US012209128B2

(12) United States Patent
Campbell et al.

(10) Patent No.: US 12,209,128 B2
(45) Date of Patent: Jan. 28, 2025

(54) ANTI-PD-L1 ANTIBODIES

(71) Applicant: KYMAB LIMITED, Cambridge (GB)

(72) Inventors: Jamie Campbell, Cambridge (GB);
Nikole Sandy, Cambridge (GB);
Cassandra Van Krinks, Cambridge (GB); Stephen John Arkinstall, Cambridge, MA (US); Volker Germaschewski, Cambridge (GB); Ian Kirby, Cambridge (GB); Miha Kosmac, Cambridge (GB); Thomas Gallagher, Cambridge (GB); Cecilia Deantonio, Cambridge (GB); Stephen Douglas Gillies, Carlisle, MA (US)

(73) Assignee: KYMAB LIMITED, Cambridge (GB)

( * ) Notice: Subject to any disclaimer, the term of this patent is extended or adjusted under 35 U.S.C. 154(b) by 556 days.

(21) Appl. No.: 17/243,372

(22) Filed: Apr. 28, 2021

(65) Prior Publication Data

US 2021/0380699 A1    Dec. 9, 2021

Related U.S. Application Data

(63) Continuation of application No. 16/311,440, filed as application No. PCT/GB2017/051796 on Jun. 20, 2017, now abandoned.

(60) Provisional application No. 62/352,291, filed on Jun. 20, 2016.

(30) Foreign Application Priority Data

Aug. 9, 2016   (GB) ..................... 1613683
Sep. 7, 2016   (GB) ..................... 1615224
Sep. 9, 2016   (GB) ..................... 1615335
Dec. 1, 2016   (GB) ..................... 1620414
Dec. 20, 2016  (GB) ..................... 1621782
Feb. 13, 2017  (GB) ..................... 1702338
Feb. 13, 2017  (GB) ..................... 1702339
Feb. 24, 2017  (GB) ..................... 1703071

(51) Int. Cl.
*C07K 16/28*    (2006.01)
*A61K 39/00*    (2006.01)
*C07K 14/55*    (2006.01)
*C07K 16/46*    (2006.01)
*C07K 19/00*    (2006.01)

(52) U.S. Cl.
CPC .......... *C07K 16/2827* (2013.01); *C07K 14/55* (2013.01); *C07K 16/28* (2013.01); *C07K 16/2803* (2013.01); *C07K 16/468* (2013.01); *C07K 19/00* (2013.01); *A61K 2039/505* (2013.01); *C07K 2317/21* (2013.01); *C07K 2317/31* (2013.01); *C07K 2317/33* (2013.01); *C07K 2317/524* (2013.01); *C07K 2317/56* (2013.01); *C07K 2317/565* (2013.01); *C07K 2317/567* (2013.01); *C07K 2317/71* (2013.01); *C07K 2317/76* (2013.01); *C07K 2317/92* (2013.01); *C07K 2319/00* (2013.01); *C07K 2319/02* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 4,663,281 A | 5/1987 | Gillies et al. | |
| 4,741,900 A | 5/1988 | Alvarez et al. | |
| 4,816,397 A | 3/1989 | Boss et al. | |
| 5,219,996 A | 6/1993 | Bodmer et al. | |
| 5,223,409 A | 6/1993 | Ladner et al. | |
| 5,314,995 A | 5/1994 | Fell, Jr. et al. | |
| 5,403,484 A | 4/1995 | Ladner et al. | |
| 5,427,908 A | 6/1995 | Dower et al. | |
| 5,516,637 A | 5/1996 | Huang et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,645,835 A | 7/1997 | Fell, Jr. et al. | |
| 5,658,727 A | 8/1997 | Barbas et al. | |
| 5,661,016 A | 8/1997 | Lonberg et al. | |
| 5,677,425 A | 10/1997 | Bodmer et al. | |

(Continued)

FOREIGN PATENT DOCUMENTS

| CN | 101023102 | 8/2007 |
|---|---|---|
| CN | 101248089 | 8/2008 |

(Continued)

OTHER PUBLICATIONS

US 9,382,325 B1, 07/2016, Bland-Ward et al. (withdrawn)
U.S. Appl. No. 14/700,896 U.S. Pat. No. 9,139,653, filed Apr. 30, 2015 Sep. 22, 2015, Jamie Campbell.
U.S. Appl. No. 14/811,163 U.S. Pat. No. 9,234,043, filed Jul. 28, 2015 Jan. 12, 2016, Jamie Campbell.
U.S. Appl. No. 14/955,843, filed Dec. 1, 2015, Jamie Campbell.
U.S. Appl. No. 15/122,298 2016/0368997 U.S. Pat. No. 10,669,342, filed Mar. 3, 2015 Dec. 22, 2016 Jun. 2, 2020, Jamie Campbell.

(Continued)

*Primary Examiner* — Nora M Rooney
(74) *Attorney, Agent, or Firm* — LATHROP GPM LLP; James H. Velema, Esq.

(57) ABSTRACT

The present invention relates to anti-PD-L1 antibodies, bispecific antibodies containing one domain with specificity to PD-L1, and to immunocytokines comprising an anti-PD-L1 antibody fused to a cytokine, such as IL-2. The present invention also provides methods of treatment, uses and pharmaceutical compositions comprising the antibodies, bispecific antibodies and immunocytokines.

6 Claims, 68 Drawing Sheets

Specification includes a Sequence Listing.

(56) References Cited

U.S. PATENT DOCUMENTS

| | | | |
|---|---|---|---|
| 5,698,426 A | 12/1997 | Huse | |
| 5,712,380 A | 1/1998 | Kendall et al. | |
| 5,733,743 A | 3/1998 | Johnson et al. | |
| 5,750,753 A | 5/1998 | Kimae et al. | |
| 5,766,886 A | 6/1998 | Studnicka et al. | |
| 5,770,429 A | 6/1998 | Lonberg et al. | |
| 5,780,225 A | 7/1998 | Wigler et al. | |
| 5,821,047 A | 10/1998 | Garrard et al. | |
| 5,869,046 A | 2/1999 | Presta et al. | |
| 5,869,619 A | 2/1999 | Studnicka | |
| 5,969,108 A | 10/1999 | McCafferty et al. | |
| 6,011,003 A | 1/2000 | Charnock-Jones et al. | |
| 6,028,176 A | 2/2000 | Greve et al. | |
| 6,100,071 A | 8/2000 | Davis-Smyth et al. | |
| 6,121,022 A | 9/2000 | Presta et al. | |
| 6,331,415 B1 | 12/2001 | Cabilly et al. | |
| 6,407,088 B1 | 6/2002 | Dong et al. | |
| 6,528,055 B2 | 3/2003 | Godfrey et al. | |
| 6,528,623 B2 | 3/2003 | Godfrey et al. | |
| 6,548,507 B1 | 4/2003 | Bountra et al. | |
| 6,599,906 B1 | 7/2003 | Ku et al. | |
| 6,803,039 B2 | 10/2004 | Tsuji et al. | |
| 6,875,432 B2 | 4/2005 | Liu et al. | |
| 6,897,294 B2 | 5/2005 | Davis-Smyth et al. | |
| 7,029,895 B2 | 4/2006 | Glucksmann et al. | |
| 7,030,225 B1 | 4/2006 | Tamatani et al. | |
| 7,045,615 B2 | 5/2006 | Tamatani et al. | |
| 7,056,509 B2 | 6/2006 | Thorpe et al. | |
| 7,098,184 B2 | 8/2006 | Godfrey et al. | |
| 7,125,551 B2 | 10/2006 | Kroczek | |
| 7,129,338 B1 | 10/2006 | Ota et al. | |
| 7,132,099 B2 | 11/2006 | Kroczek | |
| 7,166,283 B2 | 1/2007 | Tsuji et al. | |
| 7,196,175 B2 | 3/2007 | Tamatani et al. | |
| 7,226,909 B2 | 6/2007 | Tamatani et al. | |
| 7,259,247 B1 | 8/2007 | Kroczek | |
| 7,261,893 B2 | 8/2007 | Veldman et al. | |
| 7,279,560 B2 | 10/2007 | Tamatani et al. | |
| 7,291,331 B1 | 11/2007 | Croft et al. | |
| 7,300,754 B2 | 11/2007 | Abi Fadel et al. | |
| 7,304,033 B2 | 12/2007 | Larsen | |
| 7,306,800 B2 | 12/2007 | Kroczek | |
| 7,368,531 B2 | 5/2008 | Rosen et al. | |
| 7,411,051 B2 | 8/2008 | Rosen et al. | |
| 7,438,905 B2 | 10/2008 | Suzuki et al. | |
| 7,456,187 B2 | 11/2008 | Ford et al. | |
| 7,456,264 B2 | 11/2008 | Keler et al. | |
| 7,465,445 B2 | 12/2008 | Tezuka et al. | |
| 7,482,147 B2 | 1/2009 | Glucksmann et al. | |
| 7,501,496 B1 | 3/2009 | Endl et al. | |
| 7,521,541 B2 | 4/2009 | Eigenbrot et al. | |
| 7,572,618 B2 | 8/2009 | Mintier et al. | |
| 7,582,288 B2 | 9/2009 | Gillies et al. | |
| 7,704,500 B2 | 4/2010 | Papadopoulos et al. | |
| 7,722,872 B2 | 5/2010 | Kroczek | |
| 7,776,577 B2 | 8/2010 | Kapeller-Libermann et al. | |
| 7,794,710 B2 | 9/2010 | Chen et al. | |
| 7,812,133 B2 | 10/2010 | Martin | |
| 7,868,141 B2 | 1/2011 | Endl et al. | |
| 7,892,540 B2 | 2/2011 | Chen | |
| 7,932,358 B2 | 4/2011 | Tamatani et al. | |
| 7,943,743 B2 | 5/2011 | Korman et al. | |
| 7,968,689 B2 | 6/2011 | Rosen et al. | |
| 7,972,813 B2 | 7/2011 | McCormack et al. | |
| 7,988,965 B2 | 8/2011 | Tsuji et al. | |
| 7,998,478 B2 | 8/2011 | Tezuka et al. | |
| 8,008,449 B2 | 8/2011 | Korman et al. | |
| 8,030,457 B2 | 10/2011 | Jackson et al. | |
| 8,062,640 B2 | 11/2011 | Sleeman et al. | |
| 8,080,243 B2 | 12/2011 | Liang et al. | |
| 8,101,175 B1 | 1/2012 | Croft et al. | |
| 8,168,179 B2 | 5/2012 | Honjo | |
| 8,168,762 B2 | 5/2012 | Jackson et al. | |
| 8,188,233 B2 | 5/2012 | Condra et al. | |
| 8,188,234 B2 | 5/2012 | Condra et al. | |
| 8,318,905 B2 | 11/2012 | Kroczek | |
| 8,344,114 B2 | 1/2013 | Sparrow et al. | |
| 8,357,371 B2 | 1/2013 | Sleeman et al. | |
| 8,389,690 B2 | 3/2013 | Tamatani et al. | |
| 8,399,646 B2 | 3/2013 | Liang et al. | |
| 8,420,098 B2 | 4/2013 | Camphausen et al. | |
| 8,426,363 B2 | 4/2013 | Liang et al. | |
| 8,486,647 B2 | 7/2013 | Haber et al. | |
| 8,501,184 B2 | 8/2013 | Sleeman et al. | |
| 8,530,414 B2 | 9/2013 | Davies et al. | |
| 8,551,477 B1 | 10/2013 | Croft et al. | |
| 8,563,698 B2 | 10/2013 | Jackson et al. | |
| 8,598,320 B2 | 12/2013 | Hedrick | |
| 8,840,889 B2 | 9/2014 | Chen | |
| 8,916,155 B2 | 12/2014 | Kroczek | |
| 8,956,615 B1 | 2/2015 | Croft et al. | |
| 8,962,807 B2 | 2/2015 | Verdonck et al. | |
| 9,102,725 B2 | 8/2015 | Korman | |
| 9,139,653 B1 | 9/2015 | Campbell et al. | |
| 9,234,043 B1 | 1/2016 | Campbell | |
| 9,376,493 B2 | 6/2016 | Faget et al. | |
| 9,428,570 B2 | 8/2016 | Lawson | |
| 9,434,785 B1 | 9/2016 | Bland-Ward et al. | |
| 9,512,229 B2 | 12/2016 | Bland-Ward | |
| 9,567,399 B1 | 2/2017 | Campbell | |
| 9,587,030 B2 | 3/2017 | Campbell | |
| 9,617,338 B1 | 4/2017 | Campbell | |
| 9,868,789 B2 | 1/2018 | Bland-Ward | |
| 9,868,790 B2 | 1/2018 | Bland-Ward | |
| 9,957,323 B2 * | 5/2018 | Sainson | C07K 14/55 |
| 10,118,963 B2 | 11/2018 | Zhou | |
| 10,214,586 B2 | 2/2019 | Ludwig et al. | |
| 10,604,576 B2 | 3/2020 | Campbell | |
| 10,654,935 B2 | 5/2020 | Campbell et al. | |
| 10,669,342 B2 | 6/2020 | Campbell et al. | |
| 11,965,026 B2 * | 4/2024 | Cambell | C07K 16/2827 |
| 2002/0064555 A1 | 3/2002 | Chiang et al. | |
| 2002/0045571 A1 | 4/2002 | Liu et al. | |
| 2002/0081679 A1 | 6/2002 | Chiang et al. | |
| 2002/0082259 A1 | 6/2002 | Ono et al. | |
| 2002/0114814 A1 | 8/2002 | Gray | |
| 2002/0150576 A1 | 10/2002 | LaRosa et al. | |
| 2002/0156242 A1 | 10/2002 | Tamatani et al. | |
| 2003/0119038 A1 | 6/2003 | Bingham et al. | |
| 2003/0124149 A1 | 7/2003 | Shalaby et al. | |
| 2003/0158402 A1 | 8/2003 | Hall | |
| 2004/0009553 A1 | 1/2004 | Glucksmann et al. | |
| 2004/0023243 A1 | 2/2004 | Henry et al. | |
| 2004/0038242 A1 | 2/2004 | Edmonds et al. | |
| 2004/0110226 A1 | 6/2004 | Lazar | |
| 2004/0191265 A1 | 9/2004 | Schenerman et al. | |
| 2004/0248177 A1 | 12/2004 | Abi Fadel et al. | |
| 2004/0265309 A1 | 12/2004 | Kandel et al. | |
| 2005/0085433 A1 | 4/2005 | Breidenstein et al. | |
| 2005/0101529 A1 | 5/2005 | Yue et al. | |
| 2005/0118625 A1 | 6/2005 | Mounts | |
| 2005/0147612 A1 | 7/2005 | Yayon et al. | |
| 2005/0175610 A1 | 8/2005 | Wiegand et al. | |
| 2005/0197285 A1 | 9/2005 | Rosen et al. | |
| 2005/0260203 A1 | 11/2005 | Wiegand et al. | |
| 2005/0271656 A1 | 12/2005 | Huang | |
| 2005/0281822 A1 | 12/2005 | Cedarbaum et al. | |
| 2005/0281831 A1 | 12/2005 | Davis-Smyth et al. | |
| 2006/0002929 A1 | 1/2006 | Khare et al. | |
| 2006/0116508 A1 | 6/2006 | Glucksmann et al. | |
| 2006/0147945 A1 | 7/2006 | Edmonds et al. | |
| 2006/0210566 A1 | 9/2006 | Holash et al. | |
| 2006/0223088 A1 | 10/2006 | Rosen et al. | |
| 2006/0223090 A1 | 10/2006 | Rosen et al. | |
| 2006/0246071 A1 | 11/2006 | Green et al. | |
| 2006/0246483 A1 | 11/2006 | Rosen et al. | |
| 2007/0015696 A1 | 1/2007 | Rosen et al. | |
| 2007/0037206 A1 | 2/2007 | Rosen et al. | |
| 2007/0037748 A1 | 2/2007 | Stahl et al. | |
| 2007/0041963 A1 | 2/2007 | Rosen | |
| 2007/0041972 A1 | 2/2007 | Rother et al. | |
| 2007/0055056 A1 | 3/2007 | Rosen et al. | |
| 2007/0082345 A1 | 4/2007 | Ota et al. | |
| 2007/0122378 A1 | 5/2007 | Freeman et al. | |

(56) References Cited

U.S. PATENT DOCUMENTS

| | | |
|---|---|---|
| 2007/0224663 A1 | 9/2007 | Rosen et al. |
| 2007/0292440 A1 | 12/2007 | Kenyon |
| 2008/0008697 A1 | 1/2008 | Mintier et al. |
| 2008/0069795 A1 | 3/2008 | Rabb |
| 2008/0103090 A1 | 5/2008 | Rosen et al. |
| 2008/0113930 A1 | 5/2008 | Tan et al. |
| 2008/0279862 A1 | 11/2008 | Khare |
| 2009/0053230 A1 | 2/2009 | Martin |
| 2009/0055944 A1 | 2/2009 | Korman et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0252749 A1 | 10/2009 | Leister |
| 2009/0269350 A1 | 10/2009 | Glucksmann et al. |
| 2009/0326202 A1 | 12/2009 | Jackson et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068194 A1 | 3/2010 | Kim |
| 2010/0068199 A1 | 3/2010 | Liang et al. |
| 2010/0098712 A1 | 4/2010 | Adler et al. |
| 2010/0136028 A1 | 6/2010 | Sparrow et al. |
| 2010/0150937 A1 | 6/2010 | Sparrow et al. |
| 2010/0166740 A1 | 7/2010 | Endl et al. |
| 2010/0166768 A1 | 7/2010 | Sleeman et al. |
| 2010/0183591 A1 | 7/2010 | Baron |
| 2010/0183612 A1 | 7/2010 | Peach |
| 2010/0203056 A1 | 8/2010 | Irving et al. |
| 2010/0233177 A1 | 9/2010 | Yowe et al. |
| 2010/0291099 A1 | 11/2010 | Glucksmann et al. |
| 2010/0323359 A1 | 12/2010 | MacDonald et al. |
| 2011/0027287 A1 | 2/2011 | Jackson et al. |
| 2011/0033451 A1 | 2/2011 | Carreno |
| 2011/0033465 A1 | 2/2011 | Hedrick |
| 2011/0065902 A1 | 3/2011 | Sleeman et al. |
| 2011/0070239 A1 | 3/2011 | Endl et al. |
| 2011/0091481 A1 | 4/2011 | Burnette |
| 2011/0105726 A1 | 5/2011 | Rosen |
| 2011/0117011 A1 | 5/2011 | Jackson et al. |
| 2011/0135662 A1 | 6/2011 | Finney et al. |
| 2011/0142849 A1 | 6/2011 | Rue |
| 2011/0229489 A1 | 9/2011 | Pons et al. |
| 2011/0230392 A1 | 9/2011 | Chiang et al. |
| 2011/0256148 A1 | 10/2011 | Sleeman et al. |
| 2011/0307966 A1 | 12/2011 | MacDonald et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0020976 A1 | 1/2012 | Jackson et al. |
| 2012/0027751 A1 | 2/2012 | Rennert |
| 2012/0027765 A1 | 2/2012 | Jackson et al. |
| 2012/0058906 A1 | 3/2012 | Smider |
| 2012/0064621 A1 | 3/2012 | Papadopoulos et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0185956 A1 | 7/2012 | Gingras et al. |
| 2012/0195910 A1 | 8/2012 | Wu et al. |
| 2012/0208208 A1 | 8/2012 | Ni et al. |
| 2012/0208209 A1 | 8/2012 | Ichetovkin et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2012/0269723 A1 | 10/2012 | Brinkmann et al. |
| 2012/0301461 A1 | 11/2012 | Condra et al. |
| 2012/0321879 A1 | 12/2012 | Teutsch et al. |
| 2012/0328616 A1 | 12/2012 | Li et al. |
| 2013/0018175 A1 | 1/2013 | Verdonck |
| 2013/0052201 A1 | 2/2013 | Jackson et al. |
| 2013/0058944 A1 | 3/2013 | Jackson et al. |
| 2013/0064825 A1 | 3/2013 | Chan et al. |
| 2013/0064834 A1 | 3/2013 | Sleeman et al. |
| 2013/0071379 A1 | 3/2013 | Condra et al. |
| 2013/0071405 A1 | 3/2013 | Davies et al. |
| 2013/0072665 A1 | 3/2013 | Jackson et al. |
| 2013/0079501 A1 | 3/2013 | Jackson et al. |
| 2013/0079502 A1 | 3/2013 | Jackson et al. |
| 2013/0085265 A1 | 4/2013 | Jackson et al. |
| 2013/0085266 A1 | 4/2013 | Sleeman et al. |
| 2013/0095108 A1 | 4/2013 | Nadler et al. |
| 2013/0095109 A1 | 4/2013 | Nadler |
| 2013/0115171 A1 | 5/2013 | McDonough et al. |
| 2013/0115223 A1 | 5/2013 | Sparrow et al. |
| 2013/0142783 A1 | 6/2013 | Coyle |
| 2013/0183315 A1 | 7/2013 | Attinger |
| 2013/0189278 A1 | 7/2013 | Sitlani |
| 2013/0245235 A1 | 9/2013 | Jackson et al. |
| 2013/0273069 A1 | 10/2013 | Liang et al. |
| 2013/0310324 A1 | 11/2013 | Flinspach et al. |
| 2014/0044703 A1 | 2/2014 | Kato et al. |
| 2014/0086932 A1 | 3/2014 | Traber et al. |
| 2014/0161794 A1 | 3/2014 | Lugovsky |
| 2014/0093497 A1 | 4/2014 | Reimann |
| 2014/0165219 A1 | 6/2014 | Leppert et al. |
| 2014/0170157 A1 | 6/2014 | Agarwal et al. |
| 2014/0286897 A1 | 9/2014 | Podack |
| 2014/0322132 A1 | 10/2014 | Vitalis et al. |
| 2015/0203580 A1 | 7/2015 | Papadopoulos et al. |
| 2015/0239978 A1 | 8/2015 | Marodon et al. |
| 2015/0307620 A1 | 10/2015 | Vella et al. |
| 2016/0000909 A1 | 1/2016 | Eisenbach-Schwartz et al. |
| 2016/0002336 A1 | 1/2016 | Chen |
| 2016/0024211 A1 | 1/2016 | Chen |
| 2016/0145344 A1 | 5/2016 | Akbari |
| 2016/0215059 A1 | 7/2016 | Liu et al. |
| 2016/0264666 A1 | 9/2016 | Faget et al. |
| 2016/0264675 A1 | 9/2016 | Bland-Ward et al. |
| 2016/0304610 A1 | 10/2016 | Sazinsky et al. |
| 2016/0361364 A1 | 12/2016 | Corbascio |
| 2017/0037137 A1 | 2/2017 | Bland-Ward |
| 2017/0362321 A1 | 12/2017 | Campbell et al. |
| 2018/0305464 A1 | 10/2018 | Li et al. |
| 2019/0077867 A1 | 3/2019 | Zhu et al. |
| 2019/0276547 A1 | 9/2019 | Campbell |
| 2019/0330351 A1 | 10/2019 | Campbell et al. |
| 2020/0231692 A1 | 7/2020 | Hu et al. |
| 2021/0380699 A1 | 12/2021 | Campbell et al. |

FOREIGN PATENT DOCUMENTS

| | | |
|---|---|---|
| CN | 101374865 | 2/2009 |
| CN | 103221427 | 7/2013 |
| EP | 0438474 | 5/1996 |
| EP | 0463151 | 6/1996 |
| EP | 0546073 | 9/1997 |
| EP | 0984023 | 3/2000 |
| EP | 0996622 | 5/2000 |
| EP | 1067182 | 1/2001 |
| EP | 1125585 | 8/2001 |
| EP | 1158004 | 11/2001 |
| EP | 1374901 | 1/2004 |
| EP | 1502920 | 2/2005 |
| EP | 1514933 | 3/2005 |
| EP | 1286668 | 4/2005 |
| EP | 1618212 | 11/2007 |
| EP | 2481758 | 1/2012 |
| EP | 1740617 | 10/2013 |
| EP | 2650016 | 10/2013 |
| EP | 2691419 | 11/2016 |
| EP | 3369745 | 9/2018 |
| EP | 2812022 | 6/2019 |
| EP | 3495391 | 6/2019 |
| JP | 2005/130764 | 5/2005 |
| JP | 2009-518005 | 5/2007 |
| JP | 2008-512995 | 5/2008 |
| JP | 2016-555520 | 6/2017 |
| RU | 2540490 | 2/2015 |
| WO | WO 1985/004880 | 11/1985 |
| WO | WO 1990/002809 | 3/1990 |
| WO | WO 1991/004329 | 4/1991 |
| WO | WO 1991/009967 | 7/1991 |

(56) References Cited

FOREIGN PATENT DOCUMENTS

| | | |
|---|---|---|
| WO | WO 1991/010737 | 7/1991 |
| WO | WO 1991/013166 | 9/1991 |
| WO | WO 1992/001047 | 1/1992 |
| WO | WO 1992/002551 | 2/1992 |
| WO | WO 1992/008495 | 5/1992 |
| WO | WO 1992/008801 | 5/1992 |
| WO | WO 1992/018619 | 10/1992 |
| WO | WO 1992/022583 | 12/1992 |
| WO | WO 1993/011236 | 6/1993 |
| WO | WO 1993/012227 | 6/1993 |
| WO | WO 1993/020849 | 10/1993 |
| WO | WO 1995/015982 | 6/1995 |
| WO | WO 1995/020401 | 8/1995 |
| WO | WO 1995/021915 | 8/1995 |
| WO | WO 1996/008570 | 3/1996 |
| WO | WO 1997/044453 | 11/1997 |
| WO | WO 1997/049805 | 12/1997 |
| WO | WO 1998/003821 | 1/1998 |
| WO | WO 1998/013071 | 4/1998 |
| WO | WO 1998/020734 | 5/1998 |
| WO | WO 1998/024893 | 6/1998 |
| WO | WO 1998/025971 | 6/1998 |
| WO | WO 1999/003859 | 1/1999 |
| WO | WO 1999/003996 | 1/1999 |
| WO | WO 1999/015553 | 4/1999 |
| WO | WO 1999/029732 | 6/1999 |
| WO | WO 1999/043713 | 9/1999 |
| WO | WO 1999/052562 | 10/1999 |
| WO | WO 1999/053958 | 10/1999 |
| WO | WO 1999/060128 | 11/1999 |
| WO | WO 2000/011033 | 3/2000 |
| WO | WO 2000/040615 | 7/2000 |
| WO | WO 2000/047228 | 8/2000 |
| WO | WO 2000/076310 | 12/2000 |
| WO | WO 2001/007081 | 2/2001 |
| WO | WO 2001/010912 | 2/2001 |
| WO | WO 2001/014424 | 3/2001 |
| WO | WO 2001/031007 | 5/2001 |
| WO | WO 2001/057081 | 8/2001 |
| WO | WO 2001/058957 | 8/2001 |
| WO | WO 2001/087981 | 11/2001 |
| WO | WO 2001/098468 | 12/2001 |
| WO | WO 2002/000243 | 1/2002 |
| WO | WO 2002/002143 | 1/2002 |
| WO | WO 2002/014358 | 2/2002 |
| WO | WO 2002/046383 | 6/2002 |
| WO | WO 2002/057435 | 7/2002 |
| WO | WO 2002/066514 | 8/2002 |
| WO | WO 2002/072605 | 9/2002 |
| WO | WO 2002/079232 | 10/2002 |
| WO | WO 2002/079415 | 10/2002 |
| WO | WO 2002/090526 | 11/2002 |
| WO | WO 2002/090566 | 11/2002 |
| WO | WO 2002/102993 | 12/2002 |
| WO | WO 2002/102994 | 12/2002 |
| WO | WO 2003/015697 | 2/2003 |
| WO | WO 2003/048334 | 6/2003 |
| WO | WO 2003/050531 | 6/2003 |
| WO | WO 2003/059245 | 7/2003 |
| WO | WO 2004/018649 | 3/2004 |
| WO | WO 2004/051268 | 6/2004 |
| WO | WO 2004/055056 | 7/2004 |
| WO | WO 2004/094613 | 11/2004 |
| WO | WO 2004/097047 | 11/2004 |
| WO | WO 2004/106377 | 12/2004 |
| WO | WO 2005/003169 | 1/2005 |
| WO | WO 2005/003170 | 1/2005 |
| WO | WO 2005/003171 | 1/2005 |
| WO | WO 2005/007121 | 1/2005 |
| WO | WO 2005/016969 | 2/2005 |
| WO | WO 2005/021592 | 3/2005 |
| WO | WO 2005/063808 | 7/2005 |
| WO | WO 2005/063820 | 7/2005 |
| WO | WO 2005/066348 | 7/2005 |
| WO | WO 2005/086751 | 9/2005 |
| WO | WO 2005/086798 | 9/2005 |
| WO | WO 2005/094879 | 10/2005 |
| WO | WO 2005/103086 | 11/2005 |
| WO | WO 2005/113605 | 12/2005 |
| WO | WO 2005/117984 | 12/2005 |
| WO | WO 2006/029879 | 3/2006 |
| WO | WO 2006/030220 | 3/2006 |
| WO | WO 2006/061219 | 6/2006 |
| WO | WO 2006/091899 | 8/2006 |
| WO | WO 2006/133396 | 12/2006 |
| WO | WO 2007/005874 | 1/2007 |
| WO | WO 2007/023298 | 3/2007 |
| WO | WO 2007/041972 | 4/2007 |
| WO | WO 2007/062245 | 5/2007 |
| WO | WO 2007/109324 | 9/2007 |
| WO | WO 2007/113648 | 10/2007 |
| WO | WO 2007/128121 | 11/2007 |
| WO | WO 2007/133290 | 11/2007 |
| WO | WO 2008/003473 | 1/2008 |
| WO | WO 2008/027338 | 3/2008 |
| WO | WO 2008/038024 | 4/2008 |
| WO | WO 2008/057457 | 5/2008 |
| WO | WO 2008/057458 | 5/2008 |
| WO | WO 2008/057459 | 5/2008 |
| WO | WO 2008/063382 | 5/2008 |
| WO | WO 2008/083174 | 7/2008 |
| WO | WO 2008/086395 | 7/2008 |
| WO | WO 2008/090958 | 7/2008 |
| WO | WO 2008/106116 | 9/2008 |
| WO | WO 2008/109871 | 9/2008 |
| WO | WO 2008/125623 | 10/2008 |
| WO | WO 2008/130704 | 10/2008 |
| WO | WO 2008/133647 | 11/2008 |
| WO | WO 2008/137915 | 11/2008 |
| WO | WO 2009/026558 | 2/2009 |
| WO | WO 2009/033027 | 3/2009 |
| WO | WO 2009/055783 | 4/2009 |
| WO | WO 2009/061853 | 5/2009 |
| WO | WO 2009/070642 | 6/2009 |
| WO | WO 2009/100297 | 8/2009 |
| WO | WO 2009/100318 | 8/2009 |
| WO | WO 2009/126688 | 10/2009 |
| WO | WO 2009/131740 | 10/2009 |
| WO | WO 2009/141239 | 11/2009 |
| WO | WO 2010/029513 | 3/2010 |
| WO | WO 2010/031720 | 3/2010 |
| WO | WO 2010/035012 | 4/2010 |
| WO | WO 2010/036959 | 4/2010 |
| WO | WO 2010/054007 | 5/2010 |
| WO | WO 2010/056804 | 5/2010 |
| WO | WO 2010/073180 | 7/2010 |
| WO | WO 2010/077634 | 7/2010 |
| WO | WO 2010/077854 | 8/2010 |
| WO | WO 2010/089411 | 8/2010 |
| WO | WO 2010/111180 | 9/2010 |
| WO | WO 2010/117448 | 10/2010 |
| WO | WO 2011/004192 | 1/2011 |
| WO | WO 2011/020024 | 2/2011 |
| WO | WO 2011/020783 | 2/2011 |
| WO | WO 2011/025904 | 3/2011 |
| WO | WO 2011/037791 | 3/2011 |
| WO | WO 2011/041613 | 4/2011 |
| WO | WO 2011/051350 | 5/2011 |
| WO | WO 2011/051351 | 5/2011 |
| WO | WO 2011/053665 | 5/2011 |
| WO | WO 2011/053743 | 5/2011 |
| WO | WO 2011/053759 | 5/2011 |
| WO | WO 2011/053783 | 5/2011 |
| WO | WO 2011/056997 | 5/2011 |
| WO | WO 2011/066389 | 6/2011 |
| WO | WO 2011/071871 | 6/2011 |
| WO | WO 2011/072263 | 6/2011 |
| WO | WO 2011/073180 | 6/2011 |
| WO | WO 2011/097477 | 8/2011 |
| WO | WO 2011/111007 | 9/2011 |
| WO | WO 2011/158009 | 12/2011 |
| WO | WO 2012/025536 | 3/2012 |
| WO | WO 2012/027328 | 3/2012 |
| WO | WO 2012/054438 | 4/2012 |

(56) References Cited

FOREIGN PATENT DOCUMENTS

| | | |
|---|---|---|
| WO | WO 2012/062228 | 5/2012 |
| WO | WO 2012/088313 | 6/2012 |
| WO | WO 2012/088446 | 6/2012 |
| WO | WO 2012/101251 | 8/2012 |
| WO | WO 2012/101252 | 8/2012 |
| WO | WO 2012/101253 | 8/2012 |
| WO | WO 2012/107416 | 8/2012 |
| WO | WO 2012/107417 | 8/2012 |
| WO | WO 2012/109530 | 8/2012 |
| WO | WO 2012/131004 | 10/2012 |
| WO | WO 2012/132067 | 10/2012 |
| WO | WO 2012/145493 | 10/2012 |
| WO | WO 2012/146628 | 11/2012 |
| WO | WO 2012/154999 | 11/2012 |
| WO | WO 2012/162583 | 11/2012 |
| WO | WO 2012/168491 | 12/2012 |
| WO | WO 2012/170438 | 12/2012 |
| WO | WO 2012/170607 | 12/2012 |
| WO | WO 2012/174338 | 12/2012 |
| WO | WO 2012/177741 | 12/2012 |
| WO | WO 2012/178137 | 12/2012 |
| WO | WO 2013/008171 | 1/2013 |
| WO | WO 2013/008185 | 1/2013 |
| WO | WO 2013/016648 | 1/2013 |
| WO | WO 2013/028231 | 2/2013 |
| WO | WO 2013/039958 | 3/2013 |
| WO | WO 2013/039969 | 3/2013 |
| WO | WO 2013/041844 | 3/2013 |
| WO | WO 2013/061078 | 5/2013 |
| WO | WO 2013/061098 | 5/2013 |
| WO | WO 2013/063298 | 5/2013 |
| WO | WO 2013/079174 | 6/2013 |
| WO | WO 2013/148284 | 10/2013 |
| WO | WO 2013/148350 | 10/2013 |
| WO | WO 2013/170367 | 11/2013 |
| WO | WO 2013/172933 | 11/2013 |
| WO | WO 2013/173223 | 11/2013 |
| WO | WO 2013/180201 | 12/2013 |
| WO | WO 2013/181087 | 12/2013 |
| WO | WO 2013/181634 | 12/2013 |
| WO | WO 2014/023679 | 2/2014 |
| WO | WO 2014/023752 | 2/2014 |
| WO | WO 2014/033327 | 3/2014 |
| WO | WO 2014/055897 | 4/2014 |
| WO | WO 2014/089113 | 6/2014 |
| WO | WO 2014/100079 | 6/2014 |
| WO | WO 2014/109999 | 7/2014 |
| WO | WO 2014/116846 | 7/2014 |
| WO | WO 2014/159562 | 10/2014 |
| WO | WO 2014/159595 | 10/2014 |
| WO | WO 2014/165082 | 10/2014 |
| WO | WO 2014/194111 | 12/2014 |
| WO | WO 2015/036499 | 3/2015 |
| WO | WO 2015/040401 | 3/2015 |
| WO | WO 2015/049537 | 4/2015 |
| WO | WO 2015/061668 | 4/2015 |
| WO | WO 2015/103072 A1 | 7/2015 |
| WO | WO 2015/109124 | 7/2015 |
| WO | WO 2015/112800 | 7/2015 |
| WO | WO 2015/112805 | 7/2015 |
| WO | WO 2015/112900 | 7/2015 |
| WO | WO 2015/118016 | 8/2015 |
| WO | WO 2015/132580 | 9/2015 |
| WO | WO 2015/136541 | 9/2015 |
| WO | WO 2015/153514 | 10/2015 |
| WO | WO 2015/173267 | 11/2015 |
| WO | WO 2015/179654 | 11/2015 |
| WO | WO 2015/181342 | 12/2015 |
| WO | WO 2016/000619 | 1/2016 |
| WO | WO 2016/007235 | 1/2016 |
| WO | WO 2016/022468 | 2/2016 |
| WO | WO 2016/022630 | 2/2016 |
| WO | WO 2016/028656 | 2/2016 |
| WO | WO 2016/030350 | 3/2016 |
| WO | WO 2016/061142 | 4/2016 |
| WO | WO 2016/106302 | 6/2016 |
| WO | WO 2016/111645 | 7/2016 |
| WO | WO 2016/120789 | 8/2016 |
| WO | WO 2016/139482 | 9/2016 |
| WO | WO 2016/149201 | 9/2016 |
| WO | WO 2016/154177 | 9/2016 |
| WO | WO 2016/160792 | 10/2016 |
| WO | WO 2016/191643 | 12/2016 |
| WO | WO 2016/197367 | 12/2016 |
| WO | WO 2017/020291 | 2/2017 |
| WO | WO 2017/020801 | 2/2017 |
| WO | WO 2017/020802 | 2/2017 |
| WO | WO 2017/020858 | 2/2017 |
| WO | WO 2017/030823 | 2/2017 |
| WO | WO 2017/034916 | 3/2017 |
| WO | WO 2017/037707 | 3/2017 |
| WO | WO 2017/053748 | 3/2017 |
| WO | WO 2017/059095 | 4/2017 |
| WO | WO 2017/070423 | 4/2017 |
| WO | WO 2017/087547 | 5/2017 |
| WO | WO 2017/087587 | 5/2017 |
| WO | WO 2017/091429 | 6/2017 |
| WO | WO 2017/118321 | 7/2017 |
| WO | WO 2017/196867 | 11/2017 |
| WO | WO 2017/213695 | 12/2017 |
| WO | WO 2017/215590 | 12/2017 |
| WO | WO 2017/218435 | 12/2017 |
| WO | WO 2017/220569 | 12/2017 |
| WO | WO 2017/220988 | 12/2017 |
| WO | WO 2018/005682 | 1/2018 |
| WO | WO 2018/009894 | 1/2018 |
| WO | WO 2018/025221 | 2/2018 |
| WO | WO 2018/045110 | 3/2018 |
| WO | WO 2018/047178 | 3/2018 |
| WO | WO 2018/054940 | 3/2018 |
| WO | WO 2018/080812 | 5/2018 |
| WO | WO 2018/085358 | 5/2018 |
| WO | WO 2018/115859 | 6/2018 |
| WO | WO 2018/119475 | 6/2018 |
| WO | WO 2018/136553 | 7/2018 |
| WO | WO 2018/162749 | 9/2018 |
| WO | WO 2018/187191 | 10/2018 |
| WO | WO 2018/187613 | 10/2018 |
| WO | WO 2018/195226 | 10/2018 |
| WO | WO 2018/222949 | 12/2018 |
| WO | WO 2019/028367 | 2/2019 |
| WO | WO 2003/048208 | 6/2020 |

OTHER PUBLICATIONS

U.S. Appl. No. 15/259,553 2017/0002083 U.S. Pat. No. 9,587,030, filed Sep. 8, 2016 Jan. 5, 2017 Mar. 7, 2017, Jamie Campbell.
U.S. Appl. No. 15/340,497 2017/0044250 U.S. Pat. No. 10,654,935, filed Nov. 1, 2016 Feb. 16, 2017 May 19, 2020, Jamie Campbell.
U.S. Appl. No. 15/661,658 2017/0327587 U.S. Pat. No. 11,396,550, filed Jul. 27, 2017 Nov. 16, 2017 Jul. 26, 2022, Jamie Campbell.
U.S. Appl. No. 16/188,541 2019/00276547, filed Nov. 13, 2018 Sep. 12, 2019, Jamie Campbell.
U.S. Appl. No. 17/115,021 2021/0087287, filed Dec. 8, 2020 Mar. 25, 2021, Jamie Campbell.
U.S. Appl. No. 17/390,413 2021/0395378, filed Jul. 30, 2021 Dec. 23, 2021, Jamie Campbell.
U.S. Appl. No. 14/935,937 U.S. Pat. No. 9,434,785, filed Nov. 9, 2015 Sep. 6, 2016, Philip Bland-Ward.
U.S. Appl. No. 15/142,538 2016/0264675 U.S. Pat. No. 9,512,229, filed Apr. 29, 2016 Sep. 15, 2016 Dec. 6, 2016, Philip Bland-Ward.
U.S. Appl. No. 15/333,517 2017/0037137, filed Oct. 25, 2016 Feb. 9, 2017, Philip Bland-Ward.
U.S. Appl. No. 15/604,495 2017/0260279 U.S. Pat. No. 9,868,789, filed May 24, 2017 Sep. 14, 2017 Jan. 16, 2018, Philip Bland-Ward.
U.S. Appl. No. 15/661,584 2017/0327586 U.S. Pat. No. 9,868,790, filed Jul. 27, 2017 Nov. 16, 2018 Jan. 16, 2018, Philip Bland-Ward.
U.S. Appl. No. 17/725,228, filed Apr. 20, 2022, Philip Bland-Ward.
U.S. Appl. No. 16/346,675 2019/0275084, filed May 1, 2019 Sep. 12, 2019, Philip Bland-Ward.
U.S. Appl. No. 15/211,504 U.S. Pat. No. 9,567,399, filed Jul. 15, 2016 Feb. 14, 2017, Jamie Campbell.

(56) References Cited

OTHER PUBLICATIONS

U.S. Appl. No. 15/354,971 U.S. Pat. No. 9,617,338, filed Nov. 17, 2017 Apr. 11, 2017, Jamie Campbell.
U.S. Appl. No. 15/480,525 2017/0362321 U.S. Pat. No. 10,604,576, filed Apr. 6, 2017 Dec. 21, 2017 Mar. 31, 2020, Jamie Campbell.
U.S. Appl. No. 16/311,440 2019/0330351, filed Jun. 20, 2017 Oct. 31, 2019, Jamie Campbell.
U.S. Appl. No. 17/243,372 2021/0380699, filed Apr. 28, 2021 Dec. 9, 2021, Jamie Campbell.
U.S. Appl. No. 15/110,487 2017/0291951 U.S. Pat. No. 10,259,880, filed Jan. 13, 2015 Oct. 12, 2017, Jamie Campbell.
U.S. Appl. No. 15/624,765 2017/0320956, filed Jun. 16, 2017 Nov. 9, 2017, Jamie Campbell.
U.S. Appl. No. 14/472,685 U.S. Pat. No. 8,992,927, filed Aug. 29, 2014 Mar. 31, 2015, Jasper Rupert Clube.
U.S. Appl. No. 14/472,698 U.S. Pat. No. 8,986,694, filed Aug. 29, 2014 Mar. 24, 2015, Jasper Rupert Clube.
U.S. Appl. No. 14/536,129 U.S. Pat. No. 9,062,105, filed Nov. 7, 2014 Jun. 23, 2015, Jasper Rupert Clube.
U.S. Appl. No. 14/536,049 U.S. Pat. No. 9,045,545, filed Nov. 7, 2017 Jun. 2, 2015, Jasper Rupert Clube.
U.S. Appl. No. 14/659,910 U.S. Pat. No. 9,109,034, filed Mar. 17, 2015 Aug. 18, 2015, Jasper Rupert Clube.
U.S. Appl. No. 14/537,403 U.S. Pat. No. 9,067,998, filed Nov. 10, 2014 Jun. 30, 2015, Jasper Rupert Clube.
U.S. Appl. No. 14/665,532 U.S. Pat. No. 9,150,660, filed Mar. 23, 2015 Oct. 6, 2015, Jasper Rupert Clube.
U.S. Appl. No. 17/818,397, filed Aug. 9, 2022, Ben Porter-Brown.
Akiba et al., Critical contribution of OX40 ligand to T helper cell type 2 differentiation in experimental leishmaniasis, J. Exp. Med., 2000, 191(2): 375-380.
Aspeslagh et al., Rationale for anti-OX40 cancer immunotherapy, Eur. J. Cancer., 2016, 2: 50-66.
Aten et al., Strong and Selective Glomerular Localization of CD134 Ligand and TNF Receptor-1 in Proliferative Lupus Nephritis, JASN, 2000, 11(8): 1426-1438.
Attwood, The Babel of Bioinformatics, Science, 2000, 290: 471-473.
Boettler et al., OX40 Facilitates Control of a Persistent Virus Infection, PLoS, Pathog., 2012, 8(9): 1-11.
Boyerinas et al., "Antibody-dependent cellular cytotoxicity (ADCC) activity of a novel anti-PD-L1 antibody avelumab (MSB0010718C) on human tumor cells", Cancer Immunol Res., Oct. 2015, 3(10): 1148-1157.
Brando et al., Cytofluorometric methods for assessing absolute Nos. of cell subsets in blood, Cytometry, 2000, 42: 327-346.
Burrows et al., Peer Review Correspondence: OX40 blockade inhibits house dust mite driven allergic lung inflammation in mice and in vitro allergic responses in humans, European Journal of Immunology, 2014.
Byun et al., Inherited human OX40 deficiency underlying classic Kaposi sarcoma of childhood, J Exp. Med., 2013, 210(9): 1743-1759.
Carboni et al., CD134 plays a crucial role in the pathogenesis of EAE and is upregulated in the CNS of patients with multiple sclerosis, J. Neuroimmunol., 2013, 145: 1-11.
Carraway et al., New targets for therapy in breast cancer: Mammalian target of rapamycin (mTOR) antagonists, Breast Cancer Res., 2004, 6: 219-224.
Catley et al., Monoclonal antibodies for the treatment of asthma, Pharmacol Ther., Dec. 2011, 132(3): 333-351.
Cho et al., OX40 and 4-1 BB downregulate kaposi's sarcoma-associated herpes virus replication in lymphatic endothelial cells, but 4-1 BB and not OX40 inhibits viral replication in B-cells, J. Gen. Viral., 2015, 96(12): 3635-3645.
Clark et al., Determination of Absolute Counts of Circulating Regulatory T Cells in Cynomolgus Macaques Using an Optimised Flow Cytometric Method, Toxic. Pathol., 2012, 40: 107-112.
Croft et al., Clinical targeting of the TNF and TNER superfamilies, Nat Rev Drug Discov., 2013, 12(2): 147-168.
Croft et al., The significance of OX40 and OX40L to T-cell biology and immune disease, Immunol. Rev., 2009, 229(1): 173-191.
Da Silva et al., Contribution of light chain residues to high affinity binding in an HIV-1 antibody explored by combinatorial scanning mutagenesis, *Biochemistry*, 2010, 49(26): 5464-5472.
Declaration of Dr Nicholas William England under 37 C.F.R 1.132 and Exhibit B, declaration submitted in U.S. Appl. No. 15/661,658.
Dolff et al., Increased expression of costimulatory markers CD134 and COBO on interleukin-17 producing T cells in patients with systemic lupus erythematosus, Arthritis Research & Therapy, 2010, 12(4): R150.
Ekkens et al., The Role of OX40 Ligand Interactions in the Development of the Th2 Response to the Gastrointestinal Nematode Parasite Heligmosomoides polygyrus, J. Immunol., 2003, 170(1): 384-393.
Elhai et al., OX40L blockade protects against inflammation-driven fibrosis, PNAS, 2016, E3901-E3910.
Fujita et al., Lesional dendritic cells in patients with chronic atopic dermatitis and psoriasis exhibit parallel ability to activate T-cell subsets, J. Allergy Clin. Immunol., 2011, 128(3): 574-582.
Glenmark Pharmaceuticals Ltd., Glenmark's Novel Monoclonal Antibody GBR 830 to Enter Phase 2 Clinical Studies in Atopic Dermatitis and Celiac Disease in US and Europe, Glenmark Pharmaceuticals, Inc.; 2015—online only e.g. at: https://www.prnewswire.com/news-releases/glenmarks-novel-monoclonalantibody-gbr-830-to-enter-phase-2-clinical-studies-in-atopic-dermatitis-and-celiac-disease-in-us-and-europe-524062301.html.
Grogan et al., Activation and Expansion of CD81 T Effector Cells in Patients with Chronic Graft-versus-Host Disease, Biol Blood Marrow Transplant, 2011, 17: 1121-1132.
Hendricks et al., During viral infection of the respiratory tract, CD27, 4-1 BB, and OX40 collectively determine formation of CDS+ memory T cells and their capacity for secondary expansion, J. Immunol., 2005, 175(3): 1665-1676.
Hirano et al., OX40 ligand newly expressed on bronchiolar progenitors mediates influenza infection and further exacerbates pneumonia, EMBO Mol. Med., 2016, 8(4): 422-436.
Hou, Glenmark, an Indian Pharmaceutical Company in Switzerland—Innovation with a touch of spice, Neuchatel, Switzerland: Systems Biology Verification, Mar. 2014.
Humphreys et al., A critical role for OX40 in T cell-mediated immunopathology during lung viral infection, J. Exp. Med., 2003, 198(8): 1237-1242.
Humphreys et al., OX40 Costimulation Promotes Persistence of Cytomegalovirus-Specific CDS T-Cells: A CD4-Dependent Mechanism, J. Immunol., 2007, 179(4): 2195-2202.
Ilves et al., OX40 ligand and OX40 are increased in atopic dermatitis lesions but do not correlate with clinical severity, Journal of the European Academy of Dermatology and Venereology, 2013, 27: e197-e205.
International Search Report and Written Opinion dated Apr. 17, 2018, for PCT International Application No. PCT/EP2017/078202.
Ishii et al., OX40-OX40 ligand interaction in T-cell-mediated immunity and immunopathology, Advances in Immunology, 1st Ed., 2010, 105: 63-98.
Jacobsohn et al., Novel pharmacotherapeutic approaches to prevention and treatment of GVDH, Drugs, 2002, 62(6): 879-889.
Kitamura et al., OX40 costimulation can abrogate Foxp3+ regulatory T cell-mediated suppression of antitumor immunity, Int. J. Cancer, 2009, 125(3): 630-638.
Kymab News Release, Kymab Announces Positive Phase 2a Results for KY1005 in Moderate to Severe Atopic Dermatitis, Aug. 11, 2020.
Kymab, Kymab and Seattle Children's Research Institute publish impressive results using Kymab's KY1005 in a model of Acute Graft versus Host Disease (aGVHD) in Science Translational Medicine, press release issued on Sep. 21, 2017.
Kymab, Kymab announces clinical update on its promising new antibody KY1005 for treatment of autoimmune diseases, press released issued on Jul. 31, 2017.
Kymab, Kymab announces promising results from initial clinical study of new antibody KY1005 for treatment of autoimmune diseases, news release issued on Jul. 30, 2018.

(56) References Cited

OTHER PUBLICATIONS

Kymab, Kymab new therapeutic antibody for autoimmune diseases shows potential for improvement in post-transplant survival, press released issued on Dec. 5, 2016.
Lambert et al., Immunomodulatory effects of OX40 agonists in a defined antigen challenge in cynomolgus macaques, (May 20, 2015): 33, No. 15, Suppl. 1, Abstract No. 3086-3086.
Linch et al., OX40 Agonists and Combination Immunotherapy: Putting the Pedal to the Metal, Front. Oneal., 2015, 5(34): 1-14.
Maeda, Current understanding of the pathophysiology and management of acute graft versus host disease, Journal of Japan Society for Hematopoietic Cell Transplantation, 2013, vol. 2, No. 1, pp. 12-23, English abstract included.
Manku et al., Association of the co-stimulator OX40L with systemic lupus erythematosus, J. Mol. Med., 2009, 87(3): 229-234.
Matsumura et al., Expression of CD134 and CD134 ligand in lesional and nonlesional psoriatic skin, Arch. Dermatol. Res., 2003, 294: 563-566.
Mousavi et al., OX40 costimulatory signals potentiate the memory commitment of effector CDS+ T cells, J. Immunol., 2008, 181(9): 5990-6001.
Perz et al., CD4+CD25highCD127low Regulatory T cells in peripheral blood are not an independent factor for chronic graft-versus-host disease after allogeneic stem cell transplantation, The Scientific World Journal, 2012, 2012: 606839.
Pham et al., De novo proteomic sequencing of a monoclonal antibody raised against OX40 ligand, Anal Biochem, May 1, 2006, 352(1): 77-86.
Pippig et al., Robust B cell immunity but impaired T cell proliferation in the absence of CD134 (OX40), J. Immunol., 1999, 163(12): 6520-6529.
Saghari et al., KY1005 A Novel Anti-OX40L MAB with Potential in Atopic Dermatitis (AD) Results of a Phase 1 Study Assessing the Safety, Pharmacokinetics, and T-Cell-Dependent Antibody Response (TDAR) in Healthy Volunteers, Abstract from 24th World Congress of Dermatology, Milan, Jun. 10-15, 2019.
Saghari et al., KY1005 A Novel Anti-OX40L MAB with Potential in Atopic Dermatitis (AD) Results of a Phase 1 Study Assessing the Safety, Pharmacokinetics, and T-Cell-Dependent Antibody Response (TDAR) in Healthy Volunteers, Poster from 24th World Congress of Dermatology, Milan, Jun. 10-15, 2019.
Saghari et al., OX40L Blocking Monoclonal Antibody KY1005 Strongly Suppresses the Delayed-Type Hypersensitivity Skin Response to KLH in Healthy Volunteers, Abstract from 24th World Congress of Dermatology, Milan, Jun. 10-15, 2019.
Saghari et al., OX40L Blocking Monoclonal Antibody KY1005 Strongly Suppresses the Delayed-Type Hypersensitivity Skin Response to KLH in Healthy Volunteers, Poster from 24th World Congress of Dermatology, Milan, Jun. 10-15, 2019.
Simpson, Drug therapy for acute graft-versus-host disease prophylaxis, J Hemather Stem Cell Res., Jun. 2000, 9(3): 317-325.
Sochat et al., Exhibit I—Immunosuppressant targets, First Aid for the USMLE Step 1, p. 216.
Stüber et al., The expression of OX40 in immunologically mediated diseases of the gastrointestinal tract (celiac disease, Crohn's disease, ulcerative colitis), European Journal of Clinical Investigation, 2000, 30: 594-599.
Tkachev et al., AB3341- Striking Clinical, Molecular and Immunological Outcomes in Non-Human Primate Hematopoietic Stem Cell Transplantation Using a Novel OX40L Blockade Agent, KY1005, Combined with Rapamycin, ASH: 58th Annual Meeting and Exposition Experimental Transplantation: Basic Biology, Pre-Clinical Models, Dec. 3-6, 2016, San Diego, CA, USA.
Tkachev et al., Combined OX40L and mTOR blockade controls effector T cell activation while preserving Treg reconstitution after transplant, *Science Translational Medicine*, 2017, 9: eaan3085.
Tuladhar et al., Ox40L-Ox40 pathway plays distinct roles in regulating Th2 responses but does not determine outcome of cutaneous leishmaniasis caused by Leishmania mexicana and Leishmania major, Exp. Parasitol., 2015, 148: 49-55.

Wang et al., A novel agonist anti-human OX40L monoclonal antibody that stimulates T cell proliferation and enhances cytokine secretion, Hybridoma, Aug. 2009, 28(4): 269-276.
Wang et al., An Immunotherapeutic strategy for prolonging graft survival in mice, Transplant Immunology, 2015, 33(2): 84-94.
Wang et al., Characterization and functional study of five novel monoclonal antibodies against human OX40L highlight reverse signalling: Enhancement of IgG production of B cells and promotion of maturation of DCs, Tissue Antigens, 2004, 64(5): 566-557.
Wang et al., Combination of antibodies inhibits accelerated rejection mediated by memory T cells in xenoantigen-primed mice, Xenotransplantation, 2010, 17(6): 640-468.
Webb et al., "OX40, OX40L and Autoimmunity: a Comprehensive Review," Clin. Rev Allergy Immunol. 50(3):312-32 (2016).
Weinberg et al., Science gone translational: the OX40 agonist story, Immunol. Rev., 2011, 244(1): 218-231.
Willoughby et al., OX40: Structure and function—What questions remain?, Molecular Immunology, 2017, 83: 13-22.
Wu, Uniqueness of CDRH3, Analytical Molecular Biology, 2001, p. 18.
U.S. Appl. No. 15/661,584 2017/0327586 U.S. Pat. No. 9,868,790, filed Jul. 27, 2017 Nov. 16, 2017 Jan. 16, 2018, Philip Bland-Ward.
U.S. Appl. No. 15/211,504 U.S. Pat. No. 9,567,399, filed Jul. 15, 2016 Feb. 14, 2017, Jamie Cambell.
U.S. Appl. No. 15/354,971 U.S. Pat. No. 9,617,338, filed Nov. 17, 2017 Apr. 11, 2017, Jamie Cambell.
U.S. Appl. No. 15/480,525 2017/0362321 U.S. Pat. No 10,604,576, filed Apr. 6, 2017 Dec. 21, 2017 Mar. 31, 2020, Jamie Cambell.
U.S. Appl. No. 16/311,440 2019/0330351, filed Jun. 20, 2017 Oct. 31, 2019, Jamie Cambell.
U.S. Appl. No. 17/243,372 2021/0380699, filed Apr. 28, 2021 Dec. 9, 2021, Jamie Cambell.
U.S. Appl. No. 15/110,487 2017/0291951 U.S. Pat. No. 10,259,880, filed Jan. 13, 2015 Oct. 12, 2017 Apr. 16, 2019, Jamie Cambell.
U.S. Appl. No. 15/624,765 2017/0320956, filed Jun. 16, 2017 Nov. 9, 2017, Jamie Cambell.
U.S. Appl. No. 14/536,129 U.S. Pat. No. 9,062,105, filed Nov. 7, 2014 Jun. 25, 2015, Jasper Rupert Clube.
Abboud et al., Proprotein convertase subtilisin/kexin type 9 (PCSK9) gene is a risk factor of large-vessel atherosclerosis stroke PLoS One, 2(10):e1043, (2007).
Abcam Product Datasheet, Anti-ICOS antibody [C398.4A] ab81459, 2 pages.
Abifadel et al, Human Mutation, vol. 30, No. 4, pp. 520-529, 2009.
Abifadel et al. Mutations in PCSK9 cause autosomal dominant hypercholesterolemia Nat. Genet. 34, 154-156 (2003).
Abiko et al., PD-L1 on tumor cells is induced in ascites and promotes peritoneal dissemination of ovarian cancer through CTL dysfunction, Clin Cancer Res, 19(6):1363-74 (2013).
Abouelnasr et al., Defining the role of sirolimus in the management of graft-versus-host disease: from prophylaxis to treatment, Bioi Blood Marrow Transplant, 19(1):12-21 (2013).
Adebi et al., Ophthalmology 120(1):115-21 (2013). Variants in the VEGFA gene and treatment outcome after anti-VEGF treatment for neovascular age-related macular degeneration2.
Affymetrix eBioscience, Anti-Human CD278 (ICOS) Purified, obtained from url: <https://www.antibodypedia.com/gene/34168/ICOS/antibody/1028742/14-9948-80> on May 10, 2022.
Akers Michael J. et al., Formulation Development of Protein Dosage Forms Pharmaceutical Biotechnology, Kluwer, Dordrecht, NL, vol. 14, Jan. 1, 2002, pp. 47-127.
Akiba et al., CD28-independent costimulation of T cells by OX40 ligand and CD70 on activated B cells, J Immunol, 162(12):7058-66 (1999).
Akimova et al. Differing effects of rapamycin or calcineurin inhibitor on T-regulatory cells in pediatric liver and kidney transplant recipients. Am. J. Transplant. 12, 3449-3461 (2012).
Alborn et al., Serum proprotein convertase subtilisin kexin type 9 is correlated directly with serum LDL cholesterol:, Clin Chem, 53(10):1814-1819, (2007).
Alexandrov et al., Signatures of mutational processes in human cancer. Nature. Aug. 22, 2013;500(7463):415-21.

(56) References Cited

OTHER PUBLICATIONS

Alignment of Amgen Publication Heavy Chain Sequence Seq ID No. 22 and Kymab Application HCDR3 Sequence Seq ID No. 106. Alignment generated using BLAST on Aug. 10, 2017.
Allard et al., Genetic heterogeneity of autosomal dominant hypercholesterolemia: PCSK9, a third genet involved in the disease:, Current Topics in Genetics, 1, pp. 103-112, 2005.
Allard et al., Novel mutations of the PCSK9 gene cause variable phenotype of autosomal dominant hypercholesterolemia, Human mutation, 26(5), pp. 497, Nov. 2005.
Allard et al., PC9, a new actor in autosomal dominant hypercholesterolemia, Current Genomics, 6(7), pp. 535-543, Nov. 2005.
Alonso, A., et al., Subthreshold Na1-dependent theta-like rhythmicity in stellate cells of entorhinal cortex layer II, Nature, vol. 342,pp. 175-177,1989.
Anderson et al. Activation of the furin endoprotease is a multiple-step process: requirements for acidification and internal propeptide cleavage. EMBO J. 16, 1508-1518., 1997.
Anger, T., et al., Medicinal chemistry of neuronal voltage-gated sodium channel blockers, J. Med. Chem., vol. 44, No. 2 pp. 115-137, 2001.
Attie et al., Dual regulation of the LDL receptor—some clarity and new questions, Cell Metab., 1(5):290-292, (2005).
Attie et al., The mystery of PCSK9, Aterioscler Thromb Vase Biol., 24(8):1337-1339, (2004).
Augood et al., Arch Ophthalmol. 124:529e35 (2006). Prevalence of agerelated maculopathy in older Europeans: the European Eye Study (EUREYE).
Aung, et al, "The proprotein convertase subtilisin/kexin type 9 gene E670G polymorphism and serum lipid levels in the Guangxi Bai Ku Yao and Han populations", Lipids in Health and Disease, vol. 10, No. 5, pp. 1-15, 2011.
Austin et al., Genetic causes of monogenic heterozygous familial hypercholesterolemia: a HUGE prevalence review, American Journal of Epidemiology, 160 (5) pp. 407-420, 2004.
Awata et al., Diabetes. 51(5): 1635-9, (2002) A common polymorphism in the 5'-untranslated region of the VEGF gene is associated with diabetic retinopathy in type 2 diabetes.
Babcook, J., et al., A Novel Strategy for generating Monoclonal Antibodies from Single, Isolated Lymphocytes Producing Antibodies of Defined Specificities, Proc. Natl. Acad. Sci. USA, vol. 93, No. 15, pp. 7843-7848, 1996.
Bansal et al., Cord blood lipoproteins and prenatal influences, Current Opinion in Lipidology, 16(4), pp. 400-408, Aug. 2005.
Barbie et al., Systematic RNA interference reveals that oncogenic KRAS-driven cancers require TBK1. Nature, 2009; 462(7269)108-12, plus 22 pages supplemental material.
Barrios et al., Length of the Antibody Heavy Chain Complementarity Determining Region 3 as a Specificity-Determining Factor, J. Mol. Recognit., 2004, pp. 332-338, vol. 17.
Baruch et al. CNS-specific T Cells Shape Brain Function via the Choroid Plexus, Brain Behay. Immun. 34: 11-16 (2013).
Baruch et al., Aging-Induced type I Interferon Response at the Choroid Plexus Negatively Affects Brain Function, Science 346(6205): 89-93 (2014).
Baruch et al., Breaking Immune Tolerance by Targeting Foxp3(+) Regulatory T Cells Mitigates Alzheimer's Disease Pathology, Nat Commun. 6: 7967-7978 (2015).
Baruch et al., Cerebral Nitric Oxide Represses Choroid Plexus NFKB-Dependent Gateway Activity for Leukocyte Trafficking, EMBO J. 34(13): 1816-1828 (2015).
Baruch et al., CNS-Specific Immunity at the Choroid Plexus Shifts Toward Destructive Th2 Inflammation in Brain Aging, Proc. Natl. Acad. Sci. U. S. A. 110 (6): 2264-2269 (2013).
Baruch et al., PD-1 immune checkpoint blockade reduces pathology and improves memory in mouse models of Alzheimer's disease. Nat Med, 2016; 22(2):135-9, plus 296 pages supplemental material.
Basak, A., Inhibitors of Proprotien Convertases, J Mol Med 83: pp. 844-855, 2005.
Bedi et al., Inhibition of squalene synthase upregulates PCSK9 expression in rat liver, Arch Biochem Biophys., 470 (2):116-119, (2008).
Beer et al., Randomized, Double-Blind, Phase III Trial of Ipilimumab Versus Placebo in Asymptomatic or Minimally Symptomatic Patients with Metastatic Chemotherapy-Naïve Castration-Resistant Prostate Cancer, Journal of Clinical Oncology, 35(1): 40-51 (2019).
Beier et al., Induction, binding specificity and function of human ICOS. Eur J Immunol. Dec. 2000;30(12):3707-17.
Bekele-Arcuri, Z. et al., Generation and Characterization of Subtype-specific Monoclonal Antibodies to K+ Channel a- and 13-subunit Polypeptides, Neuropharmacology, vol. 35, No. 7, pp. 851-865, 1996.
Benes, J., et al., Anticonvulsant and sodium channel-blocking properties of novel 10,11-dihydro-5H-dibenz[b,f] azepine-5-carboxamide derivatives, J. Med. Chem., vol. 42, pp. 2582-2587, 1999.
Benjannet et al. (2006) The Proprotein Convertase (Pc) PCSK9 is Inactivated by Furin and/or PC5/6A, J. Biol. Chem. 281(41):30561-30572.
Benjannet et al. NARC-1/PCSK9 and its natural mutants: zymogen cleavage and effects on the low density lipoprotein (LDL) receptor and LDL cholesterol. J Biol Chem, 2004, 279 (47): 48865-48875.
Benn et al, "PCSK9R46L, Low-Density Lipoprotein Cholesterol Levels, and Risk of Ischemic Heart Disease: 3 Independent Studies and Meta-Analyses", Journal of the American College of Cardiology, vol. 55, No. 25, 2010, pp. 2833-2842.
Berge et al. Missense mutations in the PCSK9 gene are associated with hypocholesterolemia and possibly increased response to statin therapy. Arterioscler. Thromb. Vasc. Biol. (2006) 26, 1094-1100.
Biasco et al., In vivo tracking of T cells in humans unveils decade-long survival and activity of genetically modified T memory stem cells, Sci Transl Med, 7(273):273ra13 (2015).
Bingham et al. Proapoptotic Effects of NARC 1 (= PCSK9), the Gene Encoding a Novel Serine Proteinase. Cytometry Part A, 2006, 69A: 1123-1131.
Binnewies et al., Understanding the tumor immune microenvironment (TIME) for effective therapy, Nature Medicine, Published online Apr. 23, 2018 (10 pages).
Black, J.A., et al., Multiple Sodium Channel Isoforms and Mitogens-Activated Protein Kinases Are Present in Painful Human Neromas, American Neurological Association, vol. 64, pp. 664-653, 2008.
Blank et al., J. Immunol. 171:4574-81 (2013). Absence of programmed death Receptor 1 alters thymic development and enhances generation of CD4/CD8 double-negative TCR-Transgenic T Cells.
Blank et al., PD-L1/B7H-1 inhibits the effector phase of tumor rejection by T cell receptor (TCR) transgenic CD8+ T cells 64(3):1140-5 (2004).
Blazar et al., Ligation of OX40 (CD134) regulates graft-versus-host disease (GVHD) and graft rejection in allogeneic bone marrow transplant recipients, Blood, 101:3741-3748 (2003).
Bos et al., Transient regulatory T cell ablation deters oncogene-driven breast cancer and enhances radiotherapy. J Exp Med 210(11):2434-2446 (2013).
Boschetti et al., Therapy with Anti-TNF.alpha. Antibody Enhances Number and Function of FOXP3+ Regulatory T Cells in Inflammatory Bowel Diseases. AGA Abstracts, S-743 (2010).
Bossu, J.L., et al., Patch-clamp study of the tetrodotoxin-resistant sodium current in group C sensory neurons, Neuroscience Letters, vol. 51, pp. 241-246 1984.
Bottomley et al. Structural and biochemical characterization of the wild type PCSK9/EGF-AB complex and natural FH mutants. J Biol Chem Nov. 2008.
Bourgon et al., Independent filtering increases detection power for high-throughput experiments. Proc. Natl. Acad. Sci. U.S.A. 107, 9546-9551 (2010).
Brahmer et al., Phase I study of single-agent anti-programmed death-1 (MDX-1106) in refractory solid tumors: safety, clinical activity, pharmacodynamics, and immunologic correlates, J Clin Oncol, 28(19):3167-75 (2010).
Brahmer et al., Safety and activity of anti-PD-L1 antibody in patients with advanced cancer, N Engl J Med, 366 (26):2455-65 (2012).

(56) References Cited

OTHER PUBLICATIONS

Briskin, Efficacy of Anti-ICOS Agonist Monoclonal Antibodies in Preclinical Models Provides a Rationale for Clinical Development for cancer immunotherapy. Presentation SITC 2015, 22 pages.
Brown et al., Blockade of programmed death-1 ligands on dendritic cells enhances T cell activation and cytokine production, J Immunol, 170(3):1257-66 (2003).
Brown, M.S. & Goldstein, J.L. Lowering LDL—not only how low, but how long? Science 311, 1721-1723 (2006).
Brummell et al., "Probing the combining site of an anti-carbohydrate antibody by saturation-mutagenesis: role of the heavy-chain CDR3 residues", Biochemistry 32:1180-1187, 1993.
Brunger et al., Crystallography & NMR System: A new software suite for macromolecular structure determination, Acta Crystallogr D Biol Crystallogr 54, 905-21 (1998).
Bujotzek et al., VH-VL orientation prediction for antibody humanization candidate selection: A case study. MABS 8 (2):288-305 (2016).
Buonfiglio et al., The T cell activation molecule H4 and the CD28-like molecule ICOS are identical. Eur. J. Immunol., 30:3463-3467 (2000).
Burmeister et al., ICOS Controls the Pool Size of Effector-Memory and Regulatory T Cells. J. Immunol., 180(2): 774-782 (2008).
Burnett et al. New therapies for familial hypercholesterolemia Expert Opin. Ther. Patents 16(3): 349-361, 2006.
Burris III et al., Phase 1 Safety of ICOS Agonist Antibody JTX-2011 Alone and with Nivolumab (Nivo) in Advanced Solid Tumors; Predicted vs. Observed Pharmacokinetics (PK) in Iconic. (2017).
Burrows et al., OX40 blockade inhibits house dust mite driven allergic lung inflammation in mice and in vitro allergic responses in humans, Eur. J. Immunol pp. 1-13 (2015).
Butte et al., Programmed death-1 ligand 1 interacts specifically with the B7-1 costimulatory molecule to inhibit T cell responses, Immunity, 27(1):111-22 (2007).
Cameron et al. Effect of mutations in the PCSK9 gene on the cell surface LDL receptors. Hum. Mol. Genet. 15, 1551-1558 (2006).
Cameron et al., Berberine decreases PCSK9 expression in HepG2 cells, Atherosclerosis, 201(2):266-273, (2008).
Cameron et al., Characterization of novel mutations in the catalytic domain of the PCSK9 gene, J Intern Med., 263 (4):420-431, (2008).
Cameron et al., Investigations on the evolutionary conservation of PCSK9 reveal a functionally important protrusion, The FEBS Journal, pp. 1-13, 2008.
Campbell, Chapter 1, Monoclonal Antibody Technology, 1984 pp. 1-32, Elsevier Science Publishers B.V., The Netherlands.
Camus et al., Coordination of Intratumoral Immune Reaction and Human Colorectal Cancer Recurrence, Cancer Res 69:2685-93 (2009).
Cancer Discovery, "PD-1/PD-L1 Immunotherapy is Effective in Advanced Solid Tumors", 2012, 2(7): 581.
Careskey et al., Atorvastatin increases human serum levels of proprotein convertase subtilisin/kexin type 9, J Lipid Res., 49(2):394-398, (2008).
Carmenate et al., Human IL-2 Mutein with Higher Antitumor Efficacy Than Wild Type IL-2. J Immunol, published online May 15, 2013, http://http//www.jimmunol.org/content/early/2013/05/15/jimmunol.1201895, 10 pages.
Carthon et al., Preoperative CTLA-4 blockade: Tolerability and immune monitoring in the setting of a presurgical clinical trial. Clin. Cancer Res. 16:2861-2871.
Cassell et al., Therapeutic Enhancement of IL-2 Through Molecular Design. Current Pharmaceutical Design, 2002; 8:2172-2183.
Casset et al., A Peptide Mimetic of an Anti-CD4 Monoclonal Antibody by Rational Design, Biochemical and Biophysical Research Communications, 2003, vol. 307, pp. 198 205.
Cauvin et al. (2015) Advantages and Limitations of Commonly Used Nonhuman Primate Species in Research and Development of Biopharmaceuticals in the Nonhuman Primate, Nonclinical Drug Development and Safety Assessment (Academic Press), 379-395.
Cayman Chemical Company: Material Safety Data Sheet PCSK9 (human) Polyclonal Antibody Jul. 26, 2007, pp. 1-3.
Cayman Chemical Company: Material Safety Data Sheet PCSK9 (murine) Polyclonal Antibody Sep. 5, 2007, pp. 1-4.
Cayman Chemical Company: Product information PCSK9 (murine) Polyclonal Antibody Sep. 5, 2007, pp. 1-4.
Cayman Chemical Company: Product information PCSK9 Polyclonal Antibody Catalog No. 10007185 Dec. 10, 2007, pp. 1-2.
Chamow et al., Immunoadhesins: principles and applications, Trends in Biotechnology, 1996, 14(2): 52-60.
Chan et al. (2009) A proprotein convertase subtilisin/kexin type 9 neutralizing antibody reduces serum cholesterol in mice and non-human primates, Proc Natl Acad Sci USA, 106(24): 9820-9825.
Charbonnier et al. CTLA4-Ig restores rejection of MHC class-II mismatched allografts by disabling IL-2-expanded regulatory T cells. Am. J. Transplant. 12, 2313-2321 (2012).
Chattopadhyay et al., Structural Basis of Inducible Costimulatory Ligand Function: Determination of the Cell Surface Oligomeric State and Functional Mapping of the Receptor Binding Site of the Protein. J. Immunol. 177(6):3920-3929 (2006).
Chemnitz et al., Blood, 110:3226-33 (2007). RNA fingerprints provides direct evidence for the inhibitory role of TGFb and PD-1 on CD.varies.T Cells in Hodgkin lymphoma.
Chen Bei et al. Influence of histidine on the stability and physical properties of a fully human antibody in aqueous and solid forms Pharmaceutical Research, Kluwer Academic Publishers, New York, NY vol. 20, No. 12, Dec. 1, 2003, pp. 1952-1960.
Chen et al. Ox40-ligand has a critical costimulatory role in dendritic cell: T cell interactions, Immunity, 11:689-698 (1999).
Chen et al., "Enhancement and destruction of antibody function by somatic mutation: unequal occurrence is controlled by V gene combinatorial associations", EMBO J., 1995, 14(12): 2784-2794.
Chen et al., "Therapeutic efficacy of an anti-PD-L1 antibody based immunocytokine in a metastatic mouse model of colorectal cancer", Biochemical and Biophysical Research Communications, 2016, 480(2): 160-165.
Chen et al., A common PCSK9 haplotype, encompassing the E670G coding single nucleotide polymorphism, is a novel genetic marker for plasma low-density lipoprotein cholesterol levels and severity of coronary atherosclerosis, J Am Coll Cardiol. 45(10):1611-1619, (2005).
Chen et al., Asia Pac J Clin Oncol. (2014). Association between single nucleotide polymorphism of PD-L1 gene and non-small cell lung cancer susceptibility in a Chinese population.
Chen et al., Selection and Analysis of an Optimized Anti-VEGF Antibody: Crystal Structure of an Affinity Matured Fab in Complex with Antigen, J. Mol. Biol., 1999, vol. 293, pp. 865 881.
Chen, X. et al. Blockade of interleukin-6 signaling augments regulatory T-cell reconstitution and attenuates the severity of graft-versus-host disease. Blood 114, 691-900 (2009).
Cheung et al., Polymorphic variants of LIGHT (TNF superfamily-14) alter receptor avidity and bioavailability. The Journal of Immunology 185(3):1949-1958 (2010).
Chevalier et al., Phenotype Alterations in Regulatory T-Cell Subsets in Primary HIV Infection and Identification of Tr1-like Cells at the Main Interleukin 10-Producing CD4+ T Cells. JID, 211: 769-779 (2015).
Chioni, A-M. et al., A Novel Polyclonal antibody Specific lor the Nav 1.5 Voltage-Gated Na+ Channel 'Neonatal' Splice Form, Journal of Neuroscience Methods, vol. 147, pp. 88-98, 2005.
Chung et al., Treatment of malignant ascites, Current Treatment Options in Oncology, 2008, 9(2-3): 215-233.
Cieri et al., Generation of human memory stem T cells after haploidentical T-replete hematopoietic stem cell transplantation, Blood, 125(18):2865-2874 (2015).
Cieri et al., IL-7 and IL-15 instruct the generation of human memory stem T cells from naive precursors, Blood, 121 (4):573-584 (2013).
Cohen et al. Sequence variations in PCSK9, low LDL, and protection against coronary heart disease. N. Engl. J. Med. 354, 1264-1272 (2006).
Cohen et al., Erratum: Low LDL cholesterol in African Americans resulting from frequent nonsense mutations in PCSK9, Nature Genetics, 37(3), pp. 328, 2005.

(56) References Cited

OTHER PUBLICATIONS

Cohen et al., Low LDL cholesterol in individuals of African descent resulting from frequent nonsense mutations in PCSK9, Nat Genet. 37(2):161-165, (2005).
Colman, Effects of amino acid sequence changes on antibody-antigen interactions, Research in Immunology, 1994, 145(1): 33-36.
Collaborative Computational Project, No. 4 (CCP4), The CCP4 suite: programs for protein crystallography, Acta Crystallogr D. Biol Crystallogr, 50: 760-763 (1994).
Collin, Immune checkpoint inhibitors: a patent review. Expert Opinion on Therapeutic Patents, 26(5): 555-564 (2016).
Collins et al., Identification of specific residues of human interleukin 2 that affect binding to the 70-kDa subunit (p70) of the interleukin 2 receptor. Immunology, 85: 7709-7713 (1988).
Conrad et al., Plasmacytoid dendritic cells and regulatory T cells in the tumor microenvironment: A dangerous liaison. OncoImmunology. May 1, 2013;2(5):e2388.
Costet et al. Hepatic PCSK9 Expression Is Regulated by Nutritional Status via Insulin and Sterol Regulatory Element-binding Protein 1c. Journal of Biological Chemistry, Mar. 2006. 281(10): 6211-6218.
Costet et al., PCSK9 and LDL cholesterol: unraveling the target to design the bullet, Trends Biochem Sci., 33(9):426-434, (2008).
Costet et al., Proprotein Convertase Subtilisin Kexin type 9 is repressed by the peroxisome proliferator activated receptor alpha ligand fenofibric acid. Abstracts from Scientific Sessions 2006, 11-187. Basic Science.
Cox, J.J et al., An SCN9A channelopathy causes congenital inability to experience pain, Nature, vol. 444, No. 7121, pp. 894-898, 2006.
Coyle et al., The CD28-related molecule ICOS is required for effective T cell-dependent immune responses. Immunity. Jul. 2000;13(1):95-105.
Croft et al., Control of Immunity by the TNFR-Related molecule OX40 (CD134), Annu. Rev. Immunol. 28:57-78 (2010).
Crotty, T follicular helper cell differentiation, function, and roles in disease. Immunity. Oct. 16, 2014;41(4):529-42.
Culhane et al. MADE4: An R package for multivariate analysis of gene expression data. BioInformatics 21, 2789-2790 (2005).
Cummins, T. R., et al., Eiectrophysiological Properties of Mutant Nav1.7 Sodium Channels in a Painful Inherited Neuropathy, The Journal of Neuroscience, 24(38), pp. 8232-8236, 2004.
Cunningham et al., Structural and biophysical studies of PCSK9 and its mutants linked to familiar hypercholesterolemia, Nature Structural & Molecular Biology, vol. 14, No. 5, pp. 413-419 (May 2007).
Curiel et al., Nat. Med. 9:562-67 (2003). Blockade of B7-H1 improves myeloid dendritic cell-mediated antitumor immunity.
Curran et al., PD-1 and CTLA-4 combination blockade expands infiltrating cells and reduces regulatory T and myeloid cells within B16 melanoma tumors. PNAS, 107(9):4275-4280 (2010).
Currie et al., Dual Control of Antitumor CD8 T Cells through the Programmed Death-1/Programmed Death-Ligand 1 Pathway and Immunosuppressive CD4 T Cells: Regulation and Counterregulation. J. Immunol., 183(12): 7898-7908 (2009).
Cutler et al. Tacrolimus/sirolimus vs tacrolimus/methotrexate as GVHD prophylaxis after matched, related donor allogenic HCT. Blood 124, 1372-1377 (2014).
Dai et al., Anti-OX40L monoclonoal antibody prolongs secondary heart allograft survival based on CD40/CD40L and LFA-1/ICAM-1 blockade, Transplant Immunology {2015}, http://dx.doi.org/10.1016/j.trim.2015.01.001.
Dall et al., Increasing the affinity of a human IgG1 for the neonatal Fc receptor : Biological consequences. Immunol 2002; 169:5171-5180.
Damayanti et al., Serial OX40 engagement on CD+4 T cells and natural killer T cells causes allergic airway inflammation, Am J Respir Crit Care Med 181(7):688-698 (2010).
Damgaard et al., No genetic linkage or molecular evidence for involvement of the PCSK9, ARH or CYP7A1 genes in the Familial Hypercholesterolemia phenotype in a sample of Danish families without pathogenic mutations in the LDL receptor and apoB genes, Atherosclerosis 177 (2), pp. 415-422, 2004.
Dana Farber Blog, Enhancing Immunotherapy: The Race to Make 'Cold' Tumors 'Hot,' Published Jun. 6, 2018 at https://blog.dana.farber.org/insight/2018/06/enhancing-immunotherapy-race-make-cold-tumors-hot/ (7 pages).
D'Angelo et al., Many Routes to an Antibody Heavy-Chain CDR3: Necessary, Yet Insufficient, for Specific Binding, Front Immunol., 2018, vol. 9, Article 395.
Davignon et al. Erratum to NARC-1: A potential new target for drug therapy of hypercholesterolemia, Atherosclerosis, 176, pp. 429, 2004.
Davignon et al., Narc-1: A Potential New Target for Drug Therapy of Hypercholesterolemia, Xlllth International Symposium on Atherosclerosis, Sep. 28-Oct. 2, 2003, Kyoto, Japan, pp. 182-183.
Davis-Smyth et al., The EMBO Journal 15(18):4919-4927 (1996). The second immunoglobulin-like domain of the VEGF tyrosine kinase receptor Flt-1 determines ligand binding and may initiate a signal transduction cascade.
De Genst, E., et al., Molecular basis for the preferential cleft recognition by dromedary heavy-chain antibodies, PNAS, vol. 103, No. 12, pp. 4586-4591, 2006.
De Haard, Novel Strategies for Identification and Characterization of Human Antibodies Against Nav1.7 Ion Channel Target, Antibodies Against Membrane Protein Targets, 2013, pp. 1-31.
De Pascalis et al., Grafting of 'Abbreviated' Complementarity Determining Regions Containing Specificity Determining Residues Essential for Ligand Contact to Engineer a Less Immunogenic Humanized Monoclonal Antibody, J. Immunol, 2002, vol. 169, pp. 3076-3084.
Declaration of Dr. Anil K. Thotakura submitted with Statement of Opposition filed at European Patent Office against European Patent No. EP2482849 on Mar. 6, 2019 (27 pages).
Declaration of Dr. Gwenoline Borhis submitted with Statement of Opposition filed at European Patent Office against European Patent No. EP2482849 on Mar. 6, 2019 (10 pages).
Declaration of Dr. Richard C.A. Sainson, submitted with Statement of Opposition filed at European Patent Office against European Patent No. EP2482849 on Mar. 6, 2019 (8 pages).
DeDoussis et al., LDL-receptor mutations in Europe, Human Mutation, 24(6), pp. 443-459, 2004.
Dellemijn, Paul, Are opioids effective in relieving neuropathic pain?, International Association for the Study of Pain, vol. 80, No. 3, pp. 453-462, 1999.
Deng et al., An Agonist Human ICOS Monoclonal Antibody that Induces T Cell Activation and Inhibits Proliferation of a Myeloma Cell Line. Hybridoma and Hybridomics, 23(3): 176-182 (2004).
Deng et al., Extrafollicular CD4+ T-B interactions are sufficient for inducing autoimmune-like chronic graft-versus-host disease, Nature Communications 2017, 18:978, (17 pages).
Devries et al. Science 225:989-991 (1992). , The fms-like tyrosine kinase, a receptor for vascular endothelial growth factor.
Diamond et al. The broad-spectrum antiviral functions of IFIT and IFITM proteins. Nat. Rev. Immunol. 13, 46-57 (2013).
Dib-Hajj et al, Review, 2007, vol. 30, No. 11, pp. 555-563.
Dib-Hajj, et al., Genetics and molecular pathophysiology of Na(v)1.7-related pain syndromes, Advances in Genetics, vol. 63, pp. 85-110, 2008.
Dib-Hajj, et al., Voltage-gated sodium channels: therapeutic targets for pain, American Academy of Pain Medicine, vol. 10, No. 7, pp. 1260-1269, 2009.
Ding et al., Molecular population genetics of PCSK9: a signature of recent positive selection, Pharmacogenet Genomics. 18(3):169-179, (2008).
Dong et al., Angiogenesis., 17(3):553-62 (2014). Antagonism of PDGF-BB suppresses subretinal neovascularization and enhances the effects of blocking VEGF-A.
Dong et al., B7-H1, a third member of the B7 family, co-stimulates T-cell proliferation and interleukin-10 secretion Nat Med, 5(12):1365-9 (1999).
Dong et al., ICOS co-stimulatory receptor is essential for T-cell activation and function. Nature. 2001; 409(6816):97-101.

(56) References Cited

OTHER PUBLICATIONS

Dong et al., Tumor-associated B7-H1 promotes T-cell apoptosis: a potential mechanism of immune evasion, Nat Med, 8(8):793-800 (2002).
Dorfman et al., Am. J. Surg. Pathol. 30:802-10 (2006). Programmed death-1 (PD-1) is a marker of germinal centerassocaited T-cells and angioimmunoblastic T-Cell lymphoma.
Doyle, D.A., et al., The Structure of the Potassium Channel, Molecular Basis of K+ Conduction and Selectivity, Science, vol. 280, No. 5360. pp. 69-77, 1998.
Dranoff et al., Vaccination with irradiated tumor cells engineered to secrete murine granulocyte-macrophage colony-stimulating factor stimulates potent, specific, and long-lasting anti-tumor immunity, Proc. Natl. Acad. Sci. USA 90: 3539-3543 (1993).
Drenth et al. (2001) The primary erythermalgia—susceptibility gene is located on chromosome 2q31-32, Am. J. Hum. Genet., 2001, 68(5): 1277-1282.
Driessens et al., Costimulatory and coinhibitory receptors in anti-tumor immunity. Immunol. Rev. 229(1): 126-144 (2009).
Duan et al. Large scale analysis of positional effects of single-base mismatches on microarray gene expression data. BioData Min. 3, 2 (2010).
Dubuc et al. Statins upregulate PCSK9, the gene encoding the proprotein convertase neural apoptosis-regulated convertase-1 impli-cated in familial hypercholesterolemia. Arterioscler. Thromb. Vasc. Biol. 24, 1454-1459 (2004).
Duff et al. Antibody-mediated disruption of the interaction between PCSK9 and the low-density lipoprotein receptor. Biochemical Jour-nal. Published online Feb. 5, 2009 as Manuscript BJ20082407.
Dworkin, R. H., An overview of neuropathic pain: syndromes, symptoms, signs, and several mechanisms, The Clinical Journal of Pain, vol. 18, pp. 343-349, 2002.
Eager et al., GM-CSF Gene-Transduced Tumor Vaccines, Molecu-lar Therapy 12(1): 18-27 (2005).
EB 06682 Goat Anti-PCSK9 Antibody, Everest Biotech Online Catalogue,.Copyrgt. 2007, auto-generated Sep. 7, 2007.
Edwards et al., (2003) The remarkable flexibility of the human antibody repertoire; isolation of over one thousand different anti-bodies to a single protein, BLyS, J Mol Biol., 334(1): 103-118.
Ellis et al., Engineered Anti-CD38 Monoclonal Antibodies for Immunotherapy of Multiple Myeloma. The Journal of Immunology 155 (1995): 925-937.
Elpek et al., Abstract A059: Efficacy of anti-ICOS agonist mono-clonal antibodies in preclinical tumor models proves a rationale for clinical development as cancer immunotherapeutics. Cancer Immu-nology Research, (2016).
Europeanbiotechnology.com, Roche's anti-PD-L1 fails in bladder cancer, Published May 10, 2017 at https://european-biotechnology.com/up-to-date/latest-news/news/roches-anti-pd-l1-fails-in-bladder-cancer.html (2 pages).
Evans et al., The E670G Snp in the PCSK9 gene is associated with polygenic hypercholesterolemia in men but not in women, BMC Med Genet., 7:66, (2006).
Faget et al., ICOS—Ligand Expression on Plasmacytoid Dendritic Cells Supports Breast Cancer Progression by Promoting the Accu-mulation of Immunosuppressive CD4+ T Cells. Cancer Res., 72(23): (2012).
Fan et al. Self-Association of Human PCSK9 Correlates with Its LDLR-Degrading Activity, Biochemistry, 2008, 47:1631-1639.
Fan et al., Engagement of the ICOS pathway markedly enhances efficacy of CTLA-4 blockade in cancer immunotherapy. J Exp Med. Apr. 7, 2014;211(4):715-25.
Fehrenbacher et al., Atezolizumab versus docetaxel for patients with previously treated non-small-cell lung cancer (POPLAR): a multicentre, open-label, phase 2 randomised controlled trial, Lancet, 387(10030):1837-46 (2016).
Feyler et al., Tumour Cell Generation of Inducible Regulatory T-Cells in Multiple Myeloma is Contact-Dependent and Antigen-Presenting Cell-Independent. PLoS One, 7(5): 10 pages (2012).

Findlay et al., OX40L blockade is therapeutic in arthritis despite promoting osteoclastogenesis, PNAS, 111 (6):2289-2294 (2014).
Finger et al., Survey of Ophthalmology, 59(1): 1-8 (2014). Predic-tors of anti-VEGF treatment response in neovascular age-related macular degeneration.
Fisher et al., Effects of pH and low density lipoprotein (LDL) on PCSK9-dependent LDL receptor regulation, J Biol Chem, 282(28):20502-20512, (2007).
Foks et al., Interruption of the OX40-OX40 ligand pathway in LDL receptor-deficient mice causes regression of atherosclerosis, J. Immunol. 191:4573-4580 (2013).
Folsom et al., Variation in PCSK9, low LDL cholesterol, and risk of peripheral arterial disease, Atherosclerosis, 202(1):211-215, (2009).
Fong et al., Nature, 376(6):66-70 (1995). Role of the Flt-1 receptor tyrosine kinase in regulating the assembly of vascular endothelium.
Fouchier et al., PCSK9 mutations found in patients diagnosed with autosomal dominant hypercholesterolemia in the Netherlands, Cir-culation, 110 (17 Suppl. S) Oct. 26, 2004.
Fouchier et al., Update of the molecular basis of familial hyper-cholesterolemia in The Netherlands, Human Mutation, 26(6), pp. 550-556, Dec. 2005.
Frampton, J.E., et al., Pregabalin: in the treatment of painful diabetic peripheral neuropathy, vol. 64, No. 24, pp. 2813-2820, 2004.
Francisco et al., PD-L1 regulates the development, maintenance, and function of induced regulatory T cells. J. Exp. Med. 206(13): 3015-3029 (2009).
Franco et al., Blood, 118(10): 2906-2917 (2011). Pericytes promote endothelial cell survival through induction of autocrine VEGF-A signaling and Bcl-w expression.
Frank-Kamenetsky et al., Therapeutic RNAi targeting PCSK9 acutely lowers plasma cholesterol in rodents and LDL cholesterol in non-human primates, Proc Natl Acad Sci., 105(33):11915-11920, (2008).
Freeman et al., Engagement of the PD-1 immunoinhibitory receptor by a novel B7 family member leads to negative regulation of lymphocyte activation, J Exp Med, 192(7):1027-34 (2000).
French et al., A thresfold sodiumchannell in pyramidal cells in rat hippocampus, Neuroscience Letters, 56:289-294, 1985.
French et al., What is conservative substitution? J. Mol. Evol. 1983; 19;171-5.
Fu et al. (2000). Folding pathway mediated by an intramolecular chaperone. The inhibitory and chaperone functions of the subtilisin propeptide are not obligatorily linked. J. Biol. Chem. 275, 16871-16878.
Fu et al., The ICOS/ICOSL pathway is required for optimal anti-tumor responses mediated by anti-CTLA-4 therapy. Cancer Res. Aug. 15, 2011;71(16):5445-54.
Gallego-Pinazo et al., Update on the principles and novel local and systemic therapies for the treatment of non-infectious uveitis, Inflamm Allergy Drug Targets, 12(1):38-45 (2013).
Galluzzi et al., Immunological mechanisms underneath the efficacy of cancer therapy. Canc. Imm. Res. 4:895-902 (2016).
Galon et al., Approaches to treat immune hot, altered and cold tumours with combination immunotherapies, Nature Reviews Drug Discovery, Published online Jan. 4, 2019 (22 pages).
Garnett et al., Treatment and management of graft-versus-host disease: improving response and survival, Ther Adv Hematol 4(6):366-78 (2013).
Gattinoni et al., A human memory T cell subset with stem cell-like properties, Nat Med, 17(10):1290-1297 (2011).
Gattinoni, L. & Restifo, N.P., Comment on Moving T memory stem cells to the clinic, Blood, 121(4):567-568 (2013).
Gauvreau et al., OX40L blockade and allergen-induced airway responses in subjects with mild asthma, Clinical Experimental Allergy, 44:29-37 (2013).
Ge et al., CDI34-Allodepletion allows selective elimination of alloreactive human T cells without loss of virus-specific and leukemia-specific effectors, Biology of Blood and Marrow Transplantation 14:518-530 (2008).
GenomeNet Database: UniProt, Entry: A0E922, Parte, Aury et al., 2006.
Gerritsen et al., A dose-escalation trial of GM-CSF-gene transduced allogeneic prostate cancer cellular immunotherapy in combination with a fully human anti-CTLA antibody (MDX-010, ipilimumab) in

(56) References Cited

OTHER PUBLICATIONS patients with metastatic hormone-refractory prostate cancer (mHRPC) Journal of Clinical Oncology, 24(18), Published online Dec. 12, 2016 at http://ascopubs.org/doi/abs/10.1200/jco.2006.24.18_suppl. 2500 (5 pages).
Gillessen et al., A phase I dose-escalation study of the immunocytokine EMD 521873 (Selectikine) in patients with advanced solid tumours. Eur J Cancer (2012), 10 pages.
Gillies et al., A Low-Toxicity IL-2-Based Immunocytokine Retains Antitumor Activity Despite Its High Degree of IL-2 Receptor Selectivity. Clin Cancer Res, 2011; 17:3673-3682.
Gilly et al., Threshold channels—a novel type of sodium channel in squid giant axon, Nature. May 31-Jun. 6, 1984;309(5967):448-450.
Gilly, et al. (1989) Properties of appropriately and inappropriately expressed sodium channels in squid giant axon and its somata, J. Neurosci., 9(4): 1362-1374.
Goel et al. (2004) Plasticity within the Antigen-Combining Site May Manifest as Molecular Mimicry in the Humoral Immune Response, J Immunol, 173(12): 7358-7367.
Goldberg et al., Loss-of-function mutations in the Nav1.7 gene underlie congenital indifference to pain in multiple human populations, Clin Genet. Apr. 2007;71(4):311-9.
Goldstein et al. Familial hypercholesterolemia in The Metabolic & Molecular Bases of Inherited Disease (eds. Scriver, C.S et al.) 2863-2913 (McGraw-Hill, New York, 2001).
Goldstein, J.L. & Brown, M.S. The cholesterol quartet. Science 292, 1310-1312 (2001).
Golub et al. Molecular classification of cancer: Class discovery and class prediction by gene expression monitoring. Science 286, 531-537 (1999).
Gong et al., PLoS One., 8(12):e84069 (2013). Association of VEGF gene polymorphisms with diabetic retinopathy: a meta-analysis.
Gonoi, T., et al., Voltage Clamp Analysis of Tetrodotoxin-sensitive and- insensitive Sodium Channels in Rat Muscle Cells Developing in Vitro1, J. Neurosci., vol. 5, No. 9, pp. 2559-2564, 1985.
Graadt Van Roggen et al., FH Afrikaner-3 LDL receptor mutation results in defective LDL receptors and causes a mild form of familial hypercholesterolemia, Arteriosclerosis, Thrombosis, and Vascular Biology, 15(6), pp. 765-772, Jun. 1995.
Graadt Van Roggen et al., Low density lipoprotein receptor founder mutations in Afrikaner familial hypercholesterolaemic patients: A comparison of two geographical areas, Human Genetics, 88(2), pp. 204-208, 1991.
Graham et al. Antisense inhibition of proprotein convertase subtilisin/kexin type 9 reduces serum LDL in hyperlipidemic mice. J Lipid Research 2007, 48:763-767.
Graham et al., Genetic screening protocol for familial hypercholesterolemia which includes splicing defects gives an improved mutation detection rate, Atherosclerosis, 182(2), pp. 331-340, Oct. 2005.
Grefhorst et al., Plasma PCSK9 preferentially reduces liver LDL receptors in mice, J Liped Res., 49(6):1303-1311, (2008).
Gross et al., Aryl sulfonamido tetralin inhibitors of the Kv1.5 ion channel, Bioorg Med Chem Lett. Jun. 1, 2009;19(11):3063-6.
Grozdanov et al. Expression and localization of PCSK9 in rat hepatic cells Biochemistry and Cell Biology, Feb. 2006, 84(1):80-92.
Grozdanov et al. Expression of Pcsk9 in rat hepatic cells, FASEB Journal, 19(4, Suppl. S, Part 1, Mar. 4, 2005.
Gul et al., Antibody-Dependent Phagocytosis of Tumor Cells by Macrophages: A Potent Effector Mechanism of Monoclonal Antibody Therapy of Cancer. Cancer Res., 75(23), Dec. 1, 2015.
Guo et al. The type I IFN induction pathway constrains Th17-mediated autoimmune inflammation in mice. J. Clin. Invest. 118, 1680-1690 (2008).
Hallman et al., Relation of PCSK9 mutations to serum low-density lipoprotein cholesterol in childhood and adulthood (from the Bogalusa Heart Study), Am J Cardiol., 100(1):69-72, (2007).
Hamada et al., Carrier Cell-mediated Delivery of a Replication-competent Adenovirus for Cancer Gene Therapy, Molecular Therapy 15(6): 1121-1128 (2007).

Hamanishi et al., PNAS 104(9):3360-3365 (2007). Programmed cell death 1 ligand 1 and tumor-inflitrating CD8+ T lymphocytes are prognostic factors of human ovarian cancer.
Hampton et al. The Crystal Structure of PCSK9 at 1.9 Angstroms Resolution Reveals Structure Homology to Resistin within the C-Terminal Domain (Released Sep. 18, 2007).
Hampton et al., The self-inhibited structure of full-length PCSK9 at 1.9 A reveals structural homology with resistin within the C-terminal domain, Proc Nat Acad Sci USA, Sep. 2007, 104(37): 14604-14609.
Han et al., J Diabetes Res. 2014:805801 (2014). The associations between VEGF gene polymorphisms and diabetic retinopathy susceptibility: a meta-analysis of 11 case-control studies.
Hanzelmann et al., GSVA: gene set variation analysis for microarray and RNA-Seq data. BMC Bioinformatics, vol. 14, No. 1, p. 7, 2013.
Harvey et al., Efficacy of Anti-ICOS Agonist Monoclonal Antibodies in Preclinical Models Provides a Rationale for Clinical Development for cancer immunotherapy. Journal for Immunotherapy of Cancer 3(Suppl 2):09 (2015).
Hasenhindl et al., Creating stable stem regions for loop elongation in Fcabs—Insights from combining yeast surface display, in silico loop reconstruction and molecular dynamics simulations. Biochimica et Biophysica Acta 1844: 1530-1540 (2014).
Hattori et al., Blockade of the OX40 ligand prolongs corneal allograft survival, Eur. J. Immunol. 37:3597-3604 (2007).
Hayashi et al., Eur J Endocrinol. 158(6):817-22 (2008). Association of an A/C single nucleotide polymorphism in programmed cell death-ligand 1 gene with Graves' disease in Japanese patients.
Heaton et al., Human Interleukin 2 Analogues That Preferentially Bind the Intermediate-Affinity Interleukin 2 Receptor Lead to Reduced Secondary Cytokine Secretion: Implications for the Use of These Interleuken 2 Analogues in Cancer Immunotherapy. Cancer Res, 53:2597-2602 (1993).
Helfand, AstraZeneca's Imfinzi fails key Mystic trial in lung cancer. What now? Published online Nov. 16, 2018 at https://www.fiercepharma.com/pharma/astrazeneca-s-imfinzi-fails-key-mystic-trial-lung-cancer-what-now (4 pages).
Henrich et al. (2003). The crystal structure of the proprotein processing proteinase furin explains its stringent specificity. Nat Struct. Biol. 10, 520-526.
Henrich et al. (2005). Proprotein convertase models based on the crystal structures of furin and kexin: Explanation of their Specificity Journal of Molecular Biology vol. 345, Issue 2, Jan. 14, 2005, pp. 211-227.
Herbst et al., Predictive correlates of response to the anti-PD-L1 antibody MPDL3280A in cancer patients, Nature, 515(7528):563-7 (2014).
Herley et al., Biochemical and Biophysical Research Communications. 262:731-738 (1999). Characterization of the VEGF binding site on the Flt-1 receptor.
Hermann et al., Ophthalmology. 121(4):905-10. (2014). Polymorphisms in vascular endothelial growth factor receptor 2 are associated with better response rates to ranibizumab treatment in age-related macular degeneration.
Hirano et al., Blockade of B7-H1 and PD-1 by monoclonal antibodies potentiates cancer therapeutic immunity, Cancer Res, 65(3):1089-96 (2005).
Hirano et al., Cancer Res. 65:1089-96 (2005). Blockade of B7-H1 and PD-1 by monoclonal antibodies potentiates cancer therapeutic immunity.
Hirsch et al., Biomarker Driven Indication Selection in JTX-2011 ICONIC Clinical Trial. Poster presented at the American Society of Clinical Oncology (ASCO) Annual Meeting, Jun. 2-6, 2017 in Chicago, Illinois.
Hirsch, A biomarker-driven approach for the development of the ICOS agonist antibody, JTX-2011, presentation for the Society for Immunotherapy of Cancer. Nov. 8, 2017 in National Harbor, Maryland, 11 pages.
Hitt E. (2011) FDA Approves Belatacept for Kidney Transplant Patients. Accessed at http://www.medscape.com/viewarticle/744723 on Jun. 17, 2017. 2 pages.
Hodge et al., Multiple Costimulatory Modalities Enhance CTL Avidity, J. Immunol. 174: 5994-6004 (2005).

(56) References Cited

OTHER PUBLICATIONS

Hodi et al., Immunologic and clinical effects of antibody blockade of cytotoxic T lymphocyte-associated antigen 4 in previously vaccinated cancer patients. PNAS Feb. 26, 2008;105(8):3005-10.
Holla et al., Degradation of the LDL receptors by PCSK9 is not mediated by a secreted protein acted upon by PCSK9 extracellularly, BMC Cell Biol., 8:9, (2007).
Holla et al., Low-density lipoprotein receptor activity in Epstein-Barr virus-transformed lymphocytes from heterozygotes for the D374Y mutation in the PCSK9 gene, Scand J Clin Lab., 66(4):317-328, (2006).
Homer et al, (2008) Identification and characterization of two non-secreted PCSK9 mutants associated with familial hypercholesterolemia in cohorts from New Zealand and South Africa, Atherosclerosis, 196(2): 659-666.
Hooper et al., The C679X mutation in PCSK9 is present and lowers blood cholesterol in a Southern African population, Atherosclerosis, 193(2):445-448, (2007).
Hopkins et al, (2013) Abstract 17156: A Randomized Placebo-phase Clinical Trial With the Monoclonal Antibody Alirocumab Demonstrates Reductions in Low-density Lipoprotein Cholesterol in Patients With Proprotein Convertase Subtilisin/Kexin Type 9 Gain-of-Function Mutations, Circulation, 128(Suppl. 22): 17156, Abstract only.
Horkheimer et al. Induction of type I IFN is required for overcoming tumor-specific T- cell tolerance after stem cell transplantation. Blood 113, 5330-5339 (2009).
Horton et al., Molecular biology of PCSK9: its role in LDL metabolism, Trends in Biochemical Sciences, 2006, vol. 32, No. 2, pp. 71-77.
Hoshino et al., Critical role for OX40 ligand in the development of pathogenic Th2 cells in a murine model of asthma, EurJ Immunol, 33(4):861-9 (2003).
Houghten et al., Relative Importance of Position and Individual Amino Acid Residues in Peptide Antigen-Antibody Interactions: Implications in the Mechanism of Antigenic Drift and Antigenic Shift, New Approaches to Immunization, Vaccines 86, Cold Spring Harbor Laboratory, p. 21-25, 1986.
Houot et al., Therapeutic effect of CD137 immunomodulation in lymphoma and its enhancement by Treg depletion. Blood 114:3431-3438 (2009).
Hoyt et al., Benzazepinone Nav1.7 blockers: potential treatments for neuropathic pain, Bioorg Med Chem Lett. Nov. 15, 2007;17(22):6172-7.
Hsieh et al. Allogeneic hematopoietic stem-cell transplantation for sickle cell disease. N. Engl. J. Med. 361, 2309-2317 (2009).
Hu et al., Generation of low-toxicity interleukin-2 fusion proteins devoid of vasopermeability activity. Immunobiology, vol. 101, No. 12: 4853-4861 (2003).
Hua et al., Breast Cancer Res Treat. 129:195-201 (2011). PD-1 polymorphims are associated with sporadic breast cancer in Chinese Han population of northeastChina.
Huang et al. Bioinformatics enrichment tools: Paths toward the comprehensive functional analysis of large gene lists. Nucleic Acids Res. 37, 1-13 (2009).
Huang et al. Systematic and integrative analysis of large gene lists using David bioinformatics resources. Nat. Protoc. 4, 44-57 (2009).
Huang et al., Rheumatology (Oxford) 50(10):1809-13 (2011). Effects of genetic polymorphisms of programmed cell death 1 and its ligands on the development of ankylosing spondylitis.
Human Proprotein Convertase 9/PCSK9 Antibody, Antigen Affinity-purified Polyclonal Sheep IgG, Catalog No. AF3888. R & D Systems: Tools for Cell Biology ResearchTM Rev: Oct. 21, 2010 p. 1 of 1.
Human/Mouse Proprotein Convertase 9/PCSK9 Antibody, Monoclonal Rat IgG, Clone # 407119, Catalog No. MAB3888. R & D Systems: Tools for Cell Biology ResearchTM Rev. Oct. 12, 2010 p. 1 of 1. Available for sale since Jun. 2007.
Human/Mouse Proprotein Convertase 9/PCSK9 Antibody, Monoclonal Rat IgG, Clone # 407119, Catalog No. MAB38881. R & D Systems: Tools for Cell Biology ResearchTM Rev. Oct. 12, 2010 p. 1 of 1. Available for sale since Apr. 2008.
Human/Mouse Proprotein Convertase 9/PCSK9 Antibody, Monoclonal Rat IgG, Clone # 407119, Catalog No. MAB38882. R & D Systems: Tools for Cell Biology ResearchTM Rev. Oct. 12, 2010 p. 1 of 1. Available for sale since Feb. 2009.
Hutloff et al., ICOS is an inducible T-cell co-stimulator structurally and functionally related to CD28. Nature. 1999; 397(6716):263-6.
Idusogie et al., Engineered antibodies with increased activity to recruit complement. J. Immunol. 2001, 166:2571-2575.
Ikeda et al., Na+ and Ca2+ currents of acutely isolated adult rat nodose ganglion cells, J Neurophysiol. Mar. 1986;55(3):527-39.
Ikemura et al., (1987). Requirement of pro-sequence for the production of active subtilisin E in *Escherichia coli*. J. Biol. Chem. 262, 7859-7864.
Inman et al., Cancer 109:1499-505 (2007). PD-L1 (B7-H1) expression by urothelial carcinoma of the bladder and BCG-iinduced granulomata.
Inman, Costimulation, Coinhibition, and Cancer. Current Cancer Drug Targets, 7, 15-30 (2007).
International Search Report & Written Opinion dated Apr. 1, 2019, for PCT International Patent Application No. PCT/GB2018/053698.
International Search Report & Written Opinion dated Feb. 5, 2018, for PCT International Patent Application No. PCT/GB2017/052352.
International Search Report & Written Opinion dated May 27, 2019, for PCT International Patent Application No. PCT/GB2018/053701.
International Search Report & Written Opinion dated May 3, 2018, for PCT International Patent Application No. PCT/GB2017/053826.
International Search Report & Written Opinion dated May 7, 2019, for PCT International Patent Application No. PCT/GB2018/051714.
International Search Report & Written Opinion dated Oct. 4, 2017, for PCT International Patent Application No. PCT/GB2017/051796.
International Search Report & Written Opinion dated Sep. 22, 2017, for PCT International Patent Application No. PCT/GB2017/051794.
International Search Report & Written Opinion dated Sep. 25, 2017, for PCT International Patent Application No. PCT/GB2017/051795.
Irizarry et al. Exploration, normalization, and summaries of high density oligonucleotide array probe level data. Biostatistics 4, 249-264 (2003).
Ito et al. J. Biol. Chem. 273:23410-23418 (1998). Cell biology and metabolism: Identification of vascular endothelial growth factor factor receptor-1 tyrosine phosphorylation sites and binding of SH2 domain-containing molecules.
Iwai et al., Involvement of PD-L1 on tumor cells in the escape from host immune system and tumor immunotherapy by PD-L1 blockade, Proc Natl Acad Sci USA, 99(19):12293-7 (2002).
Jacquemin et al., OX40 ligand contributes to human lupus pathogenesis by promoting T follicular helper response, Immunity, 4:1-12 (2015).
Janke et al., Eminent role of ICOS costimulation for T cells interacting with plasmacytoid dendritic cells. Immunology, 11: 353-360 (2006).
Jeon, H. & Blacklow, S.C. Structure and physiologic function of the low-density lipoprotein receptor. Annu. Rev. Biochem. 74, 535-562 (2005).
Jian-Fei et al., Regulatory T cells, especially ICOS+ FOXP3(+) regulatory T cells, are increased in the hepatocellular carcinoma microenvironment and predict reduced survival. Scientific Reports, vol. 6, www.nature.com/scientificreports Published Oct. 11, 2016 (8 pages).
Jiang et al., Role of IL-2 in cancer immunotherapy. OncoImmunology, 5:6, e1163462, DOI: 10.1080/2162402X.2016.1163462, 2016, 10 pages.
Jiang et al., The principle of gating charge movement in a voltage-dependent K+ channel, Nature. May 1, 2003;423(6935):42-8.
Jirholt et al., How does mutant proprotein convertase neural apoptosis-regulated convertase 1 induce autosomal dominant hypercholersterolemia, Arteriosclerosis, Thrombosis and Vascular Biology, 24 (8) pp. 1334-1336, 2004.
Jo et al. Am J Pathol. 168(6):2036-53 (2006). Inhibition of platelet-derived growth factor B signaling enhances the efficacy of anti-vascular endothelial growth factor therapy in multiple models of ocular neovascularisation.

(56) References Cited

OTHER PUBLICATIONS

Johansson et al., Arthritis Rheum., 52(6):1665-9 (2005). Association of a PDCD1 polymorphism with renal manifestations in systemic lupus erythematosus.
Johnson, W.E., Adjusting batch effects in microarray expression data using empirical Bayes methods. Biostatistics 8, 118-127 (2007).
Johnson, Z.P., et al. Immunogenetic management software: A new tool for visualization and analysis of complex immunogenetic datasets. Immunogenetics 64, 329-336 (2012).
Johnston et al. Sirolimus and mycophenolate mofetli as GVHD prophylaxis in myeloablative, matched-related donor hematopoietic cell transplantation. Bone Marrow Transplant. 47, 581-588 (2012).
Jones, S.W., Sodium Currents in Dissociated Bull-Frog Sympathetic Neurones, J. Physiol., vol. 389, pp. 605-627, 1987.
Jounce Therapeutics Press Release, Jounce Therapeutics Initiates Phase 1/2 Iconic Study of JTX-2011 in Patients with Advanced Solid Tumors, Sep. 7, 2016, 2 pages.
Jounce Therapeutics Press Release, Jounce Therapeutics Initiates Phase 2 Portion of Iconic Study of JTX-2011 in Patients with Advanced Solid Tumors, Apr. 20, 2017, 3 pages.
Jounce Therapeutics Press Release, Jounce Therapeutics Presents Data Highlighting Advances From Two Programs in its Immuno-Oncology Pipeline at the 2016 AACR Annual Meeting, Apr. 17, 2016, 2 pages.
Jounce Therapeutics Press Release, Jounce Therapeutics Presents Phase 1 Data from ICONIC Study of JTX-2011 in Patients with Advanced Solid Tumors at 2017 ASCO Annual Meeting, Jun. 5, 2017, 6 pages.
Jounce Therapeutics Press Release, Jounce Therapeutics to Present at AACR Annual Meeting on JTX-2011 Cancer Immunotherapy Program, Mar. 22, 2017, 5 pages.
Jounce Therapeutics Press Release, Jounce Therapeutics to Present Phase 1 Data from JTX-2011 Iconic Trial at 2017 American Society of Clinical Oncology Annual Meeting, May 17, 2017, 5 pages.
Jounce Therapeutics Press Release, Jounce Therapeutics to Present Program Updates at AACR Annual Meeting 2016, Mar. 16, 2016, 2 pages.
Jounce Therapeutics, Advancing Cancer Immunotherapy Worldwide. Presentation for SITC Conference, Nov. 8-12, 2017.
Kabelitz, Expression and function of Toll-like receptors in T lymphocytes. Curr. Opin. Immunol. 19, 39-45 (2007).
Kahn et al. 'Adjustable Locks and Flexible Keys: Plasticity of Epitope-Paratope Interactions in Germline Antibodies.' J. Immunol. 192:5398-5405, 2014.
Kaiser et al., Reduced tumor-antigen density leads to PD-1/PD-L1-mediated impairment of partially exhausted CD8+ T cells, Eur J Immunol, 42(3):662-71 (2012).
Kala et al., Phage Displayed Antibodies to Heat Stable Alkaline Phosphatase: Framework Region as a Determinant of Specificity, J. Biochem., 2002, pp. 535-541, vol. 132.
Kastelein et al., What promise does PCSK9 hold?, J Am Coll Cardiol., 45(10):1620-1621, (2005).
Kathiresan et al., A PCSK9 missense variant associated with a reduced risk of early-onset myocardial infarction, N Engl J Med., 358(21):2299-2300, (2008).
Kegg Drug: D10354, Dupilumab, originally retrieved on Aug. 16, 2019, obtained from url: https://www.genome.jp/dbget-bin/www_bget?dr:D10354.
Keir et al., PD-1 and Its Ligands in Tolerance and Immunity, Annu. Rev. Immunol. 26: 677-704 (2008).
Kilpatrick et al., Rapid development of affinity matured monoclonal antibodies using RIMMS. Hybridoma, 1997; 16(4):381-9.
Kim et al. Long-distance PCR-based screening for large rearrangements of the LDL receptor gene in Korean patients with familial hypercholesterolemia, Clinical Chemistry, 45(9), p. 1424-1430, 1999.
Kinnear et al. A diametric role for OX40 in the response of effector/memory CD4+ T cells and regulatory T cells to alloantigen. J. Immunol. 191, 1465-1475 (2013).

Kitchens et al., Interruption of OX40L signaling prevents costimulation blockade-resistant allograft rejection, JCI Insight 2(5):e90317 (2017) https://doi.org/10.1172/jci.insight.90317.
Klionsky, L., et al., A Polyclonal Antibody to the Prepare Loop of Transient Receptor Potential Vanilloid Type1 Blocks Channel Activation, The Journal of Pharmacology and Experimental Therapeutics, vol. 319, No. 1, pp. 192-198, 2006.
Knappik et al., Fully Synthetic Human Combinatorial Antibody Libraries (HuCAL) Based on Modular Consensus Frameworks and CDRs Randomized with Trinucleotides. J Mol. Biol.296 (2000): 57-86.
Kole et al. Type I IFNs regulate effector and regulator T cell accumulation and anti-inflammatory cytokine production during T cell-mediated colitis. J. Immunol. 191, 2771-2779 (2013).
Kondo et al., Gene 208:297-305 (1998). Genomic organization of the flt-1 gene encoding for vascular endothelial growth factor (VEGF) receptor-1 suggest an intimate evolutionary relationship between the 7-Ig and the 5-Ig tyrosine kinase receptors.
Kong et al., Arthritis Rheum. 52(4): 1058-62 (2005). A new haplotype of PDCD1 is associated with rheumatoid arthritis in Hong Kong Chinese.
Konishi et al., Clin. Cancer Res. 10:5094-100 (2004). B7-H1 expression on non-small cell lung cancer cells and its relationship with tumor-infiltrating lymphocytes and their PD-1 expression.
Kopf et al. OX40-deficient mice are defective in Th cell proliferation but are competent in generating B cell and CTL Responses after virus infection. Immunity 11, 699-708 (1999).
Kostyuk et al., Ionic currents in the somatic membrane of rat dorsal root ganglion neurons-I. Sodium currents, Neuroscience. 1981;6(12):2423-30.
Kotani et al., Correlation of peripheral blood OX40+(CD134+) T cells with chronic graft-versus-host disease in patients who underwent allogeneic hematopoietic stem cell transplantation: Presented in part at the 42nd Annual Meeting and Exposition of the America Society of Hematology, Blood, 98(10):3160-3164 (2001).
Kotowski et al, A spectrum of PCSK9 alleles contributes to plasma levels of low-density lipoprotein cholesterol., Am. J. Hum. Genet. 2006;78:410-422.
Kotowski et al, The American Journal of Human Genetics, vol. 78, 2006, pp. 410-422.
Kotowski et al., Multiple sequence variations in PCSK9 contribute to decreased plasma levels of LDL cholesterol, Circulation, 112 (17, Suppl. S), Oct. 25, 2005. Abstract No. 1766.
Kotze et al., Familial hypercholesterolemia: Potential diagnostic value of mutation screening in a pediatric population of South Africa, Clinical Genetics, 54(1), pp. 74-78, Jul. 1998.
Koura et al. In vivo T cel costimulation blockade with abatacept for acute graft-versus-host disease prevention: A first-in-disease trial. Biol. BloodMarrow Transplant. 19, 1638-1649 (2013).
Kourimate et al.', Dual mechanisms for the fibrate-mediated repression of proprotein convertase subtilisin/kexin type 9, J Biol Chem., 283(15):9666-9673, (2008).
Kraman et al., A LAG-3/PD-L1 bispecific antibody inhibits tumour growth in two syngeneic colon carcinoma patients. Keystone Symposium, 2017, Poster 3005.
Kroemer et al. OX40 controls functionally different T cell subsets and their resistance to depletion therapy. J. Immunol. 179, 5584-5591 (2007).
Kroemer et al., Immunologic Cell Death in Cancer Therapy. Ann Rev Immunol. 2013; 31:51-72.
Kroner et al., Ann Neurol. 58(1):50-7 (2005). A PD-1 polymorphism is associated with disease progression in multiple sclerosis.
Kunis et al., IFN-γ-Dependent Activation of the Brain's Choroid Plexus for CNS Immune Surveillance and Repair, Brain 136: 3427-3440 (2013).
Kunis et al., Immunization with a Myelin-Derived Antigen Activates the Brain's Choroid Plexus for Recruitment of Immunoregulatory Cells to the CNS and Attenuates Disease Progression in a Mouse Model of Als, J. Neurosci. 35(16): 6381-6393 (2015).
Kuo et al., Expert Rev Ophthalmol., 8(2): 127-140 (2013). Genetic risk, ethnic variations and pharmacogenetic biomarkers in age-related macular degeneration and polypoidal choroidal vasculopathy.

(56) References Cited

OTHER PUBLICATIONS

Kussie et al. (1994) A single engineered amino acid substitution changes antibody fine specificity, J. Immunol., 152(1): 146-152.
Kwon et al. Molecular basis for LDL receptor recognition by PSK9. PNAS Feb. 12, 2008, 105(6):1820-1825.
Lagace et al. (2006) Secreted PCSK9 Decreases the Number of LDL Receptors in Hepatocytes and in Livers of Parabiotic Mice, J. Clin. Invest. 116(11):2995-3005.
Lalanne et al., Wild-type PCSK9 inhibits LDL clearance but does not affect apoB-containing lipoprotein production in mouse and cultured cells, J Lipid Res., 46(6):1312-1319, (2005).
Lambert et al. PCSK9: a promising therapeutic target for dyslipidemias? Trends Endocrinol. Metab. 17, 79-81 (2006).
Lambert et al., Fasting induces hyperlipidemia in mice overexpressing proprotein convertase subtilisin kexin type 9: lack of modulation of very-low density lipoprotein hepatic output by the low-density lipoprotein receptor, Endocrinology, 147(10):4985-4995, (2006).
Lambert et al., Molecular basis of PCSK9 function, Atherosclerosis, 203(1):1-7, (2009).
Lambert et al., Plasma PCSK9 concentrations correlate with LDL and total cholesterol in diabetic patients and are decreased by fenofibrate treatment, Clin Chem., 54(6):1038-1045, (2008).
Lambert et al., Unravelling the functional significance of PCSK9, Curr Opin Lipidol., 18(3):304-309, (2007).
Lamminmaki et al., Crystal Structure of a Recombinant Anti-estradiol Fab Fragment in Complex with 1713-Estradiol, The Journal of Biological Chemistry, vol. 276 (39), Sep. 28, 2001, pp. 36687 36694.
Langer, New methods of drug delivery. (1990) Science 249:1527-1533.
Langhi et al., Activation of the farnesoid X receptor represses PCSK9 expression in human hepatocytes, FEBS Lett., 582(6):949-955, (2008).
Lank et al. Ultra-high resolution HLA genotyping and allele discovery by highly multiplexed cDNA amplicon pyrosequencing. BMC Genomics 13, 378 (2012).
Larsen et al. An MHC-defined primate model reveals significant rejection of bone marrow after mixed chimerism induction despite full MHC matching. Am. J. Transplant. 10, 2396-2409 (2010).
Laustsen et al., Soluble OX40L is associated with presence of autoantibodies in early rheumatoid arthritis, Arthritis Research & Therapy 16:747 (2014).
Lazar et al., Engineered antibody Fc variants with enhanced effector function. 2006, Proc. Natl. Acad. Sci. U.S.A., Mar. 14; 103(11):4005-10.
Le et al., Follicular B Lymphomas Generate Regulatory T Cells via the ICOS/ICOSL Pathway and Are Susceptible to Treatment by Anti-ICOS/ICOSL Therapy. Cancer Res., 76(16):4648-4660 (2016).
Lederman et al. (1991) A single amino acid substitution in a common african allele of the CD4 molecule ablates binding of the monoclonal antibody, OKT4, Molecular Immunology 28(11): 1171-1181.
Lee et al. (2014) Retracted: A Monoclonal Antibody that Targets a NaV1.7 Channel Voltage Sensor for Pain and Itch Relief, Cell, 157(6): 1393-1404.
Lee et al., Complete humanization of the mouse immunoglobulin loci enables efficient therapeutic antibody discovery. Nature Biotechnology, 2014; 32: 356-363.
Lee, J.S. et al. Recruitment of Sprouty1 to immune synapse regulates T cell receptor signaling. J. Immunol. 183, 7178-7186 (2009).
Lefranc, IMGT unique numbering for immunoglobulin and T cell receptor variable domains and Ig superfamily V-like domains. Dev Comp Immunol. 2003; 27(1):55-77.
Leren et al., Mutations in the PCSK9 gene in Norwegian subjects with autosomal dominant hypercholesterolemia, Clin Genet., 65(5):419-422, (2004).
Levine et al., A prognostic score for acute graft-versus-host disease based on biomarkers: a multicentre study, Haematology, 2:e21-e29 (2015).

Li et al. (1980) beta-Endorphin omission analogs: dissociation of immunoreactivity from other biological activities, PNAS, 77(6): 3211-3214.
Li et al., Secreted PCSK9 promotes LDL receptor degradation independently of proteolytic activity, Biochem J. 406, 203-207 (2007).
Liakou et al., CTLA-4 blockade increases IFNgamma-producing CD4+ICOShi cells to shift the ratio of effector to regulatory T cells in cancer patients. Proc Natl Acad Sci USA. Sep. 30, 2008;105(39):14987-92.
Lin et al., The PD-1/PD-L1 complex resembles the antigen-binding Fv domains of antibodies and T cell receptors, Proc Natl Acad Sci USA, 105(8):3011-6 (2008).
Liston et al., Dicer-dependent microRNA pathway safeguards regulatory T cell function, J Exp Med 205(9): 1993-2004 (2008).
Liu et al., Blood 110:296-304 (2007). Plasma cells from multiple myeloma patients express B7-H1 (PD-L1) and increase expression after stimulation with IFN-y and TLR ligands via a MyD88-, TRAF6-, and Mek-dependent pathway.
Liu et al., Rheumatol Int., 31(2):209-13 (2011). Programmed cell death 1 gene polymorphisms is associated with ankylosing spondylitis in Chinese Han population.
Liu, J.L., et al., Isolation of anti-toxin single domain antibodies from a semi-synthetic spiny dogfish shark display library, BMC Biotechnology, vol. 7:78, 2007.
Llinas, et al., Electrophysiological properties of in vitro Purkinje cell dendrites in mammalian cerebellar slices, J. Physiol. (Land.), vol. 305, pp. 197-213, 1980.
Lloyd et al. Protein Engineering, Design & Selection 2009, 22:159-168 (Year: 2009).
Lode et al., Natural Killer Cell-Mediated Eradication of Neuroblastoma Metastases to Bone Marrow by Targeted Interleukin-2 Therapy. Blood, vol. 91, No. 5: 1706-1715 (1998).
Lohning et al., Expression of ICOS in Vivo Defines CD4+ Effector T Cells with High Inflammatory Potential and a Strong Bias for Secretion of Interleukin 10. J. Exp. Med., 197(2): 181-193 (2003).
Long et al., Crystal structure of a mammalian voltage-dependent Shaker family K+ channel, Science. Aug. 5, 2005;309(5736):897-903.
Lopez et al., Inhibition of PCSK9 as a novel strategy for the treatment of hypercholesterolemia, Drug News Perspect., 21(6):323-330, (2008).
Lopez et al., PCSK9: an enigmatic process, Biochim Biophys Acta., 1781(4):184-191, (2008).
Lu et al., BMC Ophthalmol. 13:56 (2013). Two polymorphisms (rs699947, rs2010963) in the VEGF-A gene and diabetic retinopathy: an updated meta-analysis.
Ma et al., Functional Characterization of Novel Genes Regulated in a Cell Culture Model of Neuronal Apoptosis, Neuroscience 2002 Abstract, Nov. 5, 2002, p. 1.
Mabry et al., MAbs. 2(1): 20-34 (2010). A dual-targeting PDGFRbeta/VEGF-A molecule assembled from stable antibody fragments demonstrates anti-angiogenic activity in vitro and in vivo.
MacCallum, et al. (1996) Antibody-antigen interactions: contact analysis and binding site topography, Journal of Molecular Biology, 262(5): 732-745.
Mak et al., Costimulation through the inducible costimulator ligand is essential for both T helper and B cell functions in T cell-dependent B cell responses. Nat Immunol. 2003; 4(8):765-72.
Marais et al., The diagnosis and management of familial hypercholesterolaemia, European Review for Medical and Pharmacological Sciences, 9(3), pp. 141-149, May 2005.
Mariuzza et al., Annu Rev Biophys Chem., 1987, 16: 139-159.
Martin-Orozco et al., Melanoma Cells Express ICOS Ligand to Promote the Activation and Expansion of T-Regulatory Cells. Cancer Research 70(23):9581-9590 2010.
Martin-Orozco et al., Paradoxical dampening of anti-islet self-reactivity but promotion of diabetes by OX40 ligand, J Immunol. 171:6954-6960 (2003).
Maxwell et al. Adenoviral-mediated expression of PCSK9 in mice results in a low-desnity lipoprotein receptor knockout phenotype, Proc Natl Acad Sci USA, May 2004, 101(18): 7100-7105.

(56) References Cited

OTHER PUBLICATIONS

Maxwell et al. Novel putative SREBP and LXR target genes identified by microarray analysis in liver of cholesterol-fed mice Journal of Lipid Research, vol. 14, 2109-2119, 2003.
Maxwell et al. Overexpression of PCSK9 accelerates the degradation of the LDLR in a post-endoplasmic reticulum compartment Proc. Natl. Acad. Sci. USA (2005) 102, 2069-2074.
Maxwell et al., Overexpression of Pcsk9 leads to the formation of an LDLR-Pcsk9 complex and acceleration of LDLR degredation, Circulation, 110 (17 Suppl. S) Oct. 26, 2004. Abstract No. 1171.
Maxwell, K.N. & Breslow, J.L. Proprotein convertase subtilisin kexin 9: the third locus implicated in autosomal dominant hypercholesterolemia. Curr. Opin. Lipidol. 16, 167-172 (2005).
Mayne et al. (2013) Differential effects of PCSK9 loss of function variants on serum lipid and PCSK9 levels in Caucasian and African Canadian populations, Lipids in Health and Disease, 12(70): 1-11.
Mayne et al., Plasma PCSK9 levels are significantly modified by statins and fibrates in humans, Lipids Health Dis., 7:22, (2008).
Mayne et al., Plasma PCSK9 Levels Correlate with Cholesterol in Men but not in Women. Biochemical and Biophysical Research Communications (BBRC) 361 (2007): 451-456.
Mbikay et al., Of PCSK9, cholesterol homeostasis and parasitic infections: possible survival benefits of loss-of-function PCSK9 genetic polymorphisms, Med Hypotheses, 69(5):1010-1017, (2007).
McAdam et al., Mouse Inducible Costimulatory Molecule (ICOS) Expression is Enhanced by CD28 Costimulation and Regulates Differentiation of CD4+ T Cells. J. Immunology, 165:5035-5040 (2000).
McCourt et al., KY1055, a novel anti-ICOS/PD-L1 bispecific antibody, enhances T cell activation and delivers potent monotherapy anti-tumour responses in vivo. poster, 1 page.
McCourt et al., KY1055, a novel anti-ICOS/PD-L1 bispecific antibody, enhances T cell activation and delivers potent monotherapy anti-tumour responses in vivo. PowerPoint, 13 pages.
McGarrity et al. (2017) Hippocampal Neural Disinhibition Causes Attentional and Memory Deficits, Cerebral Cortex, 27(9): 4447-4462.
McGowan et al., A peripherally acting Na(v)1.7 sodium channel blocker reverses hyperalgesia and allodynia on rat models of inflammatory and neuropathic pain, Anesth Analg. Sep. 2009; 109(3):951-8.
McNutt et al., Catalytic Activity Is Not Required for Secreted PCSK9 to Reduce Low Density Lipoprotein Receptors in HepG2 Cells, Journal of Biological Chemistry, vol. 282, No. 29, pp. 20799-20803 (Jul. 20, 2007).
McNutt, M.C. et al. Antagonism of secreted PCSK9 increases low density lipoprotein receptor expression in HepG2 cells—2009—Journal of Biological Chemistry, 284: 10561-10570.
Meiri et al., Detection of cell surface sodium channels by monoclonal antibodies—could the channels become exposed to the external surface and 'down regulated' by binding to antibodies?, Brain Res. Mar. 12, 1986;368(1):188-92.
Meiri et al., Monoclonal antibodies associated with sodium channel block nerve impulse and stain nodes of Ranvier, Brain Res. Sep. 17, 1984; 310(1):168-73.
Mendez et al. (1997) Functional transplant of megabase human immunoglobulin loci recapitulates human antibody response in mice, Nature Genetics, 15(2): 146-156.
Metzger et al., ICOS Promotes the Function of CD4$^+$ Effector T Cells during Anti-OX40-Mediated Tumor Rejection. Cancer Res, 76(13): 3684-3689 (2016).
Michaelson, Preclinical Assessment of JTX-2011, An Agonist Antibody Targeting ICOS, Supports Evaluation in Iconic Clinical Trial, Presentation 2017, 27 pages.
Miller et al. GVHD after haploidentical transplantation: A novel, MHC-defined rhesus macaque model identifies CD28-CD8+ T cells as a resevoir of breakthrough T-cell proliferation during costimulation blockade and sirolimus-based immunosuppression. Blood 116, 5403-5418 (2010).

Mitchell et al., J Clin Endocrinol Metab. 94(12):5139-45 (2009). Programmed death ligand 1 (PD-L1) gene variants contribute to autoimmune Addison's disease and Graves' disease susceptibility.
Miura et al., Molecular cloning and characterization of a novel glycoprotein, gp34, that is specifically induced by the human T-cell leukemia virus type 1 transactivator p. 40 tax, Molecular and Cellular Biology 11 (3): 1313-1325 (1991).
Miyake et al. (2008) Genetic variants in PCSK9 in the Japanese population: Rare genetic variants in PCSK9 might collectively contribute to plasma LDL cholesterol levels in the general population, Atherosclerosis, 196(1): 29-36.
Mojtahedi et al., Gene 508(2):229-32 (2012). Programmed death-1 gene polymorphism (PD-1.5 C/T) is associated with colon cancer.
Moore et al., Anti-PD1 x anti-ICOS bispecific antibody XmAb23104 brings together PD1 blockade and ICOS costimulation to promote human T cell activation and proliferation. SITC 2017 Poster p. 347.
Mootha et al. PGC-1a-responsive genes involved in oxidative phosphorylation are coordinately downregulated in human diabetes. Nat. Genet. 34, 267-273 (2003).
Moreno et al. (2016) Response to Programmed Cell Death-1 Blockade in a Murine Melanoma Syngeneic Model Requires Costimulation, CD4, and CD8 T Cells, Cancer Immunol Res, 4(10): 845-857.
Morishita et al., J Biol Chem 270:27948-27953 (1995). Nucleic Acids, Protein Synthesis, and Molecular Genetics: A novel promoter for vascular endothelial growth factor receptor (flt-1) that confers endothelial-speicific gene expression.
Moschen et al. Interferon-alpha controls IL-17 expression in vitro and in vivo. Immunobiology 213, 779-787 (2008).
Moynihan et al., Eradication of large established tumors in mice by combination immunotherapy that engages innate and adaptive immune responses. Nature Medicine, 12 pages (2016).
Munson, An improved technique for calculating relative response in cellular proliferation experiments. Cytometry A 77, 909-910 (2010).
Murata et al. Impairment of antigen-presenting cell function in mice lacking expression of OX40 ligand. J. Exp. Med. 191, 365-374 (2000).
Muto et al., Improving the Cross-Reactivity of an Antibody Using Site-Directed Mutagenesis, TOSOH Research and Technology Review, 2012, vol. 56: 3-9.
Naidoo et al. 'Toxicities of the anti-PD-1 and anti-PD-L1 immune checkpoint antibodies.' Ann Onc. 26:2375-2391, 2015.
Nair et al., A simple practice guide for dose conversion between animals and human. J Basic Clin Pharma 2016;7:27-31.
Nakanishi et al., Cancer Immunol. Immunother. 56:1173-82. (2007). Overexpression of B7-H1 (PD-L1) significantly associates with tumor grade and postoperative prognosis in human urothelial cancers.
Namaka et al., A treatment algorithm for neuropathic pain, Clin Ther. Jul. 2004;26(7):951-79.
Naoumova et al., Severe hypercholesterolemia in four British families with the D374Y mutation in the PCSK9 gene: Long-term follow-up and treatment response, Arteriosclerosis, Thrombosis, and Vascular Biology, 25(12), pp. 2654-2660, Dec. 2005.
Nassar et al. (2004) Nociceptor-specific gene deletion reveals a major role for Nav1.7 (PN1) in acute and inflammatory pain, PNAS, 101(34): 12706-12711.
Nassoury et al. The Cellular Trafficking of the Secretory Proprotein Convertase PCSK9 and Its Dependence on the LDLR, Traffic, 2007, 8: 718-732.
Natsume et al., Engineered Antibodies of IgG1/IgG3 Mixed Isotype with Enhanced Cytotoxic Activities. Cancer Res., 68: 3863-3872 (2008).
Natsume et al., Improving effector functions of antibodies for cancer treatment: Enhancing ADCC and CDC. Drug Des. Devel. Ther. 3:7-16 (2009).
Naureckiene et al. Functional Characterization of Narc1, a Novel Proteinase Related to Proteinase K, Arch Biochem Biophys. Dec. 1, 2003;420(1):55-67.
Nemunaitis, Vaccines in Cancer: GVAX®, a GM-CSF gene vaccine, Expert Rev. Vaccines 4(3): 259-274 (2005).
Neri et al., Immunocytokines for cancer treatment: past, present and future. Current Opinion in Immunology, GB vol. 40, Apr. 6, 2016, pp. 96-102.

(56) References Cited

OTHER PUBLICATIONS

Neufeld et al. FASEB Journal. 13:11-22 (1999). Vascular endothelial growth factor VEGF) and its receptors.
Newcomb et al. Human TH17 cells express a functional IL-13 receptor and IL-13 attenuates IL-17A production. J. Allergy Clin. Immunol. 127, 1006-1013 (2011).
Newman et al. Modification of the Fc region of a primatized IgG antibody to human CD4 retains its ability to modulate CD4 receptors but does not deplete CD4+ T cells in chimpanzees. Clin. Immunol. 98, 164-174 (2001).
Ngo et al. (1994) Computational Complexity, Protein Structure Prediction, and the Levinthal Paradox, The Protein Folding Problem and Tertiary Structure Prediction, pp. 433-506.
Ni Yan G et al. A PCSK9 C-terminal Domain Binding Fab Inhibits PCSK9 Internalization and Restores LDL-uptake: Circulation, vol. 120 No. 18 Suppl 2, Nov. 2009, p. S477. Abstract No. 1318.
Nielsen et al., Tissue Antigens., 62(6):492-7 (2003). Association of a putative regulatory polymorphism in the PD-1 gene with susceptibility to type 1 diabetes.
Nohara et al., Amelioration of experimental autoimmune encephalomyelitis with anti-OX40 ligand monoclonal antibody: a critical role for OX40 ligand in migration, but not development, of pathogenic T cells, J Immunol, 166 (3):2108-15 (2001).
Nomi et al., Clin. Cancer Res. 13:2151-57 (2007). Clinical Significance and therapeutic potential of the programmed Death-1 ligand/programmed Death-1 Pathway in Human Pancreatic Cancer.
Odegard et al., ICOS Controls Effector Function but Not Trafficking Receptor Expression of Kidney-Infiltrating Effector T Cells in Murine Lupus, J Immunology 182:4076-84 (2009).
Ohaegbulam et al., Human cancer immunotherapy with antibodies to the PD-1 and PD-L1 pathway. Trends Mol Med., 21(1): 24-33, 23 pages (2014).
Ong et al., J. Pers. Med. 3:40-69 (2013). Personalized Medicine in Ophthalmology: From Pharmacogenetic Biomarkers to Therapeutic and Dosage Optimization.
Orlandi, et al., Cloning immunoglobulin variable domains for expression by the polymerase chain reaction, PNAS USA, vol. 86, pp. 3833-3837, 1989.
Otwinowski et al., Multiparametric scaling of diffraction intensities, Acta Crystallogr A 59, 228-34 (2003).
Ouguerram et al, Apolipoprotein B100 metabolism in autosomal-dominant hypercholesterolemia related to mutations in PCSK9, Arterioscler thromb Vasc Biol. 24: 1448-1453, 2004.
Padlan et al. (1989) Structure of an antibody-antigen complex: Crystal structure of the HyHEL-10 Fab-lysozyme complex, PNAS, 86: 5938-5942.
Padlan et al., Structure of an Antibody-Antigen Complex: Crystal Structure of the HyHEL 10 Fab Lysozyme Complex, Proc. Natl. Acad. Sci., vol. 86, Aug. 1989, pp. 5938 5942.
Pakala et al., Prevention of diabetes in NOD mice at a late stage by targeting OX40/OX40 ligand interactions, Eur. J. Immunol. 34:3039-3046 (2004).
Pandit et al., Functional analysis of sites within PCSK9 responsible for hypercholesterolemia, J Lipid Res., 49(6):1333-1343, (2008).
Parhofer et al., What we have learned about VLDL and LDL metabolism from human kinetics studies, Journal of Lipid Research, 47(8), pp. 1620-1630, 2006.
Park et al., (2004). Post-transcriptional regulation of low density lipoprotein receptor protein by proprotein convertase subtilisin/kexin type 9a in mouse liver. J. Biol. Chem. 279, 50630-50638.
Parsa et al., Nat. Med. 13:84-88 (2007). Loss of tumor suppressor PTEN function increases B7-H1 expression and immunoresistance in glioma.
Paul, Fundamental Immunology, 3rd Edition, 1993, pp. 292-295, under the heading Fv Structure and Diversity in Three Dimensions.
Peccatori et al. Sirolimus-based graft-versus-host disease prophylaxis promotes the in vivo expansion of regulatory T cells and permits peripheral blood stem cell transplantation from haploidentical donors. Leukemia 29, 396-405 (2015).

Perkey et al. (2018) New Insights into Graft-Versus-Host Disease and Graft Rejection, Annual Rev. Pathol., 13: 219-245.
Peterson et al., PCSK9 function and physiology, J Lipid Res., 49(7):1595-1599, (2008).
Piatesi et al., Immunological Optimizatino of a Generic Hydrophobic Pocket for High Affinity Hapten Binding and Diels-Alder Activicy, ChemBio Chem, Apr. 2004, pp. 460-466, vol. 5(4).
Piche-Nicholas et al., (2018) Changes in complementarity-determining regions significantly alter IgG binding to the neonatal Fc receptor (FcRn) and pharmacokinetics, MAbs, 10(1): 81-94.
Piconese et al. A non-redundant role for OX40 in the competitive fitness of Treg in response to IL-2. Eur. J. Immunol. 40, 2902-2913 (2010).
Piconese et al. OX40 triggering blocks suppression by regulatory T cells and facilitates tumor rejection. J. Exp. Med. 205, 825-839 (2008).
Pidala et al. A randomized phase II study to evaluate tacrolimus in combination with sirolimus or methotrexate after allogeneic hematopoietic cell transplantation. Haematologica 97, 1882-1889 (2012).
Piper et al., The Crystal Structure of PCSK9: A Regulator of Plasma LDL-Cholesterol, Structure, 15, 1-8, pp. 545-552 (May 2007).
Pisciotta et al., Additive effect of mutations in LDLR and PCSK9 genes on the phenotype of familial hypercholesterolemia, Atherosclerosis 186(2), pp. 433-440, Jun. 2006.
Poirier et al., Implication of the proprotein convertase NARC-1/PCSK9 in the development of the nervous system, J Neurochem, 98(3):838-850, (2006).
Poirier et al., The proprotein convertase PCSK9 induces the degradation of the low density lipoprotein receptor (LDLR) and its closest family members VLDLR and ApoER2, J Biol Chem., 283(4):2363-2372, (2008).
Polisecki et al., Genetic variation a the PCSK9 locus moderately lowers low-density lipoprotein cholesterol levels, but does not significantly lower vascular disease risk in an elderly population, Atherosclerosis, 200(1): 95-101, (2008).
Polte et al., Different roles of C30 in the development of acute and chronic airways inflammation in a murine asthma model, Eur. J. 39:1736-1742 (2009).
Poosarla et al. 'Computational De Novo Design of Antibodies Binding to a Peptide With High Affinity.' Biotech. Bioeng. 114(6): 1331-1342, 2017.
Powell et al., Compendium of excipients for parenteral formulations. PDA J Pharm Sci Technol, 1998; 52:238-311.
Preston et al., The ratios of CD8+ T cells to CD4+CD25+ FOXP3+ and FOXP3- T cells correlate with poor clinical outcome in human serous ovarian cancer. PLoS One Nov. 14;8(11):e80063 (2013).
Proleukin (aldesleukin) FDA Fact Sheet, 2012 (19 pages).
Przepiorka et al., 1994 Consensus Conference on Acute GVHD Grading, Bone Marrow Transplant, 15(6):825-8 (1995).
Puhler et al., Generation of a recombinant oncolytic Newcastle disease virus and expression of a full IgG antibody from two transgenes, Gene Ther. 15: 371-383 (2008).
Qian et al., Advances in the treatment of acute graft-versus-host disease, J Cell Mol Med, 17(8):966-75 (2013).
Qian et al., Secreted PCSK9 downregulates low density lipoprotein receptor through receptor-mediated endocytosis, J Lipid Res., 48(7):1488-1498, (2007).
Qiang et al., Clinical cancer research : an official journal of the American Association for Cancer Research / 15 (3):971-9 (2009). Overexpression of PD-L1 significantly associates with tumor aggressiveness and postoperative recurrence in human hepatocellular carcinoma.
Quezada et al., CTLA4 blockade and GM-CSF combination immunotherapy alters the intratumor balance of effector and regulatory T cells, Journal of Clinical Investigation, 116(7): 1935-45 (2006).
Qui et al., Gene, 518(2):310-315 (2013). VEGF 634G>C polymorphism and diabetic retinopathy risk: A meta-analysis.
Rader et al. Monogenic hypercholesterolemia: New insights in pathogenesis and treatment, Journal of Clinical Investigation, 111 (12), pp. 1795-1803, 2003.

(56) References Cited

OTHER PUBLICATIONS

Rao et al. 'Anti-PD-1/PD-L1 therapy for infectious diseases: learning from the cancer paradigm.' J. Infect. Dis. 56:221-228, 2017.
Raouf et al. (2010) Pain as a channelopathy, J. Clin. Invest., 120(11): 3745-3752.
Rasband, M.N., et al., Distinct potassium channels on pain-sensing neurons, PNAS, vol. 98, No. 23, pp. 13373-13378, 2001.
Rashid et al. (2005) Decreased Plasma Cholesterol and Hypersensitivity to Statins in Mice Lacking PCSK9, Proc Natl Acad Sci USA 102(15):5374-5379.
Ratliff et al., Transgenic Expression of CYP7A1 in LDL Receptor-Deficient Mice Blocks Diet-Induced Hypercholesterolemia, Journal of Lipid Research, 47, 2006, ;; 1513-1520.
Rawlings et al. The JAK/STAT signaling pathway. J. Cell Sci. 117, 1281-1283 (2004).
Rawlings et al., (2006). MEROPS: the peptidase database. Nucleic Acids Res. 34, D270-D272.
RCSB Protein Data Bank: An Information Portal to Biological Macromolecular Structures. Search Results for keyword pcsk9, search conducted Jan. 10, 2008. Website accessed at http://www.rcsb.org/pdb/home/home.do—Piper et al. The Crystal Structure of Proprotein convertase subtilisin kexin type 9 (PCSK9) (Released May 8, 2007)—Cunningham et al. Crystal Structure of PCSK9 (Deposited Mar. 12, 2007, released Apr. 10, 2007)—Hampton et al. The Crystal Structure of PCSK9 at 1.9 Angstroms Resolution Reveals Structure Homology to with resistin within the c thermainal domain (PNAS 2007, 104:14604).
Reardon et al. (2015) Glioblastoma Eradication Following Immune Checkpoint Blockade in an Orthotopic, Immunocompetent Model, Cancer Immunol Res, 4(2):124-135.
Redoglia et al., Characterization of H4: a mouse T Lymphocyte activation molecule functionally associated with the DC3/T cell receptor. Eur. J. Immunol., 11: 2781-9 (1996).
Reimann et al. (2010) Pain perception is altered by a nucleotide polymorphism in SCN9A, PNAS, 107(11): 5148-5153.
Renfrey et al, The painful reality, Nat Rev Drug Discov. Mar. 2003;2(3):175-6.
Riella et al. Deleterious effect of CTLA4-Ig on a Treg-dependent transplant model. Am. J. Transplant. 12, 846-855 (2012).
Robb et al. The interferon-dependent orchestration of innate and adaptive immunity after transplantation. Blood 119, 5351-5358 (2012).
Robb et al. Type I-IFNs control GVHD and GVL responses after transplantation. Blood 118, 3399-3409 (2011).
Roberto et al., Role of naive-derived T memory stem cells in T-cell reconstitution following allogeneic transplantation, Blood, 125(18):2855-2864 (2015).
Rosenberg et al., Atezolizumab in patients with locally advanced and metastatic urothelial carcinoma who have progressed following treatment with platinum-based chemotherapy: a single-arm, multicentre, phase 2 trial, Lancet, 387(10031):1909-20 (2016).
Rosenzweig et al. (2019) PD-1/PD-L1 checkpoint blockade harnesses monocyte-derived macrophages to combat cognitive impairment in a tauopathy mouse model, Nature Communications, vol. 10, Article 465.
Rosnet et al., Oncogene 8: 173-179 (1993). Close physical linkage of the FLT1 and FLT3 genes on chromosome 13 in man and chromosome 5 in mouse.
Rossi et al., Optimization of multivalent bispecific antibodies and immunocytokines with improved in vivo properties, Bioconjug Chem, 24(1):63-71 (2013).
Rubio et al. Ex vivo identification, isolation and analysis of tumor-cytolytic T cells. Nat Med. 2003; 9(11):1377-82, plus 9 pages supplemental material.
Ruby et al. Cutting edge: OX40 agonists can drive regulatory T cell expansion if the cytokine milieu is right. J. Immunol. 183, 4853-4857 (2009).
Rudenko et al., Structure of the LDL Receptor Extracellular Domain at Endosomal pH, Science 298, 2353-8 (2002).
Rudikoff et al. Single Amino Acid Substitution Altering Antigen Binding Specificity Proc. Natl. Acad. Sci. 79: 1979-1983, 1982.
Ruutu et al., Prophylaxis and treatment of GVHD: EBMT-ELN working group recommendations for a standardized practice, Bone Marrow Transplant, 49(2):168-73 (2014).
Saerens, D., et al., Single Domain Antibodies Derived from Dromedary Lymph Node and Peripheral Blood Lymphocytes Sensing Conformational Variants of Prostate-specific Antigen, J. Bioi. Chem., vol. 279, No. 50, pp. 51965-51972, 2004.
Sainson et al., A novel antibody targeting ICOS increases intratumoural cytotoxic to regulatory T cell ratio and induces tumour regression, bioRxiv preprint first posted online Sep. 16, 2019, https://www.biorxiv.org/content/biorxiv/early/2019/09/16/771493.full.pdf—Retrieved Oct. 21, 2019 (80 pages).
Sainson et al., KY1044, a novel anti-ICOS antibody, elicits long term in vivo anti-tumour efficacy as monotherapy and in combination with immune checkpoint inhibitors. 1 page.
Sainson et al., KY1055, a novel ICOS/PD-L1 bispecific antibody, efficiently enhances T cell activation and delivers a potent anti-tumour response in vivo. 1 page.
Saint-Jore et al. Autosomal dominant type IIa hypercholesterolemia: Evaluation of the respective contributions of LDLR and APOB gene defects as well as a third major group of defects, European Journal of Human Genetics, 8(8), pp. 621-630, 2000.
Saito, Y. et al., Sodium Channel Mutation in Irritable Bowel Syndrome: Evidence lor an Ion C4 Channelopathy, Am. J. Physiol. Gatrointest. Liver Physiol., vol. 296, pp. G211-G218, 2009.
Sakai et al., (1998). Molecular identification of the sterol-regulated lumina! protease that cleaves SREBPs and controls lipid composition of animal cells. Mol. Cell 2, 505-514.
Salek-Ardakani et al., OX40 (CD134) controls memory T helper 2 cells that drive lung inflammation, J Exp Med, 198(2):315-24 (2003).
Salek-Ardakani, S., et al., OX40:OX40L Axis: Emerging Targets for Immunotherapy of Human Disease, Current Immunology Reviews 2: 37-53 (2006).
Sanchez et al. Kinetic of regulatory CD25high and activated CD134+ (OX40) T lymphocytes during acute and chronic graft-versus-host disease after allogeneic bone marrow transplantation. Br. J. Haematol. 126, 697-703 (2004).
Sanmamed et al., Agonists of Co-stimulation in Cancer Immunotherapy Directed Against CD137, OX40, GITR, CD27, CD28, and ICOS. Seminars in Oncology, 42(4):640-655 (2015).
Sanofi and Regeneron Report Positive Preliminary Phase 2 Program Results for Anti-PCSK9 Antibody in Hypercholesterolemia, http://www.prnewswire.com/news-releases/sanofi-and-regeneron-report-posit- ive-preliminary-phase-2-program-results-for-anti-pcsk9-antibody-in-hyperch- olesterolemia-133590188.html, PR Newswire, Nov. 10, 2011, pp. 1-3.
Saresella et al. (2012) A potential role for the PD1/PD-L1 pathway in the neuroinflammation of Alzheimer's disease, Neurobiology of Aging, 33(3): 624.e11-22.
Sato et al., Spatially selective depletion of tumor-associated regulatory T cells with near-infrared photoimmunotherapy. Science Translational Medicine, 2016; 8(352):1-12, plus 27 pages supplemental material.
Savabkar et al., Gastroenterol Hepatol Bed Bench., 6(4):178-82 (2013). Programmed death-1 gene polymorphism (PD-1.5 C/T) is associated with gastric cancer.
Schmalhofer, W.A., et al., ProTx-11, a Selective Inhibitor of Nav1.7 Sodium Channels, Blocks Action Potential Propagation in Nociceptors, Mol Pharmacal, vol. 74, pp. 1476-1484, 2008.
Schmid et al., Basophil sensitivity reflects long-term clinical outcome of subcutaneous immunotherapy in grass pollen-allergic patients, Allergy, May 2021, 76(5): 1528-1538.
Schmidt et al. A Novel Splicing Variant of Proprotein Convertase Subtilisin/Kexin Type 9, DNA Cell Biol. Apr. 2008; 27(4):183-189.
Schmidt et al., A 15-ketosterol is a liver X receptor ligand that suppresses sterol-responsive element binding prSeidah et al., The proprotein convertases and their implication in sterol and/or lipid metabolism, Biological Chemistry, 387(7), 871-877 (2006)otein-2 activity, Journal of Lipid Research, 47(5), May 2006, 1037-1044.

(56) References Cited

OTHER PUBLICATIONS

Schmidt et al., Secreted proprotein convertase subtilisin/kexin type 9 reduces both hepatic and extrahepatic low-density lipoprotein receptors in vivo, Biochem Biophys Res Commun., 370(4):634-640, (2008).
Schneider et al., Clin Cancer Res 15(17):5297-5302 (2009). The Role of Vascular Endothelial Growth Factor Genetic Variability in Cancer.
Schoggins et al. Interferon-stimulated genes and their antiviral effector functions. Curr. Opin. Virol. 1, 519-525 (2011).
Schonrich et al., The PD-1/PD-L1 Axis and Virus Infections: A Delicate Balance, Front Cell Infect Microbiol, 2019, 9: 207.
Schwartz et al. (2019) Potential immunotherapy for Alzheimer disease and age-related dementia, Dialogues Clin Neurosci., 21(1): 21-25.
Schwartz et al., The Resolution of Neuroinflammation in Neurodegeneration: Leukocyte Recruitment via the Choroid Plexus, EMBO J. 33(1): 7-20 (2014).
Sears et al., ICONIC: Phase 1/2 Trial of ICOS Agonist JTX-2011 Alone and in Combination with Nivolumab (nivo). (2017).
Seidah et al., (1999). Mammalian subtilisin/kexin isozyme SKI-1: a widely expressed proprotein convertase with a unique cleavage specificity and cellular localization. Proc. Natl. Acad. Sci. USA 96, 1321-1326.
Seidah et al., The proprotein convertases and their implication in sterol and/or lipid metabolism, Biological Chemistry, 387(7), 871-877 (2006).
Seidah et al., The proprotein convertases in health and disease, Molecular & Cellular Proteomics, 2(9), Sep. 2003.
Seidah et al., The secretory proprotein convertase neural apoptosis-regulated convertase 1 (NARC-1): Liver regeneration and neuronal differentiation PNAS 100: 928-933, 2003.
Seidah, N.G. and Pratt, A., The proprotein convertases are potential targets in the treatment of dyslipidemia, J. Mol. Med., 95:685-696, Mar. 10, 2007.
Selby et al., Anti-CTLA-4 antibodies of IgG2a isotype enhance antitumor activity through reduction of intratumoral regulatory T cells. Cancer Immunology Research, 1(1):32-42 (2013).
Seshasayee et al., In vivo blockade of OX40 ligand inhibits thymic stromal lymphopoietin driven atopic inflammation. J Clin Invest 117(12): 3868-3878 (2007).
Shan et al., PCSK9 binds to multiple receptors and can be functionally inhibited by an EGF-A peptide, Biochem. Biophys. Res. Commun., pp. 1-5 (2008).
Shanafelt et al., A T-cell-selective interleukin 2 mutein exhibits potent antitumor activity and is well tolerated in vivo. Nature Biotechnology, 18: 1197-1202 (2000).
Sharma et al., Immune Checkpoint Targeting in Cancer Therapy: Toward Combination Strategies with Curative Potential. Cell, 161: 205-214 (2015).
Sharma et al., J. Clin. Invest. 117:2570-82 (2007). Plasmacytoid dendritic cells from mouse tumor-draining lymph nodes directly activate mature tregs via indoleamine 2,3-dioxygenase.
Sharma et al., The future of immune checkpoint therapy. Science, 348(6230): 56-61 (2015).
Shen, et al., The molecular genetics of coronary artery disease and myocardial infarction, Acute Coronary Syndromes, 6 (4), pp. 129-141, 2004.
Shibata, et al, No genetic association between PCSK9 polymorphisms and Alzheimer's disease and plasma cholesterol level in Japanese patients, Psychiatric Genetics, 2005, vol. 15, pp. 239.
Shields et al., High resolution mapping of the binding site on human IgG1 for Fc gamma RI, Fc gamma RII, Fc gamma RIII, and FcRn and design of IgG1 variants with improved binding to the Fc gamma R. 2001, J. Biol. Chem., Mar. 2; 276(9):6591-604.
Shields et al., Lack of Fucose on Human IgG1 N-Linked Oligosaccharide Improves Binding to Human Fc.gamma.RIII and Antibody-dependent Cellular Toxicity. (2002) JBC 277:26733.

Shimauchi et al., Int. J. Cancer 121: 2585-90 (2007). Augmented expression of programmed death-1 in both neoplastic and non-neoplastic CD4+ T-cells in adult T-cell leukemia/lymphoma.
Shinohara et al. Engagement of the type I interferon receptor on dendritic cells inhibits T helper 17 cell development: Role of intracellular osteopontin. Immunity 29, 68-78 (2008).
Shioji et al., Genetic variants in PCSK9 affect the cholesterol level in Japanese, Journal of Human Genetics, 49 (2) pp. 109-114, 2004.
Shirakawa, The Current Status of Adenovirus-based Cancer Gene Therapy, Mol. Cells, 25(4): 462-466 (2008).
Sim et al., IL-2 therapy promotes suppressive ICOS+ Treg expansion in melanoma patients. J Clin Invest, 124(1): 99-110 (2014).
Sim et al., IL-2 variant circumvents ICOS+ regulatory T cell expansion and promotes NK cell activation. Cancer Immunol Res (2016).
Simpson et al., Fc-dependent depletion of tumor-infiltrating regulatory T cells co-defines the efficacy of anti-CTLA-4 therapy against melanoma. J. Exp. Med. 210(9):1695-1710 (2013).
Simpson et al., Regulation of CD4 T cell activation and effector function by inducible costimulatory (ICOS). Current Opinion in Immunology 22: 326-332 (2010).
Skobe et al., Nature Medicine 3:1222-1227 (1997). Halting angiogenesis suppress carcinoma cell invasion.
Skolnick et al. (2000) From genes to protein structure and function: novel applications of computational approaches in the genomic era, Trends in Biotech, 18(1): 34-39.
Slimani, et al. (Mar. 6, 2014) Effect of E670G Polymorphism in PCSK9 Gene on the Risk and Severity of Coronary Heart Disease and Ischemic Stroke in a Tunisian Cohort, J Mol Neurosci., 53(2): 150-157.
Soleimanifar et al. Inflammation, 34(6):707-12 (2011). Study of programmed cell death 1 (PDCD1) gene polymorphims in Iranian patients with ankylosing spondylitis.
Solomon et al., TIGIT: a novel immunotherapy target moving from bench to bedside. Cancer Immunol Immunother. 67(11):1659-1667 (2018).
Song et al., Overexpression of B7-H1 correlates with malignant cell proliferation in pancreatic cancer, Oncol Rep, 31(3)1191-8 (2014).
Song et al., Small-molecule modulators of the OX40-OX40 ligand co-stimulatory protein-protein interaction, British Journal of Pharmacology 171:4955-4969 (2014).
Soroosh et al., OX40-OX40 ligand interaction though T cell-T cell contact contributes to CD4 T Cell longevity, J. Immunol. 176:5975-5987 (2006).
Souza et al., Expression of lymphocyte-endothelial receptor-ligand pairs, 4beta7/MAdCAM-1 and OX40/OX40 ligand in the colon and jejunum of patients with inflammatory bowel disease, Gut 45:856-863 (1999).
Spoerl et al. Activity of therapeutic JAK 1/2 blockade in graft-versus-host disease. Blood 123, 3832-3242 (2014).
Stahl, Neil, Regeneron: Investor Day Early Clinical Development #1 REGN727: anti-PCSK9 Jul. 15, 2010: pp. 1-21.
Stallone et al., mTOR inhibitors effects on regulatory T cells and on dendritic cells, J Transl Med, 14(1):152 (2016).sub.-- 9pp.
Statement of Opposition filed at European Patent Office against European Patent No. EP2482849 on Mar. 6, 2019 (62 pages).
Stewart et al. Interferon-dependent IL-10 production by Tregs limits tumor Th17 inflammation. J. Clin. Invest. 123, 4859-4874 (2013).
Stewart et al., Identification and Characterization of MED14736 an Antagonistic Anti-PD-L1 Monoclonal Antibody, Cancer Immunol Res., 2015, 3(9): 1052-1062.
Strauss et al., Expression of ICOS on Human Melanoma-Infiltrating CD4.sup.+CD25.sup.highFoxp3.sup.+ T Regulatory Cells: Implications and Impact on Tumor-Mediated Immune Suppression. J. Immunol 180(5): 2967-2980 (2008).
Strohl, Fusion Proteins for Half-Life Extension of Biologics as a Strategy to Make Biobetters. BioDrugs (2015) 29:215-239.
Strom et al., Therapeutic approach to organ transplantation (Therapeutic Immunology, Austen et al. (Ed.) Blackwell Science, Cambridge MA, 1996, p. 451-456).
Strome et al., Cancer Res. 63:6501-6505 (2003). B7-H1 Blockade Augments adoptive T-Cells Immunotherapy for squamous cell carcinoma.

(56) References Cited

OTHER PUBLICATIONS

Stuber et al.,Involvement of OX40-OX40L interactions in the intestinal manifestations of the murine acute graft-versus-host disease, Gastroenterology, 115(5):1205-15 (1998).
Subramanian et al. Gene set enrichment analysis: A knowledge-based approach for interpreting genome-wide expression profiles. Proc. Natl. Acad. Sci. U.S.A. 102, 15545-15550 (2005).
Sugamura et al., Therapeutic targeting of the effector T-cell co-stimulatory molecule OX40, Nat Rev Immunol, 4(6):420-31 (2004).
Summary of PubMed search results, Nov. 2016, 1 page.
Sun et al., PD-1/PD-L1 in cardiovascular disease, Clinica Chimica Acta, Jun. 2020, 505: 26-30.
Sun X-M et al, Evidence for effect of mutant PCSK9 on apoliprotein B secretion as the cause of unusually severe dominant hypercholesterolemia, Human Molecular Genetics 14: 1161-1169, 2005.
Sun, Hong et al., Prevention of Chronic Rejection in Mouse Aortic Allografts by Combined Treatment with CTLA4-Ig and Anti-CD40 Ligand Monoclonal Antibody, Transplantation, 1997, 64:1838-56.
Swallow et al., B7h, a novel costimulatory homolog of B7.1 and B7.2, is induced by TNFalpha. Immunity. Oct. 1999;11(4):423-32.
Tall, Protease variants, LDL, and coronary heart disease, New England Journal of Medicine, 354(12), pp. 1310-1312, Mar. 23, 2006.
Tanaka et al., Generation and characterization of monoclonal antibodies against multiple epitopes on the c-terminal half of envelope gp46 of human t-cell leukemia virus type-I (HTLV-I), Int. J. Cancer, 46:675-681 (1990).
Tanaka et al., Jpn J Cancer Res., 88:867-876 (1997). , Characterization of the extracellular domain in vascular endothelial growth factor receptor-1 (Flt-1 Tyrosine kinase).
Tangrea et al., (2002). Solution structure of the pro-hormone convertase 1 pro-domain from Mus musculus. J. Mol. Biol. 320, 801-812.
Tao, M., et al., Structural Features of Human Immunoglobulin G that Determine Isotype-specific Differences in Complement Activation, J. Exp. Med, vol. 178, pp. 661-667, 1993.
Tao, M., et al., The Differential Ability of Human IgG1 and IgG4 to Activate Complement Is Determined by the COOH-terminal Sequence of the CH2 Domain, J. Exp. Med, vol. 173, pp. 1 025-1028, 1991.
Tarwana et al., Blockers of voltage-gated sodium channels for the treatment of central nervous system diseases, Recent Pat CNS Drug Discov. Jan. 2007;2(1):57-78.
Taylor et al., The classification of amino acid conservation. J. Theor. Biol., 1986; 119;205-218.
Taylor, AstraZeneca tremelimumab fails another phase 3 cancer trial, Published online Dec. 7, 2018 at https://fiercebiotech.com/biotech/astrazeneca-s-tremelimumab-fails-another-phase-3-cancer-trial (4 pages).
Taylor, P., D-1 inhibitors shine at ASH conference. Published online by PMLive and retrieved from http://www.pmlive.com/pharma.sub.--news/pd-1.sub.--inhibitors.sub.--shine-.sub.--at.sub.--ash.sub.--conference.sub.--622370. Published Dec. 8, 2014.
Terman et al., Biochem Biophys Res Comm 187(3): 1579-1586 (1992)., Identification of the KDR tyrosine kinase as a receptor for vascular endothelial cell growth factor.
Terman et al., Oncogene 6:1677-1683. (1991). Identification of a new endothelial cell growth factor receptor tyrosine kinase.
Thompson et al., Proc. Natl. Acad. Sci. USA 101:17174-79 (2004). Costimulatory B7-H1 in renal cell carcinoma patients: indicator of tumor aggressiveness and potential therapeutic target.
Thompson et al., Tumor B7-H1 is associated with poor prognosis in renal cell carcinoma patients with long-term follow-up, Cancer Res, 66(7):3381-5 (2006).
Tickle, S., et al., High-Throughput Screening for High Affinity Antibodies, Journal of the Association for Laboratory Automation, vol. 14, pp. 303-307, 2009.
Timms et al., A mutation in PCSK9 causing autosomal-dominant hypercholesterolemia in a Utah pedigree, Hum Genet., 114(4):349-353, (2004).

Toledo-Aral, et al. (1997) Identification of PN1, a predominant voltage-dependent sodium channel expressed principally in peripheral neurons, PNAS, 94(4): 1527-1532.
Tong et al. Molecular Vision 2010, 16:1958-1981 (2010). LOC387715/HTRA1 gene polymorphisms and susceptibility to age-related macular degeneration: A HuGE review and meta-analysis.
Topalian et al., Safety, activity, and immune correlates of anti-PD-1 antibody in cancer, N Engl J Med, 366 (26):2443-54 (2012).
Topol E.J., Cholesterol, racial variation and targeted medicines, Nature Medicine, 11(2), pp. 122-123, Feb. 2005.
Topol et al., Genetic susceptibility to myocardial infarction and coronary artery disease, Human Molecular Genetics, 15 (Rev. Issue 2), R117-R123, 2006.
Totsuka et al., Therapeutic effect of anti-OX40L and anti-TNF-beta MAbs in a murine model of chronic colitis, Am Physiol Gastrointest Liver Physiol. 284:G595-G603 (2003).
Tsukada et al., Blockade of CD134 (OX40)-CD143L interaction ameliorates lethal acute graft-versus-host in a murine model of allogeneic bone marrow transplantation, Blood, 95:2434-2439 (2000).
Tsutsumi et al., Thrombosis and Haemostasis 77(1):168-173 (1997). PEGylation of interleukin-6 effectively increases its thrombopoietic potency.
Tu et al., Regulatory T cells, especially ICOS FOXP3+ regulatory T cells, are increased in the hepatocellular carcinoma microenvironment and predict reduced survival. Scientific Reports, 6:35056 (2016).
U.S. National Library of Medicine, Anti-ICOS Monoclonal Antibody MEDI-570 in Treating Patients with Relapsed or Refractory Peripheral T-cell Lymphoma Follicular Variant or Angioimmunoblastic T-cell Lymphoma, ClinicalTrials.gov Identifier No. NCT02520791. First posted Aug. 13, 2015. Retrieved at https://clinicaltrials.gov/ct2/show/NCT02520791.
Ueha et al., Robust Antitumor Effects of Combined Anti-CD4-Depleting Antibody and Anti-PD-1/PD-LI Immune Checkpoint Antibody Treatment in Mice. Cancer Immunology Research, 3(6); pp. 631-640 (2015).
Ueno et al., OX40/OX40L axis: not a friend in autoimmunity, Obcotgarget, 6(26):21779-21780 (2015).
Ukyo et al., Costimulation through OX40 is crucial for induction of an alloreactive human T-cell response, Immunology, 109:226-231 (2003).
Vajdos et al., Comprehensive Functional Maps of the Antigen Binding Site of an Anti ErbB2 Antibody Obtained with Shotgun Scanning Mutagenesis, J. Mol. Biol., 2002, vol. 320, pp. 415 428.
Van Berkel et al., CD28 and ICOS: Similar or separate costimulators of T cells? Immunology Letters 105: 115-122 (2006).
Van Elsas et al., Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation, J Exp Med 190(3): 355-66 (1999).
Van Regenmortel et al., Mapping Epitope Structure and Activity: From One-Dimensional Prediction to Four-Dimensional Description of Antigenic Specificity. Methods: A Companion to Methods in Enzymology 9 (1996): 465-472.
Varret et al. A Third Major Locus for Autosomal Dominant Hypercholesterolema Maps to 1p. 34.1-p. 32 Am. J. Hum. Genet, 64:1378-1387, 1999.
Varret et al., ARH and HCHOLA3: Two different genes at 1p both implicated in familial hypercholesterolemia, American Journal of Human Genetics, 71(4 Supplement), Oct. 2002 abstract 1597.
Varret et al., Familial autosomal dominant hypercholesterolemia: Highly skewed contribution of mutations in the LDLR, APOB, FH3 and FH4 genes, Circulation, 106 (19 Supplement) Nov. 5, 2002 abstract 1461.
Vazquez-Lombardi et al., Potent antititumour activity of interleukin-2-Fc fusion proteins requires Fc-mediated depletion of regulatory T-cells. Nature Communications, vol. 8, May 12, 2017, pp. 1-12.
Vetterman et al., A signalling-enhanced chimeric receptor to activate the ICOS pathway in T cells. Journal of Immunological Methods, 424: 14-19 (2015).

(56) References Cited

OTHER PUBLICATIONS

Villeger, et al., Familial hypercholesterolemia: 30 years after Brown and Goldstein, Recent Research Developments in Human Genetics, 1(pt.1), pp. 35-51, 2002.
Vonderheide et al., Tremelimumab in combination with exemestane in patients with advanced breast cancer and treatment-associated modulation of inducible costimulator expression on patient T cells. Clin. Cancer Res. 16:3485-3494 (2010).
Vu et al. OX40 costimulation turns off Foxp3+ Tregs. Blood 110, 2501-2510 (2007).
Wang et al., Cancer Immunol Res. 2(9):846-856 (2014). In vitro characterization of the anti-PD-1 antibody nivolumab, BMS-936558, and in vivo toxicology in non-human primates.
Wang et al., Costimulation of T cells by B7-H2, a B7-like molecule that binds ICOS. Blood. Oct. 15, 2000;96(8):2808-13.
Wang et al., Hum Genet 132(6):641-8 (2013). A miR-570 binding site polymorphism in the B7-H1 gene is associated with the risk of gastric adenocarcinoma.
Wang et al., In Vitro Characterization of the Anti-PD-1 Antibody Nivolumab, BMS-936558, and In Vivo Toxicology in Non-Human Primates. Cancer Immunology Research, vol. 2, No. 9, May 28, 2014 (May 28, 2014), pp. 846-856.
Wang et al., J Clin Immunol., 27(6): 563-7 (2007). Polymorphisms of genes for programmed cell death 1 ligands in patients with rheumatoid arthritis.
Ward et al. (1989) Binding activities of a repertoire of single immunoglobulin variable domains secreted from *Escherichia coli*, Nature, 341: 544-546.
Ward et al., Targeting Costimulatory Pathways for Tumor Immunotherapy, International Reviews of Immunology, 26:161-196 (2007).
Webster, R.M., Nature Reviews Drug Discovery 13:883-884 (2014). From the Analyst's Couch: The Immune checkpoint inhibitors: where are we now?
Weigel et al., Mutant proteins of human interleukin 2. Eur. J. Biochem. 180: 295-300 (1989).
Weiss, R.E., et al., Functional differences between two classes of sodium channels in developing rat skeletal muscle, Science, vol. 233, pp. 361-364, 1986.
Wells (1990) Additivity of mutational effects in proteins, Biochemistry, 29(37): 8509-8517.
West et al., PD-L1 blockade synergizes with IL-2 therapy in reinvigorating exhausted T cells, J Clin Invest, 123 (6):2604-15 (2013).
Wing et al. CTLA-4 control over Foxp3+ regulator T cell function. Science 322, 271-275 (2008).
Wiseman et al. Major histocompatibility complex genotyping with massively parallel pyrosequencing. Nat. Med. 15, 1322-1326 (2009).
Wosornu et al., Genetic deficiency of proprotein convertase Subtilisin/Kexin 9: identification of a compound heterozygote with no PCSK9, Circulation, 114 (18, Suppl. S). Oct. 31, 2006.
Wozniak-Knopp et al., Introducing antigen-binding sites in structural loops of immunoglobulin constant domains : Fc fragments with engineered HER2/neu-binding sites and antibody properties. Protein Engineering, Design & Selection, 23(4) ; 289-297 (2010).
Wu et al., Acta Histochemica 108:19-24 (2006). Immunohistochemical localization of programmed death-1 ligand-1 (PD-L1) in gastric carcinoma and its clinical significance.
Wu et al., Humanization of a Murine Monoclonal Antibody by Simultaneous Optimization of Framework and CDR Residues, J. Mol. Biol., 1999, vol. 294, pp. 151 162.
Wu et al., Leuk Lymphoma , 54(10):2251-4 (2013). Association between polymorphisms in PDCD1 gene and aplastic anemia in Chinese Han population.
Xu et al., Diversity in the CDR3 region of VH is sufficient for most antibody specificities. Immunity 13(1):37-45 (2000).
Xu et al., The roles of stem cell memory T cells in hematological malignancies, J Hematol Oncol, 8:113 (2015).
Yagi et al., Research and Reports in Neonatology , 1:5-11 (2011). ; VEGF 936C>T is predictive of threshold retinopathy of prematurity in Japanese infants with a 30-week gestational age or less.
Yang et al., Clin Exp Rheumatol. 29(1):13-8 (2011). Association of polymorphisms in the programmed cell death 1 (PD-1) and PD-1 ligand genes with ankylosing spondylitis in a Chinese population.
Yang et al., Programmed cell death-ligand 1 expression in surgically resected stage I pulmonary adenocarcinoma and its correlation with driver mutations and clinical outcomes, Eur J Cancer, 50(7):1361-9 (2014).
Yang, J., et al., 3-(4-Phenoxyphenyl)pyrazoles: A Novel Class of Sodium Channel Blockers, J. Med. Chem., vol. 47, No. 6, pp. 1547-1552, 2004.
Yap et al., ICONIC : Biologic and clinical activity of first in class ICOS against antibody JTX-2011 +/− nivolumab (nivo) in patients with advanced cancers. Presented at 2018 ASCO Annual Meeting (18 pages).
Yende et al., Genetic polymorphisms that predict outcome and need for treatment in cardiovascular disease, Current Opinion in Critical Care 12(5), pp. 420-425, Oct. 2006.
Yuan et al. The Role of the CD134-CD134 Ligand Costimulatory Pathway in Alloimmune Responses In Vivo, J. Immunol. 170, 2949-2955 (2003).
Yue et al., The c.43.sub.--44insCTG variation in PCSK9 is associated with low plasma LDL-cholesterol in a Caucasian population, Human Mutation, 27(5), pp. 460-466, May 2006.
Yusa et al., A hyperactive piggyBac transposase for mammalian applications. Proc Natl Acad Sci USA. Jan. 25, 2011: 108(4): 1531-1536.
Zachary et al. Experimental Nephrology. 6:480-487 (1998). Vascular Endothelial Growth Factor: How it transmits its signal.
Zaid et al., Proprotein convertase subtilisin/kexin type 9 (PCSK9): hepatocyte-specific low-density lipoprotein receptor degradation and critical role in mouse liver regeneration, Hepatology, 48(2):646-654, (2008).
Zang et al., The B7 family and cancer therapy: costimulation and coinhibition. Clinical Cancer Research, 13(18): 5271-5279 (2007).
Zhang et al. An obligate cell-intrinsic function for CD28 in Tregs. J. Clin. Invest. 123, 580-593 (2013).
Zhang et al. Binding of PCSK9 to EGF-A Repeat of LDL Receptor Decreases Receptor Recycling and Increases Degradation, Journal of Biological Chemistry Apr. 23, 2007.
Zhang et al. Structural requirements for PCSK9-mediated degradation of the low-density lipoprotein receptor. PNAS, Sep. 2, 2008, 105 (35): 13045-13050.
Zhang et al., Activation of OX40 augments Th17 cytokine expression and antigen-specific uveitis, The American Journal of Pathology, 177(6):2912-2920 (2010).
Zhang et al., Binding of Proprotein Convertase Subtilisin/Kexin Type 9 to Epidermal Growth Factor-like Repeat a of Low Density Lipoprotein Receptor Decreases Receptor Recycling and Increases Degradation, Journal of Biological Chemistry, vol. 282, No. 25, pp. 18602-18612, Jun. 22, 2007.
Zhao et al., (2006). Molecular characterization of loss-of-function mutations in PCSK9 and identification of a compound heterozygote. Am. J. Hum. Genet. 79, 514-523.
Zhao et al., Functional characterization of sequence variations in PCSK9, Circulation, 112 (17, Suppl. S.), Oct. 25, 2005.
Zucker, L.S., et al., Chimeric Human-Mouse IgG Antibodies with Shuffled Constant Region Exons Demonstrate that Multiple Domains Contribute to in Vivo Half-Life, Cancer Research, vol. 58, pp. 3905-3908, 1998.
Ni et al., "A PCSK9-binding antibody that structurally mimics the EGF(A) domain of LDL-receptor reduces LDL cholesterol in vivo", J Lipid Res., Jan. 2011, 52(1): 78-86, ePublished Oct. 19, 2010.

\* cited by examiner

SEQUENCE LISTING

<160> NUMBER OF SEQ ID NOS: 545

<210> SEQ ID NO 1
<211> LENGTH: 290
<212> TYPE: PRT
<213> ORGANISM: Homo Sapien

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 241
<212> TYPE: PRT
<213> ORGANISM: Cynomologus

<400> SEQUENCE: 2

Met Gly Trp Ser Cys Ile Ile Leu Phe Leu Val Ala Thr Ala Thr Gly
1               5                   10                  15

Val His Ser Met Phe Thr Val Thr Val Pro Lys Asp Leu Tyr Val Val

```
                20                  25                  30
Glu Tyr Gly Ser Asn Met Thr Ile Glu Cys Lys Phe Pro Val Glu Lys
             35                  40                  45
Gln Leu Asp Leu Thr Ser Leu Ile Val Tyr Trp Glu Met Glu Asp Lys
         50                  55                  60
Asn Ile Ile Gln Phe Val His Gly Glu Glu Asp Leu Lys Val Gln His
 65                  70                  75                  80
Ser Asn Tyr Arg Gln Arg Ala Gln Leu Leu Lys Asp Gln Leu Ser Leu
                 85                  90                  95
Gly Asn Ala Ala Leu Arg Ile Thr Asp Val Lys Leu Gln Asp Ala Gly
             100                 105                 110
Val Tyr Arg Cys Met Ile Ser Tyr Gly Gly Ala Asp Tyr Lys Arg Ile
         115                 120                 125
Thr Val Lys Val Asn Ala Pro Tyr Asn Lys Ile Asn Gln Arg Ile Leu
         130                 135                 140
Val Val Asp Pro Val Thr Ser Glu His Glu Leu Thr Cys Gln Ala Glu
145                 150                 155                 160
Gly Tyr Pro Lys Ala Glu Val Ile Trp Thr Ser Ser Asp His Gln Val
                 165                 170                 175
Leu Ser Gly Lys Thr Thr Thr Thr Asn Ser Lys Arg Glu Glu Lys Leu
             180                 185                 190
Leu Asn Val Thr Ser Thr Leu Arg Ile Asn Thr Thr Ala Asn Glu Ile
         195                 200                 205
Phe Tyr Cys Ile Phe Arg Arg Leu Asp Pro Glu Glu Asn His Thr Ala
     210                 215                 220
Glu Leu Val Ile Pro Glu Leu Pro Leu Ala Leu Pro Pro Asn Glu Arg
225                 230                 235                 240
Thr

<210> SEQ ID NO 3
<211> LENGTH: 245
<212> TYPE: PRT
<213> ORGANISM: Homo Sapien

<400> SEQUENCE: 3

Met Arg Ile Phe Ala Val Phe Ile Phe Met Thr Tyr Trp His Leu Leu
1               5                   10                  15
Asn Ala Phe Thr Val Thr Val Pro Lys Asp Leu Tyr Val Val Glu Tyr
             20                  25                  30
Gly Ser Asn Met Thr Ile Glu Cys Lys Phe Pro Val Glu Lys Gln Leu
         35                  40                  45
Asp Leu Ala Ala Leu Ile Val Tyr Trp Glu Met Glu Asp Lys Asn Ile
     50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
             100                 105                 110
Arg Cys Met Ile Ser Tyr Gly Gly Ala Asp Tyr Lys Arg Ile Thr Val
         115                 120                 125
Lys Val Asn Ala Pro Tyr Asn Lys Ile Asn Gln Arg Ile Leu Val Val
         130                 135                 140
Asp Pro Val Thr Ser Glu His Glu Leu Thr Cys Gln Ala Glu Gly Tyr
```

```
              145                 150                 155                 160
      Pro Lys Ala Glu Val Ile Trp Thr Ser Ser Asp His Gln Val Leu Ser
                      165                 170                 175

Gly Lys Thr Thr Thr Thr Asn Ser Lys Arg Glu Glu Lys Leu Phe Asn
                      180                 185                 190

Val Thr Ser Thr Leu Arg Ile Asn Thr Thr Thr Asn Glu Ile Phe Tyr
                      195                 200                 205

Cys Thr Phe Arg Arg Leu Asp Pro Glu Glu Asn His Thr Ala Glu Leu
                      210                 215                 220

Val Ile Pro Glu Leu Pro Leu Ala His Pro Pro Asn Glu Arg Thr His
      225                 230                 235                 240

His His His His His
                      245

<210> SEQ ID NO 4
<211> LENGTH: 475
<212> TYPE: PRT
<213> ORGANISM: Homo Sapien

<400> SEQUENCE: 4

Met Arg Ile Phe Ala Val Phe Ile Phe Met Thr Tyr Trp His Leu Leu
      1               5                   10                  15

Asn Ala Phe Thr Val Thr Val Pro Lys Asp Leu Tyr Val Val Glu Tyr
                      20                  25                  30

Gly Ser Asn Met Thr Ile Glu Cys Lys Phe Pro Val Glu Lys Gln Leu
                      35                  40                  45

Asp Leu Ala Ala Leu Ile Val Tyr Trp Glu Met Glu Asp Lys Asn Ile
      50                  55                  60

Ile Gln Phe Val His Gly Glu Glu Asp Leu Lys Val Gln His Ser Ser
      65                  70                  75                  80

Tyr Arg Gln Arg Ala Arg Leu Leu Lys Asp Gln Leu Ser Leu Gly Asn
                      85                  90                  95

Ala Ala Leu Gln Ile Thr Asp Val Lys Leu Gln Asp Ala Gly Val Tyr
                      100                 105                 110

Arg Cys Met Ile Ser Tyr Gly Gly Ala Asp Tyr Lys Arg Ile Thr Val
                      115                 120                 125

Lys Val Asn Ala Pro Tyr Asn Lys Ile Asn Gln Arg Ile Leu Val Val
                      130                 135                 140

Asp Pro Val Thr Ser Glu His Glu Leu Thr Cys Gln Ala Glu Gly Tyr
      145                 150                 155                 160

Pro Lys Ala Glu Val Ile Trp Thr Ser Ser Asp His Gln Val Leu Ser
                      165                 170                 175

Gly Lys Thr Thr Thr Thr Asn Ser Lys Arg Glu Glu Lys Leu Phe Asn
                      180                 185                 190

Val Thr Ser Thr Leu Arg Ile Asn Thr Thr Thr Asn Glu Ile Phe Tyr
                      195                 200                 205

Cys Thr Phe Arg Arg Leu Asp Pro Glu Glu Asn His Thr Ala Glu Leu
                      210                 215                 220

Val Ile Pro Glu Leu Pro Leu Ala His Pro Pro Asn Glu Arg Thr Ile
      225                 230                 235                 240

Glu Gly Arg Glu Pro Lys Ser Cys Asp Lys Thr His Thr Cys Pro Pro
                      245                 250                 255

Cys Pro Ala Pro Glu Leu Leu Gly Gly Pro Ser Val Phe Leu Phe Pro
                      260                 265                 270
```

```
Pro Lys Pro Lys Asp Thr Leu Met Ile Ser Arg Thr Pro Glu Val Thr
            275                 280                 285

Cys Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 5
<211> LENGTH: 249
<212> TYPE: PRT
<213> ORGANISM: Cynomologus

<400> SEQUENCE: 5

Met Gly Trp Ser Cys Ile Ile Leu Phe Leu Val Ala Thr Ala Thr Gly
1               5                   10                  15

Val His Ser Met Phe Thr Val Thr Val Pro Lys Asp Leu Tyr Val Val
                20                  25                  30

Glu Tyr Gly Ser Asn Met Thr Ile Glu Cys Lys Phe Pro Val Glu Lys
            35                  40                  45

Gln Leu Asp Leu Thr Ser Leu Ile Val Tyr Trp Glu Met Glu Asp Lys
        50                  55                  60

Asn Ile Ile Gln Phe Val His Gly Glu Glu Asp Leu Lys Val Gln His
65                  70                  75                  80

Ser Asn Tyr Arg Gln Arg Ala Gln Leu Leu Lys Asp Gln Leu Ser Leu
                85                  90                  95

Gly Asn Ala Ala Leu Arg Ile Thr Asp Val Lys Leu Gln Asp Ala Gly
            100                 105                 110

Val Tyr Arg Cys Met Ile Ser Tyr Gly Gly Ala Asp Tyr Lys Arg Ile
        115                 120                 125

Thr Val Lys Val Asn Ala Pro Tyr Asn Lys Ile Asn Gln Arg Ile Leu
    130                 135                 140

Val Val Asp Pro Val Thr Ser Glu His Glu Leu Thr Cys Gln Ala Glu
145                 150                 155                 160

Gly Tyr Pro Lys Ala Glu Val Ile Trp Thr Ser Ser Asp His Gln Val
                165                 170                 175
```

-continued

```
Leu Ser Gly Lys Thr Thr Thr Asn Ser Lys Arg Glu Glu Lys Leu
            180                 185                 190

Leu Asn Val Thr Ser Thr Leu Arg Ile Asn Thr Thr Ala Asn Glu Ile
            195                 200                 205

Phe Tyr Cys Ile Phe Arg Arg Leu Asp Pro Glu Glu Asn His Thr Ala
210                 215                 220

Glu Leu Val Ile Pro Glu Leu Pro Leu Ala Leu Pro Pro Asn Glu Arg
225                 230                 235                 240

Thr Asp Tyr Lys Asp Asp Asp Lys
                245

<210> SEQ ID NO 6
<211> LENGTH: 405
<212> TYPE: PRT
<213> ORGANISM: Homo Sapien

<400> SEQUENCE: 6

Met Gly Trp Ser Cys Ile Ile Leu Phe Leu Val Ala Thr Ala Thr Gly
1               5                   10                  15

Val His Ser Leu Asp Ser Pro Asp Arg Pro Trp Asn Pro Pro Thr Phe
            20                  25                  30

Ser Pro Ala Leu Leu Val Val Thr Glu Gly Asp Asn Ala Thr Phe Thr
            35                  40                  45

Cys Ser Phe Ser Asn Thr Ser Glu Ser Phe Val Leu Asn Trp Tyr Arg
        50                  55                  60

Met Ser Pro Ser Asn Gln Thr Asp Lys Leu Ala Ala Phe Pro Glu Asp
65                  70                  75                  80

Arg Ser Gln Pro Gly Gln Asp Cys Arg Phe Arg Val Thr Gln Leu Pro
                85                  90                  95

Asn Gly Arg Asp Phe His Met Ser Val Val Arg Ala Arg Arg Asn Asp
            100                 105                 110

Ser Gly Thr Tyr Leu Cys Gly Ala Ile Ser Leu Ala Pro Lys Ala Gln
        115                 120                 125

Ile Lys Glu Ser Leu Arg Ala Glu Leu Arg Val Thr Glu Arg Arg Ala
130                 135                 140

Glu Val Pro Thr Ala His Pro Ser Pro Ser Pro Arg Pro Ala Gly Gln
145                 150                 155                 160

Lys Leu Glu Asn Leu Tyr Phe Gln Gly Ile Glu Gly Arg Met Asp Glu
                165                 170                 175

Pro Lys Ser Cys Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
```

-continued

```
                    290                 295                 300
Glu Pro Gln Val Tyr Thr Leu Pro Pro Ser Arg Asp Glu Leu Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
                340                 345                 350

Thr Thr Pro Pro Val Leu Asp Ser Asp Gly Ser Phe Phe Leu Tyr Ser
            355                 360                 365

Lys Leu Thr Val Asp Lys Ser Arg Trp Gln Gln Gly Asn Val Phe Ser
        370                 375                 380

Cys Ser Val Met His Glu Ala Leu His Asn His Tyr Thr Gln Lys Ser
385                 390                 395                 400

Leu Ser Leu Ser Pro
                405

<210> SEQ ID NO 7
<211> LENGTH: 8
<212> TYPE: PRT
<213> ORGANISM: Homo Sapien

<400> SEQUENCE: 7

Gly Phe Thr Phe Asp Asp Tyr Ala
1               5

<210> SEQ ID NO 8
<211> LENGTH: 8
<212> TYPE: PRT
<213> ORGANISM: Homo Sapien

<400> SEQUENCE: 8

Ile Ser Trp Lys Ser Asn Ile Ile
1               5

<210> SEQ ID NO 9
<211> LENGTH: 15
<212> TYPE: PRT
<213> ORGANISM: Homo Sapien

<400> SEQUENCE: 9

Ala Arg Asp Ile Thr Gly Ser Gly Ser Tyr Gly Trp Phe Asp Pro
1               5                   10                  15

<210> SEQ ID NO 10
<211> LENGTH: 5
<212> TYPE: PRT
<213> ORGANISM: Homo Sapien

<400> SEQUENCE: 10

Asp Tyr Ala Met His
1               5

<210> SEQ ID NO 11
<211> LENGTH: 17
<212> TYPE: PRT
<213> ORGANISM: Homo Sapien

<400> SEQUENCE: 11

Gly Ile Ser Trp Lys Ser Asn Ile Ile Gly Tyr Ala Asp Ser Val Lys
1               5                   10                  15

Gly
```

<210> SEQ ID NO 12
<211> LENGTH: 13
<212> TYPE: PRT
<213> ORGANISM: Homo Sapien

<400> SEQUENCE: 12

Asp Ile Thr Gly Ser Gly Ser Tyr Gly Trp Phe Asp Pro
1               5                   10

<210> SEQ ID NO 13
<211> LENGTH: 122
<212> TYPE: PRT
<213> ORGANISM: Homo Sapien

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser
        115                 120

<210> SEQ ID NO 14
<211> LENGTH: 508
<212> TYPE: DNA
<213> ORGANISM: Homo Sapien

<400> SEQUENCE: 14
caagaaaaag cttgccgcca ccatggagtt tgggctgagc tggattttcc ttttggctat       60
tttaaaaggt gtccagtgtg aagtacaatt ggtggagtcc gggggaggct tggtacagcc      120
tggcaggtcc ctgagactct cctgtgcagc ctctggattc acctttgatg attatgccat      180
gcactgggtc cgacaaactc cagggaaggg cctggagtgg gtctcaggta taagttggaa      240
gagtaatatc ataggctatg cggactctgt gaagggccga ttcaccatct ccagagacaa      300
cgccaagaac tccctgtatc tgcaaatgaa cagtctgaga gctgaggaca cggccttgta      360
ttattgtgca agagatataa cggggttcggg gagttatggc tggttcgacc cctgggccca      420
gggaaccctg gtcaccgtct cctcagccaa aacgacaccc ccatctgtct atccactggc      480
ccctgaatct gctaaaactc agcctccg                                         508

<210> SEQ ID NO 15
<211> LENGTH: 449
<212> TYPE: PRT
<213> ORGANISM: Homo Sapien

<400> SEQUENCE: 15

Glu Val Gln Leu Val Glu Ser Gly Gly Gly Leu Val Gln Pro Gly Arg

-continued

```
1               5                   10                  15
Ser Leu Arg Leu Ser Cys Ala Ala Ser Gly Phe Thr Phe Asp Asp Tyr
                20                  25                  30
Ala Met His Trp Val Arg Gln Thr Pro Gly Lys Gly Leu Glu Trp Val
                35                  40                  45
Ser Gly Ile Ser Trp Lys Ser Asn Ile Ile Gly Tyr Ala Asp Ser Val
                50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Arg Asp Ile Thr Gly Ser Gly Ser Tyr Gly Trp Phe Asp Pro Trp
                100                 105                 110
Gly Gln Gly Thr Leu Val Thr Val Ser Ala Ser Thr Lys Gly Pro
                115                 120                 125
Ser Val Phe Pro Leu Ala Pro Cys Ser Arg Ser Thr Ser Glu Ser Thr
                130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
                195                 200                 205
His Lys Pro Ser Asn Thr Lys Val Asp Lys Arg Val Glu Ser Lys Tyr
                210                 215                 220
Gly Pro Pro Cys Pro Pro Cys Pro Ala Pro Glu Phe Glu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
                260                 265                 270
Pro Glu Val Gln Phe Asn Trp Tyr Val Asp Gly Val Glu Val His Asn
                275                 280                 285
Ala Lys Thr Lys Pro Arg Glu Glu Gln Phe Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
                420                 425                 430
```

Ala Leu His Asn His Tyr Thr Gln Lys Ser Leu Ser Leu Ser Leu Gly
          435                 440                 445

Lys

<210> SEQ ID NO 16
<211> LENGTH: 1356
<212> TYPE: DNA
<213> ORGANISM: Homo Sapien

<400> SEQUENCE: 16

```
gaagtgcagc tggtggaatc tgccggcgga ctggtgcagc ctggcagatc cctgagactg     60
tcttgtgccg cctccggctt caccttcgac gactacgcta tgcactgggt gcgacagacc    120
cctggcaagg gcctggaatg ggtgtccggc atctcctgga gtccaacat catcggctac    180
gccgactccg tgaagggccg gttcaccatc tcccgggaca cgccaagaa ctccctgtac    240
ctgcagatga acagcctgcg ggccgaggac accgccctgt actactgcgc cagagacatc    300
accggctccg gctcctacgg atggttcgat ccttggggcc agggcaccct cgtgaccgtg    360
tcctctgcca gcaccaaggg ccctctgtg ttccctctgg ccccttccag caagtccacc    420
tctggcggaa cagccgctct gggctgcctc gtgaaggact acttccccga gcctgtgacc    480
gtgtcctgga actctggcgc tctgaccagc ggagtgcaca ccttccctgc tgtgctgcag    540
tcctccggcc tgtactccct gtcctccgtc gtgaccgtgc cttccagctc tctgggcacc    600
cagacctaca tctgcaacgt gaaccacaag ccctccaaca ccaaggtgga caagaaggtg    660
gaacccaagt cctgcgacaa gacccacacc tgtcccccctt gtcctgcccc tgaactgctg    720
ggcggaccctt ccgtgttcct gttccccccca agcccaagg acaccctgat gatctcccgg    780
accccccgaag tgacctgcgt ggtggtggat gtgtcccacg aggaccctga agtgaagttc    840
aattggtacg tggacggcgt ggaagtgcac aacgccaaga ccaagcctag agaggaacag    900
tacaactcca cctaccgggt ggtgtccgtg ctgaccgtgc tgcaccagga ttggctgaac    960
ggcaaagagt acaagtgcaa ggtgtccaac aaggccctgc ctgcccccat cgaaaagacc   1020
atctccaagg ccaagggcca gccccgggaa ccccaggtgt acacactgcc ccctagcagg   1080
gacgagctga ccaagaacca ggtgtccctg acctgtctcg tgaaaggctt ctacccctcc   1140
gatatcgccg tggaatggga gtccaacggc cagcctgaga caactacaa gaccacccc    1200
cctgtgctgg actccgacgg ctcattcttc ctgtacagca agctgacagt ggacaagtcc   1260
cggtggcagc agggcaacgt gttctcctgc tccgtgatgc acgaggccct gcacaaccac   1320
tacacccaga gtccctgtc cctgagcccc ggcaag                              1356
```

<210> SEQ ID NO 17
<211> LENGTH: 6
<212> TYPE: PRT
<213> ORGANISM: Homo Sapien

<400> SEQUENCE: 17

Gln Ser Ile Ser Ser Tyr
1               5

<210> SEQ ID NO 18
<211> LENGTH: 3
<212> TYPE: PRT
<213> ORGANISM: Homo Sapien

<400> SEQUENCE: 18

```
Val Ala Ser
1

<210> SEQ ID NO 19
<211> LENGTH: 9
<212> TYPE: PRT
<213> ORGANISM: Homo Sapien

<400> SEQUENCE: 19

Gln Gln Ser Tyr Ser Asn Pro Ile Thr
1               5

<210> SEQ ID NO 20
<211> LENGTH: 11
<212> TYPE: PRT
<213> ORGANISM: Homo Sapien

<400> SEQUENCE: 20

Arg Ala Ser Gln Ser Ile Ser Ser Tyr Leu Asn
1               5                   10

<210> SEQ ID NO 21
<211> LENGTH: 7
<212> TYPE: PRT
<213> ORGANISM: Homo Sapien

<400> SEQUENCE: 21

Val Ala Ser Ser Leu Gln Ser
1               5

<210> SEQ ID NO 22
<211> LENGTH: 9
<212> TYPE: PRT
<213> ORGANISM: Homo Sapien

<400> SEQUENCE: 22

Gln Gln Ser Tyr Ser Asn Pro Ile Thr
1               5

<210> SEQ ID NO 23
<211> LENGTH: 107
<212> TYPE: PRT
<213> ORGANISM: Homo Sapien

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys
            100                 105

<210> SEQ ID NO 24
<211> LENGTH: 321
```

```
<212> TYPE: DNA
<213> ORGANISM: Homo Sapien

<400> SEQUENCE: 24
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagcccct gatctatgtt gcatccagtt tgcaaagtgg ggtcccatca     180
agtttcagtg gcagtggatc tgggacagat ttcactctca ccatcagcag tctgcaacct     240
gaagattttg caacttacta ctgtcaacag agttacagta atccgatcac cttcggccaa     300
gggacacgac tggagatcaa a                                               321

<210> SEQ ID NO 25
<211> LENGTH: 214
<212> TYPE: PRT
<213> ORGANISM: Homo Sapien

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 642
<212> TYPE: DNA
<213> ORGANISM: Homo Sapien

<400> SEQUENCE: 26
gacatccaga tgacccagtc tccatcctcc ctgtctgcat ctgtaggaga cagagtcacc      60
atcacttgcc gggcaagtca gagcattagc agctatttaa attggtatca gcagaaacca     120
```

```
gggaaagccc ctaagcccct gatctatgtt gcatccagtt tgcaaagtgg ggtcccatca    180
agtttcagtg gcagtggatc tgggacagat ttcactctca ccatcagcag tctgcaacct    240
gaagattttg caacttacta ctgtcaacag agttacagta atccgatcac cttcggccaa    300
gggacacgac tggagatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga aagcacaag gtgtacgcct gcgaagtgac ccaccagggc    600
ctgtctagcc ccgtgaccaa gtctttcaac cggggcgagt gt                       642
```

<210> SEQ ID NO 27
<211> LENGTH: 8
<212> TYPE: PRT
<213> ORGANISM: Homo Sapien

<400> SEQUENCE: 27

Gly Phe Thr Phe Asp Asp Tyr Ala
1               5

<210> SEQ ID NO 28
<211> LENGTH: 8
<212> TYPE: PRT
<213> ORGANISM: Homo Sapien

<400> SEQUENCE: 28

Ile Ser Trp Ile Arg Thr Gly Ile
1               5

<210> SEQ ID NO 29
<211> LENGTH: 16
<212> TYPE: PRT
<213> ORGANISM: Homo Sapien

<400> SEQUENCE: 29

Ala Lys Asp Met Lys Gly Ser Gly Thr Tyr Gly Gly Trp Phe Asp Thr
1               5                   10                  15

<210> SEQ ID NO 30
<211> LENGTH: 5
<212> TYPE: PRT
<213> ORGANISM: Homo Sapien

<400> SEQUENCE: 30

Asp Tyr Ala Met His
1               5

<210> SEQ ID NO 31
<211> LENGTH: 17
<212> TYPE: PRT
<213> ORGANISM: Homo Sapien

<400> SEQUENCE: 31

Gly Ile Ser Trp Ile Arg Thr Gly Ile Gly Tyr Ala Asp Ser Val Lys
1               5                   10                  15

Gly

<210> SEQ ID NO 32
<211> LENGTH: 14
<212> TYPE: PRT

```
<213> ORGANISM: Homo Sapien

<400> SEQUENCE: 32

Asp Met Lys Gly Ser Gly Thr Tyr Gly Gly Trp Phe Asp Thr
1               5                   10

<210> SEQ ID NO 33
<211> LENGTH: 123
<212> TYPE: PRT
<213> ORGANISM: Homo Sapien

<400> SEQUENCE: 33

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser
        115                 120

<210> SEQ ID NO 34
<211> LENGTH: 482
<212> TYPE: DNA
<213> ORGANISM: Homo Sapien

<400> SEQUENCE: 34
aagcttgccg ccaccatgga gtttgggctg agctggattt tccttttggc tattttaaaa      60
ggtgtccagt gtgaagtgca gctggtggag tctgggggag gcttggtgca gcctggcagg     120
tccctgagac tctcctgtgc agcctctgga ttcacctttg atgattatgc catgcactgg     180
gtccggcaag ttccagggaa gggcctggaa tgggtctcag gcattagttg gattcgtact     240
ggcataggct atgcggactc tgtgaagggc cgattcacca ttttcagaga caacgccaag     300
aattccctgt atctgcaaat gaacagtctg agagctgagg acacggcctt gtattactgt     360
gcaaaagata tgaagggttc ggggacttat gggggtggt tcgacacctg gggccaggga     420
accctggtca ccgtctcctc agccaaaaca acagccccat cggtctatcc actggcccct     480
gc                                                                    482

<210> SEQ ID NO 35
<211> LENGTH: 450
<212> TYPE: PRT
<213> ORGANISM: Homo Sapien

<400> SEQUENCE: 35

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

-continued

```
Ala Met His Trp Val Arg Gln Val Pro Gly Lys Gly Leu Glu Trp Val
         35                  40                  45

Ser Gly Ile Ser Trp Ile Arg Thr Gly Ile Gly Tyr Ala Asp Ser Val
 50                  55                  60

Lys Gly Arg Phe Thr Ile Phe Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Met Lys Gly Ser Gly Thr Tyr Gly Gly Trp Phe Asp Thr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
                210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
```

<210> SEQ ID NO 36
<211> LENGTH: 1359
<212> TYPE: DNA
<213> ORGANISM: Homo Sapien

<400> SEQUENCE: 36

| | | | | |
|---|---|---|---|---|
| gaagtgcagc | tggtggaatc | tggcggcgga | ctggtgcagc | ctggcagatc cctgagactg | 60 |
| tcttgtgccg | cctccggctt | caccttcgac | gactacgcta | tgcactgggt gcgacaggtg | 120 |
| ccaggcaagg | gcctggaatg | ggtgtccggc | atctcttgga | tccggaccgg catcggctac | 180 |
| gccgactctg | tgaagggccg | gttcaccatc | tccgggaca | acgccaagaa ctccctgtac | 240 |
| ctgcagatga | acagcctgcg | ggccgaggac | accgccctgt | actactgcgc caaggacatg | 300 |
| aagggctccg | gcacctacgg | cggatggttc | gatacttggg | gccagggcac cctcgtgacc | 360 |
| gtgtcctctg | ccagcaccaa | gggcccctct | gtgttccctc | tggccccttc cagcaagtcc | 420 |
| acctctggcg | gaacagccgc | tctgggctgc | ctcgtgaagg | actacttccc cgagcctgtg | 480 |
| accgtgtcct | ggaactctgg | cgctctgacc | agcggagtgc | acaccttccc tgctgtgctg | 540 |
| cagtcctccg | gcctgtactc | cctgtcctcc | gtcgtgaccg | tgccttccag ctctctgggc | 600 |
| acccagacct | acatctgcaa | cgtgaaccac | aagccctcca | acaccaaggt ggacaagaag | 660 |
| gtggaaccca | gtcctgcga | caagacccac | acctgtcccc | cttgtcctgc ccctgaactg | 720 |
| ctgggcggac | cttccgtgtt | cctgttcccc | ccaaagccca | aggacaccct gatgatctcc | 780 |
| cggacccccg | aagtgacctg | cgtggtggtg | gatgtgtccc | acgaggaccc tgaagtgaag | 840 |
| ttcaattggt | acgtggacgg | cgtggaagtg | cacaacgcca | agaccaagcc tagagaggaa | 900 |
| cagtacaact | ccacctaccg | ggtggtgtcc | gtgctgaccg | tgctgcacca ggattggctg | 960 |
| aacggcaaag | agtacaagtg | caaggtgtcc | aacaaggccc | tgcctgcccc catcgaaaag | 1020 |
| accatctcca | aggccaaggg | ccagccccgg | gaacccagg | tgtacacact gcccctagc | 1080 |
| agggacgagc | tgaccaagaa | ccaggtgtcc | ctgacctgtc | tcgtgaaagg cttctacccc | 1140 |
| tccgatatcg | ccgtggaatg | ggagtccaac | ggccagcctg | agaacaacta caagaccacc | 1200 |
| cccctgtgc | tggactccga | cggctcattc | ttcctgtaca | gcaagctgac agtggacaag | 1260 |
| tcccggtggc | agcagggcaa | cgtgttctcc | tgctccgtga | tgcacgaggc cctgcacaac | 1320 |
| cactacaccc | agaagtccct | gtccctgagc | cccggcaag | | 1359 |

<210> SEQ ID NO 37
<211> LENGTH: 6
<212> TYPE: PRT
<213> ORGANISM: Homo Sapien

<400> SEQUENCE: 37

Gln Ser Ile Ser Ser Tyr
1               5

<210> SEQ ID NO 38
<211> LENGTH: 3
<212> TYPE: PRT
<213> ORGANISM: Homo Sapien

<400> SEQUENCE: 38

Val Ala Ser
1

-continued

<210> SEQ ID NO 39
<211> LENGTH: 9
<212> TYPE: PRT
<213> ORGANISM: Homo Sapien

<400> SEQUENCE: 39

Gln Gln Ser Tyr Ser Thr Pro Ile Thr
1               5

<210> SEQ ID NO 40
<211> LENGTH: 11
<212> TYPE: PRT
<213> ORGANISM: Homo Sapien

<400> SEQUENCE: 40

Arg Ala Ser Gln Ser Ile Ser Ser Tyr Leu Asn
1               5                   10

<210> SEQ ID NO 41
<211> LENGTH: 7
<212> TYPE: PRT
<213> ORGANISM: Homo Sapien

<400> SEQUENCE: 41

Val Ala Ser Ser Leu Gln Ser
1               5

<210> SEQ ID NO 42
<211> LENGTH: 9
<212> TYPE: PRT
<213> ORGANISM: Homo Sapien

<400> SEQUENCE: 42

Gln Gln Ser Tyr Ser Thr Pro Ile Thr
1               5

<210> SEQ ID NO 43
<211> LENGTH: 107
<212> TYPE: PRT
<213> ORGANISM: Homo Sapien

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 44
<211> LENGTH: 418
<212> TYPE: DNA
<213> ORGANISM: Homo Sapien

<400> SEQUENCE: 44

```
aaagcttgcc gccaccatga ggctccctgc tcagcttctg gggtcctgc tactctggct      60 ccgaggtgcc agatgtgaca tccagatgac ccagtctcca tcctccctgt ctgcatctgt     120
aggagacaga gtcaccatca cttgccgggc aagtcagagc attagcagct atttaaattg    180
gtatcagcag aaaccaggga aagcccctaa actcctgatc tatgttgcat ccagtttgca    240
aagtggggtc ccatcaaggt tcagtggcag tggatctggg acagatttca ctctcactat    300
cagcagtctg caacctgaag attttgcaac ttactactgt caacagagtt acagtacccc    360
gatcaccttc ggccaaggga cacgtctgga gatcaaacgt acggatgctg caccaact     418

<210> SEQ ID NO 45
<211> LENGTH: 214
<212> TYPE: PRT
<213> ORGANISM: Homo Sapien

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 642
<212> TYPE: DNA
<213> ORGANISM: Homo Sapien

<400> SEQUENCE: 46
gacatccaga tgacccagtc cccctccagc ctgtctgctt ccgtgggcga cagagtgacc     60
atcacctgtc gggcctccca gtccatctcc tcctacctga actggtatca gcagaagccc    120
ggcaaggccc ccaagctgct gatctacgtg gccagctctc tgcagtccgg cgtgccctct    180
```

```
agattctccg gctctggctc tggcaccgac tttaccctga ccatcagctc cctgcagccc    240
gaggacttcg ccacctacta ctgccagcag tcctactcca cccctatcac cttcggccag    300
ggcacccggc tggaaatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga aagcacaag gtgtacgcct gcgaagtgac caccagggc     600 ctgtctagcc ccgtgaccaa gtctttcaac cggggcgagt gt                       642
```

```
<210> SEQ ID NO 47
<211> LENGTH: 450
<212> TYPE: PRT
<213> ORGANISM: Homo Sapien

<400> SEQUENCE: 47

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 48
<211> LENGTH: 450
<212> TYPE: PRT
<213> ORGANISM: Homo Sapien

<400> SEQUENCE: 48

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
                35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Cys Ser Arg Ser Thr Ser Glu Ser
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205
```

```
Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 49
<211> LENGTH: 448
<212> TYPE: PRT
<213> ORGANISM: Homo Sapien

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125
```

```
Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 50
<211> LENGTH: 214
<212> TYPE: PRT
<213> ORGANISM: Homo Sapien

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

Ser Gly Ser Gly Thr Asp Phe Thr Leu Thr Ile Ser Ser Leu Gln Pro
65                  70                      75                      80

Glu Asp Phe Ala Thr Tyr Tyr Cys Gln Gln Ser Tyr Ser Thr Pro Ile
                    85                      90                      95

Thr Phe Gly Gln Gly Thr Arg Leu Glu Ile Lys Arg Thr Val Ala Ala
                100                     105                     110

Pro Ser Val Phe Ile Phe Pro Pro Ser Asp Glu Gln Leu Lys Ser Gly
                115                     120                     125

Thr Ala Ser Val Val Cys Leu Leu Asn Asn Phe Tyr Pro Arg Glu Ala
                130                     135                     140

Lys Val Gln Trp Lys Val Asp Asn Ala Leu Gln Ser Gly Asn Ser Gln
145                     150                     155                     160

Glu Ser Val Thr Glu Gln Asp Ser Lys Asp Ser Thr Tyr Ser Leu Ser
                    165                     170                     175

Ser Thr Leu Thr Leu Ser Lys Ala Asp Tyr Glu Lys His Lys Val Tyr
                180                     185                     190

Ala Cys Glu Val Thr His Gln Gly Leu Ser Ser Pro Val Thr Lys Ser
                195                     200                     205

Phe Asn Arg Gly Glu Cys
210

<210> SEQ ID NO 51
<211> LENGTH: 214
<212> TYPE: PRT
<213> ORGANISM: Homo Sapien

<400> SEQUENCE: 51

Asp Ile Gln Met Thr Gln Ser Pro Ser Ser Leu Ser Ala Ser Val Gly
1               5                       10                      15

Asp Arg Val Thr Ile Thr Cys Arg Ala Ser Gln Ser Ile Ser Ser Tyr
                20                      25                      30

Leu Asn Trp Tyr Gln Gln Lys Pro Gly Lys Ala Pro Lys Leu Phe Ile
                35                      40                      45

Tyr Val Ala Ser Ser Leu Gln Ser Gly Val Pro Ser Arg Phe Ser Gly
50                      55                      60

Ser Gly Ser Gly Thr Asp Phe Thr Leu Thr Ile Ser Ser Leu Gln Pro
65                  70                      75                      80

Glu Asp Phe Ala Thr Tyr Tyr Cys Gln Gln Ser Tyr Ser Thr Pro Ile
                    85                      90                      95

Thr Phe Gly Gln Gly Thr Arg Leu Glu Ile Lys Arg Thr Val Ala Ala
                100                     105                     110

Pro Ser Val Phe Ile Phe Pro Pro Ser Asp Glu Gln Leu Lys Ser Gly
                115                     120                     125

Thr Ala Ser Val Val Cys Leu Leu Asn Asn Phe Tyr Pro Arg Glu Ala
                130                     135                     140

Lys Val Gln Trp Lys Val Asp Asn Ala Leu Gln Ser Gly Asn Ser Gln
145                     150                     155                     160

Glu Ser Val Thr Glu Gln Asp Ser Lys Asp Ser Thr Tyr Ser Leu Ser
                    165                     170                     175

Ser Thr Leu Thr Leu Ser Lys Ala Asp Tyr Glu Lys His Lys Val Tyr
                180                     185                     190

Ala Cys Glu Val Thr His Gln Gly Leu Ser Ser Pro Val Thr Lys Ser
                195                     200                     205

Phe Asn Arg Gly Glu Cys
    210

<210> SEQ ID NO 52
<211> LENGTH: 8
<212> TYPE: PRT
<213> ORGANISM: Homo Sapien

<400> SEQUENCE: 52

Gly Phe Thr Phe Ser Ser Tyr Trp
1               5

<210> SEQ ID NO 53
<211> LENGTH: 8
<212> TYPE: PRT
<213> ORGANISM: Homo Sapien

<400> SEQUENCE: 53

Ile Lys Glu Asp Gly Ser Glu Lys
1               5

<210> SEQ ID NO 54
<211> LENGTH: 12
<212> TYPE: PRT
<213> ORGANISM: Homo Sapien

<400> SEQUENCE: 54

Ala Arg Asn Arg Leu Tyr Ser Asp Phe Leu Asp Asn
1               5                   10

<210> SEQ ID NO 55
<211> LENGTH: 5
<212> TYPE: PRT
<213> ORGANISM: Homo Sapien

<400> SEQUENCE: 55

Ser Tyr Trp Met Ser
1               5

<210> SEQ ID NO 56
<211> LENGTH: 17
<212> TYPE: PRT
<213> ORGANISM: Homo Sapien

<400> SEQUENCE: 56

Asn Ile Lys Glu Asp Gly Ser Glu Lys Tyr Tyr Val Asp Ser Val Lys
1               5                   10                  15

Gly

<210> SEQ ID NO 57
<211> LENGTH: 10
<212> TYPE: PRT
<213> ORGANISM: Homo Sapien

<400> SEQUENCE: 57

Asn Arg Leu Tyr Ser Asp Phe Leu Asp Asn
1               5                   10

<210> SEQ ID NO 58
<211> LENGTH: 119
<212> TYPE: PRT
<213> ORGANISM: Homo Sapien

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
            85                  90                  95

Ala Arg Asn Arg Leu Tyr Ser Asp Phe Leu Asp Asn Trp Gly Gln Gly
            100                 105                 110

Thr Leu Val Thr Val Ser Ser
            115
```

<210> SEQ ID NO 59
<211> LENGTH: 358
<212> TYPE: DNA
<213> ORGANISM: Homo Sapien

<400> SEQUENCE: 59

```
gaggtgcagc tggtggagtc tgggggaggc ttggtccagc ctggggggtc cctgagactc      60
tcctgtgcag cctctggatt cacgtttagt agctattgga tgagttgggt ccgccaggct     120
ccagggaagg ggctggagtg ggtggccaac atcaaagaag atggaagtga aaatactat     180
gtcgactctg tgaagggccg attcaccatc tccagagaca acgccaagaa ctcactgtat     240
ctgcaaatga acagcctgag agccgaggac acgtctgtgt attactgtgc gagaaatcga     300
ctctacagtg acttccttga caactgggc cagggaaccc tggtcaccgt ctcctcag       358
```

<210> SEQ ID NO 60
<211> LENGTH: 449
<212> TYPE: PRT
<213> ORGANISM: Homo Sapien

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
            85                  90                  95

Ala Arg Asn Arg Leu Tyr Ser Asp Phe Leu Asp Asn Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 61
<211> LENGTH: 1347
<212> TYPE: DNA
<213> ORGANISM: Homo Sapien

<400> SEQUENCE: 61
gaggtgcagc tggtggagtc tgggggaggc ttggtccagc ctggggggtc cctgagactc     60
tcctgtgcag cctctggatt cacgtttagt agctattgga tgagttgggt ccgccaggct    120
ccagggaagg ggctggagtg ggtggccaac atcaaagaag atggaagtga aaatactat    180 gtcgactctg tgaagggccg attcaccatc tccagagaca acgccaagaa ctcactgtat    240
ctgcaaatga acagcctgag agccgaggac acgtctgtgt attactgtgc gagaaatcga    300
ctctacagtg acttccttga caactggggc cagggaaccc tggtcaccgt ctcctcagcc    360

-continued

```
agcaccaagg gcccctctgt gttccctctg gcccctccca gcaagtccac ctctggcgga    420
acagccgctc tgggctgcct cgtgaaggac tacttccccg agcctgtgac cgtgtcctgg    480
aactctggcg ctctgaccag cggagtgcac accttccctg ctgtgctgca gtcctccggc    540
ctgtactccc tgtcctccgt cgtgaccgtg ccttccagct ctctgggcac ccagacctac    600
atctgcaacg tgaaccacaa gccctccaac accaaggtgg acaagaaggt ggaacccaag    660
tcctgcgaca gacccacac ctgtcccct tgtcctgccc ctgaactgct gggcggacct    720
tccgtgttcc tgttcccccc aaagcccaag gacaccctga tgatctcccg gacccccgaa    780
gtgacctgcg tggtggtgga tgtgtcccac gaggaccctg aagtgaagtt caattggtac    840
gtggacggcg tggaagtgca acgccaag accaagccta gagaggaaca gtacaactcc    900
acctaccggg tggtgtccgt gctgaccgtg ctgcaccagg attggctgaa cggcaaagag    960
tacaagtgca aggtgtccaa caaggccctg cctgccccca tcgaaaagac catctccaag   1020
gccaagggcc agccccggga accccaggtg tacacactgc ccctagcag ggacgagctg    1080
accaagaacc aggtgtccct gacctgtctc gtgaaaggct tctacccctc cgatatcgcc    1140
gtggaatggg agtccaacgg ccagcctgag aacaactaca agaccacccc cctgtgctg    1200
gactccgacg gctcattctt cctgtacagc aagctgacag tggacaagtc ccggtggcag    1260
cagggcaacg tgttctcctg ctccgtgatg cacgaggccc tgcacaacca ctacacccag    1320
aagtccctgt ccctgagccc cggcaag                                        1347
```

<210> SEQ ID NO 62
<211> LENGTH: 6
<212> TYPE: PRT
<213> ORGANISM: Homo Sapien

<400> SEQUENCE: 62

Gln Gly Val Ser Ser Trp
1               5

<210> SEQ ID NO 63
<211> LENGTH: 3
<212> TYPE: PRT
<213> ORGANISM: Homo Sapien

<400> SEQUENCE: 63

Gly Ala Ser
1

<210> SEQ ID NO 64
<211> LENGTH: 9
<212> TYPE: PRT
<213> ORGANISM: Homo Sapien

<400> SEQUENCE: 64

Gln Gln Ala Asn Ser Ile Pro Phe Thr
1               5

<210> SEQ ID NO 65
<211> LENGTH: 11
<212> TYPE: PRT
<213> ORGANISM: Homo Sapien

<400> SEQUENCE: 65

Arg Ala Ser Gln Gly Val Ser Ser Trp Leu Ala
1               5                   10

```
<210> SEQ ID NO 66
<211> LENGTH: 7
<212> TYPE: PRT
<213> ORGANISM: Homo Sapien

<400> SEQUENCE: 66

Gly Ala Ser Ser Leu Gln Ser
1               5

<210> SEQ ID NO 67
<211> LENGTH: 9
<212> TYPE: PRT
<213> ORGANISM: Homo Sapien

<400> SEQUENCE: 67

Gln Gln Ala Asn Ser Ile Pro Phe Thr
1               5

<210> SEQ ID NO 68
<211> LENGTH: 107
<212> TYPE: PRT
<213> ORGANISM: Homo Sapien

<400> SEQUENCE: 68

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105

<210> SEQ ID NO 69
<211> LENGTH: 322
<212> TYPE: DNA
<213> ORGANISM: Homo Sapien

<400> SEQUENCE: 69
gacatccaga tgacccagtc tccatcttcc gtgtctgcat ctgtcggaga cagagtcacc      60
atcacttgtc gggcgagtca gggtgttagc agctggttag cctggtatca gcagaaatca     120
gggaaagccc ctaagctcct gatctatggt gcatccagtt tgcaaagtgg ggtcccatca     180
agattcagcg gcagtggatc tgggacagag ttcattctca ccatcagcag cctgcagcct     240
gaagattttg caacttacta ttgtcaacag gctaacagta tcccattcac tttcggccct     300
gggaccaaag tggatatcaa ac                                              322

<210> SEQ ID NO 70
<211> LENGTH: 214
<212> TYPE: PRT
<213> ORGANISM: Homo Sapien

<400> SEQUENCE: 70

Asp Ile Gln Met Thr Gln Ser Pro Ser Ser Val Ser Ala Ser Val Gly
1               5                   10                  15
```

```
              1               5              10              15
            Asp Arg Val Thr Ile Thr Cys Arg Ala Ser Gln Gly Val Ser Ser Trp
                           20                  25                  30

Leu Ala Trp Tyr Gln Gln Lys Ser Gly Lys Ala Pro Lys Leu Leu Ile
                           35                  40                  45

Tyr Gly Ala Ser Ser Leu Gln Ser Gly Val Pro Ser Arg Phe Ser Gly
                           50                  55                  60

Ser Gly Ser Gly Thr Glu Phe Ile Leu Thr Ile Ser Ser Leu Gln Pro
            65                  70                  75                  80

Glu Asp Phe Ala Thr Tyr Tyr Cys Gln Gln Ala Asn Ser Ile Pro Phe
                                85                  90                  95

Thr Phe Gly Pro Gly Thr Lys Val Asp Ile Lys Arg Thr Val Ala Ala
                          100                 105                 110

Pro Ser Val Phe Ile Phe Pro Pro Ser Asp Glu Gln Leu Lys Ser Gly
                          115                 120                 125

Thr Ala Ser Val Val Cys Leu Leu Asn Asn Phe Tyr Pro Arg Glu Ala
                          130                 135                 140

Lys Val Gln Trp Lys Val Asp Asn Ala Leu Gln Ser Gly Asn Ser Gln
            145                 150                 155                 160

Glu Ser Val Thr Glu Gln Asp Ser Lys Asp Ser Thr Tyr Ser Leu Ser
                                165                 170                 175

Ser Thr Leu Thr Leu Ser Lys Ala Asp Tyr Glu Lys His Lys Val Tyr
                          180                 185                 190

Ala Cys Glu Val Thr His Gln Gly Leu Ser Ser Pro Val Thr Lys Ser
                          195                 200                 205

Phe Asn Arg Gly Glu Cys
                          210

<210> SEQ ID NO 71
            <211> LENGTH: 642
            <212> TYPE: DNA
            <213> ORGANISM: Homo Sapien

<400> SEQUENCE: 71
gacatccaga tgacccagtc tccatcttcc gtgtctgcat ctgtcggaga cagagtcacc       60
atcacttgtc gggcgagtca gggtgttagc agctggttag cctggtatca gcagaaatca      120
gggaaagccc ctaagctcct gatctatggt gcatccagtt tgcaaagtgg ggtcccatca      180
agattcagcg gcagtggatc tgggacagag ttcattctca ccatcagcag cctgcagcct      240
gaagattttg caacttacta ttgtcaacag gctaacagta tcccattcac tttcggccct      300
gggaccaaag tggatatcaa acgtacggtg gccgctccct ccgtgttcat cttcccacct      360
tccgacgagc agctgaagtc cggcaccgct tctgtcgtgt gcctgctgaa caacttctac      420
ccccgcgagg ccaaggtgca gtggaaggtg gacaacgccc tgcagtccgg caactcccag      480
gaatccgtga ccgagcagga ctccaaggac agcacctact ccctgtcctc cacccctgacc     540 ctgtccaagg ccgactacga gaagcacaag gtgtacgcct gcgaagtgac ccaccagggc      600
ctgtctagcc ccgtgaccaa gtctttcaac cggggcgagt gt                        642

<210> SEQ ID NO 72
            <211> LENGTH: 8
            <212> TYPE: PRT
            <213> ORGANISM: Homo Sapien

<400> SEQUENCE: 72
```

-continued

```
Gly Phe Thr Phe Ser Ser Tyr Trp
1               5

<210> SEQ ID NO 73
<211> LENGTH: 8
<212> TYPE: PRT
<213> ORGANISM: Homo Sapien

<400> SEQUENCE: 73

Ile Lys Glu Asp Gly Ser Glu Lys
1               5

<210> SEQ ID NO 74
<211> LENGTH: 12
<212> TYPE: PRT
<213> ORGANISM: Homo Sapien

<400> SEQUENCE: 74

Ala Arg Val Arg Leu Tyr Ser Asp Phe Leu Asp Tyr
1               5                   10

<210> SEQ ID NO 75
<211> LENGTH: 5
<212> TYPE: PRT
<213> ORGANISM: Homo Sapien

<400> SEQUENCE: 75

Ser Tyr Trp Met Ser
1               5

<210> SEQ ID NO 76
<211> LENGTH: 17
<212> TYPE: PRT
<213> ORGANISM: Homo Sapien

<400> SEQUENCE: 76

Asn Ile Lys Glu Asp Gly Ser Glu Lys Tyr Tyr Val Asp Ser Leu Lys
1               5                   10                  15
Gly

<210> SEQ ID NO 77
<211> LENGTH: 10
<212> TYPE: PRT
<213> ORGANISM: Homo Sapien

<400> SEQUENCE: 77

Val Arg Leu Tyr Ser Asp Phe Leu Asp Tyr
1               5                   10

<210> SEQ ID NO 78
<211> LENGTH: 119
<212> TYPE: PRT
<213> ORGANISM: Homo Sapien

<400> SEQUENCE: 78

Glu Val Gln Leu Val Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Leu
    50                  55                  60
```

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Val Arg Leu Tyr Ser Asp Phe Leu Asp Tyr Trp Gly Gln Gly
            100                 105                 110

Thr Leu Val Thr Val Ser Ser
            115

<210> SEQ ID NO 79
<211> LENGTH: 358
<212> TYPE: DNA
<213> ORGANISM: Homo Sapien

<400> SEQUENCE: 79
gaggtgcagc tggtggactc tgggggaggc ttggtccagc ctggggggtc cctgagactc    60
tcctgtgcag cctctggatt cacgtttagt agctattgga tgagttgggt ccgccaggct   120
ccaggaaagg ggctggagtg ggtggccaac ataaagaag atggaagtga aaatactat    180 gtagactctt tgaagggccg attcaccatc tccagagaca acgccaagaa ctcactgtat   240
ctgcaaatga acagcctgag agccgaggac acgtctgtgt attactgtgc gagagttcga   300
ctctacagtg acttccttga ctactggggc cagggaaccc tggtcaccgt ctcctcag    358

<210> SEQ ID NO 80
<211> LENGTH: 449
<212> TYPE: PRT
<213> ORGANISM: Homo Sapien

<400> SEQUENCE: 80

Glu Val Gln Leu Val Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Glu Asp Gly Ser Glu Lys Tyr Tyr Val Asp Ser Leu
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Val Arg Leu Tyr Ser Asp Phe Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

```
<210> SEQ ID NO 81
<211> LENGTH: 1347
<212> TYPE: DNA
<213> ORGANISM: Homo Sapien

<400> SEQUENCE: 81
```

| | | | | |
|---|---|---|---|---|
| gaggtgcagc tggtggactc tgggggaggc ttggtccagc ctgggggtc cctgagactc | | | | 60 |
| tcctgtgcag cctctggatt cacgtttagt agctattgga tgagttgggt ccgccaggct | | | | 120 |
| ccaggaaagg ggctggagtg ggtggccaac ataaaagaag atggaagtga aaatactat | | | | 180 |
| gtagactctt tgaagggccg attcaccatc tccagagaca acgccaagaa ctcactgtat | | | | 240 |
| ctgcaaatga acagcctgag agccgaggac acgtctgtgt attactgtgc gagagttcga | | | | 300 |
| ctctacagtg acttccttga ctactgggc agggaaccc tggtcaccgt ctcctcagcc | | | | 360 |
| agcaccaagg gcccctctgt gttccctctg gccccttcca gcaagtccac ctctggcgga | | | | 420 |
| acagccgctc tgggctgcct cgtgaaggac tacttcccg agcctgtgac cgtgtcctgg | | | | 480 |
| aactctggcg ctctgaccag cggagtgcac accttccctg ctgtgctgca gtcctccggc | | | | 540 |
| ctgtactccc tgtcctccgt cgtgaccgtg ccttccagct ctctgggcac ccagacctac | | | | 600 |
| atctgcaacg tgaaccacaa gccctccaac accaaggtgg acaagaaggt ggaacccaag | | | | 660 |
| tcctgcgaca gacccacac ctgtcccct tgtcctgccc ctgaactgct gggcggacct | | | | 720 |

```
tccgtgttcc tgttcccccc aaagcccaag dacaccctga tgatctcccg gacccccgaa      780
gtgacctgcg tggtggtgga tgtgtcccac gaggaccctg aagtgaagtt caattggtac      840
gtggacggcg tggaagtgca caacgccaag accaagccta gagaggaaca gtacaactcc      900
acctaccggg tggtgtccgt gctgaccgtg ctgcaccagg attggctgaa cggcaaagag      960
tacaagtgca aggtgtccaa caaggccctg cctgccccca tcgaaaagac catctccaag     1020
gccaagggcc agccccggga acccagggtg tacacactgc ccctagcag ggacgagctg      1080 accaagaacc aggtgtccct gacctgtctc gtgaaaggct tctaccctc cgatatcgcc      1140 gtggaatggg agtccaacgg ccagcctgag aacaactaca agaccacccc ccctgtgctg     1200
gactccgacg gctcattctt cctgtacagc aagctgacag tggacaagtc ccggtggcag     1260
cagggcaacg tgttctcctg ctccgtgatg cacgaggccc tgcacaacca ctacacccag     1320
aagtccctgt ccctgagccc cggcaag                                          1347
```

```
<210> SEQ ID NO 82
<211> LENGTH: 6
<212> TYPE: PRT
<213> ORGANISM: Homo Sapien

<400> SEQUENCE: 82

Gln Gly Val Ser Ser Trp
1               5

<210> SEQ ID NO 83
<211> LENGTH: 3
<212> TYPE: PRT
<213> ORGANISM: Homo Sapien

<400> SEQUENCE: 83

Gly Ala Ser
1

<210> SEQ ID NO 84
<211> LENGTH: 9
<212> TYPE: PRT
<213> ORGANISM: Homo Sapien

<400> SEQUENCE: 84

Gln Gln Ala Asn Ser Ile Pro Phe Thr
1               5

<210> SEQ ID NO 85
<211> LENGTH: 11
<212> TYPE: PRT
<213> ORGANISM: Homo Sapien

<400> SEQUENCE: 85

Arg Ala Ser Gln Gly Val Ser Ser Trp Leu Ala
1               5                   10

<210> SEQ ID NO 86
<211> LENGTH: 7
<212> TYPE: PRT
<213> ORGANISM: Homo Sapien

<400> SEQUENCE: 86

Gly Ala Ser Ser Leu Gln Ser
1               5
```

```
<210> SEQ ID NO 87
<211> LENGTH: 9
<212> TYPE: PRT
<213> ORGANISM: Homo Sapien

<400> SEQUENCE: 87

Gln Gln Ala Asn Ser Ile Pro Phe Thr
1               5

<210> SEQ ID NO 88
<211> LENGTH: 107
<212> TYPE: PRT
<213> ORGANISM: Homo Sapien

<400> SEQUENCE: 88

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Glu Phe Ile Leu Ser Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105

<210> SEQ ID NO 89
<211> LENGTH: 322
<212> TYPE: DNA
<213> ORGANISM: Homo Sapien

<400> SEQUENCE: 89
gacatccaga tgacccagtc tccatcttcc gtgtctgcat ctgtcggaga cagagtcacc      60
atcacttgtc gggcgagtca gggtgttagc agttggttag cctggtatca gcagaaatca    120
gggaaagccc ctaagctcct gatctatggt gcctccagtt tgcaaagtgg ggtcccatca    180
agattcagcg gcagtggatc tgggacagag ttcattctca gcatcagcag cctgcagcct    240
gaagattttg caacttacta ttgtcaacag gctaacagta tcccattcac tttcggccct    300
gggaccaaag tggatatcaa ac                                             322

<210> SEQ ID NO 90
<211> LENGTH: 214
<212> TYPE: PRT
<213> ORGANISM: Homo Sapien

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60
```

Ser Gly Ser Gly Thr Glu Phe Ile Leu Ser Ile Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 642
<212> TYPE: DNA
<213> ORGANISM: Homo Sapien

<400> SEQUENCE: 91
gacatccaga tgacccagtc tccatcttcc gtgtctgcat ctgtcggaga cagagtcacc      60
atcacttgtc gggcgagtca gggtgttagc agttggttag cctggtatca gcagaaatca     120
gggaaagccc ctaagctcct gatctatggt gcctccagtt tgcaaagtgg ggtcccatca     180
agattcagcg gcagtggatc tgggacagag ttcattctca gcatcagcag cctgcagcct     240
gaagattttg caacttacta ttgtcaacag gctaacagta tcccattcac tttcggccct     300
gggaccaaag tggatatcaa acgtacggtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg gacaacgccc tgcagtccgg caactcccag     480
gaatccgtga ccgagcagga ctccaaggac agcacctact ccctgtcctc caccctgacc     540
ctgtccaagg ccgactacga gaagcacaag gtgtacgcct gcgaagtgac ccaccagggc     600
ctgtctagcc ccgtgaccaa gtctttcaac cggggcgagt gt                        642

<210> SEQ ID NO 92
<211> LENGTH: 9
<212> TYPE: PRT
<213> ORGANISM: Homo Sapien

<400> SEQUENCE: 92

Gly Gly Ser Ile Ile Ser Ser Asp Trp
1               5

<210> SEQ ID NO 93
<211> LENGTH: 7
<212> TYPE: PRT
<213> ORGANISM: Homo Sapien

<400> SEQUENCE: 93

Ile Phe His Ser Gly Arg Thr
1               5

<210> SEQ ID NO 94
<211> LENGTH: 8
<212> TYPE: PRT
<213> ORGANISM: Homo Sapien

<400> SEQUENCE: 94

Ala Arg Asp Gly Ser Gly Ser Tyr
1               5

<210> SEQ ID NO 95
<211> LENGTH: 6
<212> TYPE: PRT
<213> ORGANISM: Homo Sapien

<400> SEQUENCE: 95

Ser Ser Asp Trp Trp Asn
1               5

<210> SEQ ID NO 96
<211> LENGTH: 16
<212> TYPE: PRT
<213> ORGANISM: Homo Sapien

<400> SEQUENCE: 96

Glu Ile Phe His Ser Gly Arg Thr Asn Tyr Asn Pro Ser Leu Lys Ser
1               5                   10                  15

<210> SEQ ID NO 97
<211> LENGTH: 6
<212> TYPE: PRT
<213> ORGANISM: Homo Sapien

<400> SEQUENCE: 97

Asp Gly Ser Gly Ser Tyr
1               5

<210> SEQ ID NO 98
<211> LENGTH: 115
<212> TYPE: PRT
<213> ORGANISM: Homo Sapien

<400> SEQUENCE: 98

Gln Val Gln Leu Gln Glu Ser Gly Pro Gly Leu Val Lys Pro Ser Gly
1               5                   10                  15

Thr Leu Ser Leu Thr Cys Ile Val Ser Gly Gly Ser Ile Ile Ser Ser
            20                  25                  30

Asp Trp Trp Asn Trp Val Arg Gln Pro Pro Gly Lys Gly Leu Glu Trp
        35                  40                  45

Ile Gly Glu Ile Phe His Ser Gly Arg Thr Asn Tyr Asn Pro Ser Leu
    50                  55                  60

Lys Ser Arg Val Thr Ile Ser Ile Asp Lys Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Asp Gly Ser Gly Ser Tyr Trp Gly Gln Gly Thr Leu Val Thr
            100                 105                 110

Val Ser Ser
        115

<210> SEQ ID NO 99
<211> LENGTH: 346
<212> TYPE: DNA
<213> ORGANISM: Homo Sapien

<400> SEQUENCE: 99
caggtgcagc tgcaggagtc gggcccagga ctggtgaagc cttcgggac cctgtccctc      60 acctgcattg tctctggtgg ctccatcatc agtagtgact ggtggaattg ggtccgccag     120
cccccaggga aggggctgga gtggattgga gaaatctttc atagtgggag gaccaactac     180
aacccgtccc tcaagagtcg agtcaccata tcaatagaca gtccaagaa tcagttctcc     240 ctgaggctga gctctgtgac cgccgcggac acggccgtgt attactgtgc gagagatggt     300
tcggggagtt actggggcca gggaaccctg gtcaccgtct cctcag                   346

<210> SEQ ID NO 100
<211> LENGTH: 445
<212> TYPE: PRT
<213> ORGANISM: Homo Sapien

<400> SEQUENCE: 100

Gln Val Gln Leu Gln Glu Ser Gly Pro Gly Leu Val Lys Pro Ser Gly
1               5                   10                  15

Thr Leu Ser Leu Thr Cys Ile Val Ser Gly Gly Ser Ile Ile Ser Ser
            20                  25                  30

Asp Trp Trp Asn Trp Val Arg Gln Pro Pro Gly Lys Gly Leu Glu Trp
        35                  40                  45

Ile Gly Glu Ile Phe His Ser Gly Arg Thr Asn Tyr Asn Pro Ser Leu
    50                  55                  60

Lys Ser Arg Val Thr Ile Ser Ile Asp Lys Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Asp Gly Ser Gly Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

```
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 101
<211> LENGTH: 1335
<212> TYPE: DNA
<213> ORGANISM: Homo Sapien

<400> SEQUENCE: 101
caggtgcagc tgcaggagtc gggcccagga ctggtgaagc cttcggggac cctgtccctc        60
acctgcattg tctctggtgg ctccatcatc agtagtgact ggtggaattg ggtccgccag       120
cccccaggga aggggctgga gtggattgga gaaatctttc atagtgggag gaccaactac       180
aacccgtccc tcaagagtcg agtcaccata tcaatagaca gtccaagaa tcagttctcc        240 ctgaggctga gctctgtgac cgccgcggac acggccgtgt attactgtgc gagagatggt       300
tcggggagtt actggggcca gggaaccctg gtcaccgtct cctcagccag caccaagggc       360
ccctctgtgt tccctctggc ccttccagc aagtccacct ctggcggaac agccgctctg        420
ggctgcctcg tgaaggacta cttccccgag cctgtgaccg tgtcctggaa ctctggcgct       480
ctgaccagcg gagtgcacac cttccctgct gtgctgcagt cctccggcct gtactccctg       540
tcctccgtcg tgaccgtgcc ttccagctct ctgggcaccc agacctacat ctgcaacgtg       600
aaccacaagc cctccaacac caaggtggac aagaaggtgg aacccaagtc ctgcgacaag       660
acccacacct gtccccttg tctgcccct gaactgctgg gcggaccttc cgtgttcctg         720
ttccccccaa agcccaagga caccctgatg atctcccgga cccccgaagt gacctgcgtg       780
gtggtggatg tgtcccacga ggaccctgaa gtgaagttca ttggtacgt ggacggcgtg        840 gaagtgcaca cgccaagac caagcctaga gaggaacagt acaactccac ctaccgggtg        900
gtgtccgtgc tgaccgtgct gcaccaggat tggctgaacg gcaaagagta caagtgcaag       960
gtgtccaaca aggccctgcc tgccccatc gaaaagacca tctccaaggc caagggccag       1020
ccccgggaac cccaggtgta cactgcccc ctagcaggg acgagctgac caagaaccag       1080
gtgtccctga cctgtctcgt gaaaggcttc taccctccg atatcgccgt ggaatgggag       1140
```

```
tccaacggcc agcctgagaa caactacaag accaccccccc ctgtgctgga ctccgacggc    1200
tcattcttcc tgtacagcaa gctgacagtg dacaagtccc ggtggcagca gggcaacgtg    1260
ttctcctgct ccgtgatgca cgaggccctg cacaaccact acacccagaa gtccctgtcc    1320
ctgagccccg gcaag                                                     1335
```

<210> SEQ ID NO 102
<211> LENGTH: 12
<212> TYPE: PRT
<213> ORGANISM: Homo Sapien

<400> SEQUENCE: 102

Gln Ser Val Leu Tyr Ser Ser Asn Asn Lys Asn Tyr
1               5                   10

<210> SEQ ID NO 103
<211> LENGTH: 3
<212> TYPE: PRT
<213> ORGANISM: Homo Sapien

<400> SEQUENCE: 103

Trp Ala Ser
1

<210> SEQ ID NO 104
<211> LENGTH: 8
<212> TYPE: PRT
<213> ORGANISM: Homo Sapien

<400> SEQUENCE: 104

Gln Gln Tyr Tyr Ser Asn Arg Ser
1               5

<210> SEQ ID NO 105
<211> LENGTH: 17
<212> TYPE: PRT
<213> ORGANISM: Homo Sapien

<400> SEQUENCE: 105

Lys Ser Ser Gln Ser Val Leu Tyr Ser Ser Asn Asn Lys Asn Tyr Leu
1               5                   10                  15
Ala

<210> SEQ ID NO 106
<211> LENGTH: 7
<212> TYPE: PRT
<213> ORGANISM: Homo Sapien

<400> SEQUENCE: 106

Trp Ala Ser Thr Arg Glu Ser
1               5

<210> SEQ ID NO 107
<211> LENGTH: 8
<212> TYPE: PRT
<213> ORGANISM: Homo Sapien

<400> SEQUENCE: 107

Gln Gln Tyr Tyr Ser Asn Arg Ser
1               5

<210> SEQ ID NO 108
<211> LENGTH: 112

<212> TYPE: PRT
<213> ORGANISM: Homo Sapien

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Gln Gln
                85                  90                  95

Tyr Tyr Ser Asn Arg Ser Phe Gly Gln Gly Thr Lys Leu Glu Ile Lys
            100                 105                 110

<210> SEQ ID NO 109
<211> LENGTH: 337
<212> TYPE: DNA
<213> ORGANISM: Homo Sapien

<400> SEQUENCE: 109
gacatcgtga tgacccagtc tccagactcc ctggctgtgt ctctgggcga gagggccacc      60
atcaactgca gtccagcca gagtgtttta tacagctcca acaataagaa ttacttagct     120
tggtaccagc agaaatcagg acagcctcct aagttgctca tttactgggc atctacccgg     180
gaatccgggg tccctgaccg attcagtggc agcgggtctg ggacagattt cactctcacc     240
atcagcagcc tgcagactga agatgtggca gtttattact gtcagcaata ttatagtaat     300
cgcagttttg gccaggggac caagctggag atcaaac                              337

<210> SEQ ID NO 110
<211> LENGTH: 219
<212> TYPE: PRT
<213> ORGANISM: Homo Sapien

<400> SEQUENCE: 110

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Gln Gln
                85                  90                  95

Tyr Tyr Ser Asn Arg Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 111
<211> LENGTH: 657
<212> TYPE: DNA
<213> ORGANISM: Homo Sapien

<400> SEQUENCE: 111
gacatcgtga tgacccagtc tccagactcc ctggctgtgt ctctgggcga gagggccacc       60
atcaactgca gtccagcca gagtgtttta tacagctcca acaataagaa ttacttagct      120
tggtaccagc agaaatcagg acagcctcct aagttgctca tttactgggc atctacccgg      180
gaatccgggg tccctgaccg attcagtggc agcgggtctg ggacagattt cactctcacc      240
atcagcagcc tgcagactga agatgtggca gtttattact gtcagcaata ttatagtaat      300
cgcagttttg gccaggggac caagctggag atcaaacgta cggtggccgc tcccctccgtg      360
ttcatcttcc caccttccga cgagcagctg aagtccggca ccgcttctgt cgtgtgcctg      420
ctgaacaact tctaccccg cgaggccaag gtgcagtgga aggtggacaa cgccctgcag      480
tccggcaact cccaggaatc cgtgaccgag caggactcca aggacagcac ctactccctg      540
tcctccaccc tgaccctgtc caaggccgac tacgagaagc acaaggtgta cgcctgcgaa      600
gtgacccacc agggcctgtc tagccccgtg accaagtctt tcaaccgggg cgagtgt         657

<210> SEQ ID NO 112
<211> LENGTH: 8
<212> TYPE: PRT
<213> ORGANISM: Homo Sapien

<400> SEQUENCE: 112

Gly Phe Thr Phe Ser Ser Tyr Trp
1               5

<210> SEQ ID NO 113
<211> LENGTH: 8
<212> TYPE: PRT
<213> ORGANISM: Homo Sapien

<400> SEQUENCE: 113

Ile Lys Glu Asp Gly Ser Glu Lys
1               5

<210> SEQ ID NO 114
<211> LENGTH: 12
<212> TYPE: PRT
<213> ORGANISM: Homo Sapien

<400> SEQUENCE: 114

Ala Arg Asn Arg Leu Tyr Ser Asp Phe Leu Asp Asn
1               5                   10
```

<210> SEQ ID NO 115
<211> LENGTH: 5
<212> TYPE: PRT
<213> ORGANISM: Homo Sapien

<400> SEQUENCE: 115

Ser Tyr Trp Met Ser
1               5

<210> SEQ ID NO 116
<211> LENGTH: 17
<212> TYPE: PRT
<213> ORGANISM: Homo Sapien

<400> SEQUENCE: 116

Asn Ile Lys Glu Asp Gly Ser Glu Lys Tyr Tyr Val Asp Ser Val Lys
1               5                   10                  15

Gly

<210> SEQ ID NO 117
<211> LENGTH: 10
<212> TYPE: PRT
<213> ORGANISM: Homo Sapien

<400> SEQUENCE: 117

Asn Arg Leu Tyr Ser Asp Phe Leu Asp Asn
1               5                   10

<210> SEQ ID NO 118
<211> LENGTH: 119
<212> TYPE: PRT
<213> ORGANISM: Homo Sapien

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Asn Arg Leu Tyr Ser Asp Phe Leu Asp Asn Trp Gly Gln Gly
            100                 105                 110

Thr Leu Val Thr Val Ser Ser
        115

<210> SEQ ID NO 119
<211> LENGTH: 358
<212> TYPE: DNA
<213> ORGANISM: Homo Sapien

<400> SEQUENCE: 119
gaggtgcagc tggtggagtc tgggggaggc ttggtccagc ctggggggtc cctgagactc      60
tcctgtgcag cctctggatt cacgtttagt agctattgga tgagttgggt ccgccaggct     120

-continued

```
ccagggaagg ggctggagtg ggtggccaac atcaaagaag atggaagtga gaaatactat      180
gtcgactctg tgaagggccg attcaccatc tccagagaca acgccaagaa ctcactgtat      240
ctgcaaatga acagcctgag agccgaggac acgtctgtgt attactgtgc gagaaatcga      300
ctctacagtg acttccttga caactggggc cagggaaccc tggtcaccgt ctcctcag        358
```

<210> SEQ ID NO 120
<211> LENGTH: 449
<212> TYPE: PRT
<213> ORGANISM: Homo Sapien

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Asn Arg Leu Tyr Ser Asp Phe Leu Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
        435                 440                 445
Lys
```

<210> SEQ ID NO 121
<211> LENGTH: 1347
<212> TYPE: DNA
<213> ORGANISM: Homo Sapien

<400> SEQUENCE: 121

| | | | | | |
|---|---|---|---|---|---|
| gaggtgcagc | tggtggagtc | tgggggaggc | ttggtccagc | ctgggggtc | cctgagactc | 60 |
| tcctgtgcag | cctctggatt | cacgtttagt | agctattgga | tgagttgggt | ccgccaggct | 120 |
| ccagggaagg | gctggagtg | gtggccaac | atcaaagaag | atggaagtga | aaatactat | 180 |
| gtcgactctg | tgaagggccg | attcaccatc | tccagagaca | acgccaagaa | ctcactgtat | 240 |
| ctgcaaatga | acagcctgag | agccgaggac | acgtctgtgt | attactgtgc | gagaaatcga | 300 |
| ctctacagtg | acttccttga | caactgggc | cagggaaccc | tggtcaccgt | ctcctcagcc | 360 |
| agcaccaagg | gcccctctgt | gttccctctg | gccccttcca | gcaagtccac | ctctggcgga | 420 |
| acagccgctc | tgggctgcct | cgtgaaggac | tacttcccg | agcctgtgac | cgtgtcctgg | 480 |
| aactctggcg | ctctgaccag | cggagtgcac | accttcctg | ctgtgctgca | gtcctccggc | 540 |
| ctgtactccc | tgtcctccgt | cgtgaccgtg | ccttccagct | ctctgggcac | ccagacctac | 600 |
| atctgcaacg | tgaaccacaa | gccctccaac | accaaggtgg | acaagaaggt | ggaacccaag | 660 |
| tcctgcgaca | agacccacac | ctgtcccct | tgtcctgccc | tgaactgct | gggcggacct | 720 |
| tccgtgttcc | tgttcccccc | aaagcccaag | gacacctga | tgatctcccg | gaccccgaa | 780 |
| gtgacctgcg | tggtggtgga | tgtgtcccac | gaggaccctg | aagtgaagtt | caattggtac | 840 |
| gtggacggcg | tggaagtgca | caacgccaag | accaagccta | gaggaaca | gtacaactcc | 900 |
| acctaccggg | tggtgtccgt | gctgaccgtg | ctgcaccagg | attggctgaa | cggcaaagag | 960 |
| tacaagtgca | aggtgtccaa | caaggccctg | cctgccccca | tcgaaaagac | catctccaag | 1020 |
| gccaagggcc | agccccggga | accccaggtg | tacacactgc | cccctagcag | ggacgagctg | 1080 |
| accaagaacc | aggtgtccct | gacctgtctc | gtgaaaggct | tctaccccc | cgatatcgcc | 1140 |
| gtggaatggg | agtccaacgg | ccagcctgag | aacaactaca | agaccacccc | ccctgtgctg | 1200 |
| gactccgacg | gctcattctt | cctgtacagc | aagctgacag | tggacaagtc | ccggtggcag | 1260 |
| cagggcaacg | tgttctcctg | ctccgtgatg | cacgaggccc | tgcacaacca | ctacacccag | 1320 |
| aagtccctgt | ccctgagccc | cggcaag | | | | 1347 |

```
<210> SEQ ID NO 122
<211> LENGTH: 6
<212> TYPE: PRT
<213> ORGANISM: Homo Sapien

<400> SEQUENCE: 122

Gln Gly Val Ser Ser Trp
1               5

<210> SEQ ID NO 123
<211> LENGTH: 3
<212> TYPE: PRT
<213> ORGANISM: Homo Sapien

<400> SEQUENCE: 123

Gly Ala Ser
1

<210> SEQ ID NO 124
<211> LENGTH: 9
<212> TYPE: PRT
<213> ORGANISM: Homo Sapien

<400> SEQUENCE: 124

Gln Gln Ala Asn Ser Ile Pro Phe Thr
1               5

<210> SEQ ID NO 125
<211> LENGTH: 11
<212> TYPE: PRT
<213> ORGANISM: Homo Sapien

<400> SEQUENCE: 125

Arg Ala Ser Gln Gly Val Ser Ser Trp Leu Ala
1               5                   10

<210> SEQ ID NO 126
<211> LENGTH: 7
<212> TYPE: PRT
<213> ORGANISM: Homo Sapien

<400> SEQUENCE: 126

Gly Ala Ser Ser Leu Gln Ser
1               5

<210> SEQ ID NO 127
<211> LENGTH: 9
<212> TYPE: PRT
<213> ORGANISM: Homo Sapien

<400> SEQUENCE: 127

Gln Gln Ala Asn Ser Ile Pro Phe Thr
1               5

<210> SEQ ID NO 128
<211> LENGTH: 107
<212> TYPE: PRT
<213> ORGANISM: Homo Sapien

<400> SEQUENCE: 128

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30
```

```
Leu Ala Trp Tyr Gln Gln Lys Ser Gly Lys Ala Pro Lys Leu Leu Ile
         35                  40                  45

Tyr Gly Ala Ser Ser Leu Gln Ser Gly Val Pro Ser Arg Phe Ser Gly
 50                  55                  60

Ser Gly Ser Gly Thr Glu Phe Ile Leu Thr Ile Ser Ser Leu Gln Pro
 65              70                  75                  80

Glu Asp Phe Ala Thr Tyr Tyr Cys Gln Gln Ala Asn Ser Ile Pro Phe
                 85                  90                  95

Thr Phe Gly Pro Gly Thr Lys Val Asp Ile Lys
                100                 105
```

<210> SEQ ID NO 129
<211> LENGTH: 322
<212> TYPE: DNA
<213> ORGANISM: Homo Sapien

<400> SEQUENCE: 129

```
gacatccaga tgacccagtc tccatcttcc gtgtctgcat ctgtcggaga cagagtcacc      60
atcacttgtc gggcgagtca gggtgttagc agctggttag cctggtatca gcagaaatca     120
gggaaagccc ctaagctcct gatctatggt gcatccagtt tgcaaagtgg ggtcccatca     180
agattcagcg gcagtggatc tgggacagag ttcattctca ccatcagcag cctgcagcct     240
gaagattttg caacttacta ttgtcaacag gctaacagta tcccattcac tttcggccct     300
gggaccaaag tggatatcaa ac                                              322
```

<210> SEQ ID NO 130
<211> LENGTH: 214
<212> TYPE: PRT
<213> ORGANISM: Homo Sapien

<400> SEQUENCE: 130

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Val Ser Ser Trp
             20                  25                  30

Leu Ala Trp Tyr Gln Gln Lys Ser Gly Lys Ala Pro Lys Leu Leu Ile
         35                  40                  45

Tyr Gly Ala Ser Ser Leu Gln Ser Gly Val Pro Ser Arg Phe Ser Gly
 50                  55                  60

Ser Gly Ser Gly Thr Glu Phe Ile Leu Thr Ile Ser Ser Leu Gln Pro
 65              70                  75                  80

Glu Asp Phe Ala Thr Tyr Tyr Cys Gln Gln Ala Asn Ser Ile Pro Phe
                 85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 131
<211> LENGTH: 642
<212> TYPE: DNA
<213> ORGANISM: Homo Sapien

<400> SEQUENCE: 131
gacatccaga tgacccagtc tccatcttcc gtgtctgcat ctgtcggaga cagagtcacc    60
atcacttgtc gggcgagtca gggtgttagc agctggttag cctggtatca gcagaaatca   120
gggaaagccc ctaagctcct gatctatggt gcatccagtt tgcaaagtgg ggtcccatca   180
agattcagcg gcagtggatc tgggacagag ttcattctca ccatcagcag cctgcagcct   240
gaagattttg caacttacta ttgtcaacag gctaacagta tcccattcac tttcggccct   300
gggaccaaag tggatatcaa acgtacggtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg gacaacgccc tgcagtccgg caactcccag   480
gaatccgtga ccgagcagga ctccaaggac agcacctact ccctgtcctc caccctgacc   540
ctgtccaagg ccgactacga aagcacaag gtgtacgcct gcgaagtgac ccaccagggc   600
ctgtctagcc ccgtgaccaa gtctttcaac cggggcgagt gt                     642

<210> SEQ ID NO 132
<211> LENGTH: 8
<212> TYPE: PRT
<213> ORGANISM: Homo Sapien

<400> SEQUENCE: 132

Gly Phe Thr Phe Arg Ile Tyr Gly
1               5

<210> SEQ ID NO 133
<211> LENGTH: 8
<212> TYPE: PRT
<213> ORGANISM: Homo Sapien

<400> SEQUENCE: 133

Ile Trp Tyr Asp Gly Ser Asn Lys
1               5

<210> SEQ ID NO 134
<211> LENGTH: 11
<212> TYPE: PRT
<213> ORGANISM: Homo Sapien

<400> SEQUENCE: 134

Ala Arg Asp Met Asp Tyr Phe Gly Met Asp Val
1               5                   10

<210> SEQ ID NO 135
<211> LENGTH: 5
<212> TYPE: PRT
<213> ORGANISM: Homo Sapien

<400> SEQUENCE: 135

Ile Tyr Gly Met His
1               5

<210> SEQ ID NO 136
<211> LENGTH: 17
<212> TYPE: PRT
<213> ORGANISM: Homo Sapien

<400> SEQUENCE: 136

Val Ile Trp Tyr Asp Gly Ser Asn Lys Tyr Tyr Ala Asp Ser Val Lys
1               5                   10                  15

Gly

<210> SEQ ID NO 137
<211> LENGTH: 9
<212> TYPE: PRT
<213> ORGANISM: Homo Sapien

<400> SEQUENCE: 137

Asp Met Asp Tyr Phe Gly Met Asp Val
1               5

<210> SEQ ID NO 138
<211> LENGTH: 118
<212> TYPE: PRT
<213> ORGANISM: Homo Sapien

<400> SEQUENCE: 138

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Asp Tyr Phe Gly Met Asp Val Trp Gly Gln Gly Thr
            100                 105                 110

Thr Val Thr Val Ser Ser
        115

<210> SEQ ID NO 139
<211> LENGTH: 355
<212> TYPE: DNA
<213> ORGANISM: Homo Sapien

<400> SEQUENCE: 139
caggtgcagc tggtggagtc tgggggaggc gtggtccagc ctggagggtc cctgagactc     60
tcctgtgcag cgtctggatt caccttccgt atttatggca tgcactgggt ccgccaggct    120
ccaggcaagg ggctggagtg ggtggcagtt atatggtatg atggaagtaa taaatactat    180
gctgactccg tgaagggccg attcaccatc tccagagaca attccgacaa cacgctgtat    240
ctgcaaatga acagcctgag agccgaggac acggctgtgt attactgtgc gagagatatg    300
gactacttcg gtatggacgt ctggggccaa gggaccacgg tcaccgtctc ctcag        355

<210> SEQ ID NO 140

```
<211> LENGTH: 448
<212> TYPE: PRT
<213> ORGANISM: Homo Sapien

<400> SEQUENCE: 140

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Asp Tyr Phe Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
                    385                 390                 395                 400
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 141
<211> LENGTH: 1344
<212> TYPE: DNA
<213> ORGANISM: Homo Sapien

<400> SEQUENCE: 141

```
caggtgcagc tggtggagtc tgggggaggc gtggtccagc ctgggaggtc cctgagactc    60
tcctgtgcag cgtctggatt caccttccgt atttatggca tgcactgggt ccgccaggct   120
ccaggcaagg gctggagtg gtggcagtt atatggtatg atggaagtaa taaatactat    180
gctgactccg tgaagggccg attcaccatc tccagagaca attccgacaa cacgctgtat   240
ctgcaaatga acagcctgag agccgaggac acggctgtgt attactgtgc gagagatatg   300
gactacttcg gtatggacgt ctggggccaa gggaccacgg tcaccgtctc ctcagccagc   360
accaagggcc cctctgtgtt ccctctggcc cttccagca agtccacctc tggcggaaca   420
gccgctctgg gctgcctcgt gaaggactac ttccccgagc ctgtgaccgt gtcctggaac   480
tctggcgctc tgaccagcgg agtgcacacc ttccctgctg tgctgcagtc ctccggcctg   540
tactccctgt cctccgtcgt gaccgtgcct ccagctctc tgggcaccca gacctacatc   600
tgcaacgtga accacaagcc ctccaacacc aaggtggaca gaaggtggaa acccaagtcc   660
tgcgacaaga cccacacctg tcccccttgt cctgcccctg aactgctggg cggaccttcc   720
gtgttcctgt ccccccaaa gcccaaggac ccctgatga tctcccggac ccccgaagtg    780
acctgcgtgg tggtggatgt gtcccacgag accctgaagt gaagttcaa ttggtacgtg    840
gacggcgtgg aagtgcacaa cgccaagacc aagcctagag aggaacagta caactccacc    900
taccgggtgg tgtccgtgct gaccgtgctg caccaggatt ggctgaacgg caaagagtac    960
aagtgcaagg tgtccaacaa ggcccctgcct gcccccatcg aaaagaccat ctccaaggcc   1020
aagggccagc ccgggaacc ccaggtgtac acactgcccc ctagcaggga cgagctgacc    1080
aagaaccagg tgtccctgac ctgtctcgtg aaaggcttct acccctccga tatcgccgtg   1140
gaatgggagt ccaacggcca gcctgagaac aactacaaga ccaccccccc tgtgctggac   1200
tccgacggct cattcttcct gtacagcaag ctgacagtgg acaagtcccg gtggcagcag   1260
ggcaacgtgt tctcctgctc cgtgatgcac gaggccctgc acaaccacta cacccagaag   1320
tccctgtccc tgagccccgg caag                                          1344
```

<210> SEQ ID NO 142
<211> LENGTH: 6
<212> TYPE: PRT
<213> ORGANISM: Homo Sapien

<400> SEQUENCE: 142

```
Gln Gly Ile Arg Asn Asp
1               5
```

<210> SEQ ID NO 143
<211> LENGTH: 3

```
<212> TYPE: PRT
<213> ORGANISM: Homo Sapien

<400> SEQUENCE: 143

Ala Ala Ser
1

<210> SEQ ID NO 144
<211> LENGTH: 9
<212> TYPE: PRT
<213> ORGANISM: Homo Sapien

<400> SEQUENCE: 144

Leu Gln His Asn Ser Tyr Pro Arg Thr
1               5

<210> SEQ ID NO 145
<211> LENGTH: 11
<212> TYPE: PRT
<213> ORGANISM: Homo Sapien

<400> SEQUENCE: 145

Arg Ala Ser Gln Gly Ile Arg Asn Asp Leu Gly
1               5                   10

<210> SEQ ID NO 146
<211> LENGTH: 7
<212> TYPE: PRT
<213> ORGANISM: Homo Sapien

<400> SEQUENCE: 146

Ala Ala Ser Ser Leu Gln Ser
1               5

<210> SEQ ID NO 147
<211> LENGTH: 9
<212> TYPE: PRT
<213> ORGANISM: Homo Sapien

<400> SEQUENCE: 147

Leu Gln His Asn Ser Tyr Pro Arg Thr
1               5

<210> SEQ ID NO 148
<211> LENGTH: 107
<212> TYPE: PRT
<213> ORGANISM: Homo Sapien

<400> SEQUENCE: 148

Asp Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
```

<210> SEQ ID NO 149
<211> LENGTH: 322
<212> TYPE: DNA
<213> ORGANISM: Homo Sapien

<400> SEQUENCE: 149

```
gacctccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctcggac gttcggccaa     300
gggaccaagg tggaaatcaa ac                                              322
```

<210> SEQ ID NO 150
<211> LENGTH: 214
<212> TYPE: PRT
<213> ORGANISM: Homo Sapien

<400> SEQUENCE: 150

Asp Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 151
<211> LENGTH: 642
<212> TYPE: DNA
<213> ORGANISM: Homo Sapien

<400> SEQUENCE: 151

```
gacctccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctcggac gttcggccaa     300
gggaccaagg tggaaatcaa acgtacggtg gccgctccct ccgtgttcat cttcccacct     360
tccgacgagc agctgaagtc cggcaccgct tctgtcgtgt gcctgctgaa caacttctac     420
ccccgcgagg ccaaggtgca gtggaaggtg acaacgccc tgcagtccgg caactcccag     480
gaatccgtga ccgagcagga ctccaaggac agcacctact ccctgtcctc caccctgacc     540
ctgtccaagg ccgactacga aaagcacaag gtgtacgcct gcgaagtgac ccaccagggc     600
ctgtctagcc ccgtgaccaa gtctttcaac cggggcgagt gt                       642
```

```
<210> SEQ ID NO 152
<211> LENGTH: 9
<212> TYPE: PRT
<213> ORGANISM: Homo Sapien

<400> SEQUENCE: 152

Gly Gly Ser Ile Ser Ser Ser Asp Trp
1               5

<210> SEQ ID NO 153
<211> LENGTH: 7
<212> TYPE: PRT
<213> ORGANISM: Homo Sapien

<400> SEQUENCE: 153

Ile Phe His Ser Gly Asn Thr
1               5

<210> SEQ ID NO 154
<211> LENGTH: 8
<212> TYPE: PRT
<213> ORGANISM: Homo Sapien

<400> SEQUENCE: 154

Val Arg Asp Gly Ser Gly Ser Tyr
1               5

<210> SEQ ID NO 155
<211> LENGTH: 6
<212> TYPE: PRT
<213> ORGANISM: Homo Sapien

<400> SEQUENCE: 155

Ser Ser Asp Trp Trp Ser
1               5

<210> SEQ ID NO 156
<211> LENGTH: 16
<212> TYPE: PRT
<213> ORGANISM: Homo Sapien

<400> SEQUENCE: 156

Glu Ile Phe His Ser Gly Asn Thr Asn Tyr Asn Pro Ser Leu Lys Ser
1               5                   10                  15
```

```
<210> SEQ ID NO 157
<211> LENGTH: 6
<212> TYPE: PRT
<213> ORGANISM: Homo Sapien

<400> SEQUENCE: 157

Asp Gly Ser Gly Ser Tyr
1               5

<210> SEQ ID NO 158
<211> LENGTH: 115
<212> TYPE: PRT
<213> ORGANISM: Homo Sapien

<400> SEQUENCE: 158

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Pro Pro Gly Lys Gly Leu Glu Trp
        35                  40                  45

Ile Gly Glu Ile Phe His Ser Gly Asn Thr Asn Tyr Asn Pro Ser Leu
    50                  55                  60

Lys Ser Arg Val Thr Ile Ser Val Asp Lys Ser Lys Asn Gln Ile Ser
65                  70                  75                  80

Leu Arg Leu Asn Ser Val Thr Ala Ala Asp Thr Ala Val Tyr Tyr Cys
                85                  90                  95

Val Arg Asp Gly Ser Gly Ser Tyr Trp Gly Gln Gly Thr Leu Val Thr
            100                 105                 110

Val Ser Ser
        115

<210> SEQ ID NO 159
<211> LENGTH: 346
<212> TYPE: DNA
<213> ORGANISM: Homo Sapien

<400> SEQUENCE: 159
caggtgcagc tgcaggagtc gggcccagga ctggtgaagc cttcggggac cctgtccctc      60
acctgcgctg tctctggtgg ctccatcagc agtagtgact ggtggagttg ggtccgccag     120
cccccaggga aggggctgga gtggattggg gaaatctttc atagtgggaa caccaactac     180
aacccgtccc tcaagagtcg agtcaccata tcagtagaca gtccaagaa ccagatctcc      240 ctgaggctga actctgtgac cgccgcggac acggccgtgt attactgtgt gagagatggt     300
tcggggagtt actggggcca gggaaccctg gtcaccgtct cctcag                    346

<210> SEQ ID NO 160
<211> LENGTH: 445
<212> TYPE: PRT
<213> ORGANISM: Homo Sapien

<400> SEQUENCE: 160

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Pro Pro Gly Lys Gly Leu Glu Trp
        35                  40                  45
```

```
Ile Gly Glu Ile Phe His Ser Gly Asn Thr Asn Tyr Asn Pro Ser Leu
 50                  55                  60
Lys Ser Arg Val Thr Ile Ser Val Asp Lys Ser Lys Asn Gln Ile Ser
 65                  70                  75                  80
Leu Arg Leu Asn Ser Val Thr Ala Ala Asp Thr Ala Val Tyr Tyr Cys
                 85                  90                  95
Val Arg Asp Gly Ser Gly Ser Tyr Trp Gly Gln Gly Thr Leu Val Thr
            100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 161
<211> LENGTH: 1335
<212> TYPE: DNA
```

-continued

<213> ORGANISM: Homo Sapien

<400> SEQUENCE: 161

```
caggtgcagc tgcaggagtc gggcccagga ctggtgaagc cttcgggac cctgtccctc        60
acctgcgctg tctctggtgg ctccatcagc agtagtgact ggtggagttg ggtccgccag      120
cccccaggga aggggctgga gtggattggg gaaatctttc atagtgggaa caccaactac      180
aacccgtccc tcaagagtcg agtcaccata tcagtagaca agtccaagaa ccagatctcc      240
ctgaggctga actctgtgac cgccgcggac acggccgtgt attactgtgt gagagatggt      300
tcggggagtt actggggcca gggaaccctg gtcaccgtct cctcagccag caccaagggc      360
ccctctgtgt tccctctggc cccttccagc aagtccacct ctggcggaac agccgctctg      420
ggctgcctcg tgaaggacta cttccccgag cctgtgaccg tgtcctggaa ctctggcgct      480
ctgaccagcg gagtgcacac cttccctgct gtgctgcagt cctccggcct gtactccctg      540
tcctccgtcg tgaccgtgcc ttccagctct ctgggcaccc agacctacat ctgcaacgtg      600
aaccacaagc cctccaacac caaggtggac aagaaggtgg aacccaagtc ctgcgacaag      660
acccacacct gtccccttg tcctgcccct gaactgctgg gcggaccttc cgtgttcctg      720
ttccccccaa agcccaagga cacctgatg atctcccgga cccccgaagt gacctgcgtg      780
gtggtggatg tgtcccacga ggaccctgaa gtgaagttca attggtacgt ggacggcgtg      840
gaagtgcaca cgccaagac caagcctaga gaggaacagt acaactccac ctaccgggtg      900
gtgtccgtgc tgaccgtgct gcaccaggat tggctgaacg gcaaagagta caagtgcaag      960
gtgtccaaca aggccctgcc tgcccccatc gaaaagacca tctccaaggc caagggccag     1020
cccgggaac cccaggtgta cacactgccc ctagcaggg acgagctgac caagaaccag      1080
gtgtccctga cctgtctcgt gaaaggcttc taccctccg atatcgccgt ggaatgggag      1140
tccaacggcc agcctgagaa caactacaag accacccccc ctgtgctgga ctccgacggc     1200
tcattcttcc tgtacagcaa gctgacagtg gacaagtccc ggtggcagca gggcaacgtg     1260
ttctcctgct ccgtgatgca cgaggccctg cacaaccact acacccagaa gtccctgtcc     1320
ctgagccccg gcaag                                                      1335
```

<210> SEQ ID NO 162
<211> LENGTH: 12
<212> TYPE: PRT
<213> ORGANISM: Homo Sapien

<400> SEQUENCE: 162

Gln Ser Val Leu Tyr Ser Ser Asn Asn Lys Asn Tyr
1               5                   10

<210> SEQ ID NO 163
<211> LENGTH: 3
<212> TYPE: PRT
<213> ORGANISM: Homo Sapien

<400> SEQUENCE: 163

Trp Ala Ser
1

<210> SEQ ID NO 164
<211> LENGTH: 8
<212> TYPE: PRT
<213> ORGANISM: Homo Sapien

<400> SEQUENCE: 164

Gln Gln Tyr Tyr Ser Thr Arg Ser
1               5

<210> SEQ ID NO 165
<211> LENGTH: 17
<212> TYPE: PRT
<213> ORGANISM: Homo Sapien

<400> SEQUENCE: 165

Lys Ser Ser Gln Ser Val Leu Tyr Ser Ser Asn Asn Lys Asn Tyr Leu
1               5                   10                  15

Ala

<210> SEQ ID NO 166
<211> LENGTH: 7
<212> TYPE: PRT
<213> ORGANISM: Homo Sapien

<400> SEQUENCE: 166

Trp Ala Ser Thr Arg Glu Ser
1               5

<210> SEQ ID NO 167
<211> LENGTH: 8
<212> TYPE: PRT
<213> ORGANISM: Homo Sapien

<400> SEQUENCE: 167

Gln Gln Tyr Tyr Ser Thr Arg Ser
1               5

<210> SEQ ID NO 168
<211> LENGTH: 112
<212> TYPE: PRT
<213> ORGANISM: Homo Sapien

<400> SEQUENCE: 168

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Arg Ser Phe Gly Gln Gly Thr Lys Leu Glu Ile Lys
                100                 105                 110

<210> SEQ ID NO 169
<211> LENGTH: 337
<212> TYPE: DNA
<213> ORGANISM: Homo Sapien

<400> SEQUENCE: 169
gacatcgtga tgacccagtc tccagactcc ctggctgtgt ctctgggcga gagggccacc      60
atcaactgca agtccagcca gagtgtttta tacagctcca acaataagaa ctacttagct     120

| | |
|---|---:|
| tggtaccagc agaaaccagg acagcctcct aaactgctca tttactgggc atctacccgg | 180 |
| gaatccgggg tccctgaccg attcagtggc agcgggtctg ggacagattt cactctcacc | 240 |
| atcagcagcc tgcaggctga agatgtggca gtttattact gtcagcaata ttatagtact | 300 |
| cgcagttttg gccaggggac caagctggag atcaaac | 337 |

<210> SEQ ID NO 170
<211> LENGTH: 219
<212> TYPE: PRT
<213> ORGANISM: Homo Sapien

<400> SEQUENCE: 170

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Arg Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 171
<211> LENGTH: 657
<212> TYPE: DNA
<213> ORGANISM: Homo Sapien

<400> SEQUENCE: 171

| | |
|---|---:|
| gacatcgtga tgacccagtc tccagactcc ctggctgtgt ctctgggcga gagggccacc | 60 |
| atcaactgca agtccagcca gagtgtttta tacagctcca acaataagaa ctacttagct | 120 |
| tggtaccagc agaaaccagg acagcctcct aaactgctca tttactgggc atctacccgg | 180 |
| gaatccgggg tccctgaccg attcagtggc agcgggtctg ggacagattt cactctcacc | 240 |
| atcagcagcc tgcaggctga agatgtggca gtttattact gtcagcaata ttatagtact | 300 |
| cgcagttttg gccaggggac caagctggag atcaaacgta cggtggccgc tcccctccgtg | 360 |

```
ttcatcttcc caccttccga cgagcagctg aagtccggca ccgcttctgt cgtgtgcctg    420
ctgaacaact tctaccccg cgaggccaag gtgcagtgga aggtggacaa cgccctgcag     480
tccggcaact cccaggaatc cgtgaccgag caggactcca aggacagcac ctactccctg    540
tcctccaccc tgaccctgtc caaggccgac tacgagaagc acaaggtgta cgcctgcgaa    600
gtgacccacc agggcctgtc tagccccgtg accaagtctt tcaaccgggg cgagtgt       657
```

<210> SEQ ID NO 172
<211> LENGTH: 10
<212> TYPE: PRT
<213> ORGANISM: Homo Sapien

<400> SEQUENCE: 172

Gly Gly Ser Ile Ser Ser Ser Ser Tyr Tyr
1               5                   10

<210> SEQ ID NO 173
<211> LENGTH: 7
<212> TYPE: PRT
<213> ORGANISM: Homo Sapien

<400> SEQUENCE: 173

Ile Tyr Ser Thr Gly Tyr Thr
1               5

<210> SEQ ID NO 174
<211> LENGTH: 13
<212> TYPE: PRT
<213> ORGANISM: Homo Sapien

<400> SEQUENCE: 174

Ala Ile Ser Thr Ala Ala Gly Pro Glu Tyr Phe His Arg
1               5                   10

<210> SEQ ID NO 175
<211> LENGTH: 7
<212> TYPE: PRT
<213> ORGANISM: Homo Sapien

<400> SEQUENCE: 175

Ser Ser Ser Tyr Tyr Cys Gly
1               5

<210> SEQ ID NO 176
<211> LENGTH: 16
<212> TYPE: PRT
<213> ORGANISM: Homo Sapien

<400> SEQUENCE: 176

Ser Ile Tyr Ser Thr Gly Tyr Thr Tyr Tyr Asn Pro Ser Leu Lys Ser
1               5                   10                  15

<210> SEQ ID NO 177
<211> LENGTH: 11
<212> TYPE: PRT
<213> ORGANISM: Homo Sapien

<400> SEQUENCE: 177

Ser Thr Ala Ala Gly Pro Glu Tyr Phe His Arg
1               5                   10

<210> SEQ ID NO 178
<211> LENGTH: 120

```
<212> TYPE: PRT
<213> ORGANISM: Homo Sapien

<400> SEQUENCE: 178

Gln Leu Gln Glu Ser Gly Pro Gly Leu Val Lys Pro Ser Glu Thr Leu
1               5                   10                  15

Ser Leu Thr Cys Thr Val Ser Gly Gly Ser Ile Ser Ser Ser Ser Tyr
            20                  25                  30

Tyr Cys Gly Trp Ile Arg Gln Pro Pro Gly Lys Gly Leu Asp Trp Ile
        35                  40                  45

Gly Ser Ile Tyr Ser Thr Gly Tyr Thr Tyr Tyr Asn Pro Ser Leu Lys
    50                  55                  60

Ser Arg Val Thr Ile Ser Ile Asp Thr Ser Lys Asn Gln Phe Ser Cys
65                  70                  75                  80

Leu Ile Leu Thr Ser Val Thr Ala Ala Asp Thr Ala Val Tyr Tyr Cys
                85                  90                  95

Ala Ile Ser Thr Ala Ala Gly Pro Glu Tyr Phe His Arg Trp Gly Gln
            100                 105                 110

Gly Thr Leu Val Thr Val Ser Ser
        115                 120

<210> SEQ ID NO 179
<211> LENGTH: 361
<212> TYPE: DNA
<213> ORGANISM: Homo Sapien

<400> SEQUENCE: 179
cagctgcagg agtcgggccc aggcctggtg aagccttcgg agaccctgtc cctcacctgc      60
actgtctctg gtggctccat cagcagtagt agttattact gcggctggat ccgccagccc     120
cctgggaagg ggctggactg gattgggagt atctattcta ctgggtacac ctactacaac     180
ccgtccctca agagtcgagt caccatttcc atagacacgt ccaagaacca gttctcatgc     240
ctgatactga cctctgtgac cgccgcagac acggctgtgt attactgtgc gataagtaca     300
gcagctggcc ctgaatactt ccatcgctgg ggccagggca ccctggtcac cgtctcctca     360
g                                                                     361

<210> SEQ ID NO 180
<211> LENGTH: 450
<212> TYPE: PRT
<213> ORGANISM: Homo Sapien

<400> SEQUENCE: 180

Gln Leu Gln Glu Ser Gly Pro Gly Leu Val Lys Pro Ser Glu Thr Leu
1               5                   10                  15

Ser Leu Thr Cys Thr Val Ser Gly Gly Ser Ile Ser Ser Ser Ser Tyr
            20                  25                  30

Tyr Cys Gly Trp Ile Arg Gln Pro Pro Gly Lys Gly Leu Asp Trp Ile
        35                  40                  45

Gly Ser Ile Tyr Ser Thr Gly Tyr Thr Tyr Tyr Asn Pro Ser Leu Lys
    50                  55                  60

Ser Arg Val Thr Ile Ser Ile Asp Thr Ser Lys Asn Gln Phe Ser Cys
65                  70                  75                  80

Leu Ile Leu Thr Ser Val Thr Ala Ala Asp Thr Ala Val Tyr Tyr Cys
                85                  90                  95

Ala Ile Ser Thr Ala Ala Gly Pro Glu Tyr Phe His Arg Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 181
<211> LENGTH: 1350
<212> TYPE: DNA
<213> ORGANISM: Homo Sapien

<400> SEQUENCE: 181
cagctgcagg agtcgggccc aggcctggtg aagccttcgg agaccctgtc cctcacctgc      60
actgtctctg gtggctccat cagcagtagt agttattact gcggctggat ccgccagccc     120

```
cctgggaagg ggctggactg gattgggagt atctattcta ctgggtacac ctactacaac      180
ccgtccctca agagtcgagt caccatttcc atagacacgt ccaagaacca gttctcatgc      240
ctgatactga cctctgtgac cgccgcagac acggctgtgt attactgtgc gataagtaca      300
gcagctggcc ctgaatactt ccatcgctgg ggcagggca cctggtcac cgtctcctca       360 gccagcacca agggcccctc tgtgttccct ctggccccctt ccagcaagtc cacctctggc     420
ggaacagccg ctctgggctg cctcgtgaag gactacttcc ccgagcctgt gaccgtgtcc      480
tggaactctg gcgctctgac cagcggagtg cacaccttcc ctgctgtgct gcagtcctcc     540
ggcctgtact ccctgtcctc cgtcgtgacc gtgccttcca gctctctggg cacccagacc     600
tacatctgca acgtgaacca caagccctcc aacaccaagg tggacaagaa ggtggaaccc     660
aagtcctgcg acaagaccca cacctgtccc ccttgtcctg ccctgaact gctgggcgga     720 ccttccgtgt tcctgttccc cccaaagccc aaggacaccc tgatgatctc ccggacccc     780 gaagtgacct gcgtggtggt ggatgtgtcc cacgaggacc ctgaagtgaa gttcaattgg     840
tacgtggacg gcgtggaagt gcacaacgcc aagaccaagc ctagagagga acagtacaac     900
tccacctacc gggtggtgtc cgtgctgacc gtgctgcacc aggattggct gaacggcaaa     960
gagtacaagt gcaaggtgtc caacaaggcc ctgcctgccc ccatcgaaaa gaccatctcc    1020
aaggccaagg gccagccccg ggaacccag gtgtacacac tgccccctag cagggacgag    1080
ctgaccaaga accaggtgtc cctgacctgt ctcgtgaaag gcttctaccc ctccgatatc    1140
gccgtggaat gggagtccaa cggccagcct gagaacaact acaagaccac ccccctgtg    1200 ctggactccg acggctcatt cttcctgtac agcaagctga cagtggacaa gtcccggtgg    1260
cagcagggca acgtgttctc ctgctccgtg atgcacgagg ccctgcacaa ccactacacc    1320
cagaagtccc tgtccctgag ccccggcaag                                     1350
```

<210> SEQ ID NO 182
<211> LENGTH: 12
<212> TYPE: PRT
<213> ORGANISM: Homo Sapien

<400> SEQUENCE: 182

Gln Ser Val Leu Tyr Ser Ser Asn Ser Lys Asn Phe
1               5                   10

<210> SEQ ID NO 183
<211> LENGTH: 3
<212> TYPE: PRT
<213> ORGANISM: Homo Sapien

<400> SEQUENCE: 183

Trp Ala Ser
1

<210> SEQ ID NO 184
<211> LENGTH: 9
<212> TYPE: PRT
<213> ORGANISM: Homo Sapien

<400> SEQUENCE: 184

Gln Gln Tyr Tyr Ser Thr Pro Arg Thr
1               5

<210> SEQ ID NO 185
<211> LENGTH: 17
<212> TYPE: PRT

<213> ORGANISM: Homo Sapien

<400> SEQUENCE: 185

Lys Ser Ser Gln Ser Val Leu Tyr Ser Ser Asn Ser Lys Asn Phe Leu
1               5                   10                  15

Ala

<210> SEQ ID NO 186
<211> LENGTH: 7
<212> TYPE: PRT
<213> ORGANISM: Homo Sapien

<400> SEQUENCE: 186

Trp Ala Ser Thr Arg Gly Ser
1               5

<210> SEQ ID NO 187
<211> LENGTH: 9
<212> TYPE: PRT
<213> ORGANISM: Homo Sapien

<400> SEQUENCE: 187

Gln Gln Tyr Tyr Ser Thr Pro Arg Thr
1               5

<210> SEQ ID NO 188
<211> LENGTH: 113
<212> TYPE: PRT
<213> ORGANISM: Homo Sapien

<400> SEQUENCE: 188

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Ser Lys Asn Phe Leu Ala Trp Tyr Gln Gln Lys Pro Gly Gln
            35                  40                  45

Pro Pro Lys Leu Phe Ile Tyr Trp Ala Ser Thr Arg Gly Ser Gly Val
    50                  55                  60

Pro Asp Arg Ile Ser Gly Ser Gly Ser Gly Thr Asp Phe Asn Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 189
<211> LENGTH: 340
<212> TYPE: DNA
<213> ORGANISM: Homo Sapien

<400> SEQUENCE: 189
gacatcgtga tgacccagtc tccagactcc ctggctgtgt ctctgggcga gagggccacc      60
atcaactgca agtccagcca gagtgtttta tacagctcca acagtaagaa cttcttagct     120
tggtaccagc agaaaccggg acagcctcct aagctgttca tttactgggc atctacccgg     180
ggatccgggg tccctgaccg aatcagtggc agcgggtctg ggacagattt caatctcacc     240
atcagcagcc tgcaggctga agatgtggca gtttattact gtcaacaata ttatagtact     300

```
cctcggacgt tcggccaagg gaccaaggtg gagatcaaac                          340
```

<210> SEQ ID NO 190
<211> LENGTH: 220
<212> TYPE: PRT
<213> ORGANISM: Homo Sapien

<400> SEQUENCE: 190

| Asp | Ile | Val | Met | Thr | Gln | Ser | Pro | Asp | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Glu | Arg | Ala | Thr | Ile | Asn | Cys | Lys | Ser | Ser | Gln | Ser | Val | Leu | Tyr | Ser |
|---|---|---|---|---|---|---|---|---|---|---|---|---|---|---|---|
| | | | 20 | | | | | 25 | | | | | 30 | | |

| Ser | Asn | Ser | Lys | Asn | Phe | Leu | Ala | Trp | Tyr | Gln | Gln | Lys | Pro | Gly | Gln |
|---|---|---|---|---|---|---|---|---|---|---|---|---|---|---|---|
| | | 35 | | | | | 40 | | | | | 45 | | | |

| Pro | Pro | Lys | Leu | Phe | Ile | Tyr | Trp | Ala | Ser | Thr | Arg | Gly | Ser | Gly | Val |
|---|---|---|---|---|---|---|---|---|---|---|---|---|---|---|---|
| | 50 | | | | | 55 | | | | | 60 | | | | |

| Pro | Asp | Arg | Ile | Ser | Gly | Ser | Gly | Ser | Gly | Thr | Asp | Phe | Asn | Leu | Thr |
|---|---|---|---|---|---|---|---|---|---|---|---|---|---|---|---|
| 65 | | | | | 70 | | | | | 75 | | | | | 80 |

| Ile | Ser | Ser | Leu | Gln | Ala | Glu | Asp | Val | Ala | Val | Tyr | Tyr | Cys | Gln | Gln |
|---|---|---|---|---|---|---|---|---|---|---|---|---|---|---|---|
| | | | | 85 | | | | | 90 | | | | | 95 | |

| Tyr | Tyr | Ser | Thr | Pro | Arg | Thr | Phe | Gly | Gln | Gly | Thr | Lys | Val | Glu | Ile |
|---|---|---|---|---|---|---|---|---|---|---|---|---|---|---|---|
| | | | 100 | | | | | 105 | | | | | 110 | | |

| Lys | Arg | Thr | Val | Ala | Ala | Pro | Ser | Val | Phe | Ile | Phe | Pro | Pro | Ser | Asp |
|---|---|---|---|---|---|---|---|---|---|---|---|---|---|---|---|
| | | 115 | | | | | 120 | | | | | 125 | | | |

| Glu | Gln | Leu | Lys | Ser | Gly | Thr | Ala | Ser | Val | Val | Cys | Leu | Leu | Asn | Asn |
|---|---|---|---|---|---|---|---|---|---|---|---|---|---|---|---|
| | 130 | | | | | 135 | | | | | 140 | | | | |

| Phe | Tyr | Pro | Arg | Glu | Ala | Lys | Val | Gln | Trp | Lys | Val | Asp | Asn | Ala | Leu |
|---|---|---|---|---|---|---|---|---|---|---|---|---|---|---|---|
| 145 | | | | | 150 | | | | | 155 | | | | | 160 |

| Gln | Ser | Gly | Asn | Ser | Gln | Glu | Ser | Val | Thr | Glu | Gln | Asp | Ser | Lys | Asp |
|---|---|---|---|---|---|---|---|---|---|---|---|---|---|---|---|
| | | | | 165 | | | | | 170 | | | | | 175 | |

| Ser | Thr | Tyr | Ser | Leu | Ser | Ser | Thr | Leu | Thr | Leu | Ser | Lys | Ala | Asp | Tyr |
|---|---|---|---|---|---|---|---|---|---|---|---|---|---|---|---|
| | | | 180 | | | | | 185 | | | | | 190 | | |

| Glu | Lys | His | Lys | Val | Tyr | Ala | Cys | Glu | Val | Thr | His | Gln | Gly | Leu | Ser |
|---|---|---|---|---|---|---|---|---|---|---|---|---|---|---|---|
| | | | 195 | | | | | 200 | | | | | 205 | | |

| Ser | Pro | Val | Thr | Lys | Ser | Phe | Asn | Arg | Gly | Glu | Cys |
|---|---|---|---|---|---|---|---|---|---|---|---|
| | 210 | | | | | 215 | | | | | 220 |

<210> SEQ ID NO 191
<211> LENGTH: 660
<212> TYPE: DNA
<213> ORGANISM: Homo Sapien

<400> SEQUENCE: 191

```
gacatcgtga tgacccagtc tccagactcc ctggctgtgt ctctgggcga gagggccacc      60
atcaactgca agtccagcca gagtgtttta tacagctcca acagtaagaa cttcttagct     120
tggtaccagc agaaaccggg acagcctcct aagctgttca tttactgggc atctacccgg     180
ggatccgggg tccctgaccg aatcagtggc agcgggtctg gacagattt caatctcacc      240
atcagcagcc tgcaggctga agatgtggca gtttattact gtcaacaata ttatagtact     300
cctcggacgt tcggccaagg gaccaaggtg gagatcaaac gtacggtggc cgctcccctcc    360
gtgttcatct tcccaccttc cgacgagcag ctgaagtccg gcaccgcttc tgtcgtgtgc     420
ctgctgaaca acttctaccc ccgcgaggcc aaggtgcagt ggaaggtgga caacgccctg     480
cagtccggca actcccagga atccgtgacc gagcaggact ccaaggacag cacctactcc     540
```

-continued

```
ctgtcctcca ccctgaccct gtccaaggcc gactacgaga agcacaaggt gtacgcctgc    600
gaagtgaccc accagggcct gtctagcccc gtgaccaagt ctttcaaccg gggcgagtgt    660
```

<210> SEQ ID NO 192
<211> LENGTH: 981
<212> TYPE: DNA
<213> ORGANISM: Homo Sapien

<400> SEQUENCE: 192

```
gcttccacca agggcccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc atcatgccca gcacctgagt tcctgggggg accatcagtc    360
ttcctgttcc cccaaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a                                              981
```

<210> SEQ ID NO 193
<211> LENGTH: 327
<212> TYPE: PRT
<213> ORGANISM: Homo Sapien

<400> SEQUENCE: 193

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
```

```
                130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 194
<211> LENGTH: 981
<212> TYPE: DNA
<213> ORGANISM: Homo Sapien

<400> SEQUENCE: 194
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc cccgtgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcgtgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac gcagaagagc     960
ctctccctgt ctctgggtaa a                                               981
```

<210> SEQ ID NO 195
<211> LENGTH: 327
<212> TYPE: PRT
<213> ORGANISM: Homo Sapien

<400> SEQUENCE: 195

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 196
<211> LENGTH: 981
<212> TYPE: DNA
<213> ORGANISM: Homo Sapien

<400> SEQUENCE: 196

```
gcttccacca agggcccatc cgtcttcccc ctggcgccct gctccaggag caccctccgag    60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaagctc accgtggaca agagcaggtg gcaggagggg    900
aacgtcttct catgctccgt gatgcatgag gctctgcaca accactacac gcagaagagc    960
ctctccctgt ctctgggtaa a                                              981

<210> SEQ ID NO 197
<211> LENGTH: 327
<212> TYPE: PRT
<213> ORGANISM: Homo Sapien

<400> SEQUENCE: 197

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 198
<211> LENGTH: 981
<212> TYPE: DNA
<213> ORGANISM: Homo Sapien

<400> SEQUENCE: 198
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctgaat tgaggggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggatcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa a                                               981

<210> SEQ ID NO 199
<211> LENGTH: 327
<212> TYPE: PRT
<213> ORGANISM: Homo Sapien

<400> SEQUENCE: 199

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
             100                 105                 110

Glu Phe Glu Gly Gly Pro Ser Val Phe Leu Phe Pro Pro Lys Pro Lys
         115                 120                 125

Asp Thr Leu Met Ile Ser Arg Thr Pro Glu Val Thr Cys Val Val Val
     130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                 165                 170                 175

Asn Ser Thr Tyr Arg Val Val Ser Val Leu Thr Val Leu His Gln Asp
             180                 185                 190

Trp Leu Asn Gly Lys Glu Tyr Lys Cys Lys Val Ser Asn Lys Gly Leu
         195                 200                 205

Pro Ser Ser Ile Glu Lys Thr Ile Ser Lys Ala Lys Gly Gln Pro Arg
     210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                 245                 250                 255

Ile Ala Val Glu Trp Glu Ser Asn Gly Gln Pro Glu Asn Asn Tyr Lys
             260                 265                 270

Thr Thr Pro Pro Val Leu Asp Ser Asp Gly Ser Phe Phe Leu Tyr Ser
         275                 280                 285

Arg Leu Thr Val Asp Lys Ser Arg Trp Gln Glu Gly Asn Val Phe Ser
     290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 200
<211> LENGTH: 981
<212> TYPE: DNA
<213> ORGANISM: Homo Sapien

<400> SEQUENCE: 200
gcctccacca agggacctag cgtgttccct ctcgcccct  gttccaggtc cacaagcgag      60
tccaccgctg ccctcggctg tctggtgaaa gactactttc cgagcccgt  gaccgtctcc    120 tggaatagcg gagccctgac ctccggcgtg cacacatttc ccgccgtgct gcagagcagc    180
ggactgtata gcctgagcag cgtggtgacc gtgcccagct ccagcctcgg caccaaaacc    240
tacacctgca acgtggacca caagcccctcc aacaccaagg tggacaagcg ggtggagagc    300
```

| | |
|---|---|
| aagtacggcc cccccttgccc tccttgtcct gccccctgagt tcgagggagg accctccgtg | 360 |
| ttcctgtttc cccccaaacc caaggacacc ctgatgatct cccggacacc cgaggtgacc | 420 |
| tgtgtggtcg tggacgtcag ccaggaggac cccgaggtgc agttcaactg gtatgtggac | 480 |
| ggcgtggagg tgcacaatgc caaaaccaag cccagggagg agcagttcaa ttccacctac | 540 |
| agggtggtga gcgtgctgac cgtcctgcat caggattggc tgaacggcaa ggagtacaag | 600 |
| tgcaaggtgt ccaacaaggg actgcccagc tccatcgaga agaccatcag caaggctaag | 660 |
| ggccagccga gggagcccca ggtgtatacc ctgcctccta gccaggaaga gatgaccaag | 720 |
| aaccaagtgt ccctgacctg cctggtgaag ggattctacc cctccgacat cgccgtggag | 780 |
| tgggagagca atggccagcc cgagaacaac tacaaaacaa cccctcccgt gctcgatagc | 840 |
| gacggcagct tctttctcta cagccggctg acagtggaca gagcaggtg gcaggagggc | 900 |
| aacgtgttct cctgttccgt gatgcacgag gccctgcaca tcactacac ccagaagagc | 960 |
| ctctcccctgt ccctgggcaa g | 981 |

<210> SEQ ID NO 201
<211> LENGTH: 981
<212> TYPE: DNA
<213> ORGANISM: Homo Sapien

<400> SEQUENCE: 201

| | |
|---|---|
| gccagcacca agggcccttc cgtgttcccc ctggcccctt gcagcaggag cacctccgaa | 60 |
| tccacagctg ccctgggctg tctggtgaag gactactttc ccgagcccgt gaccgtgagc | 120 |
| tggaacagcg gcgctctgac atccggcgtc cacacctttc ctgccgtcct gcagtcctcc | 180 |
| ggcctctact ccctgtcctc cgtggtgacc gtgcctagct cctcccctcgg caccaagacc | 240 |
| tacacctgta acgtggacca caaaccctcc aacaccaagg tggacaaacg ggtcgagagc | 300 |
| aagtacggcc ctccctgccc tccttgtcct gccccgagt tcgaaggcgg acccagcgtg | 360 |
| ttcctgttcc ctcctaagcc caaggacacc ctcatgatca gccggacacc cgaggtgacc | 420 |
| tgcgtggtgg tggatgtgag ccaggaggac cctgaggtcc agttcaactg gtatgtggat | 480 |
| ggcgtggagg tgcacaacgc caagacaaag ccccgggaag agcagttcaa ctccacctac | 540 |
| agggtggtca gcgtgctgac cgtgctgcat caggactggc tgaacggcaa ggagtacaag | 600 |
| tgcaaggtca gcaataaggg actgcccagc agcatcgaga agaccatctc caaggctaaa | 660 |
| ggccagcccc gggaacctca ggtgtacacc ctgcctccca gccaggagga gatgaccaag | 720 |
| aaccaggtga gcctgacctg cctggtgaag ggattctacc cttccgacat cgccgtggag | 780 |
| tgggagtcca acggccagcc cgagaacaat tataagacca cccctcccgt cctcgacagc | 840 |
| gacggatcct tctttctgta ctccaggctg accgtggata gtccaggtg gcaggaaggc | 900 |
| aacgtgttca gctgctccgt gatgcacgag gccctgcaca tcactacac ccagaagtcc | 960 |
| ctgagcctgt ccctgggaaa g | 981 |

<210> SEQ ID NO 202
<211> LENGTH: 981
<212> TYPE: DNA
<213> ORGANISM: Homo Sapien

<400> SEQUENCE: 202

| | |
|---|---|
| gcctccacca agggcccatc cgtcttcccc ctggcgccct gctccaggag cacctccgag | 60 |
| agcacggccg ccctgggctg cctggtcaag gactacttcc ccgaaccagt gacggtgtcg | 120 |
| tggaactcag gcgccctgac cagcggcgtg cacacctcc cggctgtcct acagtcctca | 180 |

```
ggactctact ccctcagcag cgtggtgacc gtgccctcca gcagcttggg cacgaagacc      240
tacacctgca acgtagatca caagcccagc aacaccaagg tggacaagag agttgagtcc      300
aaatatggtc ccccatgccc accatgccca gcgcctccag ttgcgggggg accatcagtc      360
ttcctgttcc ccccaaaacc caaggacact ctcatgatct cccggacccc tgaggtcacg      420
tgcgtggtgg tggacgtgag ccaggaagac cccgaggtcc agttcaactg gtacgtggat      480
ggcgtggagg tgcataatgc caagacaaag ccgcgggagg agcagttcaa cagcacgtac      540
cgtgtggtca gcgtcctcac cgtcctgcac caggactggc tgaacggcaa ggagtacaag      600
tgcaaggtct ccaacaaagg cctcccgtca tcgatcgaga aaaccatctc caaagccaaa      660
gggcagcccc gagagccaca ggtgtacacc ctgcccccat cccaggagga gatgaccaag      720
aaccaggtca gcctgacctg cctggtcaaa ggcttctacc ccagcgacat cgccgtggag      780
tgggagagca atgggcagcc ggagaacaac tacaagacca cgcctcccgt gctggactcc      840
gacggatcct tcttcctcta cagcaggcta accgtggaca agagcaggtg gcaggagggg      900
aatgtcttct catgctccgt gatgcatgag gctctgcaca accactacac acagaagagc      960
ctctccctgt ctctgggtaa a                                               981
```

<210> SEQ ID NO 203
<211> LENGTH: 327
<212> TYPE: PRT
<213> ORGANISM: Homo Sapien

<400> SEQUENCE: 203

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

-continued

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 204
<211> LENGTH: 990
<212> TYPE: DNA
<213> ORGANISM: Homo Sapien

<400> SEQUENCE: 204

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agtggagccc     300
aaatcttgtg acaaaactca cacatgccca ccgtgcccag cacctgaact cgcggggggca     360
ccgtcagtct tcctcttccc cccaaaaccc aaggacaccc tcatgatctc ccggaccccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990
```

<210> SEQ ID NO 205
<211> LENGTH: 330
<212> TYPE: PRT
<213> ORGANISM: Homo Sapien

<400> SEQUENCE: 205

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 206
<211> LENGTH: 321
<212> TYPE: DNA
<213> ORGANISM: Homo Sapien

<400> SEQUENCE: 206
cgtacggtgg ccgctccctc cgtgttcatc ttcccacctt ccgacgagca gctgaagtcc    60
ggcaccgctt ctgtcgtgtg cctgctgaac aacttctacc ccgcgaggc caaggtgcag   120 tggaaggtgg acaacgccct gcagtccggc aactcccagg aatccgtgac cgagcaggac   180
tccaaggaca gcacctactc cctgtcctcc accctgaccc tgtccaaggc cgactacgag   240
aagcacaagg tgtacgcctg cgaagtgacc caccagggcc tgtctagccc cgtgaccaag   300
tctttcaacc ggggcgagtg t                                            321

<210> SEQ ID NO 207
<211> LENGTH: 107
<212> TYPE: PRT
```

<213> ORGANISM: Homo Sapien

<400> SEQUENCE: 207

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 208
<211> LENGTH: 321
<212> TYPE: DNA
<213> ORGANISM: Homo Sapien

<400> SEQUENCE: 208
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggag    180
agcaaggaca gcacctacag cctcagcagc accctgacgc tgagcaaagc agactacgag    240
aaacacaaag tctacgccgg cgaagtcacc catcagggcc tgagctcgcc cgtcacaaag    300
agcttcaaca ggggagagtg t                                              321

<210> SEQ ID NO 209
<211> LENGTH: 107
<212> TYPE: PRT
<213> ORGANISM: Homo Sapien

<400> SEQUENCE: 209

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 210
<211> LENGTH: 321
<212> TYPE: DNA
<213> ORGANISM: Homo Sapien

<400> SEQUENCE: 210

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
cggaaggtgg ataacgccct ccaatcgggt aactcccagg agagtgtcac agagcaggag     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                321
```

<210> SEQ ID NO 211
<211> LENGTH: 107
<212> TYPE: PRT
<213> ORGANISM: Homo Sapien

<400> SEQUENCE: 211

```
Arg Thr Val Ala Ala Pro Ser Val Phe Ile Phe Pro Pro Ser Asp Glu
 1               5                  10                  15
Gln Leu Lys Ser Gly Thr Ala Ser Val Val Cys Leu Leu Asn Asn Phe
            20                  25                  30
Tyr Pro Arg Glu Ala Lys Val Gln Arg Lys Val Asp Asn Ala Leu Gln
        35                  40                  45
Ser Gly Asn Ser Gln Glu Ser Val Thr Glu Gln Glu Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 212
<211> LENGTH: 321
<212> TYPE: DNA
<213> ORGANISM: Homo Sapien

<400> SEQUENCE: 212

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaac tctacgcctg cgaagtcacc catcagggcc tgagctcgcc cgtcacaaag     300
agcttcaaca ggggagagtg t                                                321
```

<210> SEQ ID NO 213
<211> LENGTH: 107
<212> TYPE: PRT
<213> ORGANISM: Homo Sapien

<400> SEQUENCE: 213

```
Arg Thr Val Ala Ala Pro Ser Val Phe Ile Phe Pro Pro Ser Asp Glu
 1               5                  10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
```

```
                35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Leu Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 214
<211> LENGTH: 321
<212> TYPE: DNA
<213> ORGANISM: Homo Sapien

<400> SEQUENCE: 214
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcaac accctgacgc tgagcaaagc agactacgag   240
aaacacaaag tctacgcctg cgaagtcacc catcagggcc tgagctcgcc cgtcacaaag   300
agcttcaaca ggggagagtg c                                             321

<210> SEQ ID NO 215
<211> LENGTH: 107
<212> TYPE: PRT
<213> ORGANISM: Homo Sapien

<400> SEQUENCE: 215

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Asn Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 216
<211> LENGTH: 312
<212> TYPE: DNA
<213> ORGANISM: Homo Sapien

<400> SEQUENCE: 216
cccaaggcca accccacggt cactctgttc ccgccctcct ctgaggagct ccaagccaac    60
aaggccacac tagtgtgtct gatcagtgac ttctacccgg gagctgtgac agtggcttgg   120
aaggcagatg gcagccccgt caaggcggga gtggagacga ccaaaccctc aaacagagc   180 aacaacaagt acgcggccag cagctacctg agcctgacgc cgagcagtg gaagtcccac   240
```

-continued agaagctaca gctgccaggt cacgcatgaa gggagcaccg tggagaagac agtggcccct    300
acagaatgtt ca    312

<210> SEQ ID NO 217
<211> LENGTH: 104
<212> TYPE: PRT
<213> ORGANISM: Homo Sapien

<400> SEQUENCE: 217

Pro Lys Ala Asn Pro Thr Val Thr Leu Phe Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 218
<211> LENGTH: 318
<212> TYPE: DNA
<213> ORGANISM: Homo Sapien

<400> SEQUENCE: 218
ggtcagccca aggccaaccc cactgtcact ctgttcccgc cctcctctga ggagctccaa    60
gccaacaagg ccacactagt gtgtctgatc agtgacttct acccgggagc tgtgacagtg    120
gcctggaagg cagatggcag ccccgtcaag gcgggagtgg agaccaccaa accctccaaa    180
cagagcaaca acaagtacgc ggccagcagc tacctgagcc tgacgcccga gcagtggaag    240
tcccacagaa gctacagctg ccaggtcacg catgaaggga gcaccgtgga agacagtg    300 gcccctacag aatgttca    318

<210> SEQ ID NO 219
<211> LENGTH: 106
<212> TYPE: PRT
<213> ORGANISM: Homo Sapien

<400> SEQUENCE: 219

Gly Gln Pro Lys Ala Asn Pro Thr Val Thr Leu Phe Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

```
Glu Lys Thr Val Ala Pro Thr Glu Cys Ser
        100                 105
```

<210> SEQ ID NO 220
<211> LENGTH: 318
<212> TYPE: DNA
<213> ORGANISM: Homo Sapien

<400> SEQUENCE: 220

```
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag   240
tcccacagaa gctacagctg ccaggtcacg catgaaggga gcaccgtgga agacagtg    300
gcccctacag aatgttca                                                 318
```

<210> SEQ ID NO 221
<211> LENGTH: 318
<212> TYPE: DNA
<213> ORGANISM: Homo Sapien

<400> SEQUENCE: 221

```
ggccagccta aggccgctcc ttctgtgacc ctgttccccc catcctccga ggaactgcag    60
gctaacaagg ccaccctcgt gtgcctgatc agcgacttct accctggcgc cgtgaccgtg   120
gcctggaagg ctgatagctc tcctgtgaag gccggcgtgg aaaccaccac ccccttccaag  180
cagtccaaca acaaatacgc cgcctcctcc tacctgtccc tgacccctga gcagtggaag   240
tcccaccggt cctacagctg ccaagtgacc cacgagggct ccaccgtgga aaagaccgtg   300
gctcctaccg agtgctcc                                                 318
```

<210> SEQ ID NO 222
<211> LENGTH: 318
<212> TYPE: DNA
<213> ORGANISM: Homo Sapien

<400> SEQUENCE: 222

```
ggccagccta aagctgcccc cagcgtcacc ctgtttcctc cctccagcga ggagctccag    60
gccaacaagg ccaccctcgt gtgcctgatc tccgacttct atcccggcgc tgtgaccgtg   120
gcttggaaag ccgactccag ccctgtcaaa gccggcgtgg agaccaccac accctccaag   180
cagtccaaca acaagtacgc cgcctccagc tatctctccc tgacccctga gcagtggaag   240
tcccaccggt cctactcctg tcaggtgacc cacgagggct ccaccgtgga aaagaccgtc   300
gccccaccg agtgctcc                                                  318
```

<210> SEQ ID NO 223
<211> LENGTH: 106
<212> TYPE: PRT
<213> ORGANISM: Homo Sapien

<400> SEQUENCE: 223

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45
```

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 224
<211> LENGTH: 318
<212> TYPE: DNA
<213> ORGANISM: Homo Sapien

<400> SEQUENCE: 224
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcggagtgg agaccaccac accctccaaa      180
caaagcaaca caagtacgc ggccagcagc tatctgagcc tgacgcctga gcagtggaag      240
tcccacagaa gctacagctg ccaggtcacg catgaaggga gcaccgtgga agacagtg       300 gccctacag aatgttca                                                    318

<210> SEQ ID NO 225
<211> LENGTH: 106
<212> TYPE: PRT
<213> ORGANISM: Homo Sapien

<400> SEQUENCE: 225

Gly Gln Pro Lys Ala Ala Pro Ser Val Thr Leu Phe Pro Pro Ser Ser
 1                5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 226
<211> LENGTH: 312
<212> TYPE: DNA
<213> ORGANISM: Homo Sapien

<400> SEQUENCE: 226
cccaaggctg ccccctcggt cactctgttc ccaccctcct ctgaggagct tcaagccaac      60
aaggccacac tggtgtgtct cataagtgac ttctacccgg gagccgtgac agttgcctgg     120
aaggcagata gcagccccgt caaggcgggg gtggagacca ccacacctc caaacaaagc      180 aacaacaagt acgcggccag cagctacctg agcctgacgc tgagcagtg gaagtccac      240 aaaagctaca gctgccaggt cacgcatgaa gggagcaccg tggagaagac agttgcccct     300
acggaatgtt ca                                                    312

<210> SEQ ID NO 227
<211> LENGTH: 104
<212> TYPE: PRT
<213> ORGANISM: Homo Sapien

<400> SEQUENCE: 227

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 228
<211> LENGTH: 318
<212> TYPE: DNA
<213> ORGANISM: Homo Sapien

<400> SEQUENCE: 228
ggtcagccca aggctgcccc ctcggtcact ctgttcccac cctcctctga ggagcttcaa     60
gccaacaagg ccacactggt gtgtctcata agtgacttct acccgggggcc agtgacagtt   120 gcctggaagg cagatagcag ccccgtcaag gcggggggtgg agaccaccac accctccaaa   180
caaagcaaca acaagtacgc ggccagcagc tacctgagcc tgacgcctga gcagtggaag   240
tcccacaaaa gctacagctg ccaggtcacg catgaaggga gcaccgtgga agacagtg      300 gccccctacgg aatgttca                                                 318

<210> SEQ ID NO 229
<211> LENGTH: 106
<212> TYPE: PRT
<213> ORGANISM: Homo Sapien

<400> SEQUENCE: 229

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Pro Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

```
                    100              105
```

<210> SEQ ID NO 230
<211> LENGTH: 318
<212> TYPE: DNA
<213> ORGANISM: Homo Sapien

<400> SEQUENCE: 230

```
ggtcagccca aggctgcccc ctcggtcact ctgttcccac cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tacctgagcc tgacgcctga gcagtggaag   240
tcccacaaaa gctacagctg ccaggtcacg catgaaggga gcaccgtgga agacagtg     300 gcccctacag aatgttca                                                 318
```

<210> SEQ ID NO 231
<211> LENGTH: 106
<212> TYPE: PRT
<213> ORGANISM: Homo Sapien

<400> SEQUENCE: 231

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 232
<211> LENGTH: 318
<212> TYPE: DNA
<213> ORGANISM: Homo Sapien

<400> SEQUENCE: 232

```
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tacctgagcc tgacgcctga gcagtggaag   240
tcccacagaa gctacagctg ccaggtcacg catgaaggga gcaccgtgga agacagtg    300 gcccctacag aatgttca                                                 318
```

<210> SEQ ID NO 233
<211> LENGTH: 106
<212> TYPE: PRT
<213> ORGANISM: Homo Sapien

<400> SEQUENCE: 233

```
Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Ser Ser Pro
        35                  40                  45
Val Lys Ala Gly Val Glu Thr Thr Thr Pro Ser Lys Gln Ser Asn Asn
50                  55                  60
Lys Tyr Ala Ala Ser Ser Tyr Leu Ser Leu Thr Pro Glu Gln Trp Lys
65                  70                  75                  80
Ser His Arg Ser Tyr Ser Cys Gln Val Thr His Glu Gly Ser Thr Val
                85                  90                  95
Glu Lys Thr Val Ala Pro Thr Glu Cys Ser
            100                 105

<210> SEQ ID NO 234
<211> LENGTH: 318
<212> TYPE: DNA
<213> ORGANISM: Homo Sapien

<400> SEQUENCE: 234
ggtcagccca aggctgcccc atcggtcact ctgttcccgc cctcctctga ggagcttcaa      60
gccaacaagg ccacactggt gtgcctgatc agtgacttct acccgggagc tgtgaaagtg     120
gcctggaagg cagatggcag ccccgtcaac acgggagtgg agaccaccac ccctccaaa     180 cagagcaaca caagtacgc ggccagcagc tacctgagcc tgacgcctga gcagtggaag     240
tcccacagaa gctacagctg ccaggtcacg catgaaggga gcaccgtgga agacagtg     300 gcccctgcag aatgttca                                                  318

<210> SEQ ID NO 235
<211> LENGTH: 106
<212> TYPE: PRT
<213> ORGANISM: Homo Sapien

<400> SEQUENCE: 235

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Lys Val Ala Trp Lys Ala Asp Gly Ser Pro
        35                  40                  45
Val Asn Thr Gly Val Glu Thr Thr Thr Pro Ser Lys Gln Ser Asn Asn
50                  55                  60
Lys Tyr Ala Ala Ser Ser Tyr Leu Ser Leu Thr Pro Glu Gln Trp Lys
65                  70                  75                  80
Ser His Arg Ser Tyr Ser Cys Gln Val Thr His Glu Gly Ser Thr Val
                85                  90                  95
Glu Lys Thr Val Ala Pro Ala Glu Cys Ser
            100                 105

<210> SEQ ID NO 236
<211> LENGTH: 318
<212> TYPE: DNA
<213> ORGANISM: Homo Sapien

<400> SEQUENCE: 236
ggtcagccca aggctgcccc atcggtcact ctgttcccac cctcctctga ggagcttcaa      60
```

```
gccaacaagg ccacactggt gtgtctcgta agtgacttct acccgggagc cgtgacagtg    120
gcctggaagg cagatggcag ccccgtcaag gtgggagtgg agaccaccaa accctccaaa    180
caaagcaaca acaagtatgc ggccagcagc tacctgagcc tgacgcccga gcagtggaag    240
tcccacagaa gctacagctg ccgggtcacg catgaaggga gcaccgtgga agacagtg     300 gccccctgcag aatgctct                                                318
```

<210> SEQ ID NO 237
<211> LENGTH: 106
<212> TYPE: PRT
<213> ORGANISM: Homo Sapien

<400> SEQUENCE: 237

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Val Ser Asp
            20                  25                  30
Phe Tyr Pro Gly Ala Val Thr Val Ala Trp Lys Ala Asp Gly Ser Pro
        35                  40                  45
Val Lys Val Gly Val Glu Thr Thr Lys Pro Ser Lys Gln Ser Asn Asn
    50                  55                  60
Lys Tyr Ala Ala Ser Ser Tyr Leu Ser Leu Thr Pro Glu Gln Trp Lys
65                  70                  75                  80
Ser His Arg Ser Tyr Ser Cys Arg Val Thr His Glu Gly Ser Thr Val
                85                  90                  95
Glu Lys Thr Val Ala Pro Ala Glu Cys Ser
            100                 105

<210> SEQ ID NO 238
<211> LENGTH: 8
<212> TYPE: PRT
<213> ORGANISM: Homo Sapien

<400> SEQUENCE: 238

Gly Phe Thr Phe Ser Asp Tyr Tyr
1               5

<210> SEQ ID NO 239
<211> LENGTH: 8
<212> TYPE: PRT
<213> ORGANISM: Homo Sapien

<400> SEQUENCE: 239

Ile Ser Thr Ser Gly Ser Thr Ile
1               5

<210> SEQ ID NO 240
<211> LENGTH: 16
<212> TYPE: PRT
<213> ORGANISM: Homo Sapien

<400> SEQUENCE: 240

Ala Arg Gly Ile Thr Gly Thr Asn Phe Tyr His Tyr Gly Leu Gly Val
1               5                   10                  15

<210> SEQ ID NO 241
<211> LENGTH: 5
<212> TYPE: PRT
<213> ORGANISM: Homo Sapien

```
<400> SEQUENCE: 241

Asp Tyr Tyr Met Ser
1               5

<210> SEQ ID NO 242
<211> LENGTH: 17
<212> TYPE: PRT
<213> ORGANISM: Homo Sapien

<400> SEQUENCE: 242

Tyr Ile Ser Thr Ser Gly Ser Thr Ile Tyr Tyr Ala Asp Ser Val Lys
1               5                   10                  15

Gly

<210> SEQ ID NO 243
<211> LENGTH: 14
<212> TYPE: PRT
<213> ORGANISM: Homo Sapien

<400> SEQUENCE: 243

Gly Ile Thr Gly Thr Asn Phe Tyr His Tyr Gly Leu Gly Val
1               5                   10

<210> SEQ ID NO 244
<211> LENGTH: 123
<212> TYPE: PRT
<213> ORGANISM: Homo Sapien

<400> SEQUENCE: 244

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Val Pro Gly Lys Gly Leu Glu Trp Val
        35                  40                  45

Ser Tyr Ile Ser Thr Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ala Ala Val Tyr His Cys
                85                  90                  95

Ala Arg Gly Ile Thr Gly Thr Asn Phe Tyr His Tyr Gly Leu Gly Val
            100                 105                 110

Trp Gly Gln Gly Thr Thr Val Thr Val Ser Ser
        115                 120

<210> SEQ ID NO 245
<211> LENGTH: 370
<212> TYPE: DNA
<213> ORGANISM: Homo Sapien

<400> SEQUENCE: 245
caggtgcagc tggtggagtc tgggggaggc ttggtcaagc ctggagggtc cctgagactc      60
tcctgtgcag cctctggatt caccttcagt gactactaca tgagctggat ccgccaggtt     120
ccagggaagg ggctggagtg ggtttcatac attagtacta gtggtagtac catatactac     180
gcagactctg tgaagggccg attcaccatc tccagggaca cgccaagaa ctcactgtat      240 ctacaaatga acagcctgag agccgaggac gcggccgtgt atcactgtgc gagaggtata     300
```

```
actggaacta acttctacca ctacggtttg ggcgtctggg gccaagggac cacggtcacc    360
gtctcctcag                                                           370
```

<210> SEQ ID NO 246
<211> LENGTH: 453
<212> TYPE: PRT
<213> ORGANISM: Homo Sapien

<400> SEQUENCE: 246

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Val Pro Gly Lys Gly Leu Glu Trp Val
        35                  40                  45

Ser Tyr Ile Ser Thr Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ala Ala Val Tyr His Cys
                85                  90                  95

Ala Arg Gly Ile Thr Gly Thr Asn Phe Tyr His Tyr Gly Leu Gly Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
```

Val Ser Leu Thr Cys Leu Val Lys Gly Phe Tyr Pro Ser Asp Ile Ala
355                 360                 365
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 247
<211> LENGTH: 1359
<212> TYPE: DNA
<213> ORGANISM: Homo Sapien

<400> SEQUENCE: 247

| | |
|---|---|
| caggtgcagc tggtggagtc tgggggaggc ttggtcaagc ctggagggtc cctgagactc | 60 |
| tcctgtgcag cctctggatt caccttcagt gactactaca tgagctggat ccgccaggtt | 120 |
| ccagggaagg ggctggagtg ggtttcatac attagtacta gtggtagtac catatactac | 180 |
| gcagactctg tgaagggccg attcaccatc tccagggaca acgccaagaa ctcactgtat | 240 |
| ctacaaatga acagcctgag agccgaggac gcggccgtgt atcactgtgc gagaggtata | 300 |
| actggaacta acttctacca ctacggtttg gcgtctggg gccaagggac cacggtcacc | 360 |
| gtctcctcag ccagcaccaa gggcccctct gtgttccctc tggccccttc cagcaagtcc | 420 |
| acctctggcg gaacagccgc tctgggctgc ctcgtgaagg actacttccc cgagcctgtg | 480 |
| accgtgtcct ggaactctgg cgctctgacc agcggagtgc acaccttccc tgctgtgctg | 540 |
| cagtcctccg gcctgtactc cctgtcctcc gtcgtgaccg tgccttccag ctctctgggc | 600 |
| acccagacct acatctgcaa cgtgaaccac aagccctcca caccaaggt ggacaagaag | 660 |
| gtggaaccca gtcctgcga caagacccac acctgtcccc cttgtcctgc ccctgaactg | 720 |
| ctgggcggac cttccgtgtt cctgttcccc ccaaagccca aggacaccct gatgatctcc | 780 |
| cggacccccg aagtgacctg cgtggtggtg gatgtgtccc acgaggaccc tgaagtgaag | 840 |
| ttcaattggt acgtggacgg cgtggaagtg cacaacgcca agaccaagcc tagagaggaa | 900 |
| cagtacaact ccacctaccg ggtggtgtcc gtgctgaccg tgctgcacca ggattggctg | 960 |
| aacggcaaag agtacaagtg caaggtgtcc aacaaggccc tgcctgcccc catcgaaaag | 1020 |
| accatctcca aggccaaggg ccagccccgg gaaccccagg tgtacacact gcccctagc | 1080 |
| agggacgagc tgaccaagaa ccaggtgtcc ctgacctgtc tcgtgaaagg cttctacccc | 1140 |
| tccgatatcg ccgtggaatg ggagtccaac ggccagcctg agaacaacta caagaccacc | 1200 |
| cccctgtgc tggactccga cggctcattc ttcctgtaca gcaagctgac agtggacaag | 1260 |
| tcccggtggc agcagggcaa cgtgttctcc tgctccgtga tgcacgaggc cctgcacaac | 1320 |
| cactacaccc agaagtccct gtccctgagc cccggcaag | 1359 |

<210> SEQ ID NO 248
<211> LENGTH: 6
<212> TYPE: PRT
<213> ORGANISM: Homo Sapien

-continued

```
<400> SEQUENCE: 248

Gln Gly Ile Asn Ser Trp
1               5

<210> SEQ ID NO 249
<211> LENGTH: 3
<212> TYPE: PRT
<213> ORGANISM: Homo Sapien

<400> SEQUENCE: 249

Ala Ala Ser
1

<210> SEQ ID NO 250
<211> LENGTH: 9
<212> TYPE: PRT
<213> ORGANISM: Homo Sapien

<400> SEQUENCE: 250

Gln Gln Val Asn Ser Phe Pro Leu Thr
1               5

<210> SEQ ID NO 251
<211> LENGTH: 11
<212> TYPE: PRT
<213> ORGANISM: Homo Sapien

<400> SEQUENCE: 251

Arg Ala Ser Gln Gly Ile Asn Ser Trp Leu Ala
1               5                   10

<210> SEQ ID NO 252
<211> LENGTH: 7
<212> TYPE: PRT
<213> ORGANISM: Homo Sapien

<400> SEQUENCE: 252

Ala Ala Ser Thr Leu Gln Ser
1               5

<210> SEQ ID NO 253
<211> LENGTH: 9
<212> TYPE: PRT
<213> ORGANISM: Homo Sapien

<400> SEQUENCE: 253

Gln Gln Val Asn Ser Phe Pro Leu Thr
1               5

<210> SEQ ID NO 254
<211> LENGTH: 107
<212> TYPE: PRT
<213> ORGANISM: Homo Sapien

<400> SEQUENCE: 254

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
```

```
              50                  55                  60
Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

Thr Phe Gly Gly Gly Thr Lys Val Glu Ile Lys
                100                 105
```

<210> SEQ ID NO 255
<211> LENGTH: 322
<212> TYPE: DNA
<213> ORGANISM: Homo Sapien

<400> SEQUENCE: 255

```
gacatccaga tgacccagtc tccatcttcc gtgtctgcat ctgtaggaga cagagtcacc      60
atcacttgtc gggcgagtca gggtattaac agctggttag cctggtatca gcagaaacca    120
gggaaagccc ctaagctcct gatctatgct gcatccactt tgcaaagtgg ggtcccatca    180
aggttcagcg gcagtgggtc tgggcagat ttcactctca ccatcagcag cctgcagcct    240
gaagattttg caacttacta ttgtcaacag gttaacagtt tcccgctcac tttcggcgga    300
gggaccaagg tggagatcaa ac                                             322
```

<210> SEQ ID NO 256
<211> LENGTH: 214
<212> TYPE: PRT
<213> ORGANISM: Homo Sapien

<400> SEQUENCE: 256

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 257
<211> LENGTH: 642
<212> TYPE: DNA
<213> ORGANISM: Homo Sapien

<400> SEQUENCE: 257
gacatccaga tgacccagtc tccatcttcc gtgtctgcat ctgtaggaga cagagtcacc    60
atcacttgtc gggcgagtca gggtattaac agctggttag cctggtatca gcagaaacca   120
gggaaagccc ctaagctcct gatctatgct gcatccactt tgcaaagtgg ggtcccatca   180
aggttcagcg gcagtgggtc tggggcagat ttcactctca ccatcagcag cctgcagcct   240
gaagattttg caacttacta ttgtcaacag gttaacagtt tcccgctcac tttcggcgga   300
gggaccaagg tggagatcaa acgtacggtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg acaacgccc tgcagtccgg caactcccag   480
gaatccgtga ccgagcagga ctccaaggac agcacctact ccctgtcctc caccctgacc   540
ctgtccaagg ccgactacga aagcacaag gtgtacgcct gcgaagtgac ccaccagggc   600
ctgtctagcc ccgtgaccaa gtctttcaac cggggcgagt gt                      642

<210> SEQ ID NO 258
<211> LENGTH: 8
<212> TYPE: PRT
<213> ORGANISM: Homo Sapien

<400> SEQUENCE: 258

Gly Phe Thr Phe Ser Tyr Tyr Ala
1               5

<210> SEQ ID NO 259
<211> LENGTH: 8
<212> TYPE: PRT
<213> ORGANISM: Homo Sapien

<400> SEQUENCE: 259

Ile Ser Gly Gly Gly Gly Asn Thr
1               5

<210> SEQ ID NO 260
<211> LENGTH: 16
<212> TYPE: PRT
<213> ORGANISM: Homo Sapien

<400> SEQUENCE: 260

Ala Lys Asp Arg Met Lys Gln Leu Val Arg Ala Tyr Tyr Phe Asp Tyr
1               5                   10                  15

<210> SEQ ID NO 261
<211> LENGTH: 5
<212> TYPE: PRT
<213> ORGANISM: Homo Sapien

<400> SEQUENCE: 261

Tyr Tyr Ala Met Ser
1               5

<210> SEQ ID NO 262
<211> LENGTH: 17

```
<212> TYPE: PRT
<213> ORGANISM: Homo Sapien

<400> SEQUENCE: 262

Thr Ile Ser Gly Gly Gly Gly Asn Thr His Tyr Ala Asp Ser Val Lys
1               5                   10                  15

Gly

<210> SEQ ID NO 263
<211> LENGTH: 14
<212> TYPE: PRT
<213> ORGANISM: Homo Sapien

<400> SEQUENCE: 263

Asp Arg Met Lys Gln Leu Val Arg Ala Tyr Tyr Phe Asp Tyr
1               5                   10

<210> SEQ ID NO 264
<211> LENGTH: 123
<212> TYPE: PRT
<213> ORGANISM: Homo Sapien

<400> SEQUENCE: 264

Glu Val Pro Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Asp Trp Val
        35                  40                  45

Ser Thr Ile Ser Gly Gly Gly Gly Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Arg Met Lys Gln Leu Val Arg Ala Tyr Tyr Phe Asp Tyr
            100                 105                 110

Trp Gly Gln Gly Thr Leu Val Thr Val Ser Ser
        115                 120

<210> SEQ ID NO 265
<211> LENGTH: 370
<212> TYPE: DNA
<213> ORGANISM: Homo Sapien

<400> SEQUENCE: 265
gaggtgccgc tggtggagtc tgggggaggc ttggtacagc ctgggggtc cctgagactc     60 tcctgtgcag cctctggatt cacgtttagc tactatgcca tgagctgggt ccgtcaggct    120
ccagggaagg ggctggactg gtctcaact attagtggtg gtggtggtaa cacacactac    180
gcagactccg tgaagggccg attcactata tccagagaca attccaagaa cacgctgtat    240
ctgcacatga acagcctgag agccgaagac acggccgtct attactgtgc gaaggatcgg    300
atgaaacagc tcgtccgggc ctactacttt gactactggg gccagggaac cctggtcacc    360
gtctcctcag                                                           370

<210> SEQ ID NO 266
<211> LENGTH: 453
<212> TYPE: PRT
```

<213> ORGANISM: Homo Sapien

<400> SEQUENCE: 266

```
Glu Val Pro Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Asp Trp Val
        35                  40                  45

Ser Thr Ile Ser Gly Gly Gly Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Arg Met Lys Gln Leu Val Arg Ala Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 267
<211> LENGTH: 1359
<212> TYPE: DNA
<213> ORGANISM: Homo Sapien

<400> SEQUENCE: 267
gaggtgccgc tggtggagtc tgggggaggc ttggtacagc ctgggggtc cctgagactc      60 tcctgtgcag cctctggatt cacgtttagc tactatgcca tgagctgggt ccgtcaggct    120
ccagggaagg ggctggactg ggtctcaact attagtggtg gtggtggtaa cacacactac    180
gcagactccg tgaagggccg attcactata tccagagaca attccaagaa cacgctgtat    240
ctgcacatga acagcctgag agccgaagac acggccgtct attactgtgc gaaggatcgg    300
atgaaacagc tcgtccgggc ctactacttt gactactggg gccagggaac cctggtcacc    360
gtctcctcag ccagcaccaa ggccccctct gtgttccctc tggccccctt cagcaagtcc    420
acctctggcg gaacagccgc tctgggctgc ctcgtgaagg actacttccc cgagcctgtg    480
accgtgtcct ggaactctgg cgctctgacc agcggagtgc acacctttcc tgctgtgctg    540
cagtcctccg gcctgtactc cctgtcctcc gtcgtgaccg tgccttccag ctctctgggc    600
acccagacct acatctgcaa cgtgaaccac aagccctcca acaccaaggt ggacaagaag    660
gtggaaccca gtcctgcga caagacccac acctgtcccc cttgtcctgc ccctgaactg    720
ctgggcggac cttccgtgtt cctgttcccc ccaaagccca aggacaccct gatgatctcc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaact ccacctaccg ggtggtgtcc gtgctgaccg tgctgcacca ggattggctg    960
aacggcaaag agtacaagtg caaggtgtcc aacaaggccc tgcctgcccc catcgaaaag   1020
accatctcca aggccaaggg ccagccccgg gaaccccagg tgtacacact gcccctagc    1080 agggacgagc tgaccaagaa ccaggtgtcc ctgacctgtc tcgtgaaagg cttctacccc   1140
tccgatatcg ccgtggaatg ggagtccaac ggccagcctg agaacaacta caagaccacc   1200 cccctgtgc tggactccga cggctcattc ttcctgtaca gcaagctgac agtggacaag   1260
tcccggtggc agcagggcaa cgtgttctcc tgctccgtga tgcacgaggc cctgcacaac   1320
cactacaccc agaagtccct gtccctgagc cccggcaag                           1359

<210> SEQ ID NO 268
<211> LENGTH: 6
<212> TYPE: PRT
<213> ORGANISM: Homo Sapien

<400> SEQUENCE: 268

Gln Asp Ile Ser Thr Tyr
1               5

<210> SEQ ID NO 269
```

```
<211> LENGTH: 3
<212> TYPE: PRT
<213> ORGANISM: Homo Sapien

<400> SEQUENCE: 269

Gly Thr Ser
1

<210> SEQ ID NO 270
<211> LENGTH: 9
<212> TYPE: PRT
<213> ORGANISM: Homo Sapien

<400> SEQUENCE: 270

Gln Gln Leu His Thr Asp Pro Ile Thr
1               5

<210> SEQ ID NO 271
<211> LENGTH: 11
<212> TYPE: PRT
<213> ORGANISM: Homo Sapien

<400> SEQUENCE: 271

Trp Ala Ser Gln Asp Ile Ser Thr Tyr Leu Gly
1               5                   10

<210> SEQ ID NO 272
<211> LENGTH: 7
<212> TYPE: PRT
<213> ORGANISM: Homo Sapien

<400> SEQUENCE: 272

Gly Thr Ser Ser Leu Gln Ser
1               5

<210> SEQ ID NO 273
<211> LENGTH: 9
<212> TYPE: PRT
<213> ORGANISM: Homo Sapien

<400> SEQUENCE: 273

Gln Gln Leu His Thr Asp Pro Ile Thr
1               5

<210> SEQ ID NO 274
<211> LENGTH: 107
<212> TYPE: PRT
<213> ORGANISM: Homo Sapien

<400> SEQUENCE: 274

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Thr Tyr
            20                  25                  30

Leu Gly Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu His Thr Asp Pro Ile
                85                  90                  95
```

Thr Phe Gly Gln Gly Thr Arg Leu Glu Ile Lys
            100                 105

<210> SEQ ID NO 275
<211> LENGTH: 322
<212> TYPE: DNA
<213> ORGANISM: Homo Sapien

<400> SEQUENCE: 275
gacatccagt tgacccagtc tccatccttc ctgtctgcat ctgtaggaga cagagtcacc    60
atcacttgct gggccagtca ggacattagc acttatttag ctggtatca gcaaaaacca    120 gggaaagccc ctaagctcct gatctatggt acatccagtt tgcaaagtgg ggtcccatca    180
aggttcagcg gcagtggatc tgggacagaa ttcactctca caatcagcag cctgcagcct    240
gaagattttg caacttatta ctgtcaacag cttcatactg acccgatcac cttcggccaa    300
gggacacgac tggagatcaa ac                                             322

<210> SEQ ID NO 276
<211> LENGTH: 214
<212> TYPE: PRT
<213> ORGANISM: Homo Sapien

<400> SEQUENCE: 276

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Thr Tyr
            20                  25                  30

Leu Gly Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu His Thr Asp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 277
<211> LENGTH: 642
<212> TYPE: DNA
<213> ORGANISM: Homo Sapien

```
<400> SEQUENCE: 277
gacatccagt tgacccagtc tccatccttc ctgtctgcat ctgtaggaga cagagtcacc      60
atcacttgct gggccagtca ggacattagc acttatttag ctggtatca gcaaaaacca     120
gggaaagccc ctaagctcct gatctatggt acatccagtt tgcaaagtgg ggtcccatca    180
aggttcagcg gcagtggatc tgggacagaa ttcactctca caatcagcag cctgcagcct    240
gaagattttg caacttatta ctgtcaacag cttcatactg acccgatcac cttcggccaa    300
gggacacgac tggagatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg acaacgccc tgcagtccgg caactcccag     480
gaatccgtga ccgagcagga ctccaaggac agcacctact ccctgtcctc caccctgacc    540
ctgtccaagg ccgactacga aagcacaag gtgtacgcct gcgaagtgac ccaccagggc     600
ctgtctagcc ccgtgaccaa gtctttcaac cggggcgagt gt                       642
```

```
<210> SEQ ID NO 278
<211> LENGTH: 8
<212> TYPE: PRT
<213> ORGANISM: Homo Sapien

<400> SEQUENCE: 278

Gly Phe Thr Phe Ser Ser Tyr Trp
1               5
```

```
<210> SEQ ID NO 279
<211> LENGTH: 8
<212> TYPE: PRT
<213> ORGANISM: Homo Sapien

<400> SEQUENCE: 279

Ile Lys Gln Asp Gly Ser Glu Lys
1               5
```

```
<210> SEQ ID NO 280
<211> LENGTH: 12
<212> TYPE: PRT
<213> ORGANISM: Homo Sapien

<400> SEQUENCE: 280

Ala Arg Val Arg Gln Trp Ser Asp Tyr Ser Asp Tyr
1               5                   10
```

```
<210> SEQ ID NO 281
<211> LENGTH: 5
<212> TYPE: PRT
<213> ORGANISM: Homo Sapien

<400> SEQUENCE: 281

Ser Tyr Trp Met Asn
1               5
```

```
<210> SEQ ID NO 282
<211> LENGTH: 17
<212> TYPE: PRT
<213> ORGANISM: Homo Sapien

<400> SEQUENCE: 282

Asn Ile Lys Gln Asp Gly Ser Glu Lys Tyr Tyr Val Asp Ser Val Lys
1               5                   10                  15
```

```
<210> SEQ ID NO 283
<211> LENGTH: 10
<212> TYPE: PRT
<213> ORGANISM: Homo Sapien

<400> SEQUENCE: 283

Val Arg Gln Trp Ser Asp Tyr Ser Asp Tyr
1               5                   10

<210> SEQ ID NO 284
<211> LENGTH: 119
<212> TYPE: PRT
<213> ORGANISM: Homo Sapien

<400> SEQUENCE: 284

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gln Trp Ser Asp Tyr Ser Asp Tyr Trp Gly Gln Gly
            100                 105                 110

Thr Pro Val Thr Val Ser Ser
            115

<210> SEQ ID NO 285
<211> LENGTH: 358
<212> TYPE: DNA
<213> ORGANISM: Homo Sapien

<400> SEQUENCE: 285
gaggtgcacc tggtggagtc tgggggaggc ttggtccagc ctggggggtc cctgagactc    60
tcctgtgcag cctctggatt cacctttagt agctattgga tgaactgggt ccgccaggct   120
ccagggaagg ggctggagtg ggtggccaac ataaagcaag atggaagtga aaaatactat   180
gtggactctg tgaagggccg cttcaccgtc tccagagaca acgccaagaa ctcactgtat   240
ctgcaaatga acagcctgag agccgaggac acggctgtgt attactgtgc gagagttcga   300
caatggtccg actactctga ctactggggc cagggaaccc cggtcaccgt ctcctcag     358

<210> SEQ ID NO 286
<211> LENGTH: 449
<212> TYPE: PRT
<213> ORGANISM: Homo Sapien

<400> SEQUENCE: 286

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

Trp Met Asn Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
 50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg Val Arg Gln Trp Ser Asp Tyr Ser Asp Tyr Trp Gly Gln Gly
             100                 105                 110

Thr Pro Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Asp Glu Leu Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445

Lys

<210> SEQ ID NO 287
<211> LENGTH: 1347
<212> TYPE: DNA
<213> ORGANISM: Homo Sapien

<400> SEQUENCE: 287

```
gaggtgcacc tggtggagtc tgggggaggc ttggtccagc ctggggggtc cctgagactc      60
tcctgtgcag cctctggatt cacctttagt agctattgga tgaactgggt ccgccaggct     120
ccagggaagg ggctggagtg ggtggccaac ataaagcaag atggaagtga aaatactat      180
gtggactctg tgaagggccg cttcaccgtc tccagagaca acgccaagaa ctcactgtat     240
ctgcaaatga acagcctgag agccgaggac acggctgtgt attactgtgc gagagttcga     300
caatggtccg actactctga ctactgggc agggaaccc cggtcaccgt ctcctcagcc       360
agcaccaagg gcccctctgt gttccctctg gccccttcca gcaagtccac ctctggcgga     420
acagccgctc tgggctgcct cgtgaaggac tacttccccg agcctgtgac cgtgtcctgg     480
aactctggcg ctctgaccag cggagtgcac accttccctg ctgtgctgca gtcctccggc     540
ctgtactccc tgtcctccgt cgtgaccgtg ccttccagct ctctgggcac ccagacctac     600
atctgcaacg tgaaccacaa gccctccaac accaaggtgg acaagaaggt ggaacccaag     660
tcctgcgaca gacccacac ctgtccccct tgtcctgccc ctgaactgct gggcggacct      720
tccgtgttcc tgttcccccc aaagcccaag gacaccctga tgatctcccg gacccccgaa     780
gtgacctgcg tggtggtgga tgtgtcccac gaggaccctg aagtgaagtt caattggtac     840
gtggacggcg tggaagtgca acgccaag accaagccta gagaggaaca gtacaactcc      900
acctaccggg tggtgtccgt gctgaccgtg ctgcaccagg attggctgaa cggcaaagag     960
tacaagtgca aggtgtccaa caaggccctg cctgcccca tcgaaaagac catctccaag    1020
gccaagggcc agccccggga acccaggtg tacacactgc ccctagcag ggacgagctg     1080
accaagaacc aggtgtccct gacctgtctc gtgaaaggct tctacccctc cgatatcgcc    1140
gtggaatggg agtccaacgg ccagcctgag aacaactaca agaccacccc cctgtgctg     1200
gactccgacg gctcattctt cctgtacagc aagctgacag tggacaagtc ccggtggcag    1260
cagggcaacg tgttctcctg ctccgtgatg cacgaggccc tgcacaacca ctacacccag    1320
aagtccctgt ccctgagccc cggcaag                                        1347
```

<210> SEQ ID NO 288
<211> LENGTH: 6
<212> TYPE: PRT
<213> ORGANISM: Homo Sapien

<400> SEQUENCE: 288

Gln Gly Ile Ser Ser Trp
1               5

<210> SEQ ID NO 289
<211> LENGTH: 3
<212> TYPE: PRT
<213> ORGANISM: Homo Sapien

<400> SEQUENCE: 289

Ala Ala Ser
1

<210> SEQ ID NO 290

```
<211> LENGTH: 9
<212> TYPE: PRT
<213> ORGANISM: Homo Sapien

<400> SEQUENCE: 290

Gln Gln Ala Asn Ser Phe Pro Phe Thr
1               5

<210> SEQ ID NO 291
<211> LENGTH: 11
<212> TYPE: PRT
<213> ORGANISM: Homo Sapien

<400> SEQUENCE: 291

Arg Ala Ser Gln Gly Ile Ser Ser Trp Leu Ala
1               5                   10

<210> SEQ ID NO 292
<211> LENGTH: 7
<212> TYPE: PRT
<213> ORGANISM: Homo Sapien

<400> SEQUENCE: 292

Ala Ala Ser Ser Leu Gln Ser
1               5

<210> SEQ ID NO 293
<211> LENGTH: 9
<212> TYPE: PRT
<213> ORGANISM: Homo Sapien

<400> SEQUENCE: 293

Gln Gln Ala Asn Ser Phe Pro Phe Thr
1               5

<210> SEQ ID NO 294
<211> LENGTH: 107
<212> TYPE: PRT
<213> ORGANISM: Homo Sapien

<400> SEQUENCE: 294

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 295
<211> LENGTH: 322
<212> TYPE: DNA
<213> ORGANISM: Homo Sapien

<400> SEQUENCE: 295
```

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccattcac tttcggccct   300
gggaccaaag tggatatcaa ac                                            322
```

<210> SEQ ID NO 296
<211> LENGTH: 214
<212> TYPE: PRT
<213> ORGANISM: Homo Sapien

<400> SEQUENCE: 296

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 297
<211> LENGTH: 642
<212> TYPE: DNA
<213> ORGANISM: Homo Sapien

<400> SEQUENCE: 297

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccattcac tttcggccct   300
```

```
gggaccaaag tggatatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtctagcc ccgtgaccaa gtctttcaac cggggcgagt gt                       642
```

<210> SEQ ID NO 298
<211> LENGTH: 214
<212> TYPE: PRT
<213> ORGANISM: Homo Sapien

<400> SEQUENCE: 298

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 299
<211> LENGTH: 453
<212> TYPE: PRT
<213> ORGANISM: Homo Sapien

<400> SEQUENCE: 299

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45
```

```
Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 300
<211> LENGTH: 347
<212> TYPE: PRT
<213> ORGANISM: Homo Sapien

<400> SEQUENCE: 300

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Pro Thr Ser Ser Ser Thr Lys Lys Thr
    210                 215                 220

Gln Leu Gln Leu Glu His Leu Leu Leu Asp Leu Gln Met Ile Leu Asn
225                 230                 235                 240

Gly Ile Asn Asn Tyr Lys Asn Pro Lys Leu Thr Arg Met Leu Thr Phe
                245                 250                 255

Lys Phe Tyr Met Pro Lys Lys Ala Thr Glu Leu Lys His Leu Gln Cys
            260                 265                 270

Leu Glu Glu Glu Leu Lys Pro Leu Glu Glu Val Leu Asn Leu Ala Gln
        275                 280                 285

Ser Lys Asn Phe His Leu Arg Pro Arg Asp Leu Ile Ser Asn Ile Asn
    290                 295                 300

Val Ile Val Leu Glu Leu Lys Gly Ser Glu Thr Thr Phe Met Cys Glu
305                 310                 315                 320

Tyr Ala Asp Glu Thr Ala Thr Ile Val Glu Phe Leu Asn Arg Trp Ile
                325                 330                 335

Thr Phe Cys Gln Ser Ile Ile Ser Thr Leu Thr
            340                 345
```

<210> SEQ ID NO 301
<211> LENGTH: 133
<212> TYPE: PRT
<213> ORGANISM: Homo Sapien

<400> SEQUENCE: 301

| Ala | Pro | Thr | Ser | Ser | Thr | Lys | Lys | Thr | Gln | Leu | Gln | Leu | Glu | His |
| 1 | | | | 5 | | | | | 10 | | | | | 15 |

| Leu | Leu | Leu | Asp | Leu | Gln | Met | Ile | Leu | Asn | Gly | Ile | Asn | Asn | Tyr | Lys |
| | | | 20 | | | | | 25 | | | | | 30 | | |

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 302
<211> LENGTH: 586
<212> TYPE: PRT
<213> ORGANISM: Homo Sapien

<400> SEQUENCE: 302

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Val Pro Gly Lys Gly Leu Glu Trp Val
            35                  40                  45

Ser Gly Ile Ser Trp Ile Arg Thr Gly Ile Gly Tyr Ala Asp Ser Val
        50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Asp Glu Leu Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys Ala Pro Thr Ser Ser Ser Thr Lys Lys Thr Gln
450                 455                 460

Leu Gln Leu Glu His Leu Leu Leu Asp Leu Gln Met Ile Leu Asn Gly
465                 470                 475                 480

Ile Asn Asn Tyr Lys Asn Pro Lys Leu Thr Arg Met Leu Thr Phe Lys
            485                 490                 495

Phe Tyr Met Pro Lys Lys Ala Thr Glu Leu Lys His Leu Gln Cys Leu
        500                 505                 510

Glu Glu Glu Leu Lys Pro Leu Glu Glu Val Leu Asn Leu Ala Gln Ser
    515                 520                 525

Lys Asn Phe His Leu Arg Pro Arg Asp Leu Ile Ser Asn Ile Asn Val
530                 535                 540

Ile Val Leu Glu Leu Lys Gly Ser Glu Thr Thr Phe Met Cys Glu Tyr
545                 550                 555                 560

Ala Asp Glu Thr Ala Thr Ile Val Glu Phe Leu Asn Arg Trp Ile Thr
            565                 570                 575

Phe Cys Gln Ser Ile Ile Ser Thr Leu Thr
        580                 585

<210> SEQ ID NO 303
<211> LENGTH: 14
<212> TYPE: PRT
<213> ORGANISM: Homo Sapien

<400> SEQUENCE: 303

Ala Pro Thr Ser Thr Gln Leu Gln Leu Glu Leu Leu Leu Asp

-continued

```
1               5                   10

<210> SEQ ID NO 304
<211> LENGTH: 11
<212> TYPE: PRT
<213> ORGANISM: Homo Sapien

<400> SEQUENCE: 304

Thr Gln Leu Gln Leu Glu His Leu Leu Leu Asp
1               5                   10

<210> SEQ ID NO 305
<211> LENGTH: 17
<212> TYPE: PRT
<213> ORGANISM: Homo Sapien

<400> SEQUENCE: 305

Ala Pro Thr Ser Lys Lys Thr Gln Leu Gln Leu Glu His Leu Leu Leu
1               5                   10                  15

Asp

<210> SEQ ID NO 306
<211> LENGTH: 19
<212> TYPE: PRT
<213> ORGANISM: Homo Sapien

<400> SEQUENCE: 306

Pro Thr Ser Ser Ser Thr Lys Lys Thr Gln Leu Gln Leu Glu His Leu
1               5                   10                  15

Leu Leu Asp

<210> SEQ ID NO 307
<211> LENGTH: 18
<212> TYPE: PRT
<213> ORGANISM: Homo Sapien

<400> SEQUENCE: 307

Thr Ser Ser Ser Thr Lys Lys Thr Gln Leu Gln Leu Glu His Leu Leu
1               5                   10                  15

Leu Asp

<210> SEQ ID NO 308
<211> LENGTH: 17
<212> TYPE: PRT
<213> ORGANISM: Homo Sapien

<400> SEQUENCE: 308

Ser Ser Ser Thr Lys Lys Thr Gln Leu Gln Leu Glu His Leu Leu Leu
1               5                   10                  15

Asp

<210> SEQ ID NO 309
<211> LENGTH: 16
<212> TYPE: PRT
<213> ORGANISM: Homo Sapien

<400> SEQUENCE: 309

Ser Ser Thr Lys Lys Thr Gln Leu Gln Leu Glu His Leu Leu Leu Asp
1               5                   10                  15

<210> SEQ ID NO 310
<211> LENGTH: 15
```

<212> TYPE: PRT
<213> ORGANISM: Homo Sapien

<400> SEQUENCE: 310

Ser Thr Lys Lys Thr Gln Leu Gln Leu Glu His Leu Leu Leu Asp
1               5                   10                  15

<210> SEQ ID NO 311
<211> LENGTH: 14
<212> TYPE: PRT
<213> ORGANISM: Homo Sapien

<400> SEQUENCE: 311

Thr Lys Lys Thr Gln Leu Gln Leu Glu His Leu Leu Leu Asp
1               5                   10

<210> SEQ ID NO 312
<211> LENGTH: 13
<212> TYPE: PRT
<213> ORGANISM: Homo Sapien

<400> SEQUENCE: 312

Lys Lys Thr Gln Leu Gln Leu Glu His Leu Leu Leu Asp
1               5                   10

<210> SEQ ID NO 313
<211> LENGTH: 12
<212> TYPE: PRT
<213> ORGANISM: Homo Sapien

<400> SEQUENCE: 313

Lys Thr Gln Leu Gln Leu Glu His Leu Leu Leu Asp
1               5                   10

<210> SEQ ID NO 314
<211> LENGTH: 19
<212> TYPE: PRT
<213> ORGANISM: Homo Sapien

<400> SEQUENCE: 314

Ala Pro Thr Ser Ser Thr Lys Thr Gln Leu Gln Leu Glu His Leu
1               5                   10                  15

Leu Leu Asp

<210> SEQ ID NO 315
<211> LENGTH: 18
<212> TYPE: PRT
<213> ORGANISM: Homo Sapien

<400> SEQUENCE: 315

Ala Pro Thr Ser Ser Ser Thr Thr Gln Leu Gln Leu Glu His Leu Leu
1               5                   10                  15

Leu Asp

<210> SEQ ID NO 316
<211> LENGTH: 17
<212> TYPE: PRT
<213> ORGANISM: Homo Sapien

<400> SEQUENCE: 316

Ala Pro Thr Ser Ser Ser Thr Gln Leu Gln Leu Glu His Leu Leu Leu
1               5                   10                  15

Asp

```
<210> SEQ ID NO 317
<211> LENGTH: 16
<212> TYPE: PRT
<213> ORGANISM: Homo Sapien

<400> SEQUENCE: 317

Ala Pro Thr Ser Ser Thr Gln Leu Gln Leu Glu His Leu Leu Leu Asp
1               5                   10                  15

<210> SEQ ID NO 318
<211> LENGTH: 14
<212> TYPE: PRT
<213> ORGANISM: Homo Sapien

<400> SEQUENCE: 318

Ala Pro Thr Thr Gln Leu Gln Leu Glu His Leu Leu Leu Asp
1               5                   10

<210> SEQ ID NO 319
<211> LENGTH: 13
<212> TYPE: PRT
<213> ORGANISM: Homo Sapien

<400> SEQUENCE: 319

Ala Pro Thr Gln Leu Gln Leu Glu His Leu Leu Leu Asp
1               5                   10

<210> SEQ ID NO 320
<211> LENGTH: 12
<212> TYPE: PRT
<213> ORGANISM: Homo Sapien

<400> SEQUENCE: 320

Ala Thr Gln Leu Gln Leu Glu His Leu Leu Leu Asp
1               5                   10

<210> SEQ ID NO 321
<211> LENGTH: 15
<212> TYPE: PRT
<213> ORGANISM: Homo Sapien

<400> SEQUENCE: 321

Ala Thr Lys Lys Thr Gln Leu Gln Leu Glu His Leu Leu Leu Asp
1               5                   10                  15

<210> SEQ ID NO 322
<211> LENGTH: 15
<212> TYPE: PRT
<213> ORGANISM: Homo Sapien

<400> SEQUENCE: 322

Ala Pro Lys Lys Thr Gln Leu Gln Leu Glu His Leu Leu Leu Asp
1               5                   10                  15

<210> SEQ ID NO 323
<211> LENGTH: 15
<212> TYPE: PRT
<213> ORGANISM: Homo Sapien

<400> SEQUENCE: 323

Ala Pro Thr Lys Thr Gln Leu Gln Leu Glu His Leu Leu Leu Asp
1               5                   10                  15
```

```
<210> SEQ ID NO 324
<211> LENGTH: 113
<212> TYPE: PRT
<213> ORGANISM: Homo Sapien

<400> SEQUENCE: 324
```

Leu Gln Met Ile Leu Asn Gly Ile Asn Asn Tyr Lys Asn Pro Lys Leu
1               5                   10                  15

Thr Arg Met Leu Thr Phe Lys Phe Tyr Met Pro Lys Lys Ala Thr Glu
            20                  25                  30

Leu Lys His Leu Gln Cys Leu Glu Glu Glu Leu Lys Pro Leu Glu Glu
        35                  40                  45

Val Leu Asn Leu Ala Gln Ser Lys Asn Phe His Leu Arg Pro Arg Asp
50                  55                  60

Leu Ile Ser Asn Ile Asn Val Ile Val Leu Glu Leu Lys Gly Ser Glu
65                  70                  75                  80

Thr Thr Phe Met Cys Glu Tyr Ala Asp Glu Thr Ala Thr Ile Val Glu
                85                  90                  95

Phe Leu Asn Arg Trp Ile Thr Phe Cys Gln Ser Ile Ile Ser Thr Leu
            100                 105                 110

Thr

```
<210> SEQ ID NO 325
<211> LENGTH: 290
<212> TYPE: PRT
<213> ORGANISM: Mus Musculus

<400> SEQUENCE: 325
```

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 326
<211> LENGTH: 226
<212> TYPE: PRT
<213> ORGANISM: Mus Musculus

<400> SEQUENCE: 326

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His His His His
    210                 215                 220

His His
225

<210> SEQ ID NO 327
<211> LENGTH: 251
<212> TYPE: PRT
<213> ORGANISM: Homo Sapien

<400> SEQUENCE: 327

Glu Leu Cys Asp Asp Pro Pro Glu Ile Pro His Ala Thr Phe Lys
1               5                   10                  15

```
Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln Val Ala Val Ala Gly
            210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
            245                 250

<210> SEQ ID NO 328
<211> LENGTH: 525
<212> TYPE: PRT
<213> ORGANISM: Homo Sapien

<400> SEQUENCE: 328

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
```

```
                130             135             140
Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525

<210> SEQ ID NO 329
<211> LENGTH: 347
<212> TYPE: PRT
<213> ORGANISM: Homo Sapien
```

<400> SEQUENCE: 329

| | | | | | | | | | | | | | | |
|---|---|---|---|---|---|---|---|---|---|---|---|---|---|---|
| Leu | Asn | Thr | Thr | Ile | Leu | Thr | Pro | Asn | Gly | Asn | Glu | Asp | Thr | Thr | Ala |
| 1 | | | | 5 | | | | | 10 | | | | | 15 | |

Asp Phe Phe Leu Thr Thr Met Pro Thr Asp Ser Leu Ser Val Ser Thr
            20            25            30

Leu Pro Leu Pro Glu Val Gln Cys Phe Val Phe Asn Val Glu Tyr Met
      35              40              45

Asn Cys Thr Trp Asn Ser Ser Glu Pro Gln Pro Thr Asn Leu Thr
50              55              60

Leu His Tyr Trp Tyr Lys Asn Ser Asp Asn Asp Lys Val Gln Lys Cys
65              70            75            80

Ser His Tyr Leu Phe Ser Glu Glu Ile Thr Ser Gly Cys Gln Leu Gln
          85            90            95

Lys Lys Glu Ile His Leu Tyr Gln Thr Phe Val Val Gln Leu Gln Asp
        100            105          110

Pro Arg Glu Pro Arg Arg Gln Ala Thr Gln Met Leu Lys Leu Gln Asn
      115            120          125

Leu Val Ile Pro Trp Ala Pro Glu Asn Leu Thr Leu His Lys Leu Ser
130              135           140

Glu Ser Gln Leu Glu Leu Asn Trp Asn Asn Arg Phe Leu Asn His Cys
145              150          155          160

Leu Glu His Leu Val Gln Tyr Arg Thr Asp Trp Asp His Ser Trp Thr
          165          170          175

Glu Gln Ser Val Asp Tyr Arg His Lys Phe Ser Leu Pro Ser Val Asp
        180          185          190

Gly Gln Lys Arg Tyr Thr Phe Arg Val Arg Ser Arg Phe Asn Pro Leu
      195            200          205

Cys Gly Ser Ala Gln His Trp Ser Glu Trp Ser His Pro Ile His Trp
      210            215          220

Gly Ser Asn Thr Ser Lys Glu Asn Pro Phe Leu Phe Ala Leu Glu Ala
225              230          235          240

Val Val Ile Ser Val Gly Ser Met Gly Leu Ile Ile Ser Leu Leu Cys
          245          250          255

Val Tyr Phe Trp Leu Glu Arg Thr Met Pro Arg Ile Pro Thr Leu Lys
        260          265          270

Asn Leu Glu Asp Leu Val Thr Glu Tyr His Gly Asn Phe Ser Ala Trp
      275            280          285

Ser Gly Val Ser Lys Gly Leu Ala Glu Ser Leu Gln Pro Asp Tyr Ser
      290            295          300

Glu Arg Leu Cys Leu Val Ser Glu Ile Pro Pro Lys Gly Gly Ala Leu
305              310          315          320

Gly Glu Gly Pro Gly Ala Ser Pro Cys Asn Gln His Ser Pro Tyr Trp
        325          330          335

Ala Pro Pro Cys Tyr Thr Leu Lys Pro Glu Thr
        340          345

<210> SEQ ID NO 330
<211> LENGTH: 152
<212> TYPE: PRT
<213> ORGANISM: Homo Sapien

<400> SEQUENCE: 330

Asp Cys Asp Ile Glu Gly Lys Asp Gly Lys Gln Tyr Glu Ser Val Leu
1              5              10            15

```
Met Val Ser Ile Asp Gln Leu Leu Asp Ser Met Lys Glu Ile Gly Ser
         20                  25                  30

Asn Cys Leu Asn Asn Glu Phe Asn Phe Phe Lys Arg His Ile Cys Asp
         35                  40                  45

Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
             115                 120                 125

Cys Phe Leu Lys Arg Leu Leu Gln Glu Ile Lys Thr Cys Trp Asn Lys
         130                 135                 140

Ile Leu Met Gly Thr Lys Glu His
145                 150

<210> SEQ ID NO 331
<211> LENGTH: 133
<212> TYPE: PRT
<213> ORGANISM: Homo Sapien

<400> SEQUENCE: 331

Gly Ile His Val Phe Ile Leu Gly Cys Phe Ser Ala Gly Leu Pro Lys
  1               5                  10                  15

Thr Glu Ala Asn Trp Val Asn Val Ile Ser Asp Leu Lys Lys Ile Glu
             20                  25                  30

Asp Leu Ile Gln Ser Met His Ile Asp Ala Thr Leu Tyr Thr Glu Ser
                 35                  40                  45

Asp Val His Pro Ser Cys Lys Val Thr Ala Met Lys Cys Phe Leu Leu
 50                  55                  60

Glu Leu Gln Val Ile Ser Leu Glu Ser Gly Asp Ala Ser Ile His Asp
 65                  70                  75                  80

Thr Val Glu Asn Leu Ile Ile Leu Ala Asn Asn Ser Leu Ser Ser Asn
                 85                  90                  95

Gly Asn Val Thr Glu Ser Gly Cys Lys Glu Cys Glu Glu Leu Glu Glu
                100                 105                 110

Lys Asn Ile Lys Glu Phe Leu Gln Ser Phe Val His Ile Val Gln Met
             115                 120                 125

Phe Ile Asn Thr Ser
    130

<210> SEQ ID NO 332
<211> LENGTH: 133
<212> TYPE: PRT
<213> ORGANISM: Homo Sapien

<400> SEQUENCE: 332

Gln Gly Gln Asp Arg His Met Ile Arg Met Arg Gln Leu Ile Asp Ile
  1               5                  10                  15

Val Asp Gln Leu Lys Asn Tyr Val Asn Asp Leu Val Pro Glu Phe Leu
             20                  25                  30

Pro Ala Pro Glu Asp Val Glu Thr Asn Cys Glu Trp Ser Ala Phe Ser
                 35                  40                  45
```

```
Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
            130

<210> SEQ ID NO 333
<211> LENGTH: 127
<212> TYPE: PRT
<213> ORGANISM: Homo Sapien

<400> SEQUENCE: 333

Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
 50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
                100                 105                 110

Phe Leu Leu Val Ile Pro Phe Asp Cys Trp Glu Pro Val Gln Glu
            115                 120                 125

<210> SEQ ID NO 334
<211> LENGTH: 171
<212> TYPE: PRT
<213> ORGANISM: Homo Sapien

<400> SEQUENCE: 334

Cys Asp Leu Pro Gln Asn His Gly Leu Leu Ser Arg Asn Thr Leu Val
 1               5                  10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Lys Gly Ser Gln Leu
            35                  40                  45

Gln Lys Ala His Val Met Ser Val Leu His Glu Met Leu Gln Gln Ile
 50                  55                  60

Phe Ser Leu Phe His Thr Glu Arg Ser Ser Ala Ala Trp Asn Met Thr
 65                  70                  75                  80

Leu Leu Asp Gln Leu His Thr Glu Leu His Gln Gln Leu Gln His Leu
                85                  90                  95

Glu Thr Cys Leu Leu Gln Val Val Gly Glu Gly Glu Ser Ala Gly Ala
                100                 105                 110
```

-continued

```
Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser
                165                 170

<210> SEQ ID NO 335
<211> LENGTH: 177
<212> TYPE: PRT
<213> ORGANISM: Homo Sapien

<400> SEQUENCE: 335

Gly Pro Gln Arg Glu Glu Phe Pro Arg Asp Leu Ser Leu Ile Ser Pro
1               5                   10                  15

Leu Ala Gln Ala Val Arg Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Arg Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu

<210> SEQ ID NO 336
<211> LENGTH: 197
<212> TYPE: PRT
<213> ORGANISM: Homo Sapien

<400> SEQUENCE: 336

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80
```

```
Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
            130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
            165                 170                 175

Leu His Ala Phe Arg Ile Arg Ala Val Thr Ile Asp Arg Val Met Ser
            180                 185                 190

Tyr Leu Asn Ala Ser
            195

<210> SEQ ID NO 337
<211> LENGTH: 306
<212> TYPE: PRT
<213> ORGANISM: Homo Sapien

<400> SEQUENCE: 337

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255
```

-continued

```
Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
            275                 280                 285

Gln Asp Arg Tyr Tyr Ser Ser Trp Ser Glu Trp Ala Ser Val Pro
        290                 295                 300

Cys Ser
305

<210> SEQ ID NO 338
<211> LENGTH: 103
<212> TYPE: PRT
<213> ORGANISM: Homo Sapien

<400> SEQUENCE: 338

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Trp Glu Lys Gln Val Ser Gln Lys Lys Lys Gln Lys Asn Gly
65                  70                  75                  80

Lys Lys His Gln Lys Lys Lys Val Leu Lys Val Arg Lys Ser Gln Arg
                85                  90                  95

Ser Arg Gln Lys Lys Thr Thr
            100

<210> SEQ ID NO 339
<211> LENGTH: 77
<212> TYPE: PRT
<213> ORGANISM: Homo Sapien

<400> SEQUENCE: 339

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 340
<211> LENGTH: 330
<212> TYPE: PRT
<213> ORGANISM: Homo Sapien

<400> SEQUENCE: 340

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 341
<211> LENGTH: 996
<212> TYPE: DNA
<213> ORGANISM: Homo Sapien

<400> SEQUENCE: 341
gccagcacca agggcccctc tgtgttccct ctggcccctt ccagcaagtc cacctctggc     60
ggaacagccg ctctgggctg cctcgtgaag gactacttcc ccgagcctgt gaccgtgtcc    120
tggaactctg gcgctctgac cagcggagtg cacaccttcc ctgctgtgct gcagtcctcc    180
ggcctgtact ccctgtcctc cgtcgtgacc gtgccttcca gctctctggg cacccagacc    240
tacatctgca acgtgaacca caagccctcc aacaccaagg tggacaagaa ggtggaaccc    300
aagtcctgcg acaagaccca cacctgtccc cttgtcctg ccctgaact gctgggcgga    360 ccttccgtgt tcctgttccc cccaaagccc aaggacaccc tgatgatctc ccggacccc     420

```
gaagtgacct gcgtggtggt ggatgtgtcc cacgaggacc ctgaagtgaa gttcaattgg    480
tacgtggacg gcgtggaagt gcacaacgcc aagaccaagc ctagagagga acagtacaac    540
tccacctacc gggtggtgtc cgtgctgacc gtgctgcacc aggattggct gaacggcaaa    600
gagtacaagt gcaaggtgtc caacaaggcc ctgcctgccc ccatcgaaaa gaccatctcc    660
aaggccaagg ccagccccg ggaaccccag gtgtacacac tgcccctag cagggacgag     720 ctgaccaaga accaggtgtc cctgacctgt ctcgtgaaag gcttctaccc ctccgatatc    780
gccgtggaat gggagtccaa cggccagcct gagaacaact acaagaccac cccccctgtg    840
ctggactccg acggctcatt cttcctgtac agcaagctga cagtggacaa gtcccggtgg    900
cagcagggca acgtgttctc ctgctccgtg atgcacgagg ccctgcacaa ccactacacc    960
cagaagtccc tgtccctgag ccccggcaag tgatga                              996
```

```
<210> SEQ ID NO 342
<211> LENGTH: 450
<212> TYPE: PRT
<213> ORGANISM: Homo Sapien

<400> SEQUENCE: 342

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270
```

```
Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
                385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 343
<211> LENGTH: 8
<212> TYPE: PRT
<213> ORGANISM: Homo Sapien

<400> SEQUENCE: 343

Gly Phe Thr Phe Ser Asn Tyr Ala
1               5

<210> SEQ ID NO 344
<211> LENGTH: 8
<212> TYPE: PRT
<213> ORGANISM: Homo Sapien

<400> SEQUENCE: 344

Ile Ser Phe Ser Gly Gly Thr Thr
1               5

<210> SEQ ID NO 345
<211> LENGTH: 14
<212> TYPE: PRT
<213> ORGANISM: Homo Sapien

<400> SEQUENCE: 345

Ala Lys Asp Glu Ala Pro Ala Gly Ala Thr Phe Phe Asp Ser
1               5                   10

<210> SEQ ID NO 346
<211> LENGTH: 5
<212> TYPE: PRT
<213> ORGANISM: Homo Sapien

<400> SEQUENCE: 346

Asn Tyr Ala Met Ser
1               5
```

<210> SEQ ID NO 347
<211> LENGTH: 17
<212> TYPE: PRT
<213> ORGANISM: Homo Sapien

<400> SEQUENCE: 347

Ala Ile Ser Phe Ser Gly Gly Thr Thr Tyr Tyr Ala Asp Ser Val Lys
1               5                   10                  15
Gly

<210> SEQ ID NO 348
<211> LENGTH: 12
<212> TYPE: PRT
<213> ORGANISM: Homo Sapien

<400> SEQUENCE: 348

Asp Glu Ala Pro Ala Gly Ala Thr Phe Phe Asp Ser
1               5                   10

<210> SEQ ID NO 349
<211> LENGTH: 121
<212> TYPE: PRT
<213> ORGANISM: Homo Sapien

<400> SEQUENCE: 349

Glu Val Gln Leu Ala Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Gly Lys Gly Leu Glu Trp Val
        35                  40                  45

Ser Ala Ile Ser Phe Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Asp Asp Thr Ala Val Tyr Tyr Cys
                85                  90                  95

Ala Lys Asp Glu Ala Pro Ala Gly Ala Thr Phe Phe Asp Ser Trp Gly
            100                 105                 110

Gln Gly Thr Leu Val Thr Val Ser Ser
        115                 120

<210> SEQ ID NO 350
<211> LENGTH: 364
<212> TYPE: DNA
<213> ORGANISM: Homo Sapien

<400> SEQUENCE: 350
gaagtgcaac tggcggagtc tgggggaggc ttggtacagc cggggggtc cctgagactc        60 tcctgtgcag cctctggatt cacctttagc aactatgcca tgagttgggt ccgccagact      120
ccaggaaagg gctggagtg gtctcagct attagttta gtggtggtac tacatactac        180
gctgactccg tgaagggccg gttcaccatc tccagagaca attccaagaa cacgctgtat      240
ttgcacatga acagcctgag agccgatgac acggccgtat attactgtgc gaaagatgag      300
gcaccagctg gcgcaacctt ctttgactcc tggggccagg gaacgctggt caccgtctcc      360
tcag                                                                   364

<210> SEQ ID NO 351
<211> LENGTH: 448
<212> TYPE: PRT
<213> ORGANISM: Homo Sapien

<400> SEQUENCE: 351

```
Glu Val Gln Leu Ala Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Gly Lys Gly Leu Glu Trp Val
        35                  40                  45

Ser Ala Ile Ser Phe Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu His Met Asn Ser Leu Arg Ala Asp Asp Thr Ala Val Tyr Tyr Cys
                85                  90                  95

Ala Lys Asp Glu Ala Pro Ala Gly Ala Thr Phe Phe Asp Ser Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
        435                 440                 445

<210> SEQ ID NO 352
<211> LENGTH: 1344
<212> TYPE: DNA
<213> ORGANISM: Homo Sapien

<400> SEQUENCE: 352

```
gaagtgcaac tggcggagtc tgggggaggc ttggtacagc cggggggggtc cctgagactc    60
tcctgtgcag cctctggatt cacctttagc aactatgcca tgagttgggt ccgccagact   120
ccaggaaagg ggctggagtg ggtctcagct attagtttta gtggtggtac tacatactac   180
gctgactccg tgaagggccg gttcaccatc tccagagaca attccaagaa cacgctgtat   240
ttgcacatga acagcctgag agccgatgac acggccgtat attactgtgc gaaagatgag   300
gcaccagctg gcgcaaacctt cttgactcc tggggcagg gaacgctggt caccgtctcc   360
tcagccagca ccaagggccc ttccgtgttc ccctggccc cttgcagcag gagcacctcc   420
gaatccacag ctgccctggg ctgtctggtg aaggactact ttcccgagcc cgtgaccgtg   480
agctggaaca gcggcgctct gacatccggc gtccacacct ttcctgccgt cctgcagtcc   540
tccggcctct actccctgtc ctccgtggtg accgtgccta gctcctcct cggcaccaag   600
acctacacct gtaacgtgga ccacaaaccc tccaacacca aggtggacaa acgggtcgag   660
agcaagtacg gccctcccctg ccctccttgt cctgcccccg agttcgaagg cggacccagc   720
gtgttcctgt tccctcctaa gcccaaggac acctcatga tcagccggac acccgaggtg   780
acctgcgtgg tggtggatgt gagccaggag gaccctgagg tccagttcaa ctggtatgtg   840
gatggcgtgg aggtgcacaa cgccaagaca aagccccggg aagagcagtt caactccacc   900
tacagggtgg tcagcgtgct gaccgtgctg catcaggact ggctgaacgg caaggagtac   960
aagtgcaagg tcagcaataa gggactgccc agcagcatcg agaagaccat ctccaaggct  1020
aaaggccagc ccgggaacc tcaggtgtac accctgcctc ccagccagga ggagatgacc  1080
aagaaccagg tgagcctgac ctgcctggtg aagggattct accttccga catcgccgtg  1140
gagtgggagt ccaacggcca gcccgagaac aattataaga ccaccctcc cgtcctcgac  1200
agcgacggat ccttctttct gtactccagg ctgaccgtgg ataagtccag gtggcaggaa  1260
ggcaacgtgt tcagctgctc cgtgatgcac gaggccctgc acaatcacta cacccagaag  1320
tccctgagcc tgtccctggg aaag                                         1344
```

<210> SEQ ID NO 353
<211> LENGTH: 6
<212> TYPE: PRT
<213> ORGANISM: Homo Sapien

<400> SEQUENCE: 353

Gln Gly Ile Arg Arg Trp
1               5

```
<210> SEQ ID NO 354
<211> LENGTH: 3
<212> TYPE: PRT
<213> ORGANISM: Homo Sapien

<400> SEQUENCE: 354

Gly Ala Ser
1

<210> SEQ ID NO 355
<211> LENGTH: 9
<212> TYPE: PRT
<213> ORGANISM: Homo Sapien

<400> SEQUENCE: 355

Gln Gln Ala Asn Ser Phe Pro Ile Thr
1               5

<210> SEQ ID NO 356
<211> LENGTH: 11
<212> TYPE: PRT
<213> ORGANISM: Homo Sapien

<400> SEQUENCE: 356

Arg Ala Ser Gln Gly Ile Arg Arg Trp Leu Ala
1               5                   10

<210> SEQ ID NO 357
<211> LENGTH: 7
<212> TYPE: PRT
<213> ORGANISM: Homo Sapien

<400> SEQUENCE: 357

Gly Ala Ser Ser Leu Gln Ser
1               5

<210> SEQ ID NO 358
<211> LENGTH: 9
<212> TYPE: PRT
<213> ORGANISM: Homo Sapien

<400> SEQUENCE: 358

Gln Gln Ala Asn Ser Phe Pro Ile Thr
1               5

<210> SEQ ID NO 359
<211> LENGTH: 107
<212> TYPE: PRT
<213> ORGANISM: Homo Sapien

<400> SEQUENCE: 359

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Arg Trp
            20                  25                  30

Leu Ala Trp Tyr Gln Gln Lys Pro Gly Lys Ala Pro Lys Leu Leu Ile
        35                  40                  45

Ser Gly Ala Ser Ser Leu Gln Ser Gly Val Pro Ser Arg Phe Ser Gly
    50                  55                  60

Ser Gly Ser Gly Thr Asp Phe Thr Leu Ile Ile Thr Ser Leu Gln Pro
65                  70                  75                  80

Glu Asp Phe Ala Thr Tyr Tyr Cys Gln Gln Ala Asn Ser Phe Pro Ile
                85                  90                  95
```

```
Thr Phe Gly Gln Gly Thr Arg Leu Glu Ile Lys
            100                 105
```

<210> SEQ ID NO 360
<211> LENGTH: 322
<212> TYPE: DNA
<213> ORGANISM: Homo Sapien

<400> SEQUENCE: 360

```
gacatccaga tgacccagtc tccatcttcc gtgtctgcat ctgtaggaga cagagtcacc      60
atcacttgtc gggcgagtca gggtattagg aggtggttag cctggtatca gcagaaacca    120
gggaaagccc ctaaactcct gatctctggt gcatccagtt tgcaaagtgg ggtcccatca    180
aggttcagcg gcagtggatc tgggacagat ttcactctca tcattaccag tctgcagcct    240
gaagattttg caacttacta ttgtcaacag gctaacagtt cccgatcac cttcggccaa     300
gggacacgac tggagatcaa ac                                              322
```

<210> SEQ ID NO 361
<211> LENGTH: 214
<212> TYPE: PRT
<213> ORGANISM: Homo Sapien

<400> SEQUENCE: 361

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Arg Trp
            20                  25                  30

Leu Ala Trp Tyr Gln Gln Lys Pro Gly Lys Ala Pro Lys Leu Leu Ile
        35                  40                  45

Ser Gly Ala Ser Ser Leu Gln Ser Gly Val Pro Ser Arg Phe Ser Gly
    50                  55                  60

Ser Gly Ser Gly Thr Asp Phe Thr Leu Ile Ile Thr Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 362
<211> LENGTH: 642
<212> TYPE: DNA
<213> ORGANISM: Homo Sapien

<400> SEQUENCE: 362

```
gacatccaga tgacccagtc tccatcttcc gtgtctgcat ctgtaggaga cagagtcacc    60
atcacttgtc gggcgagtca gggtattagg aggtggttag cctggtatca gcagaaacca   120
gggaaagccc ctaaactcct gatctctggt gcatccagtt tgcaaagtgg ggtcccatca   180
aggttcagcg gcagtggatc tgggacagat ttcactctca tcattaccag tctgcagcct   240
gaagattttg caacttacta ttgtcaacag gctaacagtt tcccgatcac cttcggccaa   300
gggacacgac tggagatcaa acgtacggtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg acaacgccc tgcagtccgg caactcccag   480
gaatccgtga ccgagcagga ctccaaggac agcacctact ccctgtcctc caccctgacc   540
ctgtccaagg ccgactacga gaagcacaag gtgtacgcct gcgaagtgac ccaccagggc   600
ctgtctagcc ccgtgaccaa gtctttcaac cggggcgagt gt                      642
```

<210> SEQ ID NO 363
<211> LENGTH: 8
<212> TYPE: PRT
<213> ORGANISM: Homo Sapien

<400> SEQUENCE: 363

Gly Tyr Thr Phe Ser Thr Phe Gly
1               5

<210> SEQ ID NO 364
<211> LENGTH: 8
<212> TYPE: PRT
<213> ORGANISM: Homo Sapien

<400> SEQUENCE: 364

Ile Ser Ala Tyr Asn Gly Asp Thr
1               5

<210> SEQ ID NO 365
<211> LENGTH: 14
<212> TYPE: PRT
<213> ORGANISM: Homo Sapien

<400> SEQUENCE: 365

Ala Arg Ser Ser Gly His Tyr Tyr Tyr Gly Met Asp Val
1               5                   10

<210> SEQ ID NO 366
<211> LENGTH: 121
<212> TYPE: PRT
<213> ORGANISM: Homo Sapien

<400> SEQUENCE: 366

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Phe
                20                  25                  30

Gly Ile Thr Trp Val Arg Gln Ala Pro Gly Gln Gly Leu Glu Trp Met
            35                  40                  45

Gly Trp Ile Ser Ala Tyr Asn Gly Asp Thr Asn Tyr Ala Gln Asn Leu
        50                  55                  60

Gln Gly Arg Val Ile Met Thr Thr Asp Thr Ser Thr Ser Thr Ala Tyr

```
                65                  70                  75                  80
Met Glu Leu Arg Ser Leu Arg Ser Asp Asp Thr Ala Val Tyr Tyr Cys
                    85                  90                  95

Ala Arg Ser Ser Gly His Tyr Tyr Tyr Gly Met Asp Val Trp Gly
                100                 105                 110

Gln Gly Thr Thr Val Thr Val Ser Ser
                115                 120

<210> SEQ ID NO 367
<211> LENGTH: 363
<212> TYPE: DNA
<213> ORGANISM: Homo Sapien

<400> SEQUENCE: 367
caggttcagg tggtgcagtc tggagctgag gtgaagaagc ctggggcctc agtgaaggtc      60
tcctgcaagg cttctggtta caccttttcc acctttggta tcacctgggt gcgacaggcc     120
cctggacaag gcttgaatg gatgggatgg atcagcgctt acaatggtga cacaaactat      180
gcacagaatc tccagggcag agtcatcatg accacagaca catccacgag cacagcctac     240
atggagctga ggagcctgag atctgacgac acggccgttt attactgtgc gaggagcagt     300
ggccactact actactacgg tatggacgtc tggggccaag gaccacggt caccgtctcc     360 tca                                                                    363

<210> SEQ ID NO 368
<211> LENGTH: 451
<212> TYPE: PRT
<213> ORGANISM: Homo Sapien

<400> SEQUENCE: 368

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Phe
                20                  25                  30

Gly Ile Thr Trp Val Arg Gln Ala Pro Gly Gln Gly Leu Glu Trp Met
                35                  40                  45

Gly Trp Ile Ser Ala Tyr Asn Gly Asp Thr Asn Tyr Ala Gln Asn Leu
        50                  55                  60

Gln Gly Arg Val Ile Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Ser Ser Gly His Tyr Tyr Tyr Gly Met Asp Val Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205
```

```
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450

<210> SEQ ID NO 369
<211> LENGTH: 1359
<212> TYPE: DNA
<213> ORGANISM: Homo Sapien

<400> SEQUENCE: 369
caggttcagg tggtgcagtc tggagctgag gtgaagaagc tggggcctc  agtgaaggtc      60 tcctgcaagg cttctggtta cacctttcc  acctttggta tcacctgggt gcgacaggcc     120
cctggacaag gcttgaatg  gatgggatgg atcagcgctt acaatggtga cacaaactat     180
gcacagaatc tccagggcag agtcatcatg accacagaca catccacgag cacagcctac     240
atggagctga ggagcctgag atctgacgac acggccgttt attactgtgc gaggagcagt     300
ggccactact actactacgg tatggacgtc tggggccaag ggaccacggt caccgtctcc     360
tcagccagca ccaagggccc ctctgtgttc cctctggccc cttccagcaa gtccacctct     420
ggcggaacag ccgctctggg ctgcctcgtg aaggactact ccccgagcc  tgtgaccgtg     480 tcctggaact ctggcgctct gaccagcgga gtgcacacct ccctgctgt  gctgcagtcc     540 tccggcctgt actccctgtc ctccgtcgtg accgtgcctt ccagctctct gggcacccag     600
acctacatct gcaacgtgaa ccacaagccc tccaacacca  aggtggacaa gaaggtggaa     660
```

-continued

```
cccaagtcct gcgacaagac ccacacctgt cccccttgtc ctgcccctga actgctgggc    720
ggaccttccg tgttcctgtt cccccccaaag cccaaggaca ccctgatgat ctcccggacc   780
cccgaagtga cctgcgtggt ggtggatgtg tcccacgagg accctgaagt gaagttcaat    840
tggtacgtgg acggcgtgga agtgcacaac gccaagacca gcctagaga ggaacagtac     900 aactccacct accgggtggt gtccgtgctg accgtgctgc accaggattg gctgaacggc    960
aaagagtaca gtgcaaggt gtccaacaag gccctgcctg cccccatcga aaagaccatc    1020
tccaaggcca agggccagcc ccgggaaccc caggtgtaca cactgccccc tagcagggac   1080
gagctgacca gaaccaggt gtccctgacc tgtctcgtga aaggcttcta ccctcccgat    1140
atcgccgtgg aatgggagtc caacggccag cctgagaaca actacaagac cacccccct    1200 gtgctggact ccgacggctc attcttcctg tacagcaagc tgacagtgga caagtcccgg   1260
tggcagcagg gcaacgtgtt ctcctgctcc gtgatgcacg aggccctgca caaccactac   1320
acccagaagt ccctgtccct gagccccggc aagtgatga                          1359
```

<210> SEQ ID NO 370
<211> LENGTH: 11
<212> TYPE: PRT
<213> ORGANISM: Homo Sapien

<400> SEQUENCE: 370

Gln Ser Leu Leu His Ser Asn Glu Tyr Asn Tyr
1               5                   10

<210> SEQ ID NO 371
<211> LENGTH: 3
<212> TYPE: PRT
<213> ORGANISM: Homo Sapien

<400> SEQUENCE: 371

Leu Gly Ser
1

<210> SEQ ID NO 372
<211> LENGTH: 9
<212> TYPE: PRT
<213> ORGANISM: Homo Sapien

<400> SEQUENCE: 372

Met Gln Ser Leu Gln Thr Pro Leu Thr
1               5

<210> SEQ ID NO 373
<211> LENGTH: 112
<212> TYPE: PRT
<213> ORGANISM: Homo Sapien

<400> SEQUENCE: 373

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Glu Tyr Asn Tyr Leu Asp Trp Tyr Leu Gln Lys Pro Gly Gln Ser
            35                  40                  45

Pro Gln Leu Leu Ile Phe Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Ile Tyr Tyr Cys Met Gln Ser
            85                  90                  95

Leu Gln Thr Pro Leu Thr Phe Gly Gly Gly Thr Lys Val Glu Ile Lys
            100                 105                 110

<210> SEQ ID NO 374
<211> LENGTH: 336
<212> TYPE: DNA
<213> ORGANISM: Homo Sapien

<400> SEQUENCE: 374
gatattgtga tgactcagtc tccactctcc ctgcccgtca cccctggaga gccggcctcc      60
atctcctgca ggtctagtca gagcctcctg catagtaatg aatacaacta tttggattgg     120
tacctgcaga agccagggca gtctccacag ctcctgatct ttttgggttc taatcgggcc     180
tccggggtcc ctgacaggtt cagtggcagt ggatcaggca cagatttttac actgaaaatc     240 accagagtgg aggctgagga tgttggaatt tattactgca tgcaatctct acaaactccg     300
ctcactttcg gcggagggac caaggtggag atcaaa                               336

<210> SEQ ID NO 375
<211> LENGTH: 219
<212> TYPE: PRT
<213> ORGANISM: Homo Sapien

<400> SEQUENCE: 375

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Glu Tyr Asn Tyr Leu Asp Trp Tyr Leu Gln Lys Pro Gly Gln Ser
        35                  40                  45

Pro Gln Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Ile Tyr Tyr Cys Met Gln Ser
            85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 376

<211> LENGTH: 657
<212> TYPE: DNA
<213> ORGANISM: Homo Sapien

<400> SEQUENCE: 376

```
gatattgtga tgactcagtc tccactctcc ctgcccgtca cccctggaga gccggcctcc      60
atctcctgca ggtctagtca gagcctcctg catagtaatg aatacaacta tttggattgg     120
tacctgcaga agccagggca gtctccacag ctcctgatct ttttgggttc taatcgggcc     180
tccggggtcc ctgacaggtt cagtggcagt ggatcaggca cagattttac actgaaaatc     240
accagagtgg aggctgagga tgttggaatt tattactgca tgcaatctct acaaactccg     300
ctcactttcg gcggagggac caaggtggag atcaaacgta cggtggccgc tcccteegtg     360
ttcatcttcc caccttccga cgagcagctg aagtccggca ccgcttctgt cgtgtgcctg     420
ctgaacaact ctacccccg cgaggccaag gtgcagtgga aggtggacaa cgccctgcag     480
tccggcaact cccaggaatc cgtgaccgag caggactcca aggacagcac ctactccctg     540
tcctccaccc tgaccctgtc caaggccgac tacgagaagc acaaggtgta cgcctgcgaa     600
gtgacccacc agggcctgtc tagccccgtg accaagtctt caaccgggg cgagtgt         657
```

<210> SEQ ID NO 377
<211> LENGTH: 8
<212> TYPE: PRT
<213> ORGANISM: Homo Sapien

<400> SEQUENCE: 377

Gly Tyr Thr Phe Thr Ser Tyr Gly
1               5

<210> SEQ ID NO 378
<211> LENGTH: 8
<212> TYPE: PRT
<213> ORGANISM: Homo Sapien

<400> SEQUENCE: 378

Ile Ser Ala Tyr Asn Gly Asn Thr
1               5

<210> SEQ ID NO 379
<211> LENGTH: 17
<212> TYPE: PRT
<213> ORGANISM: Homo Sapien

<400> SEQUENCE: 379

Ala Arg Ser Thr Tyr Phe Tyr Gly Ser Gly Thr Leu Tyr Gly Met Asp
1               5                   10                  15
Val

<210> SEQ ID NO 380
<211> LENGTH: 124
<212> TYPE: PRT
<213> ORGANISM: Homo Sapien

<400> SEQUENCE: 380

Gln Val Gln Leu Val Gln Ser Gly Gly Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
                100                 105                 110

Val Trp Gly Gln Gly Thr Thr Val Thr Val Ser Ser
            115                 120

<210> SEQ ID NO 381
<211> LENGTH: 372
<212> TYPE: DNA
<213> ORGANISM: Homo Sapien

<400> SEQUENCE: 381
caggttcaac tggtgcagtc tggaggtgag gtgaagaagc ctggggcctc agtgaaggtc     60
tcctgcaagg cttctggtta cacctttacc agctatggtt tcagctgggt gcgacaggcc    120
cctggacaag actagagtg gatgggatgg atcagcgctt acaatggtaa cacaaactat    180
gcacagaagc tccagggcag agtcaccatg accacagaca tccacgag cacagcctac     240 atggagctga ggagcttgag atctgacgac acggccgtgt attactgtgc gagatctacg    300
tatttctatg gttcggggac cctctacggt atggacgtct ggggccaagg gaccacggtc    360
accgtctcct ca                                                        372

<210> SEQ ID NO 382
<211> LENGTH: 454
<212> TYPE: PRT
<213> ORGANISM: Homo Sapien

<400> SEQUENCE: 382

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Phe Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 383
<211> LENGTH: 1368
<212> TYPE: DNA
<213> ORGANISM: Homo Sapien

<400> SEQUENCE: 383
caggttcaac tggtgcagtc tggaggtgag gtgaagaagc tggggcctc agtgaaggtc      60 tcctgcaagg cttctggtta caccttacc agctatggtt tcagctgggt gcgacaggcc     120
cctggacaag actagagtg gatgggatgg atcagcgctt acaatggtaa cacaaactat    180
gcacagaagc tccagggcag agtcaccatg accacagaca catccacgag cacagcctac    240
atggagctga ggagcttgag atctgacgac acggccgtgt attactgtgc agatctacg    300 tatttctatg gttcggggac cctctacggt atggacgtct ggggccaagg gaccacggtc    360
accgtctcct cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540

```
ctgcagtcct ccggcctgta ctccctgtcc tccgtcgtga ccgtgccttc cagctctctg      600
ggcacccaga cctacatctg caacgtgaac cacaagccct ccaacaccaa ggtggacaag      660
aaggtggaac ccaagtcctg cgacaagacc cacacctgtc cccttgtcc tgcccctgaa       720 ctgctgggcg gaccttccgt gttcctgttc cccccaaagc caaggacac cctgatgatc       780 tcccggaccc ccgaagtgac ctgcgtggtg gtggatgtgt cccacgagga ccctgaagtg      840
aagttcaatt ggtacgtgga cggcgtgaa gtgcacaacg ccaagaccaa gcctagagag       900
gaacagtaca actccaccta ccgggtggtg tccgtgctga ccgtgctgca ccaggattgg      960
ctgaacggca aagagtacaa gtgcaaggtg tccaacaagg ccctgcctgc ccccatcgaa     1020
aagaccatct ccaaggccaa gggccagccc cgggaacccc aggtgtacac actgcccccct   1080 agcagggacg agctgaccaa gaaccaggtg tccctgacct gtctcgtgaa aggcttctac     1140
ccctccgata tcgccgtgga atgggagtcc aacggccagc tgagaacaa ctacaagacc      1200 accccccctg tgctggactc cgacggctca ttcttcctgt acagcaagct gacagtggac     1260
aagtcccggt ggcagcaggg caacgtgttc tcctgctccg tgatgcacga ggccctgcac     1320
aaccactaca cccagaagtc cctgtccctg agccccggca agtgatga                   1368
```

<210> SEQ ID NO 384
<211> LENGTH: 11
<212> TYPE: PRT
<213> ORGANISM: Homo Sapien

<400> SEQUENCE: 384

Gln Ser Leu Leu His Ser Asp Gly Tyr Asn Tyr
1               5                   10

<210> SEQ ID NO 385
<211> LENGTH: 3
<212> TYPE: PRT
<213> ORGANISM: Homo Sapien

<400> SEQUENCE: 385

Leu Gly Ser
1

<210> SEQ ID NO 386
<211> LENGTH: 9
<212> TYPE: PRT
<213> ORGANISM: Homo Sapien

<400> SEQUENCE: 386

Met Gln Ala Leu Gln Thr Pro Leu Ser
1               5

<210> SEQ ID NO 387
<211> LENGTH: 112
<212> TYPE: PRT
<213> ORGANISM: Homo Sapien

<400> SEQUENCE: 387

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Tyr Asn Tyr Leu Asp Trp Tyr Leu Gln Lys Pro Gly Gln Ser
            35                  40                  45

```
Pro Gln Leu Leu Ile Tyr Leu Gly Ser Thr Arg Ala Ser Gly Phe Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ser Phe Gly Gln Gly Thr Lys Leu Glu Ile Lys
                100                 105                 110
```

<210> SEQ ID NO 388
<211> LENGTH: 336
<212> TYPE: DNA
<213> ORGANISM: Homo Sapien

<400> SEQUENCE: 388

```
gatattgtga tgactcagtc tccactctcc ctgcccgtca cccctggaga gccggcctcc    60
atctcctgca ggtctagtca gagcctcctg catagtgatg gatacaactg tttggattgg   120
tacctgcaga agccagggca gtctccacag ctcctgatct atttgggttc tactcgggcc   180 tccggggttcc ctgacaggtt cagtggcagt ggatcaggca cagattttac actgaaaatc   240
agcagagtgg aggctgagga tgttggggtt tattactgca tgcaagctct acaaactccg   300
tgcagttttg gccaggggac caagctggag atcaaa                             336
```

<210> SEQ ID NO 389
<211> LENGTH: 219
<212> TYPE: PRT
<213> ORGANISM: Homo Sapien

<400> SEQUENCE: 389

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Tyr Asn Tyr Leu Asp Trp Tyr Leu Gln Lys Pro Gly Gln Ser
            35                  40                  45

Pro Gln Leu Leu Ile Tyr Leu Gly Ser Thr Arg Ala Ser Gly Phe Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ser Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 390
<211> LENGTH: 657
<212> TYPE: DNA
<213> ORGANISM: Homo Sapien

<400> SEQUENCE: 390
gatattgtga tgactcagtc tccactctcc ctgcccgtca cccctggaga gccggcctcc      60
atctcctgca ggtctagtca gagcctcctg catagtgatg gatacaactg tttggattgg    120
tacctgcaga agccagggca gtctccacag ctcctgatct atttgggttc tactcgggcc    180
tccgggttcc ctgacaggtt cagtggcagt ggatcaggca cagattttac actgaaaatc    240
agcagagtgg aggctgagga tgttggggtt tattactgca tgcaagctct acaaactccg    300
tgcagttttg gccaggggac caagctggag atcaaacgta cggtggccgc tcccccgtg     360 ttcatcttcc caccttccga cgagcagctg aagtccggca ccgcttctgt cgtgtgcctg    420
ctgaacaact tctaccccg cgaggccaag gtgcagtgga aggtggacaa cgccctgcag     480
tccggcaact cccaggaatc cgtgaccgag caggactcca aggacagcac ctactccctg    540
tcctccaccc tgaccctgtc aaggccgac tacgagaagc acaaggtgta cgcctgcgaa     600
gtgacccacc agggcctgtc tagccccgtg accaagtctt tcaaccgggg cgagtgt     657

<210> SEQ ID NO 391
<211> LENGTH: 8
<212> TYPE: PRT
<213> ORGANISM: Homo Sapien

<400> SEQUENCE: 391

Gly Tyr Thr Phe Thr Ser Tyr Gly
1               5

<210> SEQ ID NO 392
<211> LENGTH: 8
<212> TYPE: PRT
<213> ORGANISM: Homo Sapien

<400> SEQUENCE: 392

Ile Ser Ala Tyr Asn Gly Asn Thr
1               5

<210> SEQ ID NO 393
<211> LENGTH: 17
<212> TYPE: PRT
<213> ORGANISM: Homo Sapien

<400> SEQUENCE: 393

Ala Arg Ser Thr Tyr Phe Tyr Gly Ser Gly Thr Leu Tyr Gly Met Asp
1               5                   10                  15

Val

<210> SEQ ID NO 394
<211> LENGTH: 124
<212> TYPE: PRT
<213> ORGANISM: Homo Sapien

<400> SEQUENCE: 394

Gln Val Gln Leu Val Gln Ser Gly Gly Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
                100                 105                 110

Val Trp Gly Gln Gly Thr Thr Val Thr Val Ser Ser
            115                 120
```

<210> SEQ ID NO 395
<211> LENGTH: 372
<212> TYPE: DNA
<213> ORGANISM: Homo Sapien

<400> SEQUENCE: 395

```
caggttcaac tggtgcagtc tggaggtgag gtgaagaagc ctggggcctc agtgaaggtc      60
tcctgcaagg cttctggtta cacctttacc agctatggtt tcagctgggt gcgacaggcc     120
cctggacaag gactagagtg gatgggatgg atcagcgctt acaatggtaa cacaaactat     180
gcacagaagc tccagggcag agtcaccatg accacagaca catccacgag cacagcctac     240
atggagctga ggagcttgag atctgacgac acggccgtgt attactgtgc gagatctacg     300
tatttctatg gttcggggac cctctacggt atggacgtct ggggccaagg gaccacggtc     360
accgtctcct ca                                                         372
```

<210> SEQ ID NO 396
<211> LENGTH: 454
<212> TYPE: PRT
<213> ORGANISM: Homo Sapien

<400> SEQUENCE: 396

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Val | Thr | Val | Ser | Trp | Asn | Ser | Gly | Ala | Leu | Thr | Ser | Gly | Val | His | Thr |
|     |     |     |     |     | 165 |     |     |     |     | 170 |     |     |     |     | 175 |

Phe Pro Ala Val Leu Gln Ser Ser Gly Leu Tyr Ser Leu Ser Ser Val
                180                    185                    190

Val Thr Val Pro Ser Ser Ser Leu Gly Thr Gln Thr Tyr Ile Cys Asn
        195                    200                    205

Val Asn His Lys Pro Ser Asn Thr Lys Val Asp Lys Lys Val Glu Pro
  210                    215                    220

Lys Ser Cys Asp Lys Thr His Thr Cys Pro Pro Cys Pro Ala Pro Glu
225                  230                    235                    240

Leu Leu Gly Gly Pro Ser Val Phe Leu Phe Pro Pro Lys Pro Lys Asp
                245                    250                    255

Thr Leu Met Ile Ser Arg Thr Pro Glu Val Thr Cys Val Val Val Asp
        260                    265                    270

Val Ser His Glu Asp Pro Glu Val Lys Phe Asn Trp Tyr Val Asp Gly
    275                    280                    285

Val Glu Val His Asn Ala Lys Thr Lys Pro Arg Glu Glu Gln Tyr Asn
290                  295                    300

Ser Thr Tyr Arg Val Val Ser Val Leu Thr Val Leu His Gln Asp Trp
305                  310                    315                    320

Leu Asn Gly Lys Glu Tyr Lys Cys Lys Val Ser Asn Lys Ala Leu Pro
                325                    330                    335

Ala Pro Ile Glu Lys Thr Ile Ser Lys Ala Lys Gly Gln Pro Arg Glu
        340                    345                    350

Pro Gln Val Tyr Thr Leu Pro Pro Ser Arg Asp Glu Leu Thr Lys Asn
    355                    360                    365

Gln Val Ser Leu Thr Cys Leu Val Lys Gly Phe Tyr Pro Ser Asp Ile
370                  375                    380

Ala Val Glu Trp Glu Ser Asn Gly Gln Pro Glu Asn Asn Tyr Lys Thr
385                  390                    395                    400

Thr Pro Pro Val Leu Asp Ser Asp Gly Ser Phe Phe Leu Tyr Ser Lys
                405                    410                    415

Leu Thr Val Asp Lys Ser Arg Trp Gln Gln Gly Asn Val Phe Ser Cys
        420                    425                    430

Ser Val Met His Glu Ala Leu His Asn His Tyr Thr Gln Lys Ser Leu
    435                    440                    445

Ser Leu Ser Pro Gly Lys
    450

<210> SEQ ID NO 397
<211> LENGTH: 1368
<212> TYPE: DNA
<213> ORGANISM: Homo Sapien

<400> SEQUENCE: 397
caggttcaac tggtgcagtc tggaggtgag gtgaagaagc ctggggcctc agtgaaggtc    60
tcctgcaagg cttctggtta cacctttacc agctatggtt tcagctgggt gcgacaggcc   120
cctggacaag gactagagtg gatgggatgg atcagcgctt acaatggtaa cacaaactat   180
gcacagaagc tccagggcag agtcaccatg accacagaca tccacgag cacagcctac   240 atggagctga ggagcttgag atctgacgac acggccgtgt attactgtgc gagatctacg   300
tatttctatg gttcggggac cctctacggt atggacgtct ggggccaagg gaccacggtc   360

-continued

```
accgtctcct cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540
ctgcagtcct ccggcctgta ctccctgtcc tccgtcgtga ccgtgccttc agctctctg     600
ggcacccaga cctacatctg caacgtgaac cacaagccct ccaacaccaa ggtggacaag    660
aaggtggaac ccaagtcctg cgacaagacc cacacctgtc cccttgtcc tgcccctgaa     720
ctgctgggcg gaccttccgt gttcctgttc cccccaaagc ccaaggacac cctgatgatc    780
tcccggaccc ccgaagtgac ctgcgtggtg gtggatgtgt cccacgagga ccctgaagtg    840
aagttcaatt ggtacgtgga cggcgtggaa gtgcacaacg ccaagaccaa gcctagagag    900
gaacagtaca actccaccta ccgggtggtg tccgtgctga ccgtgctgca ccaggattgg    960
ctgaacggca aagagtacaa gtgcaaggtg tccaacaagg ccctgcctgc ccccatcgaa   1020
aagaccatct ccaaggccaa gggccagccc cgggaacccc aggtgtacac actgcccct    1080
agcagggacg agctgaccaa gaaccaggtg tccctgacct gtctcgtgaa aggcttctac   1140
ccctccgata tcgccgtgga atgggagtcc aacggccagc ctgagaacaa ctacaagacc   1200
acccccctg tgctggactc cgacggctca ttcttcctgt acagcaagct gacagtggac    1260
aagtcccggt ggcagcaggg caacgtgttc tcctgctccg tgatgcacga ggccctgcac   1320
aaccactaca cccagaagtc cctgtccctg agccccggca agtgatga               1368
```

<210> SEQ ID NO 398
<211> LENGTH: 11
<212> TYPE: PRT
<213> ORGANISM: Homo Sapien

<400> SEQUENCE: 398

Gln Ser Leu Leu His Ser Asp Gly Tyr Asn Cys
1               5                   10

<210> SEQ ID NO 399
<211> LENGTH: 3
<212> TYPE: PRT
<213> ORGANISM: Homo Sapien

<400> SEQUENCE: 399

Leu Gly Ser
1

<210> SEQ ID NO 400
<211> LENGTH: 9
<212> TYPE: PRT
<213> ORGANISM: Homo Sapien

<400> SEQUENCE: 400

Met Gln Ala Leu Gln Thr Pro Cys Ser
1               5

<210> SEQ ID NO 401
<211> LENGTH: 112
<212> TYPE: PRT
<213> ORGANISM: Homo Sapien

<400> SEQUENCE: 401

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser

```
                  20                  25                  30

Asp Gly Tyr Asn Cys Leu Asp Trp Tyr Leu Gln Lys Pro Gly Gln Ser
                35                  40                  45

Pro Gln Leu Leu Ile Tyr Leu Gly Ser Thr Arg Ala Ser Gly Phe Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110

<210> SEQ ID NO 402
<211> LENGTH: 336
<212> TYPE: DNA
<213> ORGANISM: Homo Sapien

<400> SEQUENCE: 402
gatattgtga tgactcagtc tccactctcc ctgcccgtca cccctggaga gccggcctcc      60
atctcctgca ggtctagtca gagcctcctg catagtgatg gatacaactg tttggattgg     120
tacctgcaga agccagggca gtctccacag ctcctgatct atttgggttc tactcgggcc     180
tccgggttcc ctgacaggtt cagtggcagt ggatcaggca cagattttac actgaaaatc     240
agcagagtgg aggctgagga tgttggggtt tattactgca tgcaagctct acaaactccg     300
tgcagttttg gccagggac caagctggag atcaaa                                336

<210> SEQ ID NO 403
<211> LENGTH: 219
<212> TYPE: PRT
<213> ORGANISM: Homo Sapien

<400> SEQUENCE: 403

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Tyr Asn Cys Leu Asp Trp Tyr Leu Gln Lys Pro Gly Gln Ser
                35                  40                  45

Pro Gln Leu Leu Ile Tyr Leu Gly Ser Thr Arg Ala Ser Gly Phe Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

180                 185                 190
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 404
<211> LENGTH: 657
<212> TYPE: DNA
<213> ORGANISM: Homo Sapien

<400> SEQUENCE: 404
gatattgtga tgactcagtc tccactctcc ctgcccgtca cccctggaga gccggcctcc      60
atctcctgca ggtctagtca gagcctcctg catagtgatg gatacaactg tttggattgg     120
tacctgcaga agccagggca gtctccacag ctcctgatct atttgggttc tactcgggcc     180
tccggggttcc ctgacaggtt cagtggcagt ggatcaggca cagattttac actgaaaatc    240
agcagagtgg aggctgagga tgttggggtt tattactgca tgcaagctct acaaactccg     300
tgcagttttg gccaggggac caagctggag atcaaacgta cggtggccgc tcccccgtg     360
ttcatcttcc caccttccga cgagcagctg aagtccggaa ccgcttctgt cgtgtgcctg     420
ctgaacaact tctaccccg cgaggccaag gtgcagtgga aggtggacaa cgccctgcag     480
tccggcaact cccaggaatc cgtgaccgag caggactcca aggacagcac ctactccctg     540
tcctccaccc tgaccctgtc caaggccgac tacgagaagc acaaggtgta cgcctgcgaa     600
gtgacccacc agggcctgtc tagccccgtg accaagtctt tcaaccgggg cgagtgt       657

<210> SEQ ID NO 405
<211> LENGTH: 8
<212> TYPE: PRT
<213> ORGANISM: Homo Sapien

<400> SEQUENCE: 405

Gly Val Thr Phe Asp Asp Tyr Gly
1               5

<210> SEQ ID NO 406
<211> LENGTH: 8
<212> TYPE: PRT
<213> ORGANISM: Homo Sapien

<400> SEQUENCE: 406

Ile Asn Trp Asn Gly Gly Asp Thr
1               5

<210> SEQ ID NO 407
<211> LENGTH: 17
<212> TYPE: PRT
<213> ORGANISM: Homo Sapien

<400> SEQUENCE: 407

Ala Arg Asp Phe Tyr Gly Ser Gly Ser Tyr Tyr His Val Pro Phe Asp
1               5                   10                  15
Tyr

<210> SEQ ID NO 408
<211> LENGTH: 124
<212> TYPE: PRT
<213> ORGANISM: Homo Sapien

<400> SEQUENCE: 408

Glu Val Gln Leu Val Glu Ser Gly Gly Gly Val Val Arg Pro Gly Gly
1               5                   10                  15

Ser Leu Arg Leu Ser Cys Val Ala Ser Gly Val Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Asp Thr Asp Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Phe Tyr Gly Ser Gly Ser Tyr Tyr His Val Pro Phe Asp
            100                 105                 110

Tyr Trp Gly Gln Gly Ile Leu Val Thr Val Ser Ser
        115                 120

<210> SEQ ID NO 409
<211> LENGTH: 372
<212> TYPE: DNA
<213> ORGANISM: Homo Sapien

<400> SEQUENCE: 409
gaggtgcagc tggtggagtc tgggggaggt gtggtacggc ctgggggtc cctgagactc      60
tcctgtgtag cctctggagt cacctttgat gattatggca tgagctgggt ccgccaagct    120
ccagggaagg gctggartg ggtctctggt attaattgga atggtggcga cacagattat    180
tcagactctg tgaagggccg attcaccatc tccagagaca cgccaagaa ctccctgtat    240
ctacaaatga atagtctgag agccgaggac acggccttgt attactgtgc gagggatttc    300
tatggttcgg ggagttatta tcacgttcct tttgactact ggggccaggg aatcctggtc    360
accgtctcct ca                                                       372

<210> SEQ ID NO 410
<211> LENGTH: 454
<212> TYPE: PRT
<213> ORGANISM: Homo Sapien

<400> SEQUENCE: 410

Glu Val Gln Leu Val Glu Ser Gly Gly Gly Val Val Arg Pro Gly Gly
1               5                   10                  15

Ser Leu Arg Leu Ser Cys Val Ala Ser Gly Val Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Asp Thr Asp Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Phe Tyr Gly Ser Gly Ser Tyr Tyr His Val Pro Phe Asp
            100                 105                 110

Tyr Trp Gly Gln Gly Ile Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 411
<211> LENGTH: 1368
<212> TYPE: DNA
<213> ORGANISM: Homo Sapien

<400> SEQUENCE: 411
gaggtgcagc tggtggagtc tgggggaggt gtggtacggc ctgggggtc cctgagactc      60 tcctgtgtag cctctggagt cacctttgat gattatggca tgagctgggt ccgccaagct    120
ccagggaagg gctggartg ggtctctggt attaattgga atggtggcga cacagattat    180
tcagactctg tgaagggccg attcaccatc tccagagaca acgccaagaa ctccctgtat    240

```
ctacaaatga atagtctgag agccgaggac acggccttgt attactgtgc gagggatttc    300
tatggttcgg ggagttatta tcacgttcct tttgactact ggggccaggg aatcctggtc    360
accgtctcct cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540
ctgcagtcct ccgcctgta ctccctgtcc tcgtcgtga ccgtgccttc agctctctg    600 ggcacccaga cctacatctg caacgtgaac cacaagccct ccaacaccaa ggtggacaag    660
aaggtggaac ccaagtcctg cgacaagacc cacacctgtc ccccttgtcc tgcccctgaa    720
ctgctgggcg gaccttccgt gttcctgttc ccccaaagc caaggacac cctgatgatc    780 tcccggaccc ccgaagtgac ctgcgtggtg gtggatgtgt cccacgagga ccctgaagtg    840
aagttcaatt ggtacgtgga cggcgtggaa gtgcacaacg ccaagaccaa gcctagagag    900
gaacagtaca actccaccta ccgggtggtg tccgtgctga ccgtgctgca ccaggattgg    960
ctgaacggca agagtacaa gtgcaaggtg tccaacaagg ccctgcctgc ccccatcgaa   1020
aagaccatct ccaaggccaa gggccagccc cgggaacccc aggtgtacac actgcccct   1080 agcagggacg agctgaccaa gaaccaggtg tccctgacct gtctcgtgaa aggcttctac   1140
ccctccgata tcgccgtgga atgggagtcc aacggccagc tgagaacaa ctacaagacc   1200 accccccctg tgctggactc cgacggctca ttcttcctgt acagcaagct gacagtggac   1260
aagtcccggt ggcagcaggg caacgtgttc tcctgctccg tgatgcacga ggccctgcac   1320
aaccactaca cccagaagtc cctgtccctg agccccggca gtgatga               1368
```

<210> SEQ ID NO 412
<211> LENGTH: 7
<212> TYPE: PRT
<213> ORGANISM: Homo Sapien

<400> SEQUENCE: 412

Gln Ser Val Ser Arg Ser Tyr
1               5

<210> SEQ ID NO 413
<211> LENGTH: 3
<212> TYPE: PRT
<213> ORGANISM: Homo Sapien

<400> SEQUENCE: 413

Gly Ala Ser
1

<210> SEQ ID NO 414
<211> LENGTH: 9
<212> TYPE: PRT
<213> ORGANISM: Homo Sapien

<400> SEQUENCE: 414

His Gln Tyr Asp Met Ser Pro Phe Thr
1               5

<210> SEQ ID NO 415
<211> LENGTH: 108
<212> TYPE: PRT
<213> ORGANISM: Homo Sapien

<400> SEQUENCE: 415

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Arg Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Asp Gly Ser Gly Thr Asp Phe Thr Leu Ser Ile Ser Arg Leu Glu
65                  70                  75                  80

Pro Glu Asp Phe Ala Val Tyr Tyr Cys His Gln Tyr Asp Met Ser Pro
                85                  90                  95

Phe Thr Phe Gly Pro Gly Thr Lys Val Asp Ile Lys
            100                 105
```

<210> SEQ ID NO 416
<211> LENGTH: 324
<212> TYPE: DNA
<213> ORGANISM: Homo Sapien

<400> SEQUENCE: 416

```
gaaattgtgt tgacgcagtc tccagggacc ctgtctttgt ctccagggga aagagccacc      60
ctctcctgca gggccagtca gagtgttagc agaagctact tagcctggta ccagcagaaa     120
cgtggccagg ctcccaggct cctcatctat ggtgcatcca gcagggccac tggcatccca     180
gacaggttca gtggcgatgg gtctgggaca gacttcactc tctccatcag cagactggag     240
cctgaagatt ttgcagtgta ttactgtcac cagtatgata tgtcaccatt cactttcggc     300
cctgggacca agtggatat caaa                                             324
```

<210> SEQ ID NO 417
<211> LENGTH: 215
<212> TYPE: PRT
<213> ORGANISM: Homo Sapien

<400> SEQUENCE: 417

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Arg Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Asp Gly Ser Gly Thr Asp Phe Thr Leu Ser Ile Ser Arg Leu Glu
65                  70                  75                  80

Pro Glu Asp Phe Ala Val Tyr Tyr Cys His Gln Tyr Asp Met Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 418
<211> LENGTH: 645
<212> TYPE: DNA
<213> ORGANISM: Homo Sapien

<400> SEQUENCE: 418
gaaattgtgt tgacgcagtc tccagggacc ctgtctttgt ctccagggga aagagccacc    60
ctctcctgca gggccagtca gagtgttagc agaagctact tagcctggta ccagcagaaa   120
cgtggccagg ctcccaggct cctcatctat ggtgcatcca gcagggccac tggcatccca   180
gacaggttca gtggcgatgg gtctgggaca gacttcactc tctccatcag cagactggag   240
cctgaagatt ttgcagtgta ttactgtcac cagtatgata tgtcaccatt cactttcggc   300
cctgggacca agtggatat caaacgtacg gtggccgctc cctccgtgtt catcttccca   360
ccttccgacg agcagctgaa gtccggcacc gcttctgtcg tgtgcctgct gaacaacttc   420
taccccgcg aggccaaggt gcagtggaag gtggacaacg ccctgcagtc cggcaactcc   480
caggaatccg tgaccgagca ggactccaag gacagcacct actccctgtc ctccaccctg   540
accctgtcca aggccgacta cgagaagcac aaggtgtacg cctgcgaagt gacccaccag   600
ggcctgtcta gccccgtgac caagtctttc aaccggggcg agtgt              645

<210> SEQ ID NO 419
<211> LENGTH: 8
<212> TYPE: PRT
<213> ORGANISM: Homo Sapien

<400> SEQUENCE: 419

Gly Leu Thr Phe Asp Asp Tyr Gly
1               5

<210> SEQ ID NO 420
<211> LENGTH: 8
<212> TYPE: PRT
<213> ORGANISM: Homo Sapien

<400> SEQUENCE: 420

Ile Asn Trp Asn Gly Asp Asn Thr
1               5

<210> SEQ ID NO 421
<211> LENGTH: 17
<212> TYPE: PRT
<213> ORGANISM: Homo Sapien

<400> SEQUENCE: 421

Ala Arg Asp Tyr Tyr Gly Ser Gly Ser Tyr Tyr Asn Val Pro Phe Asp
1               5                   10                  15

Tyr

```
<210> SEQ ID NO 422
<211> LENGTH: 124
<212> TYPE: PRT
<213> ORGANISM: Homo Sapien

<400> SEQUENCE: 422

Glu Val Gln Leu Val Glu Ser Gly Gly Gly Val Val Arg Pro Gly Gly
1               5                   10                  15

Ser Leu Arg Leu Ser Cys Ala Ala Ser Gly Leu Thr Phe Asp Asp Tyr
            20                  25                  30

Gly Met Ser Trp Val Arg Gln Val Pro Gly Lys Gly Leu Glu Trp Val
        35                  40                  45

Ser Gly Ile Asn Trp Asn Gly Asp Asn Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Tyr Tyr Gly Ser Gly Ser Tyr Tyr Asn Val Pro Phe Asp
            100                 105                 110

Tyr Trp Gly Gln Gly Thr Leu Val Thr Val Ser Ser
        115                 120

<210> SEQ ID NO 423
<211> LENGTH: 372
<212> TYPE: DNA
<213> ORGANISM: Homo Sapien

<400> SEQUENCE: 423
gaggtgcagc tggtggagtc tgggggaggt gtggtacggc ctggggggtc cctgagactc      60
tcctgtgcag cctctggact cacctttgat gattatggca tgagctgggt ccgccaagtt     120
ccagggaagg ggctggagtg ggtctctggt attaattgga atggtgataa cacagattat     180
gcagactctg tgaagggccg attcaccatc tccagagaca acgccaagaa ctccctgtat     240
ctgcaaatga acagtctgag agccgaggac acggccttgt attactgtgc gagggattac    300
tatggttcgg ggagttatta taacgttcct tttgactact ggggccaggg aaccctggtc    360
accgtctcct ca                                                        372

<210> SEQ ID NO 424
<211> LENGTH: 454
<212> TYPE: PRT
<213> ORGANISM: Homo Sapien

<400> SEQUENCE: 424

Glu Val Gln Leu Val Glu Ser Gly Gly Gly Val Val Arg Pro Gly Gly
1               5                   10                  15

Ser Leu Arg Leu Ser Cys Ala Ala Ser Gly Leu Thr Phe Asp Asp Tyr
            20                  25                  30

Gly Met Ser Trp Val Arg Gln Val Pro Gly Lys Gly Leu Glu Trp Val
        35                  40                  45

Ser Gly Ile Asn Trp Asn Gly Asp Asn Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Arg Asp Tyr Tyr Gly Ser Gly Ser Tyr Tyr Asn Val Pro Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 425
<211> LENGTH: 1368
<212> TYPE: DNA
<213> ORGANISM: Homo Sapien

<400> SEQUENCE: 425
gaggtgcagc tggtggagtc tgggggaggt gtggtacggc ctggggggtc cctgagactc     60

-continued

```
tcctgtgcag cctctggact cacctttgat gattatggca tgagctgggt ccgccaagtt    120
ccagggaagg ggctggagtg ggtctctggt attaattgga atggtgataa cacagattat    180
gcagactctg tgaagggccg attcaccatc tccagagaca acgccaagaa ctccctgtat    240
ctgcaaatga acagtctgag agccgaggac acggccttgt attactgtgc gagggattac    300
tatggttcgg ggagttatta taacgttcct tttgactact ggggccaggg aaccctggtc    360
accgtctcct cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540
ctgcagtcct ccggcctgta ctccctgtcc tccgtcgtga ccgtgccttc cagctctctg    600
ggcacccaga cctacatctg caacgtgaac cacaagccct ccaacaccaa ggtggacaag    660
aaggtggaac ccagtcctg cgacaagacc cacacctgtc ccccttgtcc tgcccctgaa     720
ctgctgggcg gaccttccgt gttcctgttc cccccaaagc ccaaggacac cctgatgatc    780
tcccggaccc ccgaagtgac ctgcgtggtg gtggatgtgt cccacgagga ccctgaagtg    840
aagttcaatt ggtacgtgga cggcgtggaa gtgcacaacg ccaagaccaa gcctagagag    900
gaacagtaca actccaccta ccgggtggtg tccgtgctga ccgtgctgca ccaggattgg    960
ctgaacggca agagtacaa gtgcaaggtg tccaacaagg ccctgcctgc cccatcgaa    1020 aagaccatct ccaaggccaa ggccagcccc cgggaacccc aggtgtacac actgcccccct   1080 agcagggacg agctgaccaa gaaccaggtg tccctgacct gtctcgtgaa aggcttctac    1140
ccctccgata tcgccgtgga atgggagtcc aacggccagc tgagaacaa ctacaagacc    1200 accccccctg tgctggactc cgacggctca ttcttcctgt acagcaagct gacagtggac    1260
aagtcccggt ggcagcaggg caacgtgttc tcctgctccg tgatgcacga ggcctgcac    1320 aaccactaca cccagaagtc cctgtccctg agccccggca agtgatga             1368
```

<210> SEQ ID NO 426
<211> LENGTH: 7
<212> TYPE: PRT
<213> ORGANISM: Homo Sapien

<400> SEQUENCE: 426

Gln Ser Val Ser Ser Tyr
1               5

<210> SEQ ID NO 427
<211> LENGTH: 3
<212> TYPE: PRT
<213> ORGANISM: Homo Sapien

<400> SEQUENCE: 427

Gly Ala Ser
1

<210> SEQ ID NO 428
<211> LENGTH: 8
<212> TYPE: PRT
<213> ORGANISM: Homo Sapien

<400> SEQUENCE: 428

Gln Gln Tyr Gly Ser Ser Pro Phe
1               5

<210> SEQ ID NO 429

-continued

```
<211> LENGTH: 107
<212> TYPE: PRT
<213> ORGANISM: Homo Sapien

<400> SEQUENCE: 429

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Ser Ser Pro
                85                  90                  95

Phe Phe Gly Pro Gly Thr Lys Val Asp Ile Lys
            100                 105

<210> SEQ ID NO 430
<211> LENGTH: 321
<212> TYPE: DNA
<213> ORGANISM: Homo Sapien

<400> SEQUENCE: 430
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag aagactggag   240
cctgaagatt ttgcagtgta ttactgtcag cagtatggta gttcaccatt cttcggccct   300
gggaccaaag tggatatcaa a                                             321

<210> SEQ ID NO 431
<211> LENGTH: 323
<212> TYPE: DNA
<213> ORGANISM: Homo Sapien

<400> SEQUENCE: 431
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag aagactggag   240
cctgaagatt ttgcagtgta ttactgtcag cagtatggta gttcaccatt cacttcggcc   300
ctgggaccaa agtggatatc aaa                                           323

<210> SEQ ID NO 432
<211> LENGTH: 214
<212> TYPE: PRT
<213> ORGANISM: Homo Sapien

<400> SEQUENCE: 432

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                20                  25                  30
Tyr Leu Ala Trp Tyr Gln Gln Lys Pro Gly Gln Ala Pro Arg Leu Leu
             35                  40                  45
Ile Tyr Gly Ala Ser Ser Arg Ala Thr Gly Ile Pro Asp Arg Phe Ser
         50                  55                  60
Gly Ser Gly Ser Gly Thr Asp Phe Thr Leu Thr Ile Arg Arg Leu Glu
 65                  70                  75                  80
Pro Glu Asp Phe Ala Val Tyr Tyr Cys Gln Gln Tyr Gly Ser Ser Pro
                 85                  90                  95
Phe Phe Gly Pro Gly Thr Lys Val Asp Ile Lys Arg Thr Val Ala Ala
             100                 105                 110
Pro Ser Val Phe Ile Phe Pro Pro Ser Asp Glu Gln Leu Lys Ser Gly
         115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 433
<211> LENGTH: 642
<212> TYPE: DNA
<213> ORGANISM: Homo Sapien

<400> SEQUENCE: 433

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag aagactggag   240
cctgaagatt ttgcagtgta ttactgtcag cagtatggta gttcaccatt cttcggccct   300
gggaccaaag tggatatcaa acgtacggtg gccgctccct ccgtgttcat cttcccacct   360
tccgacgagc agctgaagtc cggcaccgct tctgtcgtgt gcctgctgaa caacttctac   420
ccccgcgagg ccaaggtgca gtggaaggtg gacaacgccc tgcagtccgg caactcccag   480
gaatccgtga ccgagcagga ctccaaggac agcacctact ccctgtcctc caccctgacc   540
ctgtccaagg ccgactacga gaagcacaag gtgtacgcct gcgaagtgac ccaccagggc   600
ctgtctagcc ccgtgaccaa gtctttcaac cggggcgagt gt                      642
```

<210> SEQ ID NO 434
<211> LENGTH: 644
<212> TYPE: DNA
<213> ORGANISM: Homo Sapien

<400> SEQUENCE: 434

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
```

-continued

```
cctggccagg ctcccaggct cctcatatat ggtgcatcca gcagggccac tggcatccca    180
gacaggttca gtggcagtgg gtctgggaca gacttcactc tcaccatcag aagactggag    240
cctgaagatt ttgcagtgta ttactgtcag cagtatggta gttcaccatt cacttcggcc    300
ctgggaccaa agtggatatc aaacgtacgg tggccgctcc ctccgtgttc atcttcccac    360
cttccgacga gcagctgaag tccggcaccg cttctgtcgt gtgcctgctg aacaacttct    420 accccgcga ggccaaggtg cagtggaagg tggacaacgc cctgcagtcc ggcaactccc    480
aggaatccgt gaccgagcag gactccaagg acagcaccta ctccctgtcc tccaccctga    540
ccctgtccaa ggccgactac gagaagcaca aggtgtacgc ctgcgaagtg acccaccagg    600
gcctgtctag ccccgtgacc aagtctttca accggggcga gtgt                     644
```

<210> SEQ ID NO 435
<211> LENGTH: 8
<212> TYPE: PRT
<213> ORGANISM: Homo Sapien

<400> SEQUENCE: 435

Gly Tyr Thr Phe Asn Ser Tyr Gly
1               5

<210> SEQ ID NO 436
<211> LENGTH: 8
<212> TYPE: PRT
<213> ORGANISM: Homo Sapien

<400> SEQUENCE: 436

Ile Ser Val His Asn Gly Asn Thr
1               5

<210> SEQ ID NO 437
<211> LENGTH: 17
<212> TYPE: PRT
<213> ORGANISM: Homo Sapien

<400> SEQUENCE: 437

Ala Arg Ala Gly Tyr Asp Ile Leu Thr Asp Phe Ser Asp Ala Phe Asp
1               5                   10                  15

Ile

<210> SEQ ID NO 438
<211> LENGTH: 124
<212> TYPE: PRT
<213> ORGANISM: Homo Sapien

<400> SEQUENCE: 438

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Gly Ile Ile Trp Val Arg Gln Ala Pro Gly Gln Gly Leu Glu Trp Met
            35                  40                  45

Gly Trp Ile Ser Val His Asn Gly Asn Thr Asn Cys Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Thr Asp Asp Thr Ala Val Tyr Tyr Cys
                85                  90                  95

```
Ala Arg Ala Gly Tyr Asp Ile Leu Thr Asp Phe Ser Asp Ala Phe Asp
            100                 105                 110

Ile Trp Gly His Gly Thr Met Val Thr Val Ser Ser
            115                 120

<210> SEQ ID NO 439
<211> LENGTH: 372
<212> TYPE: DNA
<213> ORGANISM: Homo Sapien

<400> SEQUENCE: 439
caggttcagt tggtgcagtc tggagctgag gtgaagaagc ctggggcctc agtgaaggtc    60
tcctgcaagg cttctggtta cacctttaat agttatggta tcatctgggt gcgacaggcc   120
cctggacaag gcttgagtg gatgggatgg atcagcgttc acaatggtaa cacaaactgt    180
gcacagaagc tccagggtag agtcaccatg accacagaca catccacgag cacagcctac   240
atggagctga ggagcctgag aactgacgac acggccgtgt attactgtgc gagagcgggt   300
tacgatattt tgactgattt ttccgatgct tttgatatct ggggccacgg gacaatggtc   360
accgtctctt ca                                                      372

<210> SEQ ID NO 440
<211> LENGTH: 454
<212> TYPE: PRT
<213> ORGANISM: Homo Sapien

<400> SEQUENCE: 440
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Gly Ile Ile Trp Val Arg Gln Ala Pro Gly Gln Gly Leu Glu Trp Met
            35                  40                  45

Gly Trp Ile Ser Val His Asn Gly Asn Thr Asn Cys Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Thr Asp Asp Thr Ala Val Tyr Tyr Cys
                85                  90                  95

Ala Arg Ala Gly Tyr Asp Ile Leu Thr Asp Phe Ser Asp Ala Phe Asp
            100                 105                 110

Ile Trp Gly His Gly Thr Met Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
        210                 215                 220

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 441
<211> LENGTH: 1368
<212> TYPE: DNA
<213> ORGANISM: Homo Sapien

<400> SEQUENCE: 441
caggttcagt tggtgcagtc tggagctgag gtgaagaagc ctggggcctc agtgaaggtc      60
tcctgcaagg cttctggtta cacctttaat agttatggta tcatctgggt gcgacaggcc    120
cctggacaag gcttgagtg gatgggatgg atcagcgttc acaatggtaa cacaaactgt     180
gcacagaagc tccagggtag agtcaccatg accacagaca catccacgag cacagcctac    240
atggagctga ggagcctgag aactgacgac acggccgtgt attactgtgc gagagcgggt    300
tacgatattt tgactgattt ttccgatgct tttgatatct ggggccacgg gacaatggtc    360
accgtctctt cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540
ctgcagtcct ccggcctgta ctccctgtcc tcgtcgtga ccgtgccttc agctctctg     600 ggcacccaga cctacatctg caacgtgaac cacaagccct ccaacaccaa ggtggacaag    660
aaggtggaac ccagtcctg cgacaagacc cacacctgtc cccttgtcc tgcccctgaa     720 ctgctgggcg accttccgt gttcctgttc cccccaaagc ccaaggacac cctgatgatc    780
```

-continued

```
tcccggaccc cgaagtgac ctgcgtggtg gtggatgtgt cccacgagga ccctgaagtg    840
aagttcaatt ggtacgtgga cggcgtggaa gtgcacaacg ccaagaccaa gcctagagag    900
gaacagtaca actccaccta ccgggtggtg tccgtgctga ccgtgctgca ccaggattgg    960
ctgaacggca agagtacaa gtgcaaggtg tccaacaagg ccctgcctgc ccccatcgaa   1020
aagaccatct ccaaggccaa gggccagccc cgggaacccc aggtgtacac actgcccct   1080 agcagggacg agctgaccaa gaaccaggtg tccctgacct gtctcgtgaa aggcttctac   1140
ccctccgata tcgccgtgga atgggagtcc aacggccagc ctgagaacaa ctacaagacc   1200
accccccctg tgctggactc cgacggctca ttcttcctgt acagcaagct gacagtggac   1260
aagtcccggt ggcagcaggg caacgtgttc tcctgctccg tgatgcacga ggccctgcac   1320
aaccactaca cccagaagtc cctgtccctg agccccggca agtgatga                1368
```

<210> SEQ ID NO 442
<211> LENGTH: 6
<212> TYPE: PRT
<213> ORGANISM: Homo Sapien

<400> SEQUENCE: 442

Gln Asn Ile Asn Asn Phe
1               5

<210> SEQ ID NO 443
<211> LENGTH: 3
<212> TYPE: PRT
<213> ORGANISM: Homo Sapien

<400> SEQUENCE: 443

Ala Ala Ser
1

<210> SEQ ID NO 444
<211> LENGTH: 8
<212> TYPE: PRT
<213> ORGANISM: Homo Sapien

<400> SEQUENCE: 444

Gln Gln Ser Tyr Gly Ile Pro Trp
1               5

<210> SEQ ID NO 445
<211> LENGTH: 106
<212> TYPE: PRT
<213> ORGANISM: Homo Sapien

<400> SEQUENCE: 445

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Phe
                20                  25                  30

Leu Asn Trp Tyr Gln Gln Lys Glu Gly Lys Pro Lys Leu Leu Ile
            35                  40                  45

Tyr Ala Ala Ser Ser Leu Gln Arg Gly Ile Pro Ser Thr Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Ile Cys Gln Gln Ser Tyr Gly Ile Pro Trp
                85                  90                  95

Val Gly Gln Gly Thr Lys Val Glu Ile Lys
            100                 105

<210> SEQ ID NO 446
<211> LENGTH: 318
<212> TYPE: DNA
<213> ORGANISM: Homo Sapien

<400> SEQUENCE: 446
gacatccaga tgacccagtc tccatcctcc ctgtctgcat ctgtaggaga cagagtcacc    60
atcacttgcc gggcaagtca gaacattaat aactttttaa attggtatca gcagaaagaa   120
gggaaaggcc ctaagctcct gatctatgca catccagtt tgcaaagagg ataccatca   180 acgttcagtg gcagtggatc tgggacagac ttcactctca ccatcagcag tctgcaacct   240
gaagattttg caacttacat ctgtcaacag agctacggta tcccgtgggt cggccaaggg   300
accaaggtgg aaatcaaa                                                 318

<210> SEQ ID NO 447
<211> LENGTH: 213
<212> TYPE: PRT
<213> ORGANISM: Homo Sapien

<400> SEQUENCE: 447

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Phe
            20                  25                  30

Leu Asn Trp Tyr Gln Gln Lys Glu Gly Lys Gly Pro Lys Leu Leu Ile
        35                  40                  45

Tyr Ala Ala Ser Ser Leu Gln Arg Gly Ile Pro Ser Thr Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ile Cys Gln Gln Ser Tyr Gly Ile Pro Trp
                85                  90                  95

Val Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 448
<211> LENGTH: 639
<212> TYPE: DNA
<213> ORGANISM: Homo Sapien

<400> SEQUENCE: 448

```
gacatccaga tgacccagtc tccatcctcc ctgtctgcat ctgtaggaga cagagtcacc     60
atcacttgcc gggcaagtca gaacattaat aacttttaa attggtatca gcagaaagaa    120
gggaaaggcc ctaagctcct gatctatgca gcatccagtt tgcaaagagg gataccatca   180
acgttcagtg gcagtggatc tgggacagac ttcactctca ccatcagcag tctgcaacct   240
gaagattttg caacttacat ctgtcaacag agctacggta tcccgtgggt cggccaaggg   300
accaaggtgg aaatcaaacg tacggtggcc gctcccctccg tgttcatctt cccaccttcc  360
gacgagcagc tgaagtccgg caccgcttct gtcgtgtgcc tgctgaacaa cttctacccc   420
cgcgaggcca aggtgcagtg gaaggtggac aacgccctgc agtccggcaa ctcccaggaa   480
tccgtgaccg agcaggactc caaggacagc acctactccc tgtcctccac cctgaccctg   540
tccaaggccg actacgagaa gcacaaggtg tacgcctgcg aagtgaccca ccagggcctg   600
tctagccccg tgaccaagtc tttcaaccgg ggcgagtgt                          639
```

<210> SEQ ID NO 449
<211> LENGTH: 8
<212> TYPE: PRT
<213> ORGANISM: Homo Sapien

<400> SEQUENCE: 449

```
Gly Phe Thr Phe Ser Asp Tyr Phe
1               5
```

<210> SEQ ID NO 450
<211> LENGTH: 8
<212> TYPE: PRT
<213> ORGANISM: Homo Sapien

<400> SEQUENCE: 450

```
Ile Ser Ser Ser Gly Ser Thr Ile
1               5
```

<210> SEQ ID NO 451
<211> LENGTH: 21
<212> TYPE: PRT
<213> ORGANISM: Homo Sapien

<400> SEQUENCE: 451

```
Ala Arg Asp His Tyr Asp Gly Ser Gly Ile Tyr Pro Leu Tyr Tyr Tyr
1               5                   10                  15
Tyr Gly Leu Asp Val
            20
```

<210> SEQ ID NO 452
<211> LENGTH: 128
<212> TYPE: PRT
<213> ORGANISM: Homo Sapien

<400> SEQUENCE: 452

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Phe Met Ser Trp Ile Arg Gln Ala Pro Gly Lys Gly Leu Glu Trp Ile
        35                  40                  45
Ser Tyr Ile Ser Ser Ser Gly Ser Thr Ile Tyr Tyr Ala Asp Ser Val
    50                  55                  60
```

Arg Gly Arg Phe Thr Ile Ser Arg Asp Asn Ala Lys Tyr Ser Leu Tyr
65                  70                  75                  80

Leu Gln Met Asn Ser Leu Arg Ser Glu Asp Thr Ala Val Tyr Tyr Cys
                85                  90                  95

Ala Arg Asp His Tyr Asp Gly Ser Gly Ile Tyr Pro Leu Tyr Tyr Tyr
            100                 105                 110

Tyr Gly Leu Asp Val Trp Gly Gln Gly Thr Thr Val Thr Val Ser Ser
        115                 120                 125

<210> SEQ ID NO 453
<211> LENGTH: 384
<212> TYPE: DNA
<213> ORGANISM: Homo Sapien

<400> SEQUENCE: 453
caggtgcagc tggtggagtc tgggggaggc ttggtcaagc ctggagggtc cctgagactc      60
tcctgtgcag cctctggatt caccttcagt gactacttca tgagctggat ccgccaggcg     120
ccagggaagg gctggagtg gatttcatac attagttcta gtggtagtac catatactac      180
gcagactctg tgaggggccg attcaccatc tccaggaca cgccaagta ctcactgtat       240 ctgcaaatga acagcctgag atccgaggac acggccgtgt attactgtgc gagagatcac    300
tacgatggtt cggggattta tcccctctac tactattacg gtttggacgt ctggggccag    360
gggaccacgg tcaccgtctc ctca                                            384

<210> SEQ ID NO 454
<211> LENGTH: 458
<212> TYPE: PRT
<213> ORGANISM: Homo Sapien

<400> SEQUENCE: 454

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Arg Gly Arg Phe Thr Ile Ser Arg Asp Asn Ala Lys Tyr Ser Leu Tyr
65                  70                  75                  80

Leu Gln Met Asn Ser Leu Arg Ser Glu Asp Thr Ala Val Tyr Tyr Cys
                85                  90                  95

Ala Arg Asp His Tyr Asp Gly Ser Gly Ile Tyr Pro Leu Tyr Tyr Tyr
            100                 105                 110

Tyr Gly Leu Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

```
Leu Ser Ser Val Val Thr Val Pro Ser Ser Leu Gly Thr Gln Thr
            195                 200                 205
Tyr Ile Cys Asn Val Asn His Lys Pro Ser Asn Thr Lys Val Asp Lys
210                 215                 220
Lys Val Glu Pro Lys Ser Cys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Asp Glu
        355                 360                 365
Leu Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455

<210> SEQ ID NO 455
<211> LENGTH: 1380
<212> TYPE: DNA
<213> ORGANISM: Homo Sapien

<400> SEQUENCE: 455
caggtgcagc tggtggagtc tgggggaggc ttggtcaagc ctggagggtc cctgagactc     60
tcctgtgcag cctctggatt caccttcagt gactacttca tgagctggat ccgccaggcg    120
ccagggaagg ggctggagtg gatttcatac attagttcta gtggtagtac catatactac    180
gcagactctg tgaggggccg attcaccatc tccaggaca acgccaagta ctcactgtat    240
ctgcaaatga acagcctgag atccgaggac acggccgtgt attactgtgc gagagatcac    300
tacgatggtt cggggattta tccctctac tactattacg gtttggacgt ctggggccag    360
gggaccacgg tcaccgtctc ctcagccagc accaagggcc cctctgtgtt ccctctggcc    420
ccttccagca agtccacctc tggcggaaca gccgctctgg gctgcctcgt gaaggactac    480
ttccccgagc tgtgaccgt gtcctggaac tctggcgctc tgaccagcgg agtgcacacc    540
ttccctgctg tgctgcagtc ctccggcctg tactccctgt cctccgtcgt gaccgtgcct    600
```

```
tccagctctc tgggcaccca gacctacatc tgcaacgtga accacaagcc ctccaacacc    660
aaggtggaca agaaggtgga acccaagtcc tgcgacaaga cccacacctg tccccctttgt   720 cctgcccctg aactgctggg cggaccttcc gtgttcctgt tcccccaaa gcccaaggac     780 accctgatga tctcccggac ccccgaagtg acctgcgtgg tggtggatgt gtcccacgag    840
gaccctgaag tgaagttcaa ttggtacgtg gacggcgtgg aagtgcacaa cgccaagacc    900
aagcctagag aggaacagta caactccacc taccgggtgg tgtccgtgct gaccgtgctg    960
caccaggatt ggctgaacgg caaagagtac aagtgcaagg tgtccaacaa ggccctgcct   1020
gcccccatcg aaaagaccat ctccaaggcc aagggccagc ccgggaacc ccaggtgtac    1080 acactgcccc ctagcaggga cgagctgacc aagaaccagg tgtccctgac ctgtctcgtg   1140
aaaggcttct acccctccga tatcgccgtg aatggagt ccaacggcca gcctgagaac     1200
aactacaaga ccaccccccc tgtgctggac tccgacggct cattcttcct gtacagcaag   1260
ctgacagtgg acaagtcccg gtggcagcag ggcaacgtgt tctcctgctc cgtgatgcac   1320
gaggccctgc acaaccacta cacccagaag tccctgtccc tgagccccgg caagtgatga  1380
```

```
<210> SEQ ID NO 456
<211> LENGTH: 11
<212> TYPE: PRT
<213> ORGANISM: Homo Sapien

<400> SEQUENCE: 456

Gln Ser Leu Leu His Ser Asn Gly Tyr Asn Tyr
1               5                   10

<210> SEQ ID NO 457
<211> LENGTH: 3
<212> TYPE: PRT
<213> ORGANISM: Homo Sapien

<400> SEQUENCE: 457

Leu Gly Ser
1

<210> SEQ ID NO 458
<211> LENGTH: 9
<212> TYPE: PRT
<213> ORGANISM: Homo Sapien

<400> SEQUENCE: 458

Met Gln Ala Leu Gln Thr Pro Arg Ser
1               5

<210> SEQ ID NO 459
<211> LENGTH: 111
<212> TYPE: PRT
<213> ORGANISM: Homo Sapien

<400> SEQUENCE: 459

Ile Val Met Thr Gln Ser Pro Leu Ser Leu Pro Val Thr Pro Gly Glu
1               5                   10                  15

Pro Ala Ser Ile Ser Cys Arg Ser Ser Gln Ser Leu Leu His Ser Asn
            20                  25                  30

Gly Tyr Asn Tyr Leu Asp Tyr Tyr Leu Gln Lys Pro Gly Gln Ser Pro
        35                  40                  45

Gln Leu Leu Ile Tyr Leu Gly Ser Tyr Arg Ala Ser Gly Val Pro Asp
    50                  55                  60
```

```
Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Met Gln Ala Leu
                 85                  90                  95

Gln Thr Pro Arg Ser Phe Gly Gln Gly Thr Thr Leu Glu Ile Lys
            100                 105                 110
```

<210> SEQ ID NO 460
<211> LENGTH: 333
<212> TYPE: DNA
<213> ORGANISM: Homo Sapien

<400> SEQUENCE: 460

```
attgtgatga ctcagtctcc actctcccta cccgtcaccc ctggagagcc ggcctccatc    60
tcctgcaggt ctagtcagag cctcctgcat agtaatggat acaactattt ggattattac   120
ctgcagaagc cagggcagtc tccacagctc ctgatctatt tgggttctta tcgggcctcc   180
ggggtccctg acaggttcag tggcagtgga tcaggcacag attttacact gaaaatcagc   240
agagtggagg ctgaggatgt tggggtttat tactgcatgc aagctctaca aactcctcgc   300
agttttggcc aggggaccac gctggagatc aaa                                333
```

<210> SEQ ID NO 461
<211> LENGTH: 218
<212> TYPE: PRT
<213> ORGANISM: Homo Sapien

<400> SEQUENCE: 461

```
Ile Val Met Thr Gln Ser Pro Leu Ser Leu Pro Val Thr Pro Gly Glu
  1               5                  10                  15

Pro Ala Ser Ile Ser Cys Arg Ser Ser Gln Ser Leu Leu His Ser Asn
             20                  25                  30

Gly Tyr Asn Tyr Leu Asp Tyr Tyr Leu Gln Lys Pro Gly Gln Ser Pro
         35                  40                  45

Gln Leu Leu Ile Tyr Leu Gly Ser Tyr Arg Ala Ser Gly Val Pro Asp
     50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Met Gln Ala Leu
                 85                  90                  95

Gln Thr Pro Arg Ser Phe Gly Gln Gly Thr Thr Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 462
<211> LENGTH: 654
<212> TYPE: DNA
<213> ORGANISM: Homo Sapien

<400> SEQUENCE: 462

```
attgtgatga ctcagtctcc actctcccta cccgtcaccc ctggagagcc ggcctccatc    60
tcctgcaggt ctagtcagag cctcctgcat agtaatggat acaactattt ggattattac   120
ctgcagaagc cagggcagtc tccacagctc ctgatctatt tgggttctta tcgggcctcc   180
ggggtccctg acaggttcag tggcagtgga tcaggcacag atttacact gaaaatcagc    240
agagtggagg ctgaggatgt tggggtttat tactgcatgc aagctctaca aactcctcgc   300
agttttggcc aggggaccac gctggagatc aaacgtacgg tggccgctcc ctccgtgttc   360
atcttcccac cttccgacga gcagctgaag tccggcaccg cttctgtcgt gtgcctgctg   420
aacaacttct accccgcga ggccaaggtg cagtggaagg tggacaacgc cctgcagtcc    480
ggcaactccc aggaatccgt gaccgagcag gactccaagg acagcaccta ctccctgtcc   540
tccaccctga ccctgtccaa ggccgactac gagaagcaca aggtgtacgc ctgcgaagtg   600
acccaccagg gcctgtctag ccccgtgacc aagtctttca ccggggcga gtgt           654
```

<210> SEQ ID NO 463
<211> LENGTH: 10
<212> TYPE: PRT
<213> ORGANISM: Homo Sapien

<400> SEQUENCE: 463

Gly Phe Ser Leu Ser Thr Thr Gly Val Gly
1               5                   10

<210> SEQ ID NO 464
<211> LENGTH: 7
<212> TYPE: PRT
<213> ORGANISM: Homo Sapien

<400> SEQUENCE: 464

Ile Tyr Trp Asp Asp Asp Lys
1               5

<210> SEQ ID NO 465
<211> LENGTH: 16
<212> TYPE: PRT
<213> ORGANISM: Homo Sapien

<400> SEQUENCE: 465

Thr His Gly Tyr Gly Ser Ala Ser Tyr Tyr His Tyr Gly Met Asp Val
1               5                   10                  15

<210> SEQ ID NO 466
<211> LENGTH: 124
<212> TYPE: PRT
<213> ORGANISM: Homo Sapien

<400> SEQUENCE: 466

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Thr
            20                  25                  30

Gly Val Gly Val Gly Trp Ile Arg Gln Pro Pro Gly Lys Ala Leu Glu
        35                  40                  45

Trp Leu Ala Val Ile Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Phe
                 85                  90                  95

Cys Thr His Gly Tyr Gly Ser Ala Ser Tyr Tyr His Tyr Gly Met Asp
                100                 105                 110

Val Trp Gly Gln Gly Thr Thr Val Thr Val Ser Ser
            115                 120

<210> SEQ ID NO 467
<211> LENGTH: 372
<212> TYPE: DNA
<213> ORGANISM: Homo Sapien

<400> SEQUENCE: 467
cagatcacct tgaaggagtc tggtcctacg ctggtgaaac ccacacagac cctcacgctg      60
acctgcacct tctctgggtt ctcactcagc actactggag tgggtgtggg ctggatccgt     120
cagcccccag gaaaggccct ggagtggctt gcagtcattt attgggatga tgataagcgc     180
tacagcccat ctctgaagag cagactcacc atcaccaagg acacctccaa aaaccaggtg     240
gtccttacaa tgaccaacat ggaccctgtg gacacagcca catatttctg tacacacgga     300
tatggttcgg cgagttatta ccactacggt atggacgtct ggggccaagg gaccacggtc     360
accgtctcct ca                                                         372

<210> SEQ ID NO 468
<211> LENGTH: 454
<212> TYPE: PRT
<213> ORGANISM: Homo Sapien

<400> SEQUENCE: 468

Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Thr
                 20                  25                  30

Gly Val Gly Val Gly Trp Ile Arg Gln Pro Pro Gly Lys Ala Leu Glu
             35                  40                  45

Trp Leu Ala Val Ile Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Phe
                 85                  90                  95

Cys Thr His Gly Tyr Gly Ser Ala Ser Tyr Tyr His Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 469
<211> LENGTH: 1368
<212> TYPE: DNA
<213> ORGANISM: Homo Sapien

<400> SEQUENCE: 469
cagatcacct tgaaggagtc tggtcctacg ctggtgaaac ccacacagac cctcacgctg     60
acctgcacct tctctgggtt ctcactcagc actactggag tgggtgtggg ctggatccgt    120
cagcccccag gaaaggccct ggagtggctt gcagtcattt attgggatga tgataagcgc    180
tacagcccat ctctgaagag cagactcacc atcaccaagg acacctccaa aaaccaggtg    240
gtccttacaa tgaccaacat ggaccctgtg gacacagcca catatttctg tacacacgga    300
tatggttcgg cgagttatta ccactacggt atggacgtct ggggccaagg gaccacggtc    360
accgtctcct cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540

-continued

```
ctgcagtcct ccggcctgta ctccctgtcc tccgtcgtga ccgtgccttc cagctctctg    600
ggcacccaga cctacatctg caacgtgaac cacaagccct ccaacaccaa ggtggacaag    660
aaggtggaac ccaagtcctg cgacaagacc cacacctgtc cccttgtcc tgcccctgaa     720
ctgctgggcg gaccttccgt gttcctgttc cccccaaagc ccaaggacac cctgatgatc    780
tcccggaccc ccgaagtgac ctgcgtggtg gtggatgtgt cccacgagga ccctgaagtg    840
aagttcaatt ggtacgtgga cggcgtgaa gtgcacaacg ccaagaccaa gcctagagag     900
gaacagtaca actccaccta ccgggtggtg tccgtgctga ccgtgctgca ccaggattgg    960
ctgaacggca agagtacaa gtgcaaggtg tccaacaagg ccctgcctgc ccccatcgaa     1020
aagaccatct ccaaggccaa gggccagccc cgggaacccc aggtgtacac actgcccct    1080
agcagggacg agctgaccaa gaaccaggtg tccctgacct gtctcgtgaa aggcttctac    1140
ccctccgata tcgccgtgga atgggagtcc aacggccagc tgagaacaa ctacaagacc    1200
accccccctg tgctggactc cgacggctca ttcttcctgt acagcaagct gacagtggac    1260
aagtcccggt ggcagcaggg caacgtgttc tcctgctccg tgatgcacga ggccctgcac    1320
aaccactaca cccagaagtc cctgtccctg agccccggca agtgatga              1368
```

<210> SEQ ID NO 470
<211> LENGTH: 6
<212> TYPE: PRT
<213> ORGANISM: Homo Sapien

<400> SEQUENCE: 470

Gln Ser Val Thr Asn Tyr
1               5

<210> SEQ ID NO 471
<211> LENGTH: 3
<212> TYPE: PRT
<213> ORGANISM: Homo Sapien

<400> SEQUENCE: 471

Asp Ala Ser
1

<210> SEQ ID NO 472
<211> LENGTH: 9
<212> TYPE: PRT
<213> ORGANISM: Homo Sapien

<400> SEQUENCE: 472

Gln His Arg Ser Asn Trp Pro Leu Thr
1               5

<210> SEQ ID NO 473
<211> LENGTH: 107
<212> TYPE: PRT
<213> ORGANISM: Homo Sapien

<400> SEQUENCE: 473

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Asn Tyr
                20                  25                  30

Leu Ala Trp His Gln Gln Lys Pro Gly Gln Ala Pro Arg Leu Leu Ile
            35                  40                  45

```
Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His Arg Ser Asn Trp Pro Leu
                 85                  90                  95

Thr Phe Gly Gly Gly Thr Lys Val Glu Ile Lys
            100                 105

<210> SEQ ID NO 474
<211> LENGTH: 322
<212> TYPE: DNA
<213> ORGANISM: Homo Sapien

<400> SEQUENCE: 474
gaaattgtat tgacacagtc tccagccacc ctgtctttgt ctccagggga aagagccacc    60
ctctcctgca gggccagtca gagtgttacc aactacttag cctggcacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcac cgtagcaact ggcctctcac tttcggcgga   300
gggaccaagg tggagatcaa ac                                            322

<210> SEQ ID NO 475
<211> LENGTH: 214
<212> TYPE: PRT
<213> ORGANISM: Homo Sapien

<400> SEQUENCE: 475

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Thr Asn Tyr
                 20                  25                  30

Leu Ala Trp His Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His Arg Ser Asn Trp Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 476
<211> LENGTH: 643
<212> TYPE: DNA
<213> ORGANISM: Homo Sapien

<400> SEQUENCE: 476

```
gaaattgtat tgacacagtc tccagccacc ctgtctttgt ctccagggga aagagccacc    60
ctctcctgca gggccagtca gagtgttacc aactactag cctggcacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcac cgtagcaact ggcctctcac tttcggcgga    300
gggaccaagg tggagatcaa accgtacggt ggccgctccc tccgtgttca tcttcccacc    360
ttccgacgag cagctgaagt ccggcaccgc ttctgtcgtg tgcctgctga acaacttcta    420
cccccgcgag gccaaggtgc agtggaaggt ggacaacgcc ctgcagtccg gcaactccca    480
ggaatccgtg accgagcagg actccaagga cagcacctac tccctgtcct ccaccctgac    540
cctgtccaag gccgactacg agaagcacaa ggtgtacgcc tgcgaagtga cccaccaggg    600
cctgtctagc cccgtgacca gtctttcaa ccggggcgag tgt                       643
```

<210> SEQ ID NO 477
<211> LENGTH: 10
<212> TYPE: PRT
<213> ORGANISM: Homo Sapien

<400> SEQUENCE: 477

Gly Phe Ser Leu Ser Thr Ser Gly Val Gly
1               5                   10

<210> SEQ ID NO 478
<211> LENGTH: 7
<212> TYPE: PRT
<213> ORGANISM: Homo Sapien

<400> SEQUENCE: 478

Ile Tyr Trp Asp Asp Asp Lys
1               5

<210> SEQ ID NO 479
<211> LENGTH: 16
<212> TYPE: PRT
<213> ORGANISM: Homo Sapien

<400> SEQUENCE: 479

Thr His Gly Tyr Gly Ser Ala Ser Tyr Tyr His Tyr Gly Met Asp Val
1               5                   10                  15

<210> SEQ ID NO 480
<211> LENGTH: 124
<212> TYPE: PRT
<213> ORGANISM: Homo Sapien

<400> SEQUENCE: 480

Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asp Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Phe
                 85                  90                  95

Cys Thr His Gly Tyr Gly Ser Ala Ser Tyr Tyr His Tyr Gly Met Asp
                100                 105                 110

Val Trp Gly Gln Gly Thr Thr Val Thr Val Ser Ser
                115                 120

<210> SEQ ID NO 481
<211> LENGTH: 372
<212> TYPE: DNA
<213> ORGANISM: Homo Sapien

<400> SEQUENCE: 481
cagatcaccT tgaaggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcagtcattt attgggatga tgataagcgc   180
tacagcccat ctctgaagag caggctcacc atcaccaagg acacctccaa aaaccaggtg   240
gtccttacaa tgaccaacat ggaccctgtg gacacagcca catatttctg tacacacgga   300
tatggttcgg cgagttatta ccactacggt atggacgtct ggggccaagg gaccacggtc   360
accgtctcct ca                                                       372

<210> SEQ ID NO 482
<211> LENGTH: 454
<212> TYPE: PRT
<213> ORGANISM: Homo Sapien

<400> SEQUENCE: 482

Gln Ile Thr Leu Lys Glu Ser Gly Pro Thr Leu Val Lys Pro Thr Gln
 1                5                  10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
        35                  40                  45

Trp Leu Ala Val Ile Tyr Trp Asp Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Phe
                 85                  90                  95

Cys Thr His Gly Tyr Gly Ser Ala Ser Tyr Tyr His Tyr Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
    195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 483
<211> LENGTH: 1368
<212> TYPE: DNA
<213> ORGANISM: Homo Sapien

<400> SEQUENCE: 483
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcagtcattt attgggatga tgataagcgc     180
tacagcccat ctctgaagag caggctcacc atcaccaagg acacctccaa aaaccaggtg     240
gtccttacaa tgaccaacat ggaccctgtg gacacagcca catatttctg tacacacgga     300
tatggttcgg cgagttatta ccactacggt atggacgtct ggggccaagg gaccacggtc     360
accgtctcct cagccagcac caagggcccc tctgtgttcc ctctggcccc ttccagcaag     420

-continued

```
tccacctctg gcggaacagc cgctctgggc tgcctcgtga aggactactt ccccgagcct    480
gtgaccgtgt cctggaactc tggcgctctg accagcggag tgcacacctt ccctgctgtg    540
ctgcagtcct ccggcctgta ctccctgtcc tccgtcgtga ccgtgccttc cagctctctg    600
ggcacccaga cctacatctg caacgtgaac cacaagccct ccaacaccaa ggtggacaag    660
aaggtggaac ccaagtcctg cgacaagacc cacacctgtc ccccttgtcc tgcccctgaa    720
ctgctgggcg gaccttccgt gttcctgttc cccccaaagc caaggacac cctgatgatc    780 tcccggaccc ccgaagtgac ctgcgtggtg gtggatgtgt cccacgagga ccctgaagtg    840
aagttcaatt ggtacgtgga cggcgtggaa gtgcacaacg ccaagaccaa gcctagagag    900
gaacagtaca actccaccta ccgggtggtg tccgtgctga ccgtgctgca ccaggattgg    960
ctgaacggca agagtacaa gtgcaaggtg tccaacaagg ccctgcctgc ccccatcgaa   1020
aagaccatct ccaaggccaa gggccagccc cgggaacccc aggtgtacac actgccccct   1080
agcagggacg agctgaccaa gaaccaggtg tccctgacct gtctcgtgaa aggcttctac   1140
ccctccgata tcgccgtgga atgggagtcc aacggccagc ctgagaacaa ctacaagacc   1200
accccccctg tgctggactc cgacggctca ttcttcctgt acagcaagct gacagtggac   1260
aagtcccggt ggcagcaggg caacgtgttc tcctgctccg tgatgcacga ggccctgcac   1320
aaccactaca cccagaagtc cctgtccctg agccccggca agtgatga                 1368
```

<210> SEQ ID NO 484
<211> LENGTH: 6
<212> TYPE: PRT
<213> ORGANISM: Homo Sapien

<400> SEQUENCE: 484

Gln Ser Val Thr Asn Tyr
1               5

<210> SEQ ID NO 485
<211> LENGTH: 3
<212> TYPE: PRT
<213> ORGANISM: Homo Sapien

<400> SEQUENCE: 485

Asp Ala Ser
1

<210> SEQ ID NO 486
<211> LENGTH: 9
<212> TYPE: PRT
<213> ORGANISM: Homo Sapien

<400> SEQUENCE: 486

Gln Gln Arg Ser Asn Trp Pro Leu Thr
1               5

<210> SEQ ID NO 487
<211> LENGTH: 107
<212> TYPE: PRT
<213> ORGANISM: Homo Sapien

<400> SEQUENCE: 487

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Asn Tyr
            20                  25                  30

-continued

Leu Ala Trp His Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
                100                 105

<210> SEQ ID NO 488
<211> LENGTH: 321
<212> TYPE: DNA
<213> ORGANISM: Homo Sapien

<400> SEQUENCE: 488
gaaattgtgt tgacacagtc tccagccacc ctgtctttgt ctccagggga aagagccacc     60
ctctcctgca gggccagtca gagtgttacc aactacttag cctggcacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctctcac tttcggcgga    300
gggaccaagg tggagatcaa a                                              321

<210> SEQ ID NO 489
<211> LENGTH: 214
<212> TYPE: PRT
<213> ORGANISM: Homo Sapien

<400> SEQUENCE: 489

Glu Ile Val Leu Thr Gln Ser Pro Ala Thr Leu Ser Leu Ser Pro Gly
 1               5                   10                  15

Glu Arg Ala Thr Leu Ser Cys Arg Ala Ser Gln Ser Val Thr Asn Tyr
             20                  25                  30

Leu Ala Trp His Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 490
<211> LENGTH: 642
<212> TYPE: DNA
<213> ORGANISM: Homo Sapien

<400> SEQUENCE: 490
gaaattgtgt tgacacagtc tccagccacc ctgtctttgt ctccagggga aagagccacc      60
ctctcctgca gggccagtca gagtgttacc aactacttag cctggcacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctctcac tttcggcgga    300
gggaccaagg tggagatcaa acgtacggtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg gacaacgccc tgcagtccgg caactcccag    480
gaatccgtga ccgagcagga ctccaaggac agcacctact ccctgtcctc caccctgacc    540
ctgtccaagg ccgactacga aagcacaag gtgtacgcct gcgaagtgac ccaccagggc    600
ctgtctagcc ccgtgaccaa gtctttcaac cggggcgagt gt                      642

<210> SEQ ID NO 491
<211> LENGTH: 8
<212> TYPE: PRT
<213> ORGANISM: Homo Sapien

<400> SEQUENCE: 491

Gly Phe Thr Phe Ser Asp Tyr Tyr
1               5

<210> SEQ ID NO 492
<211> LENGTH: 8
<212> TYPE: PRT
<213> ORGANISM: Homo Sapien

<400> SEQUENCE: 492

Ile Ser Ser Ser Gly Ser Thr Ile
1               5

<210> SEQ ID NO 493
<211> LENGTH: 20
<212> TYPE: PRT
<213> ORGANISM: Homo Sapien

<400> SEQUENCE: 493

Ala Arg Asp Phe Tyr Asp Ile Leu Thr Asp Ser Pro Tyr Phe Tyr Tyr
1               5                   10                  15

Gly Val Asp Val
            20

<210> SEQ ID NO 494
<211> LENGTH: 127
<212> TYPE: PRT
<213> ORGANISM: Homo Sapien

<400> SEQUENCE: 494

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Ala Glu Asp Thr Ala Val Tyr Tyr Cys
                85                  90                  95

Ala Arg Asp Phe Tyr Asp Ile Leu Thr Asp Ser Pro Tyr Phe Tyr Tyr
            100                 105                 110

Gly Val Asp Val Trp Gly Gln Gly Thr Thr Val Thr Val Ser Ser
        115                 120                 125

<210> SEQ ID NO 495
<211> LENGTH: 381
<212> TYPE: DNA
<213> ORGANISM: Homo Sapien

<400> SEQUENCE: 495
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtttcatac attagtagta gtggtagtac catatactac       180
gcagactctg tgaagggccg attcaccatc tccaggaca acgccaagaa ctcactgtat      240
ctgcaaatta acagcctgag agccgaggac acggccgtgt attactgtgc gagagatttt    300
tacgatattt tgactgatag tccgtacttc tactacggtg tggacgtctg gggccaaggg    360
accacggtca ccgtctcctc a                                              381

<210> SEQ ID NO 496
<211> LENGTH: 457
<212> TYPE: PRT
<213> ORGANISM: Homo Sapien

<400> SEQUENCE: 496

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Ala Glu Asp Thr Ala Val Tyr Tyr Cys
                85                  90                  95

Ala Arg Asp Phe Tyr Asp Ile Leu Thr Asp Ser Pro Tyr Phe Tyr Tyr
            100                 105                 110

Gly Val Asp Val Trp Gly Gln Gly Thr Thr Val Thr Val Ser Ser Ala
        115                 120                 125

| | | | | | | | | | | | | |
|---|---|---|---|---|---|---|---|---|---|---|---|---|
|Ser|Thr|Lys|Gly|Pro|Ser|Val|Phe|Pro|Leu|Ala|Pro|Ser|Ser|Lys|Ser|
| |130| | | |135| | | |140| | | | | | |

Ser Thr Lys Gly Pro Ser Val Phe Pro Leu Ala Pro Ser Ser Lys Ser
 130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 497
<211> LENGTH: 1377
<212> TYPE: DNA
<213> ORGANISM: Homo Sapien

<400> SEQUENCE: 497
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg gctggagtg gtttcatac attagtagta gtggtagtac catatactac   180
gcagactctg tgaagggccg attcaccatc tccagggaca acgccaagaa ctcactgtat   240

-continued

```
ctgcaaatta acagcctgag agccgaggac acggccgtgt attactgtgc gagagatttt    300
tacgatattt tgactgatag tccgtacttc tactacggtg tggacgtctg gggccaaggg    360
accacggtca ccgtctcctc agccagcacc aagggcccct ctgtgttccc tctggcccct    420
tccagcaagt ccacctctgg cggaacagcc gctctgggct gcctcgtgaa ggactacttc    480
cccgagcctg tgaccgtgtc ctggaactct ggcgctctga ccagcggagt gcacaccttc    540
cctgctgtgc tgcagtcctc cggcctgtac tccctgtcct ccgtcgtgac cgtgccttcc    600
agctctctgg gcacccagac ctacatctgc aacgtgaacc acaagccctc caacaccaag    660
gtggacaaga aggtggaacc caagtcctgc gacaagaccc acacctgtcc cccttgtcct    720
gcccctgaac tgctgggcgg accttccgtg ttcctgttcc cccaaagcc caaggacacc     780
ctgatgatct cccggacccc cgaagtgacc tgcgtggtgg tggatgtgtc ccacgaggac    840
cctgaagtga agttcaattg gtacgtggac ggcgtggaag tgcacaacgc caagaccaag    900
cctagagagg aacagtacaa ctccacctac cgggtggtgt ccgtgctgac cgtgctgcac    960
caggattggc tgaacggcaa agagtacaag tgcaaggtgt ccaacaaggc cctgcctgcc   1020
cccatcgaaa agaccatctc caaggccaag ggccagcccc gggaacccca ggtgtacaca   1080
ctgcccccta gcagggacga gctgaccaag aaccaggtgt ccctgacctg tctcgtgaaa   1140
ggcttctacc cctccgatat cgccgtggaa tgggagtcca acggccagcc tgagaacaac   1200
tacaagacca ccccccctgt gctggactcc gacggctcat tcttcctgta cagcaagctg   1260
acagtggaca gtcccggtgt gcagcagggc aacgtgttct cctgctccgt gatgcacgag   1320
gccctgcaca accactacac ccagaagtcc ctgtccctga ccccggcaa gtgatga      1377
```

<210> SEQ ID NO 498
<211> LENGTH: 11
<212> TYPE: PRT
<213> ORGANISM: Homo Sapien

<400> SEQUENCE: 498

Gln Ser Leu Leu His Ser Asn Gly Tyr Asn Tyr
1               5                   10

<210> SEQ ID NO 499
<211> LENGTH: 3
<212> TYPE: PRT
<213> ORGANISM: Homo Sapien

<400> SEQUENCE: 499

Leu Gly Ser
1

<210> SEQ ID NO 500
<211> LENGTH: 9
<212> TYPE: PRT
<213> ORGANISM: Homo Sapien

<400> SEQUENCE: 500

Met Gln Ala Leu Gln Thr Pro Arg Thr
1               5

<210> SEQ ID NO 501
<211> LENGTH: 112
<212> TYPE: PRT
<213> ORGANISM: Homo Sapien

<400> SEQUENCE: 501

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110
```

<210> SEQ ID NO 502
<211> LENGTH: 336
<212> TYPE: DNA
<213> ORGANISM: Homo Sapien

<400> SEQUENCE: 502

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
cggacgttcg gccaagggac caaggtggaa atcaaa                             336
```

<210> SEQ ID NO 503
<211> LENGTH: 219
<212> TYPE: PRT
<213> ORGANISM: Homo Sapien

<400> SEQUENCE: 503

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215
```

<210> SEQ ID NO 504
<211> LENGTH: 657
<212> TYPE: DNA
<213> ORGANISM: Homo Sapien

<400> SEQUENCE: 504

```
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc aatcggggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cggacgttcg gccaagggac caaggtggaa atcaaacgta cggtggccgc tcccctccgtg    360
ttcatcttcc caccttccga cgagcagctg aagtccggaa ccgcttctgt cgtgtgcctg    420
ctgaacaact tctaccccg cgaggccaag gtgcagtgga aggtggacaa cgccctgcag    480
tccggcaact cccaggaatc cgtgaccgag caggactcca aggacagcac ctactccctg    540
tcctccaccc tgaccctgtc aaggccgac tacgagaagc acaaggtgta cgcctgcgaa    600
gtgacccacc agggcctgtc tagccccgtg accaagtctt tcaaccgggg cgagtgt      657
```

<210> SEQ ID NO 505
<211> LENGTH: 239
<212> TYPE: PRT
<213> ORGANISM: Homo Sapien

<400> SEQUENCE: 505

```
Phe Thr Val Thr Val Pro Lys Asp Leu Tyr Val Val Glu Tyr Gly Ser
1               5                  10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160
```

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
        180                 185                 190

Phe Arg Arg Leu Asp Pro Glu Asn His Thr Ala Glu Leu Val Ile
        195                 200                 205

Pro Glu Leu Pro Leu Ala His Pro Pro Asn Glu Arg Thr Ile Glu Gly
    210                 215                 220

Arg Asp Tyr Lys Asp Asp Asp Lys His His His His His His
225                 230                 235

<210> SEQ ID NO 506
<211> LENGTH: 179
<212> TYPE: PRT
<213> ORGANISM: Homo Sapien

<400> SEQUENCE: 506

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu

<210> SEQ ID NO 507
<211> LENGTH: 121
<212> TYPE: PRT
<213> ORGANISM: Homo Sapien

<400> SEQUENCE: 507

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

-continued

Ser Gln Leu Ser Asn Asn Ser Val Ser Phe Phe Leu Tyr Asn Leu Asp
 65                  70                  75                  80

His Ser His Ala Asn Tyr Tyr Phe Cys Asn Leu Ser Ile Phe Asp Pro
                 85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe
        115                 120

<210> SEQ ID NO 508
<211> LENGTH: 199
<212> TYPE: PRT
<213> ORGANISM: Homo Sapien

<400> SEQUENCE: 508

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Tyr Ser Ser Val His Asp Pro
        165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 509
<211> LENGTH: 33
<212> TYPE: PRT
<213> ORGANISM: Homo Sapien

<400> SEQUENCE: 509

Lys Tyr Ser Ser Ser Val His Asp Pro Asn Gly Glu Tyr Met Phe Met
1               5                   10                  15

Arg Ala Val Asn Thr Ala Lys Lys Ser Arg Leu Thr Asp Val Thr Leu
            20                  25                  30

Met

<210> SEQ ID NO 510
<211> LENGTH: 128
<212> TYPE: PRT

<213> ORGANISM: Mus Musculus

<400> SEQUENCE: 510

Glu Ile Asn Gly Ser Ala Asp His Arg Met Phe Ser Phe His Asn Gly
1               5                   10                  15
Gly Val Gln Ile Ser Cys Lys Tyr Pro Glu Thr Val Gln Gln Leu Lys
            20                  25                  30
Met Arg Leu Phe Arg Glu Arg Glu Val Leu Cys Glu Leu Thr Lys Thr
        35                  40                  45
Lys Gly Ser Gly Asn Ala Val Ser Ile Lys Asn Pro Met Leu Cys Leu
    50                  55                  60
Tyr His Leu Ser Asn Asn Ser Val Ser Phe Phe Leu Asn Asn Pro Asp
65                  70                  75                  80
Ser Ser Gln Gly Ser Tyr Tyr Phe Cys Ser Leu Ser Ile Phe Asp Pro
                85                  90                  95
Pro Phe Gln Glu Arg Asn Leu Ser Gly Gly Tyr Leu His Ile Tyr
            100                 105                 110
Glu Ser Gln Leu Cys Cys Gln Leu Lys Ile Val Val Gln Val Thr Glu
            115                 120                 125

<210> SEQ ID NO 511
<211> LENGTH: 121
<212> TYPE: PRT
<213> ORGANISM: Mus Musculus

<400> SEQUENCE: 511

Glu Ile Asn Gly Ser Ala Asp His Arg Met Phe Ser Phe His Asn Gly
1               5                   10                  15
Gly Val Gln Ile Ser Cys Lys Tyr Pro Glu Thr Val Gln Gln Leu Lys
            20                  25                  30
Met Arg Leu Phe Arg Glu Arg Glu Val Leu Cys Glu Leu Thr Lys Thr
        35                  40                  45
Lys Gly Ser Gly Asn Ala Val Ser Ile Lys Asn Pro Met Leu Cys Leu
    50                  55                  60
Tyr His Leu Ser Asn Asn Ser Val Ser Phe Phe Leu Asn Asn Pro Asp
65                  70                  75                  80
Ser Ser Gln Gly Ser Tyr Tyr Phe Cys Ser Leu Ser Ile Phe Asp Pro
                85                  90                  95
Pro Phe Gln Glu Arg Asn Leu Ser Gly Gly Tyr Leu His Ile Tyr
            100                 105                 110
Glu Ser Gln Leu Cys Cys Gln Leu Lys
            115                 120

<210> SEQ ID NO 512
<211> LENGTH: 147
<212> TYPE: PRT
<213> ORGANISM: Mus Musculus

<400> SEQUENCE: 512

Met Gly Trp Ser Cys Ile Ile Leu Phe Leu Val Ala Thr Ala Thr Gly
1               5                   10                  15
Val His Ser Glu Ile Asn Gly Ser Ala Asp His Arg Met Phe Ser Phe
            20                  25                  30
His Asn Gly Gly Val Gln Ile Ser Cys Lys Tyr Pro Glu Thr Val Gln
        35                  40                  45
Gln Leu Lys Met Arg Leu Phe Arg Glu Arg Glu Val Leu Cys Glu Leu
    50                  55                  60

Thr Lys Thr Lys Gly Ser Gly Asn Ala Val Ser Ile Lys Asn Pro Met
65                  70                  75                  80

Leu Cys Leu Tyr His Leu Ser Asn Asn Ser Val Ser Phe Phe Leu Asn
                85                  90                  95

Asn Pro Asp Ser Ser Gln Gly Ser Tyr Tyr Phe Cys Ser Leu Ser Ile
            100                 105                 110

Phe Asp Pro Pro Pro Phe Gln Glu Arg Asn Leu Ser Gly Gly Tyr Leu
            115                 120                 125

His Ile Tyr Glu Ser Gln Leu Cys Cys Gln Leu Lys Ile Val Val Gln
        130                 135                 140

Val Thr Glu
145

<210> SEQ ID NO 513
<211> LENGTH: 199
<212> TYPE: PRT
<213> ORGANISM: Cynomologus

<400> SEQUENCE: 513

Met Lys Ser Gly Leu Trp Tyr Phe Phe Leu Phe Cys Leu His Met Lys
1               5                   10                  15

Val Leu Thr Gly Glu Ile Asn Gly Ser Ala Asn Tyr Glu Met Phe Ile
                20                  25                  30

Phe His Asn Gly Gly Val Gln Ile Leu Cys Lys Tyr Pro Asp Ile Val
            35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Lys Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp Arg Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Thr Phe Val Val Cys Ile Phe Gly Cys Ile Leu
145                 150                 155                 160

Ile Cys Trp Leu Thr Lys Lys Lys Tyr Ser Ser Thr Val His Asp Pro
                165                 170                 175

Asn Gly Glu Tyr Met Phe Met Arg Ala Val Asn Thr Ala Lys Lys Ser
            180                 185                 190

Arg Leu Thr Gly Thr Thr Pro
        195

<210> SEQ ID NO 514
<211> LENGTH: 120
<212> TYPE: PRT
<213> ORGANISM: Cynomologus

<400> SEQUENCE: 514

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
                20                  25                  30

```
Met Gln Leu Leu Lys Gly Gly Gln Ile Leu Cys Asp Leu Thr Lys Thr
                35                  40                  45

Lys Gly Ser Gly Asn Lys Val Ser Ile Lys Ser Leu Lys Phe Cys His
 50                  55                  60

Ser Gln Leu Ser Asn Asn Ser Val Ser Phe Phe Leu Tyr Asn Leu Asp
 65                  70                  75                  80

Arg Ser His Ala Asn Tyr Tyr Phe Cys Asn Leu Ser Ile Phe Asp Pro
                 85                  90                  95

Pro Phe Lys Val Thr Leu Thr Gly Gly Tyr Leu His Ile Tyr Glu
            100                 105                 110

Ser Gln Leu Cys Cys Gln Leu Lys
            115                 120

<210> SEQ ID NO 515
<211> LENGTH: 240
<212> TYPE: PRT
<213> ORGANISM: Homo Sapien

<400> SEQUENCE: 515

Asp Thr Gln Glu Lys Glu Val Arg Ala Met Val Gly Ser Asp Val Glu
 1               5                  10                  15

Leu Ser Cys Ala Cys Pro Glu Gly Ser Arg Phe Asp Leu Asn Asp Val
                20                  25                  30

Tyr Val Tyr Trp Gln Thr Ser Glu Ser Lys Thr Val Thr Tyr His
                35                  40                  45

Ile Pro Gln Asn Ser Ser Leu Glu Asn Val Asp Ser Arg Tyr Arg Asn
 50                  55                  60

Arg Ala Leu Met Ser Pro Ala Gly Met Leu Arg Gly Asp Phe Ser Leu
 65                  70                  75                  80

Arg Leu Phe Asn Val Thr Pro Gln Asp Glu Gln Lys Phe His Cys Leu
                 85                  90                  95

Val Leu Ser Gln Ser Leu Gly Phe Gln Glu Val Leu Ser Val Glu Val
                100                 105                 110

Thr Leu His Val Ala Ala Asn Phe Ser Val Pro Val Val Ser Ala Pro
                115                 120                 125

His Ser Pro Ser Gln Asp Glu Leu Thr Phe Thr Cys Thr Ser Ile Asn
130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
                180                 185                 190

Val Asn Ile Gly Cys Cys Ile Glu Asn Val Leu Leu Gln Gln Asn Leu
                195                 200                 205

Thr Val Gly Ser Gln Thr Gly Asn Asp Ile Gly Glu Arg Asp Lys Ile
            210                 215                 220

Thr Glu Asn Pro Val Ser Thr Gly Glu Lys Asn Ala Ala Thr Trp Ser
225                 230                 235                 240

<210> SEQ ID NO 516
<211> LENGTH: 302
<212> TYPE: PRT
<213> ORGANISM: Homo Sapien

<400> SEQUENCE: 516
```

```
Met Arg Leu Gly Ser Pro Gly Leu Leu Phe Leu Phe Ser Ser Leu
1               5                   10                  15

Arg Ala Asp Thr Gln Glu Lys Glu Val Arg Ala Met Val Gly Ser Asp
                20                  25                  30

Val Glu Leu Ser Cys Ala Cys Pro Glu Gly Ser Arg Phe Asp Leu Asn
                35                  40                  45

Asp Val Tyr Val Tyr Trp Gln Thr Ser Glu Ser Lys Thr Val Val Thr
50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
                100                 105                 110

Cys Leu Val Leu Ser Gln Ser Leu Gly Phe Gln Glu Val Leu Ser Val
                115                 120                 125

Glu Val Thr Leu His Val Ala Ala Asn Phe Ser Val Pro Val Val Ser
                130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
                180                 185                 190

Met Arg Gly Leu Tyr Asp Val Val Ser Val Leu Arg Ile Ala Arg Thr
                195                 200                 205

Pro Ser Val Asn Ile Gly Cys Cys Ile Glu Asn Val Leu Leu Gln Gln
210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
                260                 265                 270

Ile Gly Trp Val Cys Arg Asp Arg Cys Leu Gln His Ser Tyr Ala Gly
                275                 280                 285

Ala Trp Ala Val Ser Pro Glu Thr Glu Leu Thr Gly His Val
290                 295                 300

<210> SEQ ID NO 517
<211> LENGTH: 113
<212> TYPE: PRT
<213> ORGANISM: Homo Sapien

<400> SEQUENCE: 517

Leu Gln Met Ile Leu Asn Gly Ile Asn Asn Tyr Lys Asn Pro Lys Leu
1               5                   10                  15

Thr Ala Met Leu Thr Phe Lys Phe Tyr Met Pro Lys Lys Ala Thr Glu
                20                  25                  30

Leu Lys His Leu Gln Cys Leu Glu Glu Glu Leu Lys Pro Leu Glu Glu
                35                  40                  45

Val Leu Asn Leu Ala Gln Ser Lys Asn Phe His Leu Arg Pro Arg Asp
50                  55                  60

Leu Ile Ser Asn Ile Asn Val Ile Val Leu Glu Leu Lys Gly Ser Glu
```

```
                65                  70                  75                  80
Thr Thr Phe Met Cys Glu Tyr Ala Asp Glu Thr Ala Thr Ile Val Glu
                    85                  90                  95

Phe Leu Asn Arg Trp Ile Thr Phe Cys Gln Ser Ile Ile Ser Thr Leu
                100                 105                 110

Thr
```

```
<210> SEQ ID NO 518
<211> LENGTH: 113
<212> TYPE: PRT
<213> ORGANISM: Homo Sapien

<400> SEQUENCE: 518

Leu Gln Met Ile Leu Asn Gly Ile Asn Asn Tyr Lys Asn Pro Lys Leu
1               5                   10                  15

Thr Gln Met Leu Thr Phe Lys Phe Tyr Met Pro Lys Lys Ala Thr Glu
                20                  25                  30

Leu Lys His Leu Gln Cys Leu Glu Glu Glu Leu Lys Pro Leu Glu Glu
            35                  40                  45

Val Leu Asn Leu Ala Gln Ser Lys Asn Phe His Leu Arg Pro Arg Asp
    50                  55                  60

Leu Ile Ser Asn Ile Asn Val Ile Val Leu Glu Leu Lys Gly Ser Glu
65                  70                  75                  80

Thr Thr Phe Met Cys Glu Tyr Ala Asp Glu Thr Ala Thr Ile Val Glu
                85                  90                  95

Phe Leu Asn Arg Trp Ile Thr Phe Cys Gln Ser Ile Ile Ser Thr Leu
                100                 105                 110

Thr
```

```
<210> SEQ ID NO 519
<211> LENGTH: 336
<212> TYPE: DNA
<213> ORGANISM: Homo Sapien

<400> SEQUENCE: 519
gatattgtga tgactcagtc tccactctcc ctgcccgtca cccctggaga gccggcctcc      60
atctcctgca ggtctagtca gagcctcctg catagtgatg gatacaacta tttggattgg    120
tacctgcaga agccagggca gtctccacag ctcctgatct atttgggttc tactcgggcc    180 tccggggttcc ctgacaggtt cagtggcagt ggatcaggca cagattttac actgaaaatc   240
agcagagtgg aggctgagga tgttggggtt tattactgca tgcaagctct acaaactccg    300
ctcagttttg gccaggggac caagctggag atcaaa                               336
```

```
<210> SEQ ID NO 520
<211> LENGTH: 657
<212> TYPE: DNA
<213> ORGANISM: Homo Sapien

<400> SEQUENCE: 520
gatattgtga tgactcagtc tccactctcc ctgcccgtca cccctggaga gccggcctcc      60
atctcctgca ggtctagtca gagcctcctg catagtgatg gatacaacta tttggattgg    120
tacctgcaga agccagggca gtctccacag ctcctgatct atttgggttc tactcgggcc    180 tccggggttcc ctgacaggtt cagtggcagt ggatcaggca cagattttac actgaaaatc   240
agcagagtgg aggctgagga tgttggggtt tattactgca tgcaagctct acaaactccg    300
```

```
ctcagttttg gccaggggac caagctggag atcaaacgta cggtggccgc tccctccgtg    360
ttcatcttcc caccttccga cgagcagctg aagtccggca ccgcttctgt cgtgtgcctg    420
ctgaacaact tctaccccg cgaggccaag gtgcagtgga aggtggacaa cgccctgcag     480
tccggcaact cccaggaatc cgtgaccgag caggactcca aggacagcac ctactccctg    540
tcctccaccc tgaccctgtc aaggccgac tacgagaagc acaaggtgta cgcctgcgaa     600
gtgacccacc agggcctgtc tagccccgtg accaagtctt tcaaccgggg cgagtgt       657
```

```
<210> SEQ ID NO 521
<211> LENGTH: 372
<212> TYPE: DNA
<213> ORGANISM: Homo Sapien

<400> SEQUENCE: 521
```

```
gaggtgcagc tggtggagtc tgggggaggt gtggtacggc ctgggggtc cctgagactc      60 tcctgtgtag cctctggagt caccttttgat gattatggca tgagctgggt ccgccaagct   120
ccagggaagg ggctggagtg ggtctctggt attaattgga atggtggcga cacagattat    180
tcagactctg tgaagggccg attcaccatc tccagagaca acgccaagaa ctccctgtat    240
ctacaaatga atagtctgag agccgaggac acggccttgt attactgtgc gagggatttc    300
tatggttcgg ggagttatta tcacgttcct tttgactact ggggccaggg aatcctggtc    360
accgtctcct ca                                                        372
```

```
<210> SEQ ID NO 522
<211> LENGTH: 1368
<212> TYPE: DNA
<213> ORGANISM: Homo Sapien

<400> SEQUENCE: 522
```

```
gaggtgcagc tggtggagtc tgggggaggt gtggtacggc ctgggggtc cctgagactc      60 tcctgtgtag cctctggagt caccttttgat gattatggca tgagctgggt ccgccaagct   120
ccagggaagg ggctggagtg ggtctctggt attaattgga atggtggcga cacagattat    180
tcagactctg tgaagggccg attcaccatc tccagagaca acgccaagaa ctccctgtat    240
ctacaaatga atagtctgag agccgaggac acggccttgt attactgtgc gagggatttc    300
tatggttcgg ggagttatta tcacgttcct tttgactact ggggccaggg aatcctggtc    360
accgtctcct cagccagcac caagggcccc tctgtgttcc ctctggcccc ttccagcaag    420
tccacctctg gcggaacagc cgctctgggc tgcctcgtga aggactactt ccccgagcct    480
gtgaccgtgt cctggaactc tggcgctctg accagcggag tgcacacctt ccctgctgtg    540
ctgcagtcct ccggcctgta ctccctgtcc tccgtcgtga ccgtgccttc agctctctg     600 ggcacccaga cctacatctg caacgtgaac cacaagccct caacaccaa ggtggacaag    660 aagtggaac ccaagtcctg cgacaagacc cacacctgtc cccttgtcc tgcccctgaa     720 ctgctgggcg accttccgt gttcctgttc ccccaaagc caaggacac cctgatgatc      780 tccccggaccc ccgaagtgac ctgcgtggtg gtggatgtgt cccacgagga ccctgaagtg    840
aagttcaatt ggtacgtgga cggcgtggaa gtgcacaacg ccaagaccaa gcctagagag    900
gaacagtaca actccaccta ccgggtggtg tccgtgctga ccgtgctgca ccaggattgg    960
ctgaacggca aagagtacaa gtgcaaggtg tccaacaagg ccctgcctgc ccccatcgaa   1020
aagaccatct ccaaggccaa gggccagccc cgggaacccc aggtgtacac actgccccct   1080
agcagggacg agctgaccaa gaaccaggtg tccctgacct gtctcgtgaa aggcttctac   1140
```

-continued

| | |
|---|---|
| ccctccgata tcgccgtgga atgggagtcc aacggccagc ctgagaacaa ctacaagacc | 1200 |
| acccccctg tgctggactc cgacggctca ttcttcctgt acagcaagct gacagtggac | 1260 |
| aagtccggt ggcagcaggg caacgtgttc tcctgctccg tgatgcacga ggccctgcac | 1320 |
| aaccactaca cccagaagtc cctgtccctg agccccggca agtgatga | 1368 |

<210> SEQ ID NO 523
<211> LENGTH: 990
<212> TYPE: DNA
<213> ORGANISM: Homo Sapien

<400> SEQUENCE: 523

| | |
|---|---|
| gcctccacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagag agttgagccc | 300 |
| aaatcttgtg acaaaactca cacatgccca ccgtgcccag cacctgaact cctggggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcaaggtctc caacaaagcc ctcccagccc ccatcgagaa aaccatctcc | 660 |
| aaagccaaag gcagccccg agaaccacag gtgtacaccc tgcccccatc ccggaggag | 720 |
| atgaccaaga accaggtcag cctgacctgc ctggtcaaag gcttctatcc cagcgacatc | 780 |
| gccgtggagt gggagagcaa tgggcagccg gagaacaact acaagaccac gcctcccgtg | 840 |
| ctggactccg acggctcctt cttcctctat agcaagctca ccgtggacaa gagcaggtgg | 900 |
| cagcagggga acgtcttctc atgctccgtg atgcatgagg ctctgcacaa ccactacacg | 960 |
| cagaagagcc tctccctgtc cccgggtaaa | 990 |

<210> SEQ ID NO 524
<211> LENGTH: 330
<212> TYPE: PRT
<213> ORGANISM: Homo Sapien

<400> SEQUENCE: 524

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 525
<211> LENGTH: 990
<212> TYPE: DNA
<213> ORGANISM: Homo Sapien

<400> SEQUENCE: 525
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc catcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
```

```
ctggactccg acggctcctt cttcctctac agcaagctca ccgtggacaa gagcaggtgg    900
cagcagggga acatcttctc atgctccgtg atgcatgagg ctctgcacaa ccactacacg    960
cagaagagcc tctccctgtc tccgggtaaa                                     990
```

<210> SEQ ID NO 526
<211> LENGTH: 330
<212> TYPE: PRT
<213> ORGANISM: Homo Sapien

<400> SEQUENCE: 526

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Ile Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 527

```
<211> LENGTH: 978
<212> TYPE: DNA
<213> ORGANISM: Homo Sapien

<400> SEQUENCE: 527
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc      420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac tcccatgctg gactccgac    840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                   978

<210> SEQ ID NO 528
<211> LENGTH: 326
<212> TYPE: PRT
<213> ORGANISM: Homo Sapien

<400> SEQUENCE: 528

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
```

```
                    165                 170                 175
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 529
<211> LENGTH: 978
<212> TYPE: DNA
<213> ORGANISM: Homo Sapien

<400> SEQUENCE: 529
gcctccacca agggcccatc ggtcttcccc ctggcgccct gctccaggag cacctccgag     60
agcacagcgg ccctgggctg cctggtcaag gactacttcc ccgaaccggt gacggtgtcg    120
tggaactcag gcgctctgac cagcggcgtg cacaccttcc cggctgtcct acagtcctca    180
ggactctact ccctcagcag cgtggtgacc gtgacctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
atggaggtgc ataatgccaa gacaaagcca cgggaggagc agttcaacag cacgttccgt    540
gtggtcagcg tcctcaccgt cgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac tcccatgct ggactccgac    840 ggctccttct tcctctacag caagctcacc gtggacaaga gcaggtggca gcagggaac     900 gtcttctcat gctccgtgat gcatgaggct ctgcacaacc actacacaca gaagagcctc    960
tccctgtctc cgggtaaa                                                  978

<210> SEQ ID NO 530
<211> LENGTH: 326
<212> TYPE: PRT
<213> ORGANISM: Homo Sapien
```

<400> SEQUENCE: 530

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65              70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 531
<211> LENGTH: 978
<212> TYPE: DNA
<213> ORGANISM: Homo Sapien

<400> SEQUENCE: 531
gcctccacca agggcccatc ggtcttcccc ctggcgccct gctccaggag cacctccgag        60
agcacagcgg ccctgggctg cctggtcaag gactacttcc ccgaaccggt gacggtgtcg       120
tggaactcag gcgctctgac cagcggcgtg cacaccttcc cagctgtcct acagtcctca       180

```
ggactctact ccctcagcag cgtggtgacc gtgccctcca gcagcttggg cacccagacc      240
tacacctgca acgtagatca caagcccagc aacaccaagg tggacaagac agttgagcgc      300
aaatgttgtg tcgagtgccc accgtgccca gcaccacctg tggcaggacc gtcagtcttc      360
ctcttccccc caaacccaa ggacaccctc atgatctccc ggacccctga ggtcacgtgc       420
gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac ctcccatgct ggactccgac      840
ggctccttct cctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaa                                                    978
```

<210> SEQ ID NO 532
<211> LENGTH: 326
<212> TYPE: PRT
<213> ORGANISM: Homo Sapien

<400> SEQUENCE: 532

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 533
<211> LENGTH: 978
<212> TYPE: DNA
<213> ORGANISM: Homo Sapien

<400> SEQUENCE: 533
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt cgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctaccccg cgacatctcc gtggagtgg      780
gagagcaatg ggcagccgga gaacaactac aagaccacac ctcccatgct ggactccgac     840
ggctccttct cctctacag caagctcacc gtggacaaga gcaggtggca gcaggggaac     900
gtcttctcat gctccgtgat gcatgaggct ctgcacaacc actacacaca gaagagcctc     960
tccctgtctc cgggtaaa                                                   978

<210> SEQ ID NO 534
<211> LENGTH: 326
<212> TYPE: PRT
<213> ORGANISM: Homo Sapien

<400> SEQUENCE: 534

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 535
<211> LENGTH: 318
<212> TYPE: DNA
<213> ORGANISM: Homo Sapien

<400> SEQUENCE: 535
ggtcagccca aggctgcccc ctcggtcact ctgttcccac cctcctctga ggagcttcaa     60
gccaacaagg ccacactggt gtgtctcgta agtgacttca acccgggagc cgtgacagtg    120
gcctggaagg cagatggcag ccccgtcaag gtgggagtgg agaccaccaa accctccaaa    180
caaagcaaca caagtatgc ggccagcagc tacctgagcc tgacgcccga gcagtggaag    240
tcccacagaa gctacagctg ccgggtcacg catgaaggga gcaccgtgga agacagtg    300 gccccctgcag aatgctct                                                318

<210> SEQ ID NO 536
<211> LENGTH: 106
<212> TYPE: PRT

<213> ORGANISM: Homo Sapien

<400> SEQUENCE: 536

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 537
<211> LENGTH: 990
<212> TYPE: DNA
<213> ORGANISM: Homo Sapien

<400> SEQUENCE: 537
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gggtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990

<210> SEQ ID NO 538
<211> LENGTH: 106
<212> TYPE: PRT
<213> ORGANISM: Homo Sapien

<400> SEQUENCE: 538

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp

```
                    20                  25                  30
Phe Tyr Pro Gly Ala Val Thr Val Ala Trp Lys Ala Asp Ser Ser Pro
            35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 539
<211> LENGTH: 157
<212> TYPE: PRT
<213> ORGANISM: Homo Sapien

<400> SEQUENCE: 539

Met Gly Trp Ser Cys Ile Ile Leu Phe Leu Val Ala Thr Ala Thr Gly
1               5                   10                  15

Val His Ser Met Met Thr Gly Thr Ile Glu Thr Thr Gly Asn Ile Ser
            20                  25                  30

Ala Glu Lys Gly Gly Ser Ile Ile Leu Gln Cys His Leu Ser Ser Thr
        35                  40                  45

Thr Ala Gln Val Thr Gln Val Asn Trp Glu Gln Gln Asp Gln Leu Leu
    50                  55                  60

Ala Ile Cys Asn Ala Asp Leu Gly Trp His Ile Ser Pro Ser Phe Lys
65                  70                  75                  80

Asp Arg Val Ala Pro Gly Pro Gly Leu Gly Leu Thr Leu Gln Ser Leu
                85                  90                  95

Thr Val Asn Asp Thr Gly Glu Tyr Phe Cys Ile Tyr His Thr Tyr Pro
            100                 105                 110

Asp Gly Thr Tyr Thr Gly Arg Ile Phe Leu Glu Val Leu Glu Ser Ser
        115                 120                 125

Val Ala Glu His Gly Ala Arg Phe Gln Ile Pro Ile Glu Gly Arg Asp
    130                 135                 140

Tyr Lys Asp Asp Asp Asp Lys His His His His His His
145                 150                 155

<210> SEQ ID NO 540
<211> LENGTH: 123
<212> TYPE: PRT
<213> ORGANISM: Homo sapiens

<400> SEQUENCE: 540

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
```

-continued

```
                  85                  90                  95

Ala Lys Asp Met Lys Gly Ser Gly Thr Tyr Gly Gly Trp Phe Asp Thr
                100                 105                 110

Trp Gly Gln Gly Thr Leu Val Thr Val Ser Ser
            115                 120

<210> SEQ ID NO 541
<211> LENGTH: 123
<212> TYPE: PRT
<213> ORGANISM: Homo sapiens

<400> SEQUENCE: 541

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
                100                 105                 110

Trp Gly Gln Gly Thr Leu Val Thr Val Ser Ser
            115                 120

<210> SEQ ID NO 542
<211> LENGTH: 123
<212> TYPE: PRT
<213> ORGANISM: Homo sapiens

<400> SEQUENCE: 542

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
                100                 105                 110

Trp Gly Gln Gly Thr Leu Val Thr Val Ser Ser
            115                 120

<210> SEQ ID NO 543
<211> LENGTH: 105
<212> TYPE: PRT
<213> ORGANISM: Homo sapiens

<400> SEQUENCE: 543
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu
                100                 105

<210> SEQ ID NO 544
<211> LENGTH: 105
<212> TYPE: PRT
<213> ORGANISM: Homo sapiens

<400> SEQUENCE: 544

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu
                100                 105

<210> SEQ ID NO 545
<211> LENGTH: 107
<212> TYPE: PRT
<213> ORGANISM: Homo sapiens

<400> SEQUENCE: 545

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Phe Ile
        35                  40                  45

Tyr Val Ala Ser Ser Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

```
Thr Phe Gly Gln Gly Thr Arg Leu Glu Ile Lys
            100                 105
```

ANTI-PD-L1 ANTIBODIES

This application is a continuation of U.S. patent application Ser. No. 16/311,440, filed on Dec. 19, 2018, which is a national stage filing under 35 U.S.C. § 371 of International Application No. PCT/GB2017/051796, filed on Jun. 20, 2017, which claims priority of U.S. Provisional Application No. 62/352,291, filed Jun. 20, 2016, British Patent Application No. 1613683.0, filed Aug. 9, 2016, British Patent Application No. 1615224.1, filed Sep. 7, 2016, British Patent Application No. 1615335.5, filed Sep. 9, 2016, British Patent Application No. 1620414.1, filed Dec. 1, 2016, British Patent Application No. 1621782.0, filed Dec. 20, 2016, British Patent Application No. 1702338.3, filed Feb. 13, 2017, British Patent Application No. 1702339.1, filed Feb. 13, 2017, and British Patent Application No. 1703071.9, filed Feb. 24, 2017. The contents of these applications are each incorporated herein by reference.

SEQUENCE LISTING

The instant application contains a Sequence Listing which has been submitted electronically in ASCII format and is hereby incorporated by reference in its entirety. Said ASCII file, created on Aug. 9, 2024, is named 719437_SA9-614USCON_ST25.txt and is 510,612 bytes in size.

FIELD OF THE INVENTION

Antibodies and methods of using the antibodies are described. In particular, antibodies that specifically bind human PD-L1 antigen and their use in treating various diseases are described.

INTRODUCTION

Immunocytokines (antibody-cytokine fusion proteins) were first reported in the literature in the early 1990s and consisted of whole antibody fusions with cytokines such as lymphotoxin (TNF-α) or interleukin 2 (IL-2). Subsequent studies in GD2-expressing tumour models in mice indicated that the ch14.18 antibody and ch14.18-IL2 immunocytokine both had anti-tumour activity but that the immunocytokine was far more potent than the antibody, even when combined with free IL-2, (see Sabzevari H et al., Proc. Natl. Acad. Sci. USA, 1994, 91:9626-30; Pancook J D, et al., Cancer Immunol. Immunother., 1996, 42:88-92; Becker J C, et al., Proc. Natl. Acad. Sci. USA, 1996, 93:2702-7). In addition, immune-competent mice treated with the immunocytokine, but not the antibody plus IL-2, developed an adaptive immune response dependent on CD8$^+$ T-cells that prevented subsequent tumour challenge (Becker J C, et al., J. Exp. Med., 1996, 183:2361-6; Becker J C, et al., Proc. Natl. Acad. Sci. USA, 1996, 93:7826-31). Thus, the targeting of IL-2 to the tumour microenvironment induces an anti-tumour vaccine effect that is not possible with the antibody, either alone or together with the free cytokine. A related humanized immunocytokine, hu 14.18-IL2, achieved clinical proof of concept in relapsed non-bulky neuroblastoma as monotherapy where it induced a significant number of complete responses in patients with no other treatment options (see Shusterman et al., Journal of Clinical Oncology, 2010, 28(33), 4969-4975). A number of publications describe the ability of this molecule to activate several components of the immune system to kill tumour cells (particularly NK cells and CD8$^+$ T-cells), and develop T-cell memory in order to resist subsequent tumour challenge (Yamane et al. 2009; Expert Opi, Investig. Drugs, 18(7): 991-1000; Neal et al., 2004, Clin. Cancer Res., 1010, 4839-4847).

As IL-2 based immunocytokines can have significant side effects, recent efforts have focused on the reduction of toxicity whilst maintaining efficacy. One example is Selectikine (EMD 521873), which has a substitution of aspartic acid for threonine at position 20 of IL-2, a key residue in the binding of IL-2Rβ (Gillies et al., Clinical Cancer Research, 2011, 17(11), 3673-3685). Selectikine, which binds necrotic tissue, has been shown to have good anti-tumour activity, despite its selectivity for the high affinity IL-2R, over the intermediate IL-2R and good tolerability in Phase I studies (Laurent et al., Journal of Translational Medicine, 2013, 11(1), 5. http://doi.org/10.1186/1479-5876-11-5)

WO2012/178137 (Gillies) and an associated journal article (Gilles, Protein Engineering, Design and Selection, 2013, 26(10), 561-569) describe light chain immunocytokine fusions with tumour targeting antibodies, and modulation of IL-2 activity by the introduction of truncations in the N-terminal part of the cytokine, which decreases signalling through IL-2Rβγ. IL-2 fusion proteins that specifically target IL-2Rβγ have been shown to have increased toxicity compared with wild-type (Vasquez-Lombardi et al. Nat Comm, 2017, DOI: 10.1038/ncomms15373), supporting the notion that decreasing IL-2Rβγ binding may be beneficial in terms of side effects.

An adaptive immune response involves activation, selection, and clonal proliferation of two major classes of lymphocytes termed T-cells and B-cells. After encountering an antigen, T-cells proliferate and differentiate into antigen-specific effector cells, while B-cells proliferate and differentiate into antibody-secreting cells. T-cell activation is a multi-step process requiring several signalling events between the T-cell and an antigen-presenting cell (APC). For T-cell activation to occur, two types of signals must be delivered to a resting T-cell. The first type is mediated by the antigen-specific. T-cell receptor (TcR), and confers specificity to the immune response. The second signal, a costimulatory type signal, regulates the magnitude of the response and is delivered through accessory receptors on the T-cell.

A primary costimulatory signal is delivered through the activating CD28 receptor upon engagement of its ligands B7-1 or B7-2. In contrast, engagement of the inhibitory CTLA-4 receptor by the same B7-1 or 67-2 ligands results in attenuation of a T-cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and Inhibitory signals and ensures the development of an effective immune response, while safeguarding against the development of autoimmunity.

Programmed death-1 (PD-1) is a 50-55 kDa type I transmembrane receptor that is a member of the CD28 family. PD-1 is involved in the regulation of T-cell activation and is expressed on T-cells, B cells, and myeloid cells. Two ligands for PD-1, PD ligand 1 (PD-L1) and ligand 2 (PD-L2) have been identified and have co-stimulatory features.

Programmed cell death 1 ligand 1 (PD-L1), also known as cluster of differentiation (CD274) or B7 homolog 1 (B7-H1), is a member of the B7 family that modulates activation or inhibition of the PD-1 receptor. The open reading frame of PD-L1 encodes a putative type 1 transmembrane protein of 290 amino acids, which includes two extracellular Ig domains (a N-terminal V-like domain and a Ig C-like domain), a hydrophobic transmembrane domain and a cytoplasmic tail of 30 amino acids. The 30 amino acid intracellular (cytoplasmic) domain contains no obvious signalling motifs, but does have a potential site for protein kinase C phosphorylation.

The complete amino acid sequence for PD-L1 can be found in NCBI Reference Sequence: NP_054862.1 (SEQ ID NO: 1), which refers to many journal articles, including, for example, Dong, H., et al. (1999), "PD-L1, a third member of the B7 family, co-stimulates T-cell proliferation and interleukin-10 secretion," Nat. Med. 5 (12), 1365-1369. The PD-L1 gene is conserved in chimpanzee, Rhesus monkey, dog, cow, mouse, rat, chicken, and zebrafish. The murine form of PD-L1 bears 69% amino acid identity with the human form of PD-L1, and also shares a conserved structure.

In humans, PD-L1 is expressed on a number of immune cell types including activated and anergic/exhausted T-cells, on naive and activated B-cells, as well as on myeloid dendritic cells (DC), monocytes and mast cells. It is also expressed on non-immune cells including islets of the pancreas, Kupffer cells of the liver, vascular endothelium and selected epithelia, for example airway epithelia and renal tubule epithelia, where its expression is enhanced during inflammatory episodes. PD-L1 expression is also found at increased levels on a number of tumours including, but not limited to breast (including but not limited to triple negative breast cancer and inflammatory breast cancer), ovarian, cervical, colon, colorectal, lung, including non-small cell lung cancer, renal, including renal cell carcinoma, gastric, oesophageal, bladder, hepatocellular cancer, squamous cell carcinoma of the head and neck (SCCHN) and pancreatic cancer, melanoma and uveal melanoma.

PD-1/PD-L1 signalling is believed to serve a critical non-redundant function within the immune system by negatively regulating T-cell responses. This regulation is involved in T-cell development in the thymus, in regulation of chronic inflammatory responses and in maintenance of both peripheral tolerance and immune privilege. It appears that upregulation of PD-L1 may allow cancers to evade the host immune system and, in many cancers, the expression of PD-L1 is associated with reduced survival and an unfavourable prognosis. Therapeutic monoclonal antibodies that are able to block the PD-1/PD-L1 pathway may enhance antitumoural immune responses in patients with cancer. Published clinical data suggest a correlation between clinical responses with tumoural membranous expression of PD-L1 (Brahmer et al., Journal of Clinical Oncology, 2010, Topalian et al., NEJM, 2012) and a stronger correlation between lack of clinical responses and a lack of PD-L1 protein localized to the membrane (Brahmer et al., Journal of Clinical Oncology, 2010, Topalian et al., NEJM, 2012). Thus, PD-L1 expression in tumours or tumour-infiltrating leukocytes (Herbst R S, et al., "Predictive correlates of response to the anti-PD-L1 antibody MPDL3280A in cancer patients", Nature, 2014, Nov. 27, 515(7528):563-7, doi: 10.1038/nature14011) is a candidate molecular marker for use in selecting patients for immunotherapy, for example, immunotherapy using anti-PD-L1 antibodies. Patient enrichment based on surface expression of PD-L1 may significantly enhance the clinical success of treatment with drugs targeting the PD-1/PD-L1 pathway. There is also evidence of an on-going immune response, such as the tumour infiltrating CD8+ T-cells, or the presence of signature of cytokine activation, such as IFNγ.

Further evidence of PD-L1 expression and correlation to disease will emerge from the numerous ongoing clinical trials. Atezolizumab is the most advanced, and recent data from Phase II trials shows therapeutic effects in metastatic urothelial carcinoma and NSCLC, particularly in patients with PD-L1+ immune cells in the tumour microenvironment (see Fehrenbacher et al., 2016, The Lancet, http://doi.org/10.1016/50140-6736(16)00587-0; Rosenberg et al., 2016, The Lancet, http://doi.org/10.1016/S0140-6736(16)00561-4). Recent results from a Phase III trial of 1225 patients with NSCLC showed improved survival in patients taking atezolizumab, compared with chemotherapy, regardless of tumour expression of PD-L1 (Rittmeyer et al., 2017, The Lancet, 389(10066), 255-265).

SUMMARY OF THE INVENTION

Antibodies

Disclosed herein are antibodies and antigen binding fragments thereof that specifically bind to PD-L1. In one embodiment, the antibody or antigen binding fragment thereof specifically binds to surface expressed PD-L1.

In a first configuration, there is provided an antibody or a fragment thereof, that specifically binds to hPD-L1 as defined by Seq ID No:1, and competes for binding to said hPD-L1 with the antibody 1D05, wherein the antibody or fragment comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In a second configuration, there is provided an antibody or a fragment thereof which specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions.

In a third configuration, there is provided an antibody or fragment thereof which specifically binds to an epitope that is identical to an epitope to which the antibody 1D05 specifically binds.

In a fourth configuration, there is provided an antibody or fragment thereof which competes for binding to hPD-L1 with the antibody 1D05.

In a fifth configuration, there is provided a bispecific antibody or fusion protein comprising an antibody or fragment thereof as defined in any other configuration, embodiment or concept.

In a sixth configuration, there is provided an antibody or fragment as defined in any other configuration, embodiment or concept for use in treating or preventing a hPD-L1-mediated disease or condition.

In a seventh configuration, there is provided the use of an antibody or fragment as defined in any other configuration, embodiment or concept in the manufacture of a medicament for administration to a human for treating or preventing a hPD-L1 mediated disease or condition in the human.

In an eighth configuration, there is provided a method of treating or preventing a hPD-L1 mediated disease or condition in a human, comprising administering to said human a therapeutically effective amount of an antibody or fragment as defined in any other configuration, embodiment or concept, wherein the hPD-L1 mediated disease or condition is thereby treated or prevented.

In a ninth configuration, there is provided a pharmaceutical composition comprising an antibody of fragment as defined in any other configuration, embodiment or concept and a pharmaceutically acceptable excipient, diluent or carrier.

In a tenth configuration, there is provided a kit comprising a pharmaceutical composition comprising an antibody of fragment as defined in any other configuration, embodiment or concept and a pharmaceutically acceptable excipient, diluent or carrier.

In an eleventh configuration, there is provided a method of modulating PD-1/PD-L1 interaction in a patient, comprising administering an effective amount of an antibody or fragment as defined in any other configuration, embodiment or concept to said patient.

In a twelfth configuration, there is provided a method of inhibiting PD-L1 activity in a patient, comprising administering an effective amount of an antibody or fragment as defined in any other configuration, embodiment or concept to said patient.

In a thirteenth configuration, there is provided a method of treating a proliferative disease in an animal (e.g. a human), comprising administering an effective amount of an antibody or fragment as defined in any other configuration, embodiment or concept to said patient.

In a fourteenth configuration, there is provided a method of detecting PD-L1 expression in a sample, comprising contacting the sample with an antibody or fragment as defined in any other configuration, embodiment or concept.

In a fifteenth configuration, there is provided a method comprising contacting a biological sample with an antibody or fragment as defined in any other configuration, embodiment or concept to form a complex with PD-L1 present in the sample and measuring the presence, absence or level of the complex in the biological sample.

In a sixteenth configuration, there is provided a method of detecting PD-L1 expression in a sample, comprising contacting the sample with an antibody or fragment as defined in any other configuration, embodiment or concept.

In a seventeenth configuration, there is provided a method comprising contacting a biological sample with an antibody or fragment as defined in any other configuration, embodiment or concept to form a complex with PD-L1 present in the sample and measuring the presence, absence or level of the complex in the biological sample.

In a eighteenth configuration, there is provided a method for identifying binding partners for PD-L1, the method comprising immunoprecipitating an intact protein complex comprising PD-L1 using an antibody or fragment as defined in any other configuration, embodiment or concept.

In a nineteenth configuration, there is provided a method of diagnosing a disease in a human subject associated with altered PD-L1 expression comprising the steps of contacting a biological sample from the human subject with an antibody as defined in other configuration, embodiment or concept to form a complex between the antibody and PD-L1 present in the sample; and detecting the amount of the complex.

In a twentieth configuration, there is provided a nucleic acid that encodes the CDRH3 of an antibody or fragment as defined in any other configuration, embodiment or concept.

In a twenty-first configuration, there is provided a nucleic acid that encodes a VH domain and/or a VL domain of an antibody or fragment as defined in any other configuration, embodiment or concept.

In a twenty-second configuration, there is provided a vector comprising the nucleic acid of any other configuration, embodiment or concept; optionally wherein the vector is a CHO or HEK293 vector.

In a twenty-third configuration, there is provided a host comprising the nucleic acid of any other configuration, embodiment or concept or the vector of any other configuration, embodiment or concept.

Immunocytokines

In a first configuration, there is provided an immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1 as defined by Seq ID No:1, and competes for binding to said hPD-L1 with the antibody 1D05; and
wherein the immunocytokine comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In a second configuration, there is provided an immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions.

In a third configuration, there is provided an immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1; and
wherein the $V_H$ domain comprises a CDRH3 of from 12 to 20 amino acids and which is derived from the recombination of a human $V_H$ gene segment, a human D gene segment and a human $J_H$ gene segment, wherein the human $J_H$ gene segment is IGHJ5 (e.g. IGHJ5*02).

In a fourth configuration, there is provided an immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to an epitope that is identical to an epitope to which the antibody 1D05 specifically binds.

In a fifth configuration, there is provided an immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site which competes for binding to hPD-L1 with the antibody 1D05.

In a sixth configuration, there is provided an immunocytokine as defined in any other configuration, embodiment or aspect for use in treating or preventing a hPD-L1-mediated disease or condition.

In a seventh configuration, there is provided the use of an immunocytokine as defined in any other configuration, embodiment or aspect in the manufacture of a medicament for administration to a human for treating or preventing a hPD-L1 mediated disease or condition in the human.

In an eighth configuration, there is provided a method of treating or preventing a hPD-L1 mediated disease or condition in a human, comprising administering to said human a therapeutically effective amount of an immunocytokine as defined in any other configuration, embodiment or aspect, wherein the hPD-L1 mediated disease or condition is thereby treated or prevented.

In a ninth configuration, there is provided a pharmaceutical composition comprising an immunocytokine as defined in any other configuration, embodiment or aspect, and a pharmaceutically acceptable excipient, diluent or carrier.

In a tenth configuration, there is provided a kit comprising a pharmaceutical composition comprising an immunocytokine as defined in any other configuration, embodiment or aspect, and a pharmaceutically acceptable excipient, diluent or carrier.

In an eleventh configuration, there is provided a nucleic acid that encodes a heavy chain and/or a light chain of an immunocytokine as defined in any other configuration, embodiment or aspect.

In a twelfth configuration, there is provided a vector comprising the nucleic acid that encodes a heavy chain and/or a light chain of an immunocytokine as defined in any other configuration, embodiment or aspect.

In a thirteenth configuration, there is provided a host comprising the nucleic acid of any other configuration, embodiment or aspect or the vector as defined in any other configuration, embodiment or aspect.

Anti-ICOS Bispecific Antibodies

In a first configuration, there is provided a multispecific antibody (e.g. bispecific antibody or a dual-binding antibody) which binds (and optionally has specificity for) ICOS (e.g. human ICOS) and another target antigen.

In a second configuration, there is provided a composition comprising a multispecific, bispecific or dual-binding antibody as described herein and a pharmaceutically acceptable excipient, diluent or carrier.

In a third configuration, there is provided a multispecific, bispecific or dual-binding antibody as described herein for use in treating or preventing a disease or condition, selected from neurological disease, neoplastic or non-neoplastic disease, chronic viral infections, and malignant tumours; such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

In a fourth configuration, there is provided a use of a multispecific, bispecific or dual-binding antibody as described herein in the manufacture of a medicament for administration to a human for treating or preventing a disease or condition in the human selected from neurological disease, neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

In a fifth configuration, there is provided a method of treating or preventing a disease or condition selected from neurological disease, neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas) in a human, comprising administering to said human a therapeutically effective amount of a multispecific, bispecific or dual-binding antibody as described herein, wherein the disease or condition is thereby treated or prevented.

In a sixth configuration, there is provided a nucleic acid that encodes a heavy chain and/or a light chain of a multispecific antibody as described herein.

In a seventh configuration, there is provided a vector comprising the nucleic acid that encodes a heavy chain and/or a light chain of a multispecific antibody as described herein.

DESCRIPTION OF THE FIGURES

FIG. 10(a) Bispecific 1, FIG. 10(b) Bispecific 2, FIG. 10(c) Bispecific 3, FIG. 10(d) Bispecific 4. For detailed construction information of each Bispecific construct, see Table 6

FIG. 14(a): shows the group mean (n=8/9) tumour growth curve, for this graph when an animal is removed from the study due to tumour size, the last reading is used for the rest of the study. The shaded area shows the area where the last reading is being used FIGS. 14(b) to 14(e): show the individual animal tumour growth curves for each group. FIG. 14(b) A375 tumours alone; FIG. 14(c) A375 tumours co-injected with CD4$^+$/8$^+$ T-cells at a 6:1 ratio. For panels FIG. 14(d) and FIG. 14(e) A375 tumour cell were co-injected with CD4$^+$/8$^+$ T-cells at a 6:1 ratio; FIG. 14(d) Isotype Control antibody at 10 mg/kg and FIG. 14(e) anti-PD-L1 antibody 1D05 at 10 mg/kg.

Dosing was at 1-hour post tumour/T-cell implantation and on days 3, 6, 8 and 10, shown on the graph by the dotted lines

FIG. 25(a) Titration of FIT-Ig molecules; FIG. 25(b) Titration of monospecific antibodies. Data shown are representative of one unique experiment FIG. 26(a) Titration of FIT-Ig molecules; FIG. 26(b) Titration of monospecific antibodies. Data shown are representative of one unique experiment FIG. 31(b) IL-8; FIG. 31(c) IL-6; FIG. 31(d) IFN$\gamma$; FIG. 31(e) G-CSF, FIG. 31(f) IL-2, FIG. 31(g) IL-4 and FIG. 31(h) IL-5. Where no bar is included, cytokine levels were below the limit of quantification of the assay. IL-1$\beta$ was not detectable in any samples and so is not included in the graphs

DETAILED DESCRIPTION

1. Definitions

Figure 1:
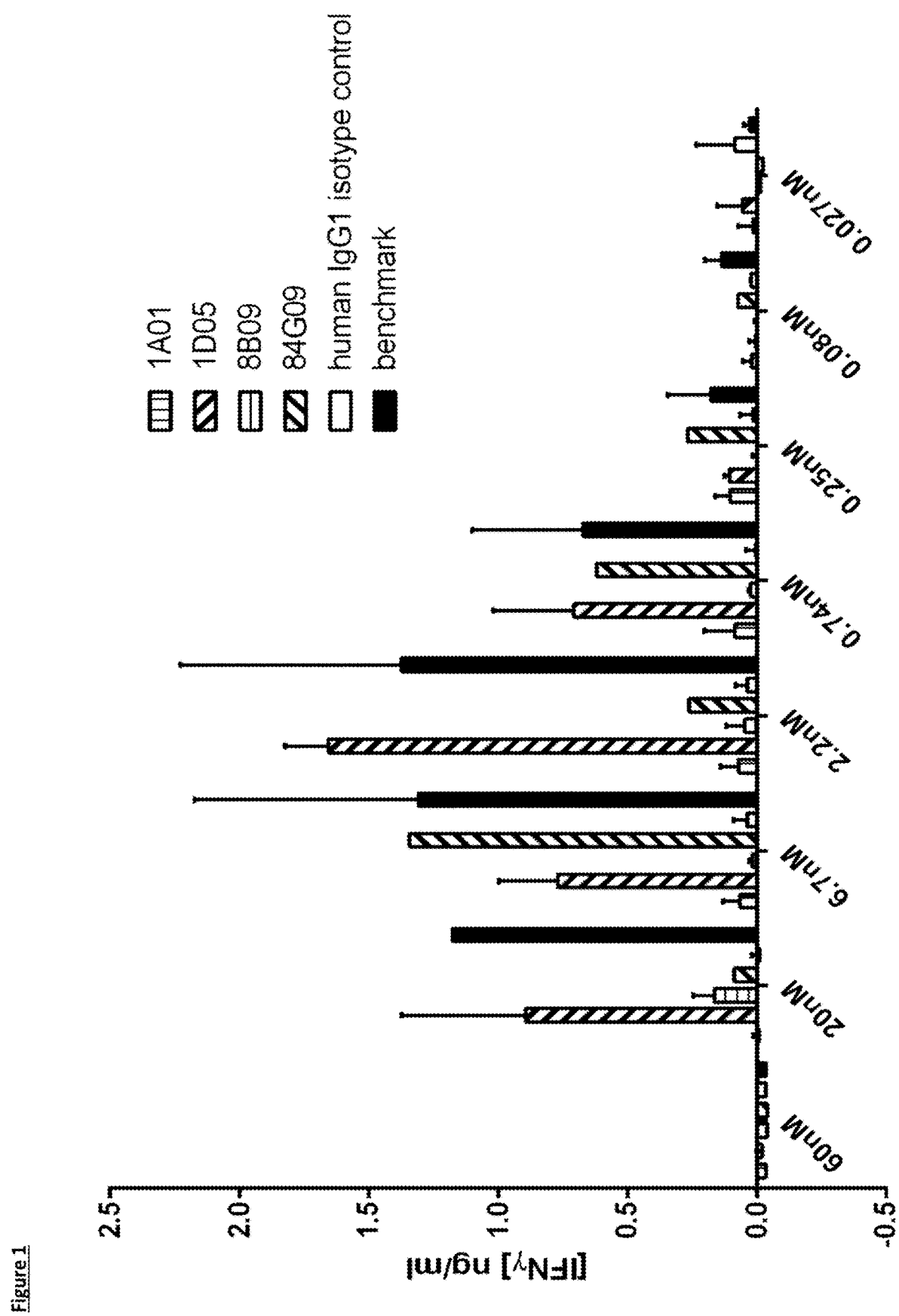
FIG. 1: Analysis of selected antibodies in a dendritic cell—T-cell mixed lymphocyte reaction. Monocytes were cultured with GM-CSF and IL-4 for seven days, before addition of allogeneic purified CD3$^+$ T-cells and titrations of antibodies. Supernatants were taken at day 5 for analysis of IFNγ production. Data is shown from one experiment. Note that for 84G09, there is a single point per concentration, as one replicate failed

Unless otherwise defined herein, scientific and technical terms shall have the meanings that are commonly understood by those of ordinary skill in the art. Further, unless otherwise required by context, singular terms shall include pluralities and plural terms shall include the singular.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, "administer" or "administration" refers to the act of injecting or otherwise physically delivering a substance as it exists outside the body (e.g., an anti-hPD-L1 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The term "antibody", "immunoglobulin" or "Ig" may be used interchangeably herein and means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies (including dual binding antibodies), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha (α), delta (δ), epsilon (ε), gamma (γ), and mu (μ). The type of heavy chain defines the class of antibody, i.e., IgA, IgD, IgE, IgG, and IgM, respectively. The γ and α classes are further divided into subclasses on the basis of differences in the constant domain sequence and function, e.g., IgG1, hIgG2, mIgG2A, mIgG2B, IgG3, IgG4, IgA1 and IgA2. In mammals, there are two types of immunoglobulin light chains, λ and κ. The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The antibodies described herein may be oligoclonal, polyclonal, monoclonal (including full-length monoclonal antibodies), camelised, chimeric, CDR-grafted, multi-specific, bi-specific (including dual-binding antibodies), catalytic, chimeric, humanized, fully human, anti-idiotypic, including antibodies that can be labelled in soluble or bound form as well as fragments, variants or derivatives thereof, either alone or in combination with other amino acid sequences provided by known techniques. An antibody may be from any species. Antibodies described herein can be naked or conjugated to other molecules such as toxins, radioisotopes, etc.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g. the complementarity determining regions (CDRs)). The antigen binding region can be derived from any animal species, such as rodents (e.g. rabbit, rat or hamster) and humans. Preferably, the antigen binding region will be of human origin.

Antigen binding fragments described herein can include single-chain Fvs (scFv), single-chain antibodies, single domain antibodies, domain antibodies, Fv fragments, Fab fragments, F(ab') fragments, F(ab')$_2$ fragments, antibody fragments that exhibit the desired biological activity, disulfide-stabilised variable region (dsFv), dimeric variable region (diabody), anti-idiotypic (anti-Id) antibodies (including, e.g. anti-Id antibodies to antibodies), intrabodies, linear antibodies, single-chain antibody molecules and multispecific antibodies formed from antibody fragments and epitope-binding fragments of any of the above. In particular, antibodies and antibody fragments described herein can include immunoglobulin molecules and immunologically active fragments of immunoglobulin molecules, i.e., molecules that contain an antigen-binding site. Digestion of antibodies with the enzyme, papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognized by Fc receptors (FcR) found on certain types of cells. Digestion of antibodies with the enzyme, pepsin, results in a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody obtained from a population of substantially homogeneous antibodies, i.e. the individual antibodies comprising the population are identical except for possible naturally occurring mutations and/or post-translation modifications (e.g. isomerizations, amidations) that may be present in minor amounts. Monoclonal antibodies are highly specific, and are directed against a single antigentic determinant or epitope. In contrast, polyclonal antibody preparations typically include different antibodies directed against different antigenic determinants (or epitopes). The term "monoclonal antibody" as used herein encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

The monoclonal antibodies herein can include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies that exhibit the desired biological activity.

The term "humanized antibody" refers to a subset of chimeric antibodies in which a "hypervariable region" from a non-human immunoglobulin (the donor antibody) replaces residues from a hypervariable region in a human immunoglobulin (recipient antibody). In general, a humanized antibody will include substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more substitutions that improve antibody performance, such as binding affinity, isomerization, immunogenicity, etc.

The term "bispecific antibody" means an antibody which comprises specificity for two target molecules, and includes, but is not limited to, formats such as DVD-Ig (see DiGiammarino et al., "Design and generation of DVD-Ig™ molecules for dual-specific targeting", Meth. Mo. Biol., 2012, 889, 145-156), mAb$^2$ (see WO2008/003103, the description of the mAb$^2$ format is incorporated herein by reference), FIT-Ig (see WO2015/103072, the description of the FIT-Ig scaffold is incorporated herein by reference), mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody. For a review of bispecific formats, see Spiess, C., et al., Mol. Immunol. (2015). In another embodiment, the bispecific molecule comprises an antibody which is fused to another non-Ig format, for example a T-cell receptor binding domain; an immunoglobulin superfamily domain; an agnathan variable lymphocyte receptor; a fibronectin domain (e.g. an Adnectin™); an antibody constant domain (e.g. a CH$_3$ domain, e.g., a CH$_2$ and/or CH$_3$ of an Fcab™) wherein the constant domain is not a functional CH$_1$ domain; an scFv; an (scFv)$_2$; an sc-diabody; an scFab; a centyrin and an epitope binding domain derived from a scaffold selected from CTLA-4 (Evibody™); a lipocalin domain; Protein A such as Z-domain of Protein A (e.g. an Affibody™ or SpA); an A-domain (e.g. an Avimer™ or Maxibody™); a heat shock protein (such as and epitope binding domain derived from GroEI and GroES); a transferrin domain (e.g. a trans-body); ankyrin repeat protein (e.g. a DARPin™); peptide aptamer; C-type lectin domain (e.g. Tetranectin™); human γ-crystallin or human ubiquitin (an affilin); a PDZ domain; scorpion toxin; and a kunitz type domain of a human protease inhibitor.

In one embodiment, the bispecific antibody is a mAb$^2$. A mAb$^2$ comprises a V$_H$ and V$_L$ domain from an intact antibody, fused to a modified constant region, which has been engineered to form an antigen-binding site, known as an "Fcab". The technology behind the Fcab/mAb$^2$ format is described in more detail in WO2008/003103, and the description of the mAb$^2$ format is incorporated herein by reference.

In one embodiment, a "bispecific antibody" does not include a FIT-Ig format. In one embodiment, a "bispecific antibody" does not include a mAb$^2$ format. In one embodiment, a "bispecific antibody" does not include either a FIT-Ig format or a mAb$^2$ format.

In another embodiment, the bispecific antibody is a "dual binding antibody". As used herein, the term "dual binding antibody" is a bispecific antibody wherein both antigen-binding domains are formed by a V$_H$/V$_L$ pair, and includes FIT-Ig (see WO2015/103072, incorporated herein by reference), mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv and scFv4-Ig.

The term "hypervariable region", "CDR region" or "CDR" refers to the regions of an antibody variable domain which are hypervariable in sequence and/or form structurally defined loops. Generally, antigen binding sites of an antibody include six hypervariable regions: three in the V$_H$ (CDRH1, CDRH2, CDRH3), and three in the V$_L$ (CDRL1, CDRL2, CDRL3). These regions of the heavy and light chains of an antibody confer antigen-binding specificity to the antibody. CDRs may be defined according to the Kabat system (see Kabat, E. A. et al., 1991, "Sequences of Proteins of Immunological Interest", 5$^{th}$ edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", 3. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR.

A "human antibody" is an antibody that possesses an amino-acid sequence corresponding to that of an antibody produced by a human and/or has been made using any of the techniques for making human antibodies and specifically excludes a humanized antibody comprising non-human antigen-binding residues. The term "specifically binds to" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g. by a radioimmunoassay (RIA).

An antibody or a fragment thereof that specifically binds to a hPD-L1 antigen may be cross-reactive with related antigens. Preferably, an antibody or a fragment thereof that specifically binds to a hPD-L1 antigen does not cross-react with other antigens (but may optionally cross-react with PD-L1 of a different species, e.g. rhesus, or murine). An antibody or a fragment thereof that specifically binds to a hPD-L1 antigen can be identified, for example, by immunoassays, BIAcore™, or other techniques known to those of skill in the art. An antibody or a fragment thereof binds specifically to a PD-L1 antigen when it binds to a hPD-L1 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times (such as more than 15 times, more than 20 times, more than 50 times or more than 100 times) background. See, e.g. Paul, ed., 1989, Fundamental Immunology Second Edition, Raven Press, New York at pages 332-336 for a discussion regarding antibody specificity.

The term "aliphatic amino acid" means that the amino acid R groups are nonpolar and hydrophobic. Hydrophobicity increases with increasing number of C atoms in the hydrocarbon chain. Glycine, Alanine, Valine, Leucine and Isoleucine are aliphatic amino acids.

The term "aromatic amino acid" means that the amino acid R groups contain an aromatic ring system. Phenylalanine, Tyrosine and Tryptophan are aromatic amino acids.

The term "hydroxyl-containing amino acid" means that the amino acid R groups contain a hydroxyl group, and are hydrophilic. Serine, Cysteine, Threonine and Methionine are hydroxyl-containing amino acids.

The term "basic amino acid" means that the amino acid R groups are nitrogen containing and are basic at neutral pH. Histidine, Lysine and Arginine are basic amino acids.

The term "cyclic amino acid" means that the amino acid R groups have an aliphatic cyclic structure. Proline is the only cyclic aliphatic amino acid.

The term "acidic amino acid" means that the amino acid R groups are polar and are negatively charged at physiological pH. Aspartate and Glutamate are acidic amino acids.

The term "amide amino acid" means that the amino acid R groups contain an amide group. Asparagine and Glutamine are amide amino acids.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g. the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, the term "biomarker" refers to a gene that is differentially expressed in individuals having a disease of interest, for example, a gene that is differentially expressed in individuals having cancer. In one embodiment, PD-L1 is a biomarker whose expression in tumours may be indicative as to whether or not a patient would respond to a particular type of treatment, in particular, whether a patient would response to treatment targeting PD-L1, for example, immunotherapy using anti-PD-L1 antibodies. In one embodiment, PD-L1 is a biomarker whose expression in tumours may be indicative as to whether or not a patient would respond to a particular type of treatment, in particular, whether a patient would response to treatment targeting PD-1, for example, immunotherapy using anti-PD-1 antibodies. In another embodiment, PD-L1 may be free or membrane bound. In another embodiment, PD-L1 may be fixed or unfixed.

As used herein, a "buffer" refers to a chemical agent that is able to absorb a certain quantity of acid or base without undergoing a strong variation in pH.

As used herein, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

The term "chemotherapeutic agent" or "chemotherapy" refers to a therapeutic agent whose primary purpose is to destroy cancer cells, typically by interfering with the tumour cell's ability to grow or multiply. There are many different types of chemotherapeutic agents, with more than 50 approved chemotherapy drugs available. Chemotherapeutic drugs can be classified based on how they work. Alkylating drugs kill cancer cells by directly attacking DNA, the genetic material of the genes. Cyclophosphamide is an alkylating drug. Antimetabolites interfere with the production of DNA and keep cells from growing and multiplying. An example of an antimetabolite is 5-fluorouracil (5-FU). Anti-tumour antibiotics are made from natural substances such as fungi in the soil. They interfere with important cell functions, including production of DNA and cell proteins. Doxorubicin and bleomycin belong to this group of chemotherapy drugs. Plant alkaloids prevent cells from dividing normally. Vinblastine and vincristine are plant alkaloids obtained from the periwinkle plant. Steroid hormones slow the growth of some cancers that depend on hormones. For example, tamoxifen is used to treat breast cancers that depend on the hormone estrogen for growth. DNA damage response (DDR) inhibitors, such as PARP inhibitors, block DNA repair mechanisms following single or double stranded breaks.

Examples of chemotherapeutic agents include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed. (Mack Publishing Co. 1995), and in Goodman and Gilman's The Pharmacological Basis of Therapeutics, $7^{th}$ Ed. (MacMillan Publishing Co. 1985). Another example of chemotherapeutic agents is the class of antibody-conjugated toxins, including, but not limited to pyrrolobenzodiazepiness, maytansanoids, calicheamicin, etc. Other suitable toxins and/or chemotherapeutic agents are known to those of skill in the art.

As used herein, the term "composition" is intended to encompass a product containing the specified ingredients (e.g. an antibody of the invention) in, optionally, the specified amounts, as well as any product which results, directly or indirectly, from combination of the specified ingredients in, optionally, the specified amounts.

As used herein the term "comprising" or "comprises" is used with reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

In the context of a polypeptide, the term "derivative" as used herein refers to a polypeptide that comprises an amino acid sequence of a hPD-L1 polypeptide, a fragment of a hPD-L1 polypeptide, or an antibody that specifically binds to a hPD-L1 polypeptide which has been altered by the introduction of amino acid residue substitutions, deletions or additions. The term "derivative" as used herein also refers to a hPD-L1 polypeptide, a fragment of a hPD-L1 polypeptide, or an antibody that specifically binds to a hPD-L1 polypeptide which has been chemically modified, e.g. by the covalent attachment of any type of molecule to the polypeptide. For example, but not by way of limitation, a hPD-L1 polypeptide, a fragment of a hPD-L1 polypeptide, or a hPD-L1 antibody may be chemically modified, e.g. by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hPD-L1 polypeptide, a fragment of a hPD-L1 polypeptide, or a hPD-L1 antibody may be chemically modified by chemical modifications using techniques known to those of skill in the art, including, but not limited to specific chemical cleavage, acetylation, formulation, metabolic synthesis of tunicamycin, etc. Further, a derivative of a hPD-L1 polypeptide, a fragment of a hPD-L1 polypeptide, or a hPD-L1 antibody may contain one or more non-classical amino acids. A polypeptide derivative possesses a similar or identical function as a hPD-L1 polypeptide, a fragment of a hPD-L1 polypeptide, or a hPD-L1 antibody described herein.

The term "effector function" as used herein is meant to refer to one or more of antibody dependant cell mediated cytotoxic activity (ADCC), complement-dependant cytotoxic activity (CDC) mediated responses, Fc-mediated phagocytosis or antibody dependant cellular phagocytosis (ADCP) and antibody recycling via the FcRn receptor.

An "effective amount" refers to an amount effective, at dosages and for periods of time necessary, to achieve the desired effect, including a therapeutic or prophylactic result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which toxic or detrimental effects of the antibody are outweighed by the therapeutically beneficial effects. A "prophylactically effective amount" refers to an amount effective, at the dosages and for periods of time necessary, to achieve the desired prophylactic result. In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g. inhibition of a hPD-L1 biological activity of a cell).

The term "epitope" as used herein refers to a localized region on the surface of an antigen, such as hPD-L1 polypeptide or hPD-L1 polypeptide fragment, that is capable of being bound to one or more antigen binding regions of an antibody, and that has antigenic or immunogenic activity in an animal, preferably a. mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hPD-L1 epitope is a three-dimensional surface feature of a hPD-L1 polypeptide (e.g. in a trimeric form of a hPD-L1 polypeptide). In other embodiments, a hPD-L1 epitope is linear feature of a hPD-L1 polypeptide (e.g. in a trimeric form or monomeric form of the hPD-L1 polypeptide). Antibodies provided herein may specifically bind to an epitope of the monomeric (denatured) form of hPD-L1, an epitope of the trimeric (native) form of hPD-L1, or both the monomeric (denatured) form and the trimeric (native) form of hPD-L1. In specific embodiments, the antibodies provided herein specifically bind to an epitope of the trimeric form of hPD-L1 but do not specifically bind the monomeric form of hPD-L1.

The term "excipients" as used herein refers to inert substances which are commonly used as a diluent, vehicle, preservatives, binders, or stabilizing agent for drugs and includes, but not limited to, proteins (e.g. serum albumin, etc.), amino acids (e.g. aspartic acid, glutamic acid, lysine, arginine, glycine, histidine, etc.), fatty acids and phospholipids (e.g. alkyl sulfonates, caprylate, etc.), surfactants (e.g. SDS, polysorbate, nonionic surfactant, etc.), saccharides (e.g. sucrose, maltose, trehalose, etc.) and polyols (e.g. mannitol, sorbitol, etc.). See, also, Remington's Pharmaceutical Sciences (1990) Mack Publishing Co., Easton, Pa., which is hereby incorporated by reference in its entirety.

As used herein, the term "fixed" or "fixation" refers to a chemical process by which biological tissues are preserved from decay, to prevent autolysis or putrefaction. In general, fixation involves exposing the tissue to chemical compounds such as alcohols or aldehydes such as formaldehyde to terminate ongoing biochemical reactions. In some instances, fixation may also increase the mechanical strength or stability of the treated tissues. The term "unfixed" refers to a tissue that has not been subjected to a chemical process to prevent tissue decay. As used herein, the term "surface expressed" means that the protein is embedded in or spans a cell membrane or is associated with a protein that is embedded in or spans a cell membrane (i.e. a membrane associated protein). In one embodiment, a surface expressed protein includes one or more transmembrane domains. In another embodiment, the protein is associated with the exterior or interior surface of a cell membrane indirectly via association with another membrane spanning protein (i.e. the surface expressed protein is not spanning the cell membrane itself). In general, surface expressed proteins that are integrated into a cell membrane or expressed endogenously within a cell are more likely to fold in the correct conformation than recombinantly produced free forms of the same protein.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, PD-L1 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hPD-L1 polypeptide or an antibody that specifically binds to a hPD-L1 polypeptide. In a specific embodiment, a fragment of a hPD-L1 polypeptide or an antibody that specifically binds to a hPD-L1 antigen retains at least 1, at least 2, or at least 3 functions of the polypeptide or antibody.

The term "free" refers to a polypeptide, for example, PD-L1 or fragments and variants thereof, that is combined with a buffer, wherein the polypeptide is not associated with a cell surface or cell membrane. As such, the term "free" can refer to a polypeptide that is capable of surface expression (i.e. includes one or more transmembrane domains or membrane association domains), but that is not, in its present state, expressed on the surface of a cell or bound to a protein that is expressed on the surface of a cell. A free polypeptide can also refer to a free recombinant or native or unbound polypeptide. In the context of phage display, a free antigen can be selected in solution (referred to herein as a "soluble selection") or adsorbed to a surface, for example, adsorbed to the surface of a 96-well plate (referred to herein as "biopanning selection").

The term "fusion protein" as used herein refers to a polypeptide that comprises an amino acid sequence of an antibody and an amino acid sequence of a heterologous polypeptide or protein (i.e. a polypeptide or protein not normally a part of the antibody (e.g. a non-anti-hPD-L1 antigen antibody)). The term "fusion" when used in relation to hPD-L1 or to an anti-hPD-L1 antibody refers to the joining of a peptide or polypeptide, or fragment, variant and/or derivative thereof, with a heterologous peptide or polypeptide. Preferably, the fusion protein retains the biological activity of the hPD-L1 or anti-hPD-L1 antibody. In certain embodiments, the fusion protein comprises a hPD-L1 antibody VH domain, VL domain, VH CDR (one, two or three VH CDRs), and/or VL CDR (one, two or three VL CDRs), wherein the fusion protein specifically binds to a hPD-L1 epitope.

The term "heavy chain" when used with reference to an antibody refers to five distinct types, called alpha ($\alpha$), delta ($\delta$), epsilon ($\epsilon$), gamma ($\gamma$) and mu ($\mu$), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG2, IgG3 and IgG4. Preferably the heavy chain is a human heavy chain. In the human population, multiple heavy chain constant region alleles, of each immunoglobulin or immunoglobulin subclass, exist. The nucleotide and amino acid sequences of these allelic variants are accessible on publicly available databases such as IMGT, ENSEMBL Swiss-Prot and Uniprot. Allelic variants may also be identified in various genome sequencing projects. In one embodiment, the antibodies and antibody fragments disclosed herein comprise a heavy chain encoded by a IgG1 constant region allele, which includes, but is not limited to, human IGHG1*01 (Seq ID Nos:340, 341 & 537), IGHG1*02 (Seq ID Nos:340, 341 &537), IGHG1*03 (Seq ID Nos:523 & 524), IGHG1*04 (Seq ID Nos:525 & 526) and IGHG1*05 (Seq ID Nos:340, 341 & 537). In one embodiment, the antibodies and antibody fragments disclosed herein comprise a protein encoded by a IgG2 constant region allele, which includes, but is not limited to, human IGHG2*01 (Seq ID Nos:527 & 528), IGHG2*02 (Seq ID Nos:529 & 530), IGHG2*03 (Seq ID Nos:527 & 528), IGHG2*04 (Seq ID Nos:531 & 532), IGHG2*05 (Seq ID Nos:527 & 528) and IGHG2*06 (Seq ID Nos:533 & 534). In one embodiment, the antibodies or antibody fragments disclosed herein comprise a protein encoded by a IgG3 constant region allele, which includes but is not limited to human IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19. In one embodiment, the antibodies or antibody fragments disclosed herein comprise a protein encoded by a IgG4 constant region allele, which includes but is not limited to human IGHG4*01 (Seq ID Nos:192 & 193), IGHG4*02 (Seq ID Nos:194 & 195), IGHG4*03 (Seq ID Nos:196 & 197) and IGHG4*04 (Seq ID Nos:192 & 193). In another example, the heavy chain is a disabled IgG isotype, e.g. a disabled IgG4. In certain embodiments, the antibodies of the invention comprise a human gamma 4 constant region. In another embodiment, the heavy chain constant region does not bind Fc-$\gamma$ receptors, and e.g. comprises a Leu235Glu mutation. In another embodiment, the heavy chain constant region comprises a Ser228Pro mutation to increase stability. In another embodiment, the heavy chain constant region is IgG4-PE (SEQ ID No:199. In another embodiment, the antibodies and antibody fragments disclosed herein comprise a heavy chain constant region encoded by a murine IgG1 constant region allele, which includes but is not limited to mouse IGHG1*01 or IGHG1*02. In one embodiment, the antibodies and antibody fragments disclosed herein comprise a heavy chain constant region encoded by a murine IgG2 constant region allele, which includes, but is not limited to, mouse IGHG2A*01, IGHG2A*02, IGHG2B*01, IGHG2B*02, IGHG2C*01, IGHG2C*02 or IGHG2C*03. In one embodiment, the antibodies or antibody fragments disclosed herein comprise a protein encoded by a murine IgG3 constant region allele, which includes but is not limited to mouse IGHG3*01.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "an IL-2 cytokine" as used herein refers to a cytokine-like molecule which has a similar activity to a wild-type IL-2. It may have activity at the high ($\alpha\beta\gamma$) affinity IL-2 receptor and/or the intermediate affinity ($\alpha\beta$) IL-2 receptor. The cytokine may be a variant IL-2 cytokine having one or more amino acid deletions, substitutions or additions. Variant cytokines are described in more detail hereinbelow.

The term "immunomodulatory agent" and variations thereof including, but not limited to, immunomodulatory agents, as used herein refer to an agent that modulates a host's immune system. In certain embodiments, an immunomodulatory agent is an immunosuppressant agent. In certain other embodiments, an immunomodulatory agent is an immunostimulatory agent. In accordance with the invention, an immunomodulatory agent used in the combination therapies of the invention does not include an anti-hPD-L1 antibody or antigen-binding fragment. Immunomodulatory agents include, but are not limited to, small molecules, peptides, polypeptides, proteins, fusion proteins, antibodies, inorganic molecules, mimetic agents, and organic molecules.

The term "in combination" in the context of the administration of other therapies refers to the use of more than one therapy. The use of the term "in combination" does not restrict the order in which therapies are administered to a subject with a disease. A first therapy can be administered before (e.g. 1. minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a hPD-L1-mediated disease. Any additional therapy can be administered in any order with the other additional therapies. In certain embodiments, the antibodies of the invention can be administered in combination with one or more therapies (e.g. therapies that are not the antibodies of the invention that are currently administered to prevent, treat, manage, and/or ameliorate a hPD-L1-mediated disease. Non-limiting examples of therapies that can be administered in combination with an antibody of the invention include analgesic agents, anaesthetic agents, antibiotics, or immunomodulatory agents or any other agent listed in the U.S. Pharmacopoeia and/or Physician's Desk Reference.

The term "immunocytokine", as used herein refers to an antibody format which is fused to a cytokine molecule. The antibody format may be any of those described herein, and the cytokine may be fused directly, or by means of a linker or chemical conjugation to either the N- or C-terminus of the heavy or the light chain of the antibody format.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g. the blood in a vein. A common, but non-limiting example of an injection device is a needle and syringe.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

An "isolated" or "purified" antibody or protein is one that has been identified, separated and/or recovered from a component of its production environment (e.g. natural or recombinant). For example, the antibody or protein is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e. culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly, such preparations of the antibody have less than about 30%, 20%, 10%, 5% (by dry weight) of chemical precursors or compounds other than the antibody of interest. In a preferred embodiment, antibodies of the invention are isolated or purified.

The terms "Kabat numbering," and like terms are recognized in the art and refer to a system of numbering amino acid residues which are more variable (i.e. hypervariable) than other amino acid residues in the heavy chain variable regions of an antibody, or an antigen binding portion thereof (Kabat et al., (1971) Ann. NY Acad. Sci., 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

"Label" or "labelled" as used herein refers to the addition of a detectable moiety to a polypeptide, for example, a radiolabel, fluorescent label, enzymatic label, chemiluminescent label or a biotinyl group or gold. Radioisotopes or radionuclides may include $^{3}H$, $^{14}C$, $^{15}N$, $^{35}S$, $^{90}Y$, $^{99}Tc$, $^{115}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes (e.g. cyanine dyes, e.g. Cy5™, Cy5.5™. or Cy7™); additional fluorescent labels or fluorescers include, such as fluorescein and its derivatives, fluorochrome, GFP (GFP for "Green Fluorescent Protein"), other fluorescent proteins (e.g. mCherry, mTomato), dansyl, umbelliferone, phycoerythrin, phycocyanin, allophycocyanin, o-phthaldehyde, and fluorescamine; fluorophores such as lanthanide cryptates and chelates e.g. Europium etc. (Perkin Elmer and Cisbio Assays); chemiluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "light chain" when used in reference to an antibody refers to the immunoglobulin light chains, of which there are two types in mammals, lambda (λ) and kappa (κ). Preferably, the light chain is a human light chain. Preferably the light chain constant region is a human constant region. In the human population, multiple light chain constant region alleles exist. The nucleotide and amino acid sequences of these allelic variants are accessible on publicly available databases such as IMGT, ENSEMBL, Swiss-Prot and Uniprot. In one embodiment, the antibodies or antibody fragments disclosed herein comprise a protein encoded by a human κ constant region allele, which includes, but is not limited to, IGKC*01 (Seq ID Nos:206 & 207), IGKC*02 (Seq ID Nos:208 & 209), IGKC*03 (Seq ID Nos:210 & 211), IGKC*04 (Seq ID Nos:212 & 213) and IGKC*05 (Seq ID Nos:214 & 215). In one embodiment, the antibodies or antibody fragments disclosed herein comprise a protein encoded by a human λ constant region allele, which includes but is not limited to IGLC1*01 (Seq ID Nos:216 & 217), IGLC1*02 (Seq ID Nos:218, 219 & 220), IGLC2*01 (Seq ID Nos:221, 222 & 538), IGLC2*02 (Seq ID Nos:224 & 225), IGLC2*03 (Seq ID Nos:224 & 225), IGLC3*01 (Seq ID Nos:226 & 227), IGLC3*02 (Seq ID Nos:228 & 229), IGLC3*03 (Seq ID Nos:230 & 231), IGLC3*04 (Seq ID Nos:232 & 233), IGLC6*01 (Seq ID Nos:234 & 235), IGLC7*01 (Seq ID Nos:236 & 237), IGLC7*02 (Seq ID Nos:236 & 237), IGLC7*03 (Seq ID Nos:535 & 536). In another embodiment, the antibodies and antibody fragments disclosed herein comprise a light chain constant region encoded by a mouse κ constant region allele, which includes, but is not limited to, IGKC*01, IGKC*03 or IGKC*03. In another embodiment, the antibodies and antibody fragments disclosed herein comprise a light chain constant region encoded by a mouse λ constant region allele, which includes, but is not limited to, IGLC1*01, IGLC2*01 or IGLC3*01.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEG ALIGN™ (DNASTAR) software. In one embodiment, the % homology is about 70%. In one embodiment, the % homology is about 75%. In one embodiment, the % homology is about 80%. In one embodiment, the % homology is about 85%. In one embodiment, the % homology is about 90%. In one embodiment, the % homology is about 92%. In one embodiment, the % homology is about 95%. In one embodiment, the % homology is about 97%. In one embodiment, the % homology is about 98%. In one embodiment, the % homology is about 99%. In one embodiment, the % homology is 100%.

The term "naturally occurring" or "native" when used in connection with biological materials such as nucleic acid molecules, polypeptides, host cells, and the like, refers to those which are found in nature and not manipulated by a human being.

As used herein, "packaging" refers to how the components are organized and/or restrained into a unit fit for distribution and/or use. Packaging can include, e.g. boxes, bags, syringes, ampoules, vials, tubes, clamshell packaging, barriers and/or containers to maintain sterility, labelling, etc.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein, the term "polynucleotide," "nucleotide," nucleic acid" "nucleic acid molecule" and other similar terms are used interchangeable and include DNA, RNA, mRNA and the like.

As used herein, the terms "prevent", "preventing", and "prevention" refer to the total or partial inhibition of the development, recurrence, onset or spread of a hPD-L1-mediated disease and/or symptom related thereto, resulting from the administration of a therapy or combination of therapies provided herein (e.g. a combination of prophylactic or therapeutic agents, such as an antibody of the invention).

The term "soluble" refers to a polypeptide, such as PD-L1 and variants or fragments thereof, that is lacking one or more transmembrane or cytoplasmic domains found in the native or membrane-associated form. In one embodiment, the "soluble" form of PD-L1 lacks both the transmembrane domain and the cytoplasmic domain.

The term "subject" or "patient" refers to any animal, including, but not limited to, mammals. As used herein, the term "mammal" refers to any vertebrate animal that suckle their young and either give birth to living young (eutharian or placental mammals) or are egg-laying (metatharian or nonplacental mammals). Examples of mammalian species include, but are not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like.

As used herein "substantially all" refers to refers to at least about 60%, at least about 70%, at least about 75%, at least about 80%, at least about 85%, at least about 90%, at least about 95%, at least about 98%, at least about 99%, or about 100%.

The term "substantially free of surfactant" as used herein refers to a formulation of an antibody that specifically binds to a hPD-L1 antigen, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of an antibody that specifically binds to a hPD-L1 antigen, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and non-ionic surfactants. Surfactants are often used as wetting, emulsifying, solubilizing, and dispersing agents for various pharmaceutical compositions and preparations of biological materials.

As used herein, the term "tag" refers to any type of moiety that is attached to, e.g. a polypeptide and/or a polynucleotide that encodes a hPD-L1 or hPD-L1 antibody or antigen binding fragment thereof. For example, a polynucleotide that encodes a hPD-L1, hPD-L1 antibody or antigen binding fragment thereof can contain one or more additional tag-encoding nucleotide sequences that encode e.g. a detectable moiety or a moiety that aids in affinity purification. When translated, the tag and the antibody can be in the form of a fusion protein. The term "detectable" or "detection" with reference to a tag refers to any tag that is capable of being visualized or wherein the presence of the tag is otherwise able to be determined and/or measured (e.g. by quantitation). A non-limiting example of a detectable tag is a fluorescent tag.

As used herein, the term "therapeutic agent" refers to any agent that can be used in the treatment, management or amelioration of a hPD-L1-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a hPD-L1-mediated disease or one or more symptoms related thereto. In specific embodiments, the therapeutic agent is a fully human anti-hPD-L1 antibody, such as a fully human anti-hPD-L1 monoclonal antibody.

As used herein, the term "therapy" refers to any protocol, method and/or agent that can be used in the prevention, management, treatment and/or amelioration of a hPD-L1-mediated disease (e.g. cancer). In certain embodiments, the terms "therapies" and "therapy" refer to a biological therapy, supportive therapy, and/or other therapies useful in the prevention, management, treatment and/or amelioration of a hPD-L1-mediated disease known to one of skill in the art such as medical personnel.

The terms "treat", "treatment" and "treating" refer to the reduction or amelioration of the progression, severity, and/or duration of a hPD-L1-mediated disease (e.g. cancer) resulting from the administration of one or more therapies (including, but not limited to, the administration of one or more prophylactic or therapeutic agents, such as an antibody of the invention). In specific embodiments, such terms refer to the reduction or inhibition of the binding of hPD-L1 to PD-1, the reduction or inhibition of the binding of hPD-L1 to CD80, and/or the inhibition or reduction of one or more symptoms associated with a hPD-L1-mediated disease, such as cancer. In specific embodiments, such terms refer to the reduction or inhibition of the binding of hPD-L1 to PD-1 and/or CD80, and/or the inhibition or reduction of one or more symptoms associated with a hPD-L1-mediated disease, such as cancer. In an example, the cell is a human cell. In specific embodiments, a prophylactic agent is a fully human anti-hPD-L1 antibody, such as a fully human anti-hPD-L1 monoclonal antibody.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the PD-L1 and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) $5^{th}$ ed. ("Kabat et al."). In preferred embodiments, the variable region is a human variable region.

Definitions of common terms in cell biology and molecular biology can be found in "The Merck Manual of Diagnosis and Therapy", $19^{th}$ Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (Eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan eta., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

2. PD-L1 Antibodies

Many tumour cells express surface molecules that are specific to cancer that can serve as diagnostic and/or therapeutic antibody targets. Examples of cell surface proteins expressed by tumour molecules that can be useful as biomarkers include, for example, members of the B7 family of proteins, major histocompatibility complex molecules (MHC), cytokine and growth factor receptors such as the receptor for epidermal growth factor (EGFR). The B7 family is a group of proteins that are members of the immunoglobulin (Ig) superfamily of cell-surface proteins that bind to receptors on lymphocytes to regulate immune responses. The family includes transmembrane or glycosylphosphatidylinositol (GPI)-linked proteins characterized by extracellular Ig-like domains (IgV and IgC domains related to the variable and constant domains of immunoglobulins). All members have short cytoplasmic domains. There are seven known members of the B7 family: B7-1, B7-2, PD-L1 (B7-H1), PD-L2, B7-H2, B7-H3, and B7-H4.

The complete amino acid sequence for PD-L1 can be found in NCBI Reference Sequence: NP_054862.1 (SEQ ID No:1), which refers to many journal articles, including, for example, Dong, H., et al. (1999), "PD-L1, a third member of the B7 family, co-stimulates T-cell proliferation and interleukin-10 secretion," Nat. Med. 5 (12), 1365-1369, the disclosure of which is hereby incorporated by reference herein in its entirety. The amino acid sequence of PD-L1 includes a 30 amino acid long cytoplasmic domain that is unique to PD-L1, which shows little homology to other molecules, including other B7 family members.

In one embodiment, the antibody is a polyclonal antibody. Methods for generating polyclonal antibodies are known, and include, for example, inoculating a suitable mammal with an antigen to induce the immune system of the animal to produce immunoglobulins (IgGs) that specifically bind the injected antigen. Examples of suitable mammals include, for example, mouse, guinea pig, hamster, rat, rabbit sheep or goat. The polyclonal IgG is then typically purified from the mammal's serum. In one embodiment, the antibody is a polyclonal antibody that binds to a surface expressed protein. In another embodiment, the antibody is a polyclonal antibody that specifically binds to a member of the B7 family of proteins. In a more specific embodiment, the antibody is a polyclonal antibody that specifically binds PD-L1. In another embodiment, the antibody is a polyclonal antibody that specifically binds surface expressed PD-L1. In a more particular embodiment, the polyclonal antibody or antigen binding fragment thereof specifically binds human PD-L1. In another embodiment, the antibody is a polyclonal antibody that specifically binds soluble PD-L1. The term "soluble" also refers to a protein, such as PD-L1 that is lacking one or more transmembrane domain or cytoplasmic domains. In one embodiment, the "soluble" form of PD-L1 lacks both the transmembrane domain and the cytoplasmic domain. In one embodiment, the antibody is a polyclonal antibody that binds "free" PD-L1 (i.e. PD-L1 that is not associated with a cell membrane or surface, either directly or indirectly).

In another embodiment, the antibody can be a monoclonal antibody. Methods of making monoclonal antibodies are known and include, for example, fusing myeloma cells with the cells from an animal that was immunized with the desired antigen. In other embodiments, the monoclonal antibodies may be generated using recombinant DNA technology. In one embodiment, the antibody is a monoclonal antibody that specifically binds a surface expressed protein. In one embodiment, the antibody is a fully human monoclonal antibody. In another embodiment, the antibody is a monoclonal antibody that specifically binds to a member of the B7 family of proteins. In a more specific embodiment, the antibody is a monoclonal antibody that specifically binds PD-L1. In another embodiment, the antibody is a monoclonal antibody that specifically binds surface expressed PD-L1. In a more particular embodiment, the monoclonal antibody or antigen binding fragment thereof specifically binds human PD-L1. In another embodiment, the antibody is a monoclonal antibody that specifically binds soluble PD-L1. In one embodiment, the antibody is a monoclonal antibody that specifically binds soluble PD-L1 that is lacking one or more transmembrane domain or cytoplasmic domains. In one embodiment, the antibody is a monoclonal antibody that specifically binds soluble PD-L1 that is lacking both the transmembrane domain and the cytoplasmic domain. In one embodiment, the antibody is a monoclonal antibody that binds "free" PD-L1 (i.e. PD-L1 that is not associated with a cell membrane or surface, either directly or indirectly).

In an example the binding site(s) of the antibody or fragment are selected from a plurality (e.g. library) of binding sites. For example, the plurality of binding sites comprises or consists of a plurality of 4-chain antibodies or fragments thereof, e.g. dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (e.g. a rodent, e.g. a mouse or rat, e.g. a Velocimousem, Kymouse™, Xenomouse™, Aliva Mousem, HuMab Mouse™, Omnimouse™, Omnirat™ or MeMo Mouse™) with hPD-L1 or a hPD-L1 epitope and isolation of a repertoire of antibody-producing cells (e.g. a B-cell, plasma cell or plasmablast repertoire) and/or a repertoire of isolated antibodies, fragments or binding sites.

PD-L1 binding ability, specificity and affinity (Kd, $K_{off}$ and/or $K_{on}$) can be determined by any routine method in the art, e.g. by surface plasmon resonance (SPR). The term "Kd" or "$K_D$", as used herein, is intended to refer to the equilibrium dissociation constant of a particular antibody-antigen interaction. Such binding measurements can be made using a variety of binding assays known in the art, e.g. using surface plasmon resonance (SPR), such as by Biacore™ or using the ProteOn XPR36™ (Bio-Rad®), using KinExA® (Sapidyne Instruments, Inc), or using ForteBio Octet (Pall ForteBio Corp.).

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (e.g. using Hepes buffered saline at pH 7.6 (also referred to as HBS-EP)).

In one embodiment, the SPR is carried out at a physiological salt level, e.g. 150 mM NaCl.

In one embodiment, the SPR is carried out at a detergent level of no greater than 0.05% by volume, e.g. in the presence of P20 (polysorbate 20; e.g. Tween 20™) at 0.05% and EDTA at 3 mM.

In one example, the SPR is carried out at 25° C. or 37° C. in a buffer at pH 7.6, 150 mM NaCl, 0.05% detergent (e.g. P20) and 3 mM EDTA. The buffer can contain 10 mM Hepes. In one example, the SPR is carried out at 25° C. or 37° C. in HBS-EP. HBS-EP is available from Teknova Inc. (California; catalogue number H8022).

In an example, the affinity of the antibody or fragment is determined using SPR by:
1. Coupling anti-mouse (or other relevant human, rat or non-human vertebrate antibody constant region species-matched) IgG (e.g. Biacore™ BR-1008-38) to a biosensor chip (e.g. GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, e.g. under an SPR condition discussed above (e.g. at 25° C. in physiological buffer). SPR can be carried out using any standard SPR apparatus, such as by Biacorem or using the ProteOn XPR36™ (Bio-Rad®).

Regeneration of the capture surface can be carried out with 10 mM glycine at pH 1.7. This removes the captured antibody and allows the surface to be used for another interaction. The binding data can be fitted to 1:1 model inherent using standard techniques, e.g. using a model inherent to the ProteOn XPR36™ analysis software.

The present inventors have identified a number of antibodies having specificity for hPD-L1, which have a number of potential utilities and benefits over existing antibodies. For example, the antibodies described herein may have one or more of the following properties:
a. Specificity for blocking only one of the ligands of PD-L1 (e.g. blocks CD80/PD-L1 interaction, but not PD-1/PD-L1 interaction)
b. Immunogenicity/lack of side effects
c. Solubility
d. Stability
e. Ease of formulation
f. Frequency of dosing and/or route of administration, for example due to improved half-life over existing anti-PDL1 antibodies
g. Manufacturability (e.g. expression, ease of purification, isoforms)

1D05 has a heavy chain variable region ($V_H$) amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36). A full length light chain amino acid sequence is Seq ID No:45 (light chain nucleic acid sequence Seq ID No:46).

84G09 has a heavy chain variable ($V_H$) region amino acid sequence of Seq ID No:13, comprising the CDRH1 amino acid sequence of Seq ID No:7 (IMGT) or Seq ID No:10 (Kabat), the CDRH2 amino acid sequence of Seq ID No:8 (IMGT) or Seq ID No:11 (Kabat), and the CDRH3 amino acid sequence of Seq ID No:9 (IMGT) or Seq ID No:12 (Kabat). The heavy chain nucleic acid sequence of the $V_H$ domain is Seq ID No:14. 84G09 has a light chain variable region ($V_L$) amino acid sequence of Seq ID No:23, comprising the CDRL1 amino acid sequence of Seq ID No:17 (IMGT) or Seq ID No:20 (Kabat), the CDRL2 amino acid sequence of Seq ID No:18 (IMGT) or Seq ID No:21 (Kabat), and the CDRL3 amino acid sequence of Seq ID No:19 (IMGT) or Seq ID No:22 (Kabat). The light chain nucleic acid sequence of the $V_L$ domain is Seq ID No:24. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:15 (heavy chain nucleic acid sequence Seq ID No:16). A full length light chain amino acid sequence is Seq ID No:25 (light chain nucleic acid sequence Seq ID No:26).

1D05 HC mutant 1 has a heavy chain variable ($V_H$) region amino acid sequence of Seq ID No:47, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 1 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 HC mutant 2 has a heavy chain variable ($V_H$) region amino acid sequence of Seq ID No:48, comprising the CDRH1 amino acid sequence of Seq ID No:27. (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 2 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 HC mutant 3 has a heavy chain variable ($V_H$) region amino acid sequence of Seq ID No:49, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 3 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 HC mutant 4 has a heavy chain variable ($V_H$) region amino acid sequence of Seq ID No:342, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 4 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 LC mutant 1 has a heavy chain variable ($V_H$) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 LC mutant 1 has a light chain variable region ($V_L$) amino acid sequence of Seq ID No:50, comprising the CDRL1 amino acid sequence of Seq ID No:37 (IMGT) or Seq ID No:40 (Kabat), and the CDRL3 amino acid sequence of Seq ID No:39 (IMGT) or Seq ID No:42 (Kabat). The CDRL2 sequence of 1D05 LC Mutant 1 is as defined by the Kabat or IMGT systems from the $V_L$ sequence of Seq ID No:50. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The VL domain may be combined with any of the light chain constant region sequences described herein, e.g. Seq ID Nos:207., 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36).

1D05 LC mutant 2 has a heavy chain variable ($V_H$) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 LC mutant 2 has a light chain variable region ($V_L$) amino acid sequence of Seq ID No:51, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36).

1D05 LC mutant 3 has a heavy chain variable ($V_H$) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 LC mutant 3 has a light chain variable region ($V_L$) amino acid sequence of Seq ID No:298, comprising the CDRL1 amino acid sequence of Seq ID No:37 (IMGT) or Seq ID No:40 (Kabat), and the CDRL3 amino acid sequence of Seq ID No:39 (IMGT) or Seq ID No:42 (Kabat). The CDRL2 sequence of 1D05 LC Mutant 3 is as defined by the Kabat or IMGT systems from the $V_L$ sequence of Seq ID No:298. The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic add sequence Seq ID No:36). A full length light chain amino acid sequence is Seq ID No:45 (light chain nucleic acid sequence Seq ID No:46).

411B08 has a heavy chain variable ($V_H$) region amino acid sequence of Seq ID No:58, comprising the CDRH1 amino acid sequence of Seq ID No:52 (IMGT) or Seq ID No:55 (Kabat), the CDRH2 amino acid sequence of Seq ID No:53 (IMGT) or Seq ID No:56 (Kabat), and the CDRH3 amino acid sequence of Seq ID No:54 (IMGT) or Seq ID No:57 (Kabat). The heavy chain nucleic acid sequence of the $V_H$ domain is Seq ID No:59. 411B08 has a light chain variable region ($V_L$) amino acid sequence of Seq ID No:68, comprising the CDRL1 amino acid sequence of Seq ID No:62 (IMGT) or Seq ID No:65 (Kabat), the CDRL2 amino acid sequence of Seq ID No:63 (IMGT) or Seq ID No:66 (Kabat), and the CDRL3 amino acid sequence of Seq ID No:64 (IMGT) or Seq ID No:67 (Kabat). The light chain nucleic acid sequence of the $V_L$ domain is Seq ID No:69. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:60 (heavy chain nucleic acid sequence Seq ID No:61). A full length light chain amino acid sequence is Seq ID No:70 (light chain nucleic acid sequence Seq ID No:71).

411C04 has a heavy chain variable ($V_H$) region amino acid sequence of Seq ID No:78, comprising the CDRH1 amino acid sequence of Seq ID No:72 (IMGT) or Seq ID No:75 (Kabat), the CDRH2 amino acid sequence of Seq ID No:73 (IMGT) or Seq ID No:76 (Kabat), and the CDRH3 amino acid sequence of Seq ID No:74 (IMGT) or Seq ID No:77 (Kabat). The heavy chain nucleic acid sequence of the $V_H$ domain is Seq ID No:79. 411C04 has a light chain variable region ($V_L$) amino acid sequence of Seq ID No:88, comprising the CDRL1 amino acid sequence of Seq ID No:82 (IMGT) or Seq ID No:85 (Kabat), the CDRL2 amino acid sequence of Seq ID No:83 (IMGT) or Seq ID No:86 (Kabat), and the CDRL3 amino acid sequence of Seq ID No:84 (IMGT) or Seq ID No:87 (Kabat). The light chain nucleic acid sequence of the $V_L$ domain is Seq ID No:89. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:80 (heavy chain nucleic acid sequence Seq ID No:81). A full length light chain amino acid sequence is Seq ID No:90 (light chain nucleic acid sequence Seq ID No:91). 411D07 has a heavy chain variable ($V_H$) region amino acid sequence of Seq ID No:98, comprising the CDRH1 amino acid sequence of Seq ID No:92 (IMGT) or Seq ID No:95 (Kabat), the CDRH2 amino acid sequence of Seq ID No:93 (IMGT) or Seq ID No:96 (Kabat), and the CDRH3 amino acid sequence of Seq ID No:94 (IMGT) or Seq ID No:97 (Kabat). The heavy chain nucleic acid sequence of the $V_H$ domain is Seq ID No:99. 411D07 has a light chain variable region ($V_L$) amino acid sequence of Seq ID No:108, comprising the CDRL1 amino acid sequence of Seq ID No:102 (IMGT) or Seq ID No:105 (Kabat), the CDRL2 amino acid sequence of Seq ID No:103 (IMGT) or Seq ID No:106 (Kabat), and the CDRL3 amino acid sequence of Seq ID No:104 (IMGT) or Seq ID No:107 (Kabat). The light chain nucleic acid sequence of the $V_L$ domain is Seq ID No:109. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:100 (heavy chain nucleic acid sequence Seq ID No:101). A full length light chain amino acid sequence is Seq ID No:110 (light chain nucleic acid sequence Seq ID No:111).

385F01 has a heavy chain variable ($V_H$) region amino acid sequence of Seq ID No:118, comprising the CDRH1 amino acid sequence of Seq ID No:112 (IMGT) or Seq ID No:115 (Kabat), the CDRH2 amino acid sequence of Seq ID No:113 (IMGT) or Seq ID No:116 (Kabat), and the CDRH3 amino acid sequence of Seq ID No:114 (IMGT) or Seq ID No:117 (Kabat). The heavy chain nucleic acid sequence of the $V_H$ domain is Seq ID No:119. 385F01 has a light chain variable region ($V_L$) amino acid sequence of Seq ID No:128, comprising the CDRL1 amino acid sequence of Seq ID No:122 (IMGT) or Seq ID No:125 (Kabat), the CDRL2 amino add sequence of Seq ID No:123 (IMGT) or Seq ID No:126 (Kabat), and the CDRL3 amino acid sequence of Seq ID No:124 (IMGT) or Seq ID No:127 (Kabat). The light chain nucleic acid sequence of the $V_L$ domain is Seq ID No:129. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:120 (heavy chain nucleic acid sequence Seq ID No:121). A full length light chain amino acid sequence is Seq ID No:130 (light chain nucleic acid sequence Seq ID No:131).

386H03 has a heavy chain variable ($V_H$) region amino acid sequence of Seq ID No:158, comprising the CDRH1 amino acid sequence of Seq ID No:152 (IMGT) or Seq ID No:155 (Kabat), the CDRH2 amino acid sequence of Seq ID No:153 (IMGT) or Seq ID No:156 (Kabat), and the CDRH3 amino acid sequence of Seq ID No:154 (IMGT) or Seq ID No:157 (Kabat). The heavy chain nucleic acid sequence of the $V_H$ domain is Seq ID No:159. 386H03 has a light chain variable region ($V_L$) amino acid sequence of Seq ID No:168, comprising the CDRL1 amino acid sequence of Seq ID No:162 (IMGT) or Seq ID No:165 (Kabat), the CDRL2 amino acid sequence of Seq ID No:163 (IMGT) or Seq ID No:166 (Kabat), and the CDRL3 amino acid sequence of Seq ID No:164 (IMGT) or Seq ID No:167 (Kabat). The light chain nucleic acid sequence of the $V_L$ domain is Seq ID No:169. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:160 (heavy chain nucleic acid sequence Seq ID No:161). A full length light chain amino acid sequence is Seq ID No:170 (light chain nucleic acid sequence Seq ID No:171).

389A03 has a heavy chain variable ($V_H$) region amino acid sequence of Seq ID No:178, comprising the CDRH1 amino acid sequence of Seq ID No:172 (IMGT) or Seq ID No:175 (Kabat), the CDRH2 amino acid sequence of Seq ID No:173 (IMGT) or Seq ID No:176 (Kabat), and the CDRH3 amino acid sequence of Seq ID No:174 (IMGT) or Seq ID No:177 (Kabat). The heavy chain nucleic acid sequence of the $V_H$ domain is Seq ID No:179. 389A03 has a light chain variable region ($V_L$) amino acid sequence of Seq ID No:188, comprising the CDRL1 amino acid sequence of Seq ID No:182 (IMGT) or Seq ID No:185 (Kabat), the CDRL2 amino acid sequence of Seq ID No:183 (IMGT) or Seq ID No:186 (Kabat), and the CDRL3 amino acid sequence of Seq ID No:184 (IMGT) or Seq ID No:187 (Kabat). The light chain nucleic acid sequence of the $V_L$ domain is Seq ID No:189. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:180 (heavy chain nucleic acid sequence Seq ID No:181). A full length light chain amino acid sequence is Seq ID No:190 (light chain nucleic acid sequence Seq ID No:191).

413D08 has a heavy chain variable ($V_H$) region amino acid sequence of Seq ID No:138, comprising the CDRH1 amino acid sequence of Seq ID No:132 (IMGT) or Seq ID No:135 (Kabat), the CDRH2 amino acid sequence of Seq ID No:133 (IMGT) or Seq ID No:136 (Kabat), and the CDRH3 amino acid sequence of Seq ID No:134 (IMGT) or Seq ID No:137 (Kabat). The heavy chain nucleic acid sequence of the $V_H$ domain is Seq ID No:139. 413D08 has a light chain variable region ($V_L$) amino acid sequence of Seq ID No:148, comprising the CDRL1 amino acid sequence of Seq ID No:142 (IMGT) or Seq ID No:145 (Kabat), the CDRL2 amino acid sequence of Seq ID No:143 (IMGT) or Seq ID No:146 (Kabat), and the CDRL3 amino acid sequence of Seq ID No:144 (IMGT) or Seq ID No:147 (Kabat). The light chain nucleic acid sequence of the $V_L$ domain is Seq ID No:149. The $V_H$ domain may be combined with any of the heavy chain constant region sequences described herein, e.g. Seq ID No:193, Seq ID No:195, Seq ID No:197, Seq ID No199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No: 140 (heavy chain nucleic acid sequence Seq ID No:141). A full length light chain amino acid sequence is Seq ID No:150 (light chain nucleic acid sequence Seq ID No:151).

413G05 has a heavy chain variable ($V_H$) region amino acid sequence of Seq ID No:244, comprising the CDRH1 amino acid sequence of Seq ID No:238 (IMGT) or Seq ID No:241 (Kabat), the CDRH2 amino acid sequence of Seq ID No:239 (IMGT) or Seq ID No:242 (Kabat), and the CDRH3 amino acid sequence of Seq ID No:240 (IMGT) or Seq ID No:243 (Kabat). The heavy chain nucleic acid sequence of the $V_H$ domain is Seq ID No:245. 413G05 has a light chain variable region ($V_L$) amino acid sequence of Seq ID No:254, comprising the CDRL1 amino acid sequence of Seq ID No:248 (IMGT) or Seq ID No:251 (Kabat), the CDRL2 amino acid sequence of Seq ID No:249 (IMGT) or Seq ID No:252 (Kabat), and the CDRL3 amino acid sequence of Seq ID No:250 (IMGT) or Seq ID No:253 (Kabat). The light chain nucleic acid sequence of the $V_L$ domain is Seq ID No:255. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:246 (heavy chain nucleic acid sequence Seq ID No:247). A full length light chain amino acid sequence is Seq ID No:256 (light chain nucleic acid sequence Seq ID No:257).

413F09 has a heavy chain variable (V$_H$) region amino acid sequence of Seq ID No:264, comprising the CDRH1 amino acid sequence of Seq ID No:258 (IMGT) or Seq ID No:261 (Kabat), the CDRH2 amino acid sequence of Seq ID No:259 (IMGT) or Seq ID No:262 (Kabat), and the CDRH3 amino acid sequence of Seq ID No:260 (IMGT) or Seq ID No:263 (Kabat). The heavy chain nucleic acid sequence of the V$_H$ domain is Seq ID No:265. 413F09 has a light chain variable region (V$_L$) amino acid sequence of Seq ID No:274, comprising the CDRL1 amino acid sequence of Seq ID No:268 (IMGT) or Seq ID No:271 (Kabat), the CDRL2 amino acid sequence of Seq ID No:269 (IMGT) or Seq ID No:272 (Kabat), and the CDRL3 amino acid sequence of Seq ID No:270 (IMGT) or Seq ID No:273 (Kabat). The light chain nucleic acid sequence of the V$_L$ domain is Seq ID No:275. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:266 (heavy chain nucleic acid sequence Seq ID No:267). A full length light chain amino acid sequence is Seq ID No:276 (light chain nucleic acid sequence Seq ID No:277).

414B06 has a heavy chain variable (V$_H$) region amino acid sequence of Seq ID No:284, comprising the CDRH1 amino acid sequence of Seq ID No:278 (IMGT) or Seq ID No:281 (Kabat), the CDRH2 amino acid sequence of Seq ID No:279 (IMGT) or Seq ID No:282 (Kabat), and the CDRH3 amino acid sequence of Seq ID No:280 (IMGT) or Seq ID No:283 (Kabat). The heavy chain nucleic acid sequence of the V$_H$ domain is Seq ID No:285. 414B06 has a light chain variable region (V$_L$) amino acid sequence of Seq ID No:294, comprising the CDRL1 amino acid sequence of Seq ID No:288 (IMGT) or Seq ID No:291(Kabat), the CDRL2 amino acid sequence of Seq ID No:289 (IMGT) or Seq ID No:292 (Kabat), and the CDRL3 amino acid sequence of Seq ID No:290 (IMGT) or Seq ID No:293 (Kabat). The light chain nucleic acid sequence of the V$_L$ domain is Seq ID No:295. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:286 (heavy chain nucleic acid sequence Seq ID No:287). A full length light chain amino acid sequence is Seq ID No:296 (light chain nucleic acid sequence Seq ID No:297).

416E01 has a heavy chain variable region (V$_H$) amino acid sequence of Seq ID No:349, comprising the CDRH1 amino acid sequence of Seq ID No:343 (IMGT) or Seq ID No:346 (Kabat), the CDRH2 amino acid sequence of Seq ID No:344 (IMGT) or Seq ID No:347 (Kabat), and the CDRH3 amino acid sequence of Seq ID No:345 (IMGT) or Seq ID No:348 (Kabat). The heavy chain nucleic acid sequence of the V$_H$ domain is Seq ID No:350. 416E01 has a light chain variable region (Vi) amino acid sequence of Seq ID No:359, comprising the CDRL1 amino acid sequence of Seq ID No:353 (IMGT) or Seq ID No:356 (Kabat), the CDRL2 amino acid sequence of Seq ID No:354 (IMGT) or Seq ID No:357 (Kabat), and the CDRL3 amino acid sequence of Seq ID No:355 (IMGT) or Seq ID No:358 (Kabat). The light chain nucleic acid sequence of the V$_L$ domain is Seq ID No:360. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:351 (heavy chain nucleic acid sequence Seq ID No:352). A full length light chain amino acid sequence is Seq ID No:361 (light chain nucleic acid sequence Seq ID No:362).

The antibodies of the invention are described with respect to the following concepts, aspects, sentences, arrangements and embodiments. Unless otherwise stated, all concepts, embodiments, sentences, arrangements and aspects are to be read as being able to be combined with any other concept, aspect, sentence, arrangement or embodiment, unless such combination would not make technical sense or is explicitly stated otherwise.

Concept 1. An antibody or a fragment thereof, which specifically binds to hPD-L1 as defined by Seq ID No:1, and competes for binding to said hPD-L1 with the antibody 1D05, wherein the antibody or fragment comprises a V$_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In these concepts, antibodies or fragments may include or may not include bispecific antibodies. In one embodiment, in these concepts, antibodies or fragments includes bispecific antibodies. In one embodiment, a bispecific antibody does not include a FIT-Ig format. In one embodiment, a bispecific antibody does not include a mAb$^2$ format. In one embodiment, a bispecific antibody does not include either a FIT-Ig format or a mAb$^2$ format. In one embodiment, the antibody or fragment in these concepts includes a bispecific antibody, but does not include a bispecific antibody having a FIT-Ig format. In one embodiment, the antibody or fragment in these concepts includes a bispecific antibody, but does not include a bispecific antibody having a mAb$^2$ format. In one embodiment, the antibody or fragment in these concepts includes a bispecific antibody, but does not include a bispecific antibody having a FIT-Ig format or a mAb$^2$ format. In another embodiment, in these concepts, antibodies or fragments include dual binding antibodies.

Preferably, an antibody or a fragment thereof that specifically binds to a hPD-L1 antigen does not cross-react with other antigens (but may optionally cross-react with PD-L1 of a different species, e.g., rhesus, cynomolgus, or murine). An antibody or a fragment thereof that specifically binds to a hPD-L1 antigen can be identified, for example, by immunoassays, BIAcore™, or other techniques known to those of skill in the art. An antibody or a fragment thereof binds specifically to a hPD-L1 antigen when it binds to a hPD-L1 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times background. See, e.g. Paul, ed., 1989, Fundamental Immunology Second Edition, Raven Press, New York at pages 332-336 for a discussion regarding antibody specificity.

In one embodiment, the antibody or fragment is a human antibody. In one embodiment, the antibody or fragment is a human antibody or fragment. In one embodiment, the antibody or fragment is a fully human antibody or fragment. In one embodiment, the antibody or fragment is a fully human monoclonal antibody or fragment.

There is also provided concept 1a: An antibody or a fragment thereof, that specifically binds to hPD-L1 as defined by Seq ID No:1, and competes for binding to said hPD-L1 with the antibody 411B08, wherein the antibody or fragment comprises a $V_H$ domain which comprises a CDRH3 comprising the motif $ARX_1RX_2X_3SDX_4X_5D$, wherein $X_1$, $X_2$, $X_3$, $X_4$ and $X_5$ are independently any amino acid.

There is also provided concept 1b: An antibody or a fragment thereof, that specifically binds to hPD-L1 as defined by Seq ID No:1, and competes for binding to said hPD-L1 with the antibody 411B08, wherein the antibody or fragment comprises a $V_H$ domain which comprises a CDRH3 comprising the motif $X_1RDGSGSY$, wherein $X_1$ is any amino acid.

As provided in the concepts or aspects herein, an anti-PD-L1 antibody or immunocytokine may bind to PD-L1, e.g. human PD-L1 with a $K_D$ of less than 50 nM, less than 40 nM, less than 30 nM as determined by surface plasmon resonance. Another embodiment, anti-PD-L1 antibody or immunocytokine may bind to PD-L1, e.g. human PD-L1 with a $K_D$ of less than 20 nM, less than 15 nM, less than 10 nM as determined by surface plasmon resonance. anti-PD-L1 antibody or immunocytokine may bind to PD-L1, e.g. human PD-L1 with a $K_D$ of less than 8 nM, less than 5 nM, less than 4 nM, less than 3 nM, less than 2 nM or less than 1 nM as determined by surface plasmon resonance. The KD may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

In another embodiment, the $K_D$ is within a range of 0.01 to 1 nM, or a range of 0.05 to 2 nM, or a range of 0.05 to 1 nM. The $K_D$ may be with regard to hPD-L1, cynoPD-L1 and/or mouse PD-L1.

In another embodiment, the anti-PD-L1 antibodies described herein have a $K_{ON}$ rate (e.g. as measured by SPR, e.g. at 25° C. or at 37° C.) of approximately 0.5 to 10 μM, for example approximately 1 to 8 μM or approximately 1 to 7 μM. In another embodiment, the $K_{ON}$ rate is approximately 1 to 5 μM, e.g. approximately 1 μM, approximately 1.5 μM, approximately 2 μM, approximately 2.5 μM or approximately 3 μM. In another embodiment, the $K_{ON}$ rate is approximately 3.5 μM, approximately 4 μM, approximately 4.5 μM, approximately 5 μM or approximately 5.5 μM.

In another embodiment, the anti-PD-L1 antibodies described herein have a $K_{OFF}$ rate (e.g. as measured by SPR, e.g. at 25° C. or at 37° C.) of approximately 0.01 to 100 mM, for example approximately 0.1 to 50 mM or approximately 0.5 to 50 mM. In another embodiment, the $K_{OFF}$ rate is approximately 0.5 to 10 mM, or approximately 0.5 to 10 mM, e.g. approximately 1 mM, approximately 2 mM, approximately 3 mM, approximately 4 mM or approximately 5 mM. In another embodiment, the $K_{OFF}$ rate is approximately 0.6 mM, approximately 0.7 mM, approximately 0.8 mM or approximately 0.9 mM.

In another embodiment, the anti-PD-L1 antibodies (and immunocytokines) described in the concepts and aspects herein provide improved transient expression levels over other anti-PD-L1 antibodies and immunocytokines. Thus, in one embodiment, the anti-PD-L1 antibody (or immunocytokine) is expressed in a HEK293 cell, e.g. a HEK293T cell, at an expression level of approximately 100 μg/mL, or in a range of approximately 100 to 350 μg/mL. In another embodiment, the expression level is above approximately 350 μg/mL.

In another embodiment, the anti-PD-L1 antibody (or immunocytokine) is expressed in a CHO cell, e.g. an Expi-CHO cell, at an expression level of approximately 100 μg/mL, or in a range of approximately 100 to 350 μg/mL. In another embodiment, the expression level is above approximately 350 μg/mL.

In another embodiment, the anti-PD-L1 antibody (or immunocytokine) is expressed in a CHO cell, e.g. an Expi-CHO cell or a CHO-E7 EBNA cell, at an expression level of approximately 100 μg/mL, or in a range of approximately 100 to 350 μg/mL. In another embodiment, the expression level is above approximately 350 μg/mL. The antibody described herein as 1D05, formatted as a human IgG1 (Seq ID No:340), at 2 L volume in CHO-E7 EBNA cells has an expression level of approximately 115 μg/mL. The antibody described herein as 416E01, formatted as a human IgG1 (Seq ID No:340), at 2 L volume in CHO-E7 EBNA cells has an expression level of approximately 160 μg/mL. The antibody described herein as 1414B06, formatted as a human IgG1 (Seq ID No:340), at 2 L volume in CHO-E7 EBNA cells has an expression level of approximately 783 μg/mL. The antibody described herein as 413G05, formatted as a human IgG1 (Seq ID No:340), at 2 L volume in CHO-E7 EBNA cells has an expression level of approximately 383 μg/mL.

In any of these expression systems, the expression is carried out of a scale of between approximately 0.5 mL and 3 mL, for example between approximately 0.5 mL and 2 mL. In any of these expression systems, the anti-PD-L1 antibody (or immunocytokine) may be expressed from a pTT5 vector. In any of these expression systems, the anti-PD-L1 antibody (or immunocytokine) may be expressed in conjunction with a lipid transfection reagent, and may optionally be expressed in a CHO cell, e.g. an Expi-CHO cell. In any of these expression systems, the anti-PD-L1 antibody (or immunocytokine) may be expressed in conjunction with a PEI transfection reagent, and may optionally be expressed in a CHO cell, e.g. an CHO-E7 EBNA cell. In any of these expression systems, the anti-PD-L1 antibody (or immunocytokine) may be expressed in conjunction with a helper plasmid (e.g. an AKT helper plasmid), and may optionally be expressed in a CHO cell, e.g. an CHO-E7 EBNA cell.

In any of these expression systems, the expression level is between approximately 100 μg/mL and approximately 1500 μg/mL, for example between approximately 100 μg/mL and approximately 1000 μg/mL, or between approximately 200 μg/mL and approximately 1000 μg/mL, or between approximately 350 μg/mL and approximately 1000 μg/mL. In any of these expression systems, the lower limit of expression may be approximately 100 μg/mL, approximately 200 μg/mL, approximately 300 μg/mL, or approximately 400 μg/mL. In another embodiment, the lower limit of expression may be approximately 500 μg/mL, approximately 600 μg/mL, approximately 700 μg/mL, or approximately 800 μg/mL. In any of these expression systems, the upper limit of expression may be approximately 200 μg/mL, approximately 1800 μg/mL, approximately 1600 μg/mL, or approximately 1500 μg/mL. In another embodiment, the upper limit of expression may be approximately 1250 μg/mL, approximately 1000 μg/mL, approximately 900 μg/mL, or approximately 800 μg/mL.

In another embodiment, the expression system is a Lonza expression system, e.g. Lonza X-Ceed® system. In the Lonza expression system, the expression may be carried out at a scale of approximately 30 mL to 2 L, for example 50 mL to 1 L, or 1 L to 2 L. In the Lonza expression system, the anti-PD-L1 antibody (or immunocytokine) may be expressed in conjunction with electroporation, and optionally without any helper plasmids. In the Lonza expression system, the anti-PD-L1 antibody (or immunocytokine) may be expressed at a level of approximately 1 g/L, or approximately 900 mg/L, or approximately 800 mg/L, or approximately 700 mg/L. In another embodiment, In the Lonza expression system, the anti-PD-L1 antibody (or immunocytokine) may be expressed at a level of approximately 600 mg/L or approximately 500 mg/L or approximately 400 mg/L. In the Lonza expression system, the anti-PD-L1 antibody (or immunocytokine) may be expressed at a level of between approximately 400 mg/L and approximately 2 g/L, for example between approximately 500 mg/L and approximately 1.5 g/L, or between approximately 500 mg/L and approximately 1 g/L. In another embodiment, the expression level is above 1 g/L. In another embodiment, the anti-PD-L1 antibodies described in the concepts provide improved half-life over other anti-PD-L1 antibodies as further described in Aspect 1 hereinbelow.

Concept 2. The antibody or fragment according to concept 1, wherein $X_1$ is a hydroxyl-containing amino acid, optionally T.

In one embodiment, the hydroxyl-containing amino acid is Serine. In one embodiment, the hydroxyl-containing amino acid is Cysteine. In one embodiment, the hydroxyl-containing amino acid is Threonine. In one embodiment, the hydroxyl-containing amino acid is Methionine. In one embodiment, the hydroxyl-containing amino acid is Serine or Cysteine. In one embodiment, the hydroxyl-containing amino acid is Serine or Threonine. In one embodiment, the hydroxyl-containing amino acid is Serine or Methionine. In one embodiment, the hydroxyl-containing amino acid is Cysteine or Threonine. In one embodiment, the hydroxyl-containing amino acid is Cysteine or Methionine. In one embodiment, the hydroxyl-containing amino acid is Threonine or Methionine.

In one embodiment, the hydroxyl-containing amino acid is selected from serine, cysteine, threonine and methionine.

Concept 2a. The antibody or fragment according to concept 1a, wherein $X_1$ is an aliphatic amino acid or an amide amino acid.

In one embodiment, $X_1$ is selected from Asparagine (N) and valine (V). In one embodiment, $X_1$ is valine. In one embodiment, $X_1$ is asparagine.

Concept 2b. The antibody or fragment according to concept 1b, wherein $X_1$ is an aliphatic amino acid.

In one embodiment, $X_1$ is selected from alanine (A) or valine (V). In one, embodiment, $X_1$ is valine. In one embodiment, $X_1$ is alanine.

Concept 3. The antibody or fragment according to concept 1 or concept 2, wherein $X_2$ is a basic amino acid, optionally K.

In one embodiment, the hydroxyl-containing amino acid is Histidine. In one embodiment, the hydroxyl-containing amino acid is Lysine. In one embodiment, the hydroxyl-containing amino acid is Arginine. In one embodiment, the hydroxyl-containing amino acid is Histidine or Lysine. In one embodiment, the hydroxyl-containing amino acid is Histidine or Arginine. In one embodiment, the hydroxyl-containing amino acid is Lysine or Arginine.

In one embodiment, the hydroxyl-containing amino acid is selected from Histidine, Lysine and Arginine.

Concept 3a. The antibody or fragment according to concept 1a or concept 2a, wherein $X_1$ is an aliphatic amino acid or an amide amino acid.

In one embodiment, $X_2$ is selected from leucine (L), isoleucine (I), Valine (V), Asparagine (N) and glutamine (Q). In one embodiment, $X_2$ is selected from leucine (L), isoleucine (I) and Valine (V). In one embodiment, $X_2$ is selected from Asparagine (N) and glutamine (Q) In one embodiment, $X_1$ is selected from leucine (L) and glutamine (Q). In one embodiment, $X_1$ is leucine (L). In one embodiment, $X_2$ is glutamine (Q).

Concept 4. The antibody or fragment according to any one of concepts 1 to 3, wherein $X_2$ is a hydroxyl-containing amino acid, optionally S or T.

In one embodiment, the hydroxyl-containing amino acid is Serine. In one embodiment, the hydroxyl-containing amino acid is Cysteine. In one embodiment, the hydroxyl-containing amino acid is Threonine. In one embodiment, the hydroxyl-containing amino acid is Methionine. In one embodiment, the hydroxyl-containing amino acid is Serine or Cysteine. In one embodiment, the hydroxyl-containing amino acid is Serine or Threonine. In one embodiment, the hydroxyl-containing amino acid is Serine or Methionine. In one embodiment, the hydroxyl-containing amino acid is Cysteine or Threonine. In one embodiment, the hydroxyl-containing amino acid is Cysteine or Methionine. In one embodiment, the hydroxyl-containing amino acid is Threonine or Methionine.

In one embodiment, the hydroxyl-containing amino acid is selected from serine, cysteine, threonine and methionine.

Concept 4a. The antibody or fragment according to any one of concepts 1a, 2a or 3a, wherein $X_3$ is an aromatic amino acid.

In one embodiment, $X_3$ is selected from Phenylalanine (F), Tyrosine (Y) and Tryptophan (W). In one embodiment, $X_3$ is selected from Tyrosine (Y) and Tryptophan (W). In one embodiment, $X_3$ is Tyrosine (Y). In one embodiment, $X_3$ is Tryptophan (W).

Concept 5. The antibody or fragment according to any one of concepts 1 to 4, wherein $X_3$ is an aromatic amino acid, optionally W.

In one embodiment, the hydroxyl-containing amino acid is Phenylalanine. In one embodiment, the hydroxyl-containing amino acid is Tyrosine. In one embodiment, the hydroxyl-containing amino acid is Tryptophan. In one embodiment, the hydroxyl-containing amino acid is Phenylalanine or Tyrosine. In one embodiment, the hydroxyl-containing amino acid is Phenylalanine or Tryptophan. In one embodiment, the hydroxyl-containing amino acid is Tyrosine or Tryptophan.

In one embodiment, the hydroxyl-containing amino acid is selected from Phenylalanine, Tyrosine and Tryptophan.

Concept 5a. The antibody or fragment according to any one of concepts 1a, 2a, 3a or 4a wherein $X_4$ is an aromatic amino acid.

In one embodiment, $X_4$ is selected from Phenylalanine (F), Tyrosine (Y) and Tryptophan (W). In one embodiment, $X_4$ is selected from Tyrosine (Y) and Phenylalanine (F). In one embodiment, $X_4$ is Tyrosine (Y). In one embodiment, $X_4$ is Phenylalanine (F).

Concept 6. The antibody or fragment according to any one of concepts 1 to 5, wherein $X_4$ is absent.

Concept 6a. The antibody or fragment according to any one of concepts 1a, 2a, 3a, 4a or 5a wherein $X_5$ is an aliphatic amino acid or an hydroxyl-containing amino acid.

In one embodiment, $X_5$ is selected from leucine (L), isoleucine (I), Valine (V), Serine (S), Cysteine (C) and Threonine (T). In one embodiment, $X_5$ is selected from leucine (L), isoleucine (I) and Valine (V). In one embodiment, $X_5$ is selected from Serine (S), Cysteine (C) and Threonine (T). In one embodiment, $X_5$ is selected from leucine (L) and Serine (S). In one embodiment, $X_5$ is Serine (S). In one embodiment, $X_5$ is leucine (L).

Concept 7. The antibody or fragment according to any one of concepts 1 to 5, wherein $X_4$ is present.

Concept 8. The antibody or fragment according to concept 7, wherein $X_4$ is an aliphatic amino acid, optionally G.

In one embodiment, the hydroxyl-containing amino acid is selected from Glycine, Alanine, Valine, Leucine and Isoleucine.

In one embodiment, the hydroxyl-containing amino acid is selected from Glycine and Alanine. In one embodiment, the hydroxyl-containing amino acid is selected from Glycine and Valine. In one embodiment, the hydroxyl-containing amino acid is selected from Glycine and Leucine. In one embodiment, the hydroxyl-containing amino acid is selected from Glycine and Isoleucine. In one embodiment, the hydroxyl-containing amino acid is selected from Alanine and Valine. In one embodiment, the hydroxyl-containing amino acid is selected from Alanine and Leucine. In one embodiment, the hydroxyl-containing amino acid is selected from Alanine and Isoleucine. In one embodiment, the hydroxyl-containing amino acid is selected from Valine and Leucine. In one embodiment, the hydroxyl-containing amino acid is selected from Valine and Isoleucine. In one embodiment, the hydroxyl-containing amino acid is selected from, Leucine and Isoleucine.

In one embodiment, the hydroxyl-containing amino acid selected from three of each of Glycine, Alanine, Valine, Leucine and Isoleucine. In one embodiment, the hydroxyl-containing amino acid selected from four of each of Glycine, Alanine, Valine, Leucine and Isoleucine.

Concept 9. An antibody or a fragment thereof, optionally according to any one of concepts 1 to 8, which specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions.

Concept 9a: An antibody or a fragment thereof, optionally according to any one of concepts 1 to 8, which specifically binds to hPD-L1, and competes for binding to said hPD-L1 with the antibody 84G09, wherein the antibody or fragment comprises a $V_H$ domain which comprises the CDRH3 sequence of SEQ ID NO:9 or 12, or the CDRH3 sequence of SEQ ID NO:9 or 12 comprising 6 or fewer amino acid substitutions.

Concept 9b: An antibody or a fragment thereof, optionally according to any one of concepts 1 to 8, which specifically binds to hPD-L1, and competes for binding to said hPD-L1 with the antibody 411B08, wherein the antibody or fragment comprises a $V_H$ domain which comprises the CDRH3 sequence of SEQ ID NO:54 or 57, or the CDRH3 sequence of SEQ ID NO:54 or 57 comprising 6 or fewer amino acid substitutions.

Concept 9c: An antibody or a fragment thereof, optionally according to any one of concepts 1 to 8, which specifically binds to hPD-L1, and competes for binding to said hPD-L1 with the antibody 411C04, wherein the antibody or fragment comprises a $V_H$ domain which comprises the CDRH3 sequence of SEQ ID No:74 or 77, or the CDRH3 sequence of SEQ ID NO:74 or 77 comprising 6 or fewer amino acid substitutions.

Concept 9d: An antibody or a fragment thereof, optionally according to any one of concepts 1 to 8, which specifically binds to hPD-L1, and competes for binding to said hPD-L1 with the antibody 411D07, wherein the antibody or fragment comprises a $V_H$ domain which comprises the CDRH3 sequence of SEQ ID NO:94 or 97, or the CDRH3 sequence of SEQ ID NO:94 or 97 comprising 3 or fewer amino acid substitutions.

Concept 9e: An antibody or a fragment thereof, optionally according to any one of concepts 1 to 8, which specifically binds to hPD-L1, and competes for binding to said hPD-L1 with the antibody 385F01, wherein the antibody or fragment comprises a $V_H$ domain which comprises the CDRH3 sequence of SEQ ID NO:114 or 117, or the CDRH3 sequence of SEQ ID NO:114 or 117 comprising 6 or fewer amino acid substitutions.

Concept 9f: An antibody or a fragment thereof, optionally according to any one of concepts 1 to 8, which specifically binds to hPD-L1, and competes for binding to said hPD-L1 with the antibody 386H03, wherein the antibody or fragment comprises a $V_H$ domain which comprises the CDRH3 sequence of SEQ ID NO:144 or 147, or the CDRH3 sequence of SEQ ID NO:144 or 147 comprising 3 or fewer amino acid substitutions.

Concept 9g: An antibody or a fragment thereof, optionally according to any one of concepts 1 to 8, which specifically binds to hPD-L1, and competes for binding to said hPD-L1 with the antibody 389A03, wherein the antibody or fragment comprises a $V_H$ domain which comprises the CDRH3 sequence of SEQ ID NO:174 or 177, or the CDRH3 sequence of SEQ ID NO:174 or 177 comprising 6 or fewer amino acid substitutions.

Concept 9h: An antibody or a fragment thereof, optionally according to any one of concepts 1 to 8, which specifically binds to hPD-L1, and competes for binding to said hPD-L1 with the antibody 413D08, wherein the antibody or fragment comprises a $V_H$ domain which comprises the CDRH3 sequence of SEQ ID NO:134 or 137, or the CDRH3 sequence of SEQ ID NO:134 or 137 comprising 5 or fewer amino acid substitutions.

Concept 9i: An antibody or a fragment thereof, optionally according to any one of concepts 1 to 8, which specifically binds to hPD-L1, and competes for binding to said hPD-L1 with the antibody 413G05, wherein the antibody or fragment comprises a $V_H$ domain which comprises the CDRH3 sequence of SEQ ID NO:240 or 243, or the CDRH3 sequence of SEQ ID NO:240 or 243 comprising 6 or fewer amino acid substitutions.

Concept 9j: An antibody or a fragment thereof, optionally according to any one of concepts 1 to 8, which specifically binds to hPD-L1, and competes for binding to said hPD-L1 with the antibody 413F09, wherein the antibody or fragment comprises a $V_H$ domain which comprises the CDRH3 sequence of SEQ ID NO:260 or 263, or the CDRH3 sequence of SEQ ID NO:260 or 263 comprising 6 or fewer amino acid substitutions.

Concept 9k: An antibody or a fragment thereof, optionally according to any one of concepts 1 to 8, which specifically binds to hPD-L1, and competes for binding to said hPD-L1 with the antibody 414B06, wherein the antibody or fragment comprises a $V_H$ domain which comprises the CDRH3 sequence of SEQ ID NO:280 or 283, or the CDRH3 sequence of SEQ ID NO:280 or 283 comprising 6 or fewer amino acid substitutions.

Concept 9l: An antibody or a fragment thereof, optionally according to any one of concepts 1 to 8, which specifically binds to hPD-L1, and competes for binding to said hPD-L1 with the antibody 416E01, wherein the antibody or fragment comprises a $V_H$ domain which comprises the CDRH3 sequence of SEQ ID No:345 or 348, or the CDRH3 sequence of SEQ ID No:345 or 348 comprising 6 or fewer amino acid substitutions.

In all of concepts 9, 9a to l, 17, 17a to l, 18, 18a to l, 19, 19a to l, 22, 22a to l, 23, 23a to l, 24 and 24a to l, in one embodiment, the CDR comprises one amino acid substitution, which may be a conservative amino acid substitution. In all of concepts 9, 9a to l, 17, 17a to l, 18, 18a to l, 19, 19a to l, 22, 22a to l, 23, 23a, 24 and 24a to l, in one embodiment, the CDR comprises two amino acid substitutions, which may be conservative amino acid substitutions. In all of concepts 9, 9a to l, 17, 17a to l, 18, 18a to l, 19, 19a to l, 22, 22a, 22b, 22d, 22f, 22g, 24 and 24a to l, in one embodiment, the CDR comprises three amino acid substitutions, which may be conservative amino acid substitutions. In all of concepts 9, 9a to c, 9e, 9g to I, 17, 17a to c, 17e, 17g to I, 19, 19a, 22, 22d, 22f, 22g, 24 and 24a to l, in one embodiment, the CDR comprises four amino acid substitutions, which may be conservative amino acid substitutions. In all of concepts 9, 9a to c, 9e, 9g to l, 17, 17a to c, 17e, 17g to l, 22d, 22f and 22g, in one embodiment, the CDR comprises five amino acid substitutions, which may be conservative amino acid substitutions. In all of concepts 9, 9a to c, 9e, 9g, 9i to l, 17, 17a to c, 17e, 17g and 17i to l, in one embodiment, the CDR comprises six amino acid substitutions, which may be conservative amino acid substitutions.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g. substituting a charged or hydrophobic amino; acid with alanine), or alternatively, in which a naturally-occurring amino acid is substituted with a non-conventional amino acid.

In one embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

Concept 10. An antibody or fragment which specifically binds to hPD-L1 and comprises a $V_H$ domain comprising a CDRH3 of from 12 to 20 amino acids and which is derived from the recombination of a human $V_H$ gene segment, a human D gene segment and a human $J_H$ gene segment, wherein the human $J_H$ gene segment is IGHJ5 (e.g. IGHJ5*02).

In one embodiment, the CDRH3 is from 14 to 17 amino acids and the human $J_H$ gene segment is IGHJ5 (e.g. IGHJ5*02).

There is also provided as concept 10a an antibody or fragment which specifically binds to hPD-L1 and comprises a $V_H$ domain comprising a CDRH3 of from 8 to 16 amino acids and which is derived from the recombination of a human $V_H$ gene segment, a human D gene segment and a human $J_H$ gene segment, wherein the human $J_H$ gene segment is selected from IGHJ4 (e.g. IGHJ4*02), IGHJ5 (e.g. IGHJ5*02) and IGHJ6 (e.g. IGHJ6*02).

In another embodiment, the human $J_H$ gene segment is IGHJ6 (e.g. IGHJ6*02). In another embodiment, the CDRH3 is of from 10 to 17 amino acids and the human $J_H$ gene segment is IGHJ6 (e.g. IGHJ6*02).

In another embodiment, the human $J_H$ gene segment is IGHJ4 (e.g. IGHJ4*02). In another embodiment, the CDRH3 is from 7 to 17 amino acids and the human $J_H$ gene segment is IGHJ4 (e.g. IGHJ4*02).

Optionally, the antibody of concept 10 or 10a has any of the features of concepts 1 to 9, including the binding affinities, Kon and Koff rates, expression levels, half-life etc.

Concept 11. The antibody or fragment according to concept 10 or 10a, wherein the human $V_H$ gene segment is IGHV3 (e.g. IGHV3-9, such as IGHV3-9*01).

There is also provided as concept 11a an antibody or fragment according to concept 10 or 10a, wherein the human $V_H$ gene segment is selected from IGHV3 (e.g. IGHV3-9, such as IGHV3-9*01 or e.g. IGHV3-7, such as IGHV3-7*01 or e.g. IGHV3-33, such as IGHV3-33*01 or e.g. IGHV3-11, such as IGHV3-11*01 or e.g. IGHV3-23, such as IGHV3-23*04), or IGHV4 (e.g. IGHV4-4, such as IGHV4-4*02 or e.g. IGHV4-39, such as IGHV4-39*01).

In one embodiment, the human $V_H$ gene segment is IGHV3 (e.g. IGHV3-7, such as IGHV3-7*01). In one embodiment, the human $V_H$ gene segment is IGHV3 (e.g. IGHV3-33, such as IGHV3-33*01). In one embodiment, the human $V_H$ gene segment is IGHV3 (e.g. IGHV3-11, such as IGHV3-11*01). In one embodiment, the human $V_H$ gene segment is IGHV3 (e.g. IGHV3-23, such as IGHV3-23*04).

In one embodiment, the human $V_H$ gene segment is IGHV4 (e.g. e.g. IGHV4-4, such as IGHV4-4*02). In one embodiment, the human $V_H$ gene segment is IGHV4 (e.g. IGHV4-39, such as IGHV4-39*01).

There is also provided as concept 11b an antibody or fragment according to concept 10, 10a, 11 or 11a, wherein the human D gene segment is selected from IGHD1 (e.g. IGHD1-20, such as IGHD1-20*01), IGHD3 (e.g. IGHD3-10, such as IGHD3-10*01), IGHD4 (e.g. IGHD4-11, such as IGHD4-11*01), IGHD5 (e.g. IGHD5-7, such as IGHD5-18*01), and IGHD6 (e.g. IGHD6-13, such as IGHD6-13*01).

In one embodiment, the human D gene segment is IGHD1 (e.g. IGHD1-20, such as IGHD1-20*01). In one embodiment, the human D gene segment is IGHD3 (e.g. IGHD3-10, such as IGHD3-10*01). In one embodiment, the human D gene segment is IGHD4 (e.g. IGHD4-11, such as IGHD4-11*01). In one embodiment, the human D gene segment is IGHD5 (e.g. IGHD5-18, such as IGHD5-19*01). In one embodiment, the human D gene segment is IGHD6 (e.g. IGHD6-13, such as IGHD6-13*01).

In any of concepts 10, 11 and 11a, the $V_H$, $D_H$ and $J_H$ gene segments are as described in the combinations for the antibodies in Table 5 hereinbelow. In one embodiment, the antibody heavy chain is derived from a combination of IGHV3 (e.g. IGHV3-7 such as IGHV3-7*01), IGHD4 (e.g. IGHD4-11 such as IGHD4-11*01) and IGHJ4 (e.g. IGHJ4*02). In one embodiment, the antibody heavy chain is derived from a combination of IGHV4 (e.g. IGHV4-4 such as IGHV4-4*02), IGHD3 (e.g. IGHD3-10 such as IGHD3-10*01) and IGHJ4 (e.g. IGHJ4*02). In one embodiment, the antibody heavy chain is derived from a combination of IGHV4 (e.g. IGHV4-39 such as IGHV4-39*01), IGHD6 (e.g. IGHD6-13 such as IGHD6-13*01) and IGHJ1 (e.g. IGHJ1*01). In one embodiment, the antibody heavy chain is derived from a combination of IGHV3 (e.g. IGHV3-33 such as IGHV3-33*01), IGHD5 (e.g. IGHD5-18 such as IGHD5-18*01) and IGHJ6 (e.g. IGHJ6*02). In one embodiment, the antibody heavy chain is derived from a combination of IGHV3 (e.g. IGHV3-11 such as IGHV3-11*01), IGHD1 (e.g. IGHD1-20 such as IGHD1-20*01) and IGHJ6 (e.g. IGHJ6*02). In one embodiment, the antibody heavy chain is derived from a combination of IGHV3 (e.g. IGHV3-23 such as IGHV3-23*04), IGHD5 (e.g. IGHD5-18 such as IGHD5-18*01) and IGHJ4 (e.g. IGHJ4*02). In one embodiment, the antibody heavy chain is derived from a combination of IGHV3 (e.g. IGHV3-7 such as IGHV3-7*01), IGHD5 (e.g. IGHD5-24 such as IGHD5-24*01) and IGHJ4 (e.g. IGHJ4*02). In one embodiment, the antibody heavy chain is derived from a combination of IGHV3 (e.g. IGHV3-23 such as IGHV3-23*04), IGHD6 (e.g. IGHD6-13 such as IGHD6-13*01) and IGHJ4 (e.g. IGHJ4*02).

Concept 12. The antibody or fragment according to concept 10, 10a, 11, 11a or 11b, wherein the antibody or fragment comprises a $V_L$ domain which is derived from the recombination of a human Vκ gene segment, and a human Jκ gene segment, wherein the human Vκ gene segment is IGκV1D (e.g. IGκV1D-39, such as IGκV1D-39*01).

There is also provided as concept 12a an antibody or fragment according to any of concepts 10, 10a, 11, 11a or 11b, wherein the human Vκ gene segment is selected from IGκV1 (e.g. IGκV1-17, such as IGκV1-17*01 or e.g. IGκV1-9, such as IGκV1-9*d01 or e.g. IGκV1D-12, such as IGκV1D-12*02 or e.g. IGκV1D-39, such as IGκV1D-39*01), and IGκV4 (e.g. IGκV4-1, such as IGκV4-1*01).

In one embodiment, the human Vκ gene segment is IGκV1 (e.g. IGκV1-17, such as IGκV1-17*01). In one embodiment, the human Vκ gene segment is IGκV1 (e.g. IGκV1-9, such as IGκV1-9*d01). In one embodiment, the human Vκ gene segment is IGκV1 (e.g. IGκV1D-12, such as IGκV1D-12*02). In one embodiment, the human Vκ gene segment is IGκV1 (e.g. IGκV1D-39, such as IGκV1D-39*01).

In one embodiment, the human Vκ gene segment is IGκV1 IGκV4 (e.g. IGκV4-1, such as IGκV4-1*01)

There is also provided as concept 12b an antibody or fragment according to concept 10, 10a, 11 or 11a, wherein the human Jκ gene segment is selected from IGκJ1 (e.g. IGκJ1*01), IGκJ2 (e.g. IGκJ2*04), IGκJ3 (e.g. IGκJ3*01), IGκJ4 (e.g. IGκJ4*01) or IGκJ5 (e.g. IGκJ5*01).

In one embodiment, the human Jκ gene segment is IGκJ1 (e.g. IGκJ1*01). In one embodiment, the human Jκ gene segment is IGκJ2 (e.g. IGκJ2*04). In one embodiment, the human Jκ gene segment is IGκJ3 (e.g. IGκJ3*01). In one embodiment, the human Jκ gene segment is IGκJ4 (e.g. IGκJ4*01). In one embodiment, the human Jκ gene segment is IGκJ5 (e.g. IGκJ5*01).

In any of concepts 12 and 12a, the Vκ and Jκ gene segments are as described in the combinations for the antibodies in Table 5 hereinbelow. In one embodiment, the antibody light chain is derived from a combination of IGKV1D (e.g. IGKV1D-12 such as IGKV1D-12*02) and IGKJ3 (e.g. IGKJ3*01). In one embodiment, the antibody light chain is derived from a combination of IGKV4 (e.g. IGKV4-1 such as IGKV14-1*01) and IGKJ2 (e.g. IGKJ2*04). In one embodiment, the antibody light chain is derived from a combination of IGKV1 (e.g. IGKV1-17 such as IGKV1-17*01) and IGKJ1 (e.g. IGKJ1*01). In one embodiment, the antibody light chain is derived from a combination of IGKV1D (e.g. IGKV1D-12, such as IGKV1D-12*02) and IGKJ4 (e.g. IGKJ4*01). In one embodiment, the antibody light chain is derived from a combination of IGKV1 (e.g. IGKV1-9 such as IGKV1-9*d01) and IGKJ5 (e.g. IGKJ5*01). In one embodiment, the antibody light chain is derived from a combination of IGKV1D (e.g. IGKV1D-12 such as IGKV1D-12*02) and IGKJ5 (e.g. IGKJ5*01).

Concept 13. An antibody or fragment thereof which specifically binds to an epitope that is identical to an epitope to which the antibody 1D05 specifically binds.

Concept 13a. An antibody or fragment thereof which specifically binds to an epitope that is identical to an epitope to which the antibody 84G09 specifically binds.

Concept 13b. An antibody or fragment thereof which specifically binds to an epitope that is identical to an epitope to which the antibody 411B08 specifically binds.

Concept 13c. An antibody or fragment thereof which specifically binds to an epitope that is identical to an epitope to which the antibody 411C04 specifically binds.

Concept 13d. An antibody or fragment thereof which specifically binds to an epitope that is identical to an epitope to which the antibody 411D07 specifically binds.

Concept 13e. An antibody or fragment thereof which specifically binds to an epitope that is identical to an epitope to which the antibody 385F01 specifically binds.

Concept 13f. An antibody or fragment thereof which specifically binds to an epitope that is identical to an epitope to which the antibody 386H03 specifically binds.

Concept 13g. An antibody or fragment thereof which specifically binds to an epitope that is identical to an epitope to which the antibody 389A03 specifically binds.

Concept 13h. An antibody or fragment thereof which specifically binds to an epitope that is identical to an epitope to which the antibody 413D08 specifically binds.

Concept 13i. An antibody or fragment thereof which specifically binds to an epitope that is identical to an epitope to which the antibody 413G05 specifically binds.

Concept 13j. An antibody or fragment thereof which specifically binds to an epitope that is identical to an epitope to which the antibody 413F09 specifically binds.

Concept 13k. An antibody or fragment thereof which specifically binds to an epitope that is identical to an epitope to which the antibody 414B06 specifically binds.

Concept 131. An antibody or fragment thereof which specifically binds to an epitope that is identical to an epitope to which the antibody 416E01 specifically binds.

The antibodies described in these concepts have the sequences as described hereinabove.

In one embodiment, there is provided an antibody which specifically binds to an epitope which is substantially similar to an epitope to which any of the antibodies in concept 13, 13 a to 13l bind.

Contact amino acid residues involved in the interaction of antibody and antigen may be determined by various known methods to those skilled in the art.

In one embodiment, sequential replacement of the amino acids of the antigen sequence (using standard molecular biology techniques to mutate the DNA of the coding sequence, of the antigen), in this case hPD-L1 with Alanine (a.k.a Alanine scan), or another unrelated amino acid, may provide residues whose mutation would reduce or ablate the ability of the antibody to recognise the antigen in question. Binding may be assessed using standard techniques, such as, but not limited to, SPR, HTRF, ELISA (which are described elsewhere herein). Other substitutions could be made to enhance the disruption of binding such as changing the charge on the side chain of antigen sequence amino acids (e.g. Lysine change to glutamic acid), switching polar and non-polar residues (e.g. Serine change to leucine). The alanine scan or other amino substitution method may be carried out either with recombinant soluble antigen, or where the target is a cell membrane target, directly on cells using transient or stable expression of the mutated versions.

In one embodiment, protein crystallography may be used to determine contact residues between antibody and antigen (i.e. to determine the epitope to which the antibody binds), crystallography allows the direct visualisation of contact residues involved in the antibody-antigen interaction. As well as standard X-ray crystallography, cryo-electro microscopy has been used to determine contact residues between antibodies and HIV capsid protein (see Lee, Jeong Hyun, et al. "Antibodies to a conformational epitope on gp41 neutralize HIV-1 by destabilizing the Env spike.", Nature communications, 6, (2015)).

In one embodiment, if the antibody recognises a linear epitope, short peptides based on the antigen sequence can be produced and binding of the antibody to these peptides can be assessed using standard techniques, such as, but not limited to, SPR, HTRF, ELISA (which are described elsewhere herein). Further investigation of the epitope could be provided by performing an Alanine scan on any peptides that show binding. Alternative to linear peptides, conformational scans could be carried out using Pepscan technology (http://www.pepscan.com/) using their chemical linkage of peptides onto scaffolds, which has been used to determine discontinuous epitopes on CD20 targeting antibodies (Niederfellner, Gerhard, et al. "Epitope characterization and crystal structure of GA101 provide insights into the molecular basis for type I/II distinction of CD20 antibodies.", Blood, 118.2, (2011), 358-367.).

In one embodiment, limited proteolytic digestion and mass spectrophotometry can be used to identify binding epitopes. The antibody-antigen complex is digested by a protease, such as, but not limited to, trypsin. The digested complex peptides are compared to antibody-alone and antigen-alone digestion mass spectrophotometry to determine if a particular epitope is protected by the complexation. Further work involving amino acid substitution, competition binding, may then be employed to narrow down to individual amino acid residues involved in the interaction (see, for example, Suckau, Detlev, et al. "Molecular epitope identification by limited proteolysis of an immobilized antigen-antibody complex and mass spectrometric peptide mapping.", Proceedings of the National Academy of Sciences, 87.24, (1990), 9848-9852).

Thus, in one embodiment, the contact residues of the epitope are identified with an unrelated amino acid scan (e.g. alanine scan). In another embodiment, an unrelated amino acid scan (e.g. alanine scan) is carried out using a technique selected from SPR, HTRF, ELISA, X-ray crystallography, cryo-electro microscopy and a combination of limited proteolytic digestion and mass spectrometry. In one embodiment, the unrelated amino acid scan (e.g. alanine scan) is carried out using HTRF. In one embodiment, the unrelated amino acid scan (e.g. alanine scan) is carried out using ELISA.

When the alanine scan is carried out with either ELISA or HTRF, an amino acid residue is identified as contributing to the epitope if the reduction in signal is at least 25%. In one embodiment, the reduction in signal is at least 30%. In one embodiment, the reduction in signal is at least 35%. In one embodiment, the reduction in signal is at least 40%. In one embodiment, the reduction in signal is at least 45%. In one embodiment, the reduction in signal is at least 50%. In one embodiment, the reduction in signal is at least 55%. In one embodiment, the reduction in signal is at least 60%. In one embodiment, the reduction in signal is at least 70%. In one embodiment, the reduction in signal is at least 75%. In one embodiment, the reduction in signal is at least 80%. In one embodiment, the reduction in signal is at least 85%. In one embodiment, the reduction in signal is at least 90%.

When the alanine scan is carried out with SPR, an amino acid residue is identified as contributing to the epitope if there is at least a 10-fold reduction in affinity. In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

Concept 14. The antibody or fragment according to concept 13, wherein the epitope is identified by unrelated amino acid scanning, or by X-ray crystallography.

Concept 15. The antibody or fragment according to concept 14, wherein the contact residues of the epitope are defined by a reduction in affinity of at least 10-fold in an unrelated amino acid scan, e.g. an alanine scan as determined by SPR.

In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

SPR may be carried out as described hereinabove.

Concept 16. An antibody or fragment thereof which competes for binding to hPD-L1 with the antibody 1D05.

Competition may be determined by surface plasmon resonance (SPR), such techniques being readily apparent to the skilled person. SPR may be carried out using Biacore™, Proteon™ or another standard SPR technique. Such competition may be due, for example, to the antibodies or fragments binding to identical or overlapping epitopes of hPD-L1. In one embodiment, competition is determined by ELISA, such techniques being readily apparent to the skilled person. In one embodiment, competition is determined by homogenous time resolved fluorescence (HTRF), such techniques being readily apparent to the skilled person. In one embodiment, competition is determined by fluorescence activated cell sorting (FACS), such techniques being readily apparent to the skilled person. In one embodiment, competition is determined by ForteBio Octet® Bio-Layer Interferometry (BLI) such techniques being readily apparent to the skilled person.

In one embodiment, the antibody or fragment competes (e.g. in a dose-dependent manner) with hPD-1 (or a fusion protein thereof) for binding to cell surface-expressed hPD-L1. In one embodiment, the antibody or fragment competes (e.g. in a dose-dependent manner) with hPD-1 (or a fusion protein thereof) for binding to soluble hPDL-1.

In one embodiment, the antibody or fragment partially or completely inhibits binding of PD-1 and/or CD80 to cell surface-expressed PD-L1, such as hPD-L1. In another embodiment, the antibody or fragment partially or completely inhibits binding of hPD-1 and/or CD80 to soluble hPD-L1. In some embodiments, the antibody or fragment partially or completely increases the secretion of IFNγ, CD25 and IL-2 from a cell having cell surface-expressed PD-1. In one embodiment, the antibody or fragment partially or completely inhibits binding of CD80 to soluble hPD-L1, but does not show any detectable inhibition of the binding of PD-1 to cell surface-expressed PD-L1. In one embodiment, the antibody or fragment partially or completely inhibits binding of CD80 to soluble hPD-L1, but does not show any detectable inhibition of the binding of PD-1 to soluble PD-L1.

As used herein, "inhibits", "inhibition", "inhibiting" and the like, as used herein refers to the ability of an antagonist (e.g. an antibody or fragment thereof) to bind to an epitope which either partially or completely prevents the binding of the receptor (e.g. CD80 or PD-1) to the ligand (e.g. PD-L1). If the epitope to which the antagonist binds completely blocks the binding site of the ligand, then ligand binding is completely prevented (which may be a physical blocking—in the case of overlapping epitopes—or steric blocking—where the antagonist is large such that it prevents the ligand binding to its distinct epitope), and the ligand is not removed from circulation. The concentration of circulating ligand may therefore appear to be increased. If the epitope to which the antagonist binds partially blocks the binding site of the ligand, the ligand may be able to bind, but only weakly (in the case of partial inhibition), or in a different orientation to the natural binding interaction. In this case, some of the ligand may be removed from circulation, but not as much as when the ligand binding site is completely free and available for binding. Inhibition thus refers to the physical interaction of ligand arid receptor. Inhibition can be measured by HTRF, which is described in more detail elsewhere herein and in Mathis (1995) Clinical Chemistry 41(9), 1391-1397. Inhibition can also be measured by flow cytometry, where receptor is expressed on cells, or by ELISA, where receptor is adsorbed onto plates.

Concept 16a. An antibody or fragment thereof which competes for binding to hPD-L1 with the antibody 84G09.
Concept 16b. An antibody or fragment thereof which competes for binding to hPD-L1 with the antibody 411B08.
Concept 16c. An antibody or fragment thereof which competes for binding to hPD-L1 with the antibody 411C04.
Concept 16d. An antibody or fragment thereof which competes for binding to hPD-L1 with the antibody 411D07.
Concept 16e. An antibody or fragment thereof which competes for binding to hPD-L1 with the antibody 385F01.
Concept 16f. An antibody or fragment thereof which competes for binding to hPD-L1 with the antibody 386H03.
Concept 16g. An antibody or fragment thereof which competes for binding to hPD-L1 with the antibody 389A03.
Concept 16h. An antibody or fragment thereof which competes for binding to hPD-L1 with the antibody 413D08.
Concept 16i. An antibody or fragment thereof which competes for binding to hPD-L1 with the antibody 413G05.
Concept 16j. An antibody or fragment thereof which competes for binding to hPD-L1 with the antibody 413F09.
Concept 16k. An antibody or fragment thereof which competes for binding to hPD-L1 with the antibody 414B06.
Concept 16l. An antibody or fragment thereof which competes for binding to hPD-L1 with the antibody 416E01.

The antibodies have the sequences as described hereinabove.

Concept 17. The antibody or fragment according to any one of concepts 10 to 16, wherein the $V_H$ domain comprises the CDRH3 sequence of SEQ ID NO:29 or 32, or the CDRH3 sequence of SEQ ID NO:29 or 32 comprising 6 or fewer amino acid substitutions.

Concept 17a: An antibody or a fragment thereof according to any one of concepts 10 to 16 (but when dependent on concept 13, it is dependent on concept 13a, and when dependent on concept 16, it is dependent on concept 16a), wherein the $V_H$ domain comprises the CDRH3 sequence of SEQ ID NO:9 or 12, or the CDRH3 sequence of SEQ ID NO:9 or 12 comprising 6 or fewer amino acid substitutions.

Concept 17b: An antibody or a fragment thereof according to any one of concepts 10 to 16 (but when dependent on concept 13, it is dependent on concept 13b, and when dependent on concept 16, it is dependent on concept 16b), wherein the $V_H$ domain comprises the CDRH3 sequence of SEQ ID NO:54 or 57, or the CDRH3 sequence of SEQ ID NO:54 or 57 comprising 6 or fewer amino acid substitutions.

Concept 17c: An antibody or a fragment thereof according to any one of concepts 10 to 16 (but when dependent on concept 13, it is dependent on concept 13c, and when dependent on concept 16, it is dependent on concept 16c), wherein the a $V_H$ domain comprises the CDRH3 sequence of SEQ ID NO:74 or 77, or the CDRH3 sequence of SEQ ID NO:74 or 77 comprising 6 or fewer amino acid substitutions.

Concept 17d: An antibody or a fragment thereof according to any one of concepts 10 to 16 (but when dependent on concept 13, it is dependent on concept 13d, and when dependent on concept 16, it is dependent on concept 16d), wherein the V$_H$ domain comprises the CDRH3 sequence of SEQ ID NO:94 or 97, or the CDRH3 sequence of SEQ ID NO:94 or 97 comprising 3 or fewer amino acid substitutions.

Concept 17e: An antibody or a fragment thereof according to any one of concepts 10 to 16 (but when dependent on concept 13, it is dependent on concept 13e, and when dependent on concept 16, it is dependent on concept 16e), wherein the V$_H$ domain comprises the CDRH3 sequence of SEQ ID NO:114 or 117, or the CDRH3 sequence of SEQ ID NO:114 or 117 comprising 6 or fewer amino acid substitutions.

Concept 17f: An antibody or a fragment thereof according to any one of concepts 10 to 16 (but when dependent on concept 13, it is dependent on concept 13f, and when dependent on concept 16, it is dependent on concept 16f), wherein the V$_H$ domain comprises the CDRH3 sequence of SEQ ID NO:144 or 147, or the CDRH3 sequence of SEQ ID NO:144 or 147 comprising 3 or fewer amino acid substitutions.

Concept 17g: An antibody or a fragment thereof according to any one of concepts 10 to 16 (but when dependent on concept 13, it is dependent on concept 13g, and when dependent on concept 16, it is dependent on concept 16g), wherein the V$_H$ domain comprises the CDRH3 sequence of SEQ ID NO:174 or 177, or the CDRH3 sequence of SEQ ID NO:174 or 177 comprising 6 or fewer amino acid substitutions.

Concept 17h: An antibody or a fragment thereof according to any one of concepts 10 to 16 (but when dependent on concept 13, it is dependent on concept 13h, and when dependent on concept 16, it is dependent on concept 16h), wherein the V$_H$ domain comprises the CDRH3 sequence of SEQ ID NO:134 or 137, or the CDRH3 sequence of SEQ ID NO:134 or 137 comprising 5 or fewer amino acid substitutions.

Concept 17i: An antibody or a fragment thereof according to any one of concepts 10 to 16 (but when dependent on concept 13, it is dependent on concept 13i, and when dependent on concept 16, it is dependent on concept 16i), wherein the V$_H$ domain comprises the CDRH3 sequence of SEQ ID NO:240 or 243, or the CDRH3 sequence of SEQ ID NO:240 or 243 comprising 6 or fewer amino acid substitutions.

Concept 17j: An antibody or a fragment thereof according to any one of concepts 10 to 16 (but when dependent on concept 13, it is dependent on concept 13j, and when dependent on concept 16, it is dependent on concept 16j), wherein the a V$_H$ domain comprises the CDRH3 sequence of SEQ ID NO:260 or 263, or the CDRH3 sequence of SEQ ID NO:260 or 263 comprising 6 or fewer amino acid substitutions.

Concept 17k: An antibody or a fragment thereof according to any one of concepts 10 to 16 (but when dependent on concept 13, it is dependent on concept 13k, and when dependent on concept 16, it is dependent on concept 16k), wherein the V$_H$ domain comprises the CDRH3 sequence of SEQ ID NO:280 or 283, or the CDRH3 sequence of SEQ ID NO:280 or 283 comprising 6 or fewer amino acid substitutions.

Concept 17l: An antibody or a fragment thereof according to any one of concepts 10 to 16 (but when dependent on concept 13, it is dependent on concept 13l, and when dependent on concept 16, it is dependent on concept 16l), wherein the V$_H$ domain comprises the CDRH3 sequence of SEQ ID NO:345 or 348, or the CDRH3 sequence of SEQ ID NO:345 or 348 comprising 6 or fewer amino acid substitutions.

Concept 18. The antibody or fragment according to any preceding concept, wherein the V$_H$ domain comprises the CDRH1 sequence of SEQ ID NO:27 or 30 or the CDRH1 sequence of SEQ ID NO:27 or 30 comprising 3, 2 or 1 amino acid substitution(s).

Concept. 18a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, and when dependent on concept 17, it is dependent on concept 17a), wherein the V$_H$ domain comprises the CDRH1 sequence of SEQ ID NO:7 or 10, or the CDRH1 sequence of SEQ ID NO:7 or 10 comprising 3, 2 or 1 amino acid substitution(s).

Concept 18b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, and when dependent on concept 17, it is dependent on concept 17b), wherein the V$_H$ domain comprises the CDRH1 sequence of SEQ ID NO:52 or 55, or the CDRH1 sequence of SEQ ID NO:52 or 55 comprising 3, 2 or 1 amino acid substitution(s).

Concept 18c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, and when dependent on concept 17, it is dependent on concept 17c), wherein the V$_H$ domain comprises the CDRH1 sequence of SEQ ID NO:72 or 75, or the CDRH1 sequence of SEQ ID NO:72 or 75 comprising 3, 2 or 1 amino acid substitution(s).

Concept 18d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, and when dependent on concept 17, it is dependent on concept 17d), wherein the V$_H$ domain comprises the CDRH1 sequence of SEQ ID NO:92 or 95, or the CDRH1 sequence of SEQ ID NO:92 or 95 comprising 3, 2 or 1 amino acid substitution(s).

Concept 18e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, and when dependent on concept 17, it is dependent on concept 17e), wherein the V$_H$ domain comprises the CDRH1 sequence of SEQ ID NO:112 or 115, or the CDRH1 sequence of SEQ ID NO:112 or 115 comprising 3, 2 or 1 amino acid substitution(s).

Concept 18f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, and when dependent on concept 17, it is dependent on concept 17f), wherein the V$_H$ domain comprises the CDRH1 sequence of SEQ ID NO:142 or 145, or the CDRH1 sequence of SEQ ID NO:142 or 145 comprising 3, 2 or 1 amino acid substitution(s).

Concept 18g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, and when dependent on concept 17, it is dependent on concept 17g), wherein the $V_H$ domain comprises the CDRH1 sequence of SEQ ID NO:172 or 175, or the CDRH1 sequence of SEQ ID NO:172 or 175 comprising 3, 2 or 1 amino acid substitution(s).

Concept 18h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, and when dependent on concept 17, it is dependent on concept 17h), wherein the $V_H$ domain comprises the CDRH1 sequence of SEQ ID NO:132 or 135, or the CDRH1 sequence of SEQ ID NO:132 or 135 comprising 3, 2 or 1 amino acid substitution(s).

Concept 18i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, and when dependent on concept 17, it is dependent on concept 17i), wherein the $V_H$ domain comprises the CDRH1 sequence of SEQ ID NO:238 or 241, or the CDRH1 sequence of SEQ ID NO:238 or 241 comprising 3, 2 or 1 amino acid substitution(s).

Concept 18j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, and when dependent on concept 17, it is dependent on concept 17j), wherein the $V_H$ domain comprises the CDRH1 sequence of SEQ ID NO:258 or 261, or the CDRH1 sequence of SEQ ID NO:258 or 261 comprising 3, 2 or 1 amino acid substitution(s).

Concept 18k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, and when dependent on concept 17, it is dependent on concept 17k), wherein the $V_H$ domain comprises the CDRH1 sequence of SEQ ID NO: 278 or 281, or the CDRH1 sequence of SEQ ID NO: 278 or 281 comprising 3, 2 or 1 amino acid substitution(s).

Concept 18l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, and when dependent on concept 17, it is dependent on concept 17l), wherein the $V_H$ domain comprises the CDRH1 sequence of SEQ ID NO: 343 or 346, or the CDRH1 sequence of SEQ ID NO: 343 or 346 comprising 3, 2 or 1 amino acid substitution(s).

Concept 19. The antibody or fragment according to any preceding concept, wherein the $V_H$ domain comprises the CDRH2 sequence of SEQ ID NO:28 or 31, or the CDRH2 sequence of SEQ ID NO:28 or 31 comprising 4 or fewer amino acid substitutions.

Concept 19a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, and when dependent on concept 18, it is dependent on concept 18a), wherein the $V_H$ domain comprises the CDRH2 sequence of SEQ ID NO:8 or 11, or the CDRH2 sequence of SEQ ID NO:8 or 11 comprising 4 or fewer amino acid substitutions.

Concept 19b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, and when dependent on concept 18, it is dependent on concept 18b), wherein the $V_H$ domain comprises the CDRH2 sequence of SEQ ID NO:53 or 56, or the CDRH2 sequence of SEQ ID NO:53 or 56 comprising 3, 2 or 1 amino acid substitution(s).

Concept 19c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, and when dependent on concept 18, it is dependent on concept 18c), wherein the $V_H$ domain comprises the CDRH2 sequence of SEQ ID NO:73 or 76, or the CDRH2 sequence of SEQ ID NO:73 or 76 comprising 3, 2 or 1 amino acid substitution(s).

Concept 19d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, and when dependent on concept 18, it is dependent on concept 18d), wherein the $V_H$ domain comprises the CDRH2 sequence of SEQ ID NO:93 or 96, or the CDRH2 sequence of SEQ ID NO:93 or 96 comprising 3, 2 or 1 amino acid substitution(s).

Concept 19e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, and when dependent on concept 18, it is dependent on concept 18e), wherein the $V_H$ domain comprises the CDRH2 sequence of SEQ ID NO:113 or 116, or the CDRH2 sequence of SEQ ID NO:113 or 116 comprising 3, 2 or 1 amino acid substitution(s).

Concept 19f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, and when dependent on concept 18, it is dependent on concept 18f), wherein the V$_H$ domain comprises the CDRH2 sequence of SEQ ID NO:143 or 146, or the CDRH2 sequence of SEQ ID NO:143 or 146 comprising 3, 2 or 1 amino acid substitution(s).

Concept 19g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, and when dependent on concept 18, it is dependent on concept 18g), wherein the V$_H$ domain comprises the CDRH2 sequence of SEQ ID NO:173 or 176, or the CDRH2 sequence of SEQ ID NO:173 or 176 comprising 3, 2 or 1 amino acid substitution(s).

Concept 19h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, and when dependent on concept 18, it is dependent on concept 18h), wherein the V$_H$ domain comprises the CDRH2 sequence of SEQ ID NO:133 or 136, or the CDRH2 sequence of SEQ ID NO:133 or 136 comprising 3, 2 or 1 amino acid substitution(s).

Concept 19i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, and when dependent on concept 18, it is dependent on concept 18i), wherein the V$_H$ domain comprises the CDRH2 sequence of SEQ ID NO:239 or 242, or the CDRH2 sequence of SEQ ID NO:239 or 242 comprising 3, 2 or 1 amino acid substitution(s).

Concept 19j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, and when dependent on concept 18, it is dependent on concept 18j), wherein the V$_H$ domain comprises the CDRH2 sequence of SEQ ID NO:259 or 262, or the CDRH2 sequence of SEQ ID NO:259 or 262 comprising 3, 2 or 1 amino acid substitution(s).

Concept 19k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, and when dependent on concept 18, it is dependent on concept 18k), wherein the V$_H$ domain comprises the CDRH2 sequence of SEQ ID NO:279 or 282, or the CDRH2 sequence of SEQ ID NO:279 or 282 comprising 3, 2 or 1 amino acid substitution(s).

Concept 19l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, when dependent on concept 17, it is dependent on concept 17l, and when dependent on concept 18, it is dependent on concept 18l), wherein the V$_H$ domain comprises the CDRH2 sequence of SEQ ID NO:344 or 347, or the CDRH2 sequence of SEQ ID NO:344 or 347 comprising 3, 2 or 1 amino acid substitution(s).

Concept 20. The antibody or fragment according to any preceding concept, wherein the V$_H$ domain comprises an amino acid sequence of SEQ ID NO:33, or a heavy chain variable domain amino acid sequence that is at least 80% (e.g. at least 85%, or at least 90%) identical to SEQ ID NO:33.

Concept 20a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, and when dependent on concept 19, it is dependent on concept 19a), wherein the V$_H$ domain comprises an amino acid sequence of SEQ ID NO:13, or a heavy chain variable domain amino acid sequence that is at least 80% (e.g. at least 85%, or at least 90%) identical to SEQ ID NO:13.

Concept 20b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept. 17b, when dependent on concept 18, it is dependent on concept 18b, and when dependent on concept 19, it is dependent on concept 19b), wherein the V$_H$ domain comprises an amino acid sequence of SEQ ID NO:58, or a heavy chain variable domain amino acid sequence that is at least 80% (e.g. at least 85%, or at least 90%) identical to SEQ ID NO:58.

Concept 20c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, and when dependent on concept 19, it is dependent on concept 19c), wherein the V$_H$ domain comprises an amino acid sequence of SEQ ID NO:78, or a heavy chain variable domain amino acid sequence that is at least 80% (e.g. at least 85%, or at least 90%) identical to SEQ ID NO:78.

Concept 20d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, and when dependent on concept 19, it is dependent on concept 19d), wherein the V$_H$ domain comprises an amino acid sequence of SEQ ID NO:98, or a heavy chain variable domain amino acid sequence that is at least 80% (e.g. at least 85%, or at least 90%) identical to SEQ ID NO:98.

Concept 20e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, and when dependent on concept 19, it is dependent on concept 19e), wherein the $V_H$ domain comprises an amino acid sequence of SEQ ID NO:118, or a heavy chain variable domain amino acid sequence that is at least 80% (e.g. at least 85%, or at least 90%) identical to SEQ ID NO:118.

Concept 20f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, and when dependent on concept 19, it is dependent on concept 19f), wherein the $V_H$ domain comprises an amino acid sequence of SEQ ID NO:158, or a heavy chain variable domain amino acid sequence that is at least 80% (e.g. at least 85%, or at least 90%) identical to SEQ ID NO:158.

Concept 20g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, and when dependent on concept 19, it is dependent on concept 19g), wherein the $V_H$ domain comprises an amino acid sequence of SEQ ID NO:178, or a heavy chain variable domain amino acid sequence that is at least 80% (e.g. at least 85%, or at least 90%) identical to SEQ ID NO:178.

Concept 20h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, and when dependent on concept 19, it is dependent on concept 19h), wherein the $V_H$ domain comprises an amino acid sequence of SEQ ID NO:138, or a heavy chain variable domain amino acid sequence that is at least 80% (e.g. at least 85%, or at least 90%) identical to SEQ ID NO:138.

Concept 20i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, and when dependent on concept 19, it is dependent on concept 19i), wherein the $V_H$ domain comprises an amino acid sequence of SEQ ID NO:244, or a heavy chain variable domain amino acid sequence that is at least 80% (e.g. at least 85%, or at least 90%) identical to SEQ ID NO:244.

Concept 20j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, and when dependent on concept 19, it is dependent on concept 19j), wherein the $V_H$ domain comprises an amino acid sequence of SEQ ID NO:264, or a heavy chain variable domain amino acid sequence that is at least 80% (e.g. at least 85%, or at least 90%) identical to SEQ ID NO:264.

Concept 20k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, and when dependent on concept 19, it is dependent on concept 19k), wherein the $V_H$ domain comprises an amino acid sequence of SEQ ID NO:284, or a heavy chain variable domain amino acid sequence that is at least 80% (e.g. at least 85%, or at least 90%) identical to SEQ ID NO:284.

Concept 20l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, when dependent on concept 17, it is dependent on concept 17l, when dependent on concept 18, it is dependent on concept 18l, and when dependent on concept 19, it is dependent on concept 19l), wherein the $V_H$ domain comprises an amino acid sequence of SEQ ID NO:349, or a heavy chain variable domain amino acid sequence that is at least 80% (e.g. at least 85%, or at least 90%) identical to SEQ ID NO:349.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 21. The antibody or fragment according to any preceding concept comprising first and second copies of said $V_H$ domain.

Concept 22. The antibody or fragment according to any preceding concept, comprising a $V_L$ domain which comprises the CDRL1 sequence of SEQ ID NO:37 or 40, or the CRDL1 sequence of SEQ ID NO:37 or 40 comprising 3 or fewer amino acid substitutions.

Concept 22a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, and when dependent on concept 20, it is dependent on concept 20a), comprising a $V_L$ domain, which comprises the CDRL1 sequence of SEQ ID NO:17 or 20, or the CDRL1 sequence of SEQ ID NO:17 or 20 comprising 3 or fewer amino acid substitutions.

Concept 22b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, and when dependent on concept 20, it is dependent on concept 20b), comprising a $V_L$ domain which comprises the CDRL1 sequence of SEQ ID NO:62 or 65, or the CDRL1 sequence of SEQ ID NO:62 or 65 comprising 3 or fewer amino acid substitutions.

Concept 22c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it independent on concept 19c, and when dependent on concept 20, it is dependent on concept 20c), comprising a $V_L$ domain which comprises the CDRL1 sequence of SEQ ID NO:82 or 85, or the CDRL1 sequence of SEQ ID NO:82 or 85 comprising 2 or 1 amino acid substitution(s).

Concept 22d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, and when dependent on concept 20, it is dependent on concept 20d), comprising a $V_L$ domain which comprises the CDRL1 sequence of SEQ ID NO:102 or 105, or the CDRL1 sequence of SEQ ID NO:102 or 105 comprising 5 or fewer amino acid substitutions.

Concept 22e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, and when dependent on concept 20, it is dependent on concept 20e), comprising a $V_L$ domain which comprises the CDRL1 sequence of SEQ ID NO:122 or 125, or the CDRL1 sequence of SEQ ID NO:122 or 125 comprising 2 or 1 amino acid substitution(s).

Concept 22f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, and when dependent on concept 20, it is dependent on concept 20f), comprising a $V_L$ domain which comprises the CDRL1 sequence of SEQ ID NO:162 or 165, or the CDRL1 sequence of SEQ ID NO:162 or 165 comprising 5 or fewer amino acid substitutions.

Concept 22g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, and when dependent on concept 20, it is dependent on concept 20g), comprising a $V_L$ domain which comprises the CDRL1 sequence of SEQ ID NO:182 or 185, or the CDRL1 sequence of SEQ ID NO:182 or 185 comprising 5 or fewer amino acid substitutions.

Concept 22h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, and when dependent on concept 20, it is dependent on concept 20h), comprising a $V_L$ domain which comprises the CDRL1 sequence of SEQ ID NO:142 or 145, or the CDRL1 sequence of SEQ ID NO:142 or 145 comprising 2 or 1 amino acid substitution(s).

Concept 22i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, and when dependent on concept 20, it is dependent on concept 20i), comprising a $V_L$ domain which comprises the CDRL1 sequence of SEQ ID NO:248 or 251, or the CDRL1 sequence of SEQ ID NO:248 or 251 comprising 2 or 1 amino acid substitution(s).

Concept 22j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, and when dependent on concept 20, it is dependent on concept 20j), comprising a $V_L$ domain which comprises the CDRL1 sequence of SEQ ID NO:268 or 271, or the CDRL1 sequence of SEQ ID NO:268 or 271 comprising 2 or 1 amino acid substitution(s).

Concept 22k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, and when dependent on concept 20, it is dependent on concept 20k), comprising a $V_L$ domain which comprises the CDRL1 sequence of SEQ ID NO:288 or 291, or the CDRL1 sequence of SEQ ID NO:288 or 291 comprising 2 or 1 amino acid substitution(s).

Concept 22l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, when dependent on concept 17, it is dependent on concept 17l, when dependent on concept 18, it is dependent on concept 18l, when dependent on concept 19, it is dependent on concept 19l, and when dependent on concept 20, it is dependent on concept 20l), comprising a $V_L$ domain which comprises the CDRL1 sequence of SEQ ID NO:353 or 356, or the CDRL1 sequence of SEQ ID NO:353 or 356 comprising 2 or 1 amino acid substitution(s).

Concept 23. The antibody or fragment according to any preceding concept, comprising a or said $V_L$ domain, which $V_L$ domain comprises the CDRL2 sequence of SEQ ID NO:38 or 41, or the CRDL2 sequence of SEQ ID NO:38 or 41 comprising 2 or 1 amino acid substitution(s), for example a CDRL2 sequence of Seq ID No:50.

Concept 23a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, when dependent on concept 20, it is dependent on concept 20a, and when dependent on concept 22, it is dependent on concept 22a), comprising a or said $V_L$ domain, which $V_L$ domain comprises the CDRL2 sequence of SEQ ID NO:18 or 21, or the CDRL2 sequence of SEQ ID NO:18 or 21 comprising 2 or 1 amino acid substitution(s).

Concept 23b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, when dependent on concept 20, it is dependent on concept 20b, and when dependent on concept 22, it is dependent on concept 22b), comprising a or said $V_L$ domain, which $V_L$ domain comprises the CDRL2 sequence of SEQ ID NO:63 or 66, or the CDRL2 sequence of SEQ ID NO:63 or 66 comprising one amino acid substitution.

Concept 23c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, when dependent on concept 20, it is dependent on concept 20c, and when dependent on concept 22, it is dependent on concept 22c), comprising a or said $V_L$ domain, which $V_L$ domain comprises the CDRL2 sequence of SEQ ID NO:83 or 86, or the CDRL2 sequence of SEQ ID NO:83 or 86 comprising one amino acid substitution.

Concept 23d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, when dependent on concept 20, it is dependent on concept 20d, and when dependent on concept 22, it is dependent on concept 22d), comprising a or said $V_L$ domain, which $V_L$ domain comprises the CDRL2 sequence of SEQ ID NO:103 or 106, or the CDRL2 sequence of SEQ ID NO:103 or 1.06 comprising one amino acid substitution.

Concept 23e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, when dependent on concept 20, it is dependent on concept 20e, and when dependent on concept 22, it is dependent on concept 22e), comprising a or said $V_L$ domain, which $V_L$ domain comprises the CDRL2 sequence of SEQ ID NO:123 or 126, or the CDRL2 sequence of SEQ ID NO:123 or 126 comprising one amino acid substitution.

Concept 23f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, when dependent on concept 20, it is dependent on concept 20f, and when dependent on concept 22, it is dependent on concept 22o, comprising a or said $V_L$ domain, which $V_L$ domain comprises the CDRL2 sequence of SEQ ID NO:153 or 156, or the CDRL2 sequence of SEQ ID NO:153 or 156 comprising one amino acid substitution.

Concept 23g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, when dependent on concept 20, it is dependent on concept 20g, and when dependent on concept 22, it is dependent on concept 22g), comprising a or said $V_L$ domain, which $V_L$ domain comprises the CDRL2 sequence of SEQ ID NO:183 or 186, or the CDRL2 sequence of SEQ ID NO:183 or 186 comprising one amino acid substitution.

Concept 23h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, when dependent on concept 20, it is dependent on concept 20h, and when dependent on concept 22, it is dependent on concept 22h), comprising a or said $V_L$ domain, which $V_L$ domain comprises the CDRL2 sequence of SEQ ID NO:143 or 146, or the CDRL2 sequence of SEQ ID NO:143 or 146 comprising one amino acid substitution.

Concept 23i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, when dependent on concept 20, it is dependent on concept 20i, and when dependent on concept 22, it is dependent on concept 22i), comprising a or said $V_L$ domain, which $V_L$ domain comprises the CDRL2 sequence of SEQ ID NO:249 or 252, or the CDRL2 sequence of SEQ ID NO:249 or 252 comprising one amino acid substitution.

Concept 23j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, when dependent on concept 20, it is dependent on concept 20j, and when dependent on concept 22, it is dependent on concept 22j), comprising a or said $V_L$ domain, which $V_L$ domain comprises the CDRL2 sequence of SEQ ID NO:269 or 272, or the CDRL2 sequence of SEQ ID NO:269 or 272 comprising one amino acid substitution.

Concept 23k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, when dependent on concept 20, it is dependent on concept 20k, and when dependent on concept 22, it is dependent on concept 22k), comprising a or said $V_L$ domain, which $V_L$ domain comprises the CDRL2 sequence of SEQ ID NO:289 or 292, or the CDRL2 sequence of SEQ ID NO:289 or 292 comprising one amino acid substitution.

Concept 23l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, when dependent on concept 17, it is dependent on concept 17l, when dependent on concept 18, it is dependent on concept 18l, when dependent on concept 19, it is dependent on concept 19l, when dependent on concept 20, it is dependent on concept 20l, and when dependent on concept 22, it is dependent on concept 22l), comprising a or said $V_L$ domain, which $V_L$ domain comprises the CDRL2 sequence of SEQ ID NO:354 or 357, or the CDRL2 sequence of SEQ ID NO:354 or 357 comprising one amino acid substitution.

Concept 24. The antibody or fragment according to any preceding concept, comprising a or said $V_L$ domain, which $V_L$ domain comprises the CDRL3 sequence of SEQ ID NO:39 or 42, or the CRDL3 sequence of SEQ ID NO:39 or 42 comprising 4 or fewer amino acid substitutions.

Concept 24a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, when dependent on concept 20, it is dependent on concept 20a, when dependent on concept 22, it is dependent on concept 22a, and when dependent on concept 23, it is dependent on concept 23a), comprising a or said $V_L$ domain, which $V_L$ domain comprises the CDRL3 sequence of SEQ ID NO:19 or 22, or the CDRL3 sequence of SEQ ID NO: 19 or 22 comprising 4 or fewer amino acid substitutions.

Concept 24b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, when dependent on concept 20, it is dependent on concept 20b, when dependent on concept 22, it is dependent on concept 22b, and when dependent on concept 23, it is dependent on concept 23b), comprising a or said $V_L$ domain, which $V_L$ domain comprises the CDRL3 sequence of SEQ ID NO:64 or 67, or the CDRL3 sequence of SEQ ID NO:64 or 67 comprising 4 or fewer amino acid substitutions.

Concept 24c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, when dependent on concept 20, it is dependent on concept 20c, when dependent on concept 22, it is dependent on concept 22c, and when dependent on concept 23, it is dependent on concept 23c), comprising a or said $V_L$ domain, which $V_L$ domain comprises the CDRL3 sequence of SEQ ID NO:84 or 87, or the CDRL3 sequence of SEQ ID NO:84 or 87 comprising 4 or fewer amino acid substitutions.

Concept 24d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, when dependent on concept 20, it is dependent on concept 20d, when dependent on concept 22, it is dependent on concept 22d, and when dependent on concept 23, it is dependent on concept 23d), comprising a or said $V_L$ domain, which $V_L$ domain comprises the CDRL3 sequence of SEQ ID NO:104 or 107, or the CDRL3 sequence of SEQ ID NO:104 or 107 comprising 4 or fewer amino acid substitutions.

Concept 24e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, when dependent on concept 20, it is dependent on concept 20e, when dependent on concept 22, it is dependent on concept 22e, and when dependent on concept 23, it is dependent on concept 23e), comprising a or said $V_L$ domain, which $V_L$ domain comprises the CDRL3 sequence of SEQ ID NO:124 or 127, or the CDRL3 sequence of SEQ ID NO:124 or 127 comprising 4 or fewer amino acid substitutions.

Concept 24f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, when dependent on concept 20, it is dependent on concept 20f, when dependent on concept 22, it is dependent on concept 22f, and when dependent on concept 23, it is dependent on concept 23f), comprising a or said $V_L$ domain, which $V_L$ domain comprises the CDRL3 sequence of SEQ ID NO:164 or 167, or the CDRL3 sequence of SEQ ID NO:164 or 167 comprising 4 or fewer amino acid substitutions.

Concept 24g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, when dependent on concept 20, it is dependent on concept 20g, when dependent on concept 22, it is dependent on concept 22g, and when dependent on concept 23, it is dependent on concept 23g), comprising a or said $V_L$ domain, which $V_L$ domain comprises the CDRL3 sequence of SEQ ID NO:184 or 187, or the CDRL3 sequence of SEQ ID NO:184 or 187 comprising 4 or fewer amino acid substitutions.

Concept 24h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, when dependent on concept 20, it is dependent on concept 20h, when dependent on concept 22, it is dependent on concept 22h, and when dependent on concept 23, it is dependent on concept 23h), comprising a or said $V_L$ domain, which $V_L$ domain comprises the CDRL3 sequence of SEQ ID NO:144 or 147, or the CDRL3 sequence of SEQ ID NO:144 or 147 comprising 4 or fewer amino acid substitutions.

Concept 24i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, when dependent on concept 20, it is dependent on concept 20i, when dependent on concept 22, it is dependent on concept 22i, and when dependent on concept 23, it is dependent on concept 23i), comprising a or said $V_L$ domain, which $V_L$ domain comprises the CDRL3 sequence of SEQ ID NO:250 or 253, or the CDRL3 sequence of SEQ ID NO:250 or 253 comprising 4 or fewer amino acid substitutions.

Concept 24j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, when dependent on concept 20, it is dependent on concept 20j, when dependent on concept 22, it is dependent on concept 22j, and when dependent on concept 23, it is dependent on concept 23j), comprising a or said $V_L$ domain, which $V_L$ domain comprises the CDRL3 sequence of SEQ ID NO:270 or 273, or the CDRL3 sequence of SEQ ID NO:270 or 273 comprising 4 or fewer amino acid substitutions.

Concept 24k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, when dependent on concept 20, it is dependent on concept 20k, when dependent on concept 22, it is dependent on concept 22k, and when dependent on concept 23, it is dependent on concept 23k), comprising a or said $V_L$ domain, which $V_L$ domain comprises the CDRL3 sequence of SEQ ID NO:290 or 293, or the CDRL3 sequence of SEQ ID NO:290 or 293 comprising 4 or fewer amino acid substitutions.

Concept 24l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, when dependent on concept 17, it is dependent on concept 17l, when dependent on concept 18, it is dependent on concept 18l, when dependent on concept 19, it is dependent on concept 19l, when dependent on concept 20, it is dependent on concept 20l, when dependent on concept 22, it is dependent on concept 22l, and when dependent on concept 23, it is dependent on concept 23l), comprising, a or said $V_L$ domain, which $V_L$ domain comprises the CDRL3 sequence of SEQ ID NO:355 or 358, or the CDRL3 sequence of SEQ ID NO:355 or 358 comprising 4 or fewer amino acid substitutions.

Concept 25. The antibody or fragment according to any preceding concept, comprising a or said $V_L$ domain, which $V_L$ domain comprises an amino acid sequence of SEQ ID NO:43, or a light chain variable domain amino acid sequence that is at least 80% (e.g. at least 85%, or at least 90%) identical to SEQ ID NO:43 (for example the $V_L$ domain sequence in the light chain sequence of Seq ID No:50, 51 or 298).

Concept 25a: An antibody or a fragment thereof according to any preceding concept (but when dependent on concept 9, it is dependent on concept 9a, when dependent on concept 13, it is dependent on concept 13a, when dependent on concept 16, it is dependent on concept 16a, when dependent on concept 17, it is dependent on concept 17a, when dependent on concept 18, it is dependent on concept 18a, when dependent on concept 19, it is dependent on concept 19a, when dependent on concept 20, it is dependent on concept 20a, when dependent on concept 22, it is dependent on concept 22a, when dependent on concept 23, it is dependent on concept 23a, and when dependent on concept 24, it is dependent on concept 24a), wherein the $V_L$ domain comprises an amino acid sequence of SEQ ID NO:23, or a light chain variable domain amino acid sequence that is at least 80% (e.g. at least 85%, or at least 90%) identical to SEQ ID NO:23.

Concept 25b: An antibody or a fragment thereof according to any preceding concept (but when dependent on concept 9, it is dependent on concept 9b, when dependent on concept 13, it is dependent on concept 13b, when dependent on concept 16, it is dependent on concept 16b, when dependent on concept 17, it is dependent on concept 17b, when dependent on concept 18, it is dependent on concept 18b, when dependent on concept 19, it is dependent on concept 19b, when dependent on concept 20, it is dependent on concept 20b, when dependent on concept 22, it is dependent on concept 22a, when dependent on concept 23, it is dependent on concept 23b, and when dependent on concept 24, it is dependent on concept 24b), wherein the $V_L$ domain comprises an amino acid sequence of SEQ ID NO:68, or a light chain variable domain amino acid sequence that is at least 80% (e.g. at least 85%, or at least 90%) identical to SEQ ID NO:68.

Concept 25c: An antibody or a fragment thereof according to any preceding concept (but when dependent on concept 9, it is dependent on concept 9c, when dependent on concept 13, it is dependent on concept 13c, when dependent on concept 16, it is dependent on concept 16c, when dependent on concept 17, it is dependent on concept 17c, when dependent on concept 18, it is dependent on concept 18c, when dependent on concept 19, it is dependent on concept 19c, when dependent on concept 20, it is dependent on concept 20c, when dependent on concept 22, it is dependent on concept 22c, when dependent on concept 23, it is dependent on concept 23c, and when dependent on concept 24, it is dependent on concept 24c), wherein the $V_L$ domain comprises an amino acid sequence of SEQ ID NO:88, or a light chain variable domain amino acid sequence that is at least 80% (e.g. at least 85%, or at least 90%) identical to SEQ ID NO:88.

Concept 25d: An antibody or a fragment thereof according to any preceding concept (but when dependent on concept 9, it is dependent on concept 9d, when dependent on concept 13, it is dependent on concept 13d, when dependent on concept 16, it is dependent on concept 16d, when dependent on concept 17, it is dependent on concept 17d, when dependent on concept 18, it is dependent on concept 18d, when dependent on concept 19, it is dependent on concept 19d, when dependent on concept 20, it is dependent on concept 20d, when dependent on concept 22, it is dependent on concept 22d, when dependent on concept 23, it is dependent on concept 23d, and when dependent on concept 24, it is dependent on concept 24d), wherein the $V_L$ domain comprises an amino acid sequence of SEQ ID NO:108, or a light chain variable domain amino acid sequence that is at least 80% (e.g. at least 85%, or at least 90%) identical to SEQ ID NO:108.

Concept 25e: An antibody or a fragment thereof according to any preceding concept (but when dependent on concept 9, it is dependent on concept 9e, when dependent on concept 13, it is dependent on concept 13e, when dependent on concept 16, it is dependent on concept 16e, when dependent on concept 17, it is dependent on concept 17e, when dependent on concept 18, it is dependent on concept 18e, when dependent on concept 19, it is dependent on concept 19e, when dependent on concept 20, it is dependent on concept 20e, when dependent on concept 22, it is dependent on concept 22e, when dependent on concept 23, it is dependent on concept 23e, and when dependent on concept 24, it is dependent on concept 24e), wherein the $V_L$ domain comprises an amino acid sequence of SEQ ID NO:128, or a light chain variable domain amino acid sequence that is at least 80% (e.g. at least 85%, or at least 90%) identical to SEQ ID NO:128.

Concept 25f: An antibody or a fragment thereof according to any preceding concept (but when dependent on concept 9, it is dependent on concept 9f, when dependent on concept 13, it is dependent on concept 13f, when dependent on concept 16, it is dependent on concept 16f, when dependent on concept 17, it is dependent on concept 17f, when dependent on concept 18, it is dependent on concept 18f, when dependent on concept 19, it is dependent on concept 19f, when dependent on concept 20, it is dependent on concept 20f, when dependent on concept 22, it is dependent on concept 22f, when dependent on concept 23, it is dependent on concept 23f, and when dependent on concept 24, it is dependent on concept 24o, wherein the $V_L$ domain comprises an amino acid sequence of SEQ ID NO:168, or a light chain variable domain amino acid sequence that is at least 80% (e.g. at least 85%, or at least 90%) identical to SEQ ID NO:168.

Concept 25g: An antibody or a fragment thereof according to any preceding concept (but when dependent on concept 9, it is dependent on concept 9g, when dependent on concept 13, it is dependent on concept 13g, when dependent on concept 16, it is dependent on concept 16g, when dependent on concept 17, it is dependent on concept 17g, when dependent on concept 18, it is dependent on concept 18g, when dependent on concept 19, it is dependent on concept 19g, when dependent on concept 20, it is dependent on concept 20g, when dependent on concept 22, it is dependent on concept 22g, when dependent on concept 23, it is dependent on concept 23g, and when dependent on concept 24, it is dependent on concept 24g), wherein the $V_L$ domain comprises an amino acid sequence of SEQ ID NO:188, or a light chain variable domain amino acid sequence that is at least 80% (e.g. at least 85%, or at least 90%) identical to SEQ ID NO:188.

Concept 25h: An antibody or a fragment thereof according to any preceding concept (but when dependent on concept 9, it is dependent on concept 9h, when dependent on concept 13, it is dependent on concept 13h, when dependent on concept 16, it is dependent on concept 16h, when dependent on concept 17, it is dependent on concept 17h, when dependent on concept 18, it is dependent on concept 18h, when dependent on concept 19, it is dependent on concept 19h, when dependent on concept 20, it is dependent on concept 20h, when dependent on concept 22, it is dependent on concept 22h, when dependent on concept 23, it is dependent on concept 23h, and when dependent on concept 24, it is dependent on concept 24h), wherein the $V_L$ domain comprises an amino acid sequence of SEQ ID NO:148, or a light chain variable domain amino acid sequence that is at least 80% (e.g. at least 85%, or at least 90%) identical to SEQ ID NO:148.

Concept 25i: An antibody or a fragment thereof according to any preceding concept (but when dependent on concept 9, it is dependent on concept 9i, when dependent on concept 13, it is dependent on concept 13i, when dependent on concept 16, it is dependent on concept 16i, when dependent on concept 17, it is dependent on concept 17i, when dependent on concept 18, it is dependent on concept 18i, when dependent on concept 19, it is dependent on concept 19i, when dependent on concept 20, it is dependent on concept 20i, when dependent on concept 22, it is dependent on concept 22i, when dependent on concept 23, it is dependent on concept 23i, and when dependent on concept 24, it is dependent on concept 24i), wherein the $V_L$ domain comprises an amino acid sequence of SEQ ID NO:254, or a light chain variable domain amino acid sequence that is at least 80% (e.g. at least 85%, or at least 90%) identical to SEQ ID NO:254.

Concept 25j: An antibody or a fragment thereof according to any preceding concept (but when dependent on concept 9, it is dependent on concept 9j, when dependent on concept 13, it is dependent on concept 13j, when dependent on concept 16, it is dependent on concept 16j, when dependent on concept 17, it is dependent on concept 17j, when dependent on concept 18, it is dependent on concept 18j, when dependent on concept 19, it is dependent on concept 19j, when dependent on concept 20, it is dependent on concept 20j, when dependent on concept 22, it is dependent on concept 22j, when dependent on concept 23, it is dependent on concept 23j, and when dependent on concept 24, it is dependent on concept 24j), wherein the $V_L$ domain comprises an amino acid sequence of SEQ ID NO:274, or a light chain variable domain amino acid sequence that is at least 80% (e.g. at least 85%, or at least 90%) identical to SEQ ID NO:274.

Concept 25k: An antibody or a fragment thereof according to any preceding concept (but when dependent on concept 9, it is dependent on concept 9k, when dependent on concept 13, it is dependent on concept 13k, when dependent on concept 16, it is dependent on concept 16k, when dependent on concept 17, it is dependent on concept 17k, when dependent on concept 18, it is dependent on concept 18k, when dependent on concept 19, it is dependent on concept 19k, when dependent on concept 20, it is dependent on concept 20k, when dependent on concept 22, it is dependent on concept 22k, when dependent on concept 23, it is dependent on concept 23k, and when dependent on concept 24, it is dependent on concept 24k), wherein the $V_L$ domain comprises an amino acid sequence of SEQ ID NO:294, or a light chain variable domain amino acid sequence that is at least 80% (e.g. at least 85%, or at least 90%) identical to SEQ ID NO:294.

Concept 25l: An antibody or a fragment thereof according to any preceding concept (but when dependent on concept 9, it is dependent on concept 9l, when dependent on concept 13, it is dependent on concept 13l, when dependent on concept 16, it is dependent on concept 16l, when dependent on concept 17, it is dependent on concept 17l, when dependent on concept 18, it is dependent on concept. 18l, when dependent on concept 19, it is dependent on concept 19l, when dependent on concept 20, it is dependent on concept 20l, when dependent on concept 22, it is dependent on concept 22l, when dependent on concept 23, it is dependent on concept 23l, and when dependent on concept 24, it is dependent on concept 24l), wherein the $V_L$ domain comprises an amino acid sequence of SEQ ID NO:359, or a light chain variable domain amino acid sequence that is at least 80% (e.g. at least 85%, or at least 90%) identical to SEQ ID NO:359.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 26. The antibody or fragment according to any one of concepts 12 to 21, comprising first and second copies of a or said $V_L$ domain.

Concept 27. The antibody or fragment according to any preceding concept which specifically binds to cynomolgus PD-L1 as defined by Seq ID No:2.

In one embodiment, the antibody or fragment binds to cynomolgus PD-L1 with an affinity of less than 1 nM (e.g. from 1 nM to 0.01 µM or from 1 nM to 0.1 µM, or from 1 nM to 1 µM). In one embodiment, the antibody or fragment binds to cynomolgus PD-L1 with an affinity of less than 10 nM (e.g. from 10 nM to 0.01 µM or from 10 nM to 0.1 µM, or from 10 nM to 1 µM). In one embodiment, the antibody or fragment binds to cynomolgus PD-L1 with an affinity of less than 0.1 nM (e.g. from 0.1 nM to 0.01 µM or from 0.1 nM to 0.1 µM, or from 0.1 nM to 1 µM). In one embodiment, the antibody or fragment binds to cynomolgus PD-L1 with an affinity of less than 0.01 nM (e.g. from 0.011 nM to 0.01 µM or from 0.01 nM to 0.1 µM).

In one embodiment, the antibody or fragment binds to cynomolgus PD-L1 with an affinity of within 2-fold of the affinity to hPD-L1. In one embodiment, the antibody or fragment binds to cynomolgus PD-L1 with an affinity of within 4-fold of the affinity to hPD-L1. In one embodiment, the antibody or fragment binds to cynomolgus PD-L1 with an affinity of within 5-fold of the affinity to hPD-L1. In one embodiment, the antibody or fragment binds to cynomolgus PD-L1 with an affinity of within 6-fold of the affinity to hPD-L1. In one embodiment, the antibody or fragment binds to cynomolgus PD-L1 with an affinity of within 8-fold of the affinity to hPD-L1. In one embodiment, the antibody or fragment binds to cynomolgus PD-L1 with an affinity of within 10-fold of the affinity to hPD-L1.

In one embodiment, the antibody or fragment does not detectably bind to cynomolgus PD-L1. In one embodiment, the antibody or fragment does not detectably bind to murine PD-L1.

In one embodiment, the antibody or fragment binds to murine PD-L1 with an affinity of less than 1 nM (e.g. from 1 nM to 0.01 µM or from 1 nM to 0.1 µM, or from 1 nM to 1 µM). In one embodiment, the antibody or fragment binds to murine PD-L1 with an affinity of less than 10 nM (e.g. from 10 nM to 0.01 µM or from 10 nM to 0.1 µM, or from 10 nM to 1 µM). In one embodiment, the antibody or fragment binds to murine PD-L1 with an affinity of less than 0.1 nM (e.g. from 0.1 nM to 0.01 µM or from 0.1 nM to 0.1 µM, or from 0.1 nM to 1 µM). In one embodiment, the antibody or fragment binds to murine PD-L1 with an affinity of less than 0.01 nM (e.g. from 0.011 nM to 0.01 µM or from 0.01 nM to 0.1 µM).

Concept 28. The antibody or fragment according to any preceding concept, wherein the antibody or fragment comprises a kappa light chain.

Kappa light chain constant region amino acid and nucleotide sequences can be found in Seq ID Nos:206 to 215.

In one embodiment, the light chain may be a lambda light chain. Lambda light chain constant region amino acid and nucleotide sequences can be found in Seq ID Nos:216 to 237 and Seq ID No:535, Seq ID No:536 and Seq ID No:538.

Concept 29. The antibody or fragment according to any one of concepts 9 to 28, wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Conservative substitutions may be as described above in concept 9.

Concept 30. The antibody or fragment according to any preceding concept, wherein the antibody or fragment comprises a constant region, such as a human constant region, for example an effector-null human constant region, e.g. an IgG4 constant region or an IgG1 constant region, optionally wherein the constant region is IgG4-PE (Seq ID No:199), or a disabled IgG1 as defined in Seq ID No:205.

In other embodiments, the antibody or fragment is any of the isotypes or constant regions as defined hereinabove. In one embodiment, the constant region is wild-type human IgG1 (Seq ID No:340). For example, the constant region is an effector-enabled IgG1 constant region, optionally having ADCC and/or CDC activity. In one embodiment, the constant region is engineered for enhanced ADCC and/or CDC and/or ADCP. In another embodiment, the constant region is engineered for enhanced effector function.

The IgG4 constant region may be any of the IgG4 constant region amino acid sequences, or encoded by any of the nucleic acid sequences of Seq ID Nos:192 to 203. A heavy chain constant region may be an IgG4 comprising both the Leu235Glu mutation and the Ser228Pro mutation. This "IgG4-PE" heavy chain constant region (Seq ID Nos: 198, encoded by Seq ID Nos:199, 200 and 201) is effector null.

An alternative effector null human constant region is a disabled IgG1 being an IgG1*01 allele comprising the L235A and/or G237A mutations (e.g. LAGA, Seq ID No:204, encoded by Seq ID No:205). In one embodiment, the antibodies or antibody fragments disclosed herein comprise an IgG1 heavy chain constant region, wherein the sequence contains alanine at position 235 and/or 237 (EU index numbering).

The antibody-dependent cell phagocytosis (ADCP) mechanism is discussed in Gül et al., "Antibody-Dependent Phagocytosis of Tumor Cells by Macrophages: A Potent Effector Mechanism of Monoclonal Antibody Therapy of Cancer", Cancer Res., 75(23), Dec. 1, 2015.

The potency of Fc-mediated effects may be enhanced by engineering the Fc domain by various established techniques. Such methods increase the affinity for certain Fc-receptors, thus creating potential diverse profiles of activation enhancement. This can be achieved by modification of one or several amino acid residues (e.g. as described in Lazar et al., 2006, Proc. Natl. Acad. Sci. U.S.A., March 14; 103(11):4005-10; the modifications disclosed therein are incorporated herein by reference). Human IgG1 constant regions containing specific mutations or altered glycosylation on residue Asn297 (e.g. N297Q, EU index numbering) have been shown to enhance binding to Fc receptors. In one embodiment, such mutations are one or more of the residues selected from 239, 332 and 330 for human IgG1 constant regions (or the equivalent positions in other IgG isotypes). In one embodiment, the antibody or fragment comprises a human IgG1 constant region having one or more mutations independently selected from N297Q, S239D, I332E and A330L (EU index numbering).

In another embodiment, the increase in affinity for Fc-receptors is achieved by altering the natural glycosylation profile of the Fc domain by, for example, generating under fucosylated or de-fucosylated variants (as described in Natsume et al., 2009, Drug Des. Devel. Ther., 3:7-16 or by Zhou Q., Biotechnol. Bioeng., 2008, Feb. 15, 99(3):652-65, the modifications described therein are incorporated herein by reference). Non-fucosylated antibodies harbour a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcγRIIIa binding capacity. For example, to increase ADCC, residues in the hinge region can be altered to increase binding to Fc-γRIII (see, for example, Shields et al., 2001, J. Biol. Chem., March 2; 276(9):6591-604; the modifications described therein are incorporated herein by reference). Thus, in one embodiment, the antibody or fragment comprises a human IgG heavy chain constant region that is a variant of a wild-type human IgG heavy chain constant region, wherein the variant human IgG heavy chain constant region binds to human Fcγ receptors selected from the group consisting of FcγRIIB and FcγRIIA with higher affinity than the wild type human IgG heavy chain constant region binds to the human Fcγ receptors. In one embodiment, the antibody or fragment comprises a human IgG heavy chain constant region that is a variant of a wild type human IgG heavy chain constant region, wherein the variant human IgG heavy chain constant region binds to human FcγRIIB with higher affinity than the wild type human IgG heavy chain constant region binds to human FcγRIIB. In one embodiment, the variant human IgG heavy chain constant region is a variant human IgG1, a variant human IgG2, or a variant human IgG4 heavy chain constant region. In one embodiment, the variant human IgG heavy chain constant region comprises one or more amino acid mutations selected from G236D, P238D, S239D, S267E, L328F, and L328E (EU index numbering system). In another embodiment, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F (EU index numbering system). In another embodiment, the variant human IgG heavy chain constant region further comprises one or more amino acid mutations that reduce the affinity of the IgG for human FcγRIIIA, human FcγRIIA, or human FcγRI. In one embodiments, the FcγRIIB is expressed on a cell selected from the group consisting of macrophages, monocytes, B-cells, dendritic cells, endothelial cells, and activated T-cells. In one embodiment, the variant human IgG heavy chain constant region comprises one or more of the following amino acid mutations G236A, S239D, F243L, T256A, K290A, R292P, S298A, Y300L, V305I, A330L, I332E, E333A, K334A, A339T, and P396L (EU index numbering system). In one embodiment, the variant human IgG heavy chain constant region comprises a set of amino acid mutations selected from the group consisting of: S239D; T256A; K290A; S298A; I332E; E333A; K334A; A339T; S239D and I332E; S239D, A330L, and I332E; S298A, E333A, and K334A; G236A, S239D, and I332E; and F243L, R292P, Y300L, V305I, and P396L (EU index numbering system).

In one embodiment, the variant human IgG heavy chain constant region comprises a S239D, A330L, or I332E amino acid mutations (EU index numbering system). In one embodiment, the variant human IgG heavy chain constant region comprises an S239D and I332E amino acid mutations (EU index numbering system). In one embodiment, the variant human IgG heavy chain constant region is a variant human IgG1 heavy chain constant region comprising the S239D and I332E amino acid mutations (EU index numbering system). In one embodiment, the antibody or fragment comprises an afucosylated Fc region. In another embodiment, the antibody or fragment thereof is defucosylated. In another embodiment, the antibody or fragment is under fucosylated.

In another embodiment, the antibodies and fragments disclosed herein may comprise a triple mutation (M252Y/S254T/T256E) which enhances binding to FcRn. See Dall et al., Immunol 2002; 169:5171-5180 for a discussion of mutations affection FcRn binding in table 2, the mutations described therein are incorporated herein by reference.

Equally, the enhancement of CDC may be achieved by amino acid changes that increase affinity for C1q, the first component of the classic complement activation cascade (see Idusogie et al., J. Immunol., 2001, 166:2571-2575; the modifications described are incorporated herein by reference). Another approach is to create a chimeric Fc domain created from human IgG1 and human IgG3 segments that exploit the higher affinity if IgG3 for C1q (Natsume et al., 2008, Cancer Res., 68: 3863-3872; the modifications are incorporated herein by reference). In another embodiment, the antibody or antibody fragments disclosed herein may comprise mutated amino acids at residues 329, 331 and/or 322 to alter the C1q binding and/or reduced or abolished CDC activity. In another embodiment, the antibodies or antibody fragments disclosed herein may contain Fc regions with modifications at residues 231 and 239, whereby the amino acids are replaced to alter the ability of the antibody to fix complement. In one embodiment, the antibody or fragment has a constant region comprising one or more mutations selected from E345K, E430G, R344D and D356R, in particular a double mutation comprising R344D and D356R (EU index numbering system).

An antibody may have a heavy chain constant region that binds one or more types of Fc receptor but does not induce cellular effector functions, i.e. which does not mediate ADCC, CDC or ADCP activity. Such a constant region may be unable to bind the particular Fc receptor(s) responsible for triggering ADCC, CDC or ADCP activity. An antibody may have a heavy chain constant region that does not bind Fcγ receptors. Thus, in one embodiment, the constant region may comprise a Leu235Glu mutation (EU index numbering system).

In another embodiment, the antibodies and fragments disclosed herein are modified to increase or decrease serum half-life. In one embodiment, one or more of the following mutations: T252L, T254S or T256F are introduced to increase biological half-life of the antibody. Biological half-life can also be increased by altering the heavy chain constant region $CH_1$ domain or CL region to contain a salvage receptor binding epitope taken from two loops of a $CH_2$ domain of an Fc region of an IgG, as described in U.S. Pat. Nos. 5,869,046 and 6,121,022, the modifications described therein are incorporated herein by reference. In another embodiment, the Fc hinge region of an antibody or antigen-binding fragment of the invention is mutated to decrease the biological half-life of the antibody or fragment. One or more amino acid mutations are introduced into the CH₂-CH₃ domain interface region of the Fc-hinge fragment such that the antibody or fragment has impaired Staphylococcyl protein A (SpA) binding relative to native Fc-hinge domain SpA binding. Other methods of increasing serum half-life are known to those skilled in the art. Thus, in one embodiment, the antibody or fragment is PEGylated. In another embodiment, the antibody or fragment is fused to an albumin-bidnig domain, e.g. an albumin binding single domain antibody (dAb). In another embodiment, the antibody or fragment is PASylated (i.e. genetic fusion of polypeptide sequences composed of PAS (XL-Protein GmbH) which forms uncharged random coil structures with large hydrodynamic volume). In another embodiment, the antibody or fragment is XTENylated®/rPEGylated (i.e. genetic fusion of non-exact repeat peptide sequence (Amunix, Versartis) to the therapeutic peptide). In another embodiment, the antibody or fragment is ELPylated (i.e. genetic fusion to ELP repeat sequence (PhaseBio)). These various half-life extending fusions are described in more detail in Strohl, BioDrugs (2015) 29:215-239, which fusions, e.g. in Tables 2 and 6, are incorporated herein by reference.

The antibody may have a modified constant region which increases stability. Thus, in one embodiment, the heavy chain constant region comprises a Ser228Pro mutation. In another embodiment, the antibodies and fragments disclosed herein comprise a heavy chain hinge region that has been modified to alter the number of cysteine residues. This modification can be used to facilitate assembly of the light and heavy chains or to increase or decrease the stability of the antibody.

Concept 31. The antibody or fragment according to concept 30, wherein the constant region is a murine constant region.

In other embodiments, the constant region may be of any non-human mammalian origin, e.g. rat, mouse, hamster, guinea pig, dog, cat, horse, chicken, llama, dromedary, etc. In one embodiment, the constant region is a rat constant region. In another embodiment, the constant region is a llama constant region. The murine constant region may be any of the isotypes or alleles described hereinabove.

Concept 32. The antibody or fragment according to concept 30 or concept 31, wherein the constant region has CDC and/or ADCC activity.

Concept 33. The antibody according to any preceding concept wherein the:
a) $V_H$ domain comprises an amino acid sequence of SEQ ID No:33 and the $V_L$ domain comprises an amino acid sequence of SEQ ID No:43;
b) $V_H$ domain comprises an amino acid sequence that is at least 85% identical to SEQ ID No:33, and the $V_L$ domain comprises an amino acid sequence that is at least 85% identical to SEQ ID No:43;
c) $V_H$ domain comprises an amino acid sequence of the $V_H$ domain of SEQ ID No:47 and the $V_L$ domain comprises an amino acid sequence of SEQ ID No:43;
d) $V_H$ domain comprises an amino acid sequence of the $V_H$ domain of SEQ ID No:48 and the $V_L$ domain comprises an amino acid sequence of SEQ ID No:43;
e) $V_H$ domain comprises an amino acid sequence of the $V_H$ domain of SEQ ID No:49 and the $V_L$ domain comprises an amino acid sequence of SEQ ID No:43;
f) $V_H$ domain comprises an amino acid sequence of the $V_H$ domain of SEQ ID No:342 and the $V_L$ domain comprises an amino acid sequence of SEQ ID No:43;
g) $V_H$ domain comprises an amino acid sequence of SEQ ID No:33 and the $V_L$ domain comprises an amino acid sequence of the $V_L$ domain of SEQ ID No:50;
h) $V_H$ domain comprises an amino acid sequence of the $V_H$ domain of SEQ ID No:47 and the $V_L$ domain comprises an amino acid sequence of the $V_L$ domain of SEQ ID No:50;
i) $V_H$ domain comprises an amino acid sequence of the $V_H$ domain of SEQ ID No:48 and the $V_L$ domain comprises an amino acid sequence of the $V_L$ domain of SEQ ID No:50;
j) $V_H$ domain comprises an amino acid sequence of the $V_H$ domain of SEQ ID No:49 and the $V_L$ domain comprises an amino acid sequence of the $V_L$ domain of SEQ ID No:50;
k) $V_H$ domain comprises an amino acid sequence of the $V_H$ domain of SEQ ID No:342 and the $V_L$ domain comprises an amino acid sequence of the $V_L$ domain of SEQ ID No:50;
l) $V_H$ domain comprises an amino acid sequence of SEQ ID No:33 and the $V_L$ domain comprises an amino acid sequence of the $V_L$ domain of SEQ ID No:51;
m) $V_H$ domain comprises an amino acid sequence of the $V_H$ domain of SEQ ID No:47 and the $V_L$ domain comprises an amino acid sequence of the $V_L$ domain of SEQ ID No:51;
n) $V_H$ domain comprises an amino acid sequence of the $V_H$ domain of SEQ ID No:48 and the $V_L$ domain comprises an amino acid sequence of the $V_L$ domain of SEQ ID No:51;
o) $V_H$ domain comprise an amino acid sequence of the $V_H$ domain of SEQ ID No:49 and the $V_L$ domain comprises an amino acid sequence of the $V_L$ domain of SEQ ID No:51;
p) $V_H$ domain comprise an amino acid sequence of the $V_H$ domain of SEQ ID No:342 and the $V_L$ domain comprises an amino acid sequence of the $V_L$ domain of SEQ ID No:51;
q) $V_H$ domain comprises an amino acid sequence of SEQ ID No:33 and the $V_L$ domain comprises an amino acid sequence of the $V_L$ domain of SEQ ID No:298;
r) $V_H$ domain comprises an amino acid sequence of the $V_H$ domain of SEQ ID No:47 and the $V_L$ domain comprises an amino acid sequence of the $V_L$ domain of SEQ ID No:298; domain comprises an amino acid sequence of the $V_H$ domain of SEQ ID No:48 and the $V_L$ domain comprises an amino acid sequence of the $V_L$ domain of SEQ ID No:298;
t) $V_H$ domain comprise an amino acid sequence of the $V_H$ domain of SEQ ID No:49 and the $V_L$ domain comprises an amino acid sequence of the $V_L$ domain of SEQ ID No:298;
u) $V_H$ domain comprise an amino acid sequence of the $V_H$ domain of SEQ ID No:342 and the $V_L$ domain comprises an amino acid sequence of the $V_L$ domain of SEQ ID No:298;
v) $V_H$ domain comprises an amino acid sequence of SEQ ID No:58 and the $V_L$ domain comprises an amino acid sequence of SEQ ID No:68;
w) $V_H$ domain comprises an amino acid sequence that is at least 85% identical to SEQ ID No:58, and the $V_L$ domain comprise an amino acid sequence that is at least 85% identical to SEQ ID No:68;

x) V_H domain comprises an amino acid sequence of SEQ ID No:78 and the V_L domain comprises an amino acid sequence of SEQ ID No:88;
y) V_H domain comprises an amino acid sequence that is at least 85% identical to SEQ ID No:78, and the V_L domain comprises an amino acid sequence that is at least 85% identical to SEQ ID No:88;
z) V_H domain comprises an amino acid sequence of SEQ ID No:98 and the V_L domain comprises an amino acid sequence of SEQ ID No:108;
aa) V_H domain comprises an amino acid sequence that is at least 85% identical to SEQ ID No:98, and the V_L domain comprises an amino acid sequence that is at least 85% identical to SEQ ID No:108;
bb) V_H domain comprises an amino acid sequence of SEQ ID No:118 and the V_L domain comprises an amino acid sequence of SEQ ID No:128;
cc) V_H domain comprises an amino acid sequence that is at least 85% identical to SEQ ID No:118, and the V_L domain comprises an amino acid sequence that is at least 85% identical to SEQ ID No:128;
dd) V_H domain comprises an amino acid sequence of SEQ ID No:158 and the V_L domain comprises an amino acid sequence of SEQ ID No:168;
ee) V_H domain comprises an amino acid sequence that is at least 85% identical to SEQ ID No:158, and the V_L domain comprises an amino acid sequence that is at least 85% identical to SEQ ID No:168;
ff) V_H domain comprises an amino acid sequence of SEQ ID No:178 and the V_L domain comprises an amino acid sequence of SEQ ID No:188;
gg) V_H domain comprises an amino acid sequence that is at least 85% identical to SEQ ID No:178, and the V_L domain comprises an amino acid sequence that is at least 85% identical to SEQ ID No:188;
hh) V_H domain comprises an amino acid sequence of SEQ ID No:138 and the V_L domain comprises an amino acid sequence of SEQ ID No:148;
ii) V_H domain comprises an amino acid sequence that is at least 85% identical to SEQ ID No:138 and the V_L domain comprises an amino acid sequence that is at least 85% identical to SEQ ID No:148;
jj) V_H domain comprises an amino acid sequence of SEQ ID No:244 and the V_L domain comprises an amino acid sequence of SEQ ID No:254;
kk) V_H domain comprises an amino acid sequence that is at least 85% identical to SEQ ID No:244, and the V_L domain comprises an amino acid sequence that is at least 85% identical to SEQ ID No:254;
ll) V_H domain comprises an amino acid sequence of SEQ ID No:264 and the V_L domain comprises an amino acid sequence of SEQ ID No:274;
mm) V_H domain comprises an amino acid sequence that is at least 85% identical to SEQ ID No:264, and the V_L domain comprises an amino acid sequence that is at least 85% identical to SEQ ID No:274;
nn) V_H domain comprises an amino acid sequence of SEQ ID No:284 and the V_L domain comprises an amino acid sequence of SEQ ID No:294; and
oo) V_H domain comprises an amino acid sequence that is at least 85% identical to SEQ ID No:284, and the V_L domain comprises an amino acid sequence that is at least 85% identical to SEQ ID No:294;
pp) V_H domain comprises an amino acid sequence of SEQ ID No:349 and the VL domain comprises an amino acid sequence of SEQ ID No:359; and
qq) V_H domain comprises an amino acid sequence that is at least 85% identical to SEQ ID No:349, and the V_L domain comprises an amino acid sequence that is at least 85% identical to SEQ ID No:359.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 34. The antibody according to any preceding concept wherein the antibody comprises a heavy chain and a light chain, and
  a) the heavy chain amino acid sequence comprises an amino acid sequence of SEQ ID No:35 and the light chain amino acid sequence comprises an amino acid sequence of SEQ ID No:45;
  b) the heavy chain amino acid sequence comprises an amino acid sequence that is at least 85% identical to SEQ ID No:35 and the light chain amino acid sequence comprises an amino acid sequence that is at least 85% identical to SEQ ID No:45;
  c) the heavy chain amino acid sequence comprises an amino acid sequence of SEQ ID No:47 and the light chain amino acid sequence comprises an amino acid sequence of SEQ ID No:45;
  d) the heavy chain amino acid sequence comprises an amino acid sequence of SEQ ID No:48 and the light chain amino acid sequence comprises an amino acid sequence of SEQ ID No:45;
  e) the heavy chain amino acid sequence comprises an amino acid sequence of SEQ ID No:49 and the light chain amino acid sequence comprises an amino acid sequence of SEQ ID No:45;
  f) the heavy chain amino acid sequence comprises an amino acid sequence of SEQ ID No:342 and the light chain amino acid sequence comprises an amino acid sequence of SEQ ID No:45;
  g) the heavy chain amino acid sequence comprises an amino acid sequence of SEQ ID No:35 and the light chain amino acid sequence comprises an amino acid sequence of SEQ ID No:50;
  h) the heavy chain amino acid sequence comprises an amino acid sequence of SEQ ID No:47 and the light chain amino acid sequence comprises an amino acid sequence of SEQ ID No:50;
  i) the heavy chain amino acid sequence comprises an amino acid sequence of SEQ ID No:48 and the light chain amino acid sequence comprises an amino acid sequence of SEQ ID No:50;
  j) the heavy chain amino acid sequence comprises an amino acid sequence of SEQ ID No:49 and the light chain amino acid sequence comprises an amino acid sequence of SEQ ID No:50;
  k) the heavy chain amino acid sequence comprises an amino acid sequence of SEQ ID No:342 and the light chain amino acid sequence comprises an amino acid sequence of SEQ ID No:50;

l) the heavy chain amino acid sequence comprises an amino acid sequence of SEQ ID No:35 and the light chain amino acid sequence comprises an amino acid sequence of SEQ ID No:51;
m) the heavy chain amino acid sequence comprises an amino acid sequence of SEQ ID No:47 and the light chain amino acid sequence comprises an amino acid sequence of SEQ ID No:51;
n) the heavy chain amino acid sequence comprises an amino acid sequence of SEQ ID No:48 and the light chain amino acid sequence comprises an amino acid sequence of SEQ ID No:51;
o) the heavy chain amino acid sequence comprises an amino acid sequence of SEQ ID No:49 and the light chain amino acid sequence comprises an amino acid sequence of SEQ ID No:51;
p) the heavy chain amino acid sequence comprises an amino acid sequence of SEQ ID No:342 and the light chain amino acid sequence comprises an amino acid sequence of SEQ ID No:51;
q) the heavy chain amino acid sequence comprises an amino acid sequence of SEQ ID No:35 and the light chain amino acid sequence comprises an amino acid sequence of SEQ ID No:298;
r) the heavy chain amino acid sequence comprises an amino acid sequence of SEQ ID No:47 and the light chain amino acid sequence comprises an amino acid sequence of SEQ ID No:298;
s) the heavy chain amino acid sequence comprises an amino acid sequence of SEQ ID No:48 and the light chain amino acid sequence comprises an amino acid sequence of SEQ ID No:298;
t) the heavy chain amino acid sequence comprises an amino acid sequence of SEQ ID No:49 and the light chain amino acid sequence comprises an amino acid sequence of SEQ ID No:298;
u) the heavy chain amino acid sequence comprises an amino acid sequence of SEQ ID No:342 and the light chain amino acid sequence comprises an amino add sequence of SEQ ID No:298;
v) the heavy chain amino acid sequence comprises an amino acid sequence of SEQ ID No:60 and the light chain amino acid sequence comprises an amino add sequence of SEQ ID No:70;
w) the heavy chain amino acid sequence comprises an amino acid sequence that is at least 85% identical to SEQ ID No:60, and the light chain amino acid sequence comprises an amino acid sequence that is at least 85% identical to SEQ ID No:70;
x) the heavy chain amino acid sequence comprises an amino acid sequence of SEQ ID No:80 and the light chain amino add sequence comprises an amino acid sequence of SEQ ID No:90;
y) the heavy chain amino acid sequence comprises an amino acid sequence that is at least 85% identical to SEQ ID No:80, and the light chain amino acid sequence comprises an amino acid sequence that is at least 85% identical to SEQ ID No:90;
z) the heavy chain amino acid sequence comprises an amino acid sequence of SEQ ID No:100 and the light chain amino acid sequence comprises an amino acid sequence of SEQ ID No:110;
aa) the heavy chain amino acid sequence comprises an amino acid sequence that is at least 85% identical to SEQ ID No:100, and the light chain amino acid sequence comprises an amino acid sequence that is at least 85% identical to SEQ ID No:110;
bb) the heavy chain amino acid sequence comprises an amino acid sequence of SEQ ID No:120 and the light chain amino acid sequence comprises an amino acid sequence of SEQ ID No:130;
cc) the heavy chain amino acid sequence comprises an amino acid sequence that is at least 85% identical to SEQ ID No:120, and the light chain amino acid sequence comprises an amino acid sequence that is at least 85% identical to SEQ ID No:130;
dd) the heavy chain amino acid sequence comprises an amino acid sequence of SEQ ID No:160 and the light chain amino acid sequence comprises an amino acid sequence of SEQ ID No:170;
ee) the heavy chain amino acid sequence comprises an amino acid sequence that is at least 85% identical to SEQ ID No:160, and the light chain amino acid sequence comprises an amino acid sequence that is at least 85% identical to SEQ ID No:170;
ff) the heavy chain amino acid sequence comprises an amino acid sequence of SEQ ID No:180 and the light chain amino acid sequence comprises an amino acid sequence of SEQ ID No:190;
gg) the heavy chain amino acid sequence comprises an amino acid sequence that is at least 85% identical to SEQ ID No:180, and the light chain amino acid sequence comprises an amino acid sequence that is at least 85% identical to SEQ ID No:190
hh) the heavy chain amino acid sequence comprises an amino acid sequence of SEQ ID No:140 and the light chain amino acid sequence comprises an amino acid sequence of SEQ ID No:150;
ii) the heavy chain amino acid sequence comprises an amino acid sequence that is at least 85% identical to SEQ ID No:140, and the light chain amino acid sequence comprises an amino acid sequence that is at least 85% identical to SEQ ID No:150;
jj) the heavy chain amino acid sequence comprises an amino acid sequence of SEQ ID No:246 and the light chain amino acid sequence comprises an amino acid sequence of SEQ ID No:256;
kk) the heavy chain amino acid sequence comprises an amino acid sequence that is at least 85% identical to SEQ ID No:246, and the light chain amino acid sequence comprises an amino acid sequence that is at least 85% identical to SEQ ID No:256;
ll) the heavy chain amino acid sequence comprises an amino acid sequence of SEQ ID No:266 and the light chain amino acid sequence comprises an amino acid sequence of SEQ ID No:276;
mm) the heavy chain amino acid sequence comprises an amino acid sequence that is at least 85% identical to SEQ ID No:266, and the light chain amino acid sequence comprises an amino acid sequence that is at least 85% identical to SEQ ID No:276;
nn) the heavy chain amino acid sequence comprises an amino acid sequence of SEQ ID No:286 and the light chain amino acid sequence comprises an amino acid sequence of SEQ ID No:296; and
oo) the heavy chain amino acid sequence comprises an amino acid sequence that is at least 85% identical to SEQ ID No:286, and the light chain amino acid sequence comprises an amino acid sequence that is at least 85% identical to SEQ ID No:296;
pp) the heavy chain amino acid sequence comprises an amino acid sequence of SEQ ID No:351 and the light chain amino acid sequence comprises an amino acid sequence of SEQ ID No:361; and qq) the heavy chain amino acid sequence comprises an amino acid sequence that is at least 85% identical to SEQ ID No:351, and the light chain amino acid sequence comprises an amino acid sequence that is at least 85% identical to SEQ ID No:361.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Concept 35. The antibody or fragment according to any preceding concept which competes for binding to hPD-L1 with the antibody 1D05, optionally wherein the competition for binding to hPD-L1 is conducted using SPR.

SPR may be carried out as described hereinabove, or as described in concept 16.

Concept 36. The antibody or fragment according to any preceding concept wherein the antibody or fragment is capable of inhibiting PD-L1-mediated suppression of T-cells, optionally wherein the suppression of T-cells is measured by an increase in one or more of IFNγ, IL-2, CD25 or proliferation of T-cells in an assay that provides co-stimulation by either direct CD3/CD28 stimulation, superantigen stimulation or provides co-stimulation by co-incubation with cells capable of inducing a T-cell response.

The measurements may be carried out with any suitable technique. For example, the measurements may be taken with ELISA, HTRF, BRDU incorporation (proliferation), electrochemiluminescence (ECL) or flow cytometry (e.g. FACS). These techniques are well-known to those skilled in the art and are described elsewhere herein. In one embodiment, the assay is flow cytometry. In one embodiment, the assay is ELISA. In one embodiment, the assay is HTRF.

In one embodiment, the suppression of T-cells is measured by an increase in IFNγ. In one embodiment, the suppression of T-cells is measured by an increase in IL-2. In one embodiment, the suppression of T-cells is measured by an increase in CD25. In one embodiment, the suppression of T-cells is measured by an increase in IFNγ and IL-2. In one embodiment, the suppression of T-cells is measured by an increase in IFNγ and CD25. In one embodiment, the suppression of T-cells is measured by an increase in CD25 and IL-2. In one embodiment, the suppression of T-cells is measured by an increase in IFNγ, IL-2 and CD25.

In one embodiment, the co-stimulation is provided by direct CD3/CD28 stimulation.

In one embodiment, the co-stimulation is provided by a superantigen, such as staphylococcal enterotoxin B (SEB).

In one embodiment, the assay provides co-stimulation by co-incubation with cells capable of inducing a T-cell response. Such cells may be antigen-presenting cells (APCs), for example monocytes, B-cells or dendritic cells. In one embodiment, the assay provides co-stimulation by co-incubation with APCs. In one embodiment, the assay provides co-stimulation by co-incubation with monocytes. In one embodiment, the assay provides co-stimulation by co-incubation with B-cells. In one embodiment, the assay provides co-stimulation by co-incubation with dendritic cells.

Concept 37. A bispecific antibody or fusion protein comprising an antibody or fragment thereof as defined in any preceding concept.

Concept 37a. A dual binding antibody or fusion protein comprising an antibody or fragment thereof as defined in any preceding concept.

A dual binding antibody has the meaning as set out above.

Concept 38. The bispecific antibody according to concept 37, wherein the bispecific format is selected from DVD-Ig, mAb$^2$, FIT-Ig, mAb-dAb, dock and lock, SEEDbody, scDiabody-Fc, diabody-Fc, tandem scFv-Fc, Fab-scFv-Fc, Fab-scFv, intrabody, BITE, diabody, DART, TandAb, scDiabody, scDiabody-CH$_3$, Diabody-CH$_3$, minibody, knobs-in-holes, knobs-in-holes with common light chain, knobs-in-holes with common light chain and charge pairs, charge pairs, charge pairs with common light chain, in particular mAb$^2$, knob-in-holes, knob-in-holes with common light chain, knobs-in-holes with common light chain and charge pairs and FIT-Ig, e.g. mAb$^2$ and FIT-Ig.

In one embodiment, the bispecific format is selected from DVD-Ig, mAb$^2$, FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH$_3$, Diabody-CH$_3$, Triple body, Miniantibody, minibody, TriBi minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig and zybody.

In one embodiment, the bispecific format is selected from DVD-Ig, FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH$_3$, Diabody-CH$_3$, Triple body, Miniantibody, minibody, TriBi minibody, scFv-CH$_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, FIT-Ig, mAb-dAb, dock and lock, SEEDbody, scDiabody-Fc, diabody-Fc, tandem scFv-Fc, Fab-scFv-Fc, Fab-scFv, intrabody, BITE, diabody, DART, TandAb, scDiabody, scDiabody-CH$_3$, Diabody-CH$_3$, minibody, knobs-in-holes, knobs-in-holes with common light chain, knobs-in-holes with common light chain and charge pairs, charge pairs, charge pairs with common light chain, in particular knob-in-holes, knob-in-holes with common light chain, knobs-in-holes with common light chain and charge pairs and FIT-Ig, e.g. FIT-Ig.

In one embodiment, the bispecific format is selected from DVD-Ig, mAb$^2$, mAb-dAb, dock and lock, Fab-arm exchange, SEEDbody, Triomab, LUZ-Y, Fcab, κλ-body, orthogonal Fab, scDiabody-Fc, diabody-Fc, tandem scFv- Fc, Fab-scFv-Fc, Fab-scFv, intrabody, BITE, diabody, DART, TandAb, scDiabody, scDiabody-CH₃, Diabody-CH₃, Triple body, Miniantibody, minibody, TriBi minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, mAb², mAb-dAb, dock and lock, SEEDbody, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH₃, minibody, knobs-in-holes, knobs-in-holes with common light chain, knobs-in-holes with common light chain and charge pairs, charge pairs, charge pairs with common light chain, in particular mAb², knob-in-holes, knobs-in-holes with common light chain and charge pairs, and knob-in-holes with common light chain, e.g. mAb².

In one embodiment, the bispecific format is selected from DVD-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH₃, Diabody-CH₃, Triple body, Miniantibody, minibody, TriBi minibody, scFv-CH₃ KIH, scFv-CH-CL-scFv, F(ab')₂-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody, for example DVD-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH₃, Diabody-CH₃, minibody, knobs-in-holes, knobs-in-holes with common light chain, knobs-in-holes with common light chain and charge pairs, charge pairs, charge pairs with common light chain, in particular knob-in-holes, knobs-in-holes with common light chain and charge pairs, and knob-in-holes with common light chain.

Concept 39. The bispecific antibody according to concept 37 or concept 38, wherein the bispecific antibody specifically binds to hPD-L1 and another target antigen selected from immune checkpoint inhibitors (such as PD-1, CTLA-4, TIGIT, TIM-3, LAG-3 and VISTA, e.g. TIGIT, TIM-3 and LAG-3), immune modulators (such as BTLA, hHVEM, CSF1R, CCR4, CD39, CD40, CD73, CD96, CXCR2, CXCR4, CD200, GARP, SIRPα, CXCL9, CXCL10, CXCL11 and CD155, e.g. GARP, SIRPα, CXCR4, BTLA, hVEM and CSF1R), immune activators (such as CD137, GITR, OX40, CD40, CXCR3 (e.g. agonistic anti-CXCR3 antibodies), CD27, CD3, ICOS (e.g. agonistic anti-ICOS antibodies), for example. ICOS, CD137, GITR and OX40).

Concept 39a. A bispecific antibody which binds to hPD-L1 with a $V_H$, a $V_L$, or a paired $V_H$ and $V_L$ comprising one or more of the CDRs (e.g. CDRH3 and CDRL3) or variable region sequences of any of the antibodies described in Aspect 1a hereinbelow, and another target antigen selected from immune checkpoint inhibitors (such as PD-1, CTLA-4, TIGIT, TIM-3, LAG-3 and VISTA, e.g. TIGIT, TIM-3 and LAG-3), immune modulators (such as BTLA, hHVEM, CSF1R, CCR4, CD39, CD40, CD73, CD96, CXCR2, CXCR4, CD200, GARP, SIRPα, CXCL9, CXCL10, CXCL11 and CD155, e.g. GARP, SIRPα, CXCR4, BTLA, hVEM and CSF1R), immune activators (such as CD137, GITR, OX40, CD40, CXCR3 (e.g. agonistic anti-CXCR3 antibodies), CD27, CD3, ICOS (e.g. agonistic anti-ICOS antibodies), for example. ICOS, CD137, GITR and OX40).

Concept 39b. The bispecific antibody according to concept 37 or concept 38, wherein the bispecific antibody specifically binds to hPD-L1 and another target antigen selected from immune checkpoint inhibitors (such as PD-1, CTLA-4, TIGIT, TIM-3, LAG-3 and VISTA, e.g. TIGIT, TIM-3 and LAG-3), immune modulators (such as BRA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R), immune activators (such as CD137, GITR, OX40, CD40, CXCR3 (e.g. agonistic anti-CXCR3 antibodies), CD3, ICOS (e.g. agonistic anti-ICOS antibodies), for example. ICOS, CD137, GITR and OX40).

In one embodiment, the another target antigen is an immune checkpoint inhibitor, such as PD-1, CTLA-4, TIGIT, TIM-3, LAG-3 and VISTA, e.g. TIGIT, CTLA-4, TIM-3 and LAG-3. In one embodiment, the another target antigen is an immune modulator, such as BILA, hHVEM, CSF1R, CCR4, CD39, CD40, CD73, CD96, CXCR2, CXCR4, CD200, GARP, SIRPα, CXCL9, CXCL10, CXCL11 and CD155, or such as such as BTLA, hHVEM, CSF1R, CCR4, CD39, CD40, CD73, CD96, CXCR2, CXCR4, CD200, GARP, SIRPα, CXCL9, CXCL10 and CD155 e.g. GARP, SIRPα, CXCR4, BTLA, hVEM and CSF1R. In one embodiment, the another target antigen is an immune activator, such as CD137, GITR, OX40, CD40, CXCR3 (e.g. agonistic anti-CXCR3 antibodies), CD27, CD3 and ICOS (e.g. agonistic anti-ICOS antibodies), or CD137, GITR, OX40, CD40, CXCR3 (e.g. agonistic anti-CXCR3 antibodies), CD3 and ICOS (e.g. agonistic anti-ICOS antibodies), for example ICOS, CD137, GITR and OX40). In one embodiment, the another target antigen is CTLA-4. In one embodiment, the another target antigen is TIGIT. In one embodiment, the another target antigen is TIM-3. In one embodiment, the another target antigen is LAG-3. In one embodiment, the another target antigen is GITR. In one embodiment, the another target antigen is VISTA. In one embodiment, the another target antigen is CD137. In one embodiment, the another target antigen is SIRPα. In one embodiment, the another target antigen is CXCL10. In one embodiment, the another target antigen is CD155. In one embodiment, the another target antigen is CD40.

In another embodiment, the bispecific antibody binds another target antigen which is PD-1 and the binding to PD-1 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CTLA4 and the binding to CTLA4 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is TIGIT and the binding to TIGIT is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is TIM-3 and the binding to TIM-3 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is LAG3 and the binding to LAG3 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is VISTA and the binding to VISTA is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is BTLA and the binding to BTLA is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is hHVEM and the binding to hHVEM is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CSF1R and the binding to CSF1R is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CCR4 and the binding to CCR4 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD39 and the binding to CD39 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD40 and the binding to CD40 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD73 and the binding to CD73 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD96 and the binding to CD96 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CXCR2 and the binding to CXCR2 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CXCR4 and the binding to CXCR4 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD200 and the binding to CD200 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is GARP and the binding to GARP is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is SIRPα and the binding to SIRPα is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CXCL9 and the binding to CXCL9 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CXCL10 and the binding to CXCL10 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CXCL11 and the binding to CXCL11 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD155 and the binding to CD155 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD137 and the binding to CD137 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is GITR and the binding to GITR is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is OX40 and the binding to OX40 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD40 and the binding to CD40 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CXCR3 and the binding to CXCR3 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD27 and the binding to CD27 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is CD3 and the binding to CD3 is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in Aspect 1A hereinbelow.

In another embodiment, the bispecific antibody binds another target antigen which is ICOS and the binding to ICOS is provided by an antigen-binding domain (for example, a $V_H$, a $V_L$ or a paired $V_H$ and $V_L$) having any of the sequences, including CDR sequences (for example CDRH3 and/or CDRL3) or variable region sequences as described in arrangement 5 and arrangement 5a hereinbelow, and any of the anti-ICOS antibodies described in sentences 1 to 102 and sentences 1a to 21a.

In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds GITR (optionally wherein the GITR Fab has a sequence—including CDRs and variable regions—as defined in Aspect 1a hereinbelow). In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds GITR (optionally wherein the GITR antibody has a sequence—including CDRs and variable regions—as defined in Aspect 1a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1a hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 to 31).

In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds ICOS (e.g. binds with agonistic activity and optionally wherein the ICOS Fab has a sequence—including CDRs and variable regions—as defined in arrangement 5, or in arrangement 5a, or in sentences 1 to 102, or in sentences 1a to 21a hereinbelow). In one embodiment, the ICOS Fab has a sequence of any of the ICOS antibodies described herein in sentences 1 to 102 or in sentences 1a to 21a) In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds ICOS (e.g. binds with agonistic activity or optionally wherein the ICOS antibody has a sequence—including CDRs and variable regions—as defined in arrangement 5, or in arrangement 5a, or in sentences 1 to 102, or in sentences 1a to 21a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1A hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 or 31).

In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds TIM-3 (optionally wherein the TIM-3 Fab has a sequence—including CDRs and variable regions—as defined in Aspect 1a hereinbelow). In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds TIM-3 (optionally wherein the TIM-3 antibody has a sequence—including CDRs and variable regions—as defined in Aspect 1a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1a hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 or 31).

In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds CD137 (optionally wherein the CD137 Fab has a sequence—including CDRs and variable regions—as defined in Aspect 1a hereinbelow). In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds CD137 (optionally wherein the CD137 antibody has a sequence—including CDRs and variable regions—as defined in Aspect 1a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1a hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 or 31).

In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds CD3 (optionally wherein the CD3 Fab has a sequence—including CDRs and variable regions—as defined in Aspect 1a hereinbelow). In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds CD3 (optionally wherein the CD3 antibody has a sequence—including CDRs and variable regions—as defined in Aspect 1a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1a hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 or 31).

Any of the targets listed above (and the Fabs and/or full antibodies described in more detail in Aspect 1A) may be applied to the FIT-Ig structure.

Concept 40. The bispecific antibody according to concept 39, wherein the another target antigen is TIGIT or LAG3.

In any of concepts 37 to 40, if the antibody or fragment thereof has the heavy and light variable region sequences of 84G09, then the bispecific antibody shall be interpreted as not including a $mAb^2$ format wherein the Fcab has binding affinity to LAG3.

In one embodiment, the bispecific antibody has a FIT-Ig format which comprises a full antibody (e.g. an antibody comprising a light chain comprising a $V_L$ and $C_L$ and a heavy chain comprising $V_H$, $C_H1$, $C_H2$ and $C_H3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds TIGIT (optionally wherein the TIGIT Fab has a sequence—including CDRs and variable regions—as defined in Aspect 1a hereinbelow). In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds TIGIT (optionally wherein the TIGIT antibody has a sequence—including CDRs and variable regions—as defined in Aspect 1a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1a hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 or 31).

In one embodiment, the bispecific antibody has a FIT-Ig format which comprises a full antibody (e.g. an antibody comprising a light chain comprising a $V_L$ and $C_L$ and a heavy chain comprising $V_H$, $C_H1$, $C_H2$ and $C_H3$) which binds hPD-L1 (optionally wherein the antibody has a structure as defined in any one of concepts 1 to 40, or wherein the antibody has a sequence—including CDRs and variable regions—as defined in Aspect 1a hereinbelow) and a Fab which binds LAG3 (optionally wherein the LAG3 Fab has a sequence—including CDRs and variable regions—as defined in Aspect 1a hereinbelow). In one embodiment, the bispecific antibody has a FIT-Ig format which comprises a full antibody (e.g. an antibody comprising a light chain comprising a $V_L$ and $C_L$ and a heavy chain comprising $V_H$, $CH_1$, $CH_2$ and $CH_3$) which binds LAG3 (optionally wherein the LAG3 antibody has a sequence—including CDRs and variable regions—as defined in Aspect 1a hereinbelow) and a Fab which binds hPD-L1 (optionally wherein the antibody has a structure as defined in any one of concepts 1 to 40, or wherein the antibody has a sequence—including CDRs and variable regions—as defined in Aspect 1a hereinbelow). In one embodiment, the FIT-Ig is effector-enabled (e.g. as described in any of concepts 30 to 32). In another embodiment, the FIT-Ig is effector-disabled (e.g. is an IgG4 format, or as described in any of concepts 30 or 31).

Concept 41. An antibody or fragment as defined in any preceding concept for use in treating or preventing a hPD-L1-mediated disease or condition, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma). (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

Concept 42. Use of an antibody or fragment as defined in any one of concepts 1 to 40 in the manufacture of a medicament for administration to a human for treating or preventing a hPD-L1 mediated disease or condition in the human, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

Concept 43. A method of treating or preventing a hPD-L1 mediated disease or condition, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas) in a human, comprising administering to said human a therapeutically effective amount of an antibody or fragment as defined in any one of concepts 1 to 40, wherein the hPD-L1 mediated disease or condition is thereby treated or prevented.

In any of concepts 41 to 43, the hPD-L1 mediated disease may be any of those as described herein. In one embodiment, in any of concepts 41 to 43, the hPD-L1 mediated disease is a virally induced cancer, such as cervical cancer and nasopharyngeal cancer, for example cervical cancers caused by HPV infection. In one embodiment, in any of concepts 41 to 43, the hPD-L1 mediated disease is a chronic viral infection. In one embodiment, in any of concepts 41 to 43, the hPD-L1 mediated disease is a neoplastic disease. In one embodiment, in any of concepts 41 to 43, the hPD-L1 mediated disease is a non-neoplastic disease. In one embodiment, in any of concepts 41 to 43, the hPD-L1 mediated disease is a malignant tumour. In one embodiment, in any of concepts 41 to 43, the hPD-L1 mediated disease is a cancer which is known to be responsive to PD-L1 therapy, such as melanoma, Merkel cell carcinoma, non-small cell lung cancer (squamous and non-squamous), renal cell cancer, bladder cancer, head and neck squamous cell carcinoma, mesothelioma. In one embodiment, in any of concepts 41 to 43, the hPD-L1 mediated disease is a cancer which is a soft tissue sarcoma.

Concept 44. The antibody or fragment according to concept 41, the use according to concept 42 or the method according to concept 43, wherein the hPD-L1-mediated disease or condition is cancer.

Concept 44a. The antibody or fragment according to concept 41, the use according to concept 42 or the method according to concept 43, wherein the hPD-L1-mediated disease or condition is a neurodegenerative disease, disorder or condition, optionally wherein the neurodegenerative disease, disorder or condition is selected from Alzheimer's disease, amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia, in particular Alzheimer's disease, amyotrophic lateral sclerosis, Parkinson's disease and Huntington's disease, and e.g. Alzheimer's disease.

In concept 44a, the therapeutically effective amount of an antibody or fragment may comprise an antigen-binding site that specifically binds PD-L1, e.g. hPD-L1.

In one embodiment, the antigen-binding site specifically binds PD-L1, e.g. hPD-L1. In one embodiment, the PD-L1 antigen-binding site comprises the CDRH1, CDRH2, CDR3, CDRL1, CDRL2 and CDRL3, or the $V_H$, or the $V_L$ or the $V_H$ and $V_L$ region from any one of the anti-PD-L1 antibodies selected from atezolizumab (Roche), avelumab (Merck), BMS-936559/MDX-1105 (BMS), durvalumab/Medi4736 (Medimmune), KN-035, CA-170, FAZ-053 M7824, ABBV-368, LY-3300054, GNS-1480, YW243.55. S70, REGN3504 and any of the PD-L1 antibodies disclosed in WO2017/034916, WO2017/020291, WO2017/020858, WO2017/020801, WO2016/111645, WO2016/197367, WO2016/061142, WO2016/149201, WO2016/000619, WO2016/160792, WO2016/022630, WO2016/007235, WO2015/179654, WO2015/173267, WO2015/181342, WO2015/109124, WO2015/112805, WO2015/061668, WO2014/159562, WO2014/165082, WO2014/100079, WO2014/055897, WO2013/181634, WO2013/173223, WO2013/079174, WO2012/145493, WO2011/066389, WO2010/077634, WO2010/036959, WO2010/089411 or WO2007/005874, which antibodies and sequences are incorporated herein by reference.

In another embodiment of concept 44a, the PD-L1 antigen-binding site comprises the CDRH1, CDRH2, CDR3, CDRL1, CDRL2 and CDRL3, or the $V_H$, or the $V_L$ or the $V_H$ and $V_L$ region from any one of the anti-PD-L1 antibodies selected from an anti-PD-L1 antibody disclosed herein, particularly the anti-PD-L1 antibody clones disclosed in concepts 16a through 16l, and more particularly anti-PD-L1 antibody clone 84G09.

In another embodiment of concept 44a, the PD-L1 antigen-binding site comprises the CDRH1, CDRH2, CDR3, CDRL1, CDRL2 and CDRL3, or the $V_H$, or the $V_L$ or the $V_H$ and $V_L$ region from anti-PD-L1 antibody clone 84G09 and the hPD-L1-mediated disease or condition is Alzheimer's disease.

Concept 45. The antibody or fragment, the use or the method according to concept 44, wherein the cancer is selected from melanoma, Merkel cell carcinoma, non-small cell lung cancer (squamous and non-squamous), renal cell cancer, bladder cancer, head and neck squamous cell carcinoma and mesothelioma or is selected from virally induced cancers (such as cervical cancer and nasopharyngeal cancer) and soft tissue sarcomas.

Concept 46. The antibody or fragment, use or the method according to any one of concepts 41 to 45, further comprising administering to the human a further therapy, for example a further therapeutic agent, optionally wherein the further therapeutic agent is independently selected from the group consisting of:
  a. other immune checkpoint inhibitors (such as anti-TIM-3 antibodies, anti-CTLA-4 antibodies, anti-TIGIT antibodies and anti-LAG-3 antibodies);
  b. immune stimulators (such as anti-OX40 antibodies, anti-GITR antibodies, anti-CD137 antibodies, anti-ICOS antibodies and anti-CD40 antibodies);
  c. chemokine receptor antagonists (such as CXCR4, CCR4 and CXCR2);
  d. targeted kinase inhibitors (such as CSF-1R or VEGFR inhibitors);
  e. angiogenesis inhibitors (such as anti-VEGF-A or Delta-like Ligand-4);
  f. immune stimulating peptides or chemokines (such as CXCL9 or CXCL10);
  g. cytokines (such as IL-15 and IL-21);
  h. bispecific T-cell engagers (BiTEs) having at least one specificity against CD3 (e.g. CD3/CD19 BiTE);
  i. other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
  j. oncolytic viruses (such as HSV virus (optionally which secretes GMCSF), Newcastle disease virus and Vaccinia virus);
  k. vaccination with tumour associated antigens (such as New York Esophageal Cancer-1 [NY-ESO-1], Melanoma Associated Antigen-3 [MAGE-3]);
  l. cell-based therapies (such as chimeric Antigen Receptor-T-cells (CAR-T) for example expressing anti-CD19, anti-EpCam or anti-mesothelin);
  m. bi-specific NK cell engagers having a specificity against an activating MK receptor such as NKG2D or CD16a; and
  n. adoptive transfer of tumour specific T-cells or LAK cells,
or optionally wherein the further therapy is chemotherapy, radiotherapy and surgical removal of tumours.

Radiotherapy may be single dose or in fractionated doses, either delivered to affected tissues directly or to the whole body.

Chemotherapeutic agents may any as described hereinabove, in particular, agents that induce immunogenic cell death, for example platinum therapies, such as oxalipiatin. In one embodiment, the chemotherapy is a standard of care cytotoxic chemotherapy for the cancer being treated.

In this aspect, the bispecific molecules include "bispecific antibodies" and antibody fusion proteins, including those formats and molecules described in concepts 37 to 40.

The antibodies may be any of the sequences or antibodies described in arrangement 5, 5a or detailed in Aspect 1a.

The further therapeutic agents of this concept may be delivered by any method, which methods are well-known to those skilled in the art. For example, the further therapeutic agents may be delivered orally, systemically or locally (to the tumour environment). In one embodiment, the further therapeutic agent is delivered orally. In one embodiment, the further therapeutic agent is delivered systemically (e.g. intravenously). In one embodiment, the further therapeutic agent is delivered locally to the tumour environment.

Compositions and routes of administration are described in more detail hereinbelow.

Concept 47. The antibody or fragment, use or the method according to concept 46, wherein the further therapeutic agent is administered sequentially or simultaneously with the anti-hPD-L1 antibody or fragment.

Concept 48. A pharmaceutical composition comprising an antibody of fragment as defined in any one of concepts 1 to 40 and a pharmaceutically acceptable excipient, diluent or carrier and optionally further comprising a further therapeutic agent independently selected from the group consisting of:
  a) other immune checkpoint inhibitors (such as anti-TIM-3 antibodies, anti-CTLA-4 antibodies, anti-TIGIT antibodies and anti-LAG-3 antibodies);
  b) immune stimulators (such as anti-OX40 antibodies, anti-GITR antibodies, anti-CD137 antibodies, anti-ICOS antibodies and anti-CD40 antibodies);
  c) chemokine receptor antagonists (such as CXCR4, CCR4 and CXCR2);
  d) targeted kinase inhibitors (such as CSF-1R or VEGFR inhibitors);
  e) angiogenesis inhibitors (such as anti-VEGF-A or Delta-like Ligand-4);
  f) immune stimulating peptides or chemokines (such as CXCL9 or CXCL10);
  g) cytokines (such as IL-15 and IL-21);
  h) bispecific T-cell engagers (BiTEs) having at least one specificity against CD3 (e.g. CD3/CD19 BiTE);
  i) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
  j) oncolytic viruses (such as HSV virus (optionally which secretes GMCSF), Newcastle disease virus and Vaccinia virus);
  k) vaccination with tumour associated antigens (such as New York Esophageal Cancer-1 [NY-ESO-1], Melanoma Associated Antigen-3 [MAGE-3]);
  l) cell-based therapies (such as chimeric Antigen Receptor-T-cells (CAR-T) for example expressing anti-CD19, anti-EpCam or anti-mesothelin);
  m) bi-specific NK cell engagers having a specificity against an activating MK receptor such as NKG2D or CD16a; and n) adoptive transfer of tumour specific T-cells or LAK cells.

Pharmaceutical formulations are well-known to those skilled in the art. In one embodiment, the antibody or fragment is administered intravenously. In one embodiment, the antibody or fragment is administered subcutaneously.

In an example, an antibody or fragment as disclosed herein is contained in a medical container, e.g. a vial, syringe, IV container or an injection device (such as an intraocular or intravitreal injection device). In an example, the antibody or fragment is in vitro, for example, in a sterile container.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In this aspect, the bispecific molecules include "bispecific antibodies" and antibody fusion proteins, including those formats and molecules described in concepts 37 to 40.

The further therapeutic agents of this concept may be delivered by any method, which methods are well-known to those skilled in the art. For example, the further therapeutic agents may be delivered orally, systemically or locally (to the tumour environment). In one embodiment, the further therapeutic agent is delivered orally. In one embodiment, the further therapeutic agent is delivered systemically (e.g. intravenously). In one embodiment, the further therapeutic agent is delivered locally to the tumour environment.

The antibodies may have any of the sequences or may be any of the antibodies described in arrangement 5, 5a or detailed in aspect 1a.

Concept 49. A pharmaceutical composition according to concept 48, or a kit comprising a pharmaceutical composition as defined in concept 48, wherein the composition is for treating and/or preventing a hPD-L1-mediated condition or disease, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma.

Concept 50. A pharmaceutical composition according to concept 48 or concept 49 in combination with, or kit according to concept 49 comprising, a label or instructions for use to treat and/or prevent said disease or condition in a human; optionally wherein the label or instructions comprise a marketing authorisation number (e.g. an FDA or EMA authorisation number); optionally wherein the kit comprises an IV or injection device that comprises the antibody or fragment.

Concept 51. A method of modulating PD-1/PD-L1 interaction in a patient, comprising administering an effective amount of an antibody or fragment as defined in any one of concepts 1 to 40 to said patient.

In another embodiment, there is provided a method of modulating CD80/PD-L1 interaction in a patient, comprising administering an effective amount of an antibody or fragment as defined in any one of concepts 1 to 40 to said patient. In another embodiment, the antibody or fragment modulates CD80/PD-L1 interaction, but does not modulate PD-1/PD-L1 interaction. In another embodiment, the antibody or fragment blocks CD80/PD-L1 interaction, but does not block PD-1/PD-L1 interaction. In another embodiment, the antibody or fragment inhibits CD80/PD-L1 interaction, but does not inhibit PD-1/PD-L1 interaction.

Concept 52. A method of inhibiting PD-L1 activity in a patient, comprising administering an effective amount of an antibody or fragment as defined in any one of concepts 1 to 40 to said patient.

In one embodiment, the antibody or fragment blocks or inhibits PD-1 binding to PD-L1. In one embodiment, the antibody or fragment blocks or inhibits CD80 binding to PD-L1.

Concept 53. A method of treating a proliferative disease in an animal (e.g. a human), comprising administering an effective amount of an antibody or fragment as defined in any one of concepts 1 to 40 to said patient.

Proliferative diseases may be any as described elsewhere herein.

Concept 54. A method of detecting PD-L1 expression in a sample, comprising contacting the sample with an antibody or fragment as defined in any one of concepts 1 to 40.

Concept 55. A method comprising contacting a biological sample with an antibody or fragment as defined in any one of concepts 1 to 40 to form a complex with PD-L1 present in the sample and measuring the presence, absence or level of the complex in the biological sample.

Concept 56. The method according to concept 55, wherein the presence, absence and/or level of PD-L1 expression is detected prior to treatment and a high level of surface expressed PD-L1 is indicative of successful treatment.

Concept 57. The method according to concept 55, wherein the presence, absence and/or level of PD-L1 expression is detected during treatment as an early response biomarker.

Concept 58. The method according to concept 55 or concept 57, wherein the presence, absence and/or level of PD-L1 expression is detected during or after treatment to help determine one or more of: whether treatment has been successful, whether treatment should continue, and/or whether treatment should be modified.

Concept 59. The method according to any one of concepts 55 to 58, wherein therapy comprises treatment with an anti-PD-L1 antibody, optionally as defined in any one of concepts 1 to 40.

Concept 60. A method for monitoring therapy efficacy, the method comprising detecting expression of surface expressed PD-L1 in a patient prior to therapy, and during or after therapy, wherein an antibody or fragment as defined in any one of concepts 1 to 40 is used to detect expression of surface expressed PD-L1.

Concept 61. The method according to concept 60, wherein surface expressed PD-L1 expression is detected in vivo.

Concept 62. The method according to concept 60, wherein surface expressed PD-L1 expression is detected in a tissue sample in vitro.

Concept 63. A method for identifying binding partners for PD-L1, the method comprising immunoprecipitating an intact protein complex comprising PD-L1 using an antibody or fragment as defined in any one of concepts 1 to 40.

Concept 64. A method of diagnosing a disease in a human subject associated with altered PD-L1 expression comprising the steps of contacting a biological sample from the human subject with an antibody as defined in concepts 1 to 40 to form a complex between the'antibody and PD-L1 present in the sample; and detecting the amount of the complex.

Concept 65. A nucleic acid that encodes the CDRH3 of an antibody or fragment as defined in any one of concepts 1 to 40.

Concept 65a. There is also provided a nucleic acid that encodes the CDRH2 of an antibody or fragment as defined in any one of concepts 1 to 40.

Concept 65b. There is also provided a nucleic acid that encodes the CDRH1 of an antibody or fragment as defined in any one of concepts 1 to 40.

Concept 65c. There is also provided a nucleic acid that encodes the CDRL1 of an antibody or fragment as defined in any one of concepts 1 to 40.

Concept 65d. There is also provided a nucleic acid that encodes the CDRL2 of an antibody or fragment as defined in any one of concepts 1 to 40.

Concept 65e. There is also provided a nucleic acid that encodes the CDRL3 of an antibody or fragment as defined in any one of concepts 1 to 40.

In one embodiment, the nucleic acid is an isolated and purified nucleic acid.

Concept 66. A nucleic acid that encodes a $V_H$ domain and/or a $V_L$ domain of an antibody or fragment as defined in any one of concepts 1 to 40.

The $V_H$ and $V_L$ domain nucleic acid sequences of the invention are provided in the sequence listing. In one embodiment, the nucleic acid sequence is at least 70% identical to the specified Seq ID No. In one embodiment, the nucleic acid sequence is at least 75% identical to the specified Seq ID No. In one embodiment, the nucleic acid sequence is at least 95% identical to the specified Seq ID No. In one embodiment, the nucleic acid sequence is at least 96% identical to the specified Seq ID No. In one embodiment, the nucleic acid sequence is at least 97% identical to the specified Seq ID No. In one embodiment, the nucleic acid sequence is at least 98% identical to the specified Seq ID No. In one embodiment, the nucleic acid sequence is at least 99% identical to the specified Seq ID No. In one embodiment, the nucleic acid sequence is at least 99.5% identical to the specified Seq ID No.

Concept 67. The nucleic acid according to concept 66 comprising a nucleotide sequence that is at least 80% identical to the sequence of SEQ ID NO:36 and/or SEQ ID NO:46.

Concept 67a. A nucleic acid according to concept 66 comprising a nucleotide sequence that is at least 80% identical to the sequence of SEQ ID NO:16 and/or SEQ ID NO:26.

Concept 67b. A nucleic acid according to concept 66 comprising a nucleotide sequence that is at least 80% identical to the sequence of SEQ ID NO:61 and/or SEQ ID NO:71.

Concept 67c. A nucleic acid according to concept 66 comprising a nucleotide sequence that is at least 80% identical to the sequence of SEQ ID NO:81 and/or SEQ ID NO:91.

Concept 67d. A nucleic acid according to concept 66 comprising a nucleotide sequence that is at least 80% identical to the sequence of SEQ ID NO:101 and/or SEQ ID NO:111.

Concept 67e. A nucleic acid according to concept 66 comprising a nucleotide sequence that is at least 80% identical to the sequence of SEQ ID NO:121 and/or SEQ ID NO:131.

Concept 67f. A nucleic acid according to concept 66 comprising a nucleotide sequence that is at least 80% identical to the sequence of SEQ ID NO:161 and/or SEQ ID NO:171.

Concept 67g. A nucleic acid according to concept 66 comprising a nucleotide sequence that is at least 80% identical to the sequence of SEQ ID NO:181 and/or SEQ ID NO:191.

Concept 67h. A nucleic acid according to concept 66 comprising a nucleotide sequence that is at least 80% identical to the sequence of SEQ ID NO:141 and/or SEQ ID NO:151.

Concept 67i. A nucleic acid according to concept 66 comprising a nucleotide sequence that is at least 80% identical to the sequence of SEQ ID NO:247 and/or SEQ ID NO:257.

Concept 67j. A nucleic acid according to concept 66 comprising a nucleotide sequence that is at least 80% identical to the sequence of SEQ ID NO:267 and/or SEQ ID NO:277.

Concept 67k. A nucleic acid according to concept 66 comprising a nucleotide sequence that is at least 80% identical to the sequence of SEQ ID NO:287 and/or SEQ ID NO:297.

Concept 67l. A nucleic acid according to concept 66 comprising a nucleotide sequence that is at least 80% identical to the sequence of SEQ ID NO:352 and/or SEQ ID NO:362.

In one embodiment, the nucleic acid sequence is at least 70% identical to the specified Seq ID No. In one embodiment, the nucleic acid sequence is at least 75% identical to the specified Seq ID No. In one embodiment, the nucleic acid sequence is at least 95% identical to the specified Seq ID No. In one embodiment, the nucleic acid sequence is at least 96% identical to the specified Seq ID No. In one embodiment, the nucleic acid sequence is at least 97% identical to the specified Seq ID No. In one embodiment, the nucleic acid sequence is at least 98% identical to the specified Seq ID No. In one embodiment, the nucleic acid sequence is at least 99% identical to the specified Seq ID No. In one embodiment, the nucleic acid sequence is at least 99.5% identical to the specified Seq ID No.

Concept 68. A nucleic acid that encodes a heavy chain or a light chain of an antibody as defined in any one of concepts 1 to 40.

Concept 69. A vector comprising the nucleic acid of any one of concepts 65 to 68; optionally wherein the vector is a CHO or HEK293 vector.

Concept 70. A host comprising the nucleic acid of any one of concepts 65 to 68 or the vector of concept 69.

3. Immunocytokines

The inventors have described immunocytokines which comprise an antibody which binds to an immune checkpoint inhibitor, such as PD-L1 fused to either the N-terminus or C-terminus of the heavy chain or the light chain (for example, the C-terminus of the heavy or light chain, and in particular the light chain). The immunocytokines comprise a cytokine molecule, which may be IL-2 or a variant thereof (including variant having a 1 to 10 amino acid deletion at the N-terminus). The antibodies as described hereinabove may be used in any immunocytokine described herein.

Without being bound by theory, immunocytokines of the invention may provide one or more of the following advantageous properties:
 synergistic activity (by virtue of the therapeutic activity of antibody Fab portion in combination with the cytokine)
 improved tumour targeting
 ability to retain effector functions such as CDC, ADCC and/or ADCP
 reduced off-target effects
 reduced toxicity (e.g. compared to free cytokine or cytokine when fused to the heavy chain of an immunocytokine)
 reduced immunogenicity
 lower dose/frequency of dosing, in particular due to improved half life of light chain cytokine fusions as compared to heavy chain fusion equivalents
 Specificity for blocking only one of the ligands of PD-L1 (e.g. blocks CD80/PD-L1 interaction, but not PD-1/PD-L1 interaction)
 Solubility
 Stability
 Ease of formulation
 Frequency of dosing and/or route of administration
 Manufacturability (e.g. expression, ease of purification, isoforms)

1D05 ICK comprises a heavy chain amino acid sequence of Seq ID No:299, and a light chain amino acid sequence of Seq ID No:300. The light chain comprises a $V_L$ domain comprising the CDRs and $V_L$ sequence of antibody 1D05 described hereinabove, fused at the heavy chain to full length, wild-type, human IL-2 cytokine. It does not contain a linker peptide. The heavy chain comprises a $V_H$ domain comprising the CDRs and $V_H$ sequence of antibody 1D05 described hereinabove, fused to a disabled IgG constant region (Seq ID No:205).

1D05 D5-9 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D5-9 (Seq ID No:303), which is directly fused to amino acids 21 to 133 of hIL-2 (Seq ID No:324).

1D05 D1-9 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-9 (Seq ID No:304), which is directly fused to amino acids 21 to 133 of hIL-2 (Seq ID No:324).

1D05 D5-7 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D5-7 (Seq ID No:305), which is directly fused to amino acids 21 to 133 of hIL-2 (Seq ID No:324).

1D05 D1 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1 (Seq ID No:306), which is directly fused to amino acids 21 to 133 of hIL-2 (Seq ID No:324).

1D05 D1-2 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-2 (Seq ID No:307), which is directly fused to amino acids 21 to 133 of hIL-2 (Seq ID No:324).

1D05 D1-3 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-3 (Seq ID No:308), which is directly fused to amino acids 21 to 133 of hIL-2 (Seq ID No:324).

1D05 D1-4 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-4 (Seq ID No:309), which is directly fused to amino acids 21 to 133 of hIL-2 (Seq ID No:324).

1D05 D1-5 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-5 (Seq ID No:310), which is directly fused to amino acids 21 to 133 of hIL-2 (Seq ID No:324).

1D05 D1-6 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-6 (Seq ID No:311), which is directly fused to amino acids 21 to 133 of hIL-2 (Seq ID No:324).

1D05 D1-7 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-7 (Seq ID No:312), which is directly fused to amino acids 21 to 133 of hIL-2 (Seq ID No:324).

1D05 D1-8 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-8 (Seq ID No:313), which is directly fused to amino acids 21 to 133 of hIL-2 (Seq ID No:324).

1D05 D9 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9 (Seq ID No:314), which is directly fused to amino acids 21 to 133 of hIL-2 (Seq ID No:324).

1D05 D9-8 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-8 (Seq ID No:315), which is directly fused to amino acids 21 to 133 of hIL-2 (Seq ID No:324).

1D05 D9-7 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-7 (Seq ID No:316), which is directly fused to amino acids 21 to 133 of hiL-2 (Seq ID No:324).

1D05 D9-6 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-6 (Seq ID No:317), which is directly fused to amino acids 21 to 133 of hIL-2 (Seq ID No:324).

1D05 D9-4 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-4 (Seq ID No:318), which is directly fused to amino acids 21 to 133 of hIL-2 (Seq ID No:324).

1D05 D9-3 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-3 (Seq ID No:319), which is directly fused to amino acids 21 to 133 of hIL-2 (Seq ID No:324).

1D05 D9-2 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-2 (Seq ID No:320), which is directly fused to amino acids 21 to 133 of hIL-2 (Seq ID No:324).

1D05 D2-6 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D2-6 (Seq ID No:321), which is directly fused to amino acids 21 to 133 of hIL-2 (Seq ID No:324).

1D05 D3-7 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D3-7 (Seq ID No:322), which is directly fused to amino acids 21 to 133 of hIL-2 (Seq ID No:324).

1D05 D4-8 ICK comprises a heavy chain comprising a $V_H$ region amino acid sequence of Seq ID No:33 (comprising the CDRs of 1D05 as described hereinabove) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D4-8 (Seq ID No:323), which is directly fused to amino acids 21 to 133 of hIL-2 (Seq ID No:324).

In any of the ICK constructs above, the IL-2 binding portion may be a variant IL-2, in particular an IL-2 having an R38A mutation (as described in amino acids 21-133 of the variant IL-2 described as SEQ ID NO:517) or an R38Q mutation (as described in amino acids 21-133 of the variant IL-2 described as SEQ ID NO:518).

In any of the ICK constructs above, the $V_H$ region of the 1D05 antibody may be exchanged for the $V_H$ region of mutated 1D05—Heavy Chain mutant 1 (Seq ID No:47), mutated 1D05—Heavy Chain mutant 2 (Seq ID No:48), mutated 1D05—Heavy Chain mutant 3 (Seq ID No:49) or mutated 1D05—Heavy Chain mutant 4 (Seq ID No:342). A preferred mutated heavy chain $V_H$ region of 1D05 is mutated 1D05—Heavy Chain mutant 4 (Seq ID No:342).

Thus, certain ICK constructs comprise:

Mutated 1D05—Heavy Chain mutant 4 D5-9 ICK, which comprises a heavy chain comprising a $V_H$ region amino acid sequence of Seq ID No:342 (comprising the CDRs of mutated 1D05—Heavy Chain mutant 4 as described herein) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D5-9 (Seq ID No:303), which is directly fused to amino acids 21 to 133 of hIL-2 (Seq ID No:324).

Mutated 1D05—Heavy Chain mutant 4 D1-9 ICK, which comprises a heavy chain comprising a $V_H$ region amino acid sequence of Seq ID No:342 (comprising the CDRs of mutated 1D05—Heavy Chain mutant 4 as described herein) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-9 (Seq ID No:304), which is directly fused to amino acids 21 to 133 of hIL-2 (Seq ID No:324).

Mutated 1D05—Heavy Chain mutant 4 D1-8 ICK, which comprises a heavy chain comprising a $V_H$ region amino acid sequence of Seq ID No:342 (comprising the CDRs of mutated 1D05—Heavy Chain mutant 4 as described herein) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D1-8 (Seq ID No:313), which is directly fused to amino acids 21 to 133 of hIL-2 (Seq ID No:324).

Mutated 1D05—Heavy Chain mutant 4 D9-7 ICK, which comprises a heavy chain comprising a $V_H$ region amino acid sequence of Seq ID No:342 (comprising the CDRs of mutated 1D05—Heavy Chain mutant 4 as described herein) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-7 (Seq ID No:316), which is directly fused to amino acids 21 to 133 of hIL-2 (Seq ID No:324).

Mutated 1D05—Heavy Chain mutant 4 D9-2 ICK, which comprises a heavy chain comprising a $V_H$ region amino acid sequence of Seq ID No:342 (comprising the CDRs of mutated 1D05—Heavy Chain mutant 4 as described herein) fused to a disabled IgG1 constant region with an amino acid sequence of Seq ID No:205. The light chain comprises a $V_L$ amino acid sequence of Seq ID No:43 (comprising the CDRs of 1D05 as described hereinabove) directly fused at the C-terminus to IL-2 D9-2 (Seq ID No:320), which is directly fused to amino acids 21 to 133 of hIL-2 (Seq ID No:324).

In any of the ICK constructs above, the $V_L$ region of the 1D05 antibody may be exchanged for the $V_L$ region of mutated 1D05—Light Chain mutant 1 (Seq ID No:50), mutated 1D05—Light Chain mutant 2 (Seq ID No:51) or mutated 1D05—Light Chain mutant 3 (Seq ID No:298).

In any of the ICK constructs above, both the $V_H$ and $V_L$ region of the 1D05 antibody may be exchanged for both the $V_H$ and $V_L$ regions of any of the other antibodies described herein, i.e. 84G09, 411B08, 411C04, 411D07, 385F01, 413D08, 386H03, 389A03, 413G05, 413F09 and 414B06.

In any of the ICK constructs above, the heavy chain constant region of Seq ID No:205 may be exchanged for any of the heavy chain constant regions of Seq ID Nos:193, 195, 197, 199, 203, 205, 340, 524, 526, 528, 530, 532 or 534.

Immunocytokines may be described in the following sentences or aspects. Unless otherwise apparent, the features of any of the concepts described hereinabove apply mutatis mutandis to any of the aspects hereinbelow.

Aspect 1. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1 as defined by Seq ID No:1, and competes for binding to said hPD-L1 with the antibody 1D05; and
wherein the immunocytokine comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In the aspects described herein, CDR sequences may be determined according to any method known to those skilled in the art, such as using the Kabat method, the IMGT method or the Chothia method, each of which are described in more detail herein. In one embodiment, the CDR regions are human CDR regions.

In addition to the CDR regions, the $V_H$ and/or $V_L$ domains may further comprise framework regions, such as FW1, FW2 and FW3. The $V_H$ and/or $V_L$ domains may be of any origin described herein, and may be for example, fully human, humanised, murine or camelid. In one embodiment, the $V_H$ and/or $V_L$ domains are human $V_H$ and/or $V_L$ domains. CDRs may be of a non-human origin (e.g. mouse origin) and be grafted onto human framework regions. In another embodiment, the CDRs are synthetic.

In another embodiment, $V_H$ regions may be selected from the group consisting of an antibody variable domain (e.g. a $V_L$ or a $V_H$, an antibody single variable domain (domain antibody or dAb), a camelid $V_{HH}$ antibody single variable domain, a shark immunoglobulin single variable domain (NARV), a Nanobody™ or a camelised $V_H$ single variable domain); a T-cell receptor binding domain; an immunoglobulin superfamily domain; an agnathan variable lymphocyte receptor; a fibronectin domain (e.g. an Adnectin™); an antibody constant domain (e.g. a $CH_3$ domain, e.g. a $CH_2$ and/or $CH_3$ of an Fcab™) wherein the constant domain is not a functional $CH_1$ domain; an scFv; an (scFv)2; an sc-diabody; an scFab; a centyrin and an epitope binding domain derived from a scaffold selected from CTLA-4 (Evibody™); a lipocalin domain; Protein A such as Z-domain of Protein A (e.g. an Affibody™ or SpA); an A-domain (e.g. an Avimer™ or Maxibody™); a heat shock protein (such as and epitope binding domain derived from GroEI and GroES); a transferrin domain (e.g. a trans-body); ankyrin repeat protein (e.g. a DARPin™); peptide aptamer; C-type lectin domain (e.g. Tetranectin™); human γ-crystallin or human ubiquitin (an affilin); a PDZ domain; scorpion toxin; and a kunitz type domain of a human protease inhibitor.

The constant region comprises at least two heavy chain constant region domains selected from $CH_1$, $CH_2$, $CH_3$ and $CH_4$. In one embodiment, the constant region comprises (or consists of) a $CH_1$ domain and a $CH_2$ domain. In one embodiment, the constant region comprises (or consists of) a $CH_1$ domain, a hinge region and a $CH_2$ domain. In one embodiment, the constant region comprises (or consists of) a $CH_1$ domain and a $CH_3$ domain, and optionally a hinge region. In one embodiment, the constant region comprises (or consists of) a $CH_1$ domain and a $CH_4$ domain, and optionally a hinge region. In one embodiment, the constant region comprises (or consists of) a CH₁ domain, a CH₂ domain and a CH₃ domain, and optionally a hinge region. In one embodiment, the constant region comprises (or consists of) a CH₁ domain, a CH₂ domain and a CH₄ domain, and optionally a hinge region. In one embodiment, the constant region comprises (or consists of) a CH₁ domain, a CH₃ domain and a CH₄ domain, and optionally a hinge region. In one embodiment, the constant region comprises (or consists of) a full constant region.

The constant region may be of any isotype described herein, e.g. IgA, IgD, IgE, IgG, and IgM. In one embodiment, the constant region is of any origin described herein, and may be for example, human, murine or camelid. In one embodiment, the constant region is a (full) human constant region. In one embodiment, the constant region is a human IgG constant region. In one embodiment, the constant region is a (full) human IgG1 constant region. In one embodiment, the constant region is an effector null (full) human IgG1 constant region. In one embodiment, the constant region has CDC and/or ADCC and/or ADCP activity. In one embodiment, the constant region is engineered to enhance the CDC and/or ADCC and/or ADCP activity. The constant region may be any of the constant regions described in concepts 30 to 32 hereinabove.

The light chain constant region may be a kappa or lambda light chain constant region. The light chain constant region may be as described in concept 28 hereinabove.

An IL-2 cytokine is a cytokine molecule which confers IL-2 activity on one or both of the intermediate affinity IL-2 Receptor (αβ) and the high affinity IL-2 receptor (αβγ). An IL-2 cytokine includes variant IL-2 cytokines. An IL-2 cytokine may be of human origin or of non-human origin, for example of a non-human mammal, including, but not limited to, primates (e.g. monkeys such a rhesus macaque or cynomolgus), rodents (such as mice, rats and guinea pigs) farm animals, (such as cattle, sheep, pigs, goats, horses, chickens, turkeys, ducks and geese), and domestic mammals (such as dogs and cats). In one embodiment, an IL-2 cytokine is a human IL-2 cytokine.

As used herein, a "variant IL-2 cytokine" is a cytokine having up to 10 amino acids deleted from the N terminal sequence, in combination with up to 5 amino acid substitutions, deletions or additions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 20, or first 15, or first 10 amino acids of the wild-type IL-2 sequence in question), in combination with up to 5 (e.g. 1, 2, 3, 4 or 5) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 15 amino acids of the wild-type IL-2 sequence in question), in combination with up to 5 (e.g. 1, 2, 3, 4 or 5) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 10 amino acids of the wild-type IL-2 sequence in question), in combination with up to 5 (e.g. 1, 2, 3, 4 or 5) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 10 (e.g. 1, 2, 3, 4, 5, 6, 7, 8, 9 or 10) amino acid deletions from the N-terminal sequence (e.g. within the first 20, or first 15, or first 10 amino acids of the wild-type IL-2 sequence in question), in combination with 1 amino acid substitution elsewhere in the IL-2 cytokine.

In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 9 (e.g. 1, 2, 3, 4, 5, 6, 7, 8 or 9) amino acid deletions from the N-terminal sequence (e.g. within the first 20, or first 15, or first 10 amino adds of the wild-type IL-2 sequence in question), in combination with one amino acid substitution elsewhere in the IL-2 cytokine.

In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 8 (e.g. 1, 2, 3, 4, 5, 6, 7 or 8) amino acid deletions from the N-terminal sequence (e.g. within the first 20, or first 15, or first 10 amino acids of the wild-type IL-2 sequence in question), in combination with one amino acid substitution elsewhere in the IL-2 cytokine.

In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 7 (e.g. 1, 2, 3, 4, 5, 6 or 7) amino acid deletions from the N-terminal sequence (e.g. within the first 20, or first 15, or first 10 amino acids of the wild-type IL-2 sequence in question), in combination with one amino acid substitution elsewhere in the IL-2 cytokine.

In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine.

In one embodiment, the variant IL-2 cytokine comprises (or consists of) up to 5 (e.g. 1, 2, 3, 4 or 5) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 5 (e.g. 1, 2, 3, 4 or 5) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 6 (e.g. 1, 2, 3, 4, 5 or 6) amino acid deletions from the N-terminal sequence (e.g. within the first 20, or first 15, or first 10 amino acids of the wild-type IL-2 sequence in question), in combination with one amino acid substitution elsewhere in the IL-2 cytokine.

In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 4 (e.g. 1, 2, 3 or 4) amino acid deletions from the N-terminal sequence (e.g. within the first 20, or first 15, or first 10 amino acids of the wild-type IL-2 sequence in question), in combination with one amino acid substitution elsewhere in the IL-2 cytokine.

In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) up to 3 (e.g. 1, 2 or 3) amino acid deletions from the N-terminal sequence (e.g. within the first 20, or first 15, or first 10 amino acids of the wild-type IL-2 sequence in question), in combination with one amino acid substitution elsewhere in the IL-2 cytokine.

In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with up to 4 (e.g. 1, 2, 3 or 4) amino acid substitutions elsewhere in the IL-2 cytokine. In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with up to 3 (e.g. 1, 2 or 3) amino acid substitutions elsewhere in the IL-2 cytokine. In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with up to 2 (e.g. 1 or 2) amino acid substitutions elsewhere in the IL-2 cytokine. In one embodiment, the variant IL-2 cytokine comprises (or consists of) 1 or 2 amino acid deletions from the N-terminal sequence (e.g. within the first 20, or first 15, or first 10 amino acids of the wild-type IL-2 sequence in question), in combination with one amino acid substitution elsewhere in the IL-2 cytokine.

Substitutions elsewhere in the IL-2 cytokine are defined further in aspect 44 hereinbelow.

Particular IL-2 cytokines and variant IL-2 cytokines are further defined in aspects 40 to 45 hereinbelow.

The amino acid sequence of the α-chain of human IL-2 is provided in Seq ID No:327. The amino acid sequence of the β-chain of human IL-2 is provided in Seq ID No:328. The amino acid sequence of the γ-chain of human IL-2 is provided in Seq ID No:239.

In any of the aspects or concepts herein, an immunocytokine or anti-PDL1 antibody or fragment may have a half-life of at least 4 hours, 5 hours, 6 hours, 7 hours or 8 hours. In another embodiment, the half-life of any of the immunocytokines or anti-PD-L1 antibodies or fragments provided herein is at least 9 hours, or at least 10 hours, or at least 11 hours, or at least 12 hours. In another embodiment, the half-life of any of the immunocytokines or anti-PD-L1 antibodies or fragments provided herein is at least 13 hours, or at least 14 hours, or at least 15 hours, or at least 16 hours. In another embodiment, the half-life of any of the immunocytokines or anti-PD-L1 antibodies or fragments provided herein is at least 17 hours, or at least 18 hours, or at least 19 hours, or at least 20 hours. In another embodiment, the half-life of any of the immunocytokines or anti-PD-L1 antibodies or fragments provided herein is at least 21 hours, or at least 22 hours, or at least 23 hours, or at least 24 hours. In another embodiment, the half-life of any of the immunocytokines or anti-PD-L1 antibodies or fragments provided herein is at least 25 hours, or at least 26 hours, or at least 27 hours, or at least 30 hours. In another embodiment, the half-life of any of the immunocytokines or anti-PD-L1 antibodies or fragments provided herein is at least 32 hours, or at least 34 hours, or at least 36 hours, or at least 40 hours. In one embodiment, the half-life is determined in a mouse model (for example a human PD-L1 knock-in mouse, e.g. as described in Example 22 hereinbelow, or in an immunocompromised mouse xenografted with human T-cells). In another embodiment, the half life is determined in a single dose study in cynomolgus monkeys (e.g. as described in Example 18 or Example 23 hereinbelow). In another embodiment, the half life is determined in an extended single dose study in cynomolgus monkeys (e.g. as described in Example 19 or Example 26 hereinbelow).

Aspect 1a. An immunocytokine comprising an immunoglobulin heavy chain and an immunoglobulin light chain, wherein the heavy chain comprises in N- to C-terminal direction:
  a) A $V_H$ domain comprising CDRH1, CDRH2 and CDRH3; and
  b) A heavy chain constant region;
and wherein the light chain comprises in N- to C-terminal direction:
  c) A $V_L$ domain comprising CDRL1, CDRL2 and CDRL3;
  d) A light chain constant region, ($C_L$);
  e) Optionally, a linker, (L); and
  f) An IL-2 cytokine;
wherein the $V_H$ domain and $V_L$ domain are comprised by an antigen-binding site that specifically binds to an antigen selected from: an immune checkpoint inhibitor (such as PD-1, CTLA-4, TIGIT, TIM-3, LAG-3 and VISTA, e.g. TIGIT, TIM-3 and LAG-3), an immune modulator (such as BTLA, hHVEM, CSF1R, CCR4, CD39, CD40, CD73, CD96, CXCR2, CXCR4, CD200, GARP, SIRPα, CXCL9, CXCL10, CXCL11 and CD155, e.g. GARP, SIRPα, CXCR4, BTLA, hVEM and CSF1R), and an immune activator (such as CD137, GITR, OX40, CD40, CXCR3 (e.g. agonistic activity against CXCR3), CD27, CD3 and ICOS (e.g. agonistic activity against ICOS), for example, ICOS, CD137, GITR and OX40).

In another embodiment, the antigen-binding site that specifically binds to an antigen selected from: an immune checkpoint inhibitor (such as PD-1, CTLA-4, TIGIT, TIM-3, LAG-3 and VISTA, e.g. TIGIT, TIM-3 and LAG-3), an immune modulator (such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BILA, hVEM and CSF1R), and an immune activator (such as CD137, GITR, OX40, CD40, CXCR3 (e.g. agonistic activity against CXCR3), CD3 and ICOS (e.g. agonistic activity against ICOS), for example, ICOS, CD137, GITR and OX40).

Any of the embodiments of aspect 1 apply mutatis mutandis to aspect 1a. Any of the features or embodiments of aspects 2 to 54 apply mutatis mutandis to aspect 1a. Any of the features of the antibodies or other embodiments or features of concepts 1 to 70 apply mutatis mutandis to aspect 1a.

In one embodiment, the antigen-binding site specifically binds PD-L1, e.g. hPD-L1. In one embodiment, the PD-L1 antigen-binding site comprises the CDRH1, CDRH2, CDRH3, CDRL1, CDRL2 and CDRL3, or the $V_H$, or the $V_L$ or the $V_H$ and $V_L$ region from any one of the anti-PD-L1 antibodies selected from atezolizumab/MPDL3280A (Roche), avelumab/MSB0010718C (Merck), BMS-936559/MDX-1105 (BMS), durvalumab/Medi4736 (Medimmune), KN-035, CA-170, FAZ-053 M7824, ABBV-368, LY-3300054, GNS-1480, YW243.55.570, REGN3504 and any of the PD-L1 antibodies disclosed in WO2017/034916, WO2017/020291, WO2017/020858, WO2017/020801, WO2016/111645, WO2016/050721, WO2016/197367, WO2016/061142, WO2016/149201, WO2016/000619, WO2016/160792, WO2016/022630, WO2016/007235, WO2015/179654, WO2015/173267, WO2015/181342, WO2015/109124, WO2015/195163, WO2015/112805, WO2015/061668, WO2014/159562, WO2014/165082, WO2014/100079, WO2014/055897, WO2013/181634, WO2013/173223, WO2013/079174, WO2012/145493, WO2011/066389, WO2010/077634, WO2010/036959, WO2010/089411 or WO2007/005874, which antibodies and sequences are incorporated herein by reference.

In one embodiment, the antigen-binding site specifically binds ICOS, e.g. hICOS. In one embodiment, the antigen-binding site specifically binds ICOS, e.g. hICOS and is an agonist to ICOS, e.g. hICOS. In one embodiment, the antigen-binding site specifically binds ICOS, e.g. hICOS and is an antagonist to ICOS, e.g. hICOS. In one embodiment, the ICOS antigen-binding site comprises the CDRH1, CDRH2, CDRH3, CDRL1, CDRL2 and CDRL3, or the $V_H$, or the $V_L$ or the $V_H$ and $V_L$ region from any one of the anti-ICOS antibodies described in arrangement 5 and arrangement 5a hereinbelow, and any of the anti-ICOS antibodies described in sentences 1 to 102 and sentences 1a to 21a.

In any of the following embodiments, a particular antigen-binding site specifically binds to a human target. In one embodiment, the antigen-binding site specifically binds an immune checkpoint inhibitor. In one embodiment, the antigen-binding site specifically binds an immune checkpoint inhibitor selected from PD-1, CTLA-4, TIGIT, TIM-3, LAG-3 and VISTA. In one embodiment, the antigen-binding site specifically binds an immune checkpoint inhibitor selected from TIGIT, CTLA-4, TIM-3 and LAG-3.

In one embodiment, the antigen-binding site specifically binds PD-1, e.g. human PD-1. In one embodiment, the PD-1 antigen-binding site comprises the CDRH1, CDRH2, CDRH3, CDRL1, CDRL2 and CDRL3, or the $V_H$, or the $V_L$ or the $V_H$ and $V_L$ region from pembrolizumab (Keytruda®/MK-3475), nivolumab (Opdivo®/BMS-936558/MDX-1106), MEDI-0680/AMP514, PDR001, Lambrolizumab, BMS-936558, REGN2810, BGB-A317, BGB-108, PDR-001, SHR-1210, JS-001, JNJ-63723283, AGEN-2034, PF-06801591, genolimzumab, MGA-012, IBI-308, BCD-100, TSR-042 ANA011, AUNP-12, KD033, MCLA-134, $mDX_{400}$, $muDX_{400}$, STI-A1110, AB011, 244C8, 388D4, XCE853, or pidilizumab/CT-011, or from any one of the anti-PD-1 antibodies described in WO2015/112800 & US2015/0203579 (including the antibodies in Tables 1 to 3), U.S. Pat. Nos. 9,394,365, 5,897,862 and 7,488,802, WO2017/087599 (including antibody SSI-361 and SHB-617), WO2017/079112, WO2017/071625 (including deposit C2015132, hybridoma LT004, and antibodies 6F5/6 F5 (Re), 6F5H1 L1 and 6F5 H2L2), WO2017/058859 (including PD1AB-1 to PD1AB-6), WO2017/058115 (including 67D9, c67D9, and hu67D9), WO2017/055547 (including 12819.15384, 12748.15381, 12748.16124, 12865.15377, 12892.15378, 12796.15376, 12777.15382, 12760.15375 and 13112.15380), WO2017/040790 (including AGEN2033w, AGEN2034w, AGEN2046w, AGEN2047w, AGEN2001w and AGEN2002w), WO2017/025051 & WO2017/024515 (including 1.7.3 hAb, 1.49.9 hAb, 1.103.11 hAb, 1.103.11-v2 hAb, 1.139.15 hAb and 1.153.7 hAb), WO2017/025016 & WO2017/024465 (including antibody A to antibody I), WO2017/020858 & WO2017/020291 (including 1.4.1, 1.14.4, 1.20.15 and 1.46.11), WO2017/019896 & WO2015/112900 & US2015/0210769 (including BAP049-hum01 to BAP049-hum16 and BAP049-Clone-A to BAP049-Clone-E), WO2017/019846 (including PD-1 mAb 1 to PD-1 mAb 15), WO2017/016497 (including MHC723, MHC724, MHC725, MHC728, MHC729, m136-M13, m136-M19, m245-M3, m245-M5 and m136-M14), WO2016/201051 (including antibody EH12.2H7, antibody hPD-1 mAb2, antibody hPD-1 mAb7, antibody hPD-1 mAb9, antibody hPD-1 mAb15, or an anti-PD-1 antibody selected from Table 1), WO2016/197497 (including DFPD1-1 to DFPD1-13), WO2016/197367 (including 2.74.15 and 2.74.15. hAb4 to 2.74.15. hAb8), WO2016/196173 (including the antibodies in Table 5, and FIGS. 1-5), WO2016/127179 (including R3A1, R3A2, R4B3, and R3D6), WO2016/077397 (including the antibodies described in Table 1 of Example 9), WO2016/106159 (including the murine antibodies in Table 3 of Example 2 and the humanised antibodies in Tables 7, 8 and 9 of Example 3), WO2016/092419 (including C1, C2, C3, EH12.1, mAb7-G4, mAb15-G4, mAb-AAA, mAb15-AAA), WO2016/068801 (including clone A3 and its variants and the other antibodies described in FIGS. 1 to 4), WO2016/014688 (including 10D1, 4C10, 7D3, 13F1, 15H5, 14A6, 22A5, 6E1, 5A8, 7A4, and 7A4D and the humanised antibodies of Examples 9/10), WO2016/015685 (including 10F8, BA08-1, BA-08-2 and 15H6), WO2015/091911 & WO2015/091910 (including the anti-canine PD-1 antibodies in Examples 2, 3 and 4), WO2015/091914 (including the anti-canine PD-1 antibodies in Table 3), WO2015/085847 (including mAb005, H005-1 to H005-4), WO2015/058573 (including cAB7), WO2015/036394 (including LOPD180), WO2015/035606 (including the antibodies in Table 1 of Example 2, in Tables 14, 15 and 16 of Example 7 and in tables 20, 21 and 22 of Example 11), WO2014/194302 (including GA2, RG1B3, RG1H10, RG2A7, RG2H10, SH-A4, RG4A6, GA1, GB1, GB6, GH1, A2, C7, H7, SH-A4, SH-A9, RG1H11, and RG6B), WO2014/179664 (including 9A2, 10611, 6E9, APE1922, APE1923, APE1924, APE1950, APE1963 and APE2058), WO2014/206107 (including clone 1, 10, 11, 55, 64, 38, 39, 41 and 48), WO2012/135408 (including h409A11, h409A16, and h409A17), WO2012/145493 (including antibodies 1E3, 1E8, 1H3 and h1H3 Var 1 to h1H3 Var 14), WO2011/110621 (including antibody 949 and the modified versions disclosed in FIGS. 1 to 11), WO2011/110604 (including antibody 948 and the modified versions disclosed in FIGS. 3 to 11), WO2010/089411 (including CNCM deposit number 1-4122, 1-4080 or 1-4081), WO2010/036959 (including the antibodies in Table 1 of Example 1), WO2010/029435 & WO2010/029434 (including clones 2, 10 and 19), WO2008/156712 (including hPD-1.08A, hPD-1.09A, h409A11, h409A16 and h409A17 and the antibodies described in Example 2, Table H, Example 4 and table IV), WO2006/121168 (including clones 17D8, 4H1, 5C4, 4A11, 7D3, 5F4, and 2D3), WO2004/004771 or WO2004/056875 (including PD1-17, PD1-28, PD1-33, PD1-35, PD1-F2 and the Abs described in Table 1); the sequences and features of the anti-PD-1 antibodies are incorporated herein by reference.

In one embodiment, the antigen-binding site specifically binds CTLA-4, e.g. hCTLA-4. In one embodiment, the CTLA-4 antigen-binding site comprises the CDRH1, CDRH2, CDRH3, CDRL1, CDRL2 and CDRL3, or the $V_H$, or the $V_L$ or the $V_H$ and $V_L$ region from ipilimumab (MDX-010, CAS No. 477202-00-9), tremelimumab (ticilimumab/CP-675,206), antibody clone 2F1, clone 1F4 (Abnova Corporation), clone 9H10 (EMD Millipore), clone BNU3 (GeneTex), clone 1 E2, clone AS32 (Lifespan Biosciences) clone A3.4H2. H12 (Acris Antibodies), clone 060 (Sino Biological), clone BU5G3 (Creative Diagnostics), clone MIH8 (MBL International), clone A3.6B10. G1, or clone L3D10 (BioLegend) or from any one of the anti-CTLA-4 antibodies described in WO2017/087588 (ISVs disclosed in FIG. 2), WO2017/084078 (clones C2, C4, C10, C11, C12 and C13, and FIGS. 4-7), WO2016/196237 (including AGEN1884w, AGEN2041w, the sequences in FIGS. 19A, 19B and Tables 1-6), WO2016/130986 & WO2016/130898 (including E8, F7 and the Abs described in Table 4), WO2016/015675 (including hybridoma LT001 and anitbodies 8D2, 8D2H1L1, 8D2H2L2, 8D2H3L3, 8D2H2L15 and 8D2H2L17), WO2012/120125 (including 3610, 8H5, and the Abs identified in Examples 1, 2, 3 and 5), WO2010/097597 (including JMW-3B3 and the variants and fragments disclosed), WO2009/100140 (including 10D1, 1H5, 3A4, 6C10 and the antibodies described in FIGS. 1 to 6), WO2007/008463 & WO2006/101692 & WO2006/101691 & WO2006/048749 & WO2005/09238, (including 4.1.1, 4.8.1, 4.10.2, 4.13.1, 4.14.3, 6.1.1, 11.2.1, 11.6.1, 11.7.1, 12.3.1.1, 12.9.1.1, and 10D1), WO2006/096491 (including ATCC Deposit No. 11.2.1 11.2.1.4 PTA-5169 and 4.1.1 4.1.1.1 PTA-5166), WO2006/066568 (including TGN2122. C, TGN2422. C, 4.8H10H5 and 4.3F6B5 and the antibodies described in tables 3 to 14), WO2006/029219 (including L3D10, L1B11, K4G4, KM10, and YL2), WO2004/029069 (including ATCC deposit number PTA-4537), WO01/54732

(including antibodies 25, 26, 27, 29, 33, 34, 35, 36 and 38), WO01/14424 (including 3A4, 9A5, 2E2, 2E7, 4B6, 4E10, 5C4, 5G1, 11E8, and 11G1 and the antibodies identified in Examples 3 and 4 and table 3) and WO00/37504 (including 3.1.1, 4.1.1, 4.8.1, 4.10.2, 4.13.1, 4.14.3, 6.1.1, 11.2.1, 11.6.1, 11.7.1, 12.3.1.1, and 12.9.1.1); the sequences and features of the anti-CTLA-4 antibodies are incorporated herein by reference.

In one embodiment, the antigen-binding site specifically binds TIGIT, e.g. human TIGIT. In one embodiment, the TIGIT antigen-binding site comprises the CDRH1, CDRH2, CDRH3, CDRL1, CDRL2 and CDRL3, or the $V_H$, or the $V_L$ or the $V_H$ and $V_L$ region from RG-6058 (MTIG-7192A) or from any one of the anti-TIGIT antibodies described in WO2017/053748 (including 1A4, 1D3, 4A3, 10A7, 4.1D3. Q1E, h10A7. K4G3, 4.1D3 and the other antibodies described in Examples 1 and 2), WO2017/037707 (including VSIG9 #1 and 258-csl #4), WO2017/030823 (including 14D7, 26610 and humanized versions in Example 3), WO2016/191643 (including 313R11, 313R12, 313R14, 313R19, 313R20, ATCC PTA-122180 and ATCC PTA-122181), WO2016/106302 (including 14B2, 13E6, 6F9, 11G11, 10C9, 16F6, 11C9, 27A9, 10D7, 20G6, 24E8, 24G1, 27F1, 15A6, 4E4, 13D1, 9B11, 10B8, 22G2, 19H2, 8C8, 17G4, 25E7, 26D8 and 16A8), WO2016/028656 (including 14A6, 28H5 or 31C6 and humanized versions from Example 6), and WO2009/126688 (US2013/0251720, including 10A7 and 1F4); the sequences and features of the anti-TIGIT antibodies are incorporated herein by reference.

In one embodiment, the antigen-binding site specifically binds TIM-3, e.g. human TIM-3. In one embodiment, the TIM-3 antigen-binding site comprises the CDRH1, CDRH2, CDRH3, CDRL1, CDRL2 and CDRL3, or the $V_H$, or the $V_L$ or the $V_H$ and $V_L$ region from F38-2E2 (BioLegend), clone 2E2 (Merck Millipore), clone 666E2, clone 024 (Sino Biological) clone 344801 (R&D Systems), clone E-18, clone H-191 (Santa Cruz Biotechnology), or clone 13A224 (United States Biological), TSR-022 (Tesaro) or from any one of the anti-TIM-3 antibodies described in WO2017/079115 (including anti-TIM3 antibodies listed in tables 30-38), WO2017/055404 (including PD1TIM3-0389, PD1TIM3-0168, PD1TIM3-0166, TIM3-0038, TIM3-0018, TIM3-0028, TIM3-0438—Table C), WO2017/031242 (Table 10), WO2016/179194 (including antibodies in FIG. 1b, including mAb F38-2E2 and 2E2), WO2016/171722 (including 344823 and antibodies from the hybridomas 7D11, 10G12, 11G8, 8B.2C12 and 25F.1D6), WO2016/161270 (including APE5137 and APE5121), WO2016/111947 (including mAb5, mAb13, mAb15, mAb17, mAb21, mAb22, mAb26, mAb27, mAb48, mAb58 and mAb91), WO2016/071448 (including TIM3-0016, TIM3-0018, TIM3-0021, TIM3-0022, TIM3-0026, TIM3-0028, TIM3-0030, TIM3-0033, TIM3-0038, TIM3-0433, TIM3-0434, TIM3-0438 and TIM3-0443), WO2016/068802 (including 1B9, 1H9, 1H10, 2C7, 2F4, 2G6, 1D9, 1F4 and 2C8—FIGS. 1, 2 & 3), WO2016/068803 (including A3, 610, G6, G7, G9, A11 and A11_gl—FIGS. 1, 2 & 3), WO2015/117002 (including ABTIM3, ABTIM3-hum02, ABTIM3-hum05, ABTIM3-hum06, ABTIM3-hum09, ABTIM3-hum10, ABTIM3-hum12, ABTIM-hum01, ABTIM-hum04, ABTIM3-hum07, ABTIM3-hum08, ABTIM3-hum04, ABTIM3-hum21, ABTIM3-hum03, ABTIM3-hum11 and antibodies listed in Table 9), WO2015/048312 (including 5D12), WO2014/022332 (including 2C12), WO2013/006490 (including antibodies in Table 1), WO2011/155607 (including 512, 644, 4545, 4177, 8213, 344823 and 34823), WO2003/063792 (including antibody 8B.2012 and 25F.1D6), WO2017/019897 (including antibody molecules disclosed in Tables 1-4, including ABTIM3, ABTIM3-hum20, ABTIM3-hum22 and ABTIM3-hum23), WO2016/079050 & WO2016/079050 (including Tim3_0022, Tim3_0016, Tim3_0018, Tim3_00122, Tim3_0022, Tim3_0021, Tim3_0028, Tim3_0026, Tim3_0033, Tim3_0038, Tim3_0030, 1.7. E10, F38-2EL and 27-12E12); the sequences and features of the anti-TIM-3 antibodies are incorporated herein by reference.

In one embodiment, the antigen-binding site specifically binds LAG-3, e.g. human LAG-3. In one embodiment, the LAG-3 antigen-binding site comprises the CDRH1, CDRH2, CDRH3, CDRL1, CDRL2 and CDRL3, or the $V_H$, or the $V_L$ or the $V_H$ and $V_L$ region from antibody clone 17B4 (Enzo Life Sciences), or clone 333210 (R&D Systems), or clone 14L676 (United States Biological), or C9B7W (PharMingen), or 11E, or IMO321, or mAb C9B7W (BioXcell) or from any one of the anti-LAG-3 antibodies described in WO95/30750, WO2004/078928, WO2008/132601 (including IMP731 Lag-3 Ab, IMP321, A9H12 Lag-3 mAb and 31G11), WO2010/019570 (including 25F7, 26H10, 25E3, 8B7, 11F2 and 17E5), WO2014/140180 (including H5L7, H5L7BW, IMP731 and antibodies in Tables 3 & Table 7), WO2014/179664 (including APE03109), WO2014/008218 (including Lag3.1, Lag3.5, Lag3.6, Lag3.7 and Lag3.8), WO2015/042246, WO2015/116539 (including BMS-986016), WO2015/138920 (including BAP050-hum01 to BAP050-hum20, huBAP050(Ser), BAP050-hum01-Ser to BAP050-hum20-Ser, BAP050-Clone-F, BAP050-Clone-G, BAP050-Clone-H, BAP050-Clone-I, BAP050-Clone-J, BAP050 and BAP050-chi), WO2015/198312, WO2016/028672 (including Ab1, Ab2, Ab3, Ab4, Ab5, Ab6, Ab7, Ab8 and Ab9), WO2016/126858, WO2016/200782 (including LAG-3 mAb1 to LAG-3 mAb6), WO2017/015560 (including L32D10, L3E3, L3C5, L35D4, L35G6, L33H11, L32A9, L32A4, L3A1 and the antibodies listed in Table 3), WO2017/062888 (including mAb1, H4H15477P, H4H15483P, H4H15484P, H4H15491, H4H17823P, H4H17826P2, H4H17828P2, H4sH15460P, H4sH15462P, H4sH15463P, H4sH15464P, H4sH15466P, H4sH15467P, H4sH15470P, H4sH15475P, H4sH15479P, H4sH15480P, H4sH15482P, H4sH15488P, H4sH15496P2, H4sH15498P2, H4sH15505P2, H4sH15518P2, H4sH15523P2, H4sH15530P2, H4sH15555P2, H4sH15558P2, H4sH15567P2 and H4H17819P), WO2017/019894, WO2017/037203 (including 8E2, 13E2, 34F4, 1764 and IMP761), WO2017/087589 (including 11B09) or WO2017/087901; the sequences and features of the anti-LAG-3 antibodies are incorporated herein by reference.

In one embodiment, the antigen-binding site specifically binds VISTA, e.g. human VISTA. In one embodiment, the VISTA antigen-binding site comprises the CDRH1, CDRH2, CDRH3, CDRL1, CDRL2 and CDRL3, or the $V_H$, or the $V_L$ or the $V_H$ and $V_L$ region from any one of the anti-VISTA antibodies described in WO2016/207717 & WO2015/097536 (including VSTB50, VSTB53, VSTB60, VSTB95, VSTB112, VSTB116, VSTB174, VSTB175, VSTB149, VSTB140 and the antibodies in Table 1A and Examples 7 and 8) and WO2014/190356 (including clone 2D3 and 18C3); the sequences and features of the anti-VISTA antibodies are incorporated herein by reference.

In one embodiment, the antigen-binding site specifically binds an immune modulator. In one embodiment, the antigen-binding site specifically binds an immune modulator selected from BTLA, hHVEM, CSF1R, CCR4, CD39, CD40, CD73, CD96, CXCR2, CXCR4, CD200, GARP, SIRPα, OCL9, CXCL10, CXCL11 and CD155, or from BTLA, hHVEM, CSF1R, CCR4, CD39, CD40, CD73, CD96, CXCR2, CXCR4, CD200, GARP, SIRPα, CXCL9, CXCL10 and CD155. In one embodiment, the antigen-binding site specifically binds an immune modulator selected from GARP, SIRPα, CXCR4, BTLA, hVEM and CSF1R.

In one embodiment, the antigen-binding site specifically binds GARP, e.g. human GARP. In one embodiment, the GARP antigen-binding site comprises the CDRH1, CDRH2, CDR3, CDRL1, CDRL2 and CDRL3, or the $V_H$, or the $V_L$ or the $V_H$ and $V_L$ region from G14D9, Plato-1, 272, G6, 50 G10 or 7611 or from any of one of the anti-GARP antibodies described in WO2007/113301 & WO2015/015003 (including MHGARP8, LHG-10, LHG-10-D, LHG-10.3-D, LHG-10.4-D, LHG-10.5-D, LHG-10.6-D, LHG-10.3, LHG-10.4, LHG-10.5, LHG-10.6, 27E10, MHGARP1, MHGARP2, MHGARP3, MHGARP4, MHGARP5, MHGARP6, MHGARP7 and MHGARP9), WO2017/051888 (including 110F, 105F, c151D, c198D, h198D, h151D, h151D-H1L1 and h198D-H3L4); the sequences and features of the anti-GARP antibodies are incorporated herein by reference.

In one embodiment, the antigen-binding site specifically binds SIRPα, e.g. human SIRPα. In one embodiment, the SIRPα antigen-binding site comprises the CDRH1, CDRH2, CDRH3, CDRL1, CDRL2 and CDRL3, or the $V_H$, or the $V_L$ or the $V_H$ and $V_L$ region from ED9 (ThermoFisher), or 602411 (Novus Biologicals), or from any one of the anti-SIRPα antibodies described in WO97/48723, WO00/24869 (including 10C4), WO00/66159 (including ED9 and ED17), WO01/40307, WO02/092784 (including SE5A5, SE7C2 and SE12C3), WO2004/108923, (including SE12C3 and 2F34), WO2009/046541 (including P84), WO2011/076781, WO2012/172521, WO2012/040207 (including SE5A5 and mouse P84), WO2013/056352 (including 29-AM4-5, Ab AM4-5, AM5-1, AM5-3, AM5-5, AM5-6, SIRPalpha-AM3-35, AM4-1, SIRP29-AM3-35, SIRP29-AM4-5, SIRP29-AM4-1, 29-AM2-2, 29-AM4-4, 29-AM4-1, 29-AM4-5, 29-AM3-35 and SIRP29-AM3-63), WO2016/063233, WO2016/205042 (including P362) or WO2015/138600 (including KWAR23); the sequences and features of the anti-SIRPα antibodies are incorporated herein by reference.

In one embodiment, the antigen-binding site specifically binds CXCR4, e.g. human CXCR4. In one embodiment, the CXCR4 antigen-binding site comprises the CDRH1, CDRH2, CDRH3, CDRL1, CDRL2 and CDRL3, or the $V_H$, or the $V_L$ or the $V_H$ and $V_L$ region of ulocuplumab/BMS-936564, clone 44717.111 or PF-06747143 or from any one of the anti-CXCR4 antibodies described in WO97/49424 (including MAB12G5), WO99/50461, WO01/42308, WO03/066830 & WO2003/066830 (including Ab124 and Ab125), WO2004/059285 (including $ALX_{40}$-4C), WO2006/089141 (including mAbs 2N, 6R, 18, 19, 20, 33 and 48), WO2007/005605, WO2008/142303 (including MAB170, MAB171, MAB173 and MAB172), WO2008/060367 & WO2013/071068 & WO2015/015401 (including BMS-936564/MDX-1338), WO2009/140124 (including antibody I, II, III, IV and V), WO2009/117706 (including 701, 708, 716, 717, 718 and 4G10), WO2011/161266 (including 4CXCR100, 4CXCR103, 4CXCR104, 4CXCR101, 4CXCR238D2 and 4CXCR238D4), WO2011/098762 (including C-9P21 (Table 1), B-1M22 (Table 2), C1124 (Table 3), D-1K21 (Table 4) and 9N10 (Table 5)), WO2012/175576, WO2013/013025 (including 2A4, 6C7, 4C1, 7C8, 5C9 and 5E1), WO2013/017566 (including Mab 427aB1 and 515H7), WO2013/017562 (including 1-3859 Mab and 515H7), WO2015/069874 (including antibodies corresponding to Seq ID numbers 25 and 29), WO2015/015401 (including 12A11, 6B6, 3G10, m3G10. hIgG1, m3G10. hIgG4, h3G10. A57. hIgG1, h3G10. A57. A58A.hIgG1, h3G10.1.91. A58A.hIgG1, h3G10.1.91. A58B.hIgG1 and h3G10.2.37.2.72. hIgG1), WO2016/156570 (including 281F12, 281A6 and 281D4), WO2016/109872 (including antibodies listed in tables 1, 2, 9 & 12, M3-114-6H, AM4-272-6H, AM3-523-6H, AM4-272, AM3-114, AM3-523, AM4-746 and AM4-1121), WO2017/071625, WO2012/175576, WO2010/125162 & WO2012/055980 & WO2011/121040 & WO2010/037831 (including c414H5 (414H5), c515H7 (515H7) and 301aE5), WO2009/138519 (including ALX40-4C, 238D2, 238D4, 237B5 antibodies and sequences listed in table 1, table 1.1, table A-I, table B-1.1 & B-5), WO2011/042398 (including 238D2 and 238D4), WO2011/083140 (including those disclosed in Tables C-2, C-3, C-4 & C-5, FIG. 2 and ALX-0651, 15H3, 10E12, 10G10, 238B6, 10E9, 281E10, 10A10, 14A2 and 15A1) or WO2011/083141; the sequences and features of the anti-CXCR4 antibodies are incorporated herein by reference.

In one embodiment, the antigen-binding site specifically binds BTLA, e.g. hBTLA. In one embodiment, the BILA antigen-binding site comprises the CDRH1, CDRH2, CDRH3, CDRL1, CDRL2 and CDRL3, or the $V_H$, or the $V_L$ or the $V_H$ and $V_L$ region from antibody clone 1B7, clone 2G8, clone 4C5 (Abnova Corporation), clone 4B8 (antibodies-online), clone MIH26 (Thermo Scientific Pierce Antibodies), clone UMAB61 (OriGene Technologies), clone 330104 (R&D Systems), clone 1B4 (Lifespan Biosciences), clone 440205, clone 5E7 (Creative Diagnostics) or from any one of the anti-BTLA antibodies described in WO2016/176583 (including clone 6F4), WO2011/014438 (including 8D5, 8A3, 20H4, 21H6, 15C5, 19A7 and 4C7), WO2010/106051 (including CNCM deposit number 1-4123) and WO2008/076560 (including 1B4, E4H9, 3C2, 3C2a, 6A5, 11E2, E8D9, 10H6 and 4C9 as detailed in Example 2); the sequences and features of the anti-BTLA antibodies are incorporated herein by reference.

In one embodiment, the antigen-binding site specifically binds hVEM, e.g. human hVEM. In one embodiment, the HVEM antigen-binding site comprises the CDRH1, CDRH2, CDRH3, CDRL1, CDRL2 and CDRL3, or the $V_H$, or the $V_L$ or the $V_H$ and $V_L$ region from any one of the anti-HVEM antibodies described in WO2008/083169 (including LBH1); the sequences and features of the anti-BTLA antibodies are incorporated herein by reference.

In one embodiment, the antigen-binding site specifically binds CSF1R. In one embodiment, the CSF1R antigen-binding site comprises the CDRH1, CDRH2, CDRH3, CDRL1, CDRL2 and CDRL3, or the $V_H$, or the $V_L$ or the $V_H$ and $V_L$ region from any one of the anti-CSF1R antibodies described in WO2009/026303 (including 1.2, 1.109, 2.360 and 1.2. SM and the antibodies in FIGS. 1 and 2), WO2009/112245 (including CXIIG6), WO2011/070024 (including Mab 2F11, 2E10, 2H7 and 1G10, and their derivatives), WO2011/107553 (including 7H5.2G10/DSM ACC2922), WO2011/123381 (including antibody 1 and antibody 2), WO2011/131407 (including 7G5.3B6/DSM ACC2921), WO2011/140249 (including 0301, 0302, and 0311 their derivatives and the antibodies in tables 2, 3 and 5), WO2013/169264 & WO2014/036357 & WO2016/106180 & WO2016/168149 (including huAb1 to huAb16), WO2012/110360 & WO2013/057281 (including CXIIG6, H19K12, H27K5 and H27K15 and the humanised antibodies of tables 1 and 2), WO2013/087699 (including 9D11.2E8 and 10H2.2F12), WO2014/072441 (including H27K15), WO2014/173814 & WO2013/132044 (including Mab 2F11, Mab 2E10, Mab 2H7, Mab 1G10 and sc2-4A5 and the antibodies in Table 3 and 3b), WO2015/028455 & WO2015/028454 (including Ab535, Ab969, and derivatives, e.g. Ab969. g2), WO2015/036511 & WO2016/207312 (including 2F11, 2E10 and the derivatives described in embodiment 33) and WO2017/049038 (including ALM-423 and the antibodies listed in Table 2); the sequences and features of the anti-CSF1R antibodies are incorporated herein by reference.

In one embodiment, the antigen-binding site specifically binds CD39, e.g. human CD39. In one embodiment, the CD39 antigen-binding site comprises the CDRH1, CDRH2, CDRH3, CDRL1, CDRL2 and CDRL3, or the $V_H$, or the $V_L$ or the $V_H$ and $V_L$ region from BY40, BY12, BA54g (Biolegend), BU61 (Santa Cruz Biotech), A1 (Ebiosciences), AC2 (Immunotech), 22A9 (Abcam), 24DMS1 or any one of the anti-CD39 antibodies described in WO96/32471, WO00/04041, WO01/10205 (including CD39L4), WO2009/09547 (including CNCM-I-3889/BY40), WO2014/169255, WO2012/085132 (including antibodies VY12, BY40 and BA54g), WO2016/073845 (including R29-5-13A, R29-5-71A, R29-5-165C and R29-9-8B), WO2017/089334 (including 1-391, 1-392 and antibodies produced from hybridomas I-3889 and CNCM I-41171) and WO2009/095478; the sequences and features of the anti-CD39 antibodies are incorporated herein by reference.

In one embodiment, the antigen-binding site specifically binds CD40, e.g. human CD40. In one embodiment, the CD40 antigen-binding site comprises the CDRH1, CDRH2, CDRH3, CDRL1, CDRL2 and CDRL3, or the $V_H$, or the $V_L$ or the $V_H$ and $V_L$ region from BMS3h-56-269, CP-870,893, dacetuzumab, SEA-CD40, ADC-1013, RO7009789 and Chi Lob 7/4, or from any one of the anti-CD40 antibodies described in WO2017/059243, WO2017/059196, WO2017/040932, WO2017/040566, WO2017/004016, WO2017/004006, WO2016/196314, WO2016/028810, WO2016/023960, WO2016/023875, WO2015/134988, WO2015/091853, WO2014/070934, WO2014/065403, WO2014/065402, WO2014/04298, WO2013/164789, WO2013/034904, WO2012/149356, WO2012/145673, WO2012/125569, WO2012/111762, WO2012/075111, WO2012/065950, WO2012/041635, WO2011/123489, WO2010/123012, WO2010/104761, WO2010/121231, WO2009/062125, WO2010/104747, WO2010/104748, WO2010/104749, WO2010/024676, WO2009/094391, WO2009/062054, WO2008/091954, WO2007/130493, WO2007/129895, WO2007/124299, WO2007/053767, WO2007/053661, WO2006/128103, WO2006/073443, WO2005/063981, WO2005/063289 (US2012/0263732), WO2005/044855, WO2005/044306, WO2005/044294, WO2005/044307, WO2005/044304, WO2005/044854, WO2005/044305, WO03/040170 (U.S. Pat. Nos. 7,563,442B, 7,618,633B, 7,338,660B, 7,288,251B, 7,626,012B, 8,388,971B, 2013/0024956), WO03/029296, WO02/088186, WO01/83755, WO02/28905, WO02/28480, WO02/28481, WO02/28904, WO01/37870, WO01/16180, WO00/75348 WO99/61057, WO99/42075, WO97/31025, WO95/17202 and WO95/09653; the sequences and features of the anti-CD40 antibodies are incorporated herein by reference.

In one embodiment, the antigen-binding site specifically binds CD73, e.g. human CD73. In one embodiment, the CD73 antigen-binding site comprises the CDRH1, CDRH2, CDRH3, CDRL1, CDRL2 and CDRL3, or the $V_H$, or the $V_L$ or the $V_H$ and $V_L$ region from 1E9 (Santa Cruz Biotechnology), AD2, 7G2, 4G4 or from any one of the anti-CD73 antibodies described in WO2017/064043 (including 7H10, 12F9, 15D7, 4B11, 11D9 and 9D2), WO2016/081748 (including 4C3, 7A11, 6E11, 5F8, 4C3, 11F11, 11A6, CD73.4-1, CD73.4-2, CD73.3, 11F11-1, 11F11-2, 11F11, 4C3-1, 4C3-2, 4C3-3, 4D4, 10D2-1, 10D2-2, 11A6, 24H2, 5F8-1, 5F8-2 and 5F8-3), WO2016/131950 (including 11E1, 8C7, 3C12 and 6E1), WO2016/075176 (including MEDI9447, clone 10.3 and clone 2C5) & WO2016/075099 (including CD730004, CD730008, CD7300011, CD730021, CD730042, CD730046, CD730047, CD730068 and CD730069), WO2016/055609 (including 11E1, 6E1, 3C12 and 8C7); the sequences and features of the anti-CD73 antibodies are incorporated herein by reference.

In one embodiment, the antigen-binding site specifically binds CD96, e.g. human CD96. In one embodiment, the CD96 antigen-binding site comprises the CDRH1, CDRH2, CDRH3, CDRL1, CDRL2 and CDRL3, or the $V_H$, or the $V_L$ or the $V_H$ and $V_L$ region of 6A6, or NK92.39 (E bioscience), 1C8, 3H8, MAA6359 or from any one of the anti-CD96 antibodies described in WO2008/073316, WO2009/007124, WO2013/184912, WO2014/089169, WO2014/149310 (including antibody 3.3), WO2015/024060 or WO2015/024042, WO2015/024060 (including mAb 3.3); the sequences and features of the anti-CD96 antibodies are incorporated herein by reference.

In one embodiment, the antigen-binding site specifically binds CXCR2, e.g. human CXCR2. In one embodiment, the CXCR2 antigen-binding site comprises the CDRH1, CDRH2, CDRH3, CDRL1, CDRL2 and CDRL3, or the $V_H$, or the $V_L$ or the $V_H$ and $V_L$ region from any one of the anti-CXCR2 antibodies described in WO2015/169811 (including HY29 and HY29GL), WO2014/170317 (including $CX_2$-Mab #1 to #19), WO2012/062713, WO2013/168108 (including 163D2-127D1, 163E3-127D1, 163E3-54B12, 163D2-54B12, 2B2-163E3, 2B2-163D2, 97A9-2B2, 97A9-54B12, 127D1-163D2, 127D1-163E3, 2B2-97A9, 54B12-163D2, 54B12-163E3, 163D2-2B2, 163E3-2B2, 127D1-97A9, 54B12-97A9, 97A9-127D1 and derivatives thereof), WO2009/117706 (including 48311.211, 5E8/CXCR2, clone 19 and derivatives thereof), WO2009/120186 (including RII115, 48311 and derivatives thereof) and WO2002/26249; the sequences and features of the anti-CXCR2 antibodies are incorporated herein by reference.

In one embodiment, the antigen-binding site specifically binds CD200, e.g. human CD200. In one embodiment, the CD200 antigen-binding site comprises the CDRH1, CDRH2, CDRH3, CDRL1, CDRL2 and CDRL3, or the $V_H$, or the $V_L$ or the $V_H$ and $V_L$ region from DX-109, samalizumab/ALXN-6000, TTI-200.7 or from any one of the anti-CD200 antibodies described in WO99/24565 (including M3B5 and the antibodies in Examples 4 and 5), WO02/11762 (including 3B6 and the antibodies in the Examples), WO2004/060295 (US2004/0213783), WO2004/078938 (including scFv-9), WO2006/020266 (U.S. Pat. No. 8,840,885B2, including CG1R3A10, cG2aR3A10, cG2aR3B7, dGIR3A5, dGIR3B5, and dGIR3B10 and the antibodies described in FIGS. 9A-9C, FIGS. 21A and 21B), WO2007/084321 (U.S. Pat. No. 8,709,415B2, including ALXN5200, hB7VH3VL2, C2aB7G1, C2aB7G2/G4, V3V2-G1 and V3V2-G2/G4), WO2009/014745 (including OX90mG2a (FIG. 10), OX9ONE and OX9ONE-AG), and WO2011/100538 & US2013/0189258 (including Antibody 1 and Antibody 2); the sequences and features of the anti-CD200 antibodies are incorporated herein by reference.

In one embodiment, the antigen-binding site specifically binds CCR4, e.g. human CCR4. In one embodiment, the CCR4 antigen-binding site comprises the CDRH1, CDRH2, CDRH3, CDRL1, CDRL2 and CDRL3, or the $V_H$, or the $V_L$ or the $V_H$ and $V_L$ region from mogamulizumab, KM3060 (see Niwa et al., 2004, Cancer Research 64, 2127-2133), and KW-0761 (see Ishida et al., Annals of Oncology 2008, vol 19, supplement 4, 513) or from any one of the anti-CCR4 antibodies described in WO2016/178779 & WO2016/057488 (including mAb2-3, 1-44, 1-49, 2-1 and 2-2), WO2015/179236 (including KW-0761), WO2013/166500 (including mAb1567, c1567, h1567, mAb 1-4 and 2-3 and the antibodies in Examples 6 and 13), WO2012/076883 (including antibodies 208, 306, 308, 406, 501, 503, 601, 603 and 803—Tables 1-9), WO2010/142952 (including 17G, 9E, 11F, 9E10, 9E103 and 9E1D—see Tables 1-16), WO2009/086514 (including mAb1567 and the humanised mAbs in Example 14), WO2005/035582 (including the DG44/CCR4 antibody and the Ms705/CCR4 antibody (FERM BP-8467)), WO2005/053741 & WO01/64754 (U.S. Pat. Nos. 6,989,145B, 7,666,418B, 8,197,814B, 8,632, 996B, including KM2160 (FERM BP-10090), KM2760 (FERM deposit BP-7054)), WO2003/018635 (including KM2160, KM8759 (FERM BP-8129) and KM8760 (FERM BP-8130), WO00/42074 (U.S. Pat. Nos. 6,488,930B, 7,138, 117B, including 2610, 10E4, 1G1 and the antibodies deposited as ATCC accession number HB-12624 and HB-12625) and WO00/41724 (U.S. Pat. No. 6,881,406B, 6,245,332B, including 1G1 and the antibody deposited under ATCC accession number HB-12624); the sequences and features of the anti-CCR4 antibodies are incorporated herein by reference.

In one embodiment, the antigen-binding site specifically binds CXCL9, e.g. human CXCL9. In one embodiment, the CXCL9 antigen-binding site comprises the CDRH1, CDRH2, CDRH3, CDRL1, CDRL2 and CDRL3, or the $V_H$, or the $V_L$ or the $V_H$ and $V_L$ region from mAb 392-100 or AF392 (R&D Systems).

In one embodiment, the antigen-binding site specifically binds CXCL10, e.g. human CXCL10. In one embodiment, the CXCL10 antigen-binding site comprises the CDRH1, CDRH2, CDRH3, CDRL1, CDRL2 and CDRL3, or the $V_H$, or the $V_L$ or the $V_H$ and $V_L$ region of mAb266 (R & D systems) or from any one of the anti-CXCL10 antibodies described in WO017/8708 (including CR.G (IP-10) (IgG1) (PharMingen) ande IP-10 (IgG)(A. Luster), WO02/15932, WO03/006045, WO2004/082714, WO2004/045525, WO2004/045526, WO2004/101511 (including antibodies in table 1 and AIP12, HuAIP12, MuAIP12, AIP13, HuAIP13, MuAIP13, AIP6, AIP8, AIP14, AIP18, AIP21, AIP22, AIP5 and AIP17), WO2005/060457 (including AIP5, AIP6, AIP8, AIP10, AIP12, AIP13, AIP14, AIP17, AIP18, AIP21, AIP22, AIP32 and AIP36), WO2005/011605, WO2005/023201, WO2005/058815 (including 1D4, 1E1, 2G1, 3C4, 6A5, 6A8, 6610, 7C10, 8F6, 10A12 and 10A12S13C4), WO2005/084708, WO2006/03981.9, WO2006/118085, WO2008/047486, WO2008/044824 (including antibodies #124, #31, #28, #43 and #137), WO2008/106200, WO2009/023566, WO2012/149320 (including MSX-1100 and 6A5), WO2014/003742 (including the antibody of Example 14), WO2013/170735, WO2014/189306, WO2015/063187; the sequences and features of the anti-CXCL10 antibodies are incorporated herein by reference.

In one embodiment, the antigen-binding site specifically binds CD155, e.g. human CD155. In one embodiment, the CD155 antigen-binding site comprises the CDRH1, CDRH2, CDRH3, CDRL1, CDRL2 and CDRL3, or the $V_H$, or the $V_L$ or the $V_H$ and $V_L$ region from clone SKII.4 (BioLegend).

In one embodiment, the antigen-binding site specifically binds an immune activator. In one embodiment, the antigen-binding site specifically binds an immune activator selected from CD137, GITR, OX40, CD40, CXCR3 (e.g. agonistic activity against CXCR3), CD3 and ICOS (e.g. agonistic activity against ICOS). In one embodiment, the antigen-binding site specifically binds an immune activator selected from ICOS, CD137, GITR and OX40.

In one embodiment, the antigen-binding site specifically binds CD137, e.g. hCD137. In one embodiment, the CD137 antigen-binding site comprises the CDRH1, CDRH2, CDRH3, CDRL1, CDRL2 and CDRL3, or the $V_H$, or the $V_L$ or the $V_H$ and $V_L$ region from urelumab, BMS-663513, PF-05082566 (Pfizer), 1D8 and 3E1, 4B4 (BioLegend 309809), H4-1BB-M127 (BD Pharmingen 552532), BBK.2 (Thermo Fisher M S621PABX), 145501 (Leinco Technologies B591), the antibody produced by cell line deposited as ATCC No. HB-11248 (U.S. Pat. No. 6,974,863) or XmAb-5592, or from any one of the anti-CD137 antibodies described in WO2017/04945, WO2016/134358, WO2015/179236, WO2012/177788, WO2012/145183, WO2012/032433, WO2009/135019, WO2005/035584, U.S. Pat. No. 6,974,863, WO2004/055513 and WO2004/010947; the sequences and features of the anti-CD137 antibodies are incorporated herein by reference.

In one embodiment, the antigen-binding site specifically binds GITR, e.g. hGITR. In one embodiment, the GITR antigen-binding site comprises the CDRH1, CDRH2, CDRH3, CDRL1, CDRL2 and CDRL3, or the $V_H$, or the $V_L$ or the $V_H$ and $V_L$ region from MK4166, $TRX_{518}$, $TRX_{385}$, MAB689 (R & D Systems), YGITR765 (Novus Biologicals) or 1D8 (Novus Biologicals), or from any one of the anti-GITR antibodies described in WO2015/187835 (including 28F3, 3C3-1, 3C3-2, 2G6, 8A6, 9G7-1, 9G7-2, 14E3, 19H8-1, 19H8-2, 19D3, 18E10, and 6G10), WO2015/184099 (including 1042-7, 32-15, 1039-45, 1333-21, 231-1039-45, 231-32-15, Hum231 #1, Hum231 #2, m6C8, pab1964, to pab1973, pab1975 to pab1977, pab1979 to pab1981, pab1983, pab2159, pab2160, pab2161 and the antibodies in tables 1 and 2), WO2015/031667 (including antibodies Ab1 to Ab59 in table 1), WO2015/026684 (including an antibody with a CDR sequence of Seq ID 1-66), WO2013/039954 (including, 2155, 1718, 1649, 1362, 954, 827, 698, 706 and antibodies listed in Tables 1 & 3), WO2011/051726 (including antibodies containing CDRs a-f listed on page 17), WO2011/028683 (including antibodies 36E5, 61F6, 61G6, 3D6, 6H6, 1D8, 17F10, 35D8, 49A1, 9E5, 31H6 and antibodies from hybridomas PTA-9889, PTA-9890, PTA-9891, PTA-9892, PTA-9893, PTA-10286, PTA-10287, PTA-10288, PTA-10289, PTA-10290, and PTA-10291), WO2009/009116 (including antibody 2F8), WO2007/133822 (including antibodies listed in Table 1), WO2006/105021 (including 6C8, 2F8, HuN6C8-Agly, HuQ6C8-Gly, and HuQ6C8-Agly), WO2006/050172 & WO2004/084942 (including DTA-1), WO03/006058 (including anti-GITR/TNFRSF18 #AF524), WO2016/054638 (including mAb #1-81, #3-167, #5-139, #7-192, #10-116, #11-126, #12-46, #13-169, #14-182, #15-68 and #17-60), WO2016/196792 (including 6G10, 28F3, 19D3, 18E10, 3C3, 2G6, 8A6, 9G7, 14E3 and 191-18), WO2017/087678 (including 28F3, 19D3, 18E10, 30-1, 3C3-2, 2G6, 8A6, 9G7-1, 9G7-2, 14E3, 19H8-1, 19H8-2 and 6G10); the sequences and features of the anti-GITR antibodies are incorporated herein by reference.

In one embodiment, the antigen-binding site specifically binds OX40, e.g. hOX40. In one embodiment, the OX40 antigen-binding site comprises the CDRH1, CDRH2, CDRH3, CDRL1, CDRL2 and CDRL3, or the $V_H$, or the $V_L$ or the $V_H$ and $V_L$ region from GSK3174998, L106 BD (Pharmingen Product #340420), ACT35 (Santa Cruz Biotechnology, Catalog #20073), MOXR0916, MEDI-6469, MEDI-0562, 9612 (Weinberg, A. D., et al., J Immunother 29, 575-585 (2006)), the humanised anti-OX40 Ab described in Morris et al., Mol Immunol. May 2007; 44(12): 3112-3121, or from any one of the anti-OX40 antibodies described in WO2017/077085 (including SAP9, SAP28.2, SAP15.3, SAP29-50, SAP25-29 and SAP29-23 and humanised versions described in Examples 4 and 5), WO2017/063162 (including O3, O19, O21 and the affinity matured version in Example 5—Table 2, including 21 #H28H33, 21 #H65, 21 #H96, 21 #VHnew-L80, 21 #H96-L80), WO2017/050729 (including SP197), WO2017/021912 & WO2017/021910 (including ANTIBODY 106-222, OX86, and the antibodies described in FIGS. 6 and 7), WO2016/200836 & WO2016/200835 (including MOXR0916/1A7. gr1 IgG1), WO2016/196228 (including 3F4, 14B6-1, 14B6-2, 23H3, 18E9, 8611, 20B3, 20C1, 6E1-1, 6E1-2, 14A2, 14A2-1, 14A2-2, L106, OX40.1, OX40.5, OX40.8, OX40.6, and OX40.16 and OX40.21—FIGS. 1 to 10), WO2016/179517 (including 11D4, pab1949, pab1949-1, pab2044, pab2193-1, Tables 1 to 4), WO2016/057667 (including 9612 and OX40mAb24), WO2015/153513 (including 3C8, 1D2, 1A7 and their variants described in the sequence listing, including A1A7. gr1 and 3C8. gr.5, the antibodies described in FIG. 1), WO2014/148895 (including ACT35, 12H3, 12H3 (FIG. 25)—and humanised versions VL1H1, VL1VH2, VL1VH3, VL2H1, VL2VH2 and VL2VH3 (FIGS. 43 & 44) and 20E5 (FIG. 24)), WO2013/068563 (including A26 [FIG. 2]), WO2013/038191 (including ACT35, 12H3 and 12H3), WO2013/028231 (including 119-122, 119-43-1, 106-222 and the antibodies in Table 1), WO2013/008171 (including 2F8, 1D4 and their derivatives, including VH6/VL9, and the antibodies in FIGS. 4 and 5 and tables 6 and 7), WO2012/027328 (including 119-122, 119-43-1, Hu106 and Hu106-222), WO2010/096418 (including A26), WO2008/106116 (including the antibodies in Tables 1 and 2, and A10 (inc A10A-F), B66—FIG. 14—B2, B24, B36, B37, and B39) and WO2007/062245 (including 112V8 (ATCC No. PTA-7219), 112Y55 (ATCC No. PTA-7220), 112Y131 (ATCC No. PTA-7218), 112F32 (ATCC No. PTA-7217) and 112Z5 (ATCC No. PTA-7216); the sequences and features of the anti-OX40 antibodies are incorporated herein by reference.

In one embodiment, the antigen-binding site specifically binds CXCR3, e.g. CXCR3. In one embodiment, the CXCR3 antigen-binding site comprises the CDRH1, CDRH2, CDRH3, CDRL1, CDRL2 and CDRL3, or the $V_H$, or the $V_L$ or the $V_H$ and $V_L$ region from GSK3174998 or from any one of the anti-CXCR3 antibodies described in WO2016/200836, WO2016/200835, WO2016/196228, WO2016/179517, WO2016/057667, WO2015/153513, WO2014/148895, WO2013/068563, WO2013/038191, WO2013/028231, WO2013/008171, WO2012/027328, WO2010/096418, WO2011/073180, WO2008/106116 and WO2007/062245; the sequences and features of the anti-CXCR3 antibodies are incorporated herein by reference.

In one embodiment, the antigen-binding site specifically binds CD27, e.g. hCD27. In one embodiment, the CD27 antigen-binding site comprises the CDRH1, CDRH2, CDRH3, CDRL1, CDRL2 and CDRL3, or the $V_H$, or the $V_L$ or the $V_H$ and $V_L$ region from any one of the anti-CD27 antibodies described in WO2016/145085 (including 1F5), WO2015/016718 (including hCD27.15 and 1F5), WO2014/140374 (including 2F2, 5F24, 5F32, 10F13, 10F31, 11F26, 1052 to 015, F2A4B2 and their derivatives, including hz5F24VH+V5Q, hz5F24VL+K45Q), WO2013/138586 (including C2177, C2186, C2191, and C2192 and the derivatives in Examples 8 to 12, and tables 7 to 42), WO2012/004367 (including hCD27.15/ATCC number PTA-11008), WO2011/130434 (including 1G5, 1H8, 3H12, 3H8, 2G9, 1F5, 3A10, 2C2, ms 1A4, ms 9F4 and ms M-T271), WO2011/081164 & WO2010/001908 (including KM4027, KM4028, KM4026, KM4030, KM4032 and derivatives thereof), WO2008/051424 (including LG3A10 and AT124-1); the sequences and features of the anti-CD27 antibodies are incorporated herein by reference.

In one embodiment, the antigen-binding site specifically binds CD3, e.g. hCD3. In one embodiment, the CD3 antigen-binding site comprises the CDRH1, CDRH2, CDRH3, CDRL1, CDRL2 and CDRL3, or the $V_H$, or the $V_L$ or the $V_H$ and $V_L$ region from OKT3 antibody, otelixizumab, teplizumab or visilizumab, or from any one of the anti-CD3 antibodies described in WO2017/010874, WO2017/009442, WO2016/204966, WO2016/180721, WO2016/179003, WO2016/116626, WO2016/014974, WO2015/104346, WO2015/095392, WO2015/001085, WO2014/047231, WO2013/188693, WO2013/186613, WO2013/158856, WO2012/173819, WO2012/162067, WO2005/118635, WO2004/108158, WO2004/052397, WO2004/024771, WO01/51644, WO00/05268, WO97/44362, WO93/19196, WO92/06193 and WO91/09968; the sequences and features of the anti-CD3 antibodies are incorporated herein by reference.

Aspect 1b. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
c) Optionally, a linker, (L); and
d) An IL-2 cytokine;
and wherein the light chain comprises in N- to C-terminal direction:
e) A $V_L$ domain comprising CDRL1, CDRL2 and CDRL3; and
f) A light chain constant region, ($C_L$);
wherein the $V_H$ domain and $V_L$ domain are comprised by an antigen-binding site that specifically binds to an antigen selected from: an immune checkpoint inhibitor (such as PD-1, CTLA-4, TIGIT, TIM-3, LAG-3 and VISTA, e.g. TIGIT, TIM-3 and LAG-3), an immune modulator (such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R), and an immune activator (such as CD137, GITR, OX40, CD40, CXCR3 (e.g. agonistic anti-CXCR3 antibodies), CD27, CD3 and ICOS (e.g. agonistic anti-ICOS antibodies), for example ICOS, CD137, GITR and OX40).

In another embodiment, the antigen-binding site that specifically binds to an antigen selected from: an immune checkpoint inhibitor (such as PD-1, CTLA-4, TIGIT, TIM-3, LAG-3 and VISTA, e.g. TIGIT, TIM-3 and LAG-3), an immune modulator (such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R), and an immune activator (such as CD137, GITR, OX40, CD40, CXCR3 (e.g. agonistic anti-CXCR3 antibodies), CD3 and ICOS (e.g. agonistic anti-ICOS antibodies), for example ICOS, CD137, GITR and OX40).

Any of the embodiments of aspect 1 and/or aspect 1a apply mutatis mutandis to aspect 1b. Any of the features or embodiments of aspects 2 to 54 apply mutatis mutandis to aspect 1b. Any of the features of the antibodies or other embodiments or features of concepts 1 to 70 apply mutatis mutandis to aspect 1b.

In one embodiment, the antigen binding site specifically binds any of the antigens as set out in aspect 1a.

In one embodiment, the antigen-binding site specifically bind to hPD-L1 as defined by Seq ID No:1, and competes for binding to said hPD-L1 with the antibody 1D05; and wherein the immunocytokine comprises a $V_H$ domain which comprises a CDRH3 comprising the motif $X_1GSGX_2YGX_3X_4FD$, wherein $X_1$, $X_2$ and $X_3$ are independently any amino acid, and $X_4$ is either present or absent, and if present, may be any amino acid.

In either of aspect 1 or 1a, the wording of part f) may be substituted to read: "f) a cytokine, e.g. selected from IL-7, IL-15, IL-21, IL-12, GM-CSF, TNFα, TGFβ, CXCL9, CXCL10 and interferon-α". In 1b, the wording of part d) may be substituted for "d) a cytokine, e.g. selected from IL-7, IL-15, IL-21, IL-12, GM-CSF, TNFα, TGFβ, CXCL9, CXCL10 and interferon-α". Thus, the immunocytokines as disclosed herein may contain cytokines other than a cytokine having IL-2 cytokine activity. In one embodiment, the cytokine is IL-7 (Seq ID No:330). In one embodiment, the cytokine is IL-15 (Seq ID No:331). In one embodiment, the cytokine is IL-21 (Seq ID No:332). In one embodiment, the cytokine is IL-12, comprising the a-chain (Seq ID No:336) and the β-chain (Seq ID No:337). In one embodiment, the cytokine is GM-CSF (Seq ID No:333). In one embodiment, the cytokine is TNFα (Seq ID No:335). In one embodiment, the cytokine is TGFβ. In one embodiment, the cytokine is CXCL9 (Seq ID No:338). In one embodiment, the cytokine is CXCL10 (Seq ID No:339). In one embodiment, the cytokine is interferon-α (Seq ID No:334).

In another embodiment, the cytokine is an immune-stimulating cytokine. In another embodiment, the cytokine is a T-cell stimulating cytokine.

Aspect 2. An immunocytokine according to aspect 1, wherein $X_1$ is a hydroxyl-containing amino acid, optionally T.

Aspect 3. An immunocytokine according to aspect 1 or aspect 2, wherein $X_2$ is a basic amino acid, optionally K.

Aspect 4. An immunocytokine according to any one of aspects 1 to 3, wherein $X_2$ is a hydroxyl-containing amino acid, optionally S or T.

Aspect 5. The immunocytokine according to any one of claims 1 to 4, wherein $X_3$ is an aromatic amino acid, optionally W.

Aspect 6. An immunocytokine according to any one of aspects 1 to 5, wherein $X_4$ is absent.

Aspect 7. An immunocytokine according to any one of aspects 1 to 5, wherein $X_4$ is present.

Aspect 8. An immunocytokine according to aspect 7, wherein $X_4$ is an aliphatic amino acid, optionally G.

The features of aspects 2 to 7 may be as defined in any of concepts 2 to 7 hereinabove.

Aspect 9. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1, and competes for binding to said hPD-L1 with the antibody 1D05, wherein the antibody or fragment comprises a $V_H$ domain which comprises the CDRH3 sequence of SEQ ID NO:29 or 32, or the CDRH3 sequence of SEQ ID NO:29 or 32 comprising 6 or fewer amino acid substitutions, optionally, wherein the immunocytokine is according to any one of aspects 2 to 8.

In this aspect, any of the features of CDRH3 described in concepts 9, and 9a to 1, and any of the embodiments of concept 9 apply mutatis mutandis.

Aspect 10. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site that specifically binds to hPD-L1; and
wherein the $V_H$ domain comprises a CDRH3 of from 12 to 20 amino acids and which is derived from the recombination of a human $V_H$ gene segment, a human D gene segment and a human $J_H$ gene segment, wherein the human $J_H$ gene segment is IGHJ5 (e.g. IGHJ5*02).

In this aspect, any of the features of CDRH3 described in concepts 10 and 10a apply mutatis mutandis Aspect 11. An immunocytokine according to aspect 10, wherein the human $V_H$ gene segment is IGHV3 (e.g. IGHV3-9, such as IGHV3-9*01).

In this aspect, any of the features of the gene segments described in concept 11, 11a or 11b apply mutatis mutandis.

Aspect 12. An immunocytokine according to aspect 10 or aspect 11, wherein the antibody or fragment comprises a $V_L$ domain which is derived from the recombination of a human Vκ gene segment, and a human Jκ gene segment, wherein the human $V_L$ gene segment is IGκV1D (e.g. IGκV1D-39, such as IGκV1D-39*01).

In this aspect, any of the features of the gene segments described in concept 12, 12a or 12b apply mutatis mutandis.

Aspect 13. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);

e) optionally, a linker, (L); and
f) An IL-2 cytokine;
wherein the $V_H$ domain and $V_L$ domain are comprised by an antigen-binding site that specifically binds to an epitope that is identical to an epitope to which the antibody 1D05 specifically binds.

In this aspect, any of the features of the epitopes, assays and other embodiments described in any of concepts 13 and 13a to 13l apply mutatis mutandis Aspect 14. An immunocytokine according to aspect 13, wherein the epitope is identified by an unrelated amino acid scan, or by X-ray crystallography.

Aspect 15. An immunocytokine according to aspect 14, wherein the contact residues of the epitope are defined by a reduction in affinity of at least 10-fold in an unrelated amino acid scan, e.g. an alanine scan as determined by SPR.

In this aspect, any of the features of concept 15 apply mutatis mutandis.

Aspect 16. An immunocytokine comprising an immunoglobulin heavy chain and an immunoglobulin light chain, wherein the heavy chain comprises in N- to C-terminal direction:
a) A $V_H$ domain comprising CDRH1, CDRH2 and CDRH3; and
b) A heavy chain constant region;
and wherein the light chain comprises in N- to C-terminal direction:
c) A $V_L$ domain comprising CDRL1, CDRL2 and CDRL3;
d) A light chain constant region, ($C_L$);
e) Optionally, a linker, (L); and
f) An IL-2 cytokine;
wherein the $V_H$ domain and $V_L$ domain are comprised by an antigen-binding site which competes for binding to hPD-L1 with the antibody 1D05.

In this aspect, any of the features of the antibodies of concepts 16a to 16l or any of the competitive-assays and other embodiments described in concept 16, or the features of concept 35 apply mutatis mutandis.

Aspect 17. An immunocytokine according to any one of aspects 10 to 16, wherein the $V_H$ domain comprises the CDRH3 sequence of SEQ ID NO:29 or 32, or the CDRH3 sequence of SEQ ID NO:29 or 32 comprising 6 or fewer amino acid substitutions.

In this aspect, any of the features of the antibodies of concepts 17a to 17l apply mutatis mutandis.

Aspect 18. An immunocytokine according to any preceding aspect, wherein the $V_H$ domain comprises the CDRH1 sequence of SEQ ID NO:27 or 30 or the CDRH1 sequence of SEQ ID NO:27 or 30 comprising 3, 2 or 1 amino acid substitution(s).

In this aspect, any of the features of the antibodies of concepts 18a to 18l apply mutatis mutandis.

Aspect 19. An immunocytokine according to any preceding aspect, wherein the $V_H$ domain comprises the CDRH2 sequence of SEQ ID NO:28 or 31, or the CDRH2 sequence of SEQ ID NO:28 or 31 comprising 4 or fewer amino acid substitutions.

In this aspect, any of the features of the antibodies of concepts 19a to 19l apply mutatis mutandis.

Aspect 20. An immunocytokine according to any preceding aspect, wherein the $V_H$ domain comprises an amino acid sequence of SEQ ID NO:33, or a heavy chain variable domain amino acid sequence that is at least 80% (e.g. at least 85%, or at least 90%) identical to SEQ ID NO:33 (for example the $V_H$ domain sequence in any of the heavy chain sequences of Seq ID Nos:47 to 49).

In this aspect, any of the features of the antibodies of concepts 20a to 20l or any of the embodiments of concept 20 apply mutatis mutandis.

Aspect 21. An immunocytokine according to any preceding aspect comprising first and second copies of said heavy chain.

Aspect 22. An immunocytokine according to any preceding aspect, comprising a $V_L$ domain which comprises the CDRL1 sequence of SEQ ID NO:37 or 40, or the CRDL1 sequence of SEQ ID NO:37 or 40 comprising 3 or fewer amino acid substitutions.

In this aspect, any of the features of the antibodies of concepts 22a to 22l apply mutatis mutandis.

Aspect 23. An immunocytokine according to any preceding aspect, comprising a $V_L$ domain which comprises the CDRL2 sequence of SEQ ID NO:38 or 41, or the CRDL2 sequence of SEQ ID NO:38 or 41 comprising 2 or 1 amino acid substitution(s), for example a CDRL2 sequence of Seq ID No:50.

In this aspect, any of the features of the antibodies of concepts 23a to 23l apply mutatis mutandis.

Aspect 24. An immunocytokine according to any preceding aspect, comprising a $V_L$ domain which comprises the CDRL3 sequence of SEQ ID NO:39 or 42, or the CRDL3 sequence of SEQ ID NO:39 or 42 comprising 4 or fewer amino acid substitutions.

In this aspect, any of the features of the antibodies of concepts 24a to 24l apply mutatis mutandis.

Aspect 25. An immunocytokine according to any preceding aspect, comprising a $V_L$ domain which comprises an amino acid sequence of SEQ ID NO:43, or a light chain variable domain amino acid sequence that is at least 80%. (e.g. at least 85%, or at least 90%) identical to SEQ ID NO:43 (for example the $V_L$ domain sequence in the light chain sequence of Seq ID No:50 or 51).

In this aspect, any of the features of the antibodies of concepts 25a to 25l or any of the embodiments of concept 25 apply, mutatis mutandis.

Aspect 26. An immunocytokine according to any preceding aspect comprising first and second copies of said light chain.

Aspect 27. An immunocytokine according to any preceding aspect which specifically binds to cynomolgus PD-L1 as defined by Seq ID No:2.

In this aspect, any of embodiments of concept 27 apply mutatis mutandis.

Aspect 28. An immunocytokine according to any preceding aspect, wherein the antibody or fragment comprises a kappa light chain.

In this aspect, any of the embodiments of concept 28 apply mutatis mutandis

Aspect 29. An immunocytokine according to any one of aspects 9 to 28, wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V); and
6) Phenylalanine (F), Tyrosine (Y), Tryptophan (W).

In this aspect, any of the embodiments of concept 9 apply mutatis mutandis.

Aspect 30. An immunocytokine according to any preceding aspect, wherein the antibody or fragment comprises a constant region, e.g. an IgG1 constant region, optionally wherein the constant region is a disabled IgG1 as defined in Seq ID No:205.

In this aspect, any of the features or the embodiments of concepts 30, 31 or 32 apply mutatis mutandis.

Aspect 31. An immunocytokine according to any preceding aspect wherein the:
A) $V_H$ domain comprises an amino acid sequence of SEQ ID No:33 and the $V_L$ domain comprises an amino acid sequence of SEQ ID No:43;
B) $V_H$ domain comprises an amino acid sequence that is at least 85% identical to SEQ ID No:33, and the $V_L$ domain comprises an amino acid sequence that is at least 85% identical to SEQ ID No:43;
C) $V_H$ domain comprises an amino acid sequence of the $V_H$ domain of SEQ ID No:47 and the $V_L$ domain comprises an amino acid sequence of SEQ ID No:43;
D) $V_H$ domain comprises an amino acid sequence of the $V_H$ domain of SEQ ID No:48 and the $V_L$ domain comprises an amino acid sequence of SEQ ID No:43;
E) $V_H$ domain comprises an amino acid sequence of the $V_H$ domain of SEQ ID No:49 and the $V_L$ domain comprises an amino acid sequence of SEQ ID No:43;
F) $V_H$ domain comprises an amino acid sequence of SEQ ID No:33 and the $V_L$ domain comprises an amino acid sequence of the $V_L$ domain of SEQ ID No:50;
G) $V_H$ domain comprises an amino acid sequence of the $V_H$ domain of SEQ ID No:47 and the $V_L$ domain comprises an amino acid sequence of the $V_L$ domain of SEQ ID No:50;
H) $V_H$ domain comprises an amino acid sequence of the $V_H$ domain of SEQ ID No:48 and the $V_L$ domain comprises an amino acid sequence of the $V_L$ domain of SEQ ID No:50;
I) $V_H$ domain comprises an amino acid sequence of the $V_H$ domain of SEQ ID No:49 and the $V_L$ domain comprises an amino acid sequence of the $V_L$ domain of SEQ ID No:50;
J) $V_H$ domain comprises an amino acid sequence of SEQ ID No:33 and the $V_L$ domain comprises an amino acid sequence of the $V_L$ domain of SEQ ID No:51;
K) $V_H$ domain comprises an amino acid sequence of the $V_H$ domain of SEQ ID No:47 and the $V_L$ domain comprises an amino acid sequence of the $V_L$ domain of SEQ ID No:51;
L) $V_H$ domain comprises an amino acid sequence of the $V_H$ domain of SEQ ID No:48 and the $V_L$ domain comprises an amino acid sequence of the $V_L$ domain of SEQ ID No:51;
M) $V_H$ domain comprise an amino acid sequence of the $V_H$ domain of SEQ ID No:49 and the $V_L$ domain comprises an amino acid sequence of the $V_L$ domain of SEQ ID No:51;
N) $V_H$ domain comprises an amino acid sequence of SEQ ID No:33 and the $V_L$ domain comprises an amino acid sequence of the $V_L$ domain of SEQ ID No:298;
O) $V_H$ domain comprises an amino acid sequence of the $V_H$ domain of SEQ ID No:47 and the $V_L$ domain comprises an amino acid sequence of the $V_L$ domain of SEQ ID No:298;
P) $V_H$ domain comprises an amino acid sequence of the $V_H$ domain of SEQ ID No:48 and the $V_L$ domain comprises an amino acid sequence of the $V_L$ domain of SEQ ID No:298;
Q) $V_H$ domain comprise an amino acid sequence of the $V_H$ domain of SEQ ID No:49 and the $V_L$ domain comprises an amino acid sequence of the $V_L$ domain of SEQ ID No:298;
R) $V_H$ domain comprises an amino acid sequence of SEQ ID No:58 and the $V_L$ domain comprises an amino acid sequence of SEQ ID No:68;
S) $V_H$ domain comprises an amino acid sequence that is at least 85% identical to SEQ ID No:58, and the $V_L$ domain comprise an amino acid sequence that is at least 85% identical to SEQ ID No:68;
T) $V_H$ domain comprises an amino acid sequence of SEQ ID No:78 and the $V_L$ domain comprises an amino acid sequence of SEQ ID No:88;
U) $V_H$ domain comprises an amino acid sequence that is at least 85% identical to SEQ ID No:78, and the $V_L$ domain comprises an amino acid sequence that is at least 85% identical to SEQ ID No:88;
V) $V_H$ domain comprises an amino acid sequence of SEQ ID No:98 and the $V_L$ domain comprises an amino acid sequence of SEQ ID No:108;
W) $V_H$ domain comprises an amino acid sequence that is at least 85% identical to SEQ ID No:98, and the $V_L$ domain comprises an amino acid sequence that is at least 85% identical to SEQ ID No:108;
X) $V_H$ domain comprises an amino acid sequence of SEQ ID No:118 and the $V_L$ domain comprises an amino acid sequence of SEQ ID No:128;
Y) $V_H$ domain comprises an amino acid sequence that is at least 85% identical to SEQ ID No:118, and the $V_L$ domain comprises an amino acid sequence that is at least 85% identical to SEQ ID No:128;
Z) $V_H$ domain comprises an amino acid sequence of SEQ ID No:158 and the $V_L$ domain comprises an amino acid sequence of SEQ ID No:168;
AA) $V_H$ domain comprises an amino acid sequence that is at least 85% identical to SEQ ID No:158, and the $V_L$ domain comprises an amino acid sequence that is at least 85% identical to SEQ ID No:168;
BB) $V_H$ domain comprises an amino acid sequence of SEQ ID No:178 and the $V_L$ domain comprises an amino acid sequence of SEQ ID No:188;
CC) $V_H$ domain comprises an amino acid sequence that is at least 85% identical to SEQ ID No:178, and the $V_L$ domain comprises an amino acid sequence that is at least 85% identical to SEQ ID No:188;
DD) $V_H$ domain comprises an amino acid sequence of SEQ ID No:138 and the $V_L$ domain comprises an amino acid sequence of SEQ ID No:148;
EE) $V_H$ domain comprises an amino acid sequence that is at least 85% identical to SEQ ID No:13, and the $V_L$ domain comprises an amino acid sequence that is at least 85% identical to SEQ ID No:148;
FF) $V_H$ domain comprises an amino acid sequence of SEQ ID No:244 and the $V_L$ domain comprises an amino acid sequence of SEQ ID No:254;
GG) $V_H$ domain comprises an amino acid sequence that is at least 85% identical to SEQ ID No:244, and the $V_L$ domain comprises an amino acid sequence that is at least 85% identical to SEQ ID No:254;

HH) $V_H$ domain comprises an amino acid sequence of SEQ ID No:264 and the $V_L$ domain comprises an amino acid sequence of SEQ ID No:274;

II) $V_H$ domain comprises an amino acid sequence that is at least 85% identical to SEQ ID No:264, and the $V_L$ domain comprises an amino acid sequence that is at least 85% identical to SEQ ID No:274;

JJ) $V_H$ domain comprises an amino acid sequence of SEQ ID No:284 and the $V_L$ domain comprises an amino acid sequence of SEQ ID No:294;

KK) $V_H$ domain comprises an amino acid sequence that is at least 85% identical to SEQ ID No:284, and the $V_L$ domain comprises an amino acid sequence that is at least 85% identical to SEQ ID No:294;

LL) $V_H$ domain comprises an amino acid sequence of SEQ ID No:13 and the $V_L$ domain comprises an amino acid sequence of SEQ ID No:23; and MM) $V_H$ domain comprises an amino acid sequence that is at least 85% identical to SEQ ID No:13, and the $V_L$ domain comprises an amino acid sequence that is at least 85% identical to SEQ ID No:23;

NN) $V_H$ domain comprises an amino acid sequence of SEQ ID No:349 and the $V_L$ domain comprises an amino acid sequence of SEQ ID No:359; and OO) $V_H$ domain comprises an amino acid sequence that is at least 85% identical to SEQ ID No:349, and the $V_L$ domain comprises an amino acid sequence that is at least 85% identical to SEQ ID No:359.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Aspect 32. An immunocytokine according to any preceding aspect wherein the:

A) $V_H$ and the constant region comprise an amino acid sequence of SEQ ID No:299 and $V_L$ and $C_L$ comprise an amino acid sequence of SEQ ID No:45;

B) $V_H$ and the constant region comprise an amino acid sequence that is at least 85% identical to SEQ ID No:299, and the $V_L$ and $C_L$ comprise an amino acid sequence that is at least 85% identical to SEQ ID No:45;

C) $V_H$ and the constant region comprise an amino acid sequence of SEQ ID No:47 and $V_L$ and $C_L$ comprise an amino acid sequence of SEQ ID No:45;

D) $V_H$ and the constant region comprise an amino acid sequence of SEQ ID No:48 and $V_L$ and $C_L$ comprise an amino acid sequence of SEQ ID No:45;

E) $V_H$ and the constant region comprise an amino acid sequence of SEQ ID No:49 and $V_L$ and $C_L$ comprise an amino acid sequence of SEQ ID No:45;

F) $V_H$ and the constant region comprise an amino acid sequence of SEQ ID No:342 and $V_L$ and $C_L$ comprise an amino acid sequence of SEQ ID No:45;

G) $V_H$ and the constant region comprise an amino acid sequence of SEQ ID No:238 and $V_L$ and $C_L$ comprise an amino acid sequence of SEQ ID No:50;

H) $V_H$ and the constant region comprise an amino acid sequence of SEQ ID No:47 and $V_L$ and $C_L$ comprise an amino acid sequence of SEQ ID No:50;

I) $V_H$ and the constant region comprise an amino acid sequence of SEQ ID No:48 and $V_L$ and $C_L$ comprise an amino acid sequence of SEQ ID No:50;

J) $V_H$ and the constant region comprise an amino acid sequence of SEQ ID No:49 and $V_L$ and $C_L$ comprise an amino acid sequence of SEQ ID No:50;

K) $V_H$ and the constant region comprise an amino acid sequence of SEQ ID No:342 and $V_L$ and $C_L$ comprise an amino acid sequence of SEQ ID No:50;

L) $V_H$ and the constant region comprise an amino acid sequence of SEQ ID No:299 and $V_L$ and $C_L$ comprise an amino acid sequence of SEQ ID No:51;

M) $V_H$ and the constant region comprise an amino acid sequence of SEQ ID No:47 and $V_L$ and $C_L$ comprise an amino acid sequence of SEQ ID No:51;

N) $V_H$ and the constant region comprise an amino acid sequence of SEQ ID No:48 and $V_L$ and $C_L$ comprise an amino acid sequence of SEQ ID No:51;

O) $V_H$ and the constant region comprise an amino acid sequence of SEQ ID No:49 and $V_L$ and $C_L$ comprise an amino acid sequence of SEQ ID No:51;

P) $V_H$ and the constant region comprise an amino acid sequence of SEQ ID No:342 and $V_L$ and $C_L$ comprise an amino acid sequence of SEQ ID No:51;

Q) $V_H$ and the constant region comprise an amino acid sequence of SEQ ID No:299 and $V_L$ and $C_L$ comprise an amino acid sequence of SEQ ID No:298;

R) $V_H$ and the constant region comprise an amino acid sequence of SEQ ID No:47 and $V_L$ and $C_L$ comprise an amino acid sequence of SEQ ID No:298;

S) $V_H$ and the constant region comprise an amino acid sequence of SEQ ID No:48 and $V_L$ and $C_L$ comprise an amino acid sequence of SEQ ID No:298;

T) $V_H$ and the constant region comprise an amino acid sequence of SEQ ID No:49 and $V_L$ and $C_L$ comprise an amino acid sequence of SEQ ID No:298;

U) $V_H$ and the constant region comprise an amino acid sequence of SEQ ID No:342 and $V_L$ and $C_L$ comprise an amino acid sequence of SEQ ID No:298;

V) $V_H$ and the constant region comprise an amino acid sequence of SEQ ID No:60 and $V_L$ and $C_L$ comprise an amino acid sequence of SEQ ID No:70;

W) $V_H$ and the constant region comprise an amino acid sequence that is at least 85% identical to SEQ ID No:60, and the $V_L$ and $C_L$ comprise an amino acid sequence that is at least 85% identical to SEQ ID No:70;

X) $V_H$ and the constant region comprise an amino acid sequence of SEQ ID No:80 and $V_L$ and $C_L$ comprise an amino acid sequence of SEQ ID No:90;

Y) $V_H$ and the constant region comprise an amino acid sequence that is at least 85% identical to SEQ ID No:80, and the $V_L$ and $C_L$ comprise an amino acid sequence that is at least 85% identical to SEQ ID No:90;

Z) $V_H$ and the constant region comprise an amino acid sequence of SEQ ID No:100 and $V_L$ and $C_L$ comprise an amino acid sequence of SEQ ID No:110;

AA) $V_H$ and the constant region comprise an amino acid sequence that is at least 85% identical to SEQ ID No:100, and the $V_L$ and $C_L$ comprise an amino acid sequence that is at least 85% identical to SEQ ID No:110;
BB) $V_H$ and the constant region comprise an amino acid sequence of SEQ ID No:120 and $V_L$ and $C_L$ comprise an amino acid sequence of SEQ ID No:130;
CC) $V_H$ and the constant region comprise an amino acid sequence that is at least 85% identical to SEQ ID No:120, and the $V_L$ and $C_L$ comprise an amino acid sequence that is at least 85% identical to SEQ ID No:130;
DD) $V_H$ and the constant region comprise an amino acid sequence of SEQ ID No:160 and $V_L$ and $C_L$ comprise an amino acid sequence of SEQ ID No:170;
EE) $V_H$ and the constant region comprise an amino acid sequence that is at least 85% identical to SEQ ID No:160, and the $V_L$ and $C_L$ comprise an amino acid sequence that is at least 85% identical to SEQ ID No:170;
FF) $V_H$ and the constant region comprise an amino acid sequence of SEQ ID No:180 and $V_L$ and $C_L$ comprise an amino acid sequence of SEQ ID No:190;
GG) $V_H$ and the constant region comprise an amino acid sequence that is at least 85% identical to SEQ ID No:180, and the $V_L$ and $C_L$ comprise an amino acid sequence that is at least 85% identical to SEQ ID No:190;
HH) $V_H$ and the constant region comprise an amino acid sequence of SEQ ID No:140 and $V_L$ and $C_L$ comprise an amino acid sequence of SEQ ID No:150;
II) $V_H$ and the constant region comprise an amino acid sequence that is at least 85% identical to SEQ ID No:140, and the $V_L$ and $C_L$ comprise an amino acid sequence that is at least 85% identical to SEQ ID No:150;
JJ) $V_H$ and the constant region comprise an amino acid sequence of SEQ ID No:246 and $V_L$ and $C_L$ comprise an amino acid sequence of SEQ ID No:256;
KK) $V_H$ and the constant region comprise an amino acid sequence that is at least 85% identical to SEQ ID No:246, and the $V_L$ and $C_L$ comprise an amino acid sequence that is at least 85% identical to SEQ ID No:256;
LL) $V_H$ and the constant region comprise an amino acid sequence of SEQ ID No:266 and $V_L$ and $C_L$ comprise an amino acid sequence of SEQ ID No:276;
MM) $V_H$ and the constant region comprise an amino acid sequence that is at least 85% identical to SEQ ID No:266, and the $V_L$ and $C_L$ comprise an amino acid sequence that is at least 85% identical to SEQ ID No:276;
NN) $V_H$ and the constant region comprise an amino acid sequence of SEQ ID No:286 and $V_L$ and $C_L$ comprise an amino acid sequence of SEQ ID No:296; and
OO) $V_H$ and the constant region comprise an amino acid sequence that is at least 85% identical to SEQ ID No:286, and the $V_L$ and $C_L$ comprise an amino acid sequence that is at least 85% identical to SEQ ID No:296;
PP) $V_H$ and the constant region comprise an amino acid sequence of SEQ ID No:15 and $V_L$ and $C_L$ comprise an amino acid sequence of SEQ ID No:25; and QQ) $V_H$ and the constant region comprise an amino acid sequence that is at least 85% identical to SEQ ID No:15, and the $V_L$ and $C_L$ comprise an amino acid sequence that is at least 85% identical to SEQ ID No:25;
RR) $V_H$ and the constant region comprise an amino acid sequence of SEQ ID No:351 and $V_L$ and $C_L$ comprise an amino acid sequence of SEQ ID No:361; and
SS) $V_H$ and the constant region comprise an amino acid sequence that is at least 85% identical to SEQ ID No:351, and the $V_L$ and $C_L$ comprise an amino acid sequence that is at least 85% identical to SEQ ID No:361.

In one embodiment, the amino acid sequence is at least 70% identical to the specified Seq ID No. In one embodiment, the amino acid sequence is at least 75% identical to the specified Seq ID No. In one embodiment, the amino acid sequence is at least 95% identical to the specified Seq ID No. In one embodiment, the amino acid sequence is at least 96% identical to the specified Seq ID No. In one embodiment, the amino acid sequence is at least 97% identical to the specified Seq ID No. In one embodiment, the amino acid sequence is at least 98% identical to the specified Seq ID No. In one embodiment, the amino acid sequence is at least 99% identical to the specified Seq ID No. In one embodiment, the amino acid sequence is at least 99.5% identical to the specified Seq ID No.

Aspect 33. An immunocytokine according to any preceding aspect wherein the antigen-binding site specifically binds PD-L1, whilst the IL-2 cytokine binds the high affinity ($\alpha\beta\gamma$) IL-2 receptor (IL-2R).

In one embodiment, the antigen binding site binds PD-L1 simultaneously to the IL-2 cytokine binding the $\alpha\beta\gamma$ IL-2R. In one embodiment, the antigen binding site binds PD-L1 sequentially to the IL-2 cytokine binding the $\alpha\beta\gamma$ IL-2R. In one embodiment, the IL-2 cytokine additionally binds the intermediate ($\beta\gamma$) IL-2R.

Aspect 34. An immunocytokine according to any preceding aspect wherein the immunocytokine is capable of inhibiting PD-L1-mediated suppression of T-cells.

In one embodiment, the immunocytokine inhibits PD-L1-mediated suppression of T-cells. In one embodiment, the immunocytokine inhibits PD-L1-mediated suppression of T-cells in an in vitro assay. In another embodiment, the antigen binding site has any of the features or embodiments of concept 51 or 52.

In another embodiment, the antigen binding site blocks or inhibits PD-1 binding to PD-L1. In one embodiment, the antigen binding site blocks or inhibits CD80 binding to PD-L1.

Aspect 35. An immunocytokine according to any preceding aspect wherein the immunocytokine is capable of increasing IL-2R-mediated T-cell activation.

In one embodiment, the immunocytokine increases IL-2R-mediated T-cell activation. In one embodiment, the immunocytokine increases IL-2R-mediated T-cell activation in an in vitro assay.

Aspect 36. An immunocytokine according to aspect 34 or aspect 35, wherein the suppression of T-cells or the increase in IL-2R-mediated T-cell activation is measured by an increase in one or more of IFN$\gamma$, IL-2, CD25 or proliferation of T-cells in an assay that provides co-stimulation by either direct CD3/CD28 stimulation, superantigen stimulation or provides co-stimulation by co-incubation with cells capable of inducing a T-cell response.

The measurements may be carried out with any suitable technique. For example, the measurements may be taken with ELISA, HTRF, BRDU incorporation (proliferation), electrochemiluminescence (ECL) or flow cytometry (e.g. FACS). These techniques are well-known to those skilled in the art and are described elsewhere herein. In one embodiment, the assay is flow cytometry. In one embodiment, the assay is ELISA. In one embodiment, the assay is HTRF.

In this aspect, when aspect 36 is dependent on aspect 34, any of the features or embodiments of concept 36 apply mutatis mutandis.

When Aspect 36 is dependent on Aspect 35, in one embodiment, the increase in IL-2R-mediated T-cell activation is measured by an increase in one or both of IFNγ and CD25.

When Aspect 36 is dependent on Aspect 35, in one embodiment, the co-stimulation is provided by direct CD3/CD28 stimulation.

When Aspect 36 is dependent on Aspect 35, in one embodiment, the co-stimulation is provided by a superantigen, such as staphylococcal enterotoxin B (SEB).

When Aspect 36 is dependent on Aspect 35, in one embodiment, the assay provides co-stimulation by co-incubation with cells capable of inducing a T-cell response. Such cells may be antigen-presenting cells (APCs), for example monocytes, B-cells or dendritic cells. In one embodiment, the assay provides co-stimulation by co-incubation with APCs. In one embodiment, the assay provides co-stimulation by co-incubation with monocytes. In one embodiment, the assay provides co-stimulation by co-incubation with B-cells. In one embodiment, the assay provides co-stimulation by co-incubation with dendritic cells.

Aspect 37. An immunocytokine according to any preceding aspect which does not comprise a linker (L), or an immunocytokine according to any preceding claim wherein the $C_L$ of d) is directly fused to the cytokine of f).

In one embodiment, the $C_L$ of the light chain or the heavy chain is directly fused to the cytokine.

In one embodiment of aspect 1b, the $C_L$ of b) is directly fused to the cytokine of d).

Aspect 38. An immunocytokine according to any one of aspects 1 to 37, wherein the linker is a peptide linker of 1 to 20 amino acids in length.

In one embodiment, the linker is peptide linker of 1 to 15 amino acids in length. In one embodiment, the linker is peptide linker of 1 to 10 amino acids in length. In one embodiment, the linker is peptide linker of 1 to 5 amino acids in length.

In one embodiment, the linker may be a chemical linker. In the case of recombinant fusion proteins, the linkers are encoded by nucleic acid sequences located in frame, in between the coding regions for the different immunocytokine portions. In the case of synthetic proteins, the linker peptides are introduced during synthesis.

Linkers are well-known to those skilled in the art. For example, see described in Denardo et al., 1998, Clin. Cancer Res., 4(10):2483-90; Peterson et al., 1999, Bioconjug. Chem. 10(4):553-7; and Zimmerman et al., 1999, Nucl. Med. Biol., 26(8):943-50, the modifications described therein are incorporated herein by reference.

Aspect 39. An immunocytokine according to aspect 38, wherein the linker peptide is selected from poly-G or (G4S)x, wherein X is 1, 2, 3 or 4.

In other embodiments, the linker may be selected from STG, GSTG, RS, TVAAPS, GGGGS, GSTVAAPS, TVAAPSGS or GSTVAAPSGS. In another embodiment, the linker is Gln-Arg-Val-Asp (derived from N-terminus of canine kappa constant region). In another embodiment, the linker is GGNGT or YGNGT.

Aspect 40. An immunocytokine according to any preceding aspect wherein the IL-2 cytokine is human IL-2 (hIL-2) or a variant thereof.

IL-2 variants are as described in aspect 1.

There is also provided a variant cytokine, which may be any of the non-IL-2 cytokines described herein (including the non-IL-2 cytokines described in aspect 1, e.g. selected from IL-7, IL-15, IL-21, IL-12, GM-CSF, TNFα, CXCL9, CXCL10 and interferon-a). The definition of a variant IL-2 cytokine applies mutatis mutandis to the other cytokines (including immune stimulating cytokines and T-cell stimulating cytokines) described herein, e.g. comprising any of the N-terminal deletions described for IL-2 in aspect 1.

Aspect 41. An immunocytokine according to aspect 40, wherein the hIL-2 comprises or consists of the amino acid sequence of Seq ID No:301.

Aspect 42. An immunocytokine according to aspect 40, wherein the hIL-2 comprises a variant of IL-2 which comprises a modification at the N-terminus, optionally a deletion of from 1 to 10 amino acids.

As used in this aspect, a modification at the N-terminus of any of the cytokines described herein (including the non-IL-2 cytokines described in aspect 1, e.g. selected from IL-7, IL-15, IL-21, IL-12, GM-CSF, TNFα, CXCL9, CXCL10 and interferon-a) refers to one or more (such as 1 to 10, e.g. 1 to 5) amino acid substitutions, deletions or additions.

In one embodiment, the modification is one or more (such as 1 to 10, e.g. 1 to 5) amino acid substitutions at the N-terminus of the cytokine. Substitutions may be conservative substitutions, for example, as defined in concept 9, concept 29 or aspect 29. In one embodiment, the modification is a deletion. In another embodiment, the modification is an N-terminal deletion, for example, any of the deletions described in concept 9 and aspect 1. In one embodiment, the modification (such as a deletion of 1 to 10 amino acids) is within the final 50 amino acids of the N-terminus of the cytokine, e.g. the IL-2 cytokine. In one embodiment, the modification (such as a deletion of 1 to 10 amino acids) within the final 30 amino acids of the N-terminus of the cytokine, e.g. the IL-2 cytokine. In one embodiment, the modification (such as a deletion of 1 to 10 amino acids) within the final 25 amino acids of the N-terminus of the cytokine, e.g. the IL-2 cytokine. In one embodiment, the modification (such as a deletion of 1 to 10 amino acids) within the final 20 amino acids of the N-terminus of the cytokine, e.g. the IL-2 cytokine. In one embodiment, the modification (such as a deletion of 1 to 10 amino acids) within the final 15 amino acids of the N-terminus of the cytokine, e.g. the IL-2 cytokine. In one embodiment, the modification (such as a deletion of 1 to 10 amino acids) within the final 10 amino acids of the N-terminus of the cytokine, e.g. the IL-2 cytokine.

In one embodiment, the modification is a deletion of 1 to 9 amino acids from within the final 10 amino acids of the N-terminus of the cytokine, such as a deletion of the final 1 to 9 amino acids of the N-terminus of the cytokine. In one embodiment, the modification is a deletion of 1 to 8 amino acids from within the final 10 amino acids of the N-terminus of the cytokine, such as a deletion of the final 1 to 8 amino acids of the N-terminus of the cytokine. In one embodiment, the modification is a deletion of 1 to 7 amino acids from within the final 10 amino acids of the N-terminus of the cytokine, such as a deletion of the final 1 to 7 amino acids of the N-terminus of the cytokine. In one embodiment, the modification is a deletion of 1 to 6 amino acids from within the final 10 amino acids of the N-terminus of the cytokine, such as a deletion of the final 1 to 6 amino acids of the N-terminus of the cytokine. In one embodiment, the modification is a deletion of 1 to 5 amino acids from within the final 10 amino acids of the N-terminus of the cytokine, such as a deletion of the final 1 to 5 amino acids of the N-terminus of the cytokine. In one embodiment, the modification is a deletion of 1 to 4 amino acids from within the final 10 amino acids of the N-terminus of the cytokine, such as a deletion of the final 1 to 4 amino acids of the N-terminus of the cytokine. In one embodiment, the modification is a deletion of 1 to 3 amino acids from within the final 10 amino acids of the N-terminus of the cytokine, such as a deletion of the final 1 to 3 amino acids of the N-terminus of the cytokine. In one embodiment, the modification is a deletion of 1 or 2 amino acids from within the final 10 amino acids of the N-terminus of the cytokine, such as a deletion of the final 1 or 2 amino acids of the N-terminus of the cytokine. In one embodiment, the modification is a deletion of 1 amino acid from within the final 10 amino acids of the N-terminus of the cytokine, such as a deletion of the final amino acid of the N-terminus of the cytokine. In a particular embodiment, the cytokine is an IL-2 cytokine, such as a human IL-2 cytokine.

In one embodiment, the deletion is of the 9th amino acid from the N-terminus of the cytokine, e.g. the IL-2 cytokine, for example the human IL-2 cytokine. In one embodiment, the deletion is of the $8^{th}$ and $9^{th}$ amino acid from the N-terminus of the cytokine, e.g. the IL-2 cytokine, for example the human IL-2 cytokine. In one embodiment, the deletion is of the $7^{th}$, $8^{th}$ and $9^{th}$ amino acid from the N-terminus of the cytokine, e.g. the IL-2 cytokine, for example the human IL-2 cytokine. In one embodiment, the deletion is of the $6^{th}$ to $9^{th}$ amino acid from the N-terminus of the cytokine, e.g. the IL-2 cytokine, for example the human IL-2 cytokine. In one embodiment, the deletion is of the $4^{th}$ to $9^{th}$ amino acid from the N-terminus of the cytokine, e.g. the IL-2 cytokine, for example the human IL-2 cytokine. In one embodiment, the deletion is of the $3^{rd}$ to $9^{th}$ amino acid from the N-terminus of the cytokine, e.g. the IL-2 cytokine, for example the human IL-2 cytokine. In one embodiment, the deletion is of the $2^{nd}$ to $9^{th}$ amino acid from the N-terminus of the cytokine, e.g. the IL-2 cytokine, for example the human IL-2 cytokine. In one embodiment, the deletion is of the $2^{nd}$ to $6^{th}$ amino acid from the N-terminus of the cytokine, e.g. the IL-2 cytokine, for example the human IL-2 cytokine. In one embodiment, the deletion is of the $3^{rd}$ to $7^{th}$ amino acid from the N-terminus of the cytokine, e.g. the IL-2 cytokine, for example the human IL-2 cytokine. In one embodiment, the deletion is of the $4^{th}$ to $8^{th}$ amino acid from the N-terminus of the cytokine, e.g. the IL-2 cytokine, for example the human IL-2 cytokine. Any of the deletions described in Aspect 1 hereinabove may be applied mutatis mutandis to the non-IL-2 cytokines of this aspect.

Aspect 42a. A variant hIL-2 comprising an N-terminal modification of any of the aspects or features of aspect 42. In one embodiment of aspect 42a, the variant hIL-2 is a purified variant hIL-2. In another embodiment of aspect 42a, the variant hIL-2 is an isolated and purified variant hIL-2.

Aspect 42b. A variant cytokine selected from IL-7, IL-15, IL-21, IL-12, GM-CSF, TNFα, CXCL9, CXCL10 and interferon-α comprising an N-terminal modification of any of the aspects or features of aspect 42. In one embodiment of aspect 42a, the variant cytokine is a purified variant cytokine. In another embodiment of aspect 42a, the variant cytokine is an isolated and purified variant cytokine.

Aspect 43. An immunocytokine according to aspect 40 or aspect 42, wherein the hIL-2 comprises a variant IL-2 comprising an N-terminal sequence selected from Seq ID No:303 to 323.

Aspect 43a. A variant hIL-2 comprising an N-terminal sequence selected from Seq ID No:303 to 323.

In one embodiment of aspect 43a, the variant hIL-2 is a purified variant hIL-2. In another embodiment of aspect 43a, the variant hIL-2 is an isolated and purified variant hIL-2. In one embodiment, the variant hIL-2 comprises (or consists) of an N-term terminal sequence selected from Seq ID No:303 to 323 directly fused to an IL-2 sequence selected from Seq ID No:324, 517 and 518.

Aspect 44. An immunocytokine according to any one of aspects 40, 42 or 43 wherein the hIL-2 variant comprises one or more (such as 1 to 5, e.g. one or two) mutations independently selected from the following:
1) D20 (such as D20T);
2) R38 (such as R38W, R38A or R38Q);
3) F42 (such as F42A or F42K);
4) Y45 (such as Y45A);
5) E62 (such as E62A);
6) N88 (such as N88R);
7) C125 (such as C125S);
8) Q126 (such as Q126W); or
9) R38 and F42 (such as R38W and F42K or R38A and F42A);
wherein the residue numbering is defined with reference to the human wild-type IL-2 sequence, Seq ID No:301.

Aspect 44a. A variant hIL-2 according to any one of aspects 42a or 43a wherein the hIL-2 variant comprises one or more (such as 1 to 5, e.g. one or two) mutations independently selected from the following:
1) D20 (such as D20T);
2) R38 (such as R38W, R38A or R38Q);
3) F42 (such as F42A or F42K);
4) Y45 (such as Y45A);
5) E62 (such as E62A);
6) N88 (such as N88R);
7) C125 (such as C125S);
8) Q126 (such as Q126W); or
9) R38 and F42 (such as R38W and F42K or R38A and F42A);
wherein the residue numbering is defined with reference to the human wild-type IL-2 sequence, Seq ID No:301.

In one embodiment, the variant hIL-2 comprises (or consists) of an R38 (such as R38W, R38A or R38Q, e.g. R38A) mutation. In one embodiment, the variant hIL-2 comprises (or consists) of an F42 (such as F42A or F42K, e.g. F42A) mutation. In one embodiment, the variant hIL-2 comprises (or consists) or a Y45 (such as Y45A) mutation. In one embodiment, the variant hIL-2 comprises (or consists) of an E62 (such as E62A) mutation.

In one embodiment, the variant hIL-2 comprises (or consists) of an R38 (such as R38W, R38A or R38Q, e.g. R38A) mutation and an F42 (such as F42A or F42K, e.g. F42A) mutation. In one embodiment, the variant hIL-2 comprises (or consists) of an R38 (such as R38W, R38A or R38Q e.g. R38A) and a Y45 (such as Y45A) mutation. In one embodiment, the variant hIL-2 comprises (or consists) of an R38 (such as R38W, R38A or R38Q, e.g. R38A) mutation and an E62 (such as E62A). In one embodiment, the variant hIL-2 comprises (or consists) of a Y45 (such as Y45A) mutation and an E62 (such as E62A). In one embodiment, the variant hIL-2 comprises (or consists) of an F42 (such as F42A or F42K, e.g. F42A) mutation and an E62 (such as E62A) mutation. In one embodiment, the variant hIL-2 comprises (or consists) of an F42 (such as F42A or F42K, e.g. F42A) mutation and a Y45 (such as Y45A) mutation.

In one embodiment, the variant hIL-2 comprises (or consists) of an R38 (such as R38W, R38A or R38Q e.g. R38A) mutation, an F42 (such as F42A or F42K, e.g. F42A) mutation and a Y45 (such as Y45A) mutation. In one embodiment, the variant hIL-2 comprises (or consists) of an R38 (such as R38W, R38A or R38Q, e.g. R38A) mutation, an F42 (such as F42A or F42K, e.g. F42A) mutation and an E62 (such as E62A) mutation. In one embodiment, the variant hIL-2 comprises (or consists) of an R38 (such as R38W, R38A or R38Q; e.g. R38A) mutation, a Y45 (such as Y45A) mutation and an E62 (such as E62A) mutation.

In one embodiment, the variant hIL-2 comprises (or consists) of an R38 (such as R38W, R38A or R38Q e.g. R38A) mutation, an F42 (such as F42A or F42K, e.g. F42A) mutation, a Y45 (such as Y45A) mutation and an E62 (such as E62A) mutation. In one embodiment, the variant hIL-2 comprises (or consists) of an R38A, F42A, Y45A and an E62A mutation.

Other hIL-2 mutations are known to those skilled in the art. In one embodiment, the hIL-2 mutations are those described in WO2012/062228 (see claims 2 to 7, incorporated herein by reference). In one embodiment, the hIL-2 mutations are those described in WO1999/60128 (see claims 6, 7, 8, 10, 11 and 12 incorporated herein by reference). In one embodiment, the hIL-2 mutations are those described in WO1993/20849 (see claims 4 and 5 incorporated herein by reference). In one embodiment, the hIL-2 mutations are those described in WO2003/015697 (see claims 7 and 10 incorporated herein by reference). In one embodiment, the hIL-2 mutations are those described in WO2005/007121 (see claims 9 to 14 incorporated herein by reference). In one embodiment, the hIL-2 mutations are those described in WO2005/086798 (see claims 5 to 10 incorporated herein by reference). In one embodiment, the hIL-2 mutations are those described in WO2005/086751 (see claims 5 to 9 incorporated herein by reference). In one embodiment, the hIL-2 mutations are those described in WO2009/061853 (see claim 5 incorporated herein by reference). In one embodiment, the hIL-2 mutations are those described in WO2012/088446 (see claims 3 to 8 and 11 to 13 incorporated herein by reference). In one embodiment, the hIL-2 mutations are those described in WO2012/107417 (see claims 2, 4, 6 and 9, incorporated herein by reference). In one embodiment, the hIL-2 mutations are those described in WO2012/119093 (see claims 1 to 7, incorporated herein by reference). In one embodiment, the hIL-2 mutations are those described in WO2015/164815 (see claims 3 to 19, incorporated herein by reference).

In these aspects, where the residue numbering is defined with reference to the human wild-type IL-2 sequence, if, for example, there is a single amino acid deletion from the N-terminus of the cytokine, and the claim described an N88 amino acid mutation, then, for the variant IL-2 having the single amino acid deletion, the N will in fact be at position 87. If the cytokine has 3 amino acids deleted from the N-terminus, and the mutation is an F42A mutation, then the position to be mutated, will in fact be F39 in the variant sequence.

Aspect 45. An immunocytokine according to aspect 40, wherein the hIL-2 comprises a variant IL-2 consists of an N-terminal sequence selected from Seq ID No:242 to 262 fused to the amino acid sequence of Seq ID No:324.

In one embodiment, the variant hIL-2 comprises (or consists) of an N-terminal sequence selected from Seq ID No:303 to 323 fused to the amino acid sequence selected from Seq ID No:324, 517 and 518.

In one embodiment, the immunocytokine is 1D05 D1-9 ICK. In one embodiment, the immunocytokine is 1D05 D1-9. In one embodiment, the immunocytokine is 1D05 D9-2 ICK. In one embodiment, the immunocytokine is 1D05 D9-7 ICK.

Aspect 45a. A variant hIL-2 comprising an N-terminal sequence selected from Seq ID No:303 to 323 fused to the amino acids sequence of Seq ID No:324.

In one embodiment of aspect 45a, the variant hIL-2 is a purified variant hIL-2. In another embodiment of aspect 44a, the variant hIL-2 is an isolated and purified variant hIL-2.

Aspect 46. An immunocytokine according to any preceding aspect, wherein the IL-2 cytokine binds to the high affinity (αβγ) IL-2 receptor with a potency less than free IL-2, for example with an $EC_{50}$ of greater than 20 pM, greater than 50 pM or greater than 100 pM, e.g. when measured in a cell-based proliferative assay.

Free IL-2 has a potency of approximately 10 μM against the αβγ (high affinity) receptor in a cell-based proliferative assay. As used herein, $EC_{50}$ refers to the effective concentration to give 50% of maximal activation of the IL2R. The higher the $EC_{50}$, the less potent the substance is, thus a substance having an $EC_{50}$ of 1 μM is more potent than a substance with an $EC_{50}$ of 1 nM. The sequences of the α-chain, β-chain and γ-chain are provided in Seq ID Nos: 327, 328 and 329 respectively.

In one embodiment, the IL-2 cytokine has an $EC_{50}$ in the range of 5 pM to 20 pM. In one embodiment, the $EC_{50}$ is in the range of 5 pM to 1 nM. In one embodiment, the $EC_{50}$ is in the range of 5 pM to 750 pM, 5 pM to 500 pM, 5 pm to 250 pM or 5 pM to 100 pM, e.g. 5 pM to 50 pM.

In one embodiment, the $EC_{50}$ is in the range of 10 pM to 1 nM. In one embodiment, the $EC_{50}$ is in the range of 10 pM to 750 pM, 10 pM to 500 pM, 10 pM to 250 pM or 10 pm to 100 pM, e.g. 10 pM to 50 pM, or 10 pM to 30 pM.

In one embodiment, the $EC_{50}$ is in the range of 20 pM to 1 nM. In one embodiment, the $EC_{50}$ is in the range of 20 pM to 750 pM, 20 pM to 500 pM, 20 pM to 250 pM or 20 pm to 100 pM, e.g. 20 pM to 50 pM.

In another embodiment, the IL-2 cytokine has an $EC_{50}$ in the range of 50 pM to 1 nM. In one embodiment, the $EC_{50}$ is in the range of 50 pM to 750 pM, 50 pM to 500 pM, 50 pM to 250 pM or 50 pm to 100 pM, e.g. 50 pM to 75 pM. In another embodiment, the IL-2 cytokine has an $EC_{50}$ in the range of 100 pM to 1 nM. In one embodiment, the $EC_{50}$ is in the range of 100 pM to 800 pM, 100 pM to 700 pM, 100 pM to 600 pM or 100 pm to 500 pM, e.g. 100 pM to 400 pM. In another embodiment, the IL-2 cytokine has an $EC_{50}$ in the range of 100 pm to 300 pM. In another embodiment, the IL-2 cytokine has an $EC_{50}$ in the range of 100 pm to 200 pM.

In another embodiment, the $EC_{50}$ is greater than 5 pM. In another embodiment, the $EC_{50}$ is greater than 10 pM. In another embodiment, the $EC_{50}$ is greater than 20 pM. In another embodiment, the $EC_{50}$ is greater than 30 pM, greater than 40 pM, greater than 50 pM, greater than 60 pM or greater than 70 pM. In another embodiment, the $EC_{50}$ is greater than 100 pM, greater than 125 pM, greater than 150 pM, greater than 175 pM or greater than 200 pM. In another embodiment, the $EC_{50}$ is greater than 250 pM, greater than 300 pM, greater than 350 pM, greater than 400 pM. In another embodiment, the $EC_{50}$ is greater than 500 pM, greater than 600 pM, greater than 700 pM or greater than 800 pM.

In one embodiment, the $EC_{50}$ is less than 5 nM. In one embodiment, the $EC_{50}$ is less than 1 nM. In one embodiment, the $EC_{50}$ is less than 800 pM. In one embodiment, the $EC_{50}$ is less than 700 pM. In one embodiment, the $EC_{50}$ is less than 600 pM. In one embodiment, the $EC_{50}$ is less than 500 pM. In one embodiment, the $EC_{50}$ is less than 400 pM. In one embodiment, the $EC_{50}$ is less than 300 pM. In one embodiment, the $EC_{50}$ is less than 200 pM. In one embodiment, the $EC_{50}$ is less than 100 pM. In one embodiment, the $EC_{50}$ is less than 50 pM.

The potency of the immunocytokine against the αβγ IL-2R may be measured in a cell-based proliferative assay, which are well-known to those skilled in the art and are detailed more in the Examples hereinbelow (see Example 13 and FIG. 12).

Aspect 47. An immunocytokine according to any preceding aspect, wherein the IL-2 binds to the intermediate affinity (βγ) IL-2 receptor with a potency less than free IL-2, for example with an $EC_{50}$ of greater than 1 nM, greater than 5 nM or greater than 10 nM, e.g. when measured in a cell-based proliferative assay.

Free IL-2 has a potency of approximately 100 pM against the βγ (intermediate affinity) receptor in a cell-based proliferative assay. As used herein, $EC_{50}$ refers to the effective concentration to give 50% of maximal activation of the IL-2R. The higher the $EC_{50}$, the less potent the substance is, thus a substance having an $EC_{50}$ of 1 pM is more potent than a substance with an $EC_{50}$ of 1 nM. The sequences of the α-chain, β-chain and γ-chain are provided in Seq ID Nos: 327, 328 and 329 respectively.

In one embodiment, the $EC_{50}$ is in the range of 1 to 100 nM. In one embodiment, the $EC_{50}$ is in the range of 10 nM to 100 nM. In one embodiment, the $EC_{50}$ is in the range of 20 nM to 100 nM. In another embodiment, the IL-2 cytokine has an $EC_{50}$ in the range of 30 nM to 100 nM, 40 nM to 100 nM, 50 nM to 100 nM. In one embodiment, the $EC_{50}$ is in the range of 50 nM to 100 nM, 60 nM to 100 nM, 70 nM to 100 nM.

In one embodiment, the $EC_{50}$ is in the range of 1 to 50 nM. In one embodiment, the $EC_{50}$ is in the range of 10 nM to 50 nM. In one embodiment, the $EC_{50}$ is in the range of 20 nM to 50 nM. In another embodiment; the IL-2 cytokine has an $EC_{50}$ in the range of 30 nM to 50 nM or 40 nM to 50 nM.

In one embodiment, the $EC_{50}$ is in the range of 1 to 10 nM. In one embodiment, the $EC_{50}$ is in the range of 1 to 20 nM. In one embodiment, the $EC_{50}$ is in the range of 1 to 30 nM. In one embodiment, the $EC_{50}$ is in the range of 1 nM to 9 nM. In one embodiment, the $EC_{50}$ is in the range of 1 nM to 8 nM. In another embodiment, the IL-2 cytokine has an $EC_{50}$ in the range of 1 nM to 7 nM, 1 nM to 6 nM or 1 nM to 5 nM.

In another embodiment, the $EC_{50}$ is greater than 0.5 nM, greater than 0.6 nM, greater than 0.7 nM, greater than 0.8 nM or greater than 0.9 nM. In another embodiment, the $EC_{50}$ is greater than 1 nM, greater than 1.25 nM, greater than 1.5 nM, greater than 1.75 nM or greater than 2 nM. In another embodiment, the $EC_{50}$ is greater than 2.5 nM, greater than 3 nM, greater than 3.5 nM or greater than 4 nM. In another embodiment, the $EC_{50}$ is greater than 5 nM, greater than 6 nM, greater than 7 nM or greater than 8 nM. In a particular embodiment, the $EC_{50}$ is greater than 1 nM.

In one embodiment, the $EC_{50}$ is less than 10 nM. In one embodiment, the $EC_{50}$ is less than 20 nM. In one embodiment, the $EC_{50}$ is less than 30 nM. In one embodiment, the $EC_{50}$ is less than 40 nM. In one embodiment, the $EC_{50}$ is less than 50 nM.

In one embodiment, the $EC_{50}$ is less than 100 nM. In one embodiment, the $EC_{50}$ is less than 200 nM. In one embodiment, the $EC_{50}$ is less than 300 nM.

In another embodiment, the $EC_{50}$ is less than 75 nM or less than 50 nM.

In one embodiment, the IL-2 shows no detectable potency against the βγ IL-2R in a cell-based proliferative assay.

The potency of the immunocytokine against the βγ IL-2R may be measured in a cell-based proliferative assay, which are well-known to those skilled in the art and are detailed more in the Examples hereinbelow (see Example 13 and FIG. 12).

Aspect 48. An immunocytokine according to any preceding aspect, wherein the IL-2 preferentially binds to the high affinity (αβγ) IL-2 receptor over the intermediate affinity (βγ) IL-2 receptor.

Aspect 49. An immunocytokine according to aspect 48, wherein the ratio of IL-2 potency against the high affinity (αβγ) IL-2 receptor:intermediate affinity (βγ) IL-2 receptor is at least 2:1.

In one embodiment, the ratio is at least 3:1. In one embodiment, the ratio is at least 4:1. In one embodiment, the ratio is at least 5:1. In one embodiment, the ratio is at least 7.5:1. In one embodiment, the ratio is at least 10:1. In one embodiment, the ratio is at least 12.5:1. In one embodiment, the ratio is at least 15:1. In one embodiment, the ratio is at least 17.5:1. In one embodiment, the ratio is at least 20:1.

In another embodiment, the ratio is at least 50:1. In another embodiment, the ratio is at least 75:1. In another embodiment, the ratio is at least 100:1. In another embodiment, the ratio is at least 250:1. In another embodiment, the ratio is at least 500:1. In another embodiment, the ratio is at least 750:1. In another embodiment, the ratio is at least 1000:1.

In another embodiment, the ratio is at least 1250:1. In another embodiment, the ratio is at least 1500:1. In another embodiment, the ratio is at least 1750:1. In another embodiment, the ratio is at least 2000:1.

Aspect 50. An immunocytokine according to any preceding aspect, wherein the antigen binding site binds to hPD-L1 with an affinity of less than 500 pM (e.g. less than 300 pM or less than 200 pM), optionally wherein the immunocytokine provides a ratio of the potency of the IL-2 cytokine against the high affinity (αβγ) receptor: affinity of the anti-PD-L1 antigen binding site against hPD-L1 of at least 2:1.

In one embodiment, the antigen binding site binds to hPD-L1 with an affinity of less than 200 pM. In one embodiment, the antigen binding site binds to hPD-L1 with an affinity of less than 100 pM, or less than 50 pM.

In one embodiment, the antigen binding site binds to hPD-L1 with an affinity of between 50 pM and 500 pM, or between 75 pM and 500 pM, or between 100 pM and 500 pM or between 200 pM and 500 pM.

In one embodiment, the antigen binding site binds to hPD-L1 with an affinity of between 50 pM and 400 pM, or between 50 pM and 300 pM, or between 50 pM and 200 pM or between 50 pM and 100 pM.

In one embodiment, the antigen binding site binds to hPD-L1 with an affinity of between 100 pM and 500 pM, or between 100 pM and 400 pM, or between 100 pM and 300 pM. In one embodiment, the ratio of the potency of the IL-2 cytokine against the high affinity (αβγ) receptor: affinity of the anti-PD-L1 antigen binding site against hPD-L1 is at least 3:1. In one embodiment, the ratio of the potency of the IL-2 cytokine against the high affinity (αβγ) receptor: affinity of the anti-PD-L1 antigen binding site against hPD-L1 is at least 4:1. In one embodiment, the ratio of the potency of the IL-2 cytokine against the high affinity (αβγ) receptor: affinity of the anti-PD-L1 antigen binding site against hPD-L1 is at least 5:1. In one embodiment, the ratio of the potency of the IL-2 cytokine against the high affinity (αβγ) receptor: affinity of the anti-PD-L1 antigen binding site against hPD-L1 is at least 7:1. In one embodiment, the ratio of the potency of the IL-2 cytokine against the high affinity (αβγ) receptor: affinity of the anti-PD-L1 antigen binding site against hPD-L1 is at least 10:1.

Any of the half-life, $K_{ON}$ rates, $K_{OFF}$ rates, or binding characteristics of the anti-PD-L1 antibodies in concepts 1 to 40 applu mutatis mutandis to the immunocytokines disclosed herein.

Aspect 50a. An immunocytokine according to any preceding aspect, wherein the antigen binding site binds to mPD-L1 (Seq ID No:325) with an affinity of less than 500 nM (e.g. less than 100 nM, less than 10 nM or less than 1 nm).

In one embodiment, the antigen binding site binds to hPD-L1 with an affinity of between 1 nM and 500 nM, or between 1 nM and 250 nM, or between 1 nM and 100 nM, or between 1 nM and 50 nM.

In one embodiment, the antigen binding site binds to hPD-L1 with an affinity of between 10 nM and 500 nM, or between 10 nM and 250 nM, or between 10 nM and 100 nM, or between 1 nM and 50 nM, in particular between 10 nM and 100 nM.

In one embodiment, the antigen binding site binds to hPD-L1 with an affinity of between 100 nM and 500 nM, or between 100 nM and 400 nM, or between 100 nM and 300 nM, or between 100 nM and 200 nM.

The affinity of the antigen-binding site to hPD-L1 or mPD-L1 may be measured by any technique well-known to those skilled in the art. In one embodiment, the affinity is measured using SPR, the details of which are provided hereinabove.

Aspect 51. An immunocytokine as defined in any preceding aspect for use in treating or preventing a hPD-L1-mediated disease or condition, e.g. selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas).

Aspect 52. Use of an immunocytokine as defined in any one of aspects 1 to 50 in the manufacture of a medicament for administration to a human for treating or preventing a hPD-L1 mediated disease or condition in the human, e.g. wherein the hPD-L1 mediated disease or condition is selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas).

Aspect 53. A method of treating or preventing a hPD-L1 mediated disease or condition, e.g. selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas) in a human, comprising administering to said human a therapeutically effective amount of an immunocytokine as defined in any one of aspects 1 to 50, wherein the hPD-L1 mediated disease or condition is thereby treated or prevented.

In any of aspects 51 to 53, the hPD-L1 mediated disease may be any of those as described herein. In one embodiment, in any of aspects 51 to 53, the hPD-L1 mediated disease is a virally induced cancer, such as cervical cancer and nasopharyngeal cancer, for example cervical cancers caused by HPV infection. In one embodiment, in any of aspects 51 to 53, the hPD-L1 mediated disease is a chronic viral infection. In one embodiment, in any of aspects 51 to 53, the hPD-L1 mediated disease is a neoplastic disease. In one embodiment, in any of aspects 51 to 53, the hPD-L1 mediated disease is a non-neoplastic disease. In one embodiment, in any of aspects 51 to 53, the hPD-L1 mediated disease is a malignant tumour. In one embodiment, in any of aspects 51 to 53, the hPD-L1 mediated disease is a cancer which is known to be responsive to PD-L1 therapy, such as melanoma, Merkel cell carcinoma, non-small cell lung cancer (squamous and non-squamous), renal cell cancer, bladder cancer, head and neck squamous cell carcinoma, mesothelioma. In one embodiment, in any of aspects 51 to 53, the hPD-L1 mediated disease is a cancer which is a soft tissue sarcoma. In one embodiment, in any of aspects 51 to 53, the hPD-L1 mediated disease is a neurodegenerative disease, disorder or condition, optionally wherein the neurodegenerative disease, disorder or condition is selected from Alzheimer's disease, amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia, in particular Alzheimer's disease, amyotrophic lateral sclerosis, Parkinson's disease and Huntington's disease, and e.g. Alzheimer's disease.

Aspect 54. The immunocytokine according to aspect 51, the use according to aspect 52 or the method according to aspect 53, wherein the hPD-L1-mediated disease or condition is cancer.

Aspect 55. The immunocytokine, the use or the method according to aspect 54, wherein the cancer is selected from melanoma, Merkel cell cancer, non-small cell lung cancer, bladder cancer, Non-Hodgkin's lymphomas, colorectal cancer with microsatellite instability (MSI) or a cancer selected from breast cancer, ovarian cancer, colorectal cancer (without MSI or microsatellite instability), in particular melanoma and renal cell cancer.

In one embodiment, the cancer is a cancer which is known to be responsive to both IL-2 therapy and PD-L1 therapy, such as melanoma and renal cell cancer.

In one embodiment, the cancer is colorectal cancer with microsatellite instability (MSI). In one embodiment, the cancer is breast cancer. In one embodiment, the cancer is ovarian cancer.

Aspect 56. The immunocytokine, use or the method according to any one of aspects 51 to 55, further comprising administering to the human a further therapy, for example a further therapeutic agent, optionally wherein the further therapeutic agent is independently selected from the group consisting of:
  A) other immune checkpoint inhibitors (such as anti-TIM-3 antibodies, anti-CTLA-4 antibodies, anti-TIGIT antibodies and anti-LAG-3 antibodies);
  B) immune stimulators (such as anti-OX40 antibodies, anti-GITR antibodies, anti-CD137 antibodies, anti-ICOS antibodies and anti-CD40 antibodies);
  C) chemokine receptor antagonists (such as CXCR4, CCR4 and CXCR2);
  D) targeted kinase inhibitors (such as CSF-1R or VEGFR inhibitors);
  E) angiogenesis inhibitors (such as anti-VEGF-A or Delta-like Ligand-4);
  F) immune stimulating peptides or chemokines (such as CXCL9 or CXCL10);
  G) cytokines (such as IL-15 and IL-21);
  H) bispecific T-cell engagers (BiTEs) having at least one specificity against CD3 (e.g. CD3/CD19 BiTE);
  I) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
  J) oncolytic viruses (such as HSV virus (optionally which secretes GMCSF), Newcastle disease virus and Vaccinia virus);
  K) vaccination with tumour associated antigens (such as New York Esophageal Cancer-1 [NY-ESO-1], Melanoma Associated Antigen-3 [MAGE-3]);
  L) cell-based therapies (such as chimeric Antigen Receptor-T-cells (CAR-T) for example expressing anti-CD19, anti-EpCam or anti-mesothelin);
  M) bi-specific NK cell engagers having a specificity against an activating MK receptor such as NKG2D or CD16a; and
  N) adoptive transfer of tumour specific T-cells or LAK cells,
  or optionally wherein the further therapy is chemotherapy, radiotherapy and surgical removal of tumours.

Radiotherapy may be single dose or in fractionated doses, either delivered to affected tissues directly or to the whole body.

In this aspect, any of the features and embodiments of concept 46 apply mutatis mutandis In this aspect, the bispecific molecules include "bispecific antibodies" and antibody fusion proteins, including those formats and molecules described in concepts 37 to 40.

The antibodies may be any of the sequences or antibodies described in arrangement 5, 5a or detailed in Aspect 1a.

Aspect 57. A pharmaceutical composition comprising an immunocytokine as defined in any one of aspects 1 to 50 and a pharmaceutically acceptable excipient, diluent or carrier and optionally further comprising a further therapeutic agent independently selected from the group consisting of:
  A) other immune checkpoint inhibitors (such as anti-TIM-3 antibodies, anti-CTLA-4 antibodies, anti-TIGIT antibodies and anti-LAG-3 antibodies);
  B) immune stimulators (such as anti-OX40 antibodies, anti-G1TR antibodies, anti-CD137 antibodies, anti-ICOS antibodies and anti-CD40 antibodies);
  C) chemokine receptor antagonists (such as CXCR4, CCR4 and CXCR2);
  D) targeted kinase inhibitors (such as CSF-1R or VEGFR inhibitors);
  E) angiogenesis inhibitors (such as anti-VEGF-A or Delta-like Ligand-4);
  F) immune stimulating peptides or chemokines (such as CXCL9 or CXCL10);
  G) cytokines (such as IL-15 and IL-21);
  H) bispecific T-cell engagers (BiTEs) having at least one specificity against CD3 (e.g. CD3/CD19 BiTE);
  I) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
  J) oncolytic viruses (such as HSV virus (optionally which secretes GMCSF), Newcastle disease virus and Vaccinia virus);
  K) vaccination with tumour associated antigens (such as New York Esophageal Cancer-1 [NY-ESO-1], Melanoma Associated Antigen-3 [MAGE-3]);
  L) cell-based therapies (such as chimeric Antigen Receptor-T-cells (CAR-T) for example expressing anti-CD19, anti-EpCam or anti-mesothelin);

M) bi-specific NK cell engagers having a specificity against an activating MK receptor such as NKG2D or CD16a; and N) adoptive transfer of tumour specific T-cells or LAK cells.

In one embodiment, the further therapeutic agent is administered sequentially or simultaneously with the immunocytokine.

In this aspect, any of the features and embodiments of concept 48 apply mutatis mutandis In this aspect, the bispecific molecules include "bispecific antibodies" and antibody fusion proteins, including those formats and molecules described in concepts 37 to 40.

The antibodies may be any of the sequences or antibodies described in arrangement 5, 5a or detailed in Aspect 1a.

Aspect 58. A pharmaceutical composition according to aspect 57, or a kit comprising a pharmaceutical composition as defined in aspect 57, wherein the composition is for treating and/or preventing a hPD-L 1 mediated disease or condition, e.g. selected from neoplastic or non-neoplastic disease, chronic viral infections, and malignant tumours, such as melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma (for example melanoma, breast cancer, ovarian cancer, Merkel cell carcinoma, non-small cell lung cancer (squamous and non-squamous), renal cell cancer, bladder cancer, colorectal cancer (without MSI or microsatellite instability), head and neck squamous cell carcinoma and mesothelioma or for example virally induced cancers (such as cervical cancer and nasopharyngeal cancer) and soft tissue sarcomas).

Aspect 59. A pharmaceutical composition according to aspect 57 or aspect 58 in combination with, or kit according to aspect 58 comprising a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the immunocytokine.

Aspect 60. A method of treating a proliferative disease in an animal (e.g. a human), comprising administering an effective amount of an immunocytokine as defined in any one of aspects 1 to 50 to said patient.

Proliferative diseases may be any as described elsewhere herein.

Aspect 61. A nucleic acid that encodes a heavy chain and/or a light chain of an immunocytokine as defined in any one of aspects 1 to 50.

In one embodiment, the nucleic acid encodes a light chain of an immunocytokine as defined in any one of aspects 1 to 50.

Aspect 62. A vector comprising the nucleic acid as defined in aspect 61; optionally wherein the vector is a CHO or HEK293 vector:

Aspect 63. A host comprising the nucleic acid as defined in aspect 61 or the vector as defined in aspect 62.

4. ICOS Antibodies

ICOS antibodies are provided herein. The ICOS antibodies may be any of those described in GB patent application 1620414.1 (filed 1 Dec. 2016), the sequences of the anti-ICOS antibodies disclosed therein are incorporated herein by reference.

STIM001 has a heavy chain variable region ($V_H$) amino acid sequence of Seq ID No:366, comprising the CDRH1 amino acid sequence of Seq ID No:363, the CDRH2 amino acid sequence of Seq ID No:364, and the CDRH3 amino acid sequence of Seq ID No:365. The heavy chain nucleic acid sequence of the $V_H$ domain is Seq ID No:367. STIM001 has a light chain variable region ($V_L$) amino acid sequence of Seq ID No:373, comprising the CDRL1 amino acid sequence of Seq ID No:370, the CDRL2 amino acid sequence of Seq ID No:371, and the CDRL3 amino acid sequence of Seq ID No:372. The light chain nucleic acid sequence of the $V_L$ domain is Seq ID No:374. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:368 (heavy chain nucleic acid sequence Seq ID No:369). A full length light chain amino acid sequence is Seq ID No:375 (light chain nucleic acid sequence Seq ID No:376).

STIM002 has a heavy chain variable region ($V_H$) amino acid sequence of Seq ID No:380, comprising the CDRH1 amino acid sequence of Seq ID No:377, the CDRH2 amino acid sequence of Seq ID No:378, and the CDRH3 amino acid sequence of Seq ID No:379. The heavy chain nucleic acid sequence of the $V_H$ domain is Seq ID No:381. STIM002 has a light chain variable region ($V_L$) amino acid sequence of Seq ID No:387, comprising the CDRL1 amino acid sequence of Seq ID No:384, the CDRL2 amino acid sequence of Seq ID No:385, and the CDRL3 amino acid sequence of Seq ID No:386. The light chain nucleic acid sequence of the $V_L$ domain is Seq ID No:388 or Seq ID No:519. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:382 (heavy chain nucleic acid sequence Seq ID No:383). A full length light chain amino acid sequence is Seq ID No:389 (light chain nucleic acid sequence Seq ID No:390 or Seq ID No:520).

STIM002-B has a heavy chain variable region ($V_H$) amino acid sequence of Seq ID No:394, comprising the CDRH1 amino acid sequence of Seq ID No:391, the CDRH2 amino acid sequence of Seq ID No:392, and the CDRH3 amino acid sequence of Seq ID No:393. The heavy chain nucleic acid sequence of the $V_H$ domain is Seq ID No:395. STIM002-B has a light chain variable region (Vi) amino acid sequence of Seq ID No:401, comprising the CDRL1 amino acid sequence of Seq ID No:398, the CDRL2 amino acid sequence of Seq ID No:399, and the CDRL3 amino acid sequence of Seq ID No:400. The light chain nucleic acid sequence of the $V_L$ domain is Seq ID No:402.

The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:396 (heavy chain nucleic acid sequence Seq ID No:397). A full length light chain amino acid sequence is Seq ID No:403 (light chain nucleic acid sequence Seq ID No:404).

STIM003 has a heavy chain variable region (V$_H$) amino acid sequence of Seq ID No:408, comprising the CDRH1 amino acid sequence of Seq ID No:405, the CDRH2 amino acid sequence of Seq ID No:406, and the CDRH3 amino acid sequence of Seq ID No:407. The heavy chain nucleic acid sequence of the V$_H$ domain is Seq ID No:409 or Seq ID No:521. STIM003 has a light chain variable region (V$_L$) amino acid sequence of Seq ID No:415, comprising the CDRL1 amino acid sequence of Seq ID No:412, the CDRL2 amino acid sequence of Seq ID No:413, and the CDRL3 amino acid sequence of Seq ID No:414. The light chain nucleic acid sequence of the V$_L$ domain is Seq ID No:4416. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:410 (heavy chain nucleic acid sequence Seq ID No:411 or Seq ID No:522). A full length light chain amino acid sequence is Seq ID No:417 (light chain nucleic acid sequence Seq ID No:418).

STIM004 has a heavy chain variable region (V$_H$) amino acid sequence of Seq ID No:422, comprising the CDRH1 amino acid sequence of Seq ID No:419, the CDRH2 amino acid sequence of Seq ID No:420, and the CDRH3 amino add sequence of Seq ID No:421. The heavy chain nucleic acid sequence of the V$_H$ domain is Seq ID No:423. STIM004 has a light chain variable region (V$_L$) amino acid sequence of Seq ID No:429, comprising the CDRL1 amino acid sequence of Seq ID No:426, the CDRL2 amino acid sequence of Seq ID No:427, and the CDRL3 amino acid sequence of Seq ID No:428. The light chain nucleic acid sequence of the V$_L$ domain is Seq ID No:430 or Seq ID No:431. The VH domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino add sequence is Seq ID No:424 (heavy chain nucleic acid sequence Seq ID No:425). A full length light chain amino add sequence is Seq ID No:432 (light chain nucleic acid sequence Seq ID No:433 or Seq ID no: 434).

STIM005 has a heavy chain variable region (V$_H$) amino acid sequence of Seq ID No:438, comprising the CDRH1 amino add sequence of Seq ID No:435, the CDRH2 amino acid sequence of Seq ID No:436, and the CDRH3 amino acid sequence of Seq ID No:437. The heavy chain nucleic acid sequence of the V$_H$ domain is Seq ID No:439. STIM005 has a light chain variable region (V$_L$) amino acid sequence of Seq ID No:445, comprising the CDRL1 amino acid sequence of Seq ID No:442, the CDRL2 amino acid sequence of Seq ID No:443, and the CDRL3 amino acid sequence of Seq ID No:444. The light chain nucleic acid sequence of the V$_L$ domain is Seq ID No:446. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino add sequence is Seq ID No:440 (heavy chain nucleic acid sequence Seq ID No:441). A full length light chain amino acid sequence is Seq ID No:447 (light chain nucleic add sequence Seq ID No:448).

STIM006 has a heavy chain variable region (V$_H$) amino acid sequence of Seq ID No:452, comprising the CDRH1 amino acid sequence of Seq ID No:449, the CDRH2 amino acid sequence of Seq ID No:450, and the CDRH3 amino acid sequence of Seq ID No:451. The heavy chain nucleic acid sequence of the V$_H$ domain is Seq ID No:453. STIM006 has a light chain variable region (V$_L$) amino acid sequence of Seq ID No:459, comprising the CDRL1 amino acid sequence of Seq ID No:456, the CDRL2 amino acid sequence of Seq ID No:457, and the CDRL3 amino acid sequence of Seq ID No:458. The light chain nucleic acid sequence of the V$_L$ domain is Seq ID No:460. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The V$_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:454 (heavy chain nucleic acid sequence Seq ID No:455). A full length light chain amino acid sequence is Seq ID No:461 (light chain nucleic acid sequence Seq ID No:462).

STIM007 has a heavy chain variable region (V$_H$) amino acid sequence of Seq ID No:466, comprising the CDRH1 amino acid sequence of Seq ID No:463, the CDRH2 amino acid sequence of Seq ID No:464, and the CDRH3 amino add sequence of Seq ID No:465. The heavy chain nucleic acid sequence of the V$_H$ domain is Seq ID No:467. STIM007 has a light chain variable region (V$_L$) amino acid sequence of Seq ID No:473, comprising the CDRL1 amino acid sequence of Seq ID No:470, the CDRL2 amino acid sequence of Seq ID No:471, and the CDRL3 amino acid sequence of Seq ID No:472. The light chain nucleic acid sequence of the V$_L$ domain is Seq ID No:474. The V$_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:468 (heavy chain nucleic acid sequence Seq ID No:469). A full length light chain amino acid sequence is Seq ID No:475 (light chain nucleic acid sequence Seq ID No:476).

STIM008 has a heavy chain variable region ($V_H$) amino acid sequence of Seq ID No:480, comprising the CDRH1 amino acid sequence of Seq ID No:477, the CDRH2 amino acid sequence of Seq ID No:478, and the CDRH3 amino acid sequence of Seq ID No:479. The heavy chain nucleic acid sequence of the $V_H$ domain is Seq ID No:481. STIM008 has a light chain variable region ($V_L$) amino acid sequence of Seq ID No:487, comprising the CDRL1 amino acid sequence of Seq ID No:484, the CDRL2 amino acid sequence of Seq ID No:485, and the CDRL3 amino acid sequence of Seq ID No:486. The light chain nucleic add sequence of the $V_L$ domain is Seq ID No:488. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:482 (heavy chain nucleic acid sequence Seq ID No:483). A full length light chain amino acid sequence is Seq ID No:489 (light chain nucleic acid sequence Seq ID No:490).

STIM009 has a heavy chain variable region ($V_H$) amino acid sequence of Seq ID No:494, comprising the CDRH1 amino acid sequence of Seq ID No:491, the CDRH2 amino acid sequence of Seq ID No:492, and the CDRH3 amino acid sequence of Seq ID No:493. The heavy chain nucleic acid sequence of the $V_H$ domain is Seq ID No:495. STIM009 has a light chain variable region ($V_L$) amino acid sequence of Seq ID No:501, comprising the CDRL1 amino acid sequence of Seq ID No:498, the CDRL2 amino acid sequence of Seq ID No:499, and the CDRL3 amino acid sequence of Seq ID No:500. The light chain nucleic acid sequence of the $V_L$ domain is Seq ID No:502. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:496 (heavy chain nucleic acid sequence Seq ID No:497). A full length light chain amino acid sequence is Seq ID No:503 (light chain nucleic acid sequence Seq ID No:504).

Antibodies STIM001-009 are described in more detail in GB patent application 1620414.1 (filed 1 Dec. 2016), the contents of which are incorporated herein by reference. ICOS antibodies may also be described as in the following numbered sentences below:

Sentence 1. An isolated antibody that binds the extracellular domain of human and/or mouse ICOS, comprising:
an antibody $V_H$ domain comprising complementarity determining regions (CDRs) HCDR1, HCDR2 and HCDR3, and
an antibody $V_L$ domain comprising complementarity determining regions LCDR1, LCDR2 and LCDR3, wherein
HCDR1 is the HCDR1 of STIM001, STIM002, STIM002-B, STIM003, STIM004, STIM005, STIM006, STIM007, STIM008 or STIM009, or comprises that HCDR1 with 1, 2, 3, 4 or 5 amino acid alterations,
HCDR2 is the HCDR2 of STIM001, STIM002, STIM002-B, STIM003, STIM004, STIM005, STIM006, STIM007, STIM008 or STIM009, or comprises that HCDR2 with 1, 2, 3, 4 or 5 amino acid alterations, and/or
HCDR3 is the HCDR3 of STIM001, STIM002, STIM002-B, STIM003, STIM004, STIM005, STIM006, STIM007, STIM008 or STIM009 or comprises that HCDR3 with 1, 2, 3, 4 or 5 amino acid alterations.

Sentence 2. An antibody according to sentence 1, wherein the antibody heavy chain CDRs are those of STIM001, STIM002, STIM002-B, STIM003, STIM004, STIM005, STIM006, STIM007, STIM008 or STIM009 or comprise the STIM001, STIM002, STIM002-B, STIM003, STIM004, STIM005, STIM006, STIM007, STIM008 or STIM009 heavy chain CDRs with 1, 2, 3, 4 or 5 amino acid alterations.

Sentence 3. An antibody according to sentence 2, wherein the antibody $V_H$ domain has the heavy chain CDRs of STIM003.

Sentence 4. An isolated antibody that binds the extracellular domain of human and/or mouse ICOS, comprising:
an antibody $V_H$ domain comprising complementarity determining regions HCDR1, HCDR2 and HCDR3, and
an antibody VI domain comprising complementarity determining regions LCDR1, LCDR2 and LCDR3,
wherein LCDR1 is the LCDR1 of STIM001, STIM002, STIM002-B, STIM003, STIM004 STIM005, STIM006, STIM007, STIM008 or STIM009, or comprises that LCDR1 with 1, 2, 3, 4 or 5 amino acid alterations,
LCDR2 is the LCDR2 of STIM001, STIM002, STIM002-B, STIM003, STIM004, STIM005, STIM006, STIM007, STIM008 or STIM009, or comprises that LCDR2 with 1, 2, 3, 4 or 5 amino acid alterations, and/or
LCDR3 is the LCDR3 of STIM001, STIM002, STIM002-B, STIM003, STIM004, STIM005, STIM006, STIM007, STIM008 or STIM009 or comprises that LCDR3 with 1, 2, 3, 4 or 5 amino acid alterations.

Sentence 5. An antibody according to any preceding sentence, wherein the antibody light chain CDRs are those of STIM001, STIM002, STIM002-B, STIM003, STIM004, STIM005, STIM006, STIM007, STIM008 or STIM009, or comprise the STIM001, STIM002, STIM002-B, STIM003, STIM004, STIM005, STIM006, STIM007, STIM008 or STIM009 light chain CDRs with 1, 2, 3, 4 or 5 amino acid alterations.

Sentence 6. An antibody according to sentence 5, wherein the antibody $V_L$ domain has the light chain CDRs of STIM003.

Sentence 7. An antibody according to any of the preceding sentences, comprising $V_H$ and/or $V_l$ domain framework regions of human germline gene segment sequences.

Sentence 8. An antibody according to any of the preceding sentences, comprising a $V_H$ domain which
  (i) is derived from recombination of a human heavy chain V gene segment, a human heavy chain D gene segment and a human heavy chain 3 gene segment, wherein
    the V segment is IGHV1-18 (e.g., V1-18*01), IGVH3-20 (e.g. V3-20*d01), IGVH3-11 (e.g., V3-11*01) or IGVH2-5 (e.g., V2-5*10);
    the D gene segment is IGHD6-19 (e.g., IGHD6-19*01), IGHD3-10 (e.g., IGHD3-10*01) or IGHD3-9 (e.g., IGHD3-9*01); and/or
    the 3 gene segment is IGHJ6 (e.g., IGHJ6*02), IGHJ4 (e.g., IGHJ4*02) or IGHJ3 (e.g., IGHJ3*02), or
  (ii) comprises framework regions FR1, FR2, FR3 and FR4, wherein
    FR1 aligns with human germline V gene segment IGHV1-18 (e.g., V1-18*01), IGVH3-20 (e.g. V3-20*d01), IGVH3-11 (e.g., V3-11*01) or IGVH2-5 (e.g., V2-5*10), optionally with 1, 2, 3, 4 or 5 amino acid alterations,
    FR2 aligns with human germline V gene segment IGHV1-18 (e.g., V1-18*01), IGVH3-20 (e.g. V3-20*d01), IGVH3-11 (e.g., V3-11*01) or IGVH2-5 (e.g., V2-5*10), optionally with 1, 2, 3, 4 or 5 amino acid alterations,
    FR3 aligns with human germline V gene segment IGHV1-18 (e.g., V1-18*01), IGVH3-20 (e.g. V3-20*d01), IGVH3-11 (e.g., V3-11*01) or IGVH2-5 (e.g., V2-5*10), optionally with 1, 2, 3, 4 or 5 amino acid alterations, and/or
    FR4 aligns with human germline 3 gene segment IGJH6 (e.g., JH6*02), IGJH4 (e.g., JH4*02) or IGJH3 (e.g., JH3*02), optionally with 1, 2, 3, 4 or 5 amino acid alterations.

Sentence 9. An antibody according to any of the preceding sentences, comprising an antibody $V_L$ domain which
  (i) is derived from recombination of a human light chain V gene segment and a human light chain 3 gene segment, wherein
    the V segment is IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), and/or
    the 3 gene segment is IGKJ4 (e.g., IGKJ4*01), IGKJ2 (e.g., IGKJ2*04), IGLJ3 (e.g., IGKJ3*01) or IGKJ1 (e.g., IGKJ1*01); or
  (ii) comprises framework regions FR1, FR2, FR3 and FR4, wherein
    FR1 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations,
    FR2 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations,
    FR3 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, and/or
    FR4 aligns with human germline J gene segment IGKJ4 (e.g., IGKJ4*01), IGKJ2 (e.g., IGKJ2*04), IGKJ3 (e.g., IGKJ3*01) or IGKJ1 (e.g., IGKJ1*01), optionally with 1, 2, 3, 4 or 5 amino acid alterations.

Sentence 10. An antibody according to any of the preceding sentences, comprising an antibody VH domain which is the $V_H$ domain of STIM001, STIM002, STIM002-B, STIM003, STIM004, STIM005, STIM006, STIM007, STIM008 or STIM009, or which has an amino acid sequence at least 90% identical to the antibody $V_H$ domain sequence of STIM001, STIM002, STIM002-B, STIM003, STIM004, STIM005, STIM006, STIM007, STIM008 or STIM009.

Sentence 11. An antibody according to any of the preceding sentences, comprising an antibody VL domain which is the $V_L$ domain of STIM001, STIM002, STIM002-B, STIM003, STIM004, STIM005, STIM006, STIM007, STIM008 or STIM009, or which has an amino acid sequence at least 90% identical to the antibody $V_L$ domain sequence of STIM001, STIM002, STIM002-B, STIM003, STIM004, STIM005, STIM006, STIM007, STIM008 or STIM009.

Sentence 12. An antibody according to sentence 11, comprising
  an antibody $V_H$ domain which is selected from the $V_H$ domain of STIM001, STIM002, STIM002-B, STIM003, STIM004, STIM005, STIM006, STIM007, STIM008 or STIM009, or which has an amino acid sequence at least 90% identical to the antibody $V_H$ domain sequence of STIM001, STIM002, STIM002-B, STIM003, STIM004, STIM005, STIM006, STIM007, STIM008 or STIM009, and
  an antibody $V_L$ domain which is the $V_L$ domain of said selected antibody, or which has an amino acid sequence at least 90%, identical to the antibody $V_L$ domain sequence of said selected antibody.

Sentence 13. An antibody according to sentence 12, comprising the STIM003 $V_H$ domain and the STIM003 $V_L$ domain.

Sentence 14. An antibody according to any of the preceding sentences, comprising an antibody constant region.

Sentence 15. An antibody according to sentence 14, wherein the constant region comprises a human heavy and/or light chain constant region.

Sentence 16. An antibody according to sentence 14 or sentence 15, wherein the constant region is Fc effector positive.

Sentence 17. An antibody according to sentence 16, comprising an Fc region that has enhanced ADCC, ADCP and/or CDC function compared with a native human Fc region.

Sentence 18. An antibody according to any of sentences 14 to 17, wherein the antibody is an IgG1.

Sentence 19. An antibody according to sentence 17 or sentence 18, wherein the antibody is afucosylated.

Sentence 20. An antibody according to any of the preceding sentences which is conjugated to a cytotoxic drug or pro-drug.

Sentence 21. An antibody according to any of the preceding sentences, which is a multispecific antibody.

Sentence 22. An isolated antibody that competes for binding to human ICOS with a human IgG1 antibody comprising the heavy and light chain complementarity determining regions of STIM001, STIM002, STIM002-B, STIM003, STIM004, STIM005, STIM006, STIM007, STIM008 or STIM009.

Sentence 23. An isolated antibody that binds the extracellular domain of human and mouse ICOS with an affinity (KD) of less than 50 nM as determined by surface plasmon resonance.

Sentence 24. An antibody according to sentence 23, wherein the antibody binds the extracellular domain of human and mouse ICOS with an affinity (KD) of less than 5 nM as determined by surface plasmon resonance.

Sentence 25. An antibody according to sentence 23 or sentence 24, wherein the $K_D$ of binding the extracellular domain of human ICOS is within 10-fold of the $K_D$ of binding the extracellular domain of mouse ICOS.

Sentence 26. A composition comprising an isolated antibody according to any of the preceding sentences and a pharmaceutically acceptable excipient.

Sentence 27. A composition comprising isolated nucleic acid encoding an antibody according to any of sentences 1 to 25 and a pharmaceutically acceptable excipient.

Sentence 28. A method of depleting regulatory T-cells and/or increasing effector T-cell response in a patient comprising administering a composition according to sentence 26 to the patient.

Sentence 29. A method of treating a disease or condition amenable to therapy by depleting regulatory T-cells and/or increasing effector T-cell response in a patient, the method comprising administering a composition according to sentence 26 to the patient.

Sentence 30. A composition according to sentence 26 for use in a method of treatment of the human body by therapy.

Sentence 31. A composition for use according to sentence 30, for use in depleting regulatory T-cells and/or increasing effector T-cell response in a patient.

Sentence 32. A composition for use according to sentence 30, for use in treating a disease or condition amenable to therapy by depleting regulatory T-cells and/or increasing effector T-cell response in a patient.

Sentence 33. A method according to sentence 29, or a composition for use according to sentence 32, wherein the disease is a cancer or a solid tumour.

Sentence 34. A method or a composition for use according to any of sentences 29 to 33, wherein the method comprises administering the antibody and another therapeutic agent to the patient.

Sentence 35. A method or composition for use according to sentence 34, wherein the therapeutic agent is an anti-PDL1 antibody.

Sentence 36. A method or composition for use according to sentence 35, wherein the anti-ICOS antibody and the anti-PDL1 antibody are each able to mediate ADCC, ADCP and/or CDC.

Sentence 37. A method or composition for use according to sentence 35, wherein the anti-ICOS antibody is a human IgG1 antibody and the anti-PDL1 antibody is a human IgG1 antibody.

Sentence 38. A method or composition for use according to sentence 34, wherein the other therapeutic agent is IL-2.

Sentence 39. A method or composition for use according to any of sentences 34 to 38, wherein the method comprises administering the anti-ICOS antibody after administering the other therapeutic agent.

Sentence 40. A method or a composition for use according to any of sentences 28 to 39, wherein
the anti-ICOS antibody is conjugated to a pro-drug, and wherein
the method or use comprises
administering the anti-ICOS antibody to a patient and selectively activating the pro-drug at a target tissue site.

Sentence 41. A method or a composition for use according to sentence 40, wherein the patient has a solid tumour and the method comprises selectively activating the pro-drug in the tumour.

Sentence 42. A method or a composition for use according to sentence 40 or sentence 41, comprising selectively activating the pro-drug through photoactivation.

Sentence 43. Combination of anti-ICOS human IgG1 antibody and anti-PDL1 human IgG1 antibody for use in a method of treating cancer.

Sentence 44. Combination according to sentence 43, wherein the anti-ICOS antibody and the anti-PDL1 antibody are provided in separate compositions for administration.

Sentence 45. A method or composition for use according to sentence 37, or a combination according to sentence 43 or sentence 44, wherein the human IgG1 constant region has a wild type amino acid sequence shown in the appended sequence listing.

Sentence 46. Anti-ICOS antibody for use in a method of reducing or reversing a surge in ICOS-positive regulatory T-cells in a patient, wherein the surge results from treatment of the patient with another therapeutic agent.

Sentence 47. A method of treating a patient, the method comprising reducing or reversing a surge in ICOS-positive regulatory T-cells in the patient, wherein the surge results from treatment of the patient with another therapeutic agent.

Sentence 48. Anti-ICOS antibody for use in a method of treating a patient, the method comprising comprising administering the anti-ICOS antibody to a patient who has an increased level of ICOS-positive regulatory T-cells following treatment with another therapeutic agent.

Sentence 49. A method of treating a patient, the method comprising administering an anti-ICOS antibody to a patient who has an increased level of ICOS-positive regulatory T-cells following treatment with another therapeutic agent.

Sentence 50. An anti-ICOS antibody for use according to sentence 46 or sentence 48, or a method according to sentence 47 or sentence 49, wherein the method comprises administering a therapeutic agent to the patient, determining that the patient has an increased level of ICOS-positive regulatory T-cells following the treatment with said agent, and administering an anti-ICOS antibody to the patient to reduce the level of regulatory T-cells.

Sentence 51. An anti-ICOS antibody for use or a method according to any of sentences 46 to 50, wherein the therapeutic agent is IL-2 or an immunomodulatory antibody (e.g., anti-PDL-1, anti-PD-1 or anti-CTLA-4).

Sentence 52. An anti-ICOS antibody for use or a method according to any of sentences 46 to 51, wherein the method comprises treating a tumour, e.g., melanoma, such as metastatic melanoma.

Sentence 53. Anti-ICOS antibody for use in a method of treating cancer in a patient by in vivo vaccination of the patient against their cancer cells, the method comprising
treating the patient with a therapy that causes immunological cell death of the cancer cells, resulting in presentation of antigen to antigen-specific effector T-cells, and
administering an anti-ICOS antibody to the patient, wherein the anti-ICOS antibody enhances the antigen-specific effector T-cell response.

Sentence 54. A method of treating cancer in a patient by in vivo vaccination of the patient against their cancer cells, the method comprising
treating the patient with a therapy that causes immunological cell death of the cancer cells, resulting in presentation of antigen to antigen-specific effector T-cells, and
administering an anti-ICOS antibody to the patient, wherein the anti-ICOS antibody enhances the antigen-specific effector T-cell response.

Sentence 55. A method of treating cancer in a patient by in vivo vaccination of the patient against their cancer cells, the method comprising administering an anti-ICOS antibody to the patient, wherein
the patient is one who has been previously treated with a therapy that causes immunological cell death of the cancer cells, resulting in presentation of antigen to antigen-specific effector T-cells, and wherein
the anti-ICOS antibody enhances the antigen-specific effector T-cell response.

Sentence 56. Anti-ICOS antibody for use or a method according to any of sentences 53 to 55, wherein the therapy that causes immunological cell. death is radiation of the cancer cells, administration of a chemotherapeutic agent and/or administration of an antibody directed to a tumour-associated antigen.

Sentence 57. Anti-ICOS antibody for use or a method according to sentence 56, wherein the chemotherapeutic agent is oxaliplatin.

Sentence 58. Anti-ICOS antibody for use or a method according to sentence 56, wherein the tumour-associated antigen is HER2 or CD20.

Sentence 59. Anti-ICOS antibody for use in a method of vaccinating a patient, the method comprising administering the antibody and a vaccine composition to the patient.

Sentence 60. A method of vaccinating a patient, the method comprising administering an anti-ICOS antibody and a vaccine composition to the patient.

Sentence 61. Anti-ICOS antibody for use according to sentence 59, or a method according to sentence 60, wherein the vaccine composition is a vaccine against hepatitis B, malaria or HIV.

Sentence 62. Anti-ICOS antibody for use in a method of treating a cancer in a patient, wherein the cancer is or has been characterised as being positive for expression of ICOS ligand and/or FOXP3.

Sentence 63. A method of treating a cancer in a patient, wherein the cancer is or has been characterised as being positive for expression of ICOS ligand and/or FOXP3, the method comprising administering an anti-ICOS antibody to the patient.

Sentence 64. Anti-ICOS antibody for use according to sentence 62, or a method according to sentence 63, wherein the method comprises:
testing a sample from a patient to determine that the cancer expresses ICOS ligand and/or FOXP3;
selecting the patient for treatment with the anti-ICOS antibody; and administering the anti-ICOS antibody to the patient.

Sentence 65. Anti-ICOS antibody for use according to sentence 62, or a method according to sentence 63, wherein the method comprises administering an anti-ICOS antibody to a patient from whom a test sample has indicated that the cancer is positive for expression of ICOS ligand and/or FOXP3.

Sentence 66. Anti-ICOS antibody for use or a method according to sentence 64 or sentence 65, wherein the sample is biopsy sample of a solid tumour.

Sentence 67. Anti-ICOS antibody for use in a method of treating a cancer in a patient, wherein the cancer is or has been characterised as being refractory to treatment with an immunooncology drug, e.g., anti-CTLA-4 antibody, anti-PD1 antibody, anti-PD-L1 antibody, anti-CD137 antibody or anti-GITR antibody.

Sentence 68. A method of treating a cancer in a patient, wherein the cancer is or has been characterised as being refractory to treatment with an immunooncology drug, e.g., anti-CTLA-4 antibody, anti-PD1 antibody, anti-PD-L1 antibody, anti-CD137 antibody or anti-GITR antibody, the method comprising administering an anti-ICOS antibody to the patient.

Sentence 69. Anti-ICOS antibody for use according to sentence 67 or a method according to sentence 68, wherein the method comprises:
treating the patient with the immunooncology drug;
determining that the cancer is not responsive to the drug;
selecting the patient for treatment with the anti-ICOS antibody; and
administering the anti-ICOS antibody to the patient.

Sentence 70. Anti-ICOS antibody for use according to sentence 67, or a method according to sentence 68, wherein the method comprises administering an anti-ICOS antibody to a patient whose cancer was not responsive to prior treatment with the immunooncology drug.

Sentence 71. Anti-ICOS antibody for use or a method according to any of sentences 62 to 70, wherein the cancer is a tumour derived from cells that have acquired ability to express ICOS ligand.

Sentence 72. Anti-ICOS antibody for use or a method according to sentence 71, wherein the cancer is melanoma.

Sentence 73. Anti-ICOS antibody for use or a method according to any of sentences 62 to 70, wherein the cancer is derived from an antigen-presenting cell, such as a B lymphocyte (e.g., B cell lymphoma, such as diffused large B cell lymphoma) or a T lymphocyte.

Sentence 74. Anti-ICOS antibody for use or a method according to any of sentences 62 to 70, wherein the cancer is resistant to treatment with an anti-CD20 antibody.

Sentence 75. Anti-ICOS antibody for use or a method according to sentence 74, wherein the cancer is B cell lymphoma.

Sentence 76. Anti-ICOS antibody for use or a method according to sentence 75, wherein the anti-CD20 antibody is rituximab.

Sentence 77. Anti-ICOS antibody for use or a method according to any of sentences 74 to 76, wherein the method comprises treating the patient with the anti-CD20 antibody;
  determining that the cancer is not responsive to the anti-CD20 antibody;
  testing a sample from a patient to determine that the cancer expresses ICOS ligand;
  selecting the patient for treatment with the anti-ICOS antibody; and
  administering the anti-ICOS antibody to the patient.

Sentence 78. Anti-ICOS antibody for use or a method according to any of sentences 74 to 76, wherein the method comprises administering an anti-ICOS antibody to a patient whose cancer was not responsive to prior treatment with anti-CD20 antibody.

Sentence 79. Anti-ICOS antibody for use or a method according to any of sentences 52 to 78, wherein the cancer is a solid tumour.

Sentence 80. Anti-ICOS antibody for use or a method according to any of sentences 52 to 78, wherein the cancer is a haemotological liquid tumour.

Sentence 81. Anti-ICOS antibody for use or a method according to sentence 79 or 80, wherein the tumour is high in regulatory T-cells.

Sentence 82. Anti-ICOS antibody for use or a method according to any of sentences 43 to 81, wherein the anti-ICOS antibody is as defined in any of sentences 1 to 25 or is provided in a composition according to sentence 26.

Sentence 83. A transgenic non-human mammal having a genome comprising a human or humanised immunoglobulin locus encoding human variable region gene segments, wherein the mammal does not express ICOS.

Sentence 84. A method of producing an antibody that binds the extracellular domain of human and non-human ICOS, comprising
  (a) immunising a mammal according to sentence 83 with human ICOS antigen;
  (b) isolating antibodies generated by the mammal;
  (c) testing the antibodies for ability to bind human ICOS and non-human ICOS; and
  (d) selecting one or more antibodies that binds both human and non-human ICOS.

Sentence 85. A method according to sentence 84, comprising immunising the mammal with cells expressing human ICOS.

Sentence 86. A method according to sentence 84 or sentence 85, comprising
  (c) testing the antibodies for ability to bind human ICOS and non-human ICOS using surface plasmon resonance and determining binding affinities; and
  (d) selecting one or more antibodies for which the KD of binding to human ICOS is less than 50 nM and the KD of binding to non-human ICOS is less than 500 nM.

Sentence 87. A method according to sentence 86, comprising
  (d) selecting one or more antibodies for which the KD of binding to human ICOS is less than 10 nM and the KD of binding to non-human ICOS is less than 100 nM.

Sentence 88. A method according to any of sentences 84 to 87, comprising
  (c) testing the antibodies for ability to bind human ICOS and non-human ICOS using surface plasmon resonance and determining binding affinities; and
  (d) selecting one or more antibodies for which the KD of binding to human ICOS is within 10-fold of the KD of binding to non-human ICOS.

Sentence 89. A method according to sentence 88, comprising
  (d) selecting one or more antibodies for which the KD of binding to human ICOS is within 5-fold of the $K_D$ of binding to non-human ICOS.

Sentence 90. A method according to any of sentences 84 to 89, comprising testing the antibodies for ability to bind non-human ICOS from the same species as the mammal.

Sentence 91. A method according to any of sentences 84 to 90, comprising testing the antibodies for ability to bind non-human ICOS from a different species as the mammal.

Sentence 92. A method according to any of sentences 84 to 91, wherein the mammal is a mouse or a rat.

Sentence 93. A method according to any of sentences 84 to 92, wherein the non-human ICOS is mouse ICOS or rat ICOS.

Sentence 94. A method according to any of sentences 84 to 93, wherein the human or humanised immunoglobulin locus comprises human variable region gene segments upstream of an endogenous constant region.

Sentence 95. A method according to sentence 94, comprising
  (a) immunising a mammal according to sentence 83 with human ICOS antigen, wherein the mammal is a mouse;
  (b) isolating antibodies generated by the mouse;
  (c) testing the antibodies for ability to bind human ICOS and mouse ICOS; and
  (d) selecting one or more antibodies that binds both human and mouse ICOS.

Sentence 96. A method according to any of sentences 84 to 95, comprising isolating nucleic acid encoding an antibody heavy chain variable domain and/or an antibody light chain variable domain.

Sentence 97. A method according to any of sentences 84 to 96, wherein the mammal generates antibodies through recombination of human variable region gene segments and an endogenous constant region.

Sentence 98. A method according to sentence 96 or sentence 97, comprising conjugating the nucleic acid encoding the heavy and/or light chain variable domain to a nucleotide sequence encoding a human heavy chain constant region and/or human light chain constant region respectively.

Sentence 99. A method according to any of sentences 96 to 98, comprising introducing the nucleic acid into a host cell.

Sentence 100. A method according to sentence 99, comprising culturing the host cell under conditions for expression of the antibody, or of the antibody heavy and/or light chain variable domain.

Sentence 101. An antibody, or antibody heavy and/or light chain variable domain, produced by the method according to any of sentences 84 to 100.

Sentence 102. A method of selecting an antibody that binds ICOS, optionally for selecting an ICOS agonist antibody, the assay comprising:
providing an array of antibodies immobilised (attached or adhered) to a substrate in a test well;
adding ICOS-expressing cells (e.g., activated primary T-cells, or Mi cells) to the test well;
observing morphology of the cells;
detecting shape change in the cells from rounded to flattened against the substrate within the well; wherein the shape change indicates that the antibody is an antibody that binds ICOS, optionally an ICOS agonist antibody;
selecting the antibody from the test well;
expressing nucleic acid encoding the CDRs of the selected antibody; and
formulating the antibody into a composition comprising one or more additional components.

Alternative sentences describing anti-ICOS antibodies are described below:

Sentence 1a. An antibody or a fragment thereof which specifically binds to human ICOS (hICOS) (SEQ ID NO: 508, 507 and/or 506), and:
a) competes for binding to said hICOS with the antibody STIM001, wherein the antibody or fragment comprises a $V_H$ domain which comprises the CDRH3 sequence of SEQ ID NO:365, or the CDRH3 sequence of SEQ ID NO:365 comprising 3, 2 or 1 amino acid substitution(s);
b) competes for binding to said hICOS with the antibody STIM002, wherein the antibody or fragment comprises a $V_H$ domain which comprises the CDRH3 sequence of SEQ ID NO:379, or the CDRH3 sequence of SEQ ID NO:379 comprising 3, 2 or 1 amino acid substitution(s);
c) competes for binding to said hICOS with the antibody STIM002-B, wherein the antibody or fragment comprises a $V_H$ domain which comprises the CDRH3 sequence of SEQ ID NO:393, or the CDRH3 sequence of SEQ ID NO:393 comprising 3, 2 or 1 amino acid substitution(s);
d) competes for binding to said hICOS with the antibody STIM003, wherein the antibody or fragment comprises a $V_H$ domain which comprises the CDRH3 sequence of SEQ ID NO:407, or the CDRH3 sequence of SEQ ID NO:407 comprising 3, 2 or 1 amino acid substitution(s);
e) competes for binding to said hICOS with the antibody STIM004, wherein the antibody or fragment comprises a $V_H$ domain which comprises the CDRH3 sequence of SEQ ID NO:421, or the CDRH3 sequence of SEQ ID NO:421 comprising 3, 2 or 1 amino acid substitution(s);
f) competes for binding to said hICOS with the antibody STIM005, wherein the antibody or fragment comprises a $V_H$ domain which comprises the CDRH3 sequence of SEQ ID NO:437, or the CDRH3 sequence of SEQ ID NO:437 comprising 3, 2 or 1 amino acid substitution(s);
g) competes for binding to said hICOS with the antibody STIM006, wherein the antibody or fragment comprises a $V_H$ domain which comprises the CDRH3 sequence of SEQ ID NO:451, or the CDRH3 sequence of SEQ ID NO:451 comprising 3, 2 or 1 amino acid substitution(s);
h) competes for binding to said hICOS with the antibody STIM007, wherein the antibody or fragment comprises a $V_H$ domain which comprises the CDRH3 sequence of SEQ ID NO:465, or the CDRH3 sequence of SEQ ID NO:465 comprising 3, 2 or 1 amino acid substitution(s);
i) competes for binding to said hICOS with the antibody STIM008, wherein the antibody or fragment comprises a $V_H$ domain which comprises the CDRH3 sequence of SEQ ID NO:479, or the CDRH3 sequence of SEQ ID NO:479 comprising 3, 2 or 1 amino acid substitution(s); or
j) competes for binding to said hICOS with the antibody STIM009, wherein the antibody or fragment comprises a $V_H$ domain which comprises the CDRH3 sequence of SEQ ID NO:493, or the CDRH3 sequence of SEQ ID NO:493 comprising 3, 2 or 1 amino acid substitution(s).

Sentence 2a. The antibody or a fragment thereof according to sentence 1a, wherein the $V_H$ domain comprises the CDRH1 sequence of:
a) SEQ ID NO:363, or the CDRH1 sequence of SEQ ID NO:363 comprising 1 amino acid substitution;
b) SEQ ID NO:377, or the CDRH1 sequence of SEQ ID NO:377 comprising 1 amino acid substitution;
c) SEQ ID NO:391, or the CDRH1 sequence of SEQ ID NO:391 comprising 1 amino acid substitution;
d) SEQ ID NO:405, or the CDRH1 sequence of SEQ ID NO:405 comprising 1 amino acid substitution;
e) SEQ ID NO:419, or the CDRH1 sequence of SEQ ID NO:419 comprising 1 amino acid substitution;
f) SEQ ID NO:435, or the CDRH1 sequence of SEQ ID NO:435 comprising 1 amino acid substitution;
g) SEQ ID NO:449, or the CDRH1 sequence of SEQ ID NO:449 comprising 1 amino acid substitution;
h) SEQ ID NO:463, or the CDRH1 sequence of SEQ ID NO:463 comprising 1 amino acid substitution; or
i) SEQ ID NO:477, or the CDRH1 sequence of SEQ ID NO:477 comprising 1 amino acid substitution.
j) SEQ ID NO:491, or the CDRH1 sequence of SEQ ID NO:491 comprising 1 amino acid substitution.

Sentence 3a. The antibody or a fragment thereof according to sentence 1a or sentence 2a, wherein the $V_H$ domain comprises the CDRH2 sequence of:
a) SEQ ID NO:364, or the CDRH2 sequence of SEQ ID NO:364 comprising 2 or 1 amino acid substitution(s);
b) SEQ ID NO:378, or the CDRH2 sequence of SEQ ID NO:378 comprising 2 or 1 amino acid substitution(s);
c) SEQ ID NO:392, or the CDRH2 sequence of SEQ ID NO:392 comprising 2 or 1 amino acid substitution(s);
d) SEQ ID NO:406, or the CDRH2 sequence of SEQ ID NO:406 comprising 2 or 1 amino acid substitution(s);
e) SEQ ID NO:420, or the CDRH2 sequence of SEQ ID NO:420 comprising 2 or 1 amino acid substitution(s);
f) SEQ ID NO:436, or the CDRH2 sequence of SEQ ID NO:436 comprising 2 or 1 amino acid substitution(s);
g) SEQ ID NO:450, or the CDRH2 sequence of SEQ ID NO:450 comprising 2 or 1 amino acid substitution(s);

h) SEQ ID NO:464, or the CDRH2 sequence of SEQ ID NO:464 comprising 2 or 1 amino acid substitution(s);
i) SEQ ID NO:478, or the CDRH2 sequence of SEQ ID NO:478 comprising 2 or 1 amino acid substitution(s); or
j) SEQ ID NO:492, or the CDRH2 sequence of SEQ ID NO:492 comprising 2 or 1 amino acid substitution(s).

Sentence 4a. The antibody or a fragment thereof according to any preceding sentence, wherein the $V_H$ domain comprises:
a) an amino acid sequence of SEQ ID NO:366, or a heavy chain variable domain amino acid sequence that is at least 98% identical to SEQ ID NO:366;
b) an amino acid sequence of SEQ ID NO:380, or a heavy chain variable domain amino acid sequence that is at least 98% identical to SEQ ID NO:380;
c) an amino acid sequence of SEQ ID NO:394, or a heavy chain variable domain amino acid sequence that is at least 98% identical to SEQ ID NO:394;
d) an amino acid sequence of SEQ ID NO:408, or a heavy chain variable domain amino acid sequence that is at least 98% identical to SEQ ID NO:408;
e) an amino acid sequence of SEQ ID NO:422, or a heavy chain variable domain amino acid sequence that is at least 98% identical to SEQ ID NO:422;
f) an amino acid sequence of SEQ ID NO:438, or a heavy chain variable domain amino acid sequence that is at least 98% identical to SEQ ID NO:438;
g) an amino acid sequence of SEQ ID NO:452, or a heavy chain variable domain amino acid sequence that is at least 98% identical to SEQ ID NO:452;
h) an amino acid sequence of SEQ ID NO:466, or a heavy chain variable domain amino acid sequence that is at least 98% identical to SEQ ID NO:466;
i) an amino acid sequence of SEQ ID NO:480, or a heavy chain variable domain amino acid sequence that is at least 98% identical to SEQ ID NO:480; or
j) an amino acid sequence of SEQ ID NO:494, or a heavy chain variable domain amino acid sequence that is at least 98% identical to SEQ ID NO:494.

Sentence 5a. The antibody or fragment according to any preceding sentence comprising first and second copies of said $V_H$ domain.

Sentence 6a. The antibody or a fragment thereof according to any preceding sentence comprising a $V_L$ domain, which comprises the CDRL1 sequence of:
a) SEQ ID NO:370, or the CDRL1 sequence of SEQ ID NO:370 comprising one amino add substitution;
b) SEQ ID NO:384, or the CDRL1 sequence of SEQ ID NO:384 comprising one amino acid substitution;
c) SEQ ID NO:398, or the CDRL1 sequence of SEQ ID NO:398 comprising one amino acid substitution;
d) SEQ ID NO:412, or the CDRL1 sequence of SEQ ID NO:412 comprising one amino acid substitution;
e) SEQ ID NO:426, or the CDRL1 sequence of SEQ ID NO:426 comprising one amino acid substitution;
f) SEQ ID NO:442, or the CDRL1 sequence of SEQ ID NO:442 comprising one amino acid substitution;
g) SEQ ID NO:456, or the CDRL1 sequence of SEQ ID NO:456 comprising one amino acid substitution;
h) SEQ ID NO:470, or the CDRL1 sequence of SEQ ID NO:470 comprising one amino acid substitution; or
i) SEQ ID NO:484, or the CDRL1 sequence of SEQ ID NO:484 comprising one amino acid substitution.
j) SEQ ID NO:498, or the CDRL1 sequence of SEQ ID NO:498 comprising one amino acid substitution.

Sentence 7a. The antibody or a fragment thereof according to any preceding sentence comprising a or said $V_L$ domain, which $V_L$ domain comprises the CDRL2 sequence of:
a) SEQ ID NO:371, or the CDRL2 sequence of SEQ ID NO:371 comprising 1 amino acid substitution;
b) SEQ ID NO:385, or the CDRL2 sequence of SEQ ID NO:385 comprising 1 amino acid substitution;
c) SEQ ID NO:399, or the CDRL2 sequence of SEQ ID NO:399 comprising 1 amino acid substitution;
d) SEQ ID NO:413, or the CDRL2 sequence of SEQ ID NO:413 comprising 1 amino acid substitution;
e) SEQ ID NO:427, or the CDRL2 sequence of SEQ ID NO:427 comprising 1 amino acid substitution;
f) SEQ ID NO:443, or the CDRL2 sequence of SEQ ID NO:443 comprising 1 amino acid substitution;
g) SEQ ID NO:457, or the CDRL2 sequence of SEQ ID NO:457 comprising 1 amino acid substitution;
h) SEQ ID NO:471, or the CDRL2 sequence of SEQ ID NO:471 comprising 1 amino acid substitution;
i) SEQ ID NO:485, or the CDRL2 sequence of SEQ ID NO:485 comprising 1 amino acid substitution; or
j) SEQ ID NO:499, or the CDRL2 sequence of SEQ ID NO:499 comprising 1 amino acid substitution.

Sentence 8a. The antibody or a fragment thereof according to any preceding sentence comprising a or said $V_L$ domain, which VI domain comprises the CDRL3 sequence of:
a) SEQ ID NO:372, or the CDRL3 sequence of SEQ ID NO:372 comprising 2 or 1 amino acid substitution(s);
b) SEQ ID NO:386, or the CDRL3 sequence of SEQ ID NO:386 comprising 2 or 1 amino acid substitution(s);
c) SEQ ID NO:400, or the CDRL3 sequence of SEQ ID NO:400 comprising 2 or 1 amino acid substitution(s);
d) SEQ ID NO:414, or the CDRL3 sequence of SEQ ID NO:414 comprising 2 or 1 amino acid substitution(s);
e) SEQ ID NO:428, or the CDRL3 sequence of SEQ ID NO:428 comprising 2 or 1 amino acid substitution(s);
f) SEQ ID NO:444, or the CDRL3 sequence of SEQ ID NO:444 comprising 2 or 1 amino acid substitution(s);
g) SEQ ID NO:458, or the CDRL3 sequence of SEQ ID NO:458 comprising 2 or 1 amino acid substitution(s);
h) SEQ ID NO:472, or the CDRL3 sequence of SEQ ID NO:472 comprising 2 or 1 amino acid substitution(s);
i) SEQ ID NO:486, or the CDRL3 sequence of SEQ ID NO:486 comprising 2 or 1 amino acid substitution(s); or
j) SEQ ID NO:500, or the CDRL3 sequence of SEQ ID NO:500 comprising 2 or 1 amino acid substitution(s).

Sentence 9a. The antibody or a fragment thereof according to any preceding sentence, comprising a or said $V_L$ domain, wherein the $V_L$ domain comprises an amino acid sequence of:
a) SEQ ID NO:373, or a light chain variable domain amino acid sequence that is at least 98% identical to SEQ ID NO:373;

b) SEQ ID NO:387, or a light chain variable domain amino acid sequence that is at least 98% identical to SEQ ID NO:387;
c) SEQ ID NO:401, or a light chain variable domain amino acid sequence that is at least 98% identical to SEQ ID NO:401;
d) SEQ ID NO:415, or a light chain variable domain amino acid sequence that is at least 98% identical to SEQ ID NO:415;
e) SEQ ID NO:429, or a light chain variable domain amino acid sequence that is at least 98% identical to SEQ ID NO:429;
f) SEQ ID NO:445, or a light chain variable domain amino acid sequence that is at least 98% identical to SEQ ID NO:445;
g) SEQ ID NO:459, or a light chain variable domain amino acid sequence that is at least 98% identical to SEQ ID NO:459;
h) SEQ ID NO:473, or a light chain variable domain amino acid sequence that is at least 98% identical to SEQ ID NO:473;
i) SEQ ID NO:487, or a light chain variable domain amino acid sequence that is at least 98% identical to SEQ ID NO:487; or
j) SEQ ID NO:501, or a light chain variable domain amino acid sequence that is at least 98% identical to SEQ ID NO:501.

Sentence 10a. The antibody or fragment according to any one of sentences 6a to 9a, comprising first and second copies of the a or said $V_L$ domain.

Sentence 11. The antibody or fragment according to any preceding sentence, wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Sentence 12a. An antibody or fragment thereof which specifically binds to an epitope that is:
a) Identical to an epitope to which the antibody STIM001 specifically binds;
b) Identical to an epitope to which the antibody STIM002 specifically binds;
c) Identical to an epitope to which the antibody STIM002-B specifically binds;
d) Identical to an epitope to which the antibody STIM003 specifically binds;
e) Identical to an epitope to which the antibody STIM004 specifically binds;
f) Identical to an epitope to which the antibody STIM005 specifically binds;
g) Identical to an epitope to which the antibody STIM006 specifically binds;
h) Identical to an epitope to which the antibody STIM007 specifically binds;
i) Identical to an epitope to which the antibody STIM008 specifically binds; or
j) Identical to an epitope to which the antibody STIM009 specifically binds.

Sentence 13a. The antibody or fragment according to sentence 12a, wherein the epitope is identified by unrelated amino acid scanning, or by X-ray crystallography.

Sentence 14a. The antibody or fragment according to sentence 13a, wherein the contact residues of the epitope are defined by a reduction in affinity of at least 10-fold in an unrelated amino acid scan, e.g. an alanine scan as determined by SPR.

Sentence 15a. An antibody or fragment thereof which:
a) Competes for binding to hICOS with the antibody STIM001;
b) Competes for binding to hICOS with the antibody STIM002;
c) Competes for binding to hICOS with the antibody STIM002-B;
d) Competes for binding to hICOS with the antibody STIM003;
e) Competes for binding to hICOS with the antibody STIM004;
f) Competes for binding to hICOS with the antibody STIM005;
g) Competes for binding to hICOS with the antibody STIM006;
h) Competes for binding to hICOS with the antibody STIM007;
i) Competes for binding to hICOS with the antibody STIM008; or
j) Competes for binding to hICOS with the antibody STIM009.

Sentence 16a. The antibody or fragment according to any preceding sentence which specifically binds to cynomolgus ICOS (Seq ID No:513, SEQ ID NO: 513 or Seq ID No: 514) and/or mouse ICOS (Seq ID No:510, Seq ID No:511 or Seq ID No:512).

Sentence 17a. The antibody or fragment according to any preceding sentence which specifically binds to a hICOS isoform or natural variant, a mouse ICOS isoform or natural variant and/or a cynomolgus ICOS isoform or natural variant.

Sentence 18a. The antibody or fragment according to sentence 17a, wherein the hICOS isoform comprises an amino acid sequence as defined by Seq ID no:509.

Sentence 19a. The antibody or fragment according to any preceding sentence, wherein the antibody or fragment comprises a constant region, such as a human constant region, for example an effector-null human constant region, e.g. an IgG4 constant region or an IgG1 constant region, optionally wherein the constant region is IgG4-PE (Seq ID No:199), or a disabled IgG1 (Seq ID No:205).

Sentence 20a. The antibody or fragment according to sentence 19a, wherein the constant region is a murine constant region.

Sentence 21a. The antibody or fragment according to sentence 19a or sentence 20a, wherein the constant region has CDC and/or ADCC activity.

5. Anti-ICOS Bispecific Antibodies

As previously described, the PD-L1 antibodies as provided herein, may be formatted as a multispecific (e.g. bispecific) antibody, as disclosed hereinabove in concepts 37 to 40. In one embodiment disclosed therein, the PD-L1 antibodies as disclosed herein may be formatted in a bispecific antibody which has specificity for both PD-L1 (e.g. human PD-L1) and for ICOS (e.g. an agonist to ICOS, such as human ICOS).

Thus, there is provided a multispecific (e.g. bispecific antibody or a dual-binding antibody) which has specificity for PD-L1 (e.g. human PD-L1) and ICOS (e.g. human ICOS). In one embodiment the multispecific (e.g. bispecific or dual-binding) antibody has agonistic activity against ICOS (e.g. human ICOS).

Various ICOS-containing multispecific antibodies are described in the arrangements below:

Arrangement 1. A multispecific antibody (e.g. bispecific antibody or a dual-binding antibody) which binds (and optionally has specificity for) ICOS (e.g. human ICOS) and another target antigen.

In one embodiment, there is provided a bispecific antibody or a dual-binding antibody which binds ICOS (e.g. human ICOS) and another target antigen. In one embodiment, there is provided a bispecific antibody or a dual-binding antibody which has specificity for ICOS (e.g. human ICOS) and another target antigen. In one embodiment, there is provided a bispecific antibody antibody which binds ICOS (e.g. human ICOS) and another target antigen, and wherein the bispecific antibody format is a mAb². In one embodiment, there is provided a bispecific antibody antibody which binds ICOS (e.g. human ICOS) and another target antigen, and wherein the bispecific antibody format is a mAb², and the binding to another target antigen is provided by a modified constant region (i.e. an Fcab). In one embodiment, there is provided a bispecific antibody antibody which binds ICOS (e.g. human ICOS) and another target antigen which is PD-L1 (e.g. human PD-L1), and wherein the bispecific antibody format is a mAb2, and the binding to ICOS is provided by a modified constant region (i.e. an Fcab). In one embodiment, there is provided a bispecific antibody antibody which binds ICOS (e.g. human ICOS) and another target antigen which is PD-L1 (e.g. human PD-L1), and wherein the bispecific antibody format is a mAb2, and the binding to ICOS is provided by a modified constant region (i.e. an Fcab) and the binding to PD-L1 is provided by any of the antibodies described in concepts 1 to 70, or by any of the PD-L1 antibodies described in arrangement 5 or 5a below. In one embodiment, there is provided a bispecific antibody antibody which binds ICOS (e.g. human ICOS) and another target antigen which is PD-L1 (e.g. human PD-L1), and wherein the bispecific antibody format is a mAb², and the binding to PD-L1 is provided by a modified constant region (i.e. an Fcab). In one embodiment, there is provided a bispecific antibody antibody which binds ICOS (e.g. human ICOS) and another target antigen which is PD-L1 (e.g. human PD-L1), and wherein the bispecific antibody format is a mAb², and the binding to PD-L1 is provided by a modified constant region (i.e. an Fcab) and the binding to ICOS is provided by any of the antibodies described in sentences 1 to 102 or sentences 1a to 21a.

In one embodiment, the multispecific (e.g. bispecific or dual-binding) antibody has agonistic activity against ICOS (e.g. human ICOS). The another target antigen may be any of the target antigens specified in concept 39. In one embodiment, the another target antigen is an immune checkpoint inhibitor, such as PD-1, PD-L1, CTLA-4, TIGIT, TIM-3, LAG-3 and VISTA, e.g. PD-L1, TIGIT, CRA-4, TIM-3 and LAG-3. In one embodiment, the another target antigen is an immune modulator, such as BTLA, hHVEM, CSF1R, CCR4, CD39, CD40, CD73, CD96, CXCR2, CXCR4, CD200, GARP, SIRPα, CXCL9, CXCL10 and CD155, e.g. GARP, SIRPα, CXCR4, BTLA, hVEM and CSF1R. In one embodiment, the another target antigen is an immune activator, such as CD137, GITR, OX40, CD40, CXCR3 (e.g. agonistic anti-CXCR3 antibodies), CD27 and CD3, or CD137, GITR, OX40, CD40, CXCR3 (e.g. agonistic anti-CXCR3 antibodies) and CD3, for example CD137, GITR and OX40). In one embodiment, the another target antigen is PD-L1. In one embodiment, the another target antigen is CTLA-4. In one embodiment, the another target antigen is TIGIT. In one embodiment, the another target antigen is TIM-3. In one embodiment, the another target antigen is LAG-3. In one embodiment, the another target antigen is GITR. In one embodiment, the another target antigen is VISTA. In one embodiment, the another target antigen is CD137. In one embodiment, the another target antigen is SIRPα. In one embodiment, the another target antigen is CXCL10. In one embodiment, the another target antigen is CD155. In one embodiment, the another target antigen is CD40. The antibodies against these another target antigens may be any of those described in aspect 1a hereinabove.

The format of the multispecific, bispecific or dual-binding antibody may be any of the formats disclosed herein, for example as set out in concepts 37 to 40. In particular, the binding and/or specificity for ICOS may be provided by a non-immunoglobulin format, for example, a T-cell receptor binding domain; an immunoglobulin superfamily domain; an agnathan variable lymphocyte receptor; a fibronectin domain (e.g., an Adnectin™); an antibody constant domain (e.g., a CH3 domain, e.g., a CH2 and/or CH3 of an Fcab™) wherein the constant domain is not a functional CH1 domain; an scFv; an (scFv)2; an sc-diabody; an scFab; a centyrin and an epitope binding domain derived from a scaffold selected from CTLA-4 (Evibody™); a lipocalin domain; Protein A such as Z-domain of Protein A (e.g., an Affibody™ or SpA); an A-domain (e.g., an Avimer™ or Maxibody™); a heat shock protein (such as and epitope binding domain derived from GroEI and GroES); a transferrin domain (e.g., a trans-body); ankyrin repeat protein (e.g., a DARPin™); peptide aptamer; C-type lectin domain (e.g., Tetranectin™); human γ-crystallin or human ubiquitin (an affilin); a PDZ domain; scorpion toxin; and a kunitz type domain of a human protease inhibitor. The binding and/or specificity for another target antigen may be provided by an immunoglobulin-derived antigen-binding protein.

"Specifically binds" has the meaning provided hereinabove. Binding constants, e.g. $K_D$ may be determined as described elsewhere herein, and particular $K_D$s of interest are described in arrangement 2 below, and in concept 1 hereinabove (although specified for PD-L1 binding, the values of $K_D$ may be equally applied to anti-ICOS binding).

Arrangement 2. A multispecific antibody according to arrangement 1, wherein the ICOS is human ICOS.

Sequences of human ICOS are provided in Seq ID Nos: 506, 507 and 508. In one embodiment, the multispecific antibody is specific for wild type human ICOS. In another embodiment, the multispecific antibody is cross-reactive to an isoform or natural variant of hICOS, for example the isoform of Seq ID No:509. Other isoforms and natural variants are well known to those skilled in the art. In another embodiment, the multispecific antibody is specific for the isoform or natural variant (e.g. the ICOS isoform having the amino acid sequence of Seq ID No:509) over wild type hICOS.

One way to quantify the extent of species cross-reactivity of an antibody, e.g. a multispecific, bispecific or dual-binding antibody is as the fold-difference in its affinity for antigen compared with a different antigen (e.g. fold difference in affinity for human ICOS vs mouse ICOS or fold difference in affinity for wild-type hICOS vs an isoform of hICOS). Affinity may be quantified as $K_D$, referring to the equilibrium dissociation constant of the antibody-antigen reaction as determined by SPR (optionally with the antibody in Fab format as described elsewhere herein). A species or isoform cross-reactive anti-ICOS antibody may have a fold-difference in affinity for binding human and mouse ICOS that is 30-fold or less, 25-fold or less, 20-fold or less, 15-fold or less, 10-fold or less or 5-fold or less. To put it another way, the $K_D$ of binding the extracellular domain of hICOS may be within 30-fold, 25-fold, 20-fold, 15-fold, 10-fold or 5-fold of the $K_D$ of binding the extracellular domain of mouse ICOS.

Antibodies can also be considered cross-reactive if the $K_D$ for binding antigen of both species meets a threshold value, e.g., if the $K_D$ of binding hICOS and the $K_D$ of binding mouse ICOS are both 10 mM or less, preferably 5 mM or less, more preferably 1 mM or less. The $K_D$ may be 10 nM or less, 5 nM or less, 2 nM or less, or 1 nM or less. The KD may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

An alternative measure of cross-reactivity for binding hICOS and mouse ICOS, or WT hICOS and an isoform of hICOS is the ability of an antibody to neutralise ICOS ligand binding to ICOS receptor, such as in an HTRF assay (as described elsewhere herein). Examples of species cross-reactive antibodies are provided herein, including STIM001, STIM002, STIM002-B, STIM003, STIM005 and STIM006, each of which was confirmed as neutralising binding of human B7-H2 (ICOS ligand) to hICOS and neutralising binding of mouse B7-H2 to mouse ICOS in an HTRF assay. Any of these antibodies or their variants may be selected when an antibody cross-reactive for human and mouse ICOS is desired. A species cross-reactive anti-ICOS antibody may have an $IC_{50}$ for inhibiting binding of hICOS to human ICOS receptor that is within 25-fold, 20-fold, 15-fold, 10-fold or 5-fold of the IC50 for inhibiting mouse ICOS to mouse ICOS receptor as determined in an HTRF assay. Antibodies can also be considered cross-reactive if the $IC_{50}$ for inhibiting binding of hICOS to human ICOS receptor and the $IC_{50}$ for inhibiting binding of mouse ICOS to mouse ICOS receptor are both 1 mM or less, preferably 0.5 mM or less, e.g., 30 nM or less, 20 nM or less, 10 nM or less. The $IC_{50}$s may be 5 nM or less, 4 nM or less, 3 nM or less or 2 nM or less. In some cases, the $IC_{50}$s will be at least 0.1 nM, at least 0.5 nM or at least 1 nM.

Affinities may also be as disclosed in concept 27 hereinabove.

Arrangement 3. A multispecific antibody according to arrangement 2, which comprises a $V_H$ domain comprising a CDRH1, a CDRH2 and a CDRH3 which $V_H$ domain binds (and optionally has specificity for) hICOS.

In one embodiment, the multispecific antibody comprises at least one $V_H$ domain which binds to hICOS. For example, the multispecific antibody may comprise a single-chain Fv (scFv), single-chain antibody, a single domain antibody or a domain antibody compositing only the $V_H$ region which binds to (and optionally has specificity for) hICOS.

Arrangement 4. A multispecific antibody according to arrangement 2 or arrangement 3, which comprises a $V_L$ domain comprising a CDRL1, a CDRL2 and a CDRL3, which $V_L$ domain binds (and optionally has specificity for). hICOS.

In one embodiment, the multispecific antibody comprises at least one $V_L$ domain which binds to hICOS. For example, the multispecific antibody may comprise a single-chain Fv (scFv), single-chain antibody, a single domain antibody or a domain antibody compositing only the $V_L$ region which binds to (and optionally has specificity for) hICOS.

In another embodiment, the multispecific antibody comprises a paired $V_H$ and $V_L$ domain, including, but not limited to, an intact or full-length antibody, a Fab fragment, a Fab' fragment, a F(ab')$_2$ fragment or a Fv fragment.

Arrangement 5. A multispecific antibody according to arrangement 3 or 4, wherein the $V_H$ and/or $V_L$ domain is any of $V_H$ and/or $V_L$ domains:
  a. of the antibody 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89 or any other antibody described in WO2016/154177 and US2016/0304610;
  b. of the antibody 422.2, H2L5, or any other antibody described in WO2016/120789 and US2016/0215059;
  c. of the antibody 314-8, the antibody produced from hybridoma CNCM 1-4180, or any other antibody described in WO2014/033327 and U52015/0239978;
  d. of the antibody Icos145-1, the antibody produced by hybridoma CNCM 1-4179, or any other antibody described in WO2012/131004, U.S. Pat. No. 9,376,493 and US2016/0264666;
  e. of the antibody JMAb 136, "136", or any other antibody described in WO2010/056804;
  f. of the antibody MIC-944, 9F3 or any other antibody described in WO99/15553, U.S. Pat. Nos. 7,259,247, 7,132,099, 7,125,551, 7,306,800, 7,722,872, WO05/103086, U.S. Pat. Nos. 8,318,905 and 8,916,155;
  g. of any JMAb antibody, e.g., any of JMAb-124, JMAb-126, JMAb-127, JMAb-128, JMAb-135, JMAb-136, JMAb-137, JMAb-138, JMAb-139, JMAb-140, JMAb-141, e.g., JMAb136, or any other antibody described in WO98/3821, U.S. Pat. No. 7,932,358B2, US2002/156242, U.S. Pat. Nos. 7,030,225, 7,045,615, 7,279,560, 7,226,909, 7,196,175, 7,932,358, 8,389,690, WO02/070010, U.S. Pat. Nos. 7,438,905, 7,438,905, WO01/87981, U.S. Pat. Nos. 6,803,039, 7,166,283, 7,988,965, WO01/15732, U.S. Pat. Nos. 7,465,445 and 7,998,478;
  h. of the antibody 17G9 or any other antibody described in WO2014/08911;
  i. of any antibody described in WO2012/174338;
  j. of any antibody described in US2016/0145344;
  k. of any antibody described in WO2011/020024, US2016/002336, US2016/024211 and U.S. Pat. No. 8,840,889;
  l. of any antibody described in U.S. Pat. No. 8,497,244;
  m. of the antibody known as GSK3359609;
  n. of the antibody known as JTX-2011; or
  o. of antibody clone ISA-3 (eBioscience), clone SP98 (Novus Biologicals), clone 1 G1, clone 3G4 (Abnova Corporation), clone 669222 (R&D Systems), clone TQ09 (Creative Diagnostics), or clone C398.4A (BioLegend).

Arrangement 5a. A multispecific antibody according to any preceding arrangement, which comprises the CDRH1, CDRH2, CDR3, CDRL1, CDRL2 and CDRL3, or the $V_H$, or the $V_L$ or the $V_H$ and $V_L$ region:

a. of the antibody 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, 35A9S89 or any other antibody described in WO2016/154177 and US2016/0304610;
b. of the antibody 422.2, H2L5, or any other antibody described in WO2016/120789 and US2016/0215059;
c. of the antibody 314-8, the antibody produced from hybridoma CNCM 1-4180, or any other antibody described in WO2014/033327 and US2015/0239978;
d. of the antibody Icos145-1, the antibody produced by hybridoma CNCM 1-4179, or any other antibody described in WO2012/131004, U.S. Pat. No. 9,376,493 and US2016/0264666;
e. of the antibody JMAb 136, "136", or any other antibody described in WO2010/056804;
f. of the antibody MIC-944, 9F3 or any other antibody described in WO99/15553, U.S. Pat. Nos. 7,259,247, 7,132,099, 7,125,551, 7,306,800, 7,722,872, WO05/103086, U.S. Pat. Nos. 8.318.905 and 8,916,155;
g. of any JMAb antibody, e.g., any of JMAb-124, JMAb-126, JMAb-127, JMAb-128, JMAb-135, JMAb-136, JMAb-137, JMAb-138, JMAb-139, JMAb-140, JMAb-141, e.g., JMAb136, or any other antibody described in WO98/3821, U.S. Pat. No. 7,932,358B2, US2002/156242, U.S. Pat. Nos. 7,030,225, 7,045,615, 7,279,560, 7,226,909, 7,196,175, 7,932,358, 8,389,690, WO02/070010, U.S. Pat. Nos. 7,438,905, 7,438,905, WO01/87981, U.S. Pat. Nos. 6,803,039, 7,166,283, 7,988,965, WO01/15732, U.S. Pat. Nos. 7,465,445 and 7,998,478;
h. of the antibody 17G9 or any other antibody described in WO2014/08911;
i. of any antibody described in WO2012/174338;
j. of any antibody described in US2016/0145344;
k. of any antibody described in WO2011/020024, US2016/002336, US2016/024211 and U.S. Pat. No. 8,840,889;
l. of any antibody described in U.S. Pat. No. 8,497,244;
m. of the antibody known as GSK3359609;
n. of the antibody known as JTX-2011; or
o. of antibody clone ISA-3 (eBioscience), clone SP98 (Novus Biologicals), clone 1 G1, clone 3G4 (Abnova Corporation), clone 669222 (R&D Systems), clone TQ09 (Creative Diagnostics), or clone C398.4A (BioLegend).

Arrangement 6. A multispecific antibody according to arrangement 3 or 4, wherein the $V_H$ and/or $V_L$ domain is any of $V_H$ and/or $V_L$ domains defined in sentences 1 to 102 or sentences 1a to 21a.

In one embodiment, the anti-ICOS $V_H$ and/or $V_L$ is as described in GB patent application 1620414.1 (filed 1 Dec. 2016), the contents of which are incorporated herein by reference.

Arrangement 7. A multispecific antibody according to any preceding arrangement, which has agonistic activity against ICOS.

Agonism can be tested for in an in vitro T-cell activation assays, using antibody in soluble form (e.g. in immunoglobulin format or other antibody format comprising two spatially separated antigen-binding sites, e.g., two VH-$V_L$ pairs), either including or excluding a cross-linking agent, or using antibody (e.g. multispecific antibody) bound to a solid surface to provide a tethered array of antigen-binding sites.

Agonism assays may use a hICOS positive T-lymphocyte cell line such as MJ cells (ATCC CRL-8294) as the target T-cell for activation in such assays. One or more measures of T-cell activation can be determined for a test antibody and compared with a reference molecule or a negative control to determine whether there is a statistically significant (p<0.05) difference in T-cell activation effected by the test antibody (e.g. multispecific antibody) compared with the reference molecule or the control. One suitable measure of T-cell activation is production of cytokines, e.g., IFNγ, TNFα or IL-2. A skilled person will include suitable controls as appropriate, standardising assay conditions between test antibody and control. A suitable negative control is an antibody in the same format (e.g., isotype control) that does not bind ICOS, e.g., an antibody (e.g. multispecific antibody) specific for an antigen that is not present in the assay system. A significant difference is observed for test antibody relative to a cognate isotype control within the dynamic range of the assay is indicative that the antibody acts as an agonist of the ICOS receptor in that assay.

An agonist antibody may be defined as one which, when tested in a T-cell activation assay:
has a significantly lower $EC_{50}$ for induction of IFNγ production compared with control antibody;
induces significantly higher maximal IFNγ production compared with control antibody;
has a significantly lower $EC_{50}$ for induction of IFNγ production compared with ICOSL-Fc;
induces significantly higher maximal IFNγ production compared with ICOSL-Fc;
has a significantly lower $EC_{50}$ for induction of IFNγ production compared with reference antibody C398.4A; and/or
induces significantly higher maximal IFNγ production compared with reference antibody C398.4A.

A significantly lower or significantly higher value may for example be up to 0.5-fold different, up to 0.75-fold different, up to 2-fold different, up to 3-fold different, up to 4-fold different or up to 5-fold different, compared with the reference or control value.

Thus, in one example, an antibody (e.g. a multispecific antibody) provided herein has a significantly lower, e.g., at least 2-fold lower, $EC_{50}$ for induction of IFNγ in an MJ cell activation assay using the antibody in bead-bound format, compared with control.

The bead-bound assay uses the antibody (e.g. multispecific antibody) (and, for control or reference experiments, the control antibody, reference antibody or ICOSL-Fc) bound to the surface of beads. Magnetic beads may be used, and various kinds are commercially available, e.g., Tosyl-activated DYNABEADS M-450 (DYNAL Inc, 5 Delaware Drive, Lake Success, N.Y. 11042 Prod No. 140.03, 140.04). Beads may be coated (coating methods are well-known to those skilled in the art), or generally by dissolving the coating material in carbonate buffer (pH 9.6, 0.2 M) or other method known in the art. Use of beads conveniently allows the quantity of protein bound to the bead surface to be determined with a good degree of accuracy. Standard Fc-protein quantification methods can be used for coupled protein quantification on beads. Any suitable method can be used, with reference to a relevant standard within the dynamic range of the assay. DELFIA, ELISA or other methods could be used.

Agonism activity of an antibody can also be measured in primary human T-lymphocytes ex vivo. The ability of an antibody (e.g. multispecific antibody) to induce expression of IFNγ in such T-cells is indicative of ICOS agonism.

Preferably, an antibody will show significant (p<0.05) induction of IFNγ at 5 μg/mL compared with control antibody in a T-cell activation assay. An anti-ICOS antibody may stimulate T-cell activation to a greater degree than ICOS-L or C398.4 in such an assay. Thus, the antibody may show significantly (p<0.05) greater induction of IFNγ at 5 μg/mL compared with the control or reference antibody in a T-cell activation assay. TNFα or IL-2 induction may be measured as an alternative assay readout.

Agonism of an anti-ICOS antibody may contribute to its ability to change the balance between populations of $T_{Reg}$ and $T_{Eff}$ cells in vivo, e.g., in a site of pathology such as a tumour microenvironment, in favour of $T_{Eff}$ cells. The ability of an antibody to enhance tumour cell killing by activated ICOS-positive effector T-cells may be determined, as discussed elsewhere herein.

Arrangement 8. A multispecific antibody according to any preceding arrangement, which binds (and optionally has specificity for) mouse ICOS and/or cynomolgus ICOS.

The multispecific antibodies described herein may be cross-reactive, and may for example bind the extracellular domain of mouse ICOS as well as human ICOS. The multispecific antibodies may bind other non-human ICOS, including ICOS of primates, such as cynomolgus monkey. An anti-ICOS multispecific antibody intended for therapeutic use in humans must bind human ICOS, whereas binding to ICOS of other species would not have direct therapeutic relevance in the human clinical context. Regardless of the underlying theory, however, cross-reactive antibodies are of high value and are excellent candidates as therapeutic molecules for pre-clinical and clinical studies. Cross-reactivity may be determined as set out for arrangement 2 hereinabove.

Arrangement 9. A multispecific antibody according to any preceding arrangement which is a bispecific antibody.

A bispecific antibody has any of the meanings set out hereinabove.

Arrangement 10. A bispecific antibody according to arrangement 9, wherein the bispecific antibody format is selected from DVD-Ig, mAb², FIT-Ig, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, minibody, knobs-in-holes, knobs-in-holes with common light chain, knobs-in-holes with common light chain and charge pairs, charge pairs, charge pairs with common light chain, in particular mAb², knob-in-holes, knob-in-holes with common light chain, knobs-in-holes with common light chain and charge pairs and FIT-Ig, e.g. mAb² and FIT-Ig.

In one embodiment, the bispecific antibody format is as described in any of concepts 37 to 40 described hereinabove, or as described in the definitions section. In one embodiment, the bispecific antibody format is a mAb², wherein the ICOS binding is provided by the Fcab portion of the bispecific antibody. In another embodiment, the the bispecific antibody format is a mAb², wherein the ICOS binding is provided by the Fab portion of the bispecific antibody.

In another embodiment, the bispecific antibody is not a mAb² bispecific antibody.

Arrangement 11. A multispecific antibody according to any one of arrangements 1 to 8 which is a dual binding antibody.

A dual-binding antibody has any of the meanings set out hereinabove.

Arrangement 12. A multispecific, bispecific or dual binding antibody according to any one of arrangements 1 to 11, wherein the another target antigen is selected from immune checkpoint inhibitors, immune modulators and immune activators.

Arrangement 13. A multispecific, bispecific or dual-binding antibody according to arrangement 12, wherein the another target antigen is selected from PD-1, PD-L1, CTLA-4, TIGIT, TIM-3, LAG-3, VISTA, BTLA, HVEM, CSF1R, CCR4, CD39, CD40, CD73, CD96, CXCR2, CXCR4, CD200, GARP, SIRPα, CXCL9, CXCL10, CD155, CD137, GITR, OX40, CXCR3, CD27 and CD3.

Arrangement 13a. A multispecific, bispecific or dual-binding antibody according to arrangement 12, wherein the another target antigen is selected from PD-1, PD-L1, CTLA-4, TIGIT, TIM-3, LAG-3, VISTA, BTLA, HVEM, CSF1R, CCR4, CD39, CD40, CD73, CD96, CXCR2, CXCR4, CD200, GARP, SIRPα, CXCL9, CXCL10, CD155, CD137, GITR, OX40, CXCR3 and CD3.

In one embodiment, the antigen-binding site which binds the another target antigen is provided for by any of the CDRH1, CDRH2, CDR3, CDRL1, CDRL2 and CDRL3, or the $V_H$, or the $V_L$ or the $V_H$ and $V_L$ regions from any one of the antibodies against the targets listed in arrangement 13 which are described in more detail in aspect 1a hereinabove.

Arrangement 14. A multispecific, bispecific or dual-binding antibody according to arrangement 13, wherein the another target antigen is selected from PD-L1, TIGIT, TIM-3, LAG-3, GARP, SIRPα, CXCR4, BTLA, HVEM, CSF1R, agonistic anti-CXCR3 antibodies), CD137, GITR and OX40.

Arrangement 15. A multispecific, bispecific or dual-binding antibody according to arrangement 14, wherein the another target antigen is PD-L1 (e.g. human PD-L1).

Arrangement 16. A multispecific, bispecific or dual-binding antibody according to arrangement 15, wherein the binding (and optionally specificity for) PD-L1 is provided by any of the antibodies or fragments as defined in concepts 1 to 70.

Arrangement 17. A multispecific, bispecific or dual-binding antibody according to arrangement 15 or arrangement 16, which comprises a $V_H$ domain comprising a CDRH1, a CDRH2 and a CDRH3 which $V_H$ domain has specificity for human PD-L1.

Arrangement 18. A multispecific, bispecific or dual-binding antibody according to any one of arrangements 15 to 17, which comprises a $V_L$ domain comprising a CDRL1, a CDRL2 and a CDRL3, which $V_L$ domain as specificity for human PD-L1.

Arrangement 19. A multispecific, bispecific or dual-binding antibody according to arrangement 17 or arrangement 18, wherein the $V_H$ and/or $V_L$ domain is any of $V_H$ and/or $V_L$ domains from atezolizumab (Roche), avelumab (Merck), BMS-936559 (BMS), durvalumab (Medimmune) or from any of the PD-L1 antibodies disclosed in WO2016/061142, WO2016/022630, WO2016/007235, WO2015/173267, WO2015/181342, WO2015/109124, WO2015/112805, WO2015/061668, WO2014/159562, WO2014/165082, WO2014/100079, WO2014/055897, WO2013/181634, WO2013/173223, WO2013/079174, WO2012/145493, WO2011/066389, WO2010/077634, WO2010/036959 or WO2007/005874.

Arrangement 20. A multispecific, bispecific or dual-binding antibody according to arrangement 17 or arrangement 18, wherein the $V_H$ and/or $V_L$ domain is any of $V_H$ and/or $V_L$ domains described in concepts 1 to 70.

Arrangement 21. A multispecific, bispecific or dual-binding antibody according to any one of arrangements 15 to 20, which binds (and optionally has specificity for) mouse PD-L1 and/or cynomolgus PD-L1.

Cross reactivity may be as described hereinabove for arrangement 2 or concept 27.

Arrangement 22. A composition comprising a multispecific, bispecific or dual-binding antibody as defined in any preceding arrangement and a pharmaceutically acceptable excipient, diluent or carrier and optionally further comprising a further therapeutic agent independently selected from the group consisting of:
 a) other immune checkpoint inhibitors (such as anti-TIM-3 antibodies, anti-PD-1 antibodies, anti-CRA-4 antibodies, anti-TIGIT antibodies and anti-LAG-3 antibodies);
 b) immune stimulators (such as anti-OX40 antibodies, anti-GITR antibodies, anti-CD137 antibodies, anti-ICOS antibodies and anti-CD40 antibodies);
 c) chemokine receptor antagonists (such as CXCR4, CCR4 and CXCR2);
 d) targeted kinase inhibitors (such as CSF-1R or VEGFR inhibitors);
 e) angiogenesis inhibitors (such as anti-VEGF-A or Delta-like Ligand-4);
 f) immune stimulating peptides or chemokines (such as CXCL9 or CXCL10);
 g) cytokines (such as IL-15 and IL-21);
 h) bispecific T-cell engagers (BiTEs) having at least one specificity against CD3 (e.g. CD3/CD19 BiTE);
 i) other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
 j) oncolytic viruses (such as I-ISV virus (optionally which secretes GMCSF), Newcastle disease virus and Vaccinia virus);
 k) vaccination with tumour associated antigens (such as New York Esophageal Cancer-1 [NY-ESO-1], Melanoma Associated Antigen-3 [MAGE-3]);
 l) cell-based therapies (such as chimeric Antigen Receptor-T-cells (CAR-T) for example expressing anti-CD19, anti-EpCam or anti-mesothelin);
 m) bi-specific NK cell engagers having a specificity against an activating MK receptor such as NKG2D or CD16a; and
 n) adoptive transfer of tumour specific T-cells or LAK cells.

The antibodies may be any of the sequences or antibodies described in arrangement 5 or detailed in aspect 1a. Other features of this arrangement may be as described in concept 49.

Arrangement 22a. A pharmaceutical composition according to arrangement 22, or a kit comprising a pharmaceutical composition as defined in arrangement 22, wherein the composition is for treating and/or preventing a condition or disease selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease, diffuse large B-cell lymphoma.

Arrangement 22b. A pharmaceutical composition according to arrangement 22 or arrangement 22a in combination with, or kit according to arrangement 22a comprising, a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the multispecific, bispecific or dual-binding antibody.

Arrangement 23. A multispecific, bispecific or dual-binding antibody as defined in any one of arrangements 1 to 21 for use in treating or preventing a disease or condition, selected from neurological disease, neoplastic or non-neoplastic disease, chronic viral infections, and malignant tumours; such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas).

Arrangement 24. Use of a multispecific, bispecific or dual-binding antibody as defined in any one of arrangements 1 to 21 in the manufacture of a medicament for administration to a human for treating or preventing a disease or condition in the human selected from neurological disease, neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas). Arrangement 25. A method of treating or preventing a disease or condition selected from neurological disease, neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma (for example melanoma, Merkel cell carcinoma, non-small cell lung cancer (squamous and non-squamous), renal cell cancer, bladder cancer, head and neck squamous cell carcinoma and mesothelioma or for example virally induced cancers (such as cervical cancer and nasopharyngeal cancer) and soft tissue sarcomas) in a human, comprising administering to said human a therapeutically effective amount of a multispecific, bispecific or dual-binding antibody as defined in any one of arrangements 1 to 21, wherein the disease or condition is thereby treated or prevented.

The diseases and conditions which may be treated or prevented by the multispecific, bispecific or dual-binding antibodies provided for in these arrangements may be any of the diseases provided for in, for example concepts 41 to 45, aspects 51 to 55, or in any of the sentences described herein.

Arrangement 26. The multispecific, bispecific or dual-binding antibody according to arrangement 23, the use according to arrangement 24 or the method according to arrangement 25, wherein the neurological disease is a neurodegenerative disease, disorder or condition, optionally wherein the neurodegenerative disease, disorder or condition is selected from Alzheimer's disease, amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia, in particular Alzheimer's disease, amyotrophic lateral sclerosis, Parkinson's disease and Huntington's disease, and e.g. Alzheimer's disease.

Arrangement 27. The multispecific, bispecific or dual-binding antibody according to arrangement 23, the use according to arrangement 24 or the method according to arrangement 25, wherein the cancer is selected from melanoma, Merkel cell carcinoma, non-small cell lung cancer (squamous and non-squamous), renal cell cancer, bladder cancer, head and neck squamous cell carcinoma and mesothelioma or is selected from virally induced cancers (such as cervical cancer and nasopharyngeal cancer) and soft tissue sarcomas.

Arrangement 28. The multispecific, bispecific or dual-binding antibody, the use or the method according to any one of arrangements 23 to 27, further comprising administering to the human a further therapy, for example a further therapeutic agent, optionally wherein the further therapeutic agent is independently selected from the group consisting of:
  a. other immune checkpoint inhibitors (such as anti-TIM-3 antibodies, anti-PD-1 antibodies, anti-CTLA-4 antibodies, anti-TIGIT antibodies and anti-LAG-3 antibodies);
  b. immune stimulators (such as anti-OX40 antibodies, anti-GITR antibodies, anti-CD137 antibodies and anti-CD40 antibodies);
  c. chemokine receptor antagonists (such as CXCR4, CCR4 and CXCR2);
  d. targeted kinase inhibitors (such as CSF-1R or VEGFR inhibitors);
  e. angiogenesis inhibitors (such as anti-VEGF-A or Delta-like Ligand-4);
  f. immune stimulating peptides or chemokines (such as CXCL9 or CXCL10);
  g. cytokines (such as IL-15 and IL-21);
  h. bispecific T-cell engagers (BiTEs) having at least one specificity against CD3 (e.g. CD3/CD19 BiTE);
  i. other bi-specific molecules (for example IL-15-containing molecules targeted towards tumour associated antigens, for example Epidermal growth factor receptors such as EGFR, Her-2, New York Esophageal Cancer-1 (NY-ESO-1), GD2, EpCAM or Melanoma Associated Antigen-3 (MAGE-A3));
  j. oncolytic viruses (such as HSV virus (optionally which secretes GMCSF), Newcastle disease virus and Vaccinia virus);
  k. vaccination with tumour associated antigens (such as New York Esophageal Cancer-1 [NY-ESO-1], Melanoma Associated Antigen-3 [MAGE-3]);
  l. cell-based therapies (such as chimeric Antigen Receptor-T-cells (CAR-T) for example expressing anti-CD19, anti-EpCam or anti-mesothelin);
  m. bi-specific NK cell engagers having a specificity against an activating MK receptor such as NKG2D or CD16a; and
  n. adoptive transfer of tumour specific T-cells or LAK cells, or optionally wherein the further therapy is chemotherapy, radiotherapy and surgical removal of tumours.

Radiotherapy may be single dose or in fractionated doses, either delivered to affected tissues directly or to the whole body.

In this arrangement, any of the features and embodiments of concept 46 apply mutatis mutandis.

In this aspect, the bispecific molecules include "bispecific antibodies" and antibody fusion proteins, including those formats and molecules described in concepts 37 to 40.

Arrangement 29. A nucleic acid that encodes a heavy chain and/or a light chain of a multispecific, bispecific or dual-binding antibody as defined in any one of arrangements 1 to 21.

Arrangement 30. A vector comprising the nucleic acid as defined in arrangement 29; optionally wherein the vector is a CHO or HEK293 vector.

Arrangement 31. A host comprising the nucleic acid as defined in arrangement 29 or the vector as defined in arrangement 30.

6. Uses for Antibodies and Immunocytokines

Unless otherwise apparent from the context, the uses for antibodies or fragments applies mutatis mutandis to the immunocytokines and multispecific (e.g. bispecific or dual-binding antibodies) of the invention.

Therapeutic

In one embodiment, the PD-L1 specific antibodies described herein and antigen binding fragments thereof can be used for therapeutic modulation of the PD-1/PD-L1 pathway. In one embodiment, the PD-L1 specific antibody or fragment thereof is as described in any concept, aspect or embodiment herein.

In one embodiment, the antibody or antibody binding fragment specifically binds to PD-L1 and thereby inhibits PD-L1 activity. In another embodiment, the antibody or antibody binding fragment specifically binds to PD-L1 and thereby inhibits binding of PD-L1 to PD-1. In another embodiment, the antibody or antibody binding fragment specifically binds to PD-L1 and thereby inhibits binding of PD-L1 to B7-1. In yet another embodiment, the antibody or antigen binding fragment thereof blocks PD-L1 induced T-cell suppression and thereby enhance anti-tumour immunity.

In yet another embodiment, the antibody or antigen binding fragment thereof is capable of stimulating one or more of the following activities: T-cell proliferation, IFN-y, CD25 and/or IL-2 secretion in mixed lymphocyte reactions.

In one embodiment, the antibody or antigen binding fragment thereof specifically binds PD-L1 and inhibits PD-L1 induced cell proliferation, for example, tumour cell proliferation and/or inhibits, tumour cell survival. In another embodiment, the antibody or antigen binding fragment thereof specifically binds PD-L1 and thereby inhibits PD-L1 mediated suppression of T-cells, including, but not limited to, tumour reactive T-cells, thereby enhancing anti-tumour cytolytic T-cell activity. In other embodiments, the antibodies or binding fragments thereof as described herein inhibit tumour cell adhesion, motility, invasion and cellular metastasis, and reduce tumour growth. In other embodiments, the antibodies or binding fragments thereof can bind to cells expressing PD-L1, including tumour and non-tumour cells, and recruit, by means of interaction with the Fc portion of the antibody, cellular effector functions against the target cells by mechanisms including but not limited to antibody dependent cellular cytotoxicity (ADCC) and antibody dependent cellular phagocytosis (ADCP).

Still further embodiments include methods of treating a proliferative or invasion-related disease in a mammal by administering to the animal a therapeutically effective dose of an antibody or antigen binding fragment thereof. In another embodiment, the antibodies or antigen binding fragments thereof can be used in a method for treating a mammal suffering from a disease selected from: neoplastic or non-neoplastic disease, chronic viral infection, and a malignant tumour, wherein the method includes administering to the mammal a therapeutically effective dose of an antibody or antigen binding fragment thereof.

Still further embodiments include methods of treating a disease of immunological dysfunction in a mammal by administering to the animal a therapeutically effective dose of an antibody or antigen binding fragment thereof as described herein. Exemplary immunological dysfunction in humans includes diseases of neurological deficit, such as Alzheimer's disease.

It has further been proposed that an immune response, particularly an IFNγ-dependent systemic immune response, could be beneficial for treatment of Alzheimer's disease and other CNS pathologies that share a neuroinflammatory component. WO2015/136541 (incorporated herein by reference) proposes treatment of Alzheimer's disease using an anti-PD-1 antibody (also see Baruch K. et al., PD-1 immune checkpoint blockade reduces pathology and improves memory in mouse models of Alzheimer's disease, Nature Medicine, 2016, 22(2):137-137).

Thus, in one embodiment, the antibody or antigen binding fragment thereof specifically binds PD-L1 and reduces the level of systemic immunosuppression in an individual by release of a restraint imposed on the immune system by PD-1/PD-L1 immune checkpoint pathway. In an aspect, PD-1/PD-L1 inhibitory immune checkpoint pathway blockade results in transient relief the systemic adaptive immune activity from suppression, which results in a transiently augmented immune response in the periphery, mainly manifested by elevation of IFN-y secretion by IFN-y-producing cells. Increased IFN-γ activity may enable the brain's choroid plexus to allow selective leukocyte trafficking and infiltration of T-cells and monocytes into the damaged CNS, homing of these immune cells to sites of neurodegenerative pathology and neuroinflammation, and may modulate the environment to become less toxic and more permissive for clearance of toxic agents, rescue of neurons, regeneration and repair.

Thus, the PD-L1 mediated disease or condition is a neurodegenerative disease, disorder or condition. In one embodiment, the neurodegenerative disease, disorder or condition is Alzheimer's disease. In another embodiment, the neurodegenerative disease, disorder or condition is selected from amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia. In another embodiment, the neurodegenerative disease, disorder or condition is selected from Alzheimer's disease, amyotrophic lateral sclerosis, Parkinson's disease and Huntington's disease.

Anti-PD-L1 antibodies as described herein may be used in the treatment of Alzheimer's disease or other neurodegenerative diseases, optionally in combination with one or more other immune checkpoint inhibitors (such as anti-TIM-3 antibodies, anti-CTLA-4 antibodies, anti-TIGIT antibodies and anti-LAG-3 antibodies) or one or more other immune stimulators (such as anti-OX40 antibodies, anti-GITR antibodies, anti-CD137 antibodies, anti-ICOS antibodies and anti-CD40 antibodies, including those which are specifically described in Aspect 1a herein). Other combination partners include any of the the active agents as listed in claim 10 of WO2015/136541, which is incorporated herein by reference.

Any of the PD-L1 antibodies described herein (including at least the antibodies described in any of concepts 1 to 40, and the PD-L1 antibodies described in aspect 1a) may be used for the treatment of the neurodegenerative diseases, disorders or conditions described above.

Exemplary cancers in humans include a Merkel cell carcinoma, breast cancer, prostate cancer, basal cell carcinoma, biliary tract cancer, bladder cancer, bone cancer, brain and CNS cancer (e.g. gliomblastoma), cervical cancer, choriocarcinoma, colon and rectum cancer, connective tissue cancer, cancer of the digestive system; endometrial cancer, esophageal cancer; eye cancer; cancer of the head and neck; nasopharyngeal cancer; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma including but not limited to DLBCL; Chronic lymphocytic leukaemia, melanoma; uveal melanoma, myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer (renal cell carcinoma (RCC)), cancer of the respiratory system; sarcoma, skin cancer; stomach cancer, testicular cancer, thyroid cancer; uterine cancer, cancer of the urinary system, as well as other carcinomas and sarcomas. Further examples of virally induced cancers including; Nasopharyngeal carcinoma, certain Types of NHL (for example but not limited to EBV+ CNS lymphomas, DLBCL and BL, Hodgkins lymphoma (thought to be EBV driven) HPV-related cervical and head and neck squamous cell carcinomas); HBV hepatocellular carcinoma.

Exemplary chronic infections in humans include HIV, hepatitis B virus (HBV), and hepatitis C virus (HCV).

Proliferative or invasion-related diseases that can be treated with the antibodies or antigen binding fragments described herein include neoplastic diseases, and the metastasis associated with such neoplastic disease, such as, melanoma, uveal melanoma, skin cancer, small cell lung cancer, non-small cell lung cancer, salivary gland, glioma, hepatocellular (liver) carcinoma, gallbladder cancer, thyroid tumour, bone cancer, gastric (stomach) cancer, prostate cancer, breast cancer (including triple negative breast cancer), ovarian cancer, cervical cancer, uterine cancer, vulval cancer, endometrial cancer, testicular cancer, bladder cancer, lung cancer, glioblastoma, thyroid cancer, endometrial cancer, kidney cancer, colon cancer, colorectal cancer, pancreatic cancer, esophageal carcinoma, brain/CNS cancers, neuronal cancers, head and neck cancers (including but not limited to squamous cell carcinoma of the head and neck (SCCHN)), mesothelioma, sarcomas, biliary (cholangiocarcinoma), small bowel adenocarcinoma, pediatric malignancies, epidermoid carcinoma, sarcomas, cancer of the pleural/peritoneal membranes and leukaemia, including acute myeloid leukaemia, acute lymphoblastic leukaemia, and multiple myeloma. Treatable chronic viral infections include HIV, hepatitis B virus (HBV), and hepatitis C virus (HCV) in humans, simian immunodeficiency virus (SIV) in monkeys, and lymphocytic choriomeningitis virus (LCMV) in mice.

The antibody or antigen binding fragment thereof can be administered alone, or in combination with other antibodies or chemo therapeutic drugs, radiation therapy or therapeutic vaccines. In one embodiment, the antibody or antigen binding fragment thereof is administered as an antibody-drug conjugate in which the antibody or antigen binding fragment thereof is linked to a drug moiety such as a cytotoxic or cytostatic agent. The use of antibody-drug conjugates for the local delivery of cytotoxic or cytostatic agents in the treatment of cancer allows targeted delivery of the drug moiety to tumours, and intracellular accumulation therein, where systemic administration of unconjugated drug may result in unacceptable levels of toxicity. Drugs in antibody drug conjugates can include, but are not limited to, daunomycin, doxorubicin, methotrexate, and vindesine. Toxins can also be used in antibody-toxin conjugates, including, for example, bacterial toxins such as diphtheria toxin, plant toxins such as ricin, small molecule toxins such as geldanamycin. The toxins may effect their cytotoxic and cytostatic effects by mechanisms including tubulin binding, DNA binding, or topoisomerase.

Detection

In another embodiment, the antibodies or antigen binding fragments can be used to detect the presence, absence and/or level of surface expressed PD-L1 expression in a sample. PD-L1 surface expression can be detected in vivo and/or in vitro and is useful in helping diagnose diseases or conditions that involve expression and/or overexpression of PD-L1.

In Vitro Diagnostic

In another embodiment, the PD-L1 specific antibodies or antigen binding fragments thereof can be used for the assessment of expression and localization of PD-L1 in a biological sample from a patient. In one embodiment, the biological sample is a tissue sample and PD-L1 expression is detected using known methods such as FLOW cytometry, IHC in fresh tissue, IHC in FFPE tissue and/or IHC in frozen tissue. In other embodiments, the biological sample is blood, plasma or serum.

In one embodiment, the antibody or antibody fragment described herein is labeled with a detectable moiety, for example, a radiolabel, fluorescent label, enzymatic label chemiluminescent labeled or a biotinyl group. Radioisotopes or radionuclides may include $^3$H, $^{14}$C, $^{15}$N, $^{35}$S, $^{90}$Y, $^{99}$Tc, $^{115}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc. (Perkin Elmer and Cisbio Assays); chemiluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

In Vivo Diagnostic

In one embodiment, the antibody or antigen binding fragment thereof can be administered to a patient, wherein the antibody or antigen binding fragment is conjugated to a label. The presence of the label in the patient can be measured or observed, wherein a relatively high amount of the label may indicate a high risk of disease and a relatively low amount of the label may indicate a relatively low risk of the disease. In one embodiment, the label is a contrast agent, isotopic tag, or fluorescent marker, such as green fluorescent protein.

In one embodiment, the antibody or antigen binding fragment is used to monitor therapy that involves the use of other therapeutic agents, including, for example, chemotherapeutic agents or other antibodies that specifically bind PD-L1. In one embodiment, the antibody does not compete with the therapeutic PD-L1 antibodies.

Guide Patient Selection

In one embodiment, detection of PD-L1 expression can be used to guide patient selection. In one embodiment, the antibodies or antigen binding fragments thereof can be used to assist in patient selection for therapeutic antibody treatment with an anti-PD-L1 antibody, including, but not limited to anti-PD-L1 antibodies disclosed in WO2011/066389, entitled "Targeted Binding Agents Against B7-H1", which antibodies and sequences are incorporated herein by reference. In another embodiment, the antibodies or antigen binding fragments thereof can be used to assist in patient selection for treatment with immunotherapies such as anti- PD-L1, anti-CTLA4, anti-OX40, anti-PD-1, vaccines etc. In some cases, higher levels of PD-L1 may be indicative of successful therapy, whereas lower levels may indicate a reduced likelihood of success. Preferential expression of splice variants and/or protein processing may produce unique protein mixture profiles which may impact a patient's response to treatment or may change following treatment. These profiles may help to identify patients and define patient subsets who should receive treatment, continue to receive treatment or who should receive an alternative treatment. In another embodiment, the antibodies or antigen binding fragments thereof can be used for detection of PD-L1 isoforms. Patient samples can include, for example, blood, plasma, serum, sputum, saliva, urine, CSF, tears, exhaled exogenous particle samples, cell supernatant, cell or tissue lysate or tissue samples.

In one embodiment, the antibodies or antigen binding fragments thereof can be used to identify the presence, absence and/or level of PD-L1 expression at baseline, i.e., before treatment.

In another embodiment, the PD-L1 specific antibodies or antigen binding fragments thereof can be used as an exclusion marker to suggest treatment with therapies that do not target PD-L1. In another embodiment, the PD-L1 specific antibodies or antigen binding fragments thereof can be used as a prognostic marker for life expectancy. In particular, PD-L1 expression on tumours is linked to poor prognosis and life expectancy can be estimated based on historical data within tumour types.

Methods for detection of proteins are known, and include, for example, IHC, FLOW cytometery, Western blotting and Mass Spectroscopy, Immunoprecipitation, aptamers, immuno-PCR, and protein array.

Guide Therapy

The antibodies can be used to guide therapy. For example, the antibodies or antigen binding fragments thereof can be used to identify the presence, absence and/or level of PD-L1 expression during or after treatment. In one embodiment, the antibodies or antigen binding fragments thereof can be used as early response biomarkers to assist in patient management, drug approval and reimbursement. In another embodiment, the antibodies or antigen binding fragments thereof can be used to identify the presence, absence and/or level of PD-L1 expression to help guide therapy. For example, PD-L1 expression can help determine whether the treatment is effective, and hence, whether or not treatment should be continued, or whether the dose should be adjusted (increased or decreased) and whether a combination regimen should be changed. For example, in one embodiment, the PD-L1 specific antibodies or antigen binding fragments thereof can be used for determining receptor occupancy of PD-L1 on cells in a patient treated with anti-PD-L1 therapy for dose setting (PK/PD). In particular, receptor occupancy can be used as a measure of target engagement or target coverage. Estimates of the amount or duration of target engagement needed to elicit a biological or clinical response could be used to determine if a patient has been dosed sufficiently or not. In particular, the antibodies can be used to assist in evaluating the relationship between, dose, exposure, receptor occupancy, pharmacodynamic response and clinical benefit.

Monitor Efficacy of Therapy

In another embodiment, the PD-L1 specific antibodies or antigen binding fragments thereof can be used for patient monitoring, to help evaluate whether a course of treatment is effective and whether or not treatment should be continued. For example, in one embodiment, the antibodies or antigen binding fragments thereof can be used detect expression before a patient receives therapeutic treatment that targets PD-L1. In another embodiment, the antibodies or antigen binding fragments thereof can be used to detect expression during therapy or after a patient has received therapeutic anti-PD-L1 treatment. In another embodiment, the antibodies or antigen binding fragments thereof can be used as an early response marker to assist in the determination as to whether or not a course of therapy is effective and should be continued or discontinued. In one embodiment, the expression of PD-L1 is detected after washout, wherein the term "washout" refers to a period of time after which the administered drug has been eliminated from the body. In particular, expression of PD-L1 may be detected after washout if the patient is treated with anti-PD-L1 therapy that competes with the detection antibody. However, if the patient is treated with an antibody that does not compete with an anti-PD-L1 antibody, such as anti-CTLA-4 or anti-PD-1, detection can be performed without waiting for washout. In another embodiment, the detection antibody can bind to PD-L1 but not compete with a therapeutic antibody that binds to PD-L1. In this situation, washout may not be necessary. The washout period can vary depending upon many factors, but is generally a period of at least about 1, 2, 3, 4, 5, or 6 weeks and up to about 1, 2, 3, 4, 5 or 6 months from the most recent chemotherapy or immunotherapy treatment. The antibodies or antigen binding fragments thereof can be used to determine expression of PD-L1 on biopsy samples or on circulating tumour cells (CTC).

In one embodiment, labelled antibodies or antigen binding fragments thereof can be used to identify a peripheral correlate to enable non-invasive assessment of tumour status pre, during and post treatment.

Methods for detection of proteins are known, and include, for example, IHC, flow cytometery, Western blotting and Mass Spectroscopy, immunoprecipitation, aptamers, immuno-PCR., and protein array.

Identify Protein Binding Partners for PD-L1

In another embodiment, antibodies or antigen binding fragments thereof can be used as a capture reagent or detection reagent for examination of the protein binding partners of PD-L1 protein species in the context of a protein "pull-down." A protein "pull down" refers to immunoprecipitation of intact protein complexes, such as antigen along with any proteins or ligands that are bound to it—also known as co-immunoprecipitation (Co-IP). Co-IP works by selecting an antibody that targets a known protein that is believed to be a member of a larger complex of proteins. By targeting the known member with an antibody it may become possible to pull the entire protein complex out of solution and thereby identify unknown members of the complex. Complete understanding of the regulation of immune recognition through and PD-1 axis vs. CTLA-4 etc. is not fully understood. As such, antibodies and antigen binding fragments could improve knowledge of the interplay among accessory proteins and factors, which may determine a patient's propensity to respond to specific therapies or immunotherapy in general.

7. Pharmaceutical Compositions

Unless otherwise apparent from the context, the compositions for antibodies or fragments applies mutatis mutandis to the immunocytokines and multispecific (e.g. bispecific or dual-binding antibodies) of the invention.

In one embodiment, there is provided a pharmaceutical composition comprising an effective amount of an antibody or antigen binding fragment and a pharmaceutically acceptable carrier. An effective amount of antibody to be employed therapeutically will depend, for example, upon the therapeutic objectives, the route of administration, and the condition of the patient. In one embodiment, the composition includes other excipients or stabilizers.

Pharmaceutically acceptable carriers are known and include carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as Ethylenediaminetetraacetic acid (EDTA); sugar alcohols such as mannitol or sorbitol; salt-forming counterions such as sodium; and/or nonionic surfactants such as TWEEN™, polyethylene glycol (PEG), and PLURONICS™.

The antibodies or antigen binding fragments can be administered intravenously or through the nose, lung, for example, as a liquid or powder aerosol (lyophilized). The composition can also be administered parenterally or subcutaneously. When administered systemically, the composition should be sterile, pyrogen-free and in a physiologically acceptable solution, having due regard for pH, isotonicity and stability. These conditions are known to those skilled in the art.

Methods of administering a prophylactic or therapeutic agent (e.g., an antibody as disclosed herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody as disclosed herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. Each dose may or may not be administered by, an identical route of administration. In one embodiment, an anti-PD-L1 antibody or fragment as disclosed herein may be administered via multiple routes of administration simultaneously or subsequently to other doses of the same or a different anti-PD-L1 antibody or fragment as disclosed herein.

Various delivery systems are known and can be used to administer a prophylactic or therapeutic agent (e.g., an antibody or fragment as disclosed herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO92/19244, WO97/32572, WO97/44013, WO98/31346, and WO99/66903, each of which is incorporated herein by reference their entirety.

In a specific embodiment, it may be desirable to administer a prophylactic or therapeutic agent, or a pharmaceutical composition as described herein locally to the area in need of treatment. This may be achieved by, for example, local infusion, by topical administration (e.g., by intranasal spray), by injection, or by means of an implant, said implant being of a porous, non-porous, or gelatinous material, including membranes, such as sialastic membranes, or fibres. When administering an anti-PD-L1 antibody or fragment, care must be taken to use materials to which the antibody does not absorb.

8. Kits and Articles of Manufacture

Unless otherwise apparent from the context, the kits and articles of manufacture for antibodies or fragments applies mutatis mutandis to the immunocytokines and multispecific (e.g. bispecific or dual-binding antibodies) of the invention.

In one embodiment, the invention provides a kit for detecting PD-L1 in a biological sample. The kit can be used to screen for PD-L1 related diseases. In one embodiment, the kit includes an antibody or antigen binding fragment and a means for determining whether the antibody or antigen binding fragment is bound to PD-L1 in a sample. In one embodiment, the antibody or antigen binding fragment is labelled. In another embodiment, the antibody or antigen binding fragment is an unlabelled primary antibody and the kit includes means for detecting the primary antibody. In one embodiment, the means for detecting includes a labelled secondary antibody that is an anti-immunoglobulin antibody. The antibody may be labelled with any suitable marker, including, for example, a fluorochrome, an enzyme, a radionuclide and a radiopaque material. Suitable antibodies and antigen binding fragments are described in detail above.

In one embodiment, a kit for detecting PD-L1 is provided, wherein the kit includes an antibody or antigen binding fragment described herein. In one embodiment, the kit may also include instructions and one or more reagents for detecting PD-L1. In one embodiment, the kit includes an antigen or antigen binding fragment described herein, along with instructions for preparing a formalin-fixed paraffin-embedded (FFPE) tissue sample for IHC and/or one or more reagents for IHC. In one embodiment, the kit includes an antigen or antigen binding fragment described herein as a primary antibody and a secondary antibody that specifically binds thereto. In one embodiment, the kit includes a labeled antigen or antigen binding fragment described herein, wherein the label includes a fluorescent label such as fluoroscein or rhodamine or an enzymatic reporter such as horseradish peroxidase (HRP) or alkaline phosphatase (AP). In one embodiment, the kit includes a blocking reagent that includes at least about 1% and up to about 5%, or between about 2% and 3%, or about 2% cold water fish skin gelatin protein (CWF) in a buffer, such as phosphate buffered saline (PBS).

In one embodiment, the kit includes buffer for antigen retrieval, such as a citrate buffer, for example sodium citrate, at a concentration of at least about 1, 2, 5, or 10 mM and up to about 10, 15 or 20 mM and at a pH between about 5.5 and 9, or a pH of about 6. In another embodiment, a kit for treating diseases involving the expression of PD-L1 is provided, wherein the kit includes an antibody or antigen binding fragment described herein and instructions to administer the antibody or antigen binding fragment to a subject in need of treatment. There is also provided a pharmaceutical or diagnostic pack or kit comprising one or more containers filled with one or more of the ingredients of the pharmaceutical compositions as disclosed herein, such as one or more anti-PD-L1 antibodies or fragments provided herein. Optionally associated with such container(s) can be a notice in the form prescribed by a governmental agency regulating the manufacture, use or sale of pharmaceuticals or biological products, which notice reflects approval by the agency of manufacture, use or sale for human administration, e.g., an authorisation number.

In another embodiment, an article of manufacture that includes a container in which a composition containing an antibody or antigen binding fragment described herein and a package insert or label indicating that the composition can be used to treat diseases characterized by the expression or overexpression of PD-L1 is provided. In one embodiment, there is provided a kit for treating and/or preventing a PD-L1-mediated condition or disease, the kit comprising an antibody or fragment as disclosed herein in any embodiment or combination of embodiments (and optionally a further therapeutic agent as described elsewhere herein) optionally in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment. In another embodiment, the kit comprises an antibody or antigen binding fragment thereof contained within a container or an IV bag. In another embodiment, the container or IV bag is a sterile container or a sterile IV bag. In another embodiment, the antibody or antigen binding fragment therefore is formulated into a pharmaceutical composition contained within a (sterile) container or contained within a (sterile) IV bag. In a further embodiment, the kit further comprises instructions for use.

9. Examples

Example 1—Antigen Preparation, Immunization Procedures, and Hybridoma Generation The following example provides a detailed description of the generation and identification of a panel of anti-human PD-L1 monoclonal antibodies using the KyMouse™ system (see, e.g., WO2011/004192, WO2011/158009 and WO2013/061098). To this end, genetically engineered mice containing a large number of human immunoglobulin genes were immunized with soluble recombinant human PD-L1 or surface expressed human PD-L1 displayed on mouse embryonic fibroblast (MEF) cells. Various immunization regimens, including conventional intraperitoneal injections as well as a rapid immunisation at multiple sites (RIMMS) regimen were set up, boosting animals over several weeks (see detailed methods below). At the end of each regimen, secondary lymphoid tissue such as the spleen, and in some cases, the lymph nodes were removed. Tissues were prepared into a single cell suspension and fused with SP2/0 cells to generate a stable hybridoma cell line.

Materials and Methods a) Generation of Stably Transfected MEF and CHO-S Cells Expressing Human PD-L1:

Full length human PD-L1 sequence (SEQ ID No:1 also known as B7-H1) was codon optimized for mammalian expression and cloned into an expression vector under the CMV promoter flanked by 3' and 5' piggyBac specific terminal repeat sequences, facilitating stable integration into the cell genome (see: "A hyperactive piggyBac transposase for mammalian applications"; Yusa K., et al., Proc. Natl. Acad. Sci. USA., 108(4): 1531-6, 2011 Jan. 25). Furthermore, the expression vector contained a puromycin selection cassette to facilitate stable cell line generation. The human PD-L1 expression plasmid was co-transfected with a plasmid encoding piggyBac transposase into an in-house derived mouse embryonic fibroblast (MEF) cell line (embryos used to generate this line were obtained from a 12955 crossed to C57/BL6 female mouse) and CHO-S cells using the FreeStyle Max transfection reagent (Invitrogen) according to manufacturer instructions. 24 hours after transfection, the media was supplemented with puromycin and grown for at least two weeks to select a stable cell line with complete medium being exchanged every 3 to 4 days. The expression of hPD-L1 was assessed by flow cytometry using an anti-human PD-L1-PE conjugated antibody (eBioscience). Complete MEF media was made up of Dulbecco's Modified Eagle's Medium (Gibco) supplemented with 10% v/v fetal bovine serum (Gibco). Complete CHO-S media was made up of CD-CHO media (Gibco) supplemented with 8 mM Glutamax (Gibco). Transfected CHO cells were used for screening purposes (see Example 2).

b) Preparation of MEF Cells for Mouse Immunizations:

Cell culture medium was removed and cells washed once with 1×PBS. Cells were treated for 5 minutes with trypsin to loosen cells from tissue culture surface. Cells were collected and trypsin., neutralized by the addition of complete MEF media. Cells were then centrifuged at 300 g for 10 minutes and washed with 25 mL of 1×PBS. Cells were counted and resuspended at the appropriate concentration in 1×PBS.

c) Immunisations with PD-L1

Genetically engineered Kymouse™ HK strain, containing human immunoglobulin genes producing human kappa (HK) light chain antibodies (Lee et al, Nature Biotechnology, 32, 6-363, 2014) were immunized by various immunisation regimens for the generation of human anti-PD-L1 antibodies.

Mice were immunised either with soluble recombinant hPD-L1 (R&D Systems, 156-B7, Fc chimera) using a modified sub-cutaneous immunisation procedure (RIMMS; modified after Kilpatrick et al., "Rapid development of affinity matured monoclonal antibodies using RIMMS"; Hybridoma. 1997 August; 16(4):381-9, hereafter referred to as KM031), or by using soluble recombinant hPD-L1 in a prime-rest-boost regime by sub-cutaneous administration (hereafter referred to as KM032) or by combination of soluble recombinant hPD-L1 and stably transfected MEF cells expressing hPD-L1 administered intra-peritoneally (hereafter referred to as KM033). Sigma Adjuvant System was used for all immunisations and rest intervals were usually between 2 and 3 weeks. Where protein was used as the immunogen, CpG (Hokkaido System Science) was also administered. Serum from serial or terminal blood samples were analysed for the presence of specific antibodies by ELISA and flow cytometry and the titre data was used (where possible) to select mice to be used for hybridoma fusions. A further regimen, KM042 immunising with MEF-PD-L1 cells alone, or protein alone in a prime-rest-boost setting, was also performed, but out of six antibodies confirmed to bind to hPD-L1, no neutralising antibodies were identified.

d) Cloning and Expression of Recombinant Proteins

DNA sequences encoding PD-L1 were purchased as synthetic DNA strings and cloned into appropriate mammalian expression vectors for transient expression in Expi293 and CHO cells. The sequence listing shows the sequences of the antigens, where available, and affinity tags for purification/labelling (shown in bold and underlined), see Seq ID Nos:3 to 6.

e) Determining Serum Titre by Reverse PD-L1 ELISA Protocol

Titres in mouse serum samples were determined using a reverse PD-L1 ELISA protocol. Anti-mouse IgG capture antibody (Southern Biotech) (4 µg/mL diluted in PBS, 50 µL/well) was adsorbed to 96 well low auto-fluorescent, high protein binding plates (Costar) overnight at 4° C. Excess IgG was removed by washing three times with PBS-Tween (0.1% v/v) and the wells were blocked with 1% w/v bovine serum albumin (BSA, Sigma) in PBS for 1 hour at room temperature, after which plates were washed three times with PBS-Tween (0.1% v/v). Serial ten-fold dilutions of mouse serum were prepared, diluting samples in reagent diluent (0.1% w/v BSA/PBS). 50 µL/well of this titration was then added to ELISA plates. To determine the change in activity level due to immunization, serum from each animal prior to immunization was diluted to 1/100 in reagent diluent and 50 µL/well added to the ELISA plate. Following incubation, plates were washed as before to remove unbound proteins. Biotinylated hPD-L1-his (in-house generated protein, Seq ID No: 3, labelled in-house using Sulfo-NHS-LC-Biotin (Thermo)), used at 100 ng/mL in reagent diluent; 50 µL/well) was then added to the plates and incubated at room temperature for 1 hour. Unbound biotinylated hPD-L1 was removed by washing with PBS-Tween (0.1% v/v), while the remaining biotinylated hPD-L1 was detected by addition of streptavidin-HRP (Sigma) diluted 1/10,000 in reagent diluent. Following incubation for 1 hour at room temperature, plates were washed as described before and 50 µL TMB (Sigma) was added to the plate. The reaction was stopped by adding 50 µL 1M sulphuric acid (Fluka Analytical). The OD at 450 nm was measured on an Envision plate reader (PerkinElmer). litres were not performed for KM032 as only one mouse was immunised. For KM031, titres were performed on terminal bleeds only.

f) Determination of Serum Titres by Flow Cytometry Using CHO-S Expressed hPD-L1

CHO-S Cells Expressing hPD-L1, Suspended in FACS Buffer (PBS+1% w/v BSA+0.1% w/v sodium azide) were distributed to a 96-well, V-bottom plate (Greiner) at a density of $10^5$ cells per well. A titration of mouse serum was prepared, diluting samples in FACS buffer. 25 µL/well of this titration was then added to the cell plate. To determine the change in activity level due to immunization, serum from each animal prior to immunization was diluted to 1/100 in FACS buffer and 25 µL/well added to the cells. Cells were incubated at 4° C. for 1 hour. Cells were washed twice with 150 µL PBS, centrifuging after each wash step and aspirating supernatant (centrifuged at 300×g for 3 minutes). To detect antibody binding, PE goat-anti-mouse IgG (Jackson ImmunoResearch) was diluted 1/500 in FACS buffer and 50 µL was added to the cells. Cells were incubated 1 hour at 4° C. in the dark, then washed twice with 150 µL PBS as above. To fix cells, 100 µL 2% v/v paraformaldehyde was added and cells incubated for 30 minutes at 4° C. Cells were then pelleted by centrifugation at 300×g and the plates resuspended in 100 µL of FACS buffer. PE signal intensity (geometric mean) was measured by flow cytometry using a BD FACS Array instrument. Titres were performed by this method for KM033 only.

g) Murine Tissue Isolation and Preparation

Following final boost, mice were culled and spleens were excised from immunized mice, washed in 1×PBS and kept on ice until further processing. Tissues were prepared in buffer containing 1×PBS (Invitrogen) and 3% heat-inactivated FBS (Invitrogen). Splenocytes were dispersed by mashing the tissue through a 45 µM strainer (BD Falcon) and rinsing with 30 mL 3% FBS/PBS buffer before centrifugation at 700 g for 10 minutes at 4° C. To remove red blood cells, the pelleted splenocytes were resuspended in 4 mL Red Blood Cell Lysis Buffer (Sigma). After 4 minutes of incubation, the lysis reaction was stopped by addition of 3% FBS/1×PBS PBS buffer. Cell clumps were filtered out with a 45 pM strainer. The remaining splenocytes were pelleted for further procedures. For KM031 and KM032, axillary, inguinal and mesenteric lymph nodes were also removed and placed in sterile 1×PBS on ice until further processing. The lymph nodes were processed separately from splenocytes. Lymph node cells were prepared as above, but did not undergo red blood cell lysis. The remaining lymph node cells were pelleted for further procedures.

h) Hybridoma Fusion

Spleen and lymph node cells were pooled from KM031 and also from KM032 and subjected to a negative selection method using the MACS® Separation system. Briefly, where lymph nodes were used those cells were pooled with the splenocytes from the corresponding mice after red blood cell lysis and total cell number determined. Cells were resuspended in 100 µL 3% FBS/PBS buffer per $10^7$ cells, before adding 10 µL of Pan B Cell Biotin-Antibody Cocktail (Cat #130-095-813) per $10^7$ total cells and 10 µL of anti-IgD-Biotin antibody (Cat #130-096-979) and incubated for 10 minutes at 4° C. 2 mL FBS/PBS buffer was added and the cells were spun down at 700 g for 10 minutes. The supernatant was aspirated completely and 100 uL fresh buffer was added, then 30 uL Anti-Biotin MicroBeads (Cat #130-047-302) was added per $10^7$ cells along with 7 µL Anti-Mouse IgM MicroBeads (Miltenyi Biotec). The cells were incubated for 15 minutes in the refrigerator. The cells/MicroBeads mixture was then applied to a pre-wetted LD column (Miltenyi Biotec) placed in a magnetic MACS Separator and washed with 3% FBS/PBS buffer. The unlabelled cells that flowed through the column were collected in 3% FBS/PBS buffer.

KM033 cells were subjected to a positive selection method using the MACS® Separation system. After red blood cell lysis, splenocytes were resuspended in 80 µL 3% FBS/PBS buffer per $10^7$ cells, before adding anti-mouse IgG1 (Cat #130-047-101) plus anti-mouse IgG2a+b MicroBeads (Cat #130-047-201) and incubated for 15 minutes at 4° C. The cell/MicroBead mixture was then applied to a pre-wetted LS column (Miltenyi Biotec) placed in a magnetic MACS Separator and washed with 3% FBS/PBS buffer. IgG positive cells were collected in the labelled, column-bound fraction in 3% FBS/PBS buffer.

Enriched B-cells were treated with CpG (Hokkaido System Science) overnight (final concentration 25 µM) and the following day washed once in BSA fusion buffer (0.3 M D-Sorbitol, 0.11 mM calcium acetate hydrate, 0.5 mM magnesium acetate tetrahydrate and 0.1% BSA (v/w), adjusted to pH 7.2). Washed cells were resuspended in 200 µL BSA fusion buffer and cell count determined. SP2/0 cells were treated in the same way, but washed twice instead of once with BSA fusion buffer. B-cells fused at a ratio of 3:1 with SP2/0 myeloma cells by electrofusion using a BTX ECM 2001 Electro Cell Manipulator (Harvard Apparatus). Each fusion was left overnight in recovery medium (Dulbecco's Modified Eagle's Medium (high glucose, no phenol red) supplemented with OPI (Sigma), 1× L-Glutamax (Gibco), 20% FBS (Gibco, batch-tested for hybridoma) and 0.05 mM 2-mercaptoethanol), then resuspended in 1 part recovery medium and 9 parts semi-solid medium (Clona-Cell-HY Hybridoma Selection Medium D, Stemcell Technologies) and seeded onto 10 cm petri dishes. Visible colonies were picked 12 days later into 96-well plates and cultured for another 2 to 3 days prior to screening.

Example 2—Hybridoma Supernatant Screening

After generation of hybridoma clones, the hybridoma supernatant was assessed in a sequential primary and secondary screen and appropriate hybridoma clones selected based on criteria of antibody binding to human PD-L1 and receptor neutralization activity. In the screening cascades described, 9317 hybridoma clones were tested and 120 identified as primary hits. Thereafter, 36 hybridoma clones were confirmed by using secondary screening criteria (see details in Materials and Methods and Table 1). Among the clones identified by secondary screen, four clones were selected by the inventors to be part of the antibody shortlist, dependent upon desired selection criteria (see details in Example 3).

Materials and Methods a) Primary Screen—Binding to Cell-Expressed Human PD-L1

Supernatants collected from hybridoma cells were screened for the ability of secreted antibodies to bind to hPD-L1 expressed on the surface of CHO-S cells. To determine CHO-S hPD-L1 binding, cells were plated in black-walled, clear-bottom tissue culture treated 384-well plates (Costar) at $1 \times 10^4$/well in 80 µL F12 media (Gibco) supplemented with 10% FBS (Gibco) and cultured overnight at 37° C., 5% $CO_2$. Culture media was removed from 384-well assay plates. At least 5 µL of hybridoma supernatant or 5 µL MIH1 at 2 µg/mL in hybridoma maintaining media (HMM) or isotype IgG1 control antibody (referred to in some instances as Cm7, Sigma M9269, at a final concentration of 1 µg/mL) diluted in HMM were added to each well. HMM was made up of Advanced DMEM (Gibco) supplemented with 1× Glutamax (Gibco), 20% v/v FBS (Gibco), 0.05 mM β-Mercaptoethanol, 1× HT supplement (Gibco), and 1× penicillin/streptomycin (Gibco). 45 µL FACS buffer containing 500 ng/mL IRDye 800CW anti-Mouse Ab (LICOR) and 0.2 µM DRAQ5 (Biostatus) was added to each well. DRAQ5 was not added to background wells. Plates were incubated for 1 hour at 4° C. Supernatant was aspirated and 25 µL 4% v/v paraformaldehyde added and plates were incubated for 15 minutes at room temperature. Plates were washed twice with 100 µL PBS and then the wash buffer was completely removed. Fluorescence intensity was read by scanning plates using an Odyssey Infrared Imaging System (LI-COR®). Anti-mouse binding (800 nm channel) was normalised to cell number (700 nm channel) according to the LI-COR® recommended algorithm. Percent effect was calculated as detailed below (Equation 1). Total binding was defined using reference antibody at a final assay concentration of 0.2 µg/mL. Non-specific binding was defined using mouse IgG1 isotype control (Sigma) at a final assay concentration of 0.2 µg/mL. Criteria for hit selection were based on assay signal and visual inspection of scanned plates.

Calculation of Percentage Effect from Primary Screen (LI-COR) and HTRF

Using 800% Resp values (LI-COR) or 665/620 nm ratio (see Equation 2) (HTRF)

$$\text{Percent effect} = \frac{(\text{sample well} - \text{non-specific binding})}{(\text{total binding} - \text{non-specific binding})} \times 100 \quad \text{Equation 1}$$

Non-specific binding =
   values from wells containing isotype control mouse $IgG1$ Total Binding =
   values from wells containing reference antibody b) Primary Screen: Binding to Recombinant Human PD-L1

In parallel to screening for binding to CHO-S expressed PD-L1, supernatants collected from hybridoma wells were screened for the ability of secreted antibodies to bind to hPD-L1 expressed as a recombinant protein (produced in-house). Binding of secreted antibodies to recombinant PD-L1 were identified by HTRF® (Homogeneous Time-Resolved Fluorescence, Cisbio) assay format using biotinylated hPD-L1. 10 µL hybridoma supernatant was transferred to a white 384 well, low-volume, non-binding surface polystyrene plate (Greiner). 5 µL 230 nM biotinylated hPD-L1 his diluted in HTRF assay buffer (PBS (Sigma)+ 0.53 M KF (Sigma)+0.1% w/v BSA (Sigma)) was pre-incubated with 10 µL hybridoma supernatant or 10 µL reference antibody diluted to 3.3 nM working concentration for 1 hour at room temperature. For negative control wells, 10 µL HMM was added. Streptavidin D2 (Cisbio), and goat anti-mouse IgG (Southern Biotech) labelled with Europium cryptate (Cisbio) were both diluted 1/100 in HTRF assay buffer, and 5 µL of this mixture added to all wells. The plate was left to incubate in the dark for 2 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397.

Data were analysed by calculating 665/620 ratio and percent effect for each sample according to Equation 2 and Equation 1 respectively.

665/620 ratio=(sample 665/620 nm value)
   ×10000     Equation 2: Calculation of 665/620 ratio In general, criteria for hit selection were based on greater than or equal to 10 percent effect. In some instances, hit selection was based on greater than or equal to 20 percent effect.

Progression to secondary screen was based on a combination of data from recombinant PD-L1 binding hits and binding to human PD-L1 expressed on CHO cells.

c) Secondary Screen: Binding to Cell Expressed Recombinant Human PD-L1 or Natively Expressed hPD-L1 and Binding Affinity To determine whether wells selected using the primary screen selection criteria had the required characteristics set by the inventors, a number of assays were performed. Hybridoma clones selected as hits from primary screening were cultured for 3 days and the supernatants collected from hybridoma cells were tested to assess whether the secreted antibodies that bind to in some cases CHO-S expressed hPD-L1, or in some cases ES2 cells. In addition, the ability to neutralise recombinant hPD-1 Fc, binding to CHO-S hPD-L1 or ES2 cells was also assessed. Binding of antibodies to human PD-L1 by SPR was also tested.

d) Binding to Cell Expressed hPD-L1 and Neutralisation and hPD-L1 Binding to PD-1

Binding of hybridoma supernatants was tested for ability to bind to either CHO-S cells expressing hPD-L1 or ES2 cells. CHO-S cells expressing hPD-L1 (generated in-house), or ES2 cells (ATCC CRL-1978) natively expressing hPD-L1 were diluted in FACS buffer and were distributed to a 96-well, V-bottom plate (Greiner) at a density of 0.5 to $1 \times 10^5$ cells per well. Cells were washed with 150 μL PBS and centrifuged at 300 g for 3 minutes. Supernatant was aspirated and 150 μL PBS added. This wash step was repeated.

50 μL hybridoma supernatant or purified hybridoma material was added to the washed cells, to which 500 ng/mL human PD-1 Fc (in-house, Seq ID No:6) was added. Reference antibody was added to medium at 2 μg/mL. Where purified material was used, titrations were prepared from a top concentration of 600 nM before addition to cells. When supernatants were used, neat supernatant, and three serial two-fold dilutions were added to cells. Cells were incubated at 4° C. for 30 minutes. Cells were washed twice with 150 μL FACS buffer, centrifuging at 300 g for 3 minutes after each wash step and aspirating supernatant.

To detect antibody and receptor binding, 50 μL goat anti-human IgG-PE (Jackson ImmunoResearch) and APC anti-mouse IgG (Jackson ImmunoResearch) diluted 1/500 in FACS buffer was added to the cells. Cells were incubated for 30 minutes at 4° C. in the dark. Cells were washed twice as above and resuspended in FACS buffer for analysis. PE and APC signal intensity (geometric mean) was measured by flow cytometry using a BD FACS Array instrument. Data was plotted as geometric mean values without further calculation.

e) Determination of Affinity by Surface Plasmon Resonance

Label-free surface plasmon resonance (SPR) analysis was carried out on the ProteOn XPR36 (BioRad) array SPR machine. An anti-mouse IgG capture surface was created on a GLC biosensor chip using amine coupling of an anti-mouse IgG from GE Healthcare. Test antibodies were captured on this surface and human PD-L1 (in-house) was used as the analyte at 256 nM, 64 nM, 16 nM, 4 nM and 1 nM. The assay was carried out at 25° C. using HBS-EP (Teknova H8022). Buffer alone was used to reference the binding sensorgrams. The data was analysed using the 1:1 model inherent to the ProteOn XPR36 analysis software. In some instances, hybridoma supernatants were used as the source of antibody; in other instances, antibody was purified from hybridoma supernatant prior to analysis (see below). In some instances, a Protein A/G capture surface was used. This was created on a GLM biosensor chip using amine coupling of Protein A/G from Biorbyt.

f) Purification of Antibodies from Hybridoma Supernatant

Protein G resin in a gravity-flow column was first washed with water, then 50 mM sodium hydroxide or IgG Elute (Pierce) and was then equilibrated with tissue culture grade PBS. Clarified hybridoma supernatant containing 10% v/v 10× tissue culture grade PBS was applied several times to the equilibrated protein G column. Resin was washed with tissue culture grade PBS to remove unbound material. Antibody was then eluted with IgG Elute (Pierce) and the eluted fraction was then neutralized with 100 mM final TRIS, at pH 8.0. The eluted fraction was then concentrated down to <1.5 mL by centrifugation in a 10 kDa cut-off centrifugal filter unit. Tissue culture grade PBS was then added and the sample was concentrated down again to <1.5 mL. Protein concentration was quantified at $OD_{280}$ using the molar extinction coefficient inherent to the Nanodrop for IgG. Finally, sample was analysed on a SDS-PAGE to assess purity.

TABLE 1

Summary of hybridoma clone screening

| Experiment ID | Number of hybridoma screened | Number of Primary hits cherry picked | Number of secondary hits confirmed | Number of Lead Candidate mAbs |
|---|---|---|---|---|
| KM031 | 1872 | 41 | 4 | 0 |
| KM032 | 115 | 14 | 6 | 1 |
| KM033 | 7330 | 66 | 26 | 1 |

Example 3—Antibody Shortlist Selection Criteria

Binding to hPD-L1 natively expressed on ES2 cells, and neutralisation of recombinant human PD-1 binding to ES2 cells were used as criteria for secondary screen hit selection. Hits to progress to purification and further characterisation were determined by a combination of high affinity for human PD-L1 and neutralisation capacity.

After the selection and characterization of shortlisted antibodies, their fully-human variable domains were recovered using RT-PCR using a mixture of forward and reverse primers. Antibodies were reformatted into a human IgG1 backbone and expressed using a transient expression system in CHO-S cells.

Materials and Methods a) RNA Isolation from Hybridoma Cells

Total RNA was extracted from hybridoma cells using TRIzol™ Reagent (Invitrogen). The quantity and quality of the isolated RNA was analysed spectrophotometrically.

b) Antibody Variable Domain Recovery by RT-PCR

Selected clones were used to prepare total RNA, which was used in an RT-PCR reaction to recover the heavy and light chain V-regions. Murine IgG-specific reverse primers and human Ig-leader sequence-specific forward primer sets were used for the heavy chains. Murine kappa constant region specific reverse primers and human kappa-leader sequence specific forward primer sets were used for the kappa light chains. The RT-PCR products were separated by agarose gel electrophoresis with the DNA of the predicted size being gel purified and sequenced in the forward and reverse directions. Alternatively, the RT-PCR products were subcloned into a cloning vector and DNA of individual colonies submitted for sequencing.

Example 4—Selection of Final Lead Panel

Recombinantly expressed antibodies were analysed by SPR to confirm binding to cynomolgus monkey PD-L1, as well as human PD-L1. Antibodies were also tested in a dendritic cell-T-cell mixed lymphocyte reaction (MLR) for ability to enhance IFNγ production (FIG. 1). Antibodies with consistent immune-stimulatory effects in the MLR, and binding to both human and cynomolgus PD-L1 were selected as the final lead panel—these were designated as clone 84609 and clone 1D05. Data in FIG. 1 is from a single experiment. A further five experiments were conducted and showed similar results (84G09 showed activity in 3 out of 5 experiments, 1D05 showed activity in 3 out of 4 experiments, 1A01 showed activity is 1 out of 3 experiments and 8609 showed activity in 0 out of 3 experiments). One further experiment failed (including positive control).

Materials and Methods a) Surface Plasmon Resonance for Analysis of Antibodies with Human Constant Region Label-free surface plasmon resonance (SPR) analysis was carried out on the ProteOn XPR36 (BioRad) array SPR machine. An anti-human IgG capture surface was created on a GLC biosensor chip using a combination of anti-human Fc antibodies (Jackson Labs 09-005-008, 109-006-008 and 309-006-008) by amine coupling. Test antibodies were captured on this surface and human PD-L1-his and cynomolgus monkey PD-L1-FLAG (in-house, Seq ID No: 5) was used as the analyte at 128 nM, 32 nM, 8 nM, 2 nM, 0.5 nM and 0 nM. The data was analysed using the 1:1 model inherent to the ProteOn XPR36 analysis software.

b) Dendritic Cell—T-Cell MLR (Mixed Lymphocyte Reaction)

Dendritic cells were generated from monocytic precursors. Monocytic precursors were isolated from peripheral blood mononuclear cells (PBMCs) isolated using Ficoll-Paque plus (GE Healthcare) density gradient centrifugation from leukoreduction system chambers, (NHSBT). Monocytes were isolated from PBMCs using negative selection magnetic separation beads (Miltenyi Biotec). Monocytes were plated in 96-well, flat-bottom TC plates at $5 \times 10^4$/well and $1 \times 10^4$/well and cultured with cytokines GM-CSF and IL-4 (both Peprotech) at 100 ng/mL for 7 days in culture media (Advanced RPMI (Gibco) supplemented with 10% v/v FBS and 2 nM glutamine (culture medium).

After 7 days, T-cells were purified from allogeneic PBMC using negative selection magnetic separation beads (Miltenyi). After purification, the isolation buffer was removed by centrifugation and aspiration. The cells were resuspended at $1 \times 10^6$ cells/mL in culture medium, and 100 µL of T-cells were added to all wells with the exception of the DC-only wells. An additional 100 µL of culture medium was added to the DC-only and T-cell-only wells. Serial three-fold dilutions of antibodies were prepared in culture medium (top concentration 60 nM final). 10 µL of each dilution was added to cells.

The cells were incubated for five days at 37° C. After this period IFN-γ was measured by Duoset ELISA (R&D Systems) according to manufacturer's instructions.

Example 5—In Depth Characterisation of Lead Antibodies

Lead antibodies 84609 and 1D05 were subjected to in-depth characterisation, including SPR at 37° C., full titrations of antibodies in neutralisation assays, and confirmation of binding to PD-L1 but not PD-L2. Antibodies were also expressed with a human IgG4(PE) constant region (Seq ID No:199) for analysis by mixed lymphocyte reaction. Lead antibodies retain sub-nanomolar affinity at 37° C., and show potent neutralisation of PD-L1 binding to both PD-1 and CD80. Antibodies do not cross-read with PD-L2, bind natively expressed PD-L1 on dendritic cells, and are potent stimulators of IFNγ production in an MLR.

a) Human PD-L1/PD-1 Neutralisation Assay (ELISA)

Figure 2:
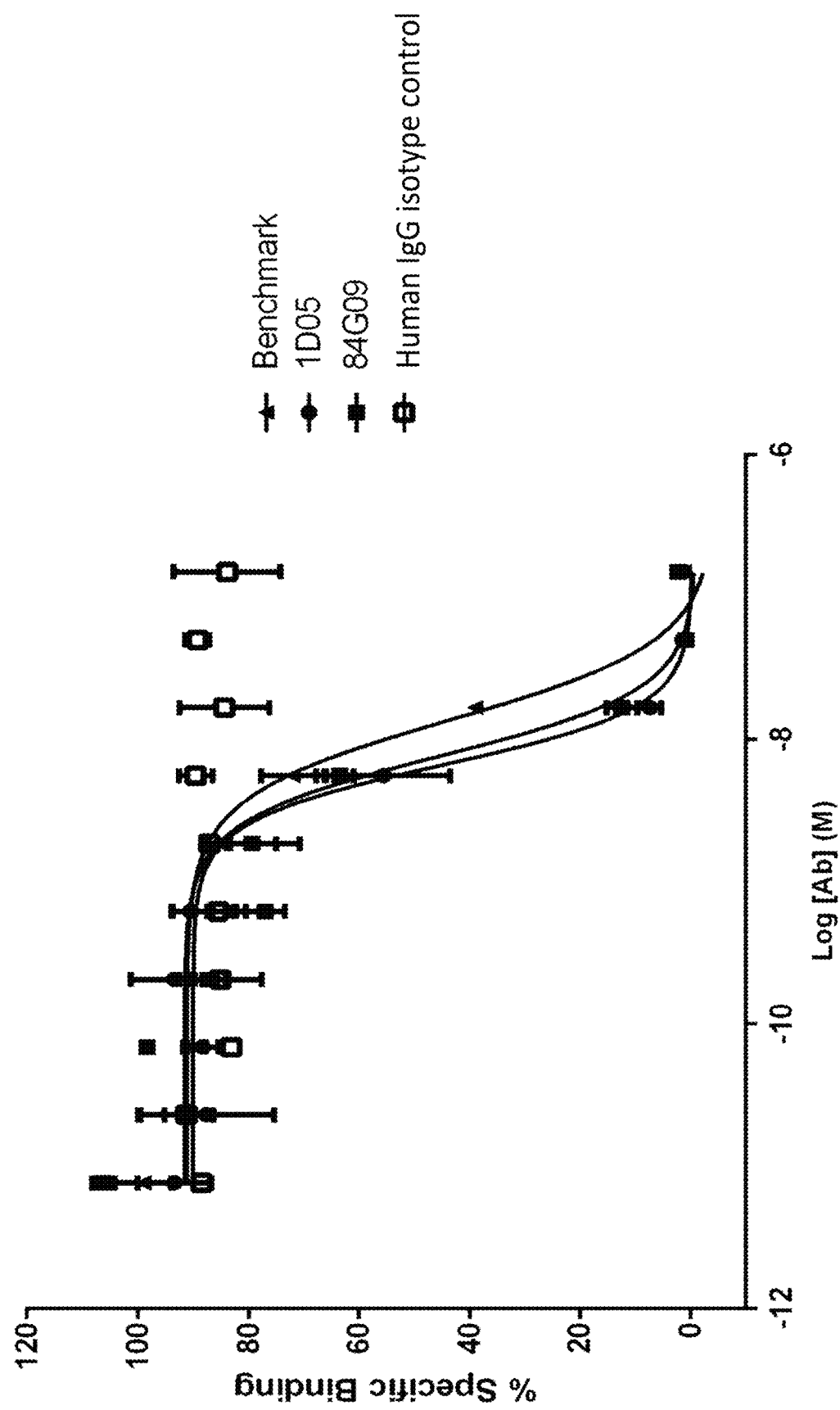
FIG. 2: PD-L1 direct neutralisation ELISA with PD-1 receptor. Neutralisation profiles of 1D05 and 84G09 compared to a benchmark anti-PD-L1 antibody and isotype control. Data representative of three independent experiments

PD-1 Fc (in house, Seq ID No:6) diluted to 1 µg/mL was adsorbed to 96-well, low auto-fluorescent, high protein binding plates (Costar) overnight at 4° C. Excess protein was removed by washing with PBS-Tween (0.1% v/v) and the wells were blocked with 1% w/v bovine serum albumin (BSA, Sigma) in PBS for 1 hour at room temperature, after which plates were washed as described previously. 30 µL titration (1/3 dilution) of antibody was added to a 96-well non-binding plate diluted in ELISA assay buffer (PBS+0.1% BSA). 30 µL biotinylated PD-L1 his (in-house, Seq ID No:3) at 50 nM working concentration (25 nM final assay concentration [FAC]) was added to the plate excluding control wells where 30 µL ELISA assay buffer was added. The plate was incubated for 30 minutes before transferring 50 µL to the coated plates. The coated plates were incubated for 1 hour at room temperature. Excess protein was removed by washing with PBS-Tween (0.1% v/v). PD-L1 binding was detected using streptavidin labelled Europium (Perkin Elmer) diluted 1/1000 in DELFIA assay buffer (Perkin Elmer). Plates were washed with TBS (Tris buffered saline)-Tween (0.1% v/v) and 50 µL/well of DELFIA Enhancement solution (Perkin Elmer) was added to the plate. Time-resolved fluorescence was measured at 615 nm on an Envision plate reader (PerkinElmer). Percentage of specific binding was calculated using Equation 3. $IC_{50}$ values were determined using GraphPad Prism software by curve fitting using a four-parameter logistic equation (Equation 4). Results are shown in FIG. 2 and summarised in Table 2.

Percentage of receptor binding (*ELISA*)
Based on fluorescence at 615 nm $$\% \text{ of specific binding} = \frac{\text{sample value} - \text{non-specific binding}}{\text{total binding} - \text{non-specific binding}} \times 100 \quad \text{Equation 3}$$

Total binding = biotinylated *PD-L1* (no antibody)

Non-specific binding = no biotinylated *PD-L1*

$Y = \text{Bottom} + (\text{Top} - \text{Bottom})/(1 + 10^{\wedge}((\text{Log IC50} - X)$
$*\text{HillSlope}))$ Equation 4: Four Parameter logistic calculation X = logarithm of concentration.
Y = specific binding (Equation 3)
Top and Bottom = Plateaus in same units as Y (specific binding)
Log $IC_{50}$ in same units as X. Y starts at Bottom and goes to Top with a sigmoid shape. Specific binding decreases as X increases.

c) CHO Human PD-L1/PD-1 or CD80 Neutralisation Assay (Flow Cytometry)

Figure 3:
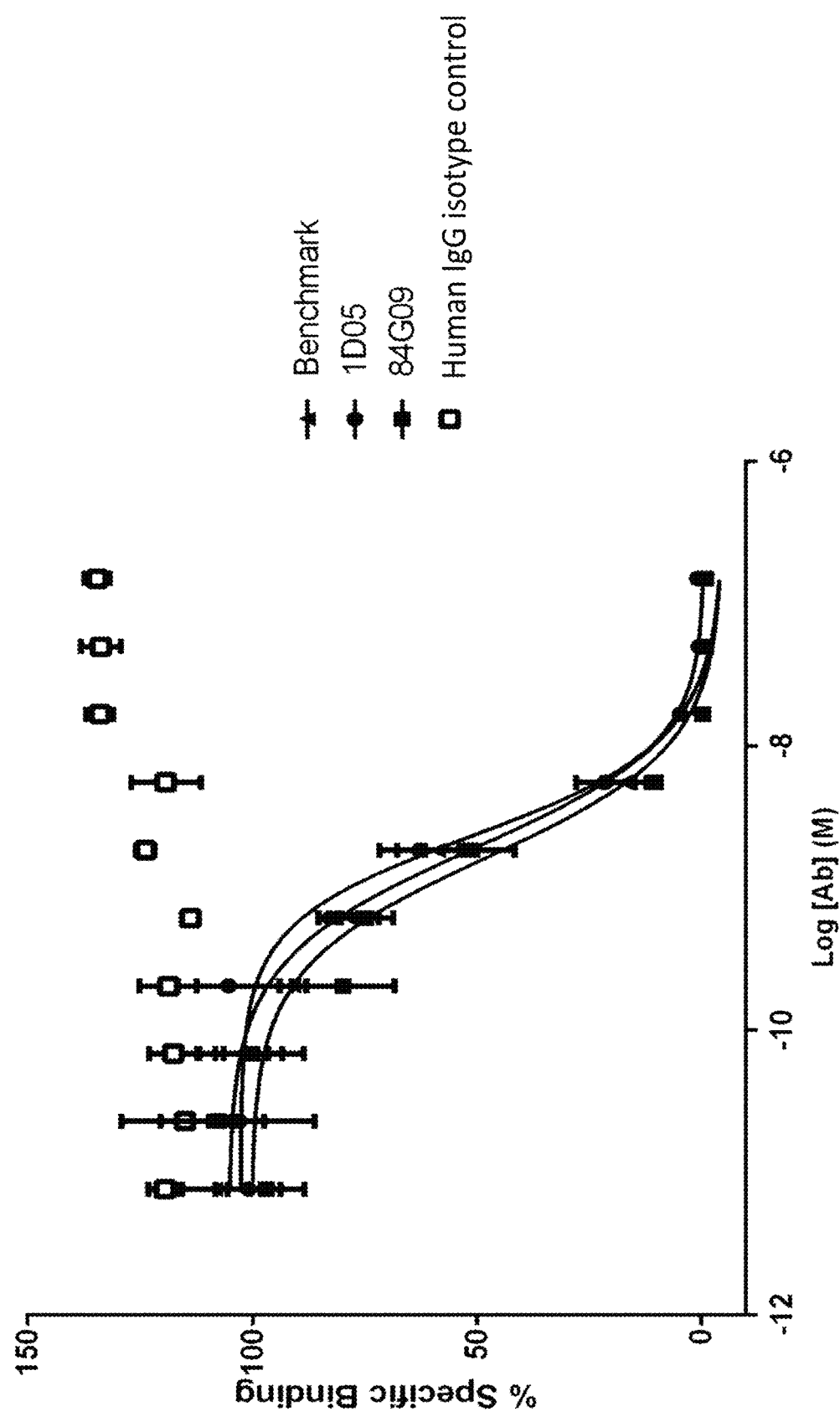
FIG. 3: Human PD-L1 CHO-S FACS neutralisation with PD-1 receptor. Neutralisation profiles of 1D05 and 84G09 compared to a benchmark anti-PD-L1 antibody and isotype control. Data representative of three independent experiments
Figure 4:
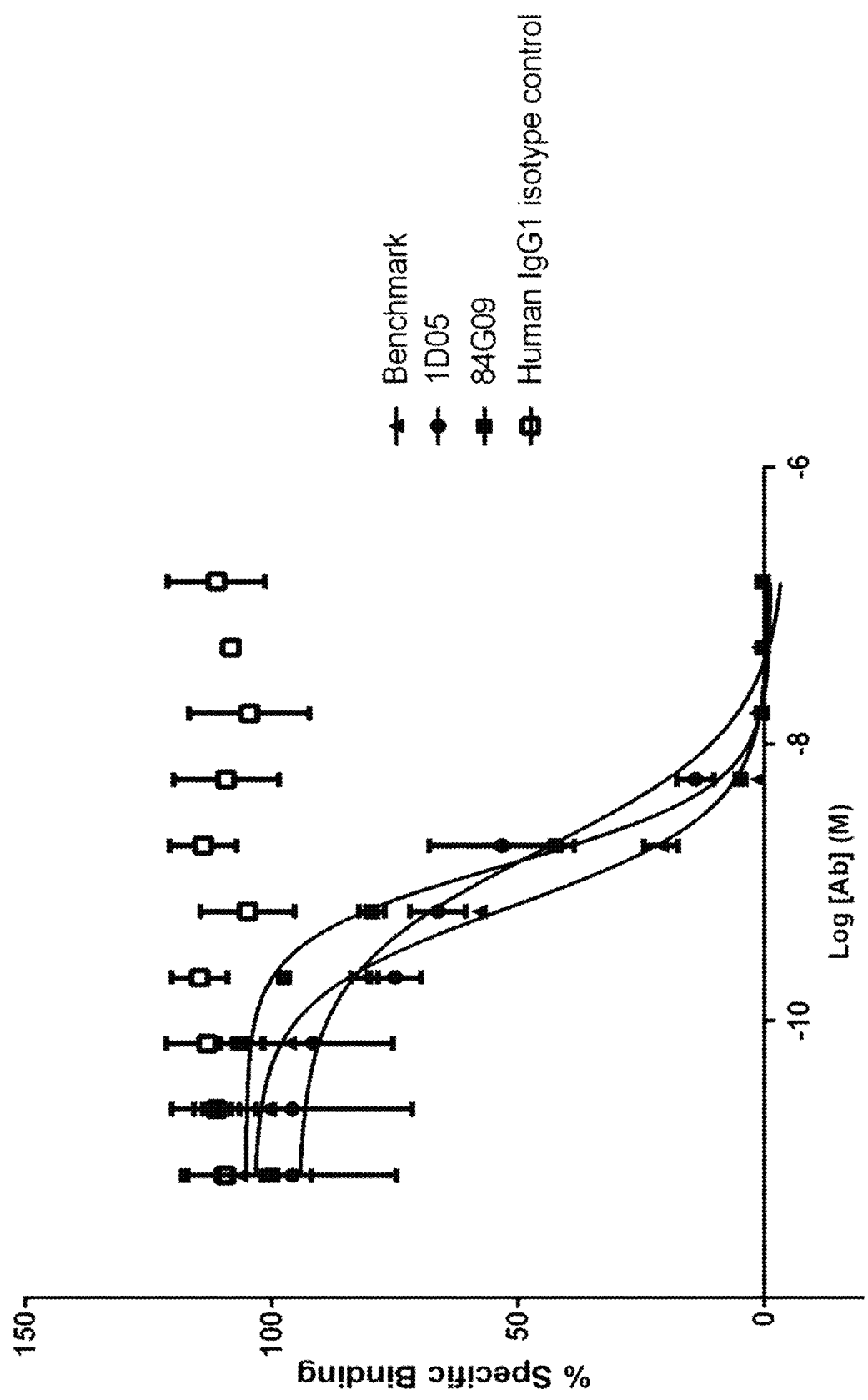
FIG. 4: Human PD-L1 CHO FACS neutralisation with CD80 receptor. Neutralisation profiles of the 1D05 and 84G09 compared to the benchmark anti-PD-L1 antibody and isotype control. Data representative of three independent experiments

CHO-S cells untransfected (referred to as WT) or transfected with hPD-L1 were diluted in FACS buffer and were distributed to a 96-well V-bottom plate (Greiner) at a density of $1 \times 10^5$ cells per well in 50 µL. Biotinylated human PD-1-Fc (in-house expressed, Seq ID No:6) or CD80-Fc (R&D Systems) were prepared as a titration from 1 µM final assay concentration (FAC), 1/2 dilution series in FACS buffer. Antibody titrations were prepared from 300 nM working concentration, 150 nM FAC, as a 1/3 dilution series in FACS buffer. Biotinylated PD-1 or CD80 were diluted in FACS buffer to 60 nM working concentration, 30 nM FAC. Plates were centrifuged at 300×g for 3 minutes to supernatant aspirated. 25 µL ligand and 25 µL antibody solution (or 50 µL of ligand titration) were added to cells and incubated at 4° C. for 1 hour. Cells were washed with 150 µL of PBS and centrifuged at 300 g for 3 minutes. Supernatant was aspirated and 150 µL PBS added. This wash step was repeated. Presence of bound CD80 or PD-1 was detected by addition of 50 µL of streptavidin-AlexaFluor 647 (Jackson ImmunoResearch) diluted 1/500 in FACS buffer. Cells were incubated 30 minutes at 4° C. in the dark. Cells were washed as described above. To fix cells, 100 µL 2% v/v paraformaldehyde was added and cells incubated for 30 minutes at 4° C., cells were pelleted by centrifugation at 300×g and the plates resuspended in 100 µL FACS buffer. AlexaFluor 647 signal intensity (geometric mean) was measured by flow cytometry using a BD FACS Array instrument. Results are shown in FIGS. 3 and 4 and summarised in Table 2.

Percentage of receptor binding (flow cytometry)
Based on geometric mean fluorescence % of specific binding =

$$\frac{\text{sample value} - \text{non-specific binding}}{\text{total binding} - \text{non-specific binding}} \times 100$$

Equation 5

Total binding =
  biotinylated *PD*-1 or *CD*80 only (no antibody)

Figure 5A:
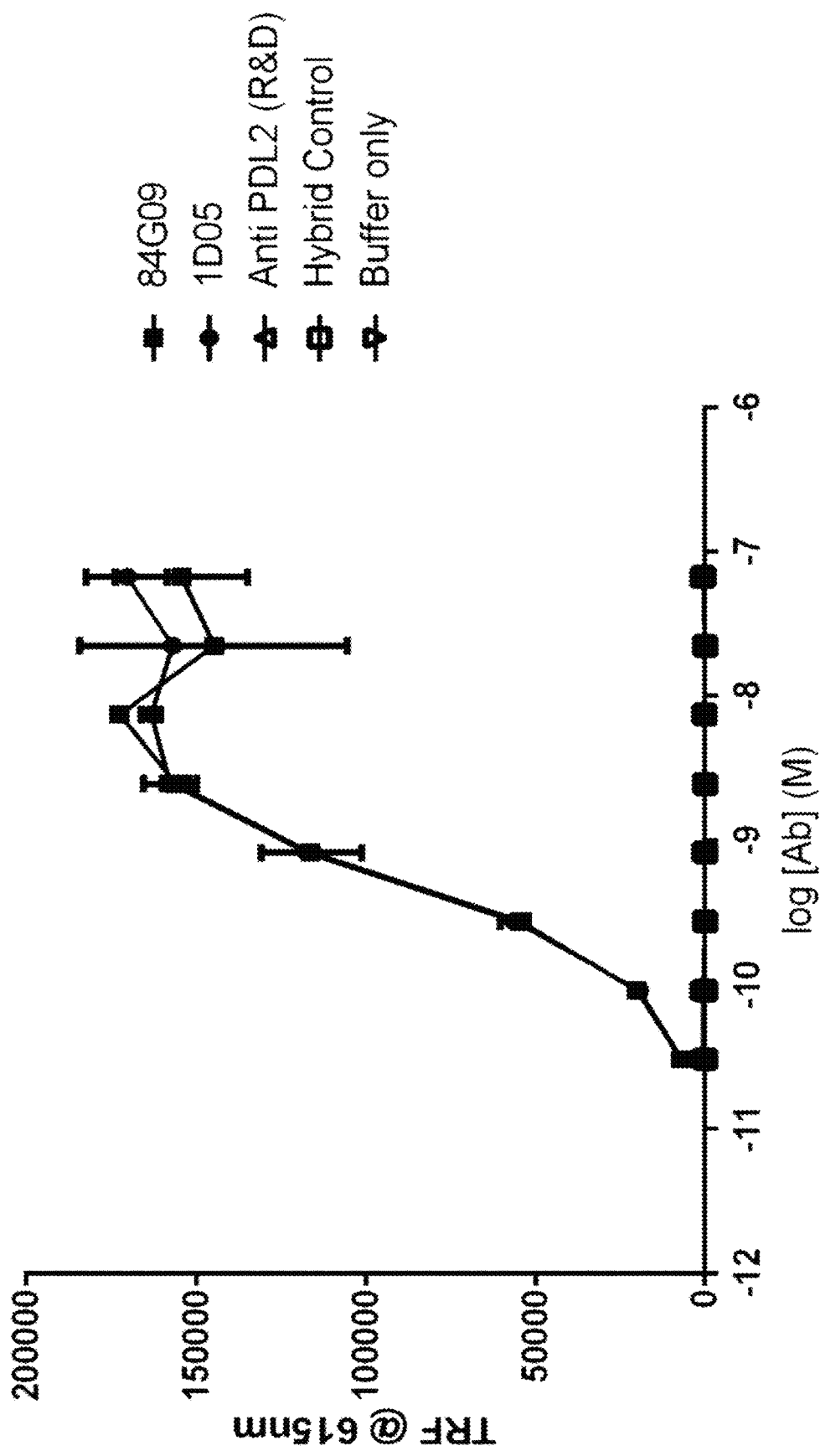
FIGS. 5(a)-5(b): Binding of lead antibodies to PD-L1 but not PD-L2. Lead antibodies bind to plate bound PD-L1 (FIG. 5a)) but not PD-L2 (FIG. 5b)). An anti-PD-L2 antibody was used as a control. Data are expressed as time resolved fluorescence units at 615 nm. Data representative of two independent experiments
Figure 5B:
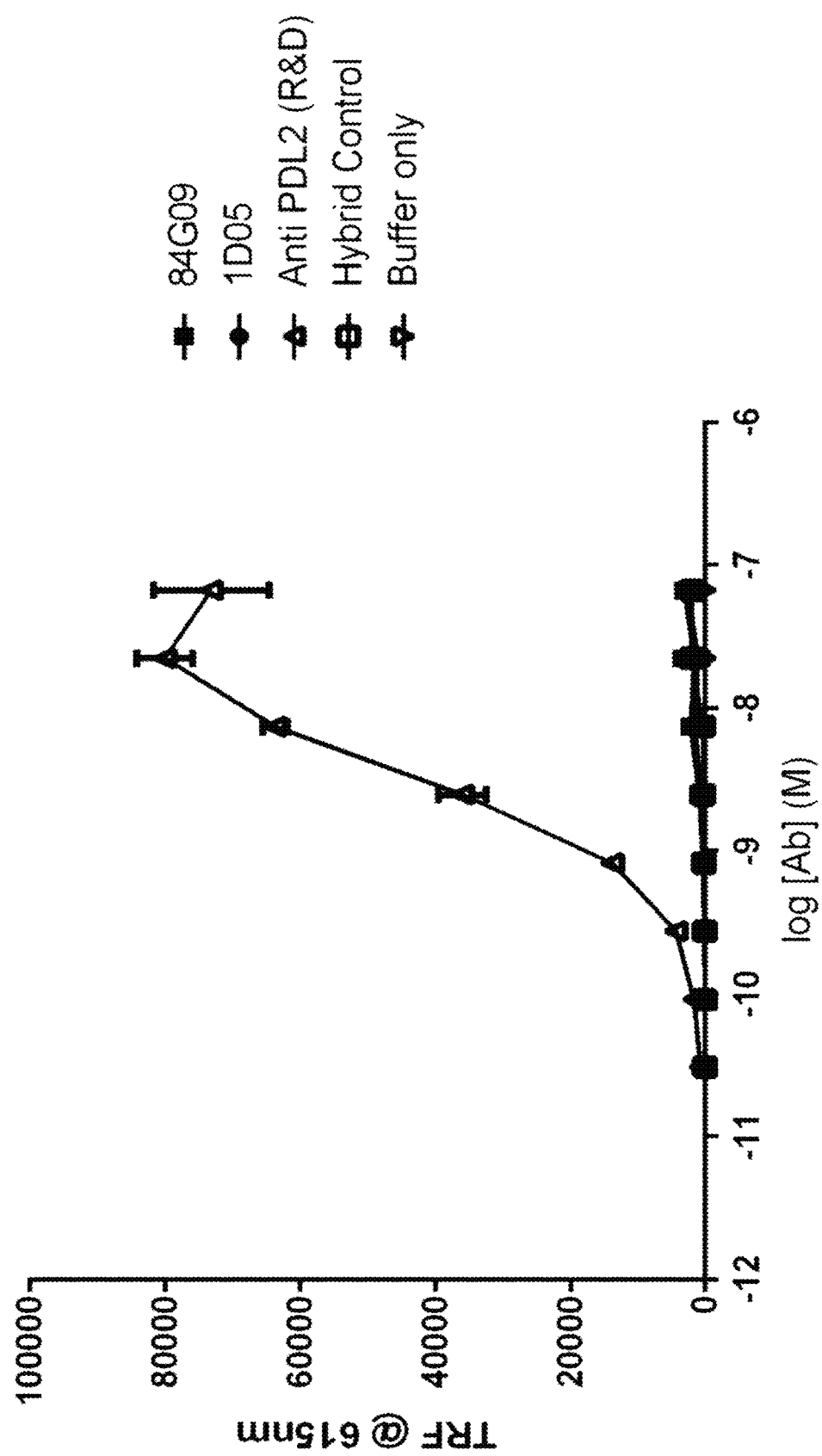

Non-specific binding =
  no ligand streptavidin AlexaFluor 647 only were diluted in blocking buffer and three-fold serial dilutions performed from 10 µg/mL. 100 µL each antibody dilution was added to the plates in duplicate and incubated for 1 hour at room temperature, before washing as stated above. Antibody binding was detected using streptavidin labelled Europium (Perkin Elmer) diluted 1/1000 in DELFIA Assay buffer (Perkin Elmer). Plates were washed with TBS (Tris buffered saline)-Tween (0.1% v/v) and 50 µL/well of DELFIA Enhancement solution (Perkin Elmer) was added to the plate. Time-resolved fluorescence was measured at 615 nm on an Envision plate reader (PerkinElmer). Results are shown in FIG. 5.

e) SPR Analysis

Label-free surface plasmon resonance (SPR) analysis was performed as per Example 4, except the assay was performed at 37° C. Additionally, due to artefacts of running the assay at 37° C., the best referencing of the binding sensorgrams was found to be using a sensorgrams from a negative control antibody using the same concentrations of human PD-L1. Results are shown in Table 2.

f) Mixed Lymphocyte Reaction

Expanded CD4$^+$ T-cells were thawed and rested in AIM V® medium (Gibco) at 37° C., 5% $CO_2$ overnight prior to the assay day. Serial dilutions of anti-human PD-L1 mAbs were prepared in the AIM medium at 4× final concentration. 50 µL of diluted mAbs was added to 96-well, U-bottom plates. 1×10$^4$ immature dendritic cells (iDC) in 50 µL AIM medium and 1×10$^5$ expanded CD4$^+$ T-cells (expanded using Dynabeads Human T-Activator CD3/CD28 by Life Technologies (Invitrogen/Applied Biosystems; Cat No: 11131D), according to manufacturer's instructions) in 100 µL AIM medium were added to the antibody dilutions in each well. Control wells include: CD4$^+$ T-cells alone, iDC alone, CD4$^+$ T-cell and iDC with or without IgG isotype control antibodies in 200 µL AIM medium. Reaction plates were incubated for 5 days in a humidified incubator (37° C. in 5% $CO_2$). At

TABLE 2

Summary of lead antibody binding and neutralisation of PD-L1 binding to PD-1 or CD80

| | | | Receptor Neutralisation (mean of n = 3) | | |
|---|---|---|---|---|---|
| Clone ID | Human PD-L1 (nM at 37° C.) | Cyno PD-L1 (nM at 37° C.) | PD-L1/PD-1 neutralisation (FACS) IC$_{50}$ (nM) | PD-L1/CD80 neutralisation (FACS) IC$_{50}$ (nM) | PD-L1/PD-1 neutralisation (ELISA) IC$_{50}$ (nM) |
| 1D05 | 0.42 $K_{on}$ = 1.85 µM $K_{off}$ = 0.779 mM | 0.43 $K_{on}$ = 1.89 µM $K_{off}$ = 0.813 mM | 2.21 | 1.18 | 5.21 |
| 84G09 | 0.43 $K_{on}$ = 2.43 µM $K_{off}$ = 1.05 mM | 0.52 $K_{on}$ = 2.61 µM $K_{off}$ = 1.35 mM | 1.82 | 1.60 | 7.90 |
| Benchmark | 0.25 | 4.79 | 1.85 | 1.42 | 14.1 | d) PD-L1/PD-L2 Binding

Figure 6:
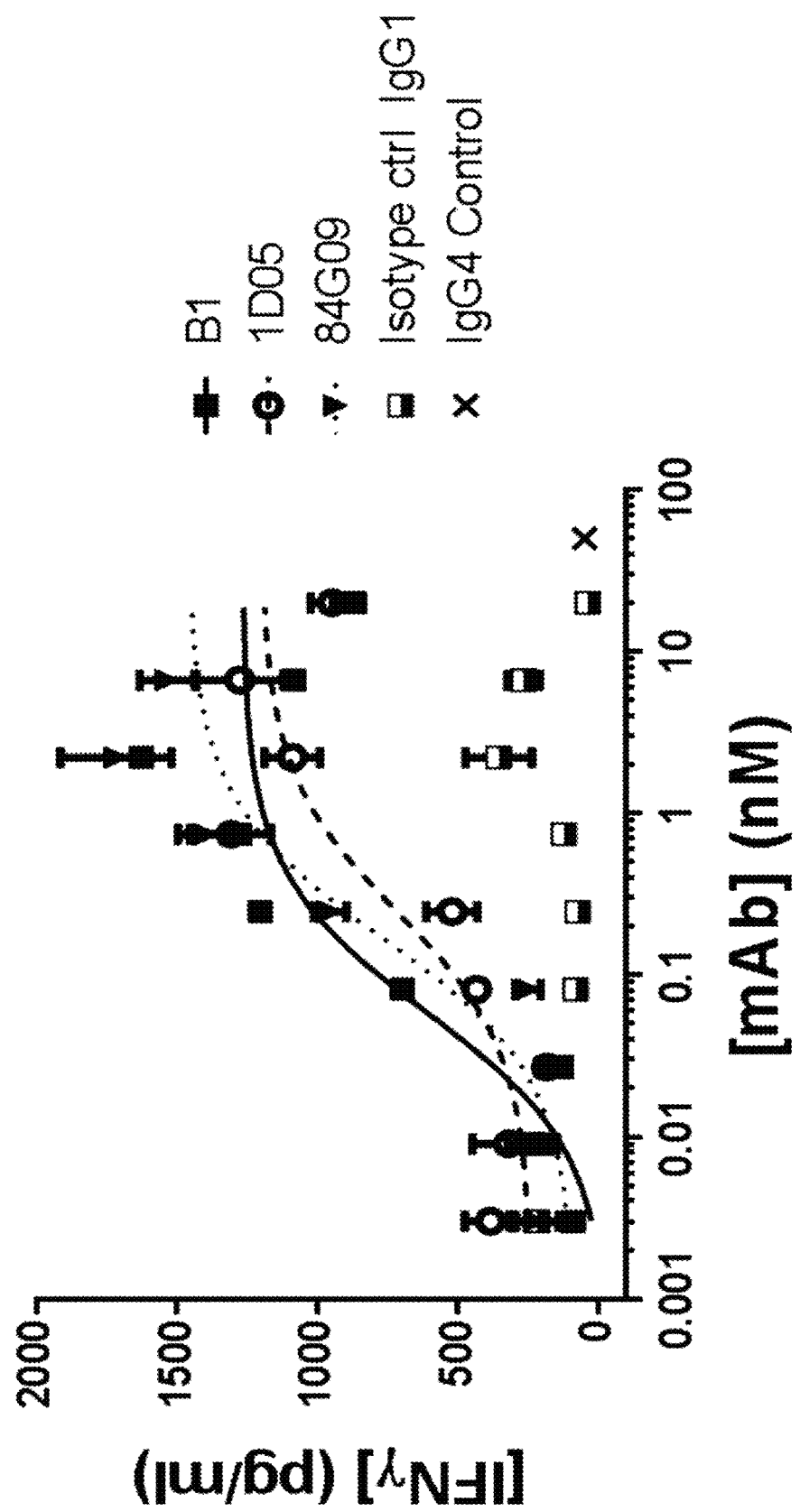
FIG. 6: Lead antibodies induce IFNγ production in a Dendritic Cell-T-cell mixed lymphocyte reaction. Immature dendritic cells were co-cultured with allogeneic CD4$^+$ T-cells in the presence of antibodies for 5 days. IFNγ was measured in supernatants by ELISA. Data are representative of three independent experiments. B1 refers to a benchmark antibody

PD-L1-Fc (R&D Systems) and PD-L2-Fc (R&D Systems) were diluted to 2 µg/mL and separately adsorbed to 96-well, high protein binding plates (Greiner) overnight at 4° C., 50 µL/well. Excess protein was removed by washing with PBS-Tween (0.1% v/v) and the wells were blocked with 250 µL/well Pierce Protein Free Blocking Buffer (Thermo, 37572) for 1 hour, after which plates were washed as described previously. Biotinylated anti-PD-L1 antibodies (in-house) or anti-PD-L2 control antibody (R&D Systems)

the end of the assay, the plate was spun down (528×g for 3 minutes) and 100 µL of supernatant was collected from the wells by gentle pipetting. Supernatants were analysed using human IFNγ Quantikine ELISA kit (R&D Systems) according to manufacturer's instructions. Results are shown in FIG. 6.

g) Sequencing and Characterisation of Gene Segment Usage of 1D05 and 84G09

Antibodies were sequenced by Source Bioscience, and V-genes were compared to germline sequences.

TABLE 3

V region usage of lead antibodies

| Antibody clone ID | V gene | D gene | J gene | CDRH3 length (aa) | non-germline CDRH3 (aa) | V gene | J gene | CDRL3 length (aa) | Non-germline CDRL3 (aa) |
|---|---|---|---|---|---|---|---|---|---|
| 1D05 | IGHV3-9*01 | IGHD3-10*01 | IGHJ5*02 | 16 | 6 | IGKV1D-39*01 | IGKJ5*1 | 9 | 0 |
| 84G09 | IGHV3-9*01 | IGHD3-10*01 | IGHJ5*02 | 15 | 4 | IGKV1D-39*01 | IGKJ5*1 | 9 | 1 | h) Binding of Lead Antibodies to Natively Expressed PD-L1

Figure 7A:
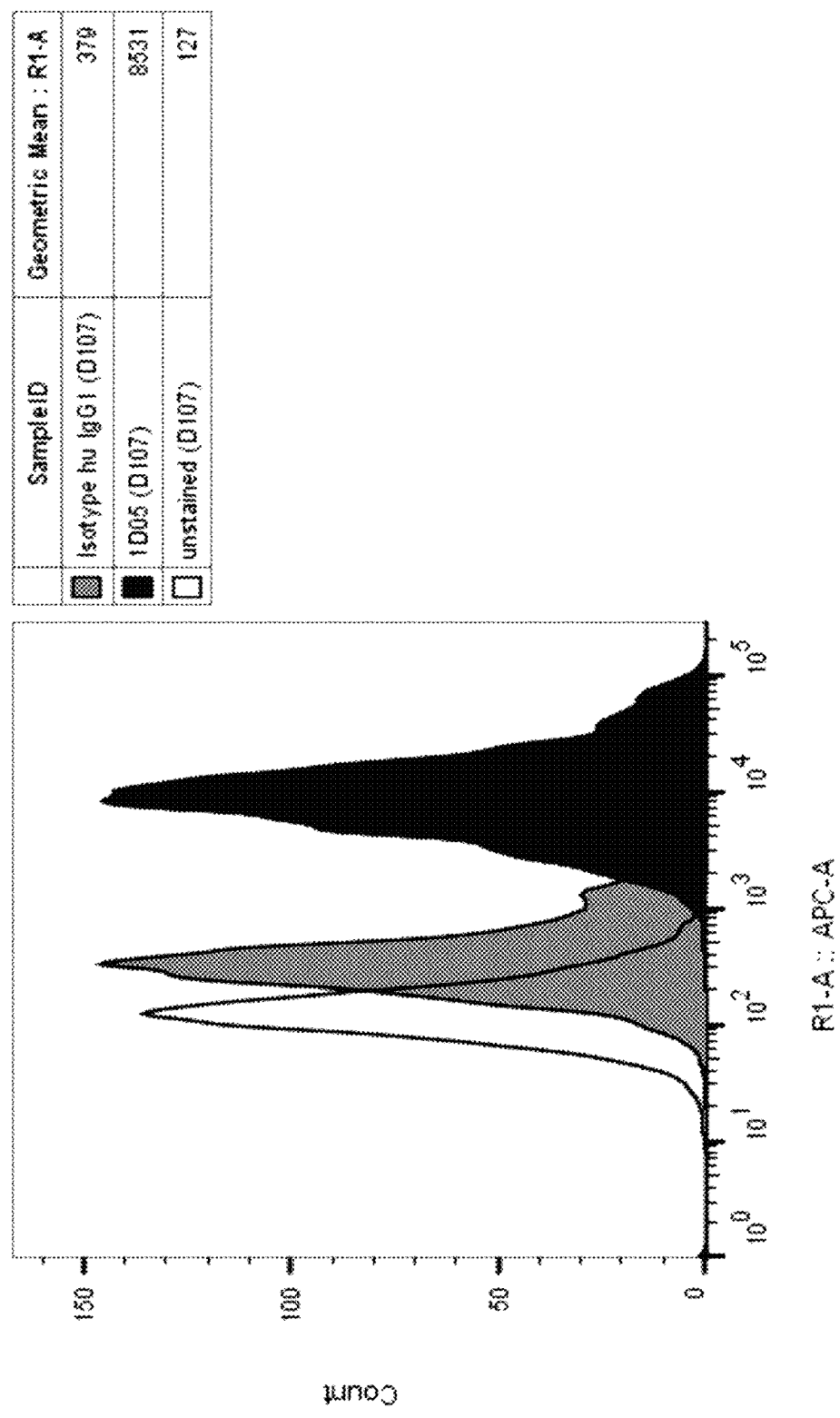
FIGS. 7(a)-7(b): Lead antibodies bind to natively expressed PD-L1 on dendritic cells. Dendritic cells were generated from monocyte precursors with GM-CSF and IL-4 and stained with lead antibodies FIG. 7(a) 1D05 and FIG. 7(b) 84G09, and isotype control directly labelled with AlexaFluor647. Data shown is from one blood donor, representative of four donors
Figure 7B:
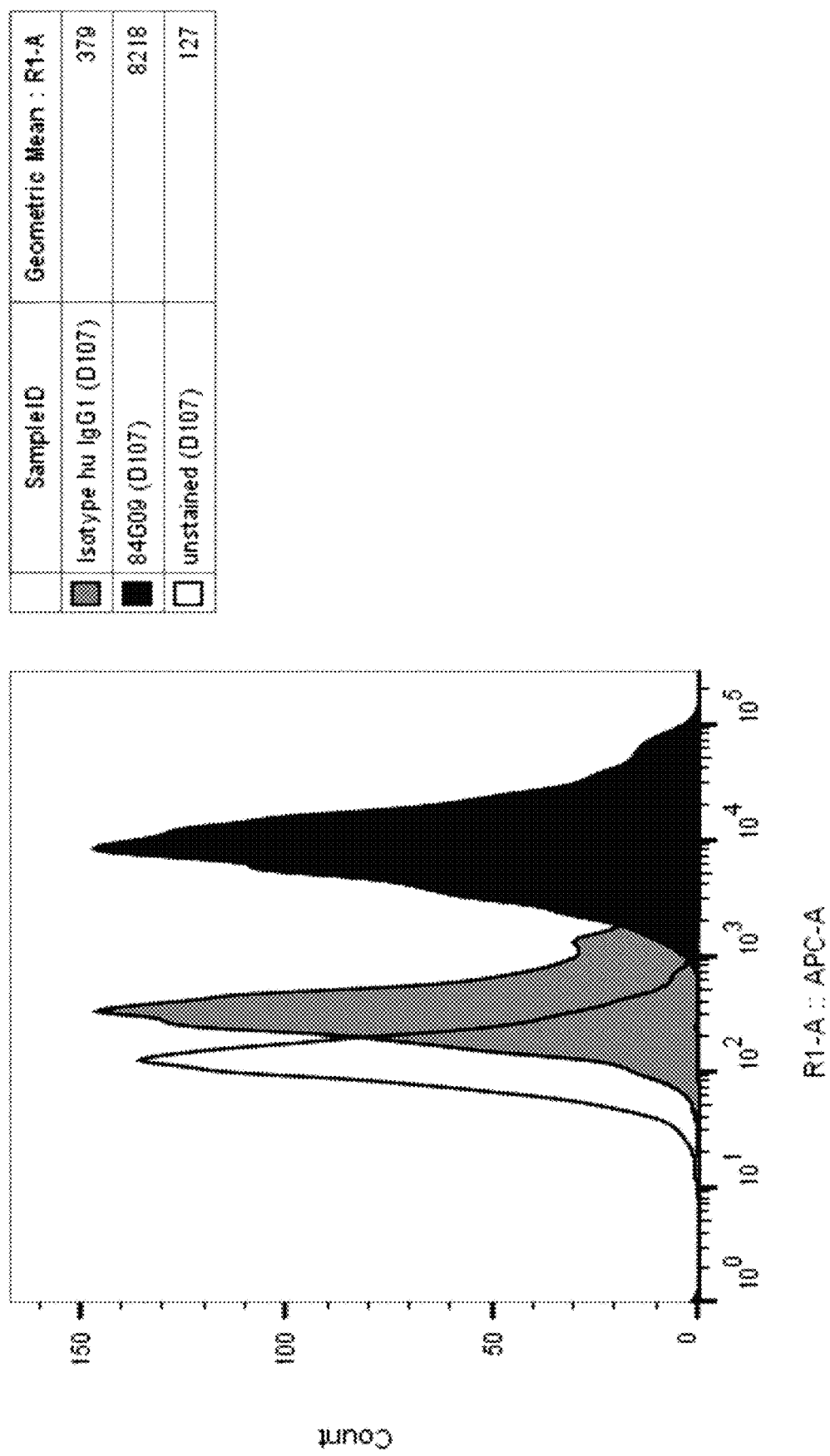

84G09 and 1D05 were labelled with AlexaFluor647 and used to stain dendritic cells derived from monocytic precursors. This shows that lead antibodies bind PD-L1 that is natively expressed on human dendritic cells. Data is shown in FIG. 7.

Materials and Methods

PBMC were suspended in RPMI 1640 medium without additives and allowed to adhere to a tissue culture flask for two hours at 37° C. Non-adherent cells were removed and the flask washed three times with PBS. PBS was removed and replaced with RPMI 10% hiFBS (Gibco) containing 100 ng/mL GM-CSF and IL-4 (both Peprotech). Cells were cultured at 37° C. for 7 days, and then removed from flask using a cell scraper.

Cells were resuspended in FACS buffer (PBS 1% w/v BSA 0.1% w/v sodium azide) and plated at $10^5$ cells/well, and incubated with Trustain FcX (Biolegend) for 10 min to prevent antibody binding to FcγR. AlexaFluor647 labelled antibodies were added at a final concentration of 5 μg/mL and incubated at 4° C. for 1 hour. Cells were then washed three times in FACS buffer and fixed for 20 min in 4% paraformaldehyde (Affymetrix). After fixation, cells were washed three times as before and resuspended in FACS buffer for analysis by flow cytometry. Data was acquired using the MACSQuant flow cytometer (Miltenyi Biotec) and analysed in FlowJo v10.

Example 6—Antigen Preparation, Immunization Procedures, and Antigen-Specific B Cell Sorting and V-Region Recovery Additional anti-human PD-L1 monoclonal antibodies were generated using the KyMouse™ system previously described. Genetically engineered HK mice were immunized with soluble recombinant human and mouse PD-L1 or surface expressed human and mouse PD-L1 displayed on mouse embryonic fibroblast (MEF) cells. Serum titres were performed by reverse ELISA and mice with the highest titres were selected for processing. At the end of each regime, spleen and lymph nodes were removed. Tissues were prepared into a single cell suspension and stained for sorting antigen-specific B-cells by FACS.

Materials and Methods a) Immunisation of Mice

Mice were immunised with soluble recombinant human PD-L1 or a combination of human and mouse PD-L1 protein (in-house) as per the schedule described in Example 1 for KM032 (hereafter described as KM121). Mice were also immunised with human PD-L1 protein, and MEF cells expressing human or mouse PD-L1, as per the schedule described in Example 1 for KM033 (hereafter described as KM122). MEF cells expressing mouse PD-L1 were generated as per Example 1, but substituting mouse PD-L1 sequences for the human PD-L1 sequences, and substituting anti-mouse PD-L1 detection antibody (eBioscience) for the anti-human PD-L1 detection antibody.

b) Determining Serum Titre by Reverse PD-L1 ELISA Protocol

Titres in mouse serum samples were determined using a reverse PD-L1 ELISA protocol as per Example 1, with the following changes. In-house generated hPD-L1-his was labelled in-house using Lightning Link kit (Innova Biosciences), and used at 1 μg/mL in reagent diluent; 50 μL/well). Bound hPD-L1 was detected by addition of streptavidin-Europium (Perkin Elmer) diluted 1/1000 in DELFIA assay buffer (Perkin Elmer). Following incubation for 1 hour at room temperature in the dark, plates were washed using TBS (Tris buffered saline)-Tween (0.1% v/v) and 50 μL/well of DELFIA Enhancement solution (Perkin Elmer) was added to the plate. Time-resolved fluorescence was measured at 615 nm on an Envision plate reader (PerkinElmer). Fluorescence data was plotted as Europium counts.

c) Sorting of Antigen-Specific B Cells and Retrieval of V-Regions

The methods used were substantially as described in Example 1 of PCT application WO2015/040401, which is incorporated herein by reference. In brief, splenocytes and lymph node cells isolated from KM121 and KM122 immunisation regimes were stained with an antibody cocktail containing markers for the selection of cells of interest (CD19), whereas unwanted cells were excluded from the final sorted population (IgM, IgD, 7AAD). CD19+ B-cells were further labelled with human PD-L1 (Seq ID No:1) and mouse PD-L1 (Seq ID No:325, labelled with AlexaFluor647 and AlexaFluor488, respectively, in-house using Lightning Link kits) to detect B-cells producing specific antibodies—cells binding human PD-L1, or both human and mouse PD-L1 were selected. These cells were single cell sorted by FACS into lysis buffer. V-region sequences were recovered using RT-PCR and two further rounds of PCR, then bridged to mouse IgG1 constant region and expressed in HEK293 cells. Supernatants from HEK293 cells were screened for the presence of PD-L1 binding antibodies. This method is hereafter referred to as BCT.

Example 7—Supernatant Screening

BCT supernatants were screened by HTRF, and selected primary hits further screened for binding to cell-expressed recombinant hPD-L1 and neutralisation of PD-1 binding, and for affinity of binding to human, cynomolgus and mouse PD-L1 recombinant protein by SPR, as described in this Example. KM121 antibodies, with an affinity of 1 nM or better for human and in some cases also cynomolgus PD-L1 were taken forward for further characterisation. For KM122, antibodies with the capacity to neutralise PD-1 binding to cell-expressed PD-L1 were taken forward, along with high affinity (<1 nM) binding to both human and cynomolgus PD-L1. Antibodies did not bind to mouse PD-L1.

a) Primary Screen—Binding to Recombinant Human PD-L1 (BCT Supernatants)

Supernatants collected from BCT expression were screened for the ability of secreted antibodies to bind to hPD-L1 expressed as a recombinant protein (produced in-house). Binding of secreted antibodies to recombinant human and mouse. PD-L1 were identified by HTRF® (Homogeneous Time-Resolved Fluorescence, Cisbio) assay format using FluoProbes®647H (Innova Biosciences) labelled PD-L1 (referred to herein as 647 hPD-L1 or 647 mPD-L1 for human PD-L1 and mouse PD-L1 labelled with FluoProbes®647H respectively). 5 µL BCT supernatant was transferred to a white 384-well, low-volume, non-binding surface polystyrene plate (Greiner). 5 µL of 25 nM 647 hPD-L1 or 647 mPD-L1 diluted in HTRF assay buffer was added to all wells. Reference antibody was diluted in BCT media (Gibco #A14351-01) to 40 nM and 5 µL added to plate. For negative control wells, 5 µL of mouse IgG1 (Sigma M9269 in some instances referred to as CM7) diluted to 40 nM in BCT media was added. Binding of secreted antibodies to PD-L1 was detected by addition of 10 µL of goat anti-mouse IgG (Southern Biotech) directly labelled with Europium cryptate (Cisbio) diluted 1/2000 in HTRF assay buffer. The plate was left to incubate in the dark for 2 hours prior to reading time resolved fluorescence at 620 nm and 665 nm emission wavelengths using an EnVision plate reader (Perkin Elmer).

Data were analysed by calculating 665/620 ratio and percent effect for each sample according to Equation 2 and Equation 1 respectively.

For KM121, primary hits were selected based on greater than or equal to 30 percent effect whereas for KM122 primary hits were selected based on greater than or equal to 40 percent effect.

Progression to secondary screen was based on data from recombinant PD-L1 binding.

b) Secondary Screen—Binding to Cell Expressed hPD-L1 and Neutralisation of hPD-L1 Binding to PD-1 (BCT Supernatants)

Binding of BCT supernatants were tested for ability to bind to CHO-S cells expressing hPD-L1. CHO-S cells expressing hPD-L1 (generated in-house), were diluted in FACS buffer (PBS 1% BSA 0.1% sodium azide) and were distributed to a 96-well, V-bottom plate (Greiner) at a density of 0.5-1×10$^5$ cells per well. Cells were washed with 150 µL PBS and centrifuged at 300 g for 3 minutes. Supernatant was aspirated and 150 µL PBS added. This wash step was repeated.

25 µL BCT neat supernatant, reference antibody or control antibody diluted to 300 nM in BCT media was added to the washed cells. 25 µL of 30 nM biotinylated human PD-1 (in-house) was added and cells were incubated at 4° C. for 60 minutes. 150 µL FACS buffer was added and cells washed as described above. To detect biotinylated PD-1 and anti-PD-L1 antibody binding, Streptavidin-647 (Jackson ImmunoResearch) and anti-Mouse PE (Jackson ImmunoResearch) were each diluted 1/500 in FACS buffer and 50 µL of this mixture added to cells. Cells were incubated 4° C. for 60 minutes. Cells were washed twice with 150 µL FACS buffer, centrifuging at 300 g for 3 minutes after each wash step and aspirating supernatant. Cells were fixed by addition of 50 µL 4% paraformaldehyde overnight. Cells were washed once as above and resuspended in FACS buffer for analysis. PE and APC signal intensity (geometric mean) was measured by flow cytometry using a BD FACS Array instrument. Data was plotted as geometric mean values without further calculation.

For KM121, secondary hits were selected based on high affinity (<1 nM) binding to human PD-L1. For KM122, secondary hits were selected based on comparable high affinity (<1 nM) binding human and cynomolgus PD-L1 and ability to neutralise PD-1 binding to cell-expressed PD-L1. Results are summarised in Table 4.

TABLE 4

Summary of BCT clone screening

| Experiment ID | Number of BCT supernatants screened | Number of Primary hits cherry picked | Number of secondary hits confirmed |
|---|---|---|---|
| KM121 | 984 | 162 | 7* |
| KM122 | 1312 | 263 | 45** |

*three of these secondary hits were not included in the primary screen and were screened by SPR and neutralisation only
**one hit was identified by primary screen but insufficient material was available for secondary screen. After re-expression, clone was shown to bind human and cynomolgus PD-L1 with affinity of <1 nM and carried forward c) Analysis of Binding by Surface Plasmon Resonance SPR analysis was carried out on the ProteOn XPR36 Array system. Anti-mouse IgG (GE Healthcare BR-1008-38) was immobilised on a GLM chip by primary amine coupling. Antibodies were directly captured from BCT supernatants. Human, mouse and cynomolgus PD-L1 were used as analytes and passed over the captured antibodies at a single concentration. The binding sensorgrams are double referenced with a 0 nM (ie buffer alone) injection, and the data is analysed using the 1:1 model inherent to the ProteOn analysis software. The assay is carried out at 25° C. and used HBS-EP as running buffer.

Example 8—Characterisation of Selected Antibodies

Figure 8A:
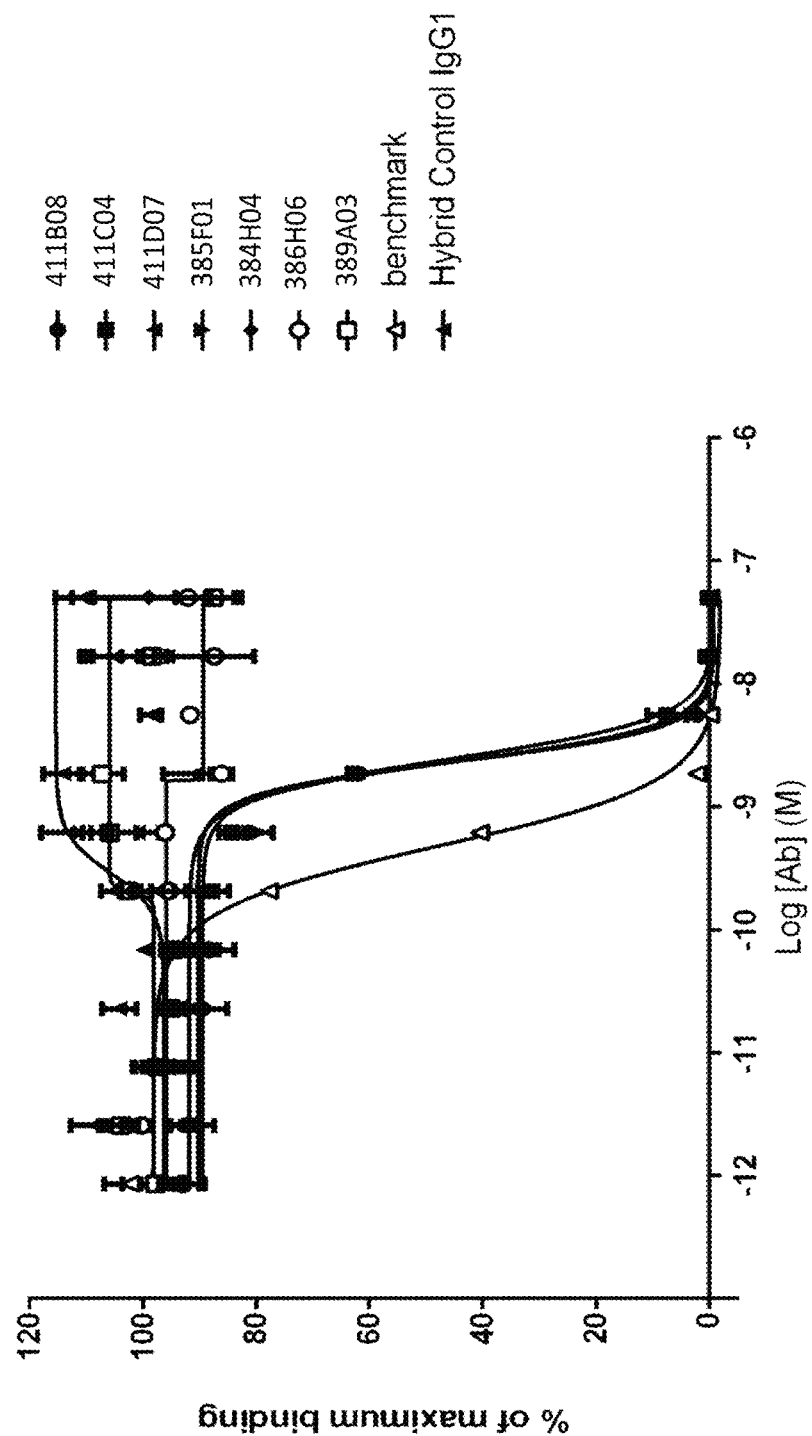
FIG. 8(a): PD-L1 direct neutralisation ELISA with PD-1 receptor. Neutralisation profiles of KM121 hits compared to a benchmark anti-PD-L1 antibody and isotype control. Data representative of three independent experiments
Figure 8B:
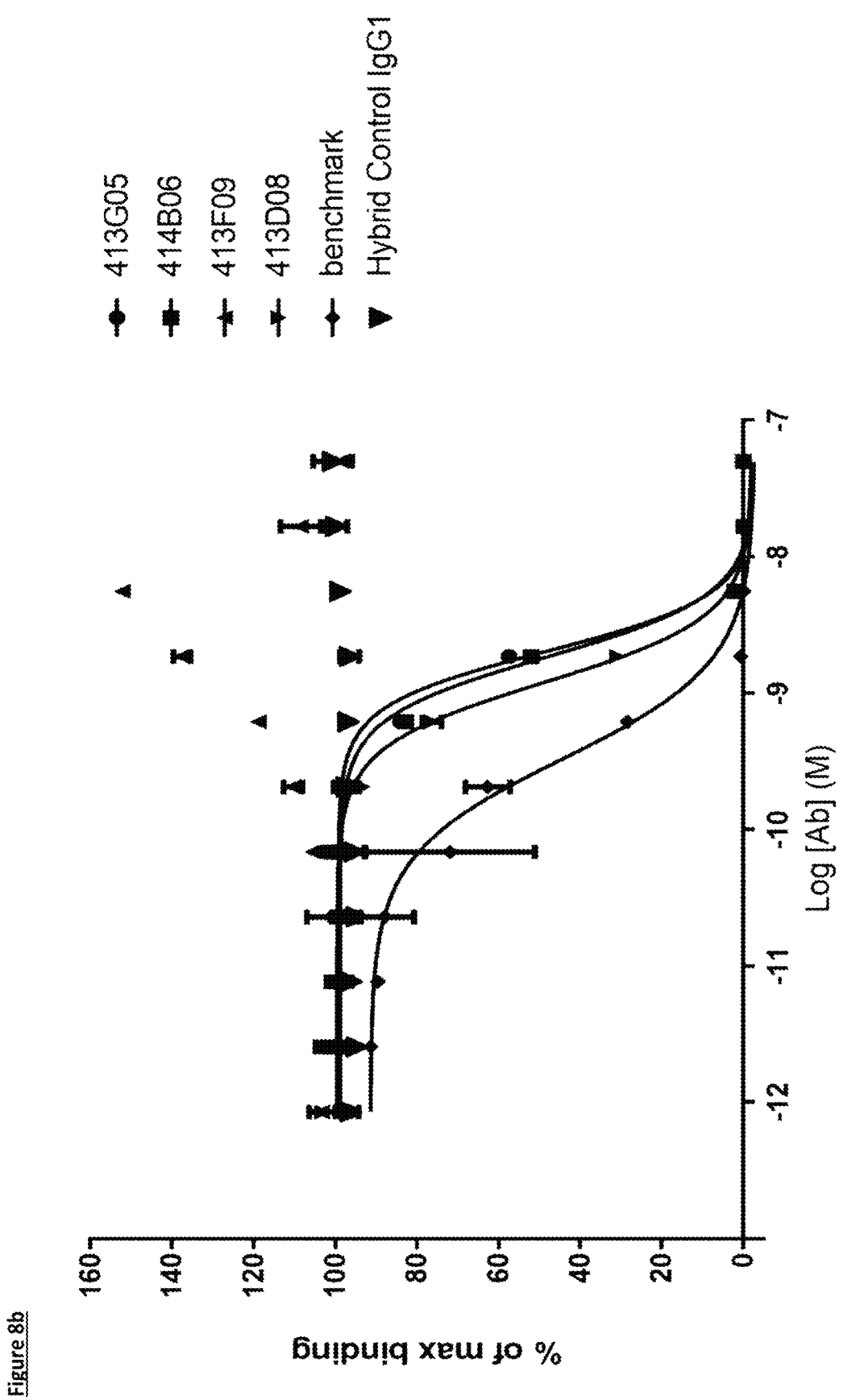
FIG. 8(b): PD-L1 direct neutralisation ELISA with PD-1 receptor. Neutralisation profiles of KM122 lead candidate molecules compared to the benchmark anti-PD-L1 antibody. Data is from a single experiment
Figure 8C:
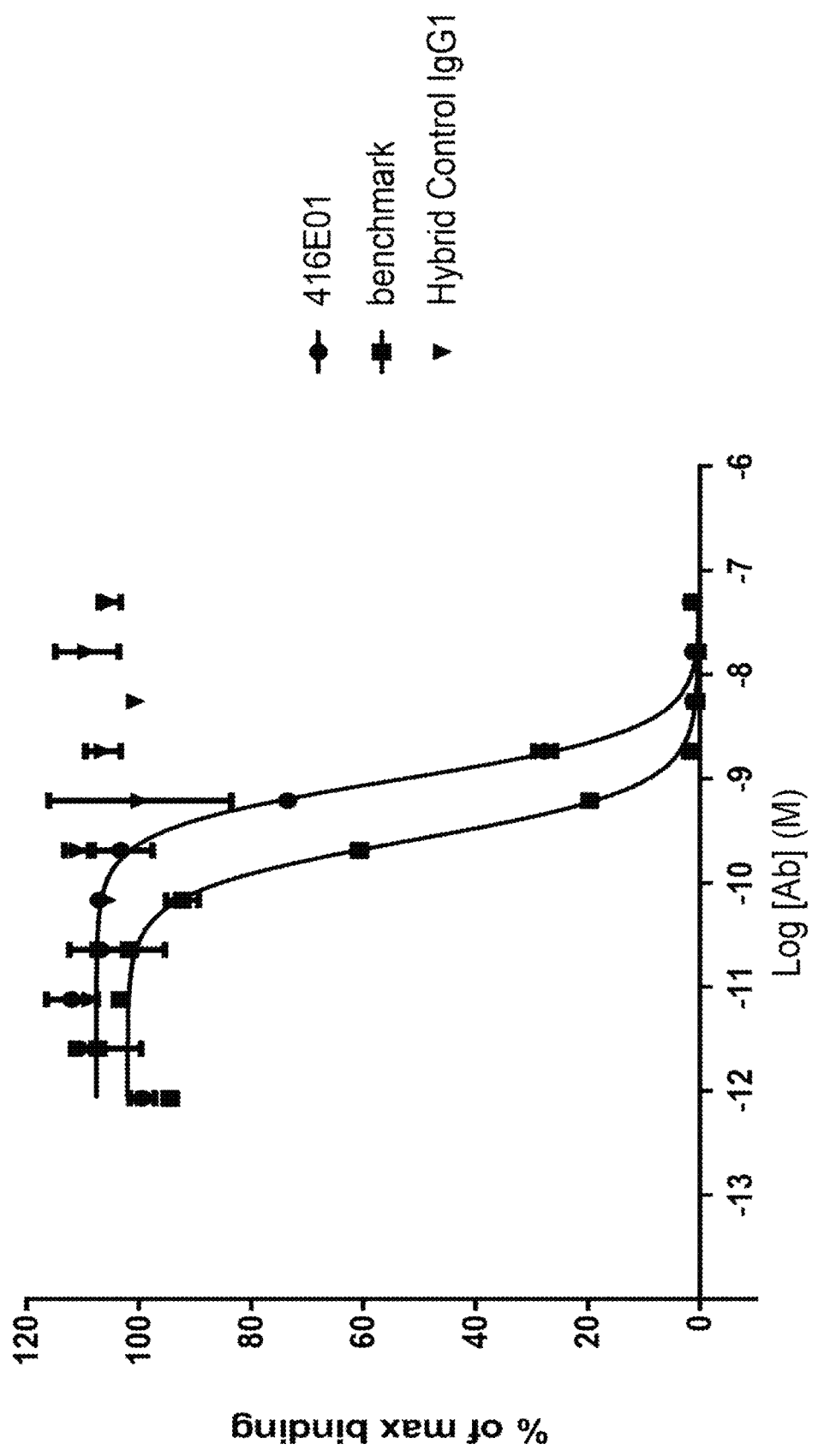
FIG. 8(c): PD-L1 direct neutralisation ELISA with PD-1 receptor. Neutralisation profile of KM122 lead candidate molecule 416E01 compared to the benchmark anti-PD-L1 antibody. Data is from a single experiment
Figure 9A:
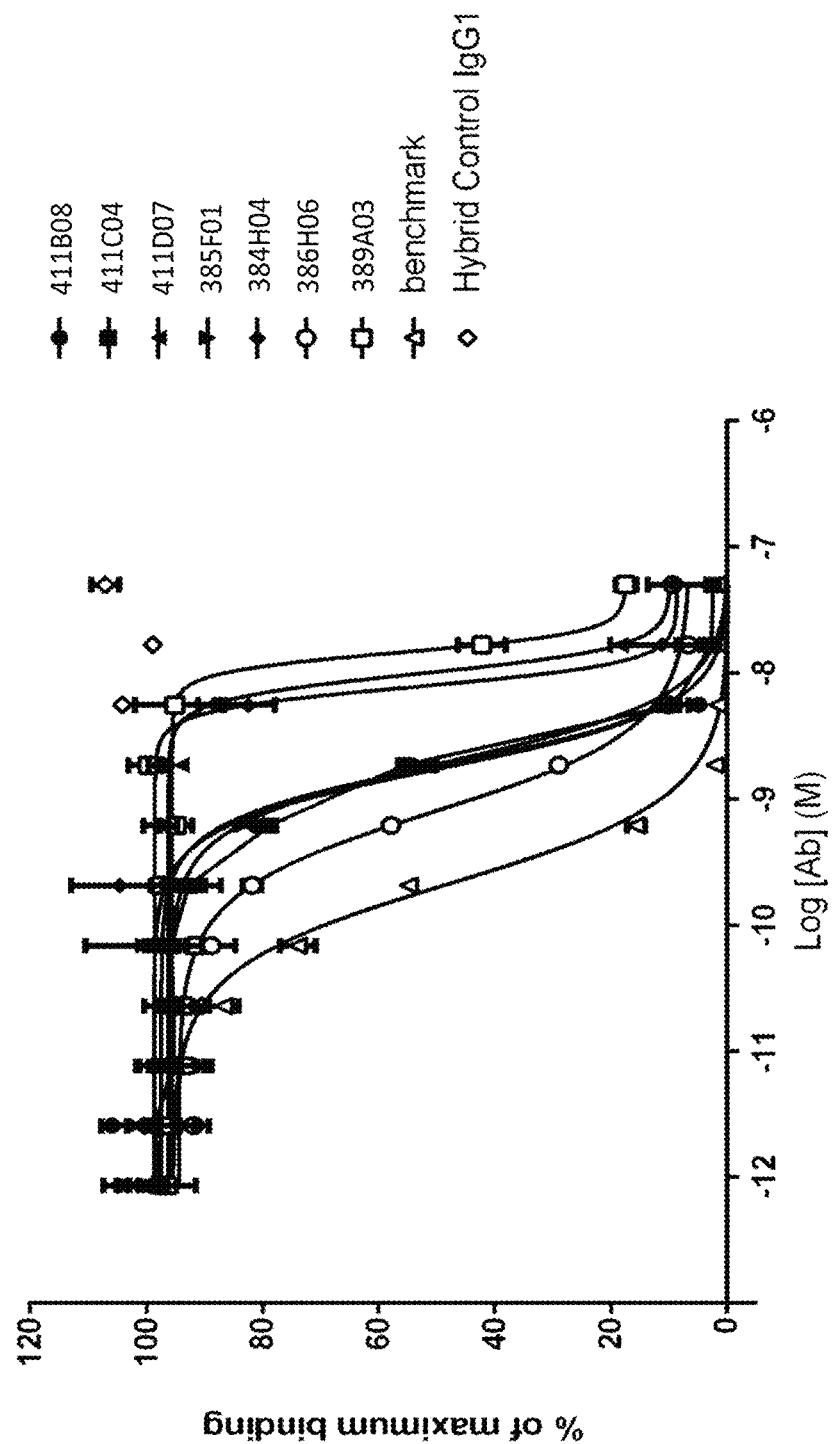
FIG. 9(a): PD-L1 direct neutralisation ELISA with CD80 receptor. Neutralisation profiles of KM121 hits compared to a benchmark anti-PD-L1 antibody and isotype control. Data representative of three independent experiments
Figure 9B:
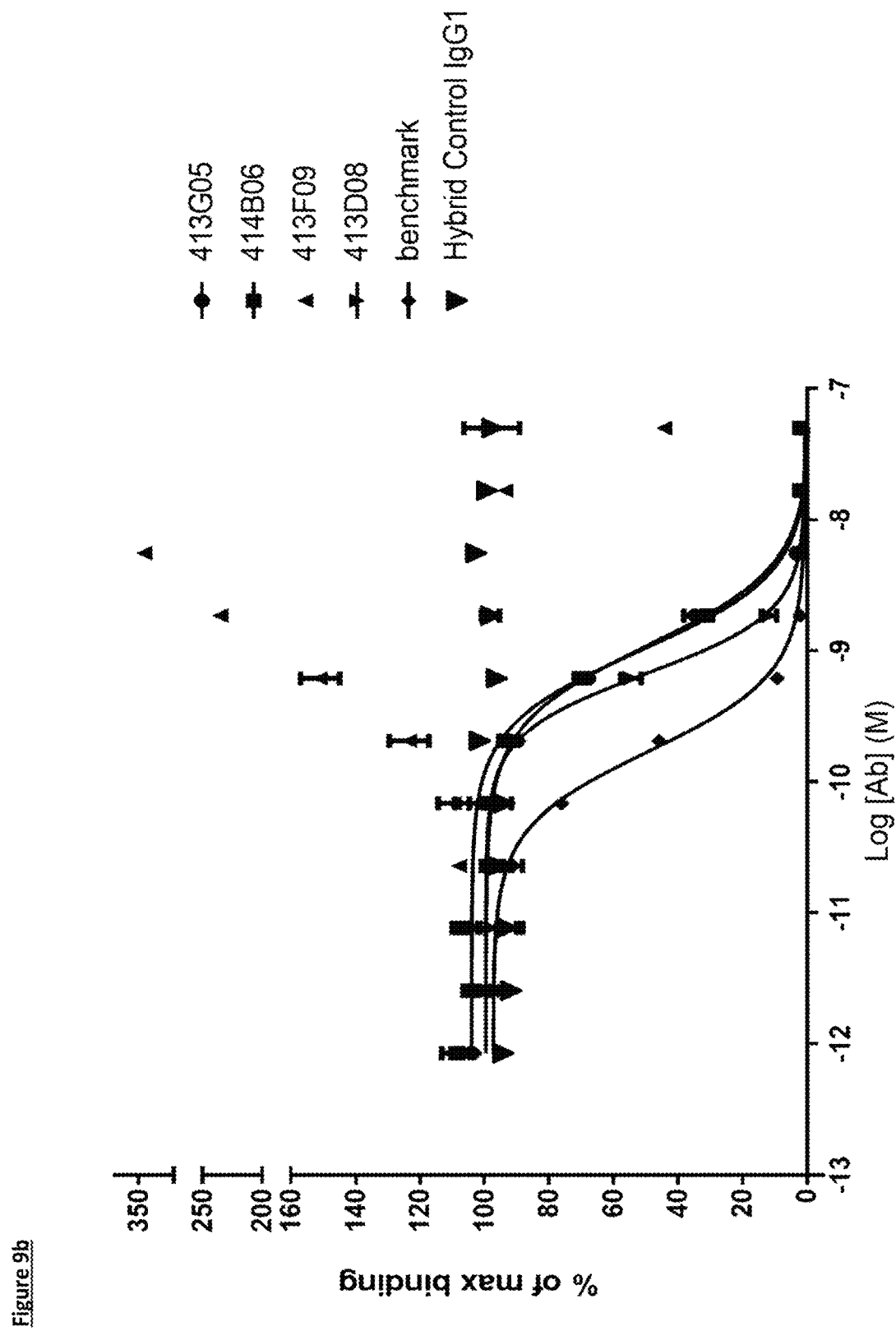
FIG. 9(b): PD-L1 direct neutralisation ELISA with CD80 receptor. Neutralisation profiles of KM122 lead candidate molecules compared to the benchmark anti-PD-L1 antibody. Data is from a single experiment
Figure 9C:
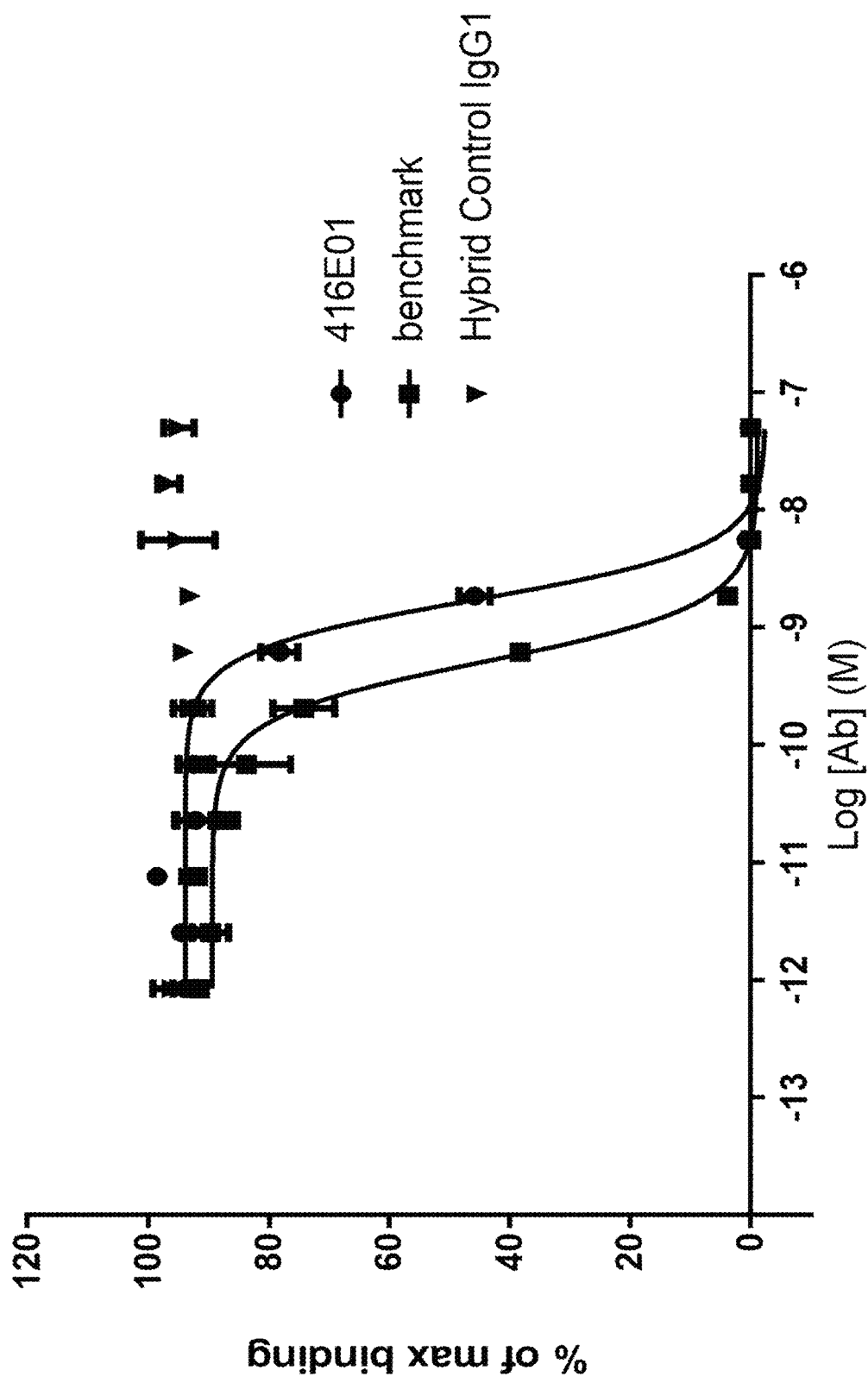
FIG. 9(c): PD-L1 direct neutralisation ELISA with CD80 receptor. Neutralisation profiles of KM122 lead candidate molecule 416E01 compared to the benchmark anti-PD-L1 antibody. Data is from a single experiment

Selected hits were re-expressed with a human IgG1 constant region and sent for sequencing at Source Bioscience. V region usage is listed in Table 5. Hits were then analysed in an ELISA to determine their ability to neutralise PD-L1/PD-1 interactions, and PD-L1/CD80 interactions. All seven KM121 hits neutralised PD-L1/CD80 interactions; however, four antibodies did not neutralise PD-L1/PD-1. Four out of five KM122 hits neutralised both PD-L1/PD-1 and PD-L1/CD80 internations. Results are shown in FIGS. 8 and 9. Antibodies shown to neutralise both PD-1 and CD80 interactions with PD-L1 were further screened for their ability to increase IFNγ in an autologous monocyte-T-cell co-culture assay.

Materials and Methods a) PD-L1/PD-1 and PD-L1/CD80 Neutralisation ELISA

CD80 (R&D Systems) or PD-1 (in-house) diluted to 2.5 µg/mL were adsorbed to 96-well, low auto-fluorescent, high protein binding plates (Costar) overnight at 4° C. Excess protein was removed by washing with PBS-Tween (0.1% v/v) and the wells were blocked with 1% w/v bovine serum albumin (BSA, Sigma) in PBS for 1 hour at room temperature, after which plates were washed with PBS-Tween as above. 60 µL of a titration (three-fold serial dilution) of antibody was added to a 96-well, non-binding plate diluted in ELISA assay buffer (PBS+0.1% BSA). 60 μL of biotin labelled PD-L1 at 16 nM working concentration (8 nM FAC) was added to the plate excluding control wells where 60 μL ELISA assay buffer was added. The plate was incubated for 30 minutes before transferring 50 μL to the coated plates. The coated plates were incubated for 1 hour at room temperature. Excess protein was removed by washing with PBS-Tween (0.1% v/v). PD-L1 binding was detected using streptavidin labelled europium (Perkin Elmer) diluted 1/1000 in DELFIA assay buffer (Perkin Elmer). The plates were washed with TBS (Tris buffered saline)-Tween (0.1% v/v) and 50 μL/well of DELFIA Enhancement solution (Perkin Elmer) was added to the plate. Time-resolved fluorescence was measured at 615 nm on an Envision plate reader (PerkinElmer). Percentage specific binding was calculated as defined in Equation 3. IC50 values were determined using GraphPad Prism software by curve fitting using a four-parameter logistic equation (Equation 4). Results are shown in Table 4a below. Values for KM121 antibodies are a mean of three independent experiments. Values for KM122 are from a single experiment. ND indicates IC50 value not determined, as a complete curve could not be generated.

TABLE 4a $IC_{50}$ values for neutralisation of PD-L1 interactions with PD-1 and CD80

| Regime | Antibody clone ID | PD-1/PD-L1 $IC_{50}$ (nM) | CD80/PD-L1 $IC_{50}$ (nM) |
|---|---|---|---|
| KM121 | 411B08 | 2.22 | 1.60 |
| KM121 | 411C04 | 2.45 | 1.93 |
| KM121 | 411D07 | ND | 9.06 |
| KM121 | 385F01 | 2.25 | 1.76 |
| KM121 | 386H03 | ND | 0.74 |
| KM121 | 389A03 | ND | 13.18 |
| KM122 | 416E01 | 1.72 | 0.98 |
| KM122 | 413G05 | 2.02 | 1.10 |
| KM122 | 414B06 | 1.84 | 1.00 |
| KM122 | 413F09 | ND | ND |
| KM122 | 413D08 | 1.20 | 0.67 |

Selected lead antibodies active in the monocyte-T-cell co-culture assay (see Example 9) were analysed by SPR at 25 and 37° C. Lead antibodies retained sub-nanomolar affinity binding to PD-L1 even at 37° C. Antibodies did not bind mouse PD-L1. Results are shown in Table 4b.

Materials and Methods

SPR analysis was performed as per Example 4 with the following amendments: analysis was performed at 37° C. as well as 25° C. to increase the stringency of the assay. Human, cynomolgus and mouse PD-L1 (his-tagged) were generated in house (Seq ID Nos 3, 5 and 326, respectively).

TABLE 4b

Binding affinities of selected lead antibodies

| Clone ID | Temperature | Antigen | KD (nM) |
|---|---|---|---|
| 413G05 | 25° C. | Human | 0.024<br>Kon = 2.57 μM<br>Koff = 62.3 μM |
| 414B06 | 25° C. | Human | 0.172<br>Kon = 4.09 μM<br>Koff = 0.702 mM |
| 416E01 | 25° C. | Human | 0.193<br>Kon = 2.34 μM<br>Koff = 45.1 mM |
| 413G05 | 25° C. | Cyno | 0.015<br>Kon = 2.66 μM<br>Koff = 38.9 mM |
| 414B06 | 25° C. | Cyno | 0.192<br>Kon = 3.78 μM<br>Koff = 0.726 mM |
| 416E01 | 25° C. | Cyno | 0.411<br>Kon = 2.44 μM<br>Koff = 1.0 mM |
| 413G05 | 37° C. | Human | 0.050<br>Kon = 4.67 μM<br>Koff = 0.235 mM |
| 414B06 | 37° C. | Human | 0.778<br>Kon = 5.88 μM<br>Koff = 4.57 mM |
| 416E01 | 37° C. | Human | 0.511<br>Kon = 4.34 μM<br>Koff = 2.22 mM |
| 413G05 | 37° C. | Cyno | 0.046<br>Kon = 4.31 μM<br>Koff = 0.197 mM |
| 414B06 | 37° C. | Cyno | 0.794<br>Kon = 5.02 μM<br>Koff = 3.98 mM |
| 416E01 | 37° C. | Cyno | 0.998<br>Kon = 4.03 μM<br>Koff = 4.02 mM |

Example 9—Testing of Lead Anti-PD-L1 Antibodies in an Autologous Co-Culture Assay The effects of anti-PD-L1 antibodies on $IFN_\gamma$ production are analysed in a co-culture of purified peripheral blood monocytes and CD45RO$^+$ memory T-cells from the same donor. In brief, monocytes are isolated by negative selection using magnetic separation beads (Miltenyi Biotec). CD45RO$^+$ T-cells are isolated by a first round of negative selection for CD3$^+$ T-cells, and one round of positive selection for CD45RO$^+$ cells (Miltenyi Biotec). Cell subsets are co-cultured at a 1:1 ratio in RPMI 10% hiFBS in the presence of anti-CD3 (UCHT1, eBioscience) to provide TCR stimulation, and antibodies under investigation. Supernatants are taken after 4 days for analysis of IFNγ by MSD (Meso Scale Discovery).

The experiments were performed as described, except IFNγ production was measured with the R&D Systems™ Human IFNγ Duoset® ELISA, using DELFIA® Eu-N1 Streptavidin detection.

Figure 37:
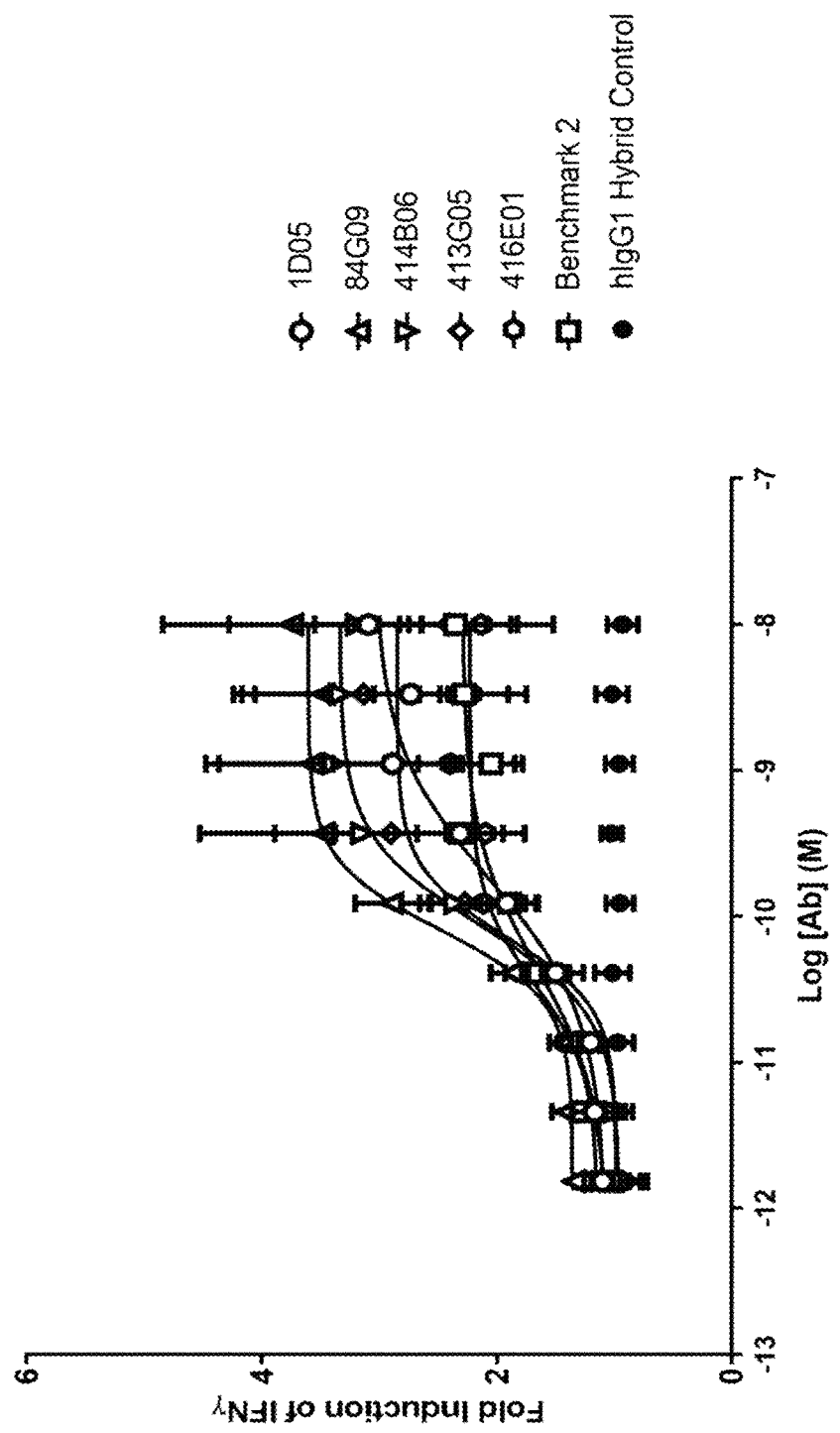
FIG. 37: Induction of IFN$\gamma$ production in a monocyte-T-cell co-culture assay by anti-PD-L1 antibodies in human IgG1 format. Each data point represents the mean fold induction of IFN$\gamma$ from at least three independent experiments, ±standard error of the mean

Response for IFNγ standard (pg/mL) was plotted versus relative fluorescence response at 615 nM. IFNγ concentration was interpolated from standard curve in pg/mL using a 4-parameter logistic fit as defined by Equation 4. Antibody-induced IFNγ is represented as fold induction compared to assay signal of wells showing background levels of response as defined in Equation 6. Each plot represents mean fold induction for individual donors with at least, 2 different donors represented versus antibody concentration Log (M). Results are shown in FIGS. 22 and 37.

Fold induction=assay response (pg/mL)/background response (pg/mL)   Equation 6

Background IFNγ response=IFNγ concentration (pg/mL) from wells containing monocyte—T-cell co-culture with anti-CD3 stimulation, without antibody.

Figure 22A:
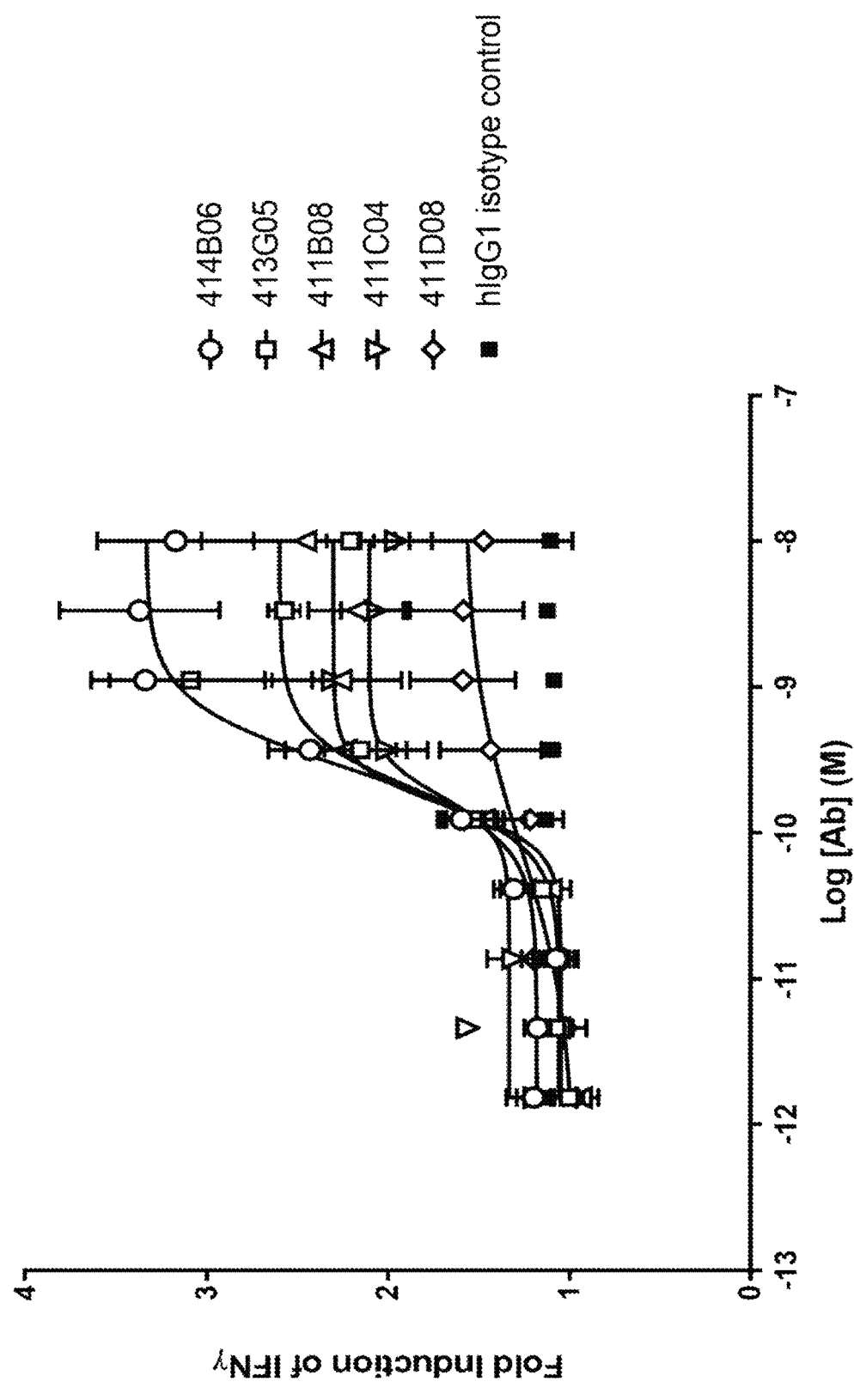
FIG. 22a: Induction of IFNγ production in a monocyte-T-cell co-culture assay by anti-PD-L1 antibodies in human IgG1 format. Each data point represents the mean fold induction from at least three independent experiments, ±standard error of the mean
Figure 22B:
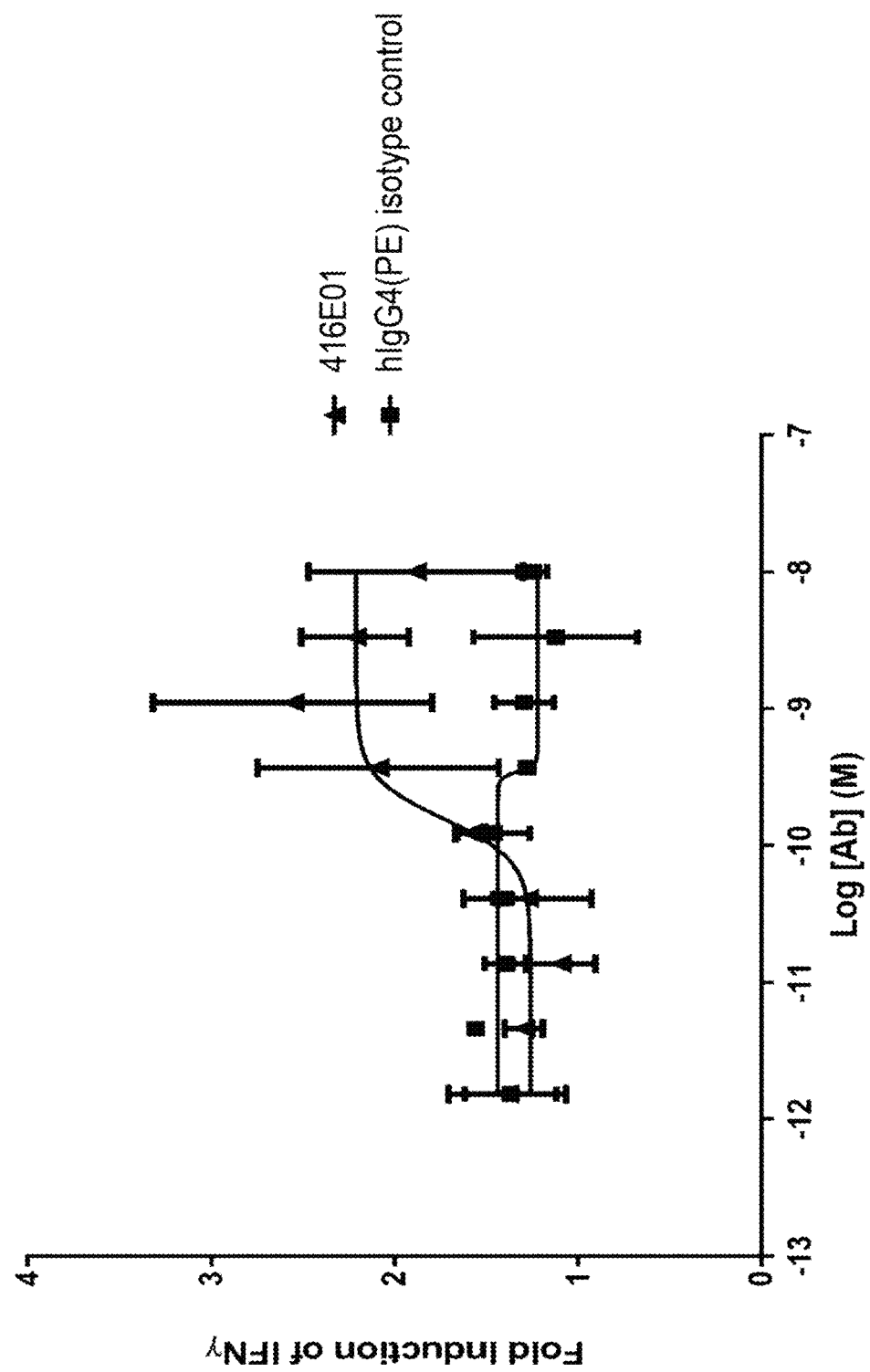
FIG. 22b: Induction of IFNγ production in a monocyte-T-cell co-culture assay by an anti-PD-L1 antibody in human IgG4(PE) format. Each data point represents the mean fold induction from two independent experiments, ±standard deviation

All five antibodies, in human IgG1 format, induced a specific, dose-dependent increase in IFNγ production by T-cells after 4 days of co-culture with autologous monocytes and anti-CD3 (see FIGS. 22a and 22b). The two antibodies that induced the highest increase in cytokine production, 413G05 and 414606, were selected for repeat characterisation by SPR (see Example 8). Antibody 416E01, in human IgG4(PE) format (Seq ID No:199), also induced specific dose-dependent increase in IFNγ production in the co-culture assay. This antibody was also selected for repeat SPR analysis.

The three selected antibodies were also analysed alongside the two lead antibodies selected in Example 4 (1D05 and 84G09), and a commercial effector enabled benchmark antibody. Antibodies were formatted as human IgG1. All antibodies induced dose-dependent IFNγ production in this assay (FIG. 37 and Table 22).

Example 10—Bispecific FIT-Ig Molecules Targeting PD-L1 and TIGIT

Bispecific FIT-Ig constructs were constructed substantially as described in Example 1 of International Application WO2015/103072 (in the name of EpiMab Biotherapeutics, and is incorporated herein by reference).

The bispecific constructs, having a FIT-Ig structure, as described in FIG. 1 of WO2015/103072 were expressed in CHO cells with a vector ratio of: Construct 1 DNA: 50%, Construct 2: DNA 25%: Construct 3 DNA 25% of total DNA in the transient transfection. The bispecific molecules were purified by standard Protein A and size exclusion chromatography. In this regard, Construct 1 is the polypeptide chain made up of $VL_A$-CL-$VH_B$-CH1-CH2-CH3 in FIG. 1 of WO2015/103072. Construct 2 is the polypeptide chain made up of $VH_A$-CH1 in FIG. 1 of WO2015/103072, and Construct 3 is the polypeptide chain made up of $VL_B$-CL in FIG. 1 of WO2015/103072.

SPR analysis was used to determine affinities of the various arms of the bispecific and the parental monospecific antibodies were used to determine if the affinities had been altered in the bispecific molecule. Sequential binding of antigens were used to test whether the bispecific constructs were capable of binding on both arms of the bispecific.

TABLE 5

V Gene usage for antibody leads

| Regime | Antibody clone ID | V gene | D gene | J gene | CDHR3 length (aa) | Non-germline CDRH3 (aa) | V gene | J gene | CDRL3 length (aa) | Non-germline CDRL3 (aa) |
|---|---|---|---|---|---|---|---|---|---|---|
| KM121 | 411B08 | IGHV3-7*01 | IGHD4-11*01 | IGHJ4*02 | 12 | 7 | IGKV1D-12*02 | IGKJ3*01 | 9 | 1 |
| KM121 | 411C04 | IGHV3-7*01 | IGHD4-11*01 | IGHJ4*02 | 12 | 6 | IGKV1D-12*02 | IGKJ3*01 | 9 | 1 |
| KM121 | 411D07 | IGHV4-4*02 | IGHD3-10*01 | IGHJ4*02 | 8 | 1 | IGKV4-1*01 | IGKJ2*04 | 8 | 2 |
| KM121 | 386H03 | IGHV4-4*02 | IGHD3-10*01 | IGHJ4*02 | 8 | 2 | IGKV4-1*01 | IGKJ2*04 | 8 | 1 |
| KM121 | 389A03 | IGHV4-39*01 | IGHD6-13*01 | IGHJ1*01 | 13 | 6 | IGKV4-1*01 | IGKJ1*01 | 9 | 1 |
| KM121 | 385F01 | IGHV3-7*01 | IGHD4-11*01 | IGHJ4*02 | 12 | 7 | IGKV1D-12*02 | IGKJ3*01 | 9 | 1 |
| KM122 | 413D08 | IGHV3-33*01 | IGHD5-18*01 | IGHJ6*02 | 11 | 3 | IGKV1-17*01 | IGKJ1*01 | 9 | 1 |
| KM122 | 413G05 | IGHV3-11*01 | IGHD1-20*01 | IGHJ6*02 | 16 | 5 | IGKV1D-12*02 | IGKJ4*01 | 9 | 1 |
| KM122 | 413F09 | IGHV3-23*04 | IGHD5-18*01 | IGHJ4*02 | 16 | 8 | IGKV1-9*d01 | IGKJ5*01 | 9 | 3 |
| KM122 | 414B06 | IGHV3-7*01 | IGHD5-24*01 | IGHJ4*02 | 12 | 6 | IGKV1D-12*02 | IGKJ3*01 | 9 | 0 |
| KM122 | 416E01 | IGHV3-23*04 | IGHD6-13*01 | IGHJ4*02 | 14 | 10 | IGKV1D-12*02 | IGKJ5*01 | 9 | 2 |

TABLE 22

Summary of data from monocyte-T cell co-culture experiments.

| Antibody name | mean EC50 (nM) | mean fold increase IFNγ |
|---|---|---|
| 1D05 | 0.21 | 3.04 |
| 84G09 | 0.081 | 3.60 |
| 413G05 | 0.082 | 2.85 |
| 414B06 | 0.012 | 3.33 |
| 416E01 | 0.064 | 2.23 |
| benchmark 2 | 0.057 | 2.30 |

TABLE 6

Bispecific antibody constructs and control monospecific antibodies

| Full name | Alias | Native variable domain[1] | Additional Domain[2] |
|---|---|---|---|
| 1D05/in-house anti-TIGIT | Bispecific 1 | 1D05 (anti-PD-L1)* | Kymab TIGIT |
| In-house anti-TIGIT/1D05 | Bispecific 2 | Kymab TIGIT | 1D05 (anti-PD-L1)* |
| Tool anti-TIGIT/Tool anti-PD-L1 | Bispecific 3 | Tool anti-TIGIT | Tool anti-PD-L1 |
| Tool anti-PD-L1/Tool anti-TIGIT | Bispecific 4 | Tool anti-PD-L1 | Tool anti-TIGIT |
| 1D05 | Antibody 1 | In-house anti-PD-L1* | na |
| Kymab TIGIT | Antibody 2 | In-house anti-TIGIT | na |

TABLE 6-continued

Bispecific antibody constructs and control monospecific antibodies

| Full name | Alias | Native variable domain[1] | Additional Domain[2] |
|---|---|---|---|
| Tool PD-L1 | Antibody 3 | Tool anti-PD-L1 | na |
| Tool TIGIT | Antibody 4 | Tool anti-TIGIT | na |

*1D05 has the $V_H$ sequence of Seq ID No: 33 and the $V_L$ sequence of Seq ID No: 43, and a heavy chain constant region of Seq ID No: 205
[1]"Native Variable domain" corresponds to the antigen-binding site formed by $VH_B$ and $VL_B$ in FIG. 1 of WO2015/103072
[2]"Additional domain" corresponds to the antigen binding site formed by VHA and VLA in FIG. 1 of WO2015/103072 a) Kinetic Analysis

An anti-human IgG capture surface was created by a mix of 3 anti-human Fc antibodies (Jackson Labs 109-005-008, 109-006-008 and 309-006-008) immobilised on a GLC chip by primary amine coupling. Control monospecific antibodies or Bispecific antibody constructs were captured on this surface and human PD-L1 or TIGIT was used as analyte at 512 nM, 128 nM, 32 nM, 8 nM and 2 nM with 0 nM (i.e. buffer alone) used to double reference the binding sensorgrams. The assay was run at 25° C., using HBS-EP as running buffer. The sensorgrams were fitted to the 1:1 model inherent to the ProteOn analysis software.

TABLE 7

TIGIT Binding

| Full name | Alias | Ka | Kd | KD (nM) |
|---|---|---|---|---|
| 1D05/in-house anti-TIGIT | Bispecific 1 | 2.38E+06 | 2.65E−03 | 1.11 |
| In-house anti-TIGIT/1D05 | Bispecific 2 | 1.12E+06 | 2.02E−03 | 1.8 |
| Tool anti-TIGIT/Tool anti-PD-L1 | Bispecific 3 | 2.10E+06 | 3.69E−03 | 1.75 |
| Tool anti-PD-L1/Tool anti-TIGIT | Bispecific 4 | 3.22E+06 | 2.98E−03 | 0.93 |
| 1D05 | Antibody 1 | nbs | nbs | nbs |
| Kymab TIGIT | Antibody 2 | 1.58E+06 | 2.27E−03 | 1.44 |
| Tool PD-L1 | Antibody 3 | nbs | nbs | nbs |
| Tool TIGIT | Antibody 4 | 3.16E+06 | 5.42E−03 | 1.72 |

TABLE 8

PD-L1 Binding

| Full name | Alias | Ka | Kd | KD (nM) |
|---|---|---|---|---|
| 1D05/in-house anti-TIGIT | Bispecific 1 | 6.03E+05 | 1.61E−04 | 0.27 |
| In-house anti-TIGIT/1D05 | Bispecific 2 | 1.04E+06 | 2.14E−04 | 0.21 |
| Tool anti-TIGIT/Tool anti-PD-L1 | Bispecific 3 | 1.25E+06 | 1.22E−04 | 0.1 |
| Tool anti-PD-L1/Tool anti-TIGIT | Bispecific 4 | 7.36E+05 | 1.57E−04 | 0.21 |
| 1D05 | Antibody 1 | 9.71E+05 | 3.36E−04 | 0.35 |
| Kymab TIGIT | Antibody 2 | nbs | nbs | nbs |
| Tool PD-L1 | Antibody 3 | 1.05E+06 | 2.08E−04 | 0.2 |
| Tool TIGIT | Antibody 4 | nbs | nbs | nbs | b) Bispecific Binding

Figure 10:
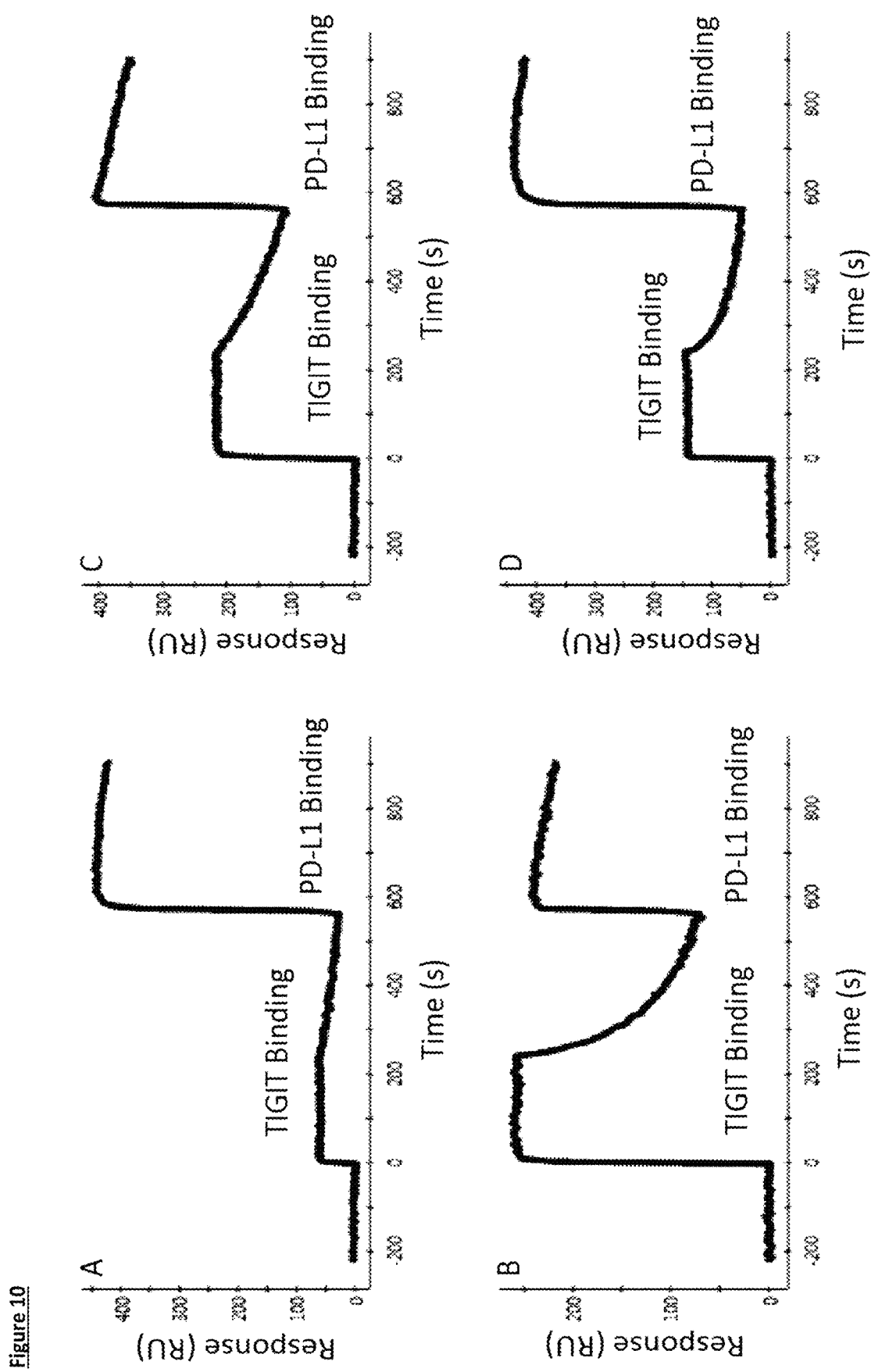
FIGS. 10(a)-10(d): Bispecific binding as measured by SPR, with PD-L1 as first antigen, and TIGIT as second antigen.
Figure 11:
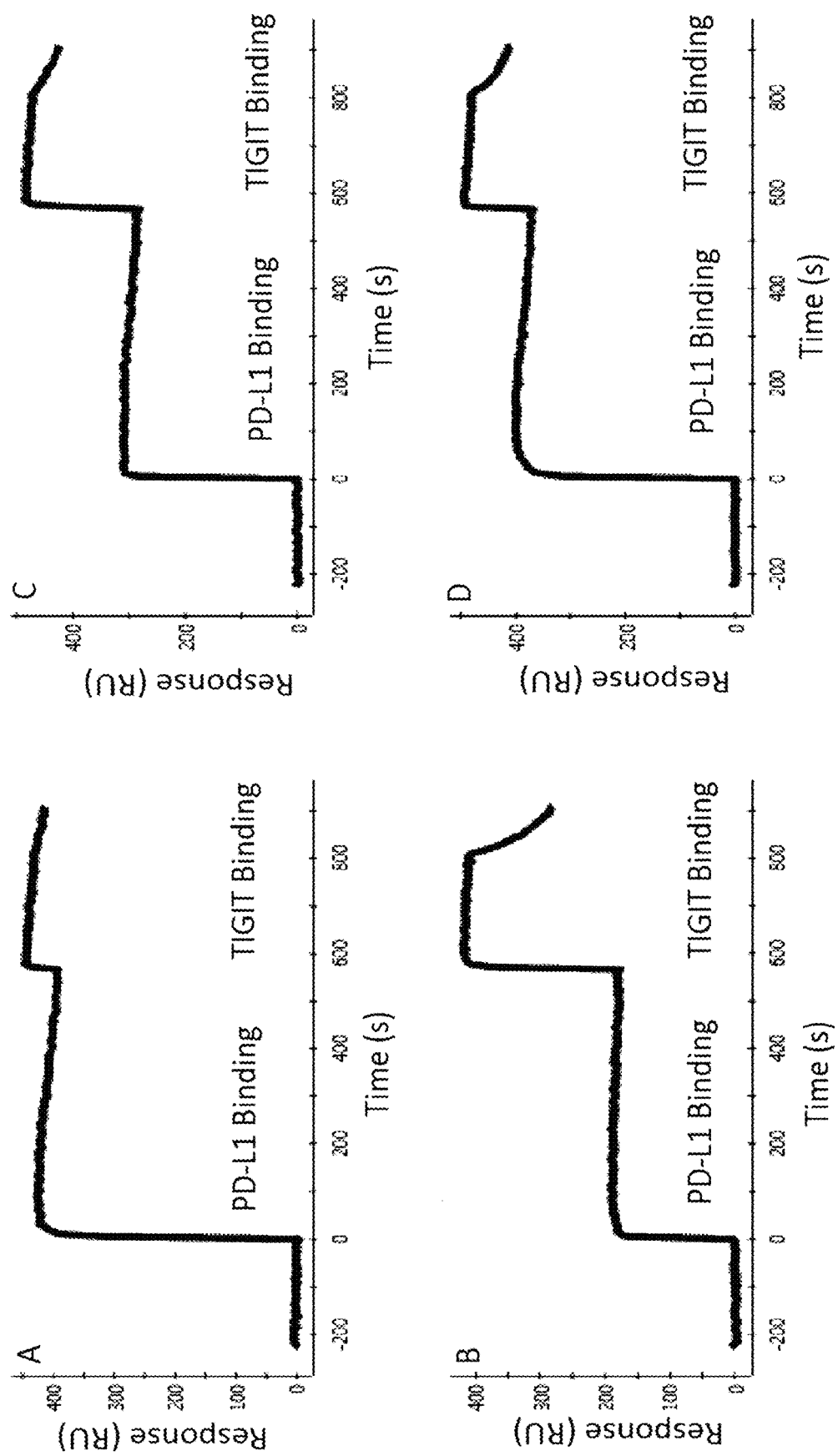
FIG. 11: Bispecific binding as measured by SPR, with TIGIT as first antigen, and PD-L1 as second antigen. A) Bispecific 1, B) Bispecific 2, C) Bispecific 3, D) Bispecific 4. For detailed construction information of each Bispecific construct, see Table 6

Using the same anti-human IgG capture surface created for kinetic analysis, the bispecific antibody constructs were captured on this surface and recombinant PD-L1 or TIGIT was used as analyte at 512 nM, 128 nM, 32 nM, 8 nM and 2 nM with 0 nM (i.e. buffer alone) used to double reference the binding sensorgrams. The assay was carried out by injecting PD-L1 followed by TIGIT with no regeneration between analyte injections, and also with TIGIT followed by PD-L1. The sensorgrams for the double referenced 512 nM are shown in FIGS. 10 and 11.

c) Characterisation of Bispecific FIT-Ig Molecules Binding to PD-L1 and TIGIT by AlphaScreen®

An AlphaScreen® binding assay was developed to assess the bispecific binding of PD-L1/TIGIT FIT-Ig molecules. The assay was set up using biotinylated (SEQ ID No:3) and His-FLAG-TIGIT (SEQ ID No:539) detected respectively with streptavidin donor beads and anti-FLAG acceptor beads (both Perkin Elmer, 6760613). Human IgG1 (Sigma 15154) and parental monospecific antibodies alone or in combination were used as negative controls, while an anti-His antibody (Qiagen 34660) was used as positive control.

Two protocols were created to investigate the ability of FIT-Ig molecules to promote proximity of TIGIT and PD-L1 coated beads with a distinct stringency. Antibodies were either incubated with PD-L1 and TIGIT proteins before adding the AlphaScreen® detection beads (Method one), or incubated with the detection beads pre-coated with their respective TIGIT and PD-L1 proteins (Method two). Method two was designed to mimic the cell recruitment by bispecific antibodies.

i) Method One

Figure 25A:
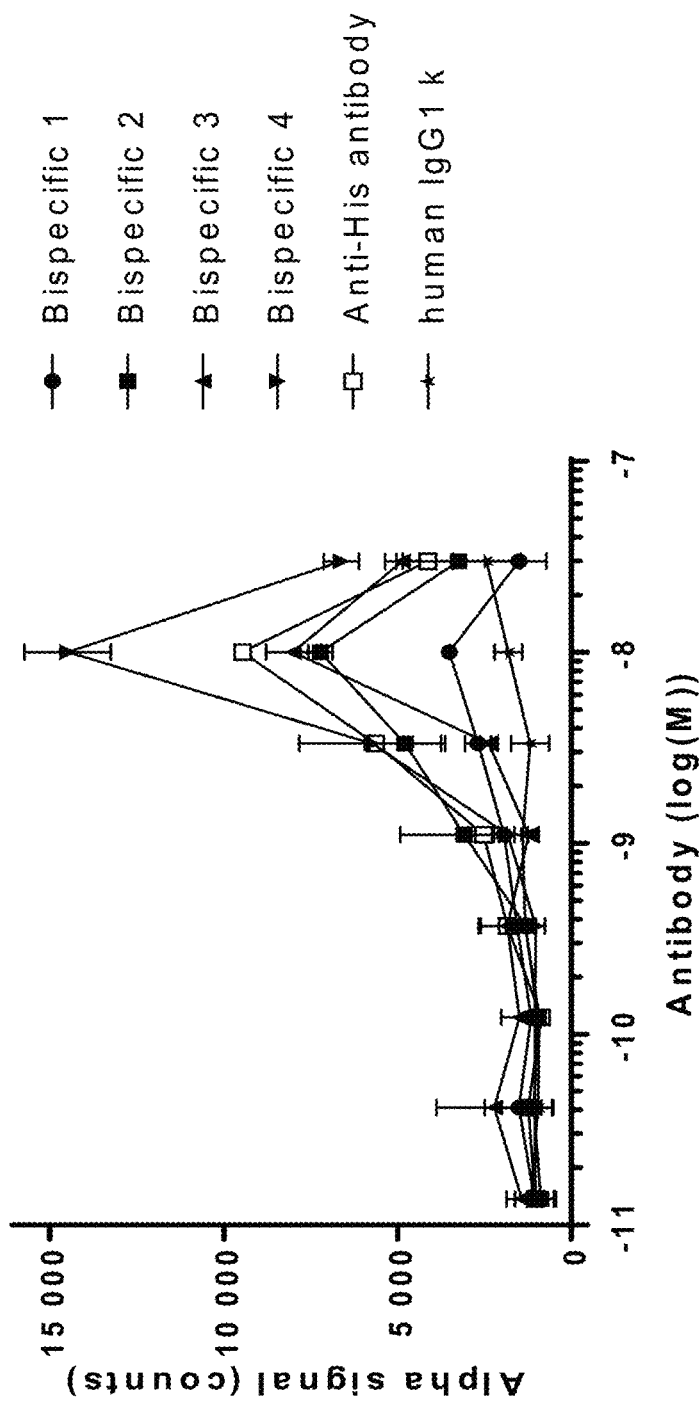
FIGS. 25(a)-25(b): Titration of FIT-Ig molecules, parental monospecific antibodies, and control antibodies in PD-L1/TIGIT AlphaScreen® Binding Assay using method one. Antibodies were incubated with PD-L1 and TIGIT proteins for an hour before the addition of AlphaScreen® acceptor beads for an hour followed by the addition of AlphaScreen® donor beads for another hour prior to the detection of fluorescence.
Figure 25B:
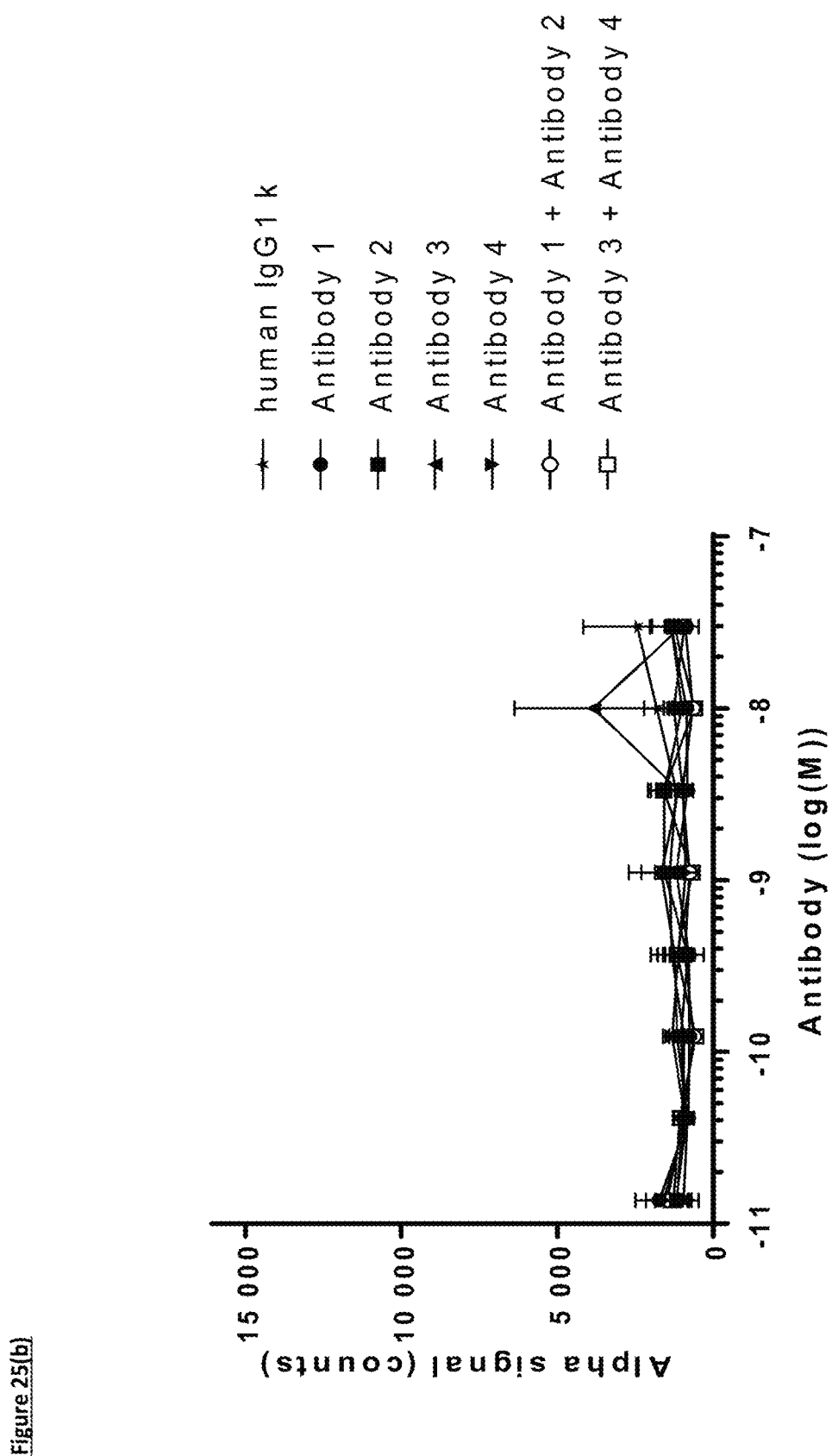

Bispecific antibodies, parental monospecific antibodies and control antibodies were prepared in buffer (PBS pH 7.4 (Gibco) and 0.1% w/v BSA (Sigma)) at 150 nM and diluted as per 1:3 series, 8 points. 5 µL of each serial dilution of antibody were mixed in a 384-well AlphaLISA® assay plate (Perkin Elmer 6005350) to 5 µL of biotinylated His-PD-L1 and 5 µL of His-FLAG-TIGIT at 50 nM in buffer. Parental monospecific antibodies were also prepared as described above starting from 300 nM to be tested in combination. 2.5 µL of the first antibody was added to the same volume of the second antibody, then 5 µL of each combination of parental monospecific antibodies were mixed in assay plates to 5 µL of biotinylated His-PD-L1 and 5 µL of His-FLAG-TIGIT at 50 nM in buffer. Assay plates were incubated for 1 hour at room temperature before adding 5 µL of anti-FLAG acceptor beads at 0.1 g/L for an additional hour at room temperature in the dark. Finally, 5 µL of streptavidin donor beads at 0.1 g/L were added to assay plates for 2 hours and 30 minutes. Assay plates were read using an EnVision plate reader (Perkin Elmer) with excitation/emission wavelengths of 680/615 nm. The fluorescent counts measured (Alpha signal) were plotted in Prism against antibody titrations. Results are shown in FIG. 25. Binding of FIT-Ig molecules to PD-L1 and TIGIT increases with the concentration of antibody up to 10 nM. No binding is observed for the monospecific parental antibodies and the isotype control.

ii) Method Two

Streptavidin donor beads prepared at 0.05 g/L in buffer (PBS pH 7.4 (Gibco 14190169) and 0.1% w/v BSA (Sigma)) were coated with biotinylated His-PD-L1 (Seq ID No:3) at 25 nM, while His-FLAG-TIGIT (Seq ID No:539) at 25 nM was used to label anti-FLAG acceptor beads at 0.05 g/L in buffer. Both acceptor and donor beads were incubated for 1 hour at room temperature in the dark.

Figure 26A:
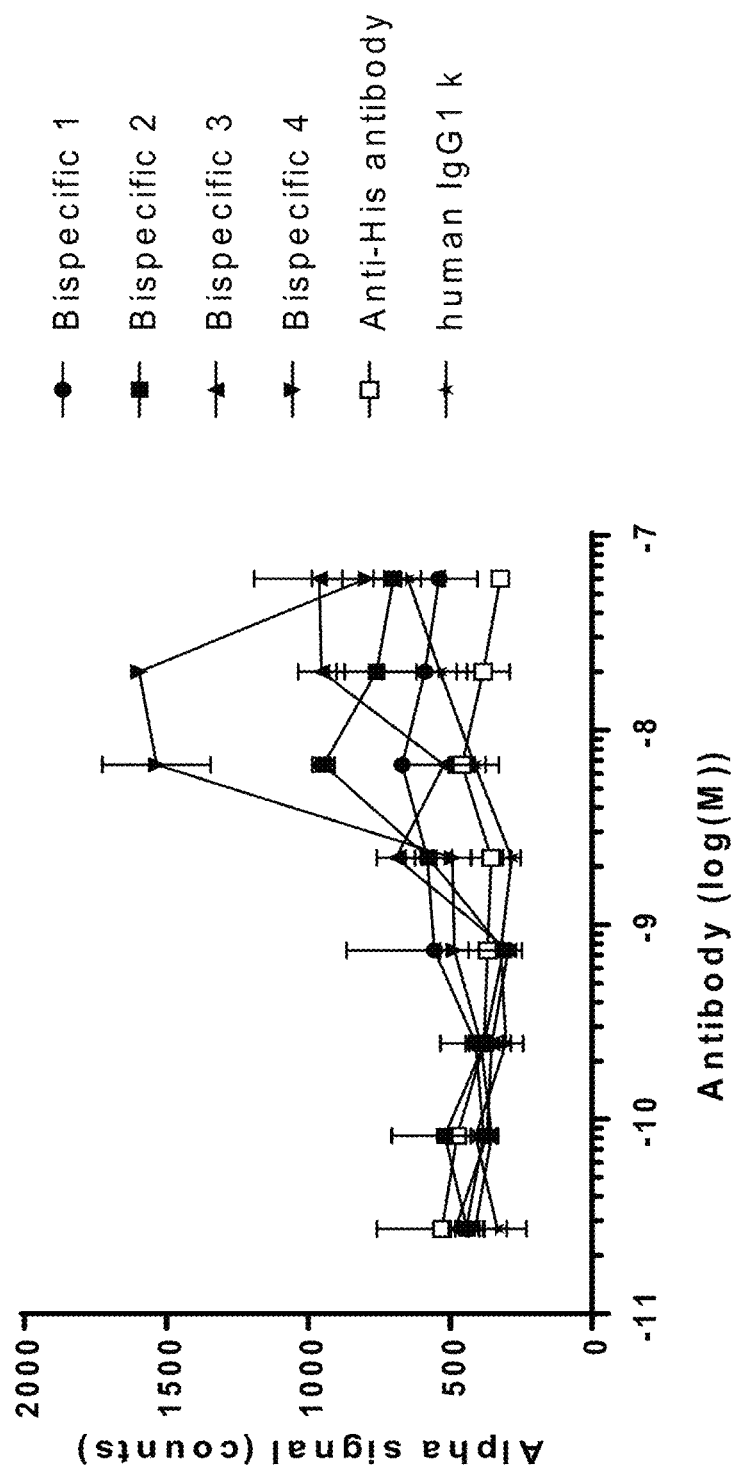
FIGS. 26(a)-26(b): Titration of FIT-Ig molecules, parental monospecific antibodies, and control antibodies in PD-L1/TIGIT AlphaScreen® Binding Assay using method two. AlphaScreen® donor and acceptor beads were coated for an hour with PD-L1 and TIGIT proteins respectively before the addition of antibodies for an hour followed by the detection of fluorescence.
Figure 26B:
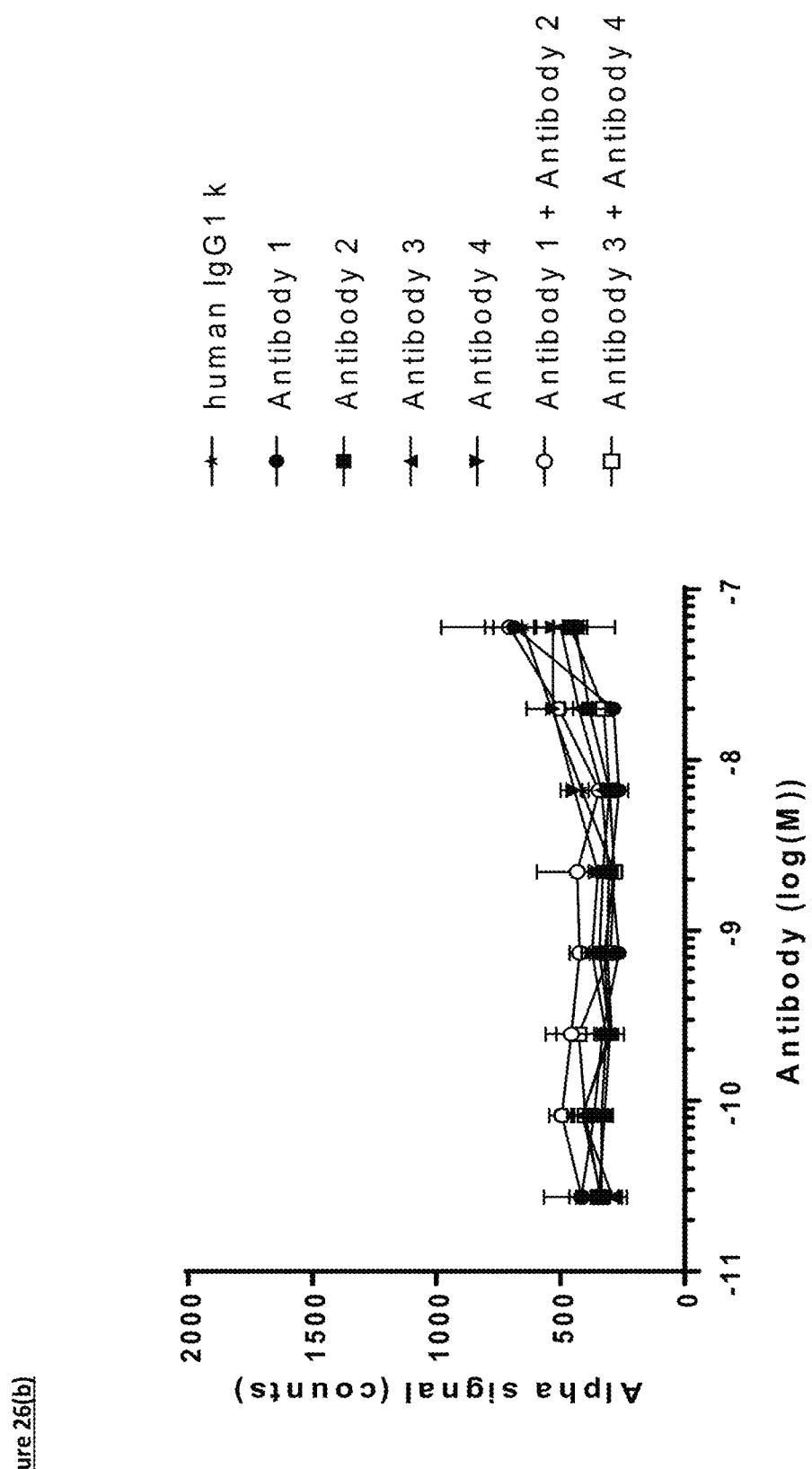

Bispecific antibodies, parental monospecific antibodies, alone and combined, and control antibodies were prepared in buffer at 300 nM and diluted as per 1:3 series, 8 points. 5 µL of each serial dilution of antibody were mixed in a 384-well AlphaLISA® assay plate (Perkin Elmer 6005350) to 10 µL of pre-coated donor beads and 10 µL of pre-coated acceptor beads. Assay plates were incubated at room temperature for 4 hours in the dark and then read as described for method one. The fluorescent counts measured (Alpha signal) were plotted in Prism against antibody titrations. Results are shown in FIG. 26. Binding of FIT-Ig molecules to PD-L1 and TIGIT increases with the concentration of antibody up to 20 nM. No binding is observed for the monospecific parental antibodies and the isotype control.

d) Characterisation of Bispecific FIT-Ig Molecules Binding to PD-L1 and TIGIT by Flow Cytometry A flow cytometry protocol was developed to assess the ability of the FIT-Ig molecules to promote the recruitment of cells expressing TIGIT and PD-L1. For this purpose, CHO cells transfected with human PD-L1 were stained with CellTrace™ Far Red (Invitrogen C34572) which emits maximally at 661 nm while HEK cells transfected with human TIGIT were stained with CellTrace™ Violet (Invitrogen C34571) which emits maximally at 450 nm.

CHO human PD-L1 and HEK human TIGIT cells were harvested, counted, washed, and re-suspended in PBS (Gibco 14190169) at 1 million of cells per mL. CellTrace™ Far Red and CellTrace™ Violet dyes were diluted 1:2000 and incubated with cells for 20 min at 37° C. in the dark, according to manufacturer's recommendations. Buffer (PBS (Gibco 14190169), 1% BSA (Sigma) 0.1% Na azide (Severn Biotech 40-2010-01)) was then added in excess for an additional 5-minute incubation step. Cells were spun down, re-suspended in buffer at 0.5 million of cells per mL and incubated for at least 10 minutes at 37° C. before proceeding with binding protocol. Unstained cells were kept and used to set up the gating strategy.

Bispecific antibodies and human IgG1 were prepared in buffer at 150 nM and diluted as per 1:3 series, 8 points. 50 µL of each serial dilution of antibody, 50 µL of CHO human PD-L1 cells labelled with CellTrace™ Far Red and 50 µL of HEK human TIGIT labelled with CellTrace™ Violet were added to a 96-well, V-bottom PS plate (Greiner 651901). Assay plates were incubated at room temperature for 1 hour under gentle agitation (450 rpm) before being read using the Attune NxT flow cytometer (Thermo Fisher). CellTrace™ Violet was excited using the Violet laser and detected in the VL1 channel with a 440/50 bandpass filter. CellTrace™ Far Red was excited using the Red laser and detected in the RL1 channel with a 670/14 bandpass filter. Sample collection was performed without vortexing samples. FCS files were analysed with FlowJo® software. Single cells and duplets were gated based on the forward and side scatter dot plot.

Figure 27:
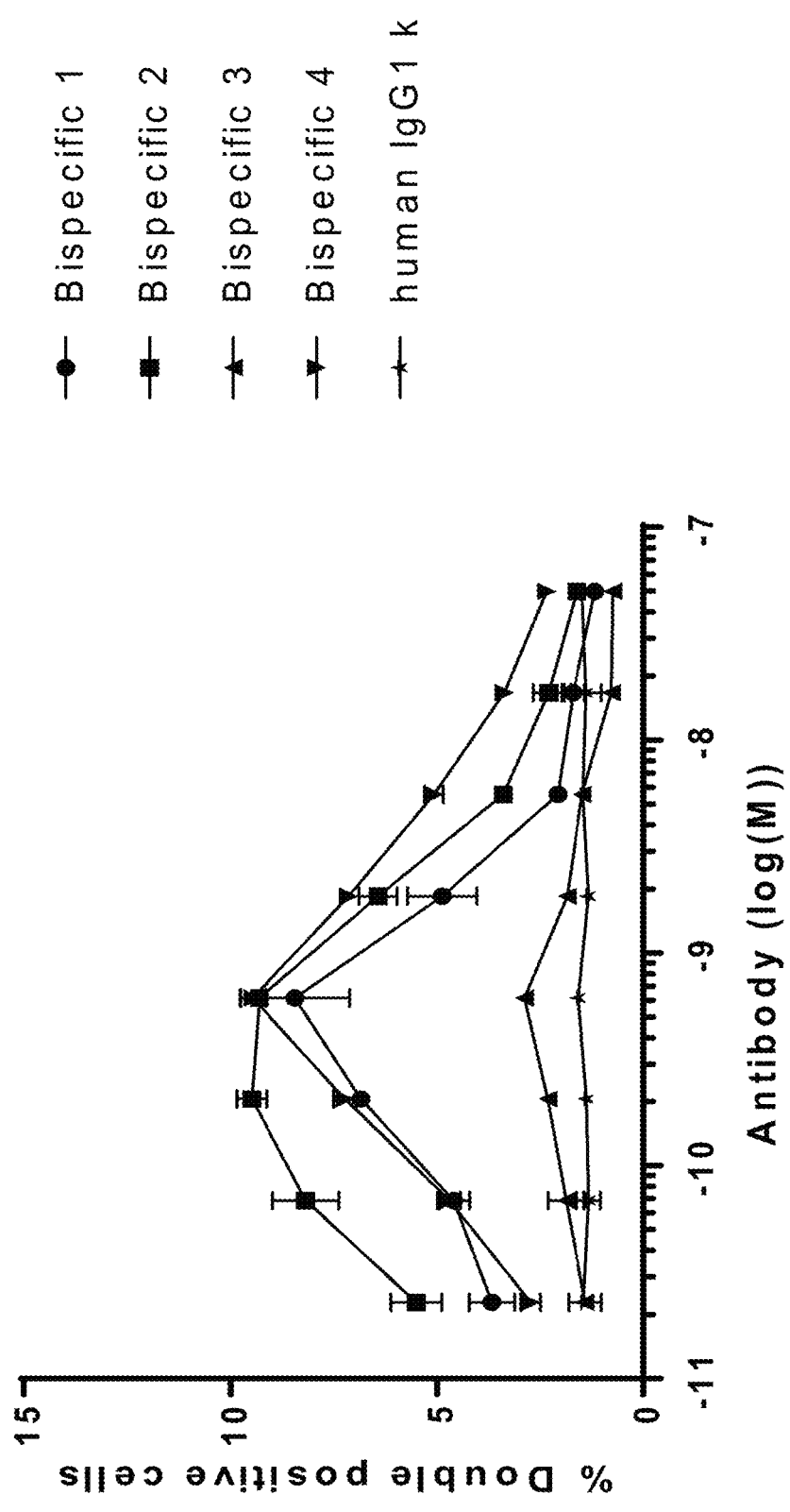
FIG. 27: Titration of FIT-Ig molecules, and control antibody in a PD-L1/TIGIT cell recruitment assay by flow cytometry. CHO human PD-L1 and HEK human TIGIT were stained with CellTrace™ Far Red and CellTrace™ Violet respectively and co-cultured in presence of antibodies for an hour prior to the detection of fluorescence and identification of double positive population. Data shown are representative of one unique experiment

Data analysis resulted in the identification of four different gates: a double negative quadrant corresponding to unstained CHO human PD-L1 and unstained HEK human TIGIT; two quadrants positive for single staining (in VL1 or RL1 channel); and a quadrant positive for dual staining (in both VL1 and RL1 channels) composed of stained CHO human PD-L1 and stained HEK human TIGIT recruited by FIT-Ig molecules. Percentages of double positive cells were plotted into Prism against antibody titrations. Results are shown in FIG. 27. Percentage of double positive cells increases with the concentration of FIT-Ig molecules up to 1 nM.

The monospecific binding of test molecules to target was confirmed on stained cells using monospecific antibodies labelled with R-Phycoerythrin (PE) which emits maximally at 590 nm. PE-labelled Antibody 1, Antibody 2 and human IgG1 were diluted in buffer at 150 nM. 50 µL of each antibody were mixed with 50 µL of stained CHO human PD-L1 and 50 µL of stained HEK human TIGIT in a 96-well, V-bottom PS plate (Greiner 651901). Following a 1 hour incubation at room temperature, cells were washed 3 times with 200 µL/well of PBS and re-suspended in 150 µL/well of buffer. Assay plates were read using the Attune NxT flow cytometer (Thermo Fisher) to record fluorescence. Cell Trace™ Violet and Far Red were detected as stated above. PE was excited using the Yellow laser and detected in the YL1 channel with a 585/16 bandpass filter. GeoMean values in the YL1 channel were used to determine monospecific binding to stained CHO human PD-L1 or stained HEK human TIGIT.

Example 11—Generation and Expression of Anti-PD-L1-IL-2 Immunocytokine Constructs Immunocytokines were generated by fusing wild type IL-2 (SEQ ID No:301), or IL-2 containing deletions in the first nine amino acids (see SEQ ID Nos:303 to 323, fused to Seq ID No:324), to the light chain of anti-PD-L1 antibody 1D05 (see Seq ID No:45). These were paired with an IgG1 effector-disabled variant of 1D05 heavy chain (Seq ID No:205). Wild type IL-2 fused to the heavy chain of 1D05 was generated for use as a control (SEQ ID No:302) and paired with the unmodified light chain of 1D05 (Seq ID No:45). Twenty-two immunocytokines were successfully expressed and characterised further. One light chain construct, 1D05 D1 did not express successfully.

Materials and Methods

The DNA sequences encoding the anti-PD-L1 (antibody 1D05) immunocytokine (C-terminal IL-2 fusion to light chain) were purchased as synthetic DNA strings and cloned into the pTT5 expression vector using the Golden Gate cloning strategy. The heavy chain sequence of 1D05, includes a constant region which is a disabled IgG1 variant with changes from wild-type shown in bold (Seq ID No:299). The light chain of antibody 1D05 has full length wild type IL-2 sequence (underlined) fused to the C-terminus of the Kappa constant region (Seq ID No:300). Overlap PCR using appropriate oligonucleotide primers were used to generate variants of N-terminal of IL-2 (see Seq ID No:300 where IL-2 the sequence is underlined and the region to be varied is shown in bold). Variant sequences were cloned into the pTT5 expression vector using the Golden Gate method. The wild type and variant constructs were transfected to Expi293™ cells for expression.

Example 12—Generation of IL-2R Transfectant Cells for Screening

In order to differentiate between immunocytokine activity on the high affinity (αβγ) and intermediate affinity (βγ) IL-2 receptors, IL-2R transfectants were generated. TF-1 cells, expressing endogenous common γ chain, were transfected with β, or α and β receptor subunits, to impart responsiveness to IL-2. The proliferative response to immunocytokines was then analysed using these cells (see Example 13).

Materials and Methods

Two recombinant cell lines were generated to distinguish between signalling through high affinity ($\alpha\beta\gamma$) and intermediate affinity ($\beta\gamma$) IL-2R. The erythroleukemia cell line TF-1 (European Collection of Authenticated Cell Cultures) shows complete growth dependency on granulocyte-macrophage colony-stimulating factor (GM-CSF) or interleukin-3 (IL-3). The first cell line generated was transfected with full length human IL-2R$\beta$ (CD122) only. The second cell line was generated by transfecting the full length human IL-2R$\alpha$ (CD25) into the first cell line.

The transfected sequences were codon optimized for mammalian expression and cloned into an expression vector under the CMV promoter flanked by 3' and 5' piggyBac specific terminal repeat sequences facilitating stable integration into the cell genome (see: "A hyperactive piggyBac transposase for mammalian applications"; Yusa K., et al., Proc. Natl. Acad. Sci. USA., 108(4): 1531-6, 2011 Jan. 25). Furthermore, the expression vector for each subunit contained a different selection cassette to facilitate stable cell line generation. The $\beta$ subunit was selected using puromycin (Sigma) and the $\alpha$ subunit using geneticin (Gibco). The a subunit was transfected into cells already expressing the $\beta$ subunit.

The expression plasmids were co-transfected with a plasmid encoding piggyBac transposase into the TF1 cell line by electroporation using the Lonza 4-D nucleofector transfection X kit system according to manufacturer instructions. 24 hours after transfection, complete media was supplemented with the appropriate selection and cells grown for at least 3 weeks to select a stable line, with media being exchanged every 3 to 4 days. The expression of the recombinant human subunits was assessed by flow cytometry using anti-human CD122 (IL-2R$\beta$) APC conjugated antibody (eBioscience) and anti-human CD25 (IL-2R$\alpha$) PE conjugated antibody (eBioscience). Endogenous common $\gamma$ chain expression was confirmed with anti-human CD132 (common $\gamma$ chain) PE conjugated antibody (eBioscience). As expression was low, CD122$^+$ cells were sorted by fluorescence activated cell sorting (FACS) and further cultured under selection. There was uniform expression of a chain after transfection, and therefore these cells were not sorted.

Complete TF1 media was made up of RPMI medium 1640 (Gibco) plus GM-CSF (2 ng/mL) and supplemented with 10% v/v heat inactivated fetal bovine serum (hiFBS, Gibco). Once responsiveness to IL-2 was confirmed, transfected cell lines were maintained in RPMI 1640, 10% hiFBS and 5 ng/mL recombinant human IL-2 with ($\alpha\beta$) or without ($\beta$) geneticin.

Figure 12A:
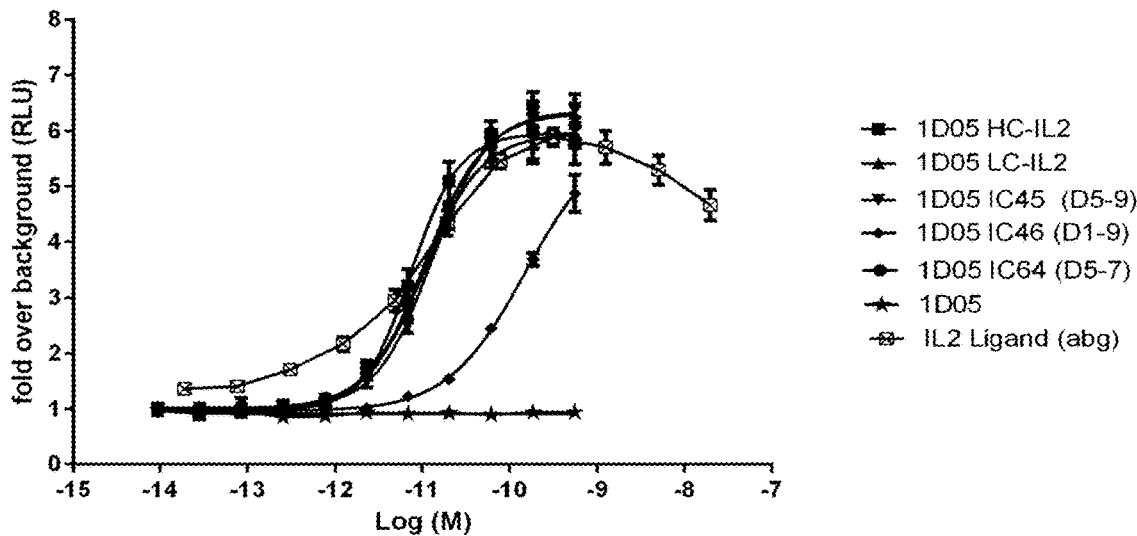
FIG. 12(a): Ability of immunocytokine constructs to induce proliferation in IL-2Rβγ expressing TF-1 cells, compared with equimolar concentrations of free IL-2. Data shown is from a single experiment, representative of three experiments
Figure 12A:
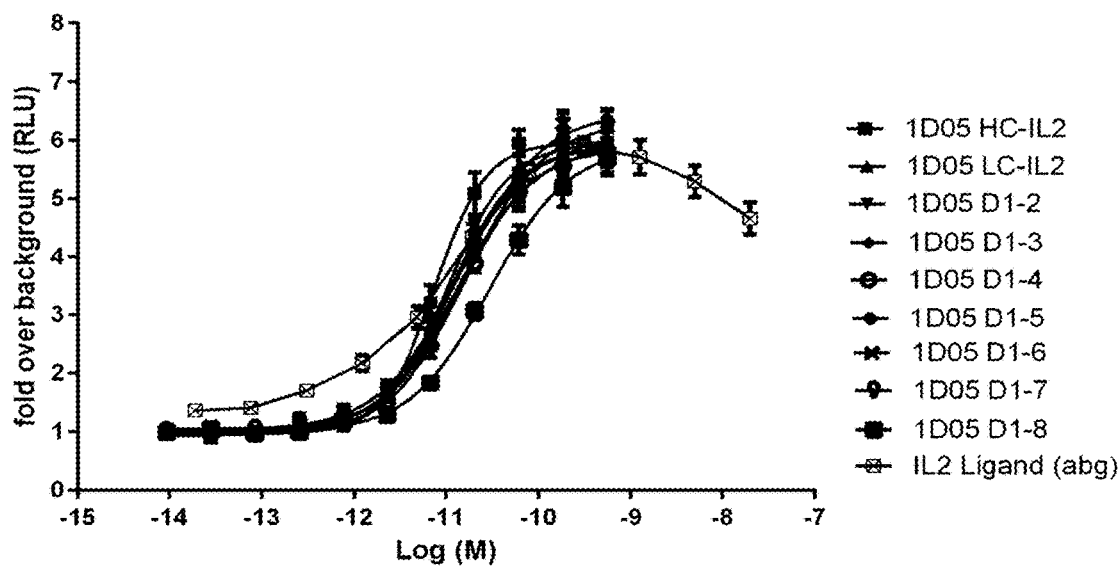
Figure 12A:
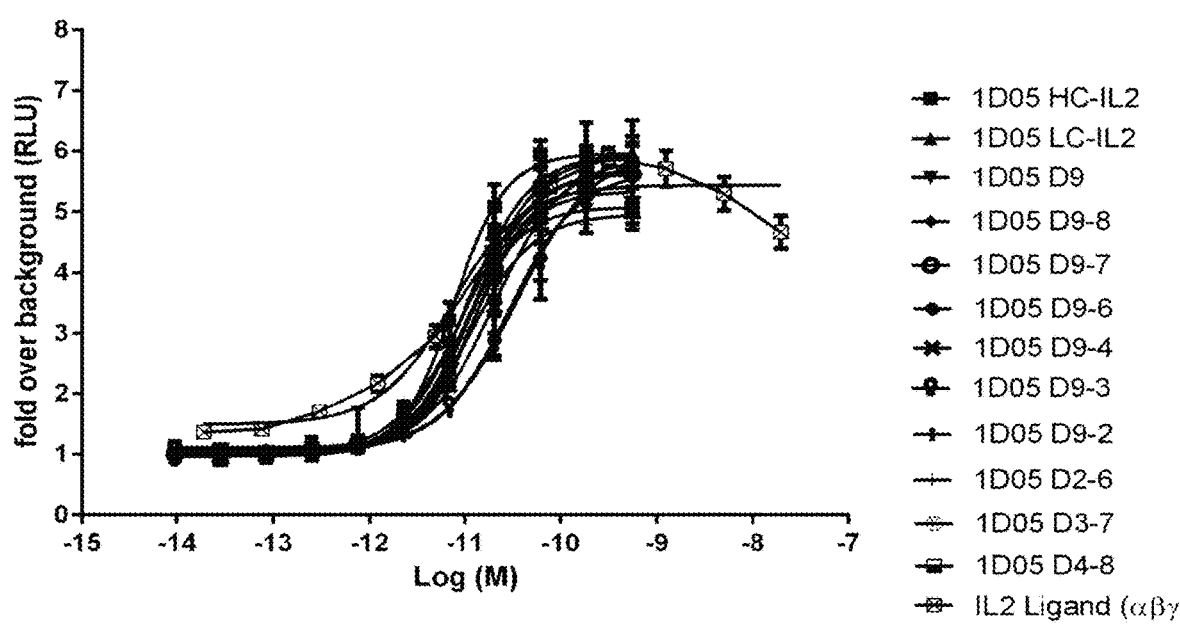
Figure 12B:
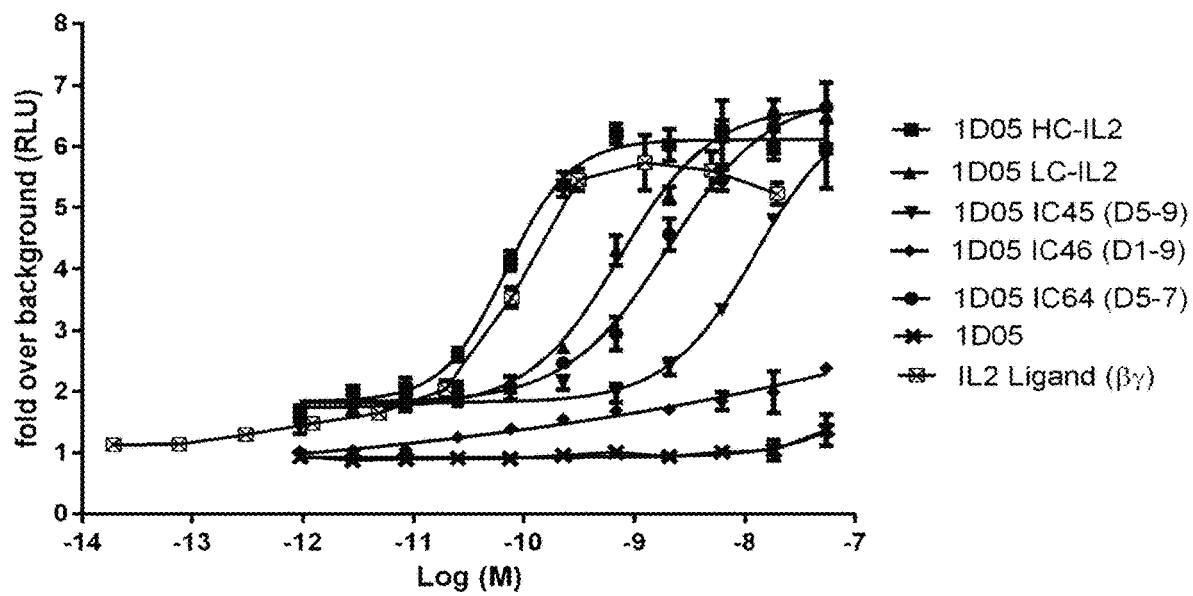
FIG. 12(b): Ability of immunocytokine constructs to induce proliferation in IL-2Rβγ expressing TF-1 cells, compared with equimolar concentrations of free IL-2. Data shown is from a single experiment, representative of four experiments
Figure 12B:
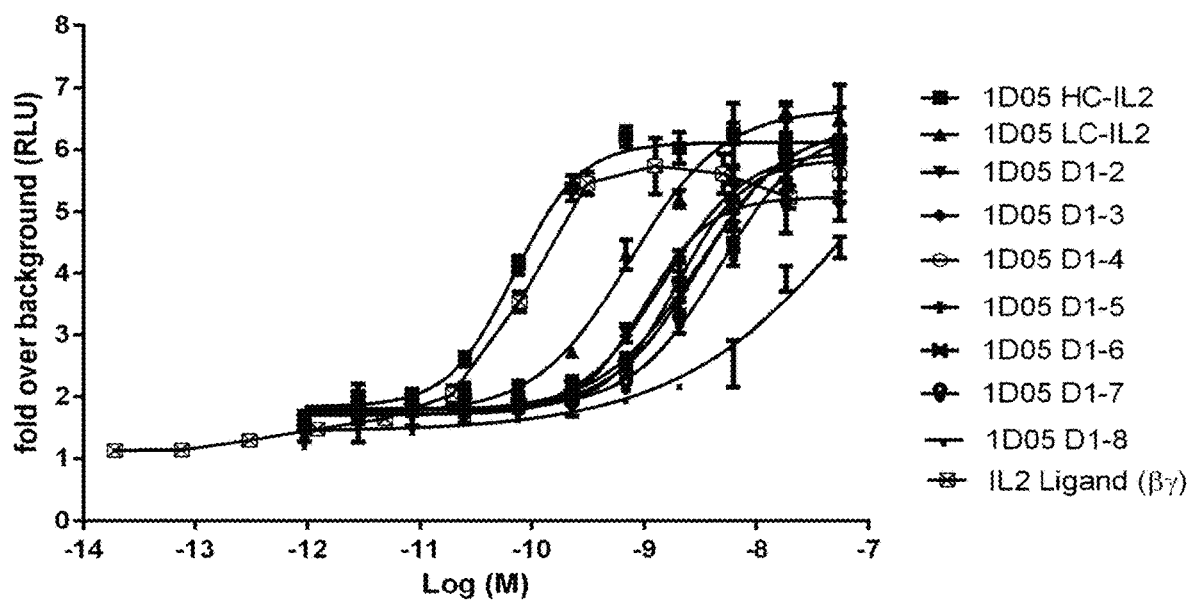
Figure 12B:
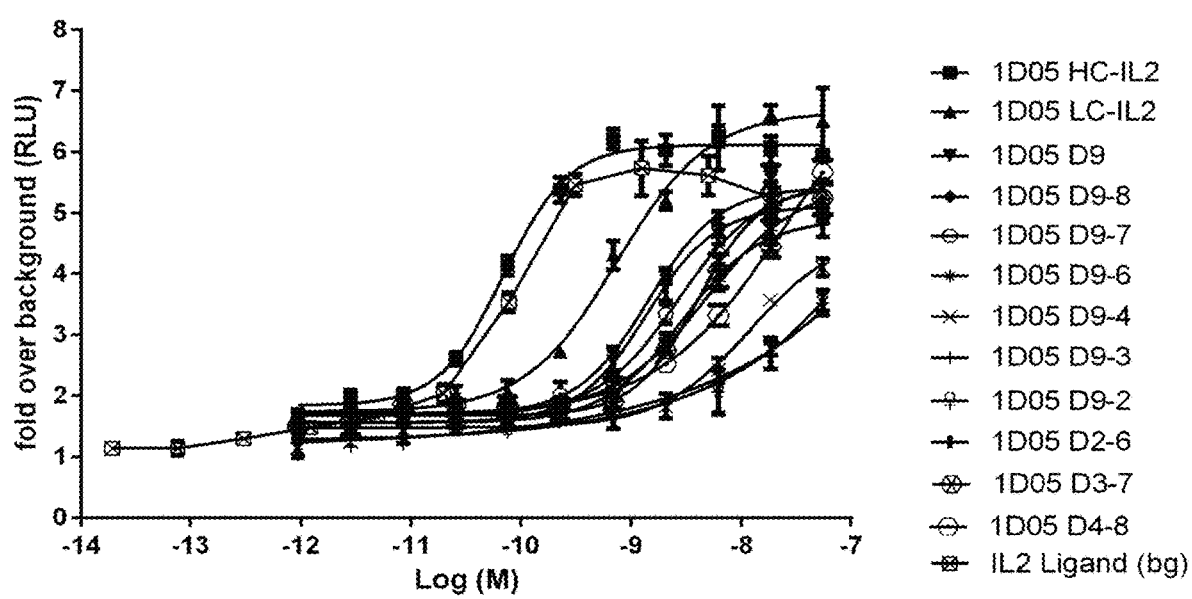

Example 13—Assessing Ability of Immunocytokine Constructs to Signal Through IL-2R Immunocytokines were assessed for their ability to induce proliferation of TF1 cell lines transfected with the $\beta$ subunit, or with both the $\alpha$ and $\beta$ subunits of IL-2R. Cells were starved of cytokines overnight, then stimulated with titrations of each immunocytokine. CellTiter-Glow® was used to determine the number of viable cells in culture after 3 days, based on quantitation of the ATP present. There was a broad range of activities of the immunocytokines on IL-2R$\beta\gamma$, with the largest IL-2 deletions having the greatest reduction on proliferation, compared with equimolar amounts of free IL-2. The effect on $\alpha\beta\gamma$ activity is not as pronounced, but again the greatest reduction in proliferation is seen with the largest IL-2 deletions. Deletions in the first few N-terminal amino acids of IL-2 allow for fine tuning of cytokine activity. A representative experiment is shown in FIGS. 12(a) and (b).

Materials and Methods

IL-2R transfected TF1 cells were routinely cultured in RPMI+10% fetal bovine serum (culture medium) with the addition of IL-2 (Peprotech) at 5 ng/mL for the $\beta$ transfected cell line and IL-2 at 5 ng/mL and Geneticin (Gibco) at 350 µg/mL for the $\alpha\beta$ transfected cell line. Prior to testing of immunocytokine constructs, the cells were harvested by centrifugation and aspirated to remove the supernatant. The cells were washed in PBS to remove cytokines and antibiotics. Cells were resuspended in fresh culture medium at $10^5$ cells/mL, without supplements and returned to the incubator overnight.

The cells were harvested by centrifugation and aspirated to remove the supernatant. Cells were resuspended in complete medium and 30 µL of cell solution was added to the plate (white walled tissue culture treated 384-well plate) wells to achieve an initial cell concentration of 1250 cells/well.

The IL-2 ligand was prepared as serial four-fold dilutions from 300 ng/mL final assay concentration (FAC) (600 ng/mL working) in culture media. The immunocytokine constructs were titrated from 0.1 µg/mL (three-fold dilutions) for testing on the $\alpha\beta\gamma$ cell line and 10 µg/mL (three-fold dilutions) for the $\beta\gamma$ cell line. 30 µL of titrations were added to the cell plate. To control wells, 30 µL of culture media without IL-2 was added. To reduce evaporation effects, the outermost rows/columns of the plate were filled with 80 µL of culture media. The plates were then incubated for 3 days at 37° C., 5% $CO_2$. Following the culture period proliferation of TF-1 cells was assessed by addition of 30 µL of Cell Titre Glo (Promega) to all wells. The plate was incubated at room temperature for 10 minutes then read using ultrasensitive luminescence filter.

Calculation of fold over background from TF-1 proliferation assay $$\text{fold over background} = \frac{\text{sample } RLU}{\text{mean over background } RLU} \quad \text{Equation 7}$$

$RLU$ = relative luminescence units

Data expressed as fold over background. Background was defined as wells containing cells but no cytokine Example 14—Binding of Immunocytokines to PD-L1

Surface plasmon resonance was used to confirm the ability of the immunocytokine constructs to bind PD-L1. The presence of the IL-2 on the light chain does not have any detrimental effect on binding (Table 9). Four constructs with a range of IL-2 activities were shortlisted for further characterisation—these were 1D05 D1-9 ICK, 1D05 D1-8 ICK, 1D05 D9-2 ICK and 1D05 D9-7 ICK.

TABLE 9

Affinity of 1D05 binding to PD-L1 is unaffected by the fusion of IL-2 to the antibody, as measured by surface plasmon resonance. Data shown is from a single experiment

| Sample Name | KD (nM) |
| --- | --- |
| 1D05 | 0.171 |
| 1D05 HC-IL2 | 0.240 |
| 1D05 LC-IL2 | 0.207 |
| 1D05 IC45 (D5-9) | 0.203 |
| 1D05 IC46 (D1-9) | 0.195 |
| 1D05 IC64 (D5-7) | 0.214 |
| 1D05 D1-2 | 0.187 |
| 1D05 D1-3 | 0.199 |
| 1D05 D1-4 | 0.186 |
| 1D05 D1-5 | 0.203 |
| 1D05 D1-6 | 0.211 |
| 1D05 D1-7 | 0.178 |
| 1D05 D1-8 | 0.190 |
| 1D05 D9 | 0.205 |
| 1D05 D9-8 | 0.225 |
| 1D05 D9-7 | 0.200 |
| 1D05 D9-6 | 0.211 |
| 1D05 D9-4 | 0.175 |
| 1D05 D9-3 | 0.171 |
| 1D05 D9-2 | 0.189 |
| 1D05 D2-6 | 0.201 |
| 1D05 D3-7 | 0.203 |
| 1D05 D4-8 | 0.208 |
| benchmark | 0.099 |

Materials and Methods

Analysis of Immunocytokines by Surface Plasmon Resonance

Label-free surface plasmon resonance (SPR) analysis was carried out on the ProteOn XPR36 (BioRad) array SPR machine. An anti-human IgG capture surface was created on a GLC biosensor chip using amine coupling of an anti-human IgG from GE Healthcare. Test antibodies were captured on this surface and human PD-L1 (in-house) was used as the analyte at 64 nM, 16 nM, 4 nM, 1 nM and 0.25 nM. The assay was carried out at 25° C. using HBS-EP (Teknova H8022). Buffer alone was used to reference the binding sensorgrams. The data was analysed using the 1:1 model inherent to the ProteOn XPR36 analysis software.

Example 15—Assessing Capacity of Immunocytokines to Neutralise the Interaction of PD-L1 and PD-1/CD80

Figure 13A:
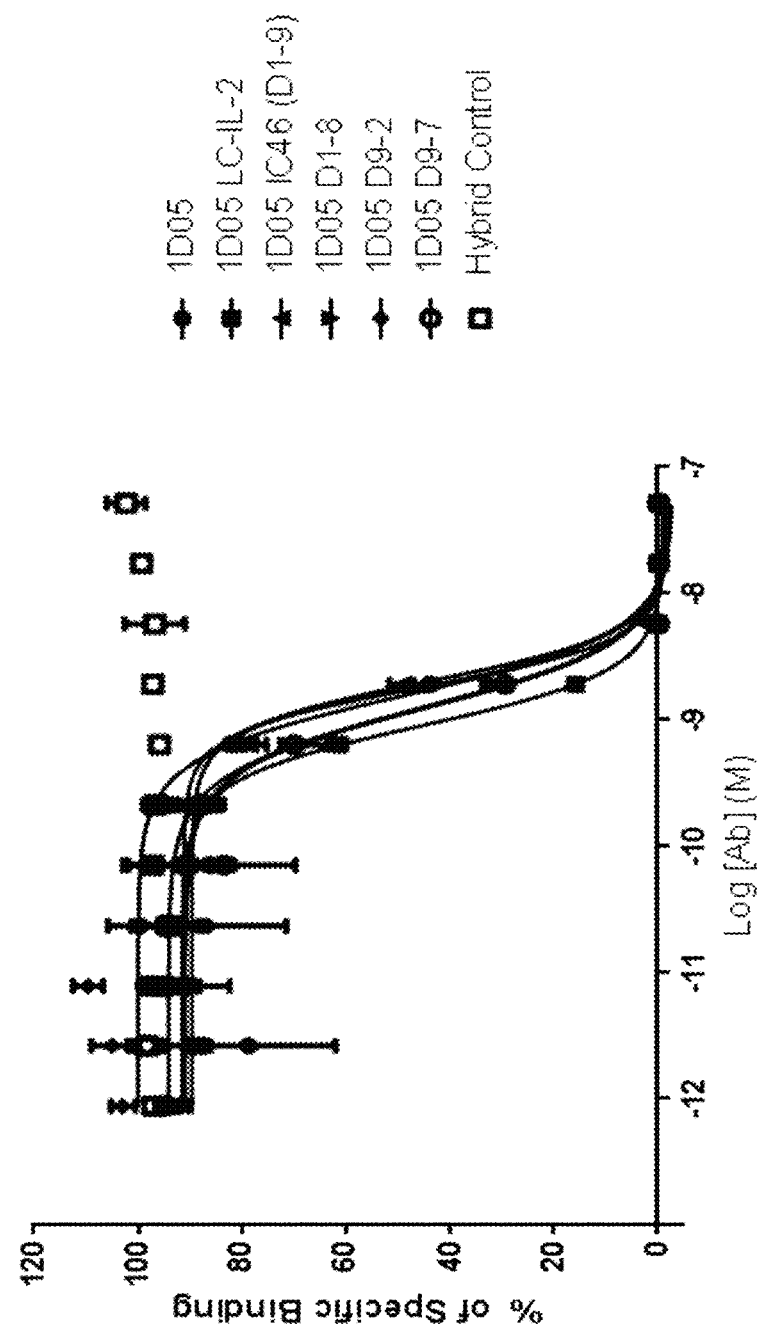
FIG. 13(a): Capacity of 1D05 antibody to neutralise the interaction between PD-1 and PD-L1 is unaffected by the fusion of IL-2 to the antibody, as measured in a neutralisation ELISA. Data shown is from a single experiment, representative of three experiments
Figure 13B:
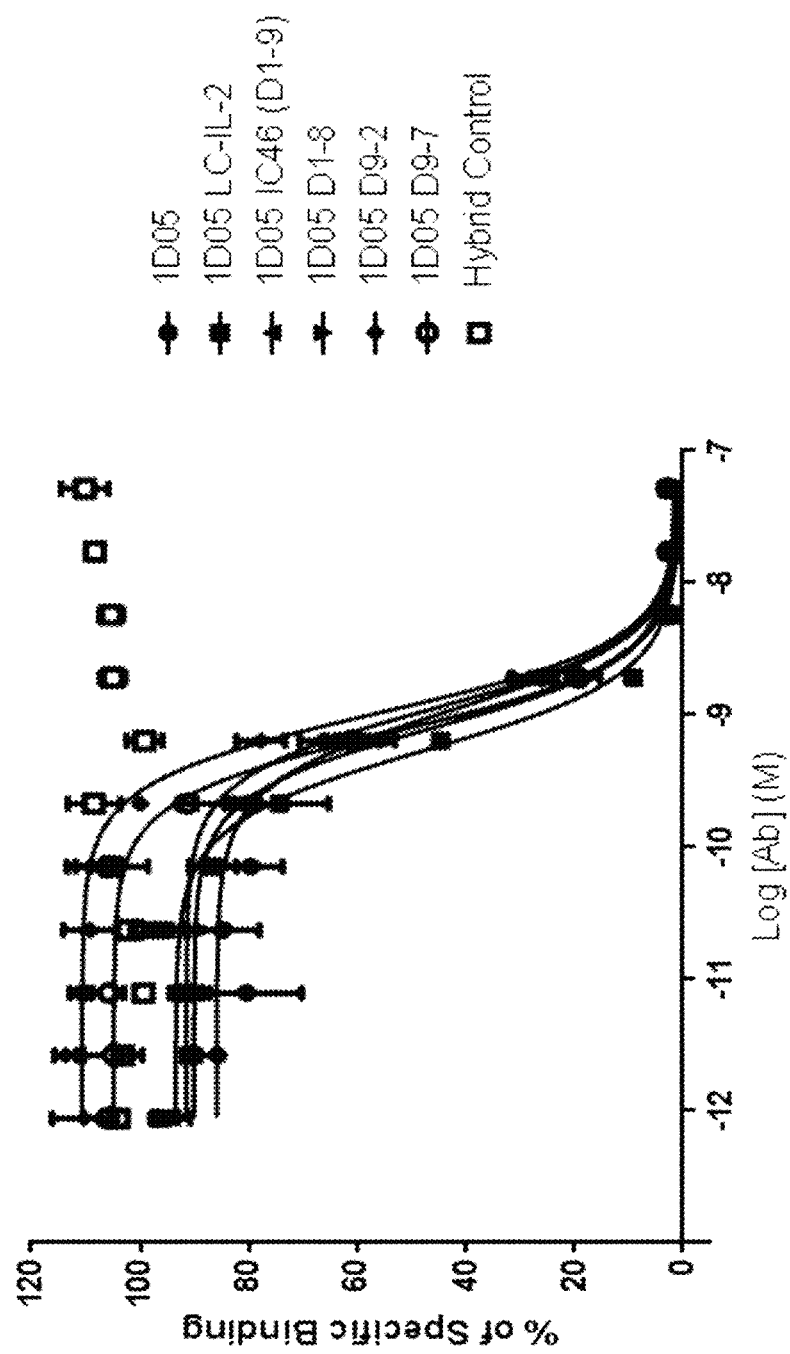
FIG. 13(b): Capacity of 1D05 antibody to neutralise the interaction between CD80 and PD-L1 is unaffected by the fusion of IL-2 to the antibody, as measured in a neutralisation ELISA. Data shown is from a single experiment, representative of three experiments

To ensure that fusion of the IL-2 molecule to the antibody did not disrupt its neutralisation capacity, shortlisted immunocytokines were tested in a neutralisation ELISA. The shortlisted immunocytokines tested did not differ from wild type antibody in their ability to neutralise interactions between PD-L1 and PD-1, and PD-L1 and CD80. Results are shown in FIG. 13 and Table 10. Values in the table are the means of three independent experiments.

TABLE 10

Summary of neutralisation ELISA data, expressed as mean of three independent experiments

| Clone | PD1-PD-L1 Neutralisation IC$_{50}$ (nM) | CD80-PD-L1 Neutralisation IC$_{50}$ (nM) |
| --- | --- | --- |
| 1D05 | 1.41 | 0.882 |
| 1D05 LC-IL-2 | 0.833 | 0.505 |
| 1D05 IC46 (D1-9) | 1.75 | 1.07 |
| 1D05 D1-8 | 1.16 | 0.745 |
| 1D05 D9-2 | 1.55 | 0.947 |
| 1D05 D9-7 | 1.15 | 0.70 |
| Hybrid Control | N/A | N/A |

Materials and Methods a) PD-L1/PD-1 or PD-L1/CD80 Neutralisation ELISA

CD80 (R&D Systems) or PD-1 (in house) diluted to 2.5 µg/mL were adsorbed to 96-well, low auto-fluorescent, high protein binding plates (Costar) overnight at 4° C. Excess protein was removed by washing with PBS-Tween (0.1% v/v) and the wells were blocked with 1% w/v bovine serum albumin (BSA, Sigma) in PBS for 1 hour at room temperature, after which plates were washed as described previously. 60 µL of a titration (three-fold dilutions from 100 nM) of antibody was added to a 96-well, non-binding plate diluted in ELISA assay buffer (PBS+0.1% BSA). 60 µL of biotinylated PD-L1 (in house, labelled with Lightning Link Biotinylation kit) at 16 nM working concentration (8 nM FAC) was added to the plate excluding control wells where 60 µL ELISA assay buffer was added. The plate was incubated for 30 min before transferring 50 µL to the coated plates.

The coated plates were incubated for 1 hour at room temperature. Excess protein was removed by washing with PBS-Tween (0.1% v/v). PD-L1 binding was detected using streptavidin labelled Europium (Perkin Elmer) diluted 1/1000 in DELFIA assay buffer (Perkin Elmer). The plates were washed with TBS (Tris buffered saline)-Tween (0.1% v/v) and 50 µL/well of DELFIA Enhancement solution (Perkin Elmer) was added to the plate. The time-resolved fluorescence was measured at 615 nm on an Envision plate reader (PerkinElmer). Percentage specific binding was calculated as defined in Equation 3.

IC$_{50}$ values were determined using Graph Pad Prism software by curve fitting using a four-parameter logistic equation (Equation 4) from the percentage specific binding (Equation 3).

Example 16—De-Immunisation of Anti-PD-L1 Antibody

To reduce the possibility of adverse immunological reactions based around the anti-PD-L1-immunocytokine, a series of 1D05 antibody mutants (Seq ID Nos:47 to 51) was created with anticipated lower potential of immunogenicity, as determined by T-cell epitope analysis software. The mutations can be single or in combination. Mutants were assessed for their ability to bind PD-L1 with the same affinity as the wild-type molecule by SPR as described in Example 14, with the addition of human PD-L1 analyte at 256 nM. Mutations under investigation are included as Seq ID Nos:47 to 51, indicated by underlined and bold text. The V$_H$ framework mutations (Seq ID Nos:47 and 48) do not have any detrimental effects on binding. The V to A mutation in CDRH2 (Seq ID No:50) was detrimental to binding, and so an alternative mutation will be analysed (V to Y, Seq ID No:298). Results are shown in Table 11.

Example 17—Inhibition of Tumour Growth by an Anti-PD-L1 Antibody in NOD/SCID: Xenograft T-Cell Model Inhibition of melanoma tumour growth by lead antibody 1D05 in the hIgG1 LAGA (Seq ID No: 205) format was demonstrated in a NOD/SCID:xenograft T-cell model. T-cells were expanded in the presence of A375, a melanoma cell line, for 20 days in the presence of IL-2 and IL-7. T-cells were co-implanted subcutaneously with fresh A375 cells, then the antibody administered intraperitoneally after 1 hour. Tumour size and animal survival were monitored. Tumours in mice treated with antibody 1D05 were smaller than in animals treated with isotype control. Survival time in 1D05-treated mice was also increased.

Materials and Methods

Efficacy studies were performed using a T-cell/Xenograft model in NOD/SCID mice employing a refinement of the methods outlined in Stewart R et al. (Cancer Immunol. Res., 2015 September; 3(9):1052-62). Leukoreduction system chambers were obtained from NHSBT. HLA-A2 positive donors were selected by staining unfractionated blood using a PE-labelled anti-human HLA-A2 (Biolegend, Clone:

TABLE 11

Deimmunisation mutations to lead 1D05 antibody

| Heavy Chain | Light Chain | KD (nM) |
|---|---|---|
| 1D05 - IgG1 disabled (LAGA) Seq ID No: 299 | 1D05 kappa (Seq ID No: 45) | 0.29 |
| 1D05 V to A change in $V_H$ (Seq ID No: 47), IgG1 disabled (LAGA, Seq ID No: 205) | 1D05 kappa (Seq ID No: 45) | 0.33 |
| 1D05 F to S change in $V_H$ (Seq ID No: 48), IgG1 disabled (LAGA, Seq ID No: 205) | 1D05 kappa (Seq ID No: 45) | 0.23 |
| 1D05 V to A & F to S change in $V_H$ (Seq ID No: 342), IgG1 disabled (LAGA, Seq ID No: 205) | 1D05 kappa (Seq ID No: 45) | 0.23 |
| 1D05 - IgG1 disabled (LAGA) Seq ID No: 299 | 1D05 kappa, V to A change (Seq ID No: 50) | 2.66 |
| 1D05 V to A change in $V_H$ (Seq ID No: 47), IgG1 disabled (LAGA, Seq ID No: 205) | 1D05 kappa, V to A change (Seq ID No: 50) | 2.8 |
| 1D05 F to S change in $V_H$ (Seq ID No: 48), IgG1 disabled (LAGA, Seq ID No: 205) | 1D05 kappa, V to A change (Seq ID No: 50) | 1.94 |
| 1D05 V to A & F to S change in $V_H$ (Seq ID No: 342), IgG1 disabled (LAGA, Seq ID No: 205) | 1D05 kappa, V to A change (Seq ID No: 50) | 1.94 |

BB7.2), the red blood cells were then lysed, followed by fixation with 4% PFA, prior to acquisition on the Attune flow cytometer. PBMCs were isolated by density gradient centrifugation over Ficoll. Primary human CD4+ and CD8+ T-cells were then isolated using an EasySep human CD4+ and CD8+ T-cell enrichment kit (Stemcell Technologies, Cat 19052 and 19053). The CD4+ and CD8+ T-cells were then cultured separately for 20 days on a monolayer of mitomycin C treated A375 cells (at day 10, T-cells were re-plated on a fresh A375 monolayer) in the presence of recombinant human IL-2 and IL-7 (Peprotech). On day 20 the cells were frozen in 90% hiFBS/10% DMSO at −80° C. in a "Mr Frosty" (Nalgene) and stored in liquid nitrogen until required. The day before starting an in vivo experiment the cells were thawed and placed in culture.

On the day of implantation, the CD4+ and CD8+ T-cells were counted and mixed together in a 1:1 ratio. The CD4+/CD8+ mixture was then added to A375 tumour cells and injected subcutaneously into mice on the rear right flank. Treated groups received their first dose of antibody or isotype control (all dosed intraperitoneally at 10 mg/kg) one-hour post implantation of the cells. The animals received further doses 3, 6, 8 and 10 days post-implantation. Tumour development was monitored three times a week using digital calipers measuring in two dimensions until end of the study. Tumour volumes (mm³) were estimated using a standard formula (L×W²)/2 (with L being the larger diameter, and W the smaller diameter of the tumour). Mice were kept on studies until their tumours developed to a mean diameter of 12 mm or they reached one of the humane endpoints outlined in the study protocol. The humane endpoint survival statistics were calculated using the Kaplan-Meier method with Prism. This approach was used to determine if PD-L1 treatment was associated with improved survival.

TABLE 12

Treatment Groups

| Groups | Number of animals | Cell Line |
|---|---|---|
| 1 | 9 | 2 × 10⁶ A375 Cells |
| 2 | 9 | 1:6 ratio T-cells:A375 Cells (2 × 10⁶ A375 Cells) |
| 3 | 8 | 10 mg/kg isotype control hIgG1 1:6 ratio T-cells:A375 Cells (2 × 10⁶ A375 Cells) |
| 4 | 8 | 10 mg/kg anti-PD-L1 1D05 hIgG1 LAGA (Seq ID No: 205) 1:6 ratio T-cells:A375 Cells (2 × 10⁶ A375 Cells) |

Figure 14:
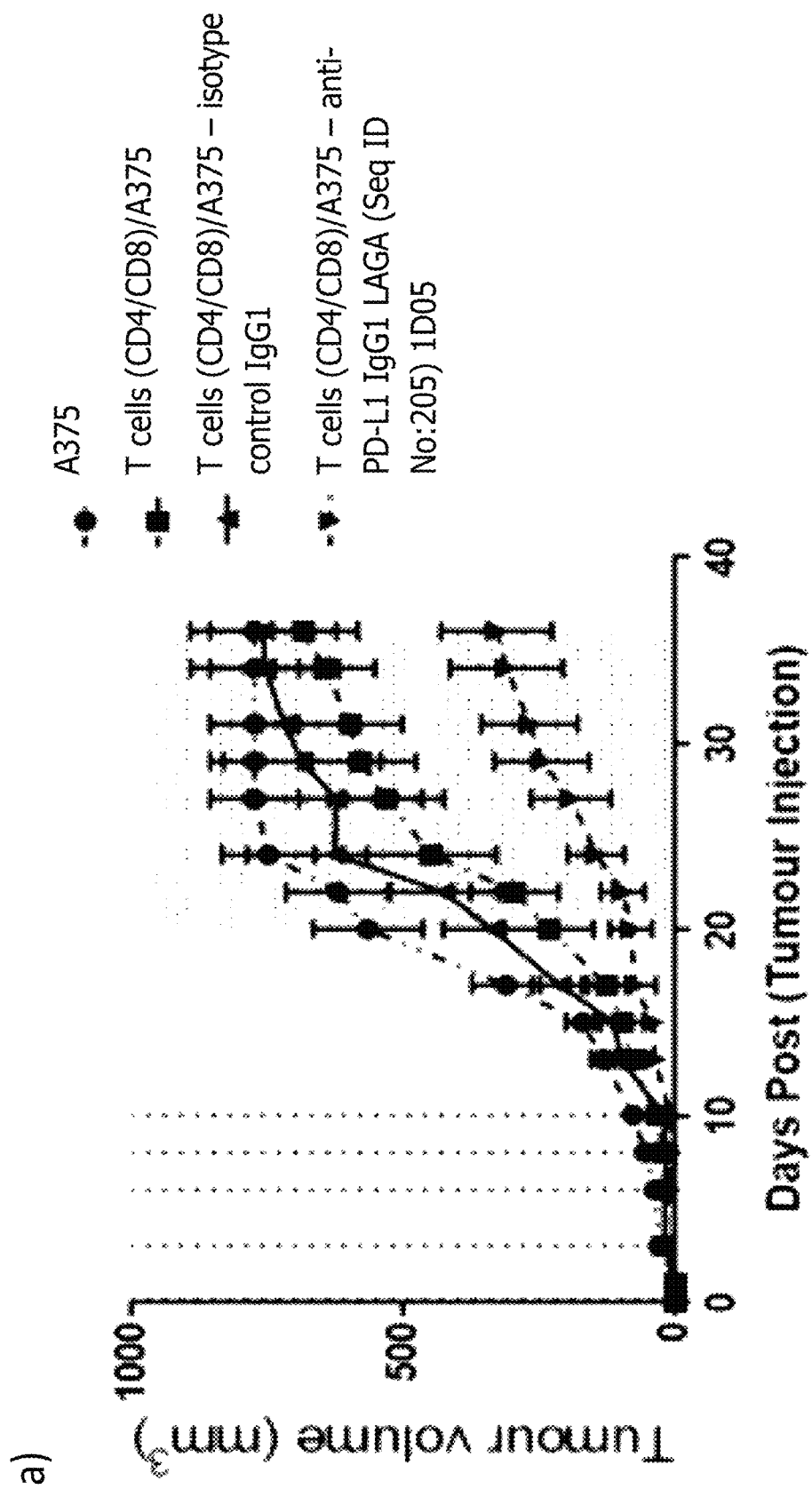
FIGS. 14(a)-14(e): Mean group and individual animal growth curves for the NOD/SCID: Xenograft in vivo efficacy study
Figure 14:
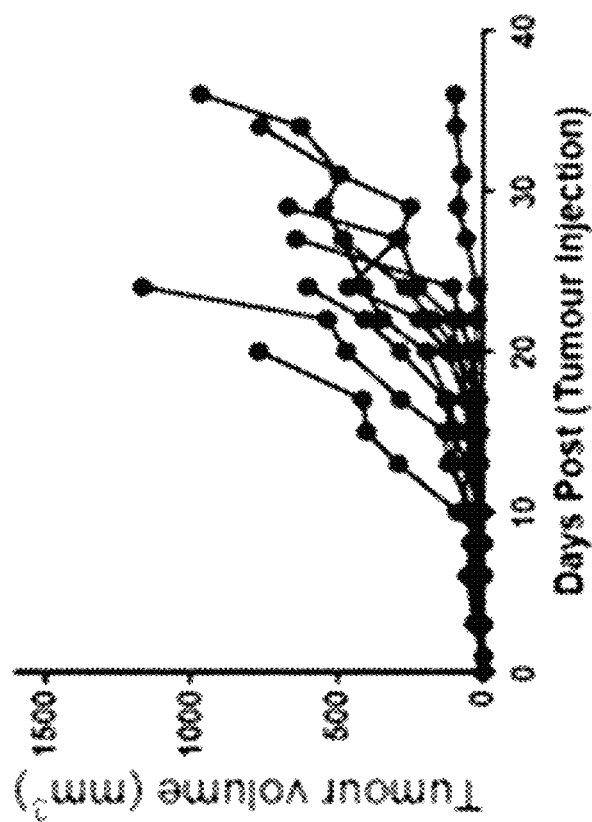
Figure 14:
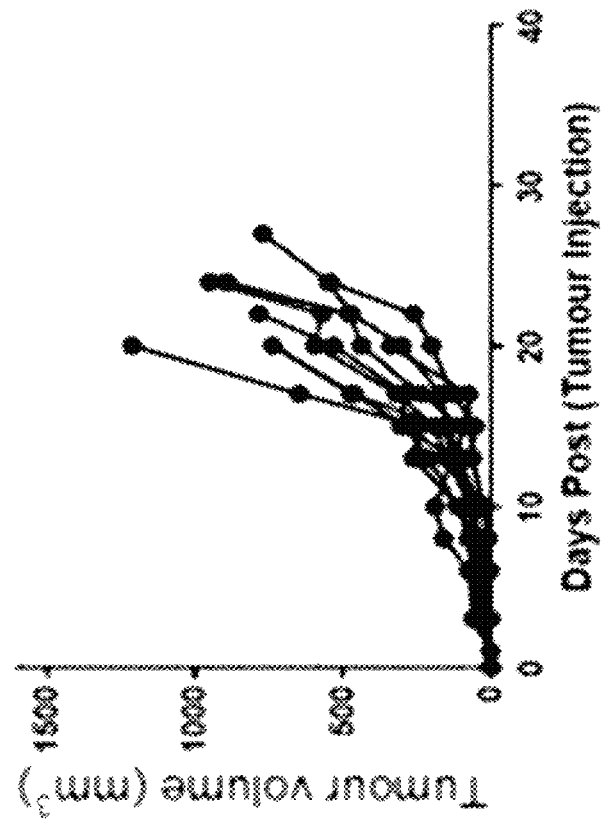
Figure 14:
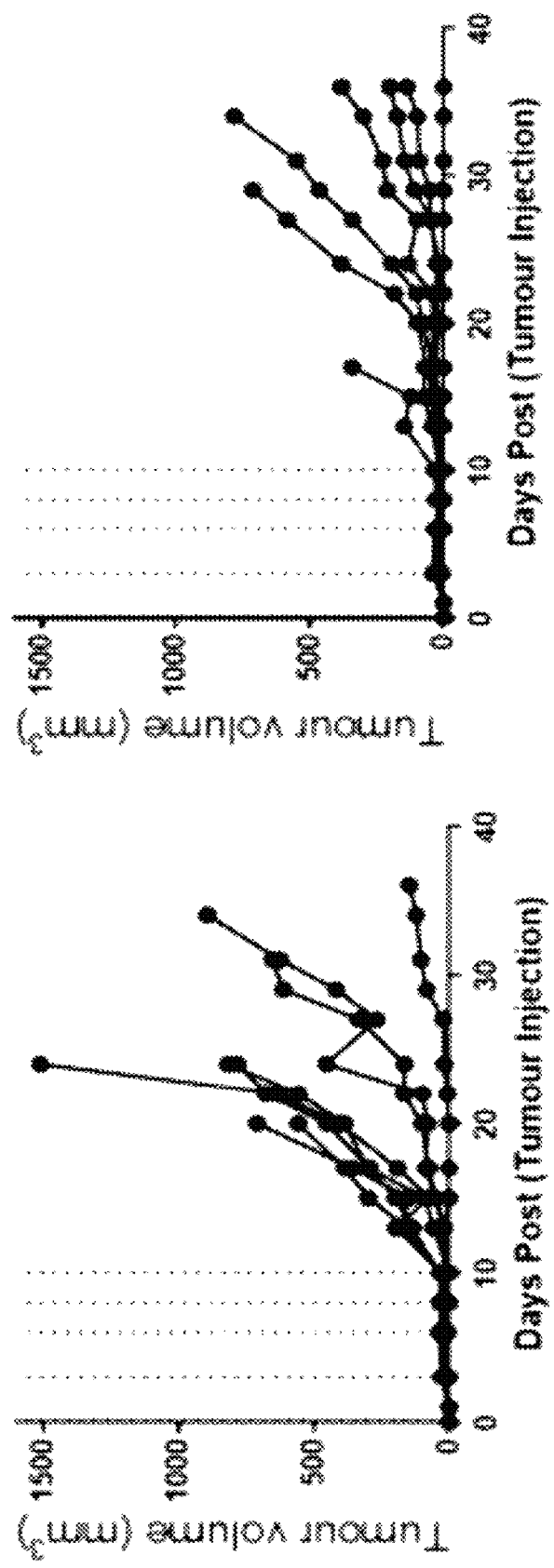

Treatment with the isotype control had no effect on tumour development when compared to the group where the CD4+/8+ T-cells are co-injected with the tumour cells. Whilst treatment with the anti-PDL1 antibody 1D05 delayed the tumour development when compared to the Isotype Control. This is shown in FIG. 14.

Figure 15:
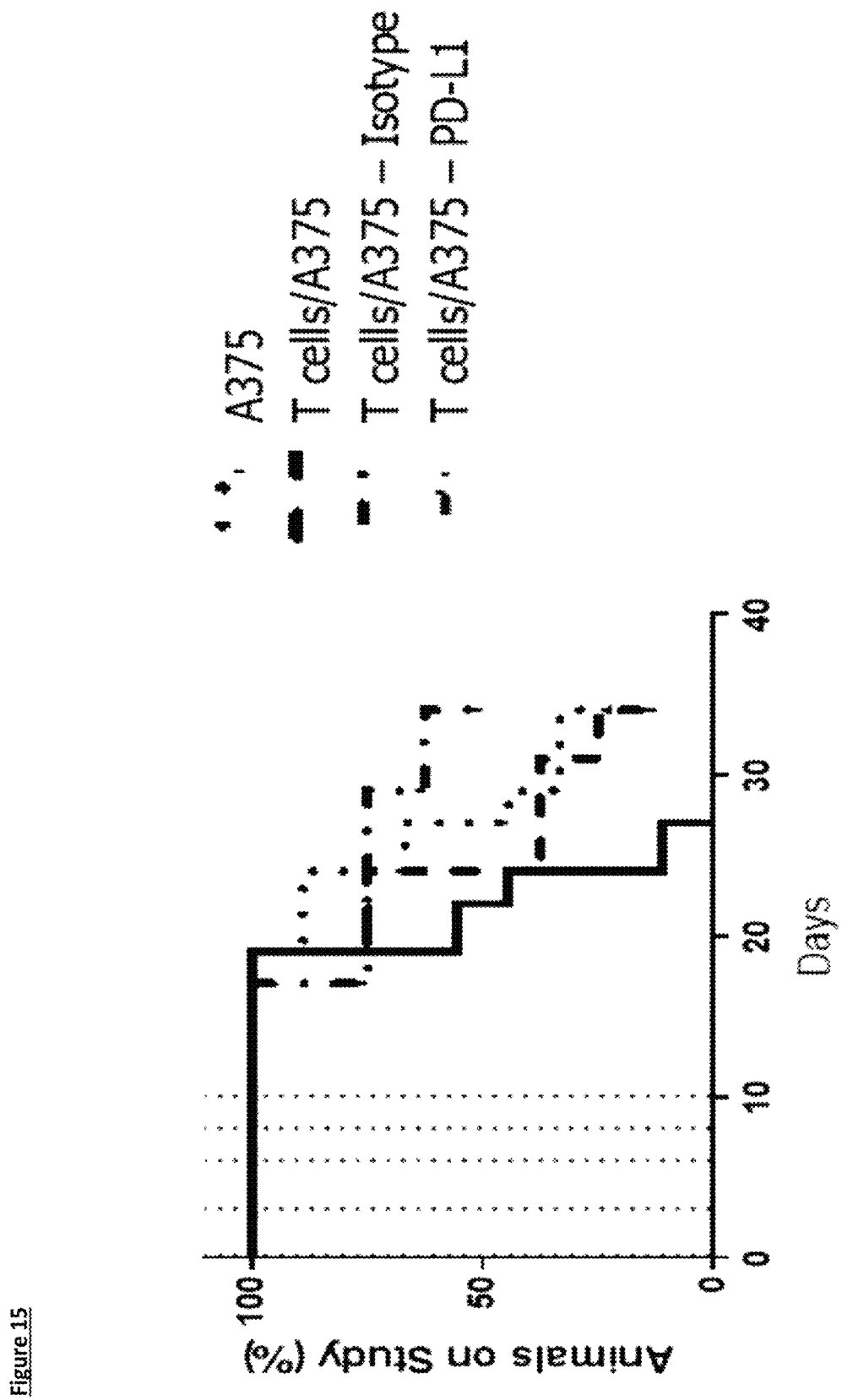
FIG. 15: Kaplan-Meier plot for the NOD/SCID:Xenograft in vivo efficacy study showing the number of animals still on study. This plot shows the slight increase in the time on study when $CD4^+/8^+$ T-cells are co-injected with the tumour cells (T-cells/A375) (n=9) when compared to the tumour cells alone A375 group (n=9). Treatment with the isotype control (T-cells/A375-Isotype (n=8)) had no effect on survival when compared to the T-cells co-injected with the tumour cells without antibody. Treatment with 10 mg/kg of the anti-PD-L1 antibody 1D05 (T-cells/A375-anti-PD-L1) (n=8)) significantly increased the time on study when compared to the isotype control group. Dosing was 1-hour post injection of the T-cells/tumour cells and on days 3, 6, 8 and 10, show on the graph by the dotted lines

All groups with T-cells co-injected with the tumours showed an increase in time on study when compared to the tumour alone group. Treatment with the isotype control had no effect on time on study, whilst treatment with the anti-PDL1 antibody 1D05 increased time on study when compared to all the other groups including the isotype control groups. Results are shown in FIG. 15.

Example 18: Single Dose Study of Immunocytokines in Cynomolgus Monkeys

To assess pharmacodynamic and pharmacokinetic (PK) parameters in the most relevant animal model, male cynomolgus monkeys received a single dose of immunocytokine (ICK) at 1 mg/kg. Animals were observed for clinical manifestations of toxicity, and blood samples were taken over the course of 7 days for the analysis of PK, production of cytokines and characterisation of leukocyte subsets. The in-life phase of the study, and haematology, flow cytometry and cytokine analysis was performed at Envigo UK (study number GF13YC). Pharmacokinetic analysis was performed in-house.

Materials and Methods

Male cynomolgus monkeys of at least 2 years of age were used for the study and body weights were recorded at 7 days and 4 days before the start of the study. Immunocytokine constructs were formulated in 50 mM sodium acetate pH 5.5, at 1 mg/mL and were diluted to 0.2 mg/mL in physiological saline for intravenous infusion at a rate of 5 mL/kg/hour. Blood pressure and body temperature were monitored pre-treatment, 1 hour and 4 hours post end-of-dose. Animals were observed twice daily for signs of ill-health. The study was performed in two phases—initial doses of 1D05 HC IL-2 ICK and 1D05 LC D9-7 ICK to ensure dose level and PK timepoints were suitable, then dosing of 1D05 LC D9-7 ICK was repeated, alongside four further constructs (see Table 1). Phase 2 dosing of 1D05 LC D9-7 ICK is indicated by a (2) next to the construct name.

TABLE 13

Treatment groups and animal numbers

| Phase | Animal | Test Item |
|---|---|---|
| 1 | 134 | 1D05 HC IL-2 ICK |
| 1 | 135 | 1D05 LC D9-7 ICK |
| 2 | 136 | 1D05 LC IL-2 ICK |
| 2 | 137 | 1D05 LC D9-7 ICK (2) |
| 2 | 138 | 1D05 LC D9-2 ICK |
| 2 | 139 | 1D05 LC D1-8 ICK |
| 2 | 140 | 1D05 LC D1-9 ICK |

Figure 16:
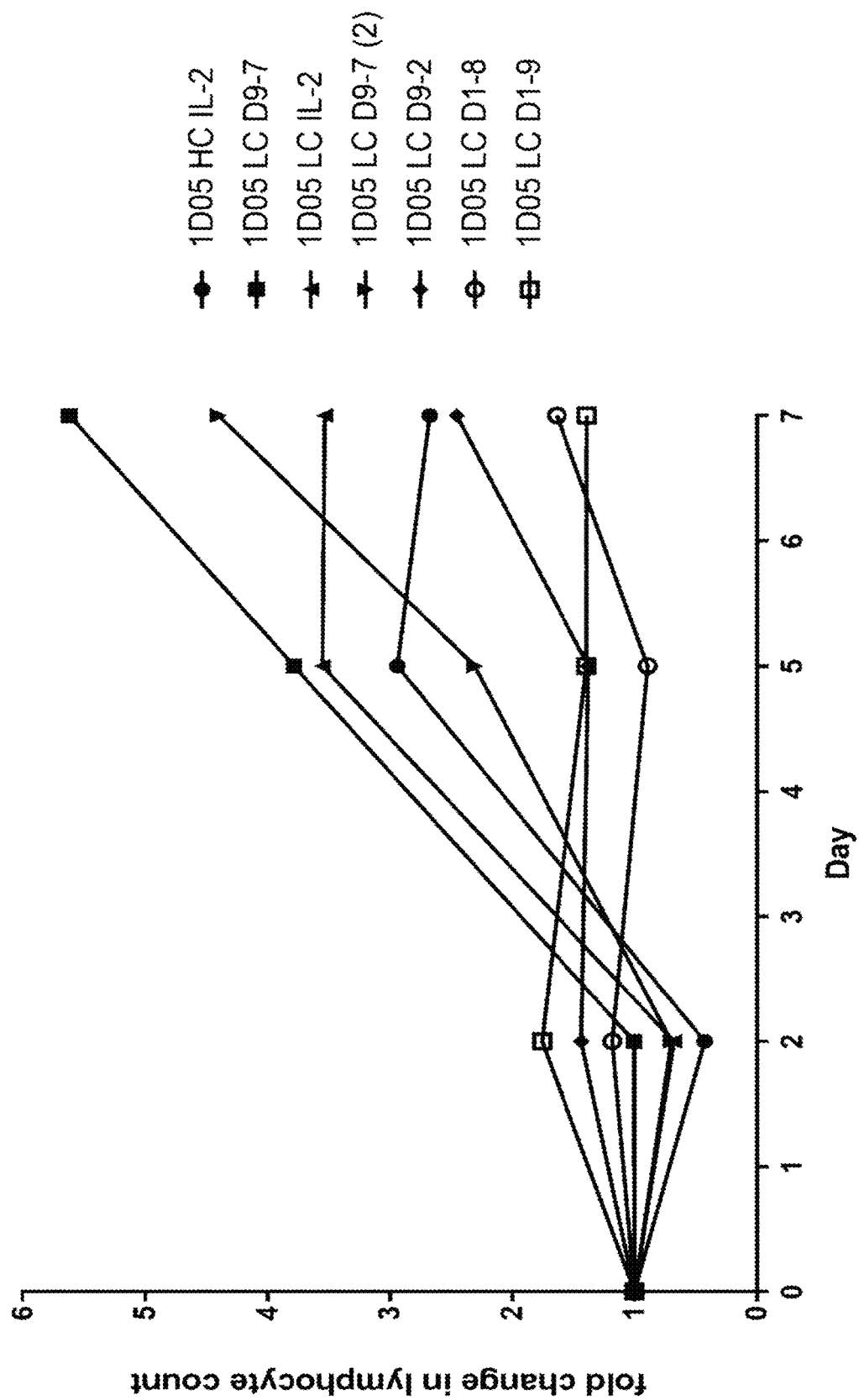
FIG. 16: Expansion of lymphocytes in response to dosing with immunocytokines. Fasting blood samples were taken into EDTA treated tubes pre-treatment (0), and 2, 5 and 7 days post-treatment. Cell counts were measured by the Bayer Advia 120. Results are expressed as fold change in lymphocyte count
Figure 17:
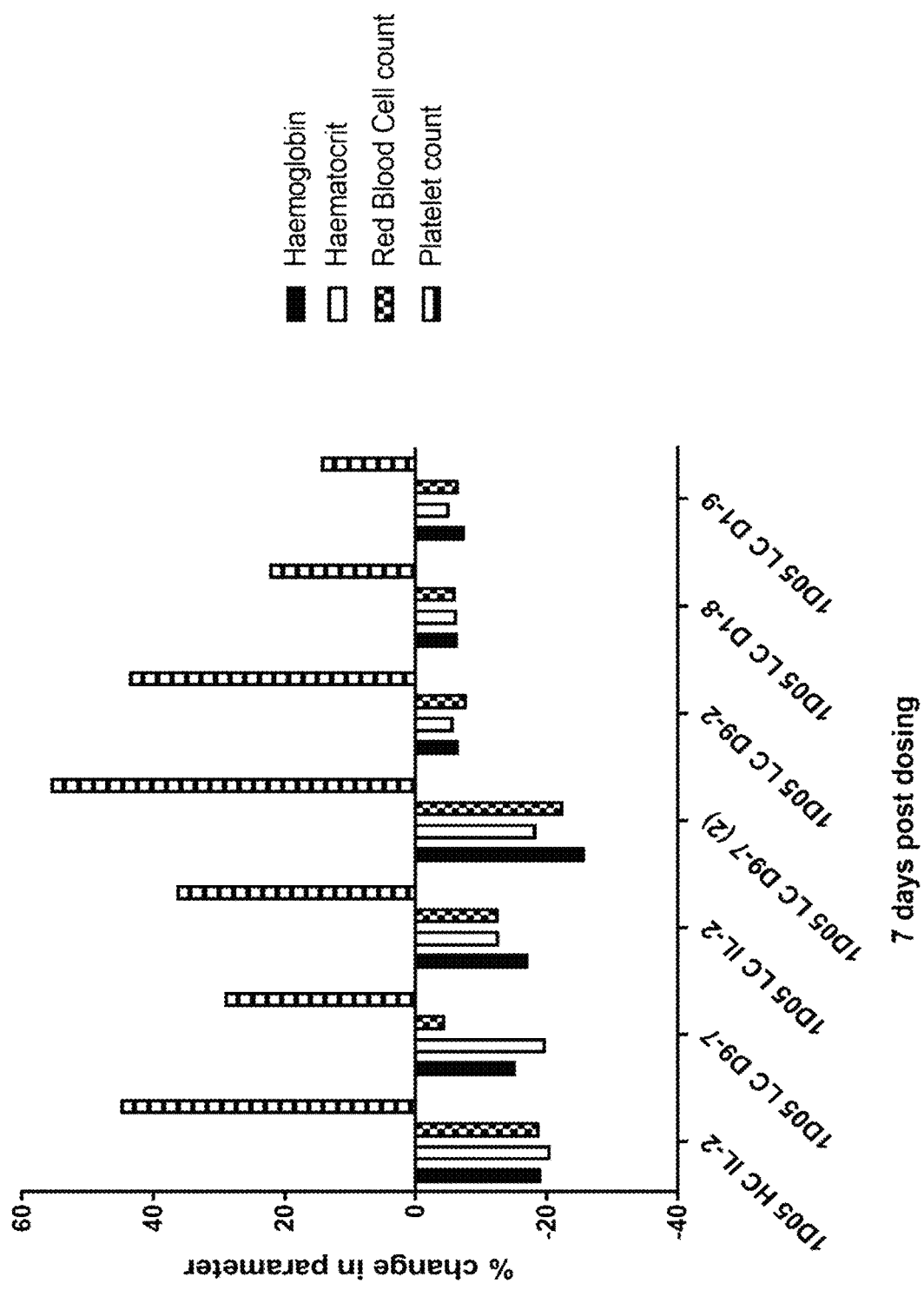
FIG. 17: Analysis of standard haematological parameters in response to dosing with immunocytokines. Fasting blood samples were taken into EDTA treated tubes pre-treatment and 7 days post-treatment. Analysis of haemoglobin, haematocrit, red blood cell counts and platelet counts were performed using the Bayer Advia 120. Results are expressed as the percentage change in parameter 7 days post-dosing

For haematological analysis, fasting blood samples were taken into EDTA treated tubes pre-treatment, and 2, 5 and 7 days post-treatment. Routine haematology parameters were measured by the Bayer Advia 120. Results are shown in FIGS. 16 and 17.

Figure 18:
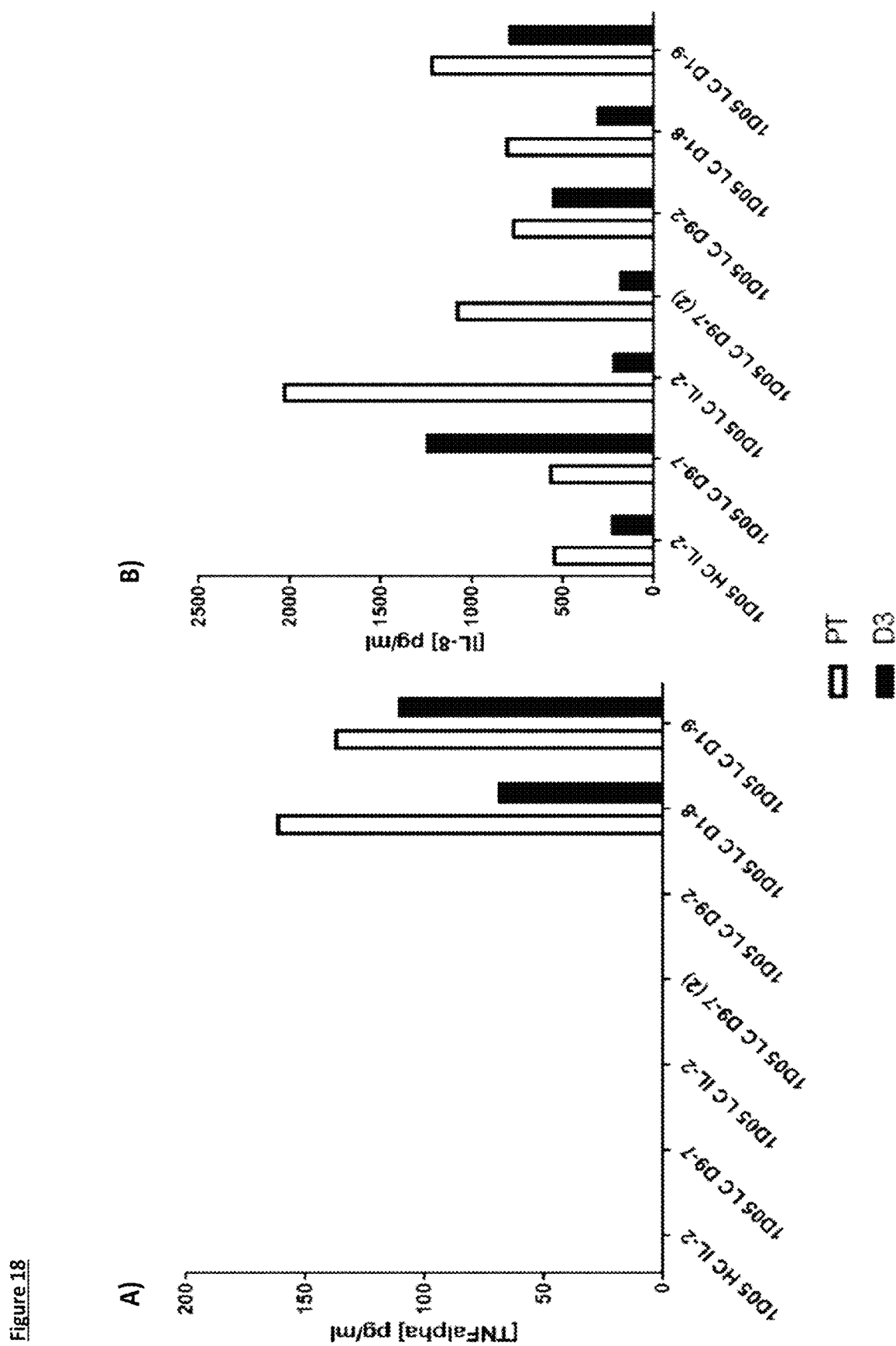
FIG. 18: Cytokine levels in plasma of cynomolgus monkeys dosed with immunocytokine molecules. Plasma samples were obtained pre-treatment (PT) and 3 days after dosing (D3) and analysed by MSD for levels of a) TNF-α; b) IL-8; c) IL-6; d) IFNγ; e) G-CSF and f) IL-2. Where no bar is included, cytokine levels were below the limit of quantification of the assay. IL4, IL-5 and IL-1β were not detectable in any sample at either timepoint and so are not included in the graphs
Figure 18:
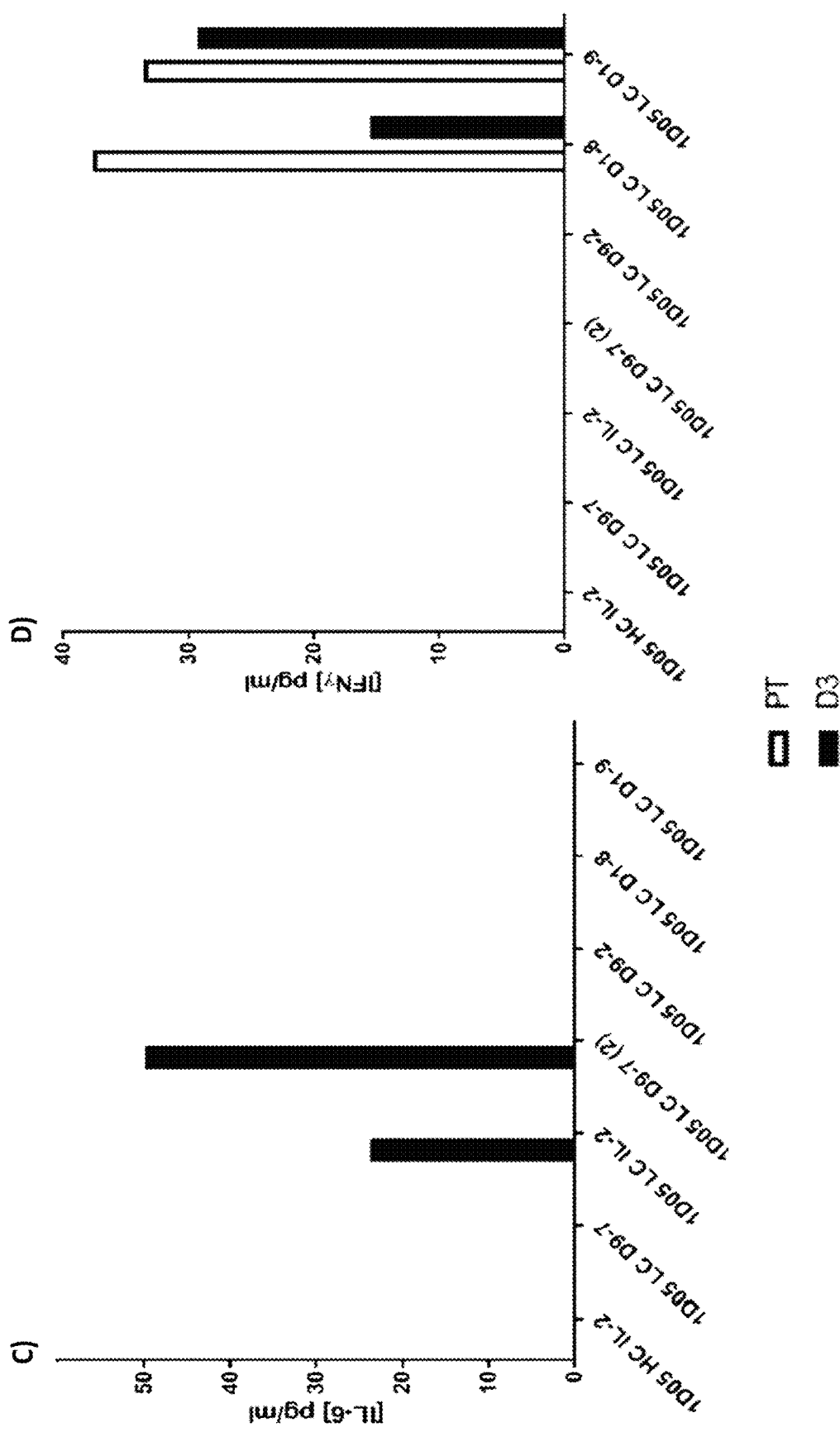
Figure 18:
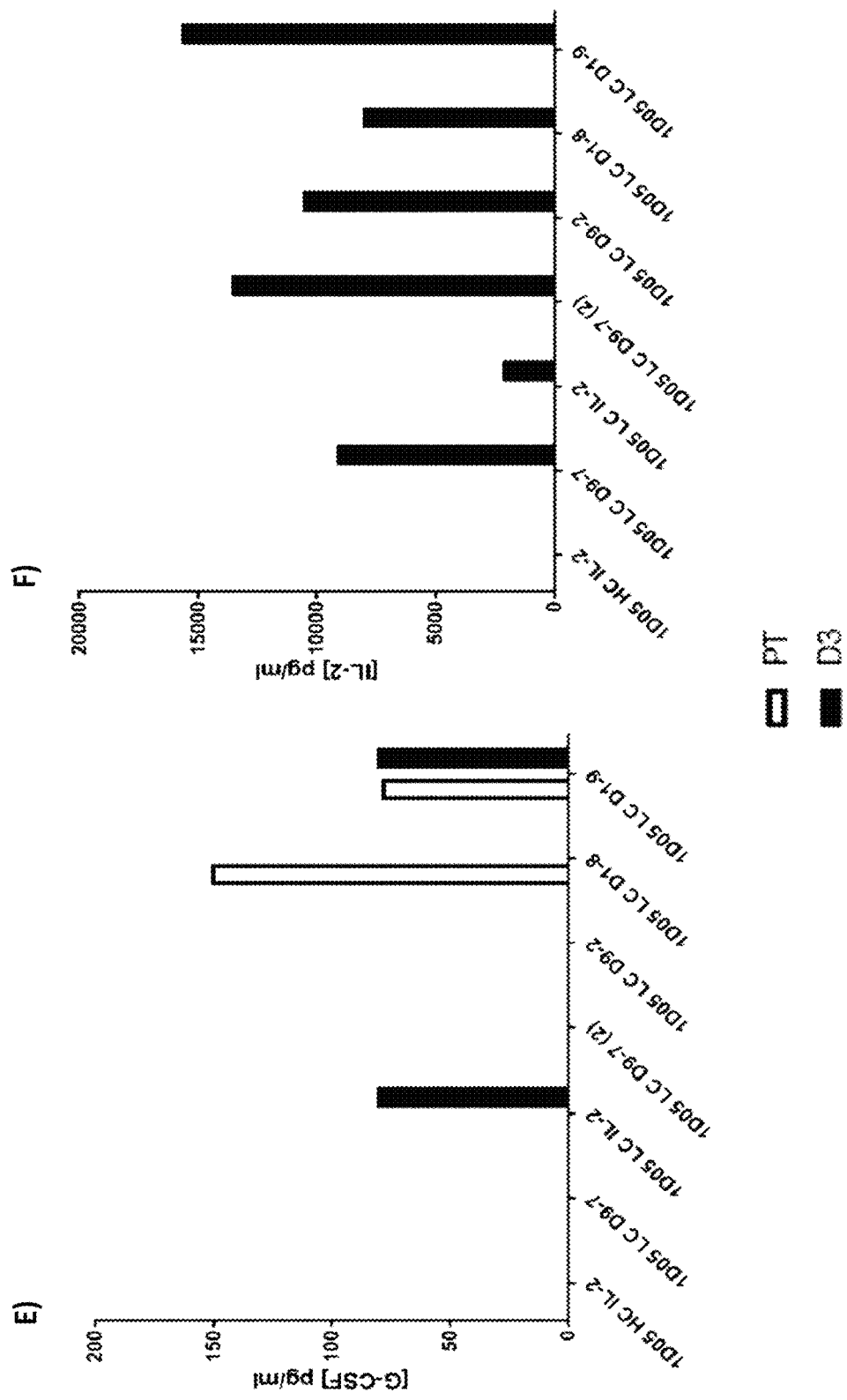
Figure 19:
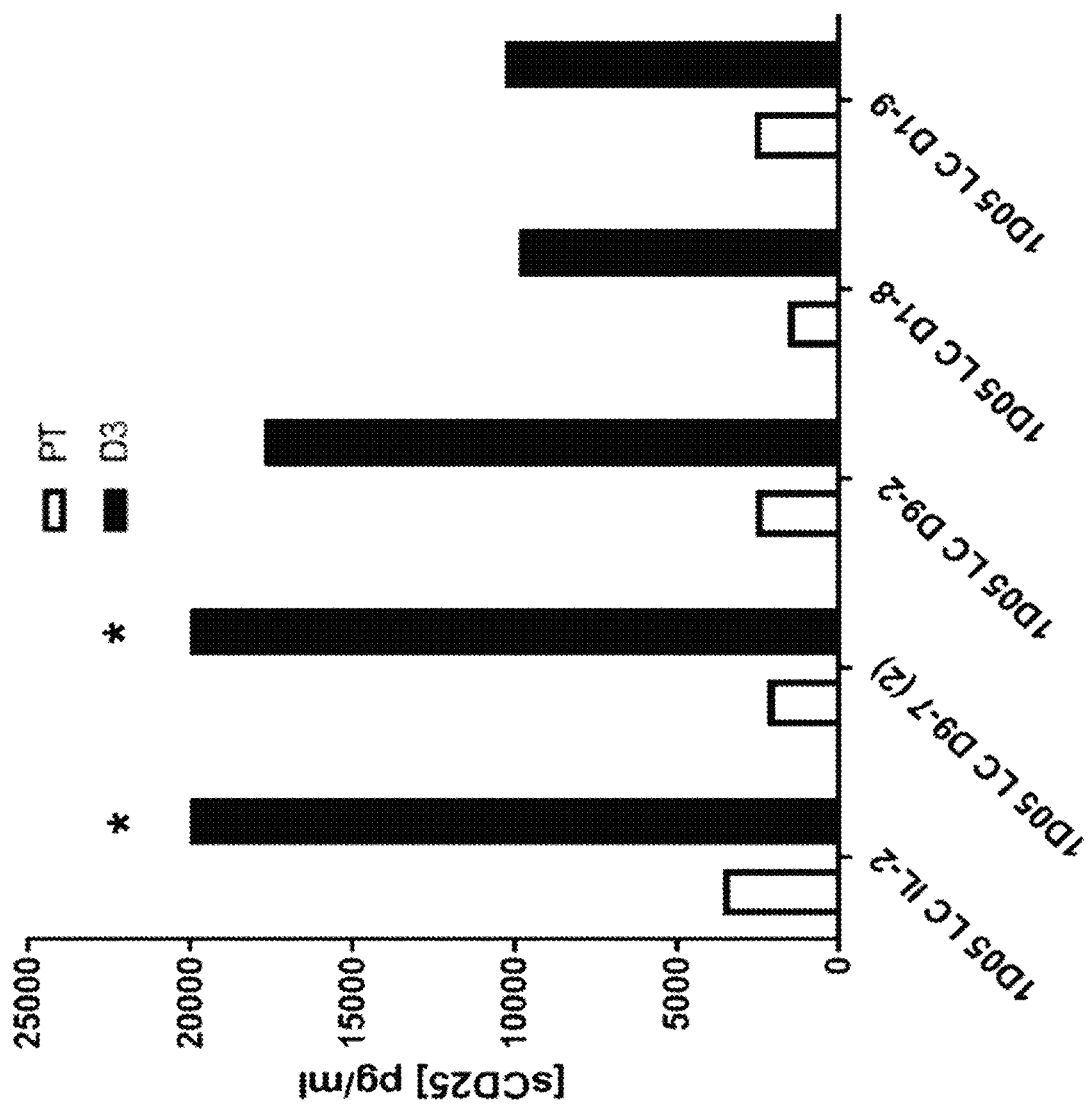
FIG. 19: Levels of soluble CD25 in plasma of cynomolgus monkeys dosed with immunocytokine molecules. Plasma samples were obtained pre-treatment (PT) and 3 days after dosing (D3) and analysed using a commercial ELISA kit. * indicates levels above limit of quantification (20,000 pg/mL)

For analysis of cytokines and soluble CD25, blood samples were taken into EDTA-treated tubes pre-treatment and 3 days post-treatment, and plasma extracted by centrifugation at 2000 g for 10 minutes. Samples were frozen until analysis by multiplex MSD (cytokines) or commercial ELISA (soluble CD25). Results are shown in FIGS. 18 and 19.

Figure 20A:
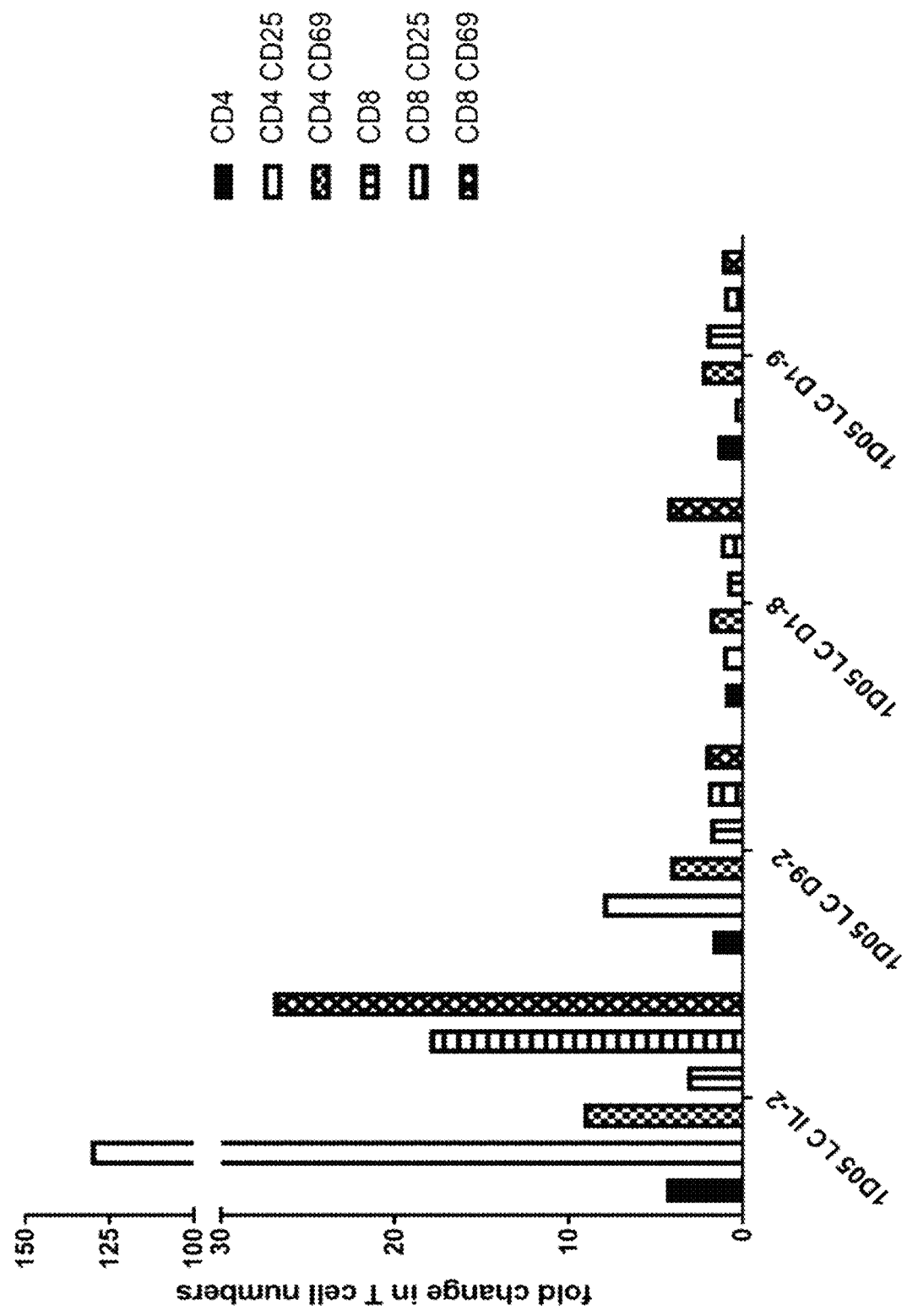
FIGS. 20(a)-20(b): Flow cytometric analysis of PBMC subsets. Whole blood was stained for markers of FIG. 20(a) T-cells and FIG. 20(b) B-cells, NK cells, neutrophils and monocytes, prior to red blood cell lysis and fixation. Data is expressed as the fold change in cell number 5 days after dosing. Data for 1D05 LC D9-7 ICK is missing due to unusable sample
Figure 20B:
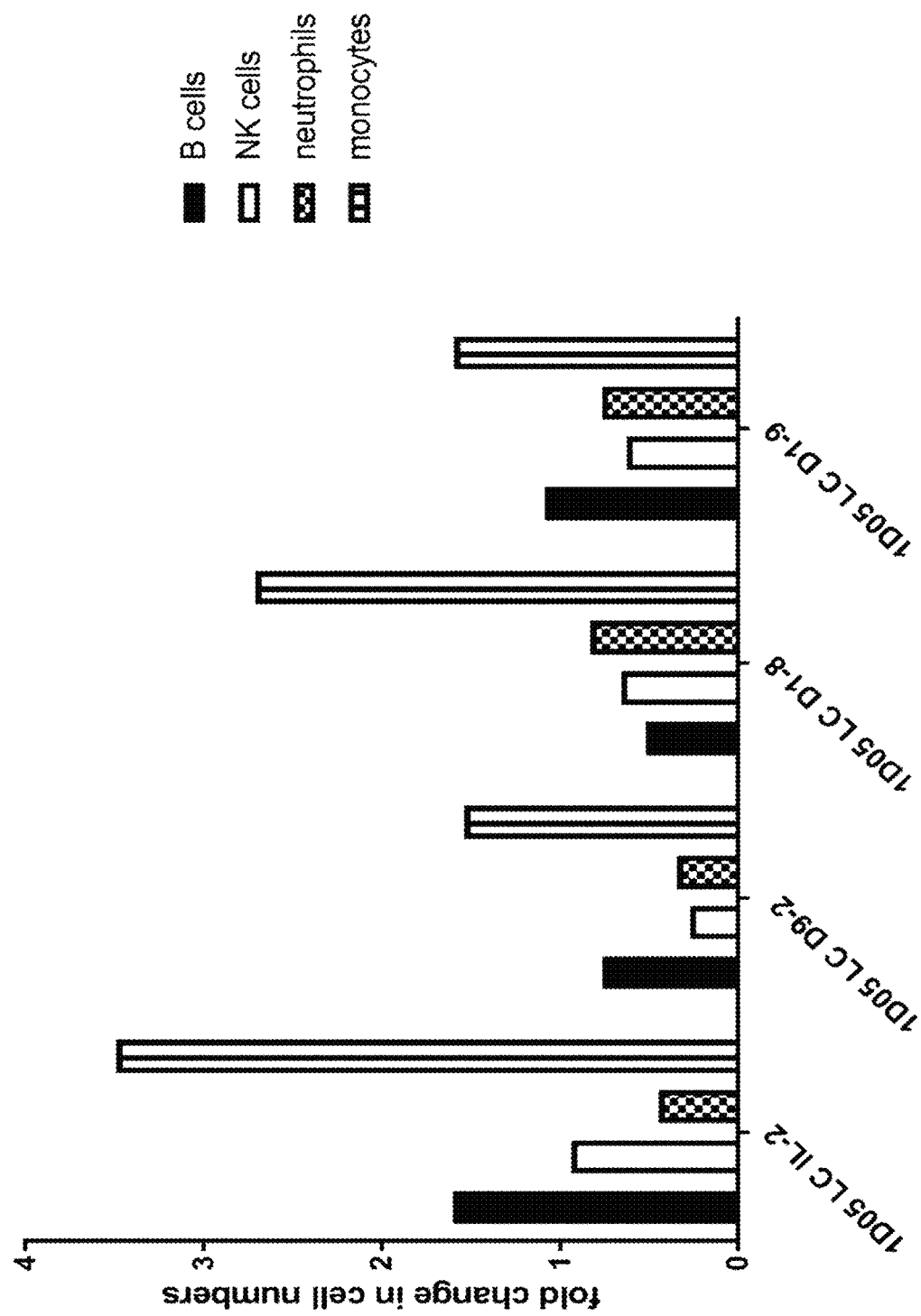

For immunophenotyping, blood samples were taken into EDTA-treated tubes pre-treatment and 5 days post-treatment. Blood samples were stained with cocktails of directly conjugated monoclonal antibodies, then red blood cells were lysed and the samples fixed by re-suspension in phosphate buffered saline containing 1% formaldehyde prior to analysis. Results are shown in FIG. 20.

For PK analysis, blood samples were taken into untreated tubes pre-treatment, end of infusion (EOI), 2, 4, 8, 16, 24, 32, 40 and 48 hours after EOI, extended to 72 hours and 96 hours for Phase 2) and serum prepared by allowing the blood to clot, then centrifugation at 2000 g for 10 min. Serum samples were frozen on dry ice for shipment to Kymab. Results are shown in FIG. 21.

Figure 21A:
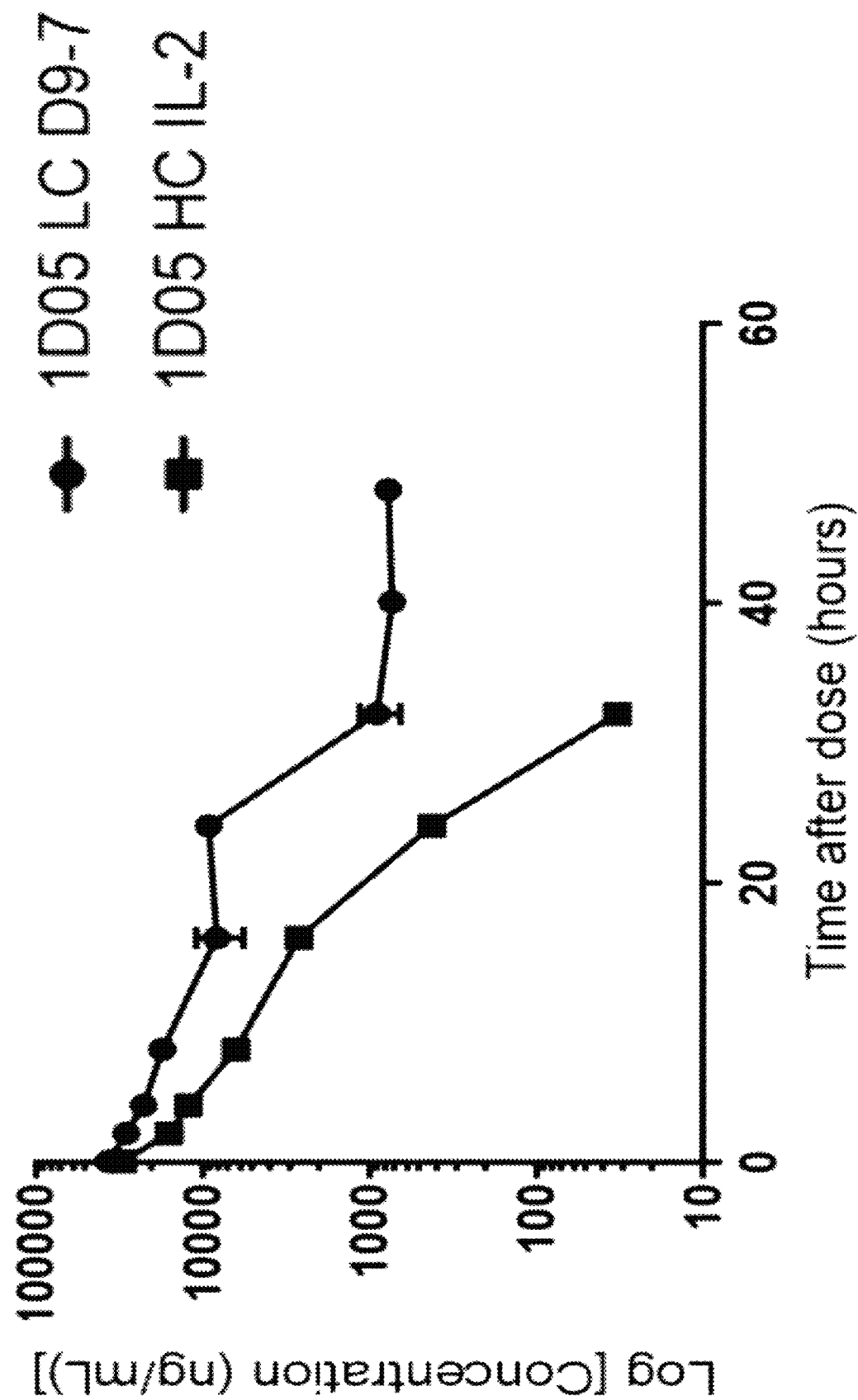
FIGS. 21(a)-21(d): Pharmacokinetic (PK) analysis of immunocytokines. Serum was prepared from blood samples taken at various time points over 96 hours. In panels FIG. 21(a) and FIG. 21(b), serum was incubated on plates coated with PD-L1 and immunocytokines detected with a biotinylated anti-human Fc detection antibody, and streptavidin-labelled Europium. In panels FIG. 21(c) and FIG. 21(d), serum was incubated on plates coated with PD-L1 and immunocytokines detected with a biotinylated anti-human IL-2 antibody, and streptavidin-labelled Europium. Results are expressed as ng/mL
Figure 21B:
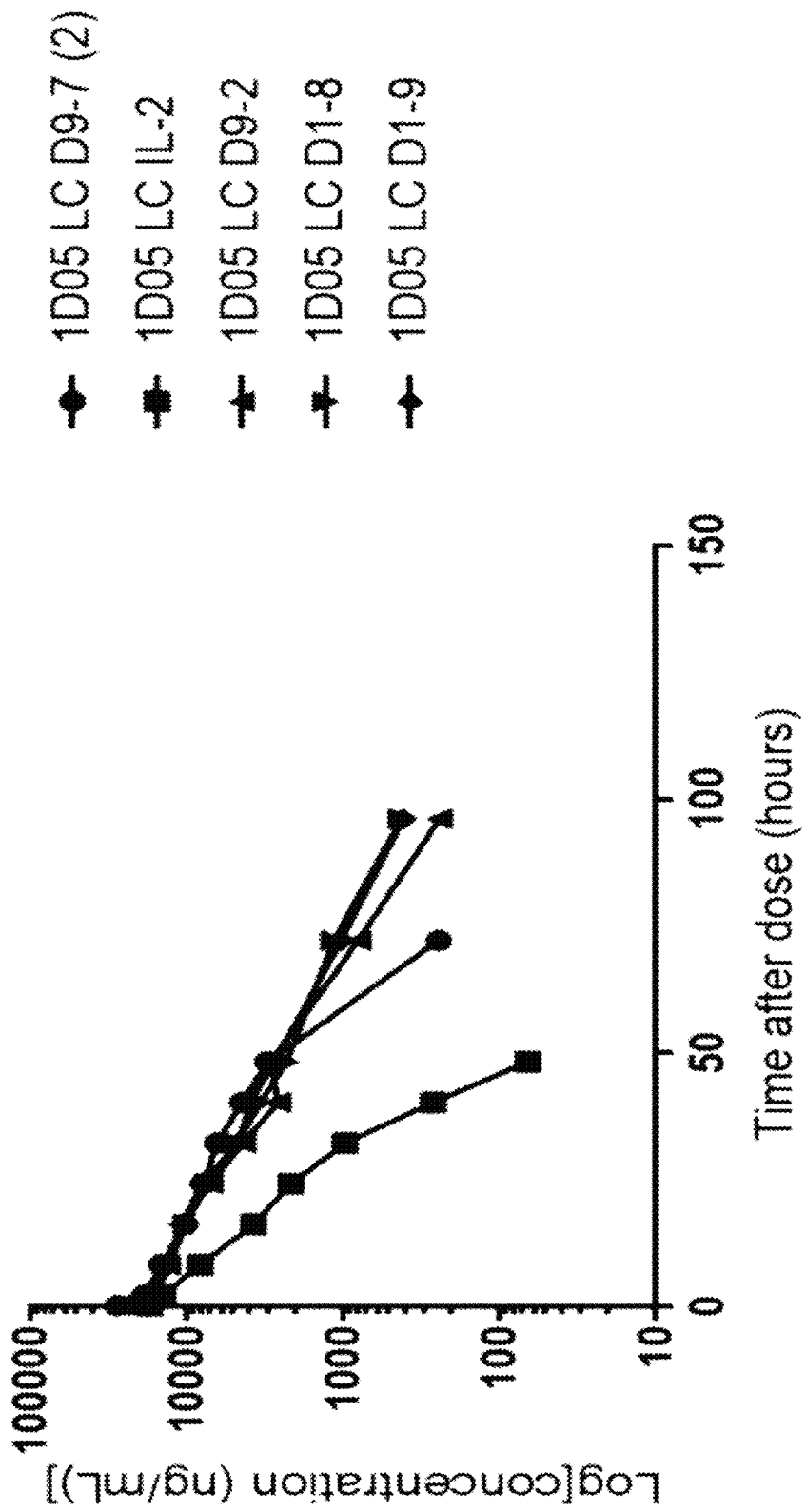

Pharmacokinetic Analysis of Serum Samples
a) PK assay for Detection of Anti-PD-L1 Antibody 50 µL/well of human PD-L1 Flag His (Seq ID No:505, in house) diluted to 2 µg/mL in PBS (Sigma, P3813-10PAK) was adsorbed to 96-well, high protein binding fluorescent plates (Greiner) overnight at 4° C. Excess protein was removed by washing 3× with 300 µL/well PBS-Tween (0.1% v/v) and the wells were blocked with 1% w/v bovine serum albumin (BSA, Sigma) in PBS for 1 hour at room temperature, after which plates were washed as described previously. Antibodies were diluted from 10,000 ng/mL to 9.77 ng/mL (1/2 dilution) in pooled cynomolgus serum (Seralab, CYNSRM) to give 12 standards including a blank. Standards, quality controls and samples were diluted at 1 in 50 MRD (minimum required dilution) in ELISA assay buffer (PBS+0.1% BSA) and were added to the coated 96-well high-binding plates at 50 µL/well. The plate was incubated for 1 hour at room temperature, after which plates were washed 3× with PBS-Tween. 50 µL biotinylated goat anti-human IgG (Southern Biotech) at 1 µg/mL was added to the plate. The plate was incubated for 1 hour at room temperature, after which plates were washed 3× with PBS-Tween. PD-L1 binding was detected using streptavidin labelled Europium (Perkin Elmer) diluted 1/1000 in DELFIA assay buffer (Perkin Elmer). Plates were washed with TBS (Tris buffered saline)-Tween (0.1% v/v) and 50 µL/well of DELFIA Enhancement solution (Perkin Elmer) was added to the plate. Time-resolved fluorescence was measured at 615 nm on an Envision plate reader (PerkinElmer). Concentrations were determined using GraphPad Prism software by interpolating from a standard curve fitted using a four-parameter logistic equation (Equation 4). Results are shown in FIGS. 21a and 21b.

b) PK Assay for Detection of Intact Immunocytokine (Antibody Fused to IL-2)

Figure 21C:
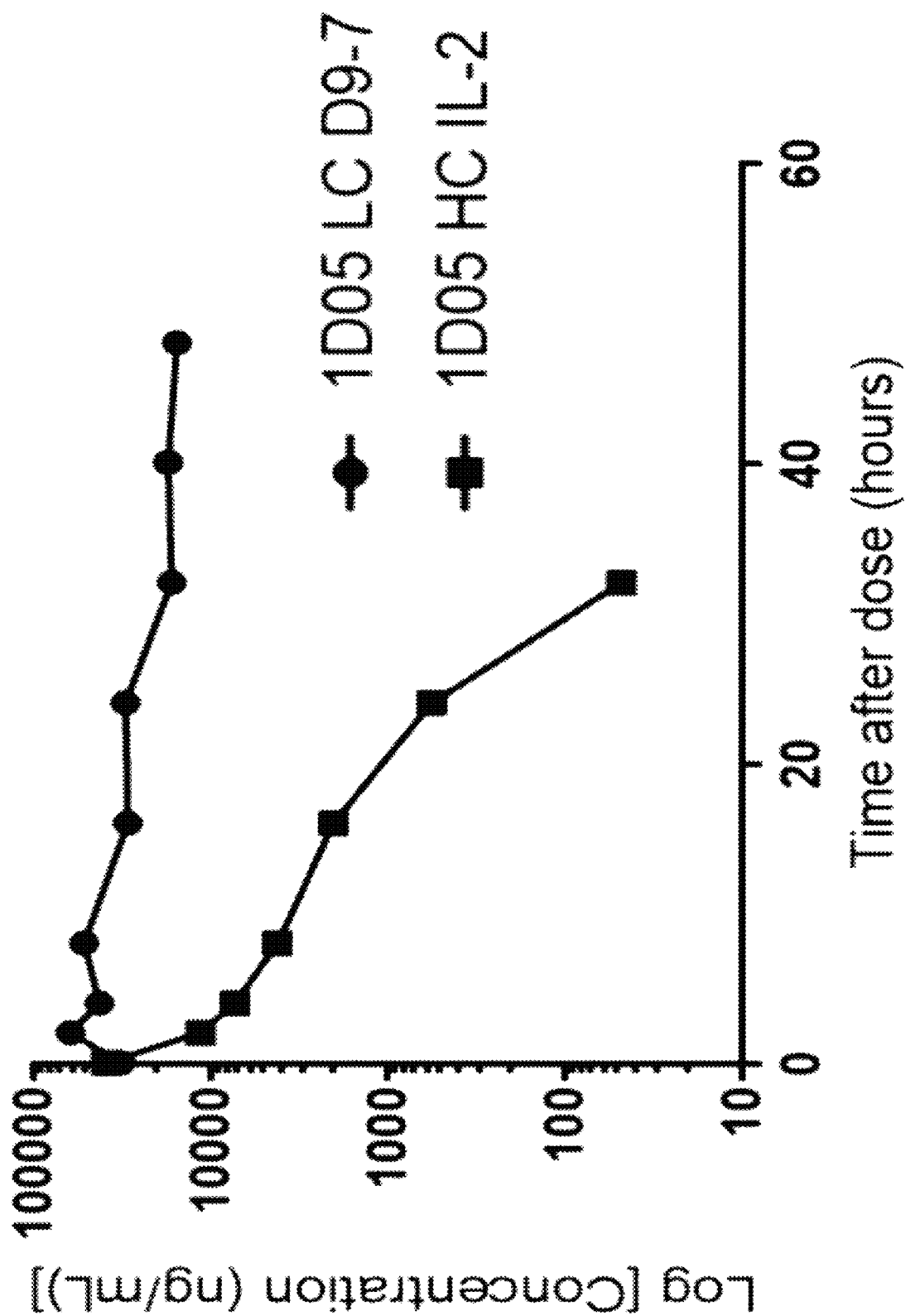
Figure 21D:
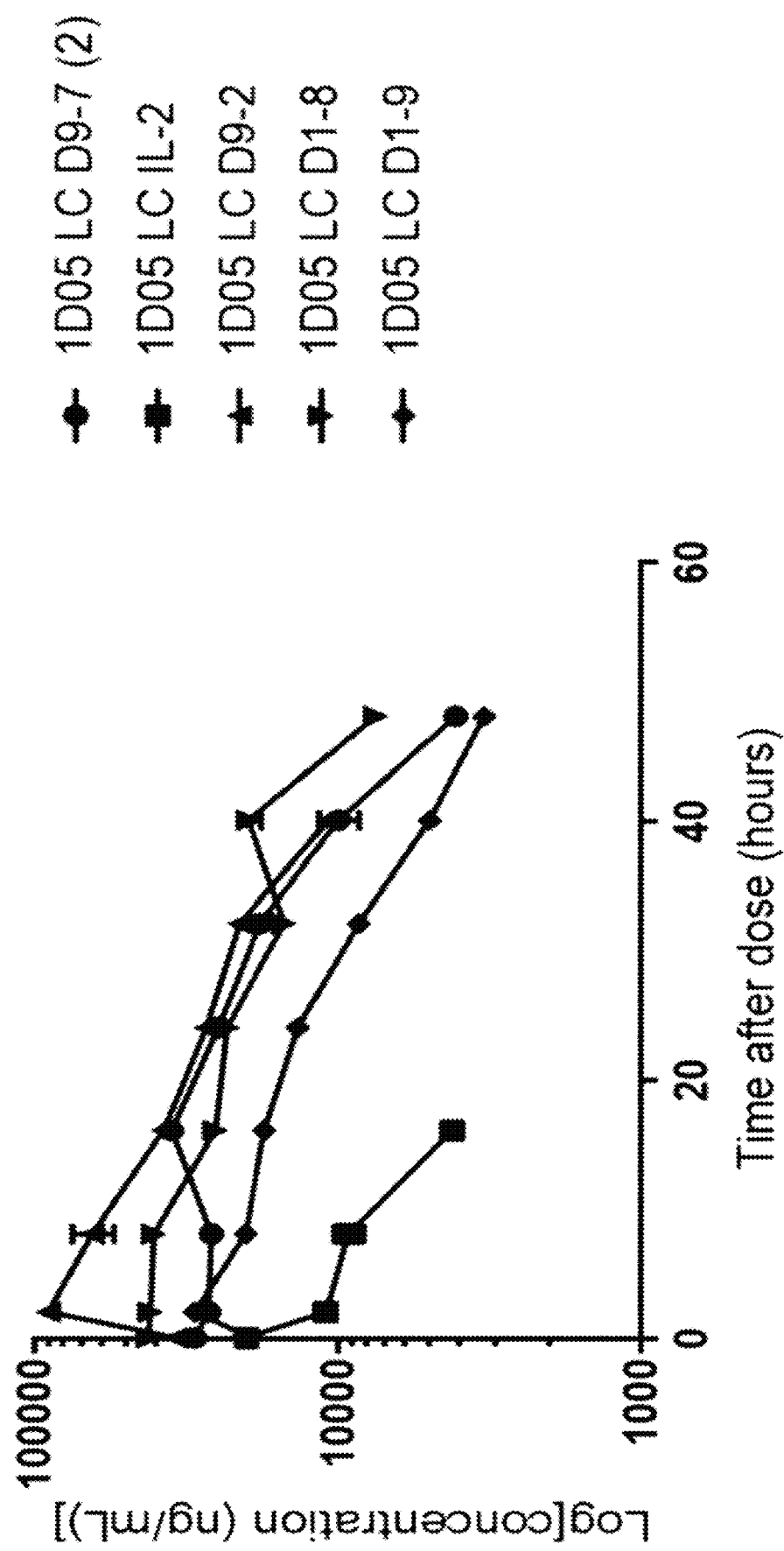

50 µL/well of human PD-L1 Flag His (Seq ID No:505 in house) diluted to 3 µg/mL in PBS (Sigma, P3813-10PAK) was adsorbed to 96-well, low auto-fluorescent, high protein binding plates (Costar) overnight at 4° C. Excess protein was removed by washing 3× with 300 µL/well PBS-Tween (0.1% v/v) and the wells were blocked with 1% w/v bovine serum albumin (BSA, Sigma) in PBS for 1 hour at room temperature, after which plates were washed 3× with PBS-Tween. Antibodies were diluted from 50,000 ng/mL to 617.3 ng/mL in pooled cynomolgus serum (Seralab, CYNSRM) to give 10 standards including a blank. Standards, quality controls and samples were diluted at 1 in 20 MRD in ELISA assay buffer (PBS+0.1% BSA) and were added to the coated 96-well high-binding plates at 50 µL/well. The plate was incubated for 1 hour at room temperature, after which plates were washed 3× with PBS-Tween. 50 µL biotinylated anti-human IL-2 (Peprotech) at 2 µg/mL was added to the plate. The plate was incubated for 1 hour at room temperature, after which plates were washed as described previously. Binding was detected using streptavidin labelled Europium (Perkin Elmer) diluted 1/1000 in DELFIA assay buffer (Perkin Elmer). Plates were washed with TBS (Tris buffered saline)-Tween (0.1% v/v) and 50 µL/well of DELFIA Enhancement solution (Perkin Elmer) was added to the plate. Time-resolved fluorescence was measured at 615 nm on an Envision plate reader (PerkinElmer). Concentrations were determined using GraphPad Prism software by interpolating from a standard curve fitted using a four-parameter logistic equation. Results are shown in FIGS. 21c and 21d.

Results Summary

No signs of overt IL-2 mediated toxicity (fever, vascular leak, diarrhoea) were observed after dosing. Lymphocyte numbers increased over the duration of the study with the different immunocytokine constructs. The constructs with the greatest truncations induced the lowest levels of lymphocyte expansion; little expansion was observed with 1D05 LC D1-9 ICK or 1D05 LC D1-8 ICK over the seven-day period, whereas 1D05 LC D9-7 ICK and the full-length IL-2 induced significant expansion. The lymphopenia observed at day 2 with some constructs is indicative of lymphocyte margination out of the circulation. This is followed by a rebound lymphocytosis which can be seen at day 5 (FIG. 16).

Administration of immunocytokine constructs did not cause significant anaemia (FIG. 17). Around a 20% reduction in haemoglobin, haematocrit and red blood cell levels was observed at day 7 with the most active constructs (1D05

HC IL-2 ICK, 1D05 LC IL2 ICK and 1D05 LC D9-7 ICK), and around a 10% reduction with the other constructs. This agrees with anecdotal evidence from studies with IL-2 heavy chain immunocytokines. Thrombocytopenia (reduced platelet count) was not observed.

IL-2 was strongly increased 3 days post-dosing, indicative of production by activated T-cells. However, there is a possibility that the assay is cross-reactive for human IL-2 and so could also detect the immunocytokine. There was no clear up- or down-regulation of any of the other cytokines post-dosing, although there was a trend for down-regulation of IL-8 levels (FIG. 18). Levels of soluble CD25, which is a biomarker of T-cell activation, were strongly increased 3 days after dosing with immunocytokines (FIG. 19). Levels of soluble CD25 correlated with the in vitro stimulatory activity of the immunocytokines described in Example 13.

Dosing with immunocytokines increases the number of activated T-cells in the blood (FIG. 20). When dosed with 1D05 LC IL-2 ICK, total $CD4^+$ and $CD8^+$ cell numbers are increased, but $CD69^+$ (early activation) and $CD25^+$ (later activation) subsets are greatly increased, compared with pre-treatment levels. The increase in cell numbers is less striking for the truncated constructs. No significant changes in B-cell, NK cell or neutrophil numbers were observed, with a moderate increase in monocyte numbers. Data for the animal dosed with 1D05 LC D9-7 ICK is not available, due to clotting of the sample.

The light chain (LC) fusions have a longer half-life than the heavy chain (HC) fusion, which agrees with previous data in mouse (Gillies S D, Protein Engineering, Design and Selection, 26:10: 561-569, 2013). The half-life of 1D05 LC IL-2 ICK was around 8 hours, and the half-life of the truncated IL-2 constructs was around two-fold longer (FIGS. 21a and 21b). The increased half-life of immunocytokines with truncated IL-2, compared with full-length IL-2, may reflect reduced binding to IL-2 receptors.

A modified assay was used to detect intact immunocytokine i.e. antibody fused to IL-2 (FIGS. 21c and 21d). This result shows that the IL-2 part of the molecule remains fused in vivo and is not cleaved.

Example 19—Extended Single Dose Study in Cynomolgus Monkeys

To determine the duration of lymphocytosis, and obtain more detailed analysis of T-cell subsets, an extended single dose study will be performed (study number HQ52PV). Female cynomolgus monkeys are dosed with 1 mg/kg immunocytokine as per Example 18 and monitored over at least 14 days. Cytokines will be analysed on days 1, 3, 7, 10 and 14, and pre-treatment. Haematology measurements will be performed on days 2, 5, 7, 10 and 14, and pre-treatment. Detection of soluble CD25 will be performed on days 3, 7 and 10, and pre-treatment. CD127 will be added to the immunophenotyping panel, to allow for detection of regulatory T-cells ($CD3^+$ $CD4^+$ $CD25^{hi}$ $CD127^{lo}$, and analysis will be performed on days 1, 5, 7, 10 and 14, and pre-treatment. PK analysis will be performed as before. Treatment groups are shown in Table 14.

TABLE 14

Treatment groups and animal numbers

| Phase | Animal | Test Item |
|---|---|---|
| 3 | 378 | 1D05 LC IL-2 ICK |
| 3 | 379 | 1D05 LC D9-7 ICK |

TABLE 14-continued

Treatment groups and animal numbers

| Phase | Animal | Test Item |
|---|---|---|
| 3 | 380 | 1D05 LC D9-2 ICK |
| 3 | 381 | 1D05 LC D1-8 ICK |
| 3 | 382 | 1D05 LC D5-9 ICK |

Figure 28:
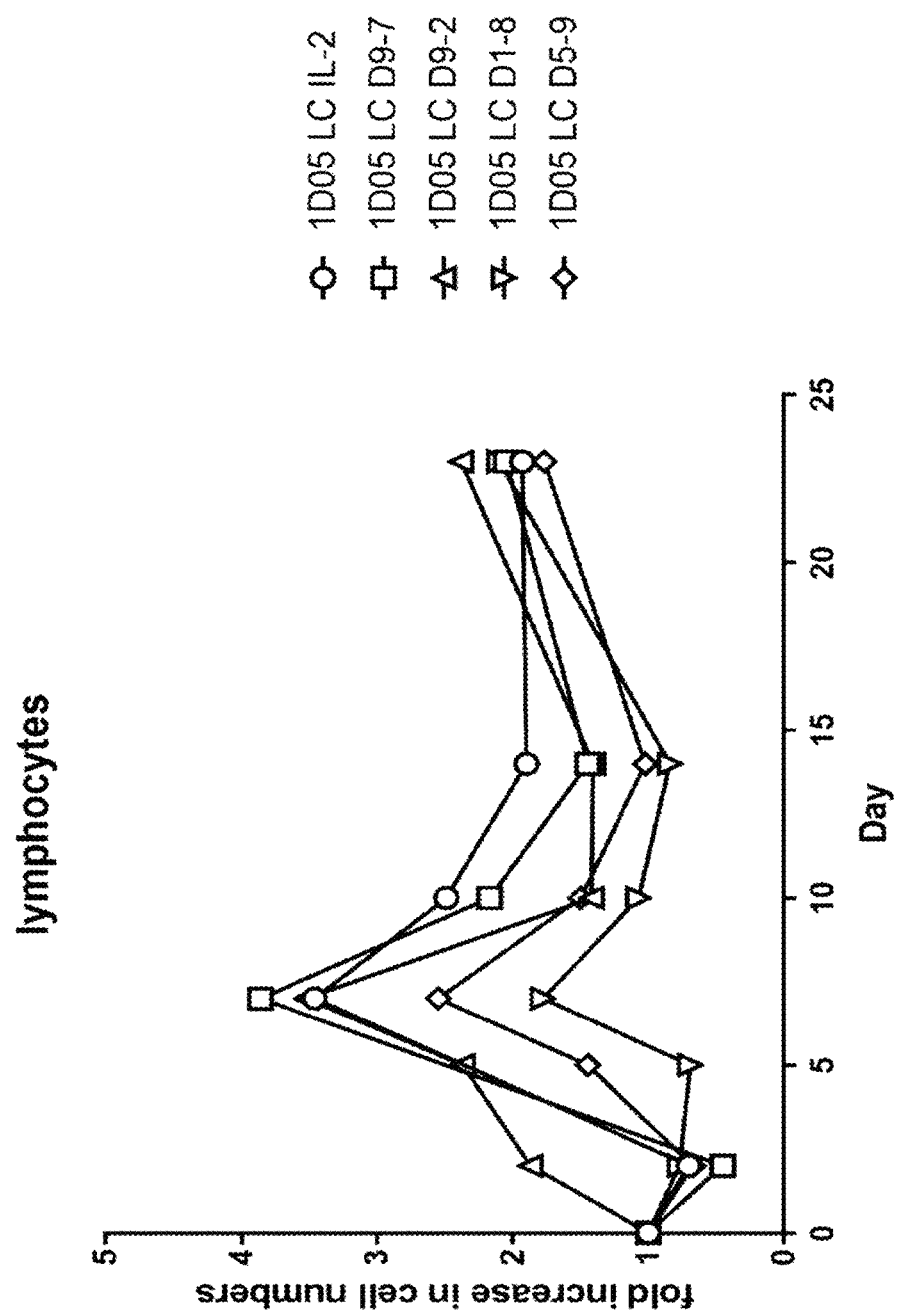
FIG. 28: Expansion of lymphocytes in response to dosing with immunocytokines. Fasting blood samples were taken into EDTA treated tubes pre-treatment (0), and 2, 5 and 7, 10, 14 and 23 days post-treatment. Cell counts were measured by the Bayer Advia 120. Results are expressed as fold change in lymphocyte count
Figure 29:
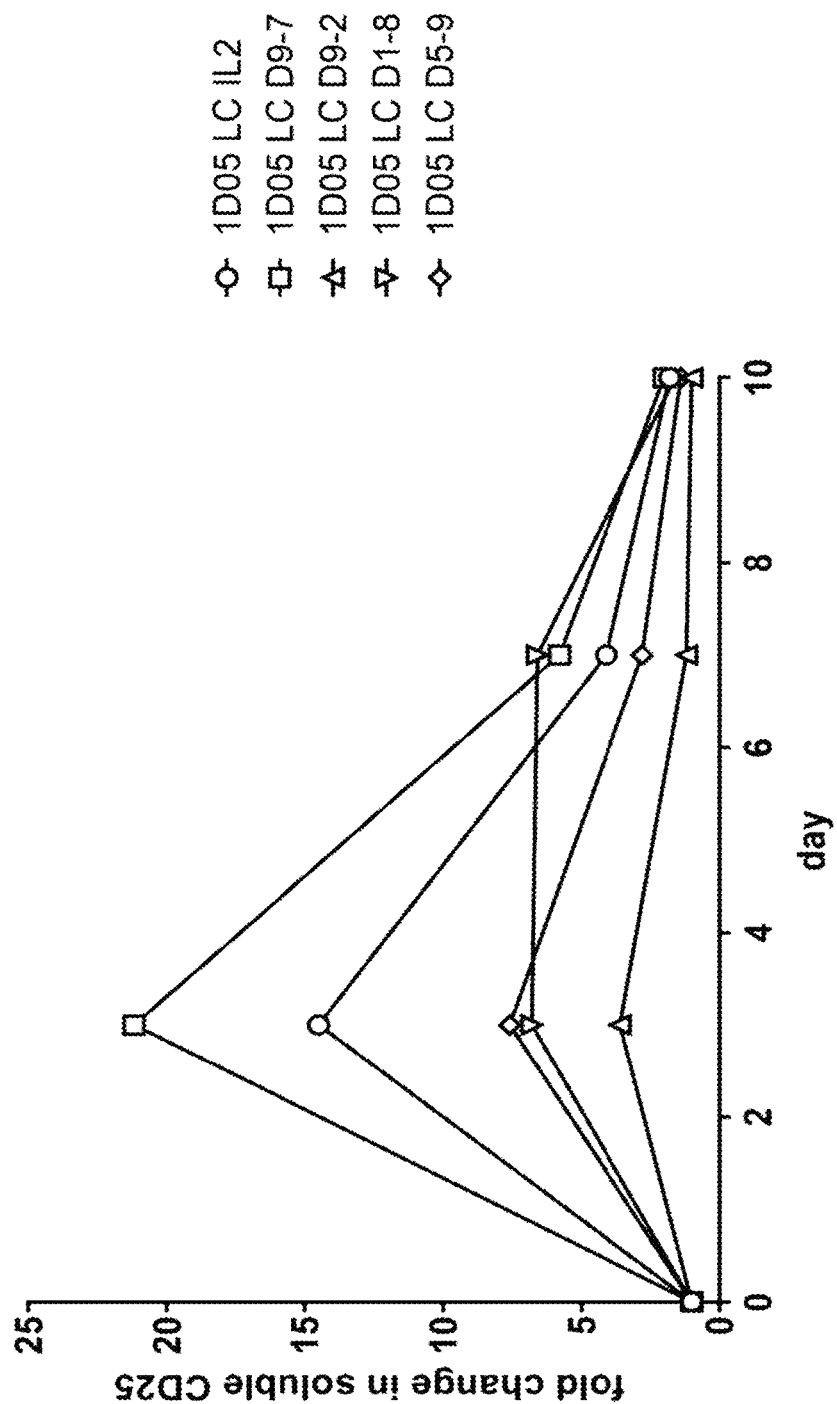
FIG. 29: Levels of soluble CD25 in plasma of cynomolgus monkeys dosed with immunocytokine molecules. Plasma samples were obtained pre-treatment (0) and 3, 7 and 10 days after dosing and analysed using a commercial ELISA kit
Figure 30A:
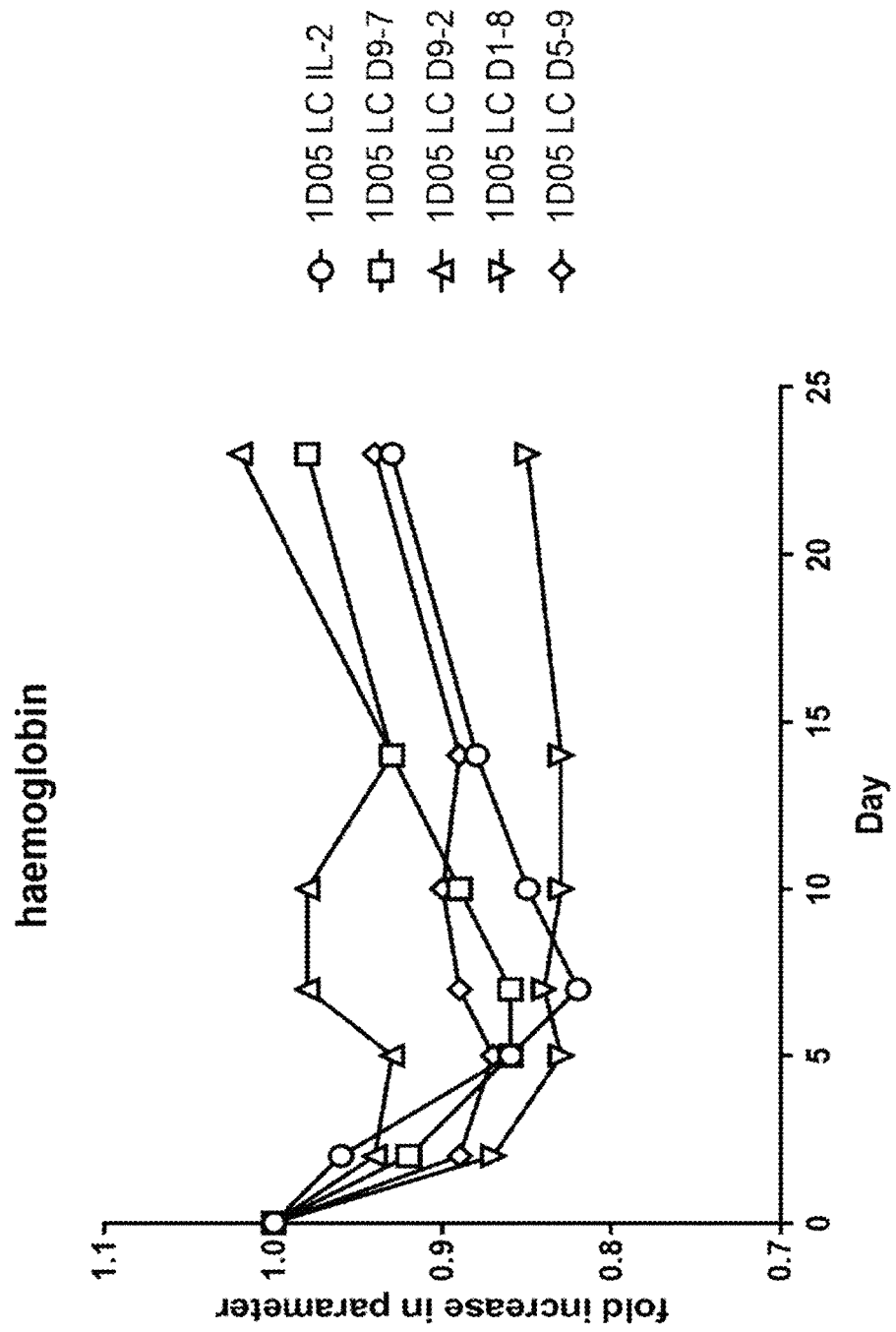
FIGS. 30(a)-30(d): Analysis of standard haematological parameters in response to dosing with immunocytokines. Fasting blood samples were taken into EDTA treated tubes pre-treatment (0) and 2, 5, 7, 10, 14 and 23 days post-treatment. Analysis of FIG. 30(a) haemoglobin, FIG. 30(b) haematocrit, FIG. 30(c) red blood cell counts and FIG. 30(d) platelet counts were performed using the Bayer Advia 120. Results are expressed as the fold change in parameter at each timepoint
Figure 30B:
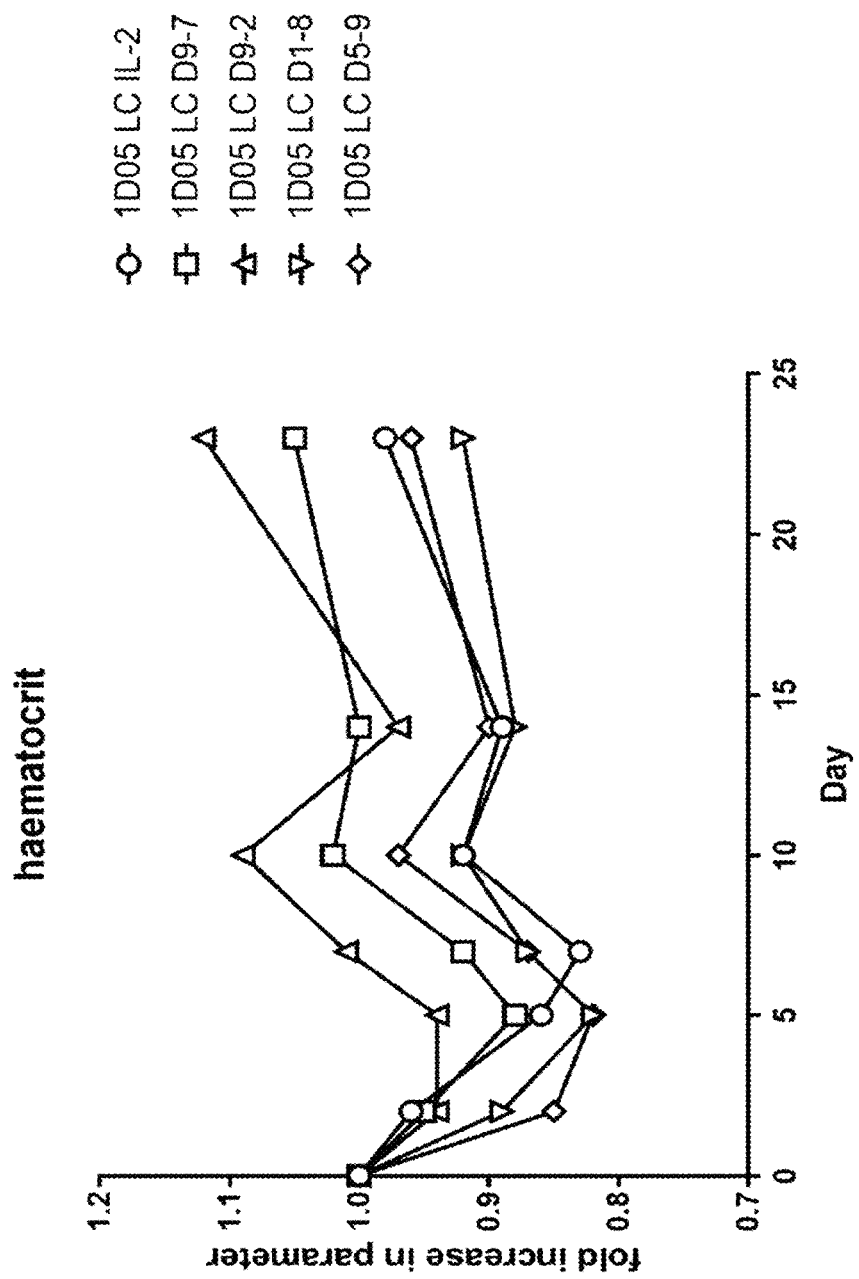
Figure 30C:
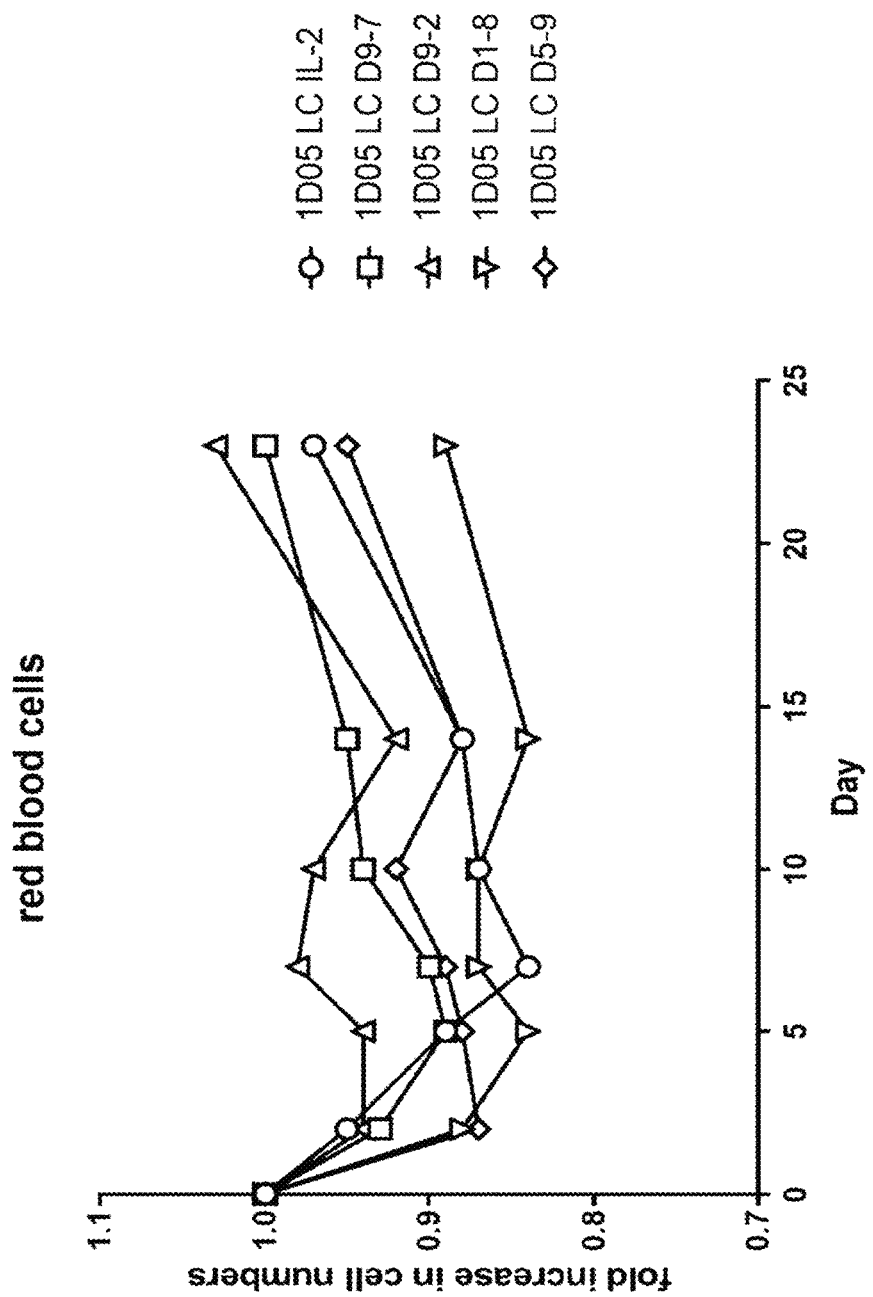
Figure 30D:
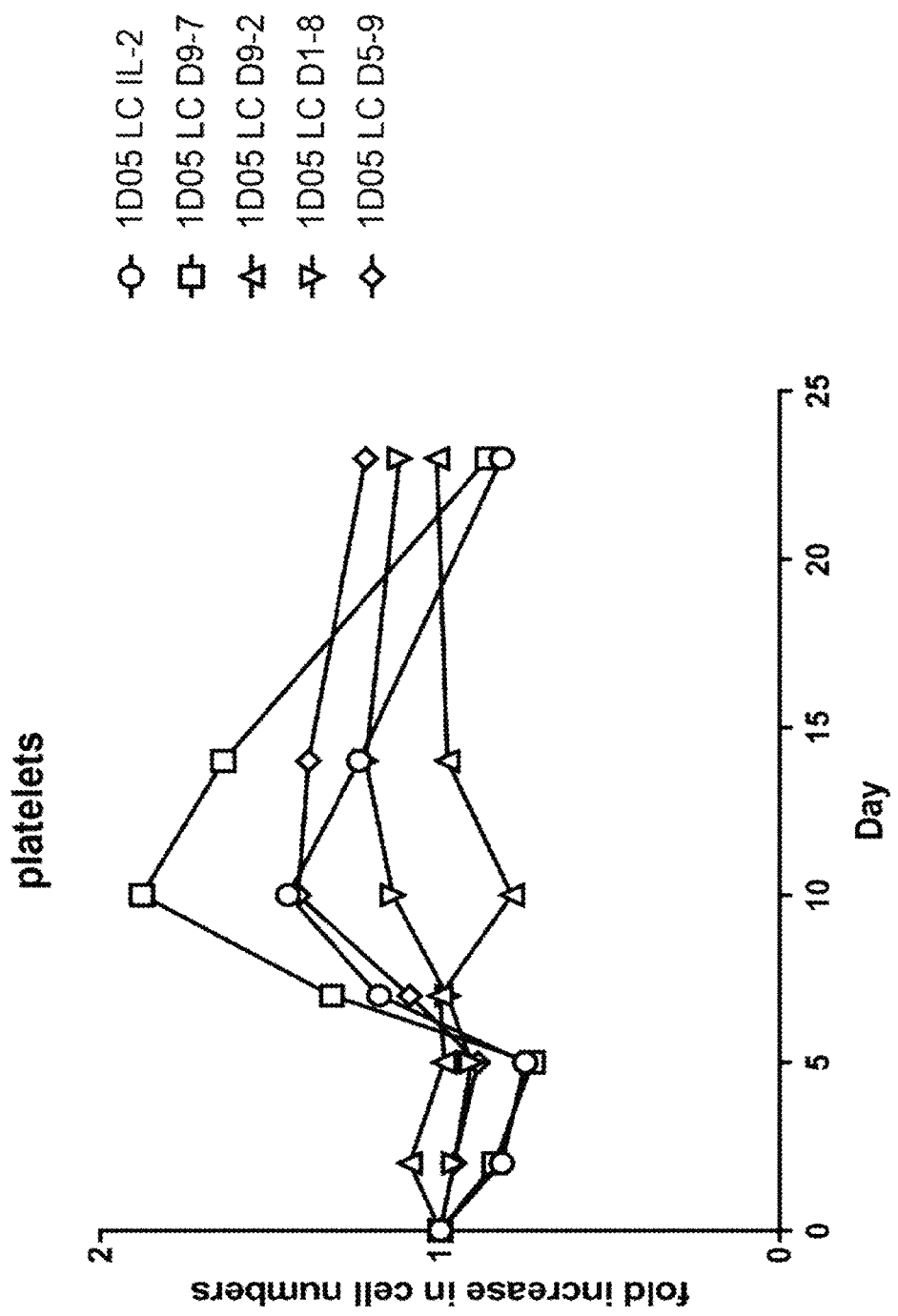

No signs of overt IL-2 mediated toxicity (fever, vascular leak, diarrhoea) were observed after dosing. Lymphocyte numbers peaked at day 7 with all immunocytokine constructs. The constructs with the greatest truncations induced the lowest levels of lymphocyte expansion; the least expansion was observed with 1D05 LC D1-8 ICK, whereas 1D05 LC D9-7 ICK and the full-length IL-2 induced the greatest expansion. The lymphopenia observed at day 2 with some constructs is indicative of lymphocyte margination out of the circulation. This is followed by a rebound lymphocytosis (FIG. 28). Levels of soluble CD25, which is a biomarker of T-cell activation, peaked 3 days after dosing with immunocytokines (FIG. 29). Levels of soluble CD25 correlated with the in vitro stimulatory activity of the immunocytokines described in Example 13.

Figure 31A:
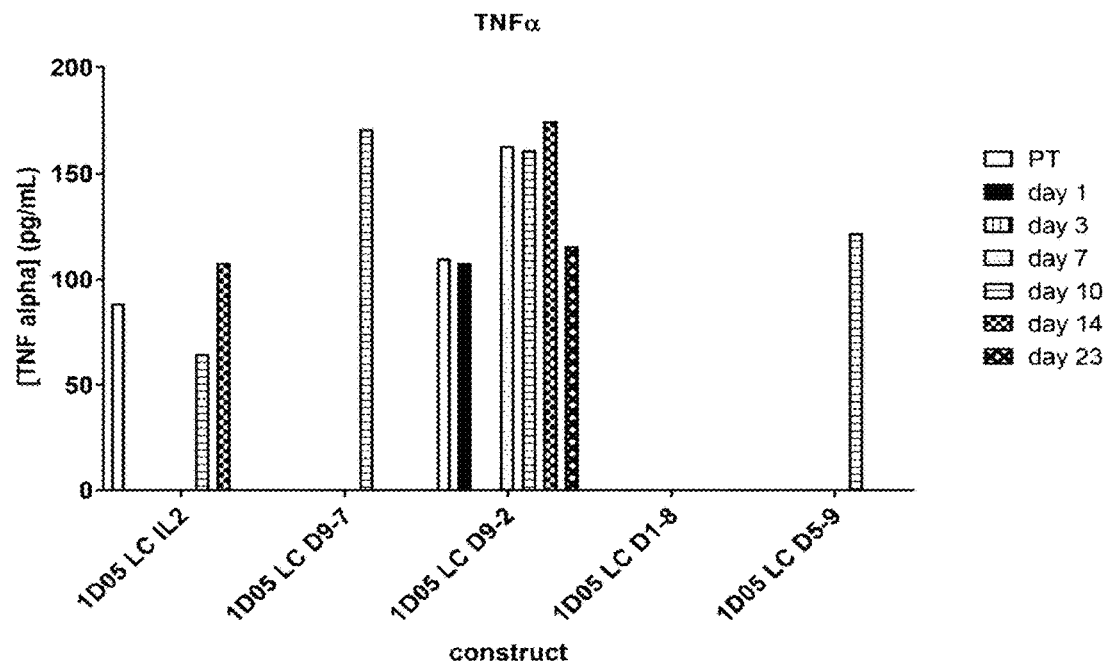
FIGS. 31(a)-31(h): Cytokine levels in plasma of cynomolgus monkeys dosed with immunocytokine molecules. Plasma samples were obtained pre-treatment (0) and 1, 3, 7, 10, 14 and 23 days after dosing and analysed by MSD for levels of FIG. 31(a) TNF-$\alpha$.
Figure 31B:
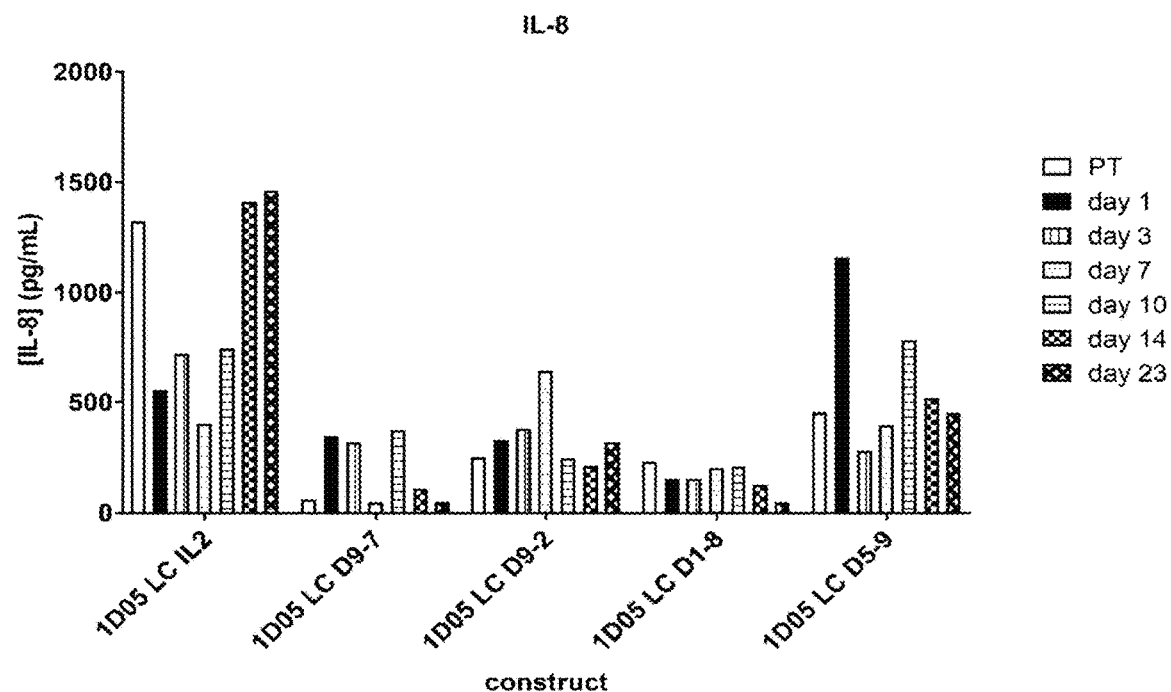
Figure 31C:
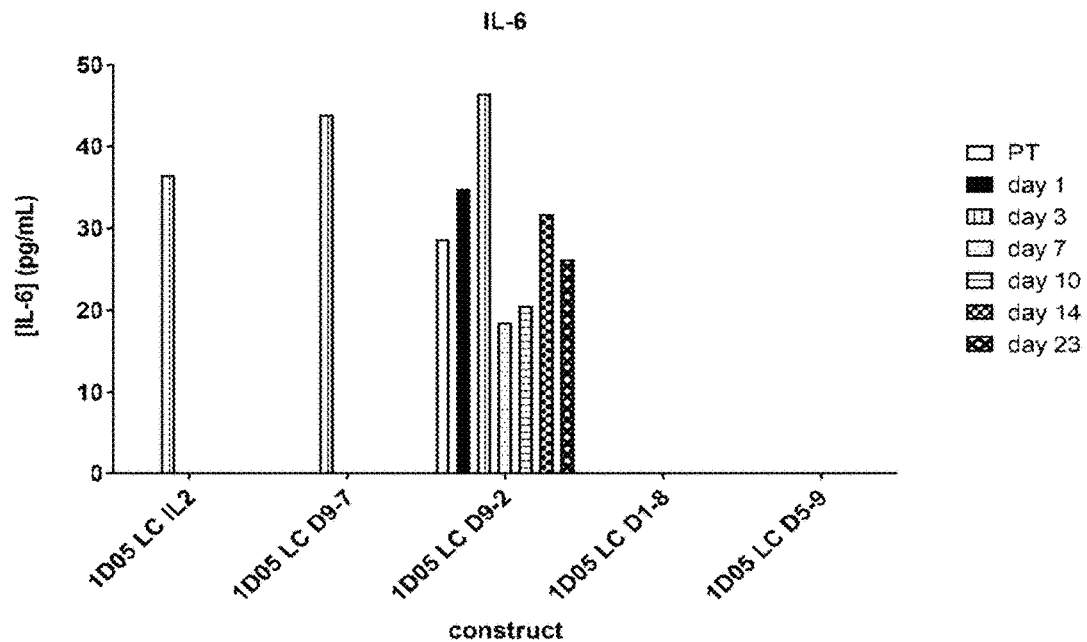
Figure 31D:
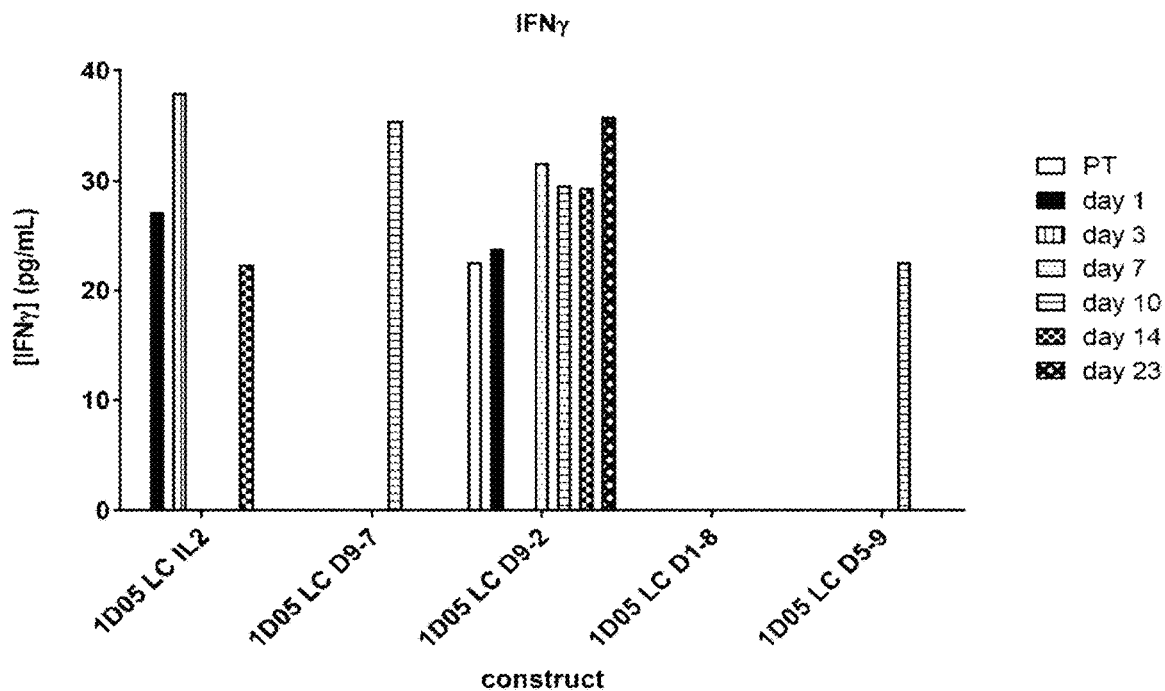
Figure 31:
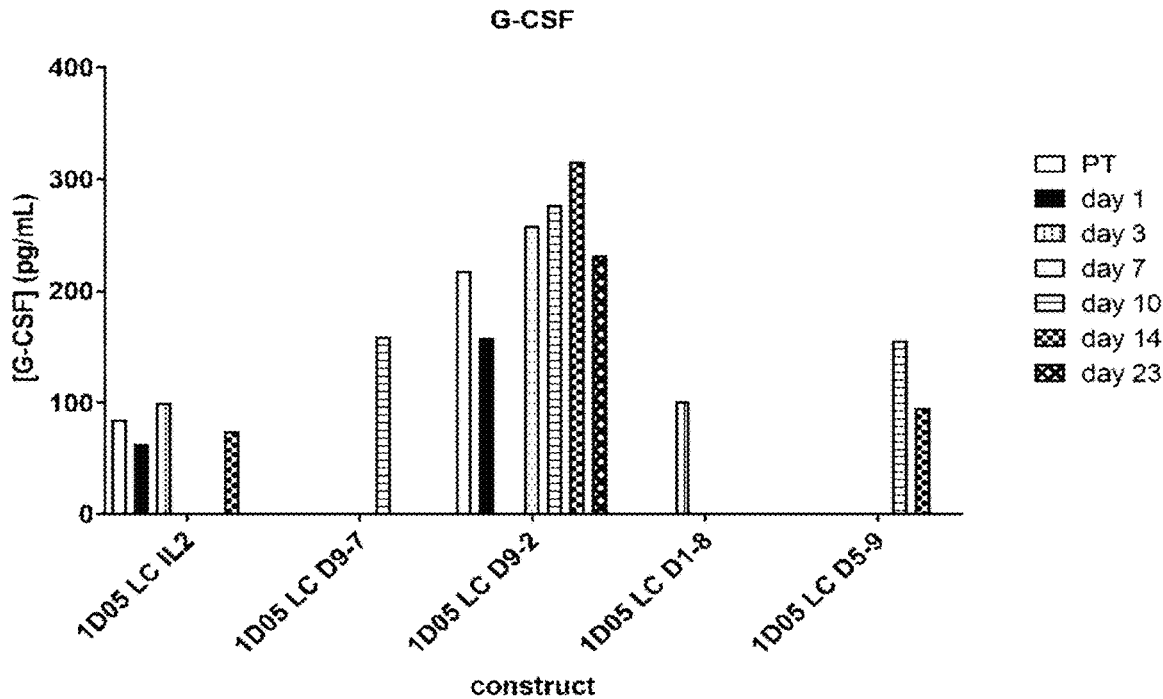
Figure 31F:
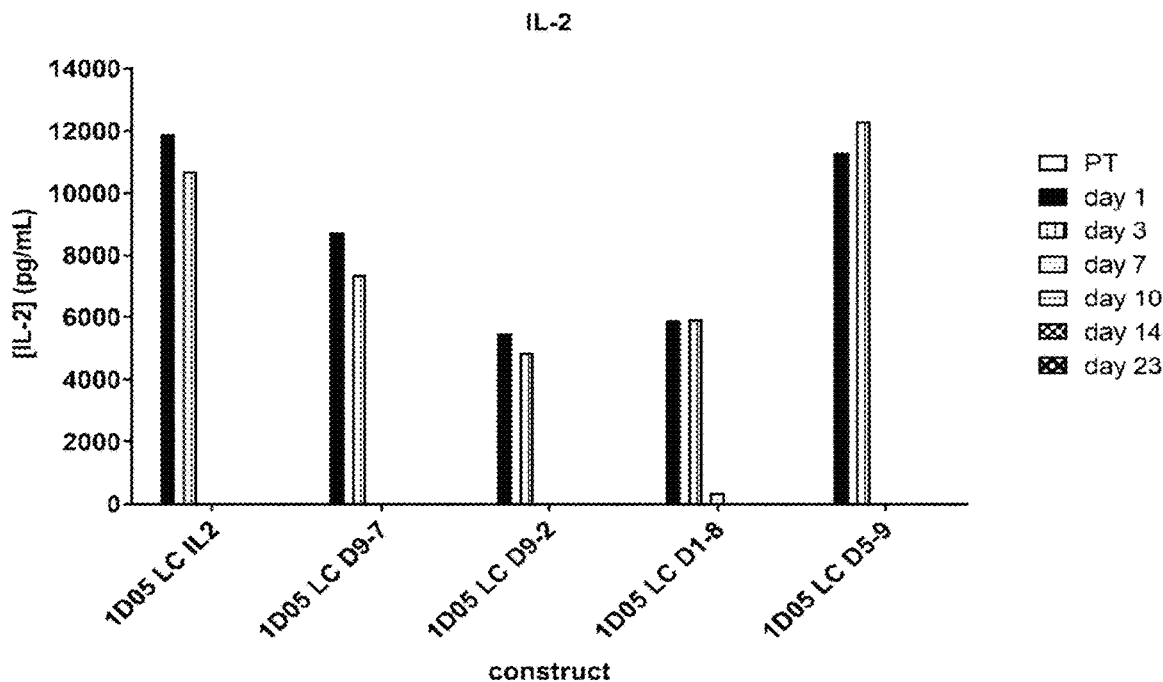
Figure 31G:
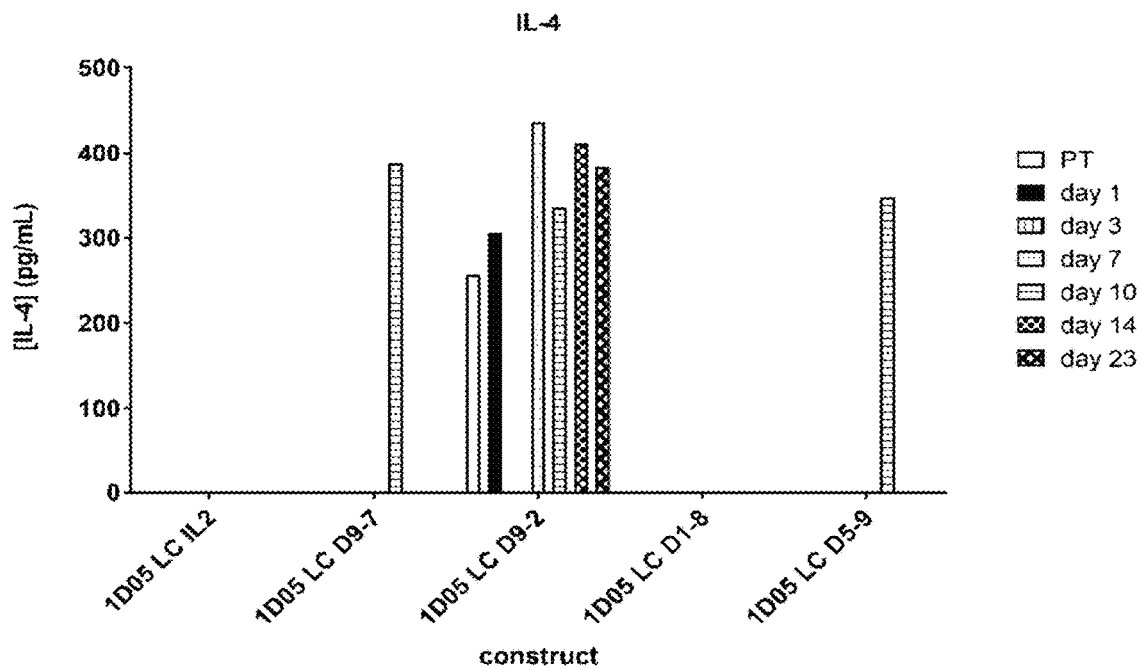
Figure 31H:
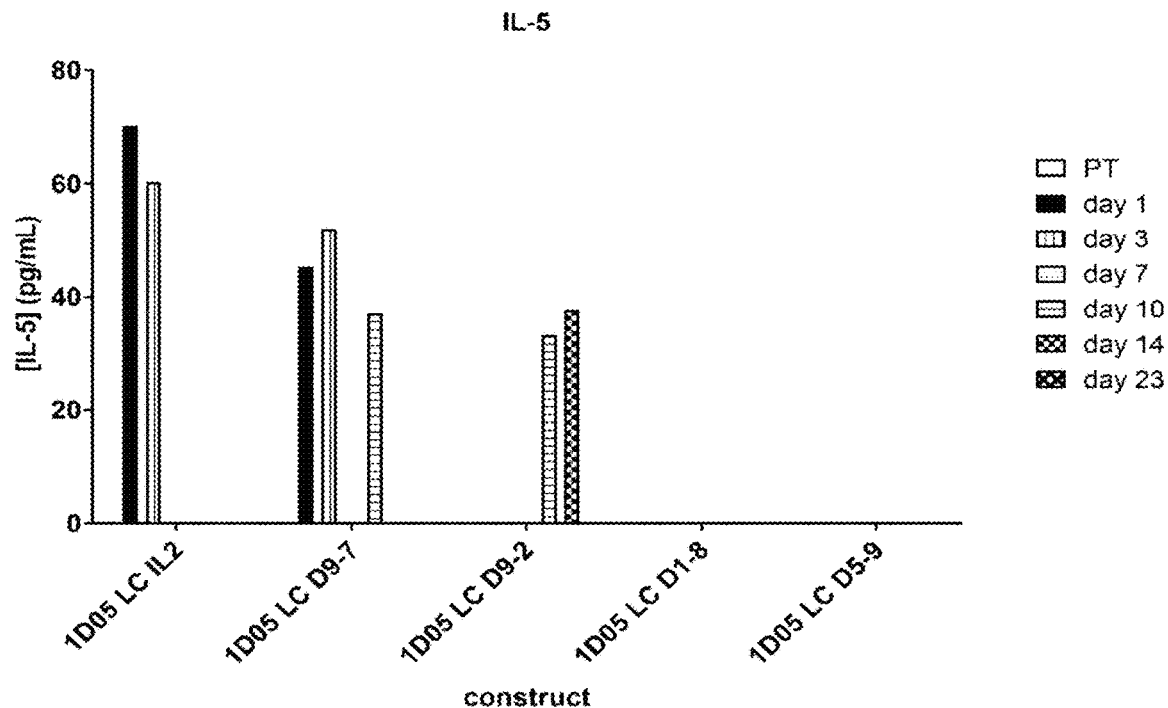

Administration of immunocytokine constructs did not cause significant anaemia (FIG. 30). A 10-20% reduction in haemoglobin, haematocrit and red blood cell levels was observed with the immunocytokine constructs. Haemoglobin levels remained lower over the entire time course in the animal dosed with 1D05 LC D1-8 ICK. Mild thrombocytopenia was observed with the two most active constructs at day 5, but levels recovered after this timepoint. IL-2 was strongly increased 3 days post-dosing, indicative of production by activated T-cells. However, there is a possibility that the assay is cross-reactive for human IL-2 and so these levels reflect the presence of the immunocytokine. There was no clear up- or down-regulation of any of the other cytokines post-dosing (FIG. 31).

Figure 32:
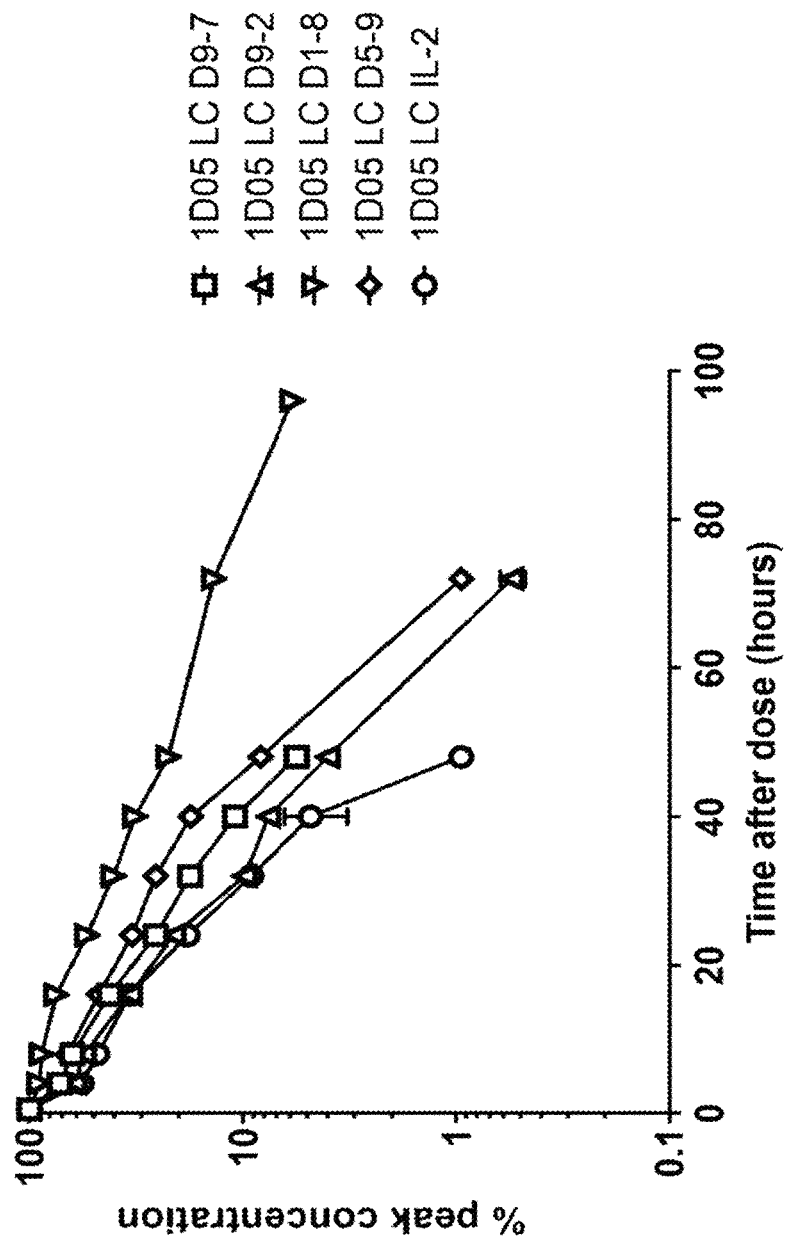
FIG. 32: Pharmacokinetic (PK) analysis of immunocytokines. Serum was prepared from blood samples taken at various time points over 96 hours. Serum was incubated on plates coated with PD-L1 and immunocytokines detected with a biotinylated anti-human Fc detection antibody, and streptavidin-labelled Europium. Results are expressed as % peak concentration

As observed previously in Example 18, the half-life of 1D05 LC IL-2 ICK was around 8 hours, and the half-life of the truncated IL-2 constructs correlated with the size of the truncation (FIG. 32). The immunocytokine construct containing the longest truncation, D1-8, had the longest half-life, of approximately 24 hours. The increased half-life of immunocytokines with truncated IL-2, compared with full-length IL-2, may reflect reduced binding to IL-2 receptors.

Figure 33A:
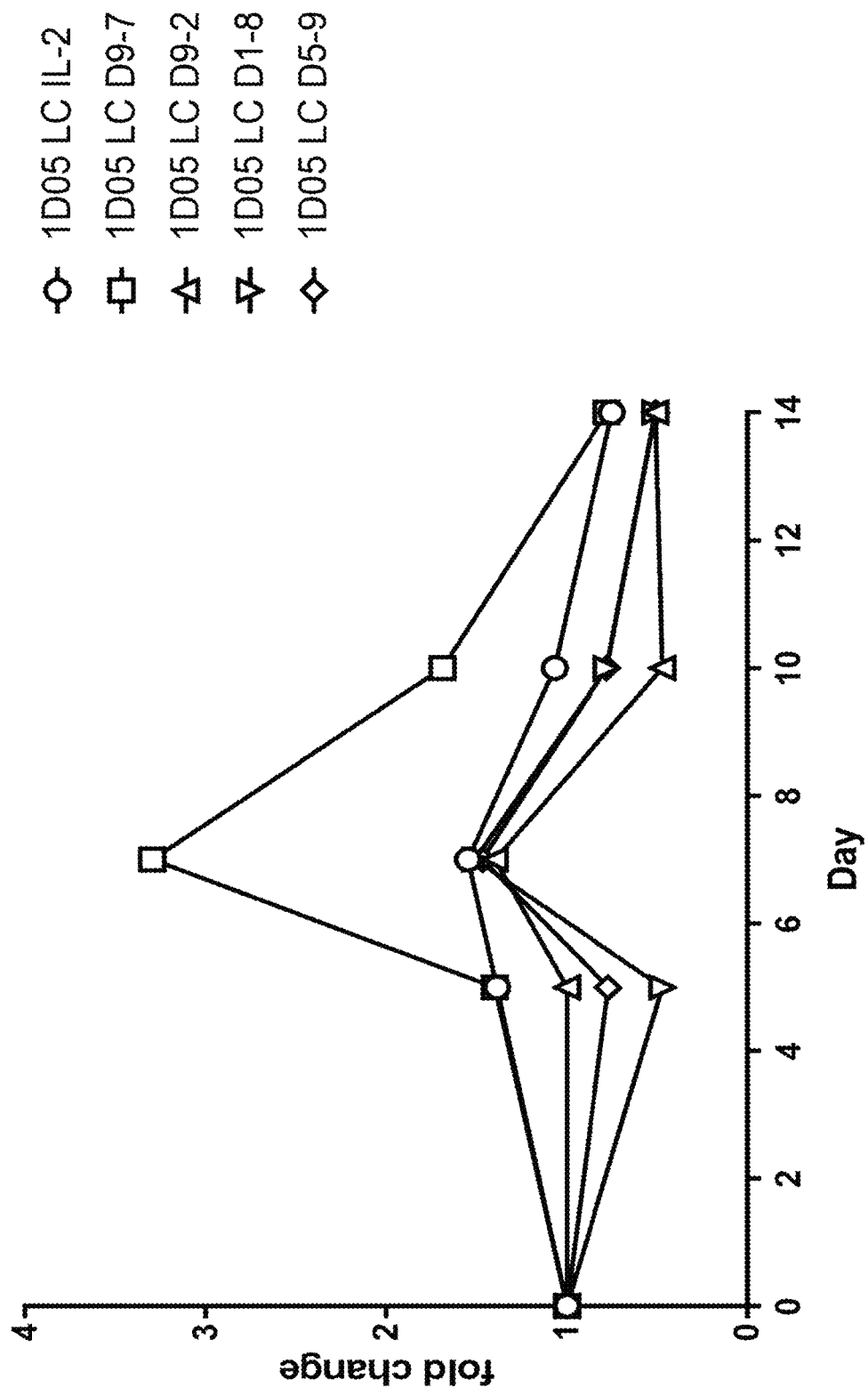
FIGS. 33(a) and 33(b): Expansion of specific T-cell subsets by ICK molecules. Whole blood was incubated with antibodies for staining, before red blood cell lysis, fixation and analysis by flow cytometry. Results are expressed as fold change in absolute (FIG. 33a) CD4$^+$ T-cell and (FIG. 33b) CD8$^+$ T-cell numbers at each timepoint.
Figure 33B:
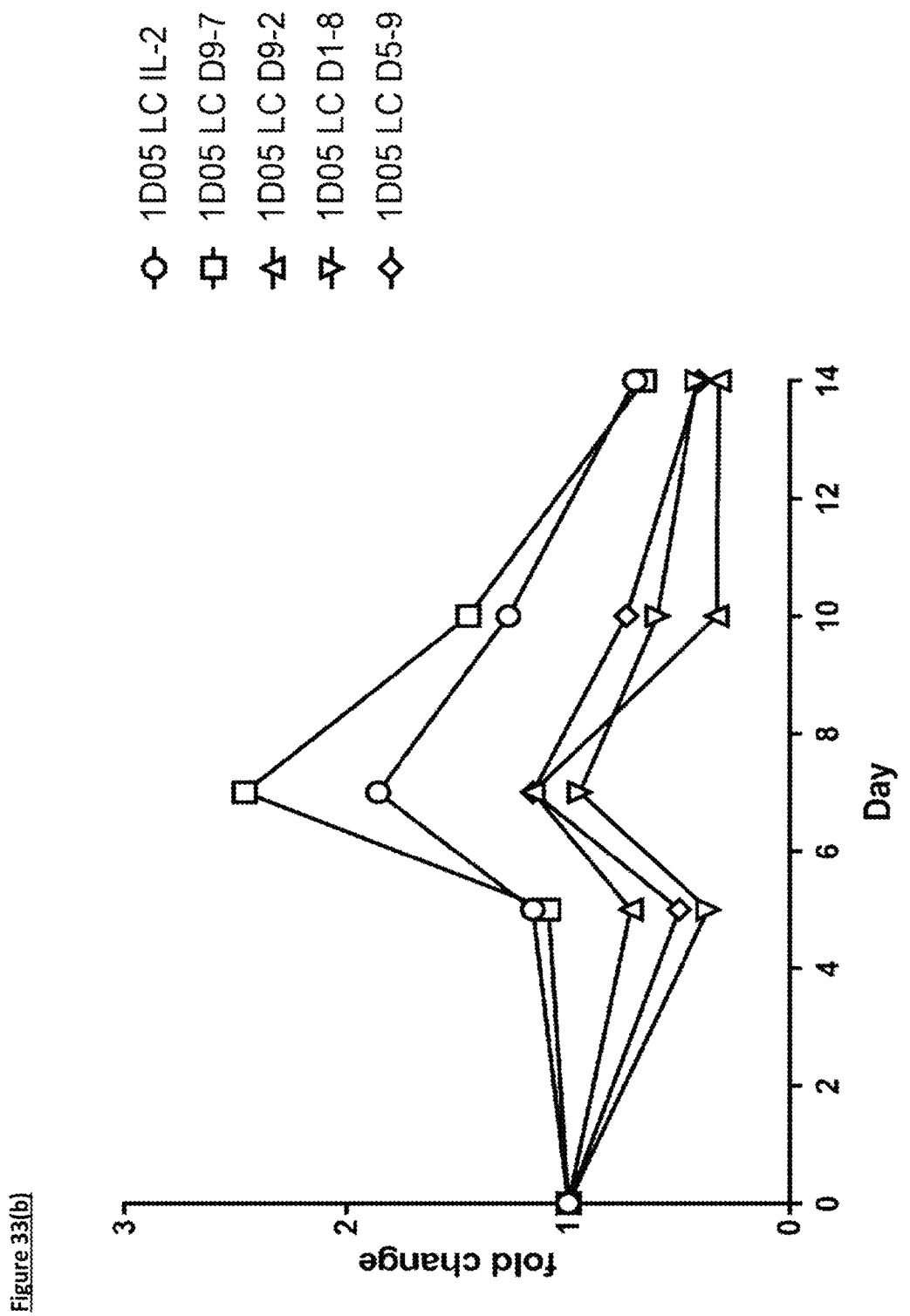

Expansion of $CD4^+$ and $CD8^+$ T-cells is shown in FIG. 33. As observed for the automated cell counts, the degree of expansion correlates well with the size of the IL-2 truncation, the greatest expansion of both T-cell subsets observed in the animal dosed with 1D05 LC ICK D9-7.

Example 20—Binding to Cell Endogenously Expressed hPD-L1 and Neutralisation of hPD-L1 Binding to PD-1 and CD80

Lead antibodies are tested for ability to bind to ES2 cells endogenously expressing hPD-L1 as well as the neutralisation of PD-L1/PD-1 interaction and PD-L1/CD80 interactions. ES2 cells endogenously expressing hPD-L1 (ATCC) are diluted in FACS buffer (PBS 1% BSA 0.1% sodium azide) and distributed to three 96-well, V-bottom plate (Greiner) at a density of $0.5-1 \times 10^5$ cells per well. Cells are washed with 150 µL PBS and centrifuged at 300 g for 3 minutes. Supernatant is aspirated and 150 µL PBS added. This wash step is repeated.

To plate 1 (PD-L1 binding), 25 µL lead antibody, reference antibody or control antibody diluted in FACS buffer is added to the washed cells. 25 µL FACS buffer is added and cells are incubated at 4° C. for 60 minutes. 150 µL FACS buffer is added and cells washed as described above. To detect anti-PD-L1 antibody binding, anti-human PE (Jackson ImmunoResearch) is diluted 1/500 in FACS buffer and 50 µL of this mixture added to cells. Cells are incubated 4° C. for 60 minutes. Cells are washed twice with 150 µL FACS buffer, centrifuging at 300 g for 3 minutes after each wash step and aspirating supernatant. Cells are fixed by addition of 50 µL 4% paraformaldehyde and overnight incubation at 4° C. Cells are washed once as above and resuspended in FACS buffer for analysis. PE signal intensity (geometric mean) is measured by flow cytometry using a Beckman Coulter Cytoflex instrument. Data is plotted as geometric mean values without further calculation.

To plate 2 (PD-1 neutralisation) 25 µL lead antibody, reference antibody or control antibody diluted in FACS buffer is added to the washed cells. 25 µL of biotinylated human PD-1 (in-house, Fc-tagged, SEQ ID No:6) is added and cells are incubated at 4° C. for 60 minutes. Biotinylation is performed in-house using Lightning Link conjugation kit (Innova Biosciences) according to manufacturer's instructions. 150 µL FACS buffer is added and cells washed as described above. To detect biotinylated PD-1, Streptavidin-Alexa Fluor 647 (AF647, Jackson ImmunoResearch) is diluted 1/500 in FACS buffer and 50 µL of this mixture added to cells. Cells are incubated at 4° C. for 60 minutes. Cells are washed twice with 150 µL FACS buffer, centrifuging at 300 g for 3 minutes after each wash step and aspirating supernatant. Cells are fixed, washed and resuspended for analysis as above. APC signal intensity (geometric mean) is measured by flow cytometry. Data is plotted as geometric mean values without further calculation.

To plate 3 (CD80 neutralisation) 25 µL lead antibody, reference antibody or control antibody diluted in FACS buffer is added to the washed cells. 25 µL biotinylated human CD80 (Fc tagged, R&D Systems, 140-B1) is added and cells are incubated at 4° C. for 60 minutes. All other steps are performed as per plate 2.

Alternatively, to simultaneously detect binding and neutralisation, ES2 cells expressing hPD-L1 are diluted in FACS buffer and are distributed to two 96-well, V-bottom plate (Greiner) at a density of 0.5-1×10$^5$ cells per well. Cells are washed with 150 µL PBS and centrifuged at 300 g for 3 minutes. Supernatant is aspirated and 150 µL PBS added. This wash step is repeated.

25 µL lead antibody, reference antibody or control antibody diluted in FACS buffer is added to the washed cells. 25 µL biotinylated human PD-1 (R&D Systems, 8986-PD-100, his-tagged) or CD80 (R&D Systems, 9050-B1-100, his-tagged) is added and cells are incubated at 4° C. for 60 minutes. 150 µL FACS buffer is added and cells washed as described above. To detect biotinylated PD-1 or CD80 and anti-PD-L1 antibody binding, streptavidin-AF647 and anti-human PE are each diluted 1:500 in FACS buffer and 50 µL of this mixture added to cells. Cells are incubated at 4° C. for 60 minutes. Cells are washed twice with 150 µL FACS buffer, centrifuging at 300 g for 3 minutes after each wash step and aspirating supernatant. Cells are fixed, washed and resuspended for analysis as above. PE and APC signal intensity (geometric mean) are measured by flow cytometry. Data is plotted as geometric mean values without further calculation. Alternatively, an anti-his tag antibody conjugated to APC (R&D Systems) may be used to detect PD-1 or CD80, or PD-1 and CD80 may be directly labelled with AF647.

Example 21—Testing of Lead Anti-PD-L1 Antibodies in Reporter Cell Bioassay

The ability of anti-PDL1 antibodies to neutralise PD-L1/PD-1 interaction on cells will be determined using a bioluminescence cell based assay (Promega®). PD-L1 aAPC/CHO-K1 cells, transfected with PD-L1 and a cell surface protein designed to promote TCR activation, are co-cultured with PD-1 expressing Jurkat cells. These cells also present a NFAT induced luciferase responsive element. Co-culture of the two cell types in the presence of an antibody able to block PD-1-PD-L1 interaction activates TCR signaling and NFAT-mediated luciferase activity.

The assay is run according to manufacturer's recommendations. Briefly, PD-L1 aAPC/CHO-K1 cells are cultured overnight in Hams F12 medium supplemented with 10% hiFBS. The next day, media is removed, effector PD-1 Jurkat cells and anti-PD-L1 antibodies are added to assay plates for 6 hours at 37° C. in RPMI 1640 supplemented with 1% hiFBS. Plates are read following 10 minutes of incubation with Bio-Glo™ on the Envision plate reader using luminescence settings. Antibody-induced luciferase activity is represented as fold induction compared to assay signal of wells showing background levels of response as defined by Equation 8. $EC_{50}$ values are calculated using a 4-parameter logistic fit (Equation 4).

Fold induction=sample well/basal luciferase response

Basal luciferase response=value from wells containing PD-L1 CHO-K1 cells and PD-1 Jurkat cells     Equation 8

Example 22—Pharmacokinetic Study of Lead Antibodies in hPD-L1 Expressing Mice

Lead antibodies, in human IgG1 effector enabled format (i.e. having a constant region of wild type IgG1, Seq ID No:341), are dosed intra-peritoneally at 10 mg/kg in mice expressing human PD-L1, eight mice per antibody. Blood samples are taken pre-treatment and at 2, 4, 8, 12, 24, 48, 72, 96, 192, 336, 508 and 672 hours. Serum is prepared and samples frozen until analysis. Samples will be analysed according to the method described for detection of antibody in Example 18 with the following exception: serum from C57BL/6 mice will be used as the vehicle in which to prepare standard curves and blanks. Minimum required dilution will differ from Example 18 due to the larger dose administered; this will be determined empirically.

Example 23—Pharmacokinetic Study of Lead Antibodies in Non-Human Primates

Lead antibodies, in human IgG1 effector enabled format (i.e. having a constant region of wild type IgG1, Seq ID No:341), are dosed intravenously at 10 mg/kg in male cynomolgus monkeys, three animals per antibody. Blood samples are taken pre-treatment and at 2, 4, 8, 12, 24, 48, 72, 96, 192, 336, 508 and 672 hours. Serum is prepared and samples frozen until analysis. Samples will be analysed according to the method described for detection of antibody in Example 18. Minimum required dilution will differ from Example 18 due to the larger dose administered; this will be determined empirically.

Example 24: Lead Antibody Activity in a Mouse B Cell:T-Cell Hybridoma Assay

Antibodies were tested in a murine B cell:T-cell hybridoma co-culture assay to assess induction of IL-2. 50 µL of human PD-L1 (SEQ ID No:1) transfected LK35.2 mouse B-lymphocyte hybridoma cells (ATCC) prepared in DMEM (Gibco) supplemented with 1% Foetal Bovine Serum (Gibco) were treated with 10 µM Ovalbumin$_{323-329}$ peptide (Thermo Scientific) and dispensed at a density of $2\times10^4$ cells/well in a 96-well tissue culture treated plate (Costar). Ovalbumin peptide loaded cells were then mixed with 50 µL 1:3 titration series of anti-PD-L1 antibodies or anti-ICOS/PD-L1 bi-specific antibodies in a mAb$^{2™}$ format from 30 nM for 9 concentration points in DMEM supplemented with 1% Foetal Bovine Serum.

Following 1 hour incubation at 37° C. 5% $CO_2$, 100 µL of murine T-helper hybridoma cell line DO-11-10 (National Jewish Health) cultured overnight in DMEM (Gibco) supplemented with 1% Foetal Bovine Serum (Gibco) were added to assay plate at $2\times10^4$ cells/well. LK35.2/DO-11-10 co-culture was incubated overnight at 37° C. 5% $CO_2$ before supernatant was collected to assess production of mouse IL-2. Cells treated with 1 or 0.1× working stock of cell stimulation cocktail (eBioscience) were used as positive control for murine IL-2 production.

Figure 23A:
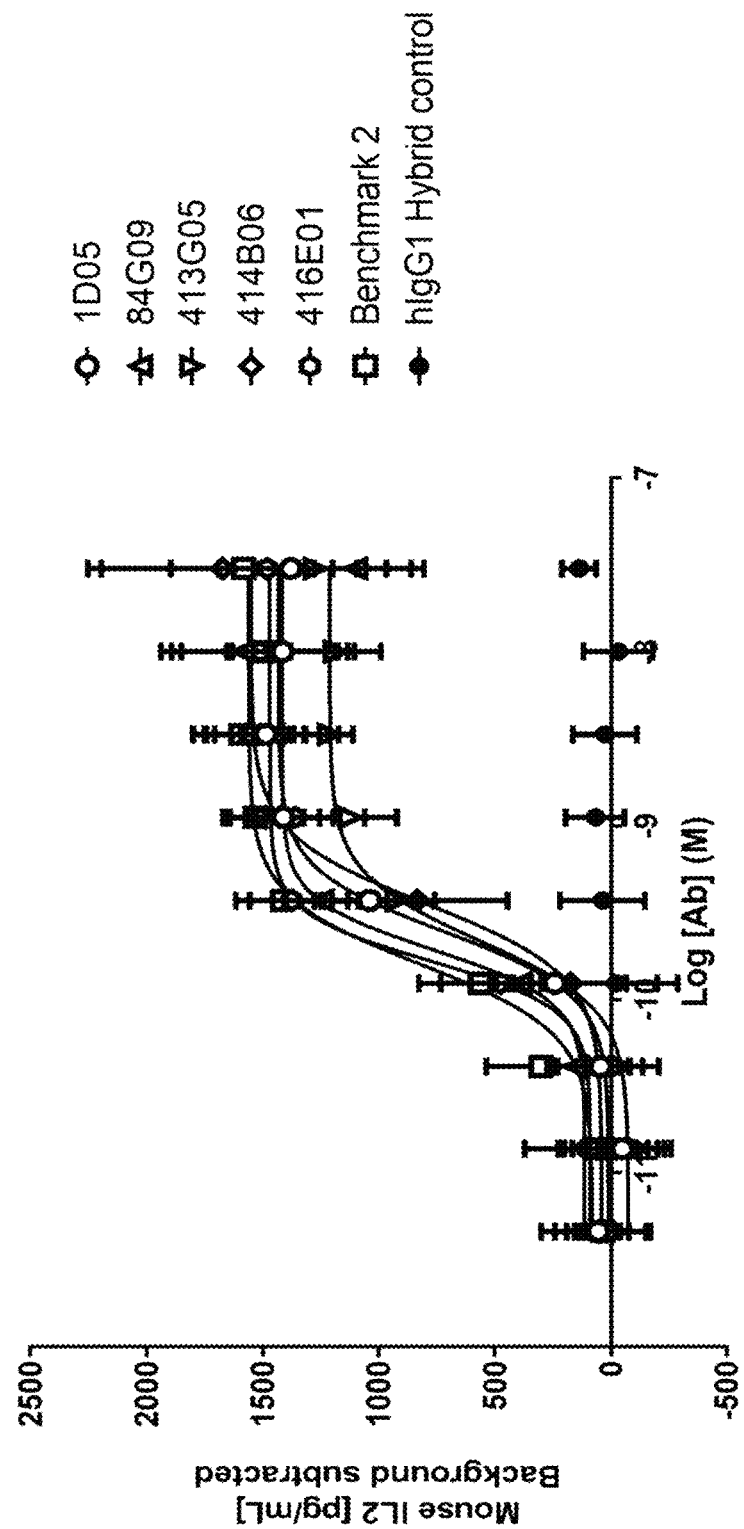
FIG. 23(a): Induction of IL-2 in a murine T-cell hybridoma assay. Human PD-L1 transfected LK35.2 cells were loaded with ovalbumin peptide and co-cultured overnight with DO-11-10 T-cell hybridoma cells in the presence of anti-PD-L1 antibodies or controls, prior to collection of supernatants and analysis of IL-2 release. Each data point indicates background-corrected mean IL-2 release from three independent experiments ±standard deviation
Figure 23B:
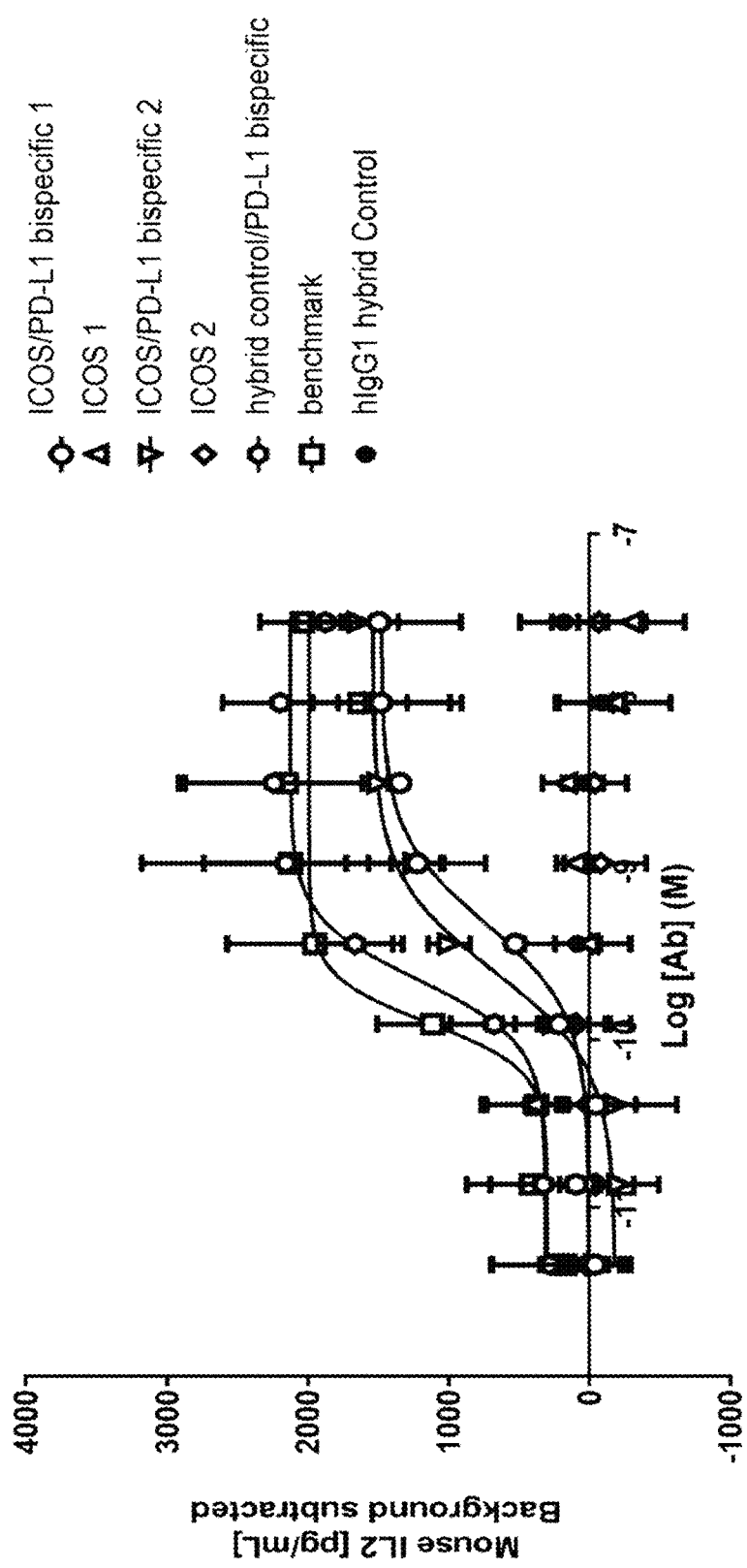
FIG. 23(b): Induction of IL-2 in a murine T-cell hybridoma assay. Human PD-L1 transfected LK35.2 cells were loaded with ovalbumin peptide and co-cultured overnight with DO-11-10 T-cell hybridoma cells in the presence of ICOS/PD-L1 bi-specific molecules, or individual antibodies, prior to collection of supernatants and analysis of IL-2 release. Each data point indicates background-corrected mean IL-2 release from three independent experiments ±standard deviation

Mouse IL-2 quantification was performed using the mouse IL-2 Duoset ELISA kit (R&D Systems) following manufacturer's protocol, modified to include streptavidin-Europium as the detection reagent (DELFIA®). Briefly, assay plates were coated overnight at 4° C. with provided capture antibody prepared in PBS at 1 µg/mL. Plates were washed three times with PBS-Tween (0.1% v/v) before adding 200 µL of 1% w/v bovine serum albumin (BSA, Sigma) in PBS for 1 hour at room temperature. 50 µL cell supernatants were added to assay plates following a washing step performed as described previously. Following one hour incubation, 50 µL of provided detection antibody at 200 µg/mL prepared in 0.1% w/v BSA in PBS was added and plates were incubated for a further hour. Plates were washed as described above and 50 µL of DELFIA® Eu-N1 streptavidin diluted 1:500 from stock solution in DELFIA® assay buffer (Perkin Elmer) were added to all wells for 1 hour. An additional washing step was performed using DELFIA wash buffer (0.5 M Tris HCL (Gibco), 1% Tween v/v (Sigma)) before the addition of 50 µL DELFIA® Enhancement Solution (Perkin Elmer). The plate was incubated for 5 minutes at room temperature protected from the light and read at 615 nm using appropriate settings for DELFIA® time resolved fluorescence on an Envision plate reader (Perkin Elmer). The concentration of mouse IL-2 was interpolated from a standard curve run alongside test samples. Final plotted values were calculated using Equation 9, where background signal was calculated using assay signal of co-culture cells treated with 50 µL of media only. Results are shown in FIG. 23. All antibodies potently enhance production of IL-2 in this co-culture system.

Equation 9= Mouse IL-2 (pg/mL)−Background

TABLE 15

EC$_{50}$ values for induction of IL-2 by of PD-L1 antibodies in a murine T cell hybridoma assay

| Antibody name | EC$_{50}$ (nM) | | |
|---|---|---|---|
| | n = 1 | n = 2 | n = 3 |
| 1D05 | 0.33 | 0.21 | 0.21 |
| 84G09 | 0.24 | 0.14 | 0.17 |
| 413G05 | 0.29 | 0.11 | 0.29 |
| 414B06 | 0.59 | 0.30 | 0.18 |
| 416E01 | 0.19 | 0.15 | 0.14 |
| benchmark 2 | 0.26 | 0.13 | 0.13 |

TABLE 16

EC$_{50}$ values for induction of IL-2 by ICOS/PD-L1 bi-specific mAb$^{2\ ™}$ antibodies in a murine T cell hybridoma assay

| Bispecific antibody name | EC$_{50}$ (nM) | | |
|---|---|---|---|
| | n = 1 | n = 2 | n = 3 |
| ICOS/PD-L1 bispecific 1 | 0.386 | n/a | 0.888 |
| Hybrid Control/PD-L1 bispecific | 0.247 | 0.311 | 0.162 |
| ICOS/PD-L1 bispecific 2 | 0.338 | 0.217 | 0.229 |
| PD-L1 benchmark | 0.122 | 0.128 | 0.123 |

Figure 24A:
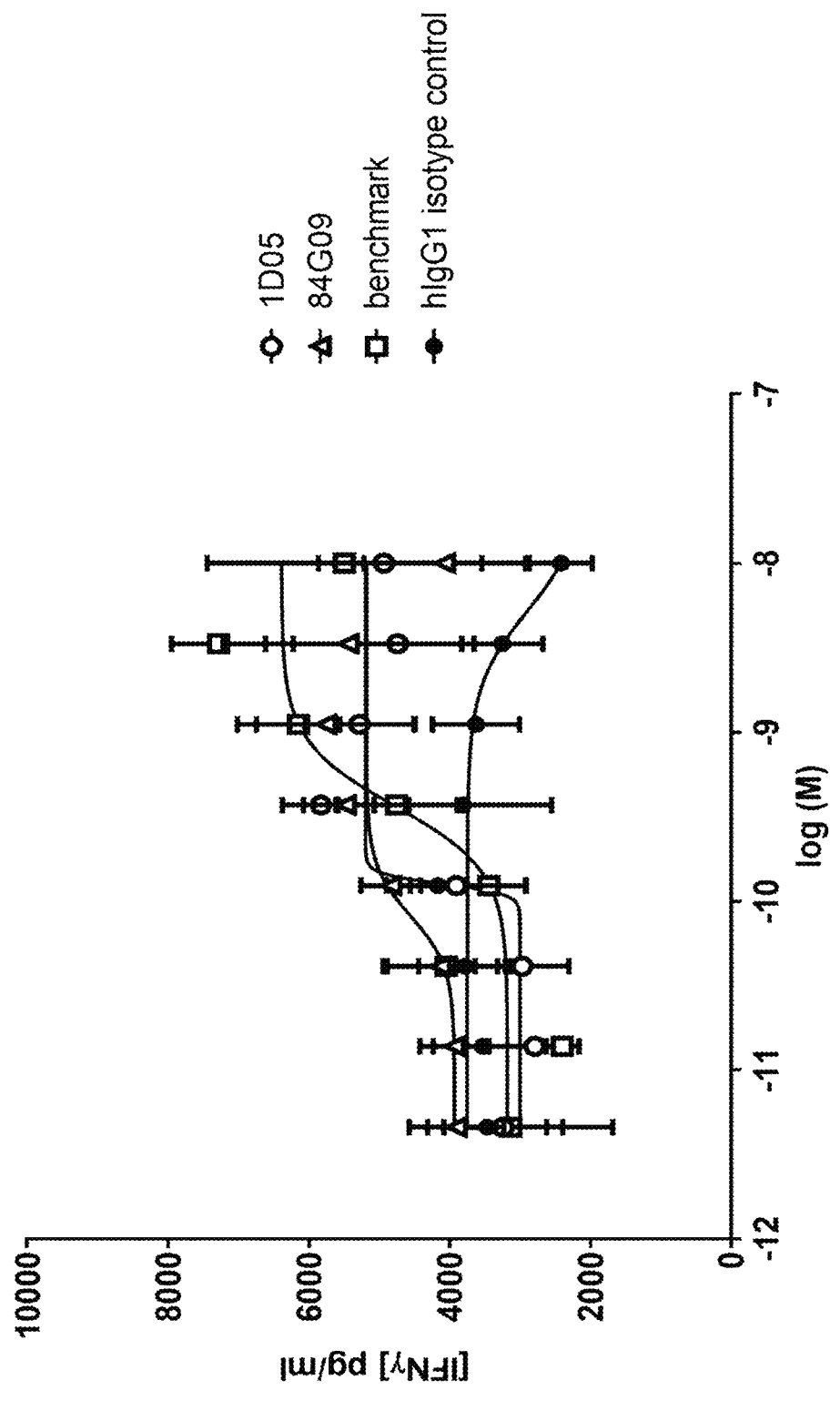
FIG. 24(a): Induction of IFNγ in a DC-T-cell MLR assay. Monocyte derived dendritic cells (DC) were activated with E. coli LPS and co-cultured with allogeneic $CD3^+$ T-cells at a 1:1 ratio. IFNγ was measured by DELFIA assay after 5 days of co-culture. Data is from a single experiment
Figure 24B:
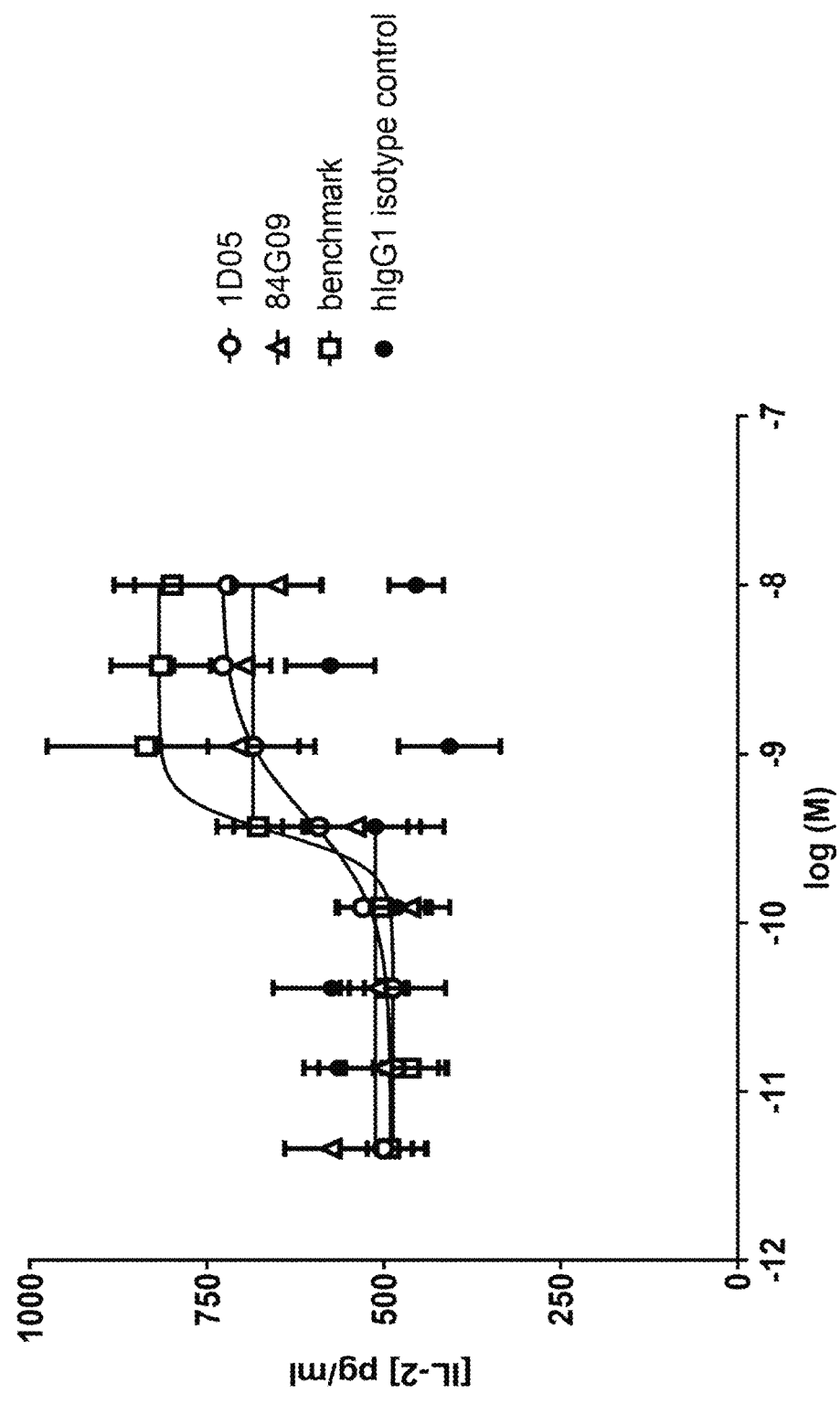
FIG. 24(b): Induction of IL-2 in a DC-T-cell MLR assay. Monocyte derived dendritic cells (DC) were activated with E. coli LPS and co-cultured with allogeneic $CD3^+$ T-cells at a 1:1 ratio. IL-2 was measured by DELFIA assay after 3 days of co-culture. Data is from a single experiment

Example 25—Testing of Lead Antibodies in an Activated DC-T-Cell Mixed Lymphocyte Reaction Monocytes were isolated from cryopreserved PBMCs by negative selection methods using a Monocyte Isolation Kit and the MACS™ magnetic separation system (Miltenyi Biotec). Monocytes were resuspended in RPMI 1640 medium containing 10% hiFBS and 100 ng/mL GM-CSF and IL-4 (both Peprotech). Cells were cultured for 5 days in non-TC treated 6-well plates (Greiner) to induce differentiation of DCs, before addition of 100 ng/mL lipopolysaccharide from *E. coli* 055: B5 (Sigma) to activate the DCs. Cells were harvested after 24 hours of activation, and washed once with PBS to remove LPS, and resuspended at $10^6$/mL in RPMI 10% hiFBS. Allogeneic CD3$^+$ T-cells were isolated from cryopreserved PBMC using a Pan T-Cell Isolation kit and the MACS system as above, and resuspended at $2\times10^6$/mL in RPMI 10% hiFBS. Serial dilutions of selected antibodies (1:3) from 10 nM were prepared in RPMI 10% hiFBS and 50 µL added to 96-well, flat-bottomed TC plates in triplicate. DCs (100 µL) and T-cells (50 µL) were added to plates and incubated at 37° C., 5% $CO_2$ for five days. Supernatants were removed after three days for measurement of IL-2, and five days for measurement of IFNγ. Supernatants were stored at −20° C. until use. Cytokine production was measured with the R&D Systems Human IFNγ and IL-2 Duoset® ELISA, using DELFIA® Eu-N1 Streptavidin detection. Results are shown in FIG. 24.

Example 26—Multi-Dose Study of Immunocytokines in Cynomolgus Monkeys

Pharmacology and toxicity of two immunocytokines, 1D05 D9-7 ICK and 1D05 D1-8 ICK (as described in Example 14), will be assessed in a multi-dose study in cynomolgus monkeys. Male juvenile monkeys are dosed with 1 mg/kg/dose according to two different regimens: Regimen 1—animals dosed on day 0 and day 14; regimen 2—animals dosed on day 0, 2, 14 and 16. Two animals will be dosed per group and monitored for 28 days. Treatment groups are shown in Table 17.

TABLE 17

Treatment groups for multi-dose study

| Treatment group | Construct | Regimen | Animals per group |
|---|---|---|---|
| 1 | 1D05 D9-7 ICK | 1 | 2 |
| 2 | 1D05 D9-7 ICK | 2 | 2 |
| 3 | 1D05 D1-8 ICK | 1 | 2 |
| 4 | 1D05 D1-8 ICK | 2 | 2 |

Heart rate, body temperature, respiration rate and blood pressure will be measured 1 hour and 4 hours after dosing. Body weight will be monitored daily. Cytokines will be analysed on days 2, 5, 7, 10, 14, 16, 19, 21, 24 and 28, and pre-treatment. Haematology measurements will be performed on days 2, 5, 7, 10, 14, 16, 19, 21, 24 and 28, and pre-treatment. Detection of soluble CD25 will be performed on days 3, 7 and 10, 17, 21, 24, and pre-treatment. Immunophenotyping will be performed on days 7, 10, 14, 24 and 28, and pre-treatment, according to the panel described in Example 19. Samples for pharmacokinetic (PK) analysis will be taken at the following timepoints at each infusion: pre-treatment, end of infusion, and at 8, 16, 24, 32, 40, 48, 72, and 96 hours.

Example 27: Immunocytokine Efficacy Study in a Syngeneic Tumour Model

An efficacy study will be performed using a CT-26 mouse tumour model, to compare surrogate immunocytokine activity with unmodified antibody, and to assess the role of effector function. On the day of implantation, BALB/c mice are injected subcutaneously into mice on the rear right flank with $1 \times 10^5$ CT-26 cells/animal. Treated groups will receive their first dose of antibody or relevant control (all dosed intraperitoneally at 10 mg/kg) 6 days post implantation of the tumour cells and will be dosed three times a week for a total of two weeks. Tumour development will be monitored three times a week using digital calipers measuring in two dimensions until end of the study. Tumour volumes (mm$^3$) will be estimated using a standard formula $(L \times W^2)/2$ (with L being the larger diameter, and W the smaller diameter of the tumour). Mice are kept on studies until their tumours developed to a mean diameter of 12 mm or they reached the one humane endpoints outlined in the study protocol. The humane endpoint survival statistics will be calculated using the Kaplan-Meier method with Prism.

TABLE 18

Treatment groups for efficacy study

| Groups | Number of animals | Treatment |
|---|---|---|
| 1 | 10 | 10 mg/kg hybrid control huIgG1$_{LAGA}$ (constant region SEQ ID No: 205) |
| 2 | 10 | 10 mg/kg hybrid control huIgG1$_{LAGA}$ IL-2 |
| 3 | 10 | 10 mg/kg anti-PD-L1 huIgG1$_{LAGA}$ |
| 4 | 10 | 10 mg/kg anti-PD-L1 huIgG1$_{LAGA}$ IL-2 |
| 5 | 10 | 10 mg/kg anti-PD-L1 huIgG1 (constant region SEQ ID No: 340) |
| 6 | 10 | 10 mg/kg anti-PD-L1 huIgG1 IL-2 |

Example 28: Immunocytokine Efficacy Study in a T-Cell: Melanoma Cell Line Xenograft Model An efficacy study will be performed using a T-cell: A375 cell line xenograft model in NOD/SCID mice employing a refinement of the methods outlined in R. Stewart et al. Briefly HLA-A2 positive donors are selected by staining whole blood using a PE labelled anti-human HLA-A2 antibody (Biolegend), followed by red blood cell lysis and analysis by flow cytometry. Primary human CD4$^+$ and CD8$^+$ T-cells will then be isolated, using an EasySep human CD4$^+$ or CD8$^+$ T-cell enrichment kit, Stemcell Technologies, Cat 19052/3). The CD4$^+$ and CD8$^+$ cells are then cultured separately for 20 days on a monolayer of mitomycin C treated A375 cells in the presence of IL-2 and IL-7. T-cells are plated on a fresh feeder layer of A375 at day 10. On day 20, the cells are cryopreserved and stored in liquid nitrogen till required. The day before implantation, T-cells are thawed and cultured in medium plus cytokines overnight. On the day of implantation, the CD4$^+$ and CD8$^+$ cells are counted and mixed together in a 1:1 ratio. The T-cells are mixed with fresh A375 tumour cells at 1:6 ratio and injected subcutaneously into mice on the rear right flank. Treated groups will receive their dose of antibody, immunocytokine or relevant control (all dosed intraperitoneally at 10 mg/kg) one-hour post implantation of the T-cells and tumour cells. Tumour development will be monitored three times a week using digital calipers measuring in two dimensions until end of the study. Tumour volumes (mm$^3$) will be estimated using a standard formula $(L \times W^2)/2$ (with L being the larger diameter, and W the smaller diameter of the tumour). Mice are kept on studies until their tumours developed to a mean diameter of 12 mm or they reached the one humane endpoints outlined in the study protocol. The humane endpoint survival statistics will be calculated using the Kaplan-Meier method with Prism. This approach will be used to determine which treatment is/are associated with improved survival. Subsequent studies will compare the immunocytokine constructs with different IL-2 activities.

TABLE 19

Treatment groups for efficacy study

| Groups | Number of animals | Treatment |
|---|---|---|
| 1 | 10 | $2 \times 10^6$ A375 Cells |
| 2 | 10 | CD4$^+$/CD8$^+$ T cells:A375 Cells |
| 3 | 10 | 10 mg/kg hybrid control CD4$^+$/CD8$^+$ T cells:A375 Cells |
| 4 | 10 | 10 mg/kg hybrid control IL-2 CD4$^+$/CD8$^+$ T cells:A375 Cells |
| 5 | 10 | 200,000 IU recombinant human IL-2 CD4$^+$/CD8$^+$ T cells:A375 Cells ($2 \times 10^6$ A375 Cells) |
| 6 | 10 | 10 mg/kg 1D05 CD4$^+$/CD8$^+$ T cells:A375 Cells ($2 \times 10^6$ A375 Cells) |
| 7 | 10 | 10 mg/kg 1D05 LC IL-2 CD4$^+$/CD8$^+$ T cells:A375 Cells ($2 \times 10^6$ A375 Cells) |

Example 29: Activity of Lead Antibodies in a Reporter Assay of Effector Function The antibody-dependent cell-mediated cytotoxicity (ADCC) activity of selected antibodies was evaluated using an ADCC Reporter Bioassay. ES2 cells (ATCC CRL-1978)

endogenously expressing human PD-L1 were co-incubated with effector cells (engineered Jurkat cells stably expressing human FcγRIIIa receptor—V158, Promega) that produce luciferase in a concentration-dependent manner in the presence of an ADCC-enabled antibody. The soluble luciferase activity is assessed by measuring the luminescence produced as the luciferase transformed a luminogenic substrate into a luminescent product.

Immediately prior to the assay, target cells (ES2) were centrifuged and resuspended in RPMI 1640+10% Ultra low IgG FBS (Thermo Fisher Scientific) and plated at 30,000 cells/well (10 µL/well) in 384-well white bottom plates. Jurkat NFAT luciferase reporter (effector) cells were resuspended in RPMI 1640+10% Ultra low IgG FBS and added to the target cells at 10,000 cells per well (10 µL/well). Eleven three-fold serial dilutions of antibodies were prepared from 2.2 nM in RPMI 1640+10% Ultra low IgG FBS and added to the target cells (10 µL/well). The plates were incubated overnight at 37° C., 5% $CO_2$, after which a luminogenic BioGlo substrate was added directly to the wells (30 µL/well) and luminescence quantified on an Envision (Perkin Elmer) plate reader.

Relative light unit (RLU) values from the raw data (Envision reads) were normalised to 'Fold of induction using the following equation:

$$\text{fold of induction} = \frac{(RLU \text{ (induced)} - RLU \text{ (background)})}{RLU \text{ (background)}} \qquad \text{Equation 10}$$

Figure 34:
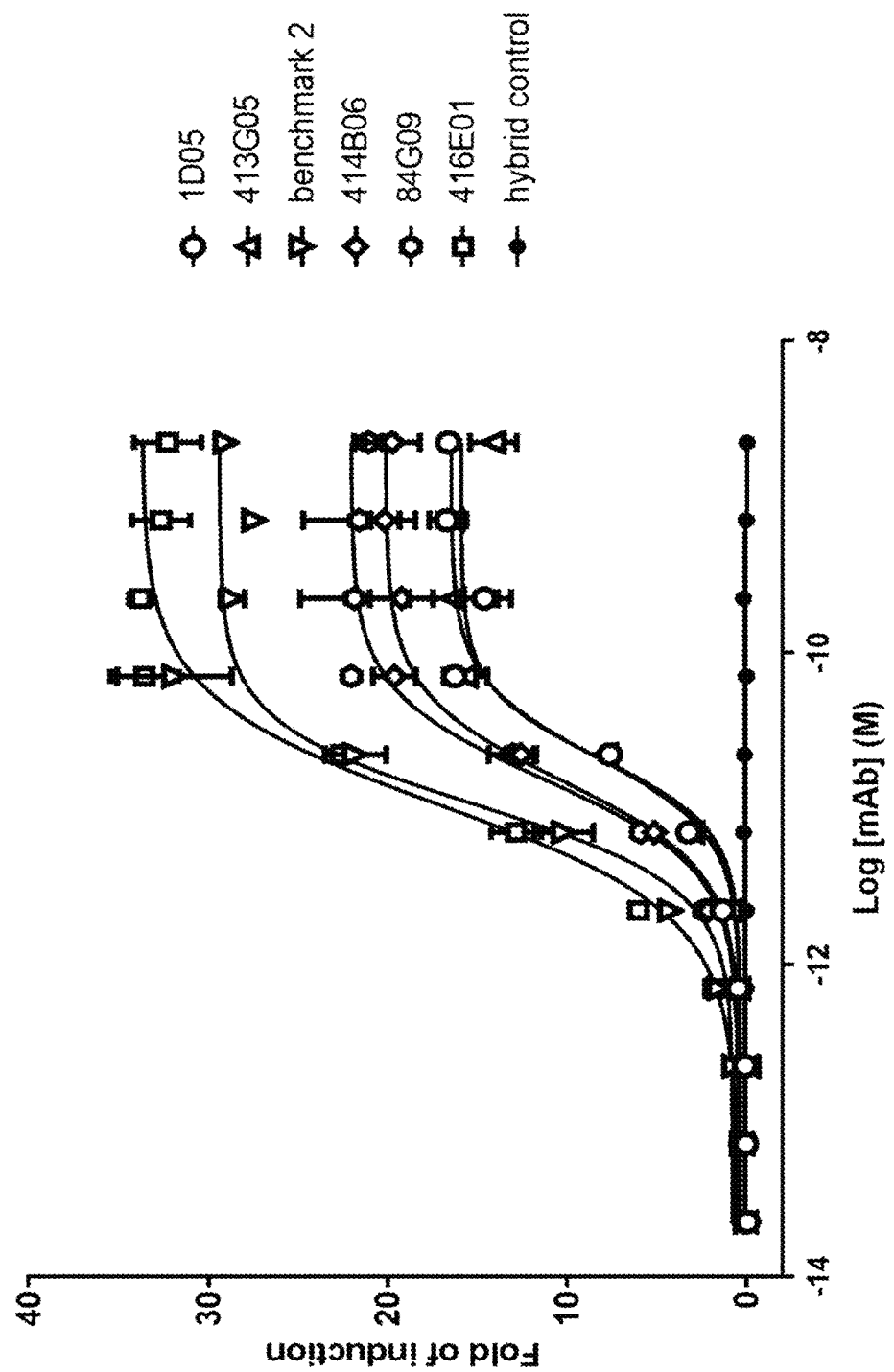
FIG. 34: Effector function of lead antibodies in a reporter cell assay. PD-L1 expressing target cells (ES2) were co-cultured overnight with Jurkat cells, engineered to express NFAT-induced luciferase and Fc$\gamma$RIIIa, in the presence of PD-L1 antibodies. Each data point indicates mean fold induction of relative light units ±standard deviation. Data is from one representative experiment, of three independent experiments

Data was plotted in GraphPad Prism, using a 4-parameter logistic fit, and a representative experiment is shown in FIG. 34. Results are summarised in Table 20. All antibodies tested induced luminescence, suggesting that all have the capacity to induce killing of target cells by ADCC. Although $EC_{50}$ values are generally similar, 416E01 induces a highest maximum level of luminescence.

TABLE 20

Summary of data from reporter cell assay

| Antibody name | $EC_{50}$ (pM) | | | max fold induction | | |
|---|---|---|---|---|---|---|
| | n = 1 | n = 2 | n = 3 | n = 1 | n = 2 | n = 3 |
| 1D05 | 24.14 | 21.53 | 34.71 | 13.70 | 16.69 | 25.04 |
| 84G09 | 24.95 | 15.30 | 25.90 | 16.33 | 22.21 | 33.82 |
| 413G05 | 21.92 | 20.87 | 27.52 | 13.22 | 16.41 | 23.45 |
| 414B06 | 19.08 | 15.02 | 24.24 | 10.94 | 20.15 | 31.51 |
| 416E01 | 79.98 | 10.58 | 22.86 | 32.11 | 33.76 | 60.16 |
| benchmark 2 | 24.81 | 10.56 | 24.93 | 19.55 | 31.88 | 43.23 |

Example 30: Binding of Lead Antibodies to Cell-Expressed Cynomolgus PD-L1

Figure 35:
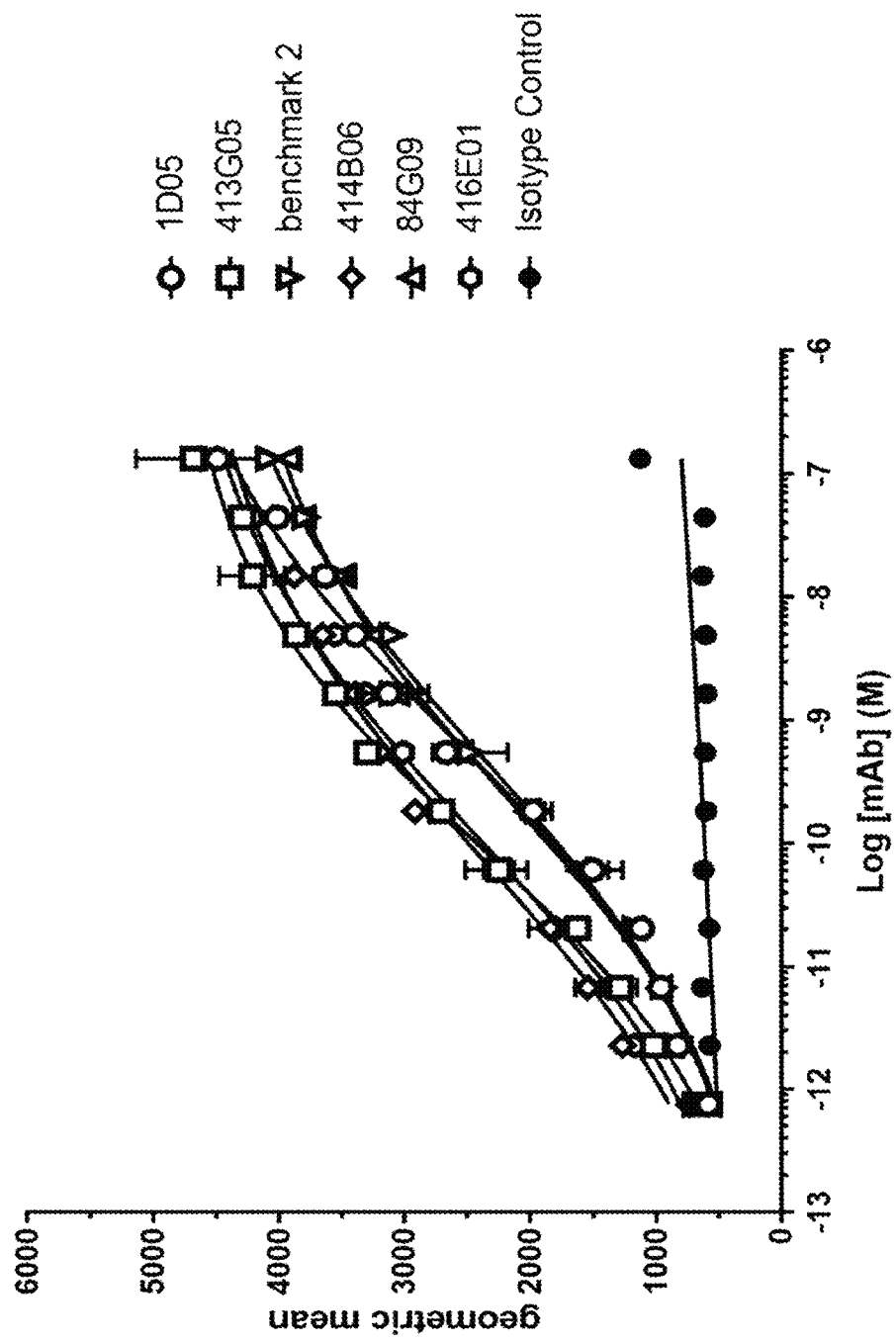
FIG. 35: Binding of lead antibodies to cell-expressed cynomolgus PD-L1. Antibodies were titrated on CHO cells expressing cynomolgus PD-L1, and bound antibody detected with an anti-human IgG AlexaFluor 647. Data is from a single experiment

CHO-S cells transfected with cynomolgus PD-L1 were diluted in FACS buffer (PBS+1% w/v BSA+0.1% w/v sodium azide) and were distributed to a 96-well V-bottom plate (Greiner) at a density of $1 \times 10^5$ cells per well. Antibody titrations were prepared from 133 nM working concentration as a 1/3 dilution series in FACS buffer. Plates were centrifuged at 300×g for 3 minutes and supernatant aspirated. 50 µL per well of antibody titrations were added to cells and incubated at 4° C. for 1 hour. Cells were washed with 150 µL of PBS and centrifuged at 300 g for 3 minutes. Supernatant was aspirated and 150 µL PBS added per well. This wash step was repeated. Presence of bound antibody was detected by addition of 50 µL per well of anti-Human IgG AlexaFluor 647 (Jackson ImmunoResearch) diluted 1/500 in FACS buffer. Cells were incubated for 1 hour at 4° C. in the dark. Cells were washed as previously described. To fix cells, 50 µL per well of 4% v/v paraformaldehyde was added and cells incubated for 20 minutes at 4° C., cells were pelleted by centrifugation at 300×g and the plates resuspended in 75 µL PBS. Geometric mean was measured by flow cytometry using a Beckman Coulter CytoFLEX instrument. Alexa Fluor 647 was excited by a 637 nm laser and detected in the Red channel with a 660/20 bandpass filter. Data was analysed using FlowJo software and is shown in FIG. 35. All antibodies bind to cynomolgus PD-L1 expressed on cells.

Example 31: Binding to CHO-Expressed hPD-L1 and Neutralisation of hPD-L1 Binding to PD-1 and CD80

CHO cells untransfected (referred to as WT) or transfected with, hPD-L1 expressing recombinant human PD-L1 were diluted in FACS buffer (PBS 1% BSA 0.1% sodium azide) and distributed to three 96-well, V-bottom plate (Greiner) at a density of $1 \times 10^5$ cells per well. Cells are washed with 150 µL PBS and centrifuged at 300 g for 3 minutes. Supernatant is aspirated and 150 µL PBS added. This wash step is repeated.

To plate 1 (PD-L1 binding), lead antibody, reference antibody or control antibody titrations were prepared from 150 nM working concentration as a 1/3 dilution series in FACS buffer. 50 µL of antibody diluted in FACS buffer is added to the washed cells and incubated at 4° C. for 60 minutes. 150 µL FACS buffer is added and cells washed as described above. To detect anti-PD-L1 antibody binding, anti-human PE (Jackson ImmunoResearch) is diluted 1/500 in FACS buffer and 50 µL of this mixture added to cells. Cells are incubated 4° C. for 60 minutes. Cells are washed twice with 150 µL FACS buffer, centrifuging at 300 g for 3 minutes after each wash step and aspirating supernatant. Cells are fixed by addition of 100 µL 4% paraformaldehyde and 30 mins at 4° C. Cells are washed once as above and resuspended in 100 µL FACS buffer for analysis. PE signal intensity (geometric mean) is measured by flow cytometry using a Beckman Coulter Cytoflex instrument. Data is plotted as geometric mean values without further calculation.

To plate 2 (PD-1 neutralisation), biotinylated human PD-1-Fc (in-house expressed, Seq ID No:6) were prepared as a titration from 1 µM final assay concentration (FAC), 1/2 dilution series in FACS buffer. Lead antibody, reference antibody or control antibody titrations were prepared from 300 nM working concentration, 150 nM FAC, as a 1/3 dilution series in FACS buffer. Biotinylated PD-1 were diluted in FACS buffer to 60 nM working concentration, 30 nM FAC. 25 µL PD-1 and 25 µL antibody solution (or 50 µL of PD1 titration) were added to cells and incubated at 4° C. for 1 hour. Biotinylation is performed in-house using Lightning Link conjugation kit (Innova Biosciences) according to manufacturer's instructions. 150 µL FACS buffer is added and cells washed as described above. To detect biotinylated PD-1, Streptavidin-Alexa Fluor 647 (AF647, Jackson ImmunoResearch) is diluted 1/500 in FACS buffer and 50 µL of this mixture added to cells. Cells are incubated at 4° C. for 60 minutes. Cells are washed twice with 150 µL FACS buffer, centrifuging at 300 g for 3 minutes after each wash step and aspirating supernatant. Cells are fixed, washed and resuspended for analysis as above. APC signal intensity (geometric mean) is measured by flow cytometry using a Beckman Coulter CYTOFLEX instrument. Data is plotted as percentage of receptor binding.

To plate 3 (CD80 neutralisation) Biotinylated human CD80 (Fc tagged, R&D Systems, 140-B1) were prepared as a titration from 1 µM final assay concentration (FAC), 1/2 dilution series in FACS buffer. Lead antibody, reference antibody or control antibody titrations were prepared from 300 nM working concentration, 150 nM FAC, as a 1/3 dilution series in FACS buffer. Biotinylated CD80 were diluted in FACS buffer to 60 nM working concentration, 30 nM FAC. 25 µL CD80 and 25 µL antibody solution (or 50 µL of CD80 titration) were added to cells and incubated at 4° C. for 1 hour. All other steps are performed as per plate 2.

Percentage of receptor binding (flow cytometry)

Based on geometric mean fluorescence $$\% \text{ of specific binding} = \frac{\text{sample value} - \text{non-specific binding}}{\text{total binding} - \text{non-specific binding}} \times 100 \quad \text{Equation 11}$$

Total binding = biotinylated PD-1 or
CD80 only (Hybrid Control at 150 nM FAC)

Non-specific binding = no PDL1 binding,
(benchmark 2 at 150 nM FAC)

Figure 36A:
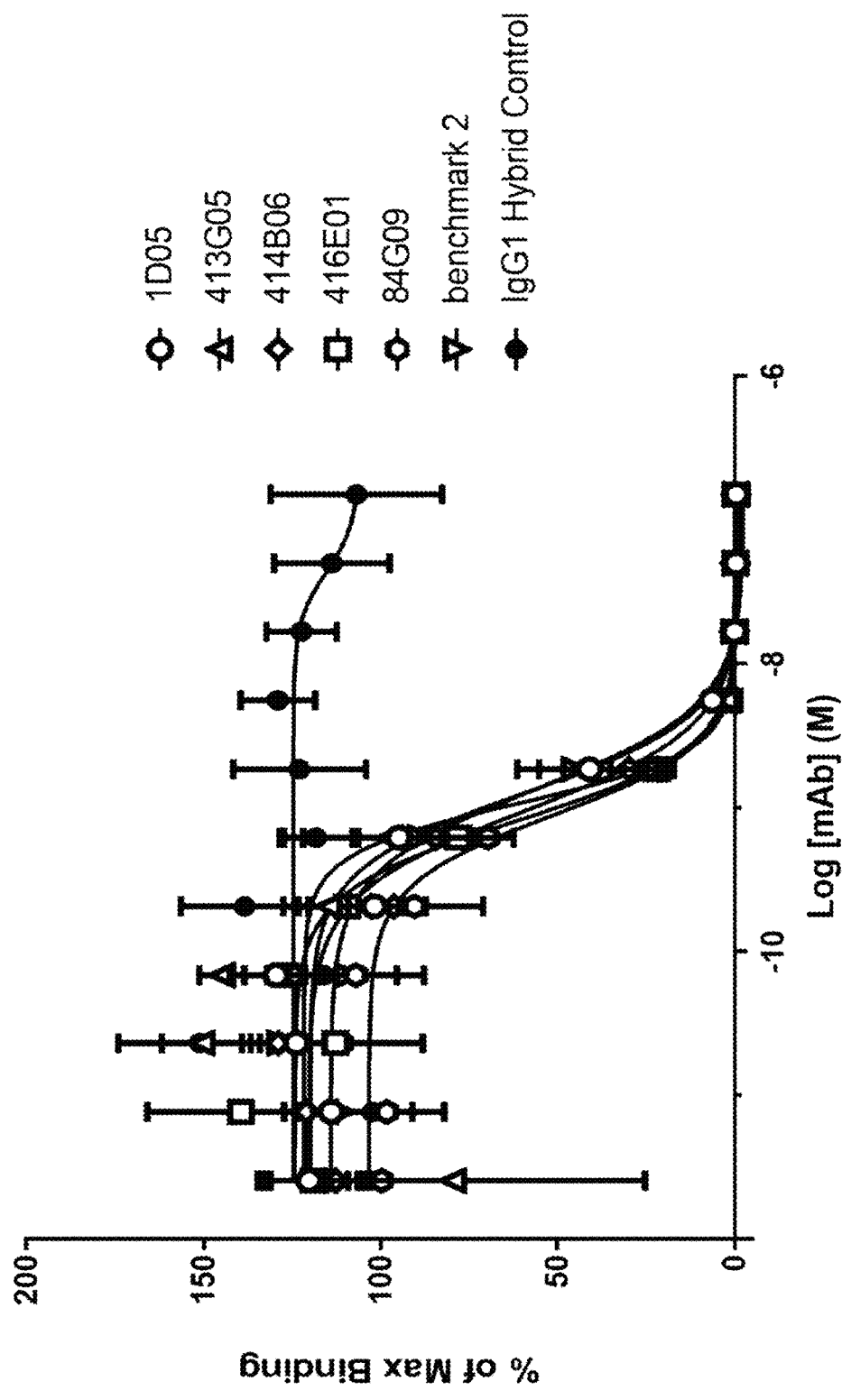
FIG. 36(a): Human PD-L1 CHO-S FACS neutralisation with PD-1 receptor. Neutralisation profiles of lead antibodies compared to a benchmark anti-PD-L1 antibody and isotype control. Data representative of two independent experiments
Figure 36B:
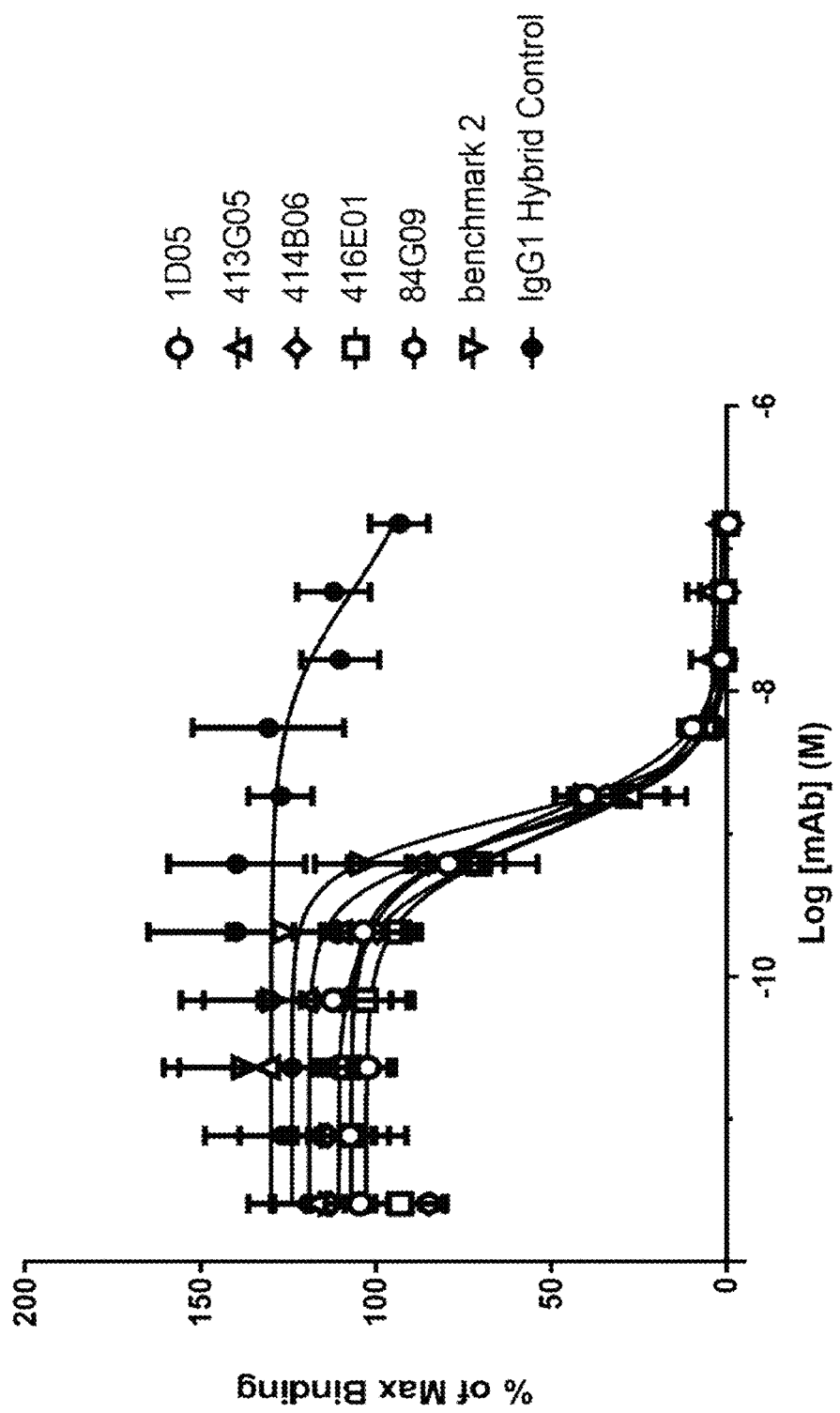
FIG. 36(b): Human PD-L1 CHO-S FACS neutralisation with CD80 receptor. Neutralisation profiles of lead antibodies compared to a benchmark anti-PD-L1 antibody and isotype control. Data representative of two independent experiments

Results are shown in FIG. 36 and in Table 21. All lead antibodies neutralise interactions of PD-L1 with both PD-1 and CD80.

TABLE 21

Summary of neutralisation of PD-1 and CD80 interactions with PD-L1

| Antibody name | PD-1 IC$_{50}$ (nM) | | CD80 IC$_{50}$ (nM) | |
|---|---|---|---|---|
| | n = 1 | n = 2 | n = 1 | n = 2 |
| 1D05 | 1.27 | 1.46 | 1.15 | 1.46 |
| 84G09 | 0.89 | 1.41 | 1.11 | 1.41 |
| 413G05 | 1.07 | 1.17 | 1.09 | 1.17 |
| 414B06 | 0.95 | 1.22 | 1.26 | 1.22 |
| 416E01 | 0.81 | 0.89 | 1.04 | 0.89 |
| benchmark 2 | 1.36 | 1.46 | 1.27 | 1.46 |

Example 32: Effector Function of Lead Antibodies in a Primary NK Cell ADCC Assay Activity of antibodies to kill PD-L1 expressing target cells via ADCC (antibody-dependent cell-mediated cytotoxicity) is measured by DELFIA cytotoxicity assay (Perkin Elmer) using human primary NK cells as effectors and ES2 as PD-L1$^+$ target cells.

This method is based on loading target cells with an acetoxymethyl ester of fluorescence enhancing ligand (BATDA) which quickly penetrates the cell membrane. Within the cell the ester bonds are hydrolysed to form a hydrophilic ligand (TDA) which no longer passes the membrane. After cytolysis the ligand is released and can be detected by addition of Europium which forms with the BATDA a highly fluorescent and stable chelate (EuTDA). The measured signal correlates directly with the degree of cell lysis.

ES2 cells are resuspended at $10^6$/mL in assay medium (RPMI+10% ultra-low IgG FBS, from Gibco) and loaded with 5 µL/mL of BATDA reagent (Perkin Elmer) for 30 min at 37° C. Cells were then washed 3 times with 50 mL PBS (300×g for 5 min) and resuspended at $8 \times 10^5$/mL in assay medium supplemented with 2 mM Probenecid (Life technologies) to reduce BATDA spontaneous release from the cells. Supernatant from ES2 cells immediately after final resuspension in assay medium is used as background control.

Seven serial three-fold dilutions of PD-L1 antibodies and isotype controls are prepared in assay media+2 mM Probenecid from 4 µg/mL (4× final concentration). NK cells are negatively isolated from fresh PBMC using Human NK Cell Isolation Kit (Miltenyi Biotec) as per manufacturer's instructions and resuspended at $4 \times 10^6$/mL in assay medium+2 mM Probenecid. 50 µL of diluted Ab, 50 µL of BATDA loaded target cells, 50 µL of NK cells and 50 µL of assay medium+2 mM Probenecid (final volume of 200 µL/well) are added in each well to give an effector: target ratio of 5:1. Wells containing ES cells only or ES2 cells+ DELFIA lysis buffer (Perkin Elmer) are used to determine spontaneous and maximum release, respectively.

Cells are incubated at 37° C., 5% CO$_2$ for 4 hours before centrifugation of plates for 5 min at 500×g, and transfer of 50 µL of cell-free supernatant into a DELFIA microtitration Plates (Perkin Elmer). 200 µL of DELFIA Europium solution (Perkin Elmer) was added to the supernatants and incubated for 15 min at Room Temperature. Fluorescent signal was then quantified with an EnVision plate reader (PerkinElmer).

Background counts are subtracted from all experimental counts. Specific release is calculated according to the following equation:

$$\% \text{ specific release} = \frac{(\text{experimental release} - \text{spontaneous release})}{(\text{maximum release} - \text{spontaneous release})} \times 100 \quad \text{Equation 12}$$

INCORPORATION BY REFERENCE

All references cited herein, including patents, patent applications, papers, text books and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention. It will be appreciated, however, that the invention may be practiced in many ways and the invention should be construed in accordance with the appended claims and any equivalents thereof.

It will be understood that particular configurations, aspects, examples, clauses and embodiments described herein are shown by way of illustration and not as limitations of the invention. Any part of this disclosure may be read in combination with any other part of the disclosure, unless otherwise apparent from the context.

SEQUENCE LISTING

| SEQ ID NO: | Name | Description | Sequence |
|---|---|---|---|
| 1 | Human PD-L1 | NCBI number: NP_054862.1 (ECD highlighted in BOLD, cytoplasmic domain underlined) | MRIFAVFIFMTYWHLLNAFTVTVPKDLYVVEYGSNMTIECKFPVEKQLDLAALIVYWEMEDKNIIQFVHGEEDLKVQHSSYRQFLARLLKDQLSLGNAALQI TDVKLQDAGVYRCMISYGGADYKRITVKVNAPYNKINQRILVVDPVTSE HELTCQAEGYPKAEVIWTSSDHQVLSGKTTTTNSKREEKLFNVTSTLRIN TTTNEIFYCTFRRLDPEENHTAELVIPELPLAHPPNERTHLVIIGAILLCLGVA LTFIFRLRKGRMDVKKCGIQDTNSKKQSDTHLEET |
| 2 | Cyno PD-L1 | NCBI number: XP_014973154.1 (ECD highlighted in BOLD) | MGWSCIILFLVATATGVHSMFTVTVPKDLYVVEYGSNMTIECKFPVEKQLDLTSLIVYWEMEDKNIIQFVHGEEDLKVQHSNYRQRAQLLKDQLSLGNAAL RITDVKLQDAGVYRCMISYGGADYKRITVKVNAPYNKINQRILVVDPVT SEHELTCQAEGYPKAEVIWTSSDHQVLSGKTTTTNSKREEKLLNVTSTLR INTTANEIFYCIFRRLDPEENHTAELVIPELPLALPPNERT |
| 3 | Human PD-L1 His | Human PD-L1 ECD with C-terminal His tag | MRIFAVFIFMTYWHLLNAFTVTVPKDLYVVEYGSNMTIECKFPVEKQLDLAALIVYW EMEDKNIIQFVHGEEDLKVQHSSYRQARLLKDQLSLGNAALQTDVKLQDAGVYR CMISYGGADYKRITVGNAPYNKINQRILVVDPVTSEHELTCQAEGYPKAEVIWTSS DHQVLSGKTTTTNSKREEKLFNVTSTLRINTTTNEIFYCTFRRLDPEENHTAELVIPE LPLAHPPNERTHHHHHH |
| 4 | Human PD-L1 Fc | Human PD-L1 ECD with C-term Fc fusion (in bold) | MRIFAVFIFMTYWHLLNAFTVTVPKDLYVVEYGSNMTIECKFPVEKQLDLAALIVYW EMEDKNIIQFVHGEEDLKVQHSSYRQRARLLKDQLSLGNAALQITDVKLQDAGVYR CMISYGGADYKRITVKVNAPYNKINQRILVVDPVTSEHELTCQAEGYPKAEVIWTSS DHQVLSGKTTTTNSKREEKLFNVTSTLRINTTTNEIFYCTFRRLDPEENHTAELVIPE LPLAHPPNERTIEGREPKSCDKTHTCPPCPAPELLGGPSVFLFPPKPKDTLM ISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |
| 5 | Cyno PD-L1 FLAG | Cynomolgus PD-L1 ECD with N-term FLAG tag | MGWSCIILFLVATATGVHSMFIVTVPKDLYVVEYGSNMTIECKFPVEKQLDLTSLIV YWEMEDKNIIQFVHGEEDLKVQHSNYRQRAQLLKDQLSLGNAALRITDVKLQDAG VYRCMISYGGADYKRITVKVNAPYNIKINQRILVVDPVTSEHELTCQAEGYPKAEVI WTSSDHQVLSGKTTTTNSKREEKLLNVTSTLRINTTANEIFYCIFRRLDPEENHTAE LVIPELPLALPPNERTDYKDDDDK |
| 6 | Human PD-1 Fc | Human PD-1 full length sequence derived from cDNA as human Fc fusion | MGWSCIILFLVATATGVHSLDSPDRPWNPPTFSPALLVVTEGDNATFTCSFSNTSE SFVLNWYRMSPSNQTDKLAAFPEDRSQPGQDCRFRVTQLPNGRDFHMSVVRARR NDSGTYLCGAISLAPKAQIKESLRAELRVTERRAEVPTAHPSPSPRPAGQKLENLY FQGIEGRMDEPKSCDKTHTCPPCPAPELLGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALPAPIEKTISKAKGQPRPEPQVYTLPP SRDELTKNQVSLTCLVKGFYPSDIAVEWESNGQPENNYKTTPPVLDSDG SFFLYSKLTVDKSRWQQGNVFSCSVMHEALHNHYTQKSLSLSP |
| 7 | 84G09 - CDRH1 (IMGT) | Amino acid sequence of CDRH1 of 84G09 using IMGT | GFTFDDYA |

-continued

SEQUENCE LISTING

| SEQ ID NO: | Name | Description | Sequence |
|---|---|---|---|
| 8 | 84G09 - CDRH2 (IMGT) | Amino acid sequence of CDRH2 of 84G09 using IMGT | ISWKSNII |
| 9 | 84G09 - CDRH3 (IMGT) | Amino acid sequence of CDRH3 of 84G09 using IMGT | ARDITGSGSYGWFDP |
| 10 | 84G09 - CDRH1 (Kabat) | Amino acid -sequence of CDRH1 of 84G09 using Kabat | DYAMH |
| 11 | 84G09 - CDRH2 (Kabat) | Amino acid sequence of CDRH2 of 84G09 using Kabat | GISWKSNIIGYADSVKG |
| 12 | 84G09 - CDRH3 (Kabat) | Amino acid sequence of CDRH3 of 84G09 using Kabat | DITGSGSYGWFDP |
| 13 | 84G09 - Heavy chain variable region | Amino acid sequence of V$_H$ of 84G09 (mutations from germline are shown in bold letters) | EVQLVESGGGLVQPCRSLRLSCAASGFTFDDYAMHWVRQTPGKGLEWVSGISWKSNIIGYADSVKGRFTISRDNAKNSLYLQMNSLRAEDTALYYCARDITGSGSYGWFDPWGQGTLVTVSS |
| 14 | 84G09 - Heavy chain variable region | Nucleic acid sequence of V$_H$ of 84G09 | CAAGAAAAGCTTGCCGCCACCATGGAGTTTGGCTGAGCTGAGTTTCCTTTTGGCTATTTTAAAGGTGTCCAGTGGAAGTACAATTGGTGGAGCTCCGGGGAGGCTTGGTACAGCCTGGCAGGTCCCTGAGACTCTCCTGTGCAGCCTGGATTCACCTTTGATGATTATGCCATGCACTGGGTCCGACAAACTCCAGGGAAGGGCCTGGAGTGGGTCTCAGGTATAAGTTGGAAGAGTAATATCATAGGCTATGCGGACTCTGTGAAGGGCCGATTCACCATCTCCAGAGACAACGCCAAGAACTCCCTGTATCTGCAAATGAACAGTCTGAGAGCTGAGGACACCGCCTTGTATTATTGTGCAAGAGATATAACGGGTTCGGGAGTTATGGCTGGTTCGACCCTGGGCCAGGAACCCTGGTCACCGTCTCCTCAGCCAAAACGACACCCCATCTGTCTATCCACTGGCCCTGAATCTGCTAAAACTCAGCCTCCG |
| 15 | 84G09 - full heavy chain sequence | Amino acid sequence of 84G09 heavy chain (mutations from germline are shown in bold letters) | EVQLVESGGGLVQPCRSLRLSCAASGFTFDDYAMHWVRQTPGKGLEWVSGISWKSNIIGYADSVKGRFTISRDNAKNSLYLQMNSLRAEDTALYYCARDITGSGSYGWFDPWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 16 | 84G09 - full heavy chain sequence | Nucleic acid sequence of 84G09 heavy chain | GAAGTGCAGCTGGTGGAATCTGGCGGCGGACTGGTGCAGCCTGCAGATCCCTGAGACTGTCTTGTGCCGCCTCCGGCTTCACCTTCGACGACTACGCTATGCACTGGGTGCGACAGACCCCTGGCAAGGGCCTGGAATGGGTGTCCGGCATCTCCTGGAAGTCCAACATCATCGGCTACGCCGACTCCGTGAAGGGCCGGTTCACCATCTCCAGGGACAACGCCAAGAACTCCCTGTACCTGCAGATGAACAGCCTGCGGGCCGAGGACACCGCCCTGTACTACTGCGCCAGAGACATCACCGGCTCCGGCTCCTACGGATGGTTCGATCCTTGGGGCCAGGGCACCCTGGTCACCGTGAGCAGCACCAAGGGCCCCTCTGTTCCCTGGCCCCTGCCTGCAAGCAAGTCCACCTCTGGCGGAA |

-continued

SEQUENCE LISTING

| SEQ ID NO: | Name | Description | Sequence |
|---|---|---|---|
| | | | CAGCCGCTCTGGGCTGCCTCGTGAAGGACTACTTCCCCGAGCCTGTGACCGTGT |
| | | | CCTGGAACTCTGGCGCTCTGACCAGCGGAGTGCACACCTTCCCTGCTGTGCTGC |
| | | | AGTCCTCCGGCCTGTACTCCCTGTCTCCGTGACCGTGCCTTCCAGCTCTCT |
| | | | GGGCACCCAGACCTACATCTGCAACGTGAACCACAAGCCCTCCAACACCAAGGT |
| | | | GGACAAGAAGGTGGAACCCAAGTCCTGCGACAAGACCCACACCTGTCCCCCTG |
| | | | TCCTGCCCCTGAACTGCTGGGCGGACCTTCCGTGTTCCTGTTCCCCCCAAAGCC |
| | | | CAAGGACACCCTGATGATCTCCCGGACCCCTGAAGTGACCTGCGTGGTGGTGGA |
| | | | TGTGTCCCACGAGGACCCTGAAGTTCAATTGGTACGTGGACGGCGTGGA |
| | | | AGTGCACAACGCCAAGACCAAGCCTAGAGAGGAACAGTACAACTCCACCTACCG |
| | | | GGTGGTGTCCGTGCTGACCGTGCTGCACCAGGATTGGCTGAACGGCAAAGAGT |
| | | | ACAAGTGCAAGGTCTCCAACAAGGCCCTGCCCGCCCCATCGAAAAGACCATCT |
| | | | CCAAGGCCAAGGGCCAGCCCCGGGAACCCCAGGTGTACACACTGCCCCCTAGCA |
| | | | GGGACGAGCTGACCAAGAACCAGGTGTCCCTGACCTGTCTGAAAGGCTTCT |
| | | | ACCCCTCCGATATCGCCGTGGAATGGGAGTCCAACGGCCAGCCTGAGAACAACT |
| | | | ACAAGACCACCCCCCCTGTGCTGGACTCCGACGGCTCATTCTTCCTGTACAGCAA |
| | | | GCTGACAGTGGACAAGTCCCGGTGGCAGGAGGGCAACGTGTTCTCCTGCTCCGT |
| | | | GATGCACGAGGCCCTGCACAACCACTACACCCAGAAGTCCCTGTCCCTGAGCCC |
| | | | CGGCAAG |
| 17 | 84G09 - CDRL1 (IMGT) | Amino acid sequence of CDRL1 of 84G09 using IMGT | QSISSY |
| 18 | 84G09 - CDRL2 (IMGT) | Amino acid sequence of CDRL2 of 84G09 using IMGT | VAS |
| 19 | 84G09 - CDRL3 (IMGT) | Amino acid sequence of CDRL3 of 84G09 using IMGT | QQSYSNPIT |
| 20 | 84G09 - CDRL1 (Kabat) | Amino acid sequence of CDRL1 of 84G09 using Kabat | RASQSISSYLN |
| 21 | 84G09 - CDRL2 (Kabat) | Amino acid sequence of CDRL2 of 84G09 using Kabat | VASSLQS |
| 22 | 84G09 - CDRL3 (Kabat) | Amino acid sequence of CDRL3 of 84G09 using Kabat | QQSYSNPIT |
| 23 | 84G09 - Light chain variable region | Amino acid sequence of $V_L$ of 84G09 | DIQMTQSPSSLSASVGDRVTITCRASQSISSYLNWYQQKPGKAPKPLIVASSLQS GVPSSFSGSGSGTDFLTISSLQPEDFATYYCQQSYSNPITFGQGTRLEIK |
| 24 | 84G09 - Light chain variable region | Nucleic acid sequence of $V_L$ or 84G09 | GACATCCAGATGACCCAGTCTCCATCCTCCCTGTCTGCATCTGTAGGAGACAGA GTCACCATCACTTGCCGGGCAAGTCAGAGCATTAGCAGCTATTTAAATTGGTAT CAGCAGAAACCAGGGAAAGCCCCTAAGCCCCTGATCTATGTTGCATCCAGTTTG CAAAGTGGGGTCCCATCAAGGTTCAGTGGCAGTGGATCTGGGACAGATTTCACT CTCACCATCAGCAGTCTGCAACCTGAAGATTTTGCAACTTACTACTGTCAACAGA GTTACAGTAATCCATCACCTTCGGCCAAGGGACCACGACTGGAGATCAAA |

SEQUENCE LISTING

| SEQ ID NO: | Name | Description | Sequence |
|---|---|---|---|
| 25 | 84G09 - full light chain sequence | Amino acid sequence of 844309 light chain | DIQMTQSPSSLSASVGDRVTITCRASQSISSYLNWYQQKPGKAPKPLIYVASSLQS GVPSSFSGSGSGTDFTLTISSLQPEDFATYYCQQSYSNPITFGQGTRLEIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 26 | 84G09 - full light chain sequence | Nucleic acid sequence of 84G09 light chain | GACATCCAGATGACCCAGTCTCCATCCTCCCTGTCTGCATCTGTAGGAGACAGA GTCACCATCACTTGCCGGGCAAGTCAGAGCATTAGCAGCTATTTAAATTGGTAT CAGCAGAAACCAGGGAAAGCCCCTAAGCCCCTGATCTATGTTGCATCCAGTTTG CAAAGTGGGGTCCCATCAAGTTCAGTGCAGTGGATCTGGGACAGATTTCACT CTCACCATCAGCAGTCTGCAACCTGAAGATTTTGCAACTTACTGTCAACAGA GTTACAGTAATCCTCCGGTCACCTTCGGCCAAGGGACACGACTGGAGATCAAACGTA CGGTGGCCGCTCCAGTCTTCATCTTCCCGCCATCTGATGAGCAGTTGAAGT CCGGAACCGCCTCTGTGTGCCTGCTGAATAACTTCTACCCGCGAGGCCA AGGTGACAGGTGGACAACGCCTGGAAGTCCAGGAATCCG TGACCGAGCAGGACTCCAAGGACAGCACCTACTCCTGTCCTCCACCCCTGACC TGTCCAAGGCGACTACGAGAAGCACAAAGTGTACGCCTGCGAAGTGACCCACC AGGGCCTGTCTAGCCCCGTGACCAAGTCTTTCAACCGGGGCGAGTGT |
| 27 | 1D05 - CDRH1 (IMGT) | Amino acid sequence of CDRH1 of 1D05 using IMGT | GFTFDDYA |
| 28 | 1D05 - CDRH2 (IMGT) | Amino acid sequence of CDRH2 of 1D05 using IMGT | ISWIRTGI |
| 29 | 1D05 - CDRH3 (IMGT) | Amino acid sequence of CDRH3 of 1D05 using IMGT | AKDMKGSGTYGGWFDT |
| 30 | 1D05 - CDRH1 (Kabat) | Amino acid sequence of CDRH1 of 1D05 using Kabat | DYAMH |
| 31 | 1D05 - CDRH2 (Kabat) | Amino acid sequence of CDRH2 of 1D05 using Kabat | GISWIRTGIGYADSVKG |
| 32 | 1D05 - CDRH3 (Kabat) | Amino acid sequence of CDRH3 of 1D05 using Kabat | DMKGSGTYGGWFDT |
| 33 | 1D05 - Heavy chain variable region | Amino acid sequence of V$_H$ of 1D05 (mutations from germline are shown in bold letters) | EVQLVESGGGLVQPGRSLRLSCAASGFTFDDYAMHWVRQVPGKGLEWVSGISWI RTGIGYADSVKGRFTIFRDNAKNSLYLQMNSLRAEDTALYYCAKDMKGSGTYGG WFDTWGQGTLVTVSS |
| 34 | 1D05 - Heavy chain variable region | Nucleic acid sequence of V$_H$ of 1D05 | AAGCTTGCCGCCACCATGAGTTTGGGCTGAGCTGGATTTTCCTTTGCTATT TTAAAAGGTGTCCAGTGTGAAGTGCAGCTGGTGGAGTCTGGGGAGGCTTGGT GCAGCCTGGCAGGTCCCTGAGACTCTCCTGTGCAGCCTCTGGATTCACCTTTGA TGATTATGCCATGCACTGGGTCCGCCAAGTTCCAGGGAAGGGCCTGGAATGGG TCTCAGGCATTAGTTGGATTCGTACAGGACAACGCCAAGAATTCCCTGTATCTGCAAATGAA GCCGATTCACCATTTTCAGACAACCGGCCTTGTATTACTGTGCAAAGATAAGGGG CAGTCTGAGAGCTGAGGACACGGCCTTGTATTACTGTGCAAAGATAATGAAGGG |

| SEQ ID NO: | Name | Description | Sequence |
|---|---|---|---|
| | | | TTCGGGGACTTATGGGGGTGGTTCGACACCTGGGGCCAGGGAACCCTGGTCA CGTCTCCTCAGCCAAACAACAGCCCCATCGGTCTATCCACTGGCCCCTGC |
| 35 | 1D05 - full heavy chain sequence | Amino acid sequence of 1D05 heavy chain | EVQLVESGGGLVQPGRSLRLSCAASGFTFDDYAMHWVRQVPGKGLEWVSGISWI RTGIGYADSVKGRFTIFRDNAKNSLYLQMNSLRAEDTALYYCAKDMKGSGTYGGW FDTWGQGTLVTVSSASTKGPSVFPLAPCSRSTSESTAALGCLVKDYFPPEVTVSWN SGALTSGVHTFPAVLQSSGLYSLSSVVTVPSSSLGTKTYTCNVDHKPSNTKVDKRV ESKYGPPCPPCPAPEFEGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLP SSIEKTISMKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQKS LSLSLGK |
| 36 | 1D05 - full heavy chain sequence | Nucleic acid sequence of 1D05 heavy chain | GAAGTGCAGCTGGTGGAATCTGGCGGCGGACTGGTGCAGCCTGGCAGATCCCT GAGACTGTCTTGTGCCGCCTCAGGCTTCACCTTCGACGACTACGCTATGCACTG GGTGCGACAGGTGCCAGGCAAGGGCCTGGAATGGGTGTCCGGCATCTCTTGGA TCCGAACCGGCATCGGCTACGCCGACTCTGTGAAGGGCCGGTTCACCATCTTCC GGGACAACGCCAAGAACTCCCTGTACCTGCAGATGAACAGCCTGCGGGCCGAGG ACACCGCCCTGTACTACTGCGCCAAGGACATGAAGGGCTCCGGCACCTACGGCG GATGGTTCGATACTTGGGGCCAGGGCACCCTGGTCACCGTGTCCTCTGCCAGCA CCAAGGGCCCCTCTGTGTTCCCTCTGGCCCCTTGCTCCAGGAGACTACTTCCCGAGGG GAACAGCCCGCTCTGGGCTGCCTCGTGAAGGACTACTTCCCCGAGCCTGTGACCG TGTCCTGGAACTCTGGCGCTCTGACCAGCGGAGTGCACACCTTCCCTGCTGTGC TGCAGTCCTCCGGCCTGTACTCCCTGTCCTCCGTGGTGACCGTGCCTTCCAGCT CTCTGGGCACCCAGACCTACATCTGCAACGTGAACCACAAGCCCTCCAACACCAA GGTGACAAGAAGGTGGAACCCAAGTCCTGCGACAAGACCCACACCTGTCCCC TTGTCCTGCCCCCAAGTCGGGGCGGACCCTCCGGACCCCAAGTCTGCGTGGT GATGTGTCCCACGAGGACCCTGAAGTGAAGTTCAATTGGTACGTGGACGGCGT GGAAGTGCACAACGCCAAGACCAAGCCTAGAGAGGAACAGTACAACTCCACCTA CCGGGTGGTGTCCGTGCTGACCGTGCTGCACCAGGATTGGCTGAACGGCAAAG AGTACAAGTGCAAGTGTCCAACAAGGCCCTGCCTGCCCCATCGAAAAGACCA TCTCCAAGGCCAAGGGCCAGCCCAGGAACCCCAGGTGTACACCCTGCCCCCTA GCAGGACGAGCTGACCAAGAACCAGGTGTCCCTGACCTGTCTGTGAAGGCT TCTACCCTTCCGATATCGCCGTGGAATGGGAGTCCAACGGCCAGCCTGAGAACA ACTACAAGACCACCCCCTGTGCTGGACAGCGGCTCATTCTTCCTGTACAG CAAGCTGACAGTGGACAAGTCCCGGTGGCAGCAGGGCAACGTGTTCTCCTGCTC CGTGATGCACGAGGCCCTGCACAACCACTACACCCAGAAGTCCCTGTCCCTGAG CCCCGGCAAG |
| 37 | 1D05 - CDRL1 (IMGT) | Amino acid sequence of CDRL1 of 1D05 using IMGT | QSISSY |
| 38 | 1D05 - CDRL2 (IMGT) | Amino acid sequence of CDRL2 of 1D05 using IMGT | VAS |
| 39 | 1D05 - CDRL3 (IMGT) | Amino acid sequence of CDRL3 of 1D05 using IMGT | QQSYSTPIT |

-continued

SEQUENCE LISTING

| SEQ ID NO: | Name | Description | Sequence |
|---|---|---|---|
| 40 | 1D05 - CDRL1 (Kabat) | Amino acid sequence of CDRL1 of 1D05 using Kabat | RASQSISSYLN |
| 41 | 1D05 - CDRL2 (Kabat) | Amino acid sequence of CDRL2 of 1D05 using Kabat | VASSLQS |
| 42 | 1D05 - CDRL3 (Kabat) | Amino acid sequence of CDRL3 of 1D05 using Kabat | QQSYSTPIT |
| 43 | 1D05 - Light chain variable region | Amino acid sequence of V$_L$ of 1D05 (mutations from germline are shown in bold letters) | DIQMTQSPSSLSASVGDRVTITCRASQSISSYLNWYQQKPGKAPKLLIYVASSLQS GVPSRFSGSGSGTDFTLTISSLQPEDFATYYCQQSYSTPITFGQGTRLEIK |
| 44 | 1D05 - Light chain variable region | Nucleic acid sequence of V$_L$ of 1D05 | AAAGTTGCCGCCACCATGAGGCTCCCTGCTCAGCTTCTGGGGCTCCTGCTACT CTGGCTCCGAGGTGCCAGATGTGACATCCAGATGACCCAGTCTCCATCTCCCT GTCTGCATCTGTAGGAGACAGAGTCACCATCACTTGCCGGGCAAGTCAGAGCAT TAGCAGCTATTTAAATTGGTATCAGCAGAAACCAGGGAAAGCCCCTAAACTCCT GATCTATGTTGCATCCAGTTTGCAAAGTGGGGTCCCATCAAGGTTCAGTGGCAG TGGATCTGGGACAGATTTCACTCTCACTATCAGCAGTCTGCAACCTGAAGATTTT GCAACTTACTACTGTCAACAGAGTTACAGTACCCCGATCACCTTCGGCCAAGGG ACACGTCTGGAGATCAAACGTACGGATGCTGCACCAACT |
| 45 | 1D05 - full light chain | Amino acid sequence of 1D05 light chain | DIQMTQSPSSLSASVGDRVTITCRASQSISSYLNWYQQKPGKAPKLLIYVASSLQS GVPSRFSGSGSGTDFTLTISSLQPEDFATYYCQQSYSTPITFGQGTRLEIKRTVAAP SVFIFPPSDEQLKSGTASVVCLLNNFYPREAINQMKVDNALQSGNSQESVTEQDSK DSTYSLSSTLTLSKADYEKHKVYACEVTHQGLSSPVTKSFNRGEC |
| 46 | 1D05 - full light chain | Nucleic acid sequence of 1D05 light chain | GACATCCAGATGACCCAGTCTCCCCTCCCCAGCCTGTCTGCTTCCGTGGGACAGA GTGACCATCACCTGTCGGGCCTCCCAGTCCATCTCCTCCTACCTGAACTGGTATC AGCAGAAGCCCGGCAAGGCCCCCAAGCTCCTGATCTACGTGGCCAGCTCTCTGC AGTCCGGCGTGCCCTCTAGATTCTCCGGCTCTGGCTCTGGCACCGACTTTACCC TGACCATCAGCTCCCTGCAGCCCGAGGACTTCGCCACCTACTACTGCCAGCAGT CCTACTCCACCCCTATCACCTTCGGCCAGGGCACCCGGCTGGAAATCAAACGTA CGGTGGCCGCTCCTGTCTTCATCTTCCCACCTTCCGACGAGCAGCTGAAGT CCGGCACCGCCTCTGTGTGCCTGCTGAACAACTTCTACCCCCGCGAGGCCA AGTCCAGTGGAAGGTGGACAACGCCCTGCAGTCCGGCAACTCCCAGGAATCCG TGACCGAGCAGGACTCCAAGGACAGCACCTACTCCCTGTCCTCCACCCTGACCC TGTCCAAGGCCGACTACGAGAAGCACAAGGTGTACGCCTGCGAAGTGACCCACC AGGGCCTGTCTAGCCCCGTGACCAAGTCTTTCAACGGGGCGAGTGT |
| 47 | Mutated 1D05 - HC mutant 1 | Amino acid sequence of 1D05 heavy chain with V to A back-mutation in framework region to germline highlighted with IgG1 disabled (LAGA) constant region | EVQLVESGGGLVQPGRSLRLSCAASGFTFDDYAMHWVRQ<u>A</u>PGKGLEWVSGISWI RTGIGYADSVKGRFTIFRDNAKNSLYLQMNSLRAEDTAL<u>Y</u>YCAKDMKGSGTYGGW FDTWGQGTLVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDKRV ESKYGPPCPPCPAPE<u>LAGA</u>PSVFLFPPKPKDTLMISRTPEVICVVVDVSQEDPEVQF NWYVDGVEVHNAKTKPREEQFNSTYRVVSVLTVLHQDWLNGKEYKCKVSNKGLP SSIERTISKAKGQPREPQVYTLPPSQEEMTKNQVSLTCLVKGFYPSDIAVEWESNG |

SEQUENCE LISTING -continued

| SEQ ID NO: | Name | Description | Sequence |
|---|---|---|---|
| 48 | Mutated 1D05 mutant 2 - HC | Amino acid sequence of 1D05 heavy chain with F to S back-mutation in framework region to germline highlighted with IgG1 disabled (LAGA) constant region | EVQLVESGGGLVQPGRSLRLSCAASGFTFDDYAMHWVRQVPGKGLEWVSGISWI RTGIGYADSVKGRFTISRDNAKNSLYLQMNSLRAEDTALYYCAKDMKGSGTYGGW FDTWGQGTLVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDKRV ESKYGPPCPPCPAPELAGAPSVFLFPPKPKDTLMISRTPEVTCVVVDVSQEDPEVQF NWYVDGVEVHNAKTKPREEQFNSTYRVVSVLTVLHQDWLNGKEYKCKVSNKGLP SSIEKTISMKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQKS LSLSLGK |
| 49 | Mutated 1D05 mutant 3 - HC | Amino acid sequence of 1D05 heavy chain with ELLG to -PVA back-mutation in constant region to germline highlighted | EVQLVESGGGLVQPGRSLRLSCAASGFTFDDYAMHWVRQVPGKGLEWVSGISWI RTGIGYADSVKGRFTIFRDNAKNSLYLQMNSLRAEDTALYYCAKDMKGSGTYGGW FDTWGQGTLVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDKRV ESKYGPPCPPCPAP-PVAGPSVFLFPPKPKDTLMISRTPEVTCVVVDVSQEDPEVQFNMYVDGVEVHNAK TKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 50 | Mutated 1D05 mutant 1 - LC | Amino acid kappa light chain with V to A back-mutation in CDRL2 to germline highlighted | DIQMTQSPSSLSASVGDRVTITCRASQSISSYLNWYQQKPGKAPKLLIYAASSLQS GVPSRFSGSGSGTDFTLTISSLQPEDFATYYCQQSYSTPITFGQGTRLEKRTVAAP SVFIFPPSDEQLKSGTASVVCLLNNFYPREAGQWKVDNALQSGNSQESVTEQDSK DSTYSLSSTLTLSKADYEKHKVYACEVTHQGLSSPVTKSFNRGEC |
| 51 | Mutated 1D05 mutant 2 - LC | Amino acid sequence of 1D05 kappa light chain with L to F back-mutation in framework to germline highlighted | DIQMTQSPSSLSASVGDRVTITCRASQSISSYLNWYQQKPGKAPKLFIYVASSLQS GVPSRFSGSGSGTDFTLTISSLQPEDFATYYCQQSYSTPITFGQGTRLEIKRTVAAP SVFIFPPSDEQLKSGTASWCLLNNFYPREAKVQMKVDNALQSGNSQESVTEQDSK DSTYSLSSTLTLSKADYEKHKVYACEVTHQGLSSPVTKSFNRGEC |
| 52 | 411B08 - CDRH1 (IMGT) | Amino acid sequence of CDRH1 of 411B08 using IMGT | GFTFSSYW |
| 53 | 411B08 - CDRH2 (IMGT) | Amino acid sequence of CDRH2 of 411B08 using IMGT | IKEDGSEK |
| 54 | 411B08 - CDRH3 (IMGT) | Amino acid sequence of CDRH3 of 411B08 using IMGT | ARNRLYSDFLDN |
| 55 | 411B08 - CDRH1 (Kabat) | Amino acid sequence of CDRH1 of 411B08 using Kabat | SYWMS |
| 56 | 411B08 - CDRH2 (Kabat) | Amino acid sequence of CDRH2 of 411B08 using Kabat | NIKEDGSEKYYVDSVKG |

-continued

SEQUENCE LISTING

| SEQ ID NO: | Name | Description | Sequence |
|---|---|---|---|
| 57 | 411B08 - CDRH3 (Kabat) | Amino acid sequence of CDRH3 of 411B08 using Kabat | NRLYSDFLDN |
| 58 | 411B08 - Heavy chain variable region | Amino acid sequence of V$_H$ of 411B08 | EVQLVESGGGLVQPGGSLRLSCAASGFTFSSYMSWVRQAPGKGLEWVANIKED GSEKYYVDSVKGRFTISRDNAKNSLYLQMNSLRAEDTSVYYCARNRLYSDFLDNW GQGTLVTVSS |
| 59 | 411B08 - Heavy chain variable region | Nucleic acid sequence of V$_H$ of 411B08 | GAGGTGCAGCTGGTGGAGTCTGGGGGAGGCTTGGTTCCAGCCTGGGGGTCCCT GAGACTCTCCTGTGCAGCCTCTGGATTCACGTTTAGTAGCTATTGGATGAGTTG GGTCCGCCAGGCTCCAGGGAAGGGGCTGGAGTGGGTGGCCAACATCAAAGAAG ATGGAAGTGAGAAATATGTCGACTCTGTGAAGGGCCGATTCACCATCTCCA GAGACAACGCCAAGAACTCACTGTATCTGCAAATGAACAGCCTGAGAGCCGAGG ACACGTCTGTATTACTGTGCGAGAAATCGACTCTACAGTGACTTCCTTGACAA CTGGGGCCAGGGAACCCTGGTCACCGTCTCCTCAG |
| 60 | 411B08 - full heavy chain sequence | Amino acid sequence of 411B08 heavy chain | EVQLVESGGGLVQPGGSLRLSCAASGFTFSSYMSWVRQAPGKGLEWVANIKED GSEKYYVDSVKGRFTISRDNAKNSLYLQMNSLRAEDTSVYYCARNRLYSDFLDNW GQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSL SPGK |
| 61 | 411B08 - full heavy chain sequence | Nucleic acid sequence of 411B08 heavy chain | GAGGTGCAGCTGGTGGAGTCTGGGGGAGGCTTGGTTCCAGCCTGGGGGTCCCT GAGACTCTCCTGTGCAGCCTCTGGATTCACGTTTAGTAGCTATTGGATGAGTTG GGTCCGCCAGGCTCCAGGGAAGGGGCTGGAGTGGGTGGCCAACATCAAAGAAG ATGGAAGTGAGAAATATGTCGACTCTGTGAAGGGCCGATTCACCATCTCCA ACACGTCTGTATTACTGTGCGAGAAATCGACTCTACAGTGACTTCCTTGACAA CTGGGGCCAGGGAACCCTGGTCACCGTCTCCTCAGCCTCCACCAAGGGCCCCTC TGTCTTCCCCCTGGCCCCCTTCCAGCAAGTCCACCTCTGGCGACACAGCCGCTCT GGGCTGCCTGGTCAAGGACTACTTCCCCGAGCCTGTGACCGTGTCGAGTCCTGG CCTGTACTCCCTGTCCTCCGTGGTGACCGTGCCCTCCAGCTCTCTGGGACCCA GACCTACATCTGCAACGTGAACCACAAGCCCTCCAACACCAAGGTGGACAAGAA GGTGGAACCCAAGTCTGCGACAAGACTCACACTCCTGTTCCCCCAAAGCCCAAGGACAC CCTGATGATCTCCAGGACCCCCGAAGTGACCTGCGTGGTGGTGGATGTGTCCCA CGAGGACCCTGAAGTGAAGTTCAATTGGTACGTGGACGGCGTGGAAGTGCACAA CGCCAAGACCAAGCCTAGAGAAGAACAGTACAACTCCACCTACCGGGTGGTGTC CGTGCTGACCGTGCTGCACCAGGATTGGCTGAACGGCAAAGAGTACAAGTGCAA GGTGTCCAACAAGGCCCTGCCCCCATCGAAAAGACCATCTCCAAGGCCAA GGGCCAGCCCCGGAACCCCAGGTGTACACACTGCCCCCTAGCAGGGAGCAGCT GACCAAGAACCAGGTGTCCCTGACCTGTCTGGTGAAAGGCTTCTACCCCTCCGA TATCGCCGTGGAATGGGAGTCCAACGGCCAGCCTGAGAACAACTACAAGACCAC CCCCCCTGTCGGACTCGACGGCTCATTCTTCCTGTACAGCAAGCTGACAGT |

SEQUENCE LISTING -continued

| SEQ ID NO: | Name | Description | Sequence |
|---|---|---|---|
| | | | GGACAAGTCCCGGTGGCAGCAGGGCAACGTGTTCTCCTGCTCCGTGATGCACGA GGCCCTGCACAACCACTACACCCAGAAGTCCCTGTCCCTGAGCCCCGGCAAG |
| 62 | 411B08 - CDRL1 (IMGT) | Amino acid sequence of CDRL1 of 411B08 using IMGT | QGVSSW |
| 63 | 411B08 - CDRL2 (IMGT) | Amino acid sequence of CDRL2 of 411B08 using IMGT | GAS |
| 64 | 411B08 - CDRL3 (IMGT) | Amino acid sequence of CDRL3 of 411B08 using IMGT | QQANSIPFT |
| 65 | 411B08 - CDRL1 (Kabat) | Amino acid sequence of CDRL1 of 411B08 using Kabat | RASQGVSSWLA |
| 66 | 411B08 - CDRL2 (Kabat) | Amino acid sequence of CDRL2 of 411B08 using Kabat | GASSLQS |
| 67 | 411B08 - CDRL3 (Kabat) | Amino acid sequence of CDRL3 of 411B08 using Kabat | QQANSIPFT |
| 68 | 411B08 - Light chain variable region | Amino acid sequence of $V_L$ of 411B08 | DIQMTQSPSSVSASVGDRVTITCRASQGVSSWLAWYQQKSGKAPKLLIYGASSLQ SGVPSRFSGSGSGTEFILTISSLQPEDFATYYCQQANSIPFTFGPGTKVDIK |
| 69 | 411B08 - Light chain variable region | Nucleic acid sequence of $V_L$ of 411B08 | GACATCCAGATGACCCAGTCTCCATCTTCCGTGTCTGCAGTCTGCAGACAGA GTCACCATCACTTGTCGGGCGAGTCAGGGTGTTAGCAGCTGGTTAGCCTGGTAT CAGCAGAAATCAGGGAAAGCCCCTAAGCTCCTGATCTATGGTGCATCCAGTTTG CAAAGTGGGGTCCCATCAAGATTCAGCGGCAGTGGATCTGGGACAGAGTTCATT CTCACCATCAGCAGCCTGCAGCCTGAAGATTTTGCAACTTACTATTGTCAACAGG CTAACAGTATCCCATTCACTTTCGGCCCTGGGACCAAAGTGGATATCAAAC |
| 70 | 411B08 - full light chain sequence | Amino acid sequence of 411B08 light chain | DIQMTQSPSSVSASVGDRVTITCRASQGVSSWLAWYQQKSGKAPKLLIYGASSLQ SGVPSRFSGSGSGTEFILTISSLQPEDFATYYCQQANSIPFTFGPGTKVDIKRTVAAP SVFIFPPSDEQLKSGTASWCLLNNFYPREAKVQWKVDNALQSGNSQESVTEQDSK DSTYSLSSTLTLSKADYEKHKVYACEVTHQGLSSPVTKSFNRGEC |
| 71 | 411B08 - full light chain sequence | Nucleic acid sequence of 411B08 light chain | GACATCCAGATGACCCAGTCTCCATCTTCCGTGTCTGCAGTCTGCAGACAGA GTCACCATCACTTGTCGGGCGAGTCAGGGTGTTAGCAGCTGGTTAGCCTGGTAT CAGCAGAAATCAGGGAAAGCCCCTAAGCTCCTGATCTATGGTGCATCCAGTTTG CAAAGTGGGGTCCCATCAAGATTCAGCGGCAGTGGATCTGGGACAGAGTCATT CTCACCATCAGCAGCCTGCAGCCTGAAGATTTTGCAACTTACTATTGTCAACAGG CTAACAGTATCCCATTCACTTTCGGCCCTGGGACCAAAGTGGATATCAAACGTAC GGTGGCCGCTCCTGTGTTCATCTTCCCACCTTCCGACGAGCAGCTGAAGTC CGGCACCGCTTCTGTCGTGTGCCTGCTGAACAACTTCTACCCCGCGAGGCCAA GGTGCAGTGGAAGGTGGACAACGCCCTGCAGTCCGGCAACTCCCAGGAATCCGT GACCGAGCAGGACTCCAAGGACTCCACCTACTCCCTGTCCTCGCCACCCTGACCCT GTCCAAGGCCGACTACGAGAAGCACAAGGTGTACGCCTGCGAAGTGACCCACCA GGGCCTGTCTAGCCCCGTGACCAAGTCTTTTCAACCGGGCGAGTGT |

-continued

SEQUENCE LISTING

| SEQ ID NO: | Name | Description | Sequence |
|---|---|---|---|
| 72 | 411C04 - CDRH1 (IMGT) | Amino acid sequence of CDRH1 of 411C04 using IMGT | GFTFSSYW |
| 73 | 411C04 - CDRH2 (IMGT) | Amino acid sequence of CDRH2 of 411C04 using IMGT | IKEDGSEK |
| 74 | 411C04 - CDRH3 (IMGT) | Amino acid sequence of CDRH3 of 411C04 using IMGT | ARVRLYSDFLDY |
| 75 | 411C04 - CDRH1 (Kabat) | Amino acid sequence of CDRH1 of 411C04 using Kabat | SYWMS |
| 76 | 411C04 - CDRH2 (Kabat) | Amino acid sequence of CDRH2 of 411C04 using Kabat | NIKEDGSEKYYVDSLKG |
| 77 | 411C04 - CDRH3 (Kabat) | Amino acid sequence of CDRH3 of 411C04 using Kabat | VRLYSDFLDY |
| 78 | 411C04 - Heavy chain variable region | Amino acid sequence of $V_H$ of 411C04 | EVQLVDSGGGLVQPGGSLRLSCAASGFTFSSYWMSWVRQAPGKGLEWVANIKED GSEKYYVDSLKGRFTISRDNAKNSLYLQMNSLRAEDTSVYYCARVRLYSDFLDYWG QGTLVIVSS |
| 79 | 411C04 - Heavy chain variable region | Nucleic acid sequence of $V_H$ of 411C04 | GAGGTGCAGCTGGTGGACTCTGGGGGAGGCTTGGTCCAGCCTGGGGGGTCCCT GAGACTCTCCTGTGCCAGCCTCTGGATTCACGTTTAGTAGCTATTGGATGAGTTG GGTCCGCCAGGCTCCAGGAAAGGGCTGGAGTGGGTGGCCAACATAAAGGAAG ATGGAAGTGAGAAATACTATGTAGACTCTTTGAAGGGCCGATTCACCATCTCCA GAGACAACGCAAGAACTCACTGTATCTGCAAATGAACAGCCTGAGACCGAGG ACACGTCTGTGTATTACTGTGCGAGAGTTCGACTCTACAGTGACTTCCTGACTA CTGGGGCCAGGGAACCCTGGTCACCGTCTCCTCAG |
| 80 | 411C04 - full heavy chain sequence | Amino acid sequence of 411C04 heavy chain | EVQLVDSGGGLVQPGGSLRLSCAASGFTFSSYWMSWVRQAPGKGLEWVANIKED GSEKYYVDSLKGRFTISRDNAKNSLYLQMNSLRAEDTSVYYCARVRLYSDFLDYWG QGTLVIVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNWY VDGVEVHNAKTKPREEQYNSTYRMVSVLTVLHQDWLNGKEYKCKVSNKALPAPIE KTISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLS PGK |
| 81 | 411C04 - full heavy chain sequence | Nucleic acid sequence of 411C04 heavy chain | GAGGTGCAGCTGGTGGACTCTGGGGGAGGCTTGGTCCAGCCTGGGGGGTCCCT GAGACTCTCCTGTGCCAGCCTCTGGATTCACGTTTAGTAGCTATTGGATGAGTTG GGTCCGCCAGGCTCCAGGAAAGGGCTGGAGTGGGTGGCCAACATAAAGAAG ATGGAAGTGAGAAATACTATGTAGACTCTTTGAAGGGCCGATTCACCATCTCCA GAGACAACGCAAGAACTCACTGTATCTGCAAATGAACAGCCTGAGAGCCGAGG ACACGTCTGTGTATTACTGTGCGAGAGTTCGACTCTACAGTGACTTCCTTGACTA CTGGGGCCAGGGAACCCTGGTCACCGTCTCCTCAGCCAGCACCAAGGGCCCCTC |

| SEQ ID NO: | Name | Description | Sequence |
|---|---|---|---|
| | | | TGTGTTCCCTCTGGCCCCTTCAGCAAGTCCACCTCTGGCGGAACAGCCGCTCT GGGCTGCCTCGTGAAGGACTACTTCCCCGAGCCTGTGACCGTGTCCTGAACTC TGGCCCTCTGACCAGCGGAGTGCACACCTTCCCTGTCTGTGCAGTCTCCGG CCTGTACTCCCTGTCCTCCGTGTGACCAGCCCTCCAGCTCTCTGGGCACCA GGTGGAACCCCAAGTCTCTGGACAAGAACCACCAAGGTGGACAAGAA GGTGGAACCCAAGTCTCTGGACAAGAAACCACACAAGGTGGACAAGAA TGAACTGCTGGGCGGACCTTCCGTGTTCCTGTTCCCCCCAAAGCCAAGGACAC CCTGATGATCTCCCGGACCCCCGAAGTGACCTGCGTGGTGGTGGATGTGTCCA CGAGGACCCTGAAGTGAAGTTCAATTGGTACGTGGACGGCGTGGAAGTGCACAA CGCCAAGACCAAGCCTAGAGAGGAACAGTACAACTCCACCTACCGGGTGTGTC CGTGCTGACCGTGCTGCACCAGGATTGGCTGAACGGCAAGGAGTACAAGTGCAA GGTGTCCAACAAGGCCCTGCCTGCCCCCATCGAAAAGACCATCTCCAAGGCCAA GGGCCAGCCCCGGAACCCCAGGTGTACACACTGCCCCTAGCAGGGACGAGCT GACCAAGAACCAGGTGTCCCTGACCTGTCTGGTGAAAGGCTTCTACCCCTCGA TATCGCCGTGGAATGGGAGTCCAACGGCCAGCCTGAGAACAACTACAAGACCAC CCCCCCTGTCCTGGACTCCGACGGCTCATTCTTCCTGTACAGCAAGCTGACAGT GGACAAGTCCCGGTGCAGCAGGCAGGGCAACGTGTTCTCCTGCTCCGTGATGCACGA GGCCCTGCACAACCACTACACCCAGAAGTCCCTGTCCCTGAGCCCCGGCAAG |
| 82 | 411C04 - CDRL1 (IMGT) | Amino acid sequence of CDRL1 of 411C04 using IMGT | QGVSSW |
| 83 | 411C04 - CDRL2 (IMGT) | Amino acid sequence of CDRL2 of 411C04 using IMGT | GAS |
| 84 | 411C04 - CDRL3 (IMGT) | Amino acid sequence of CDRL3 of 411C04 using IMGT | QQANSIPFT |
| 85 | 411C04 - CDRL1 (Kabat) | Amino acid sequence of CDRL1 of 411C04 using Kabat | RASQGVSSWLA |
| 86 | 411C04 - CDRL2 (Kabat) | Amino acid sequence of CDRL2 of 411C04 using Kabat | GASSLQS |
| 87 | 411C04 - CDRL3 (Kabat) | Amino acid sequence of CDRL3 of 411C04 using Kabat | QQANSIPFT |
| 88 | 411C04 - Light chain variable region | Amino acid sequence of $V_L$ of 411C04 | DIQMTQSPSSVSASVGDRVTITCRASQGVSSWLAWYQQKSGKAPKLLIYGASSLQ SGVPSRFSGSGSGTEFILSISSLQPEDFATYYCQQANSIPFTFGPGTKVDIK |
| 89 | 411C04 - Light chain variable region | Nucleic acid sequence of $V_L$ of 411C04 | GACATCCAGATGACCCAGTCCTCCATCTTCCGTGTCTGCATCTGTCGGAGACAGA GTCACCATCACTTGTCGGGCGAGTCAGGGTGTTAGCAGTTGGTTAGCTGGTAT CAGCAGAAATCAGGGAAAGCCCCTAAGCTCCTGATCTATGGTGCCTCCAGTTTG CAAAGTGGGGTCCCATCAAGATTCAGCGGCAGTGGATCTGGGACAGAGTTCATT CTCAGCATCAGCAGCCTGCAGCCTGAAGATTTGCAACTTACTATTGTCAACAGG CTAACAGTATCCCATTCACTTTCGGCCCTGGGACCAAAGTGGATATCAAAC |

-continued

SEQUENCE LISTING

| SEQ ID NO: | Name | Description | Sequence |
|---|---|---|---|
| 90 | 411C04 - full light chain sequence | Amino acid sequence of 411C04 light chain | DIQMTQSPSSVSASVGDRVTITCRASQGVSSWLAWYQQKSGKAPKLLIYGASSLQ SGVPSRFSGSGSGTEFILSISSLQPEDFATYYCQQANSIPFTFGPGTKVDIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 91 | 411C04 - full light chain sequence | Nucleic acid sequence of 411C04 light chain | GACATCCAGATGACCCAGTCTCCATCTTCCGTCTCTGCATCTGTCGGAGACAGA GTCACCATCACTTGTCGGGCGAGTCAGGGTGTTAGCAGTTGGTTAGCCTGGTAT CAGCAGAAATCAGGGAAAGCCCCTAAGCTCCTGATCTATGGTGCCTCCAGTTTG CAAAGTGGGGTCCCATCAAGATTCAGCGGCAGTGGATCTGGGACAGAGTTCATT CTCAGTCATCAGCCTGAGCCTGAAGATTTTGCAACTTACTATTGTCAACAGGCA CTAACAGTATCCATTCACTTTCGGCCCTGGGACCAAAGTGGATATCAAACGTAC GGTGCCGCTGTCCCTTCCTCTGTTTCATCTTCCCACCTTCCGACGAGCAGCTGAAGTC CGGCACCGCTTCTGTCGTGTGCCTGCTGAACAACTTCTACCCCCGGAGCCAA GGTGCAGTGCAGGTGGACAACGCCCTGCAGTCCGGCACACTTCTACCCCTGACCCT GACCCAGCAGGACTCCAAGGACAGCACCTACTCCCTGTCCTCCACCCTGACCCT GTCCAAGGCCGACTACGAGAAGCACAAGGTGTACGCCTGCGAAGTGACCCACCA GGGCCTGTCTAGCCCCGTGACCAAGTCTTTCAACCGGGGCGAGTGT |
| 92 | 411D07 - CDRH1 (IMGT) | Amino acid sequence of CDRH1 of 411D07 using IMGT | GGSIISSDW |
| 93 | 411D07 - CDRH2 (IMGT) | Amino acid sequence of CDRH2 of 411D07 using IMGT | IFHSGRT |
| 94 | 411D07 - CDRH3 (IMGT) | Amino acid sequence of CDRH3 of 411D07 using IMGT | ARDGSGSY |
| 95 | 411D07 - CDRH1 (Kabat) | Amino acid sequence of CDRH1 of 411D07 using Kabat | SSDWWN |
| 96 | 411D07 - CDRH2 (Kabat) | Amino acid sequence of CDRH2 of 411D07 using Kabat | EIFHSGRTNYNPSLKS |
| 97 | 411D07 - CDRH3 (Kabat) | Amino acid sequence of CDRH3 of 411D07 using Kabat | DGSGSY |
| 98 | 411D07 - Heavy chain variable region | Amino acid sequence of V$_H$ of 411D07 | QVQLQESGPGLVKPSGTLSLTCIVSGGSIISSDWWNWVRQPPGKGLEWIGEIFHS GRTNYNPSLKSRVTISIDKSNQFSLRLSSVTAADTAVYYCARDGSGSYWGQGTLV TVSS |
| 99 | 411D07 - Heavy chain variable region | Nucleic acid sequence of V$_H$ of 411D07 | CAGGTGCAGCTGCAGGAGTCGGGCCCAGGACTGGTGAAGCCTTCGGGGACCCT GTCCCTCACCTGCATTGTCTCTGGTGGCTCCATCATCAGTAGTGACTGGTGGAA TTGGGTCCGCCAGCCCCCAGGGAAGGGGCTGGAGTGGATTGGAGAAATCTTTC ATAGTGGGAGGACCAACTACTACAACCCGTCCCTCAAGAGTCGAGTCACCATATCAA TAGACAAGTCCAAGAATCAGTTCTCCCTGAAGCTGAGCTCTGTGACCGCCGCGG ACACGGCCGTGTATTACTGTGCGAGAGATGGTTCGGGAGTTACTGGGGCCAG GGAACCCTGGTCACCGTCTCCTCAG |

-continued

SEQUENCE LISTING

| SEQ ID NO: | Name | Description | Sequence |
|---|---|---|---|
| 100 | 411D07 - full heavy chain sequence | Amino acid sequence of 411D07 heavy chain | QVQLQESGPGLVKPSGTLSLTCIVSGGSIISSDWWNWVRQPPGKGLEWIGEIFHS GRTNNPSLKSRVTISIDKSKNQFSLRLSSVTAADTAVYYCARDGSGSYWGQGTLV TVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTC PPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQPENNYKTT PPVLDSDGSFFLYSKLTVDKSRWQQGNVFSCSVMHEALHNHYTQKSLSLSPGK |
| 101 | 411D07 - full heavy chain sequence | Nucleic acid sequence of 411D07 heavy chain | CAGGTGCAGCTGCAGGAGTCGGGCCCAGGACTGGTGAAGCCTTCGGGACCCT GTCCCTCACCTGCATTGTCTCTGGTGGCTCCATCATCAGTAGTGACTGGTGGAA TTGGGTCCGCCAGCCCCCAGGGAAGGGGCTGGAGTGGATTGGAGAAATCTTTC ATAGTGGGAGGACCAACTACAACCCGTCCCTGAAGAGTCGAGTCACCATATCAA TAGACAAGTCCAAGAATCAGTTCTCCCTGAGGCTGAGCTCTGTGACCGCCGGG ACACGGCCGTGTATTACTGTGCGAGAGATGGTTCGGGGAGTTACTGGGGCCAG GGAACCCTGGTCACCGTCTCCTCAGCCAGCACCAAGGGCCCCTCTGTGTTCCCT CTGGCCCCTTCCAAGTCCACCTCTGGGGGCACAGCCGCTCTGGAACTCGGGC GTGAAGGACTACTTCCCCGAGCCTGTGACCGTGTCCTGGAACTCTGGCGCTCTG ACCAGCGGAGTGCACACCTTCCCAGCTCTCCTGTCTGCAGTCCTGTACTCC CTGTCCTCCGTGACCGTGCCTCCAGCTCTCTGGGCACCCAGACCTACATC TGCAACGTGAACCACAAGCCCTCCAACACCAAGGTGGACAAGAAGGTGGAACCC AAGTCCTGCGACAAGACCCACACCTGTCCCCCTTGTCCTGCCCTGAACTGCTG GGCGACCTTCCGTGTTCCTGTTCCCCCCAAAGCCCAAGGACACCCTGATGATC TCCCGGACCCCGAAGTGACCTGCGTGGTGGACGGCGTGGAAGTGCACAACGCCAAGACC AAGCCTAGAGAGGAACAGTACAACTCCACCTACCGGGTGGTGTCCGTGCTGACC GTGCTGCACCAGGATTGGCTGAACGGCAAAGAGTACAAGTGCAAGGTGTCCAAC AAGGCCCTGCCTGCCCCATCGAAAAGACCATCTCCAAGGCCAAGGGCCAGAGCC CGGGAACCCAGGTGTACACACTGCCCCCTAGCAGGACCAGGACCAGCTGACCAAGAAC CAGGTGTCCCTGACCTGTCTGGTGAAGGCTTCTACCCCTCCGATATCGCCGTG GAATGGGAGTCCAACGGCCAGCCTGAGAACAACTACAAGACCACCCCCTGTG CTGGACTCCGACGGCTCATTCTTCCTGTACAGCAAGCTGACAGTGGACAAGTCC CGGTGGCAGCAGGGCAACGTGTTCTCCTGCTCCGTGATGCACGAGGCCCTGCAC AACCACTACACCCAGAAGTCCCTGTCCCTGAGCCCCGGCAAG |
| 102 | 411D07 - CDRL1 (IMGT) | Amino acid sequence of CDRL1 of 411D07 using IMGT | QSVLYSSNNKNY |
| 103 | 411D07 - CDRL2 (IMGT) | Amino acid sequence of CDRL2 of 411D07 using IMGT | WAS |
| 104 | 411D07 - CDRL3 (IMGT) | Amino acid sequence of CDRL3 of 411D07 using IMGT | QQYYSNRS |
| 105 | 411D07 - CDRL1 (Kabat) | Amino acid sequence of CDRL1 of 411D07 using Kabat | KSSQSVLYSSNNKWLA |

-continued

SEQUENCE LISTING

| SEQ ID NO: | Name | Description | Sequence |
|---|---|---|---|
| 106 | 411D07 - CDRL2 (Kabat) | Amino acid sequence of CDRL2 of 411D07 using Kabat | WASTRES |
| 107 | 411D07 - CDRL3 (Kabat) | Amino acid sequence of CDRL3 of 411D07 using Kabat | QQYYSNRS |
| 108 | 411D07 - Light chain variable region | Amino acid sequence of V_L of 411D07 | DIVMTQSPDSLAVSLGERATINCKSSQSVLYSSNNKNYLAWYQQKSGQPPKWYW ASTRESGVPDRFSGSGSGTDFTLTISSLQTEDVAVYYCQQYYSNRSFGQGTKLEIK |
| 109 | 411D07 - Light chain variable region | Nucleic acid sequence of V_L of 411D07 | GACATCGTGATGACCCAGTCTCCAGACTCCCTGGCTGTGTCTCTGGGCGAGAGG GCCACCATCAACTGCAAGTCCAGCCAGAGTGTTTTATACAGCTCCAACAATAAGA ATTACTTAGCTTGGTACCAGCAGAAATCAGGACAGCCTCCTAAGTTGCTCATTTA CTGGGCATCTACCCGGGAATCCGGGGTCCCTGACCGATTCAGTGGCAGCGGGT CTGGGACAGATTTCACTCTCACCATCAGCAGCCTGCAGACTGAAGATGTGGCAG TTTATTACTGTCAGCAATATTATAGTAATCAGTTTGGCCAGGGACCAAGCT GGAGATCAAAC |
| 110 | 411D07 - full light chain sequence | Amino acid sequence of 411D07 light chain | DIVMTQSPDSLAVSLGERATINCKSSQSVLYSSNNKNYLAWYQQKSGQPPKLLIYW ASTRESGVPDRFSGSGSGTDFTLTISSLQTEDVAVYYCQQYYSNRSFGQGTKLEIK RTVAAPSVFIFPPSDEQLKSGTASWCLLNNFYPREAKVQWKVDNALQSGNSQESV TEQDSKDSTYSLSSTLTLSKADYEKHKVYACEVTHQGLSSPVTKSFNRGEC |
| 111 | 411D07 - full light chain sequence | Nucleic acid sequence of 411D07 light chain | GACATCGTGATGACCCAGTCTCCAGACTCCCTGGCTGTGTCTCTGGGCGAGAGG GCCACCATCAACTGCAAGTCCAGCCAGAGTGTTTTATACAGCTCCAACAATAAGA ATTACTTAGCTTGGTACCAGCAGAAATCAGGACAGCCTCCTAAGTTGCTCATTTA CTGGGCATCTACCCGGGAATCCGGGGTCCCTGACCGATTCAGTGGCAGCGGGT CTGGGACAGATTTCACTCTCACCATCAGCAGCCTGCAGACTGAAGATGTGGCAG TTTATTACTGTCAGCAATATTATAGTAATCGAGTTTGGCCAGGGACCAAGCT GGAGATCAAACGTACGGTGGCCGCACCGCTTCTGTCGTTCATCTTCCCACCTTCCGA CCCCCGCCAGGGAGCCAAGGTGCAGTGGAAGGTGGACAACGCCCTGCAGTCCGGCA ACTCCCAGGAATCCGTGACCGAGCAGGACTCCAAGGACAGCACCTACTCCCTGT CCTCCACCCTGACCCTGTCCAAGGCCGACTACGAGAAGCACAAGGTGTACGCCT GCGAAGTGACCCACCAGGGCCTGTCTAGCCCCGTGACCAAGTCTTTCAACCGGG GCGAGTGT |
| 112 | 385F01 - CDRH1 (IMGT) | Amino acid sequence of CDRH1 of 385F01 using IMGT | GFTFSSYW |
| 113 | 385F01 - CDRH2 (IMGT) | Amino acid sequence of CDRH2 of 385F01 using IMGT | IKEDGSEK |
| 114 | 385F01 - CDRH3 (IMGT) | Amino acid sequence of CDRH3 of 385F01 using IMGT | ARNRLYSDFLDN |
| 115 | 385F01 - CDRH1 (Kabat) | Amino acid sequence of CDRH1 of 385F01 using Kabat | SYWMS |

-continued

SEQUENCE LISTING

| SEQ ID NO: | Name | Description | Sequence |
|---|---|---|---|
| 116 | 385F01 - CDRH2 (Kabat) | Amino acid sequence of CDRH2 of 385F01 using Kabat | NIKEDGSEKYYVDSVKG |
| 117 | 385F01 - CDRH3 (Kabat) | Amino acid sequence of CDRH3 of 385F01 using Kabat | NRLYSDFLDN |
| 118 | 385F01 - Heavy chain variable region | Amino acid sequence of $V_H$ of 385F01 | EVQLVESGGGLVQPGGSLRLSCAASGFTFSSYWMSWVRQAPGKGLEWVANIKED GSEKYYVDSVKGRFTISRDNAKNSLYLQMNSLRAEDTSVYYCARNRLYSDFLDNW GQGTLVTVSS |
| 119 | 385F01 - Heavy chain variable region | Nucleic acid sequence of $V_H$ of 385F01 | GAGGTGCAGCTGGTGGAGTCTGGGGGAGGCTTGGTCCAGCCTGGGGGGTCCCT GAGACTCTCCTGTGCAGCCTCTGGATTCACGTTTAGTAGCTATTGGATGAGTTG GGTCCGCCAGGCTCCAGGGAAGGGGCTGGAGTGGGTGGCCAACATCAAGAAG ATGGAAGTGAGAAATACTATGTCGACTCTGTGAAGGGCCGATTCACCATCTCCA GAGACAACGCCAAGAACTCACTGTATCTGCAAATGAACAGCCTGAGAGCCGAGG ACACCTCTGTATTACTGTGCGAGAAATCGACTCTACAGTGACTTCCTTGACAA CTGGGGCCAGGGAACCCTGGTCACCGTCTCCTCAG |
| 120 | 385F01 - full heavy chain sequence | Amino acid sequence of 385F01 heavy chain | EVQLVESGGGLVQPGGSLRLSCAASGFTFSSYWMSWVRQAPGKGLEWVANIKED GSEKYYVDSVKGRFTISRDNAKNSLYLQMNSLRAEDTSVYYCARNRLYSDFLDNW GQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSL SPGK |
| 121 | 385F01 - full heavy chain sequence | Nucleic acid sequence of 385F01 heavy chain | GAGGTGCAGCTGGTGGAGTCTGGGGGAGGCTTGGTCCAGCCTGGGGGGTCCCT GAGACTCTCCTGTGCAGCCTCTGGATTCACGTTTAGTAGCTATTGGATGAGTTG GGTCCGCCAGGCTCCAGGGAAGGGGCTGGAGTGGGTGGCCAACATCAAGAAG ATGGAAGTGAGAAATACTATGTCGACTCTGTGAAGGGCCGATTCACCATCTCCA GAGACAACGCCAAGAACTCACTGTATCTGCAAATGAACAGCCTGAGAGCCGAGG ACACCTCTGTATTACTGTGCGAGAAATCGACTCTACAGTGACTTCCTTGACAA CTGGGGCCAGGGAACCCTGGTCACCGTCTCCTCAGCCTCCACCAAGGGCCCCTC TGTGTTCCCTCTGCCAAGTCACCTCTGGGCGAACAGCCGCTCT GGGCTGCCTCTGAAGGACTACTTCCCCGAGCCTGTGACCGTGTCGTCTGGAACTC TGGCGCTCTGACCAGCGGAGTGCACACCTTCCCTGCTGTTCCTGCAGTCCTCCGG CCTGTACTCCCTGTCCTCCGTCGTGACCGTCCCTTCCAGCTCTCTGGGCACCCA GACCTACATCTGCAACGTGAACCACAAGCCCTCCAACACCAAGGTGGACAAGA GGGTGGAACCCAAGTCTGTGACAAGACACCCACCTGTCCCCCCAAGCCAAGGACAC TGAACTGCTGGGCGGACCTTCCGTTCCCTGTTCCTGTTCCCCCAAGCCCAAGGACAC CCTGATGATCTCCCGGACCCCTGAAGTGACCTGCGTGGTGGTGGATGTGTCCCA CGAGGACCCTGAAGTGAAGTTCAATTGGTACGTGGACGGCGTGGAAGTGCACAA CGCCAAGACCAAGCCTAGAGAGGAACAGTACAACTCCACCTACCGGGTGTGTC CGTGCTGACCGTGCTGCACCAGGATTGGCTGAACGGCAAAGAGTACAAGTGCAA GGTGTCCAACAAGGCCCTGCCTGCCCCCATCGAAAAGACCATCTCCAAGGCCAA GGGCCAGCCCCGGGAACCCCAGGTGTACACCCTGCCCCCTAGCAGGAGGAGCT |

| SEQ ID NO: | Name | Description | Sequence |
|---|---|---|---|
| | | | GACCAAGAACCAGGTGTCCCTGACCTGTCTCGTGAAAGGCTTTACCCCTCGA<br>TATCGCCGTGGAATGGGAGTCCAACGGCCAGCCTGAGAACAACTACAAGACCAC<br>CCCCCCTGTCCTGGACTCCGACGGCTCATTCTTCCTGTACAGCAAGCTGACAGT<br>GGACAAGTCCCGGTGGCAGCAGGGCAACGTGTTCTCCTGCTCCGTGATGCACGA<br>GGCCCTGCACAACCACTACACCCAGAAGTCCCTGTCCCTGAGCCCGGCAAG |
| 122 | 385F01 - CDRL1 (IMGT) | Amino acid sequence of CDRL1 of 385F01 using IMGT | QGVSSW |
| 123 | 385F01 - CDRL2 (IMGT) | Amino acid sequence of CDRL2 of 385F01 using IMGT | GAS |
| 124 | 385F01 - CDRL3 (IMGT) | Amino acid sequence of CDRL3 of 385F01 using IMGT | QQANSIPFT |
| 125 | 385F01 - CDRL1 (Kabat) | Amino acid sequence of CDRL1 of 385F01 using Kabat | RASQGVSSWLA |
| 126 | 385F01 - CDRL2 (Kabat) | Amino acid sequence of CDRL2 of 385F01 using Kabat | GASSLQS |
| 127 | 385F01 - CDRL3 (Kabat) | Amino acid sequence of CDRL3 of 385F01 using Kabat | QQANSIPFT |
| 128 | 385F01 - Light chain variable region | Amino acid sequence of $V_L$ of 385F01 | DIQMTQSPSSVSASVGDRVTITCRASQGVSSWLAWYQQKSGKAPKLLIYGASSLQ<br>SGVPSRFSGSGSGTEFILTISSLQPEDFATYYCQQANSIPFTFGPGTKVDIK |
| 129 | 385F01 - Light chain variable region | Nucleic acid sequence of $V_L$ of 385F01 | GACATCCAGATGACCCAGTCTCCATCTTCCGTGTCTGCATCTGTCGGAGACAGA<br>GTCACCATCACTTGTCGGGCGAGTCAGGGTGTTAGCAGCTGGTTAGCCTGGTAT<br>CAGCAGAAATCAGGGAAAGCCCCTAAGCTCCTGATCTATGGTGCATCCAGTTTG<br>CAAAGTGGGGTCCCATCAAGATTCAGCGGCAGTGGATCTGGGACAGAGTTCATT<br>CTCACCATCAGCAGCCTGAGCCTGAAGATTTTGCAACTTACTATTGTCAACAGG<br>CTAACAGTATCCCATTCACTTTCGGCCCTGGGACCAAAGTGGATATCAAAC |
| 130 | 385F01 - full light chain sequence | Amino acid sequence of 385F01 light chain | DIQMTQSPSSVSASVGDRVTITCRASQGVSSWLAWYQQKSGKAPKLLIYGASSLQ<br>SGVPSRFSGSGSGTFILTISSLQPEDFATYYCQQANSIPFTFGPGTKVDIKRTVAAP<br>SVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC |
| 131 | 385F01 - full light chain sequence | Nucleic acid sequence of 385F01 light chain | GACATCCAGATGACCCAGTCTCCATCTTCCGTGTCTGCATCTGTCGGAGACAGA<br>GTCACCATCACTTGTCGGGCGAGTCAGGGTGTTAGCAGCTGGTTAGCCTGGTAT<br>CAGCAGAAATCAGGGAAAGCCCCTAAGCTCCTGATCTATGGTGCATCCAGTTTG<br>CAAAGTGGGGTCCCATCAAGATTCAGCGGCAGTGGATCTGGGACAGAGTTCATT<br>CTCACCATCAGCAGCCTGAGCCTGAAGATTTTGCAACTTACTATTGTCAACAGG<br>CTAACAGTATCCCATTCACTTTCGGCCCTGGGACCAAAGTGGATATCAAACGTAC<br>GGTGGCGCCGCTCCTGTCGTCTTCATCTTCCCACCTTCCGACGAGCAGTTGAAGTC<br>CGGCACCGCTTCTGTCGTGTGCCTGCTGAACAACTTCTACCCCCGAGAGCCAA<br>GGTGCAGTGGAAGGTGGACAACGCCCTGCAGTCCGGCAACTCCCAGGAATCCGT |

-continued

SEQUENCE LISTING

| SEQ ID NO: | Name | Description | Sequence |
|---|---|---|---|
| | | | GACCGAGCAGGACTCCAAGGACACAGCCACCTACTCCCTGTCCTCCACCCTGACCCT GTCCAAGGCCGACTACGAGAAGCACAAGGTGTACGCCTGCGAAGTGACCCACCA GGGCCTGTCTAGCCCCGTGACCAAGTCTTTCAACCGGGGCGAGTGT |
| 132 | 413D08 - CDRH1 (IMGT) | Amino acid sequence of CDRH1 of 413D08 using IMGT | GFTFRIYG |
| 133 | 413D08 - CDRH2 (IMGT) | Amino acid sequence of CDRH2 of 413D08 using IMGT | IWYDGSNK |
| 134 | 413D08 - CDRH3 (IMGT) | Amino acid sequence of CDRH3 of 413D08 using IMGT | ARDMDYFGMDV |
| 135 | 413D08 - CDRH1 (Kabat) | Amino acid sequence of CDRH1 of 413D08 using Kabat | IYGMH |
| 136 | 413D08 - CDRH2 (Kabat) | Amino acid sequence of CDRH2 of 413D08 using Kabat | VIWYDGSNKYYADSVKG |
| 137 | 413D08 - CDRH3 (Kabat) | Amino acid sequence of CDRH3 of 413D08 using Kabat | DMDYFGMDV |
| 138 | 413D08 - Heavy chain variable region | Amino acid sequence of $V_H$ of 413D08 | QVQLVESGGGVVQPGRSLRLSCAASGFTFRIYGMHWVRQAPGKGLEWVAVIWYD GSNKYYADSVKGRFTISRDNSDNTLYLQMNSLRAEDTAVYYCARDMDYFGMDVW GQGTTVTVSS |
| 139 | 413D08 - Heavy chain variable region | Nucleic acid sequence of $V_H$ of 413D08 | CAGGTGCAGCTGGTGGAGTCTGGGGGAGGCGTGGTCCAGCCTGGGAGGTCCCT GAGACTCTCCTGTGCAGCCTCTGGATTCACCTTCCGTATTTATGGCATGCACTG GGTCCGCCAGGCTCCAGGCAAGGGGCTGGAGTGGGTGGCAGTTATATGGTATG ATGGAAGTAATAAATACTATGCTGACTCCGTGAAGGGCCGATTCACCATCTCCA GAGACAATTCCGACAACACGCTGTATCTGCAAATGAACAGCCTGAGAGCCGAGG ACACGCTGTATTACTGTGCGAGAGATATGGACTACTTCGGTATGGACGTCTT GGGGCCAAGGGACCACGGTCACCGTCTCCTCAG |
| 140 | 413D08 - full heavy chain | Amino acid sequence of 413D08 heavy chain | QVQLVESGGGVVQPGRSLRLSCAASGFTFRIYGMHWVRQAPGKGLEWVAVIWYD GSNKYYADSVKGRFTISRDNSDNTLYLQMNSLRAEDTAVYYCARDMDYFGMDVW GQGTTVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAP IEKTISMKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSL SPGK |
| 141 | 413D08 - full heavy chain sequence | Nucleic acid sequence of 413D08 heavy chain | CAGGTGCAGCTGGTGGAGTCTGGGGGAGGCGTGGTCCAGCCTGGGAGGTCCCT GAGACTCTCCTGTGCAGCCTCTGGATTCACCTTCCGTATTTATGGCATGCACTG GGTCCGCCAGGCTCCAGGCAAGGGGCTGGAGTGGCAGTTATATGGTATG ATGGAAGTAATAAATACTATGCTGACTCCGTGAAGGGCCGATTCACCATCTCCA |

| SEQ ID NO: | Name | Description | Sequence |
|---|---|---|---|
| | | | GAGACAATTCCGACAACACGCTGTATCTGCAAATGAACAGCCTGAGAGCCGAGG ACACGGCTGTGTATTACTGTGCGAGAGATATGGACTACTTCGGTATGGACGTCT GGGGCCAAGGGACCACGGTCACCGTCTCCTCAGCCTCCACCAAGGGCCCCTCTG TGTTCCCTCTGGCCCCTTGCTGAAGGACTACTTCCCCGAAGTCCACCTCTGGTGACCGTCTCTGGAACTCTG GCGCTCTGACCAGCGGAGTGCACACCTTCCCTGCTGTCCTACAGTCCTCCGGCC TGTACTCCCTGTCCTCCGTCGTGACCGTGCCCTCCAACACCAAGGTGGACAAGAAGG CCTACATCTGCAACGTGAACCACAAGCCCTCCAACACCAAGGTGGACAAGAAGG TGGAACCCAAGTCCTGCGACAAGACTCACACATGCCCTCCCCCGCCCGA ACTGCTGGGCGGACCTTCCGTGTTCCTGTTCCCCCCAAAGCCCAAGGACACCCT GATGATCTCCCGAACCCCTGAAGTGACCTGCGTGGTGGTGGATGTGTCCCACGA GGACCCTGAAGTGAAGTTCAATTGGTACGTGGACGGCGTGGAAGTGCACAACGC CAAGACCAAGCCTAGAGAGGAACAGTACAACTCCACCTACCGGGTGGTGTCCGT GCTGACCGTGCTGCACCAGGATTGGCTGAACGGCAAAGAGTACAAGTGCAAGGT GTCCAACAAGGCCCTGCCCGCCCCCATCGAAAAGACCATCTCCAAGGCCAAGGG CCAGCCCCGGGAACCCCAGGTGTACACCCTGCCCCCTAGCAGGGACGAGCTGAC CAAGAACCAGGTGTCCCTGACCTGTCTGGTGAAGGGCTTCTACCCTCCGATAT CGCCGTGGAATGGGAGTCCAACGGCCAGCCTGGAGAACAATACAAGACACCCC CCCTGTGCTGGACTCCGACGGCTCATTCTTCCTGTACAGCAAGCTGACAGTGGA CAAGTCCCGGTGGCAGCAGGGCAACGTGTTCTCCTGCTCCGTGATGCACGAGGC CCTGCACAACCACTACACCCAGAAGTCCCTGTCCCTGAGCCCCGGCAAG |
| 142 | 413D08 - CDRL1 (IMGT) | Amino acid sequence of CDRL1 of 413D08 using IMGT | QGIRND |
| 143 | 413D08 - CDRL2 (IMGT) | Amino acid sequence of CDRL2 of 413D08 using IMGT | AAS |
| 144 | 413D08 - CDRL3 (IMGT) | Amino acid sequence of CDRL3 of 413D08 using IMGT | LQHNSYPRT |
| 145 | 413D08 - CDRL1 (Kabat) | Amino acid sequence of CDRL1 of 413D08 Using Kabat | RASQGIRNDLG |
| 146 | 413D08 - CDRL2 (Kabat) | Amino acid sequence of CDRL2 of 413D08 using Kabat | AASSLQS |
| 147 | 413D08 - CDRL3 (Kabat) | Amino acid sequence of CDRL3 of 413D08 using Kabat | LQHNSYPRT |
| 148 | 413D08 - Light chain variable region | Amino acid sequence of V_L of 413D08 | DLQMTQSPSSLSASVGDRVTITCRASQGIRNDLGWYQQKPGKAPKRLIYAASSLQS GVPSRFSGSGSGTEFTLTISSLQPEDFATYYCLQHNSYPRTFGQGTKVEIK |
| 149 | 413D08 - Light chain variable region | Nucleic acid sequence of V_L of 413D08 | GACTTCACAGATGACCCAGTCTCCATCCTCCCTGTCTGCATCTGTAGGAGACAGA GTCACCATCACTTGCCGGGCAAGTCAGGGCATTAGAAATGATTTAGGCTGGTAT CAGCAGAAACCAGGGAAAGCCCCTAAGCGCCTGATCTATGCTGCATCCAGTTTG CAAAGTGGGGTCCCATCAAGGTTCAGCGGCAGTGGATCTGGGACAGAATTCACT CTCAATCAGCAGCCTGCAGCCTGAAGATTTTGCAACTTATTACTGTCTACAGC |

-continued

SEQUENCE LISTING

| SEQ ID NO: | Name | Description | Sequence |
|---|---|---|---|
| | | | ATAATAGTTACCCTCGGACGTTCGGCCAAGGGACCAAGGTGGAAATCAAAC |
| 150 | 413D08 - full light chain sequence | Amino acid sequence of 413D08 light chain | DLQMTQSPSSLSASVGDRVTITCRASQGIRNDLGWYQQKPGKAPKRLIYAASSLQS GVPSRFSGSGSGTEFTLTISSLQPEDFATYYCLQHNSYPRTFGQGTKVEIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 151 | 413D08 - full light chain sequence | Nucleic acid sequence of 413D08 light chain | GACCTCCAGATGACCCAGTCTCCATCCTCCCTGTCTGCATCTGTAGGAGACAGA GTCACCATCACTTGCCGGGCAAGTCAGGGCATTAGAAATGATTTAGGCTGGTAT CAGCAGAAACCAGGGAAAGCCCCTAAGCGCCTGATCTATGCTGCATCCAGTTTG CAAAGTGGGGTCCCATCAAGGTTCAGCGGCAGTGGATCTGGGACAGAATTCACT CTCACAATCAGCAGCCTGCAGCCTGAAGATTTTGCAACTTATTACTGTCTACAGC ATAATAGTTACCCTCGGACGTTCGGCCAAGGGACCAAGGTGGAAATCAAACGTA CGGTGGCTGCTCCATCCGTCTTCATCTTCCCACCTTCCGACGAGCAGTTGAAGT CCGGAACCGCTTCTGTTGTGTGCCTGCTGAACAACTTCTACCCCCGAGGCCA AGGTCCAGTGGAAGGTGGACAACGCCCTGCAATCCGGCAACTCCCAGGAATCCG TGACCGAGCAGGACTCCAAGGACAGCACCTATTCCCTGTCCTCCACCCTGACCC TGTCCAAGGCCGACTACGAGAAGCACAAGGTGTACGCCTGCGAAGTGACCCACC AGGGCCTGTCTAGCCCCGTGACCAAGTCTTTCAACCGCGGGGAGTGT |
| 152 | 386H03 - CDRH1 (IMGT) | Amino acid sequence of CDRH1 of 386H03 using IMGT | GGSISSSDW |
| 153 | 386H03 - CDRH2 (IMGT) | Amino acid sequence of CDRH2 of 386H03 using IMGT | IFHSGNT |
| 154 | 386H03 - CDRH3 (IMGT) | Amino acid sequence of CDRH3 of 386H03 using IMGT | VRDGSGSY |
| 155 | 386H03 - CDRH1 (Kabat) | Amino acid sequence of CDRH1 of 386H03 using Kabat | SSDWS |
| 156 | 386H03 - CDRH2 (Kabat) | Amino acid sequence of CDRH2 of 386H03 using Kabat | EIFHSGNTNYNPSLKS |
| 157 | 386H03 - CDRH3 (Kabat) | Amino acid sequence of CDRH3 of 386H03 using Kabat | DGSGSY |
| 158 | 386H03 - Heavy chain variable region | Amino acid sequence of $V_H$ of 386H03 | QVQLQESGPGLVKPSGTLSLTCAVSGGSISSSDWSWVRQPPGKGLEWIGEIFHS GNTNYNPSLKSRVTISVDKSKNQISLRLNSVTAADTAVYYCVRDGSGSYWGQGTL VTVSS |
| 159 | 386H03 - Heavy chain variable region | Nucleic acid sequence of $V_H$ of 386H03 | CAGGTGCAGCTGCAGGAGTCGGGCCCAGGACTGGTGAAGCCTTCGGGGACCCT GTCCCTCACCTGCGCTGTCTCTGGTGGCTCCATCAGCAGTAGTGACTGGTCGAG TTGGGTCCGCCAGCCCCCAGGGAAGGGGCTGGAGTGGATTGGGGAAATCTTTC ATAGTGGGAACACCAACTACAACCCGTCCCTCAAGAGTCGAGTCACCATATCAGT AGACAAGTCCAAGAACCAGATCTCCCTGAGGCTGAACTCTGTGACCGCCGCGGA CACGGCCGTGTATTACTGTGTGAGAGATGGTTCGGGAGTTACTGGGGCCAGG |

SEQUENCE LISTING -continued

| SEQ ID NO: | Name | Description | Sequence |
|---|---|---|---|
| 160 | 386H03 - full heavy chain sequence | Amino acid sequence of 386H03 heavy chain | QVQLQESGPGLVKPSGTLSLTCAVSGGSISSSDMWSWVRQPPGKGLEWIGEIFHS GNTNYNPSLKSRVTISVDKSKNQISLRLNSVTAADTAVYYCVRDGSGSYWGQTL VTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK GAACCCTGGTCACCGTCTCCTCAG |
| 161 | 386H03 - full heavy chain sequence | Nucleic acid sequence of 386H03 heavy chain | CAGGTGCAGCTGCAGGAGTCGGGCCCAGGACTGGTGAAGCCTTCGGGGACCCT GTCCCTCACCTGCGCTGTCTCTGGTGGCTCCATCAGCAGTAGTGACTGTGGAG TTGGGTCCCGCCAGCCCCCAGGGAAGGGGCTGGAGTGGATTGGGAAATCTTTC ATAGTGGGAACACCAACTACAACCCCTCCCTCAAGAGTCGAGTCACCATATCAGT AGACAAGTCCAAGAACCAGATCTCCCTGAGGCTGAACTCTGTGACCGCCCGGA CACGGCCGTGTATTACTGTGTGAGAGATGGTTCGGGAGTACTGGGGCCAGG GAACCCCTTCACCGTCTCCTCAGCCAGCACCAAGGGCCCCTCTGTTCCCTC TGGCCCCTGCTCCAGCAAGTCCACCTCTGGGGAACAGCCGGTCTGGGCTGCCTG TGAAGGACTACTTCCCCGAGCCTGTGACCGTGTCGTGGAACTCTGGCGCTCTGA CCAGCGGAGTGCACACCTTCCCTGCTGTCCTGCAGTCCTCCGGGCACCCAGCT TGTCCTCCGTCGTGACCGTGCCTTCCAGCTCTGGGGCACCCAGACCTACATCT GCAACGTGAACCACCAGCCCTCCAATACCAAGGTGGACAAGAAGGTGGAACCCA AGTCCTGCGACAAGACCCACACCTGTCCCCCCAAGCACCCTGAACTGCTGG GCGGACCCTTCCGTGTTCCTGTTCCCCCCAAAGCCTAAGGATACCCTGATGATCT CCCGACCCCTGAAGTGACCTGCGTGGTGGTGGATGTGTCCACGAGGACCCT GAAGTGAAGTTCAATTGGTACGTGGACAGCGCGTGGAAGTGCACAACGCCAAGACC AAGCCTAGAGAGGAACAGTACAACTCCACCTACCGGGTGTGTCGTGCTGACC GTGCTGCACCAGGATTGGCTGAACGGCAAAGAGTACAAGTGCAAGGTGTCCAAC AAGGCCCTGCCTGCCCCATCGAAAAGACCATCTCCAAGGCCAAGGGCCAGCC CGGGAACCCCAGGTGTACACACTGCCTCCTAGCAGGGACGAGCTGACCAAGAAC CAGGTGTCCCTGACCTGTCTGGTGAAGGGCTTCTACCCCTCCGATATCGCGTG GAATGGGAGTCCAACGGCCAGCCTGAGAACAACTACAAGACCACCCCCCTGTG CTGACTCCGACGGCTCATTCTTCCTGTACAGCAAGCTGACAGTGGACAAGTCC CGGTGGCAGCAGGGCAACGTGTTCTCCTGCTCCGTGATGCACGAGGCCCTGCAC AACCACTACACCCAGAAGTCCCTGTCCCTGAGCCCGGGCAAG |
| 162 | 386H03 - CDRL1 (IMGT) | Amino acid sequence of CDRL1 of 386H03 using IMGT | QSVLYSSNNKNY |
| 163 | 386H03 - CDRL2 (IMGT) | Amino acid sequence of CDRL2 of 386H03 using IMGT | WAS |
| 164 | 386H03 - CDRL3 (IMGT) | Amino acid sequence of CDRL3 of 386H03 using IMGT | QQYYSTRS |
| 165 | 386H03 - CDRL1 (Kabat) | Amino acid sequence of CDRL1 of 386H03 using Kabat | KSSQSVLYSSNNKNYLA |

SEQUENCE LISTING

| SEQ ID NO: | Name | Description | Sequence |
|---|---|---|---|
| 166 | 386H03 - CDRL2 (Kabat) | Amino acid sequence of CDRL2 of 386H03 using Kabat | WASTRES |
| 167 | 386H03 - CDRL3 (Kabat) | Amino acid sequence of CDRL3 of 386H03 using Kabat | QQYYSTRS |
| 168 | 386H03 - Light chain variable region | Amino acid sequence of V<sub>L</sub> of 386H03 | DIVMTQSPDSLAVSLGERATINCKSSQSVLYSSNNKNYLAWYQQKPGQPPKLLIYW ASTRESGVPDRFSGSGSGTDFTLTISSLQAEDVAVYYCQQYYSTRSFGQGTKLEIK |
| 169 | 386H03 - Light chain variable region | Nucleic acid sequence of V<sub>L</sub> of 386H03 | GACATCGTGATGACCCAGTCTCCAGACTCCCTGGCTGTGTCTCTGGGCGAGAGG GCCACCATCAACTGCAAGTCCAGCCAGAGTGTTTTATACAGTCCAACAATAAGA ACTACTTAGCTTGGTACCAGCAGAAACCAGGACAGCCTCCTAAACTGCTCATTTA CTGGGCATCTACCCGGGAATCCGGGGTCCCTGACCGATTCAGTGGCAGCGGGT CTGGGACAGATTTCACTCTCACCATCAGCAGCCTGCAGGCTGAAGATGTGGCAG TTTATTACTGTCAGCAGATTATATAGTACTCGCAGTTTTGGCCAGGGGACCAAGCT GGAGATCAAAC |
| 170 | 386H03 - full light chain sequence | Amino acid sequence of 386H03 light chain | DIVMTQSPDSLAVSLGERATINCKSSQSVLYSSNNKNYLAVYYQQKPGQPPKLLIYW ASTRESGVPDRFSGSGSGTDFTLTISSLQAEDVAVYYCQQYYSTRSFGQGTKLEIK RTVAAPSVFIFPPSDEQLKSGTASVVCLLNNFYPREAMKVDNALQSGNSQESV TEQDSKDSTYSLSSTLTLSKADYEKHKVYACEVTHQGLSSPVTKSFNRGEC |
| 171 | 386H03 - full light chain sequence | Nucleic acid sequence of 386H03 light chain | GACATCGTGATGACCCAGTCTCCAGACTCCCTGGCTGTGTCTCTGGGCGAGAGG GCCACCATCAACTGCAAGTCCAGCCAGAGTGTTTTATACAGTCCAACAATAAGA ACTACTTAGCTTGGTACCAGCAGAAACCAGGACAGCCTCCTAAACTGCTCATTTA CTGGGCATCTACCCGGGAATCCGGGGTCCCTGACCGATTCAGTGGCAGCGGGT CTGGGACAGATTTCACTCTCACCATCAGCAGCCTGCAGGCTGAAGATGTGGCAG TTTATTACTGTCAGCAGATTATATAGTACTCGCAGTTTTGGCCAGGGGACCAAGCT GGAGATCAAACGTACGGTGGCCGCACCCGTCTTCATCTTCCCACCTTCCGA CGAGCAGCTGAAGTCCGGAACTGCCTCTGTCGTGTGCCTGCTGAACAACTTCTA CCCCCGCGAGGCCAAGGTGCAGTGGAAGGTGGACAACGCCCTGCAGTCCGGCA ACTCCCAGGAATCCGTGACCGAGCAGGACTCCAAGGACAGCACCTACTCCCTGT CCTCACCCTGACCCTGTCCAAGGCCGACTACGAGAAGCACAAGGTGTACGCCT GCGAAGTGACCCACCAGGGCCTGTCTAGCCCCGTGACCAAGTCTTTCAACCGGG GCGAGTGT |
| 172 | 389A03 - CDRH1 (IMGT) | Amino acid sequence of CDRH1 of 389A03 using IMGT | GGSISSSSYY |
| 173 | 389A03 - CDRH2 (IMGT) | Amino acid sequence of CDRH2 of 389A03 using IMGT | IYSTGYT |
| 174 | 389A03 - CDRH3 (IMGT) | Amino acid sequence of CDRH3 of 389A03 using IMGT | AISTAAGPEYFHR |
| 175 | 389A03 - CDRH1 (Kabat) | Amino acid sequence of CDRH1 of 389A03 using Kabat | SSSYYCG |

SEQUENCE LISTING

| SEQ ID NO: | Name | Description | Sequence |
|---|---|---|---|
| 176 | 389A03 - CDRH2 (Kabat) | Amino acid sequence of CDRH2 of 389A03 using Kabat | SIYSTGYTYNPSLKS |
| 177 | 389A03 - CDRH3 (Kabat) | Amino acid sequence of CDRH3 of 389A03 using Kabat | STAAGPEYFHR |
| 178 | 389A03 - Heavy chain variable region | Amino acid sequence of V$_H$ of 389A03 | QLQESGPGLVKPSETLSLTCTVSGGSISSSSYYCGWIRQPPGKGLDWIGSTYSTGYT YYNPSLKSRVTISIDTSKNQFSCLILTSVTAADTAVYYCAISTAAGPEYFHRWGQGT LVTVSS |
| 179 | 389A03 - Heavy chain variable region | Nucleic acid sequence of V$_H$ of 389A03 | CAGCTGCAGGAGTCGGGCCCAGGCCTGGTGAAGCCTTCGGAGACCCTGTCCCTC ACCTGCACTGTCTCTGGTGGCTCCATCAGCAGTAGTAGTTATTACTGCGGTGG ATCCGCCAGCCCCCTGGGAAGGGCTGGACTGGATTGGGAGTATCTATTCTACT GGGTACACCTACAACCCGTCCCTCAAGAGTCGAGTCACCATTTCCATAGACA CGTCCAAGAACCAGTTCTCATGCCTGATACTGACCTCTGTAACTGCCGAGACA CGGCTGTGTATTACTGTGCGATAAGTACAGCAGCTGGCCCTGAATACTTCCATC GCTGGGGCCAGGGCACCCTGGTCACCGTCTCCTCAG |
| 180 | 389A03 - full heavy chain sequence | Amino acid sequence of 389A03 heavy chain | QLQESGPGLVKPSETLSLTCTVSGGSISSSSYYCGWIRQPPGKGLDWIGSTYSTGYT YYNPSLKSRVTISIDTSKNQFSCLILTSVTAADTAVYYCAISTAAGPEYFHRWGQGT LVTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK |
| 181 | 389A03 - full heavy chain sequence | Nucleic acid sequence of 389A03 heavy chain | CAGCTGCAGGAGTCGGGCCCAGGCCTGGTGAAGCCTTCGGAGACCCTGTCCCTC ACCTGCACTGTCTCTGGTGGCTCCATCAGCAGTAGTAGTTATTACTGCGGTGG ATCCGCCAGCCCCCTGGGAAGGGCTGGACTGGATTGGGAGTATCTATTCTACT GGGTACACCTACAACCCGTCCCTCAAGAGTCGAGTCACCATTTCCATAGACA CGTCCAAGAACCAGTTCTCATGCCTGATACTGACCAGCTGCCCTGAATACTTCCATC GGCTGTGTATTACTGTGCGATAAGTACAGCAGCTGGCCCTGAATACTTCCATC GCTGGGGCCAGGGCACCCTGGTCACCGTCTCCTCAGCCTCCACCAAGGGCCCCT CTGTTCCCCTGGCCCCTTCCAGCAAGCTCACCCTCTGGCGGCAACAGCCGCTC TGGGGCTGCCTGGTCAAGGACTACTTCCCGAAGCCTGTGACCGTGTCCTGAACT GCTGGCTCGTGACCAGCGGAGTGCACACCTTCCCGGCTGTCCTGCAGTCCTCCG GACTCTACTCCCTCAGCAGCGTGGTGACCGTGCCCTCCAGCTCTGGACCCAGA AGACCTACATCTGCAACGTGAATCACAAGCCCAGCAACACCAAGGTGGACAAGA AAGTTGAACCCAAGTCCTGCGACAAGACCCACACCTGTCCCCCATGCCCAGCA CCTGAACTGCTGGGGGACCTCTCCTGTTCCTGCCCCCAAAGCCCAAGGACA CCCTCATGATCTCCCGGACCCCCTGAAGTGACCTGCGTGGTGGTGGATGTGTCCC ACGAGGACCCTGAAGTGAAGTTCAATTGGTACGTGGACGGCGTGGAAGTGCACA ACGCCAAGACAAGCCGTGCTGCACCAGGATTGGCTGAACGGCAAGGAGTACAAGTGCA AAGGTGTCCAACAAGGCCCTGCCTGCCCCATCGAGAAAACCATCTCCAAGGCCA AGGGCCAGCCCCGGGAACCCCAGGTGTACACACTGCCCCCATCCCGGGAGCAGC |

-continued

SEQUENCE LISTING

| SEQ ID NO: | Name | Description | Sequence |
|---|---|---|---|
| | | | TGACCAAGAACCAGTGTCCCTGACCTGTCTCGTCTTCTGAAAGGCTTCTACCCCTCCG ATATCGCCTGGAATGGGAGTCCAACGGCCAGCCTGAGACAACTACAAGACCA CCCCCCTGTGCTGACTCCGACGCTCATTCTTCTGTACAGCAAGCTGACAG TGGACAAGTCCCGTGGCAGCAGGGCAACGTGTTCTCCTGCTCCGTGATGCACG AGGCCCTGCACAACCACTACACCCAGAAGTCCCTGTCCCTGAGCCCCGGCAAG |
| 182 | 389A03 - CDRL1 (IMGT) | Amino acid sequence of CDRL1 of 389A03 using IMGT | QSVLYSSNSKNF |
| 183 | 389A03 - CDRL2 (IMGT) | Amino acid sequence of CDRL2 of 389A03 using IMGT | WAS |
| 184 | 389A03 - CDRL3 (IMGT) | Amino acid sequence of CDRL3 of 389A03 using IMGT | QQYYSTPRT |
| 185 | 389A03 - CDRL1 (Kabat) | Amino acid sequence of CDRL1 of 389A03 using Kabat | KSSQSVLYSSNSKNPLA |
| 186 | 389A03 - CDRL2 (Kabat) | Amino acid sequence of CDRL2 of 389A03 using Kabat | WASTRGS |
| 187 | 389A03 - CDRL3 (Kabat) | Amino acid sequence of CDRL3 of 389A03 using Kabat | QQYYSTPRT |
| 188 | 389A03 - Light chain variable region | Amino acid sequence of V$_L$ of 389A03 | DIVMTQSPDSLAVSLGERATINCKSSQSVLYSSNSKNFLAWYQQKPGQPPKLFIYW ASTRGSGVPDRISGSGSGTDFNLTISSLQAEDVAVYYCQQYYSTPRTFGQGTKVEI K |
| 189 | 389A03 - Light chain variable region | Nucleic acid sequence of V$_L$ of 389A03 | GACATCGTGATGACCCAGTCTCCAGACTCCTGCTGTCTCTGGGCGAGAGG GCCACCATCAACTGCAAGTCCAGCCAGAGTGTTTTATACAGTCCAACAGTAAGA ACTTCTTAGCTTGGTACCAGCAGAAACCGGAGACAGCCCTCCTAAGCTGTTCATTTA CTGGGCATCTACCCGGGATCCGGGTCCCTGACCGAATCAGTGCAGCGGGT CTGGGACAGATTCAATTCACCATCAGCAGCCTGCAGGCTGAAGATGTGGCAG TTTATTACTGTCAACAATATTAGTACTCCTCGGACGTTCGGCCAAGGACCAA GGTGGAGATCAAAC |
| 190 | 389A03 - full light chain sequence | Amino acid sequence of 389A03 light chain | DIVMTQSPDSLAVSLGERATINCKSSQSVLYSSNSKNFLAWYQQKPGQPPKLFIYW ASTRGSGVPDRISGSGSGTDFNLTISSLQAEDVAVYYCQQYYSTPRTFGQGTKVEI KRTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| 191 | 389A03 - full light chain sequence | Nucleic acid sequence of 389A03 light chain | GACATCGTGATGACCCAGTCTCCAGACTCCTGCTGTCTCTGGGCGAGAGG GCCACCATCAACTGCAAGTCCAGCCAGAGTGTTTTATACAGTCCAACAGTAAGA ACTTCTTAGCTTGGTACCAGCAGAAACCGGAGACAGCCCTCCTAAGCTGTTCATTTA CTGGGCATCTACCCGGGATCCGGGTCCCTGACCGAATCAGTGCAGCGGGT CTGGGACAGATTCAATTCACCATCAGCAGCCTGCAGGCTGAAGATGTGGCAG TTTATTACTGTCAACAATATTAGTACTCCTCGGACGTTCGGCCAAGGACCAA GGTGGAGATCAAACGTACGGTGGCCGCTCCCGTCTTCATCTTCCCGTTC |

| SEQ ID NO: | Name | Description | Sequence |
|---|---|---|---|
| | | | CGAGAGCAGCTGAAGTCCGGACACCGCTTCTGTCGTGTGCCTGCTGAACAACTT<br>CTACCCCGCGAGGCCAAGGTGCAGGTGCAGGTGGACAACGCCCTGCAGTCCG<br>GCAACTCCCAGGAATCCGTGACCGAGCAGGACTCCAAGGACAGCACCTACTCCC<br>TGTCCTCCACCCTGACCCTGTCCAAGGCCGACTACGAGAAGCACAAGGTGTACG<br>CCTGCGAAGTGACCCACCAGGGCCTGTCTAGCCCCGTGACCAAGTCTTTCAACC<br>GGGGCGAGTGT |
| 192 | Human IgG4 heavy chain constant region #1 | IGHG4*01 & IGHG4*04 | Heavy Chain Constant Region Nucleotide Sequence | gcttccaccaagggcccatccgtcttccccctggcgccctgctccaggagcacctccgagagcacagccg<br>ccctgggctgcctggtcaaggactacttcccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtagatcacaagcccagcaacaccaagg<br>tggacaagagagttgagtccaaatatgtcccccatgcccatcatgcccagcacctgagttcctggggg<br>accatcagtcttcctgttccccccaaaacccaaggacactctcatgatctcccggacccctgaggtcacgtg<br>cgtggtggtggacgtgagccaggaagaccccgaggtccagttcaactggtacgtggatggcgtggagg<br>tgcataatgccaagacaaagccgcggaggagcagttcaacagtacaagtgcaaggtctccaacaaaggccctca<br>cgtcctgcaccaggactggctgaacggcaaggagtacaagtgcaaggtctccaacaaaggcctcccgt<br>cctccatcgagaaaaccatctccaaagccaaagggcagccccgagagccacaggtgtacaccctgccccc<br>atcccgggatgagctgaccaagaaccaggtcagcctgacctgcctggtcaaaggcttctacccagcg<br>acatccgcggagtgggagagcaatgggcagccggagaacaactacaagaccacgcctcccgtgctgg<br>gactccgacggctccttcttcctctacagcaggctaaccgtggacaagagcaggtggcagaggggaat<br>gtcttctcatgctccgtgatgcatgaggctctgcacaaccactacacgcagaagagcctctccctgtctctg<br>ggtaaa |
| 193 | | | Heavy Chain Constant Region Amino Acid Sequence | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPSCPAPEF<br>LGGPSVFLFPPKPKDTLMISRTPEVTCVVVDVSQEDPEVQFNWYVDGVEVHNAKTK<br>PREEQFNSTYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTPPVLDSD<br>GSFFLYSRLTVDKSRWQEGNVFSCSVMHEALHNHYTQKSLSLGK |
| 194 | Human IgG4 heavy chain constant region #2 | IGHG4*02 | Heavy Chain Constant Region Nucleotide Sequence | gcttccaccaagggcccatccgtcttccccctggcgccctgctccaggagcacctccgagagcacagccg<br>ccctgggctgcctggtcaaggactacttcccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtagatcacaagcccagcaacaccaagg<br>tggacaagagagttgagtccaaatatgtcccccatgcccatcatgcccagcacctgagttcctggggg<br>accatcagtcttcctgttccccccaaaacccaaggacactctcatgatctcccggacccctgaggtcacgtg<br>cgtggtggtggacgtgagccaggaagaccccgaggtccagttcaactggtacgtggatggcgtggagg<br>tgcataatgccaagacaaagccgcggaggagcagttcaacagtacaagtgcaaggtctccaacaaaggcctca<br>cgtcctgcaccaggactggctgaacggcaaggagtacaagtgcaaggtctccaacaaaggcctcccg<br>tctccatcgagaaaaccatctccaaagccaaagggcagccccgagagccacaggtgtacaccctgcccc<br>ccatcccgggaggagatgaccaagaaccaggtcagcctgacctgcctggtcaaagacacgcctcccagc<br>gacatcgccgtggagtgggagagcaatgggcagccggagaacaactacaagaccacgcctcccgtgct<br>ggactccgacggctccttcttcctctacagcaggctaaccgtggacaagagcaggtggcagaggggga<br>atgtcttctcatgctccgtgatgcatgaggctctgcacaaccactacacacagaagagcctctccctgtctct<br>gggtaaa |
| 195 | | | Heavy Chain Constant Region Amino Acid Sequence | ASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPSCPAPEF |

| SEQ ID NO: | Name | Description | Sequence |
|---|---|---|---|
| | | | LGGPSVFLFPPKPKDTLMISRTPEVTCVVVDVSQEDPEVQFNWYVDGVEVHNAKTK PREEQFNSTYRVVSVLTVLHQDWLNGKEYKCKVSNKGLPSSIEKTISKAKGQPREP QVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGK |
| 196 | Human IgG4 heavy chain constant region #3 | IGHG4*03 Heavy Chain Constant Region Nucleotide Sequence | gcttccaccaagggcccatccgtcttccccctggcgccctgctccaggagcacctccgagagcacagcc cctgggctgcctggtcaaggactacttccccgaaccggtgacggtgtcgtggaactcaggcgccctgac cagcggcgtgcacaccttcccggctgtcctacagtcctcaggactctactccctcagcagcgtggtgacc gtgccctcagcagcttgggcacgaagaccctacaacctcccccatgtgccagaaacacctgtgagttcgg ccccaaagagagtcttctcctgtctcccgtgccccatgtgccaaggaagaccctcatgatctcccgggaccctgaggtcacgtg cgtggtggtggacgtgagccaggaagaccccgaggtccagttcaactggtacgtggatggcgtggag tgcataatgccaagacaaagccgcgggaggagcagttcaacagtactacccgtgtggtcagcgtcctca cgtcctgcaccaggactggctgaacggcaaggagtacaagtgcaaggtctccaacaaaggcctcccg tcctccatcgagaaaaccatctccaaagccaaagggcagccccgagaaccacaggtgtacaccctgccc catcccgggacgacgggagatgaccaagaaccaggtcagcctgacctgcctggtcaaagacttctaccagc acatgcgtggagtgggagagcaatgggcagccggagaacaactacaagaccacgcctccccgtg ctctcctgtctccgggtaaacaacaagacctcagcagggcaggaacatgcagaaagaccacacgcctgc actcctgctccgtgctggactccgacggctccttcttcctctacagcaagctcaccgtggacaagagcagg tggcagcaggggaacgtcttctcatgctccgtgatgcatgaggctctgcacaaccactacacacagaagagcctctccctg tctaatcatgctctccgtgatgcatgaggctctgcacaaccactacacacagaagagcctctccctgtctg ggtaaa |
| 197 | | Heavy Chain Constant Region Amino Acid Sequence | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPSCPAPEF LGGPSVFLFPPKPKDTLMISRTPEVTCVVVDVSQEDPEVQFNWYVDGVEVHNAKTK PREEQFNSTYRVVSVLTVLHQDWLNGKEYKCKVSNKGLPSSIEKTISMKGQPREP QVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGK |
| 198 | IgG4 heavy chain constant region - IgG4-PE | IGHG4-PE Heavy Chain Constant Region Nucleotide Sequence - Synthetic Version A | gcttccaccaagggcccatccgtcttccccctggcgccctgctccaggagcacctccgagagcacggcccg cctggctgcctggtcaaggactacttccccgaaccagtgacggtgtcgtggaactcaggcgccctgac cagcggcgtgcacaccttccccgctgtcctacagtcctcaggactctactccctcagcagcgtggtgacc gtgccctcagcagcttgggcacgaagaccctacaacctcccccatgtgccagaaacacctgtgagttcgg ggacaccagtcttcctcgtctccccaaaacccaaggaagaccctcagaggtccagttcaactggtacgt gcatgggtggaacgtgagccaggaagaccccgaggtccagttcaactggtacgtggatggcgtggagt gcatgatgccaagacaaaccccgggagagaacagttcaacagtactacccgtgtggtcagcgtcctc accgtcctgcaccaggactggctgaacggcaagagtacaagtgcaaggtctccaacaaggcctcc gtcatcgatcgagaacaatctccaaagccaaagggcagccccgagagccacaggtacaccctgcccca gcgcactccgcggagagagagcaatgggcagccggagaacaactacaagaccacgcctcccgt gctgactccgcacgatcctcttcctctacagcaagctcaccgtggacaagagcaggtggcaggagggg aatgtcttctcatgctccgtgatgcatgaggctctgcacaaccactacacacagaagagcctctccgtc tctgggtaa |
| 199 | IgG4 heavy chain constant region - | Heavy Chain Constant Region Amino Acid Sequence - Encoded by Synthetic Version A, B & C (Two residues that differ | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEF EGGPSVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAKGQPRE |

SEQUENCE LISTING

| SEQ ID NO: | Name | Description | Sequence |
|---|---|---|---|
| | IgG4-PE | from the wild-type sequence are identified in bold) | PQVYTLPPSQEEMTKNQVSLTCLVKGFYPSDIAVEWESNGQPENNYKTTPPVLDSD GSFFLYSRLTVDKSRWQEGNVFSCSVMHEALHNHYTQKSLSLSLGK |
| 200 | IgG4 heavy chain constant region - IgG4-PE | Heavy Chain Constant Region Nucleotide Sequence - Synthetic Version B | Gcctccaccaaggacctagcgtgttccctctgcccctgttcaccctgagtccaccgctgc cctcggctgtctggtgaaagactacttccccgagcccgtgaccgtctcctggaatagcggagcctgacct cggcgtgcacactttccgcgctgcagagcagcggactgtatagctcagcgtggtgacccgt gcccagtcccctcggccaaaactacacctgcaacgtggaccaacccctccaaccaaggt ggaaagccggtggagacaagtacgccccccttccctcctgtcctgcccttcgaggaggag accctcccgtcctgttcctgttccccaaaccaaggacaccccgagtgcagtccgagcgggtgaccct gtgtggtcggacgtcagcaggaagccccgagtgcagtcaactggtatgtgaccggcgtggag gtgcacaatgccaaaacgagcagccaatggagacgttccaatccaccagggtggagcgtgct gacccgtccgcatccaggattgctgaacggcaaggctaaggcaagtgcaggacgcctgt ccagctccatcgagaagaccatcagcaaggctaaggaaccaagtgtccctgacctgctggtggaaggttctcaccct ccgaatccgcggaggtggagagcaatccaatgccgagaacaactacaaaaaccccccgtg ctcgatagcgacggcagctcttcttcctgtacgaggcgtgacaatcactactacacccagaaagccctgtcc aactgtgtcctgttccgtcgtgacgagcacctacgcaccaccagaagagccctcccttcc ctgggcaag |
| 201 | IgG4 heavy chain constant region - IgG4-PE | Heavy Chain Constant Region Nucleotide Sequence - Synthetic Version C | gccagcaccaaggccctccgtgttccccctggccctgagcagggagcacctccgaatcacagctg ccctgggctgtctggtgaaggatactttcctggagcccgtgaccgtgagctgaacagcggcctctgac atccggcctccacacctccctgccgtcctggtcctgagcagtcctactcctgtgtccggtgaccgtg cctagctcctccctccggcagctcaagaccgtgccctccctgccctgtgaccctgaacaaccctccaacaccaaggtgg acaacgtgtcgagagcaagtacggcccccctctgagtccctctgtgcccccagttcgaaggcggacc cagcgtgttcctgttcctctaagccaggagacctggactccagttcaactgctagttccagttcgactgc gtgtggtgggatgtgagccaggaggcagtcaacccacctacaggtggtgcaggcgtggcgtggagtg cacaacgcaaagccgggaagccccggagaagctggcttcactgtgcctacacaggtgcagctgctgac cgtgtgcatcgagaggactggtgaacggcaagtggagtcaagtgcaagtcaagtaaggcaactgccca gcagcatcgagaaggacatctccaaggctaaagctaaggccctgacctgtcgagtgccaacctcagttgtacccctgcctc ccagccaggaggatgaccaagaaccaggtgaccagccagccgagaacattataagaccacccctccccgtcctcg acatcgcctgaggctccttctcgtctcgcaggctgaccgtggatgagtcgacggtgcaggaaggcaactg gttcagctgtccgtgatgcacgagcccctgcacaataactactacaccccagaagtccctgagcctgtccctgg gaaag |
| 202 | IgG4 heavy chain constant region - inactivated | Heavy Chain Constant Region Nucleotide Sequence | gcctccaccaaggccctcatccgtcttcccctgtcccctgagggagcacctccgagagcacggccg cctgggctgcctggtcaaggactactttccccgaccagtgacggtgtgaactcaggcgccctgac cagcggcgtgcacacctccgcgctgtcctacagtcctacagcagcaccctgatcactactctcgccagcagcggtgtgaccg tgccctccagcagcttggtgcacgaagtagtcaatagtcccccaaacaaagcagccccatgaaagccaagcgccaacaccaagg tggacaagagagttgagcccaaatcttgtgacaaaactcactcgacacaccaagctcaggcctcgaggggg gaccatcagtcttcctgttctgtgacagccagaaggcggaaccccacccctgacgtccaggtcacgt gcgtggtggtgggacgtgagccaggaagccccgaggtcagttcaactgggtacgtggacggcgtggag gtgcataatgccaagaaccaagcgcgggaggaacagtacaacagtcaacagcacctaccgtgtgcagtcctc acctgccgtacctcaaagagctgccaagagtacaaagtgtcaaagcccggagccccctgaccctc gtcatcgatcgagaaaccatctccaaagccaaaaggcaagccctgcgagctgcccggaacaactacaaagaaccacgt cccatccccaggaggagatgaccacgaaggagagcaatgggcagccccgagaacctgcctggtcaaaggcttacacctgt gcgacatcgcgggtggagtggagcagtcaatggcccagcccgagaacaactacaagaccaccctcccgt gctgaactccgacggatccttcttcctacagcggcaaggccaccagcgccaagtccaggagg |

-continued

SEQUENCE LISTING

| SEQ ID NO: | Name | Description | Sequence |
|---|---|---|---|
| | | | gaatgtctctcatgctccgtgatgcatgaggctctgacaaccactcacacagaagagcctctccctgtc tctgggtaaa |
| 203 | | Heavy Chain Constant Region Amino Acid Sequence (inactivating mutations from human WT IgG4 shown in bold) | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPP VAGGPSVFLFPPKPKDTLMISRTPEVTCVVVDVSQEDPEVQFNWYVDGVEHNAK TKPREEQFNSTYRVVSVLTVLHQDWLNGKEYKCINSNKGLPSSIEKTISKAKGQPR EPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 204 | Disabled - IGHG1 | Heavy Chain Constant Region Nucleotide Sequence | gcctccaccaagggcccatccgtcttccccctggcaccctcctccaagagcacctctgggggcacagcgg ccctgggctgcctggtcaaggactacttcccgaaccggtgtgtgtgaactcaggcgccctgac cagcggcgtgcacaccttcccggctgtcctacagtcctcaggactctactcctcagcagcgtggtgaccg tgccctccagcagcttgggcaccaagacctatcaacgtcaacaccaagccagctgaaca tggacaaagttgagcccaaatcttgtgacaaaactcacacatgcccaccgtgcccagcacctgaac tcgccgggaccgtcagtcttcctcttccccccaaaacccaaggacaccctcatgatctcccggaccct gagcaatgcgtggtggtggacgtgagccacgaagaccctgaggtcaagttcaactggtacgtggac ggcgtggaggtgcataatgccaagacaaagccgcgggaggagcagtacaacagcacgtaccgtgtg tcaggtctcctcaccgtcctgcaccaggactggctgaatggcaaggagtacaagtgcaaggtctccaaca aagcctcccagccccatcgagaaaaccatctccaaagccaaagggcagcccgagaaccacaggtg tacaccctgcccccatcccgggatgagctgaccaagaaccaggtcagcctgacctgcctggtcaaaggct tctatcccagcgacatcgccgtggagtgggagagcaatgggcagccggagaacaactacaagaccac gcctcccgtgctggactccgacggctccttcttcctctacagcaagctcaccgtggacaagagcaggtggc agcaggggaacgtcttctcatgctccgtgatgcatgaggctctgcacaaccactacacgcagaagagcct ctccctgtctccgggtaaa |
| 205 | | Heavy Chain Constant Region Amino Acid Sequence (Two residues that differ from the wild-type sequence are identified in bold) | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCP APELAGAPSVFLFPPKPKDTLMISRTPEVTCVVVDVSHEDPEVKFNWYVDGVEHN AKTKPREEQYNSTYRVVSVLTVLHQDWLNGKEYKCKVSNKALPAPIEKTISMKGQ PREPQVYTLPPSRDELTKNQVSLTCLVKGFYPSDIAVEWESNGQPENNYKTIPPVL DSDGSFFLYSKLTVDKSRWQQGNVFSCSVMHEALHNHYTQKSLSLSPGK |
| 206 | Human Cκ constant region | IGKC*01 Cκ Light Chain Constant Region Nucleotide Sequence | cgtacggtggccgctcccctccgtcttcatcttcccgccatctgatgagcagttgaaatctggaactgcctct gtcgtgtgcctgctgaataacttctacccccgagagccaaggtcagtggaaggtggacaacgccctcc cagtcgagagcaggagaatcccaagacgagaggcagcacctacagcctcagcagcaccctgacgctg agcaagcagactacgagaaacacaaagtctacgcctgcgaagtcacccatcagggcctgagctcgcccgtc acaagagtttcaacaggggagagtgt |
| 207 | Human Cκ constant region | IGKC*01 Cκ Light Chain Constant Region Amino Acid Sequence | RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 208 | Human Cκ constant region | IGKC*02 Cκ Light Chain Constant Region Nucleotide Sequence | cgaactgtggctgcaccatctgtcttcatcttcccgccatctgatgagcagttgaaatctggaactgctctg ttgtgtgcctgctgaataacttctatcccagagaggccaaagtacagtggaaggtggataacgccctccaa atcgggtaactcccaggagagtgtcacagagcaggacagcaaggacagcacctacagcctcagcagc acctgacgctgagcaaagcagactacgagaaacaaagtctacgcctgcgaagtcacccatcagggcctg agctcgcccgtcacaaagagcttcaacaggggagagtgt |

| SEQ ID NO: | Name | Description | Sequence |
|---|---|---|---|
| 209 | Human Cκ constant region IGKC*03 | Cκ Light Chain Constant Region Amino Acid Sequence | RTVAAPSVFIFPPSDEQLKSGTASVVCLLNNFYPREAKVQWKVDNALQSGNSQESV TEQESKDSTYSLSSTLTLSKADYEKHKVYAGEVTHQGLSSPVTKSFNRGEC |
| 210 | | Cκ Light Chain Constant Region Nucleotide Sequence | cgaactgtggctgcaccatctgtcttcatcttcccgccatctgatgagcagtgaaatctgaactgcctctg ttgtgtgcctgctgaataacttctatcccagagaggccaaagtacagcggaagtggataacgcctcagc atcggtaactcccagagagtgtcacagagcaggagcaggacagcaggacacctacagcctcagcagc acccgacgctgagcaaagcagtaacaggagaaacacaaacttctacgcctgcgaagtcacccatcaggg cctgagctcgcccgtcacaaagacttcaacaggggagagtgt |
| 211 | Human Cκ constant region IGKC*04 | Cκ Light Chain Constant Region Amino Acid Sequence | RTVAAPSVFIFPPSDEQLKSGTASVVCLLNNFYPREAKVQRKVDNALQSGNSQESV TEQESKDSTYSLSSTLTLSKADYEKHKVYACEVTHQGLSSPVTKSFNRGEC |
| 212 | | Cκ Light Chain Constant Region Nucleotide Sequence | cgaactgtggctgcaccatctgtcttcatcttcccgccatctgatgagcagtgaaatctgaactgcctctg ttgtgtgcctgctgaataacttctatcccagagaggccaaagtacagtggaagtggataacgcctcagc atcggtaactcccagagagtgtcacagagcaggacagcaggacacctacagcctcagcagc acccgacgctgagcaaagcagtaacaggagaaacacaaacttctacgcctgcgaagtcacccatcaggg cctgagctcgcccgtcacaaagacttcaacaggggagagtgt |
| 213 | Human Cκ constant region IGKC*05 | Cκ Light Chain Constant Region Amino Acid Sequence | RTVAAPSVFIFPPSDEQLKSGTASVVCLLNNFYPREAKVQWKVDNALQSGNSQESV TEQDSKDSTYSLSSTLTLSKADYEKHKLYACEVTHQGLSSPVTKSFNRGEC |
| 214 | | Cκ Light Chain Constant Region Nucleotide Sequence | cgaactgtggctgcaccatctgtcttcatcttcccgccatctgatgagcagtgaaatctgaactgcctctg ttgtgtgcctgctgaataacttctatcccagagaggccaaagtacagtggaagtggataacgcctcagc atcggtaactcccagagagtgtcacagagcaggacagcaggacacctacagcctcagcagc acccgacgctgagcaaagcagtaacaggagaaacacaaagttctacgcctgcgaagtcacccatcaggg cctgagctcgcccgtcacaaagacttcaacaggggagagtgc |
| 215 | Human Cλ constant region IGLC1*01 | Cλ Light Chain Constant Region Amino Acid Sequence | RTVAAPSVFIFPPSDEQLKSGTASVVCLLNNFYPREAKVQWKVDNALQSGNSQESV TEQDSKDSTYSLSNTLTLSKADYEKHKVYACEVTHQGLSSPVTKSFNRGEC |
| 216 | | Cλ Light Chain Constant Region Nucleotide Sequence | cccaaggctcaaccccacgtcactcactcttgtccgcctcctctgaggagctccaagccaacaaggccac tagtgtctgatcagtgactctcaccggagtggcttgaaggcagatggcagcccgt caaggcggagtggagacgaccaaacctccaaacagagcaacaacagctgccagtacgcggcagcta cctgagcctgacgccgagcagtggaagtccaacagaggactacagctgccaggtcacgcaggtcacgcaggaagga gcaccgtggagaagacaagtggcccctacagaatgttca |
| 217 | Human Cλ constant region IGLC1*02 | Cλ Light Chain Constant Region Amino Acid Sequence | PKANPTVTLFPPSSEELQANKATLVCLISDFYPGAVTVAWKADGSPVKAGVETTKPS KQSNNKYAASSYLSLTPEQWKSHRSYSCQVTHEGSTVEKTVAPTECS |
| 218 | | Cλ Light Chain Constant Region Nucleotide Sequence - version A | ggtcagccaggccaaccccactgtcactctgttcccgccctcctctgaggagctccaagccaacaagg ccacactagtgtgtctgatcagtgacttctaccgggactggctgtgacagtggctggaagcagatggcagc ccccgtcaaggcgggagtggagacccaacaaactccaaacagagcaacaacaagtacgccgcagcagc agctacctgagcctgacgccgagcagtggaagtccaacagaggactacagctgccaggtcacgcaggtcacgcaggtcacgc agggagcaccgtggagaagacaagtggcccctacagaatgttca |
| 219 | | Cλ Light Chain Constant Region Amino Acid Sequence - encoded by version A or B | GQPKANPTVTLFPPSSEELQANKATLVCLISDFYPGAVTVAWKADGSPVKAGVETT KPSIKQSNNKYAASSYLSLTPEQWKSHRSYSCQVTHEGSTVEKTVAPTECS |

SEQUENCE LISTING -continued

| SEQ ID NO: | Name | Description | Sequence |
|---|---|---|---|
| 220 | | Cλ Light Chain Constant Region Nucleotide Sequence - Version B | ggtcagcccaaggccaacccactgtcactctgttccgccctcctgttcccgggactgcaacaagg ccacactagtgtctgatgcagtggagaccgccgagctgacagaggctgtgaagcagatggcag cccgtcaaggctgacctgagccctgaccgcagtggagaacagcctcaaacagtcccaaagtg agtacctgacctgagccgtgacgcagtggaagtccacagagaagctacagctgccagtcacgtca agggagcaccgtggagaagacagtggcccctacagaatgtca |
| 221 | Human Cλ constant region IGLC2*01 | Cλ Light Chain Constant Region Nucleotide Sequence - Version A | ggtcagcccaaggctgccctctctgtgaccctgttccccccatcctcgaggagctgcaagcaggg caccctgtgtgcctgatcagcgacttctaccctggagcgtgaccgtggagtggaaggtcgatagctc ctgaaggcggtgtggaaaccaccaccctcaaggagtccaacaacaaatacgcctcctctcta cctgacgctgagccgtgaccgtcagtgaagtcctacagctgccaagtgacccgagggtcc acgtggagaaagaccgtggctccaccgagtgctcc |
| 222 | | Cλ Light Chain Constant Region Nucleotide Sequence - Version B | ggcagccaagctgcccccgagtgcccctgttccctccctcaggagggagctccaagccaacaagg ccacctgtgcctgcctcatccgcgactctatccctgggagcgtcttgaaggcgactccagcc ctgcaaagcgggctggagacccctcaaggagtccaacaacctcaccctcaggagtccaacaacaaaagcg atcctcctgacccgtgagcagtgaccgtcagtgaagtcctactcctgtcagtgacccgagggtcc acgtggaaagacctgctccaccgagtgctcc |
| 223 | | Cλ Light Chain Constant Region Amino Acid Sequence - Encoded by Version A or B | GQPKANPTVTLFPPSSEELQANKATLVCLISDFYPGAVTVAWKADGSPVKAGVETT KPSKQSNNKYAASSYLSLTPEQWKSHRSYSCQVTHEGSTVEKTVAPTECS |
| 224 | | Cλ Light Chain Constant Region Nucleotide Sequence | ggtcagcccaaggctgccccctccgtcactctgttcccgccctcctctgaggagcttcaagcaacaaggc cacactggtgtcctcataagtgactcttacccgggagccgtgacagtggctgaaggcagatagcag ccccgtcaaggcggagtggagaaccaccaccctcaaacaaggaagcccacagctgccagtgtc agtatctgagcctgacgctgagcagtggaagtccacagaagctacagctgccagtgcacgtgcatgaa gggagcacgtggagagacagtgcccctacagaatgtca |
| 225 | Human Cλ constant region IGLC2*02 & IGLC2*03 | Cλ Light Chain Constant Region Amino Acid Sequence | GQPKAAPSVTLFPPSSEELQANKATLVCLISDFYPGAVTVAWKADSSPVKAGVETTT PSKQSNNKYAASSYLSLTPEQWKSHRSYSCQVTHEGSTVEKTVAPTECS |
| 226 | | Cλ Light Chain Constant Region Nucleotide Sequence | cccaaggctgccccctccgtcactctgttcccaccctcctctgaggagcttcaagccaacaaggccacact ggtgtctcataagtgactctacccgggagccgtgacagtgcctgaaggcagatagcggccaccccgtc aaggcggggtggagaaccaccaccctcaaacaaggaagccagcccacagctgccagtgtac tgagcctgacgctgagcagtggaagtccacagaagctacagctgccagtgcacgtgcatgaaggagc acgtggagagacagtggcccctacagaatgtca |
| 227 | | Cλ Light Chain Constant Region Amino Acid Sequence | PKAAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPTECS |
| 228 | Human Cλ constant region IGLC3*01 | Cλ Light Chain Constant Region Nucleotide Sequence | ggtcagcccaaggctgccccctccgtcactctgttccaccctcctctgaggagcttcaagccaacaaggc cacactggtgtcttcataagtccagtgacctgagtgccacaaacaagtaccgcggccagca gctactgacctgagcctgacgctgagcagtggaagtccacaaaagctacagctgccagtgcacgtgcatgaag ggagcacggtggagaagacagtggcccctacgaatgtca |
| 229 | Human Cλ constant region IGLC3*02 | Cλ Light Chain Constant Region Amino Acid Sequence | GQPKAAPSVTLFPPSSEELQANKATLVCLISDFYPGPVTVAWKADSSPVKAGVETTT |

-continued

SEQUENCE LISTING

| SEQ ID NO: | Name | Description | Sequence |
|---|---|---|---|
| 230 | Human Cλ constant region IGLC3*03 | Cλ Light Chain Constant Region Amino Acid Sequence | PSKQSNNKYAASSYLSLTPEQWKSHKSYSCQVTHEGSTVEKIVAPTECS |
| 231 | | Cλ Light Chain Constant Region Nucleotide Sequence | ggtcagcccaaggctgccccctcgtcactctgttcccaccctctgaggagcttcaagccaacaaggc cacactggtgtgtctcataagtgacttctaccggagccgtgacagtggcctgaaggcagatagcag ccccgtcaaggcgggagtggagaccaacaaggcaacctccaaacaaagcaacaagtgccacgggcagc agctacctgagcctgacgcctgagccgcctgagcctgaagccccacagagcctgcacagagcttca gggacacccgtggagagaacagtggccccctaccagaatgttca |
| 232 | Human Cλ constant region IGLC3*04 | Cλ Light Chain Constant Region Amino Acid Sequence | GQPKAAPSVTLFPPSSEELQANKATLVCLISDFYPGAVTVAWKADSSPVKAGVETTT PSKQSNNKYAASSYLSLTPEQWKSHKSYSCQVTHEGSTVEKTVAPTECS |
| 233 | | Cλ Light Chain Constant Region Nucleotide Sequence | ggtcagcccaaggctgccccctcgtcactctgttccgccctctgaggagcttcaagccaacaaggc cacactggtgtgtctcataagtgacttctaccggagccgtgacagtggcctgaaggcagatagcag ccccgtcaaggcgggagtggagaccaacaaggcaacctccaaacaaagcaacaagtaccgccagc agctacctgagcctgacgcctgagccgctgaagccaggacgctgagacgctacagagcctgcacagagcttca gggacacccgtggagagaacagtggccccctaccagaatgttca |
| 234 | Human Cλ constant region IGLC6*01 | Cλ Light Chain Constant Region Amino Acid Sequence | GQPKAAPSVTLFPPSSEELQANKATLVCLISDFYPGAVTVAWKADSSPVKAGVETTT PSKQSNNKYAASSYLSHRSYSCQVTHEGSTVEKTVAPTECS |
| 235 | | Cλ Light Chain Constant Region Nucleotide Sequence | ggtcagcccaaggctgccccatcggtcactctgttccgccctctgaggagcttcaagccaacaaggc cacactggtgcctgatcagtgacttctaccggagctgtgaaagtggcctgaaggcagatgccag ccccgtcaacacgggagtggagaccaacaaggcaacctccaaacagagcaacaagaacaaagtgccacgggcagc agctacctgagcctgagcctgagcctgagcctgagcctgagcctgagcctgagctgcacagagcttca gggagccacccgtgagagaacagtggccctgagaatgttca |
| 236 | Human Cλ constant region IGLC7*01 & IGLC7*02 | Cλ Light Chain Constant Region Amino Acid Sequence | GQPKAAPSVTLFPPSSEELQANKATLVCLISDFYPGAVKVAWKADGSPVNTGVETT TPSKQSNNKYAASSYLSLTPEQWKSHKSYSCQVTHEGSTVEKTVAPAECS |
| 237 | | Cλ Light Chain Constant Region Nucleotide Sequence | ggtcagcccaaggctgccccaagctggtcactctgttcccaccctctgaggagcttcaagccaacaaggc cacactggtgtgtctcgtaagtgacttctaccggagccgtgacagtggcctgaaggcagatggccag ccccgtcaaggtgggagtggagaccaacaacctccaaacaaagcaacaagaacaagtatgccgccagc agctacctgagcctgacgcctgagcctgagccgtgaagctgcacagagctacagagctgccaggtcacgcatga agggagcaccgggagagaacagtggcccctgagaatgtctct |
| 238 | | Cλ Light Chain Constant Region Amino Acid Sequence | GQPKAAPSVTLFPPSSEELQANKATLVCLVSDFYPGAVTVAWKADGSPVKVGVETT KPSKSNNKYAASSYLSLTPEQWKSHRSYSCRVTHEGSTVEKTVAPAECS |
| 238 | 413G05 - CDRH1 (IMGT) | Amina acid sequence of CDRH1 of 413G05 using IMGT | GFTFSDYY |
| 239 | 413G05 - CDRH2 (IMGT) | Amino acid sequence of CDRH2 of 413G05 using IMGT | ISTSGSTI |
| 240 | 413G05 - CDRH3 (IMGT) | Amino acid sequence of CDRH3 of 413G05 using IMGT | ARGITGTNFYHYGLGV |
| 241 | 413G05 - CDRH1 | Amino acid sequence of CDRH1 | DYYMS |

SEQUENCE LISTING

| SEQ ID NO: | Name | Description | Sequence |
|---|---|---|---|
| | (Kabat) | of 413G05 using Kabat | |
| 242 | 413G05 - CDRH2 (Kabat) | Amino acid sequence of CDRH2 of 413G05 using Kabat | YISTSGSTIYYADSVKG |
| 243 | 413G05 - CDRH3 (Kabat) | Amino acid sequence of CDRH3 of 413G05 using Kabat | GITGTNFYHYGLGV |
| 244 | 413G05 - Heavy chain variable region | Amino acid sequence of $V_H$ of 413G05 | QVQLVESGGGLVKPGGSLRLSCAASGFTFSDYMSWIRQVPGKGLEWVSYISTSG STIYYADSVKGRFTISRDNAKNSLYLQMNSLRAEDAAVHCARGITGTNFYHYGLG VWGQGTTVTVSS |
| 245 | 413G05 - Heavy chain variable region | Nucleic acid sequence of $V_H$ of 413G05 | CAGGTGCAGCTGGTGGAGTCTGGGGGAGGCTTGGTCAAGCCTGGAGGGTCCCT GAGACTCTCCTGTGCAGCCTCTGGATTCACCTTCAGTGACTACATGAGCTG GATCCGCCAGGTTCCAGGGAAGGGGCTGGAGTGGGTTTCATACATTAGTACTAG TGGTAGTACCATATACTACGCAGACTCTGTGAAGGGCCGATTCACCATCTCCAG GGACAACGCCAAGAACTCACTGTATCTGCAAATGAACAGCCTGAGAGCCGAGGA CGCCGCCGTGTATCACTGTGCGAGAGGTATAACTGGAACTAACTTCTACCACTA CGGTTTGGGGGTCTGGGGCCAAGGGACCACGGTCACCGTCTCCTCAG |
| 246 | 413G05 - full heavy chain sequence | Amino acid sequence of 413G05 heavy chain | QVQLVESGGGLVKPGGSLRLSCAASGFTFSDYMSWIRQVPGKGLEWVSYISTSG STIYYADSVKGRFTISRDNAKNSLYLQMNSLRAEDAAVHCARGITGTNFYHYGLG VWGQGTTVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSL SLSPGK |
| 247 | 413G05 - full heavy chain sequence | Nucleic acid sequence of 413G05 heavy chain | CAGGTGCAGCTGGTGGAGTCTGGGGGAGGCTTGGTCAAGCCTGGAGGGTCCCT GAGACTCTCCTGTGCAGCCTCTGGATTCACCTTCAGTGACTACATGAGCTG GATCCGCCAGGTTCCAGGGAAGGGGCTGGAGTGGGTTTCATACATTAGTACTAG TGGTAGTACCATATACTACGCAGACTCTGTGAAGGGCCGATTCACCATCTCCAG GGACAACGCCAAGAACTCACTGTATCTGCAAATGAACAGCCTGAGAGCCGAGGA CGCCGCCGTGTATCACTGTGCGAGAGGTATAACTGGAACTAACTTCTACCACTA CGGTTTGGGGGTCTGGGGCCAAGGGACCACGGTCACCGTCTCCTCAGCCTCTGGCGG CAAGGGCCCCTCTGGTTCCTCTGGCCGTGAAGGACTACTTCCCGAGCCTGTGACCGT GTCCTGGAACTCTGGCGCTGACCAGCGGAGTGCACACCTTCCCTGCTGTGCT GCAGTCCTCCGGCCTCTACTCCCTGTCCTCCGTGGTGACCGTGCCTTCCAGCTC TCTGGGCACCCAGACCTACATCTGCAACGTGAACCACAAGCCCTCCAACACCAAG GTGGACAAGAAGGTGGAACCCAAGTCCTGCGACAAGACCCACACCTGTCCCCCT TGTCCTGCCCTGAACTGCTGGGCACCTTCCGTGTTCCTGTTCCCCCCAAAG CCCAAGGACACCCTGATGATCTCCCGGACCCCCGAAGTGACCTGCGTGGTGGTG GATGTGTCCAGCGAGGACCCCGAAGTGAAGTTCAATTGGTACGTGGACGGCGTG GAAGTGCACAACGCCAAGACCAAGCCTAGAGAGGAACAGTACAACTCCACCTAC CGGGTGGTGTCCGTGCTGACCGTGCTGCACCAGGATTGGCTGAACGGCAAGGA |

| SEQ ID NO: | Name | Description | Sequence |
|---|---|---|---|
| | | | GTACAAGTGCAAGGTGTCCAACAAGGCCCTCCTGCCCTGCCCCATCGAAAAGACCAT CTCCAAGGCCAAGGGCCAGCCCCAGGTGTACACACTGCCCCCTAG CAGGGACGAGCTGACCAAGAACCAGGTGTCCCTGACCTGTCTGAAAGGCTT CTACCCCTCCGATATCGCCGTGGAATGGCTGAGCAACGGCCAGCCTGAGAACAA AAGTGACGAGTGACAAGTCCGGTGCAGCAGGCCAACGTGTTCTCTGCTCC GTGATGCACGAGGCCCTGCACAACCACTACACCCAGAAGTCCCTGTCCCTGAGC CCCGGCAAG |
| 248 | 413G05 - CDRL1 (IMGT) | Amino acid sequence of CDRL1 of 413G05 using IMGT | QGINSW |
| 249 | 413G05 - CDRL2 (IMGT) | Amino acid sequence of CDRL2 of 413G05 using IMGT | AAS |
| 250 | 413G05 - CDRL3 (IMGT) | Amino acid sequence of CDRL3 of 413G05 using IMGT | QQVNSFPLT |
| 251 | 413G05 - CDRL1 (Kabat) | Amino acid sequence of CDRL1 of 413G05 using Kabat | RASQGINSWLA |
| 252 | 413G05 - CDRL2 (Kabat) | Amino acid sequence of CDRL2 of 413G05 using Kabat | AASTLQS |
| 253 | 413G05 - CDRL3 (Kabat) | Amino acid sequence of CDRL3 of 413G05 using Kabat | QQVNSFPLT |
| 254 | 413G05 - Light chain variable region | Amino acid sequence of V$_L$ of 413G05 | DIQMTQSPSSVSASVGDRVTITCRASQGINSWLAWYQQKPGKAPKLLIYAASTLQS GVPSRFSGSGSGADFTLTISSLQPEDFATYYCQQVNSFPLTFGGGTKVEIK |
| 255 | 413G05 - Light chain variable region | Nucleic acid sequence of V$_L$ of 413G05 | GACATCCAGATGACCCAGTCTCCATCTCCGTGTCTGCATCTGTAGGAGACAGA GTCACCATCACTTGTCGGGCGAGTCAGGGTATTAACAGCTGGTTAGCCTGGTAT CAGCAGAAACCAGGGAAAGCCCCTAAGCTCCTGATCTATGCTGCATCCACTTTG CAAAGTGGGGTCCCATCAAGGTTCAGCGGCAGTGGGTCTGGGACAGATTTCACT CTCACCATCAGCAGCCTGCAGCCTGAAGATTTTGCAACTTACTATTGTCAACAGG TTAACAGTTTCCCGCTCACTTTCGGCGGAGGGACCAAGGTGGAGATCAAACGTA AAC |
| 256 | 413G05 - full light chain sequence | Amino acid sequence of 413G05 light chain | DIQMTQSPSSVSASVGDRVTITCRASQGINSWLAWYQQKPGKAPKLLIYAASTLQS GVPSRFSGSGSGADFTLTISSLQPEDFATYYCQQVNSFPLIFGGGTKVEIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 257 | 413G05 - full light chain sequence | Nucleic acid sequence of 413G05 light chain | GACATCCAGATGACCCAGTCTCCATCTCCGTGTCTGCATCTGTAGGAGACAGA GTCACCATCACTTGTCGGGCGAGTCAGGGTATTAACAGCTGGTTAGCCTGGTAT CAGCAGAAACCAGGGAAAGCCCCTAAGCTCCTGATCTATGCTGCATCCACTTTG CAAAGTGGGGTCCCATCAAGGTTCAGCGGCAGTGGGTCTGGGACAGATTTCACT CTCACCATCAGCAGCCTGCAGCCTGAAGATTTTGCAACTTACTATTGTCAACAGG TTAACAGTTTCCCGCTCACTTTCGGCGGAGGGACCAAGGTGGAGATCAAACGTA CGGTGGCCGCTCCGTCCTTCATCTTCCCACCTTCCGATGAACAGCTGAAGT CCGGCACCGCTTCTGTGTGCTGCTGAACAACTTCTACCCCCGAGGCCA AGGTGCAGTGGAAGGTGGACAACGCCCTGCAGTCCGGCAACTCCCAGGAATCCG TGACCGAGCAGGACTCCAAGGACAGCACCTACTCCCTGTCCTCCACCCTGACCC |

-continued

SEQUENCE LISTING

| SEQ ID NO: | Name | Description | Sequence |
|---|---|---|---|
| | | | TGTCCAAGGCCGATACGAGAAGCACAAGGTGTACGCCTGCGAAGTGACCCACC AGGGCCTGTCTAGCCCCGTGACCAAGTCTTTCAACCGGGGCGAGTGT |
| 258 | 413F09 - CDRH1 (IMGT) | Amino acid sequence of CDRH1 of 413F09 using IMGT | GFTFSYYA |
| 259 | 413F09 - CDRH2 (IMGT) | Amino acid sequence of CDRH2 of 413F09 using IMGT | ISGGGGNT |
| 260 | 413F09 - CDRH3 (IMGT) | Amino acid sequence of CDRH3 of 413F09 using IMGT | AKDRMKQLVRAYYFDY |
| 261 | 413F09 - CDRH1 (Kabat) | Amino acid sequence of CDRH1 of 413F09 using Kabat | YYAMS |
| 262 | 413F09 - CDRH2 (Kabat) | Amino acid sequence of CDRH2 of 413F09 using Kabat | TISGGGGNTHYADSVKG |
| 263 | 413F09 - CDRH3 (Kabat) | Amino acid sequence of CDRH3 of 413F09 using Kabat | DRMKQLVRAYYFDY |
| 264 | 413F09 - Heavy chain variable region | Amino acid sequence of V$_H$ of 413F09 | EVPLVESGGGLVQPGGSLRLSCAASGFTFSYYAMSWVRQAPGKGLDWVSTISGGG GNTHYADSVKGRFTISRDNSKNTLYLHMNSLRAEDTAVYYCAKDRMKQLVRAYYF DYWGQGTLVTVSS |
| 265 | 413F09 - Heavy chain variable region | Nucleic acid sequence of V$_H$ of 413F09 | GAGGTGCCCCTGGTGGAGTCTGGGGGAGGCTTGGTACAGCCTGGGGGGTCCCT GAGACTCTCCTGTGCAGCCTCTGGATTCACGTTTAGCTACTATGCCATGAGCTG GGTCCGTCAGGCTCCAGGGAAGGGGCTGGAGTGGGTCTCAACTATTAGTGGTG GTGGTGGTAACACACACTACGCAGACTCCGTGAAGGGCCGATTCACCATATCCA AGAGACAATTCCAAGAACACAGCTGTATCTGCACATGAACAGCCTGAGAGCCGAAG ACACGGCCGTCTATTACTGTGCGAAGGATCGGATGAAACAGCTCGTCCGGGCCT ACTACTTTGACTACTGGGGCCAGGGAACCCTGGTCACCGTCTCCTCAG |
| 266 | 413F09 - full heavy chain sequence | Amino acid sequence of 413F09 heavy chain | EVPLVESGGGLVQPGGSLRLSCAASGFTFSYYAMSWVRQAPGKGLDWVSTISGGG GNTHYADSVKGRFTISRDNSKNTLYLHMNSLRAEDTAVYYCAKDRMKQLVRAYYF DYWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALP APIEKTISMKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSL SLSPGK |
| 267 | 413F09 - full heavy chain sequence | Nucleic acid sequence of 413F09 heavy chain | GAGGTGCCCCTGGTGGAGTCTGGGGGAGGCTTGGTACAGCCTGGGGGGTCCCT GAGACTCTCCTGTGCAGCCTCTGGATTCACGTTTAGCTACTATGCCATGAGCTG GGTCCGTCAGGCTCCAGGGAAGGGGCTGGACTGGGTCTCAACTATTAGTGGTG GTGGTGGTAACACACACTACGCAGACTCCGTGAAGGGCCGATTCACCATATCCA GAGACAATTCCAAGAACACACGCTGTATCTGCACATGAACAGCCTGAGAGCCGAAG |

| SEQ ID NO: | Name | Description | Sequence |
|---|---|---|---|
| | | | ACACGGCCGTCTATTACTGTGCGAAGGATCGGATGAAACAGCTCGTCCGGCCT |
| | | | ACTACTTTGACTACTGGGGCCAGGGAACCCTGGTCACCGTCTCCTCAGCCAGCA |
| | | | CCAAGGGCCCCTCTGTGTTCCCTGGCCCCTTCCAGCAAGCTCACCTGGGCG |
| | | | GAACAGCCGCTCTGGGCTGCCTGGTCAAGGACTACTTCCCCGAGCCTGTGACCG |
| | | | TGTCCTGGAACTCTGGCGCTCTGACCAGCGGAGTGCACACCTTCCCTGCTGC |
| | | | TGCCTCTCCGGCCTACTACTGCCTGTCCGTGACCGTGCCCTTCCAGCT |
| | | | CTCTGGGCACCCAGACCTACATCTGCAACGTGAACCACAAGCCCTCCAACACCAA |
| | | | GGTGGACAAGAAGTGGAACCCAGTCCTGCACAAGACCCCACACTGTCCCC |
| | | | TTGTCCTGCCCCTGAACTGCTGGGCGGACCTTCCGTGTTCCTGTTCCCCCAAA |
| | | | GCCCAAGGACACCCTGATGATCTCCCGGACCCCTGAAGTGACCTGCGTGGTGGT |
| | | | GGATGTGTCCCACGAGGACCCTGAAGTGAAGTTCAATTGGTACGTGGACGGCGT |
| | | | GGAAGTGCACAACGCCAAGACCAAGCCTCGCGAGGAGCAGTACAACTCCACCTA |
| | | | CCGGGTGGTGTCCGTGCTGACCGTGCTGCACCAGGATTGGCTGAACGGCAAAG |
| | | | AGTACAAGTGCAAGGTCTCCAACAAGGCCCTGCCTGCCCCATCGAAAAGACCA |
| | | | TCTCCAAGGCCAAGGGCCAGCCCCGAGAACCCAGGTGTACACACTGCCCCCCTA |
| | | | GCAGGAGCGAGCTGACCAAGAACCAGGTGTCCCTGACCTGTCTCGTGAAAGGCT |
| | | | TCTACCCCTCCGATATCGCCGTGGAATGGGAGTCCAACGGCCAGCCTGAGAACA |
| | | | ACTACAAGACCACCCCCCCTGTGCTGGACTCCGACGGCTCATTCTTCCTGTACAG |
| | | | CAAGCTGACAGTGGACAAGTCCCGGTGGCAGCAGGGCACAGTGTTCTCTGCTC |
| | | | CGTGATGCACGAGGCCCTGCACAACCACTACACCCAGAAGTCCCTGTCCCTGAG |
| | | | CCCCGGCAAG |
| 268 | 413F09 - CDRL1 (IMGT) | Amino acid sequence of CDRL1 of 413F09 using IMGT | QDISTY |
| 269 | 413F09 - CDRL2 (IMGT) | Amino acid sequence of CDRL2 of 413F09 using IMGT | GTS |
| 270 | 413F09 - CDRL3 (IMGT) | Amino acid sequence of CDRL3 of 413F09 using IMGT | QQLHTDPIT |
| 271 | 413F09 -CDRL1 (Kabat) | Amino acid sequence of CDRL1 of 413F09 using Kabat | WASQDISTYLG |
| 272 | 413F09 - CDRL2 (Kabat) | Amino acid sequence of CDRL2 of 413F09 using Kabat | GTSSLQS |
| 273 | 413F09 - CDRL3 (Kabat) | Amino acid sequence of CDRL3 of 413F09 using Kabat | QQLHTDPIT |
| 274 | 413F09 - Light chain variable region | Amino acid sequence of $V_L$ of 413F09 | DIQLTQSPSFLSASVGDRVTITCWASQDISTYLGWYQQKPGKAPKLLIYGTSSLQS GVPSRFSGSGSGTEFTLTISSLQPEDFATYYCQQLHTDPITFGQGTRLEIK |
| 275 | 413F09 - Light chain variable region | Nucleic acid sequence of $V_L$ of 413F09 | GACATCCAGTTGACCCAGTCTCCATCCTTCCTGTCTGCATCTGTAGGAGACAGA GTCACCATCACTTGCTGGGCCAGTCAGGACATTAGCACTTATTAGGCTGGTAT CAGCAAAAACCAGGGAAAGCCCTAAGCTCCTGATCTATGGTACATCCAGTTTG CAAAGTGGGGTCCCATCAAGGTTCAGCGGCAGTGGATCTGGGACAGAATTCACT CTCAATCACAGCCTGCAGCCTGAAGATTTTGCAACTTATTACTGTCAACAGC |

SEQUENCE LISTING

| SEQ ID NO: | Name | Description | Sequence |
|---|---|---|---|
| 276 | 413F09 - full light chain sequence | Amino acid sequence of 413F09 light chain | DIQLTQSPSFLSASVGDRVTITCWASQDISTYLGWYQQKPGKAPKLLIYGTSSLQS GVPSRFSGSGSGTEFTLTISSLQPEDFATYYCQQLHTDPITFGQGTRLEIKRTVAAP SVFIFPPSDEQLKSGTASVVCLLNNFYPREAINQWKVDNALQSGNSQESVTEQDSK DSTYSLSSTLTLSKADYEKHKVYACEVTHQGLSSPVTKSFNRGEC |
| 277 | 413F09 - full light chain sequence | Nucleic acid sequence of 413F09 light chain | GACATCCAGTTGACCCAGTCTCCATCCTTCCTGTCTGCATCTGTAGGAGACAGA GTCACCATCACTTGCTGGGCCAGTCAGGACATTAGCACTTATTTAGGCTGGTAT CAGCAAAAACCAGGGAAAGCCCCTAAGCTCCTGATCTATGGTACATCCAGTTTG CAAAGTGGGGTCCCATCAAGGTTCAGCGGCAGTGGATCTGGGACAGAATTCACT CTCACAATCAGCAGCCTGCAGCCTGAGGATTTTGCAACTTATTACTGTCAACAGC TTCATACTGACCCGATCACCTTCGGTGTTCATCTTCCCACCTTCGACGAGCAGTA CGGTGGCCGCTCCTCCGTGTTCATCTTCCCACCTTCCGACGAGCAGTTGAAGT CCGGCACCGCTTCTGTTGTGCCTGCTGAACAACTTCTACCCCGCGAGGCCA AGGTCCAGTGGAAGGTGGACAACGCCCTGCAGTCCGGCAACTCCCAGGAATCCG TGACCGAGCAGGACTCCAAGGACAGCACCTACTCCCTGTCCTCCACCCTGACCC TGTCCAAGGCCGACTACGAGAAGCACAAGGTGTACGCCTGCGAAGTGACCCACC AGGGCCTGTCTAGCCCCGTGACCAAGTCTTTCAACCGGGGCGAGTGT |
| 278 | 414B306 - CDRH1 (IMGT) | Amino acid sequence of CDRH1 of 414B06 using IMGT | GFTFSSYW |
| 279 | 414B06 - CDRH2 (IMGT) | Amino acid sequence of CDRH2 of 414B06 using IMGT | IKQDGSEK |
| 280 | 414B306 - CDRH3 (IMGT) | Amino acid sequence of CDRH3 of 414B06 using IMGT | ARVRQWSDYSDY |
| 281 | 414B06 - CDRH1 (Kabat) | Amino acid sequence of CDRH1 of 414B06 using Kabat | SYWMN |
| 282 | 414B06 - CDRH2 (Kabat) | Amino acid sequence of CDRH2 of 414B06 using Kabat | NIKQDGSEKYYVDSVKG |
| 283 | 414B306 - CDRH3 (Kabat) | Amino acid sequence of CDRH3 of 414B06 using Kabat | VRQWSDYSDY |
| 284 | 414B06 - Heavy chain variable region | Amino acid sequence of $V_H$ of 414B06 | EVHLVESGGGLVQPGGSLRLSCAASGFTFSSYWMNWVRQAPGKLEWVANIKQD GSEKYYVDSVKGRFTVSRDNAKNSLYLQMNSLRAEDTAVYYCARVRQWSDYSDY WGQGTPVTVSS |
| 285 | 414B306 - Heavy chain variable region | Nucleic acid sequence of $V_H$ of 414B06 | GAGGTGCACCTGGTGGAGTCTGGGGGAGGCTTGGTCCAGCCTGGGGGGTCCCT GAGACTCTCCTGTGCAGCCTCTGGATTCACCTTTAGTAGCTATTGGATGAACTG GGTCCGCCAGGCTCCAGGGAAGGGGCTGGAGTGGGTGGCCAACATAAAGCAAG ATGGAAGTGAGAAATACTATGTGGACTCTGTGAAGGGCCGCTTCACCGTCTCCA GAGACAACGCCAAGAACTCACTGTATCTGCAAATGAACAGCCTGAGAGCCGAGG ACACGGCTGTGTATTACTGTGCGAGAGTTCGACAATGGTCCGACTACTCTGACT |

-continued

SEQUENCE LISTING

| SEQ ID NO: | Name | Description | Sequence |
|---|---|---|---|
| 286 | 414B06 - full heavy chain sequence | Amino acid sequence of 414B06 heavy chain | EVHLVESGGGLVQPGGSLRLSCAASGFTFSSYWMNWVRQAPGKGLEWVANIKQD GSEKYYVDSVKGRFIVSRDNAKNSLYLQMNSLRAEDTAVYYCARVRQWSDYSDY WGQGTPVTVSSASTKGPSVFPLAPSSKSTSGGTAALGCLVKDYFPEPVTVSNSGA LTSGVHTFPAVLQSSGLYSLSSVVTVPSSSLGTQTYICNVNHKPSNTKVDKKVEPKS CDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSL SPGK |
| 287 | 414B06 - full heavy chain sequence | Nucleic acid sequence of 414B06 heavy chain | GAGGTGCACCTGGTGGAGTCTGGGGGAGGCTTGGTCCAGCCTGGGGGGTCCCT GAGACTCTCCTGTGCAGCCTCTGGATTCACCTTTAGTAGCTATTGGATGAACTG GGTCCGCCAGGCTCCAGGGAAGGGGCTGGAGTGGGTGGCCAACATAAAGCAAG ATGGAAGTGAGAAATACTATGTGGACTCTGTGAAGGGCCGCCTTCACGTCTCCA GAGACAACGCCAAGAACTCACTGTATCTGCAAATGAACAGCCTGAGAGCCGAGG ACACGGCTGTGTATTACTGTGCGAGAGTTCGACAATGGTCCGACTACTCTGACT ACTGGGGCCAGGGAACCCCGGTCACCGTCTCCTCAGCCAGTACCAAGGGCCCCT CTGTCTTCCCTCTGGCCCCATCCAGCACTCTTCCCGGGACCTCCACCTTCCGGC TGGGCTGCTCGTGAAGGACTACTTCCCGAGCCTGTGACCGTGTCCTGGAACT CTGGCGCTGTGACCAGCGGAGTGCACACCTTCCCGGCTGTCCTCCAGTCCTCG GCCTGTACTCCCTGTCCTCGTGACCGTGCCCTCCAGCTCTCTGGGCACCC AGACCTACATCTGCAACGTGAACCACAAGCCCTCCAACACCAAGGTGGACAAGA AGGTTGAACCCAAGTCCTGCGACAAGACCCACACGTGCCCACCGTGCCCAGCACA CCCTGATGATCTCCCGGACCCCTGAAGTGACCTGCGTGGTGGTGGATGTGTCCC ACGAGGACCCTGAAGTGAAGTTCAATTGGTACGTGGACGGCGTGGAAGTGCACA ACGCCAAGACCAAGCCTAGAGAGGAACAGTACAACTCCACCTACCGGGTGGTGT CCGTGCTGACCGTGCTGCACCAGGATTGGCTGAACGGCAAAGAGTACAAGTGCA AGGTGTCCAACAAGGCCCTGCCAGCCCCCATCGAAAAGACCATCTCCAAGGCCA AGGGCCAGCCCCGGGAACCCCAGGTGTACACACTGCCCCCTAGCAGGGACGAGC TGACCAAGAACCAGGTGTCCCTGACCTGTCTCGTGAAAGGCTTCTACCCCTCCG ATATCGCCGTGGAATGGGAGTCCAACGGCCAGCCTGAGAACAACTACAAGACCA CCCCCCTGTGCTGGACTCCGACGGCTCATTCTTCCTGTACAGCAAGTCGACAG TGGACAAGTCCCGGTGGCAGCAGGGCAACGTGTTCTCCTGCTCCGTGATGCACG AGGCCCTGCACAACCACTACACCCAGAAGTCCCTGTCCCTGAGCCCCGGCAAG |
| 288 | 414B06 - CDRL1 (IMGT) | Amino acid sequence of CDRL1 of 414B06 using IMGT | QGISSW |
| 289 | 414B06 - CDRL2 (IMGT) | Amino acid sequence of CDRL2 of 414B06 using IMGT | AAS |
| 290 | 414B06 - CDRL3 (IMGT) | Amino acid sequence of CDRL3 of 414B06 using IMGT | QQANSFPFT |
| 291 | 414B06 - CDRL1 | Amino acid sequence of CDRL1 | RASQGISSWLA |

-continued

SEQUENCE LISTING

| SEQ ID NO: | Name | Description | Sequence |
|---|---|---|---|
| | | of 414B06 using Kabat | |
| 292 | 414B06 - CDRL2 (Kabat) | Amino acid sequence of CDRL2 of 414B06 using Kabat | AASSLQS |
| 293 | 414B06 - CDRL3 (Kabat) | Amino acid sequence of CDRL3 of 414B06 using Kabat | QQANSFPFT |
| 294 | 414B06 - Light chain variable region | Amino acid sequence of V_L of 414B06 | DIQMTQSPSSVSASVGDRVTITCRASQGISSWLAWYQQKPGKAPKLLIYAASSLQS GVPSRFSGSGSGTDFTLTISSLQPEDFATYYCQQANSFPFTFGPGTKVDIK |
| 295 | 414B06 - Light chain variable region | Nucleic acid sequence of V_L of 414B06 | GACATCCAGATGACCCAGTCTCCATCTTCCGTGTCTGCATCTGTAGGAGACAGA GTCACCATCACTTGTCGGGCGAGTCAGGGTATTAGCAGCTGGTTAGCTGGTAT CAGCAGAAACCAGGGAAAGCCCCTAAGCTCCTGATCTATGCTGCATCCAGTTTG CAAAGTGGGGTCCCATCAAGGTTCAGCGGCAGTGGATCTGGGACAGATTTCACT CTCACCATCAGCAGCCTGAGCCTGAAGATTTTGCAACTTACTATTGTCAACAGG CTAACAGTTTCCCATTCACTTTCGGCCCTGGGACCAAAGTGGATATCAAAC |
| 296 | 414B06 - full light chain sequence | Amino acid sequence of 414B06 light chain | DIQMTQSPSSVSASVGDRVTITCRASQGISSWLAWYQQKPGKAPKLLIYAASSLQS GVPSRFSGSGSGTDFTLTISSLQPEDKTYYCQQANSFPFTFGPGTKVDIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 297 | 414B06 - full light chain sequence | Nucleic acid sequence of 414B06 light chain | GACATCCAGATGACCCAGTCTCCATCTTCCGTGTCTGCATCTGTAGGAGACAGA GTCACCATCACTTGTCGGGCGAGTCAGGGTATTAGCAGCTGGTTAGCTGGTAT CAGCAGAAACCAGGGAAAGCCCCTAAGCTCCTGATCTATGCTGCATCCAGTTTG CAAAGTGGGGTCCCATCAAGGTTCAGCGGCAGTGGATCTGGGACAGATTTCACT CTCACCATCAGCAGCCTGAGCCTGAAGATTTTGCAACTTACTATTGTCAACAGG CTAACAGTTTCCCATTCACTTTCGGCCCTGGGACCAAAGTGGATATCAAACGTAC GGTGGCCGCTCCCTCCGTGTTCATCTTCCCACCTTCCGACGAGCAGCTGAAGTC CGGCAGTGGAAGGTGGACAACGCCCTGCAGTCCGGCAACTCCCAGGAATCCGT GACCGAGCAGGACTCCAAGGACAGCACCTACTCCCTGTCCTCCACCCTGACCCT GTCCAAGGCCGACTACGAGAAGCACAAGGTGTACGCCTGCGAAGTGACCCACCA GGGCCTGTCTAGCCCCGTGACCAAGTCTTTCAACCGGGGCGAGTGT |
| 298 | Mutated 1D05 - LC mutant 3 | Amino acid sequence of 1D05 kappa light chain with V to Y mutation in CDRL2 highlighted | DIQMTQSPSSLSASVGDRVTITCRASQSISSYLNWYQQKPGKAPKLLIYAASSLQS GVPSRFSGSGSGTDFTLTISSLQPEDFATYYCQQSYSTPITFGQGTRLEKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 299 | 1D05 - heavy chain disabled IgG1 Fc | Amino acid sequence of IgG1 disabled variant of 1D05 | EVQLVESGGGLVQPGRSLRLSCAASGFTFDDYAMHWVRQVPGKGLEWVSGISWI RTGIGYADSVKGRFTIFRDNAKNSLYLQMNSLRAEDTALYYCAKDMKGSGTYGGW FDTWGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKKVE PKSCDKTHTCPPCPAPELAGAPSVFLFPPKPKDTLMISRTPEVTCVVVDVSHEDPE VKFNWYVDGVEVHNAKTKPREEQYNSTYRVVSVLTVLHQDWLNGKEYKCKVSNK ALPAPIEKTISKAKGQPREPQVYTLPPSRDELTKNQVSLTCLVKGFYPSDIAVEWES |

-continued

SEQUENCE LISTING

| SEQ ID NO: | Name | Description | Sequence |
|---|---|---|---|
| | | | NGQPENNYKTTPPVLDSDGSFFLYSKLTVDKSRWQQGNVFSCSVMHEALHNHYT<br>QKSLSLSPGK |
| 300 | 1D05 - light chain IL-2 fusion | 1D05 Light chain sequence fused to wild-type human IL-2 sequence (IL-2 amino acid sequence is underlined and region to be varied is shown in bold) | DIQMTQSPSSLSASVGDRVTITCRASQSISSYLNWYQQKPGKAPKLLIYVASSLQS<br>GVPSRFSGSGSGTDFTLTISSLQPEDFATYYCQQSYSTPITFGQGTRLEIKRTVAAP<br>SVFIFPPSDEQLKSGTASVVCLLNNFYPREAINQWKVDNALQSGNSQESVTEQDSK<br>DSTYSLSSTLTLSKADYEKHKVYACEVTHQGLSSPVTKSFNRGECAPTSSSTKKT<br>QLQLEHLLLDLQMILNGINNYKNPKLTRMLTFKFYMPKKATELKHLQCLEEELKPL<br>EEVLNLAQSKNFHLRPRDLISNINVIVLELKGSETTFMCEYADETATIVEFLNRWITF<br>CQSIISTLT |
| 301 | Human IL-2 | Uniprot number: P60568 Full length amino acid sequence of human IL-2 (minus signal sequence) | APTSSSTKKTQLQLEHLLLDLQMILNGINNYKNPKLTRMLTFKFYMPKKATELK<br>HLQCLEEELKPLEEVLNLAQSKNFHLRPRDLISNINVIVLELKGSETTFMCEYADETA<br>TIVEFLNRWITFCQSIISTLT |
| 302 | Control 1D05 immunocytokine HC C-terminal fusion | Heavy chain 1D05 IgG1 variant fused at the N-terminus to wild-type human IL2 sequence (control) | EVQLVESGGGLVQPGRSLRLSCAASGFTFDDYAMHWVRQVPGKGLEWVSGISWI<br>RTGIGYADSVKGRFTIFRDNAKNSLYLQMNSLRAEDTALYYCAKDMKGSGTYGGW<br>FDTWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKKVE<br>PKSCDKTHTCPPCPAPELAGAPSVFLFPPKPKDTLMISRTPEVTCVVVDVSHEDPE<br>VKFNWYVDGVEVHNAKTKPREEQYNSTYRVVSVLTVLHQDWLNGKEYKCKVSNK<br>ALPAPIEKTISMKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEALHNHYT<br>QKSLSLSPGKAPTSSSTKKTQLQLEHELDLQMILNGINNYKNPKLTRMLTFKFYMP<br>KKATELKHLQCLEEELKPLEEVLNLAQSKNFHLRPRDLISNINVIVLELKGSETTFMC<br>EYADETATIVEFLNRWITFCQSIISTLT |
| 303 | IL-2 D5-9 | IL-2 IC45 (Del 5-9) N terminal IL-2 sequence | APTSTQLQLELLLD |
| 304 | IL-2 D1-9 | IL-2 IC46 (Del 1-9) N terminal IL-2 sequence | TQLQLEHLLLD |
| 305 | IL-2 D5-7 | IL-2 IC64 (Del 5-7) N terminal IL-2 sequence | APTSKKTQLQLEHLLLD |
| 306 | IL-2 D1 | IL-2 D1 N terminal IL-2 sequence | PTSSSTKKTQLQLEHLLLD |
| 307 | IL-2 D1-2 | IL-2 D1-2 N terminal IL-2 sequence | TSSSTKKTQLQLEHLLLD |
| 308 | IL-2 D1-3 | IL-2 D1-3 N terminal IL-2 sequence | SSSTKKTQLQLEHLLLD |
| 309 | IL-2 D1-4 | IL-2 D1-4 N terminal IL-2 sequence | SSTKKTQLQLEHLLLD |

-continued

SEQUENCE LISTING

| SEQ ID NO: | Name | Description | Sequence |
|---|---|---|---|
| 310 | IL-2 D1-5 | IL-2 D1-5 N terminal sequence | STKKTQLQLEHLLLD |
| 311 | IL-2 D1-6 | IL-2 D1-6 N terminal sequence | TKKTQLQLEHLLLD |
| 312 | IL-2 D1-7 | IL-2 D1-7 N terminal sequence | KKTQLQLEHLLLD |
| 313 | IL-2 D1-8 | IL-2 D1-8 N terminal sequence | KTQLQLEHLLLD |
| 314 | IL-2 D9 | IL-2 D9 N terminal sequence | APTSSSTKTQLQLEHLLLD |
| 315 | IL-2 D9-8 | IL-2 D9-8 N terminal sequence | APTSSSTTQLQLEHLLLD |
| 316 | IL-2 D9-7 | IL-2 D9-7 N terminal sequence | APTSSSTQLQLEHLLLD |
| 317 | IL-2 D9-6 | IL-2 D9-6 N terminal sequence | APTSSTQLQLEHLLLD |
| 318 | IL-2 D9-4 | IL-2 D9-4 N terminal sequence | APTQLQLEHLLLD |
| 319 | IL-2 D9-3 | IL-2 D9-3 N terminal sequence | ATQLQLEHLLLD |
| 320 | IL-2 D9-2 | IL-2 D9-2 N terminal sequence | ATKKTQLQLEHLLLD |
| 321 | IL-2 D2-6 | IL-2 D2-6 N terminal sequence | ATKKTQLQLEHLLLD |
| 322 | IL-2 D3-7 | IL-2 D3-7 N terminal sequence | APKKTQLQLEHLLLD |
| 323 | IL-2 D4-8 | IL-2 D4-8 N terminal sequence | APTKTQLQLEHLLLD |
| 324 | C-terminal amino acid sequence of hIL-2 | Amino acids 21 to 133 of hIL-2 | LQMILNGINNYKNPKLTRMLTFKFYMPKKATELKHLQCLEEELKPLEEVLNLAQSKN FHLRPRDLISNINVIVLELKGSETTFMCEYADETATIVEFLNRWITFCQSIISTLT |
| 325 | Mouse PD-L1 | Uniprot number: Q9EP73 (ECD highlighted in BOLD, and | MRIFAGIIFTACCHLLRAFTITAPKDLYVVEYGSNVTMECRFPVERELDLLAL VVWEKEDEQVIQFVAGEEDLKPQHSNFRGRASLPKDQLLKGNAALQIT |

-continued

SEQUENCE LISTING

| SEQ ID NO: | Name | Description | Sequence |
|---|---|---|---|
| | | cytoplasmic domain underlined) | DVKLQDAGVYCCIISYGGADYKRITLKVNAPYRKINQRISVDPATSEHEL<br>ICQAEGYPEAEVIWTNSDHQPVSGKRSVTTSRTEGMLLNVTSSLRVNAT<br>ANDVFYCTFWRSQPGQNHTAELIIPELPATHPPQNRTHWVLLGSILLFLIVV<br>STVLLFLRKQVRMLDVEKCGVEDTSSKNRNDTQFEET |
| 326 | Mouse PD-L1 ECD His | Mouse PD-L1 extracellular domain with his tag | FTITAPKDLYVVEYGSNVTMECRFPVERELDLLALVVWEKEDEQVIQFVAGEEDLK<br>PQHSNFRGRASLPKDQLLKGNAALQITDVKLQDAGVYCCIISYGGADYKRITLKVN<br>APYRKINQRISVDPATSEHELICQAEGYPEAEVIWTNSDHQPVSGKRSVTTSRTEG<br>MLLNVTSSLRVNATANDVFYCTFWRSQPGQNHTAELIIPELPATHPPQNRTHHHH<br>HH |
| 327 | Human IL-2Rα chain | Human IL-2 receptor alpha chain | ELCDDDPPEIPHATFKAMAYKEGTMLNCECKRGFRRIKSGSLYMLCTGNSSHSSW<br>DNQCQCTSSATRNTKQVTPQPEEQKERKTTEMQSPMQPVDQASLPGHCREPPP<br>WENEATERIYHFVVGQMVYYQCVQGYRALHRGPAESVCKMTHGKTRWTQPLIC<br>TGEMETSQFPGEEKPQASPEGRPSEETSCLVTTTDFQIQTEMAATMETSIFTTEYQ<br>VAVAGCVFLLISVLLLSGLTWQRRQRKSRRTI |
| 328 | Human IL-2Rβ chain | Human IL-2 receptor beta chain | AVNGTSQFTCFYNSRANISCVWSQDGALQDTSCQVHAWPDRRRMNQTCELLPVS<br>QASWACNLILGAPDSQKLTTVDIVTLRVLCREGVRWRVMAIQDFKPFENLRLMAPI<br>SLQVVHVETHRCNISWEISQASHYPERHLEFEARTLSPGHTWEEAPLLTLKQKQE<br>WICLETLTPDTQYEFQVRVKPLQGEFTTWSPWSQPLAPRTKPAALGKDTIPWLGH<br>LLVGLSGAFGFIIILVYLLINCRNTGPWLKKVLKCNTPDPSKFFSQLSSEHGGDVQKW<br>LSSPPPSSSFSPGGLAPEISPLEVLERDKVTQLLLQQDKVPEPASLSSNHSLTSCFTN<br>QGYFFHLPDALEIEACQVYFTDPYSEEDPDEGVAGAPTGSSPQLPLSGEDDA<br>YCTFPSRDDLLFSPSLLGGPSPSTAPGGSGAGEERMPPSLQERVPRDWDPQPLG<br>PPTPGVPDLVDFQPPPELVLREAGEEVPDAGPREGVSFPWSRPPGQGEFRALNARL<br>PLNTDAYLSLQELQGQDPTHLV |
| 329 | Human IL-2Rγ chain | Human IL-2 receptor common gamma chain | LNTTILTPNGNEDTTADFFLTTMPTDSLSVSTLPLPEVQCFVFNVEYMNCTWNSSS<br>EPQPTNLTLHYWYKNSDNDINQKCSHYLFSEETTSGCQLQKKEIHLYQTFVVQLQD<br>PREPRRQATQMLKLQNLVIPWAPENLTLHKLSESQELENWNNRFLNHCLEHLVQY<br>RTDWDHSWTEQSVDYRHKFSLPSVDGQKRYTFRVRSRFNPLCGSAQHWSEWSH<br>PIHWGSNTSKENPFLFALEAVVISVGSMGLIISLLCVYFWLERTMPRIPTLKNLEDLV<br>TEYHGNFSAWSGVSKGLAESLQPDYSERLCLVSEIPPKGGALGEGPGASPCNQHSP<br>YWAPPCYTLKPET |
| 330 | IL-7 | Human IL-7 amino acid sequence | DCDIEGKDGKQYESVLMVSIDQLLDSMKEIGSNCLNNEFNFFKRHICDANKEGMFL<br>FRAARKLRQFLKMNSTGDFDLHLLKVSEGTTILLNCTGQVKGRKPAALGEAQPTKS<br>LEENKSLKEQKKLNDLCFLKRIAEIKTCWNKILMGTKEH |
| 331 | IL-15 | Human IL-15 amino acid sequence | GIHVFILGCFSAGLPKTEANWVNVISDLKKIEDLIQSMHIDATLYTESDVHPSCKVT<br>AMKCFLLELQVISLESGDASIHDTVENLIILANNSLSSNGNVTESGCKECEELEEKNI<br>KEFLQSFVHIVQMFINTS |
| 332 | IL-21 | Human IL-21 amino acid sequence | QGQDRHMIRMRQLIDIVDQLKNYVNDLVPEFLPAPEDVETNCEWSAFSCFQKAQL<br>KSANTGNNERIINVSIKKLKRKPPSTNAGRRQKHRLTCPSCDSYEKKPPKEFLERFK<br>SLLQKMIHQHLSSRTHGSEDS |

-continued

SEQUENCE LISTING

| SEQ ID NO: | Name | Description | Sequence |
|---|---|---|---|
| 333 | GM-CSF | Human GM-CSF amino acid sequence | APARSPSPSTQPWEHVNAIQEARRLLNLSRDTAAEMNETVEVISEMFDIQEPTCLQ TRLELYKQGLRGSLTKLKGPLTMMASHYKQHCPPTPETSCATQIITFESFKENLKDF LLVIPFDCWEPVQE |
| 334 | IFNα | Human IFN-α amino acid sequence | CDLPQNHGLLSRNTLVLLHQMRRISPFLCLKDRDRFRFPQEMVKGSQLQKAHVMS VLHEMLQQIFSLFHTERSSAAWNMTLLDQLHTELHQQLQHLETCLLQVVGEGESA GAISSPALTLRRYFQGIRVYLKEKKYSDCAWEVVRMEIMKSLFLSTNMQERLRSKD RDLGS |
| 335 | TNFα | Extracellular portion of human TNF-α amino acid sequence | GPQREEFPRDLSLISPLAQAVRSSSRTPSDKPVAHVVANPQAEGQLQWLNRRANAL LANGVELRDNQLVVPSEGLYLIYSQVLFKGQGCPSTHVLLTHTISRIAVSYQTINNL LSAIKSPCQRETPEGAEAKPWYEPIYLGGVFQLEKGDRLSAEINRPDYLDFAESGQV YFGIIAL |
| 336 | IL-12α | Alpha chain of human IL-12 amino acid sequence | RNLPVATPDPGMFPCLHHSQNLLRAVSNMLQKARQTLEFYPCTSEEIDHEDITKDK TSTVEACLPLELTKNESCLNSRETSFITNGSCLASRKTSFMMALCLSSIYEDLKMYQ VEFKTMNAKLLMDPKRQIFLDQNMLAVIDELMQALNFNSETVPQKSSLEEPDFYKT KIKLCILLHAFRIRAVTIDRVMSYLNAS |
| 337 | IL-12β | Beta chain of human IL-12 amino acid sequence | IWELKKDVVVVELDWYPDAPGEMVLTCDTPEEDGITWTLDQSSEVLGSGKTLTI QVKEFGDAGQYTCHKGGEVLSHSLLLLHKKEDGIWSTDILKDQKEPKNKTFLRCEA KNYSGRFTCWWLTTISTDLTFSVKSSRGSSDPQGVTCGAATLSAERVRGDNKEYE YSVECQEDSACPAAEESLPIEVMVDAVHKLKYENYTSSFFIRDIIKPDDPPKNLQLKPL KNSRQVEVSWEYPDTWSTPHSYFSLTFCVQVQGKSKREKKDRVFTDKTSATVICR KNASISVRAQDRYYSSSWSEWASVPCS |
| 338 | CXCL9 | Human CXCL-9 amino acid sequence | TPVVRKGRCSCISTNQGTIHLQSLKDLKQFAPSPSCEKIEIIATLKNGVQTCLNPDSA DVKELIKKWEKQVSQKKKQNGKKHQKKKVLINRKSQRSRQKKT |
| 339 | CXCL10 | Human-CXCL-10 amino acid sequence | VPLSRTVRCTCISISNQPVNPRSLEKLEIIPASQFCPRVEIIATMKKKGEKRCLNPESK AIKNLLKAVSKERSKRSP |
| 340 | Human WT IgG1 constant region | IGHG1*01 & IGHG1*02 & IGHG1*05 (IgG1) | WT human IgG1 amino acid sequence | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTINDKKVEPKSCDKTHTCPPCP APELLGGPSVFLFPPKPKDTLMISRTPEVTCVVVDVSHEDPEVKFNWYVDGVEHN AKTKPREEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKTTPPVL DSDGSFFLYSKLIVDKSRWQQGNVFSCSVMHEALHNHYTQKSLSLSPGK |
| 341 | | | WT human IgG1 nucleic acid sequence | GCCAGCACCAAGGGCCCCTCTGTGTTCCCTCTGGCCCCTTCCAGCAAGTCCACC TCTGGCGGAACAGCCGCCCTGGGCTGCCTCGTGAAGGACTACTTCCCCGAGCCT GTGACCGTGTCCTGGAACTCTGGCGCTCTGACCAGCGGAGTGCACACCTTCCCT GCTGTGCTGCAGTCCTCCGGCCTGTACTCCCTGTCCTCCGTGGTGACCGTGCCT TCCAGCTCTCTGGGCACCCAGACATACATCTGCAACGTGAACCACAAGCCCTCCA ACACCAAGGTGGACAAGAAGGTGGAACCCAAGTCCTGCGACAAGACCCACACT GTCCCCCCTTGTCCTCCTGCCCCCGAGCTGCTGGGCGGACCTTCCGTGTTCCTGTTCC CCCCAAGCCCAAGGACACCCTGATGATCTCCCGGACCCCCGAAGTGACCTGCG |

-continued

SEQUENCE LISTING

| SEQ ID NO: | Name | Description | Sequence |
|---|---|---|---|
| | | | TGGTGGTGGATGTGTCCCACGAGGACCCTGAAGTGAAGTTCAATTGGTACGTG<br>ACGGCGTGGAAGTGCACAACGCCAAGACCAAGCCTAGAGAGGAACAGTACAACT<br>CCACCTACCGGGTGGTGTCCGTGCTGACCGTGCTGCACCAGGATTGGCTGAACG<br>GCAAAGAGTACAAGTGCAAGGTCTCCAACAAGGCCCTGCCTGCCCCATCGAAA<br>AGACCATCTCCAAGGCCAAGGGCCAGCCCCGGGAACCCCAGGTGTACACACTGC<br>CCCCTAGCAGGGACGAGCTGACCAAGAACCAGGTGAGTCTGACCTGTCTCGTGA<br>AAGGCTTCTACCCCTCCGATATCGCCGTGGAATGGGAGTCCAACGGCCAGCCTG<br>AGAACAACTACAAGACCACCCCCCTGTCCTGACCTCCGACGCTCATTCTTCCT<br>GTACAGCAAGCTGACAGTGGACAAGTCCCGGTGGCAGCAGGGCAACGTGTTCTC<br>CTGCTCCGTGATGCACGAGGCCCTGCACAACCACTACACCCAGAAGTCCCTGTC<br>CCTGAGCCCCGGCAAGTGATGA |
| 342 | Mutated 1D05 - HC mutant 2 | Amino acid sequence of 1D05 heavy chain with V to A and F to S back-mutation in frameworks region to germline highlighted (LAGA) with IgG1 disabled constant region | EVQLVESGGGLVQPGRSLRLSCAASGFTFDDYAMHWVRQAPGKGLEWVSGISWI<br>RTGIGYADSVKGRFTISRDNAKNSLYLQMNSLRAEDTALYYCAKDMKGSGTYGGW<br>FDTWGQGTLVTVSSASTKGPSVFPLAPCSRSTSESTAALGCLVKDYFPEPVTVSWN<br>SGALTSGVHTFPAVLQSSGLYSLSSVVTVPSSSLGTKTYTCNVDHKPSNTKVDKRV<br>ESKYGPPCPPCPAPELAGAPSVFLFPPKPKDTLMISRTPEVTCVVVDVSQEDPEVQF<br>NWYVDGVEVHNAKTKPREEQFNSTYRVVSVLTVLHQDWLNGKEYKCKVSNKGLP<br>SSIEKTISKAKGQPREPQVYTLPPSQEEMTKNQVSLTCLVKGFYPSDIAVEWESNG<br>QPENNYKTTPPVLDSDGSFFLYSRLTVDKSRWQEGNVFSCSVMHEALHNHYTQKS<br>LSLSLGK |
| 343 | 416E01 - CDRH1 (IMGT) | Amino acid sequence of CDRH1 of 416E01 using IMGT | GFTFSNYA |
| 344 | 416E01 - CDRH2 (IMGT) | Amino acid sequence of CDRH2 of 416E01 using IMGT | ISFSGGTT |
| 345 | 416E01 - CDRH3 (IMGT) | Amino acid sequence of CDRH3 of 416E01 using IMGT | AKDEAPAGATFFDS |
| 346 | 416E01 - CDRH1 (Kabat) | Amino acid sequence of CDRH1 of 416E01 using Kabat | NYAMS |
| 347 | 416E01 - CDRH2 (Kabat) | Amino acid sequence of CDRH2 of 416E01 using Kabat | AISFSGGTTYYADSVKG |
| 348 | 416E01 - CDRH3 (Kabat) | Amino acid sequence of CDRH3 of 416E01 using Kabat | DEAPAGATFFDS |
| 349 | 416E01 - Heavy chain variable region | Amino acid sequence of $V_H$ of 416E01 (mutations from germline are shown in boldletters) | EVQLAESGGGLVQPGGSLRLSCAASGFTFSNYAMSWVRQTPGKGLEWVSAISFSG<br>GTTYYADSVKGRFTISRDNSKNTLYLHMNSLRADDTAVYYCAKDEAPAGATFFD<br>SWGQGTLVTVSS |
| 350 | 416E01 - Heavy chain variable region | Nucleic acid sequence of $V_H$ of 416E01 | GAAGTGCAACTGGCGGAGTCTGGGGGAGGCTTGTGTACAGCCGGGGGGGTCCCT<br>GAGACTCTCCTGTGCAGCCTCTGGATTCACCTTTAGCAACTATGCCATGAGTTG<br>GGTCCGCCAGACTCCAGGAAAGGGGCTGGAGTGGGTCTCAGCTATTAGTTTTAG |

| SEQ ID NO: | Name | Description | Sequence |
|---|---|---|---|
| | | | TGGTGGTACTACATACTACGCTGACTCCGTGAAGGGCCCGTTCACCATCTCCAG |
| | | | AGACAATTCCAAGAACACGCTGTATTTGCAGATGAACAGCCTGAGAGCCGATGA |
| | | | CACGGCCGTATATTACTGTGCGAAAGATGAGGCACCAGCTGGCCAACCTTCTT |
| | | | TGACTCCTGGGGCCAAGGAACGCTGGTCACCGTCTCCTCAG |
| 351 | 416E01 - full heavy chain sequence | Amino acid sequence of 416E01 heavy chain | EVQLAESGGGLVQPGGSLRLSCAASGFTFSNYAMSWVRQTPGKGLEWVSAISFSG GTTYYADSVKGRFTISRDNSKNTLYLHMNSLRADDTAVYYCAKDEAPAGATFFDS WGQGTLVTVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKVDKRVESKY GPPCPPCPAPEFEGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSLSLSLG K |
| 352 | 416E01 - full heavy chain sequence | Nucleic acid sequence of 416E01 heavy chain | GAAGTGCAACTGGCCGAGTCTGGGGGAGGCTTGGTACAGCCGGGGGGGTCCCT GAGACTCTCCTGTGCAGACTCTGGATTCACCTTTAGCAACTATGCCATGAGTTG GGTCCGCCAGACTCCAGGAAAGGGCTGGAGTGGGTCTCAGCTATTAGTTTTAG TGGTGGTACTACATACTACGCTGACTCCGTGAAGGGCCGGTTCACCATCTCCAG AGACAATTCCAAGAACACGCTGTATTTGCACATGAACAGCCTGAGAGCCGATGA CACGGCCGTATATTACTGTGCGAAAGATGAGGCACCAGCTGGCGCAACCTTCTT CTACTCCTGGGGCCAAGGAACGCTGGTCACCGTCTCCTCAGCCAGCACCAAGGG CCCTTCCGTGTTCCCCCTGGCCCCCTGCAGCAGAGCACCTCCGAGAGCACAGC TGCCCTGGGCTGTCTGGTGAAGGACTACTTCCCCGAGCCCGTGACCGTGAGCTG GAACAGCGGCGCCTCTACTCCGGTCCTGCGGACCAGCCTCCACACCTTTCCGGCCCGT CTCCAGCCCTCGGTCCTCTGTTCCTGTTCCCTCCAAAGCCAAGGACACCCTC CACCAAGACCCTGAGACGAAGTACGGCCGTGTTCCTGTTCCCTCCTAAGCCCAAGGTGGAC AAACGGGTCGAGACGCCAAGTACGGCCGTGTTCCTGTTCCCTCCTAAGCCCAAGGACACCCTC ATGATCAGCCGGACCCGAGGTGACCTGCGTGGTGGTGGATGGAGTGCACAACG GGACCCTGAGGTCCAGTTGCAACTGGTATGTGGAGGTGCACAATGCCCGGGAAGAGCAGTTCAACTCCACCTACAGGGTGGTCAGCG TGCTGACCGTGCTGCATCAGGACTGGCTGAACGGCAAGGAGTACAAGTGCAAG GTCAGCAATAAGGGACTGCCCAGCAGCATCGAGAAGACCATCTCCAAGGCTAAA GGCCAGCCCCGGGAACCTCAGGTGTACACCCTGCCTCCCAGCCAGGAGGAGATG ACCAAGAACCAGGTGAGTCCAACGCGCAGCCCAGCTCCCCAGCCCAGAACAATTATAAGACCACC CCTCCCGTGCTGGACAGCGACGGATCCTTCTTTCTGTACTCCAGGCTGACCGTG GATAAGTCCAGGTGGCAGGAAGGCAACGTGTTCAGCTGTCCGTGATGCACGAG GCCCTGCACAATCACTACACCCAGAAGTCCCTGAGCCTGTCCCCAGGAAAG |
| 353 | 416E01 - CDRL1 (IMGT) | Amino acid sequence of CDRL1 of 416E01 using IMGT | QGIRRW |
| 354 | 416E01 - CDRL2 (IMGT) | Amino acid sequence of CDRL2 of 416E01 using IMGT | GAS |
| 355 | 416E01 - CDRL3 | Amino acid sequence of CDRL3 | QQANSFPIT |

SEQUENCE LISTING
-continued

| SEQ ID NO: | Name | Description | Sequence |
|---|---|---|---|
| | | of 416E01 using IMGT | |
| 356 | 416E01 - CDRL1 (Kabat) | Amino acid sequence of CDRL1 of 416E01 using Kabat | RASQGIRRWLA |
| 357 | 416E01 - CDRL2 (Kabat) | Amino acid sequence of CDRL2 of 416E01 using Kabat | GASSLQS |
| 358 | 416E01 - CDRL3 (Kabat) | Amino acid sequence of CDRL3 of 416E01 using Kabat | QQANSFPIT |
| 359 | 416E01 - Light chain variable region | Amino acid sequence of V<sub>L</sub> of 416E01 (mutations from germline are shown in bold letters) | DIQMTQSPSSVSASVGDRVTITCRASQGIRRWLAWYQQKPGKAPKLLISGASSLQ SGVPSRFSGSGSGTDFTLIITSLQPEDFATYYCQQANSFPITFGQGTRLEIK |
| 360 | 416E01 - Light chain variable region | Nucleic acid sequence of V<sub>L</sub> of 416E01 | GACATCCAGATGACCCAGTCTCCATCTTCCGTGTCTGCATCTGTAGGAGACAGA GTCACCATCACTTGTCGGGCGAGTCAGGGTATTAGGAGGTGGTTAGCCTGGTAT CAGCAGAAACCAGGGAAAGCCCCTAAACTCCTGATCTCTGGTGCATCCAGTTTG CAAAGTGGGGTCCCATCAAGGTTCAGCGGCAGTGGATCTGGGACAGATTTCACT CTCATCATTACCAGTCTGCAGCCTGAAGATTTTGCAACTTACTATTGTCAACAGG CTAACAGTTTCCCGATCACCTTCGGCCAAGGGACAACGACTGGAGATCAAAC |
| 361 | 416E01 - full light chain sequence | Amino acid sequence of 416E01 light chain | DIQMTQSPSSVSASVGDRVTITCRASQGIRRWLAWYQQKPGKAPKLLISGASSLQS GVPSRFSGSGSGTDFTLIITSLQPEDFATYYCQQANSFPITFGQGTRLEIKRIVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 362 | 416E01 - full light chain sequence | Nucleic acid sequence of 416E01 light chain | GACATCCAGATGACCCAGTCTCCATCTTCCGTGTCTGCATCTGTAGGAGACAGA GTCACCATCACTTGTCGGGCGAGTCAGGGTATTAGGAGGTGGTTAGCCTGGTAT CAGCAGAAACCAGGGAAAGCCCCTAAACTCCTGATCTCTGGTGCATCCAGTTTG CAAAGTGGGGTCCCATCAAGGTTCAGCGGCAGTGGATCTGGGACAGATTTCACT CTCATCATTACCAGTCTGCAGCCTGAAGATTTTGCAACTTACTATTGTCAACAGG CGGTGGCCGCTCCTGTCTTCATCTTCCCGCCATCTGATGAGCAGTTGAAGT CCGGAACCGCTTCTGTTGTGTGCCTGCTGAATAACTTCTACCCCCGAGGCCA AGTAGCAGTGGACTCCAGGACAGCAACAGCCCTCAGTCCAGGAGAGTCCC TGACCGAGCAGGACTCCAAGGACAGCACCTACAGCCTCAGCAGCACCCTGACCC TGTCCAAGGCCGACTACGAGAAGCACAAGGTGTACGCCTGCGAAGTGACCCACC AGGGCCTGTCTAGCCCCGTGACCAAGTCTTTCAACCGGGGCGAGTGT |
| 363 | STIM001 - CDRH1 | Amino acid sequence of CDRH1 of STIM001 using IMGT | GYTFSTFG |
| 364 | STIM001 - CDRH2 | Amino acid sequence of CDRH2 of STIM001 using IMGT | ISAYNGDT |
| 365 | STIM001 - CDRH3 | Amino acid sequence of CDRH3 | ARSSGHYYYGMDV |

-continued

SEQUENCE LISTING

| SEQ ID NO: | Name | Description | Sequence |
|---|---|---|---|
| 366 | STIM001 - Heavy chain variable region | Amino acid sequence of V_H of STIM001 using IMGT | QVQVVQSGAEVKKPGASVKVSCKASGYTFSTFGITWVRQAPGQGLEWMGWISAY NGDTNYAQNLQGRVIMTDTSTSTAYMELRSLRSDDTAVYYCARSSGHYYYYGM DVWGQGTTVTVSS |
| 367 | STIM001 - Heavy chain variable region | Nucleic acid sequence of V_H of STIM001 | CAGGTTCAGGTGGTGCAGTCTGGAGCTGAGGTGAAGAAGCCTGGGGCCTCAGT GAAGGTCTCCTGCAAGGCTTCTGGTTACACCTTTTCCACCTTTGGTATCACCTGG GTGCGACAGGCCCCTGGACAAGGGCTTGAATGGATGGGATGGATCATGACCAC CAATGGTGACACAAACTATGCACAGAATCTCCAGGGCAGAGTCATCATGACGA AGACACATCGACCAGCCTACATGGAGCTGAGGAGCCTGAGATCTGACGA CACGGCCGTTTATTACTGTGCGAGGAGCAGTGGCCACTACTACTACGGTAT GGACGTCTGGGGCCAAGGGACCACGGTCACCGTCTCCTCA |
| 368 | STIM001 - full heavy chain sequence | Amino acid sequence of STIM001 heavy chain | QVQVVQSGAEVKKIDGASMSCKASGYTFSTFGITWVRQAPGQGLEWMGWISAY NGDTNYAQNLQGRVIMTDTSTSTAYMELRSLRSDDTAVYYCARSSGHYYYYGM DVWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEV KFNWYVDGVEVHNAKTKPREEQYNSTYRVSVLTVLHQDWLNGKEYKCKVSNKA LPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPGK |
| 369 | STIM001 - full heavy chain sequence | Nucleic acid sequence of STIM001 heavy chain | CAGGTTCAGGTGGTGCAGTCTGGAGCTGAGGTGAAGAAGCCTGGGGCCTCAGT GAAGGTCTCCTGCAAGGCTTCTGGTTACACCTTTTCCACCTTTGGTATCACCTGG GTGCGACAGGCCCCTGGACAAGGGCTTGAATGGATGGGATGGATCATGACCAC CAATGGTGACACAAACTATGCACAGAATCTCCAGGGCAGAGTCATCATGACCAC AGACACATCCACGAGCACAGCCTACATGGAGCTGAGGAGCCTGAGATCTGACGA CACGGCCGTTTATTACTGTGCGAGGAGCAGTGGCCACTACTACTACTACGGTAT GGACGTCTGGGGCCAAGGGACCACGGTCACCGTCTCCTCAGCCTCCACCAAGGG CCCATCGGTCTTCCCCCTGGCACCCTCCTCCAAGAGCACCTCTGGGGGCACAGC GGCCCTGGGCTGCCTGGTCAAGGACTACTTCCCCGAACCGGTGACGGTGTCGT GGAACTCAGGCGCCCTGACCAGCGGCGTGCACACCTTCCCGGCTGTCCTACAGTC CTCCGGACTCTACTCCCTCAGCAGCGTGGTGACCGTGCCCTCCAGCTCTTGGG CACCCAGACCTACATCTGCAACGTGAATCACAAGCCCAGCAACACCAAGGTGGAC AAGAAGGTGGAACTGCAAGTCCCGGACCTTCCGTTCCTGTTCCCCCCAAAGCCCAAG GACACCCTCATGATCTCCCGGACCCCTGAAGTGACCTGCGTGGTGGTGGATGTG TCCCACGAGGACCCCGAAGTGAAGTTCAATTGGTACGTGGACGGCGTGAAGTG CACAACGCCAAGACCAAGCCTAGAGGAGCAGTACAACTCCACCTACCGGGTG GTGTCCGTGCTGACCGTGCTGCACCAGGATTGGCTGAACGGCAAAGAGTACAAG TGCAAGGTGTCCAACAAGGCCCTGCCCGCCATCGAAAAGACCATCTCCAAG GCCAAGGGCCAGCCCCGGGAACCCCAGGTGTACACACTGCCCCCTAGCAGGAC GAGCTGACCAAGAACCAGGTCCTGAATGGAGTCCAACGGCCAGCCTGAGAACAACTACAAG ACCACCCCCCTGTGCTGGACTCCGACGGCTCATTCTTCCTGTACAGCAAGCTG ACAGTGGACAAGTCCCGGTGGCAGCAGGGCAACGTGTTCTCCTGTTCCGTGATG |

| SEQ ID NO: | Name | Description | Sequence |
|---|---|---|---|
| | | | CACGAGGCCCTGCACAACCACTACACCCAGAAGTCCCTGTCCCTGAGCCCCGGC AAGTGATGA |
| 370 | STIM001 - CDRL1 | Amino acid sequence of CDRL1 of STIM001 using IMGT | QSLLHSNEYNY |
| 371 | STIM001 - CDRL2 | Amino acid sequence of CDRL2 of STIM001 using IMGT | LGS |
| 372 | STIM001 - CDRL3 | Amino acid sequence of CDRL3 of STIM001 using IMGT | MQSLQTPLT |
| 373 | STIM001 - Light chain variable region | Amino acid sequence of $V_L$ of STIM001 | DIVMTQSPLSLPVTPGEPASISCRSSQSLLHSNEYNYLDWYLQKPGQSPQLLIFLGS NRASGVPDRFSGSGSGTDFTLKITRVEAEDVGIYYCMQSLQTPLTFGGGTKVEIK |
| 374 | STIM001 - Light chain variable region | Nucleic acid sequence of $V_L$ of STIM001 | GATATTGTGATGACTCAGTCTCCACTCTCCCTGCCCGTCACCCCTGGAGAGCCG GCCTCCATCTCCTGCAGGTCTAGTCAGAGCCTCCTGCATAGTAATGAATACAACT ATTTGGATTGGTACCTGCAGAAGCCAGGGCAGTCTCCACAGCTCCTGATCTTTT TGGGTTCTAATCGGGCCTCCGGGGTCCCTGACAGGTTCAGTGGCAGTGGATCA GGCACAGATTTTACACTGAAAATCACCAGAGTGGAGGCTGAGGATGTTGGAATT TATTACTGCATGCAATCTCTACAACTCCGCTCACTTTCGGCGGAGGGACCAAG GTGGAGATCAAA |
| 375 | STIM001 - full light chain sequence | Amino acid sequence of STIM001 light chain | DIVMTQSPLSLPVTPGEPASISCRSSQSLLHSNEYNYLDWYLQKPGQSPQLLIFLGS NRASGVPDRFSGSGSGTDFTLKITRVEAEDVGIYYCMQSLQTPLTFGGGTKVEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 376 | STIM001 - full light chain sequence | Nucleic acid sequence of STIM001 light chain | GATATTGTGATGACTCAGTCTCCACTCTCCCTGCCCGTCACCCCTGGAGAGCCG GCCTCCATCTCCTGCAGGTCTAGTCAGAGCCTCCTGCATAGTAATGAATACAACT ATTTGGATTGGTACCTGCAGAAGCCAGGCCAGTCTCCACAGCTCCTGATCTTTT TGGGTTCTAATCGGGCCTCCGGGGTCCCTGACAGGTTCAGTGGCAGTGGATCA GGCACAGATTTTACACTGAAAATCACCAGAGTGGAGGCTGAGGATGTTGGAATT TATTACTGCATGCAATCTCTACAACTCCGCTCACTTTCGGCGGAGGGACCAAG GTGGAGATCAAAcgtacggtggccgctcccctccgtctcatctccacccttccagacgagcagctgaa gtccggaacggctctgtgtgttgtgtgaacaacttctaccccgcgaggccaagtgcagtggaag gtggacaacgccctgcagtccggcaactcccaggaatccgtcaccagcaggacaggacagcac ctactccctgtcctccaccctgaccctgagcaaggcgactacgagaagcacaaggtgacgcctgcgaa gtgacccaccagggcctgtctagcccgtgaccaagtctttcaacccgggcgagtgt |
| 377 | STIM002 - CDRH1 | Amino acid sequence of CDRH1 of STIM002 using IMGT | GYTFTSYG |
| 378 | STIM002 - CDRH2 | Amino acid sequence of CDRH2 of STIM002 using IMGT | ISAYNGNT |
| 379 | STIM002 - CDRH3 | Amino acid sequence of CDRH3 of STIM002 using IMGT | ARSTYFYGSSTLYGMDV |

| SEQ ID NO: | Name | Description | Sequence |
|---|---|---|---|
| 380 | STIM002 - Heavy chain variable region | Amino acid sequence of V<sub>H</sub> of STIM002 | QVQLVQSGGEVKKPGASVKVSCASGYTFTSYGFSWVRQAPGQGLEWMGWISAY NGNTNYAQKLQGRVTMTTDTSTSTAYMELRSLRSDDTAVYYCARSTYFYGSGTLY GMDVWGQGTTVTVSS |
| 381 | STIM002 - Heavy chain variable region | Nucleic acid sequence of V<sub>H</sub> of STIM002 | CAGGTTCAACTGGTGCAGTCTGGAGGTGAGGTGAAGAAGCCTGGGGCCTCAGT GAAGGTCTCCTGCAAGGCTTCTGGTTACACCTTTACCAGCTACGGTTTCAGCTG GGTGCGACAGGCCCCTGGACAAGGACTAGAGTGGATGGGATGGATCAGCGCTT ACAATGGTAACACAAACTATGCACAGAAGCTCCAGGGCAGAGTCACCATGACCA CAGACACATCCACGAGCACAGCCTACATGGAGCTGAGGAGCTTGAGGATCTGACG ACACGCCGTGATTACTGTGCGAGATCTACGTATTCTATGGTTCGGGACCC TCTACGGTATGGACGTCTGGGGCCAAGGGACCACGGTCACCGTCTCCTCA |
| 382 | STIM002 - full heavy chain sequence | Amino acid sequence of STIM002 heavy chain | QVQLVQSGGEVKKPGASVKVSCASGYTFTSYGFSWVRQAPGQGLEWMGWISAY NGNTNYAQKLQGRVTMTTDTSTSTAYMELRSLRSDDTAVYYCARSTYFYGSGTLY GMDVWGQGTTVTVSSASTKGPSVFPLAPSSKSTSGGTAALGCLVKDYFPEPVTVS WNSGALTSGVHTFPAVLQSSGLYSLSSVVPTVPSSSLGTQTYICNVNHKPSNTKVDK KVEPKSCDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKVS NKALPAPIEKTISMKGQPREPQVYTLPPSRDELTKNQVSLTCLVKGFYPSDIAVEW ESNGQPENNYKTTPPVLDSDGSFFLYSKLTVDKSRWQQGNVFSCSVMHEALHNHY TQKSLSLSPGK |
| 383 | STIM002 - full heavy chain sequence | Nucleic acid sequence of STIM002 heavy chain | CAGGTTCAACTGGTGCAGTCTGGAGGTGAGGTGAAGAAGCCTGGGGCCTCAGT GAAGGTCTCCTGCAAGGCTTCTGTTACACCTTTACCAGCTACGGTTTCAGCTG GGTGCGACAGGCCCCTGGACAAGGACTAGAGTGGATGGGATGGATCAGCGCTT ACAATGGTAACACAAACTATGCACAGAAGCTCCAGGGCAGAGTCACCATGACCA CAGACACATCCACGAGCACAGCCTACATGAGCTGAGATCTGAGGATCTGACG ACACGCCGTGATTACTGTGCGAGATCTACGTATTCTATGGTTCGGGGACCC TCTACGGTATGGACGTCTGGGGCCAAGGGACCACGGTCACCGTCTCCTCA GCCAGCACCAAGGGCCCCTCTGTCCCCTGGCCCCTGCAGCAAGTCCACC TCTGCGCAAGACCTGGCCTCTGGGCCATCCAAGAGGACTACTTCCCCGAGCCT GTGACCGTGTCCTGGAACTCTGGCGCTCTGACCAGCGGAGTGCACACCTTCCCT GCTGTCCTGCAGTCCTCTGGGCTACTCCCTGTCCTCCGTGACCGTGCCT TCCAGCTCTCTGGCACCCAGACCTACATCTGCAACGTGAACCACAAGCCCTCCA ACACCAAGGTGGACAAGAAGGTTGAACCCAAGTCCTGCGACAAGACCCACACCT GTCCCCCCTTGTCCTCTCCCCCTGAACTGCTGGGCGGACCTTCCGTGTTCCTGTTCC CCCAAAGCCCAAGGACACCCTGATGATCTCCCGGACCCCTGAAGTGAAGTTCAATTGGTACGTGG ACGGCGTGGAAGTGCACAACGCCAAGACCAAGCCTAGAGAGGAACAGTACAACT CCACCTACCGGGTGGTCCGTGCTGACCGTGCTGCACCAGGATTGGCTGAACG GCAAAGAGTACAAGTGCAAGGTGTCCAAGGCCCTGCCTGCCCCATCGAAA GACCATCTCCAAGGCCAAGGGCCAGCCCCGGGAACCCCAGGTGTACACACTGC CCCCTAGCAGGACGAGCTGACCAAGAACCAGGTGTCCCTGACCTGTCTGTGA AGGCTTCTACCCCCTCCGATATCGCCGTGGAATGGAGTCCAACGGCCAGCCTG AGAACAACTACAAGACCACCCCCCTGCTGGACTCCGACGGCTCATTCTTCCT GTACAGCAAGCTGACAGTGGACAAGTCCCGGTGGCAGCAGGGCAACGTGTTCT CTGCTCCGTGATGCACGAGGCCCTGCACAACCACTACACCCAGAAGTCCCTGTC |

-continued

SEQUENCE LISTING

| SEQ ID NO: | Name | Description | Sequence |
|---|---|---|---|
| | | | CCTGAGCCCCGGCAAGTGATGA |
| 384 | STIM002 - CDRL1 | Amino acid sequence of CDRL1 of STIM002 using IMGT | QSLLHSDGYNY |
| 385 | STIM002 - CDRL2 | Amino acid sequence of CDRL2 of STIM002 using IMGT | LGS |
| 386 | STIM002 - CDRL3 | Amino acid sequence of CDRL3 of STIM002 using IMGT | MQALQTPLS |
| 387 | STIM002 - Light chain variable region | Amino acid sequence of V<sub>L</sub> of STIM002 | DIVMTQSPLSLPVTPGEPASISCRSSQSLLHSDGYNYLDWYLQKPGQSPQLLIYLGS TRASGFPDRFSGSGSGTDFTLKISRVEAEDVGVYYCMQALQTPLSFGQGTKLEK |
| 388 | STIM002 - Light chain variable region | Nucleic acid sequence of V<sub>L</sub> of STIM002 | GATATTGTGATGACTCAGTCTCCACTCTCCCTGCCCGTCACCCCTGGAGAGCCG GCCTCCATCTCCTGCAGGTCTAGTCAGAGCCTCCTGCATAGTGATGGATACAAC TGTTTGGATTGGTACCTGCAGAAGCCAGGGCAGTCTCCACAGCTCCTGATCTAT TTGGGTTCTACTCGGGCCTCCGGGTTCCCTGACAGGTTCAGTGGCAGTGGATCA GGCACAGATTTTACACTGAAAATCAGCAGAGTGGAGGCTGAGGATGTTGGGGTT TATTACTGCATGCAAGCTCTACAAACTCCGTCAGTTTTGGCCAGGGGACCAAG CTGGAGATCAAA |
| 389 | STIM002 - full light chain sequence | Amino acid sequence of STIM002 light chain | DIVMTQSPLSLPVTPGEPASISCRSSQSLLHSDGYNYLDWYLQKPGQSPQLLIYLGS TRASGFPDRFSGSGSGTDFTLKISRVEAEDVGVYYCMQALQTPLSFGQGTKLEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 390 | STIM002 - full light chain sequence | Nucleic acid sequence of STIM002 light chain | GATATTGTGATGACTCAGTCTCCACTCTCCCTGCCCGTCACCCCTGGAGAGCCG GCCTCCATCTCCTGCAGGTCTAGTCAGAGCCTCCTGCATAGTGATGGATACAAC TGTTTGGATTGGTACCTGCAGAAGCCAGGGCAGTCTCCACAGCTCCTGATCTAT TTGGGTTCTACTCGGGCCTCCGGGTTCCCTGACAGGTTCAGTGGCAGTGGATCA GGCACAGATTTACACTGAAAATCAGCAGAGTGGAGGCTGAGGATGTTGGGGTT TATTACTGCATGCAAGCTCTACAAACTCCGTCAGTTTTGGCCAGGGGACCAAG CTGGAGATCAAAcgtacggtggcgcgtcctccatcgttctcttcatcttctacccccgaggccaagctcatcatcctccacctctaacgagtgtgctgctgaacaaacttctaccccgcgaggccaagtgcagtggaag gtgacacgccgcctctgctgctgctgcaggaatcgtgacagactggcctaccccaggacgtccaagtcctccaccgtcggccagtctaccaagcggggacacaaggcctgaccccgcgtcctctaccagggcctgtcagccccggtcctcaaccgaggcacaagggcctggaccaagctctttcaaccgggcgaagtgt |
| 391 | STIM002-B - CDRH1 | Amino acid sequence of CDRH1 of STIM002-B using IMGT | GYTFTSYG |
| 392 | STIM002-B - CDRH2 | Amino acid sequence of CDRH2 of STIM002-B using IMGT | ISAYNGNT |
| 393 | STIM002-B - CDRH3 | Amino acid sequence of CDRH3 of STIM002-B using IMGT | ARSTYFYGSGTLYGMDV |

SEQUENCE LISTING

| SEQ ID NO: | Name | Description | Sequence |
|---|---|---|---|
| 394 | STIM002-B – Heavy | Amino acid sequence of V$_H$ of chain variable region STIM002-B | QVQLVQSGGEVKKPGASMSCKASGYTFTSYGFSWVRQAPGQGLEWMGWISAY NGNTNYAQKLQGRVTMTTDTSTSTAYMELRSDDTAVYYCARSTYFYGSGTLY GMDVWGQGTTVTVSS |
| 395 | STIM002-B – Heavy | Nucleic acid sequence of V$_H$ of chain variable region STIM002-B | CAGGTTCAACTGGTGCAGTCTGGAGGTGAGGTGAAGAAGCCTGGGGCCTCAGT GAAGGTCTCCTGCAAGGCTTCTGGTTACACCTTTACCAGCTATGGTTTCAGCTG GGTGCGACAGGCCCCTGGACAAGGACTAGAGTGGATGGGATGGATCAGCGCTT ACAATGGTAACACAAACTATGCACAGCCTACACCAGAGAGTCACCATGACCA CAGACACCATCCAGCACAGCCTACATGGAGCTGAGGAGCTTCTATGGTTCGGGACCC ACACGGCCGCTGTATTACTGTGCGAGATCTACGTATTTCTATGGTTCGGGACCC TCTACGGTATGGACGTCTGGGGCCAAGGGACCACGGTCACCGTCTCCTCA |
| 396 | STIM002-B – full heavy chain sequence | Amino acid sequence of STIM002-B heavy chain | QVQLVQSGGEVKKPGASVKVSCKASGYTFTSYGFSWVRQAPGQGLEWMGWISAY NGNTNYAQKLQGRVTMTTDTSTSTAYMELRSDDTAVYYCARSTYFYGSGTLY GMDVWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVD KVEPKSCDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEALHNHY TQKSLSLSPGK |
| 397 | STIM002-B – full heavy chain sequence | Nucleic acid sequence of STIM002-B heavy chain | CAGGTTCAACTGGTGCAGTCTGGAGGTGAGGTGAAGAAGCCTGGGGCCTCAGT GAAGGTCTCCTGCAAGGCTTCTGGTTACACCTTTACCAGCTATGGTTTCAGCTG GGTGCGACAGGCCCCTGGACAAGGACTAGAGTGGATGGGATGGATCAGCGCTT ACAATGGTAACACAAACTATGCACAGCCTCCAGGGCAGAGTCACCATGACCA CAGACACAATCCACCAGCTACATGGAGCTTGAGACTGACG ACACGCCGTATGGACGTCTGGGGCCAAGGACCACGGTCACCGTCTCCTCAGCCA TCTACGGTATGGACGTCTGGGGCCAAGGACCACCGTCACCGTCTCCTCAGCCA GCCACCAAGGGCCCCTCTGTCTTCCCCCTGGCGCCCTGCTCCAGGAGCACCTCTG GCGGAACAGCGGCCCTGGGCTGCCTGGTCAAGGACTACTTCCCCGAGCCTGTGA CCGTGTCCTGGAACTCTGGCGCTCTGACCAGCGGCGTGCACACCTTCCCTGCTG TGCTGCAGTCCTCCGGCCTGTACTCCCTGTCCTCCGTGGTCACCGTGCCCTCCA GCTCTCTGGGCACCCAGACCTACATCTGCAACGTGAACCACAAGCCTCCAACAC CAAGGTGACAAGAAGGTGGAACCCAAGTCTCGCGACAAGACCCACACCTGTCC CCCTTGTCCTGCCCCTGAACTGCTGGGCGGACCTTCCGTGTTCCTGTTCCCCC AAAGCCCAAGGACACCCTGATGATCTCCCGGACCCCCGAAGTGACCTGCGTGGT GGTGGATGTGTCCACGAAGTGTCCAAGCCAAGACCAAGCCTAGAGAGAACAGTACAACTCCA CCTACCGGGTGGTGTCCGTGCTGACCGTGCTGCACCAGGATTGGCTGAACGGCA AAGAGTACAAGTGCAAGGTGTCCAACAAGGCCCTGCCTGCCCCATCGAAAAGA CCATCTCCAAGGCCAAGGGCCAGCCCCGGGAACCCAGGTGTCCCTGACCTGTGAAAG CTAGCAGGGACCAGGCTGACCAAGAACCAGGTGTCCCTGACCTGTCTGGTGAAAG GCTTCTACCCCTCCGATATCGCCGTGGAATGGGAGAGTCCAACGGCCAGCCTGAGA ACAACTACAAGACTACACCCCCCCCTGTGCTGGACTCCGACGGCAGCCAACCCTCATTCTTCCTG TACAGCAAGCTGACAGTGGACAAGTCCCGGTGGCAGCAGGGCAACGTCTTCTCCTG CTCCGTGATGCACGAGGCCCTGCACAACCACTACACCCAGAAGTCCCTGTCCCT GAGCCCCGGCAAGTGATGA |

| SEQ ID NO: | Name | Description | Sequence |
|---|---|---|---|
| 398 | STIM002-B – CDRL1 | Amino acid sequence of CDRL1 of STIM002-B using IMGT | QSLLHSDGYNC |
| 399 | STIM002-B – CDRL2 | Amino acid sequence of CDRL2 of STIM002-B using IMGT | LGS |
| 400 | STIM002-B – CDRL3 | Amino acid sequence of CDRL3 of STIM002-B using IMGT | MQALQTPCS |
| 401 | STIM002-B – Light | Amino acid sequence of $V_L$ of chain variable region STIM002-B | DIVMTQSPLSLPVTPGEPASISCRSSQSLLHSDGYNCLDWYLQKPGQSPQLLIYLGS TRASGFPDRFSGSGSGTDFTLKISRVEAEDVGVYYCMQALQTPCSFGQGTKLEIK |
| 402 | STIM002-B – Light | Nucleic acid sequence of $V_L$ of chain variable region STIM002-B | GATATTGTGATGACTCAGTCTCCACTCTCCCTGCCCGTCACCCCTGGAGAGCCG GCCTCCATCTCCTGCAGGTCTAGTCAGAGCCTCCTGCATAGTGATGGATACAAC TGTTTGGATTGGTACCTGCAGAAGCCAGGGCAGTCTCCACAGCTCCTGATCTAT TTGGGTTCTACTCGGGCCTCCGGGTTCCCTGACAGGTTCAGTGGAGGCTGGGGTT GGCACAGATTTTACACTGAAAATCAGCAGAGTGGAGGCTGAGGATGTTGGGGTT TATTACTGCATGCAAGCTCTACAAACTCCGTGCAGTTTTGGCCAGGGGACCAAG CTGGAGATCAAA |
| 403 | STIM002-B – full light chain sequence | Amino acid sequence of STIM002-B light chain | DIVMTQSPLSLPVTPGEPASISCRSSQSLLHSDGYNCLDWYLQKPGQSPQLLIYLGS TRASGFPDRFSGSGSGTDFTLKISRVEAEDVGVYYCMQALQTPCSFGQGTKLEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 404 | STIM002-B – full light chain sequence | Nucleic acid sequence of STIM002-13 light chain | GATATTGTGATGACTCAGTCTCCACTCTCCCTGCCCGTCACCCCTGGAGAGCCG GCCTCCATCTCCTGCAGGTCTAGTCAGAGCCTCCTGCATAGTGATGGATACAAC TGTTTGGATTGGTACCTGCAGAAGCCAGGGCAGTCTCCACAGCTCCTGATCTAT TTGGGTTCTACTCGGGCCTCCGGGTTCCCTGACAGGTTCAGTGGAGGCTGGGGTT GGCACAGATTTTACACTGAAAATCAGCAGAGTGGAGGCTGAGGATGTTGGGGTT TATTACTGCATGCAAGCTCTACAAACTCCGTGCAGTTTTGGCCAGGGGACCAAG CTGGAGATCAAAcgtacggtggcgcgctccctccgtgcttcatcttcccaccttccgatgagcagttgaa-gtccgcaccgctctgtgcttgtgcctgcaactcctccaggaataccgtgaccgaggaggactccaaggacagcac ctactccctcagcagcaccctgacgctgagcaaagcagactacgagaaagcacaaggtgtacgcctgcgaa gtgacccaccaggcgctgctagccccgtgaccaagtctttcaaccgggcgggtgagtgt |
| 405 | STIM003 – CDRH1 | Amino acid sequence of CDRH1 of STIM003 using IMGT | GVTFDDYG |
| 406 | STIM003 – CDRH2 | Amino acid sequence of CDRH2 of STIM003 using IMGT | INWNGGDT |
| 407 | STIM003 – CDRH3 | Amino acid sequence of CDRH3 of STIM003 using IMGT | ARDFYGSGSYYHVPFDY |
| 408 | STIM003 – Heavy | Amino acid sequence of $V_H$ of | EVQLVESGGGVVRPGGSLRLSCVASGVTFDDYGMSWVRQAPGKGLEWVSGINWN |

-continued

SEQUENCE LISTING

| SEQ ID NO: | Name | Description | Sequence |
|---|---|---|---|
| | | chain variable region STIM003 | GGDTDYSDSVKGRFTISRDNAKNSLYLQMNSLRAEDTALYYCARDFYGSGSYYHV PFDYWGQGILVTVSS |
| 409 | STIM003 – Heavy | Nucleic acid sequence of V<sub>H</sub> of chain variable region STIM003 | GAGGTGCAGCTGGTGGAGTCTGGGGGAGGTGTGTACGCCTGGGGGGTCCCT GAGACTCTCCTGTGTAGCCTCTGGAGTCACCTTTGATGATTATGGCATGAGCTG GGTCCGCCAAGCTCCAGGGAAGGGGCTGGARTGGGTCTCTGTATTAATTGGA ATGGTGGCGACACAGATTATTCAGACTCTGTGAAGGGCCGATTCACCATCTCCA GAGACAACGCCAAGAACTCCCTGTATCTACAAATGAATAGTCTGAGAGCCGAGG ACACGGCCTTGTATTACTGTGCGAGGGATTTCTATGGTTCGGGGAGTTATTATC ACGTTCCTTTTGACTACTGGGGCCAGGGAATCCTGGTCACCGTCTCCTCA |
| 410 | STIM003 – full heavy chain sequence | Amino acid sequence of STIM003 heavy chain | EVQLVESGGGVVRPGGSLRLSCVASGVTFDDYGMSWVRQAPGKGLEWVSGINWN GGDTDYSDSVKGRFTISRDNAKNSLYLQMNSLRAEDTALYYCARDFYGSGSYYHV PFDYWGQGILVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHEDP EVKFNWYVDGVEVHNAKTKPREEQYNSTYRVVSVTVLHQDWLNGKEYKCKVSN KALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYT QKSLSLSPGK |
| 411 | STIM003 – full heavy chain sequence | Nucleic acid sequence of STIM003 heavy chain | GAGGTGCAGCTGGTGGAGTCTGGGGGAGGTGTGTACGCCTGGGGGGTCCCT GAGACTCTCCTGTGTAGCCTCTGGAGTCACCTTTGATGATTATGGCATGAGCTG GGTCCGCCAAGCTCCAGGGAAGGGGCTGGARTGGGTCTCTGTATTAATTGGA ATGTGGCGACACAGATTATTCAGACTCTGTGAAGGGCCGATTCACCATCTCCA GACACAACGCCAAGAACTCCCTGTATCTACAAATGAATAGTCTGAGAGCCGAGG ACACGGCCTTGTATTACTGTGCGAGGGATTTCTATGGTTCGGGGAGTTATTATC ACGTTCCTTTTGACTACTGGGGCCAGGGAATCCTGGTCACCGTCTCCAGCCA GCACCAAGGGCCCCTCTGTGTTCCCTCTGGCCCCTGTGAAGGACTACTTCCCCGAGCCTGTGA CCGTGTCCTGGAACTCTGGCCTCTGTGAGTCACCTTTGATGATTATGGCATGAGCTG TGCTGCAGTCCTCCCGCTACTCCTCAGTCTGTGCTCCTCCGTGACCGTCCTTCCA GCTCCTGGGCACCCAGACCTACATCTGCAACGTGAACCACAAGCCCCTCCAACAC CAAGTGGACAAGAAGGTGGAACTCTGCGACAAGCCCGGACACCCTCCCCACTGTCC CCCTTGTCCTGCCCCGACCCCTGAACTCTGGCGCGGACCTTCGTGTCCTGTTCCCCCC AAAGCCCAAGGACACCCTGATGATCTCCGGACCCCTGAAGTGACCTGCGTGGT GGTGGATGTGTCCCACGAGGACCCTGAAGTGAAGTTCAATTGGTACGTGGACG GCGTGGAAGTGCACAACGCCAAGACAAGCCACGTGCGTGAGGAACAGTACAACTCCA CCTACCGGGTGGTGTCCGTGCTGACCGTGCTGCACCAGGACTGGCTGAACGGCA AAGAGTACAAGTGCAAGGTGTCAACAAGGCCCTGCCTCCCCATCGAAAAGA CCATCTCCAAGGCCAAGGGCCAGCCCCGGGAACCCCAGGTGTACACACTGCCCC CTAGCAGGGACGAGCTGACCAAGAACCAGGTGTCCTGACCTGCCTGGTCAAGG GCTTCTACCCCTCCGATATCGCCGTGGAATGGGAGTCCAACGGCCAGCCTGGA ACAACTACAAGACCACCCCCGTGCTGGACTCCGACGGCTCATTCTTCCTGTA CAGCAAGCTGACAGTGGACAAGTCCGGTGGCAGGCAGGCAACGTGTTCCTG CTCCGTGATGCACGAGGCCCTGCACAACCACTACACCCAGAAGTCCCTGTCCCT GAGCCCCGGCAAGTGATGA |

-continued

SEQUENCE LISTING

| SEQ ID NO: | Name | Description | Sequence |
|---|---|---|---|
| 412 | STIM003 - CDRL1 | Amino acid sequence of CDRL1 of STIM003 using IMGT | QSVSRSY |
| 413 | STIM003 - CDRL2 | Amino acid sequence of CDRL2 of STIM003 using IMGT | GAS |
| 414 | STIM003 - CDRL3 | Amino acid sequence of CDRL3 of STIM003 using IMGT | HQYDMSPFT |
| 415 | STIM003 - Light chain variable region | Amino acid sequence of $V_L$ of STIM003 | EIVLTQSPGTLSLSPGERATLSCRASQSVSRSYLAWYQQKRGQAPRLLIYGASSRAT GIPDRFSGDGSGTDFTLSISRLEPEDFAVYYCHQYDMSPFTFGPGTKVDIK |
| 416 | STIM003 - Light chain variable region | Nucleic acid sequence of $V_L$ of STIM003 | GAAATTGTGTTGACGCAGTCTCCAGGGACCCTGTCTTTGTCTCCAGGGGAAAGA GCCACCCTCTCCTGCAGGGCCAGTCAGAGTGTTAGCAGAAGCTACTTAGCCTGG TACCAGCAGAAACGTGGCCAGGCTCCCAGGCTCCTCATCTATGGTGCATCCAGC AGGGCCACTGGCATCCCAGACAGGTTCAGTGGCGATGGGTCTGGGACAGACTTC ACTCTCTCCATCAGCAGACTGGAGCCTGAAGATTTTGCAGTGTATTACTGTCACC AGTATGATATGTCACCATTCACTTTCGGCCCTGGGACCAAAGTGGATATCAAA |
| 417 | STIM003 - full light chain sequence | Amino acid sequence of STIM003 light chain | EIVLTQSPGTLSLSPGERATLSCRASQSVSRSYLAWYQQKRGQAPRLLIYGASSRAT GIPDRFSGDGSGTDFTLSISRLEPEDFAVYYCHQYDMSPFTFGPGMDIKRTVAAP SVFIFPPSDEQLKSGTASVVCLLNNFYPREAGQWKVDNALQSGNSQESVTEQDSK DSTYSLSSTLTLSKADYEKHKVYACEVTHQGLSSPVTKSFNRGEC |
| 418 | STIM003 - full light chain sequence | Nucleic acid sequence of STIM003 light chain | GAAATTGTGTTGACGCAGTCTCCAGGGACCCTGTCTTTGTCTCCAGGGGAAAGA GCCACCCTCTCCTGCAGGGCCAGTCAGAGTGTTAGCAGAAGCTACTTAGCCTGG TACCAGCAGAAACGTGGCCAGGCTCCCAGGCTCCTCATCTATGGTGCATCCAGC AGGGCCACTGGCATCCCAGACAGGTTCAGTGGCGATGGGTCTGGGACAGACTTC ACTCTCTCCATCAGCAGACTGGAGCCTGAAGATTTTGCAGTGTATTACTGTCACC AGTATGATATGTCACCATTCACTTTCGGCCCTGGGACCAAAGTGGATATCAAAcg tacggtggccgctccctcccgtgttcatcttcccacctctccgagcagcgagcagttgaagtcggcaccgcttctgtc gtgtgcctgctgaacaacttctaccccgaggccaaggtgcagtggaaggtggacaacgccctgcag tccggcaactccaggccgactacgagaagcacaagtgcacgacctactcctgtctccaccc tgacctgtccaaggcgactacgagaagcacaagtgctacgcctgcgaagtgacccaccaggcctgt ctagccccgtgaccaagtctttcaaccggggcgagtgt |
| 419 | STIM004 - CDRH1 | Amino acid sequence of CDRH1 of STIM004 using IMGT | GLTFDDYG |
| 420 | STIM004 - CDRH2 | Amino acid sequence of CDRH2 of STIM004 using IMGT | INWNGDNT |
| 421 | STIM004 - CDRH3 | Amino acid sequence of CDRH3 of STIM004 using IMGT | ARDYYGSSYYNVPFDY |
| 422 | STIM004 - Heavy | Amino acid sequence of $V_H$ of chain variable region STIM004 | EVQLVESGGGVVRPGGSLRLSCAASGLTFDDYGMSWVRQVPGKGLEWVSGINWN GDNTDYADSVKGRFTISRDNAKNSLYLQMNSLRAEDTALYYCARDYYGSGSYYNV PFDYWGQGTLVTVSS |

-continued

SEQUENCE LISTING

| SEQ ID NO: | Name | Description | Sequence |
|---|---|---|---|
| 423 | STIM004 - Heavy chain variable | Nucleic acid sequence of V_H of region STIM004 | GAGGTGCAGCTGGTGGAGTCTGGGGGAGGTGTGTACGCCTGGGGGTCCCT GAGACTCTCCTGTGCAGCCTCTGGACTCACCTTTGATGATTATGGCATGAGCTG GGTCCGCCAAGTTCCAGGGAAGGGGCTGGAGTGGGTCTCTGGTATTAATTGGA ATGGTGATAACACAGATTATGCAGACTCTGTGAAGGGCCGATTCACCATCTCCA GAGACAACGCCAAGAACTCCCTGTATCTGCAAATGAACAGTCTGAGAGCCGAGG ACACGGCCTTGTATTACTGTGCGAGGGATTACTATGGTTCGGGGAGTTATTATA ACGTTCCTTTTGACTACTGGGGCCAGGGAACCCTGGTCACCGTCTCCTCA |
| 424 | STIM004 - full heavy chain sequence | Amino acid sequence of STIM004 heavy chain | EVQLVESGGGVVRPGGSLRLSCAASGLTFDDYGMSWVRQVPGKGLEWVSGINWN GDNTDYADSVKGRFTISRDNAKNSLYLQMNSLRAEDTALYYCARDYYGSGSYYNV PFDYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSN KALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYT QKSLSLSPGK |
| 425 | STIM004 - full heavy chain sequence | Nucleic acid sequence of STIM004 heavy chain | GAGGTGCAGCTGGTGGAGTCTGGGGGAGGTGTGTACGCCTGGGGGTCCCT GAGACTCTCCTGTGCAGCCTCTGGACTCACCTTTGATGATTATGGCATGAGCTG GGTCCGCCAAGTTCCAGGGAAGGGGCTGGAGTGGGTCTCTGGTATTAATTGGA ATGGTGATAACACAGATTATGCAGACTCTGTGAAGGGCCGATTCACCATCTCCA GAGACAACGCCAAGAACTCCCTGTATCTGCAAATGAACAGTCTGAGAGCCGAGG ACACGGCCTTGTATTACTGTGCGAGGGATTACTATGGTTCGGGGAGTTATTATA ACGTTCCTTTTGACTACTGGGGCCAGGGAACCCTGGTCACCGTCTCCTCAGCCA GCACCAAGGGCCCCTCTGTGTTCCCCCTGGCACCCTCCTCCAAGAGCACCTCTG GCGGAACAGCCGCTCTGGGCTGCCTCGACCAGGACTACTTCCCAGCCCTGTGA CCGTGTCCTGGAACTCTGGCGCTGTACTCCCTGTCCTCCGTCGTGACCGTGCCTTCCA GCTCTCTGGGCACCCAGACCTACATCTGCAACGTGAACCACAAGCCCTCCAACAC CAAGTGGACAAGAAGGTGGAACTCTGACGACAAGAAGGTCGACACAGTACAACTCCA CCCTTGTCCTGCCCCTGACCTGTGGGCGGACCCTTCCGTTCTCCCCCCC AAAGCCCAAGGACACCCTGATGATCTCCCGGACCCCGAAGTGAAGTTCAATTGGTACGTGGACG GCGTGGAAGTGCACAACGCCAAGACCAAGCCTAGAGAGGAACAGTACAACTCCA CCTACCGGGTGGTGTCCGTGCTGACCGTGCTGCACCAGGATTGGCTGAACGGCA AAGAGTACAAGTGCAAGGTGTCCAACAAGGCCCTGCCTGCCCCATCGAAAAGA CCATCTCCAAGGCCAAGGGCCAGCCCCGAGAACCCAGGTGTACACACTGCCCC CTAGCAGGGAGCTGACCAAGAACCAGGTGTCCCTGACCTGTCTGTGAAAG GCTTCTACCCCTCCGATATCGCCGTGGAATGGGAGTCCAACGGCCAGCCTGAGA ACAACTACAAGACACCCCCTGTCTGGACTCCGACGGCTCATTCTTCCTGTA CAGCAAGCTGACAGTGGACAAGTCCGGTGGCAGCAGGGCAACGTGTTCCTG CTCCGTGATGCACGAGGCCCTGCACAACCACTACACCCAGAAGTCCCTGTCCCT GAGCCCCGGCAAGTGATGA |
| 426 | STIM004 - CDRL1 | Amino acid sequence of CDRL1 of STIM004 using IMGT | QSVSSSY |

-continued

SEQUENCE LISTING

| SEQ ID NO: | Name | Description | Sequence |
|---|---|---|---|
| 427 | STIM004 - CDRL2 | Amino acid sequence of CDRL2 of STIM004 using IMGT | GAS |
| 428 | STIM004 - CDRL3 | Amino acid sequence of CDRL3 of STIM004 using IMGT | QQYGSSPF |
| 429 | STIM004 - Corrected light chain variable region | Amino acid sequence of corrected V_L of STIM004 | EIVLTQSPGTLSLSPGERATLSCRASQSVSSSYLAWYQQKPGQAPRLLIYGASSRAT GIPDRFSGSGSGTDFTLTIRRLEPEDFAVYYCQQYGSSPFFGPGTKVDIK |
| 430 | STIM004 - Corrected light chain variable region | Nucleic acid sequence of corrected V_L of STIM004 | GAAATTGTGTTGACGCAGTCTCCAGGCACCCTGTCTTTGTCTCCAGGGGAAAGA GCCACCCTCTCCTGCAGGGCCAGTCAGAGTGTTAGCAGCAGCTACTTAGCCTGG TACCAGCAGAAACCTGGCCAGGCTCCCAGGCTCCTCATATATGGTGCATCCAGC AGGGCCACTGGCATCCCAGACAGGTTCAGTGGCAGTGGGTCTGGGACAGACTTC ACTCTCACCATCAGAGACTGGAGCCTGAAGATTTTGCAGTGTATTACTGTCAG CAGTATGGTAGTTCACCATTCTTCGGCCCTGGGACCAAAGTGGATATCAAA |
| 431 | STIM004 - Light chain variable region | Nucleic acid sequence of V_L of STIM004 | GAAATTGTGTTGACGCAGTCTCCAGGCACCCTGTCTTTGTCTCCAGGGGAAAGA GCCACCCTCTCCTGCAGGGCCAGTCAGAGTGTTAGCAGCAGCTACTTAGCCTGG TACCAGCAGAAACCTGGCCAGGCTCCCAGGTTCCTCATATATGGTCATCCAGC AGGGCCACTGGCATCCCAGACAGTTCAGTGGCAGTGGGTCTGGGACAGACTTC ACTCTCACCATCAGAGACTGGAGCCTGAAGATTTTGCAGTGTATTACTGTCAG CAGTATGGTAGTTCACCATTCACTTCGGCCCTGGGACCAAAGTGATATCAAA |
| 432 | STIM004 - full corrected light chain sequence | Amino acid sequence of corrected STIM004 light chain | EIVLTQSPGTLSLSPGERATLSCRASQSVSSSYLAWYQQKPGQAPRLLIYGASSRAT GIPDRFSGSGSGTDFTLTIRRLEPEDFAVYYCQQYGSSPFFGPGTKVDIKRTVAAPS VFIFPPSDEQLKSGTASVVCLLNNFYPREAINQMWVDNALQSGNSQESVTEQDSK DSTYSLSSTLTLSKADYEKHKVYACEVTHQGLSSPVTKSFNRGEC |
| 433 | STIM004 - full corrected light chain sequence | Nucleic acid sequence of corrected STIM004 light chain | GAAATTGTGTTGACGCAGTCTCCAGGCACCCTGTCTTTGTCTCCAGGGGAAAGA GCCACCCTCTCCTGCAGGGCCAGTCAGAGTGTTAGCAGCAGCTACTTAGCCTGG TACCAGCAGAAACCTGGCCAGGCTCCCAGACAGGTTCCTCATATATGGTCATCCAGC AGGGCCACTGGCATCCCAGACAGTTCAGTGGCAGTGGGTCTGGGACAGACTTC ACTCTCACCATCAGAGACTGGAGCCTGAAGATTTTGCAGTGTATTACTGTCAG CAGTATGGTAGTTCACCATTCTTCGGCCCTGGGACCAAAGTGGATATCAAAcgta cgtggcctgctgcatcctccgtgttcatcttcccaccttccgagctgctgaagtgcagagcagctgaagtgaagtgcaccacgcccctgtctgt tgtcctgctgaacaacttctaccccgaggccaagctccaaggcaggactccaaggaagcaggactccaaggaggactccaggtcccaaggtctgactccctgtctctccctcccacct ccggcacactcccaggatccgtgaccgaggcaggacgcaggatccgtgcagaagcaggcaaggtgaggagccctccaccct gaccctgtccaagctgacacaagtgtgtcgcctgcgaagtgaccgtgaggtgagccacaacagcagcaccaccagggcctgt ctagcccgtgaccagtcttcaaccgggcgagtgt |
| 434 | STIM004 - full light chain sequence | Nucleic acid sequence of STIM004 light chain | GAAATTGTGTTGACGCAGTCTCCAGGCACCCTGTCTTTGTCTCCAGGGGAAAGA GCCACCCTCTCCTGCAGGGCCAGTCAGAGTGTTAGCAGCAGCTACTTAGCCTGG TACCAGCAGAAACCTGGCCAGGCTCCCAGGTTCCTCATATATGGTCATCCAGC AGGGCCACTGGCATCCCAGACAGTTCAGTGGCAGTGGGTCTGGGACAGACTTC ACTCTCACCATCAGAGACTGGAGCCTGAAGATTTTGCAGTGTATTACTGTCAG CAGTATGGTAGTTCACCATTCACTTCGGCCCTGGGACCAAAGTGATATCAAAcg |

SEQUENCE LISTING

| SEQ ID NO: | Name | Description | Sequence |
|---|---|---|---|
| | | | tacggtggcgctcctccgtgtcatcttcccacctccgacgagcagtgaagtccggcaccgcttctgtc<br>gtgtgctgtgaacaacttctaccccgcgaggcaaggccaagtgcagtggaaggtgacaacgccctgcag<br>tccgcaactcccaggaatcgtgaccgagcaggactccaaggacagcacctactcccctgtcctccacc<br>tgaccctgtccaaggcgactacgagaagcacaaagtgtacgcctgcgaagtgacccaccagggcctgt<br>ctagccccgtgaccaagtctttcaaccgggcgagtgt |
| 435 | STIM005 - CDRH1 | Amino acid sequence of CDRH1 of STIM005 using IMGT | GYTFNSYG |
| 436 | STIM005 - CDRH2 | Amino acid sequence of CDRH2 of STIM005 using IMGT | ISVHNGNT |
| 437 | STIM005 - CDRH3 | Amino acid sequence of CDRH3 of STIM005 using IMGT | ARAGYDILTDFSDAFDI |
| 438 | STIM005 - Heavy chain variable region | Amino acid sequence of V$_H$ of STIM005 | QVQLVQSGAEVKKPGASVKVSCKASGYTFNSYGIIWVRQAPGQGLEWMGWISVH<br>NGNTNCAQKLQGRVTMTTDTSTSTAYMELRSLRTDDTAVYYCARAGYDILTDFSD<br>AFDIWGHGTMVTVSS |
| 439 | STIM005 - Heavy chain variable region | Nucleic acid sequence of V$_H$ of STIM005 | CAGGTTCAGTTGGTGCAGTCTGGAGCTGAGGTGAAGAAGCCTGGGGCCTCAGT<br>GAAGGTCTCCTGCAAGGCTTCTGGTTACACCTTTAATAGTTATGGTATCATCTG<br>GGTCCGACAGGCCCCTGGACAAGGGCTTGAGTGGATGGGATCAGCGTTC<br>ACAATGGTAACACAAACTGTGCACAGAAGCTCCAGGGTAGAGTCACCATGACCA<br>CAGACACATCCACAAGCTGTGCAGAAGCTACATGGAGCTGAGAACTGACG<br>ACACGGCCGTGTATTACTGTGCGAGAGCGGGTTACGATATTTTGACTGATTTTT<br>CCGATGCTTTTGATATCTGGGGCCACGGACAATGGTCACCGTCTTCA |
| 440 | STIM005 - full heavy chain sequence | Amino acid sequence of STIM005 heavy chain | QVQLVQSGAEVKKPGASVINSCKASGYTFNSYGIIWVRQAPGQGLEWMGWISVH<br>NGNTNCAQKLQGRVTMTTDTSTSTAYMELRSLRTDDTAVYYCARAGYDILTDFSD<br>AFDIWGHGTMVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDP<br>EVKFNWYDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYT<br>QKSLSLSPGK |
| 441 | STIM005 - full heavy chain sequence | Nucleic acid sequence of STIM005 heavy chain | CAGGTTCAGTTGGTGCAGTCTGGAGCTGAGGTGAAGAAGCCTGGGGCCTCAGT<br>GAAGGTCTCCTGCAAGGCTTCTGGTTACACCYTTAATAGTTATGGTATCATCTG<br>GGTCCGACAGGCCCCTGGACAAGGGCTTGAGTGGATGGGATCAGCGTTC<br>ACAATGGTAACACAAACTGTGCACAGAAGCTCCAGGGTAGAGTCACCATGACCA<br>CAGACACATCCACAGCTGTGCAGAAGCTCCAGGGTAGAGTCACCATGACCA<br>CAGACACATCCACAAGCTGTGCAGAGGCGGGTTACGATATTTTGACTGATTTTT<br>CCGATGCTTTTGATATCTGGGGCCACGGGACAATGGTCACCGTCTTCA<br>GCCAGCACCAAGGGCCCCTCTGTTCCCCTGGCGCCCTGCTCGTGAAGGACTACTTCCCCGAGCCT<br>TCTGGCGAACAGCCCCGTCCTGGACGTCTGGACGTCGGTCACACCTTCCCT<br>GTGACCGTGTCCTCAGTCCTCCGGAGCCTCTGCAGCAGCGGAGTGCACACCTTCCCT<br>GCTGTGCTGCAGTCCTCCGGACTCCCTGCTCCGTGACCGTGCCT |

-continued

SEQUENCE LISTING

| SEQ ID NO: | Name | Description | Sequence |
|---|---|---|---|
| | | | TCCAGCTCTCTGGGCACCCAGACCTACATCTGCAACGTGAACCACAAGCCCTCCA<br>ACACCAAGGTGGACAAGAAGGTTGAACCCAAGTCCTGCGACAAGACCCACACCT<br>GTCCCCCCTGTCCTCGCCCCTGAACTGCTGGGCGGACCTTCCGTTCCTGTTCC<br>CCCCAAAGCCCAAGGACACCCTGATGATCTCCCGGACCCCGAAGTGACCTGCG<br>TGGTGGTGGATGTGTCCACGAGGACGTCCAAGTGAAGTTCAATTGGTACGTGG<br>ACGGCGTGAAGTGCACAACGCCAAGACCAAGCCTAGAGGAGCAGTACAACT<br>CCACTACCGGGTGGTGTCCGTGCTGACCGTGCTGCACCAGGATTGGCTGAACG<br>GCAAAGAGTACAAGTGCAAGGTGTCCAACAAGGCCCTGCCTGCCCCCATCGAAA<br>AGACCATCTCAAGGCCAAGGGCCAGCCCCGGGAACCCCAGGTGTACACACTGC<br>CCCCTAGCAGGAGGAGATGACCAAGAACCAGGTGTCCCTGACCTGTCTCGTGA<br>AAGGCTTCTACCCCTCCGATATCGCCGTGGAATGGGAGTCCAACGGCCAGCCTG<br>AGAACAACTACAAGACCACCCCCCCTGTCCTGGACTCCGACGGCTCATTCTTCCT<br>GTACAGCAAGCTGACAGTGGACAAGTCCGGTGCAGCAGCAACGTGTTCTC<br>CTGCTCCGTGATGCACGAGGCCCTGCACAACCACTACACCCAGAAGTCCCTGTC<br>CCTGAGCCCCGGCAAGTGATGA |
| 442 | STIM005 - CDRL1 | Amino acid sequence of CDRL1 of STIM005 using IMGT | QNINNF |
| 443 | STIM005 - CDRL2 | Amino acid sequence of CDRL2 of STIM005 using IMGT | AAS |
| 444 | STIM005 - CDRL3 | Amino acid sequence of CDRL3 of STIM005 using IMGT | QQSYGIPW |
| 445 | STIM005 - Light chain variable region | Amino acid sequence of V$_L$ of STIM005 | DIQMTQSPSSLSASVGDRVTITCRASQNINNFLNWYQQKEGKGPKLLIYAASSLQR<br>GIPSTFSGSGSGTDFTLTISSLQPEDFATYICQQSYGIPWVGQGKVEIK |
| 446 | STIM005 - Light chain variable region | Nucleic acid sequence of V$_L$ of STIM005 | GACATCCAGATGACCCAGTCTCCATCTCCCGTCTCAGCTGTAGGAGACAGA<br>GTCACCATCACTTGCCGGGCAAGTCAGAACATTAATAACTTTTTAAATTGGTATC<br>AGCAGAAAGAAGGGAAAGGCCCTAAGCTCCTGATCTATGCAGCATCCAGTTTGC<br>AAAGAGGGATACCATCAACGTTCAGTGGCAGTGGATCTGGGACAGACTTCACTC<br>TCACCATCAGCAGTCTGCAACCTGAAGATTTTGCAACTTACATCTGTCAACAGAG<br>CTACGGTATCCCGTGGTCGGCCAAGGGACCAAGGTGGAAATCAAA |
| 447 | STIM005 - full light chain sequence | Amino acid sequence of STIM005 light chain | DIQMTQSPSSLSASVGDRVTITCRASQNINNFLNWYQQKEGKGPKLLIYAASSLQR<br>GIPSTFSGSGSGTDFTLTISSLQPEDFATYICQQSYGIPWVGQGTKVEIK<br>RTVAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 448 | STIM005 - full light chain sequence | Nucleic acid sequence of STIM005 light chain | GACATCCAGATGACCCAGTCTCCATCTCCCGTCTCAGCTGTAGGAGACAGA<br>GTCACCATCACTTGCCGGGCAAGTCAGAACATTAATAACTTTTTAAATTGGTATC<br>AGCAGAAAGAAGGGAAAGGCCCTAAGCTCCTGATCTATGCAGCATCCAGTTTGC<br>AAAGAGGGATACCATCAACGTTCAGTGGCAGTGGATCTGGGACAGACTTCACTC<br>TCACCATCAGCAGTCTGCAACCTGAAGATTTTGCAACTTACATCTGTCAACAGAG<br>CTACGGTATCCCGTGGTCGGCCAAGGGACCAAGGTGGAAATCAAAcgtacggtgg<br>ccgtcccccgtgttcatcttcccaccttccgacgagcagctgaagtccggaactgcctctgtcgtgtgcct<br>gctgaacaacttcacccccgaggccaaggtgcagtggaaggtggacaacgccctgcagtccggca |

-continued

SEQUENCE LISTING

| SEQ ID NO: | Name | Description | Sequence |
|---|---|---|---|
| | | | actccaggaatccgtgaccgagcaggaggactccaaggacagcacctactccctgtcctcacctgaccct gtccaaggccgactacgaagtgaagcacaaggtacgcctgcaagctgcgaagtgaccaccaggggctgtctagca ccgtgaccaagtctttcaacggggcgagtgt |
| 449 | STIM006 - CDRH1 | Amino acid sequence of CDRH1 of STIM006 using IMGT | GFTFSDYF |
| 450 | STIM006 - CDRH2 | Amino acid sequence of CDRH2 of STIM006 using IMGT | ISSSGSTI |
| 451 | STIM006 - CDRH3 | Amino acid sequence of CDRH3 of STIM006 using IMGT | ARDHYDGSGIYPLYYYGLDV |
| 452 | STIM006 - Heavy chain variable region | Amino acid sequence of V$_H$ of STIM006 | QVQLVESGGGLVKPGGSLRLSCAASGFTFSDYFMSWIRQAPGKGLEWISYISSSGS TIYYADSVRGRFTISRDNAKYSLYLQMNSLRSEDTAVYYCARDHYDGSGIYPLYYYY GLDVWGQGTTVTVSS |
| 453 | STIM006 - Heavy chain variable region | Nucleic acid sequence of V$_H$ of STIM006 | CAGGTGCAGCTGGTGGAGTCTGGGGGAGGCTTGGTCAAGCCTGGAGGGTCCCT GAGACTCTCCTGTGCAGCCTCTGGATTCACCTTCAGTGACTACTTCATGAGCTG GATCCGCCAGGCCCCAGGGAAGGGGCTGGAGTGGATTTCATACATTAGTTCTAG TGGTAGTACCATATACTACGCAGACTCTGTGAGGGGCCGATTCACCATCTCCAG GGACAACGCCAAGTACTCACTGTATCTGCAAATGAACAGCCTGAGATCCGAGA CACGGCCGTGTATTACTGTGCGAGAGATCACTACGATGTTCGGGGATTTATCC CCTCTACTACTATTACGGTTTGGACGTCTGGGGCCAGGGGACCACGGTCACCGT CTCCTCA |
| 454 | STIM006 - full heavy chain sequence | Amino acid sequence of STIM006 heavy chain | QVQLVESGGGLVKPGGSLRLSCAASGFTFSDYFMSWIRQAPGKGLEWISYISSSGS TIYYADSVRGRFTISRDNAKYSLYLQMNSLRSEDTAVYYCARDHYDGSGIYPLYYYY GLDVWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSN KALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYT QKSLSLSPGK |
| 455 | STIM006 - full heavy chain sequence | Nucleic acid sequence of STIM006 heavy chain | CAGGTGCAGCTGGTGGAGTCTGGGGGAGGCTTGGTCAAGCCTGGAGGGTCCCT GAGACTCTCCTGTGCAGCCTCTGGATTCACCTTCAGTGACTACTTCATGAGCTG GATCCGCCAGGCCCCAGGGAAGGGGCTGGAGTGGATTTCATACATTAGTTCTAG TGGTAGTACCATATACTACGCAGACTCTGTGAGGGGCCGATTCACCATCTCCAG GGACAACGCCAAGTACTCACTGTATCTGCAAATGAACAGCCTGAGATCCGAGA CACGGCCGTGTATTACTGTGCGAGAGATCACTACGATGTTCGGGGATTTATCC CCTCTACTACTATTACGGTTTGGACGTCTGGGGCCAGGGGACCACGGTCACCGT CTCCTCAGCCTCCACCAAGGGCCCATCGGTCTTCCCCCTGGCACCCTCCTCCAAGAA GTCCACCTCTGGGGGCACAGCGGCCCTGGGCTGCCTGGTCAAGGACTACTTCCC CGAACCGTGTGACCGTGTCCTGGAACTCAGGCGCCCTGACCAGCGGCGTGCACAC CTTCCCGGCTGTCCTACAGTCCTCAGGACTCTACTCCCTCAGCAGCGTGGTGAC CGTGCCCTCCAGCTCTCTGGGCACCCAGACCTACATCTGCAACGTGAATCACAA |

SEQUENCE LISTING

| SEQ ID NO: | Name | Description | Sequence |
|---|---|---|---|
| | | | GCCCTCCAACACCAAGGTGGACAGAAGGTGGAACCCAGTCCTGCACAAGAC |
| | | | CCACACCTGTCCCCCCTGTCCTGCCCCTGAACTGCTGGGCGACCTTCCGTGTT |
| | | | CCTGTTCCCCCCAAAGCCCAAGGACACCCTGATGATCTCCGGACCCCCGAAGT |
| | | | GACCTGCGTGGTGGTGGATGTGTCCCACGAGGACCCTGAAGTGAAGTTCAATTG |
| | | | GTACGTGGACGGCGTGGAAGTGCACAATGCCAAGACCAAGCCTAGAGAGGAAC |
| | | | AGTACAACTCCACCTACCGGGTGGTGTCCGTCCTGACCGTGCTGCACCAGGATT |
| | | | GGCTGAACGGCAAAGAGTACAAGTGCAAGGTCTCCAACAAGGCCCTGCCTGCCC |
| | | | CCATCGAAAAGACCATCTCCAAGGCCAAGGGCCAGCCTCGCGAGAACCCCAGGTGT |
| | | | ACACACTGCCCCCTAGCAGGGATGAGCTGACCAAGAACCAGGTGTCCCTGACCT |
| | | | GTCTCGTGAAAGGCTTCTACCCCTCCGATATCGCCGTGGAATGGGAGTCCAACG |
| | | | GCCAGCCTGAGAACAACTACAAGACCACCCCTCCTGTCTGACTCCGACGGCT |
| | | | CATTCTTCCTGTACAGCAAGCTGACAGTGGACAAGAGTCCCGTGCAGCAGGGCA |
| | | | ACGTGTTCTCCTGCTCCGTGATGCACGAGGCCCTGCACAACCACTACACCCAGA |
| | | | AGTCCCTGTCCCTGAGCCCTGGCAAGTGATGA |
| 456 | STIM006 - CDRL1 | Amino acid sequence of CDRL1 of STIM006 using IMGT | QSLLHSNGYNY |
| 457 | STIM006 - CDRL2 | Amino acid sequence of CDRL2 of STIM006 using IMGT | LGS |
| 458 | STIM006 - CDRL3 | Amino acid sequence of CDRL3 of STIM006 using IMGT | MQALQTPRS |
| 459 | STIM006 - Light chain variable region | Amino acid sequence of V_L of STIM006 | IVMTQSPLSLPVTPGEPASISCRSSQSLLHSNGYNYLDYYLQKPGQSPQLLIYLGSY RASGVPDRFSGSGSGTDFTLKISRVEAEDVGVYYCMQALQTPRSFGQGTTLEIK |
| 460 | STIM006 - Light chain variable region | Nucleic acid sequence of V_L of STIM006 | ATTGTGATGACTCAGTCTCCACTCTCCCTACCCGTCACCCCTGGAGAGCCGGCC TCCATCTCCTGCAGGTCTAGTCAGAGCCTCCTGCATAGTAATGATAACAACTATT TGGATTATTACCTGCAGAAGCCAGGCCAGTCTCCACAGCTCCTGATCTATTTGG GTTCTTATCGGGCCTCCGGGGTCCCTGACAGGTTCAGTGGCAGTGGATCAGGCA CAGATTTTACACTGAAAATCAGCAGAGTGGAGGCTGAGGATGTTGGGGTTTATT ACTGCATGCAAGCTCTACAAACTCCTCGAGTTTTGGCCAGGGGACCACGCTGG AGATCAAA |
| 461 | STIM006 - full light chain sequence | Amino acid sequence of STIM006 light chain | IVMTQSPLSLPVTPGEPASISCRSSQSLLHSNGYNYLDYYLQKPGQSPQLLIYLGSY RASGVPDRFSGSGSGTDFTLKISRVEAEDVGVYYCMQALQTPRSFGQGTTLEIKRT VAAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| 462 | STIM006 - full light chain sequence | Nucleic acid sequence of STIM006 light chain | ATTGTGATGACTCAGTCTCCACTCTCCCTACCCGTCACCCCTGGAGAGCCGGCC TCCATCTCCTGCAGGTCTAGTCAGAGCCTCCTGCATAGTAATGATAACAACTATT TGGATTATTACCTGCAGAAGCCAGGCCAGTCTCCACAGCTCCTGATCTATTTGG GTTCTTATCGGGCCTCCGGGGTCCCTGACAGGTTCAGTGGCAGTGGATCAGGCA CAGATTTTACACTGAAAATCAGCAGAGTGGAGGCTGAGGATGTTGGGGTTTATT ACTGCATGCAAGCTCTACAAACTCCTCGAGTTTTGGCCAGGGGACCACGCTGG AGATCAAAcgtacggtggctgcaccatctgtcttcatcttcccgccatctgatgagcagttgaaatctg gaactgcctctgttgtgtgcctgctgaataacttctacccccgagaggccaaagtacagtggaaggtgga |

SEQUENCE LISTING

| SEQ ID NO: | Name | Description | Sequence |
|---|---|---|---|
| | | | caacgccctgcagtccggcgaactcccaggaatccgtgaccgagcaggaatccaaggaagcacctactc ccgtcctccacctgaccctgaccctgccaaggcgacctacgagaagcacaaggtgtacgcctgcgaagtgacc caccagggcctgtctagccccgtgaccaagtcttcaaccggggcgagtgt |
| 463 | STIM007 – CDRH1 | Amino acid sequence of CDRH1 of STIM007 using IMGT | GFSLSTTGVG |
| 464 | STIM007 – CDRH2 | Amino acid sequence of CDRH2 of STIM007 using IMGT | IYWDDDK |
| 465 | STIM007 – CDRH3 | Amino acid sequence of CDRH3 of STIM007 using IMGT | THGYGSASYYHYGMDV |
| 466 | STIM007 – Heavy chain variable region | Amino acid sequence of V<sub>H</sub> of STIM007 | QITLKESGPTLVKPTQTLTLTCTFSGFSLSTTGVGVGWIRQPPGKALEWLAVIYWD DDKRYSPSLKSRLTITKDTSKNQVLTMTNMDPVDTATYFCTHGYGSASYYHYGM DVWGQGTTVTVSS |
| 467 | STIM007 – Heavy chain variable region | Nucleic acid sequence of V<sub>H</sub> of STIM007 | CAGATCACCTTGAAGGAGTCTGGTCCTACGCTGGTGAAACCCACACAGACCCTC ACGCTGACCTGCACCTTCTCTGGGTTCTCACTCAGCACTACTGGAGTGGGTGTG GGCTGGATCCGTCAGCCCCCAGGAAAGGCCCTGGAGTGGCTTGCAGTCATTTAT TGGGATGATGATAAGCGCTACAGCCCATCTCTGAAGAGCAGACTCACCATCACC AAGGACACCTCCAAAAACCAGGTCGTCCTTACAATGACCAATATGGACCCTGTG GACACAGCCACATATTTCTGTACACACGGATATGGTTCGGCGAGTTATTACCACT ACGGTATGGACGTCTGGGGCCAAGGACCACGGTCACCGTCTCCTCA |
| 468 | STIM007 – full heavy chain sequence | Amino acid sequence of STIM007 heavy chain | QITLKESGPTLVKPTQTLTLTCTFSGFSLSTTGVGVGWIRQPPGKALEWLAVIYWD DDKRYSPSLKSRLTITKDTSKNQVLTMTNMDPVDTATYFCTHGYGSASYYHYGM DVWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPGK |
| 469 | STIM007 – full heavy chain sequence | Nucleic acid sequence of STIM007 heavy chain | CAGATCACCTTGAAGGAGTCTGGTCCTACGCTGGTGAAACCCACACAGACCCTC ACGCTGACCTGCACCTTCTCTGGGTTCTCACTCAGCACTACTGGAGTGGGTGTG GGCTGGATCCGTCAGCCCCCAGGAAAGGCCCTGGAGTGGCTTGCAGTCATTTAT TGGGATGATGATAAGCGCTACAGCCCATCTCTGAAGAGCAGACTCACCATCACC AAGGACACCTCCAAAAACCAGGTCGTCCTTACAATGACCAATATGGACCCTGTG GACACAGCCACATATTTCTGTACACACGGATATGGTTCGGCGAGTTATTACCACT ACGGTATGGACGTCTGGGGCCAAGGACCACGGTCACCGTCTCCTCA GCCTCCACCAAGGGCCCCTCTGTCCTGGCCCCTTCCAGCAAGTCCACC TCTGCGGAACAGCCGCTCTGGGCTGCCTGTGAAGGACTACTTCCCCGAGCCT GTGACCGTGTCCTGGAACTCGGCCGTCCTACTCCCTGCCTGCCTCTCCTGCTCCT GCTGTGCTGCAGTCCTCGGCACCCAGACCTACATCTGCAACGTGAACCACAAGCCCTCCA ACACCAAGGTGGACAAGAAGGTGGAACCCAAGTCCTGCGACAAGACCCACACCT |

SEQUENCE LISTING

| SEQ ID NO: | Name | Description | Sequence |
|---|---|---|---|
| | | | GTCCCCCCTGTCCTGCCCCTGAACTGCTGGGCGGACCTTCCGTGTTCCTGTTCC |
| | | | CCCCAAAGCCAAGGACACCCTGATGATCTCCCGGACCCCGAAGTGACCTGCG |
| | | | TGGTGGTGGATGTGTCCCACGAGGACCCTGAAGTGAAGTTCAATTGGTACGTGG |
| | | | ACGGCGTGAAGTGCACAACGCCAAGACAAGCCTAGAGGAGCAGTACAACT |
| | | | CCACCTACCGGGTGTGTCCGTGCTGACCGTGCTGCACCAGGATTGGCTGAACG |
| | | | GCAAAGAGTACAAGTGCAAGGCCAGCAACAAGGCCCTGCCTGCCCCATCGAAA |
| | | | AGACCATCTCCAAGGCCAAGGGCCAGCCCCGGGAACCCCAGGTGTACACCCTGC |
| | | | CCCCTAGCAGGGACGAGCTGACCAAGAACCAGGTGTCCCTGACCTGTCTCGTGA |
| | | | AAGGCTTCTACCCCTCCGATATCGCCGTGGAATGGGAGTCCAACGGCCAGCCTG |
| | | | AGAACAACTACAAGACACCCCCCCTGTCCTGGACTCCGACGGCTCATTCTTCCT |
| | | | GTACAGCAAGCTGACAGTGACAAGTCCGGTGGCAGCAGGGCAACGTGTTCTC |
| | | | CTGCTCCGTGATGCACGAGGCCCTGCACAACCACTACACCCAGAAGTCCCTGTC |
| | | | CCTGAGCCCCGGCAAGTGATGA |
| 470 | STIM007- CDRL1 | Amino acid sequence of CDRL1 of STIM007 using IMGT | QSVTNY |
| 471 | STIM007- CDRL2 | Amino acid sequence of CDRL2 of STIM007 using IMGT | DAS |
| 472 | STIM007- CDRL3 | Amino acid sequence of CDRL3 of STIM007 using IMGT | QHRSNWPLT |
| 473 | STIM007 - Light chain variable region | Amino acid sequence of $V_L$ of STIM007 | EIVLTQSPATLSLSPGERATLSCRASQSVTNYLAWHQQKPGQAPRLLIYDASNRAT GIPARFSGSGSGTDFTLTISSLEPEDFAVYYCQHRSNWPLTFGGGTKVEIK |
| 474 | STIM007 - Light chain variable region | Nucleic acid sequence of $V_L$ of STIM007 | GAAATTGTATTGACACAGTCTCCAGCCACCCTGTCTTTGTCTCCAGGGGAAAGA GCCACCCTCTCTGCAGGGCCAGTCAGAGTGTTACCAACTACTTAGCCTGGCAC CAACAGAAACCTGGCCAGGCTCCCAGGCTCCTCATCTATGATGCATCCAACAGG GCCACTGGCATCCCAGCCAGGTTCAGTGGCAGTGGATCTGGGACAGACTTCACT CTCACCATCAGCAGCCTAGAGCCTGAAGATTTTGCAGTTTATTACTGTCAGCACC GTAGCAACTGGCCTCTCACTTTCGGCGGAGGGACCAAGGTGGAGATCAAAC |
| 475 | STIM007 - full light chain sequence | Amino acid sequence of STIM007 light chain | EIVLTQSPATLSLSPGERATLSCRASQSVTNYLAWHQQKPGQAPRLLIYDASNRAT GIPARFSGSGSGTDFTLTISSLEPEDFAVYYCQHRSNWPLTFGGGTKVEIKRTVAAP SVFIFPPSDEQLKSGTASVVCLLNNFYPREAKVQWKDNALQSGNSQESVTEQDSK DSTYSLSSTLTLSKADYEKHKVYACEVTHQGLSSPVTKSFNRGEC |
| 476 | STIM007 - full light chain sequence | Nucleic acid sequence of STIM007 light chain | GAAATTGTATTGACACAGTCTCCAGCCACCCTGTCTTTGTCTCCAGGGGAAAGA GCCACCCTCTCTGCAGGGCCAGTCAGAGTGTTACCAACTACTTAGCCTGGCAC CAACAGAAACCTGGCCAGGCTCCCAGGCTCCTCATCTATGATGCATCCAACAGG GCCACTGGCATCCCAGCCAGGTTCAGTGGCAGTGGATCTGGGACAGACTTCACT CTCACCATCAGCAGCCTAGAGCCTGAAGATTTTGCAGTTTATTACTGTCAGCACC GTAGCAACTGGCCTCTCACTTTCGGCGGAGGGACCAAGGTGGAGATCAAACgta cggtggccgtcccccgtctgacccatcttcccaccttccgacgagcagctgaagtccggaactgcctctgtcgt tgtgcctgctgaacaacttctacccccgagaggccaaggtacagtggaaggtggacaacgccctgcagt ccggcaactcccaggaatcgtgaccgagcaggacagcaaggacagcacctacagcctcagcagcacc gacctgtccaaggcgactacgagaagcacaaggtgtacgcctgcgaagtgacccaccagggcctgt |

-continued

SEQUENCE LISTING

| SEQ ID NO: | Name | Description | Sequence |
|---|---|---|---|
| | | | ctagcccgtgaccaagtctttcaaccgggcgagtgt |
| 477 | STIM008-CDRH1 | Amino acid sequence of CDRH1 of STIM008 using IMGT | GFSLSTSGVG |
| 478 | STIM008-CDRH2 | Amino acid sequence of CDRH2 of STIM008 using IMGT | IYWDDDK |
| 479 | STIM008-CDRH3 | Amino acid sequence of CDRH3 of STIM008 using IMGT | THGYGSASYYHYGMDV |
| 480 | STIM008 - Heavy chain variable region | Amino acid sequence of $V_H$ of STIM008 | QITLKESGPTLVKPTQTLTLTCTFSGFSLSTSGVGVGWIRQPPGKALEWLAVIYWD DDKRYSPSLKSRLITTKDTSKNQVVLTMNMDPVDTATYFCTHGYGSASYYHYGM DVWGQGTTVTVSS |
| 481 | STIM008 - Heavy chain variable region | Nucleic acid sequence of $V_H$ of STIM008 | CAGATCACCTTGAAGGAGTCTGGTCCTACGCTGGTGAAACCCACACAGACCCTC ACGCTGACCTGCACCTTCTCTGGGTTCTCACTCAGCACTAGTGGAGTGGGTGTG GGCTGGATCCGTCAGCCCCCAGGAAAGGCCCTGGAGTGGCTTGCAGTCATTTAT TGGGATGATGATAAGCGCTACAGCCCATCTCTGAAGAGCAGGCTCACCATCACC AAGGACACCTCCAAAAACCAGGTGGTCCTTACAATGAACATGGACCCTGTG GACACAGCCACATATTTCTGTACACACGGATATGGTTCGGCGAGTTATTACCACT ACGGTATGGACGTCTGGGGCCAAGGGACCACGGTCACCGTCTCCTCA |
| 482 | STIM008 - full heavy chain sequence | Amino acid sequence of STIM008 heavy chain | QITLKESGPTLVKPTQTLTLTCTFSGFSLSTSGVGVGWIRQPPGKALEWLAVIYWD DDKRYSPSLKSRLTITKDTSKNQVVLTMNMDPVDTATYFCTHGYGSASYYHYGM DVWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNA LPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPGK |
| 483 | STIM008 - full heavy chain sequence | Nucleic acid sequence of STIM008 heavy chain | CAGATCACCTTGAAGGAGTCTGGTCCTACGCTGGTGAAACCCACACAGACCCTC ACGCTGACCTGCACCTTCTCTGGGTTCTCACTCAGCACTAGTGGAGTGGGTGTG GGCTGGATCCGTCAGCCCCCAGGAAAGGCCCTGGAGTGGCTTGCAGTCATTTAT TGGGATGATGATAAGCGCTACAGCCCATCTCTGAAGAGCAGGCTCACCATCACC AAGGACACCTCCAAAAACCAGGTGGTCCTTACAATGAACATGGTTCGGCGAGTTATTACCACT ACGGTATGGACGTCTGGGGCCAAGGGACCACGGTCACCGTCTCTCAGCCAGCA CCAAGGGCCCCTCTGTTCCCCTCGGCCCCTTCCAGCAAGTCACCTCTGGGG GAACAGCCGCTCTGGGCTGCCTCGTGAAGGACTACTTCCCGGAGCCTGTGACCG TGTCCTGGAACTCTGGCGCTGTACCCCTGTCCTCGTGGTGACCCGTGGCTTCCAGCT TGCAGTCCTCCGGGCCTGTACTCCCTCAGCAGCGTGGTGACCGTGCCTTCCAGCT CTCTGGGCACCCAGACCTACATCTGCAACGTGAACCACAAGCCCTCCAACACCAA GGTGGACAAGAAGGTGGAACCCAAGTCCTGCGACAAGACCCACACCTGTCCCC TTGTCCTGCCCCTGAACTGCTGGGCGGACCTTCCGTGTTCCTGTTCCCCCAAA GCCCAAGGACACCCTGATGATCTCCCGGACCCCCGAAGTGACCTGCGTGGTGGT |

-continued

SEQUENCE LISTING

| SEQ ID NO: | Name | Description | Sequence |
|---|---|---|---|
| | | | GGATGTGTCCACGAGGACCCTGAAGTGAAGTTCAATTGGTACGTGGACGGCGT GAAGTGCACAACGCCAAGACAGCCTAAGGAACAGTAACAACTCCACCTA CCGGGTGGTGTCCGTGCTGACCGTGCTGCACCAGGATTGGCTGAACGGCAAAG AGTACAAGTGCAAGGTCTCCAACAAGGCCCTGCCTGCCCCATCGAAAAGACCA TCTCCAAGGCCAAGGCCAGCCCAGGGAACCCAGGTGTACACACTGCCCCCTA GCAGGACGAGCTGACCAAGAACCAGGTGTCCCTGACCTGTCTGTGAAGGCT TCTACCCCTCGATATCGCCGTGGAATGGGAGTCCAACGGCCAGCCTGAGAACA ACTACAAGACCACCCCCCCGTGCTGGACTCCGACGGCTCCATTCTTCCTGTACAG CAAGCTGACAGTGGACAAGTCCCGGTGGCAGCAGGGCAACGTGTTCTCCTGCTC CGTGATGCACGAGGCCCTGCACAACCACTACACCCAGAAGTCCCTGTCCCTGAG CCCCGGCAAGTGATGA |
| 484 | STIM008- CDRL1 | Amino acid sequence of CDRL1 of STIM008 using IMGT | QSVTNY |
| 485 | STIM008- CDRL2 | Amino acid sequence of CDRL2 of STIM008 using IMGT | DAS |
| 486 | STIM008- CDRL3 | Amino acid sequence of CDRL3 of STIM008 using IMGT | QQRSNWPLT |
| 487 | STIM008 - Light chain variable region | Amino acid sequence of $V_L$ of STIM008 | EIVLTQSPATLSLSPGERATLSCRASQSVTNYLAWHQQKPGQAPRLLIYDASNRAT GIPARFSGSGSGTDFTLTISSLEPEDFAVYYCQQRSNWPLTFGGGTKVEIK |
| 488 | STIM008 - Light chain variable region | Nucleic acid sequence of $V_L$ of STIM008 | GAAATTGTTGACACAGTCTCCAGCCACCCTGTCTTTGTCTCCAGGGAAAGA GCCACCCTCTCCTGCAGGGCCAGTCAGAGTGTTACCAACTACTTAGCCTGGCAC CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAGC GTAGCAACTGGCCTCTCACTTTCGGCGGAGGGACCAAGGTGGAGATCAAA |
| 489 | STIM008 - full light chain sequence | Amino acid sequence of STIM008 light chain | EIVLTQSPATLSLSPGERATLSCRASQSVTNYLAWHQQKPGQAPRLLIYDASNRAT GIPARFSGSGSGTDFTLTISSLEPEDFAVYYCQQRSNWPLTFGGGTKVEIKRTVAAP SVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC |
| 490 | STIM008 - full light chain sequence | Nucleic acid sequence of STIM008 light chain | GAAATTGTTGACACAGTCTCCAGCCACCCTGTCTTTGTCTCCAGGGAAAGA GCCACCCTCTCCTGCAGGGCCAGTCAGAGTGTTACCAACTACTTAGCCTGGCAC CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAGC GTAGCAACTGGCCTCTCACMCGGCGGAGGGACCAAGGTGGAGATCAAAcgtac ggtggccgctccctccgtgttcatcttcccacccttccgacgagcagctgaagtccggaactgcctctgtcgt gtgcctgctgaacaacttctacccccgggaggccaaggtgcagtggaaggtggacaacgccctgcagtc cggcaactcccaggaatcctgaccgaggaccaggacagcaaggacagcacctactcgtcctccacctg acctgtcccaaggccgactacgagaagcacaaggtgtacgcctgcgaagtgacccaccagggcctgtct agcccgtgaccaagtctttcaaccgggcgagtgt |

-continued

SEQUENCE LISTING

| SEQ ID NO: | Name | Description | Sequence |
|---|---|---|---|
| 491 | STIM009-CDRH1 | Amino acid sequence of CDRH1 of STIM009 using IMGT | GFTFSDYY |
| 492 | STIM009-CDRH2 | Amino acid sequence of CDRH2 of STIM009 using IMGT | ISSSGSTI |
| 493 | STIM009-CDRH3 | Amino acid sequence of CDRH3 of STIM009 using IMGT | ARDFYDILTDSPYFYGVDV |
| 494 | STIM009 - Heavy chain variable region | Amino acid sequence of $V_H$ of STIM009 | QVQLVESGGGLVKPGGSLRLSCAASGFTFSDYYMSWIRQAPGKGLEWVSYISSSGS TIYYADSVKGRFTISRDNAKNSLYLQINSLRAEDTAVYYCARDFYDILTDSPYFYYG VDVWGQGTTVTVSS |
| 495 | STIM009 - Heavy chain variable region | Nucleic acid sequence of $V_H$ of STIM009 | CAGGTGCAGCTGGTGGAGTCTGGGGGAGGCTTGGTCAAGCCTGGAGGGTCCCT GAGACTCTCGTGTGCAGCTCTGGATTCACCTTCAGTGACTACTACATGAGCTG GATCCGCCAGGCTCCAGGGAAGGGGCTGGAGTGGGTTTCATACATTAGTAGTA GTGGTAGTACCATATACTACGCAGACTCTGTGAAGGGCCGATTCACCATCTCA GGGACAACGCCAAGAACTCACTGTATCTGCAAATTAACAGCCTGAGAGCCGAGG ACACGGCCGTGTATTACTGTGCGAGAGATTTTTACGATATTTTGACTGATAGTC CGTACTTCTACTACGGTGTGACGTCTGGGCCAAGGGACCACCGTCACCGTCT CCTCA |
| 496 | STIM009 - full heavy chain sequence | Amino acid sequence of STIM009 heavy chain | QVQLVESGGGLVKPGGSLRLSCAASGFTFSDYYMSWIRQAPGKGLEWVSYISSSGS TIYYADSVKGRFTISRDNAKNSLYLQINSLRAEDTAVYYCARDFYDILTDSPYFYYG VDVWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSN KALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYT QKSLSLSPGK |
| 497 | STIM009 - full heavy chain sequence | Nucleic acid sequence of STIM009 heavy chain | CAGGTGCAGCTGGTGGAGTCTGGGGGAGGCTTGGTCAAGCCTGGAGGGTCCCT GAGACTCTCGTGTGCAGCTCTGGATTCACCTTCAGTGACTACTACATGAGCTG GATCCGCCAGGCTCCAGGGAAGGGGCTGGAGTGGGTTTCATACATTAGTAGTA GTGGTAGTACCATATACTACGCAGACTCTGTGAAGGGCCGATTCACCATCTCA GGGACAACGCCAAGAACTCACTGTATCTGCAAATTAACAGCCTGAGAGCCGAGG ACACGGCCGTGTATTACTGTGCGAGAGATTTTTACGATATTTTGACTGATAGTC CGTACTTCTACTACGGTGTGACGTCTGGGCCAAGGGACCACCGTCACCGTCT CCTCAGCCTCCACCAAGGGCCCATCGGTCTTCCCCCTGGCACCCTCCTCCAAG AGCACCTCTGGGGGCACAGCGGCCCTGGGCTGCCTGGTCAAGGACTACTTCCCCG AACCGGTGACCGTGTCCTGGAACTCAGGCGCCCTGACCAGCGGCGTGCACACCT TCCCGGCTGTCCTACAGTCCTCAGGACTCTACTCCCTCAGCAGCGTGGTGACCG TGCCCTCCAGCTCTCTGGGCACCCAGACCTACATCTGCAACGTGAATCACAAGCC CTCCAACACCAAGGTGGACAAGAAGGTGGAACCCAAGTCTTGCGACAAGACCCA CACCTGTCCCCCGTGCCCTGCCCCTGAACTGCTGGGCGGACCTTCCGTGTTCCT GTTCCCCCCAAAGCCCAAGGACACCCTGATGATCTCCCGGACCCCTGAAGTGAC CTGCGTGGTGGTGGATGTGTCCCACGAGGACCCTGAAGTGAAGTTCAATTGGTA |

SEQUENCE LISTING

| SEQ ID NO: | Name | Description | Sequence |
|---|---|---|---|
| | | | CGTGACGGCGTGAAGTGCACACGCCAAGACCAAGCCTAGAGGAACAGT<br>ACAACTCCACTACCGGGTGGTGCCTGCCTGCTGCACCAGGATTGGC<br>TGAACGGCAAAGAGTACAAGTGCAAGGTGTCCAACAAGGCCCTGCCCCA<br>TCGAAAAGACCATCTCCAAGGCCAAGGGCCAGCCCCGGGAACCCAGTGTACA<br>CACTGCCCCCTAGCAGGGACGAGCTGACCAAGAACCAGGTGTCCCTGACCTGTC<br>TCGTGAAAGGCTTCTACCCCTCCGATATCGCCGTGGAATGGGAGTCCAACGGC<br>AGCCTGAGACAACTACAGAGCTGACAGTGGACAAGTCCCGGTGGCAGCAGGGCAACG<br>TCTTCCTGTACAGCAAGCTGACAGTGGACAAGTCCCGGTGGCAGCAGGGCAACG<br>TGTTCTCCTGCTCCGTGATGCACGAGGCCCTGCACAACCACTACACCCAGAAGT<br>CCCTGTCCCTGAGCCCCGGCAAGTGATGA |
| 498 | STIM009- CDRL1 | Amino acid sequence of CDRL1 of STIM009 using IMGT | QSLLHSNGYNY |
| 499 | STIM009- CDRL2 | Amino acid sequence of CDRL2 of STIM009 using IMGT | LGS |
| 500 | STIM009- CDRL3 | Amino acid sequence of CDRL3 of STIM009 using IMGT | MQALQTPRT |
| 501 | STIM009 - Light chain variable region | Amino acid sequence of V_L of STIM009 | DIVMTQSPLSLPVTPGEPASISCRSSQSLLHSNGYNYLDWYLQKPGQSPQLLIYLGS<br>NRASGVPDRPSGSGSGTDFTLKISRVEAEDVGVYYCMQALQTPRTFGQGTKVEIK |
| 502 | STIM009 - Light chain variable region | Nucleic acid sequence of V_L of STIM009 | GATATTGTGATGACTCAGTCTCCACTCTCCCTGCCCGTCAGTCTTGGAGAGCCG<br>GCCTCCATCTCCTGCAGGTCTAGTCAGAGCCTCCTGCATAGTAATGGATACAACT<br>ATTTGGATTGGTACCTGCAGAAGCCAGGGCAGTCTCCACAGCTCCTGATCTATT<br>TGGGTTCTAATCGGGCCTCCGGGGTCCCTGACAGGTTCAGTGGCAGTGGATCA<br>GGCACAGATTTTACACTGAAAATCAGCAGAGTGGAGGCTGAGGATGTTGGGGTT<br>TATTACTGCATGCAAGCTCTACAAACTCCTCGGACGTTCGGCCAAGGGACCAAG<br>GTGGAAATCAAA |
| 503 | STIM009 - full light chain sequence | Amino acid sequence of STIM009 light chain | DIVMTQSPLSLPVTPGEPASISCRSSQSLLHSNGYNYLDWYLQKPGQSPQLLIYLGS<br>NRASGVPDRPSGSGSGTDFTLKISRVEAEDVGVYYCMQALQTPRTFGQGTKVEIKR<br>TVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC |
| 504 | STIM009 - full light chain sequence | Nucleic acid sequence of STIM009 light chain | GATATTGTGATGACTCAGTCTCCACTCTCCCTGCCCGTCAGTCTTGGAGAGCCG<br>GCCTCCATCTCCTGCAGGTCTAGTCAGAGCCTCCTGCATAGTAATGGATACAACT<br>ATTTGGATTGGTACCTGCAGAAGCCAGGGCAGTCTCCACAGCTCCTGATCTATT<br>TGGGTTCTAATCGGGCCTCCGGGGTCCCTGACAGGTTCAGTGGCAGTGGATCA<br>GGCACAGATTTTACACTGAAAATCAGCAGAGTGGAGGCTGAGGATGTTGGGGTT<br>TATTACTGCATGCAAGCTCTACAAACTCCTCGGACGTTCGGCCAAGGGACCAAG<br>GTGGAAATCAAAcgtacggtggcgcgctcctccatcttcccaccttcgacgagcagcgagctgaa<br>gtccggaaccgcctctgtgtgtgcctgctgaacaacttctaccccgaggccaaggccaagtgcagtggaag<br>gtggacaacgccctgcagtccggcaactccgtgaccgtgacctacgaggacagcaaggactgcaaggacac<br>ctactccctgtcctccaccctgaccctgtccaaggccgactacgagaagcacaaggtgtacgcctgcgaa<br>gtgacccaccaggcctgtctagcccctgaccaagtctttcaaccgggcgagtgt |

| SEQ ID NO: | Name | Description | Sequence |
|---|---|---|---|
| 505 | Human PD-L1 Flag His (KYPROT286) | Amino acid sequence of KYPROT286 with FLAG tag in bold and underlined and histidine tag in bold | FTVTVPKDLYVVEYGSNMTIECKPVEKQLDLAALIVWEMEDKNIIQFVHGEEDLK VQHSSYRQRARLLKDQLSLGNAALQITDVKLQDAGVYRCMISYGGADYKRITVKV NAPYNKINQRILVVDPVTSEHELTCQAEGYPKAEVIWTSSDHQVLSGKTTTNSKR EEKLFNVTSTLRINTTTNEIFYCTFRRLDPEENHTAELVIPELPLAHPPNERTIEGRD YKDDDDKHHHHHH |
| 506 | Mature human ICOS | Mature amino acid sequence of human ICOS | EINGSANYEMFIFHNGGVQILCKYPDIVQQFKMQLLKGGQILCDLTKTKGSGNTVSI KSLKFCHSQLSNNSVSFFLYNLDHSHANYYFCNLSIFDPPPFKVTLTGGYLHIYESQL CCQLKFWLPIGCAAFVVVCILGCILICWLTKKKYSSSVHDPNGEYMFMRAVNTAKK SRLTDVTL |
| 507 | Human ICOS extracellular domain | Amino acid sequence of human ICOS extracellular domain | EINGSANYEMFIFHNGGVQILCKYPDIVQQFKMQLLKGGQILCDLTKTKGSGNTVSI KSLKFCHSQLSNNSVSFFLYNLDHSHANYYFCNLSIFDPPPFKVTLTGGYLHIYESQL CCQLKF |
| 508 | Human ICOS with signal peptide | Amino acid sequence of human ICOS (signal peptide is underlined) | MKSGLWYFFLFCLRIKVLTGEINGSANYEMFIFHNGGVQILCKYPDIVQQFKMQLLK GGQILCDLTKTKGSGNTVSIKSLKFCHSQLSNNSVSFFLYNLDHSHANYYFCNLSIF DPPPFKVTLTGGYLHIYESQLCCQLKFWLPIGCAAFVVVCILGCILICWLTKKKYSSS VHDPNGEYMFMRAVNTAKKSRLTDVTL |
| 509 | Isoform of human ICOS (Q9Y6W8-2) | Amino acid sequence of a human ICOS isoform | The sequence of this isoform differs from the canonical sequence in its cytoplasmic domain as follows: 168-199: KYSSSVHDPNGEYMFMRAVNTAKKSRLTDVTLM |
| 510 | Mature mouse ICOS | Amino acid sequence of mature mouse ICOS | EINGSADHRMFSFHNGGVQISCKYPETVQQLKMRLFREREVLCELTKTKGSGNAVS IKNPMLCLYHLSNNSVSFFLNNPDSSQGSYYFCSLSIFDPPPFQERNLSGGYLHIYES QLCCQLKIVVQVTE |
| 511 | Mouse ICOS extracellular domain | Amino acid sequence of the extracellular domain of mouse ICOS | EINGSADHRMFSFHNGGVQISCKYPETVQQLKMRLFREREVLCELTKTKGSGNAVS IKNPMLCLYHLSNNSVSFFLNNPDSSQGSYYFCSLSIFDPPPFQERNLSGGYLHIYES QLCCQLK |
| 512 | Mouse ICOS with signal peptide | Amino acid sequence of mouse ICOS (signal peptide is underlined) | MGWSCIILFLVATATGVHSEINGSADHRMFSFHNGGVQISCKYPETVQQLKMRLFR EREVLCELTKTKGSGNAVSIKNPMLCLYHLSNNSVSFFLNNPDSSQGSYYFCSLSIF DPPPFQERNLSGGYLHIYESQLCCQLKIVVQVTE |
| 513 | Cynomolgus ICOS with signal peptide | Amino acid sequence of cynomolgus ICOS (signal peptide is underlined) | MKSGLWYFFL FCLHMKVLTG EINGSANYEM FIFHNGGVQI LCKYPDIVQQ FKMQLLKGGQILCDLTKTKGSGNKVSIKSLKFCHSQLSNNSVSFFLYNLD RSHANYYFCNLSIFDPPPFKVTLTGGYLHIYESQLCCQLKFWLPIGCATF VVVCIFGCILICWLTKKKYSSTVHDPNGEYMFMRAVNTAKKSRLTGTTP |
| 514 | Cynomolgus ICOS extracellular domain | Amino acid sequence of cynomolgus ICOS extracellular domain | EINGSANYEMFIFHNGGVQILCKYPDIVQQFKMQLLKGGQILCDLTKTKG SGNKVSIKSLKFCHSQLSNNSVSFFLYNLDRSHANYYFCNLSIFDPPPFK VTLTGGYLHIYESQLCCQLK |
| 515 | Human ICOS ligand | Amino acid sequence of human ICOS ligand comprising extracellular domain | DTQEKEVRAMVGSDVELSCACPEGSRFDLNDVVVYWQTSESKTVVTYHIPQNSSL ENVDSRYRNRALMSPAGMLRGDFSLRLFNVTPQDEQKFHCLVLSQSLGFQEVLSVE VTLHVAANFSVPVVSAPHSPSQDELTFTCTSINGYPRPNVYWINKTDNSLLDQALQ |

-continued

SEQUENCE LISTING

| SEQ ID NO: | Name | Description | Sequence |
|---|---|---|---|
| | | | NDTVFLNMRGLYDVVSVLRIARTPSVNIGCCIENVLLQQNLTVGSQTGNDIGERDK<br>ITENPVSTGEKNAATWS |
| 516 | Human ICOS ligand | | MRLGSPGLLFLLFSSLRADTQEKEVRAMVGSDVELSCACPEGSRFDLNDVYVYWQT<br>SESKTVVTYHIPQNSSLENVDSRYRNRALMSPAGMLRGDFSLRLFNVTPQDEQKFH<br>CLVLSQSLGFQEVLSVEVTLHVAANFSVPWSAPHSPSQDELTFTCTSINGYPRPNV<br>YWINKTDNSLLDQALQNDTVFLNMRGLYDVVSVLRIARTPSVNIGCCIENVLLQQN<br>LTVGSQTGNDIGERDKITENPVSTGEKNAATVVSILAVLCLLVVVAVAIGWVCRDRC<br>LQHSYAGAWAVSPETELTGHV |
| 517 | C-terminal amino acid sequence of hIL-2 | Amino adds 21 to 133 of hIL-2 with R38W mutation (bold & underlined) | LQMILNGINNYKNPKLTAMLTFKFYMPKKATELKHLQCLEEELKPLEEVLNLAQSKN<br>FHLRPRDLISNINVIVLELKGSETTFMCEYADETATIVEFLNRWITFCQSIISTLT |
| 518 | C-terminal amino acid sequence of hIL-2 | Amino acids 21 to 133 of hIL-2 with R38Q mutation (bold & underlined | LQMILNGINNYKNPKLTQMLIFKFYMPKKATELKHLQCLEEELKPLEEVLNLAQSKN<br>FHLRPRDLISNINVIVLELKGSETTFMCEYADETATIVEFLNRWITFCQSIISTLT |
| 519 | STIM002 - Corrected Light chain variable region | Nucleic acid sequence of corrected $V_L$ of STIM002 | GATATTGTGATGACTCAGTCTCCACTCTCCCTGCCCGTCACCCCTGGAGAGCCG<br>GCCTCCATCTCCTGCAGGTCTAGTCAGAGCCTCCTGCATAGTGATGGATACAAC<br>TATTTGGATTGGTACCTGCAGAAGCCAGGGCAGTCTCCACAGCTCCTGATCTAT<br>TTGGGTTCTACTCGGGCCTCCGGGTTCCCTGACAGGTTCAGTGGCAGTGGATCA<br>GGCACAGATTTTACACTGAAAATCAGCAGAGTGGAGGCTGAGGATGTTGGGGTT<br>TATTACTGCATGCAAGCTCTACAAACTCCGCTCAGTTTTGGCCAGGGGACCAAG<br>CTGGAGATCAAA |
| 520 | STIM002 - Corrected full light chain sequence | Nucleic acid sequence of corrected STIM002 light chain | GATATTGTGATGACTCAGTCTCCACTCTCCCTGCCCGTCACCCCTGGAGAGCCG<br>GCCTCCATCTCCTGCAGGTCTAGTCAGAGCCTCCTGCATAGTGATGGATACAAC<br>TATTTGGATTGGTACCTGCAGAAGCCAGGGCAGTCTCCACAGCTCCTGATCTAT<br>TTGGGTTCTACTCGGGCCTCCGGGTTCCCTGACAGGTTCAGTGGCAGTGGATCA<br>GGCACAGATTTTACACTGAAAATCAGCAGAGTGGAGGCTGAGGATGTTGGGGTT<br>TATTACTGCATGCAAGCTCTACAAACTCCGCTCAGTTTTGGCCAGGGGACCAAG<br>CTGGAGATCAAAcgtacggtggccgctccctccgtgttcatcttcccaccttccgacgagcagctgaa<br>gtccggcaccgcttctgtcgtgtgcctgctgaacaacttctacccccgcgaggccaaggtgcagtggaag<br>gtggacaacgccctgcagtccggcaactcccaggaatccgtgaccgagcaggactccaaggacagcac<br>ctactccctgtcctccaccctgaccctgtccaaggccgactacgagaagcacaaggtgtacgcctgcgaa<br>gtgacccaccagggcctgtctagccccgtgaccaagtctttcaaccggggcgagtgt |
| 521 | STIM003 - Corrected heavy chain variable region | Nucleic acid sequence of corrected $V_H$ of STIM003 | GAGGTGCAGCTGGTGGAGTCTGGGGGAGGTGTGGTACGGCCTGGGGGGTCCCT<br>GAGACTCTCCTGTGTAGCCTCTGGAGTCACCTTTGATGATTATGGCATGAGCTG<br>GGTCCGCCAAGCTCCAGGGAAGGGGCTGGAGTGGGTCTCTGGTATTAATTGGA<br>ATGGTGGCGACACAGATTATTCAGACTCTGTGAAGGGCCGATTCACCATCTCCA<br>GAGACAACGCCAAGAACTCCCTGTATCTACAAATGAATAGTCTGAGAGCCGAGG<br>ACACGGCCTTGTATTACTGTGCGAGGGATTTCTATGGTTCGGGGAGTTATTATC<br>ACGTTCCTTTTGACTACTGGGGCCAGGGAATCCTGGTCACCGTCTCCTCA |
| 522 | STIM003 - Corrected full heavy chain | Nucleic acid sequence of corrected STIM003 heavy chain | GAGGTGCAGCTGGTGGAGTCTGGGGGAGGTGTGGTACGGCCTGGGGGGTCCCT<br>GAGACTCTCCTGTGTAGCCTCTGGAGTCACCTTTGATGATTATGGCATGAGCTG |

-continued

SEQUENCE LISTING

| SEQ ID NO: | Name | Description | Sequence |
|---|---|---|---|
| | Human IgG1 constant region sequence | IGHG1*0 3 | GGTCCGCCAAGCTTCCAGGGAAGGGCTGAGTGGTCTCTGGTATTAATTGA<br>ATGGTGGCACACAGATTATTCAGACTCTGAAGGGCCGATTCACCATCTCCA<br>GAGACAACGCCAAGAACTCCCTGTATCTGCAAATGAATAGTCTGAGAGCCGAGG<br>ACACGGCCTTGTATTACTGTGCGAGGGATTTCTATGGTTCGGGGAGTTATATC<br>ACGTTCCTTTGACTACTGGGGCCAGGGAATCCTGGTCACCGTCTCCTCAGCCA<br>GCACCAAGGGCCCTCTGTGTTCCCCCTGGCTCCCTGAAGGACTACTTCCCCACCTCTG<br>GCGGAACAGCCGCTCGGGCTGCCCTGCGTCTGAAGGACTACTTCCCCGAGCCTGTGA<br>CCGTGTCCTGGAACTCTGGCGCTGTACTCCCTGTCCTCCGTGACCGTGCCTTCCA<br>GCTCTGGGCACCCAGACCTACATCTGCAACGTGAACCACAAGCCCTCCAACAC<br>CAAGTGTGACAAGAGGTGCGACAAGACCCACACATGCCCACCGTGCC<br>CCCTTGTCCTGCCCCTGAACTGTCCTGGGCGGACCTTCCTGTGTTCCTCCCCC<br>AAAGCCCAAGGACACCCTGATGATCTCCCGGACCCCTGAAGTGAAGTTCAATTGGTACGTGGACG<br>GGTGAGTGTGTCCACGAAGACCCTGAAGTGAAGTTCAATTGGTACGTGGACG<br>GCGTGGAAGTGCACAACGCCAAGACCAAGACCAAGAACCAGTACAACTCCA<br>CCTACCGGGTGGTGTCCGTGCTGACCGTCCTGCACCAGGATTGGCTGAACGGCA<br>AAGAGTACAAGTGCAAGGTGTCAACAAGGCCCTGCCTGCCCCCATCGAAAAGA<br>CCATCTCCAAGGCCAAGGGCCAGCCCCGAGAACCAGTGTACACCCTGCCCC<br>CTAGCAGGACGAGCTGACCAAGAACCAGGTGTCCCTGACCTGCCTGGTGAAAG<br>GCTTCTACCCCTCCGATATCGCCGTGGAATGGGAGTCCAACGGCCAGCCTGAGA<br>ACAACTACAAGACACACCCCCTGTGCTGGACTCCGACGGCTCATTCTTCCTGTA<br>CAGCAAGCTGACAGTGGACAAGTCCCGGTGGCAGCAGGGCAACGTGTTCTCCTG<br>CTCCGTGATGCACGAGGCCCTGCACAACCACTACACCCAGAAGTCCCTGTCCCT<br>GAGCCCGGGCAAGTGATGA |
| 523 | Human Heavy Chain Constant Region (IGHG1*03) Nucleotide Sequence | | gcttccaccaaggggcccatcggtcttccccctggcaccctcctccaagagcacctctgggggcacagcgg<br>ccctgggctgcctggtcaaggactactccctgaacccgtgacggtgtcgtggaactcaggcgccctgac<br>cagcggcgtgcacaccttcccggctgtcctacagtcctcaggactctactccctcagcagcgtggtgacc<br>gtgccctccagcagcttgggcacccagacctacatctgcaacgtgaatcacaagcccagcaacaccaagg<br>tggacaagagagttgagcccaaatcttgtgacaaaactcacacatgcccaccgtgcccagcacctgaact<br>cctggggggaccgtcagtcttcctcttccccccaaaaccccaaggacaccctcatgatctcccggacccctg<br>aggtcacatgcgtggtggtgacgtgagccacgaagaccctgaggtcaagttcaactggtacgtggacg<br>gcgtggaggtgcataatgccaagacaaagccgcgggaggagcagtacaacagcacgtaccgtgtggt<br>cagcgtcctcaccgtcctgcaccaggactggctgaatggcaaggagtacaagtgcaaggtctccaacaa<br>agccctcccagcccccatcgagaaaaccatctccaaagccaaagggcagccccgagaaccacaggtgt<br>acaccctgccccatcccgggaggagatgaccaagaaccaggtcagcctgacctgcctggtcaaaggct<br>tctatcccagcgacatcgccgtggagtggagagcaatgggcagccggagaacaactacaagaccac<br>gcctcccgtgctggactccgactccttcttcctctatagcaagctcaccgtggacaagagcaggtggc<br>agcaggggaacgtcttctcatgctccgtgatgcatgaggctctgcacaaccactacacgcagaagagcct<br>ctccctgtccccgggtaaa |
| 524 | Human Heavy Chain Constant Region (IGHG1*03) Protein Sequence | | A S T K G P S V F P L A P S S K S T S G G T A A L G C L V K D Y F P E P V T<br>V S W N S G A L T S G V H T F P A V L Q S S G L Y S L S S V V T V P S S<br>L G T Q T Y I C N V N H K P S N T K V D K R V E P K S C D K T H T C P P C<br>P A P E L L G G P S V F L F P P K P K D T L M I S R T P E V T C V V V D V S<br>H E D P E V K F N W Y V D G V E V H N A K T K P R E E Q Y N S T Y R V V<br>S V L T V L H Q D W L N G K E Y K C K V S N K A L P A P I E K T I S K A K<br>G Q P R E P Q V Y T L P P S R E E M T K N Q V S L T C L V K G F Y P S D I |

SEQUENCE LISTING

| SEQ ID NO: | Name | Description | Sequence |
|---|---|---|---|
| 525 | Human IgG1 constant region | IGHG1*04 | Human Heavy Chain Constant Region (IGHG1*04) Nucleotide Sequence | gcctccaccaaggcccatcggtcttcccctggcaccctcctccaagagcacctctgggggcacagcgg<br>ccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccg<br>tgccctccagcagcttgggcacccagacctacatctgcaacgtgaatcacaagcccagcaacaccaagg<br>tggacaagaaagttgagcccaaatcttgtgacaaaactcacacatgcccaccgtgcccagcacctgaact<br>cctgggggaccgtcagtcttcctcttccccccaaaacccaaggacaccctcatgatctcccggacccctg<br>aggtcacatgcgtggtggtggacgtgagccacgaagaccctgaggtcaagttcaactggtacgtggacg<br>gcgtggaggtgcataatgccaagacaaagccgcgggaggagcagtacaacagcacgtaccgtgtggt<br>cagcgtcctcaccgtcctgcaccaggactggctgaatggcaaggagtacaagtgcaaggtctccaacaa<br>agccctcccagcccccatcgagaaaaccatctccaaagccaaagggcagccccgagaaccacaggt<br>ctatcccagcgacatcgccgtggagtgggagagcaatgggcagccggagaacaactacaagaccacg<br>cctcccgtgctggactccgacggctccttcttcctctacagcaagctcaccgtggacaagagcaggctt<br>gcaggggaacatcttctcatgctccgtgatgcatgaggctctgcacaaccactacacgcagaagagcctc<br>tccctgtctccgggtaaa<br>A V E W E S N G Q P E N N Y K T T P P V L D S D G S F F L Y S K L T V D K<br>S R W Q Q G N V F S C S V M H E A L H N H Y T Q K S L S L S P G K |
| 526 | | Human Heavy Chain Constant Region (IGHG1*04) Protein Sequence | ASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVL<br>DSDGSFFLYSKLTVDKSRWQQGNIFSCSVMHEALHNHYTQKSLSLSPGK |
| 527 | Human IgG2 constant region | IGHG2*01 & IGHG2*03 & IGHG2*05 | Human Heavy Chain Constant Region (IGHG2*01) Nucleotide Sequence | gcctccaccaaggggcccatcggtcttccccctggcgccctgctccaggagcacctccgagagcacagcg<br>gccctgggctgcctggtcaaggactacttccccgaaccggtgacggtgtcgtggaactcaggcgctctgac<br>cagcggcgtgcacaccttcccagctgtcctacagtcctcaggactctactccctcagcagcgtggtgaccg<br>tgccctccagcaacttcggcacccagacctacacctgcaacgtagatcacaagcccagcaacaccaagg<br>tggacaagacagttgagcgcaaatgttgtgtcgagtgcccaccgtgcccagcaccacctgtggcaggac<br>cgtcagtcttcctcttccccccaaaacccaaggacaccctcatgatctcccgggaccctgaggtcacgtgcg<br>tggtggtgagcgtgagccacgaagaccccgaggtccagttcaactggtacgtggacggcgtggaggtg<br>cataatgccaagacaaagccacgggaggagcagttcaacagcacgttccgtgtggtcagcgtcctcacc<br>gttgtgcaccaggactggctgaacggcaaggagtacaagtgcaaggtctccaacaaaggcctcccagc<br>ccccatcgagaaaaccatctccaaaaccaaagggcagccccgagaaccacaggtgtacaccctgcccc<br>catcccgggaggagatgaccaagaaccaggtcagcctgacctgcctggtcaaaggcttctaccccagcg<br>acatcgccgtggagtgggagagcaatgggcagccggagaacaactacaagaccacacctcccatgctg<br>gactccgacggctccttcttcctctacagcaagctcaccgtggacaagagcaggtggcagcaggggaac<br>gtcttctcatgctccgtgatgcatgaggctctgcacaaccactacacgcagaagagcctctccctgtctccg<br>ggtaaa |
| 528 | | Human Heavy Chain Constant Region (IGHG2*01) Protein Sequence | ASTKGPSVFPLAPCSRSTSESTAALGCLVKDYFPEPVTVSWNSGALTSGVHTFPAVL<br>QSSGLYSLSSVVTVPSSNFGTQTYTCNVDHKPSNTKVDKTVERKCCVECPPCPAPP<br>VAGPSVFLFPPKPKDTLMISRTPEVTCVVVDVSHEDPEVQFNWYVDGVEVHNAKTK<br>PREEQFNSTFRVVSVLTVHQDWLNGKEYKCKVSNKGLPAPIEKTISKTKGQPREP<br>QVYTLPPSREEMTKNQVSLTCLVKGFYPSDIAVEWESNGQPENNYKTTPPMLDSD<br>GSFFLYSKLTVDKSRWQQGNVFSCSVMHEALHNHYTQKSLSLSPGK |

-continued

SEQUENCE LISTING

| SEQ ID NO: | Name | Description | Sequence |
|---|---|---|---|
| 529 | Human IgG2 constant region | IGHG2*02 | Human Heavy Chain Constant Region (IGHG2*02) Nucleotide Sequence | GCCTCCACCAAGGGCCCATCGGTCTTCCCCCTGGCGCCCTGCTCCAGGAGCACC<br>TCCGAGAGCACAGCGGCCCTGGGCTGCCTGGTCAAGGACTACTTCCCCGAACCG<br>GTGACGGTGTCGTGGAACTCAGGCGCTCTGACCAGCGCGCTGCACACCTTCCCG<br>GCTGTCCTACAGTCCTCAGGACTTCTACTCCCTCAGCAGCGTGGTGACCGTGACC<br>TCCAGCAACTTCGGCACCCAGACCTACACATGCAACGTAGATCACAAGCCCAGCA<br>ACACCAAGGTGGACAAGACAGTTGAGCGCACCGTCAGTCTTCTCATCTTCCCCCCATCC<br>GCCAGCACCTCATGATCTCCCGGACCCCTGAGGTCACGTGCGTGGTGGTGGACGT<br>GAGCCACGAAGACCCCGAGGTCCAGTTCAACTGGTACGTGGACGGCATGGAGG<br>TGCATAATGCCAAGACAAAGCCACGGGAGGAGCAGTTCAACAGCACCTTCCGTG<br>TGGTCAGCGTCCTCACCGTCCTGCACCAGGACTGGCTGAACGGCAAGGAGTACA<br>AGTGCAAGGTCTCCAACAAAGGCCTCCCAGCCCCCATCGAGAAAACCATCTCCAA<br>AACCAAAGGGCAGCCCCGAGAACCACAGGTGTACACCCTGCCCCCATCCCGGGA<br>GGAGATGACCAAGAACCAGGTCAGCTGACCTGCCTGGTCAAAGGCTTCTACCC<br>CAGCGACATCGCCGTGGAGTGGGAGAGCAATGGGCAGCCGGAGAACAACTACA<br>AGACCACACCTCCCATGCTGGACTCCGACGGCTCCTTCTTCCTCTACAGCAAGCT<br>CACCGTGGACAAGAGCAGGTGGCAGCAGGGGAACGTCTTCTCATGCTCCGTGAT<br>GCATGAGGCTCTGCACAACCACTACACAGAAGAGCCTCTCCCTGTCTCCGGG<br>TAAA |
| 530 | | Human Heavy Chain Constant Region (IGHG2*02) Protein Sequence | ASTKGPSVFPLAPCSRSTSESTAALGCLVKDYFPEPVTVSWNSGALTSGVHTFPAVL<br>QSSGLYSLSSVVTVTSSNFGTQTYTCNVDHKPSNTKVDKTVERKCCVECPPCPAPP<br>VAGPSVFLFPPKPKDTLMISRTPEVTCVVVDVSHEDPEVQFNWYVDGMEVHNAKT<br>KPREEQFNSTFRVVSVLTVVHQDWLNGKEYKCKVSNKGLPAPIEKTISKTKGQPRE<br>PQVYTLPPSREEMTKNQVSLTCLVKGFYPSDIAVEWESNGQPENNYKTTPPMLDS<br>DGSFFLYSKLTVDKSRWQQGNVFSCSVMHEALHNHYTQKSLSLSPGK |
| 531 | | IGHG2*04 | Human Heavy Chain Constant Region (IGHG2*04) Nucleotide Sequence | gcctccaccaagggcccatcggtcttccccctggcgccctgctccaggagcacctccgagagcacagcg<br>gccctgggctgcctggtcaaggactacttcccgaaccggtgacggtgtcgtggaactcaggcgctctga<br>ccagcggcgtgcacaccttcccggctgtcctacagtcctcaggactctactccctcagcagcgtggtgacc<br>gtgccctccagcaacttcggcacccagacctacacctgcaacgtagatcacaagcccagcaacaccaag<br>gtggacaagacagttgagcgcaaatgttgtgtcgagtgcccaccgtgcccagcaccacctgtggcagga<br>cgtcagtcttcctcttcccccaaaacccaaggacaccctcatgatctcccggacccctgaggtcacgtgc<br>gtggtggtggacgtgagccacgaagaccccgaggtccagttcaactggtacgtggacggcgtggaggt<br>gcataatgccaagacaaagccacgggaggagcagttcaacagcacgttccgtgtggtcagcgtcctcac<br>cgttgtgcaccaggactggctgaacggcaaggagtacaagtgcaaggtctccaacaaaggcctcccag<br>cccccatcgagaaaaccatctccaaaaccaaagggcagccccgagaaccacaggtgtacaccctgccc<br>ccatcccgggaggagatgaccaagaaccaggtcagcctgacctgcctggtcaaaggcttctaccccag<br>cgacatcgccgtggagtgggagagcaatgggcagccggagaacaactacaagaccacacctcccatgct<br>ggactccgacggctccttcttcctctacagcaagctcaccgtggacaagagcaggtggcagcagggga<br>acgtcttctcatgctccgtgatgcatgaggctctgcacaaccactacacacagaagagcctctccctgtctcc<br>gggtaaa |
| 532 | | Human Heavy Chain Constant Region (IGHG2*04) Protein Sequence | ASTKGPSVFPLAPCSRSTSESTAALGCLVKDYFPEPVTVSWNSGALTSGVHTFPAVL<br>QSSGLYSLSSVVTVPSSSLGTQTYTCNVDHKPSNTKVDKTVERKCCVECPPCPAPP<br>VAGPSVFLFPPKPKDTLMISRTPEVTCVVVDVSHEDPEVQFNWYVDGVEVHNAKTK<br>PREEQFNSTFRVVSVLTVVHQDWLNGKEYKCKVSNKGLPAPIEKTISKTKGQPREP |

| SEQ ID NO: | Name | Description | Sequence |
|---|---|---|---|
| | | | QVYTLPPSREEMTKNQVSLTCLVKGFYPSDIAVEWESNGQPENNYKTPPMLDSD GSFFLYSKLTVDKSRWQQGNVFSCSVMHEALHNHYTQKSLSLSPGK |
| 533 | Human IgG2 constant region | IGHG2*0 6 | Human Heavy Chain Constant Region (IGHG2*06) Nucleotide Sequence | GCTTCCACCAAGGGCCCATCGGTCTTCCCCCTGGCGCCCTGCTCCAGGAGCACC TCCGAGAGCACAGCGGCCCTGGGCTGCCTGGTCAAGGACTACTTCCCCGAACCG GTGACAGTGTCGTGGAACTCAGGCGCTGTGACCAGCGGCGTGCACACCTTCCCG GCTGTCCTACAGTCCTCAGGACTCTACTCCCTCAGCAGCGTGGTGACCGTGCCC TCCAGCAACTTCGGCACCCAGACCTACACCTGCAACGTAGATCACAAGCCCAGCA ACACCAAGGTGGACAAGACAGTTGAGCGCAAATGTTGTGTCGAGTGCCCACCGT GCCCAGCACCACCTGTGGCAGGACCGTCAGTCTTCCTCTTCCCCCCAAAACCCAA GGACACCCTCATGATCTCCCGGACCCCTGAGGTCACGTGCGTGGTGGTGGACGT GAGCCACGAAGACCCCGAGGTCCAGTTCAACTGGTACGTGGACGGCGTGGAGG TGCATAATGCCAAGACAAAGCCACGGGAGGAGCAGTTCAACAGCACGTTCCGTG TGGTCAGCGTCCTCACCGTCGTGCACCAGGACTGGCTGAACGGCAAGGAGTACA AGTGCAAGGTCTCCAACAAAGGCCTCCCAGCCCCCATCGAGAAAACCATCTCCAA AACCAAAGGGCAGCCCCGAGAACCACAGGTGTACACCCTGCCCCCATCCCGGGA GGAGATGACCAAGAACCAGGTCAGCCTGACCTGCCTGGTCAAAGGCTTCTACCC CAGCGACATCTCCGTGGAGTGGGAGAGCAATGGGCAGCCGGAGAACAACTACAA GACCACACCTCCCATGCTGGACTCCGACGGCTCCTTCTTCCTCTACAGCAAGCTC ACCGTGGACAAGAGCAGGTGGCAGCAGGGGAACGTCTTCTCATGCTCCGTGATG CATGAGGCTCTGCACAACCACTACACAGAAGAGCCTCTCCCTGTCTCCGGGT AAA |
| 534 | Human IgG2 constant region | | Human Heavy Chain Constant Region (IGHG2*06) Protein Sequence | ASTKGPSVFPLAPCSRSTSESTAALGCLVKDYFPEPVTVSWNSGALTSGVHTFPAVL QSSGLYSLSSVVTVPSSNFGTQTYTCNVDHKPSNTKVDKTVERKCCVECPPCPAPP VAGPSVFLFPPKPKDTLMISRTPEVTCVVVDVSHEDPEVQFNWYVDGVEVHNAKTK PREEQFNSTFRVVSVLTVVHQDWLNGKEYKCKVSNKGLPAPIEKTISKTKGQPREP QVYTLPPSREEMTKNQVSLTCLVKGFYPSDIAVEWESNGQPENNYKTPPMLDSD GSFFLYSKLTVDKSRWQQGNVFSCSVMHEALHNHYTQKSLSLSPGK |
| 535 | Human Cλ constant region | IGLC7*03 | Cλ Light Chain Constant Region (IGLC7*03) Nucleotide Sequence | GGTCAGCCCAAGGCTGCCCCCTCGGTCACTCTGTTCCCACCCTCCTCTGAGGAG CTTCAAGCCAACAAGGCCACACTGGTGTGTCTCGTAAGTGACTTCAACCCGGGA GCCGTGACAGTGGCCTGGAAGGCAGATGGCAGCCCGTCAAGGTGGGAGTGGA GACCACCAAACCCTCCAAACAACAAGCAACAACAAGTATGCGGCCAGCAGCTACCT GAGCCTGACGCCCGAGCAGTGGAAGTCCACAGAAGCTACAGCTGCCGGGTCAC GCATGAAGGGAGCACCGTGGAGAAGACAGTGGCCCCTGCAGAAATGCTCT |
| 536 | Human Cλ constant region | IGLC7*03 | Cλ Light Chain Constant Region (IGLC7*03) Amino Acid Sequence | GQPKAAPSVTLFPPSSEELQANKATLVCLVSDFNPGAVTVAWKADGSPVKVGVETT KPSKQSNNKYAASSYLSLTPEQWKSHRSYSCRVTHEGSTVEKTVAPAECS |
| 537 | Human WT IgG1 constant region | IGHG1*0 1 & IGHG1*0 5 (IgG1) | WT human IgG1 nucleotide sequence #2 | gcttccaccaagggcccatcggtcttccccctggcaccctcctccaagagcacctctgggggcacagcgg ccctgggctgcctggtcaaggactacttccccgaaccggtgacggtgtcgtggaactcaggcgccctgac cagcggcgtgcacaccttcccggctgtcctacagtcctcaggactctactccctcagcagcgtggtgaccg tgccctccagcagcttgggcacccagacctacatctgcaacgtgaatcacaagcccagcaacaccaagg tggacaagaaagttgagcccaaatcttgtgacaaaactcacacatgcccaccgtgcccagcacctgaact cctggggggaccgtcagtcttcctcttccccccaaaacccaaggacaccctcatgatctcccggacccctg aggtcacatgcgtggtggtggacgtgagccacgaagaccctgaggtcaagttcaactggtacgtggacg |

-continued

SEQUENCE LISTING

| SEQ ID NO: | Name | Description | Sequence |
|---|---|---|---|
| | | | gcgtggaggtgcataatgccaagacaaagccgggaggagcagtacaacagcacgtaccggtggt cagcgtcctcaccgtcctgaccaaggactggctggtgaatgcagtacaagtgcaagtctccaacaa agccctcccagccccatcccgagaaaccatctccaaaagcaaggcagcccgagaaccacaggtgt acacctgcccccatgccccagactgcccggatgagcttgacccaagaacccaggtcagcctgacctgcctggtcaaaggctt ctatcccagcgacatcgccgtggagtgggagagcaatgggcagccggagaacaactacaagaccacg cctcccgtgctggactccgacggctccttcttcctctacagcaagctcaccgtggacaagagcaggtggca gcagggaacgtcttctcatgctccgtgatgcatgaggctctgcacaaccactacacgcagaagagcctc tccctgtctccgggtaaa |
| 538 | Human Cλ constant region | IGLC2*01 Cλ Light Chain Constant Region Amino Acid Sequence #2 - Encoded by nucleotide sequence version A & B | GQPKAAPSVTLFPPSSEELQANKATLVCLISDFYPGAVTVAWKADSSPVKAGVETTTPSK QSNNKYAASSYLSLTPEQWKSHRSYSCQVTHEGSTVEKTVAPTECS |
| 539 | Human TIGIT-His/Flag | NCBI accession number NM_173799.3 Uniprot accession number Q495A1-1 Expressed protein corresponds to ECD only: Met 22 - Pro 141 as per full length sequence Protein domains annotated: Campath leader (double line), extracellular domain (bold), linker & Flag/His tag (italic) | MGWSCIILFLVATATGVHSMMTGTIETTGNISAEKGGSIILQCHLSSTTAQV TQVNWEQQDQLLAICNADLGWHISPSFKDRVAPGPGLGLTLQSLTVND TGEYFCIYHTYPDGTYTGRIFLEVLESSVAEHGARFQIP *IEGRDYKDDDDKH HHHHH* |

The invention claimed is:

1. An antibody or fragment thereof which specifically binds to hPD-L1, wherein the:
    a) $V_H$ domain comprises the amino acid sequence of SEQ ID NO: 540 and the $V_L$ domain comprises the amino acid sequence of SEQ ID NO: 43;
    b) $V_H$ domain comprises the amino acid sequence of SEQ ID NO: 541 and the $V_L$ domain comprises the amino acid sequence of SEQ ID NO: 43;
    c) $V_H$ domain comprises the amino acid sequence of SEQ ID NO: 542 and the $V_L$ domain comprises the amino acid sequence of SEQ ID NO: 43;
    d) $V_H$ domain comprises the amino acid sequence of SEQ ID NO: 33 and the $V_L$ domain comprises the amino acid sequence of SEQ ID NO: 544;
    e) $V_H$ domain comprises the amino acid sequence of SEQ ID NO: 540 and the $V_L$ domain comprises the amino acid sequence of the $V_L$ domain of SEQ ID NO: 544;
    f) $V_H$ domain comprises the amino acid sequence of SEQ ID NO: 541 and the $V_L$ domain comprises the amino acid sequence of SEQ ID NO: 544;
    g) $V_H$ domain comprises the amino acid sequence of SEQ ID NO: 542 and the $V_L$ domain comprises the amino acid sequence of SEQ ID NO: 544;
    h) $V_H$ domain comprises the amino acid sequence of SEQ ID NO: 33 and the $V_L$ domain comprises the amino acid sequence of SEQ ID NO: 545;
    i) $V_H$ domain comprises the amino acid sequence of SEQ ID NO: 540 and the $V_L$ domain comprises the amino acid sequence of SEQ ID NO: 544;
    j) $V_H$ domain comprises the amino acid sequence of SEQ ID NO: 541 and the $V_L$ domain comprises the amino acid sequence of SEQ ID NO: 544;
    k) $V_H$ domain comprise the amino acid sequence of SEQ ID NO: 542 and the $V_L$ domain comprises the amino acid sequence of SEQ ID NO: 544;
    l) $V_H$ domain comprises the amino acid sequence of SEQ ID NO: 33 and the $V_L$ domain comprises the amino acid sequence of SEQ ID NO: 543;
    m) $V_H$ domain comprises the amino acid sequence of the $V_H$ domain of SEQ ID NO: 540 and the $V_L$ domain comprises the amino acid sequence of SEQ ID NO: 543;
    n) $V_H$ domain comprises the amino acid sequence of SEQ ID NO: 541 and the $V_L$ domain comprises the amino acid sequence of SEQ ID NO: 543;
    o) $V_H$ domain comprise the amino acid sequence of SEQ ID NO: 542 and the $V_L$ domain comprises the amino acid sequence of SEQ ID NO: 543.

2. The antibody or fragment thereof according to claim 1, wherein the antibody or fragment thereof comprises a heavy chain and a light chain, and
    a) the heavy chain amino acid sequence comprises the amino acid sequence of SEQ ID NO: 47 and the light chain amino acid sequence comprises the amino acid sequence of SEQ ID NO: 45;
    b) the heavy chain amino acid sequence comprises the amino acid sequence of SEQ ID NO: 48 and the light chain amino acid sequence comprises the amino acid sequence of SEQ ID NO: 45;
    c) the heavy chain amino acid sequence comprises the amino acid sequence of SEQ ID NO: 49 and the light chain amino acid sequence comprises the amino acid sequence of SEQ ID NO: 45;
    d) the heavy chain amino acid sequence comprises the amino acid sequence of SEQ ID NO: 342 and the light chain amino acid sequence comprises the amino acid sequence of SEQ ID NO: 45;
    e) the heavy chain amino acid sequence comprises the amino acid sequence of SEQ ID NO: 35 and the light chain amino acid sequence comprises the amino acid sequence of SEQ ID NO: 50;
    f) the heavy chain amino acid sequence comprises the amino acid sequence of SEQ ID NO: 47 and the light chain amino acid sequence comprises the amino acid sequence of SEQ ID NO: 50;
    g) the heavy chain amino acid sequence comprises the amino acid sequence of SEQ ID NO: 48 and the light chain amino acid sequence comprises the amino acid sequence of SEQ ID NO: 50;
    h) the heavy chain amino acid sequence comprises the amino acid sequence of SEQ ID NO: 49 and the light chain amino acid sequence comprises the amino acid sequence of SEQ ID NO: 50;
    i) the heavy chain amino acid sequence comprises the amino acid sequence of SEQ ID NO: 342 and the light chain amino acid sequence comprises the amino acid sequence of SEQ ID NO: 50;
    j) the heavy chain amino acid sequence comprises the amino acid sequence of SEQ ID NO: 35 and the light chain amino acid sequence comprises the amino acid sequence of SEQ ID NO: 51;
    k) the heavy chain amino acid sequence comprises the amino acid sequence of SEQ ID NO: 47 and the light chain amino acid sequence comprises the amino acid sequence of SEQ ID NO: 51;
    l) the heavy chain amino acid sequence comprises the amino acid sequence of SEQ ID NO: 48 and the light chain amino acid sequence comprises the amino acid sequence of SEQ ID NO: 51;
    m) the heavy chain amino acid sequence comprises the amino acid sequence of SEQ ID NO: 49 and the light chain amino acid sequence comprises the amino acid sequence of SEQ ID NO: 51;
    n) the heavy chain amino acid sequence comprises the amino acid sequence of SEQ ID NO: 342 and the light chain amino acid sequence comprises the amino acid sequence of SEQ ID NO: 51;
    o) the heavy chain amino acid sequence comprises the amino acid sequence of SEQ ID NO: 35 and the light chain amino acid sequence comprises the amino acid sequence of SEQ ID NO: 298;
    p) the heavy chain amino acid sequence comprises the amino acid sequence of SEQ ID NO: 47 and the light chain amino acid sequence comprises the amino acid sequence of SEQ ID NO: 298;
    q) the heavy chain amino acid sequence comprises the amino acid sequence of SEQ ID NO: 48 and the light chain amino acid sequence comprises the amino acid sequence of SEQ ID NO: 298;

r) the heavy chain amino acid sequence comprises the amino acid sequence of SEQ ID NO: 49 and the light chain amino acid sequence comprises the amino acid sequence of SEQ ID NO: 298;

s) the heavy chain amino acid sequence comprises the amino acid sequence of SEQ ID NO: 342 and the light chain amino acid sequence comprises the amino acid sequence of SEQ ID NO: 298.

3. A pharmaceutical composition comprising the antibody or fragment thereof of claim 1 and a pharmaceutically acceptable excipient, diluent or carrier.

4. A kit comprising the pharmaceutical composition of claim 3, wherein the composition is for treating a hPD-L1-mediated condition or disease.

5. The pharmaceutical composition of claim 3, further comprising a therapeutic agent independently selected from the group consisting of:
   a) other immune checkpoint inhibitors;
   b) immune stimulators;
   c) chemokine receptor antagonists;
   d) targeted kinase inhibitors;
   e) angiogenesis inhibitors;
   f) immune stimulating peptides or chemokines;
   g) cytokines;
   h) bispecific T-cell engagers (BiTEs) having at least one specificity against CD3;
   i) other bi-specific molecules;
   j) oncolytic viruses;
   k) vaccination with tumour associated antigens;
   l) cell-based therapies;
   m) bi-specific NK cell engagers having a specificity against an activating MK receptor; and
   n) adoptive transfer of tumour specific T-cells or LAK cells.

6. The antibody or fragment thereof of claim 1, wherein the antibody or fragment comprises a human constant region comprising the amino acid sequence of SEQ ID NO: 199 or SEQ ID NO: 205.

* * * * *